United States Patent [19]

Martel et al.

[11] Patent Number: 5,672,701

[45] Date of Patent: Sep. 30, 1997

[54] 4-SUBSTITUTED ALKYL CARBAPENEM ANTIBIOTICS

[75] Inventors: Alain Martel, Delson; Carol Bachand, Candiac; Marcel Menard, Carignan, all of Canada

[73] Assignee: Bristol-Myers Squibb Company, Princeton, N.J.

[21] Appl. No.: 378,899

[22] Filed: Jan. 26, 1995

Related U.S. Application Data

[63] Continuation of Ser. No. 196,876, Feb. 15, 1994, abandoned, which is a continuation of Ser. No. 32,818, Mar. 15, 1993, abandoned, which is a continuation of Ser. No. 708,951, May 31, 1991, abandoned, which is a continuation-in-part of Ser. No. 613,921, Nov. 20, 1990, abandoned, which is a continuation-in-part of Ser. No. 466,017, Jan. 16, 1990, abandoned.

[51] Int. Cl.$^6$ ................................................ C01D 487/04
[52] U.S. Cl. ................................................ 540/350
[58] Field of Search ................................................ 540/350

[56] References Cited

U.S. PATENT DOCUMENTS

| 3,950,357 | 4/1976 | Kahan et al. . |
| 4,194,047 | 3/1980 | Christensen et al. . |
| 4,218,462 | 8/1980 | Christensen et al. . |
| 4,232,036 | 11/1980 | Christensen et al. . |
| 4,312,871 | 1/1982 | Christensen et al. . |
| 4,341,706 | 7/1982 | Christensen ............... 540/350 |
| 4,600,713 | 7/1986 | Christensen et al. . |
| 4,644,061 | 2/1987 | Kim . |
| 4,769,451 | 9/1988 | Dextraze . |
| 4,960,879 | 10/1990 | Uyeo et al. . |
| 5,102,997 | 4/1992 | Sugimura et al. . |

FOREIGN PATENT DOCUMENTS

| 10317 | 4/1980 | European Pat. Off. . |
| 30032 | 6/1981 | European Pat. Off. . |
| 45198 | 2/1982 | European Pat. Off. . |
| 71908 | 2/1983 | European Pat. Off. . |
| 160391 | 11/1985 | European Pat. Off. . |
| 160876 | 11/1985 | European Pat. Off. . |
| 170019 | 2/1986 | European Pat. Off. . |
| 235823 | 9/1987 | European Pat. Off. . |
| 336143 | 3/1989 | European Pat. Off. . |
| 433759 | 6/1991 | European Pat. Off. ............... 540/350 |

OTHER PUBLICATIONS

Vasil'Eva C.A. 72 (121120j) 1970.
Fedin C.A.72 (116554z) 1970.
E. Goetschi et al., Abstract 759 from 27th Interscience Conference on Antimicrobial Agents and Chemotheraphy Oct. 4–7, 1987.
European Search Report on EP–433,759, issued Apr. 5, 1991.

Primary Examiner—Robert Gerstl
Attorney, Agent, or Firm—Aldo A. Algieri

[57] ABSTRACT

Compounds of the formula

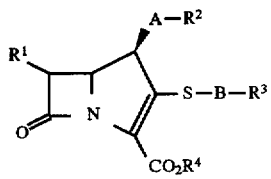

wherein

A is an unsubstituted or hydroxy-substituted straight or branched $C_{1-10}$ alkylene group or a straight or branched $C_{1-10}$ alkylene group having an intervening heteroatom selected from oxygen, sulfur and nitrogen;

$R^2$ is hydroxy, halogen, $C_{1-4}$ alkoxy, nitrile, azido, a quaternary ammonio group, $-NR^5R^6$,

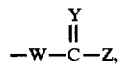

azetidinyl, or a 5- or 6-membered heterocyclic group selected from heteroaromatic and heteroalicyclic joined through a carbon atom thereof;

or a non-toxic pharmaceutically acceptable salt thereof, are novel antimicrobial agents which are useful in the treatment of infectious disease in humans and other animals. Novel intermediates and processes for their preparation are also disclosed.

77 Claims, No Drawings

4-SUBSTITUTED ALKYL CARBAPENEM ANTIBIOTICS

CROSS-REFERENCE TO RELATED APPLICATIONS

This application is a continuation of Ser. No. 08/196876 filed Feb. 15, 1994 which is a continuation of Ser. No. 08/032818 filed Mar. 15, 1993 which is a continuation of Ser. No. 07/708951 filed May 31, 1991 which is a cip of Ser. No. 07/613921 filed Nov. 20, 1990 which is a cip of Ser. No. 07/466017 Jan. 16, 1990 all now abandoned.

BACKGROUND OF THE INVENTION

1. Field of the Invention

The present invention relates to novel carbapenem antibiotics having a substituted alkyl group in the 4-position and non-toxic pharmaceutically acceptable salts thereof, which have antimicrobial activity. Therefore, the present carbapenem antibiotics and pharmaceutical compositions thereof are useful in the treatment of antibacterial infections in humans and other animals, either alone or in combination with other antibiotics (class 514, subclass 210). The present invention also provides processes for the preparation of the carbapenem antibiotics and to certain novel intermediates.

2. Nomenclature

The terminology for compounds of this class may either be based upon the root name "carbapenem" which employs a trivial system of nomenclature or on the systematic name according to Chemical Abstracts. In the present invention, the positions are numbered according to the Chemical Abstract system, for example, 3-$R^3$, 4-$R^2$, 6-$R^1$-7-oxo-1-azabicyclo[3.2.0]hept-2-ene-2-carboxylic acid as shown in the following Formula

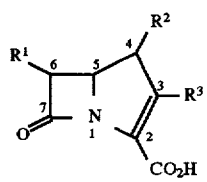

The term "carbapenem", as used herein as a class of compounds, is intended to be used interchangeably with the name 7-oxo-1-azabicyclo[3.2.0]hept-2-ene-2-carboxylic acid. However, in all instances, the numbering system employed will be the numbering system according to Chemical Abstracts as illustrated above.

3. Disclosure Statement

A great number of carbapenem antibiotics are known in the art. This class of antibiotics is typefied by thienamycin (U.S. Pat. No. 3,950,357, issued Apr. 13, 1976) which was first isolated from fermentation and exhibits a broad spectrum of antibiotic activity. Imipenem (U.S. Pat. No. 4,194,047, issued Mar. 18, 1980), a subsequent chemically more stable derivative of thienamycin, was developed. Clinical utility was limited, however, owing to its rapid decomposition in man by kidney dehydropeptidase (DHP). For this reason, imipenem is clinically administered in combination with a DHP inhibitor.

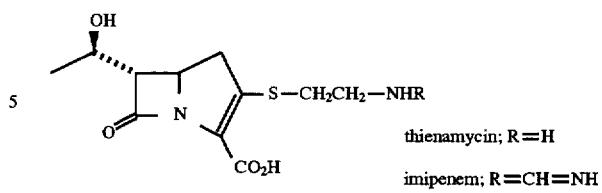

thienamycin; R=H
imipenem; R=CH=NH

Despite the broad spectrum of antibiotic activity of imipenem, there still exists a need for more effective carbapenem antibiotics which are both chemically and biologically more stable than imipenem in the treatment of infectious disease. The search for improved carbapenem antibiotics is continuing which is exemplified by the large number of patents that have been granted and published in this field. The closest carbapenem art is represented by the following publications and patents.

European Patent Publication EP-30,032, published on Jun. 10, 1981, discloses a large number of carbapenems having the Formula

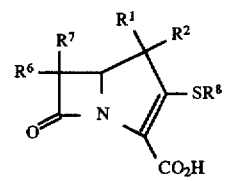

wherein $R^1$, $R^2$, $R^6$, $R^7$ and $R^8$ are independently selected from the group consisting of inter alia hydrogen, ($R^1$ and $R^2$ are not hydrogen), substituted and unsubstituted: alkyl, alkenyl and alkynyl having from 1–10 carbon atoms. The generic disclosure does not provide any distinction between the various substituents on $R^1$, $R^2$, $R^6$, $R^7$ and $R^8$ except for the proviso that $R^1$ and $R^2$ are not hydrogen.

European Patent Publication EP-45,198, published on Feb. 3, 1982, describes a series of carbapenems having the Formula

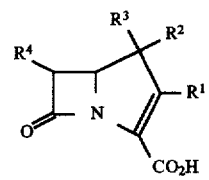

wherein $R^1$ is an alkyl, aryl, alkylthio, arylthio or acylaminoalkylthio group; $R^2$ and $R^3$ are each independently an alkoxycarbonyl or cyano group or a group of the formula $COR^1$; and $R^3$ may further be an alkyl or aryl group. The disclosure provides that the 4-position have two substituents with at least one of which is other than an alkyl group.

European Patent Publication EP-71,908, published on Feb. 16, 1983, discloses a series of carbapenems having the Formula

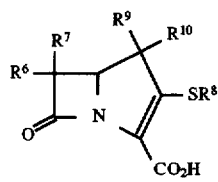

wherein $R^6$ and $R^7$, and $R^9$ and $R^{10}$ is a group of substituents which are not distinguished but are the same for both groups. Although there is a preferred list of substituents on page 57 for $R^9$ and $R^{10}$, only methyl is exemplified in the Examples.

European Patent Publication EP-160,391, published on Nov. 6, 1985, describes a series of carbapenems having the Formula

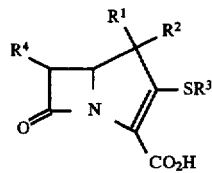

wherein $R^1$ and $R^2$ are the same or different and each represents a hydrogen atom (provided that $R^1$ and $R^2$ do not both represent hydrogen atoms), a halogen atom, a $C_2$–$C_7$ alkoxycarbonyl group or a substituted or unsubstituted $C_{1-10}$ alkyl, $C_2$–$C_6$ alkenyl, $C_2$–$C_6$ alkynyl, $C_1$–$C_6$ alkoxy, $C_1$–$C_6$ alkylthio, $C_3$–$C_8$ cycloalkyl, $C_6$–$C_{10}$ carbocyclic aryl, aralkyl, aralkenyl or aralkynyl groups wherein the groups, inter alia, are substituted by various substituents or $R^1$ and $R^2$, together with the carbon atom to which they are attached, form a $C_3$–$C_8$ alicyclic ring. The only substituents exemplified in the examples for $R^1$ and $R^2$ are those in which $R^1$ and $R^2$ is methyl, methoxy, fluoro and 1,1-dimethyl.

European Patent Publication EP-160,876, published on Nov. 13, 1985, discloses a series of carbapenems having the Formula

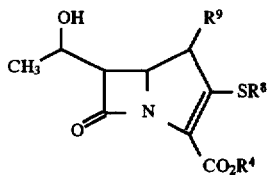

wherein $R^9$ is halogen, OR, $OSO_2R$,

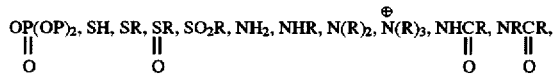

wherein R is hydrogen, $C_{1-6}$ alkyl, $C_{2-6}$ alkenyl, $C_{2-6}$ alkynyl, phenyl, phenylalkyl having 7–12 carbon atoms, cycloalkyl having 3–6 carbon atoms, cycloalkyl having 3–6 carbon atoms in the ring and 1–6 carbon atoms in the alkyl moiety, heterocyclic groups including heterocyclyl, heterocyclyalkyl, heteroaryl, and heteroarylalkyl; wherein the heterocyclic group is a long list of substituents. Fortunately, there is provided a list of representative substituents for $R^9$ on page 29 which show that the attachment of $R^9$ to the carbapenem ring is by halogen, sulfur, oxygen, nitrogen and phosphorous.

European Patent Publication EP-170,019, published on Feb. 5, 1986, discloses a series of carbapenems substituted in the 4-position with an ether group and having the Formula

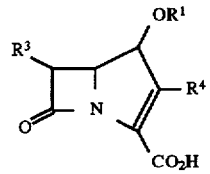

wherein $R^1$ is lower alkyl, aryl or aryl-lower alkyl and $R^3$ and $R^4$ are conventional substituents for carbapenems. The substituents exemplified in the examples are those wherein $R^1$ is methyl, ethyl, isopentyl and phenyl. However, in Abstract 759 of the Twenty-Seventh Interscience Conference on Antimicrobial Agents and Chemotherapy held on Oct. 4–7, 1987, E. Goetschi one of the inventors of EP-170, 019 disclosed some 1β-alkoxy carbapenems of which Ro 19-8928 was specifically exemplified wherein $R^1$ is hydroxyethyl.

Thus, it is the object of the present invention to provide a novel class of antibiotics which have antimicrobial activity and are useful in the treatment of infectious diseases in humans and other animals. Further objects of this invention are to provide chemical processes and intermediates for the preparation of such antibiotics and their non-toxic pharmaceutically acceptable salts and derivatives and to pharmaceutical compositions comprising such antibiotics and methods of treatment by administering such antibiotics and compositions thereof to a human or animal in need thereof.

SUMMARY OF THE INVENTION

The present invention provides novel 4-substituted alkyl carbapenem antibiotics having the Formula

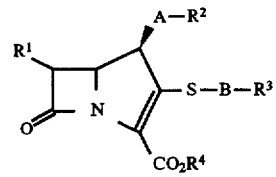

wherein $R^1$, $R^2$, $R^3$, $R^4$, A and B are as defined below, which are potent inhibitors of microorganisms and are useful as antimicrobial agents in the treatment of infectious disease in humans and other animals. Also included are pharmaceutical compositions comprising said carbapenem antibiotics and to the method of treatment comprising administering said carbapenem antibiotic or pharmaceutical composition thereof. The present invention also provides useful intermediates, processes for their preparation and processes for the preparation of compounds of Formula I.

DESCRIPTION OF THE INVENTION

The present invention provides novel 4-substituted alkyl-7-oxo-1-azabicyclo[3.2.0]hept-2-ene-2-carboxylic compounds which are antimicrobial agents useful in the treatment of infectious disease in humans and other animals, and which have the formula

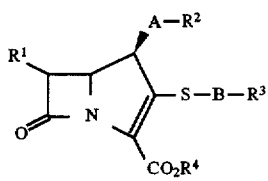

wherein

R$^1$ is hydrogen, C$_{1-2}$ alkyl, —CH$_2$OH, —CH$_2$NH$_2$,

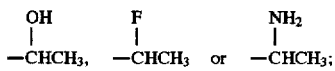

A is an unsubstituted or hydroxy-substituted straight or branched C$_{1-10}$ alkylene group or a straight or branched C$_{1-10}$ alkylene group having an intervening heteroatom selected from oxygen, sulfur and nitrogen;

R$^2$ is hydroxy, halogen, C$_{1-4}$ alkoxy, nitrile, azido, a quaternary ammonio group, —NR$^5$R$^6$,

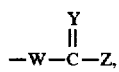

azetidinyl, or a 5- or 6-membered heterocyclic group selected from heteroaromatic and heteroalicyclic joined through a carbon atom thereof;

B is a straight or branched C$_{1-6}$ alkylene group or a direct bond when R$^3$ is joined to the sulfur atom through a carbon atom thereof;

R$^3$ is a residue of an organic group;

R$^4$ is hydrogen, a removable carboxy-protecting group or a physiologically hydrolyzable ester group;

R$^5$ and R$^6$ each are independently hydrogen, C$_{1-6}$ alkyl, C$_{1-4}$ alkoxy, hydroxyethyl, azidoethyl, aminoethyl, and when R$^5$ is hydrogen or C$_{1-4}$ alkyl, R$^6$ is hydroxy, C$_{1-4}$ alkoxy, amino, C$_{1-4}$ alkylamino, di(C$_{1-4}$)-alkylamino, substituted C$_{1-4}$ alkyl wherein said alkyl substituent is selected from hydroxy, azido, amino, guanidino, nitrile, carboxy, formimidoyl and phenyl, or an acyl residue of an amino acid or peptide; or R$^5$ and R$^6$, taken together with the nitrogen atom to which they are attached, is an unsubstituted or substituted heterocyclic group having 1 to 2 ring members and having up to four heteroatoms in each ring independently selected from oxygen, nitrogen and sulfur, wherein said substituent is selected from the group consisting of C$_{1-4}$ alkyl, C$_{1-4}$ alkoxy, trifluoromethyl, hydroxy, halogen, amino, nitrile, carboxy, formimidoyl, carbamido, carbamoyl, C$_{1-4}$ alkylamino and amino(C$_{1-4}$)alkyl;

W is a direct bond, oxygen, sulfur or NR$^{10}$;

Y is oxygen or NR$^{10}$;

Z is hydrogen, hydroxy, C$_{1-4}$ alkyl, C$_{1-4}$ alkoxy, —NR$^7$R$^8$, amino(C$_{1-4}$)alkyl, azido(C$_{1-4}$)alkyl or hydroxy(C$_{1-4}$)alkyl;

R$^7$ and R$^8$ each are independently hydrogen, C$_{1-4}$ alkyl, hydroxy, benzyloxy or alkanoyl; and R$^{10}$ is hydrogen, C$_{1-4}$ alkyl, C$_{1-4}$ alkylamino or di(C$_{1-4}$) alkylamino;

or a non-toxic pharmaceutically acceptable salt thereof.

This invention also provides stereoselective processes for the preparation of the compounds of Formula I and to novel intermediates in the preparation of compounds of Formula I.

The terms "C$_{1-2}$ alkyl", "C$_{1-4}$ alkyl", "C$_{1-6}$ alkyl", and "C$_{1-4}$ alkoxy" as used herein and in the claims (unless the context indicates otherwise) mean straight or branched chain alkyl or alkoxy groups such as methyl, ethyl, propyl, isopropyl, butyl, isobutyl, t-butyl, amyl, hexyl, and the like. Preferably, these groups contain from 1 to 4 carbon atoms and, most preferably, they contain 1 or 2 carbon atoms. The term "lower" is intended to mean 1 to 6 carbon atoms, unless otherwise indicted. The term "C$_{3-6}$ cycloalkyl" as used herein and in the claims means a carbon cyclic ring system such as cyclopropyl, cyclobutyl, cyclopentyl, cycloheptyl and cyclohexyl. The term "C$_{5-6}$ cycloalkylene" as used herein and in the claims means a cyclic ring system containing an unsaturated bond such as cyclopentene, cyclohexene and the like. The terms "straight or branched C$_{1-10}$ alkylene group" and "straight or branched C$_{1-6}$ alkylene group" as used herein and in the claims for "A" and "B", respectively means straight or branched alkylene groups such as methylene, ethylene, propylene, methylethylene, butylene, methylpropylene, ethylethylene, dimethylethylene, pentylene, methylbutylene, ethylpropylene, hexylene, methylpentylene, heptylene, and the like. The term "hydroxy-substituted straight or branched C$_{1-10}$ alkylene group" as used herein and in the claims for "A" means straight or branched alkylene groups substituted with hydroxy such as 2-hydroxyethylene, 2 or 3-hydroxypropylene, 2,3 or 4-hydroxybutylene, 2 or 3-hydroxy-methyl butylene, 2,3,4 or 5-hydroxypentylene and the like. The term "straight or branched C$_{1-10}$ alkylene group having an intervening heteroatom selected from oxygen, sulfur and nitrogen" as used herein and in the claims for "A" means straight or branched alkylene group which contains therein an oxygen, sulfur or nitrogen heteroatom such as —(CH$_2$)$_{1-6}$—O—(CH$_2$)$_{2-6}$—, —(CH$_2$)$_{1-6}$—S—(CH$_2$)$_{2-6}$—, —(CH$_2$)$_{1-6}$—NH—(CH$_2$)$_{2-6}$—, —(CH$_2$)$_{1-6}$—NCH$_3$—(CH$_2$)$_{2-6}$—, and the like. Unless otherwise specified, the term "halogen" as used herein and in the claims is intended to include bromine, chlorine, iodine and fluorine while the term "halide" is intended to include bromide, chloride and iodide anion. The term "quaternary ammonio group" as used herein and in the claims means a quaternary ammonio group which may be acyclic, cyclic, or a combination of the two, and may contain one or more additional hetero atoms selected from nitrogen, sulfur and oxygen. Suitable acyclic, cyclic and combined acyclic/cyclic quaternary ammonio groups are those illustrated herein and those as defined by —⊕≡Q in U.S. Pat. No. 4,486,586, issued Dec. 4, 1984, which is hereby incorporated by reference.

An example of an acyclic quaternary ammonio group is a group of the formula —⊕R'R"R'" in which R', R" and R'" may be the same or different and may, for example, be (lower)alkyl, (lower)alkenyl or substituted(lower)alkyl. Examples of cyclic quaternary ammonio groups are fully unsaturated monocyclic heterocyclic ring systems, and bicyclic heterocyclic ring systems in which at least one N-containing ring is fully saturated. Suitable cyclic ring systems are, for example, pyridinio, pyrimidinio, pyrazinio, thiazolio, thiadiazolio, quinolinio, isoquinolinio, thiazolo[4,5-c]-pyridinio and the like. Examples of combined acyclic/cyclic quaternary ammonio groups include, for example, 1-methyl pyrrolidino, 1-methyl piperidinio, 1-methyl morpholinio, 1-methyl piperazinio, 1-methyl imidazolidinio and 1-methyl isoindolinio.

The term "acyl residue of an amino acid or peptide" means the acyl residue of a naturally occurring amino acid or a peptide derived therefrom. Suitable amino acids are those described herein and other known amino acids such as alanine, glycine, arginine, cysteine, isoleucine, leucine, lysine, methionine, phenylalanine, proline, threonine and the like. Suitable peptides are those containing naturally occurring amino acids. However, it should be appreciated by those skilled in the art that unnatural amino acids such as those in the D-configuration may be attached to the amino acid of the acyl residue which is in the naturally occurring L-configuration. Preferably, suitable peptides are dipeptides of the natural occurring amino acids such as glycylglycine, glycylleucine, alanylalanine, alanylphenylalanine, alanylglycine and the like. It should also be appreciated by those skilled in the art that the carbapenems of Formula I wherein $R^2$ contains an acyl residue of a naturally occurring amino acid or peptide may be active in vivo as a pro-drug, i.e., the amino acid residue may be hydrolyzed by peptidase enzymes in the host to produce a more active form of the desired carbapenem antibiotic. The compounds of the present invention which contain an acyl residue of an amino acid or peptide are more active in vivo than in vitro. The term "non-toxic pharmaceutically acceptable salt" as used herein and in the claims is intended to include non-toxic acid and base salts, and salts of zwitterionic species. Salts with a base is intended to include inorganic metallic salts such as sodium, potassium, calcium and magnesium, the ammonium salt, and salts with non-toxic amines such as trialkylamines, pyridine, picoline, dibenzylamine, ethanolamine, N-methylmorpholine and other amines which have been used to form salts of carboxylic acids. Salts with an acid is intended to include inorganic acid salts such as hydrochloride, hydrobromide, hydroiodide, sulfate, phosphate, and the like, and organic acid salts such as formate, acetate, maleate, citrate, succinate, ascorbate, lactate, fumarate and tartrate which have been used to form salts of basic amines. Since the compounds of Formula I may also have an acidic or basic group in the $R^1$, $R^2$ and $R^3$ substituents, it is intended that "non-toxic pharmaceutically acceptable salt" include suitable acid or base addition salts of these functional groups such as hydrochloride, phosphate, sodium, potassium, ammonium chloride, acetate and other salts of an acidic group or a basic group as described above. Unless otherwise specified, the term "a physiologically hydrolyzable ester group" as used herein and in the claims is intended to include an ester group which is physiologically acceptable and hydrolyzable under physiological conditions such as $C_{1-6}$ alkyl, benzyl, 4-methoxybenzyl, (lower) alkanoyloxy(lower)alkyl, e.g., acetoxymethyl, propionyloxymethyl or pivaloxymethyl, (lower) alkoxycarbonyloxy(lower)alkyl, e.g., methoxycarbonyloxymethyl, ethoxycarbonyloxymethyl or 2-methoxycarbonyloxyethyl, (5-methyl-2-oxo-1,3-dioxol-4-yl)methyl and the like.

Carboxy-protecting groups which can be employed in the present invention to block or protect the carboxylic acid function are well-known to those skilled in the art and, preferably, said groups can be removed, if desired, by methods which do not result in any appreciable destruction of the remaining portion of the molecule, for example, by chemical or enzymatic hydrolysis, treatment with chemical reducing agents under mild conditions, irradiation with ultraviolet light or catalytic hydrogenation. Examples of such readily removable carboxy-protecting groups include moieties such as $C_{1-6}$ alkyl, 2,2,2-trichloroethyl, silyl such as trimethylsilyl and t-butyldimethylsilyl, phenyl, ring substituted phenyl, e.g., 4-chlorophenyl, tolyl, and t-butylphenyl, phenyl(lower)alkyl, ring substituted phenyl (lower)alkyl, e.g., benzyl, 4-methoxybenzyl, 4-nitrobenzyl, benzyhydryl and trityl, methoxymethyl, 2,2,2-trichloroethoxycarbonyl, benzyloxymethyl, (lower) alkanoyloxy(lower)alkyl such as acetoxymethyl, propionyloxymethyl, (lower)alkenyl such as vinyl and allyl, unsubstituted or substituted phenyl($C_{1-4}$)alkoxycarbonyl such as benzyloxycarbonyl and 4-nitrobenzyloxycarbonyl, and ($C_{2-4}$)alkenyloxycarbonyl such as allyoxycarbonyl. Particularly advantageous carboxy protecting groups are benzyl, 4-nitrobenzyl, 2-nitrobenzyl, 2,4-dimethoxybenzyl, 4-methoxybenzyl and the like and, preferably, allyl or substituted allyl. Other suitable protecting groups are disclosed in "Protective Groups in Organic Synthesis", Theodora W. Greene (John Wiley & Sons, 1981), Chapter 5 for carboxy, which is hereby incorporated by reference.

Amino-protecting groups which can be employed in the present invention to block or protect the amino group are well-known to those skilled in the art. Examples of conventional amino-protecting groups are described by J. W. Barton in *Protective Groups in Organic Chemistry*, J. F. W. McOmie, Ed., Plenum Press, New York, N.Y., 1973, Chapter 2 and by R. A. Boissonnas in *Advances in Organic Chemistry*, 3, 159-190 (1963). It will be evident to those skilled in the art that the particular amino-protecting group used is not critical and that one need only select a group stable to the subsequent steps of the reaction process, and which is capable of being removed under conditions which preserves the sensitive β-lactam nucleus.

Suitable amino-protecting groups include, for example, acyl groups such as formyl, acetyl and substituted acetyl (e.g., halogenated acetyl), benzoyl and substituted benzoyl, alkoxycarbonyl, halogenated alkoxycarbonyl, alkenyloxycarbonyl, aralkoxycarbonyl, halogenated aralkoxycarbonyl, benzyl and benzyl derivatives, trityl and trityl derivatives, sulfenyl derivatives, sulfonyl derivatives, diacyl derivatives such as phthalimido or succinimido or derivatives thereof and Schiff bases formed with aldehydes or ketones. Specific examples of suitable amino-protecting groups include formyl, acetyl, trifluoroacetyl, trichloroacetyl, benzoyl, toluoyl, 2,2,2-trichloroethoxycarbonyl, isopropoxycarbonyl, t-butoxycarbonyl, cyclopentyloxycarbonyl, cyclohexyloxycarbonyl, benzyloxycarbonyl, 2-nitrobenzyloxycarbonyl, 4-nitrobenzyloxycarbonyl, 4-methoxybenzyloxycarbonyl, 4-chlorobenzyloxycarbonyl, allyloxycarbonyl, 2-furfuryloxycarbonyl, trimethylsilylethoxycarbonyl, N-phenylcarbamoyl, benzyl, 4-nitrobenzyl, trityl, benzenesulfonyl, p-toluenesulfonyl, 2-nitrophenylsulfenyl, phenylthiocarbonyl, trimethylsilyl, triethylsilyl, triphenylsilyl, t-butyldimethylsilyl, methyldiphenylsilyl and diacyl amino-protecting groups such as phthalimido, succinimido and derivatives thereof.

The compounds of the present invention have several asymmetric carbon atoms and can thus exist in several stereochemical forms. The invention includes the mixture of isomers and the individual stereoisomers. Preferred compounds of the Formula I wherein $R^1$ is other than hydrogen are those having the 4R, 5S, 6S configuration on the 1-azabicyclo[3.2.0]heptane ring structure which is the same stereochemical configuration as the antibiotic thienamycin. In addition, the substituents $R^1$ and A may themselves contain asymmetric carbon atoms. Where appropriate, the $R^1$ substituent can exist in either the R or S configuration. It is intended that both the R and S configurations of $R^1$ are included in the present invention, for example, the R and S isomers of 1-hydroxyethyl, 1-fluoroethyl and 1-aminoethyl substituents. Preferably, the $R^1$ substituent is in the R configuration such as 1R-hydroxyethyl and 1R-aminoethyl. In the instance when the alkylene group of substituent A has a branched alkyl substituent or a hydroxy substituent, the compounds of Formula I will have an additional asymmetric carbon atom. It is intended that the present invention include both isomers of the compounds of Formula I, for example, the compounds of Example 57, 58 and 152.

In the definition of $R^3$ the term "a residue of an organic group" as used herein and in the claims means any organic residue containing at least one carbon atom such as methyl. In addition, the organic group is intended to include but not limited to all the organic groups illustrated herein and 3-substituent groups which are known in the carbapenem art. Suitable quaternized nitrogen-containing heterocycles are disclosed in the U.S. Pat. No. 4,642,341, issued Feb. 10, 1987 and U.S. Pat. No. 4,644,061, issued on Feb. 17, 1987, which are hereby incorporated by reference. Other suitable groups are disclosed in U.S. Pat. No. 4,745,188, issued May 17, 1988, especially in the definition of $R^8$ which is hereby incorporated by reference. Additional organic groups suitable in the definition of $R^3$ are disclosed in U.S. Pat. No. 4,822,787, issued Apr. 18, 1989; U.S. Pat. No. 4,840,946, issued Jun. 20, 1989; U.S. Pat. No. 4,863,916, issued Sep. 5, 1989; U.S. Pat. No. 4,888,344, issued Dec. 19, 1989, U.S. Pat. No. 4,952,397, issued Aug. 28, 1990 and U.S. Pat. No. 4,962,103, issued Oct. 9, 1990, which are all hereby incorporated by reference.

Preferably $R^3$ is hydrogen, $C_{3-6}$ cycloalkyl or substituted $C_{3-6}$ cycloalkyl, $C_{5-6}$ cycloalkenyl or substituted $C_{5-6}$ cycloalkenyl, phenyl or substituted phenyl, hydroxy, $C_{1-4}$ alkoxy, $C_{1-4}$ alkylthio, phenylthio or substituted phenylthio, halogen, nitrile, nitro, $—NR^7R^8$, $—\oplus R^9R^9R^9$,

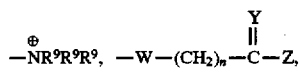

or an unsubstituted or substituted heterocyclic group selected from heteroaromatic, heteroalicyclic,

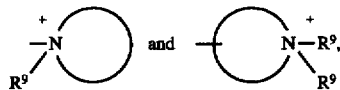

having from one to two rings with 4 to 7 ring members in each ring and having up to four heteroatoms in each ring independently selected from oxygen, nitrogen and sulfur, in which said heterocyclic group may be joined through a sulfur atom attached to a carbon atom of said heterocyclic group, wherein said $C_{3-6}$ cycloalkyl, $C_{5-6}$ cycloalkenyl, phenyl and heterocyclic substituent is selected from the group consisting of one or two $C_{1-4}$ alkyl, $C_{1-4}$ alkoxy, trifluoromethyl, hydroxy, halogen, amino, $C_{1-4}$ alkylamino, di($C_{1-4}$)alkylamino, nitrile, carboxy, formimidoyl, carbamido, carbamoyl, amino($C_{1-4}$)alkyl, $C_{1-4}$ alkylamino($C_{1-4}$)alkyl, di($C_{1-4}$)alkylamino($C_{1-4}$)alkyl, $C_{1-4}$alkoxycarbonyl, $C_{1-4}$ alkoxycarbonyl($C_{1-4}$)alkyl, amino($C_{1-4}$)alkylamino($C_{1-4}$)alkyl and $C_{1-4}$ alkylcarbonyloxy, and said heterocyclic group may also be substituted with

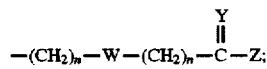

In the definition of $R^2$, the term "azetidinyl" as used herein and in the claims means unsubstituted or substituted and, in the definitions of $R^2$, $R^3$, $R^5$ and $R^6$ of the compounds of Formula I, the term "heterocyclic group" which is unsubstituted or substituted includes the heterocyclic groups illustrated herein and it is also intended to include but not limited to furyl, thienyl, thiazolyl, imidazolyl, imidazolinyl, oxazolyl, oxadiazolyl, thiadiazolyl, triazolyl, tetrazolyl, isoxazolyl, isothiazolyl, pyrrolyl, 3-pyrrolidin-1-yl pyranyl, tetrahydropyranyl, pyrazolyl, pyridyl, pyrimidinyl, tetrahydrofuryl, pyridazinyl, pyrazinyl, triazinyl, azetidinyl, pyrrolidinyl, piperidyl, piperazinyl, thiazolidin-5-yl, morpholinyl, thiomorpholinyl, 1,4-thiazin-2-yl, benzoxazolyl, indolyl, benzimidazolyl, quinolinyl, isoquinolinyl, quinoxalinyl and quinazolinyl, 6,7-dihydro-5H-pyrazolo[1,2-a][1,2,4]triazolium-6-yl wherein said azetidinyl and heterocyclic substituent of $R^2$, $R^3$, $R^5$ and $R^6$ is selected from the group comprising one or two $C_{1-4}$ alkyl, $C_{1-4}$ alkoxy, trifluoromethyl, hydroxy, halogen, amino, $C_{1-4}$ alkylamino, di($C_{1-4}$)alkylamino, nitrile, carboxy, formimidoyl, carbamido, carbamoyl, amino($C_{1-4}$)alkyl, $C_{1-4}$ alkylamino, di($C_{1-4}$)alkylamino($C_{1-4}$)alkyl, $C_{1-4}$ alkoxycarbonyl, $C_{1-4}$ alkoxycarbonyl($C_{1-4}$)alkyl, $C_{1-4}$ alkylcarbonyloxy and

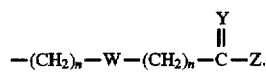

Compounds of Formula I wherein $R^4$ is hydrogen, an anionic charge or a physiologically hydrolyzable ester group together with non-toxic pharmaceutically acceptable salts thereof are useful as antimicrobial agents. The remaining compounds of Formula I are valuable intermediates which can be converted into the above-mentioned biologically active compounds.

The carbapenem compounds of Formula I may be prepared by various procedures. In one embodiment, the compounds of Formula I are preferably prepared from novel compounds of Formula II

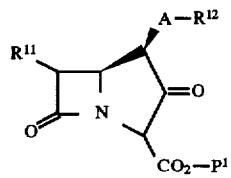

wherein $R^{11}$ is hydrogen, $C_{1-2}$ alkyl, $—CH_2OH$, $—CH_2O—P^2$, $—CH_2NH_2$, $—CH_2N—P^4$,

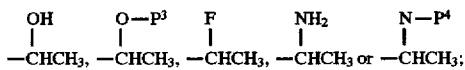

A is an unsubstituted or hydroxy-substituted straight or branched $C_{1-10}$ alkylene group or a straight or branched $C_{1-10}$ alkylene group having an intervening heteroatom selected from oxygen, sulfur and nitrogen; $P^1$ is a conventional readily removable carboxy-protecting group; $R^{12}$ is hydroxy, halogen, $C_{1-4}$ alkoxy, azido, $O—P^3$, $N—P^4$, $N(C_{1-4}$ alkyl$)$-$P^4$, or an optionally protected azetidinyl or 5- or 6-membered heterocyclic group selected from heteroaromatic and heteroalicyclic joined through a carbon atom thereof; $P^2$ and $P^3$ each are independently a conventional hydroxy-protecting group; and $P^4$ is a conventional amino-protecting group.

In another embodiment, the compounds of Formula II may be prepared from novel intermediates of Formula III

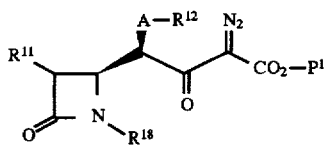

wherein $R^{11}$, A, $R^{12}$ and $P^1$ are as defined above and $R^{18}$ is hydrogen or $P^4$ in which $P^4$ is a conventional amino-protecting group.

In yet another embodiment, the compounds of Formula III may be prepared from novel intermediates of Formula IV

wherein $R^{11}$, A, $R^{12}$ and $R^{18}$ are as defined above.

The compounds of Formula IV may be prepared by various procedures, and, by way of illustration, the process for preparing one of the more preferred embodiments of compounds of Formula IV may be summarized for the preparation of intermediate compounds of Formula IVa by the reaction sequence illustrated in Reaction Scheme I.

In this sequence, the thioester VI which is prepared in Step(A) from the thiol V is converted to the silyl enol ether VII in Step(B), and without separation is coupled, in Step (C), to the azetidinone VIII by nucleophilic displacement of the 4-position leaving group "L". The resulting intermediate IX (illustrated in the β-isomer form) can then be saponified in Step(D) to yield the corresponding carboxylic acid IVa. The general process and methods of the reactions illustrated in Reaction Scheme I is described by the present inventor in U.S. Pat. No. 4,772,683 patented Sep. 20, 1988 and is hereby incorporated by reference.

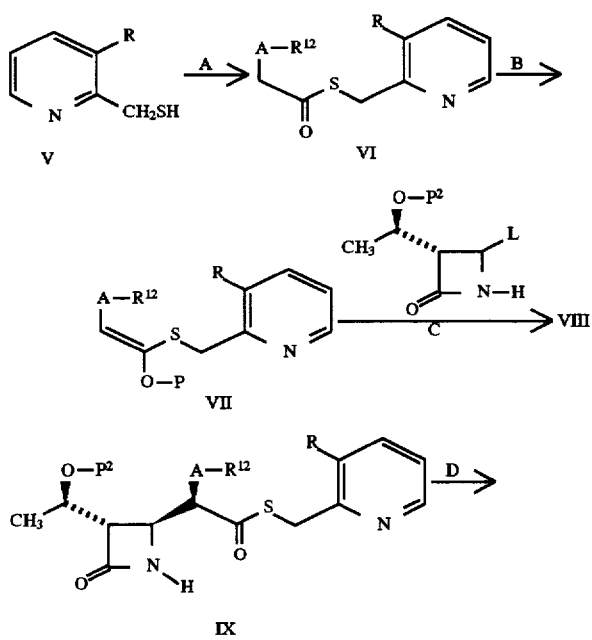

-continued
Reaction Scheme 1

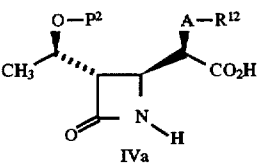

Referring now to Reaction Scheme 1, Step(A) illustrates the esterification reaction of a thiol V to a thioester VI. The reaction of Step(A) is well-known to those skilled in the art and may be carried out with 2-picolyl mercaptan wherein R is hydrogen or methyl and an appropriately activated carboxy moiety as described herein wherein A and $R^{12}$ are as previously defined.

Step(B) illustrates the reaction between thioester VI and a triorganosilyl triflate silylating agent to form the silyl enol ether VII. The reaction of Step(B) is carried out in an inert organic solvent and in the presence of an organic base. Suitable inert organic solvents which can be used include methylene chloride, tetrahydrofuran, carbon tetrachloride, cyclohexane, dioxane, dimethoxyethane, diethyl ether and chloroform. Reaction temperatures can be in the range of from about −40° C. to +30° C. Most conveniently, the reaction is carried out by mixing the reactants under cooling, advantageously between about −15° C. and 0° C. and then allowing them to gradually warm to room temperature.

Triorganosilyl triflate silylating agents are well known, and include trimethylsilyl trifluoromethanesulfonate, triisopropylsilyl trifluoromethanesulfonate, triethylsilyl trifluoromethanesulfonate, t-butyldimethylsilyl trifluoromethanesulfonate, t-butyldiphenylsilyl trifluoromethanesulfonate, or 2,4,6-tri(t-butylphenoxy) dimethylsilyl trifluoromethanesulfonate. Advantageous results have been obtained using t-butyldimethylsilyl trifluoromethanesulfonate. Thus, P will be the triorganosilyl residue of the particular triorganosilyl triflate silylating agent used.

Suitable organic amine bases include diisopropylethylamine, DBU (1,8-diazabicyclo[5.4.0] undec-7-ene),DBN (1,5-diazabicyclo[4.3.0]non-5-ene), but especially preferred are the tri($C_1$–$C_4$)alkylamines such as trimethylamine, triethylamine, tributylamine and tripropylamine. It has been found, however, that in certain instances a stronger base may be necessary to carry out the reaction of Step(A).

Generally, the organic base and triorganosilyl triflate silylating agent are present in an approximately twofold molar excess when compared to the thioester VI, with the base being slightly in excess of the triorganosilyl triflate silyating agent. Reaction times usually vary from about one hour to about five hours, but generally a maximum yield will be obtained in about three hours. Advantageously, the reaction is carried out under an inert atmosphere.

In Step(B), the silyl enol ether VII is reacted with a 4-position substituted azetidinone VIII to yield intermediate IX. The reaction is carried out in the presence of a Lewis acid catalyst and a solvent which is inert in the presence of the Lewis acid catalyst, and preferably under an inert atmosphere.

Suitable inert solvents, which are discussed above, are advantageously dry, and will generally comprise about 10% of the total reaction mixture volume. Dichloromethane has been found to provide satisfactory results.

Suitable Lewis acid catalysts include zinc halides, zirconium halides and boron trifluoride. Zinc chloride has been found to provide satisfactory results.

The silyl enol ether VII is substituted by a group "—A—R¹²" wherein A is an unsubstituted or hydroxy-substituted straight or branched $C_{1-10}$ alkylene group or a straight or branched $C_{1-10}$ alkylene group having an intervening heteroatom selected from oxygen, sulfur and nitrogen and $R^{12}$ is hydroxy, halogen, $C_{1-4}$ alkoxy, azido, O—$P^3$, N—$P^4$, N($C_{1-4}$ alkyl)-$P^4$, or an optionally protected azetidinyl or 5- or 6-membered heterocyclic group selected from heteroaromatic and heteroalicyclic joined through a carbon atom thereof in which $P^3$ is a conventional hydroxy-protecting group and $P^4$ is a conventional amino-protecting group.

The 3,4-disubstituted azetidinone intermediates such as that of Formula VIII wherein $P^2$ represents a conventional hydroxy-protecting group and L represents a conventional leaving group are known per se and are key intermediates in the synthesis of carbapenem and penem antibiotics having an (R)-hydroxyethyl substituent at the 6-position of the carbapenem or penem nucleus.

The 4-position substituent of the compound of Formula VIII is designated by "L", which represents a leaving group capable of being displaced by nucleophiclic substitution of the silyl enol ether VII. Such leaving groups include acyloxy (e.g., acetoxy, propionyloxy or t-butyryloxy), halogen (e.g., chloro), arylsulfonyl (e.g., phenylsulfonyl), mesyl and tosyl. Advantageously, "L" is acetoxy because 4-acetoxyazetidinone is a readily available starting material.

The hydroxy-protecting group "$P^2$" of azetidinone VIII and the hydroxy-protecting group of "$P^3$" in substituent "$R^{12}$" of the silyl enol ether of Formula VII may be the same or different. Preferably, "$P^2$" and "$P^3$" are the same and, more preferably, "P", "$P^2$" and "$P^3$" are the same.

Hydroxy-protecting groups, which are known to those skilled in the art, are desirable because they prevent side reactions and provide increased yields in later steps of the reaction sequence. Suitable hydroxy-protecting groups may be, for example, acyl groups such as benzyloxycarbonyl, benzhydryloxycarbonyl, trityloxycarbonyl, p-nitrobenzyloxycarbonyl and 2,2,2-trichloroethoxycarbonyl, aralkyl groups such as benzyl, benzhydryl, trityl or p-nitrobenzyl, or triorganosilyl groups such as tri($C_1$-$C_6$) alkylsilyl (e.g. trimethylsilyl, triethylsilyl, triisopropylsilyl, isopropyldimethylsilyl, t-butyldimethylsilyl, methyldiisopropylsilyl or methyldi-t-butylsilyl), triarylsilyl (e.g. triphenylsilyl, tri-p-xylsilyl) or triaralkylsilyl (e.g. tribenzylsilyl). Examples of these and other suitable hydroxy-protecting groups and methods for their formation and removal are known in the art, e.g. see *Protective Groups in Organic Synthesis*, T. W. Greene, John Wiley & Sons, New York 1981, Chapter 2.

The hydroxy-protecting group selected for "$P^2$" and "$P^3$" is preferably one that is removable at a later stage of the reaction process. Bulky triorganosilyl groups such as triisopropylsilyl, t-butyldiphenylsilyl or t-butyldimethylsilyl are advantageously employed because they provide for an essentially stereo-controlled reduction step. Such groups can be readily removed under mild conditions, e.g., by treatment with methanolic HCl or with fluoride ion (e.g., tetra-n-butyl ammonium fluoride/tetrahydrofuran), which preserves the sensitive β-lactam nucleus.

The reaction of Step(C) is advantageously carried out under an inert atmosphere, and at a temperature of from about −30° C. to about room temperature. Preferably, the reactants are added under cooling, about −15° C. to about +5° C., and allowed to react at about 0°–5° C. and then, if desired, allowed to gradually warm to room temperature. The reaction can be stirred, if desired, for up to 30 hours to achieve maximum yield.

The β-isomer of the resulting intermediate IX can be separated from the corresponding α-isomer by conventional chromatography or HPLC, or preferably, by crystallization. Alternatively, the β-isomer can be separated from the α-isomer upon saponification of intermediate IX, as discussed below in Step(D), which yields the corresponding carboxylic acid IVa because the β-isomer preferentially crystallizes when the β/α ratio is about 2/1 or greater.

In Step(D), the compound of Formula IX is saponified to yield the corresponding carboxylic acid IVa. Saponification is well-known to those skilled in the art and can be carried out as follows. The compound of Formula IX may first be dissolved in a solvent such as tetrahydrofuran and aqueous tetrahydrofuran and then, under cooling, an excess of inorganic base, such as sodium hydroxide, is added. Hydrogen peroxide may also be added. It is preferred that hydrogen peroxide be added to the saponification reaction and, more preferably, it may be added prior to the addition of the inorganic base. The reaction is usually complete within 1–2 hours at about 0° C. to about room temperature and the carboxylic acid IVa is produced upon subsequent acidification with an inorganic acid such as hydrochloric acid.

The process for preparing diazo intermediates of Formula IIIa may conveniently be summarized by Reaction Scheme 2. Briefly, in this reaction sequence, the carboxylic acid moiety of azetidinone IVa is activated and displaced with a mono carboxy-protected magnesium malonate in Step(E) to produce the β-keto ester X which is then followed by diazotization in Step(F) to yield the corresponding diazo intermediate IIIa.

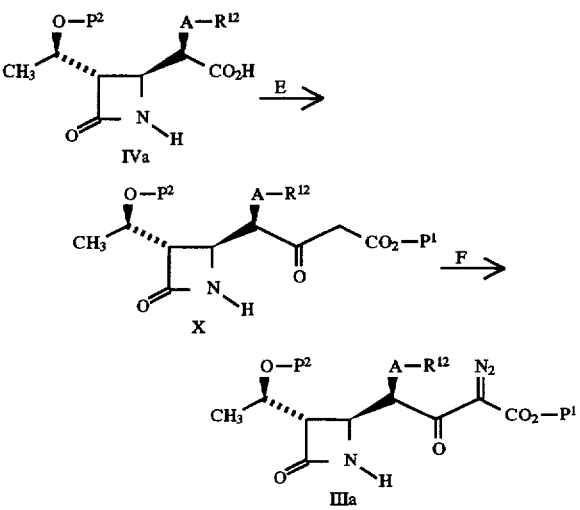

Referring now to Reaction Scheme 2, the reaction of the acid IVa to the keto ester X in Step(E) is conveniently carried out by a 2-step process. The carboxylic acid moiety is first activated by a conventional carboxy-activating group well-known to those skilled in the art and, preferably, with carbonyl-diimidazole in an inert solvent such as tetrahydrofuran, dimethoxyethane, acetonitrile, benzene and toluene, and preferably in benzene or toluene or a mixture of acetonitrile-benzene. Reaction temperatures can be in the range of from about −15° C. to about 70° C. and, preferably at about 0°–20° C. The activated carboxy intermediate may be isolated but it is preferred that the intermediated be reacted in situ under an inert atmosphere in the second step with a magnesium malonate which has been preferably dried prior to use such as azetropically removing any residual water with a Dean-Stark trap. Preferably, the magnesium malonate is a monoalkyl or monoaryl malonate such as monoallyl or substituted allyl malonate, mono benzyl, 2-nitrobenzyl, 4-nitrobenzyl, 4-methoxybenzyl or 2,4-dimethoxybenzyl malonate.

The reaction of a magnesium malonate with the activated carboxy moiety is carried out in an inert organic solvent such as tetrahydrofuran, dioxane, dichloromethane, acetonitrile, benzene and toluene and, preferably, in benzene or acetonitrile at a temperature of about 0° C. to about 80° C. Advantageously, the reaction is allowed to proceed at about 60° C. until the reaction is essentially complete which is usually about 18 hours. Generally, the magnesium malonate is advantageously present in an excess of about 1.1 to about 3.0 mole equivalent per equivalent of acid IVa. The excess of magnesium malonate may be added all at once to the reaction or, if desired, may be added stepwise until the reaction is complete and maximum yield has been achieved.

In Step(F), the keto ester X is diazotized to yield the corresponding diazo intermediate IIIa. Diazotization is well-known in the art and can be carried out in an inert solvent such as acetonitrile, dichloromethane, toluene, benzene and the like. Preferably, the reaction is carried out in acetonitrile with an azide such as 4-carboxybenzenesulfonylazide, p-toluenesulfonylazide, methanesulfonylazide and the like. The reaction is conducted in the presence of a base such as triethylamine, diethylamine, pyridine, lutidine or the like for about 1 to 30 hours at a temperature of about 0° to 50° C.

In Reaction Scheme 3, $R^{12}$, A, $P^1$ and $P^2$ are as previously defined. Generally, the diazo compound of Formula IIIa is cyclized directly in Step(G) to the bicyclic ketone of Formula IIa. Alternatively, if desired, the diazo compound of Formula IIIa is deprotected at the 6-position in Step(H) before cyclization to the bicyclic ketone of Formula IIb.

such as bis(acetylacetonate)Cu(II), copper sulfate, copper powder, rhodium acetate [$Rh_2(OAc)_4$], rhodium (II) octanoate, $Pd(OAc)_2$, $Pb(OAc)_4$ and the like and, preferably, rhodium (II) acetate or octanoate. Alternatively, the cyclization may be carried out by irradiation of the compound of Formula IIIa from a light source through a Pyrex filter (wavelength greater than 300 nm) in a solvent such as benzene, diethyl ether or the like at a temperature from about 0° to about room temperature for 30 minutes to about 2 hours.

In an alternate reaction route, the diazo compound of Formula IIIa wherein $P^2$ is preferably a triorganosilyl protecting group and, most preferably, a t-butyldimethylsilyl group is removed in Step(H) by subjecting the compound of Formula IIIa to acidic hydrolysis in a solvent such as acetonitrile, methanol, ethanol, tetrahydrofuran, dioxane and the like in the presence of an acid such as hydrochloric acid, sulfuric acid and acetic acid and, preferably, with about 3 equivalents of 1N aqueous hydrochloric acid at about −10° to about 30° C. Preferably, the reaction is carried out from about 0° to about room temperature for about 6 to 18 hours, and, advantageously, at room temperature for 18 hours. The diazo compound of Formula IIIb is then subjected to cyclizing conditions in Step(I) which are the same as those for Step(G) discussed above to yield the bicyclic ketone of Formula IIb.

The compounds of Formula Ia wherein A, B, $R^3$, $R^4$, and $R^{12}$ are as previously defined may be prepared from the bicyclic ketones of Formula IIa or IIb following the sequence of reactions illustrated in Reaction Scheme 4. It should be appreciated by those skilled in the art that both reaction routes are suitable for the preparation of compounds of Formula Ia. Nevertheless, the choice of reaction route will Reaction Scheme 3

Cyclization of the diazo compound of Formula IIIa to the bicyclic compound of Formula IIa in Step(G) may be carried out in an inert organic solvent such as tetrahydrofuran, ethyl acetate, benzene, toluene, hexane, cyclohexane or the like at a temperature from about room temperature to about 110° C. for 15 minutes to about 5 hours in the presence of a catalyst depend on the starting material to be used such as compounds of Formula IIa or IIb and the definition of the substituents A, B, $R^3$ and $R^{12}$. Thus Steps(J) and (K) are carried out with and Steps(J') and (K') are carried out without the presence of a hydroxy-protecting group in the substituent at position 6 of the carbapenem nucleus.

Reaction Scheme 4

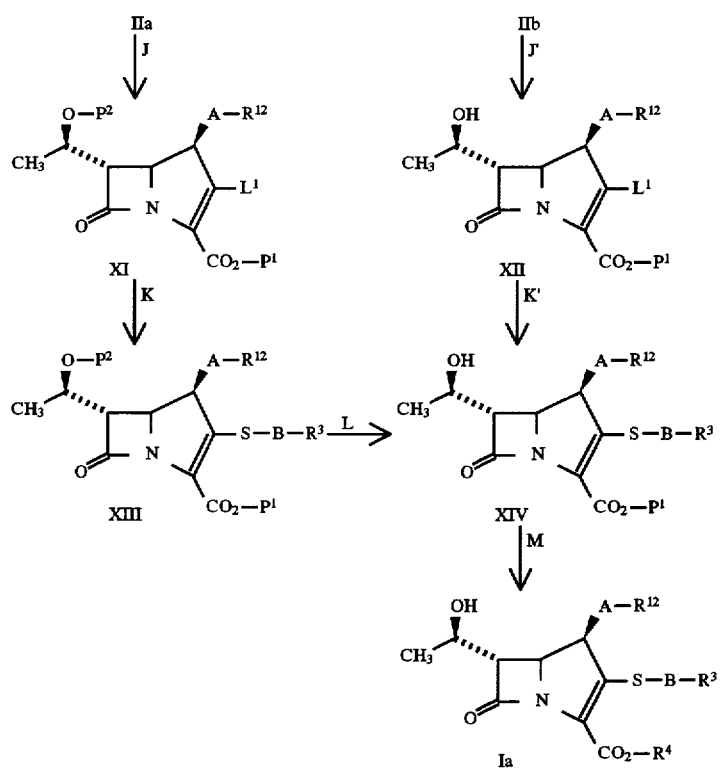

To elaborate on the processes of Reaction Scheme 4, Steps(J) and (J') illustrate the acylation or activation of the keto esters IIa and IIb. The reaction of Steps(J) and (J') are well-known to those skilled in the art and may be carried out with suitable acylating agents to provide a leaving group $L^1$ suitable for the displacement reaction of Steps(K) and (K').

Suitable acylating agents to prepare $L^1$ may include acid anhydrides such as acetic acid anhydride, methanesulfonic acid anhydride, p-toluenesulfonic acid anhydride, p-nitrophenylsulfonic acid anhydride, 2,4,6-triisopropylphenylsulfonic acid anhydride, trifluoromethanesulfonic acid anhydride and the like or acid halides such as acetyl chloride, propionyl chloride, diethyl chlorophosphate, diphenyl chlorophosphate, toluenesulfonyl chloride, p-bromophenylsulfonyl chloride and the like or other agents which provide a leaving group $L^1$ by conventional procedures and are well-known in the art. Advantageously, the acylation is carried out with diphenyl chlorophosphate to establish the diphenylphosphonyloxy leaving group at the 2-position of the intermediates XI and XII.

Typically, the acylation reaction of Step(J) or (J') is conducted in an inert organic solvent such as methylene chloride, acetonitrile, dimethylformamide, tetrahydrofuran and the like in the presence of a base such as diisopropylethylamine, triethylamine, 4-dimethylaminopyridine, imidazole, lutidine, N-methylmorpholine, N-methylpiperidine, 1,8-diazabicyclo[5.4.0]undec-7-ene, 1,5-diazabicyclo[4.3.0]non-5-ene and the like, at a temperature from about −20° to 40° C. for about 0.5 to 18 hours and preferably for 1 to 3 hours at 0° to room temperature. The intermediates XI and XII may be isolated if desired, but is conveniently used for the next step without isolation or purification.

The intermediates of Formula XI and XII are next converted in Steps(K) and (K') to the intermediates XIII and XIV, respectively, by a conventional displacement reaction. Thus, the intermediates of Formula XI or XII may be reacted with at least an equimolar amount of a mercaptan reagent of the formula

HS—B—$R^3$ wherein B is as previously defined and $R^3$ is a residue of an organic group in an inert organic solvent such as methylene chloride, dioxane, tetrahydrofuran, acetonitrile, dimethylformamide, dimethylsulfoxide, hexamethylene phosphoramide and the like, and preferably, in the presence of a base such as diisopropylethylamine, triethylamine, 4-dimethylaminopyridine, sodium hydrogen carbonate, potassium carbonate and the like. The temperature is not critical for the displacement but is advantageously carried out from about −40° to 30° C. for 30 minutes to 24 hours. Most conveniently, the reaction is carried out at about 0° to 5° C. for 2 to 4 hours. In the displacement reaction of Step(K'), about an equimolar amount of trimethylsilylchloride may optionally be added to the reaction mixture prior to the addition of said mercaptan reagent to temporarily protect the 1R-hydroxyethyl group. After the displacement is complete, the trimethylsilyl protecting group may readily be removed as described herein for removal of the $P^2$ protecting group and, preferably, by treatment with acetic acid in tetrahydrofuran, tetrahydrofuran-water and the like at about 0° C. to room temperature for about 1 to 4 hours.

In Step(L), the compound of Formula XIII is deprotected to produce the compound of Formula XIV. The deprotection is carried out in a conventional manner and when the hydroxy-protecting group is a triorganosilyl group such as t-butyldimethylsilyl, the deprotection is preferably carried out in the presence of a tetra(lower)alkylammonium fluoride such as tetrabutylammonium fluoride. Although the reaction conditions are not critical, it is advantageously carried out with about three equivalents of an ammonium fluoride derivative and optionally in the presence of about six equivalents of glacial acetic acid in an inert organic solvent such as methanol, ethanol, dioxane, acetonitrile, dichloromethane, tetrahydrofuran and the like or a mixture thereof. The deprotection is usually carried out from about −40° to 30° C. and, preferably, from −15° to 0° C. for about 4 hours to 1 week and preferably for about 3 days.

It should be appreciated by those skilled in the art that the final deblocking step, Step(M), will naturally vary depending on the protecting groups present in substituents $P^1$, $R^{12}$ and $R^3$. The deblocking Step(M) to remove the carboxy-protecting group $P^1$ of intermediate of Formula XIV to produce compounds of Formula Ia wherein $R^4$ is hydrogen or a non-toxic pharmaceutically acceptable cation such as sodium, potassium, ammonium and other cations of salts described herein is accomplished by conventional procedures such as hydrolysis, chemical reduction or hydrogenation. Where a protecting group such as p-nitrobenzyl, benzyl, benzhydryl or 2-naphthylmethyl is used which can be removed by catalytic hydrogenation, intermediate of Formula XIV in a suitable solvent such as water, dioxane, tetrahydrofuran, ethanol, isopropanol, n-butanol or mixtures thereof containing a buffer solution such as phosphate buffer, dipotassium hydrogen phosphate, sodium bicarbonate, acetate buffer and the like may be treated under a hydrogen pressure of from 1 to about 4 atmospheres in the presence of a hydrogenation catalyst such as palladium on carbon, palladium hydroxide on carbon, platinum oxide, palladium on barium sulfate, Raney nickel and the like at a temperature of from 0° to 50° C. for about 15 minutes to 4 hours. When $P^1$ is a group such as o-nitrobenzyl, photolysis may also be used for deblocking. Protecting groups such as 2,2,2-trichloroethyl may be removed by mild zinc reduction.

When the carboxy-protecting group $P^1$ is an allyl group, it may be removed with a catalyst comprising a palladium compound and preferably a palladium-ligand complex such as tetrakis(triphenylphosphine)palladium[0], bis(dibenzylideneacetone)palladium[0], di[1,2-bis(diphenylphosphino)ethane]palladium[0], tetrakis(triphenyl phosphite)palladium[0] and the like. The reduction is preferably carried out in the presence of an allyl scavenger, for example, an amine such as N-methylaniline or morpholine, an activated methylene compound such as benzoylacetate or 2-methyl-3-oxovaleric acid, an alkanoic acid or a salt thereof such as sodium acetate, sodium 2-ethylhexanoate and the like.

The reaction is usually carried out in a non-reducing solvent such as tetrahydrofuran, water, ethanol, dioxane, acetonitrile, dichloromethane, ethyl acetate or mixtures thereof at a temperature from 0° to 50° C. for about 15 minutes to 4 hours. Advantageously, the catalytic reduction is carried out in ethyl acetate or dichloromethane at about 0° C. in the presence of tetrakis(triphenylphosphine)palladium [0] containing about 1.1 molar equivalents of potassium ethyl-2-hexanoate. Similarly, other conventional carboxy-protecting groups may be removed by methods known to those skilled in the art. Finally, as mentioned above, compounds of Formula Ia wherein $R^4$ is a physiologically hydrolyzable ester group such as acetoxymethyl, pivaloyloxymethyl and methoxymethyl and the like may be administered directly to the host without deblocking since such esters are hydrolyzed in vivo under physiological conditions.

As mentioned above, the compounds of Formula XIV may optionally contain additional hydroxy-protecting groups O—$P^3$ and/or amino-protecting groups N—$P^4$ wherein $P^3$ and $P^4$ are as previously defined. Thus, reaction Step(M) may, if desired, contain an additional deblocking procedure for removing said protecting groups. The reaction may be carried out by conventional methods known per se for removing a protecting group such as hydrolysis, reduction and the like and includes the methods illustrated for the removal of the carboxy-protecting group $P^1$ and the hydroxy-protecting group $P^2$.

In the particular instance when $R^{12}$ is azido in the compound of Formula XIV, it may be desired to reduce said azido to an amine in the deblocking procedure of Step(M). The reduction may be carried out in an aqueous or aqueous buffered solution at about pH 6–9 and preferably in an aqueous solution at about −10° to 30° C. and preferably at about 0°–5° C. under a hydrogen pressure of from 1 to 4 atmospheres in the presence of a hydrogenation catalyst such as 30% palladium on Celite, 10% palladium on carbon, palladium hydroxide on carbon, platinum oxide, 5% palladium on barium sulfate, 5% palladium on alumina and the like, and preferably, on 5% palladium on barium sulfate and 5% palladium on alumina, for about 30 minutes to 3 hours until the reduction is completed.

It should be appreciated by those skilled in the art that the deblocking of the carboxy- and/or hydroxy- and/or amino-protecting groups in Step(M) may be removed at the same time during the reaction. Alternatively, or, if desired, the protecting groups may selectively be removed stepwise. Nevertheless, it should be evident to those skilled in the art that the sequence of removing the protecting groups will depend on the nature and selection of the protecting groups, and whether it is desired to prepare an intermediate of Formula XIV or Formula Ia containing some of the protecting groups such as $P^1$, $P^2$, O—$P^3$ and N—$P^4$ to prepare additional compounds of Formula I.

In another embodiment, the compounds of Formula I may be prepared from novel intermediates of the Formula XVI

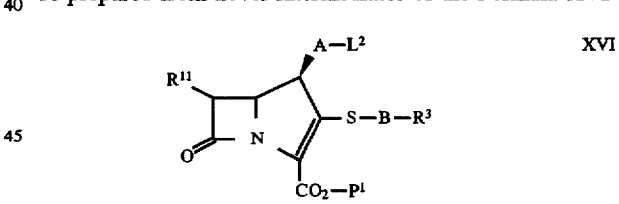

wherein A, B, $R^3$ and $R^{11}$ are as previously defined, $P^1$ is a conventional readily removable carboxy-protecting group and $L^2$ is a conventional leaving group.

The compounds of Formula XVI may be used to prepare compounds of Formula I, and, by way of illustration, the process for preparing one of the more preferred embodiments of Formula I is illustrated in Reaction Scheme 5 for the preparation of compounds of Formula Ib. Briefly, the protected intermediate of Formula XIII wherein $R^{12}$ is O—$P^3$ is selectively deprotected in Step(N) to the alcohol of Formula XV. The alcohol moiety in the 4-position of carbapenem XV is converted in Step(O) to compounds of the Formula XVIa having a conventional leaving group "$L^2$" which is susceptible to displacement by a nucleophile in Step(P) to produce the compounds of Formula XVIII. Deblocking of the protecting groups in Step(L+M) will yield the compounds of Formula Ib wherein A, B, $R^3$ and $R^4$ are as previously defined and $R^{13}$ is a nucleophilic residue wherein $R^{13}$ may be azido, —$NR^5R^6$, $$\begin{matrix} & Y \\ & \| \\ -NH-C-Z, \end{matrix}$$

nitrile, substituted alkoxy or substituted alkylthio in which $R^5$, $R^6$, Y and Z are as previously defined.

Reaction Scheme 5

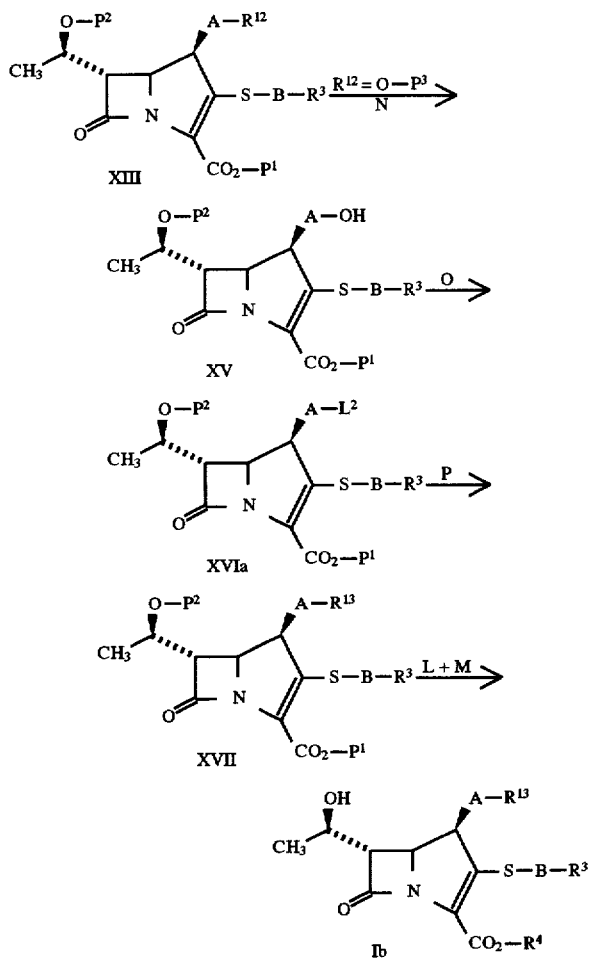

Referring now to Reaction Scheme 5, Step(N) illustrates the removal of a hydroxy-protecting group from the intermediate of Formula XIII wherein $R^{12}$ is O—$P^3$ in which $P^3$ is a conventional hydroxy-protecting group. Preferably, the protecting group $P^3$ is a triorganosilyl protecting group and, most preferably, is t-butyldimethylsilyl. The reaction of Step(N) is carried out in an inert organic solvent such as tetrahydrofuran, dioxane, ethyl acetate, dimethoxyethane, methylene chloride, carbon tetrachloride, toluene, cyclohexane and the like with about 1 to 10 mole equivalents of tetra(lower)alkyl fluoride, boron trifluoride or potassium fluoride and optionally containing about 1 to 20 equimolar amount of a lower alkyl organic acid, aromatic acid or heteroaromatic acid at a temperature of about −40° to 40° C. for about 1 to 60 hours. Advantageously, the reaction is conducted in tetrahydrofuran with about 3 equivalents of tetrabutylammonium fluoride in the presence of about 6 equivalents of acetic acid at a temperature from about −15° to 0° C. for about 18 to 24 hours.

Step(O) illustrates the reaction between the alcohol XV and a suitable acylating agent or activating agent to form the intermediate of Formula XVIa having a leaving group "$L^2$" which can be displaced by a nucleophile. Suitable acylating agents for Step(O) may be the same as the agents used to prepare the leaving group "$L^1$" in Step(K) of Reaction Scheme 4 or other agents which provide a leaving group by conventional procedures and are well-known in the art. Preferably, $L^2$ includes chloro, bromo, iodo, fluorosulfonyl, —$OSO_2R^{14}$ and —O⊕P($R^{15}$)$_3$ wherein $R^{14}$ is lower alkyl, trifluoromethyl, phenyl or substituted phenyl and $R^{15}$ is phenyl or substituted phenyl in which said substituent may be methyl, isopropyl, chloro, bromo or nitro.

The reaction of Step(O) may be conducted in an inert organic solvent such as tetrahydrofuran, dimethoxyethane, dioxane, ethyl acetate, methylene chloride, chloroform, carbon tetrachloride, toluene, benzene, cyclohexane and the like with an acylating or activating agent in the presence of a non-nucleophilic base such as triethylamine, diisopropylethylamine, 2,6-lutidine, 1,8-diazobicyclo[5.4.0]undec-7-ene, 1,5-diazobicyclo[4.3.0]non-5-ene and the like at a temperature of from about −78° to room temperature. Advantageously, the reaction is carried out in methylene chloride with about 1.2 equivalents of trifluoromethanesulfonic anhydride in the presence of about 1.5 to 2 equivalents of diisopropylethylamine at about −78° C. or in tetrahydrofuran with a mixture of triphenylphosphine and diethyl azodicarboxylate at about −40° C.

Preparation of the desired compounds of Formula XVII is carried out in Step(P) by a nucleophilic displacement of the $L^2$ leaving group of intermediate XVIa by the desired nitrogen, carbon, oxygen or sulfur-containing nucleophile $R^{13}$ wherein $R^{13}$ is preferrably as previously defined. The intermediate of Formula XVIa is reacted with at least one equivalent, and preferably an excess, of the desired nucleophilic reagent in an inert organic solvent such as methylene chloride, tetrahydrofuran, chloroform, carbon tetrachloride, dioxane, ethyl acetate, diglyme, dimethoxyethane, cyclohexane, toluene and the like over a wide temperature range from −78° to about 30° C., but preferably from about −15° to 5° C. until the reaction is complete as monitored by conventional methods of detection such as thin layer chromatography and high pressure liquid chromatography.

The preparation of the desired carbapenem of Formula Ib is accomplished by deblocking the protecting groups of intermediate XVII by conventional procedures. Suitable deblocking procedures for hydroxy, carboxy and aminoprotecting groups are as previously discussed above in the processes of Steps(L) and (M).

In another reaction route, the compounds of Formula Ic may be prepared from the compounds of Formula XVIII in Step(Q) as illustrated in Reaction Scheme 6 wherein A, B, $R^3$, $R^4$ and $P^2$ are as previously defined, $R^{16}$ is hydrogen or $C_{1-4}$ alkyl and $R^{17}$ is $C_{1-4}$ alkyl or $$\begin{matrix} & Y \\ & \| \\ & -C-Z. \end{matrix}$$

Reaction Scheme 6

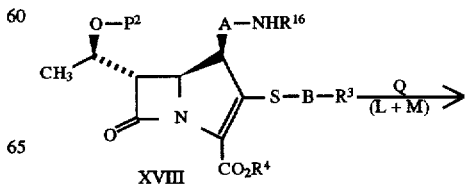

-continued
Reaction Scheme 6

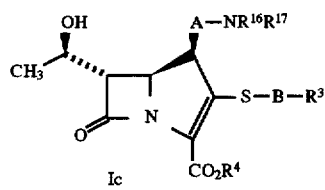

Generally, the derivatization of the amino group of Formula XVIII or salts thereof is carried out in Step(Q) with suitable imidoylating agents, acylating agents or alkylating agents. The reaction is optionally carried out with compounds of the Formula XVIII wherein $P^2$ is a conventional hydroxy-protecting group and $R^4$ is a conventional carboxy-protecting group. Advantageously, the reaction is carried out without a hydroxy-protecting group (i.e., $P^2$ is hydrogen) and $R^4$ is hydrogen or salt thereof.

Suitable imidoylating agents include formimidates and lower alkylimidates such as methyl formimidate, ethyl formimidate, benzyl formimidate, methyl acetimidate, ethyl propionimidate, ethyl butyrimidate, ethyl pentanimidate and lower alkanimidoyl halide such as formimidoyl chloride, acetimidoyl chloride, propionimidoyl chloride, butyrimidoyl chloride and the like. The reaction is usually carried out in a conventional solvent such as tetrahydrofuran, dioxane, methanol, ethanol, water, buffer solution or a mixture thereof at a temperature from about −20° to 40° C. for about 10 minutes to 18 hours. Advantageously, the reaction is carried out in an aqueous phosphate buffer solution at a slightly basic pH for about 10 to 30 minutes at about 5° C.

Suitable acylating agents to prepare compounds of Formula Ic include acid halides, acid anhydrides, mixed anhydrides, activated esters, thiolesters and the like such as acetyl chloride, azidoacetyl chloride, acetic anhydride, methyl isocyanate, ethyl isocyanate, N,N-dimethylcarbamoyl chloride, activated esters of N-protected amino acids, aminoiminomethanesulfonic acid, methylaminoiminomethanesulfonic acid and the like. The acylating reaction may be conducted in a variety of solvent systems including solvents such as tetrahydrofuran, dioxane, acetonitrile, ethanol, methanol, dimethylformamide, water and the like and mixtures thereof. It should be appreciated by those skilled in the art that the reaction may be conducted, when necessary, in the presence of a base or acid acceptor such as magnesium oxide, potassium carbonate, potassium bicarbonate, pyridine, lutidine, 2,6-lutidine, 4-dimethylaminopyridine, triethylamine, N,N-diisopropylethylamine and the like. Advantageously, the reaction is conducted in an aqueous organic mixture or aqueous buffered solution at a temperature of from −20° to 50° C. for 15 minutes to 18 hours.

Suitable alkylating agents are well-known in the art and include lower alkyl or substituted(lower)alkyl halides, lower alkyl or trifluoromethanesulfonates, formaldehyde, lower alkyl or substituted(lower)alkyl aldehydes, aromatic or heteroaromatic aldehydes, heterocycloalkyl or substituted heterocycloalkyl aldehydes wherein said aldehydes are reacted in the presence of reducing agents such as sodium cyanoborohydride, sodium borohydride and the like. The reaction may be concluded in a variety of solvents systems including tetrahydrofuran, dioxane, acetonitrile, ethanol, methanol, dimethylformamide, water and the like and mixtures thereof at a temperature from about −20° to 50° C. for 15 minutes to 20 hours. Advantageously, when the alkylating agent is formaldehyde the reaction is conducted with 37% formaldehyde in the presence of sodium cyanoborohydride in aqueous acetonitrile or aqueous buffered solution at slightly acid condition and at about 0°–5° C. for 15 minutes to 10 hours.

As mentioned above, the compounds of Formula XVIII may optionally contain a hydroxy-protecting group and/or a carboxy-protecting group. Thus, Reaction Scheme 6 may contain additional deblocking procedures for removing said protecting groups. Suitable deblocking procedures may be carried out by methods known per se or by the procedures for removal of protecting groups previously described in Steps (L) and (M).

In still another reaction route when it is desired to prepare compounds of Formula I wherein $R^2$ is

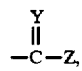

it is advantageous to convert a compound of Formula XV by controlled or stepwise oxidation to the corresponding aldehydes of Formula I wherein $R^2$ is —CHO or the corresponding acids of Formula I wherein $R^2$ is —CO$_2$H as illustrated herein or by the use of well-known conventional oxidation procedures. In addition, the aldehydes and acids of Formula I may be converted by standard chemical procedures well-known to those skilled in the art to other derivatives of $R^2$ such as oximes, nitriles, hydrazones, esters, amides, peptides, variations thereof and the like.

The preparation of compounds of Formula I in the present invention is based upon any of several available beta lactam intermediates for the synthesis of carbapenem compounds of the thienamycin series. By way of illustration, the previous Reaction Schemes illustrated the preparation of compounds of Formula I wherein $R^1$ is a 1-hydroxyethyl group in the 6-position of the beta lactam ring structure.

When it is desired to prepare compounds of the Formula I wherein $R^1$ is a 1-aminoethyl group, the process to transform the 1-hydroxyethyl group to a 1-aminoethyl group via a 1-azidoethyl intermediate in the 6-position of the azabicyclo ring structure is illustrated in Reaction Scheme 7 for the preparation of the desired 1(S) and 1(R)-configuration.

Reaction Scheme 7

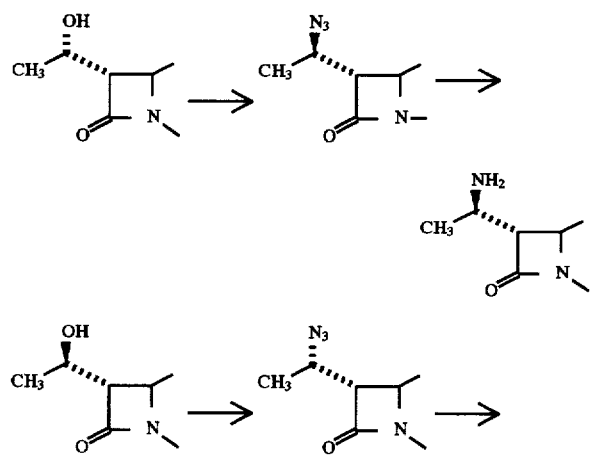

-continued
Reaction Scheme 7

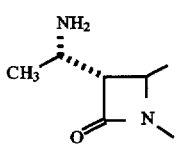

The method involves protecting other reaction sensitive substituents with conventional hydroxy, carboxy and/or amino-protecting groups, then reacting the suitable protected 1-hydroxyethyl starting material with triphenylphosphine, hydrazoic acid and diethyl azodicarboxylate (DEAD). The resulting azido group is substituted for the hydroxy group with inversion of configuration relative to the 1-hydroxyethyl starting material. Thus, for example, the 1(S)—OH starting material yields the 1(R)—$N_3$ product, and the 1(R)—OH starting material yields the 1(S)—$N_3$ product. This method was first used by D. F. Corbett et al and described in J. Chem. Soc. Perkin Trans. I, 3011 (1982) and in Tetrahedron Letters, 24, No. 49, 5543–5546 (1983). The reduction of the appropriate 1-azidoethyl intermediate to the corresponding 1-aminoethyl product is advantageously carried out by methods well-known in the art and also as described herein for the reduction of the azido group. Finally, where appropriate, the protecting groups are removed by well-known conventional procedures and the procedures described herein.

In cases where the hydroxyethyl starting material of the require 1(S)— or 1(R)— configuration is not readily available, but the related starting material of the opposite configuration is available, the latter can be transformed into the former by the method of O. Mitsunobu, Synthesis, 1–28 (1981) or O. Mitsunobu et al, Bull. Chem. Soc. Japan, 49 510 (1976). This method is similar to the above, and involves the reaction of the hydroxy compound with triphenylphosine, formic acid rather than hydrazoic acid, and diethyl azodicarboxylate to yield the formate ester of opposite configuration, for example, 1(S)—OH yields 1(R)—OCHO, and 1(R)—OH yields 1(S)—OCHO. The formate ester is then hydrolyzed to yield the required hydroxyethyl starting material.

In the case when it is desired to prepare compounds of the Formula I wherein $R^1$ is aminomethyl, the process described above to transform 1-hydroxyethyl to 1-aminoethyl may also be used to transform a beta lactam intermediate wherein $R^1$ is hydroxymethyl to an intermediate wherein $R^1$ is aminomethyl. However, in this instance, there is no difference in the relative configuration.

The preparation of compounds of Formula I wherein $R^1$ is a 1-fluoroethyl group is carried out by reacting a suitable protected 1-hydroxyethyl starting material with diethylaminosulfur trifluoride (DAST). The resulting fluoro group is substituted for the hydroxy group with inversion of configuration relative to the 1-hydroxyethyl starting material, for example, the 1(S)—OH starting material yields the 1(R)—F product, and the 1(R)—OH starting material yields the 1(S)—F product. When the hydroxyethyl starting material of the required 1(S)— or 1(R)— configuration is not readily available, but the related starting material of the opposite configuration is available, the latter can be transformed into the former by the method described previously. The method is more fully described by C. P. Mak and K. Wagner, Synthesis of florinated carbapenems. Reaction of monocyclic and bicyclic β-lactams with diethylaminosulfur trifluoride. In "Recent Advances in the Chemistry of β-Lactam Antibiotics" Eds. A. G. Brown and S. M. Roberts, Third International Symposium, pp. 366–370 (1984). The Royal Society of Chemistry, Burlington House, London and references cited therein. More recently, the DAST method and a new method using a mixture of diethylaminohexafluoropropane and diethylaminopentafluoropropene was described by T. Yoshioka et al in Journal of Antibiotics, 42, No. 10, 1520–1522 (1989). Both methods are hereby incorporated by reference.

Other methods for the preparation of intermediates of Formula I wherein $R^1$ is hydrogen, $C_{1-2}$ alkyl or hydroxymethyl are known per se and may be found in references such as Penems, Synthetic approach to thienamycin analogs by S. Oida in "Recent Advances in the Chemistry of β-Lactam Antibiotics" Ed. G. I. Gregory, Second International Symposium, 1980, and The Chemistry of Thienamycin and other Carbapenem Antibiotics by R. W. Ratcliffe and G. Alkers-Schonberg in "Chemistry and Biology of β-Lactam Antibiotics" Ed. R. B. Morin and M. Gorman, Vol. 2, Academic Press, 1982 which are also incorporated by reference.

Biological Activity and Stability

To illustrate the potent antibacterial activity and the superior chemical and biological stability of the carbapenems of the present invention, a representative member of Examples of the present invention for purposes of illustration are presented in Table I with in vitro activities (MIC), chemical stability (T ½) and biological stability (DHPI).

In vitro antibacterial activity was determined by serial 2-fold dilution of the compound in Mueller-Hinton agar and inoculation of the agar surface or broth with an appropriately diluted 18–24 h broth culture. Agar plates and tubes were incubated at 37° C. for 17 h, and the lowest concentration causing inhibition of visible growth was considered to be the minimum inhibitory concentration (MIC).

Chemical stability in aqueous solution at pH 7.4 and 37° C. is reported as half-life (T ½) in hours. These values were determined by the method of Woodward et al, J. Am. Chem. Soc., 102, 2042 (1980).

Biological stability toward renal dehydropeptidase I [renal dipeptidase (EC 3.4.13.11)] decomposition was determined and the values reported are relative to that observed with imipenem. Pure hog renal dipeptidase was prepared as described by Hitchcock et al, J. Anal. Biochem., 163, 219 (1987), while human renal dipeptidase was prepared as described by Campbell et al., J. Biol. Chem., 259, 14586–14590 (1984).

Solutions of carbapenem (0.10 mM) in buffer (50 mM) 4-morpholinepropanesulfonic acid, pH 7.1, were freshly prepared. The UV/vis spectrum of a 2.5 ml aliquot was measured and then 0.025 ml of 1M $NH_2OH$ was added to degrade the β-lactam bond. The spectrum was again measured after 30 min at 25° C. for hog dipeptidase and at 37° C. for human dipeptidase and again at 5–10 min intervals until no further decrease in absorbance was observed. The different spectrum between intact and degraded β-lactam was used to calculate a λ max and ε. A similar aliquot of carbapenem solution was incubated at 25° C. for hog dipeptidase and at 37° C. for human dipeptidase and the rate of change in absorbance at λ max was determined. Enzyme was then added to give a rate of at least $10^{-4}$ absorbance units per second. The rate of enzymatic hydrolysis was corrected for spontaneous hydrolysis and then converted with ε to nmol $min^{-1}$ (ml of enzyme)$^{-1}$. All rates are reported relative to that observed with imipenem.

The compounds of the present invention are significantly less subject to degradation by renal dehydropeptidase (DHP)

enzyme as shown in Table I. However, if DHP inhibition is desired or necessary, the compounds of the present invention may be combined or used with known DHP inhibitors such as cilastatin. Although such use is optional it is contemplated to be part of the present invention.

TABLE I

BIOLOGICAL ACTIVITY AND STABILITY OF REPRESENTATIVE COMPOUNDS

| Example | Antibacterial Activity MIC[a] (μg/ml) | | | Half-life[e] (T ½) | Dipeptidase hydrolysis (rel rate) |
|---|---|---|---|---|---|
| | S. pn. | E. coli | P. aer. | | |
| 3 | 0.13 | 0.016 | 2 | 3.2 | 0.04[g] |
| 19 | 0.06 | 0.004 | 1 | 117 | 0.05[g] |
| 24 | 0.13 | 0.016 | 1 | 3.5 | 0.08[g] |
| 32 | 0.25 | 0.004 | 0.25 | 76 | |
| 36 | 0.13 | 0.008 | 0.25 | 3.8 | 0.02[g] |
| 40 | 0.06 | 0.008 | 1.0 | 32.5 | |
| 41 | 0.25 | 0.008 | 0.5 | 70 | 0.7[h] |
| 44 | 0.03 | 0.03 | 8.0 | 89 | |
| 47 | 0.5 | 0.03 | 1 | 2.5 | 0.3[h] |
| 49 | 0.008 | 0.03 | 63 | 33.5 | |
| 63 | 0.008 | 0.016 | 1 | 18 | 0.07[h] |
| 73 | 0.03 | 0.008 | 0.25 | 37 | |
| 91 | 0.5 | 0.016 | 4.0 | 150 | |
| 92 | 2.0 | 0.06 | 2.0 | 247 | |
| 94 | 0.06 | 0.008 | 8.0 | 88 | |
| 100 | 0.25 | 0.008 | 2.0 | 180 | |
| 117 | 0.13 | 0.13 | 0.25 | 33 | |
| 120 | 0.03 | 0.13 | 0.25 | 23 | |
| 121 | 0.13 | 0.004 | 1 | 136 | |
| 124 | 0.016 | 0.03 | 2 | 21 | |
| 126 | 0.016 | 0.008 | 2 | 47 | |
| 127 | 0.06 | 0.13 | 1 | 31 | |
| 130 | 0.13 | 0.13 | 0.06 | 16 | |
| 131 | 0.25 | 0.13 | 2 | 46 | |
| 135 | 0.03 | 0.015 | 0.06 | 37 | |
| 136 | 0.015 | 0.007 | 4 | 17 | |
| 145 | 0.125 | 0.125 | 8 | | |
| 146 | 0.25 | 0.125 | 128 | | |
| 154 | 0.5 | 0.25 | 1 | 79 | |
| 177 | 0.03 | 0.13 | 1 | 17 | |
| 196 | 0.06 | 0.016 | 1 | 58 | |
| 215 | 0.03 | 0.015 | 0.5 | 49 | |
| 263 | 0.03 | 0.015 | 1 | 9.7 | |
| 294 | 0.03 | 0.125 | 0.25 | 45 | |
| 310 | 0.06 | 0.03 | 0.125 | 27 | |
| 315 | 0.015 | 0.015 | 16 | 137.5 | |
| 316 | 0.015 | 0.06 | 0.25 | 40.5 | |
| Imipenem | 0.002 | 0.03 | 2 | 15 | 1[g,h] |

[a]Minimum Inhibitory Concentration, in Mueller-Hinton broth.
[b]Streptococcus pneumoniae, A9585
[c]Escherichia coli, A15119
[d]Pseudomonas aeruginosa, A9843
[e]Half-life, 37° C., $10^{-4}$M, pH 7.4, in hours.
[f]Rate of degradation by DeHydroPeptidate I enzyme, relative to Imipenem = 1 (the smaller the number, the more stable to degradation)
[g]Relative rate using hog renal dipeptidase.
[h]Relative rate using human renal dipeptidase.

As in the case of other β-lactam antibiotics, compounds of general formula I may be converted by known procedures to pharmaceutically acceptable salts which, for purposes of the present invention, are substantially equivalent to the non-salted compounds. Thus, for example, one may dissolve a compound of formula I wherein $R^4$ is an anionic charge in a suitable inert solvent and then add an equivalent of a pharmaceutically acceptable acid. The desired acid addition salt may be recovered by conventional procedures, e.g. solvent precipitation, lyophilization, etc. Where other basic or acidic functional groups are present in the compound of formula I, pharmaceutically acceptable base addition salts and acid addition salts may be similarly prepared by known methods.

A compound of formula I wherein $R^4$ is hydrogen or an anionic charge, or a pharmaceutically acceptable salt thereof may also be converted by conventional procedures to a corresponding compound wherein $R^4$ is a physiologically hydrolyzable ester group, or a compound of formula I wherein $R^4$ is a conventional carboxy-protecting group may be converted to the corresponding compound wherein $R^4$ is hydrogen, an anionic charge or a physiologically hydrolyzable ester group, or a pharmaceutically acceptable salt thereof.

The novel carbapenem derivatives of general formula I wherein $R^4$ is hydrogen, an anionic charge or a physiologically hydrolyzable carboxy-protecting group, or the pharmaceutically acceptable salts thereof, are potent antibiotics active against various gram-positive and gram-negative bacteria and they may be used, for example, as animal feed additives for promotion of growth, as preservatives in food, as bactericides in industrial applications, for example in waterbased paint and in the white water of paper mills to inhibit the growth of harmful bacteria and as disinfectants for destroying or inhibiting the growth of harmful bacteria on medical and dental equipment. They are especially useful, however, in the treatment of infectious disease in humans and other animalscaused by gram-positive or gram-negative bacteria.

The pharmaceutically active compounds of this invention may be used alone or formulated as pharmaceutical compositions comprising, in addition to the active carbapenem ingredient, a pharmaceutically acceptable carrier or diluent. The compounds may be administered by a variety of means; those of principal interest include: orally, topically or parenterally (intravenous or intramuscular injection). The pharmaceutical compositions may be in solid form such as capsules, tablets, powders, etc. or in liquid form such as solutions, suspensions or emulsions. Compositions for injection, the preferred route of delivery, may be prepared in unit dose form in ampules or in multidose containers and may contain formulatory agents such as suspending, stabilizing and dispersing agents. The compositions may be in ready to use form or in powder form for reconstitution at the time of delivery with a suitable vehicle such as sterile water.

The dosage to be administered depends to a large extent on the particular compound being used, the particular composition formulated, the route of administration, the nature and condition of the host and the particular situs and organism being treated. Selection of the particular preferred dosage and route of application, then, is left to the discretion of the physician. In general, however, the compounds may be administered parenterally or orally to mammalian hosts in an amount of from about 5 to 200 mg/kg/day. Administration is generally carried out in divided doses, e.g. two to four times a day.

The following examples which illustrate specific embodiments of the invention are given for illustration and do not limit the scope of the present invention. The abbreviations used in the present invention are conventional abbreviations well-known to those skilled in the art. Some of which are included below.

Abbreviations

TBDMS: tert-butyldimethylsilyl
TBDMS-OTf: tert-butyldimethylsilyl trifluoromethanesulfonate
pet-ether: petroleum ether (b.p. 20–60)
TsN₃(TosN₃): p-toluenesulfonyl azide
DPCP: ClPO(OPh)₂ or diphenyl chlorophosphate
DIPEA: N,N-diisopropylethylamine TMSCl: trimethylsilyl chloride (chloro trimethylsilane)
DMAP: 4-N,N-dimethylaminopyridine
TsNH₂: p-toluenesulfonamide
TBAF: tetrabutylammonium fluoride
DEAD: diethyl azodicarboxylate
HOBT: 1-hydroxybenzotriazole hydrate
DCC: 1,3-dicyclohexylcarbodiimide
HN₃: hydrazoic acid

DESCRIPTION OF SPECIFIC EMBODIMENTS

In the following examples, all temperatures are given in degrees Centigrade. Melting points were recorded on a Gallenkamp capillary melting point apparatus and boiling points were measured at specific pressures (mm Hg) and both temperatures are uncorrected. Proton magnetic resonance ($^1$H NMR) spectra were recorded on a Bruker AC-200. All spectra were determined in the solvents indicated and chemical shifts are reported in δ units downfield from the internal standard tetramethylsilane (TMS) and interproton coupling constants are reported in Hertz (HZ). Splitting patterns are designated as follows: S, singlet; d, doublet; t, triplet; q, quartet; m, multiplet; br, broad peak; dd, doublet of doublet; bd, broad doublet, dt doublet of triplet; bs, broad singlet, dq, doublet of quartet. Infrared (IR) spectra were determined on a Perkin Elmer 781 spectrometer from 4000 cm⁻¹ to 400 cm⁻¹, calibrated to 1601 cm⁻¹ absorption of a polystyrene film and reported in reciprocal centimeters (cm⁻¹). Relative intensities are indicted as follows: s (strong), m (medium) and w (weak). Optical rotations [α]$_D^{25}$ were determined on a Perkin-Elmer 41 polarimeter in the solvents indicated. Ultraviolet spectra were determined on a Hewlett Packard 8451A diode array spectrophotometer in the solvent and concentration indicated.

Analytical thin-layer chromatography (TLC) was carried out on precoated silica gel plates (60F-254, 0.25 mm) and visualized using UV light, iodine vapors and/or staining with one of the following reagents: (a) methanolic phosphomolybdic acid (2%) and heating; (b) reagent (a) followed by 2% cobalt sulphate in 5M H₂SO₄ and heating. Column chromatography, also referred to as flash column chromatography, was performed in a glass column using finely divided silica gel (40–63 m on silica gel-H) and pressures somewhat above atmospheric pressure with the indicated solvents. Preparative thin layer chromatography was carried out on precoated silica gel plate (60F-254,2 mm) and visualized using UV light.

Reversed phase analytical thin-layer chromatography was carried out on Analtech precoated reversed phase F (250 microns) plates and visualized suing UV light or iodine vapors.

Reversed phase column chromatography was performed in a glass column using μ Bondapek C₁₈ (55–100 m) prep 500. High pressure liquid chromatography was performed on a Waters 501 HPLC pump using a Varian 2550 UV detector and a Varian 4290 integrator. The column specifications are as follows: μBondapak C₁₈ packing, 30 cm length, 3.9 mm I.D., particle size 10μ and the mobile phase is CH₃CN/aqueous K₂HPO₄ 0.01M at pH 7.4.

All evaporations of solvents were performed under reduced pressure. As used herein, the term hexanes is a mixture of isomeric C₆ hydrocarbons, as specified by the American Chemical Society, petroleum ether refers to the 30°–60° C. fractions, and the term "inert" atmosphere is an argon or nitrogen atmosphere unless otherwise indicated.

EXAMPLE 1

Sodium (4R,5S,6S)-4-(2"-fluoroethyl)-6-[(1'R)-1'-hydroxyethyl]-3-[(pyridin-2-yl)methylthio]-7-oxo-1-azabicyclo[3.2.0]hept-2-ene-2-carboxylate

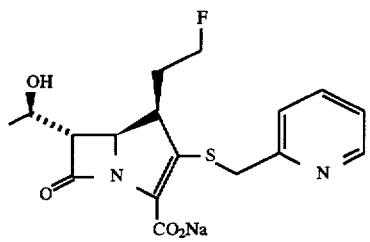

A. 4-Fluoro-[(pyridin-2-yl)methylthio]butyrate

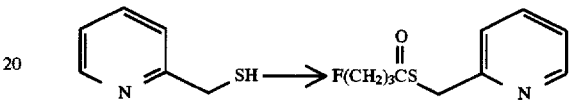

To a cold (ice bath) solution of 2-mercaptomethyl pyridine (5.26 g, 4.2 mmol) and pyridine (4.1 mL, 50 mmol) in CH₂Cl₂ (50 mL) was added dropwise 4-fluorobutyryl chloride (5.23 g, 4.2 mmol) prepared according to the procedure of F. L. Pattison et al. in J. Org. Chem., 21, 887 (1956). The mixture was stirred at 0° C. for 1 h, diluted with ethyl acetate (100 mL) washed with cold water (3×100 mL), brine (100 mL) and dried (MgSO₄). The crude mixture (9 g) was passed through a silica gel (250 g) pad to give the title compound (7.6 g, 85%) as an oil;

IR (CH₂Cl₂) ν$_{max}$: 1690 cm⁻¹ (C=O);
$^1$H NMR (CDCl₃) δ: 8.55–8.51 (1H, m, pyridine-H), 7.67–7.58 (1H, m, pyridine-H), 7.35–7.31 (1H, bd, J=7.8 Hz, pyridine-H), 7.2–7.12 (1H, m, pyridine-H), 4.61, 4.58, 4.55, 4.37, 4.34, 4.3 (2H, dt, J=5.8 Hz, J=47.1 Hz, CH₂—F), 4.27 (2H, s, CH₂—S), 2.74 (2H, t, J=7.2 Hz, CH₂C=O) and 2.2–1.92 ppm (2H, m, CH₂).

B. Enolsilyl ether of 4-fluoro-[pyridin-2-yl)methylthio] butyrate

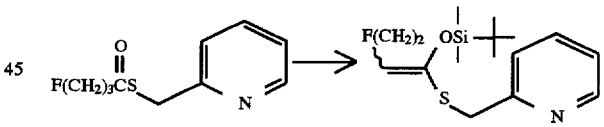

A cold (ice bath) solution of 4-fluoro-[(pyridin-2-yl) methylthio]butyrate (427 mg, 2.00 mmol) and triethylamine (0.6 mL, 4 mmol) in CH₂Cl₂ (10 mL) was treated dropwise with tert-butyldimethylsilyl trifluoromethanesulfonate (0.7 mL, 3 mmol). The ice bath was removed and the mixture was stirred for 5 h, diluted with petroleum ether (50 mL), washed with ice cold water (3×25 mL), brine (25 mL) and dried (MgSO₄). The solution was treated with neutral activated charcoal to give the title compound (0.68 g, 100%) as a red oil;

$^1$H NMR (CDCl₃, 200 MHz) δ: 8.56–8.52 (1H, m, aromatic H), 7.67–7.58 (1H, m, aromatic-H), 7.28–7.23 (1H, m, aromatic H), 7.18–7.11 (1H, m, aromatic-H), 5.02 (0.4H, t, J=7.5 Hz, vinylic H), 4.85 (0.6H, t, J=7.2 Hz, vinylic H), 4.40 and 4.16 (d, 2H, dt, J=6.7 Hz, J=47.2 Hz, CH₂F), 4.28, 4.05 (0.8H, dt, J=6.4 Hz, J=47.2 Hz, CH₂F), 4.05 (0.8H, s, CH₂-pyridine), 3.98 (1.2H, s, CH₂-pyridine), 2.5–2.2 (2H, m, CH₂), 0.98 and 0.97 (9H, 2s, t-butyl), 0.25 and 0.21 ppm (6H, 2s, dimethyl).

C. (3S,4S)-3-[(1'R)-1'-tert-Butyldimethylsilyloxyethyl]-4-[(1"R)-1"-(pyridin-2-yl)methylthiocarbonyl-3"-fluoropropyl]azetidin-2-one

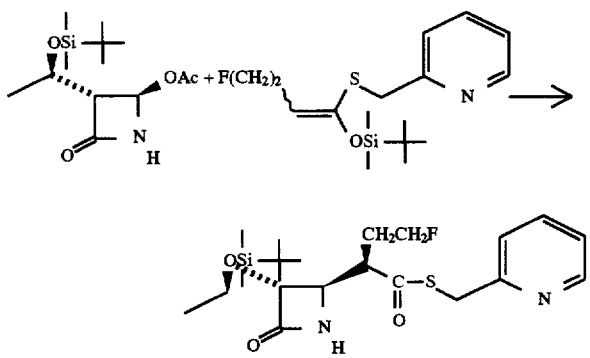

To a cold (ice bath) freshly fused ZnCl$_2$ (5.45 g, 40 mmol) under argon was added (3S,4R)-4-acetoxy-3-[(1'R)-1'-tert-butyldimethylsilyloxyethyl]azetidin-2-one (5.75 g, 20 mmol) in CH$_2$Cl$_2$ (60 mL) followed by the dropwise addition of the silylenol ether (14 g, 40 mmol) prepared in Step B in CH$_2$Cl$_2$ (20 mL). The mixture was stirred for 20 h at 5° C. (cold room), then poured over a cold saturated aqueous NaHCO$_3$ solution and extracted with ethyl acetate (2×100 mL). The ethyl acetate extracts were washed with saturated NH$_4$Cl, brine and dried (MgSO$_4$). The residue upon solvent evaporation was triturated with petroleum ether and filter to give the product (4.0 g, 45%). Recrystallization from ethyl acetate gave the title compound; m.p.=114°–115° C.

IR (CH$_2$Cl$_2$) $v_{max}$: 3410 (NH), 1770 and 1680 cm$^{-1}$ (C=O);

$^1$H NMR (CDCl$_3$) δ: 8.55–8.52 (1H, m, aromatic-H), 7.68, 7.59 (1H, m, aromatic-H), 7.33–7.29 (1H, bd, J=7.8 Hz, aromatic-H), 7.21–7.14 (1H, m, aromatic-H), 5.86 (1H, bs, NH), 5.71–4.29 (2H, 2 sets of m, CH$_2$F), 4.277 (2H, s, CH$_2$S), 4.22–4.11 (1H, m, H-1'), 3.88 (1H, dd, J=2.0 Hz, J=6.7 Hz, H-4), 3.075–2.97 (2H, m, H=3 and H-1"), 2.3–1.8 (2H, 2 sets of m, CH$_2$-2"), 1.01 (3H, d, J=6.3 Hz, CH$_3$), 0.855 (9H, s, tert-butyl) and 0.048 ppm (6H, s, dimethyl);

Anal. Calcd. for C$_{21}$H$_{33}$N$_2$O$_3$SSiF: C, 57.24; H, 7.55; N, 6.36; S, 7.28. Found: C, 57.01; H, 7.74; N, 6.17; S, 7.24.

D. (3S,4S)-3-[(1'R)-1'-tert-Butyldimethylsilyloxyethyl]-4-[(1"R)-1"-carboxy-3"-fluoropropyl]azetidin-2-one

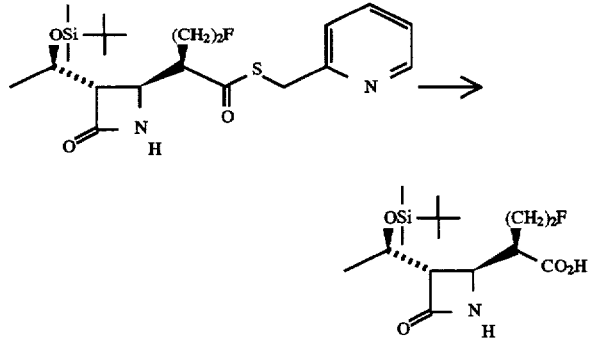

A cold (ice bath) solution of (3S,4S)-3-[(1'R)-1'-tert-butyldimethylsilyloxyethyl]-4-[(1"R)-1"-(pyridin-2-yl)methylthiocarbonyl-3"-fluoropropyl]azetidin-2-one (110 mg, 0.25 mmol) in THF (5 mL) was treated with 30% H$_2$O$_2$ (45 μL, 0.5 mmol) and a 1.0N aqueous NaOH (0.5 mL, 0.5 mmol). The ice bath was removed and the mixture was stirred for 1 h, then diluted with ethyl acetate (20 mL). The mixture was washed with 1N aqueous HCl (1×40 mL), water (3×20 mL), brine (1×20 mL) and dried (MgSO$_4$). Evaporation of the solvent afforded the title compound (82 mg, 100%) as a solid; m.p.=104°–105° C. (EtOAc);

IR (CH$_2$Cl$_2$) $v_{max}$: 3410 (NH), 1770 1750 and 1715 cm$^{-1}$ (C=O);

$^1$H NMR (CDCl$_3$, 200 MHz) δ: 6.34 (1H, bs, NH), 4.8–4.6 and 4.6–4.35 (2H, 2 sets of m, CH$_2$F), 4.35–4.1 (1H, m, H-1'), 3.95 (1H, dd, J=1.9 Hz, J=6.0 Hz, H-4), 3.15–3.12 (1H, m, H-3), 2.95–2.8 (1H, m, H=1"), 2.3–1.8 (2H, m, CH$_2$), 1.18 (3H, d, J=6.3 Hz, CH$_3$), 0.87 (9H, s, tert-butyl), 0.072 and 0.063 ppm (6H, 2s, dimethyl);

Anal. Calcd. for C$_{15}$H$_{28}$NO$_4$SiF: C, 54.03; H, 8.46; N, 4.20. Found: C, 53.75; H, 8.55; N, 4.05.

E. (3S,4R)-3-[(1'R)-1'-tert-Butyldimethylsilyloxyethyl]-4-[(1"R)-1"-(2-fluoroethyl)-3"-allyloxycarbonyl-2"-oxopropyl]azetidin-2-one

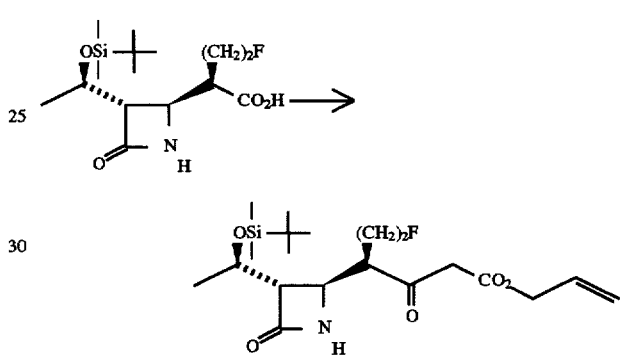

A suspension (3S,4S)-3-[(1'R)-1'-tert-butyldimethylsilyloxyethyl]-4-[(1'R )-1"-carboxy-3"-fluoropropyl]azetidin-2-one (0.75 g, 2.3 mmol) in CH$_3$CN (15 mL) was treated with carbonyl-diimidazole (0.39 g, 2.4 mmol) and stirred for 1 h at 22° C. The resulting acyl imidazole was treated with anhydrous magnesium monoallyl malonate (0.73 g, 2.4 mmol) and stirred for 50 h at 22° C. The mixture was diluted with EtOAc (60 mL), washed with cold 1N aqueous HCl (1×60 mL), water (2×60 mL), saturated aqueous NaHCO$_3$ (1×60 mL), water (2×60 mL), brine (60 mL) and dried (MgSO$_4$). Evaporation of solvent left a residue (1.7 g) that was passed through a silica gel (100 g) pad to give the title compound (Hexane→20% EtOAc/hexane) as an oil (96 mg, 10%).

IR (CH$_2$Cl$_2$) $v_{max}$: 3410 (NH), 1770, 1715, 1655 and 1630 cm$^{-1}$ (C=O);

$^1$H NMR (CDCl$_3$, 200 MHz) δ: 6.01, 6.00 (1H, 2 bs, NH), 6.0–5.8 (1H, m, vinylic H), 5.4–5.15 (2H, m, vinylic H), 5.14 (0.5H, s, vinyl H of enol), 4.7–4.6 (2H, m, CH$_2$-vinyl), 4.7–4.2 (2H, 2 sets of m, CH$_2$F), 4.21–4.13 (1H, m, H-1'), 3.91 (0.5H, dd, J=2.1 Hz, J=4.4 Hz, H4), 3.88 (0.5H, dd, J=2.1 Hz, J=6.9 Hz, H-4), 3.60 (1H, s, CH$_2$CO), 3.26–3.17 (0.5H, m, H-1"), 2.99 (0.5H, dd, J=2.2 Hz, J=4.4 Hz, H-3), 2.95–2.92 (0.5H, m, H-3), 2.55–2.35 (0.5H, m, H-1"), 2.3–1.7 (2H, m, CH$_2$), 1.175 and 1.12 (3H, 2d, J=6.28 Hz and J=6.34 Hz, CH$_3$), 0.86 (9H, s, tert-butyl), 0.067 and 0.055 (6H, 2s, dimethyl).

F. (3S,4R)-3-[(1'R)-1'-tert-Butyldimethylsilyloxyethyl]-4-[(1"R)-1"-(2-fluoroethyl)-3"-diazo-3"-allyloxycarbonyl-2"-oxopropyl]azetidin-2-one

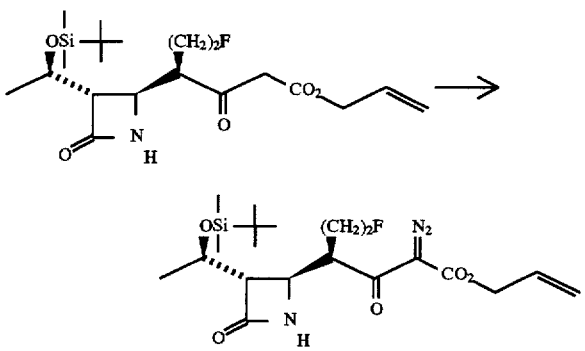

A cold (ice bath) solution of (3S,4R)-3-[(1'R)-1'-tert-butyldimethylsilyloxyethyl]-4-[(1"R)-1"-(2-fluoroethyl)-3"-allyloxycarbonyl-2"-oxopropyl]azetidin-2-one (0.20 g, 0.48 mmol) in $CH_3CN$ was treated with triethylamine (64 mL, 0.48 mmol) and p-toluenesulfonyl azide (95 mg, 0.48 mmol). The ice bath was removed and the mixture was stirred for 1 h. Evaporation of $CH_3CN$ gave a semi-solid residue that was triturated with petroleum ether (10 mL). The solid was removed by filtration and the solution was applied on a silica gel column (6 g, 10% EtOAc-hexane) to give the title compound (190 mg, 90%).

IR ($CH_2Cl_2$) $v_{max}$: 3410 (NH), 2150 ($N_2$), 1777, 1715 and 1650 cm$^{-1}$ (C=O);

$^1$H NMR (CDCl$_3$, 200 MHz) δ: 6.03–5.83 (1H, m, vinylic H), 5.90 (1H, bs, NH), 5.40–5.28 (2H, m, vinylic H), 4.73–4.7 (2H, m, $CH_2$ vinylic) 4.7–4.4, 4.4–4.2 (2H, 2 sets of m, $CH_2$-F), 4.3–4.1 (2H, m, H-1' and H-1"), 3.90 (1H, dd, J=2.0 Hz, J=5.2 Hz, H-4), 3.06–3.03 (1H, dd, J=2.1 Hz, J=3.5 Hz, H-3), 2.2–2.0, 2.0–1.8 (2H, 2 sets of m, $CH_2$), 1.18 (3H, d, J=6.3 Hz, $CH_3$), 0.86 (9H, s, tert-butyl), 0.061 and 0.051 ppm (6H, 2s, dimethyl).

G. (3S,4R)-3-[(1'R)-1'-Hydroxyethyl]-4-[(1"R)-1"-(2-fluoroethyl)-3"-diazo-3"-allyloxycarbonyl-2"-oxopropyl]azetidin-2-one

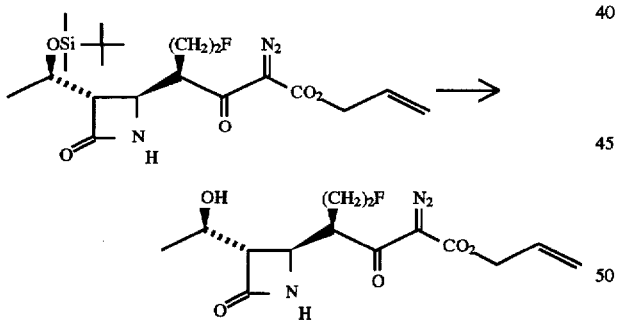

A cold (ice bath) solution of (3S,4R)-3-[(1'R)-1'-tert-butyldimethylsilyloxyethyl]-4-[(1"R)-1"-(2-fluoroethyl)-3"-diazo-3"-allyloxycarbonyl-2"-oxopropyl]azetidin-2-one (170 mg, 0.390 mmol) in $CH_3CN$ (2 mL) was treated with a 1N aqueous HCl solution (0.78 mL, 0.78 mmol). The ice bath was removed and the mixture was stirred 4 h. The solvent was removed under vacuum and the residue was diluted with EtOAc (15 mL). The organic phase was washed with 0.1M aqueous NaHCO$_3$ (10 mL), water (10 mL), brine (10 mL) and dried (MgSO$_4$). The solvent was evaporated and the residue was passed through a silica gel (5 g) pad (1:1 ethyl acetate:hexane) to give the title compound (130 mg, 100%).

IR ($CH_2Cl_2$) $v_{max}$: 3680, 3600 (OH), 3400 (NH), 2150 ($N_2$), 1765, 1715 and 1650 cm$^{-1}$ (C=O);

$^1$H NMR (CDCl$_3$, 200 MHz) δ: 6.04 (1H, bs, NH), 6.0–5.8 (1H, m, vinylic-H), 5.4–5.29 (2H, m, vinylic-H), 4.75–4.71 (2H, m, $CH_2$-vinylic), 4.7–4.5, 4.5–4.3 (2H, 2 sets of m, $CH_2$F), 2.2–2.0 (2H, m H-1' and H-1"), 3.88 (1H, dd, J=2.0 Hz, J=6.5 Hz, H-4), 2.98 (1H, dd, J=2.0 Hz, J=7.2 Hz, H-3), 2.34 (1H, d, J=3.6 Hz, OH), 2.4–1.8 (2H, 2 sets of m, $CH_2$), and 1.31 ppm (3H, d, J=6.3 Hz, $CH_3$).

H. Allyl-(2R,4R,5R,6S)-4-(2"-fluoroethyl)-6-[(1'R)-1'-hydroxy-ethyl]-3,7-dioxo-1-azabicyclo[3.2.0]heptane-2-carboxylate

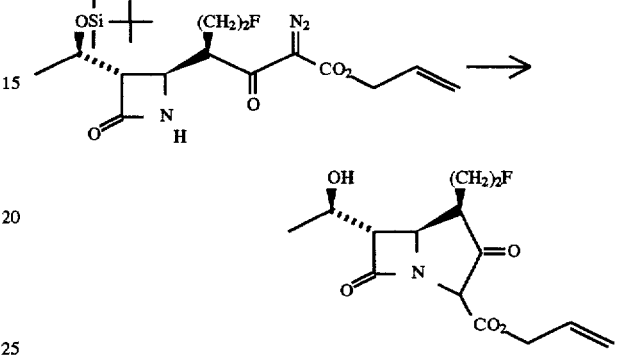

A solution of (3S,4R)-3-[(1'R)-1'-hydroxyethyl]-4-[(1"R)-1"-(2-fluoroethyl)-3"-diazo-3"-allyloxycarbonyl-2"-oxopropyl]azetidin-2-one (150 mg, 0.46 mmol) in 25% hexane-ethyl acetate (5 mL) was refluxed for 2.5 h using Rh(OAc)$_2$ as catalyst. The solvent was evaporated to give the title bicyclic ketone (140 mg, 100%).

IR ($CH_2Cl_2$) $v_{max}$: 3680, 3600 (OH), 1770, 1745 and 1735 cm$^{-1}$ (C=O);

$^1$H NMR (CDCl$_3$, 200 MHz) δ: 6.0–5.80 (1H, m, vinylic-H), 5.4–5.26 (2H, m, vinylic H), 4.79–4.68 (1H, m, HC H-F), 4.69–4.65 (2H, m, $CH_2$-vinyl), 4.68 (1H, s, H-2), 4.57–4.44 (1H, m, HCHF), 4.37 (1H, dd, J=2.5 Hz, J=8.6 Hz, H-5), 4.38–4.24 (1H, m, H-1'), 3.29 (1H, dd, J=2.5 Hz, J=7.2 Hz, H-6), 3.02–2.9 (1H, m, H-4), 2.3–1.7 (3H, 2 sets of m and bs, $CH_2$ and OH) and 1.39 (3H, d, J=6.3 Hz, $CH_3$).

I. Allyl (4R,5S,6S)-4-(2"-fluoroethyl)-6-[(1'R)-1'-hydroxyethyl]-3-[(pyridin-2-yl)methylthio]-7-oxo-1-azabicyclo[3.2.0]hept-2-ene-2-carboxylate

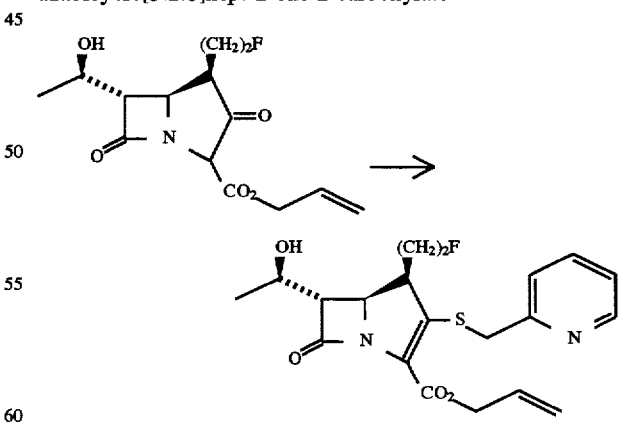

A cold (ice bath) solution of allyl (2R,4R,5R,6S)-4-(2"-fluoroethyl)-6-[(1'R)-1'-hydroxyethyl]-3,7-dioxo-1-azabicyclo[3.2.0]heptane-2-carboxylate (0.14 g, 0.55 mmol) in $CH_3CN$ (2 mL) was treated with ClPO(OPh)$_2$ (0.11 mL, 0.50 mmol) and N,N-diisopropylethylamine (0.098 mL, 0.55 mmol) and stirred for 2 h. The resulting enol phosphate was then treated with TMSCl (0.065 mL, 0.5 mmol) and N,N-diisopropylethylamine (0.098 mL, 0.55 mmol), stirred for 15 min and treated finally with 2-picolyl mercaptan (63 mg, 0.55 mmol) and N,N-diisopropylethylamine (0.098 mL, 0.55 mmol). The mixture was stirred for 3 h, diluted with ethyl acetate (20 mL), washed with H$_2$O (3×10 mL) and dried (MgSO$_4$). The residue obtained upon solvent evaporation was passed through a silica gel (10 g) column (1/1: ethyl acetate/hexane). The trimethylsilyl ether intermediate obtained (170 mg) was diluted with THF (2 mL), H$_2$O (1 mL), treated with AcOH (30 μl, 0.46 mmol) and stirred for 1 h. The mixture was diluted with ethyl acetate (20 mL), washed with 1M aqueous NaHCO$_3$ (10 mL), water (10 mL), brine (10 mL) and dried (MgSO$_4$) to give the title material (0.125 g, 69%) as an oil;

IR (CH$_2$Cl$_2$) $v_{max}$: 3600 (OH) 1775 and 1715 cm$^{-1}$ (C=O);

$^1$H NMR (CDCl$_3$, 200 MHz) δ: 8.53–8.51 (1H, bd, aromatic H), 7.71–7.62 (1H, m, aromatic H), 7.38, 7.34 (1H, bd, J=7.8 z, aromatic —H), 7.23–7.16 (1H, m, aromatic —H), 6.0–5.85 (1H, m, vinylic —H), 5.47–5.21 (2H, m, vinylic H), 4.86–4.6 (3H, m, CH$_2$-vinylic and HCHF), 4.52–4.44 (1H, m, HCHF), 4.26–4.19, 4.06, 3.99 (2H, ABq, J=13.9 Hz, CH$_2$-pyridine), 4.28–4.18 (2H, m, H-1' and H-5), 3.85–3.73 (1H, m, H-4), 3.23 (1H, dd, J=2.7 Hz, J=7.3 Hz, H-6), 2.4–1.6 (3H, m and bs, CH$_2$ and OH) and 1.36 ppm (3H, d, J=6.3 Hz, CH$_3$).

J. Sodium (4R,5S,6S)-4-(2"-fluoroethyl)-6-[(1'R)-1'-hydroxyethyl]-3-[(pyridin-2-yl)methylthio]-7-oxo-1-azabicyclo[3.2.0]hept-2-ene-2-carboxylate

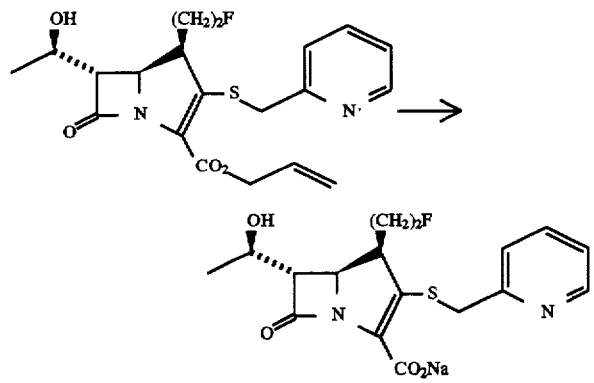

A cold (ice bath) solution of allyl (4R,5S,6S)-4-(2"-fluoroethyl)-6-[(1'R)-1'-hydroxyethyl]-3-[(pyridin-2-yl)methylthio]-7-oxo-1-azabicyclo[3.2.0]hept-2-ene-2-carboxylate (125 mg, 0.320 mmol) in THF (3 mL) was treated with Pd(PPh$_3$)$_4$ (10 mg) and N-methylaniline (60 μl, 0.55 mmol). The ice bath was removed and the mixture was stirred for 1.5 h. The mixture was diluted with EtOAc (20 mL) and extracted with an aqueous 0.05M pH 7.0 phosphate buffer (1×10 mL and 1×5 mL). The aqueous phases were combined, washed with ethyl acetate (10 mL) and passed through a μ-Bondapak C$_{18}$ column (20 g, H$_2$O, 2%, 5%, 7%, 10%, CH$_3$CN/H$_2$O) to give the title compound (50 mg, 40%).

Purity by HPLC: 99.23%, retention time 15.90 min (10% CH$_3$CN/KH$_2$PO$_4$, 0.01M, pH 7.4);

UV (H$_2$O) λ$_{max}$: 266 (6300), 304 (8700);

IR (Nujol) $v_{max}$: 1750 and 1600 cm$^{-1}$ (C=O);

$^1$H NMR (CDCl$_3$, 200 MHz) δ: 8.47–8.45 (1H, m, aromatic-H), 7.89–7.81 (1H, m, aromatic-H), 7.53–7.49 (1H, bd, J=7.9 Hz, aromatic H), 7.39–7.32 (1H, m, aromatic-H), 4.8–4.6, 4.55–4.35 (2H, 2 sets of m, CH$_2$-F), 4.24, 4.17, 4.10, 4.03 (2H, ABq, J=13.8 Hz, CH$_2$-pyridine), 4.3–4.17 (1H, m, H-1'), 4.10 (1H, dd, J=9.5 Hz, J=2.6 Hz, H-5), 3.43 (1H, dd, J=6.1 Hz, J=2.6 Hz, H-6), 3.41–3.29 (1H, m, H-4) and 1.27 ppm (1H, d, J=6.4 Hz, CH$_3$).

EXAMPLE 2

(4R,5S,6S)-4-(2"-Aminoethyl)-6-[(1'R)-1'-hydroxyethyl]-3-[(pyridin-2-yl)methylthio]-7-oxo-1-azabicyclo[3.2.0]hept-2-ene-2-carboxylic acid

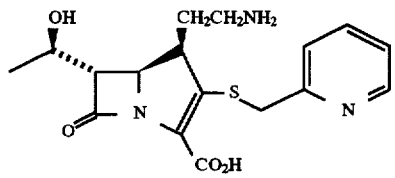

4-Azido-[(pyridin-2-yl)methylthio]butyrate

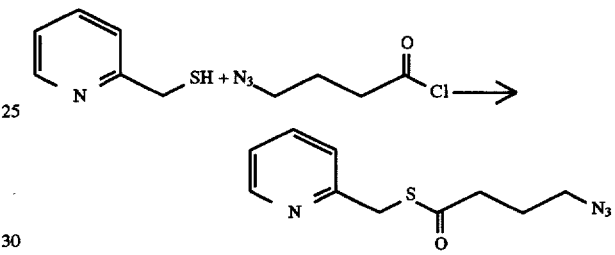

A cold (ice bath) solution 2-mercaptomethylpyridine (46.5 g, 0.372 mol) in CH$_2$Cl$_2$ was treated with pyridine (37.5 mL, 0.465 mol), followed by the dropwise addition of 4-azidobutyryl chloride (54.9 g, 0.372 mol) in CH$_2$Cl$_2$ (100 mL). The mixture was stirred at 5° C. for 1 h, diluted with EtOAc (2 L), washed with cold water (500 mL), aqueous 1M NaHSO$_3$ (500 mL), water (500 mL) then with aqueous 1M NaHCO$_3$ (500 mL), water (500 mL) and brine. The residue was passed through a silica gel (900 g) pad to give the title compound (88.9 g, 91%) as an oil.

IR (CH$_2$Cl$_2$) $v_{max}$: 2100 (N$_3$), and 1690 cm$^{-1}$ (C=O);

$^1$H NMR (CDCl$_3$, 200 MHz) δ: 8.55–8.52 (1H, m, aromatic H), 7.66–7.58 (1H, m, aromatic H), 7.34–7.31 (1H, bd, aromatic H), 7.19–7.12 (1H, m, aromatic H), 4.26 (2H, s, CH$_2$-pyridine), 3.335 (2H, t, J=6.6 Hz, CH$_2$N$_3$), 2.688 (2H, t, J=7.2 Hz, CH$_2$CO) and 2.03–1.87 ppm (2H, m, CH$_2$).

B. tert-Butyldimethylsilylenol ether of 4-azido-[(pyridin-2-yl)methylthio]butyrate

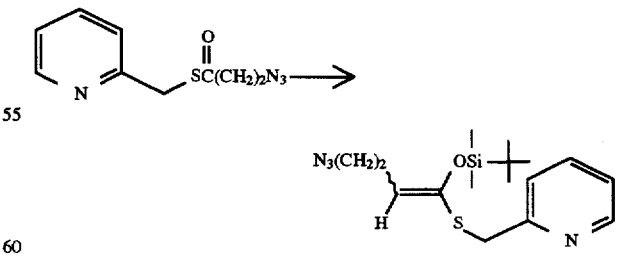

A cold (ice bath) solution of 4-azido-[(pyridin-2-yl)methylthio]butyrate (191 g, 0.809 mol) in CH$_2$Cl$_2$ (1L) was treated with triethylamine (141 mL, 1.01 mol) followed by dropwise addition of tert-butyldimethylsilyl trifluoromethanesulfonate (223 mL, 0.970 mol) and stirred for 45 min at about 22° C. The mixture was cooled down (ice bath), treated in the same manner with triethylamine and tert-butyldimethylsilyl trifluoromethanesulfonate and stirred for 45 min. This process was repeated once more and the mixture was stirred for 1 h. The mixture was cooled down (ice bath), diluted with cold petroleum ether (2 L), and washed with cold water (4×1 L), 1M aqueous NaHCO₃ (5×1 L), water (1 L), brine and dried (MgSO₄). The organic phase was treated with charcoal and filtered to give the title compound (327 g, 100%);

¹H NMR (CDCl₃, 200 MHz) δ: 8.56–8.53 (1H, m, aromatic H), 7.67–7.59 (1H, m, aromatic H), 7.28–7.25 (1H, bd, aromatic H), 7.18–7.12 (1H, m, aromatic H), 3.989 (0.45H, t, J=7.6 Hz, vinylic H), 4.828 (0.55H, t, J=7.2 Hz, vinylic H), 4.048 (0.9H, s, CH₂-pyridine), 3.978 (1.1H, s, CH₂-pyridine), 3.128 (1.1H, t, J=7.2 Hz, CH₂N₃), 3.004 (0.9H, t, J=6.9 Hz, CH₂N₃), 2.35–2.22 (2H, m, CH₂), 0.985, 0.969 (9H, 2s, tert-butyl), 0.251 and 0.215 ppm (6H, 2s, dimethyl).

C. (3S,4S)-3-[(1'R)-1'-tert-Butyldimethylsilyloxyethyl]-4-[(1'R)-1"-(pyridin-2-yl)methylthiocarbonyl-3"-azidopropyl]azetidin-2-one

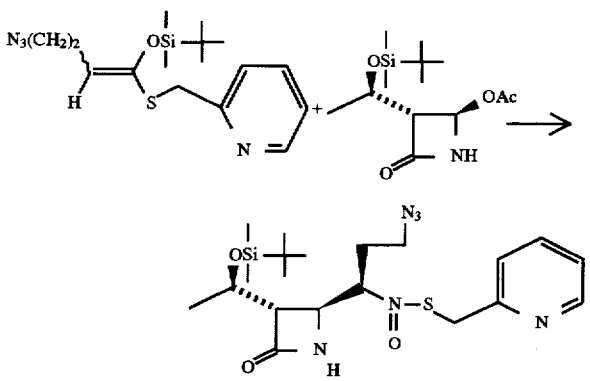

To freshly fused ZnCl₂ (38.6 g, 0.284 mol) was added first at 0° C. (ice bath), under an Argon atmosphere (3S,4R)-4-acetoxy-3-[(1'R)-1'-tert-butyldimethylsilyloxyethyl]azetidin-2-one (40.75 g, 0.142 mol) in CH₂Cl₂ (500 mL) and then dropwise a solution of tert-butyldimethylsilylenol ether of 4-azido-[(pyridin-2-yl)methylthio]butyrate (100 g, 0.284 mol) prepared in Step B in CH₂Cl₂ 140 mL. The mixture was stirred (ice bath) for 1 h then was allowed to stand for 15 h at 5° C. (cold room). The mixture was stirred again for 4 h at about 22° C., then diluted with aqueous saturated NH₄Cl (700 mL) and extracted twice with EtOAc (2×1 L). The organic phases were combined, washed with water (3×500 mL), brine (500 mL) and dried (MgSO₄). Evaporation of the solvent afforded a residue that was diluted with petroleum ether (200 mL), seeded with title compound and allowed to crystallize for 18 h at 5° C. (cold room). The crystals were collected and the mother liquor was purified on a silica gel flash (500 g) pad [8/2:CH₂Cl₂/hexane→50% EtOAc/CH₂Cl₂] to give a total of 50.5 g (74%) of the title compound; m.p.=95°–6° C. (petroleum ether).

IR (CH₂Cl₂) ν$_{max}$: 3400 (NH), 2100 (N₃), 1770 and 1680 cm⁻¹ (C=O);

¹H NMR (CDCl₃, 200 MHz) δ: 8.55–8.52 (1H, m, aromatic H), 7.67–7.59 (1H, m, aromatic H), 7.34–7.30 (1H, bd, aromatic H), 7.21–7.14 (1H, m, aromatic H), 5.93 (1H, bs, NH), 4.278 (2H, s, CH₂-pyridine), 4.2–4.09 (1H, m, H-1') 3.839 (1H, dd, J=2.1 Hz, J=6.7 Hz, H-4), 3.47–3.22 (2H, m, CH₂-N₃), 3.053 (1H, dd, J=2.3 Hz, J=3.3 Hz, H-3), 2.99–2.89 (1H, m, H-1"), 2.09–1.97 (1H, m, HCH), 1.79–1.65 (1H, m, HCH), 1.009 (3H, d, J=6.3 Hz, CH₃), 0.852 (9H, s, tert-butyl) and 0.044 (6H, s, dimethyl).

D. (3S,4S)-3-[(1'R)-1'-tert-Butyldimethylsilyloxyethyl]-4-[(1"R)-1"-carboxy-3"-azidopropyl]azetidin-2-one

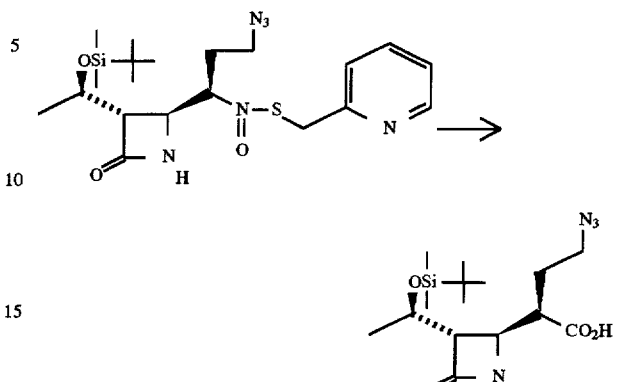

A cold (ice bath) solution of (3S,4S)-3-[(1'R)-1'-tert-butyldimethylsilyloxyethyl]-4-[(1"R)-1"-(pyridin-2-yl)methylthiocarbonyl-3"-azidopropyl] azetidin-2-one (4.79 g, 10 mmol) in THF (50 mL) was treated with H₂O₂ 30% (2.58 mL, 30.0 mmol) followed by the dropwise addition of a 1N aqueous NaOH solution (30 mL, 30 mmol). The ice bath was removed and the mixture was stirred for 1 h then cooled again (ice bath). The reaction mixture was acidified with 1N aqueous HCl (60 mL, 60 mmol) and extracted with EtOAc (3×50 mL). The organic extracts were combined, washed with water (50 mL), 1M aqueous NaHSO₃, water (50 mL), brine (50 mL) and dried (MgSO₄). Evaporation of the solvent afforded the title compound (3.64 g, 98%) as a white solid; m.p.=138°–139° C. (diethyl ether, petroleum ether).

IR (CH₂Cl₂) ν$_{max}$: 3410 (NH), 2100 (N₃), 1770, 1740 and 1710 cm⁻¹ (C=O);

¹H NMR (CDCl₃, 200 MHz) δ: 6.57 (1H, bs, NH), 4.23–4.18 (1H, m, H-1'), 3.932 (1H, dd, J=2.0 Hz, J=5.8 Hz, H-4), 3.52–3.36 (2H, m, CH₂N₃), 3.146 (1H, dd, J=1.8 Hz, J=3.7 Hz, H-3), 2.85–2.74 (1H, m, H-1"), 2.1–1.94 (1H, m, HCH), 1.9–1.7 (1H, m, HCH), 1.1830 (3H, t, J=6.3 Hz, CH₃), 0.868 (9H, s, tert-butyl), 0.072 and 0.059 ppm (6H, 2s, dimethyl).

E. (3S,4R)-3-[(1'R)-1'-tert-Butyldimethylsilyloxyethyl]-4-[(1"R)-1"-(2-azidoethyl)-3"-diazo-3"-allyloxycarbonyl-2"-oxopropyl]azetidin-2-one

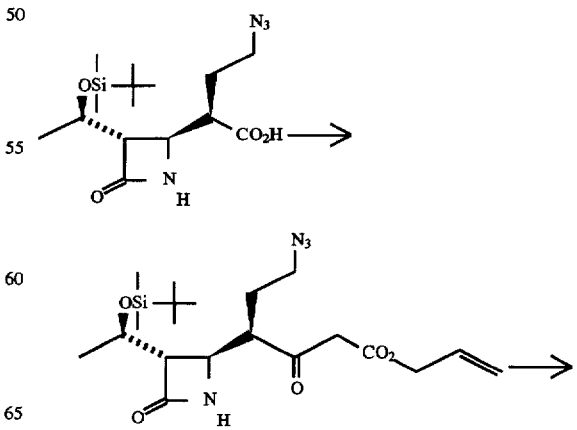

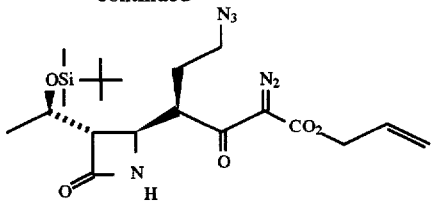

A suspension of (3S,4S)-3-[(1'R)-1'-tert-butyldimethylsilyloxyethyl]-4-[(1" R)-1"-carboxy-3"-azidopropyl]azetidin-2-one (3.56 g, 10 mmol) in anhydrous CH₃CN, under a nitrogen atmosphere, was first treated with carbonyldiimidazole (1.94 g, 12 mmol) and stirred for 30 min. To the clear solution was added monoallyl magnesium malonate (3.73 g, 12 mmol) and the mixture was stirred for 18 h at 60° C. Then more malonate (932 mg, 3 mmol) was added and the mixture was heated at 60° C. for 4 additional hours. This process was repeated twice with a heating period of 18 and 4 h respectively. Acetonitrile was then evaporated and the residue was taken up in EtOAc (200 mL). This solution was washed with cold water (100 mL), 1N aqueous HCl (100 mL), 10% aqueous Na₂CO₃ (100 mL), brine (100 mL) and dried (MgSO₄). Evaporation of the solvent afforded crude (3S,4R)-3-[(1' R)-1'-tert-butyldimethylsilyloxyethyl)-4 -[(1" R)-1"-(2-azidoethyl)-3"-allyloxycarbonyl-2"-oxopropyl] azetidin-2-one (4.2 g, 100%). Part of this crude material (1.85 g, 4.22 mmol) in CH₃CN (19 mL) was cooled down (ice bath), treated successively with triethylamine (0.6 mL, 4.3 mmol) and p-toluenesulfonyl azide (847 mg, 3.2 mmol) and stirred at about 22° C. for 3.5 h. The solvent was evaporated and the residue was passed through a silica gel (20 g, CH₂Cl₂, 10% EtOAc/CH₂Cl₂) column to give the title compound (1.21 g, 62%) contaminated with a small amount of p-toluenesulfonamide.

IR (CH₂Cl₂) ν$_{max}$: 3410 (NH), 2150 (N₂), 2100 (N₃), 1765, 1715 and 1645 cm$^{-1}$ (C=O);

¹H NMR (CDCl₃, 200 MHz) δ: 6.1–5.8 (1H, m, vinylic H), 5.87 (1H, bs, NH), 5.41–5.29 (2H, m, vinylic H), 4.75–4.7 (2H, m, CH₂), 4.23–4.1 (2H, m, H-1' and H-1"), 3.873 (1H, dd, J=2.1 Hz, J=5.2 Hz, H-4), 3.39–3.24 (2H, m, CH₂N₃), 3.049 (1H, dd, J=2.1 Hz, J=3.7 Hz, H-3), 2.21–2.05 (1H, m, HCH), 1.75–1.60 (1H, m, HCH), 1.179 (3H, d, J=6.3 Hz, CH₃), 0.864 (9H, s, tert-butyl), 0.064 and 0.052 ppm (6H, 2s, dimethyl).

F. (3S,4R) -3-[(1'R)-1'-Hydroxyethyl]-4-(1"R)-1"-(2-azidoethyl)-3"-diazo-3"-allyloxycarbonyl-2"-oxopropyl] azetidin-2-one

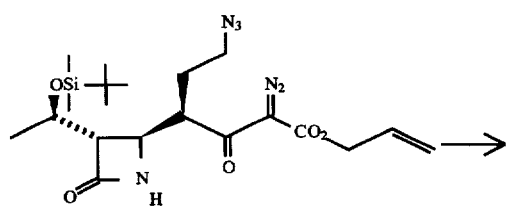

To a cold (ice bath) solution of (3S,4R)-3-[(1'R)-1'-tert-butyldimethylsilyloxyethyl]-4-[(1" R)-1"-(2-azidoethyl)-3"-diazo-3"-allyloxycarbonyl-2"-oxopropyl]azetidin-2-one (1.21 g, 2.61 mmol) in EtOH (20 mL) was added slowly 2N aqueous HCl (2.61 mL, 5.22 mmol). The ice bath was removed and the mixture was stirred for 22 h, then neutralized to pH 7 with 1M aqueous NaHCO₃. The mixture was concentrated under vacuum and the residue was taken up in EtOAc (50 mL), washed with water (20 mL), 1M aqueous NaHCO₃ (20 mL), brine (20 mL) and dried (MgSO₄). The residue was passed through a silica gel (20 g) column (CH₂Cl₂→8/2:EtOAc/CH₂Cl₂) to give the title compound (760 mg, 83%).

IR (CH₂Cl₂) ν$_{max}$: 3600, 3500 (OH) 2150 (N₂) 2100 (N₃), 1765, 1715 and 1645 cm$^{-1}$ (C=O);

¹H NMR (CDCl₃, 200 MHz) δ: 6.25 (1H, bs, NH), 6.04–5.8 (1H m, vinylic H), 5.4–5.2 (2H, m, vinylic H), 4.9–4.8 (2H, m, CH₂), 4.17–4.01 (2H, m, H-1' and H-1"), 3.844 (1H, dd, J=2.1 Hz, J=6.1 Hz, H-4), 3.42–3.2 (2H, m, CH₂N₃), 3.017 (1H, dd, J=2.1 Hz, J=6.7 Hz, H-3), 2.5 (1H, bs, OH), 2.2–2.0 (1H, m, HCH), 1.85–1.7 (1H, m, HCH) and 1.286 ppm (3H, d, J=6.4 Hz, CH₃).

G. Allyl (2R,4R,5R,6S)-4-(2"-azidoethyl)-6-[(1'R)-1'-hydroxyethyl]-3,7-dioxo-1-azabicyclo[3.2.0]heptane-2-carboxylate

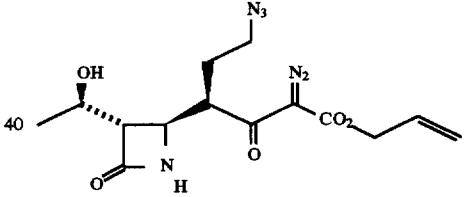

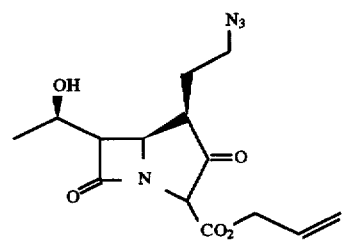

A solution of (3S,4R)-3-[(1' R)-1'-hydroxyethyl]-4-[(1"R)-1"-(2-azidoethyl)-3"-diazo-3"-allyloxycarbonyl-2"-oxopropyl]azetidin-2-one (350 mg, 1 mmol) and Rh(OAc)₂ (6 mg) in EtOAc (15 mL) and hexanes (5 mL) was heated at 80°–85° C. (bath temperature) for 2 h. The solvent was removed under vacuum to produce the title compound (340 mg, 100%) as an oil.

¹H NMR (CDCl₃, 200 MHz) δ: 6.05–5.9 (1H, m, vinylic H), 5.5–5.2 (2H, m, vinylic H), 4.77 (1H, s, H-2), 4.48–4.6 (2H, m, CH₂), 4.329 (1H, dd, J=2.5 Hz, J=8.7 Hz, H-5), 4.3–4.1 (1H, m, H-1'), 3.568 (2H, t, J=6.5 Hz, CH₂N₃), 3.234 (1H, dd, J=2.5 Hz, J=8.0 Hz, H-6), 2.95–2.75 (1H, m, H-4), 2.1–1.9 (1H, m, HCH), 1.8–1.6 (1H, m, HCH) and 1.412 ppm (3H, d, J=6.2 Hz, CH₃).

H. Allyl (4R,5S,6S)-4-(2"-azidoethyl)-6-[(1'R)-1'-hydroxyethyl]-3-[(pyridin-2-yl)methylthio]-7-oxo-1-azabicyclo-[3.2.0]hept-2-ene-2-carboxylate

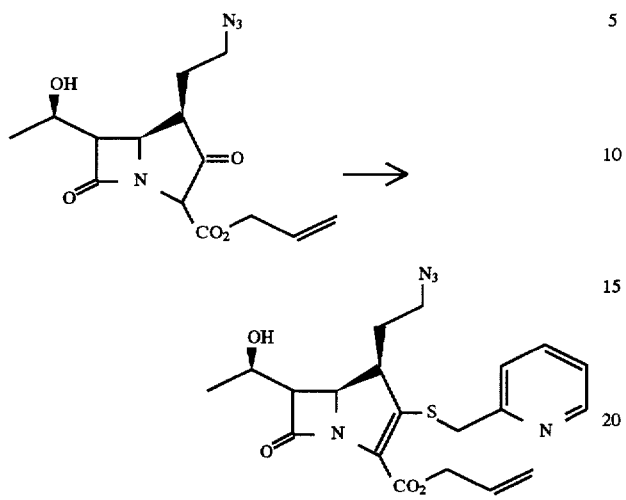

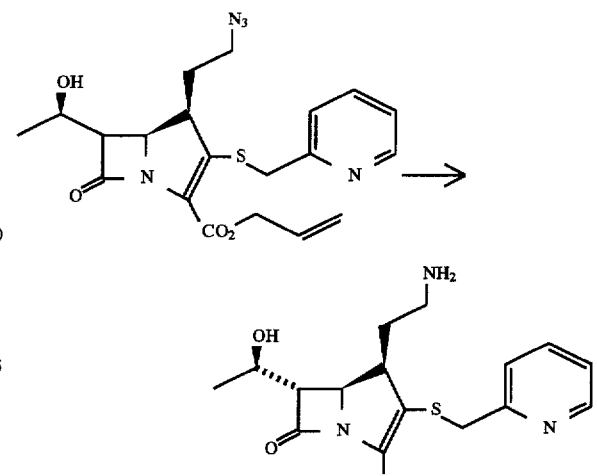

A cold (ice-CH₃OH bath) of allyl (2R,4R,5R,6S)-4-(2"-azidoethyl)-6-[(1'R)-1'-hydroxyethyl]-3,7-dioxo-1-azabicyclo[3.2.0] heptane-2-carboxylate (338 mg, 1 mmol) in $CH_3CN$ (8 mL) was treated successively with ClPO(OPh)₂ (0.23 mL, 1.1 mmol) and N,N-diisopropylethylamine (0.19 mL, 1.1 mmol) and stirred for 45 min. The resulting enol phosphate was then treated with trimethylsilyl chloride (0.14 mL, 1.1 mmol) and N,N-diisopropylethylamine (0.19 mL, 1.1 mmol) and was stirred for another 45 min. The resulting protected enol phosphate was then treated with 2-picolyl mercaptan (250 mg, 2.0 mmol) in $CH_3CN$ (1 mL) and N,N-diisopropylethylamine (0.34 mL, 2.0 mmol) and afterwards was stirred for 2 h. The reaction mixture was diluted with EtOAc (30 mL), washed with cold water (10 mL), 1M aqueous NaHSO₃ (10 mL), water (10 mL), 1M aqueous NaHCO₃ (10 mL), water (10 mL), brine (10 mL) and dried (MgSO₄). The residue after solvent removal was taken up in cold (ice bath) THF (10 mL), treated with 2N aqueous $CH_3CO_2H$ (3 mL, 6 mmol) and stirred for 1 h in cold and 1.5 h at about 22° C. The mixture was diluted with ethyl acetate (20 mL), washed with cold water (10 mL), 1M aqueous NaHCO₃ (10 mL), water (10 mL), brine and dried (MgSO₄). The residue was eluded through a silica gel (15 g) column ($CH_2Cl_2 \rightarrow 60\%$ EtOAc/$CH_2Cl_2$) to give the title compound (175 mg, 38%).

IR 3600, 3500–3400 (OH), 2100 (N₃), 1775 and 1710 $cm^{-1}$ (C=O);

¹H NMR (CDCl₃, 200 MHz), δ: 8.54–8.51 (1H, m, aromatic H), 7.7–7.6 (1H, m, aromatic H), 7.38, 7.34 (1H, m, aromatic H), 7.25–7.15 (1H, m, aromatic H), 6.1–5.8 (1H, m, allyl H), 5.5 (2H, m, allyl H), 4.8–4.55 (2H, m, $CH_2$-allyl), 4.294, 4.225, 4.072, 4.002 (2H, ABq, J=14.0 Hz, $CH_2$-pyridyl), 4.3–4.1 (1H, m, H-1'), 4.166 (1H, dd, J=2.7 Hz, J=9.5 Hz, H-5), 3.8–3.65 (1H, m, H-4), 3.6–3.3 (2H, m, $CH_2$—N₃), 3.162 (1H, dd, J=2.7 Hz, J=7.7 Hz, H-6), 2.2–2 (1H, m, HCH), 1.95 (1H, bs, OH), 1.9–1.6 (1H, m, HCH) and 1.382 ppm (3H, d, J=6.2 Hz, CH₃).

I. (4R,5S,6S)-4-(2"-Aminoethyl)-6-[(1'R)-1'-hydroxyethyl]-3-[(pyridin-2-yl)methylthio]-7-oxo-1-azabicyclo[3.2.0]-hept-2-ene-2-carboxylic acid A cold (ice bath) solution of allyl (4R,5S,6S)-4-(2"-azidoethyl)-6-[(1'R)-1'-hydroxyethyl]-3-[(pyridin-2-yl)-methylthio]-7-oxo-1-azabicyclo[3.2.0]hept-2-ene-2-carboxylate (43 mg, 0.1 mmol) in $CH_2Cl_2$ was treated with (PPh₃)₄Pd (21 mg, 0.018 mmol) and with N-methylaniline (0.03 mL, 0.26 mmol). The mixture was stirred for 1 h at about 22° C., diluted with diethyl ether (10 mL), then extracted with a 0.1M aqueous pH 7.0 phosphate buffer solution (2×1.5 mL, 0.15 mmol), water (2×1.5 mL). The aqueous phases were washed with diethyl ether (5 mL) and the pH adjusted to pH 5.9–6.0 with a 1M aqueous pH 4.2 phosphate buffer. The aqueous layer was then hydrogenolyzed at 45–50 p.s.i. and at 5° C. to 15° C. (temperature at the end of the reaction) for 1 h, using 10% Pd/C (75 mg) as catalyst. The catalyst was filtered, rinsed with a pH 6 phosphate buffer and purified on a $C_{18}$ μBondapak (12 g) reversed phase column (2% $CH_3CN/H_2O$) then repurified in the same way to give the title compound (6 mg, 16%).

Purity by HPLC: 98.11%, retention time=6.08 min. (302 mm, 10% $CH_3CN$, 0.01M pH 7.4 phosphate buffer);

UV (H₂O) $\lambda_{max}$: 266 (4600), 302 (5300);

IR (Nujol) $\nu_{max}$: 1755 and 1590 $cm^{-1}$ C=O);

¹H NMR (D₂O, 200 MHz) δ: 8.48–8.45 (1H, m, aromatic), 7.9–7.8 (1H, m, aromatic H), 7.51, 7.47 (1H, bd, aromatic H), 7.4–7.33 (1H, m, aromatic H), 4.22, 4.15, 4.09, 4.02 (2H, ABq, J=14.5 Hz, $CH_2$-picolyl), 4.3–4.14 (1H, m, H-1'), 4.097 (1H, dd, J=2.8 Hz, J=9.6 Hz, H-5), 3.374 (1H, dd, J=2.8 Hz, J=6.6 Hz, H-6), 3.3–3.16 (1H, m, H-4), 3.03 (1H, t, J=7.8 Hz, $CH_2N$), 2.2–2.05 (1H, m HCH), 1.82–1.6 (1H, m, HCH) and 1.299 ppm (3H, d, J=6.4 Hz, CH₃).

EXAMPLE 3

(4R,5S,6S)-4-(2"-Aminoethyl)-6-[(1'R)-1'-hydroxyethyl]-3-[(pyridin-2-yl)methylthio]-7-oxo-1-azabicyclo[3.2.0]hept-2-ene-2-carboxylic acid

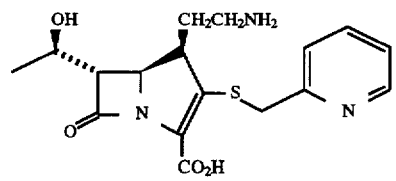

A. (3S,4R)-3-[(1'R)-1'-Hydroxyethyl]-4-[(1'R)-1"-(2-azidoethyl)-3"-diazo-3"-p-nitrobenzyloxycarbonyl-2"-oxopropyl]azetidin-2-one

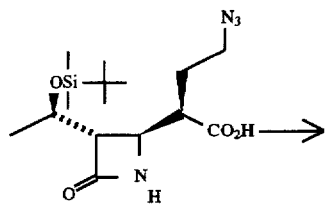

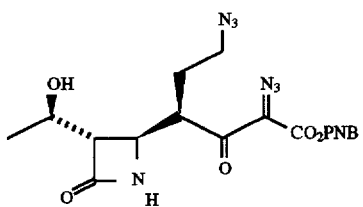

A suspension of (3S,4S)-3-[(1'R)-1'-tert-butyldimethylsilyloxyethyl]-4-[(1"R)-1"-carboxy-3"-azidopropyl]azetidin-2-one (100 mg, 0.27 mmol) in CH$_3$CN (4 mL) was treated with carbonyldiimidazole (52 mg, 0.32 mmol) and stirred for 0.5 h at about 22° C. Magnesium monop-nitrobenzyl malonate (200 mg, 0.400 mmol) was added and the mixture was heated at 60° C. (bath temperature) for 18 h. The mixture was diluted with EtOAc (20 mL), washed with 1N aqueous HCl (10 mL) water (10 mL), 10% aqueous K$_2$CO$_3$ (10 mL), brine (10 mL) and dried (MgSO$_4$) to give crude (3S,4R)-3-[(1'R)-1-tert-butyldimethylsilyloxyethyl]-4-[(1"R)-1"-(2-azidoethyl)-3"-p-nitrobenzyloxycarbonyl-2"-oxopropyl]azetidin-2-one (1.37 g, 92%). Part of this crude material (109 mg, 0.198 mmol) was dissolved in CH$_3$CN (2 mL) and treated successively with triethylamine (0.030 mL, 0.22 mmol) and p-toluenesulfonyl azide (43 mg, 0.22 mmol) and stirred at about 22° C. for 1.3 h. The solvent was evaporated and the residue applied on a preparative TLC plate (diethyl ether) to give after extraction (3S,4R)-3-[(1'R)-1'-tert-butyldimethylsilyloxyethyl]-4-[(1"R)-1"-(2-azidoethyl)-3"-diazo-3"-p-nitrobenzyloxycarbonyl-2"-oxopropyl]azetidin-2-one (R$_f$ 0.71, 84 mg) contaminated with p-toluenesulfonyl azide (65 mg, 57% adjusted yield). A similar mixture (from another reaction) (2.7 g, 4.7 mmol) was dissolved in cold (ice bath) ethanol (40 mL) and treated dropwise with 2N aqueous HCl (4.7 mL, 9.4 mmol). The ice bath was removed and the mixture was stirred for 23 h after which it was neutralized (ice bath) with 1M aqueous NaHCO$_3$ (about 10 mL) and concentrated under vacuum. The residue was diluted with EtOAc (100 mL), washed with cold 1M aqueous NaHCO$_3$ (200 mL) water(20 mL), brine and dried (MgSO$_4$). The residue was passed through a silica gel (30 g) pad (CH$_2$Cl$_2$→80% EtOAc/CH$_2$Cl$_2$→EtOAc) to give the title compound (1.45 g, 67%) as a yellow solid.

$^1$H NMR (CDCl$_3$, 200 MHz) δ: 8.3–8.23 (2H, m, aromatic H), 7.56, 7.52 (2H, bd, J=8.7 Hz, aromatic H), 6.02 (1H, bs, NH), 5.44, 5.37, 5.35, 5.29 (2H, Abq, J=13.1 Hz, CH$_2$), 4.16–4.01 (2H, m, H-1' and H-1"), 3.849 (1H, dd, J=2.2 Hz, J=6.0 Hz, H-4), 3.43–3.25 (2H, m, CH$_2$N$_3$), 3.041 (1H, dd, J=2.1 Hz, J=6.9 Hz, H-3), 2.3–2.0 (1H, m, HCH), 2.130 (1H, d, J=4.1 Hz, OH), 1.9–1.7 (1H, m, HCH) and 1.30 ppm (3H, d, J=6.3 Hz, CH$_3$).

B. p-Nitrobenzyl (4R,5S,6S)-4-(2"azidoethyl)-6-[(1'R)-1'-hydroxyethyl]-3-[(pyridin-2-yl)methylthio]-7-oxo-1-azabicyclo[3.2.0]hept-2-ene-2-carboxylate

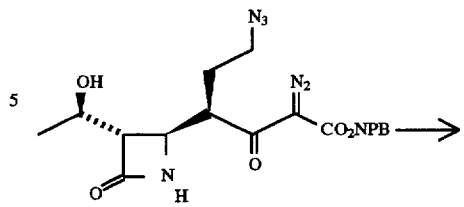

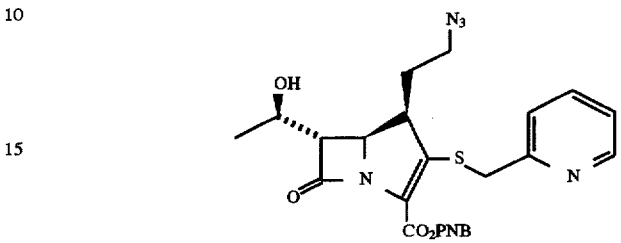

A solution of (3S,4R)-3-[(1'R)-1'-hydroxyethyl]-4-[(1"R)-1"-[(2-azidoethyl)-3"-diazo-3"-p-nitrobenzyloxycarbonyl-2"-oxopropyl]azetidin-2-one (856 mg, 1.86 mmol) in 3/1:EtOAc/hexane (40 mL) and Rh(OAc)$_2$ (20 mg) was heated at 80°–85° C. (bath temperature) for 1.5 h. The solvent was removed to leave the crude bicyclic ketone: p-nitrobenzyl (2R,4R,5R,6S)-4-(2"-azidoethyl)-6-[(1'R)-1'-hydroxyethyl]-3,7-dioxo-1-azabicyclo[3.2.0] heptane-2-carboxylate (860 mg, 100%);

$^1$H NMR (CDCl$_3$, 200 MHz) δ: 8.2 (2H, d, aromatic H), 7.5 (2H, d, aromatic H), 5.4 (1H, s, H-2), 5.3 (2H, center of ABq, CH$_2$ aromatic), 4.3 (1H, dd, H-5), 4.3–4.1 (1H, m, H-1'), 3.5 (2H, t, CH$_2$N$_3$), 3.3 (1H, dd, H-6), 3.0–2.8 (1H, m, H-4); 2.1–1.9 (1H, m, HCH), 1.9–1.7 (1H, m, HCH), 1.43 (3H, d, CH$_3$).

A cold (ice-CH$_3$OH bath) solution of the crude ketone (860 mg, 1.86 mmol) in CH$_3$CN (20 mL) was treated with diphenyl chlorophosphate (0.43 mL, 2.05 mmol) followed by the slow addition of N,N-diisopropylethylamine (0.35 mL, 2.05 mmol) and a trace of 4-dimethylaminopyridine. The mixture was stirred for 30 min after which trimethylsilyl chloride (0.26 mL, 2.05 mmol) and N,N-diisopropylethylamine (0.35 mL, 2.05 mmol) were successively added in and stirring was continued for 30 more min. The resulting O-trimethylsilyl enol phosphate was treated with 2-picolyl mercaptan (517 mg, 4.10 mmol) in CH$_3$CN (1 mL) followed by the dropwise addition of N,N-diisopropylethylamine (0.70 mL, 0.41 mmol) and stirred for 1 h. The mixture was diluted with EtOAc (40 mL), washed with cold water (20 mL), pH 7.4 phosphate buffer (20 mL), brine (20 mL) and dried (MgSO$_4$). The residue obtained after evaporation of the solvent was taken up in THF (100 mL), cooled to 5° C. (ice bath), treated with 2N aqueous CH$_3$CO$_2$H (5 mL) and stirred for 2 h. The mixture was diluted with ethyl acetate (25 mL), washed with water, pH 7.5 phosphate buffer (20 mL), brine and dried (MgSO$_4$). The residue was purified on a silica gel flash (20 g) chromatography column (CH$_2$Cl$_2$→EtOAc) to give the title compound (500 mg, 49%).

IR (CH$_2$Cl$_2$) ν$_{max}$: 3600, 3509, 3400 (OH), 2100 (N$_3$), 1775, 1710 (C=O) and 1525 cm$^{-1}$ (NO$_2$);

$^1$H NMR (CDCl$_3$, 200 MHz) δ: 8.54, 8.52 (1H, bd, aromatic H), 8.198 (2H, d, J=8.7 Hz, p-NB ester), 7.7–7.5 (3H, m, and d, J=8.7, aromatic H, p-NB ester), 7.36–7.32 (1H, bd, aromatic H), 7.24–7.17 (1H, m, aromatic H), 5.517, 5.448, 5.230, 5.161 (2H, ABq, J=14.8 Hz, CH$_2$-pNB), 4.305, 4.236, 4.087, 4.018 (2H, ABq, J=13.9 Hz, CH$_2$-pyridyl), 4.3–4.2 (1H, m, H-1'), 4.190, 4.177 (part of dd, J=2.6 Hz, part of H-5), 3.85–3.72 (1H, m, H-4), 3.7–3.3 (2H, m, CH$_2$N$_3$), 3.198 (1H, dd, J=2.6 Hz, J=7.6 Hz, H-6), 2.2–1.95 (1H, m, H-CH), 1.9–1.6 (1H, m, HCHH), 1.64 (1H, bs, OH) and 1.399 ppm (3H, d, J=6.3 Hz, CH$_3$).

C. (4R,5S,6S)-4-(2"-Aminoethyl)-6-[(1'R)-1'-hydroxyethyl]-3-[(pyridin-2-yl)methylthio]-7-oxo-1-azabicyclo[3.2.0]hept-2-ene-2-carboxylic acid

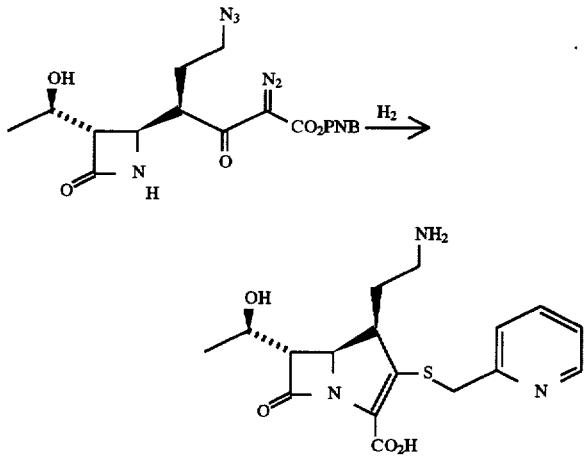

A solution of p-nitrobenzyl (4R,5S,6S)-4-(2"-azidoethyl)-6-[(1'R)-1'-hydroxyethyl]-3-[(pyridin-2-yl)methylthio]-7-oxo-1-azabicyclo[3.2.0]hept-2-ene-2-carboxylate (55 mg, 0.1 mmol) in a two phase system of diethyl ether:THF (1:1, 20 mL) and water 0.05M, pH 7.0 phosphate buffer (7 mL+3 mL) was hydrogenolyzed over 10% Pd/C (84 mg) at 50 psi for 5 h in the cold (ice bath). The catalyst was filtered off and the organic layer was washed with water. The aqueous layers were combined and passed through a μBondapak C$_{18}$ reversed phase column to give the title compound (6 mg) whose spectral data were identical to the compound prepared in Example 2 Step I.

EXAMPLE 4

(4R,5S,6S)-4-[3-(N-Formimidoyl)-aminoethyl]-6-[(1'R)-1'-hydroxyethyl]-3-[(pyridin-2-yl)methylthio]-7-oxo-1-azabicyclo[3.2.0]hept-2-ene-2-carboxylic acid

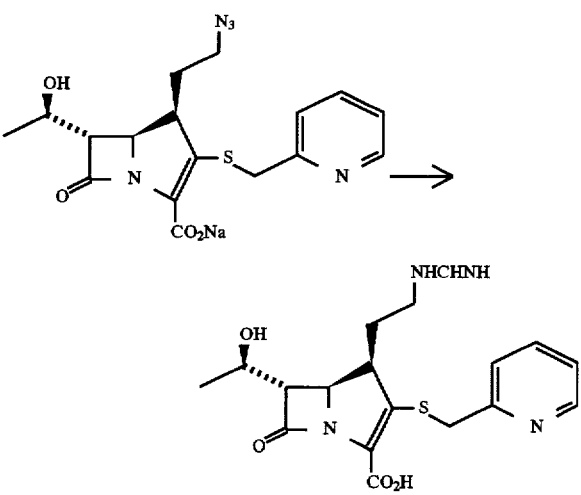

A cold (ice bath) solution of sodium (4R,5S,6S)-4-(2"-azidoethyl)-6-[(1' R)-1'-hydroxyethyl]-3-[(pyridin-2-yl)methylthio]-7-oxo-1-azabicyclo[3.2.0]hept-2-en-2-carboxylate (100 mg, 0.24 mmol) in water (12 mL) and a 0.1M pH 6.0 phosphate buffer (7 mL) was hydrogenolyzed for 2 h using 10% Pd/C as catalyst. The catalyst was filtered off and the pH of the aqueous solution (ice bath) was adjusted to 8.5 with a 1N and 0.1N aqueous NaOH. The mixture was treated portionwise with benzyl formimidate hydrochloride (410 mg, 2.4 mmol) and the pH was kept between 8–8.3 with 0.1N NaOH. The reaction mixture was stirred for 15 min and passed through a μBondapak C$_{18}$ column (10 g, H$_2$O→1.2 and 3% CH$_3$CN/H$_2$O) to give the title compound (30 mg). The product was repurified on the same material (C$_{18}$, 6 g) to give pure title compound (13 mg, 13%).

Purity by HPLC: 92.6% (μBondapak C$_{18}$, 8% CH$_3$CN/KH$_2$PO$_4$ 0.01M pH 7.4, r.t.=7.095 min);

UV (H$_2$O) $\lambda_{max}$: 304 (6445), 266 (5592);

IR (NuJol) $\nu_{max}$: 1755, 1595 (C=O) and 1715 cm$^{-1}$ (C=N);

$^1$H NMR (D$_2$O, 200 MHz) δ: 8.47, 8.45 (1H, bd, aromatic H), 7.9–7.8 (1H, m, aromatic H), 7.805 (1H, s, C=NH), 7.5–7.2 (2H, m, aromatic H), 4.3–4.1 (1H, m, H-1'), 4.217, 4.141, 4.078, 4.008 (2H, ABq, J=15.2 Hz, CH$_2$-pyridine), 4.14–4.07 (1H, hidden H-5), 3.5–3.1 (4H, m, H-6, CH$_2$N, H-4), 2.1–1.1 (1H, m, HCH), 1.75–1.5 (1H, m, HCH) and 1.296 ppm (3H, d, J=6.3 Hz, CH$_3$).

EXAMPLE 5

Sodium (4R,5S,6S)-6-[(1'R)-1'-hydroxyethyl]-4-(2"-hydroxyethyl)-3-[(pyridin-2-yl)methylthio]-7-oxo-1-azabicyclo[3.2.0]hept-2-ene-2-carboxylate A. 4-tert-Butyldimethylsilyloxy-[(pyridin-2-yl)methylthio] butyrate

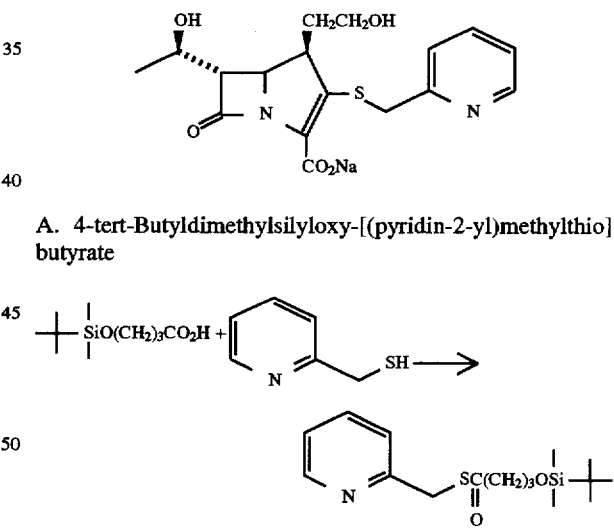

A cold (ice bath) solution of 4-tert-butyldimethylsilyloxybutyric acid (2.7 g, 13 mmol) and 2-picolyl mercaptan (1.67 g, 13 mmol) in CH$_2$Cl$_2$ (40 mL) was treated with 1,3-dicyclohexyl carbodiimide (2.8 g, 13 mmol) and 1-hydroxybenzotriazole hydrate (1.81 g, 13 mmol) and stirred at about 22° C. for 20 h. The mixture was diluted with ethyl acetate, washed with water, brine and dried (MgSO$_4$). Evaporation of solvent gave a residue which was passed through a silica gel pad (EtOAc:Hexane, 1:3) to give the title compound (3.08 g, 71%).

IR (neat) $\nu_{max}$: 1690 cm$^{-1}$ C=O;

$^1$H NMR (CDCl$_3$, 200 MHz) δ: 8.54, 8.52 (1H, bd, aromatic), 7.68, 7.66, 1.63, 7.62, 7.59, 7.58 (1H, dt, aromatic), 7.36, 7.32 (1H, d, aromatic), 7.26, 7.19, 7.166, 7.16, 7.15, 7.13 (1H, m, aromatic), 4.25 (2H, s, CH₂), 3.62 (2H, t, J=6.1 Hz, CH₂), 2.68 (2H, t, J=7.5 Hz, CH₂), 1.90 (2H, center of 5 lines; CH₂), 0.87 (9H, s, t-butyl) and 0.019 ppm (6H, s, dimethyl).

B. tert-Butyldimethylsilylenol ether of 4-tert-butyldimethylsilyloxy-[(pyridin-2-yl)methylthio]butyrate

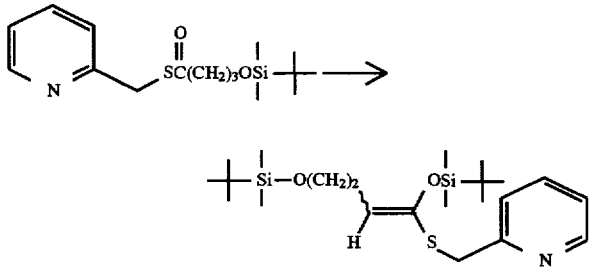

A cold (ice bath) solution of S-(2-picolylthio)4-tert-butyldimethylsilyloxybutyrate (1.3 g, 4.0 mmol) in CH₂Cl₂ (15 mL) was treated dropwise with tert-butyldimethylsilyltrifluoromethanesulfonate (1.1 mL, 6.0 mmol), triethylamine (1.14, 8.00 mmol) and stirred for 3 h at room temperature (about 22° C.). The mixture was diluted with petroleum ether (60 mL), washed with cold water (3×50 mL), brine (50 mL) and dried (MgSO₄). The solution was treated with charcoal, filtered and the solvent was evaporated to give the title compound (1.8 g, 100%) as an oil.

IR (neat) $v_{max}$: 1630 cm⁻¹ olefine;

¹H NMR (CDCl₃, 200 MHz) δ: 8.54, 8.53, 8.52, 8.51 (1H, d, aromatic-H), 7.30–7.24 (1H, m, aromatic-H), 7.16–7.10 (1H, m, aromatic-H), 6.00 (0.6H, t, J=7.5 Hz, olefinic H), 4.89 (0.4H, t, J=7.1 Hz, olefinic H), 4.04 (1.2H, s, CH₂), 3.97 (0.8H, s, CH₂), 3.47 (0.8H, t, J=7.1 Hz, CH₂), 3.38 (0.8H, t, J=6.8 Hz, CH₂), 2.28–2.15 (2H, m, CH₂), 0.98, 0.96 (2s, 9H, t-butyl), 0.864, 0.861 (9H, 2s, t-butyl), 0.237, 0.196 (6H, 2s, dimethyl), 0.014 and 0.003 ppm (6H, 2s, dimethyl).

C. (3S,4S)-3-[(1'-R)-1'-tert-Butyldimethylsilyloxyethyl]-4-[(1"R)-1"-(pyridin-2-yl)methylthtocarbonyl-3"-tert-butyl dimethylsilyloxypropyl]azetidin-2-one

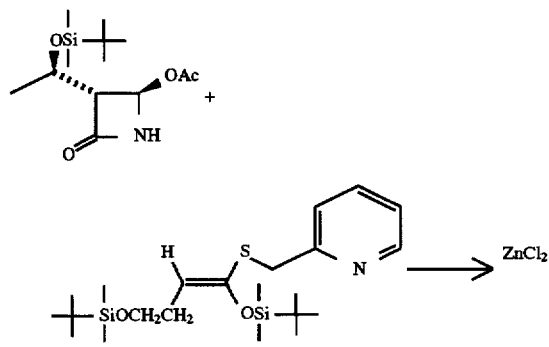

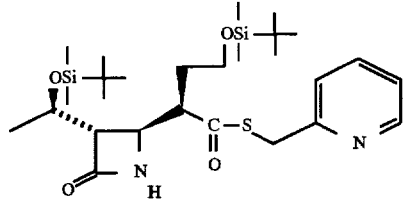

To a cold (ice bath) freshly fused ZnCl₂ (545 mg, 4 mmole) under Argon was added (3S,4R)-4-acetoxy-3-[(1'R)-1'-tert-butyl-dimethylsilyloxyethyl] azetidin-2-one (575 mg, 2 mmol) in CH₂Cl₂ (10 mL) followed by the dropwise addition of the silylenol ether (1.8 g, 4 mmol) prepared in Step B in CH₂Cl₂ (5 mL). The mixture was stirred at 5° C. for 18 h, diluted with ethyl acetate (60 mL), washed with saturated aqueous NaHCO₃ (50 mL), saturated aqueous NH₄Cl (50 mL), brine (50 mL) and dried (MgSO₄). The residue upon evaporation of solvent was purified on a silica gel column (80 g, 1:5 ethyl acetate/hexane) to give the title compound as a solid (500 mg, 45%) m.p.=103°–105° C. (hexane).

IR (CH₂Cl₂) $v_{max}$: 3410 (NH) 1765 and 1680 cm⁻¹ (C=O);

¹H NMR (CDCl₃, 200 MHz) δ: 8.54–8.51 (1H, m, aromatic H), 7.66–7.57 (1H, m, aromatic H), 7.34 (1H, d, J=7.8 Hz, aromatic H), 7.20–7.12 (1H, m, aromatic H); 5.99 (1H, bs, NH), 4.24 (2H, s, CH₂), 4.2–4.09 (1H, m, H-1'), 3.83 (1H, dd, J=2.0 Hz, J=6.9 Hz, H-4), 3.73–3.49 (2H, m, CH₂O), 3.04–2.94 (2H, m, H-1" and H-3), 2.01–1.89 (1H, m, H-2"), 1.80–1.64 (1H, m, H-2"), 1.00 3H, d, J=6.4 Hz, CH₃), 0.861, 0.850 (18H, 2s, tert-butyl), 0.040 and 0.004 ppm (12H, 2s, dimethyl);

Anal. Calcd. for C₂₇H₄₇N₂O₄SSi₂: C 58.76, H 8.58, N 5.08, S 5.81. Found: C 58.57, H 9.00, N 4.97, S 5.89.

D. (3S,4S)-3-[(1'R)-1'-tert-Butyldimethylsilyloxyethyl]-4-[(1"R)-1"-carboxy-3"-tert-butyldimethylsilyloxypropyl] azetidin-2-one

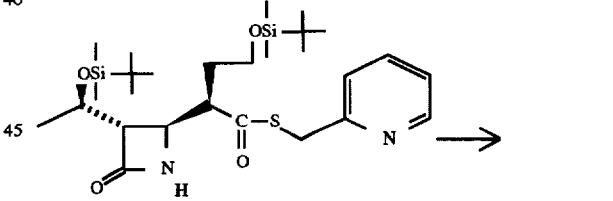

A cold (ice bath) solution of (3S,4S)-3-[(1'R)-1'-tert-butyldimethylsilyloxyethyl]-4-[(1"R)-1"-(pyridin-2-yl) methyl-thiocarbonyl-3"-tert-butyldimethylsilyloxypropyl]-azetidin-2-one (480 mg, 0.87 mmol) in THF (5 mL) was treated with 30% H₂O₂ (0.15 mL, 1.7 mmol) followed by the dropwise addition of a 1N aqueous NaOH (1.7 mL, 1.7 mmol) solution. The ice bath was removed and the mixture was stirred for 90 min after which it was diluted with ethyl acetate (30 mL), washed with 1N aqueous HCl (25 mL), 1N aqueous NaHSO₃ (25 mL), water and brine, and dried.

Evaporation of the solvent afforded the title compound (0.37 g, 96%) as a white solid; m.p.=125°–127° C. (ethyl acetate).

IR (CH$_2$Cl$_2$) v$_{max}$: 3410 (NH), 1765 (β-lactam) and 1710 cm$^{-1}$ (acid);

$^1$H NMR (CDCl$_3$) δ: 6.23 (1H, bs, NH), 4.204 (1H, m, H-1'), 2.94 (1H, dd, J=2.0 Hz, J=5.9 Hz, H-4), 3.72 (2H, bt, J=5.7 Hz, CH$_2$), 3.07 (1H, dd, J=1.7 Hz, J=4.1 Hz, H-3), 2.84–2.74 (1H, m, H-1''), 2.02–1.81 (1H, m, HC<u>H</u>), 1.78–1.69 (1H, m, <u>H</u>CH), 1.18 (3H, d, J=6.3 Hz, CH$_3$), 0.889, 0.866 (18H, 2s, tert-butyl), and 0.065 ppm (12H, s, dimethyl);

Anal. Calcd. for C$_{21}$H$_{42}$NO$_5$Si$_2$: C 56.71, H 9.52, N 3.15. Found C 56.55, H 9.67, N 3.13.

E. (3S,4R)-3-[(1'R)-1'-tert-Butyldimethylsilyloxyethyl]-4-[(1''R)-1''-(2-tert-butyldimethylsilyloxyethyl)-3''-allyloxycarbonyl-2''-oxopropyl]azetidin-2-one

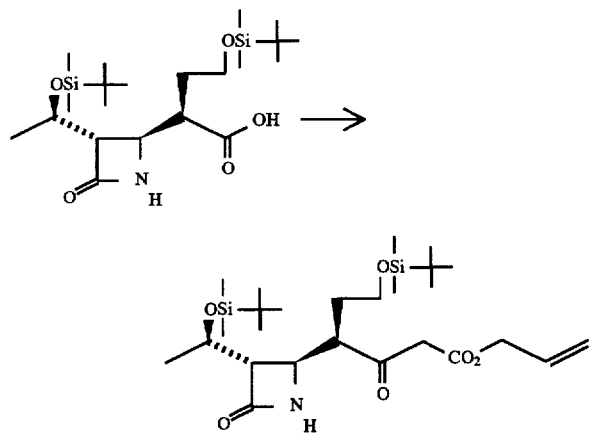

A suspension of (3S,4S)-3-[(1'R)-1'-tert-butyldimethylsilyloxymethyl]-4-[(1''R)-1''-carboxy-3''-tert-butyldimethylsilyloxypropyl]azetidin-2-one (7.5 g, 17 mmol) in CH$_3$CN (75 mL) was treated with carbonyldiimidazole (2.92 g, 18.0 mmol) and stirred for 1 h at 22° C. The mixture was then treated with anhydrous monoalkyl magnesium malonate (5.3 g, 17 mmol) and heated at 80° C. (bath temperature) for 18 h. The solvent was partially evaporated. The concentrated solution was diluted with EtOAc (250 mL), washed with 1N aqueous HCl (100 mL), water (100 mL), saturated aqueous NaHCO$_3$ (100 mL), water and brine (100 mL) and dried (MgSO$_4$). The residue (15 g) was passed through a flash silica gel (300 g) column (1:3 EtOAc/hexane) to give the title compound (5.15 g, 57%) as a mixture of ketone and enol form.

IR (Nujol) v$_{max}$: 3150–3100 (OH), 1760, 1710, 1650 and 1620 cm$^{-1}$ (C=O and enol);

$^1$H NMR (CDCl$_3$, 200 MHz) δ: 6.03–5.80 (2H, 2 bs and m, NH and allyl), 5.38–5.23 (2H, m, allyl), 5.07 (0.5H, s, vinylic H of enol), 4.67–4.60 (2H, m, CH$_2$), 4.24–4.12 (1H, m, H-1'), 3.90 (0.47H, dd, J=2.2 Hz, J=5.6 Hz, H-4), 3.83 (0.53H, dd, J=2.1 Hz, J=7.1 Hz, H-4), 3.75–3.48 (32H, m, C<u>H</u>$_2$OSi and COC<u>H</u>$_2$CO), 3.10 (0.47H, m, H-1''), 2.94 (1H, m, H-3), 2.55–2.40 (0.45H, m, H-1''), 1.97–1.6 (2H, m, CH$_2$), 1.17 (1.3H, d, J=6.3 Hz, CH$_3$), 1.11 (1.4H, d, J=6.3 Hz, CH$_3$), 0.882, 0.878, 0.865 (18H, 3s, tert-butyl), 0.064, 0.056, 0.049 and 0.031 ppm (12H, 4s, dimethyl);

Anal. Calcd. for C$_{26}$H$_{49}$NO$_6$Si$_2$: C 59.16, H 9.36, N 2.65. Found: C 59.11, H 9.36, N 2.60.

F. (3S,4R)-3-[(1'R)-1'-tert-Butyldimethylsilyloxyethyl]-4-[(1''R)-1''-(2-tert-butyldimethylsilyloxyethyl)-3''-diazo-3''-allyloxycarbonyl-2''-oxopropyl]azetidin-2-one

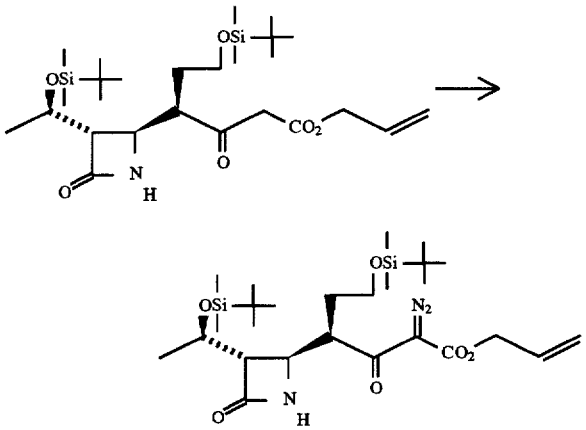

A solution of (3S,4R)-3-[(1'R)-1'-tert-butyldimethylsilyloxyethyl]-4-[(1''R)-1''-(2-tert-butyldimethylsilyloxymethyl)-3''-allyloxycarbonyl-2''-oxopropyl]azetidine-2-one (0.60 g, 1.1 mmol) in CH$_3$CN (10 ml) was treated with p-toluenesulfonyl azide (240 mg, 1.2 mmol) and triethylamine (160 μl, 1.1 mmol) and stirred for 2 h at about 22° C. The solvent was removed and the residue titurated with petroleum ether (20 mL) in order to precipitate p-toluenesulfonamide. The yellow oil (0.61 g) was passed through a silica gel (25 g, 10%–20% EtOAc/hexane) to give pure title compound (420 mg); m.p.= 53°–55° C.

IR (CH$_2$Cl$_2$) v$_{max}$: 3400 (NH), 3140 (N$_2$), 1765, 1715 and 1050 cm$^{-1}$ (C=O);

$^1$H NMR (CDCl$_3$, 200 MHz) δ: 6.02–5.8 (2H, bs and m, NH, allyl), 5.4–5.27 (2H, m, allyl), 4.72–4.68 (2H, m, CH$_2$), 4.23–4.13 (2H, m, H-1' and H-1''), 3.87 (1H, dd, J=2.1 Hz, J-5.5 Hz, H-4), 3.67–3.52 (2H, m, CH$_2$O), 3.04 (1H, bt, J=4.0 Hz, H-3), 2.10–2.01 (1H, m, HC<u>H</u>), 1.66–1.57 (1H, m, <u>H</u>CH), 1.165 (3H, d, J=6.4 Hz, CH$_3$), 0.862 and 0.849 (18H, 2s, tert-butyl), 0.058, 0.053, 0.0005 and 0.0061 ppm (12H, 4s, dimethyl);

Anal. Calcd. for C$_{26}$H$_{47}$N$_3$O$_6$Si$_2$: C 56.39, H 8.55, N 7.59. Found: C 56.44, H 8.80, N 7.50.

G. Allyl (4R,5R,6S)-6-[(1'R)-1'-tert-butyldimethylsilyloxyethyl]-4-(2''-tert-butyldimethylsilyloxyethyl)-3,7-dioxo-1-azabicyclo[3.2.0]heptane-2-carboxylate

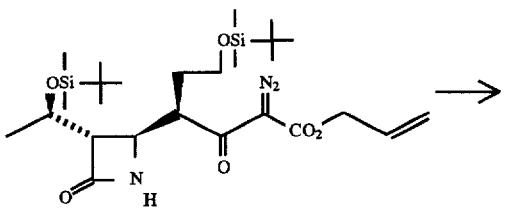

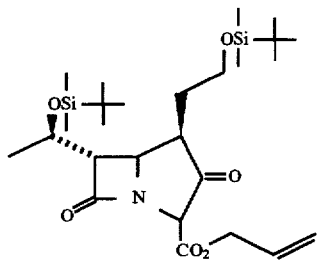

A solution of (3S,4R)-3-[(1'R)-1'-tert-butyldimethylsilyloxyethyl]-4-[(1"R)-1"-(2-tert-butyldimethylsilyloxyethyl)-3"-diazo-3"-allyloxycarbonyl-2"-oxopropyl]azetidin-2-one (1.0 g, 1.8 mmol), Rhodium (II) octanoate (3 mg) in 75% hexane-EtOAc (10 mL) was heated under reflux for 3 h and evaporated down to give the title compound as an oil, in quantitative yield (1 g, 100%).

IR (neat) $v_{max}$: 1765 (C=O) 1745 (shoulder C=O) and 1735 cm$^{-1}$ (shoulder, C=O);

$^1$H NMR (CDCl$_3$, 200 MHz) δ: 5.99–8.79 (1H, m, allyl), 5.39 (2H, m, allyl), 4.7–4.6 (2H, m, CH$_2$), 4.63 (1H, s, H-2), 4.35–4.2 (1H, m, H-1'), 4.25 (1H, dd, J=2.4 Hz, J=8.4 Hz, H-5), 3.8–3.6 (2H, m, CH$_2$—O), 3.21 (1H, dd, J=2.4 Hz, J=5.8 Hz, H-6), 2.99–2.87 (1H, m, H-4), 2.0–1.58 (2H, m, CH$_2$), 1.28 (3H, d, J=6.2 Hz, CH$_3$), 0.886, 0.879 (18H, 2s, tert-butyl), 0.094, 0.087, 0.054 and 0.045 ppm (12H, 4s, dimethyl).

H. Allyl (4R,5S,6S)-6-[(1'R)-1'-(tert-butyldimethylsilyloxyethyl]-4-(2"-tert-butyldimethylsilyloxyethyl)-3-[(pyridin-2-yl)methylthio]-7-oxo-1-azabicyclo[3.2.0]hept-2-ene-2-carboxylate

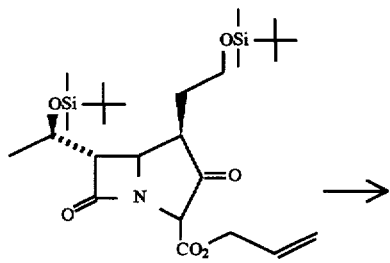

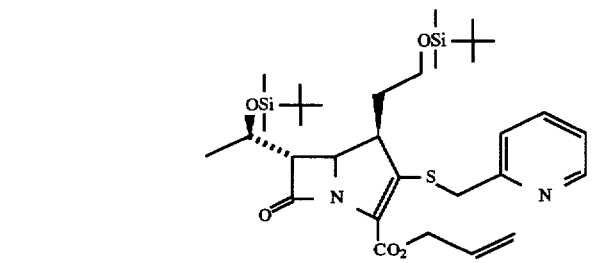

A cold (ice bath) solution of allyl (4R-5R-6S)-6-[(1'R)-1'-tert-butyldimethylsilyloxyethyl]-4-(2"-tert-butyldimethylsilyloxyethyl)-3,7-dioxo-1-azabicyclo[3.2.0]heptane-2-carboxylate (0.92 g, 1.8 mmol) in CH$_3$CN (10 mL) was treated with diphenyl chlorophosphate (0.4 mL, 2 mmol), N,N-diisopropylethylamine (0.36 mL, 2 mmol), dimethylaminopyridine (1 mg) and stirred for 1 h at 22° C. The mixture was cooled again (ice bath), treated with 2-picolyl mercaptan (0.38 g, 3 mmol) and N,N-diisopropylethylamine (0.6 μl, 3.2 mmol) and stirred for 20 h at 5° C. The reaction mixture was diluted with EtOAc (60 mL), washed with cold NaHCO$_3$, water (3×50 mL), brine and dried (MgSO$_4$). The residue obtained upon solvent evaporation was passed through a silica gel column (16 g, 1:9→1.3 EtOAc:Hexane) to give the title compound (0.63 g, 56%).

IR (CH$_2$Cl$_2$) $v_{max}$: 1775 and 1710 cm$^{-1}$ (C=O);

$^1$H NMR (CDCl$_3$, 200 MHz) δ: 8.52–8.49 (1H, m aromatic), 7.68–7.59 (1H, m, aromatic), 7.34–7.30 (1H, d, aromatic), 7.20–7.13 (1H, m, aromatic), 6.03–5.84 (1H, m, allylic H), 5.47–5.18 (1H, m, allylic H), 3.82–4.6 (2H, m, CH$_2$), 4.354, 4.287 (1H, part of ABq, J=13.5 Hz, CH$_2$-pyridyl), 4.28–4.14 (1H, m, H-1'), 4.143, 4.075 (1H, part of ABq, J=13.5 Hz, CH$_2$-pyridyl) 4.08 (1H, dd, J=2.4 Hz, J=9.2 Hz, H-5), 3.84–3.70 (2H, m, CH$_2$O), 3.65–3.51 (1H, m, H-4), 3.100 (1H, dd, J=2.4 Hz, J=6.9 Hz, H-6), 2.12–1.69 (1H, m, HCH), 1.56–1.56 (1H, m, HCH), 1.284 (3H, d, J=6.1, CH$_3$), 0.888, 0.850 (18H, 2s, tert-butyl), 0.081 (6H, s, dimethyl), 0.051 and 0.045 ppm (6H, 2s, dimethyl).

I. Allyl (4R,5S,6S)-6-[(1'R)-1'-hydroxyethyl]-4-(2"-hydroxyethyl)-3-[(pyridin-2yl)methylthio]-7-oxo-1-azabicyclo[3.2.0]hept-2-ene-2-carboxylate

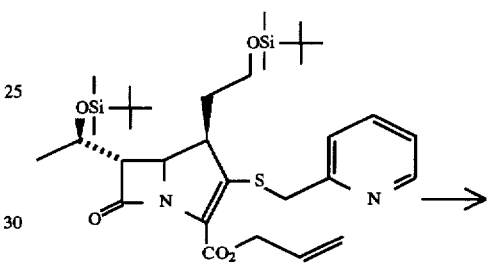

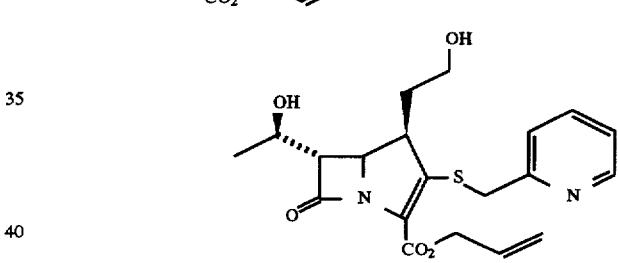

A cold (ice-MeOH bath) solution of allyl (4R,5S,6S)-6-[(1'R)-1'-tert-butyldimethylsilyloxyethyl]-4-(2"-tert-butyldimethylsilyloxyethyl)-3-[(pyridin-2-yl)methylthio]-7-oxo-1-azabicyclo[3.2.0]hept-2-ene-2-carboxylate (230 mg, 0.36 mmol) in THF (freshly distilled) (5 mL) was treated first with acetic acid (250 μl, 4.2 mmol) and dropwise with a 1M solution of tetrabutylammonium fluoride in THF (2.2 mL, 2.2 mmol). The mixture was stirred for 120 h at 22° C., diluted with EtOAc (20 mL), washed with cold 1M aqueous NaHCO$_3$ (15 mL), water (15 mL), brine (15 mL) and dried (MgSO$_4$). The residue upon solvent evaporation was purified on a silica gel (10 g) column (10% CH$_3$CN/CH$_2$Cl$_2$, CH$_3$CN, acetone) to give the title compound (60 mg, 41%).

IR (CH$_2$Cl) $v_{max}$: 3690, 3610, 3530 (OH), 1775 and 1710 cm$^{-1}$ (C=O);

$^1$H NMR (CDCl$_3$, 200 MHz) δ: 8.5–8.47 (1H, m, aromatic H), 7.75–7.66 (1H, m, aromatic H), 7.42, 7.38 (1H, d, aromatic H), 7.23–7.19 (1H, aromatic H), 6.05–5.86 (1H, m, allylic H), 5.48–5.21 (2H, m, allylic H), 4.87–4.60 (2H, m, CH$_2$), 4.343, 4.273 (1H part of ABq, J=14.1 Hz, CH$_2$-pyridyl), 4.204 (1H, dd, J=2.7 Hz, J=9.6 Hz, H-5), 4.142, 4.072 (1H, part of ABq, J=14.1 Hz, CH$_2$-pyridyl), 4.27–4.14 (1H, m, H-1'), 3.89–3.70 (3H, m, CH$_2$—O and H-4), 3.261 (1H, dd, J=2.7 Hz, J=7.8 Hz, H-6), 2.17–2.02 (1H, m, HC H), 1.89–1.67 (1H, m, HCH), 1.66 (2H, bs, OH) and 1.364 ppm (3H, d, J=6.3 Hz, CH₃).

J. Sodium (4R,5S,6S)-6-[(1'R)-1'-hydroxyethyl]-4-(2"-hydroxyethyl)-3-[(pyridin-2-yl)methylthio]-7-oxo-1-azabicyclo[3.2.0]hept-2-ene-2-carboxylate

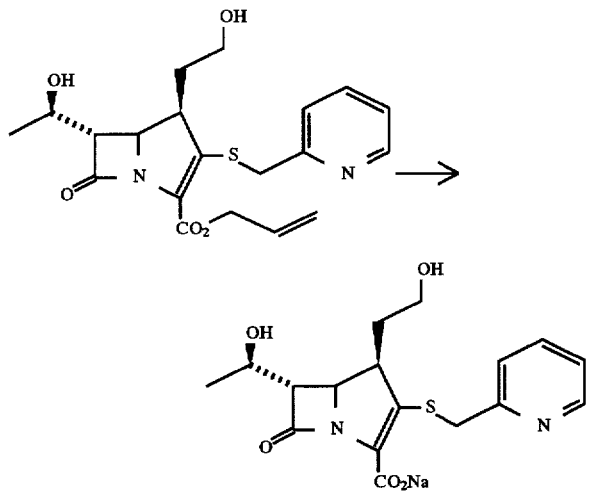

A cold (ice bath) solution of allyl (4R,5S,6S)-6-[(1'R)-1'-hydroxyethyl]-4-(2"-hydroxyethyl)-3-[(pyridin-2-yl)methylthio]-7-oxo-1-azabicyclo[3.2.0]hept-2-ene-2-carboxylate (60 mg, 0.15 mmol) in freshly distilled THF (2 mL) was treated with PPh₃ (5 mg), (PPh₃)₄Pd (5 mg) and N-methylaniline (33 μl, 0.3 mmol). The ice bath was removed and the mixture was stirred for 1 h, then diluted with EtOAc (8 mL) and extracted twice with 0.1M, pH7 aqueous buffer solution(4 mL+2 mL). The aqueous phases were combined, washed with EtOAc (5 mL), pumped under vacuum and passed through a reversed phase silica gel C₁₈ column (10 g, H₂O -10% CH₃CN/H₂O) to give the title compound as a lyophilized powder (25 mg, 43%).

Purity by HPLC: 99.5% (10% CH₃CN/KH₂PO₄ 0.01M, pH 7.4, C₁₈ μBondapak, r.t. 4.49 min).

IR (Nujol) $v_{max}$: 1750 and 1600 cm⁻¹ (C=O);

UV: (H₂O) $\lambda_{max}$ 266 (5100), 306 (6800);

¹H NMR (D₂O, 200 MHz) δ: 8.48–8.45 (1H, m, aromatic H), 7.89–7.81 (1H m, aromatic H), 7.53–7.49 (1H, d, J=7.9 Hz, aromatic H), 7.39–7.33 (1H, m, aromatic H), 4.25–4.186, 4.103, 4.033 (2H, ABq, J=13.8, CH₂-pyridyl), 4.25–4.18 (1H, m, H-1'), 4.0587, 4.0457 (part of dd, J=2.6, H-5), 3.74–3.61 (1H, m, H—CH—O), 3.57–3.44 (1H, m, HCH—O), 3.383 (1H, dd, J=2.6 Hz, J=5.9 Hz, H-6), 3.31–3.19 (1H, m, H-4), 2.1–1.9 (1H, m, HCH), 1.69–1.5 (1H m, HCH), and 1.285 ppm (3H, d, J-6.4 Hz, CH₃).

EXAMPLE 6

Sodium (4R,5S,6S)-4-(2"-azidoethyl)-6-[(1'R)-1'-hydroxyethyl]-3-[(pyridin-2-yl)methylthio]-7-oxo-1-azabicyclo[3.2.0]hept-2-ene-2-carboxylate

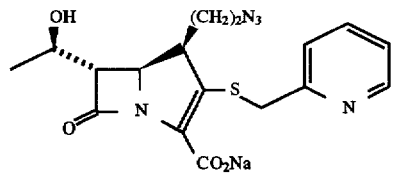

A. Allyl (4R,5S,6S)-6-[(1'R)-1'-tert-butyldimethylsilyloxyethyl]-4-(2"-hydroxyethyl)-3-[(pyridin-2-y)methylthio]-7-oxo-1-azabicyclo[3.2.0]hept-2-ene-2-carboxylate

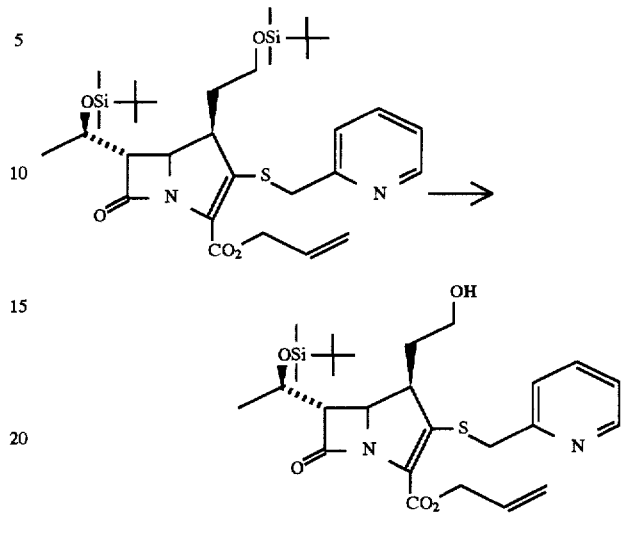

A cold (ice bath) solution of allyl (4R,5S,6 S)-6-[(1'R)-1'-tert-butyldimethylsilyloxyethyl]-4-(2"-tert-butyldimethylsilyloxyethyl)-3-[(pyridin-2-yl)methylthio]-7-oxo-1-azabicyclo[3.2.0]hept-2-ene-2-carboxylate (630 mg, 1.00 mmol) prepared as in Example 5 Step H in freshly distilled THF (10 mL) was treated first with AcOH (0.35 mL, 6 mmol) and then dropwise with a 1M THF solution of tetrabutylammonium fluoride (3.0 mL, 3 mmol). The mixture was stirred for 20 h at 5° C., neutralized to pH 7.0 with a 1M aqueous NaHCO₃ solution and extracted with EtOAc (2×15 mL). The organic solution was washed with 1M aqueous NaHCO₃ (1×20 mL), water (3×20 mL) brine and dried (MgSO₄). The residue (0.6 g) was passed through a flash silica gel (20 g) column to give the title compound (1:1 hexane, EtOAc) as an oil (0.39 g, 75%).

IR (CH₂Cl₂) $v_{max}$: 3680 3610 (OH) 1770 and 1710 cm⁻¹ (C=O);

¹H NMR (CDCl₃, 200 MHz) δ: 8.479 (1H, bd, J=4.1 Hz, aromatic H), 7.710 (1H, dt, J=7.7 Hz, J=1.78 Hz, aromatic H), 7.40 (1H, d, J=8.8 Hz, aromatic H), 7.26–7.19 (1H, m, aromatic H), 6.04–5.85 (1H, m, allylic-H), 5.48–5.20 (2H, m, allylic H), 4.83–4.61 (2H, m, CH₂), 4.387, 4.317, 4.178, 4.109 (2H, ABq, J=14.0 Hz, CH₂-pyridine), 4.27–4.12 (1H, m, H-1'), 4.122, 4.075, 4.063 (1H, dd, J=2.4 Hz, J=9.4 Hz, H-5), 3.93–3.82 (2H, m, H-4 and HCH—O), 3.65–3.55 (2H, m, H—CH—O and OH), 3.130 (1H, dd, J=2.4 Hz, J=7.0 Hz, H-6), 2.2–2.0 (1H, m, HCH), 1.9–1.6 (1H, m, HCH), 1.279 (3H, t, J=7.1 Hz, CH₃), 0.889 (9H, s, tert-butyl) and 0.076 ppm (6H, s, dimethyl).

B. Allyl (4R,5S,6S)-4-(2"-azidoethyl)-6-[(1'R)-1'-tert-butyldimethylsilyloxyethyl]-3-[(pyridin-2-yl)methylthio]-7-oxo-1-azabicyclo[3.2.0]hept-2-ene-2-carboxylate

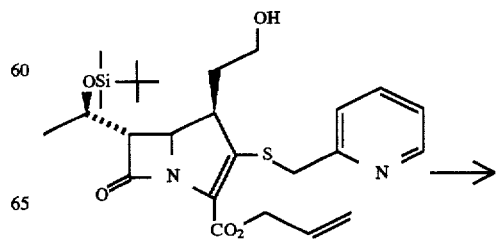

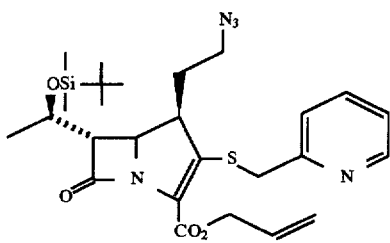

A cold (−20° C.) solution of allyl (4R,5S,6S)-6-[(1'R)-1'-tert-butyldimethylsilyloxyethyl]-4-(2"-hydroxyethyl)-3-[(pyridin-2-yl)methylthio]-7-oxo-1-azabicyclo[3.2.0]hept-2-ene-2-carboxylate (0.39 g, 0.75 mmol) in THF (80 mL) was treated with triphenylphosphine (315 mg, 1.2 mmol), a 0.43M solution of hydrazoic acid in toluene (0.21 mL, 1.3 mmol) and diethyl azodicarboxylate (0.21 mL, 1.3 mmol). The mixture was stirred for 30 min at −20° C., diluted with EtOAc (30 mL), washed with 1M aqueous NaHCO$_3$, (1×20 mL), water (2×20 mL), brine and dried (MgSO$_4$). The residue (about 1 g) was passed through a silica gel (50 g) column (1/3:AcOEt/hexane) to give the title compound (0.30 g, 74%).

IR (CH$_2$Cl$_2$) $v_{max}$: 2105 (N$_3$), 1775 and 1710 cm$^{-1}$ (C=O);

$^1$H NMR (CDCl$_3$, 200 MHz) δ: 8.53–8.50 (1H, m, aromatic H), 7.71–7.62 (1H, m, aromatic H), 7.38, 7.34 (1H, d, aromatic H), 7.22–7.16 (1H, m, aromatic H), 6.03–5.84 (1H, m, allylic H), 5.46–5.20 (2H, m, allylic H), 4.83–4.59 (2H, m, CH$_2$), 4.306, 4.237, 4.096, 4.628 (2H, ABq, J=13.7 Hz, CH$_2$ pyridyl), 4.23–4.1 (1H, m, H-1'), 4.076, 4.063, 4.016 (1H, dd, J=2.6 Hz, J=9.4 Hz, H-5), 3.75–3.6 (1H, m, H-4), 3.6–3.45 (1H, m, HCH—O), 3.45–3.25 (1H, m, HCH—O), 3.071 (1H, dd, J=2.6 Hz, J=7.8 Hz, H-6), 2.13–1.95 (1H, m, HCH), 1.8–1.5 (1H, m, HCH), 1.302 (3H, d, J=6.0 Hz, CH$_3$), 0.892 (9H, s, tert-butyl), 0.086 and 0.081 ppm (6H, 2s, dimethyl).

C. Allyl (4R,5S,6S)-4-(2"-azidoethyl)-6-[(1'R)-1'-hydroxyethyl]-3-[pyridin-2-yl)methylthio]-7-oxo-1-azabicyclo[3.2.0]hept-2-ene-2-carboxylate

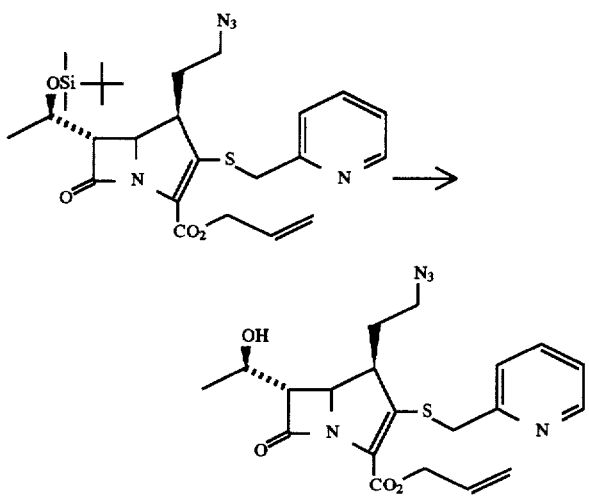

A cold (−20° C.) solution of allyl (4R,5S,6S)-4-(2"-azidoethyl)-6-[(1'R)-1'-tert-butyldimethylsilyloxyethyl]-3-[(pyridin-2-yl)methylthio]-7-oxo-1-azabicyclo[3.2.0]hept-2-ene-2-carboxylate (0.30 g, 0.55 mmol) in freshly distilled THF (10 mL) was treated with AcOH (0.2 mL, 3.3 mmol) and dropwise with a 1M THF solution of tetrabutylammonium fluoride (1.7 mL, 1.7 mmol). The mixture was then stirred at 5° C. for 90 h, diluted with EtOAc (40 mL), washed with 1M aqueous NaHCO$_3$ (1×30 mL), water (2×30 mL), brine and dried (MgSO$_4$). The residue 0.3 g was passed through a silica gel (10 g) column (1:1 hexane:EtOAc) to give the title compound (0.21 g, 89%).

IR (CH$_2$Cl$_2$) $v_{max}$: 3680–3600 (OH), 2100 (N$_3$) 1775 and 1710 cm$^{-1}$ (C=O);

$^1$H NMR (CDCl$_3$, 200 MHz) δ: 8.54–8.51 (1H, m, aromatic H), 7.7–7.6 (1H, m, aromatic H), 7.38, 7.34 (1H, m, aromatic H), 7.25–7.15 (1H, m, aromatic H), 6.1–5.8 (1H, m, allyl H), 5.5 (2H, m, allyl H), 4.8–4.55 (2H, m, CH$_2$-allyl), 4.294, 4.225, 4.072, 4.002 (2H, ABq, J=14.0 Hz, CH$_2$-pyridyl), 4.3–4.1 (1H, m, H-1'), 4.166 (1H, dd, J=2.7 Hz, J=9.5 Hz, H-5), 3.8–3.65 (1H, m, H-4), 3.6–3.3 (2H, m, CH$_2$—N$_3$), 3.162 (1H, dd, J=2.7 Hz, J=7.7 Hz, H-6), 2.2–2 (1H, m, HCH), 1.95 (1H, bs, OH), 1.9–1.6 (1H, m, HCH) 1.382 (3H, d, J=6.2 Hz, CH$_3$).

D. Sodium (4R,5S,6S)-4-(2"-azidoethyl)-6-[(1'R)-1'-hydroxyethyl]-3-[(pyridin-2-yl)methylthio]-7-oxo-1-azabicyclo[3.2.0]hept-2-ene-2-carboxylate

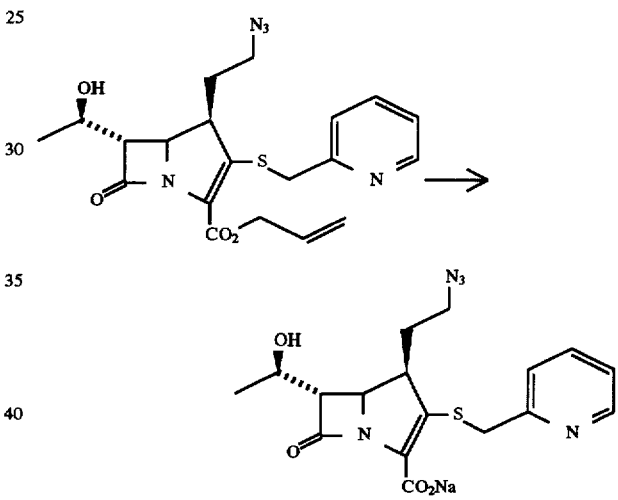

A cold (ice bath) solution of allyl (4R,5S,6S)-4-(2"-azidoethyl)-6-[(1'R)-1'-hydroxyethyl]-3- [(pyridin-2-yl)]-7-oxo-1-azabicyclo[3.2.0]hept-2-ene-2-carboxylate (74 mg, 0.17 mmol) in CH$_2$Cl$_2$ (3 mL) was treated with Pd(PPh$_3$)$_4$ (35 mg) followed by the addition of N-methylaniline (0.5 mL, 0.45 mmol). The resulting mixture was stirred at about 22° C. for 1 h, then diluted with a 0.1M pH 7.1 aqueous phosphate buffer solution (0.35 mmol) and diethyl ether (10 mL). The phases were separated and the aqueous phase was washed with diethyl ether (2×10 mL), pumped under high vacuum, and passed through a C$_{18}$ microBondapak reversed phase column (35 g, 4%→10% CH$_3$CN/H$_2$O) to give the title compound (55 mg, 41%) after lyophilization.

UV: (H$_2$O) λ$_{max}$: 266 (7800), 304 (10500);

Purity by HPLC: 99.5% (304 nm, 10% CH$_3$CN/KH$_2$PO$_4$ 0.01M pH 7.4).

IR (Nujol) $v_{max}$: 2100 (N$_3$), 1750 and 1600 cm$^{-1}$ (C=O);

$^1$H NMR (D$_2$O, 200 MHz) δ: 8.5–8.4 (1H, m, aromatic H), 7.9–7.8 (1H, m, aromatic H), 7.54, 7.50 (1H, dd, aromatic H), 7.4–7.3 (1H, m, aromatic H), 4.27, 4.20, 4.11, 4.04 (2H, ABq, J=14.2 Hz, CH$_2$-pyridine), 4.25–4.15 (1H, m, H-1'), 4.067, 4.054 (part of dd, J=2.6 Hz, part of H-5), 3.52–3.17 (4H, m, CH$_2$N$_3$, H-4 and H-6), 3.389 (1H, dd, J=2.7 Hz, J=6.3 Hz, H-6), 2.1–1.9 (1H, m, HCH), 1.75–1.5 (1H, m, HCH) and 1.297 ppm (3H, d, J=6.4 Hz, CH$_3$).

EXAMPLE 7

(4R,5S,6S)-4-(3"-Aminopropyl)-6-[(1'R)-1'-hydroxyethyl]-3-[(pyridin-2-yl)methylthio]-7-oxo-1-azabicyclo[3.2.0]hept-2-ene-2-carboxylic acid

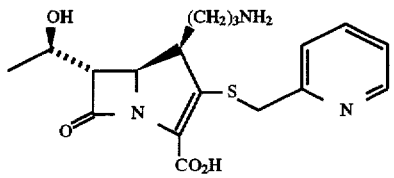

A. 5-Azido-[(pyridin-2-yl)methylthio]-valerate

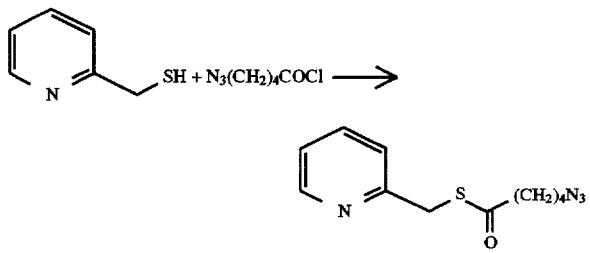

A cold (ice bath) solution of 2-picolyl mercaptan (20.2 g, 162 mmol) in CH$_2$Cl$_2$ (200 mL) was treated with pyridine (16.3 mL, 203 mmol) followed by dropwise addition of 5-azidovaleryl chloride (27.0 g, 167 mmol) in CH$_2$Cl$_2$ (50 mL). The mixture was stirred for 30 min, diluted with diethyl ether (1 L), washed with cold water (500 mL), 1M aqueous NaHSO$_3$ (2×500 mL), water (500 mL), 1M aqueous NaHCO$_3$ (500 mL), water (500 mL), brine (500 mL) and dried (MgSO$_4$). Evaporation of the solvent afforded the title compound (40.8 g, 100%).

$^1$H NMR (CDCl$_3$, 200 MHz) δ: 8.54, 8.52 (1H, bd, aromatic H), 7.6–7.5 (1H, m, aromatic H), 7.35–7.31 (1H, bd, aromatic H), 7.19–7.12 (1H, m, aromatic H), 4.25 (2H, s, CH$_2$), 3.27 (2H, t, J=6.6 Hz, CH$_2$N$_3$), 2.62 (2H, t, J=6.9 Hz, CH$_2$CO), and 1.8–1.5 ppm (4H, m, CH$_2$CH$_2$).

B. tert-Butyldimethylsilylenol ether of 5-azido-[(pyridin-2-yl)methylthio]valerate

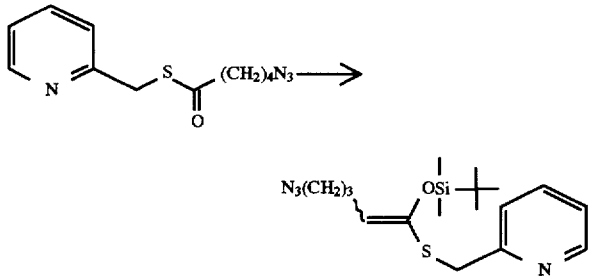

A cold (ice-MeOH bath) solution of 5-azido-[(pyridin-2-yl)methylthio]valerate (44.0 g, 162 mmol) in CH$_2$Cl$_2$ (400 mL) was successively treated with triethylamine (50 mL, 356 mmol) and dropwise with tert-butyldimethylsilyl trifluoromethanesulfonate (76.6 mL, 333 mmol). The cold bath was removed and the mixture was stirred for 2 h. The reaction mixture was then diluted with petroleum ether (1.5 L), washed with cold water (2×500 mL), 1M aqueous NaHCO$_3$ (2×500 mL), water (2×500 mL), brine (500 mL) and dried (MgSO$_4$). The organic phase was then treated with neutral activated charcoal to give, after filtration and evaporation of solvent, title compound (48.9 g, 83%).

$^1$H NMR (CDCl$_3$, 200 MHz) δ: 8.56–8.53 (1H, m, aromatic H), 7.67–7.57 (1H, m, aromatic H), 7.28–7.23 (1H, m, aromatic H), 7.18–7.11 (1H, m, aromatic H), 4.96 (0.5H, t, J=7.6 Hz, vinylic H), 4.80 (0.5H, t, J=7.3 Hz, vinylic H), 4.030 and 3.955 (2H, 2s, CH$_2$-pyridyl), 3.097 and 3.040 (2H, 2t, J=7.0 Hz, J=7.3 Hz, CH$_2$), 2.06 (2H, center of 4 lines, J=7.1 Hz, CH$_2$ vinyl), 1.57–1.38 (2H, m, CH$_2$), 0.989, 0.970 (9H, 2s, tert-butyl) and 0.243, 0.205 ppm (6H, 2s, dimethyl).

C. (3S,4S)-3-[(1'R)-1'-tert-Butyldimethylsilyloxyethyl]-4-[(1"R)-1"-(pyridin-2-yl)methylthiocarbonyl-4"-azidobutyl]azetidin-2-one

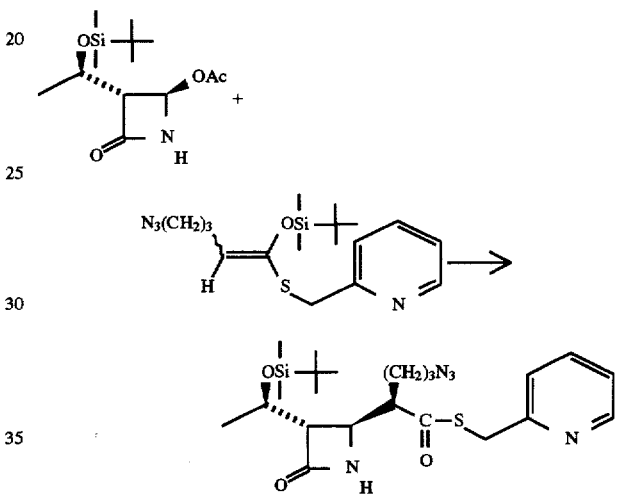

To a cold (ice bath) freshly fused ZnCl$_2$ (18.0 g, 133 mmol) was added successively (3S,4R)-4-acetoxy-3-[(1' R)-1'-tert-butyldimethylsilyloxyethyl]azetidin-2-one (19.0 g, 67.0 mmol) in CH$_2$Cl$_2$ (200 mL) and dropwise a solution of tert-butyldimethylsilylenol ether of 5-azido-[(pyridin-2-yl)methylthio]-valerate (48.5 g, 133 mmol) prepared in Step B in CH$_2$Cl$_2$ (100 mL). The mixture was stirred for 1 h and left overnight (18 h) at 5° C. (cold room). The reaction mixture was diluted with petroleum ether (1.2 L) and ice cold water (500 mL). The organic phase was washed with cold water (2×500 mL), 1M aqueous (NH$_4$Cl) (1×500 mL) water (500 mL), 1M aqueous NaHCO$_3$ (2×500 mL), water (2×500 mL), brine and dried (MgSO$_4$). The residue was passed through a silica gel pad (400 g, hexane, CH$_2$Cl$_2$, EtOAc) to give the title compound (14.2 g, 44%) as an oil.

IR (CH$_2$Cl$_2$) $v_{max}$: 3400 (NH), 2100 (N$_3$), 1770 and 1680 cm$^{-1}$ (C=O).

$^1$H NMR (CDCl$_3$, 200 MHz) δ: 8.55–8.51 (1H, m, aromatic H), 7.68–7.59 (1H, m, aromatic H), 7.35–7.30 (1H, m, aromatic H), 7.21–7.14 (1H, m, aromatic H), 5.89 (1H, bs, NH), 4.27 (2H, s, CH$_2$-pyridyl), 4.20–4.10 (1H, m, H-1'), 3.81 (1H, dd, J=2.1 Hz, J=7.0 Hz, H-4), 3.279 (2H, bt, J=6.3 Hz, CH$_2$N$_3$), 3.048 (1H, dd, J=2.4 Hz, J=3.2 Hz, H-3), 2.9–1.7 (1H, m, H-1"), 1.9–1.7 (1H, m, HCH), 1.7–1.5 (3H, m, HCH and CH$_2$), 0.987 (3H, d, J=6.3 Hz, CH$_3$), 0.851 (9H, s, tert-butyl) and 0.042 ppm (6H, s, dimethyl).

D. (3S,4S)-3-[(1'R)-1'-tert-Butyldimethylsilyloxyethyl]-4-[(1"R)-1"-carboxy-4"-azidobutyl]azetidin-2-one

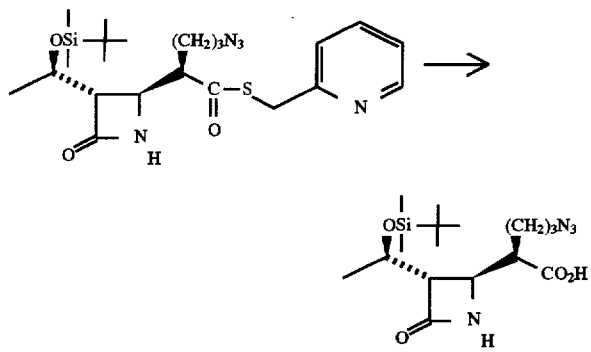

A cold (ice bath) solution of (3S,4S)-3-[(1'R)-1'-tert-butyldimethylsilyloxyethyl]-4-[(1"R)-1"- (pyridin-2-yl)-methylthiocarbonyl-4"-azidobutyl]azetidin-2-one (14.0 g, 28.4 mmol) in THF (140 mL) was treated first with 30% $H_2O_2$ (9.8 mL, 714 mmol) followed by the dropwise addition of 1M aqueous NaOH (85.2 mL, 85.2 mmol). The ice bath was removed and the mixture was stirred for 0.5 h, after which it was acidified with 1N aqueous HCl (170 mL, 170 mmol) and extracted with EtOAc (3×125 mL). The ethyl acetate extracts were combined, washed with water (1×125 mL), 1M aqueous $NaHSO_3$ (1×125 mL), water (2×125 mL), brine (1×125 mL) and dried ($MgSO_4$). Evaporation of the solvent and trituration of the solid (hexane) afforded the title compound (8.3 g, 76%) as a white solid; m.p.=147°–148° C. (diethyl ether).

IR ($CH_2Cl_2$) $v_{max}$: 3410 (NH) 2100 ($N_3$) 1765, 1740 and 1710 cm$^{-1}$ (C=O);

$^1$H NMR ($CDCl_3$, 200 MHz) δ: 6.43 (1H, bs, NH), 4.3–4.1 (1H, m, H-1'), 3.89 (1H, dd, J=2.0 Hz, J=6.1 Hz, H-4), 3.337 (2H, bt, J=6.1 Hz, $CH_2N_3$), 3.148 (1H, dd, J=2.0 Hz, J=3.7 Hz, H-3), 2.75–2.6 (1H, m, H-1"), 1.9–1.5 (4H, m, $CH_2CH_2$), 1.176 (3H, d, J=6.3 Hz, $CH_3$), 0.868 (9H, s, tert-butyl), 0.071 and 0.060 ppm (6H, 2s, dimethyl).

E. (3S,4R)-3-[(1'R)-1'-tert-Butyldimethylsilyloxyethyl]-4-[(1"R)-1"-(3-azidopropyl)-3"-diazo-3"-allyloxycarbonyl-2"-oxopropyl]azetidin-2-one

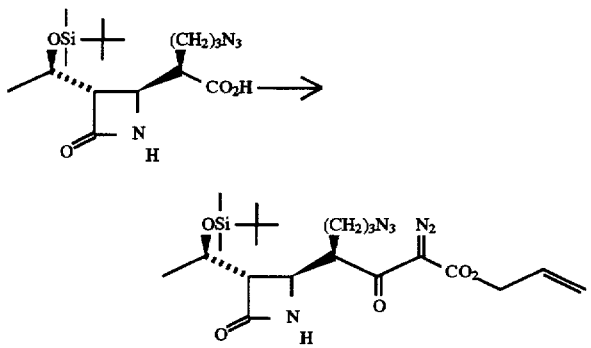

A suspension of (3S,4R)-3-[(1'R)-1'-tert-butyldimethylsilyloxyethyl]-4-[(1"R)-1"-carboxy-4"-azidobutyl]azetidin-2-one (5.0 g, 13 mmol) in $CH_3CN$ (50 mL) was treated with carbonyldiimidazole (2.5 g, 15.6 mmol) and stirred for 30 min. To the resulting clear solution (acyl imidazole) was added magnesium monoallyl malonate (5.0 g, 16 mmol). The mixture was heated at 70° C. (bath temperature) for 18 h. More malonate (1.25 g, 4 mmol) was added and the mixture was heated for 5 more hours. Then magnesium monoallyl malonate (1.25 g, 4 mmol) was added in again and heating was continued for 18 h. The solvent was partially evaporated. The residue was taken up in ethyl acetate (100 mL), washed with water 100 mL, 1N aqueous HCl (100 mL), water (2×100 mL), 10% aqueous $K_2CO_3$ (100 mL), water (100 mL), brine (100 mL) and dried ($MgSO_4$). The residue after solvent evaporation was taken up in $CH_3CN$ (50 mL), cooled to 5° C. (ice bath) under nitrogen, treated successively with triethylamine (1.82 mL, 13.0 mmol) and dropwise with p-toluenesulfonyl azide (2.56 mL, 13.0 mmol) in $CH_3CN$ (5 mL) and stirred for 3 h at room temperature (22° C.). The solvent was evaporated and the residue obtained was passed through a silica gel pad (100 g, hexane→40% ether/hexane) to give the title compound (1.6 g, 25%) as a yellow oil.

IR ($CH_2Cl_2$) $v_{max}$: 3400 (NH), 2150 ($N_2$), 2100 ($N_3$), 1765, 1715 and 1650 cm$^{-1}$ (C=O);

$^1$H NMR ($CDCl_3$, 200 MHz) δ: 6.1–5.8 (1H, m, vinylic H), 5.85 (1H, bs, NH), 5.41–5.29 (2H, m, vinylic H), 4.74–4.70 (2H, m, allylic $CH_2$), 4.3–4.0 (2H, m, H-1' and H-1"), 3.85 (1H, dd, J=2.1 Hz, J=5.3 Hz, H-4), 3.267 (2H, m, $CH_2N_3$), 3.044 (1H, dd, J=2.1 Hz, J=3.6 Hz, H-3), 2.0–1.8 (1H, m, HCH), 1.7–1.4 (3H, m, $CH_2HCH$), 1.172 (3H, d, J=6.3 Hz, $CH_3$), 0.863 (9H, s, tert-butyl) 0.063 and 0.052 (6H, 2s, dimethyl).

F. Allyl (4R,5R,6S)-6-[(1'R)-1'-tert-butyldimethylsilyloxyethyl]-4-(3"-azidopropyl)-3,7-dioxo-1-azabicyclo[3.2.0]heptane-2-carboxylate

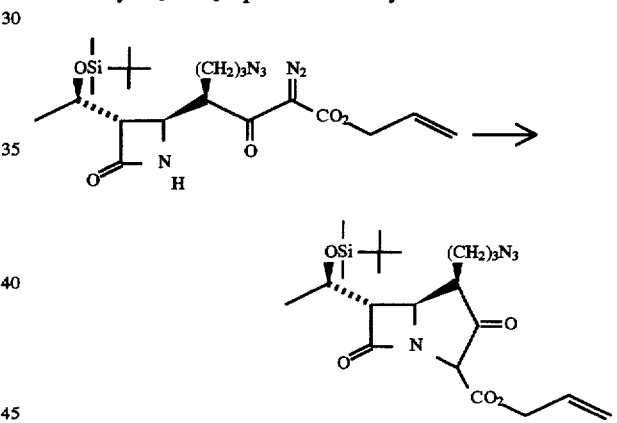

A solution of (3S,4R)-3-[(1'R)-1'-tert-butyldimethylsilyloxyethyl]-4-[(1"R)-1" -(3-azidopropyl)-3"-diazo-3"-allyloxycarbonyl-2"-oxopropyl] azetidin-2-one (1.45 g, 303 mmol) in benzene (50 mL) previously purged with Argon (10 min) was heated under reflux for 40 min using $Rh(OAc)_2$ (40 mg) as catalyst. The solvent was then evaporated to give title compound (1.45 g, 100%) as an oil.

IR ($CH_2Cl_2$) δ: 2100 ($N_3$) 1770 and 1745 cm$^{-1}$ (C=O);

$^1$H NMR ($CDCl_3$, 200 MHz) δ: 6.0–5.8 (1H, m, vinylic H), 5.4–5.25 (2H, m, vinylic H), 4.67 (1H, s, H-2), 4.64 (2H, m, $CH_2$), 4.4–4.2 (1H, m, H-1'), 4.255, 1H, dd, J=2.4 Hz, J=8.3 Hz, H-5), 3.5–3.2 (2H, m, $CH_2N_3$), 3.24 (1H, dd, J=2.4 Hz, J=6.2 Hz, H-6), 2.8–2.6 (1H, m, H-4), 1.85–1.55 (4H, m, $CH_2CH_2CO$), 1.304 (3H, d, J=6.2 Hz, $CH_3$), 0.886 (9H, s, tert-butyl), 0.102 and 0.090 ppm (6H, 2s, dimethyl).

G. Allyl (4R,5S,6S)-4-(3"-azidopropyl)-6-[(1'R)-1'-(tert-butyl-dimethylsilyloxyethyl)]-3-[(pyridin-2-yl)methylthio]-7-oxo-1-azabicyclo[3.2.0]hept-2-ene-2-carboxylate

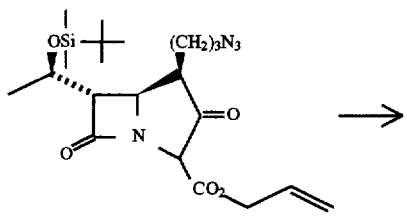

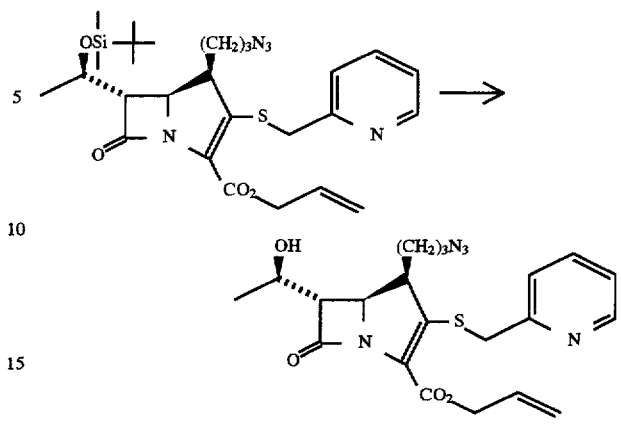

A cold (ice-MeOH bath) solution of allyl (4R,5R,6 S)-4-(3"-azidopropyl)-6-[(1'R)-1'-tert-butyldimethylsilyloxyethyl]-3,7-dioxo-1-azabicyclo[3.2.0]heptane-2-carboxylate (1.45 g, 3.03 mmol) in CH$_3$CN (25 mL) was treated with diphenyl chlorophosphate (0.67 mL, 3.3 mmol) and dropwise with N,N-diisopropylethylamine (0.55 mL, 3.3 mmol) and stirred for 45 min. The resulting enol phosphate was then treated with 2-picolyl mercaptan (2.90 g, 23.2 mmol) and dropwise with N,N-diisopropylethylamine (3.86 mL, 23.2 mmol). The ice-MeOH bath was replaced with an ice bath and the mixture was stirred for 2 h after which it was diluted with EtOAc (100 mL), washed with cold water (50 mL), cold 1M aqueous NaHSO$_3$ (3×50 mL), water (2×50 mL), cold 1M aqueous NaHCO$_3$ (2×50 mL), water (1×50 mL), brine (50 mL) and dried (MgSO$_4$). The residue was passed through a silica gel column (30 g, hexane→40% EtOAc/hexane) to give the title product contaminated with the starting thiol. This material was diluted with diethyl ether (50 mL) and washed again with cold water (20 mL), 1M aqueous NaHSO$_3$ (3×20 mL), H$_2$O (2×20 mL), 1M aqueous NaHCO$_3$ (2×20 mL), water (20 mL), brine (20 mL) and dried (MgSO$_4$) to give pure title compound (1.45 g, 86%).

IR (CH$_2$Cl$_2$) $v_{max}$: 2105 (N$_3$), 1775 and 1710 cm$^{-1}$ (C=O);

$^1$H NMR (CDCl$_3$, 200 MHz) δ: 8.5–8.4 (1H, m, aromatic H), 7.8–7.6 (1H, m, aromatic H), 7.4–7.39 (1H, bd, aromatic H), 7.3–7.18 (1H, m, aromatic H), 6.05–5.80 (1H, m, vinylic H), H-1'), 4.01 (1H, dd, J=2.6 Hz, J=9.5 Hz, H-5), 3.6–3.4 (1H, m, 5.5.–5.2 (2H, m, vinylic H), 4.9–4.6 (2H, m, CH$_2$), 4.287, 4.217, 4.083, 4.013 (2H, ABq, J=14.0 Hz, CH$_2$-pyridyl), 4.21–4.08 (1H, m, H-4), 3.4–3.2 (2H, m, CH$_2$N$_3$), 3.145 (1H, dd, J=2.6 Hz, J=7.5 Hz, H-6), 2.0–1.4 (4H, m, CH$_2$CH$_2$), 1.288 (3H, d, J=6.1 Hz, CH$_3$), 0.874 (9H, s, tert-butyl), 0.073 and 0.059 (6H, 2s, dimethyl).

H. Allyl (4R,5S,6S)-4-(3"-azidopropyl)-6-[(1'R)-1'-hydroxyethyl]-3-[(pyridin-2-yl)methylthio]-7-oxo-1-azabicyclo[3.2.0]hept-2-ene-2-carboxylate A cold (ice-MeOH bath) THF (30 mL) solution of allyl (4 R,5S,6S)-4-(3"-azidopropyl)-6-[(1'R)-1'-tert-butyldimethyl-silyloxyethyl]-3-[(pyridin-2-yl)methylthio]-7-oxo-1-azabicyclo[3.2.0]hept-2-ene-2-carboxylate (1.5 g, 2.6 mmol) was treated dropwise with CH$_3$CO$_2$H (0.9 mL, 15.6 mmol) and with a 1M THF solution of tetrabutylammonium fluoride (7.8 mL, 7.8 mmol). The mixture was stirred at that temperature for 1 h, allowed to stand for 56 h at 5° C. and then stirred at room temperature for 24 h. The mixture was cooled down to 0° C., neutralized with 1M aqueous NaHCO$_3$ (16 mL) and the aqueous phase extracted with EtOAc/diethyl ether (1:1) (2×100 mL). The organic extracts were combined, washed with cold 1M aqueous NaHCO$_3$ (50 mL), water (2×50 mL) brine and dried (MgSO$_4$). The residue was passed through a silica gel column (30 g, hexane/CH$_2$Cl$_2$→CH$_2$Cl$_2$/EtOAc→EtOAc) to give the title compound (679 mg, 64%) and starting material (160 mg, 11%).

IR (CH$_2$Cl$_2$) $v_{max}$: 3600, 3500 (OH), 2100 (N$_3$), 1775 and 1710 cm$^{-1}$ (C=O);

$^1$H NMR (CDCl$_3$, 200 MHz) δ: 8.51–8.49 (1H, m, aromatic H), 7.7–7.6 (1H, m, aromatic H), 7.41, 7.37 (1H, bd, aromatic H), 7.23–7.16 (1H, m, aromatic H), 6.05–5.8 (1H, m, vinylic H), 5.5–5.2 (2H, m, vinylic H), 4.86–4.6 (2H, m, vinylic CH$_2$), 4.256, 4.185, 4.056, 3.985 (2H, ABq, J=14.2 Hz, CH$_2$-pyridyl), 4.25–4.15 (1H, m, H-1'), 1.121 (1H, dd, J=2.7 Hz, J=9.5 Hz, H-5), 3.6–3.45 (1H, hidden, H-4), 3.45–3.24 (2H, m, CH$_2$N$_3$), 3.214 (1H, dd, J=2.7 Hz, J=7.5 Hz, H-6), 1.87 (1H, bd, J=6.5, OH), 2.0–1.5 (4H, m, CH$_2$CH$_2$), and 1.37 ppm (3H, d, J=6.3 Hz, CH$_3$).

I. (4R,5S,6S)-4-(3"-Aminopropyl)-6-[(1'R)-1'-hydroxyethyl]-3-[pyridin-2-yl)methylthio]-7-oxo-1-azabicyclo[3.2.0]hept-2-ene-2-carboxylic acid

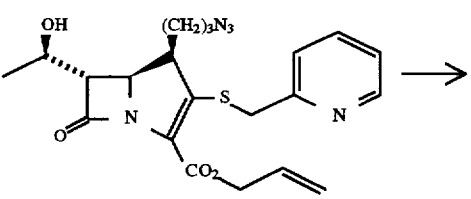

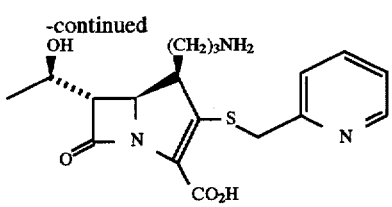

A cold (ice bath) solution of allyl (4R,5S,6 S)-4-(3"-azidopropyl)-6-[(1' R)-1'-hydroxyethyl]-3-[(pyridin-2-yl)methylthio]-7-oxo-1-azabicyclo[3.2.0]hept-2-ene-2-carboxylate (133 mg, 0.3 mmol) in $CH_2Cl_2$ (10 mL) was treated with $(Ph_3P)_4Pd$ (63 mg) and N-methyl aniline (0.1 mL, 0.6 mmol). The ice bath was removed and the mixture was stirred for 1 h after which it was cooled again (ice bath). The reaction mixture was diluted with diethyl ether (40 mL) and extracted with a 0.05M pH 7.0 phosphate buffer (2×6 mL). The aqueous extracts were combined, washed with diethyl ether (2×20 mL) and acidified to pH 5.8–5.9 with a 0.05M, pH 4.2 phosphate buffer. The aqueous layer was hydrogenolyzed at 50 psi for 1 h at 5° C.→15° C. using 10% Pd/C (225 mg) as catalyst. At the end of hydrogenolysis the catalyst was removed, passed on a $C_{18}$ µBondapak column (35 g, $H_2O$→4% $CH_3CN/H_2O$) and lyophilized to give the title compound which was repurified again on a $C_{18}$ µBondapak column (15 g) and lyophilized (17 mg, 11%).

Purity: 97.5% determined by HPLC (10% $CH_3CN$/ $KH_2PO_4$ 0.01M, pH 7.4, r.t. 5.66 min, µBondapak $C_{18}$ 10µ);

UV ($H_2O$) $\lambda_{max}$: 304 (9383), 266 (6895);

IR (Nujol) $\lambda_{max}$: 1755 and 1590 $cm^{-1}$ (C=O);

$^1$H NMR ($D_2O$, 200 MHz) δ: 8.48–8.45 (1H, bd, aromatic H), 7.9–7.8 (1H, m, aromatic H), 7.54, 7.49 (1H, bd, aromatic H), 7.4–7.3 (1H, m, aromatic H), 4.3–4.1 (1H, m, H-1'), 4.225, 4.157, 4.106, 4.043 (2H, ABq, J=13.2 Hz, $CH_2$-pyridine), 4.056, 4.043 (part of dd, J=2.6 Hz, H-5), 3.31 (1H, dd, J=2.6 Hz, J=6.5 Hz, H-6), 3.197 (1H, bt, J=9.4 Hz, H-4), 3.0–2.85 (2H, m, $CH_2N_3$), 1.9–1.55 (3H, m, HCH and $CH_2$), 1.55–1.2 (1H, m, HCH) and 1.295 ppm (3H, d, J=6.4 Hz, $CH_3$).

EXAMPLE 8

(4R,5S,6S)-4-[3"-(N-Formimidoyl)aminopropyl]-6-[(1'R)-1'-hydroxyethyl]-3-[(pyridin-2-yl)methylthio]-7-oxo-1-azabicyclo[3.2.0]hept-2-ene-2-carboxylic acid

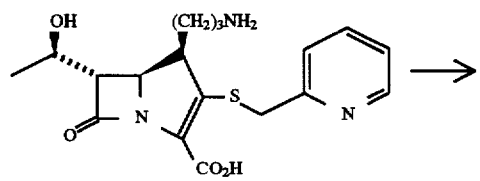

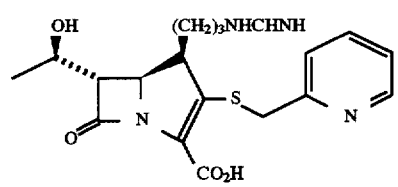

The pH of the crude hydrogenolyzed product (4R,5S,6 S)-4-(3"-aminopropyl)-6-[(1' R)-1'-hydroxyethyl]-3-[(pyridin-2-yl)-methylthio]-7-oxo-1-azabicyclo[3.2.0]hept-2-ene-2-carboxylic acid obtained from the deprotection of allyl (4R,5S,6 S)-4-(3"-azidopropyl)-6-[(1'R)-1-hydroxyethyl]-3-[(pyridin- 2-yl)methylthio]-7-oxo- 1-azabicyclo[3.2.0] hept-2-ene-2-carboxylate (150 mg, 0.338 mmol) as described in Example 7 Step I was adjusted to 8.5 with 1M aqueous NaOH at 5° C. (ice bath). To the aqueous mixture was added portionwise benzyl formimidate hydrochloride (583 mg, 3.41 mmol) while maintaining the pH at 8.3–8.4 with 1M aqueous NaOH. At the end of the addition, the mixture was stirred for 6 min and then applied on a µBondapak $C_{18}$ reversed phase column (40 g, $H_2O$→1,2,3,4 and 6% $CH_3CN/H_2O$) to give the title product which was repurified on a µBondapak $C_{18}$ reversed phase column ($H_2O$→2,3,4, and 6% $CH_3CN/H_2O$). Pure title compound (19 mg, 11%) was obtained as a white fluffy solid.

Purity: 98.9% as determined by HPLC(10% $CH_3CN$/ $K_2PO_4$ 0.01M, pH 7.4, r.t. 6.77 min, µBondapak $C_{18}$ 10µ);

UV ($H_2O$) $\lambda_{max}$: 304 (7791), 266 (5941);

IR (Nujol) $v_{max}$: 1755, 1690 (C=O), and 1715 $cm^{-1}$ (C=NH);

$^1$H NMR ($D_2O$, 200 MHz) δ: 8.45–8.42 (1H, bd, aromatic H), 7.87–7.75 (1H, m, aromatic H), 7.77 (1H, bs, C=NH), 7.51, 7.47 (1H, bd, aromatic H), 7.37, 7.3 (1H, m, aromatic H), 4.3–4.1 (1H, m, H-1'), 4.198, 4.134, 4.072, 4.001 (2H, ABq, J=13.5 Hz, $CH_2$pyridine), 4.045–4.07 (1H, hidden H-5), 3.4–3.05 (4H, m, $CH_2N$, H-4, H-6), 1.8–1.4 (3H, m, HCH and $CH_2$), 1.4–1.15 (1H, m, HCH) and 1.259 ppm (3H, d, J=6.3 Hz, $CH_3$).

EXAMPLE 9

Sodium (4R,5S,6S)-6-[(1'R)-1'-hydroxyethyl]-4-(3"-hydroxypropyl)-3-[(pyridin-2-yl)methylthio]-7-oxo-1-azabicyclo[3.2.0]hept-2-ene-2-carboxylate

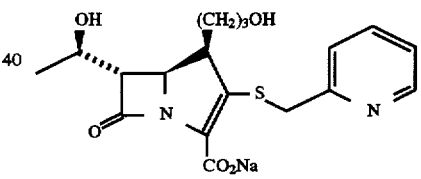

A. Sodium 5-hydroxyvalerate

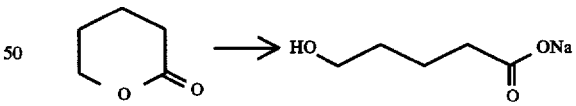

A cold (ice bath) suspension of valerolactone (20 g, 0.20 mol) in water (100 mL) was treated dropwise with a solution of NaOH (8.0 g, 0.20 mol) in water (100 mL). The mixture was stirred for 15 min after which the cold bath was removed and stirring was continued for 15 more min. The mixture was then filtered to remove the solid and lyophilization of the filtrate gave the title compound (26.2 g, 94%) as a white solid.

IR (Nujol) $v_{max}$: 3600–3100 (OH) and 1560 $cm^{-1}$ (C=O);

$^1$H NMR ($D_2O$, 200 MHz) δ: 3.61 (2H, t, J=6.1 Hz, $CH_2OH$), 2.20 (2H, t, J=7.0 Hz, $CH_2CO_2$) and 1.58, 1.57, 1.55 ppm (4H, m, $CH_2CH_2$).

B. t-Butyldimethylsilyl 5-(t-butyldimethylsilyloxy)valerate

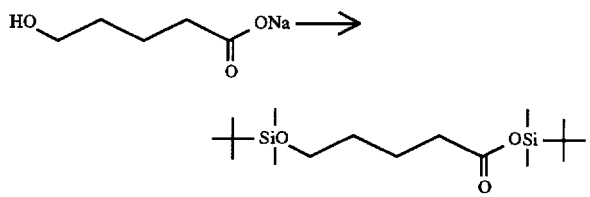

To a cold (ice bath) suspension of sodium 5-hydroxyvalerate (25.0 g, 179 mmol) in DMF (250 mL) was added portionwise t-butyldimethylsilyl chloride (80.8 g, 536 mmol) followed by the dropwise addition of triethylamine (32 mL, 232 mmol). The ice bath was removed and the mixture was stirred for 2.5 days at about 22° C. The reaction mixture was diluted with ice cold water (700 mL) and extracted with diethyl ether (2×800 mL). The organic extracts were combined, washed with cold water (5×500 mL), brine (500 mL) and dried (MgSO$_4$). Evaporation of the solvent gave the title compound (70 g, >100%) as an oil.

IR (neat) $v_{max}$: 1720 cm$^{-1}$ (C=O);

$^1$H NMR (CDCl$_3$, 200 MHz) δ: 3.61 (2H, t, J=6.0 Hz, CH$_2$O), 2.33 (2H, t, J=7.0 Hz, CH$_2$CO$_2$), 2.8–2.5 (4H, m, (CH$_2$)$_2$), 0.92, 0.88 (18H, 2s, t-butyl), 0.25, 0.09, and 0.04 ppm (12H, 3s, CH$_3$).

C. 5-(t-Butyldimethylsilyloxy)valeric acid

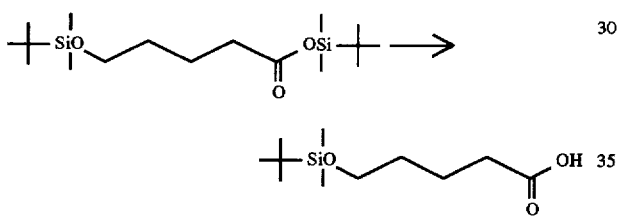

A solution of t-butyldimethylsilyl 5-(t-butyldimethylsilyloxy)valerate (70 g, from 178.6 mmol of sodium hydroxyvalerate) in MeOH (550 mL) was treated with a 5N solution of AcOH in water (50 mL, 250 mmol) and then stirred for 1.5–2.0 h. The solvent was removed and the residue was taken up in CH$_2$Cl$_2$ (1 L) and washed with ice cold water (4×500 mL), brine (500 mL) and dried (MgSO$_4$). The residue (58 g) upon solvent evaporation was taken up in diethyl ether (600 mL) and extracted with 1M aqueous NaHCO$_3$ (3×200 mL). The aqueous extracts were combined, washed with diethyl ether (3×200 mL), acidified with 5M aqueous AcOH to pH 5.0 and then extracted with diethyl ether (4×200 mL). The organic extracts were combined, washed with cold water (4×200 mL), brine (200 mL) and dried (MgSO$_4$) to give the title compound (25 g, 60%) as an oil.

IR (CH$_2$Cl$_2$) $v_{max}$: 3660–2500 (OH), 1750–1710 cm$^{-1}$ (C=O);

$^1$H NMR (CDCl$_3$, 200 MHz) δ: 3.63 (2H, t, J=6.0 Hz, CH$_2$O), 2.39 (2H, t, J=7.2 Hz, CH$_2$CO$_2$), 1.78–1.49 (4H, m, (CH$_2$)$_2$), 0.89 (9H, s, t-butyl) and 0847 ppm (6H, s, CH$_3$).

D. 5-(tert-Butyldimethylsilyloxy)-1-[(pyridin-2-yl)methylthio]valerate

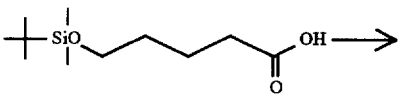

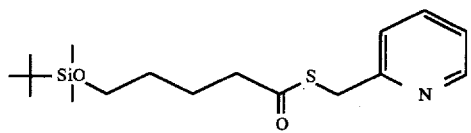

To a cold (ice bath) solution of 5-(t-butyldimethylsilyloxy)valeric acid (25.0 g, 108 mmol) in CH$_2$Cl$_2$ (350 mL) was added 2-picolyl mercaptan (13.5 g, 108 mmol), 1,3-dicyclohexyl carbodiimide (22.2 g, 108 mmol) and 1-hydroxybenzotriazole hydrate (14.6 g, 108 mmol). The ice bath was removed and the mixture was stirred for 20 h, then diluted with ethyl acetate (1 L), washed with ice cold water (1 L), ice cold 1M aqueous NaHSO$_3$ (1 L), ice cold water (1 L), 1M aqueous NaHCO$_3$ (1 L), ice cold water (2×1 L), brine (1 L) and dried (MgSO$_4$). The residue upon solvent evaporation was purified on a silica gel flash column (250 g, hexane, 5%, 10%, 15% EtOAc/hexane) to give the title compound (30.2 g, 83%) as an oil.

IR (CH$_2$Cl$_2$) $v_{max}$: 1690 cm$^{-1}$ (C=O);

$^1$H NMR (CDCl$_3$, 200 MHz) δ: 8.55–8.52 (1H, m, pyridine-H), 7.68–7.59 (1H, m, pyridine-H), 7.37–7.33 (1H, bd, J=7.7 Hz, pyridine-H), 7.20–7.14 (1H, m, pyridine-H), 4.26 (2H, s, CH$_2$S), 3.60 (2H, t, J=6.1 Hz, CH$_2$O), 2.61 (2H, t, J=7.1 Hz, CH$_2$CO$_2$), 1.85–1.6 (2H, m, CH$_2$), 1.6–1.4 (2H, m, CH$_2$), 0.88 (9H, s, t-butyl) and 0.03 (6H, s, CH$_3$).

E. t-Butyldimethylsilylenol ether of 5-(tert-butyldimethylsilyloxy)-1-[(pyridin-2-yl)methylthio]valerate

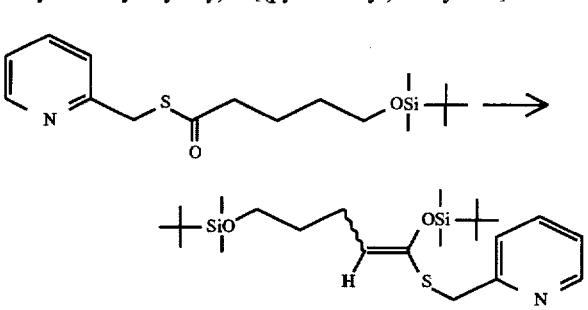

To a cold (ice-MeOH bath) solution of 5-(tert-butyldimethylsilyloxy)-1-[(pyridin-2-yl)methylthio]valerate (30.2 g, 89.0 mmol) in CH$_2$Cl$_2$ (300 mL) was added triethylamine (27 mL, 196 mmol) followed by the dropwise addition of tert-butyldimethylsilyl trifluoromethanesulfate (41 mL, 178 mmol). The cold bath was removed and the mixture was stirred for 2 h. The mixture was diluted with cold petroleum ether (2.7 L), washed with ice cold water (2×500 mL), ice cold aqueous 1M NaHCO$_3$ (1×500 mL), ice cold water (2×500 mL), brine (500 mL) and dried. Treatment of the organic solution with neutral activated charcoal and filtration afforded the title compound (33 g, 83%) as a red oil in a 45:55 ratio of geometric isomers.

$^1$H NMR (CDCl$_3$, 200 MHz) δ: 8.54–8.51 (1H, m, pyridine-H), 7.65–7.56 (1H, m, pyridine-H), 7.31–7.23 (1H, m, pyridine-H), 7.16–7.09 (1H, m, pyridine H), 5.02 (0.55H, t, J=7.6 Hz, vinylic H), 4.87 (0.45H, t, J=7.2 Hz, vinylic H), 4.03 (1.1H, s, CH$_2$S), 3.96 (0.9H, s, CH$_2$S), 3.55, 3.52, 3.49, 3.46 (2H, 4 lines, J=6.4 Hz, CH$_2$O), 2.1–1.96 (2H, m, CH$_2$-vinyl), 1.52–1.29 (2H, m, CH$_2$), 0.985, 0.977 (9H, 2s, t-butyl), 0.879, 0.873 (9H, 2s, t-butyl), 0.236 g, 0.194 g, 0.02 g and 0.013 ppm (12H, 4s, CH$_3$).

F. (3S,4S)-3-[(1'R)-1'-tert-Butyldimethylsilyloxyethyl]-4-[(1"R)-1"-(pyridin-2-yl)methylthiocarbonyl-4"-tert-butyldimethylsilyloxybutyl]azetidin-2-one

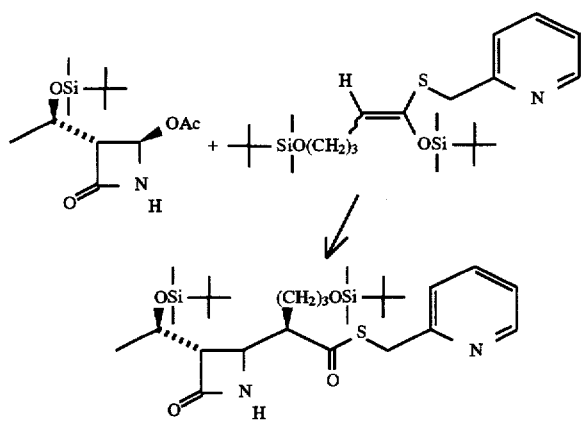

To a cold (ice bath) freshly melt ZnCl₂ (10.0 g, 73.5 mmol) under nitrogen was added (3S,4R)-4-acetoxy-3-[(1'R)-1'-tert-butyldimethylsilyloxyethyl]azetidin-2-one (10.5 g, 36.7 mmol) in CH₂Cl₂ (100 mL) followed by the slow addition of the enol silyl ether (33.2 g, 73.3 mmol) prepared in Step E in CH₂Cl₂ (50 mL). The mixture was stirred for 18.5 h at 5° C. after which it was diluted with petroleum ether (1 L) and poured on ice and water (500 mL). The organic phase was washed with cold water (2×500 mL), 1M aqueous NH₄Cl (500 mL), water (500 mL), 1M aqueous NaHCO₃ (500 mL), water (2×500 mL) brine (500 mL) and dried (MgSO₄). The residue was passed through a silica gel pad (100 g, CH₂Cl₂, 3%, 5%, 8%, 10%, 20% EtOAc/CH₂Cl₂) to give the title compound (9.2 g, 44%) as a solid; m.p.=110°–111° C. (diethyl ether-petroleum ether:1/4).

IR (CH₂Cl₂) ν$_{max}$: 3400 (NH), 1770 and 1680 cm⁻¹ (C=O);

¹H NMR (CDCl₃, 200 MHz) δ: 8.54–8.50 (1H, m, pyridine-H), 7.66–7.58 (1H, m, pyridine-H), 7.34, 7.30 (1H, bd, J=7.5 Hz, pyridine-H), 7.2–7.13 (1H, m, pyridine-H), 5.85 (1H, bs, NH), 4.25 (2H, s, CH₂S), 4.20–4.09 (1H, m, H-1'), 3.82 (1H, dd, J=2.0 Hz, J=7.1 Hz, H-4), 3.61–3.55 (2H, m, CH₂O), 3.05–3.02 (1H, m, H-3), 2.84–2.75 (1H, m, H-1"), 1.9–1.4 (4H, m, (CH₂)₂), 0.98 (3H, d, J=6.3 Hz, CH₃), 0.87, 0.85 (18H, 2s, t-butyl), 0.04 and 0.023 ppm (12H, 2s, CH₃).

Anal. Calcd. for C₂₈H₅₀N₂O₄SSi: C, 59.32; H, 8.89; N, 4.94. Found: C, 59.35; H, 9.03; N, 4.95.

G. (3S,4S)-3-[(1'R)-1'-tert-Butyldimethylsilyloxyethyl]-4-[(1"R)-1"-carboxy-4"-tert-butyldimethylsilyloxybutyl]azetidin-2-one

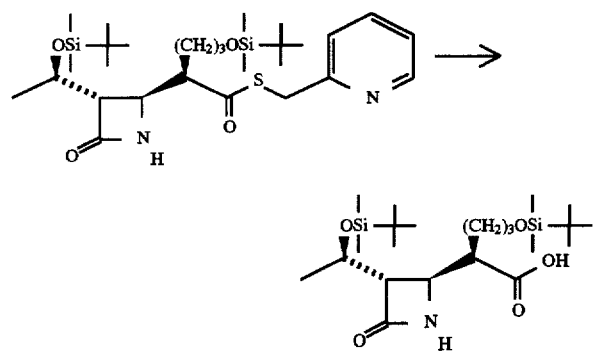

A cold (ice bath) solution of (3S,4S)-3-[(1'R)-1'-tert-butyldimethylsilyloxyethyl]-4-[(1"R)-1"-(pyridin-2-yl)-methylthiocarbonyl-4"-tert-butyldimethylsilyloxybutyl]azetidin-2-one (7.30 g, 12.9 mmol) in THF (70 mL) was treated with 30% v/v H₂O₂ (4.45 mL, 51.0 mmol) followed by the dropwise addition of 1M aqueous NaOH (38.7 mL, 38.7 mmol). The ice bath was removed and the mixture was stirred for 30 min after which it was cooled again (ice bath). Then 1N aqueous HCl (77 mL) was added in and the mixture was extracted with EtOAc (3×50 mL). The organic extracts were washed with ice cold water (2×50 mL), 1M aqueous NaHSO₃ (2×50 mL), ice cold water (3×50 mL), brine and dried (MgSO₄) to give the title compound (5.5 g, 92%) as a white solid; m.p.=127°–128° C. (petroleum ether/diethyl ether:1/2).

IR (CH₂Cl₂) ν$_{max}$: 3410 (NH), 1755, 1740 and 1710 cm⁻¹ (C=O);

¹H NMR (CDCl₃, 200 MHz) δ: 6.28 (1H, bs, NH), 4.23–4.18 (1H, m, H-1'), 3.89 (1H, dd, J=2.0 Hz, J=6.3 Hz, H-4), 3.7–3.55 (2H, m, CH₂O), 3.15–3.05 (1H, m, H-3), 2.8–2.6 (1H, m, H-1"), 1.8–1.5 (4H, m, (CH₂)₂), 1.17 (3H, d, J=6.3 Hz, CH₃), 0.89, 0.86 (18H, 2s, t-butyl), 0.064, 0.057 and 0.051 (12H, 3s, CH₃).

Anal. Calc'd. for C₂₈H₄₅NO₅Si₂: C, 57.47, H, 9.86, N, 3.05. Found: C, 57.41, H, 10.04, N, 3.07.

H. (3S,4R)-3-[(1'R)-1'-tert-Butyldimethylsilyloxyethyl]-4-[(1"R)1"-(3"-tert-butyldimethylsilyloxypropyl)-3"-allyloxycarbonyl-2"-oxopropyl]azetidin-2-one

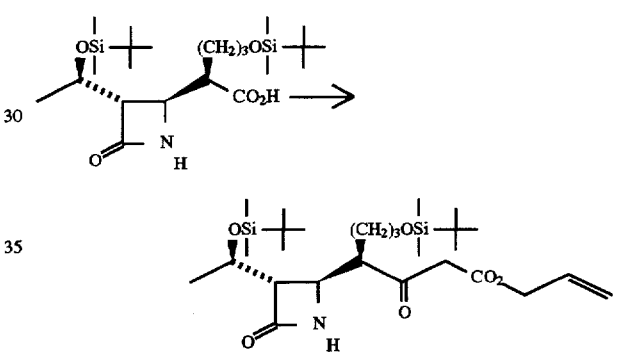

A solution of magnesium bis-allyl malonate (5.7 g, 18.1 mmol) in benzene (80 mL) was heated under reflux, using a Dean Stark condenser. The first 20 mL of benzene were removed and the Dean Stark was replaced by a dropping funnel filled with 3A molecular sieves. The refluxing period was continued for 3 more hours and this solution was allowed to cool down.

In a separate flask, a solution of (3S,4S)-3-[(1'R)-1'-tert-butyldimethylsilyloxyethyl]-4-[(1"R)-1"-carboxy-4"-tert-butyldimethylsilyloxybutyl]azetidin-2-one (5.50 g, 12.1 mmol) in toluene (100 mL) was treated with carbonyl diimidazole (2.15 g, 13.3 mmol). The mixture was stirred for 2 h and the solvent was evaporated to give an oil which was pumped under high vacuum for 2 h. The acyl imidazole was then diluted with benzene (20 mL) and added to the benzene solution of magnesium bis-allyl malonate. The mixture was heated at 67°–70° C. for 18 h, cooled down, diluted with cold EtOAc, washed with ice cold water (2×100 mL), HCl (100 mL), ice cold water (2×100 mL), 10% aqueous Na₂CO₃ (1×100 mL), ice cold water (1×100 mL), brine 100 mL, dried (MgSO₄) and treated with activated charcoal. Evaporation of solvent afforded the title compound (6.2 g, 95%) as an oil.

IR (CH₂Cl₂) ν$_{max}$: 3410 (NH), 1765 and 1715 cm⁻¹ (C=O);

¹H NMR (CDCl₃, 200 MHz) δ: 12.03, 12.02 (0.5H, 2s, enolylic-H), 6.0–5.8 (1H, m, vinylic-H), 5.87 (1H, bs, NH), 5.38–5.24 (2H, m, vinylic-H), 5.07 (0.52H, s, vinylic-H of enol form), 4.65–4.61 (2H, m, $CH_2$-vinyl), 4.19–4.1 (1H, m, H-1'), 3.89 (0.5H, dd, J=2.0 Hz, J=6.2 Hz, H-4), 3.82 (0.5H, dd, J=2.0 Hz, J=7.4 Hz, H-4), 3.64–3.4 (2.5H, m, $CH_2O$ and H-1"), 2.97–2.91 (1H, m, H-3), 2.3–2.1 (0.5H, m, H-1"), 1.8–1.4 (4H, m, $(CH_2)_2$), 1.17 (1.5H, d, J=6.2 Hz, $CH_3$), 1.11 (1.5H, d, J=6.4 Hz, $CH_3$), 0.88, 0.86 (18H, 2s, tert-butyl), 0.06 and 0.054 ppm (12H, 2s, $CH_3$).

I. (3S,4R)-3-[(1'R)-1'-tert-Butyldimethylsilyloxyethyl]-4-[(1"R)-1"-(3-tert-butyldimethylsilyloxylpropyl)-3"-diazo-3"-allyloxycarbonyl-2"-oxopropyl]azetidin-2-one

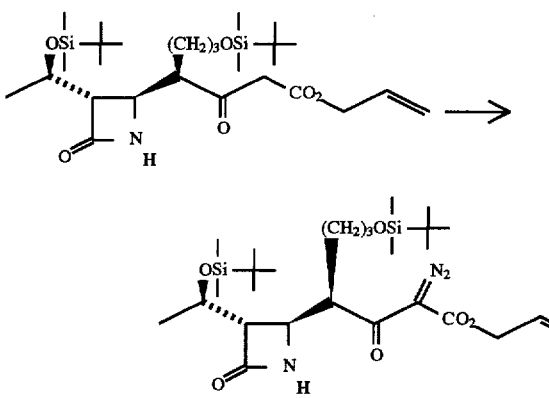

A cold (ice bath) solution of (3S,4R)-3-[(1'R)-1'-tert-butyldimethylsilyloxyethyl]-4-[(1"R)-1"-(3-tert-butyldimethylsilyloxypropyl)-3"-allyloxycarbonyl-2"-oxopropyl]azetidin-2-one (6.20 g, 11.5 mmol) in anhydrous $CH_3CN$ (50 mL) was treated with triethylamine (1.16 mL, 11.5 mmol) followed by the dropwise addition of p-toluenesulfonyl azide (2.27 g, 11.5 mmol) in $CH_3CN$ (10 mL). The mixture was stirred for 3 h at about 22° C. and the solvent was removed under vacuum. The oily residue was triturated with hexane and the solid was removed by filtration. The residue, upon evaporation of hexane, was passed through a silica gel pad (100 g, hexane, 20%, 30%, 40% ether/hexane) to give the title compound as a yellow oil (4.88 g, 75.0%).

IR ($CH_2Cl_2$) $v_{max}$: 3410 (NH), 2150 ($N_2$), 1765, 1715 and 1650 cm$^{-1}$ (C=O);

$^1$H NMR ($CDCl_3$, 200 MHz) δ: 6.03–5.80 (1H, m, vinylic-H), 5.84 (1H, bs, NH), 5.4–5.28 (2H, m, vinylic-H), 4.73–4.68 (2H, m, vinylic —$CH_2$), 4.23–4.12 (1H, m, H-1'), 4.07–4.0 (1H, m, H-1"), 3.88 (1H, dd, J=2.0 Hz, J=5.5 Hz, H-4), 3.59, 3.56, 3.54 (2H, 3 lines, $CH_2O$), 3.04 (1H, t, J=2.5 Hz, H-3), 1.9–1.7 (1H, m, H—C—H), 1.6–1.4 (3H, m, HCH and $CH_2$), 1.16 (3H, d, J=6.3 Hz, $CH_3$), 0.87, 0.86 (18H, 2s, tert-butyl), 0.056, 0.050 and 0.027 ppm (12H, 3s, $CH_3$).

J. Allyl (2R,4R,5R,6S)-6-[(1'R)-1'-tert-butyldimethylsilyloxyethyl]-4-(3"-tert-butyldimethylsilyloxypropyl)-3,7-dioxo-1-azabicyclo [3.2.0]heptane-2-carboxylate

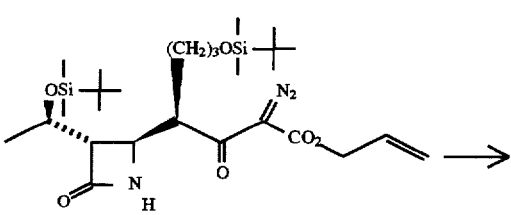

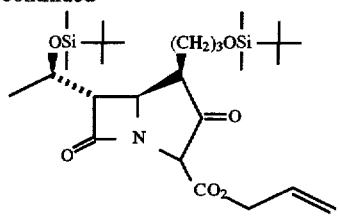

A solution of (3S,4R)-3-[(1'R)-1'-tert-butyldimethylsilyloxyethyl]-4-[(1"R)-1"-(3-tert-butyldimethylsilyloxypropyl)-3"-diazo-3"-allyloxycarbonyl-2"-oxopropyl]azetidin-2-one (3.8 g, 6.7 mmol) in benzene (300 mL) was purged with Argon for 10 min. Then $Rh(OAc)_2$ (100 mg) was added in and the mixture was heated under reflux for 70 min. The solvent was removed under vacuum to give the title compound (3.9 g, >100%) as an oil.

IR ($CH_2Cl_2$) $v_{max}$: 1765 and 1745 cm$^{-1}$ (C=O);

$^1$H NMR ($CDCl_3$, 200 MHz) δ: 5.99–5.79 (1H, m, vinylic H), 5.39–5.20 (2H, m, vinylic H), 4.66–4.60 (2H, m, $CH_2$-vinyl), 4.63 (1H, s, H-2), 4.36, 4.33, 4.30, 4.27 (1H, 4 lines out of 5, H-1'), 4.24 (1H, dd, J=2.4 Hz, J=8.1 Hz, H-5), 2.7–2.5 (2H, m, $CH_2O$), 3.31 (1H, dd, J=2.3 Hz, J=5.8 Hz, H-6), 2.8–2.6 (1H, m, H-4), 1.8–1.5 (4H, m, $(CH_2)_2$), 1.29 (3H, d, J=6.2 Hz, $CH_3$), 0.881, 0.878 (18H, 2s, tert-butyl), 0.093, 0.085 and 0.033 ppm (12H, 3s, $CH_3$).

K. Allyl (4R,5S,6S)-6-[(1'R)-1'-tert-butyldimethylsilyloxyethyl]-4-(3"-tert-butyldimethylsilyloxxpropyl)-3-[(pyridin-2-yl)methylthio]-7-oxo-1-azabicyclo[3.2.0]hept-2-ene-2-carboxylate

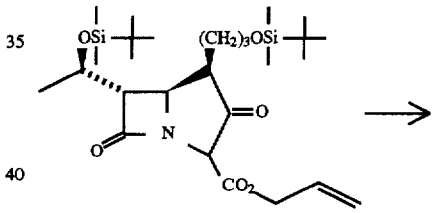

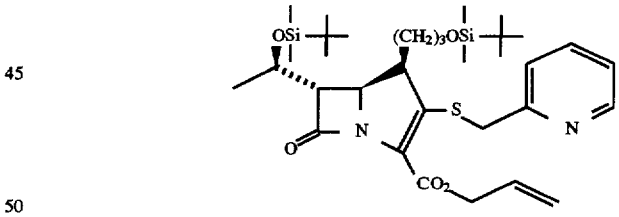

A cold (ice-MeOH bath) solution of allyl (2R,4R,5R,6S)-6-[(1'R)-1'-tert-butyldimethylsilyloxyethyl]-4-(3"-tert-butyldimethylsilyloxypropyl)-3,7-dioxo-1-azabicyclo [3.2.0]heptane-2-carboxylate (from 3.8 g, 6.7 mmol of the corresponding diazo) in $CH_3CN$ (40 mL) was treated dropwise with diphenyl chlorophosphate (1.52 mL, 7.37 mmol) and N,N-diisopropylethylamine (1.03 mL, 7.37 mmol). The mixture was stirred for 1 h at −15° C. to −10° C. The resulting enol phosphate was then treated in the cold (−15° C.) with 2-picolylmercaptan (1.68 g, 13.4 mmol) in $CH_3CN$ (10 mL) followed by the dropwise addition of N,N-diisopropylethylamine (2.36 mL, 13.4 mmol). The mixture was stirred for 1 h at −10° C. to 0° C. and then for 1.5 h at 5° C. (ice bath). The reaction mixture was diluted with cold EtOAc (300 mL), washed with cold water (2×100 mL), ice cold 1M aqueous $NaHSO_3$ (3×100 mL), ice cold water (2×100 mL), 1M aqueous NaHCO₃ (2×100 mL) ice cold water (2×100 mL), brine (100 mL) and dried (MgSO₄). The residue was passed through a silica gel flash column (60 g, hexane, 5%, 10%, 15%, 20% EtOAc/hexane) to give the title compound (3.2 g, 74%) as an oil.

IR (CH₂Cl₂) ν$_{max}$: 1770 and 1715 cm⁻¹ (C=O);
¹H NMR (CDCl₃, 200 MHz) δ: 8.50–8.48 (1H, m, pyridine-H), 7.7–7.6 (1H, pyridine-H), 7.41–7.36 (1H, bd, J=7.9, pyridine-H), 7.21–7.15 (1H, m, pyridine-H, 6.05–5.8 (1H, m, vinylic H), 5.47–5.19 (2H, m, vinylic-H), 4.9–4.6 (2H, m, CH₂-vinyl), 4.28, 4.21, 4.09, 4.02 (2H, ABq, J=13.8 Hz, CH₂-picolyl), 4.21–4.08 (1H, m, H-1'), 4.01 (1H, dd, J=2.4 Hz, J=9.3 Hz, H-5), 3.7–3.5 (2H, m, CH₂—O), 3.5–3.4 (1H, m, H-4), 3.27 (1H, dd, J=2.5 Hz, J=7.3 Hz, H-6), 1.9–1.4 [4H, m, (CH₂)₂], 1.28 (3H, d, J=6.3 Hz, CH₃), 0.877, 0.871 (18H, 2s, tert-butyl), 0.066, 0.057, 0.036 and 0.029 ppm (12H, 4s, CH₃).

L. Allyl (4R,5S,6S)-6-[(1'R)-1'-hydroxyethyl]-4-(3"-hydroxypropyl)-3-[(pyridin-2-yl)methylthio]-7-oxo-1-azabicyclo[3.2.0]hept-2-ene-2-carboxylate

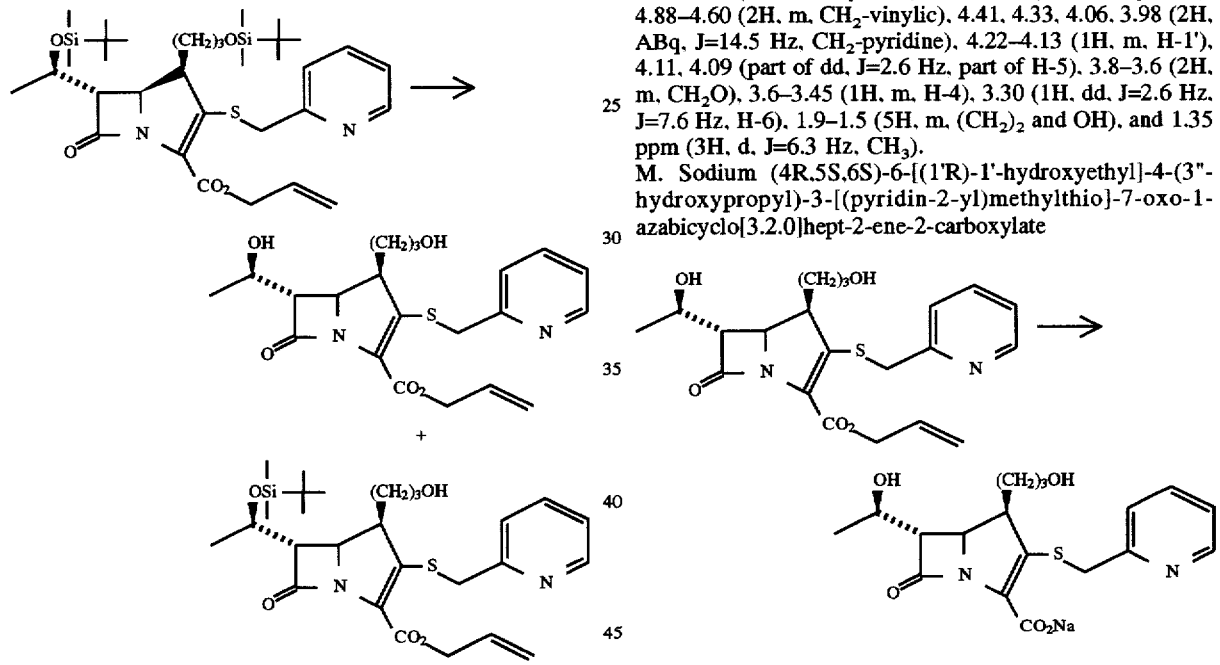

A cold (ice-MeOH bath) solution of allyl (4R,5S,6 S)-6-[(1'R)1'-tert-butyldimethylsilyloxyethyl]-4-(3"-tert-butyldimethylsilyloxypropyl)-3-[(pyridin-2-yl) methylthio]-7-oxo-1-azabicyclo[3.2.0]hept-2-ene-2-carboxylate (3.20 g, 4.95 mmol) in dry THF (60 mL) was treated with CH₃CO₂H (1.72 mL, 30 mmol) followed by the dropwise addition of a 1M solution of tetrabutylammonium fluoride in THF (15 mL, 15 mmol). The mixture was kept in a cold room (5° C.) for 30 h, then neutralized (ice bath) with 1M NaHCO₃ (30 mL, 30 mmol). The mixture was diluted with EtOAc (200 mL) and the aqueous phase was extracted twice with EtOAc (2×200 mL). The organic extracts were washed with ice cold 1M aqueous NaHCO₃ (4×100 mL), ice cold water (2×100 mL), brine (100 mL) and dried (MgSO₄). The residue was passed through a silica gel flash column (75 g, CH₂Cl₂, 5%, 10%, 20%, 30%, 40%, 60% EtOAc/CH₂Cl₂) to give allyl (4R,5S,6S)-6-[(1'R)-1'-tert-butyldimethylsilyl-oxyethyl]-4-(3"-hydroxypropyl)-3-[(pyridin-2-yl)methylthio]-7-oxo-1-azabicyclo[3.2.0]hept-2-ene-2-carboxylate (1.5 g, 57%) as a white solid.

IR (CH₂Cl₂) ν$_{max}$: 3600–3300 (OH), 1770 and 1720 cm⁻¹ (C=O);
¹H NMR (CDCl₃, 200 MHz) δ: 8.48–8.45 (1H, m, pyridine-H), 7.77–7.67 (1H, m, pyridine-H), 7.50–7.46 (1H, d, J=7.9 Hz, pyridine-H), 7.26–7.19 (1H, m, pyridine —H), 6.05–5.85 (1H, m, vinylic —H), 5.47–5.20 (2H, m, vinylic-H), 4.84–4.61 (2H, m, vinylic —CH₂), 4.46, 4.39, 4.05, 3.98 (2H, ABq, J=14.4 Hz, CH₂— pyridine), 4.20, 4.16, 4.13 (1H, 3 lines out of 5, H-1'), 3.96 (1H, dd, J=2.5 Hz, J=9.5 Hz, H-5), 3.8–3.6 (2H, m, CH₂O), 3.5–3.3 (1H, m, H-4), 3.22 (1H, dd, J=2.5 Hz, J=7.3 Hz, H-6), 1.9–1.6 (4H, m, (CH₂)₂), 1.64 (1H, bs, OH), 1.27 (3H, d, J=6.1 Hz, CH₃), 0.857 (9H, s, tert-butyl), 0.059 and 0.039 (6H, 2s, CH₃).

Elution of the above column with acetone gave the title compound (411 mg, 20%).

IR (CH₂Cl₂) ν$_{max}$: 3700–3200 (OH), 1770 and 1710 cm⁻¹ (C=O);
¹H NMR (CDCl₃, 200 MHz) δ: 8.49–8.46 (1H, m, pyridine-H), 7.75–7.66 (1H, m, pyridine-H), 7.48–7.45 (1H, bd, J=8.9 Hz, pyridine-H), 7.23–7.19 (1H, m, pyridine-H), 6.06–5.86 (1H, m, vinylic-H), 5.48–5.21 (1H, m vinylic-H), 4.88–4.60 (2H, m, CH₂-vinylic), 4.41, 4.33, 4.06, 3.98 (2H, ABq, J=14.5 Hz, CH₂-pyridine), 4.22–4.13 (1H, m, H-1'), 4.11, 4.09 (part of dd, J=2.6 Hz, part of H-5), 3.8–3.6 (2H, m, CH₂O), 3.6–3.45 (1H, m, H-4), 3.30 (1H, dd, J=2.6 Hz, J=7.6 Hz, H-6), 1.9–1.5 (5H, m, (CH₂)₂ and OH), and 1.35 ppm (3H, d, J=6.3 Hz, CH₃).

M. Sodium (4R,5S,6S)-6-[(1'R)-1'-hydroxyethyl]-4-(3"-hydroxypropyl)-3-[(pyridin-2-yl)methylthio]-7-oxo-1-azabicyclo[3.2.0]hept-2-ene-2-carboxylate

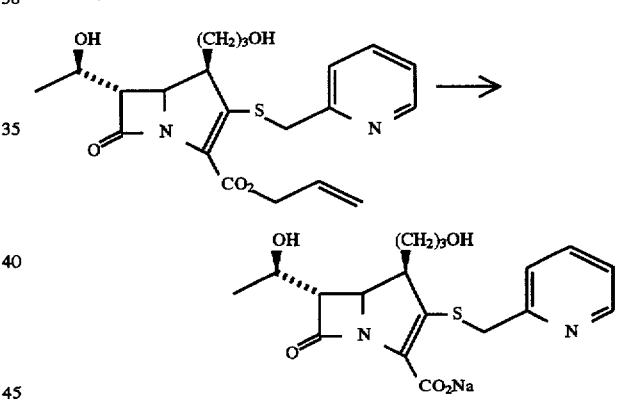

To a cold (ice bath) solution of allyl (4R,5S,6S)-6-[(1' R)-1'-hydroxyethyl]-4-(3"-hydroxypropyl)-3-[(pyridin-2-yl)-methylthio]-7-oxo-1-azabicyclo[3.2.0]hept-2-ene-2-carboxylate (166 mg, 0.400 mmol) in CH₂Cl₂ (10 mL) was added Pd(PPh₃)₄ followed by the dropwise addition of potassium 2-ethylhexanoate (0.5M in EtOAc, 1 mL, 0.5 mmol). The mixture was stirred for 15 min, diluted with diethyl ether (25 mL) and extracted with an ice cold 0.04M aqueous pH 7.0 buffer (3×5 mL). The aqueous extracts were washed with diethyl ether (2×25 mL) and passed through a C₁₈ μBondapak reversed phase column (40 g, H₂O, 1%, 2%, 3%, 5% CH₃CN/H₂O) to give the title compound (120 mg, 75%) as a lyophilized powder.

Purity 99.6% as determined by HPLC;
UV (H₂O) λ$_{max}$: 306 (11900), 266 (8000);
IR (Nujol) ν$_{max}$: 1745 and 1590 cm⁻¹ (C=O);
¹H NMR (D₂O, 200 MHz) δ: 8.47, 8.45 (1H, bd, J=4.8 Hz, pyridine-H), 7.85 (1H, bt, J=7.8 Hz, pyridine-H), 7.52 (1H, bd, J=7.8 Hz, pyridine-H), 7.39–7.33 (1H, m, pyridine-H), 4.22, 4.17, 4.11, 4.06 (2H, ABq, J=10.5 Hz, CH₂-pyridine), 4.3–4.0 (2H, m, hidden H-1' and H-5), 3.57, 3.54, 3.51 (2H, m, hidden H-1' and H-5), 3.57, 3.54, 3.51 (2H, m, CH₂O), 3.35 (1H, dd, J=2.3 Hz, J=6.0 Hz, H-6), 3.21, 3.17, 3.12 (1H, m, H-4), 2.8–2.2 (4H, m, (CH₂)₂) and 1.28 ppm (3H, d, J=6.3 Hz, CH₃).

EXAMPLE 10

(4R,5S,6S)-4-(2"-Aminoethyl)-6-[(1'R)-1'-hydroxyethyl]-3-[(1-methylpyridinium-2-yl)methylthio]-7-oxo-1-azabicyclo[3.2.0]hept-2-ene-2-carboxylic acid, phosphate monobasic salt

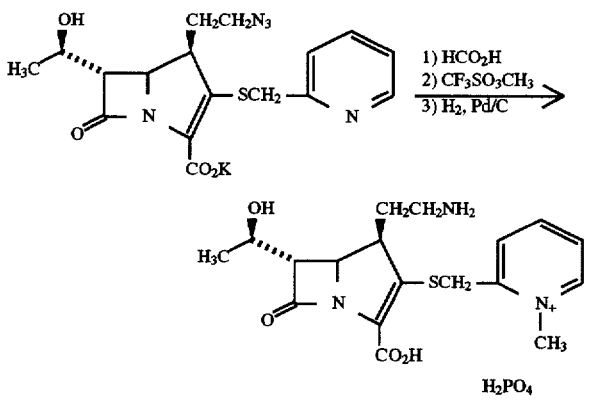

A suspension of potassium (4R,5S,6S)-4-(2"-azidoethyl)-6-(1'R)-1'-hydroxyethyl]-3-[(pyridin-2-yl)methylthio]-7-oxo-1-azabicyclo[3.2.0]hept-2-ene-2-carboxylate (prepared as in Example 6) (0.300 g, 0.70 mmol) in dry acetonitrile (3 mL) was cooled to −20° C. and treated with 98% formic acid (0.030 mL, 0.79 mmol). After 15 min, the clear solution was treated with methyl trifluoromethanesulfonate (0.12 mL, 1.06 mmol) and stirred for 1.5 h. The reaction mixture was then quenched by addition of 20 mL of 0.1M pH 7.4 phosphate buffer and the acetonitrile was evaporated under vacuum. The aqueous phase was diluted with 40 mL of 0.1M pH 6.0 phosphate buffer and hydrogenated at 0° C. over 30% palladium on Celite (0.40 g) under 45 psi of hydrogen for 1.5 h. The catalyst was filtered on a celite pad and the filtrate was chromatographed on reversed phase silica gel (μ-Bondapak C₁₈, 3×15 cm). Elution with a gradient of acetonitrile (0–5%) in water gave 0.062 g (19%) of the title compound as a white amorphous solid after freeze drying. The purity of the product by ¹H NMR was estimated to 80%.

Purity by HPLC: 97% (μ-Bondapak C₁₈, 3.9 mm×30 cm), elution 10% CH₃CN—H₂O pH 7.4 phosphate buffer, flow rate 1.5 mL/min, uv detector 300 nm, retention time 10.0 min.

UV (H₂O, pH 7.4 phosphate buffer) $\lambda_{max}$: 270 nm (6,630) and 300 nm (sh, 3480);

IR (KBr) $v_{max}$: 1765 (C=O of β-lactam), 1635, 1610and 1585 cm⁻¹;

¹H NMR (200 MHz, D₂O) δ: 1.32 (d, J=6.39 Hz, CH₃CHO), 1.7–2.3 (m, 2H, CH₂-4), 3.1–3.3 (m, 2H, CH₂NH₂), 3.37 (dt, J$_{H4, CH2}$=10.1 Hz, J$_{H4,H5}$=3.86 Hz, 1H, H-4), 3.53 (dd, J$_{H6, H5}$=3.20 Hz, J$_{H6,H1}$=6.42 Hz, 1H, H-6), 4.2–4.4 (m, H-5 and H-1' overlapping), 4.40 (s, 3H, CH₃ of pyridinium), 7.79 (~d, J=7.8 Hz, 1H, H-3 of pyridinium), 7.92 (m, 1H, H-5), 8.44 (m, 1H, H-4 of pyridinium) and 8.78 ppm (d, J=5.5 Hz, 1H, H-6 of pyridinium).

EXAMPLE 11

(4R,5S,6S)-4-(2"-N,N-Dimethylaminoethyl)-6-[(1'R)-1'-hydroxyethyl]-3-[(pyridin-2-yl)methylthio]-7-oxo-1-azabicyclo[3.2.0]-hept-2-ene-2-carboxylic acid

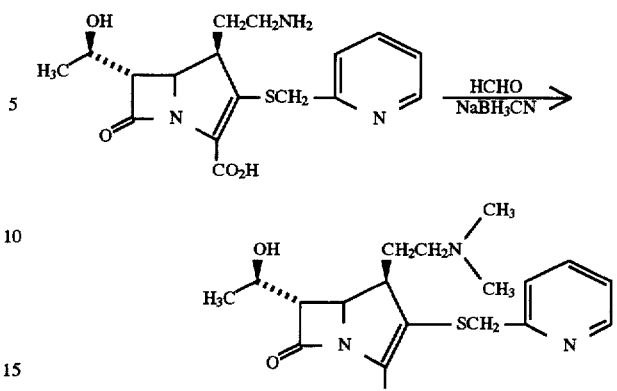

A solution of (4R,5S,6S)-4-(2"-aminoethyl)-6-[(1'R)-1'-hydroxyethyl]3-[(pyridin-2-yl)methylthio]-7-oxo-1-azabicyclo[3.2.0]hept-2-ene-2-carboxylic acid (Example 2) (0.187 g, 0.51 mmol) in cold water(3 mL) was diluted with CH₃CN (2 mL) and then treated at 0°–5° C. with 37% aqueous formaldehyde (0.21 mL). The pH of the solution (pH-meter) was 7.2. Then sodium cyanoborohydride (0.058 g, 0.93 mmol) was added all at once (pH 8.5–9.0) followed after 2 min by glacial acetic acid (3 drops, pH 5.2–5.5). The resulting homogeneous mixture was stirred at 0°–5° C. for 30 min. Then 20 mL of 0.1M pH 6.0 phosphate buffer were added and the acetonitrile was removed under vacuum (<15° C.). The residual aqueous phase was chromatographed on reversed phase silica gel (μ-Bondapak C₁₈, 2.5×10 cm) using a gradient of acetonitrile (0–10%) in water as eluent. The UV active fractions were collected, freeze dried and chromatographed a second time using the same system. The title compound was obtained as a white amorphous powder: 0.117 g (58%); $[\alpha]_D^{22}$ −4.0° (c 1.0, H₂O).

Purity by HPLC: 88% on μ-Bondapak C₁₈, 3.9 mm×30 cm, flow rate 2 mL/min, 5% CH₃CN—H₂O pH 7.4 phosphate buffer, uv detector 300 nm, retention time 9.02 min.

UV (H₂O, pH 7.4 phosphate buffer) $\lambda_{max}$: 266 (7,039) and 302 nm (7,707);

IR (KBr) $v_{max}$: 1762 (C=O of β-lactam) and 1595 cm⁻¹ (C=O of carboxylic acid);

¹H NMR (200 MHz, D₂O) δ: 1.30 (d, J=6.35 Hz, 3H, CH₃CHO), 1.6–2.2 (m, 2H, CH₂-4), 2.86 (s, 6H, N(CH₃)₂), 3.15 (m, 3H, H-4 and CH₂N), 3.32 (dd, J$_{H6,H5}$=2.91 Hz, J$_{H6,H1}$=6.75 Hz, 1H, H-6), 4.10 (ABq, J$_{AB}$=14.06 Hz, Δv=25.4 Hz, SCH₂), 4.1–4.3 (m, 2H, H-5 and CH₃CHO overlapping), 7.38 (m, 1H, H-3 of pyridine), 7.47 (d, J=7.87 Hz, 1H, H-5 of pyridine), 7.86 (m, 1H, H-4 of pyridine) and 8.47 ppm (d, J=5.0 Hz, 1H, H-2 of pyridine).

EXAMPLE 12

(4R,5S,6S)-4-(4"-Aminobutyl)-6-[(1'R)-1'-hydroxyethyl]-3-[(pyridin-2-yl)methylthio]-7-oxo-1-azabicyclo[3.2.0] hept-2-ene-2-carboxylic acid

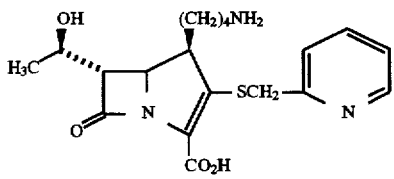

A. tert-Butyldimethylsilyl 6-(tert-butyldimethylsilyloxy) hexanoate

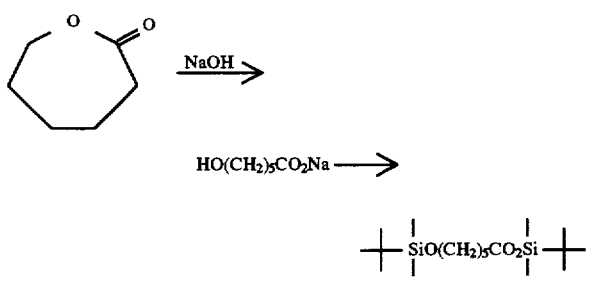

Saponification of ε-caprolactone (20.6 g, 0.18 mol) as described by P. A. Aristoff et al. in *J. Org. Chem.*, 48, 5341 (1983) gave 30.0 g of the sodium salt as a white solid: $^1$H NMR (200 MHz, $D_2O$) δ: 1.2–1.7 (m, 6H), 2.19 (t, J=7.32 Hz, 2H, $\underline{CH_2}CO_2Na$) and 3.61 ppm (t, J=6.51 Hz, 2H, $\underline{CH_2}OH$).

The crude salt was suspended in N,N-dimethylformamide (250 mL) cooled to 0°–5° C. and treated with tert-butyldimethylsilyl chloride (81.6 g, 0.54 mol) followed by triethylamine (32.6 mL, 0.23 mol) added dropwise. After 26 h at 22° C., the solid formed was filtered and washed with petroleum ether (bp 20°–60° C). After dilution with more petroleum ether (500 mL) the filtrate was washed with saturated $NaHCO_3$, brine and dried ($MgSO_4$). After evaporation of the solvent, the residue was distilled under vacuum to give 60.8 g (93%) of the title ester as a clear oil: bp=106°–107° C./0.015 torr.

IR (NaCl, film) $v_{max}$: 1722 cm$^{-1}$ (C=O of ester);

$^1$H NMR (200 MHz, $CDCl_3$) δ: 0.04 and 0.26 (2s, 2×6H, $SiCH_3$), 0.88 and 0.92 (2s, 2×9H, tert-butyl), 1.2–1.7 ppm (m, 6H, $CH_2$-3,4 and 5).

B. 6-(tert-Butyldimethylsilyloxy)hexanoic acid

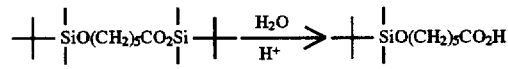

A solution of the silyl ester prepared in Step A (82.0 g, 0.227 mol) in a mixture of tetrahydrofuran (800 mL) and water (800 mL) was treated at 22° C. with oxalic acid (8.2 g, 0.09 mol) and stirred for 2 h. The reaction mixture was then diluted with EtOAc (1 L), washed with water and brine and dried ($MgSO_4$). Evaporation of the solvent gave 72 g of an oil which is a mixture of the title acid and disiloxane. This product was used without purification in the next step:

IR (NaCl, film) $v_{max}$: 1715 cm$^{-1}$ (C=O of carboxylic acid);

$^1$H NMR (200 MHz, $CDCl_3$) δ: 0.41 (s, $SiCH_3$), 0.88 (s, Si-tert-butyl), 1.3–1.8 (m, $CH_2$-3, 4 and 5), 2.3–2.4 (m, $\underline{CH_2}CO_2H$) and 3.6–3.7 ppm (m, $\underline{CH_2}OSi$).

C. 6-(tert-Butyldimethylsilyloxy)-(pyridin-2-yl)methylthiohexanoate

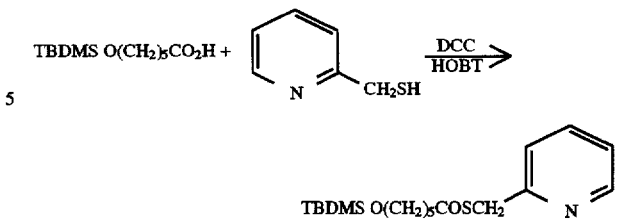

A solution of the crude 6-(tert-butyldimethylsilyloxy) hexanoic acid from Step B (~0.227 mol) in dry $CH_2Cl_2$ (500 mL) was treated at 0°–5° C. with 2-picolyl mercaptan (28.4 g, 0.227 mol), 1-hydroxybenzotriazole hydrate (34.8 g, 0.227 mol) and 1,3-dicyclohexylcarbodiimide (46.9 g, 0.227 mol). After 16 h at 22° C., the solid formed was filtered and washed with EtOAc. The flitrates were washed with water, brine and then dried ($MgSO_4$). Evaporation of the solvent gave an oil which was chromatographed on silica gel (9×10 cm). Elution with a mixture of toluene and EtOAc (95:5) gave 40.0 g (50%) of the title thioester as a clear oil:

IR (NaCl, film) $v_{max}$: 1695 cm$^{-1}$ (C=O of thioester);

$^1$H NMR (200 MHz, $CDCl_3$) δ: 0.28 (s, 6H, $SiCH_3$), 0.88 (s, 9H, t-Bu), 1.3–1.8 (m, 6H, $CH_2$-3,4 and 5), 2.58 (t, J=7.5 Hz, 2H, $CH_2$-2), 3.57 (t, J=6.2 Hz, 2H, $CH_2$-6), 4.24 (s, 2H, $CH_2$ of picolyl), 7.15 (m, 1H, H-5 of pyridine), 7.33 (d, J=7.8 Hz, 1H, H-3 of pyridine), 7.62 (m, 1H, H-4 of pyridine) and 8.52 ppm (d, J=8.5 Hz, 1H, H-6 of pyridine).

D. O-tert-Butyldimethylsilylenol ether of 6-(tert-butyldimethylsilyloxy)-1-(pyridin-2-yl) methylthiohexanoate

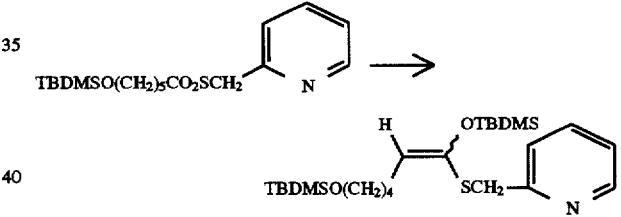

A solution of 6-(tert-butyldimethylsilyloxy)-1-(pyridin-2-yl)methylthiohexanoate (40.0 g, 0.113 mol) in dry $CH_2Cl_2$ (400 mL) was treated at 0°–5° C. with triethylamine (32 mL, 0.23 mol) followed by tert-butyldimethylsilyl trifluoromethanesulfonate (40 mL, 0.174 mol) added dropwise. The reaction mixture was then stirred at 22° C. for 3 h. After dilution with petroleum ether (bp 30°–60° C., 1 L), the organic phase was washed with water, dried ($MgSO_4$) and evaporated under reduced pressure. The residual hard oil (53.0 g) was immediately used as such for the coupling in the next step.

$^1$H NMR (200 MHz, $CDCl_3$) indicated a 1:1 mixture of E and Z isomers; δ: 3.95 and 4.03 (2×s, $SCH_2$), 4.85 (t, J=7.25 Hz, C=CH) and 5.0 ppm (t, J=7.54 Hz, C=CH).

E. (3S,4S)-3-[(-1'R)-1'-tert-butyldimethylsilyloxyethyl]-4-[1R")-1"-(pyridin-2-yl)methylthiocarbonyl-5"-tert-butyldimethylsilyloxypentyl]azetidin-2-one

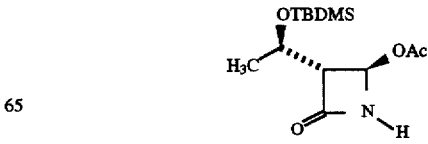

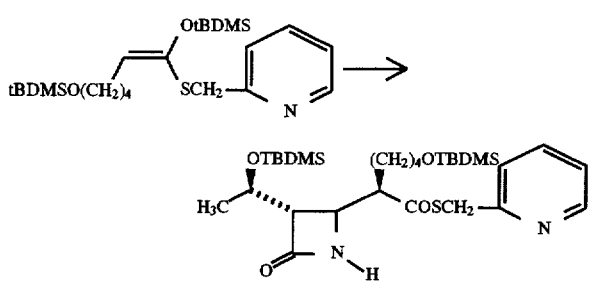

To a suspension of freshly fused zinc chloride (15.4 g, 0.113 mol) in dry CH$_2$Cl$_2$ (200 mL) at 0°–5° C. was added (3S,4R)-4-acetoxy-3-[(1' R)-1'-tert-butyldimethylsilyloxyethyl]azetidin-2-one (16.25 g 0.056 mol). Then a solution of the crude silyl enol ether (0.113 mol) prepared in Step D in dry CH$_2$Cl$_2$ (200 mL) was added dropwise (~15 min) and the resulting mixture was stirred at 0°–5° C. for 18 h. The reaction mixture was then diluted with EtOAc, washed with saturated aqueous ammonium chloride, saturated NaHCO$_3$, brine and dried (MgSO$_4$). Evaporation of the solvent gave a dark residue which was chromatographed on silica gel (15×11 cm). Elution with a mixture of toluene and EtOAc (1:1) gave 23 g (70%) of the title compound as a gum which was used as such in the next step. $^1$H NMR indicates a 9:1 β to α ratio of isomers. Crystallization of an aliquot from hexanes gave the pure β isomer of the title compound as white plates; mp=82°–83° C.; [α]$_D^{22}$ –9.0° (c 1.0, CHCl$_3$).

UV (EtOH) λ$_{max}$: 238 (5,080) and 264 nm (4,600);

IR (KBr) ν$_{max}$: 1770 (C=O) of β-lactam and 1682 cm$^{-1}$ (C=O of thioester);

$^1$H NMR (200 MHz, CDCl$_3$) δ: 0.02 and 0.04 (2×s, 2×6H, SiCH$_3$), 0.84 and 0.87 (2×s, 2×9H, Si tert-butyl), 0.97 (d, J=6.31 Hz, 3H, CH$_3$CHO), 1.2–2.0 (m, 6H, CH$_2$-2,3,4 of pentyl), 2.8 (m, 1H, H-1 of pentyl), 3.03 (m, 1H, H-6), 3.56 (t, J=5.9 Hz, 2H, CH$_2$-5 of pentyl), 3.80 (dd, J$_{H4,H3}$=2.05 Hz, J$_{H4,H}$=7.08 Hz, 1H, H-4), 4.14 (m, 1H, CH$_3$CHO), 4.26 (ABq, J$_{AB}$=14.0 Hz, Δν=7.3 Hz, 2H, SCH$_2$), 5.88 (broad s, 1H, NH), 7.18 (m, 1H, H-5 of pyridine), 7.33 (d, J=7.8 Hz, 1H, H-3 of pyridine), 7.64 (m, 1H, H-4 of pyridine), and 8.52 ppm (d, J=4.8 Hz, 1H, H-6 of pyridine).

Anal. Calcd for C$_{29}$H$_{51}$N$_2$O$_4$SSi$_2$: C, 60.06; H, 8.86; N, 4.83; S, 5.53; Found: C, 60.30; H, 8.82; N, 4.72; S, 5.67.

F. (3S,4S)-3-[(1'R)-1'-tert-Butyldimethylsilyloxyethyl]-4-[(1"R)-1"-carboxy-5"-tertbutyldimethylsilyloxypentyl]azetidin-2-one

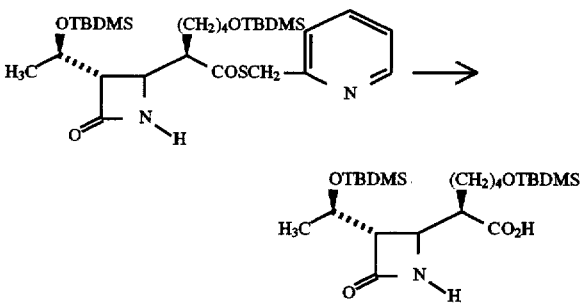

A solution of (3S,4R)-3-[(1'R)-1'-tert-butyldimethylsilyloxyethyl]-4-[(1"R)-1"-(pyridin-2-yl)methylthiocarbonyl-5"-tert-butyldimethyl-silyloxypentyl]azetidin-2-one (23.0 g, 39.7 mmol, mixture of β and α isomer in a ~9:1 ratio) in tetrahydrofuran (200 mL) was treated at 0°–5° C. with 30% hydrogen peroxide (7.0 mL, 81.2 mmol) followed by 80 mL (80.0 mmol) of 1M sodium hydroxide added dropwise. After 2 h at 22° C., the reaction mixture was diluted with EtOAc (500 mL) and acidified with 1N HCl (100 mL). The organic phase was washed with 1N sodium bisulfite (100 mL), brine and dried (MgSO$_4$). Evaporation of the solvent gave a solid which was recrystallized from AcOEt-hexanes to give 12.4 g (66%) of the title compound as a white solid: mp=136°–138° C.; [α]$_D^{22}$ –3.6° (c 1.0, CHCl$_3$).

IR (KBr) ν$_{max}$: 1760 (sh), 1715 (C=O of acid) and 1690 cm$^{-1}$;

$^1$H NMR (200 MHz, CDCl$_3$) δ: 0.04, 0.05 and 0.06 (3×s, 6H, 3H and 3H, SiCH$_3$), 0.86 and 0.88 (2×s, 2×9H, sit-Bu), 1.16 (d, J=6.28 Hz, 3H, CH$_3$CHO), 1.2–1.8 (m, 6H, CH$_2$-2,3 and 4 of pentyl), 2.6 (m, 1H, H-1 of pentyl), 3.13 (m, 1H, H-3), 3.60 (t, J=5.82 Hz, 2H, CH$_2$-5 of pentyl), 3.86 (dd, J$_{H4,H3}$=1.92 Hz, J$_{H4,H}$=6.46 Hz, 1H, H-4), 4.20 (dq, J$_{H1'}$, CH$_3$=6.28 Hz, J$_{H1,H3}$=3.86 Hz, 1H, CH$_3$CHO), and 6.32 ppm (broad s, 1H, NH).

Anal. Calcd. for C$_{23}$H$_{47}$NO$_5$Si$_2$: C, 58.31; H, 10.00; N, 2.96; Found: C, 58.18; H, 10.18; N, 2.91.

G. (3S,4R)-3-[(1'R)-1'-tert-Butyldimethylsilyloxyethyl]-4-[(1"R)-1"-(4-tert-butyldimethylsilyloxybutyl)-3"-allyloxycarbonyl-2"-oxopropyl]azetidin-2-one

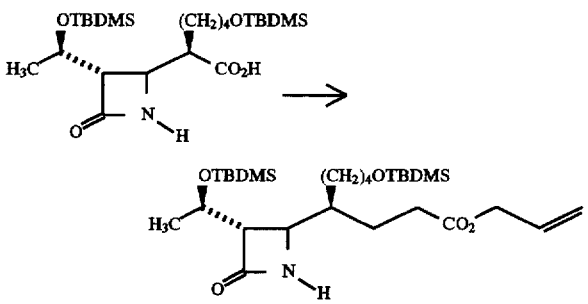

A suspension of (3S,4S)-3-[(1'R)-1'-tert-butyldimethylsilyloxyethyl]-4-[(1"R)-1"-carboxy-5"-tert-butyldimethylsilyloxypentyl]azetidin-2-one (4.70 g, 9.92 mmol) in dry toluene (125 mL) was treated at 22° C. with 1,1-carbonyldiimidazole (1.80 g, 11.1 mmol). After 5 h, the solvent was evaporated under reduced pressure and the residue was dissolved in dry benzene (15 mL). This solution was added to a solution of magnesium monoallyl malonate (4.7 g, 15.3 mmol) in dry benzene (100 mL) and the resulting mixture was stirred at 80° C. for 18 h. The reaction mixture was then diluted with EtOAc, washed with cold 1N HCl, saturated NaHCO$_3$, brine and dried (MgSO$_4$). Evaporation of the solvent gave a residue which was chromatographed on silica gel (6.5×11 cm). Elution with a mixture of toluene and EtOAc (8:2) gave 3.48 g (63%) of the title compound as a white solid. $^1$H NMR of this product indicated a 1:1 mixture of keto and enol form of the acetoacetate. Recrystallization of the solid in petroleum ether (30°–60° C.) at −20° C. gave some pure enol form of the product as white needles: mp=72°–73° C.; [α]$_D^{22}$ 0° (c 1.0, CHCl$_3$).

UV (EtOH) λ$_{max}$: 248 nm (11,090);

IR (KBr) ν$_{max}$: 1761 (C=O of β-lactam) 1718, 1650 and 1625 cm$^{-1}$;

$^1$H NMR (200 MHz, CDCl$_3$) δ: 0.03 and 0.05 (2×s, 2×6H, SiCH$_3$), 0.86 and 0.88 (2×s, 2×9H, Sit-Bu), 1.10 (d, J=6.29 Hz, 3H, CH$_3$CHO), 1.2–1.8 (m, 6H, CH$_2$-1, 2 and 3 of butyl), 2.19 (m, 1H, H-1 of oxopropyl), 2.90 (m, 1H, H-3), 3.59 (t, J=5.96 Hz, CH$_2$-4 of butyl), 3.81 (dd, J$_{H4,H3}$=2.03 Hz, J$_{H4,H1}$=7.41 Hz, 1H, H-4), 4.18 (dq, J$_{H,CH3}$=6.29 Hz, J$_{H,H3}$=3.67 Hz, CH$_3$CHO), 4.63 (m, 2H, CH$_2$ of allyl), 5.06 (s, 1H, H-3 of oxopropyl enol form), 5.2–5.4 (m, 2H, CH of allyl) and 5.8–6.1 ppm (m, 2H, CH of allyl and NH).

Anal. Calcd for C$_{28}$H$_{53}$NO$_6$Si$_2$: C, 60.50; H, 9.61; N, 2.52; Found: C, 60.62; H, 9.64; N, 2.45.

H. (3S,4R)-3-(1'R)-1'-tert-Butyldimethylsilyloxyethyl)-4-[(1"R)-1"-(4-tert-butyldimethylsilyloxybutyl)-3"-diazo-3"-allyloxycarbonyl-2"-oxopropyl]azetidin-2-one

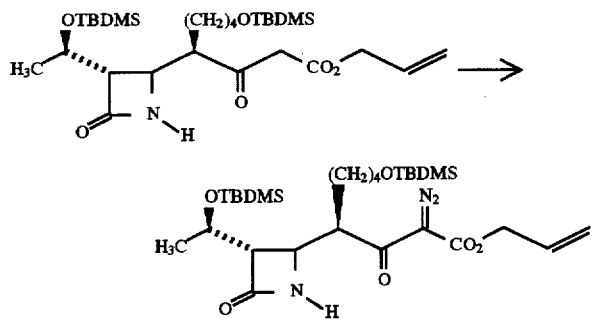

A solution of (3S,4R)-3-[(1'R)-1'-tert-butyldimethylsilyloxyethyl]-4-[(1"R)-1"-(4-tert-butyldimethylsilyloxybutyl)-3"-allyloxycarbonyl-2"-oxopropyl]azetidin-2-one (3.4 g, 6.12 mmol) in acetonitrile (50 mL) was treated at 22° C. with p-toluenesulfonyl azide (6.9 mmol, 2.3 mL of a 3M solution in CH$_3$CN) and triethylamine (0.85 mL, 6.1 mmol). After 1.5 h, the reaction mixture was diluted with EtOAc (200 mL) washed with water, saturated aqueous NaHCO$_3$, brine and dried (MgSO$_4$). Evaporation of the solvent gave a residue which was triturated with a mixture of toluene and EtOAc (9:1~30 mL). The crystalline p-toluenesulfonamide was filtered and the filtrate was chromatographed on silica gel (5×11 cm). Elution with a mixture of toluene and EtOAc (9:1) gave 3.56 g (100%) of the title compound as a clear oil:

IR (NaCl, film) v$_{max}$: 2140 (N$_2$), 1760 (C=O of β-lactam), 1720 (C=O of ester) and 1650 cm$^{-1}$;

$^1$H NMR (200 MHz, CDCl$_3$) δ: 0.03 and 0.05 (2×s, 2×6H, SiCH$_3$), 0.9 (s, 18H, Si t-Bu), 1.16 (d, J=6.29 Hz, 3H, CH$_3$CHO), 1.2–1.9 (m, 6H, CH$_2$-1, 2 and 3 of butyl), 3.04 (m, 1H, H-3), 3.57 (t, J=6.2 Hz, 1H, CH$_2$-4 of butyl), 3.85 (dd, J$_{H4,H3}$=2.11 Hz, J$_{H4,H}$=5.48 Hz, 1H, H-4), 4.05 (m, 1H, H-1 of oxopropyl), 4.17 (dq, J$_{H,CH3}$=6.29 Hz, J$_{H2,H3}$=3.68 Hz, 1H, CH$_3$CHO), 4.7 (m, 2H, CH$_2$ of allyl), 5.3–5.5 (m, 2H, CH of allyl), and 5.8–6.1 ppm (m, 2H, NH and CH of allyl).

I. Allyl (4R,5R,6S)-6-[(1'R)-1'-tert-butyldimethylsilyloxyethyl]-4-(4"-tertbutyldimethylsilyloxybutyl)-3,7-dioxo-1-azabicyclo[3.2.0]heptane-2-carboxylate

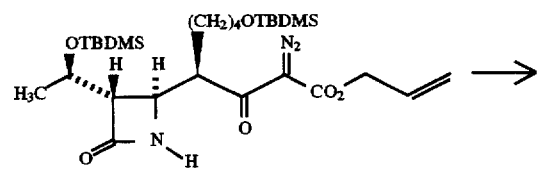

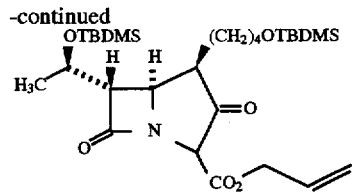

A solution of (3S,4R)-3-[(1'R)-1'-tert-butyldimethylsilyloxyethyl]-4-[(1"R)-1"-(4-tert-butyldimethylsilyloxybutyl)-3"-diazo-3"-allyloxycarbonyl-2"-oxopropyl]azetidin-2-one (3.50 g, 6.0 mmol) in dry benzene (350 mL) was treated under nitrogen with Rhodium (II) octanoate (0.14 g) and heated under reflux for 45 min. Evaporation of the solvent gave the crude bicyclic ketone as an oil which was used in the next step.

IR (NaCl, film) v$_{max}$: 1770 (C=O of β-lactam) and 1745 cm$^{-1}$ (C=O of keto ester);

$^1$H NMR (200 MHz, CDCl$_3$) δ: 0.03, 0.08 and 0.09 (3×s, 6H, 3H and 3H, SiCH$_3$), 0.86 (s, 18H, SitBu), 1.1–1.8 (m, 6H, CH$_2$-1, 2 and 3 of butyl), 1.28 (d, J=6.16 Hz, 3H, CH$_3$CHO), 2.64 (m, 1H, H-4), 3.22 dd, J$_{H6,H5}$=2.36 Hz, J$_{H6,H1'}$=5.54 Hz, 1H, H-6), 3.6 (m, 2H, CH$_2$OSi), 4.24 (dd, J$_{H5,H6}$=2.36 Hz, J$_{H5,H4}$=8.03 Hz, 1H, H-5), 4.30 (m, 1H, CH$_3$CHO), 4.61 (s, 1H, H-2), 4.64 (m, 2H, CH$_2$ of allyl), 5.2–5.4 and 5.8–6.0 ppm (2×m, 2H and 1H, CH of allyl).

J. Allyl (4R,5S,6S)-6-[(1'R)-1'-tert-butyldimethylsilyloxyethyl)-4-(4"-tert-butyldimethylsilyloxybutyl)-3-[(pyridin-2-yl)methyl-thio]-7-oxo-1-azabicyclo[3.2.0]hept-2-ene-2-carboxylate

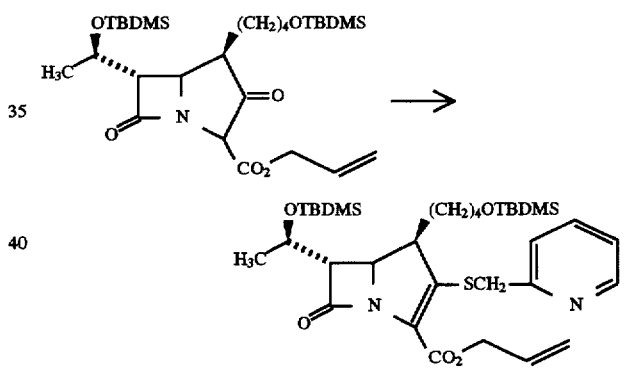

A solution of allyl (4R,5R,6S)-6-[(1'R)-1'-tert-butyldimethylsilyloxyethyl)-4-(4"-tert-butyldimethylsilyloxybutyl)-3,7-dioxo-1-azabicyclo[3.2.0]heptane-2-carboxylate (6.0 mmol) in dry CH$_3$CN (35 mL) at 0–5° C. was treated, under nitrogen, with diphenyl chlorophosphate (1.4 mL, 6.8 mmol) and N,N-diisopropylethylamine (1.2 mL, 6.9 mmol) added simultaneously over 5 min. 4-N,N-dimethylaminopyridine (~3 mg) was then added and the resulting mixture was stirred at the same temperature for 1 h. After the addition of 2-picolyl mercaptan (1.5 g, 12.0 mmol) and N,N-diisopropylethylamine, the mixture was stirred at 0°–5° C. for 16 h. The reaction mixture was then diluted with EtOAc, washed with saturated NaHCO$_3$, brine and dried (MgSO$_4$). Evaporation of the solvent gave an oil which was chromatographed on silica gel (5×10 cm). Elution with a mixture of toluene and EtOAc (9:1) gave 2.95 g (74%) of title compound as an oil.

IR (NaCl, film) v$_{max}$: 1775 (C=O of β-lactam) and 1710 cm$^{-1}$ (C=O of ester);

$^1$H NMR (200 MHz, CDCl$_3$) δ: 0.04, 0.05 and 0.06 (3×s, 6H, 3H and 3H, SiCH$_3$), 0.87 and 0.88 (2×s, 2×9H, Si t-Bu), 1.2–2.0 (m, 6H, CH$_2$-1, 2 and 3 of butyl), 1.26 (d, J=6.13 Hz, 3H, CH$_3$CHO), 3.12 (dd, J$_{H6,H5}$=2.48 Hz, J$_{H6,H1}$=6.68 Hz, 1H, H-6), 3.40 (m, 1H, H-4), 3.59 (m, 2H, CH$_2$-4 of butyl), 4.03 (dd, J$_{H5,H6}$=2.48 Hz, J$_{H5,H4}$=9.17 Hz, 1H, H-5), 4.13 (ABq, J$_{AB}$=14.3 Hz, Δv=30.4 Hz, 2H, SCH$_2$), 4.20 (m, 1H, CH$_3$CHO), 4.72 (m, 2H, CH$_2$ of allyl), 5.2–5.5 and 5.8–6.1 (2×m, 2H and 1H, CH of allyl), 7.20 (m, 1H, H-5 of pyridyl), 7.4 (d, J=7.9 Hz, 1H, H-3 of pyridine), 7.67 (m, 1H, H-4 of pyridine) and 8.5 ppm (m, 1H, H-6 of pyridine).

K. Allyl (4R,5S,6S)-6-[(1'R)-1'-tert-butyldimethylsilyloxyethyl]-4-(4"-hydroxybutyl)-3-[(pyridin-2-yl)methylthio]-7-oxo-1-azabicyclo[3.2.0]hept-2-ene-2-carboxylate

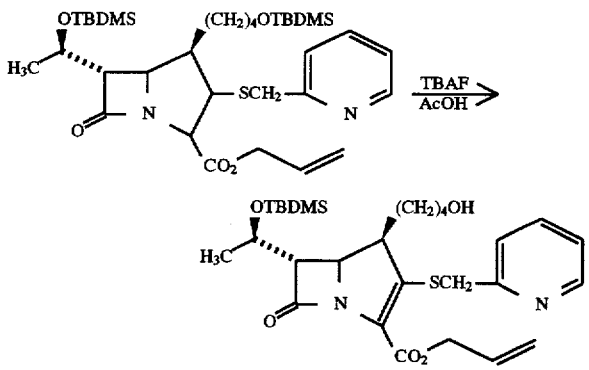

A solution of allyl (4R,5S,6S)-6-[(1'R)-1'-tert-butyldimethylsilyloxyethyl]-4-(4"-tert-butyldimethylsilyloxybutyl)-3-[(pyridin-2-yl)methylthio]-7-oxo-1-azabicyclo[3.2.0]hept-2-ene-2-carboxylate (2.95 g, 4.46 mmol) in dry tetrahydrofuran (70 mL) was treated at −10° C. and under nitrogen with glacial acetic acid (1.6 mL, 28.0 mmol) followed by 13.4 mL of 1.0M tetrabutylammonium fluoride in tetrahydrofuran. The resulting mixture was then stirred at 0° C. for 17 h. The reaction mixture was then diluted with EtOAc, washed with cold saturated NaHCO$_3$, brine and dried (MgSO$_4$). Evaporation of the solvent gave an oil which was chromatographed on silica gel (6×8 cm). Elution with a gradient of EtOAc (50→100%) in toluene gave 1.64 g (67%) of the title compound as a clear oil.

IR (NaCl, film) ν$_{max}$: 1775 (C=O of β-lactam) and 1710 cm$^{-1}$ (C=O of ester);

$^1$H NMR (200 MHz, CDCl$_3$) δ: 0.06 and 0.07 (2s, 2×3H, SiCH$_3$), 0.87 (s, 9H, Si t-Bu), 1.28 (d, J=6.08 Hz, 3H, CH$_3$CHO), 1.3–2.0 (m, 6H, CH$_2$-1, 2 and 3 of butyl), 3.14 (dd, J$_{H6,H5}$=2.54 Hz, J$_{H6,H1}$=7.19 Hz, 1H, H-6), 3.37 (m, 1H, H-4), 3.65 (m, 2H, CH$_2$-4 of butyl), 4.02 (dd, J$_{H5,H6}$=2.54 Hz, J$_{H5,H4}$=9.37 Hz, 1H, H-5), 4.14 (ABq, J$_{AB}$=13.8 Hz, Δv=33.2 Hz, 2H, SCH$_2$), 4.2 (m, 1H, CH$_3$CHO), 4.72 (m, 2H, CH$_2$ of allyl), 5.2–5.5 and 5.9–6.1 (2×m, 2H and 1H, CH of allyl), 7.2 (m, 1H, H-5 of pyridine), 7.4 (d, J=7.9 Hz, 1H, H-3 of pyridine ), 7.68 (m, 1H, H-4 of pyridine) and 8.50 ppm (1H, H-6 of pyridine).

L. Allyl (4R,5S,6S)-4-(4"-azidobutyl)-6-[(1'R)-1'-tert-butyldimethylsilyloxyethyl]-3-[(pyridin-2-yl)methylthio]-7-oxo-1-azabicyclo[3.2.0]hept-2-ene-2-carboxylate

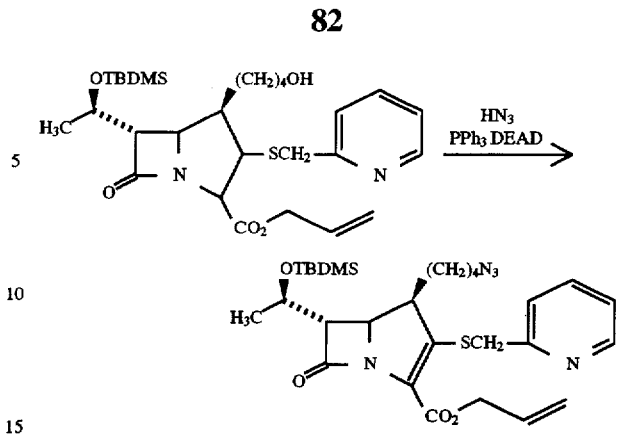

A solution of allyl (4R,5S,6S)-6-[(1'R)-1'-tert-butyldimethylsilyloxy]-4-(4"-hydroxybutyl)-3-[(pyridin-2-yl)methylthio]-7-oxo-1-azabicyclo[3.2.0]hept-2-ene-2-carboxylate (1.64 g, 3.0 mmol) in dry tetrahydrofuran (250 mL) was treated at −20° C. and under nitrogen with triphenylphosphine (1.26 g, 4.8 mmol) and 8.5 mL (5.1 mmol) of a 0.6M solution of hydrazoic acid in toluene. Then diethyl azodicarboxylate (0.80 mL, 5.08 mmol) was added dropwise over 5 min. After 30 min at −20° C., the reaction mixture was quenched by addition of EtOAc and saturated aqueous NaHCO$_3$. The organic phase was washed with brine and dried (MgSO$_4$). Evaporation of the solvent under reduced pressure gave an oil which was triturated with toluene (~25 mL). The crystalline diethyl hydrazine dicarboxylate was filtered and the filtrate was treated in the same manner with diethyl ether to crystallize the triphenylphosphine oxide. The residue was finally chromatographed on silica gel (5×9 cm) using a mixture of, toluene and EtOAc (8:2) as eluent. Evaporation of the UV active fractions gave 1.60 g (93%) of the title compound as a clear oil.

IR (NaCl, film) ν$_{max}$: 2100 (N$_3$), 1775 (C=O of β-lactam) and 1710 cm$^{-1}$ (C=O of ester);

$^1$H NMR (200 MHz, CDCl$_3$) δ: 0.06 and 0.07 (2×s, 2×3H, SiCH$_3$), 0.88 (s, 9H, Si t-Bu), 1.29 (d, J=6.07 Hz, 3H, CH$_3$CHO), 1.2–1.9 (m, 6H, CH$_2$-1, 2 and 3 of butyl), 3.10 (dd, J$_{H6,H5}$=2.55 Hz, J$_{H6,H1}$=7.20 Hz, 1H, H-6), 3.29 (t, J=6.2 Hz, 2H, CH$_2$N$_3$) 3.42 (m, 1H, H-4), 4.02 (dd, J$_{H5,H6}$=2.55 Hz, J$_{H5,H4}$=9.36 Hz, 1H, H-5), 4.13 (ABq, J$_{AB}$=14.0 Hz, Δv=31.9 Hz, 2H, SCH$_2$), 4.19 (m, 1H, overlapping with SCH$_2$, CH$_3$CHO), 4.72 (m, 2H, SCH$_2$ of allyl), 5.2–5.5 and 5.9–6.1 (2×m, 2H and 1H, CH of allyl), 7.21 (m, 1H, H-5 of pyridine), 7.41 (d, J=7.8 Hz, 1H, H-3 of pyridine), 7.69 (m, 1H, H-4 of pyridine) and 8.50 ppm (m, 1H, H-6 of pyridine).

M. Allyl (4R,5S,6S)-4-(4"-azidobutyl)-6-[(1'R)-1'-hydroxyethyl]-3-[(pyridin-2-yl)methylthio]-7-oxo-1-azabicyclo[3.2.0]hept-2-ene-2-carboxylate

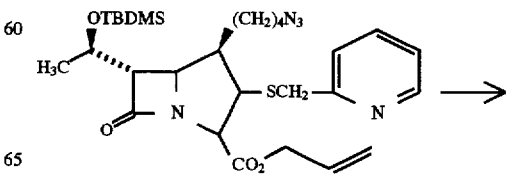

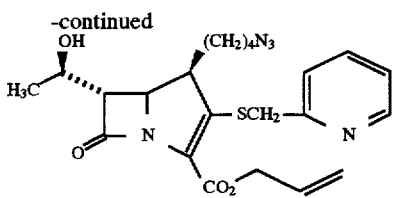

A solution of allyl (4R,5S,6S)-4-(4"-azidobutyl)-6-[(1'R)-1'-tert-butyldimethylsilyloxyethyl]-3-[(pyridin-2-yl)methylthio]-7-oxo-1-azabicyclo[3.2.0]hept-2-ene-2-carboxylate (1.60 g, 2.80 mmol) in dry tetrahydrofuran (40 mL) was treated at 5° C. with acetic acid (1.0 mL, 17.5 mmol) and then 8.4 mL (8.4 mmol) of a 1.0M solution of tetrabutylammonium fluoride in tetrahydrofuran. After 112 h at 5° C. the reaction mixture was diluted with EtOAc, washed with saturated $NaHCO_3$ and brine and dried ($MgSO_4$). Evaporation of the solvent gave an oil which was chromatographed on silica gel (4×11 cm). Elution with a mixture of toluene and EtOAc (1:1) gave 0.57 g (36%) of recovered starting material. Then elution with EtOAc gave 0.76 g (59%, 92% based on recovered starting material) of the title compound as an oil.

IR (NaCl, film) $v_{max}$: 2100 ($N_2$), 1772 (C=O of β-lactam) and 1708 $cm^{-1}$ (C=O of ester);

$^1$H NMR (200 MHz, $CDCl_3$) δ: 1.38 (d, J=6.28 Hz, 3H, $CH_3$CHO), 1.3–1.9 (m, 6H, $CH_2$-1, 2 and 3 of butyl), 1.84 (d, J=5.2 Hz, 1H, OH), 3.15 (dd, $J_{H6,H5}$=2.64 Hz $J_{H6,H1}$= 7.28 Hz, 1H, H-6), 3.31 (t, J=6.2 Hz, 2H, $CH_2N_3$), 3.48 (m, 1H, H-4), 4.13 (dd, $J_{H5,H6}$=2.64 Hz, $J_{H5,H4}$=9.43 Hz, 1H, H-5), 4.11 (ABq, $J_{AB}$=14.16 Hz, Δv=33.3 Hz, 2H, $SCH_2$), 4.2 (m, 1H, $CH_3CHO$), 4.74 (m, 2H, $CH_2$ of allyl), 5.2–5.5 and 5.9–6.1 (m, 2H, CH of allyl), 7.2 (m, 1H, H-5 of pyridine), 7.40 (d, J=7.9 Hz, 1H, H-3 of pyridine), 7.67 (m, 1H, H-4 of pyridine) and 8.50 ppm (m, 1H, H-6 of pyridine).

N. (4R,5S,6S)-4-(4"-Aminobutyl)-6-[(1'R)-1'-hydroxyethyl]-3-[(pyridin-2-yl)methylthio]-7-oxo-1-azabicyclo[3.2.0]hept-2-ene-2-carboxylic acid

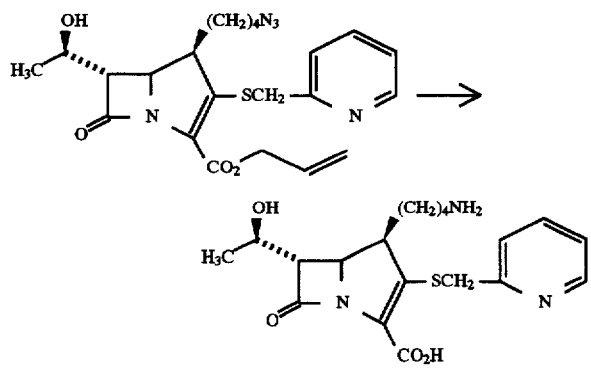

A solution of allyl (4R,5S,6S)-4-(4"-azidobutyl)-6-[(1'R)-1'-hydroxyethyl]-3-[(pyridin-2-yl)methylthio]-7-oxo-1-azabicyclo[3.2.0]hept-2-ene-2-carboxylate (0.76 g, 1.66 mmol) in dry $CH_2Cl_2$ was treated at 0°–5° C. and under nitrogen with tetrakis(triphenylphosphine)palladium[0] (0.14 g) and 3.6 mL (1.8 mmol) of a 0.5M solution of potassium 2-ethylhexanoate in EtOAc. After 30 min the reaction mixture was diluted with diethyl ether (150 mL) and extracted three times with 75 mL of 0.05M pH 7.0 phosphate buffer. The combined aqueous extracts were diluted with 75 mL of 1M $NaH_2PO_4$ (resulting pH 5.8) and then hydrogenated over 30% Palladium on Celite (0.8 g) under 45 psi at 0°–5° C. for 1.5 h. The catalyst was then filtered and the filtrate was concentrated to ~50 mL under vacuum (<15° C.). Chromatography of the residue on reversed phase silica gel (μ-Bondapak $C_{18}$, 5×9 cm) using a gradient of acetonitrile (0–10%) in water gave first 0.125 g (17%) of potassium (4R,5S,6S)-6-[(1'R)-1'-hydroxyethyl]-4-(4"-hydroxybutyl)-3-[(pyridin-2-yl)methylthio]-7-oxo-1-azabicyclo[3.2.0]hept-2-ene-2-carboxylate as a white powder after lyophilisation.

The end fractions then gave 0.273 g (42%) of the title compound as a white powder after freeze drying. By $^1$H NMR and HPLC this product was contaminated by 7% of the above hydroxybutyl side product. A portion of the product, 0.175 g, was purified a second time by chromatography to give 0.152 g (87% recovery) of the pure title compound: $[\alpha]_D$ 0° (c 1.0, $H_2O$, Purity by HPLC: 94% on μ-Bondapak $C_{18}$, 3.9 mm×30 cm, elution 5% $CH_3CN$-$H_2O$ pH 7.4 phosphate buffer, flow rate 1.5 mL/min, uv detector 306 nm, retention time 8.92 min.

UV ($H_2O$, pH 7.4 phosphate buffer) $\lambda_{max}$: 266 (6,490) and 306 nm (9,377);

IR (KBr) $v_{max}$: 1758 (C=O of β-lactam) and 1590 $cm^{-1}$ (C=O of carboxylate);

$^1$H NMR (200 MHz, $CDCl_3$) δ: 1.29 (d, J=6.36 Hz, 3H, $CH_3$CHO), 1.2–1.8 (m, 6H, $CH_2$-1, 2 and 3 of butyl), 2.97 (t, J=7.6 Hz, 2H, $CH_2NH_2$), 3.16 (m, 1H, H-4), 3.29 (dd, $J_{H6,H5}$=2.52 Hz, $J_{H6,H1}$=6.35 Hz, 1H, H-6), 4.0–4.3 (m, 4H, H-5, $CH_3CHN$ and $SCH_2$ overlapping), 7.37 (m, 1H, H-5 of pyridine), 7.52 (d, J=7.9 Hz, 1H, H-3 of pyridine), 7.86 (m, 1H, H-4 of pyridine), and 8.47 ppm (m, 1H, H-6 of pyridine).

EXAMPLE 13

Potassium (4R,5S,6S)-6-[(1'R)-1'-hydroxyethyl]-4-(4"-hydroxybutyl)-3-[(pyridin-2-yl)methylthio]-7-oxo-1-azabicyclo[3.2.0]-hept-2-ene-2-carboxylate A. Allyl (4R,5S,6S)-6-[(1'R)-1'-hydroxyethyl]-4-(4"-hydroxybutyl)-3-[(pyridin-2-yl)methylthio]-7-oxo-1-azabicyclo[3.2.0]hept-2-ene-2-carboxylate

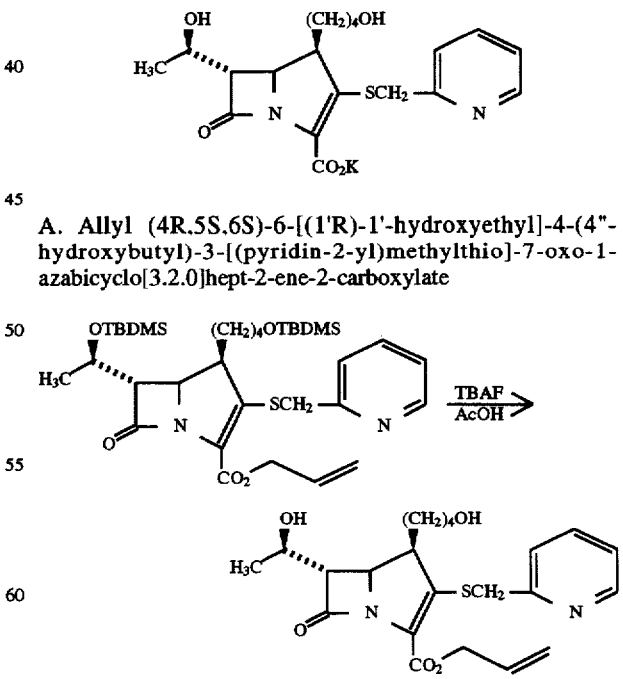

A solution of allyl (4R,5S,6S)-6-[(1'R)-1'-tert-butyldimethylsilyloxyethyl]-4-(4"-tert-butyldimethylsilyloxybutyl)-3-[(pyridin-2-yl)methylthio]-

7-oxo-1-azabicyclo[3.2.0]hept-2-ene-2-carboxylate (prepared in Example 12, Step J) (0.67 g, 1.01 mmol) in dry tetrahydrofuran (15 mL) was treated at −10° C. and under nitrogen with acetic acid (0.7 mL, 12.2 mmol) followed by 6.0 mL (6.0 mmol) of a 1.0M solution of tetrabutylammonium fluoride in tetrahydrofuran. After 140 h at 0°–5° C., the reaction mixture was diluted with EtOAc, washed with saturated NaHCO$_3$, brine and dried (MgSO$_4$). Evaporation of the solvent gave an oil which was chromatographed on silica gel (3×7 cm). Elution with a gradient of CH$_3$CN in EtOAc first gave 0.17 g (30%) of the monodeprotected allyl (4R,5S,6S)-6-[(1'R)-1'-tert-butyldimethylsilyloxyethyl]-4-(4"-hydroxybutyl)-3-[(pyridin-2-yl)methylthio]-7-oxo-1-azabicyclo[3.2.0]hept-2-ene-2-carboxylate as an oil which is identical to compound of Example 12, Step K.

Elution with acetonitrile then gave 0.20 g (45%) of the title compound as an oil.

IR (NaCl, film) $v_{max}$: 3400 (OH), 1770 (C=O of β-lactam) and 1705 cm$^{-1}$ (C=O of carboxylate);

$^1$H NMR (200 MHz, CDCl$_3$) δ: 1.37 (d, J=6.26 Hz, 3H, CH$_3$CHO), 1.3–2.0 (m, 6H, CH$_2$-1, 2 and 3 of butyl), 3.21 (dd, J$_{H6,H5}$=2.65 Hz, J$_{H6, H1'}$=8.09 Hz, 1H, H-6), 3.44 (m, 1H, H-4) 3.68 (~t, J=5.0, 2H, CH$_2$OH), 4.1–4.2 (m, overlapping with SCH$_2$, 2H, H-5 and CH$_3$CHO), 4.14 (ABq, J$_{AB}$=14.08 Hz, Δv=35.7 Hz, 2H, SCH$_2$), 4.74 (m, 2H, CH$_2$ of allyl), 5.2–5.5 and 5.9–6.1 (2×m, 2H and 1H, CH of allyl),7.21 (m, 1H, H-5 of pyridine), 7.42 (d, J=7.8 Hz, 1H, H-3 of pyridine), 7.69 (m, 1H, H-4 of pyridine) and 8.5 ppm (m, 1H, H-6 of pyridine).

B. Potassium (4R,5S,6S)-6-[(1'R)-1'-hydroxyethyl]-4-(4"-hydroxybutyl)-3-[(pyridin-2-yl)methylthio]-7-oxo-1-azabicyclo[3.2.0]hept-2-ene-2-carboxylate

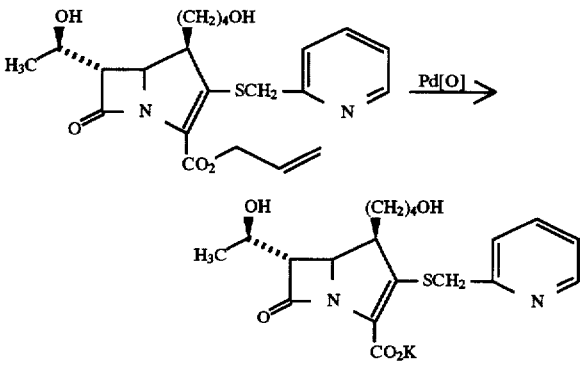

A solution of allyl (4R,5S,6S)-6-[(1'R)-1'-hydroxyethyl]-4-(4"-hydroxybutyl)-3-[(pyridin-2-yl)methylthio]-7-oxo-1-azabicyclo[3.2.0]hept-2-ene-2-carboxylate (0.20 g, 0.46 mmol) in dry dichloromethane (10 mL) was treated at 22° C. and under nitrogen with triphenylphosphine (0.020 g), tetrakis (triphenylphosphine) palladium[O] (0.020 g) and 1.0 mL (0.5 mmol) of a 0.5M solution of potassium 2-ethylhexanoate in ethyl acetate. After 20 min, the reaction mixture was extracted with water (3×10 mL) and the combined aqueous extracts were maintained under vacuum to remove traces of organic solvent. Chromatography on reversed phase silica gel (μ-Bondapak C-18, 3.5×6.5 cm, elution 0–5% CH$_3$CN in water) gave 0.151 g (75%) of the title compound as a white amorphous solid after freeze drying: [α]$_D^{22}$−4.1° (c 1.0, H$_2$O).

Purity by HPLC: 99% (μ-Bondapak C-18, 3.9 mm×30 cm, elution 5% CH$_3$CN-H$_2$O pH 7.4 phosphate buffer, flow rate 2 mL/min, uv detector 304 nm, retention time 10.0 min.

UV (H$_2$O, pH 7.4 phosphate buffer) λ$_{max}$: 266 (7,243) and 306 nm (10,819);

IR (KBr) $v_{max}$: 1750 (C=O of β-lactam) and 1590 cm$^{-1}$ (C=O of carboxylate);

$^1$H NMR (200 MHz, D$_2$O) δ: 1.28 (d, J=6.33 Hz, 3H, CH$_3$CHO), 1.1–1.7 (m, 6H, CH$_2$CH$_2$CH$_2$CH$_2$OH) 3.13 (m, 1H, H-4) 3.32 (dd, J$_{H6,H5}$=2.50 Hz, J$_{H6,H1'}$=5.93 Hz, 1H, H-6), 3.56 (t, J=6.3 Hz, CH$_2$OH), 4.14 (ABq, J$_{AB}$=14.5 Hz, Δv=24.6 Hz, 2H, SCH$_2$), 4.0–4.3 (m overlapping with SCH$_2$, 2H, H-5 and CH$_3$CHO), 7.37 (m, 1H, H-5 of pyridine), 7.52 (d, J=7.9 Hz, 1H, H-3 of pyridine), 7.86 (m, 1H, H-4 of pyridine) and 8.47 ppm (d, J=4.9 Hz, 1H, H-6 of pyridine).

EXAMPLE 14

(4R,5S,6S)-4-[4"-(N-Formimidoyl)aminobutyl]-6-[(1'R)-1'-hydroxyethyl]-3-[(pyridin-2-yl)methylthio]-7-oxo-1-azabicyclo[3.2.0]-hept-2-ene-2-carboxylic acid

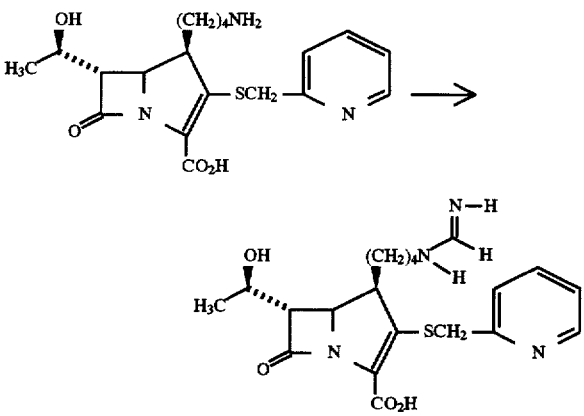

A solution of (4R,5S,6S)-4-(4"-aminobutyl)-6-[(1'R)-1'-hydroxyethyl]-3-[(pyridin-2-yl)methylthio]-7-oxo-1-azabicyclo[3.2.0]hept-2-ene-2-carboxylic acid (0.098 g, 0.25 mmol) in 25 mL of 0.04M pH 7.0 phosphate buffer at 0° C., was adjusted to pH 8.5 with 0.1M sodium hydroxide. Benzylformimidate hydrochloride (0.43 g, 2.5 mmol) was then added in small portions (~10min) while maintaining the pH around 8.3 with 0.1M NaOH. After 15 min at 0°–5° C., the pH of the solution was adjusted to 7.0 with 0.1M HCl, and the aqueous phase was washed with EtOAc. The aqueous phase was then maintained under vacuum to remove traces of organic solvent and then chromatographed on reversed phase silica gel (μ-Bondapak C-18, 3.5×6.5 cm, elution with a gradient of acetonitrile 0–5% in water). Lyophilization of the UV active fractions gave 0.076 g (72%) of the title compound as a white amorphous powder: [α]$_D^{22}$+2.4° (c 1.0, H$_2$O).

Purity by HPLC: 97.9% on μ-Bondapak c-18, 3.9 mm×30 cm, elution 10% CH$_3$CN-H$_2$O, pH 7.4 phosphate buffer, flow rate 1 mL/min, uv detector 306 nm, retention time 8.68 min.

UV (H$_2$O, pH 7.4 phosphate buffer) λ$_{max}$: 266 (6,680) and 306 nm (8,980);

IR (KBr) $v_{max}$: 1758 (C=O of β-lactam), 1715 and 1590 (C=O of carboxylate);

$^1$H NMR (200 MHz, D$_2$O) δ: 1.28 (d, J=6.31 Hz, CH$_3$CHO), 1.2–1.7 (m, 6H, CH$_2$CH$_2$CH$_2$CH$_2$NH), 3.16 (~t, 1H, H-4), 3.3 (m, 3H, H-6 and CH$_2$NHCH=NH overlapping), 4.0–4.3 (m, 4H, H-5, CH$_3$CHO and SCH$_2$ overlapping), 7.37 (m, 1H, H-5 of pyridine), 7.53 (d, J=7.9 Hz, 1H, H-3 of pyridine), 7.79 (s, 1H, NH—CH=NH), 7.86(m, 1H, H-4 of pyridine) and 8.47 ppm (d, J=4.4 Hz, 1H, H-6 of pyridine).

EXAMPLE 15

(4R,5S,6S)-4-[2"-(N-Guanidinyl)aminopropyl]-6-[(1'R)-1'-hydroxyethyl]-3-[(pyridin-2-yl)methylthio]-7-oxo-1-azabicyclo[3.2.0]hept-2-ene-2-carboxylic acid

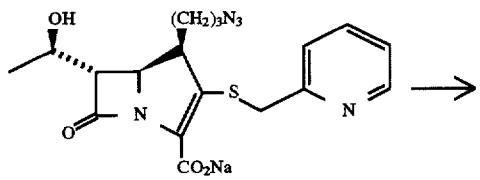

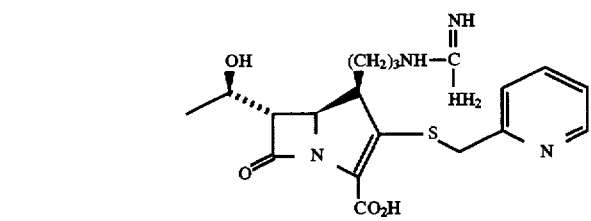

A solution of sodium (4R,5S,6S)-4-(3"-azidopropyl)-6-[(1'R)-1'-hydroxyethyl]-3-[(pyridin-2-yl)methylthio]-7-oxo-1-azabicyclo[3.2.0]hept-2-ene-2-carboxylate (120 mg, 0.28 mmol) [obtained by treating the compound of Example 7, Step H by the general procedure described in Example 6, Step D] in a 0.1M aqueous pH 5.9 phosphate buffer (8.4 mL, 0.84 mmol), water (8 mL) was shaken in a Parr hydrogenator at 40–50 psi hydrogen for 90 min at 5° C. to 15° C. (temperature at the end of the reaction) using 30% Pd on Celite (60 mg) as catalyst. The catalyst was removed by filtration and the pH of the aqueous solution was adjusted to 8.5 with 0.1N aqueous NaOH solution. To this solution was added at 5° C. (ice bath) aminoiminomethanesulfonic acid (360 mg, 3.0 mmol) and the pH was kept at 8–8.5 by addition of the 0.10N aqueous NaOH solution. This mixture was stirred for 30 min and then neutralized to pH 7.0 with a 0.1N aqueous HCl solution. It was passed twice through a $C_{18}$ µBondapak (6 g and 3 g) column ($H_2O \rightarrow 15\%$ $CH_3CN/H_2O$) to give the title compound (15 mg, 13%).

Purity by HPLC: 100% (304 nm, 10% $CH_3CN/KH_2PO_4$ 0.01M, 7.4), r.t. 7.3 min;

UV ($H_2O$) $\lambda_{max}$: 266 (5830), 306 (8250);

IR (Nujol) $\nu_{max}$: 3500–3000 (OH and $NH_2$), 1755, 1590 (C=O), and 1660, 1630 cm$^{-1}$ (C=N);

1H NMR ($D_2O$, 200 MHz) δ: 8.47–8.45 (1H, m, aromatic-H), 7.9–7.81 (1H, m, aromatic-H), 7.54–7.50 (1H, bd, J=7.9 Hz, aromatic-H), 7.40–7.34 (1H, m, aromatic-H), 4.25–4.16 (1H, m, H-1'), 4.22, 4.17, 4.10, 4.03 (2H, ABq, J=14.4 Hz, $CH_2$ pyridine), 4.06 (≈0.5H, d, J=2.3 Hz, part of H-5), 3.24 (1H, dd, J=2.7 Hz, J=6.3 Hz, H-6), 3.2–3.1 (2H, m, $CH_2$—N), 3.27–3.1 (1H, m, hidden H-4), 1.7–1.1 (4H, m, $CH_2CH_2$) and 1.28 (3H, d, J=6.3 Hz, $CH_3$).

EXAMPLE 16

Sodium (4R,5S,6S)-6-[(1'R)-1'-hydroxyethyl]-4-(2"-methylcarbamoyloxyethyl)-3-[(pyridin-2-yl)methylthio]-7-oxo-1-azabicyclo[3.2.0]hept-2-ene-2-carboxylate

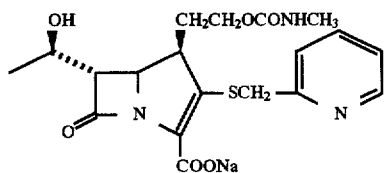

A. Allyl (4R,5S,6S)-6-[(1'R)-1'-(tert-butyldimethylsilyloxyethyl]-4-(2"-methylcarbamoyloxyethyl)-3-[(pyridin-2-yl)-methylthio]-7-oxo-1-azabicyclo[3.2.0]hept-2-ene-2-carboxylate

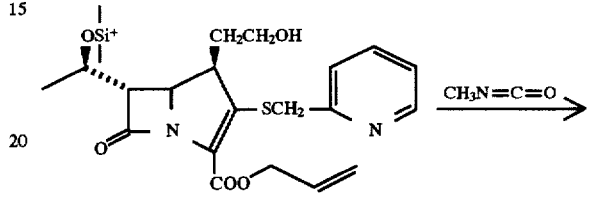

To a cold (0° C.) solution of allyl (4R,5S,6S)-[(1'R)-1'-(tert-butyldimethylsilyloxyethyl)]-4-(2"-hydroxyethyl)-3-[(pyridin-2-yl)methylthio]-7-oxo-1-azabicyclo[3.2.0]hept-2-ene-2-carboxylate (0.27 g, 0.52 mmol) prepared in Example 6, Step A in $CH_2Cl_2$ (5 mL), under Argon, was added methyl isocyanate (0.31 mL, 5.23 mmol). The reaction mixture was stirred between 0° and 5° C. for 48 h at which time ~10% of the starting material remained unreacted. The solvent was evaporated to give a foam which was chromatographed on silica (2.5×9 cm) packed in $CH_2Cl_2$ and eluted with a mixture of $CH_2Cl_2$ and EtOAc (1:1, gradient elution) to give the title compound (0.26 g, 87%).

$^1$H NMR (200 MHz, $CDCl_3$ 7.24) δ: 0.02 (s, 3H, $SiCH_3$), 0.04 (s, 3H, $SiCH_3$), 0.82 (s, 9H, $SiC(CH_3)_3$), 1.24 (d, $CH_3$, $J_{CH3, 1}$=6.14 Hz), 1.69–1.85 (m, 1H, $CH_2$), 2.05–2.18 (m, 1H, $CH_2$), 2.79 (d, $NHCH_3$, J=4.81 Hz), 3.16 (dd, H-6, $J_{5,6}$=2.33 Hz, $J_{6,1}$=6.74 Hz), 3.47 (t, H-4, J=9.69 Hz), 3.84–4.39 (m, 6H, $CH_2O$, $CHOH$, H-5, $SCH_2$), 4.57–4.83 (m, $OCH_2$, allyl), 5.18–5.46 (m, =$CH_2$, allyl), 5.8–6.02 (m, $CH$=, allyl), 7.19 (m, H-5, py, $J_{4,5}$=7.72 Hz, $J_{5,6}$=4.77 Hz), 7.48 (d, H-3, py, $J_{3,4}$=7.82 Hz), 7.69 (dt, H-4, py, $J_{4,6}$=1.64 Hz), 8.45 (dd, H-6, py).

B. Allyl (4R,5S,6S)-6-[(1'R)-1'-hydroxyethyl]-4-(2"-methylcarbamoyloxyethyl)-3-[(pyridin-2-yl)methylthio]-7-oxo-1-azabicyclo[3.2.0]hept-2-ene-2-carboxylate

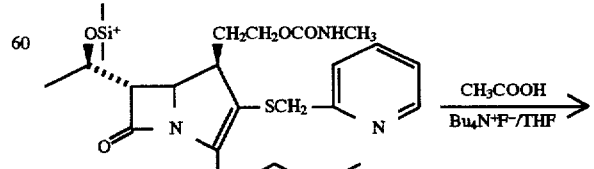

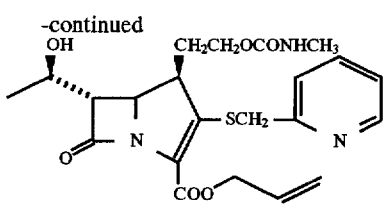

A cold (0° C.) solution of allyl (4R,5S,6S)-6-[(1'R)-1'-(tert-butyldimethylsilyloxyethyl)]-4-(2"-methylcarbamoyloxyethyl)-3-[(pyridin-2-yl)methylthio]-7-oxo-1-azabicyclo[3.2.0]hept-2-ene-2-carboxylate (0.25 g, 0.43 mmol) in dry THF (5 mL) was treated with acetic acid (0.15 mL, 2.6 mmol) followed by a 1M solution of tetrabutylammonium fluoride in THF (1.3 mL, 1.3 mmol). The mixture was stirred between 0° and 5° C. for 120 h at which time about half the starting material remained unreacted. The mixture was neutralized at 0° C. with a 1M NaHCO$_3$ solution (2.6 mL, 2.6 mmol) and extracted with EtOAc (3×50 mL). The combined organic extract was washed successively with a cold 1M NaHCO$_3$ solution, water and brine, dried (MgSO$_4$) and solvent evaporated to a solid plus syrup which was chromatographed on silica (2.5×9 cm) packed in CH$_2$Cl$_2$ and eluted first with a mixture of CH$_2$Cl$_2$ and EtOAc (gradient elution), then with EtOAc and finally with a mixture of CH$_3$CN and CH$_2$Cl$_2$ (1:1, gradient elution) to give the title compound as a white powder (0.1 g, 50%).

$^1$H NMR (200 MHz, CDCl$_3$ 7.24) δ: 1.37 (d, CH$_3$, J$_{CH3,1}$=6.25 Hz), 1.66–1.84 (m, 1H, CH$_2$), 2.11–2.27 (m, 1H, CH$_2$), 2.78 (d, NHC$\underline{H}_3$, J=4.95 Hz), 3.32 (dd, H-6, J$_{5,6}$=2.52 Hz, J$_{6,1}$=8.47 Hz), 3.45 (t, H-4, J=10.26 Hz), 3.93–4.31 (m, 6H, C$\underline{H}_2$O, C$\underline{H}$OH, H-5, SC$\underline{H}_2$), 4.59–4.87 (m, OC$\underline{H}_2$, allyl), 5.19–5.48 (m, =CH$_2$, allyl), 5.84–6.04 (m, CH=, allyl), 7.19 (m, H-5, py, J$_{4,5}$=7.71 Hz, J$_{5,6}$=5.31 Hz), 7.41 (d, H-3, py, J$_{3,4}$=7.85 Hz), 7.66 (dt, H-4, py, J$_{4,6}$=1.77 Hz), 8.45 (m, H-6, py, J$_{3,6}$=0.96 Hz).

C. Sodium (4R,5S,6S)-6-[(1'R)-1'-hydroxyethyl]-4-(2"-methylcarbamoyloxyethyl)-3-[(pyridin-2-yl)methylthio]-7-oxo-1-azabicyclo[3.2.0]hept-2-ene-2-carboxylate

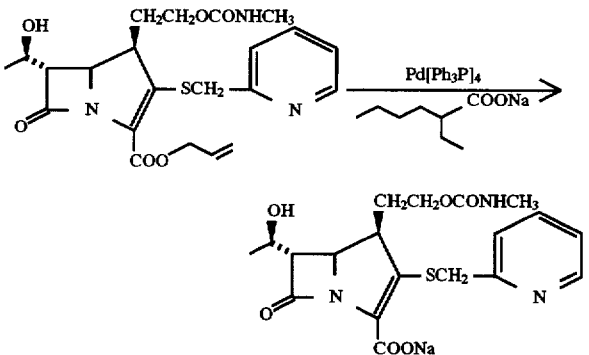

A cold (0° C.) solution of allyl (4R,5S,6S)-6-[(1'R)-1'-hydroxyethyl]-4-(2"-methylcarbamoyloxyethyl)-3-[(pyridin-2-yl)methylthio]-7-oxo-1-azabicyclo[3.2.0]hept-2-ene-2-carboxylate (0.094 g, 0.204 mmol) in CH$_2$Cl$_2$ (10 mL) was treated with Pd[Ph$_3$P]$_4$ (0.03 g, 0.026 mmol) followed by a 0.5M solution of sodium 2-ethylhexanoate in EtOAc (0.45 mL, 0.224 mmol). The mixture was stirred at 0° C. for 2 h and then extracted with water (3×15 mL). The combined aqueous phase was passed through a column of µ-Bondapak C-18 reverse phase silica (2.5×9 cm). The title compound was eluted with a mixture of water and CH$_3$CN (95:5, gradient elution) and was obtained as a white fluffy solid after lyophilization (0.062 g, 69%).

Purity by HPLC: 99.7%, UV detection at 304 nm on µ-Bondapak C-18 (4 mm×30 cm), 8% CH$_3$CN in pH 7.4 phosphate buffer, flow rate 1 mL/min, retention time 9.04 min.

UV (pH 7.4) λ$_{max}$: 304 (8778).

IR (nujol) ν$_{max}$: 1750 cm$^{-1}$ (C=O, β-lactam), 1710 cm$^{-1}$ (NHCO).

$^1$H NMR (200 MHz, D$_2$O) δ: 1.305 (d, CH$_3$, J$_{CH3,1}$=6.38 Hz), 1.6–1.73 (m, 1H, CH$_2$), 2.00–2.07 (m, 1H, CH$_2$), 2.71 (s, NCH$_3$), 3.23 (t, H-4, J=9.7 Hz), 3.48 (dd, H-6, J$_{5,6}$=2.61 Hz, J$_{6,1}$=5.84 Hz), 3.93–4.31 (m, 6H, C$\underline{H}_2$O , C$\underline{H}$OH, H-5, SC$\underline{H}_2$), 7.39 (dd, H-5, py, J$_{5,6}$=4.84 Hz, J$_{4,5}$=7.74 Hz), 7.52 (d, H-3, py, J$_{3,4}$=7.84 Hz), 7.89 (dt, H-4, py, J$_{4,6}$=1.72 Hz), 8.48 (d, H-6, py).

EXAMPLE 17

(4R,5S,6S)-4-(4"-Aminobutyl)-3-[(2-cyanoethyl)thio]-6-[(1'R)-1'-hydroxyethyl]-7-oxo-1-azabicyclo[3.2.0]hept-2-ene-2-carboxylic acid

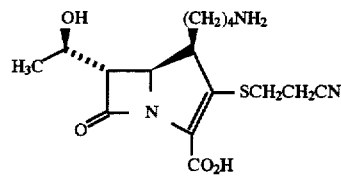

A. Allyl (4R,5S,6S)-6-[(1'R)-1'-tert-butyldimethylsilyloxyethyl]-4-(4"-tert-butyldimethylsilyloxybutyl)-3-[(2-cyanoethyl)thio]-7-oxo-1-azabicyclo[3.2.0]hept-2-ene-2-carboxylate

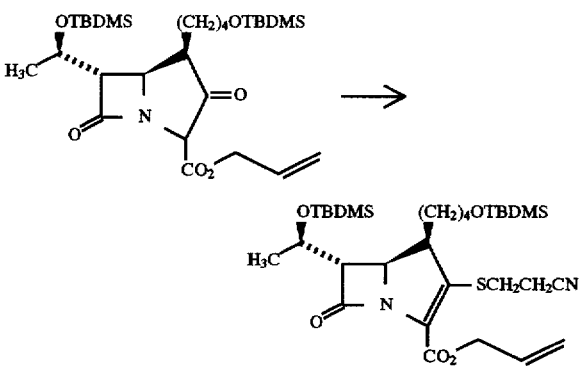

A solution of allyl (4R,5R,6S)-6-[(1'R)-1'-tert-butyldimethylsilyloxyethyl]-4-(4"-tert-butyldimethylsilyloxybutyl)-3,7-dioxo-1-azabicyclo[3.2.0]heptane-2-carboxylate (6.87 mmol, prepared from 4.0 g, 6.87 mmol of diazo precursor according to the procedure of Example 12, Step I), in dry CH$_3$CN (40 mL) was treated at 0°–5° C. and under nitrogen with diphenyl chlorophosphate (1.56 mL, 7.52 mmol) and N,N-diisopropylethylamine (1.31 mL, 7.52 mmol) added simultaneously over 5 min. A small crystal of 4-N,N-dimethylaminopyridine was then added and the mixture was stirred for 1 h. The solution was then cooled to −20° C. and treated with β-mercaptopropionitrile [L. Bauer and T. L. Welsh, J. Org. Chem., 26, 1443 (1961)] (1.23 g, 14.1 mmol) in acetonitrile (5 mL), followed by N,N-diisopropylethylamine (1.31 mL, 7.52 mmol). The temperature of the solution was then allowed to reach 0°–5° C., and the mixture was stirred for 2 h. The reaction mixture was then diluted with EtOAc, washed with saturated aqueous NaHCO$_3$, brine and dried (MgSO$_4$). Evaporation of the solvent gave an oil which was chromatographed on silica gel (5×9 cm). Elution with a gradient of EtOAc (0–5%) in toluene gave 3.42 g (80%) of the title compound as an oil.

IR (NaCl, film) $v_{max}$: 2260 (CN), 1778 (C=O of β-lactam) and 1715 cm$^{-1}$ (C=O of ester);

$^1$H NMR (200 MHz, CDCl$_3$) δ: 0.04 and 0.08 (2×s, 2×6H, SiCH$_3$), 0.88 and 0.89 (2×s, 2×9H, Si tert-Bu) 1.27 (d, J=6.14 Hz, 3H, CH$_3$CHO), 1.3–1.8 (m, 6H, CH$_2$-1, 2 and 3 of butyl), 2.5–3.2 (m, 6H, SCH$_2$CH$_2$CN, H-4 and H-6 overlapping), 3.61 (m, 2H, CH$_2$OSi), 4.1–4.3 (m, 2H, H-5 and CH$_3$CHO overlapping), 4.7 (m, 2H, CH$_2$ of allyl), 5.2–5.5 and 5.9–6.1 ppm (2×m, 2H and 1H, CH of allyl).

B. Allyl (4R,5S,6S)-6-[(1'R)-1'-tert-butyldimethylsilyloxyethyl]-3-[(2-cyanoethyl)thio]-4-(4"-hydroxybutyl)-7-oxo-1-azabicyclo[3.2.0]hept-2-ene-2-carboxylate

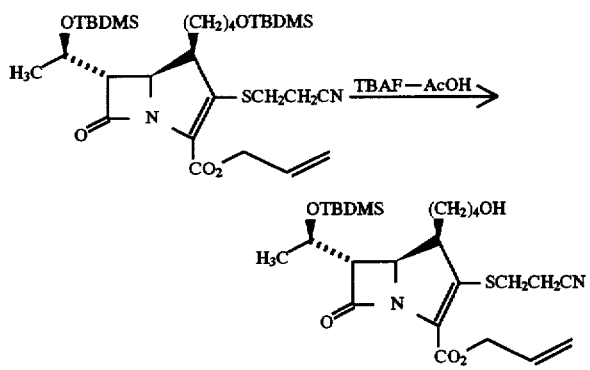

A solution of allyl (4R,5S,6S)-6-[(1'R)-1'-tert-butyldimethylsilyloxyethyl]-4-(4"-tert-butyldimethylsilyloxybutyl)-3-[(2-cyanoethyl)thio]-7-oxo-1-azabicyclo[3.2.0]hept-2-ene-2-carboxylate (3.42 g, 5.49 mmol) in dry tetrahydrofuran (75 mL) was treated at 0°–5° C. with acetic acid (1.9 mL, 33.2 mmol) followed by 16.5 mL (16.5 mmol) of a 1.0M solution of tetrabutylammonium fluoride in tetrahydrofuran. After 24 h at 4° C., the reaction mixture was diluted with EtOAc, washed with saturated aqueous NaHCO$_3$, brine and dried (MgSO$_4$). Evaporation of the solvent gave an oil which was chromatographed on silica gel (5×11 cm). Elution with a mixture of toluene and EtOAc (1:1 to AcOEt) gave 1.67 g (68%) of the title compound as an oil.

IR (NaCl, film) $v_{max}$: 3500 (OH), 2250 (CN), 1775 (C=O of β-lactam) and 1710 cm$^{-1}$ (C=O of ester);

$^1$H NMR (200 MHz, CDCl$_3$) δ: 0.08 (s, 6H, SiCH$_3$), 0.88 (s, 9H, Sit-Bu), 1.29 (d, J=6.12 Hz, 3H, CH$_3$CHO), 1.2–1.9 (m, 6H, CH$_2$-1, 2 and 3 of butyl), 2.68 (m, 2H, CH$_2$CN), 2.7–3.2 (m, 3H, H-4 and SCH$_2$), 3.21 (dd, $J_{H6,H5}$=2.62 Hz, $J_{H6,H1}$=6.78 Hz, 1H, H-6), 3.66 (m, 2H, CH$_2$OH), 4.2 (m, 2H, H-5 and CH$_3$CHO overlapping), 4.74 (m, 2H, CH$_2$ of allyl), 5.2–5.5 and 5.9–6.1 ppm (2×m, 2H and 1H, CH of allyl).

C. Allyl (4R,5S,6S)-4-(4"-azidobutyl)-6-[(1'R)-1'-tert-butyldimethylsilyloxyethyl]-3-[(2-cyanoethyl)thio]-7-oxo-1-azabicyclo[3.2.0]hept-2-ene-2-carboxylate

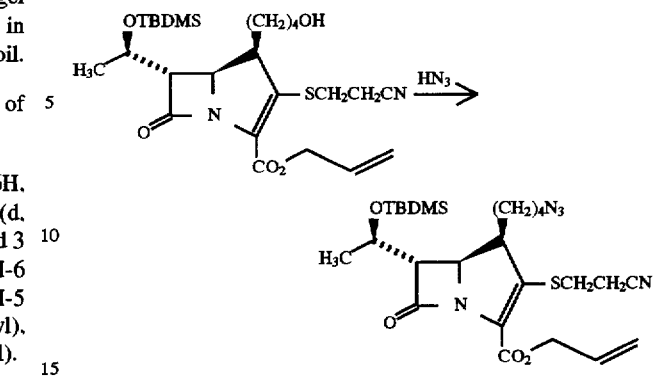

A solution of allyl (4R,5S,6S)-6-[(1'R)-1'-tert-butyldimethylsilyloxyethyl]-3-[(2-cyanoethyl)thio]-4-(4"-hydroxybutyl)-7-oxo-1-azabicyclo[3.2.0]hept-2-ene-2-carboxylate (1.67 g, 3.28 mmol) in dry tetrahydrofuran (250 mL) was treated at –20° C. with triphenylphosphine (1.38 g, 5.26 mmol) and 7.6 mL (5.7 mmol) of a 0.75M solution of hydrazoic acid in toluene. Then diethyl azodicarboxylate (0.90 mL, 5.7 mmol) was added dropwise over 5 min and the resulting mixture was stirred at the same temperature for 30 min. The reaction mixture was quenched by addition of EtOAc and saturated aqueous sodium bicarbonate. The organic phase was washed with brine, dried (MgSO$_4$) and concentrated under reduced pressure. The residual oil was triturated with toluene (25 mL) and filtered to remove the crystalline diethyl hydrazine dicarboxylate. After a similar treatment with diethyl ether to remove the triphenylphosphine oxide, the filtrate was chromatographed on silica gel (4.5×11 cm). Elution with a mixture of toluene and EtOAc (8:2) gave 1.40 g (80%) of the title compound as an oil.

IR (NaC$_1$, film) $v_{max}$: 2250 (CN), 2100 (N$_3$), 1765 (C=O of β-lactam) and 1710 cm$^{-1}$ (C=O of ester);

$^1$H NMR (200 MHz, CDCl$_3$) δ: 0.08 (s, 6H, SiCH$_3$), 0.89 (s, 9H, t-Bu), 1.30 (d, J=6.12 Hz, 3H, CH$_3$CHO), 1.2–1.9 (m, 6H, CH$_2$-1, 2 and 3 of butyl), 2.68 (m, 2H, CH$_2$CN), 2.9–3.2 (m, 3H, H-4 and SCH$_2$), 3.17 (dd, $J_{H6, H5}$=2.58 Hz, $J_{H6,H1}$=6.9 Hz, H-6), 3.32 (broad t, J=6.0 Hz, 2H, CH$_2$N$_3$), 4.1–4.3 (m, 2H, H-5 and CH$_3$CHO overlapping), 4.74 (m, 2H, CH$_2$ of allyl), 5.2–5.5 and 5.9–6.1 ppm (2×m, 2H and 1H, CH of allyl).

D. Allyl (4R,5S,6S)-4-(4"-azidobutyl)-3-[(2-cyanoethyl)thio]-6-[(1'R)-1'-hydroxyethyl]-7-oxo-1-azabicyclo[3.2.0]hept-2-ene-2-carboxylate

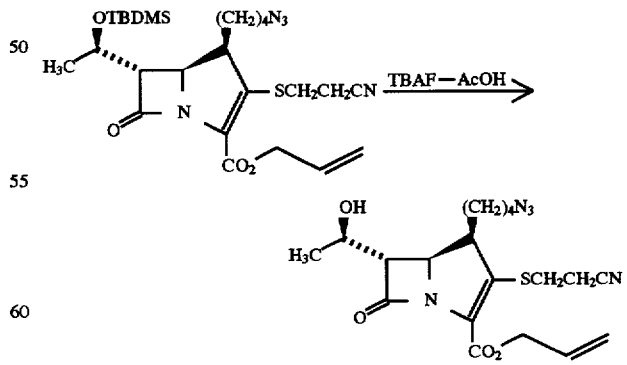

A solution of allyl (4R,5S,6S)-4-(4"-azidobutyl)-6-[(1'R)-1'-tert-butyldimethylsilyloxyethyl]-3-[(2-cyanoethyl)thio]-7-oxo-1-azabicyclo[3.2.0]hept-2-ene-2-carboxylate (1.40 g, 2.62 mmol) in dry tetrahydrofuran (40 mL) was treated at 0°–5° C. with acetic acid (1.0 mL, 17.5 mmol) followed by 8.4 mL (8.4 mmol) of a 1.0M solution of tetrabutylammonium fluoride in tetrahydrofuran. The solution was stored at 5° C. for 10 days. The reaction mixture was then diluted with cold EtOAc, washed with saturated NaHCO$_3$, brine and dried (MgSO$_4$). Evaporation of the solvent gave an oil which was chromatographed on silica gel (4.5×11 cm) using a gradient of EtOAc in toluene (1:1 to EtOAc) as eluent.

The early fractions gave 0.23 g (16%) of recovered starting material. The following fractions then gave 0.78 g (71%) of the title compound as an oil.

IR (NaCl, film) $v_{max}$: 3500 (OH), 2250 (CN), 2100 (N$_3$), 1770 (C=O of β-lactam) and 1710 cm$^{-1}$ (C=O of ester);

$^1$H NMR (200 MHz, CDCl$_3$) δ: 1.40 (d, J=6.26 Hz, 3H, C$\underline{H}_3$CHO), 1.4–1.8 (m, 6H, CH$_2$-1, 2 and 3 of butyl), 1.83 (d, J=5.1 Hz, 1H, OH), 2.9–3.3 (m, 3H, H-4 and SCH$_2$), 3.22 (dd, J$_{H6,H5}$=2.75 Hz, J$_{H6,H1}$=7.37 Hz, 1H, H-6), 3.34 (broad t, J=6.0 Hz, 2H, CH$_2$N$_3$), 4.25 (m overlapping with H-5, 1H, CH$_3$C$\underline{H}$O), 4.28 (dd, J$_{H5,H6}$=2.75 Hz, J$_{H5,H4}$=9.58 Hz, 1H, H-5), 4.77 (m, 2H, CH$_2$ of allyl), 5.2–5.5 and 5.9–6.1 ppm (2×m, 2H and 1H, CH of allyl).

E. (4R,5S,6S)-4-(4"-Aminobutyl)-3-[(2-cyanoethyl)thio]-6-[(1'R)-1'-hydroxyethyl]-7-oxo-1-azabicyclo[3.2.0]hept-2-ene-2-carboxylic acid

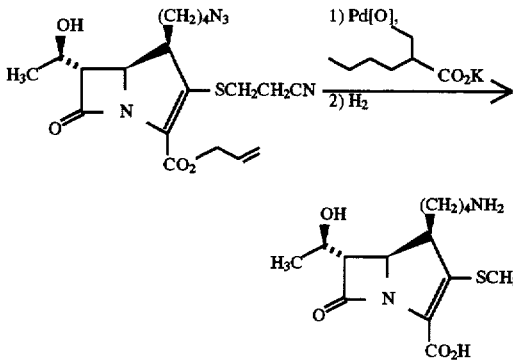

A solution of allyl (4R,5S,6S)-4-(4"-azidoethyl)-3-[(2-cyanoethyl)thio]-6-[(1'R)-1'-hydroxyethyl]-7-oxo-1-azabicyclo[3.2.0]hept-2-ene-2-carboxylate (0.78 g, 1.86 mmol) in dry CH$_2$Cl$_2$ (50 mL) was treated at 0°–5° C. and under nitrogen, with tetrakis(triphenylphosphine)palladium [O] (0.1 g) and 4.1 mL (2.05 mmol) of a 0.5M solution of potassium 2-ethylhexanoate in EtOAc. After 30 min, the reaction mixture was diluted with diethyl ether (150 mL) and extracted with 0.05M pH 7.0 aqueous phosphate buffer (3×75 mL). The combined aqueous phase was adjusted to pH 5.8 with 1M NaH$_2$PO$_4$ and the traces of organic solvent were removed under vacuum. The aqueous solution was hydrogenated at 0°–5° C. over 30% palladium on Celite under 45 psi for 2 h. The catalyst was then filtered on a Celite pad and washed with water. HPLC (μ-Bondapak C-18, elution 5% CH$_3$CN—H$_2$O pH 6.8 phosphate buffer) indicated a 70:30 mixture of the 4"-aminobutyl compound (eluted first) and the 4-hydroxybutyl compound.

The solution was then chromatographed rapidly on reversed phase silica gel (μ-Bondapak C-18, 4×7 cm, elution H$_2$O—CH$_3$CN 5%) to remove the inorganic salts. The UV active fractions were lyophilized and chromatographed on the same column using 5% CH$_3$CN—H$_2$O, 0.01M pH 6.8 phosphate buffer as eluent. Two main fractions were obtained which were again desalted on reversed phase silica gel. Lyophilisation of the first fraction gave 0.33 g (50%) of the title 4"-aminobutyl compound as a white amorphous powder. By HPLC and $^1$H NMR this fraction was ~90% pure and was contaminated by some 4"-hydroxybutyl compound and other impurities.

The second fraction gave 0.102 g (14%) of the 4-hydroxybutyl compound as a white amorphous powder, 90% pure by HPLC and $^1$H NMR which is used in Example 18.

Careful chromatography of the above, 4'-aminobutyl compound on reversed phase (μ-Bondapak C-18, same conditions as above) gave pure fractions of the title compound: [α]$_D^{22}$+60.4° (c 1.0, H$_2$O).

Purity by HPLC: 98.5% on μ-Bondapak C-18, 3.9 mm×30 cm, elution 5% CH$_3$CN—H$_2$O pH 7.4 phosphate buffer, flow rate 1 mL/min, UV detector 306 nm, retention time 5.25 min;

UV (H$_2$O, pH 7.4 phosphate buffer) λ$_{max}$: 300 nm (10, 267);

IR (KBr) $v_{max}$: 2250 (CN), 1760 (C=O of β-lactam) and 1690 cm$^{-1}$ (C=O of carboxylate);

$^1$H NMR (200 MHz, D$_2$O) δ: 1.33 (d, J=6.38 Hz, 1H, C$\underline{H}_3$CHO), 1.3–1.9 (m, 6H, CH$_2$-1, 2 and 3 of buryl), 2.86 (m, 2H, CH$_2$CN), 2.9–3.2 (m, 2H, SCH$_2$), 3.02 (t, J=7.6 Hz, 2H, C$\underline{H}_2$NH$_2$), 3.4 (m, J$_{H6,H5}$=2.66 Hz, 2H, H-6 and H-4 overlapping), and 4.3 ppm (m, 2H, H-5 and CH$_3$C$\underline{H}$O overlapping).

EXAMPLE 18

Potassium (4R,5S,6S)-3-[(2-cyanoethyl)thio]-4-(4"-hydroxybutyl)-6-[(1'R)-1'-hydroxyethyl]-7-oxo-1-azabicyclo[3.2.0]hept-2-ene-2-carboxylate

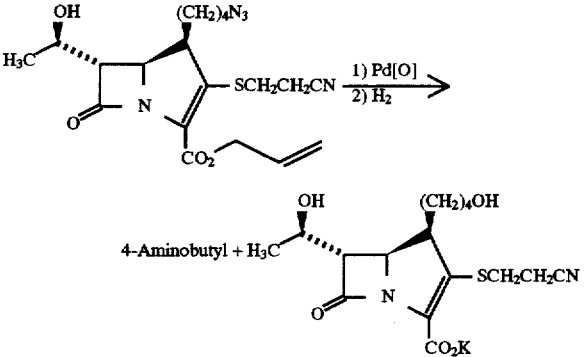

The crude fraction containing the 4"-hydroxybutyl compound (0.102 g, 90% pure) obtained by hydrogenation of the azido precursor in Example 17, Step E was purified by preparative HPLC (Zorbax ODS, Dupont, 21.2 mm×25 cm, elution 5% CH$_3$CN—H$_2$O pH 6.8 potassium phosphate buffer, UV detector) followed by desalting on μ-Bondapak C-18. Lyophilization gave 0.045 g (45% recovery) of the title compound as a white amorphous powder.

Purity by HPLC: 99% on μ-Bondapak c-18, 3.9 mm×30 cm, elution 10% CH$_3$CN—H$_2$O pH 7.4 phosphate buffer, flow rate 0.6 mL/min, uv detector 306 nm, retention time 6.93 min;

UV (H$_2$O, pH 7.4 phosphate buffer) λ$_{max}$: 302 nm (7,364);

IR (KBr) $v_{max}$: 2250 (CN) 1750 (C=O of β-lactam) and 1600 cm$^{-1}$ (C=O of carboxylate);

$^1$H NMR (200 MHz, D$_2$O) δ: 1.33 (d, J=6.41 Hz, 3H, C$\underline{H}_3$CHO), 1.3–2.0 (m, 6H, CH$_2$-1, 2 and 3 of butyl), 2.86 (m, 2H, CH$_2$CN), 2.8–3.3 (m, 2H, SCH$_2$), 3.35 (m, 1H, H-4), 3.43 (dd, J$_{H6,H5}$=2.59 Hz, J$_{H6,H1}$=6.0 Hz, 1H, H-6), 3.62 (t, J=6.3 Hz, 2H, CH$_2$OH), and 4.3 ppm (m, 2H, H-5 and CH$_3$C$\underline{H}$O overlapping).

EXAMPLE 19

(4R,5S,6S)-3-[(2-Cyanoethyl)thio]-4-[4"-(N-formimidoyl)amino-butyl]-6-[(1'R)-1'-hydroxyethyl]-7-oxo-1-azabicyclo[3.2.0]hept-2-ene-2-carboxylic acid

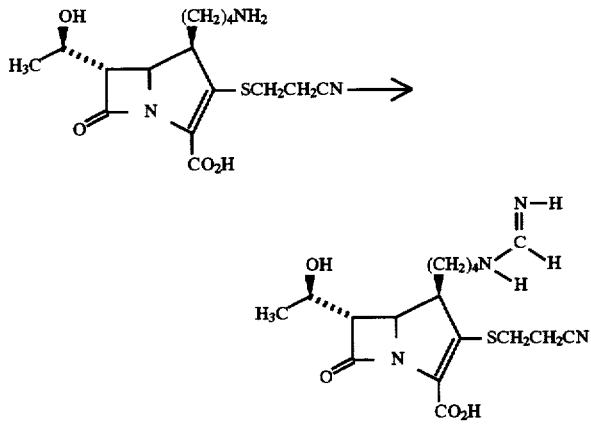

A cold (0°–5° C.) solution of (4R,5S,6S)-4-(4"-aminobutyl)-3-[(2-cyanoethyl)thio]-6-[(1'R)-1'-hydroxyethyl]-7-oxo-1-azabicyclo[3.2.0]hept-2-ene-2-carboxylic acid (0.113 g, 0.32 mmol) in 30 mL of 0.04M pH 7.0 phosphate buffer was adjusted to pH 8.5 with 0.1M NaOH. Then benzylformimidate hydrochloride (0.54 g, 3.17 mmol) was added in small portions while maintaining the pH at 8.0–8.5 with 0.1N NaOH (~10 min). After 10 min, the pH was adjusted to 7.0 with 0.1N HCl, and the reaction mixture was washed with EtOAc. The aqueous phase was maintained under vacuum to remove traces of organic solvent and then chromatographed on reversed phase silica gel (μ-Bondapak c-18, 3.5×7 cm). Elution with a gradient of acetonitrile (0–10%) in water gave 0.106 g (86%) of the title compound as a white amorphous powder after freeze drying: $[\alpha]_D^{22}$+53.5° (c 1.0, H$_2$O ).

Purity by HPLC: 93% on μ-Bondapak C-18, 3.9 mm×30 cm, elution 5% CH$_3$CN—H$_2$O pH 7.4 phosphate buffer, flow rate 1 mL/min, uv detector 300 nm, retention time 7.74 min.

UV (H$_2$O, pH 7.4 phosphate buffer) $\lambda_{max}$: 300 nm (10, 481);

IR (KBr) $\nu_{max}$: 2250 (CN), 1760 (C=O of β-lactam) and 1715 cm$^{-1}$ (C=O of carboxylate);

$^1$H NMR (200 MHz, D$_2$O) δ: 1.34 (d, J=6.34 Hz, 3H, CH$_3$CHO), 1.3–2.0 (m, 6H, CH$_2$-1, 2 and 3 of butyl), 2.8–2.9 (m, 2H, CH$_2$CN), 2.9–3.3 (m, 2H, SCH$_2$), 3.3–3.5 (m, 4H, H-4, H-6 and CH$_2$N), 4.3 (m, 2H, H-5 and CH$_3$CHO overlapping), and 7.81 ppm (s, 1H, CH=N).

EXAMPLE 20

(4R,5S,6S)-3-[(2-Cyanoethyl)thio]-4-(4"-N,N-dimethylaminobutyl)-6-[(1'R)-1'-hydroxyethyl]-7-oxo-1-azabicyclo[3.2.0]hept-2-ene-2-carboxylic acid

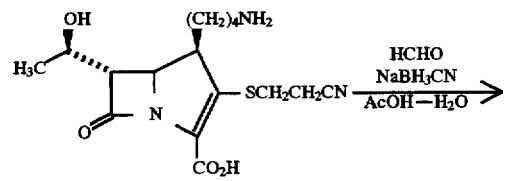

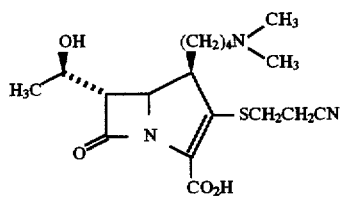

A solution of (4R,5S,6S)-4-(4"-aminobutyl)-3-[(2-cyanoethyl)thio]-6-[(1'R)-1'-hydroxyethyl]-7-oxo-1-azabicyclo[3.2.0]hept-2-ene-2-carboxylic acid (0.054 g, 0.15 mmol) in water (1 mL) at 0°–5° C., was diluted with acetonitrile (1 mL) and then treated with 37% aqueous formaldehyde (0.075 mL, 0.81 mmol) followed by sodium cyanoborohydride (0.024 g, 0.38 mmol) and one drop of acetic acid. After 15 min, the reaction mixture was quenched by the addition of 0.2M pH 6.0 phosphate buffer and the organic solvent was removed in vacuo. The aqueous phase was then chromatographed on reversed phase silica gel (μ-Bondapak C-18, 3.5×6.5 cm). Elution with a gradient of acetonitrile (0–10%) in water gave 0.016 g (27%) of the title compound as a white amorphous powder after lyophilization.

Purity by HPLC: 96% on μ-Bondapak C-18, 3.9 mm×30 cm, elution 5% CH$_3$CN—H$_2$O pH 7.0 phosphate buffer, flow rate 1 mL/min, UV detector 300 nm, retention time 10.9 min.

UV (H$_2$O, pH 7.4 phosphate buffer) $\lambda_{max}$: 300 nm (9,907);

IR (KBr) $\nu_{max}$: 2250 (weak CN), 1759 (C=O of β-lactam) and 1590 cm$^{-1}$ (C=O of carboxylate);

$^1$H NMR (200 MHz, D$_2$O) δ: 1.33 (d, J=6.37 Hz, 3H, CH$_3$CHO), 1.3–1.9 (m, 6H, CH$_2$-1, 2 and 3 of butyl), 2.87 (s, 6H, N(CH$_3$)$_2$), 2.87 (m overlapping with NCH$_3$, 2H, CH$_2$CN), 2.9–3.2 (m, 2H, SCH$_2$), 3.15 (~t overlapping with SCH$_2$, 2H CH$_2$N(CH$_3$)$_2$), 3.38 (dd, J$_{H6,H5}$=2.6 Hz, J$_{H6,H1}$= 6.25 Hz, 1H, H-6), 3.38 (m overlapping with H-6, 1H, H-4), and 4.27 ppm (m, 2H, H-5 and CH$_3$CHO).

EXAMPLE 21

Sodium (4R,5S,6S)-4-(3"-azidopropyl)-6-[(1'R)-1'-hydroxyethyl]-3-[(2-hydroxyethyl)thio]-7-oxo-1-azabicyclo[3.2.0]hept-2-ene-2-carboxylate

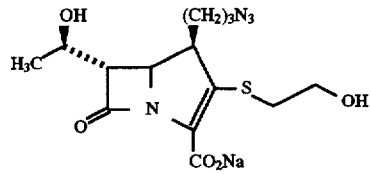

A. (3S,4R)-3-[(1'R)-1'-Hydroxyethyl]-4-[(1"R)-1"-(3-azidopropyl)-3"-diazo-3"-allyloxycarbonyl-2"-oxopropyl]azetidin-2-one

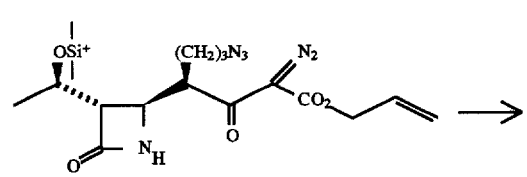

-continued

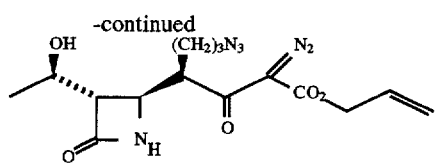

To a cold (ice bath) solution of (3S,4R)-3-[(1'R)-1'-tert-butyldimethylsilyloxyethyl]-4-[(1" R)-1"-(3-azidopropyl)-3"-diazo-3"-allyloxycarbonyl-2"-oxopropyl]azetidin-2-one (2.4 g, 5.0 mmol) from Example 7, Step E in EtOH (50 mL) was added a 2N aqueous HCl solution (7 mL). The ice bath was removed and the mixture was stirred for 20 h. The pH of the solution was adjusted to 7 with a 1M aqueous NaHCO₃ solution (15 mL) and ethanol was removed under vacuum. The residue obtained was diluted with EtOAc, washed with a 1M aqueous NaHCO₃ solution (18 mL), water (10 mL), brine (10 mL) and dried (MgSO₄). The residue was passed through a silica gel flash (40 g) column (5, 10, 20, 40, 60, 80% EtOAc/$CH_2Cl_2$) to give the title compound (1.7 g, 93%) as an oil that crystallized out.

IR ($CH_2Cl_2$) $v_{max}$: 3600, 3500 (OH) 3400 (NH) 2150 ($N_2$), 2100 ($N_3$), 1765, 1715 and 1650 cm$^{-1}$ (C=O);

$^1$H NMR (CDCl₃, 200 MHz) δ: 6.04–5.84 (1H, m, vinylic-H), 6.01 (1H, bs, NH), 5.42–5.29 (2H, m, vinylic-H), 4.75–4.63 (2H, m, $CH_2$vinyl), 4.19–4.01 (1H, m, H-1'), 4.02–3.89 (1H, m, H-1"), 3.83 (1H, dd, J=6.5 Hz, J=2.1 Hz, H-4), 3.31–3.25 (2H, m, $CH_2N_3$), 3.01 (1H, dd, J=1.9 Hz, J=6.9 Hz, H-3), 2.23 (1H, d, J=3.9 Hz, OH), 1.98–1.75 (1H, m, HCH), 1.73–1.48 (3H, m, $CH_2$—HCH) and 1.29 ppm (3H, d, J=6.3 Hz, $CH_3$).

B. Allyl (2R,4R,5R,6S)-4-(3"-azidopropyl)-6-[(1'R)-1'-hydroxyethyl]-3,7-dioxo-1-azabicyclo[3.2.0]heptane-2-carboxylate

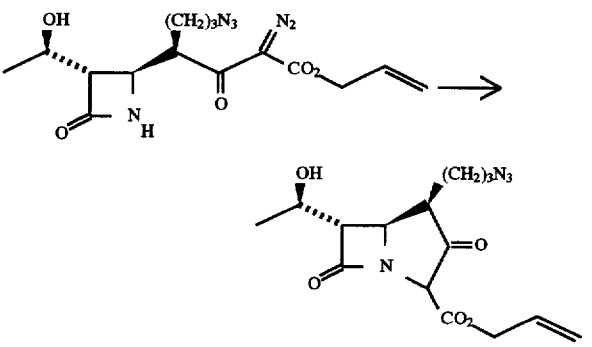

A solution of (3S,4R)-3-[(1'R)-1'-hydroxyethyl]-4-[(1" R)-1"-(3-azidopropyl)-3"-diazo-3"-allyloxycarbonyl-2"-oxopropyl]azetidin-2-one (1.46 g, 4.00 mmol) and Rh(OAc)₂ (56 mg) in benzene (140 mL) was heated under reflux for 40 min. Benzene was removed under vacuum to give the title compound (1.5 g, 100%) as an oil;

IR ($CH_2Cl_2$) $v_{max}$: 3610 (OH), 2100 ($N_3$), 1770 and 1745 cm$^{-1}$ (C=O);

$^1$H NMR (CDCl₃, 200 MHz) δ: 5.96–5.8 (1H, m, vinylic H), 5.39–5.25 (2H, m, vinylic H), 4.75–4.64 (2H, m, $CH_2$-vinylic), 4.66 (1H, s, H-2), 4.35–4.26 (1H, m, H-1'), 4.29 (1H, dd, J=2.2 Hz, J=8.1 Hz, H-5), 3.45–3.25 (2H, m, $CH_2N_3$), 3.29 (1H, dd, J=2.4 Hz, J=7.7 Hz, H-6), 2.8–2.6 (1H, m, H-4), 1.9–1.5 (4H, m, OH, $CH_2$—$CH_2$) and 1.42 ppm (3H, t, J=6.2 Hz, $CH_3$).

C. Allyl (4R,5S,6S)-4-(3"-azidopropyl)-6-[(1'R)-1'-hydroxyethyl]-3-[(2-hydroxyethyl)thio]-7-oxo-1-azabicyclo [3.2.0]-hept-2-ene-2-carboxylate

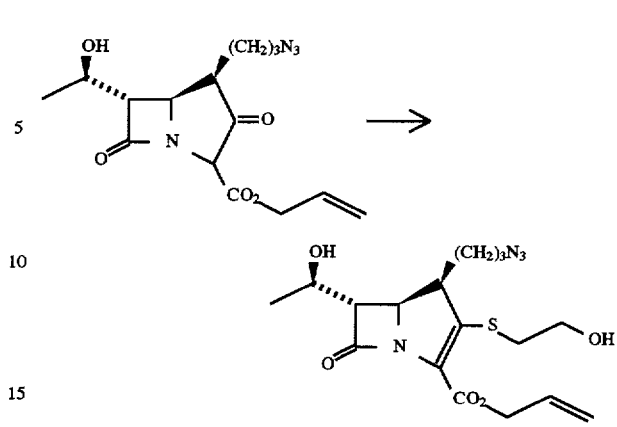

A cold (ice-MeOH bath) solution of allyl (2R,4R,5R,6 S)-4-(3"-azidopropyl)-6-[(1' R)-1'-hydroxyethyl]-3,7-dioxo-1-azabicyclo[3.2.0]heptan-2-carboxylate (1.5 g, 4.00 mmol) in CH₃CN (30 mL) was treated dropwise with diphenyl chlorophosphate (0.88 mL, 4.4 mmol) and N,N-diisopropylethylamine (0.76 mL, 4.4 mmol). The mixture was stirred for 45 min and the resulting enol phosphate was silylated by the successive addition of trimethylsilyl chloride (0.57 mL, 4.4 mmol) and N,N-diisopropylethylamine (0.76 mL, 4.4 mmol). The mixture was stirred for 35 min and the protected enol phosphate was then treated with 2-mercaptoethanol (624 mg, 8.00 mmol) and N,N-diisopropylethylamine (1.39 mL, 8.00 mmol). The mixture was stirred, allowed to stand at 5° C. for 24 h and then was diluted with cold EtOAc (100 mL). It was washed with cold 1N aqueous HCl (1×50 mL), ice cold water (2×50 mL), a cold 1M NaHCO₃ solution (1×50 mL), ice cold water (2×50 mL), brine (50 mL) and dried (MgSO₄). The residue obtained upon evaporation of the solvent was diluted with THF (30 mL, distilled over Na/benzophenone) and treated first with AcOH (1.3 mL, 24 mmol) and then dropwise with a 1M tetrabutylammonium fluoride solution in THF (12.0 mL, 12 mmol) at −25° C. (CH₃CN/dry ice bath). The mixture was stirred for 20 min, then diluted with cold EtOAc (150 mL). It was washed with an ice cold 1M aqueous NaHCO₃ solution (3×50 mL), ice cold water (3×50 mL), brine (50 mL) and dried (MgSO₄). The residue obtained upon solvent evaporation was passed through a silica gel flash (100 g) column (EtOAc-$CH_2Cl_2$; 10%→100%) to give title compound (795 mg, 50 %) as a semi-crystalline oil;

IR ($CH_2Cl_2$) $v_{max}$: 3600 (OH), 2100 ($N_3$), 1775 and 1710 cm$^{-1}$ (C=O);

$^1$H NMR (CDCl₃, 200 MHz) δ: 6.04–5.90 (1H, m, vinylic H), 5.50–5.23 (2H, m, vinylic-H), 4.82–4.63 (2H, m, $CH_2$-vinylic), 4.27–4.19 (1H, m, H-1'), 4.22 (1H, dd, J=2.7 Hz, J=9.5 Hz, H-5), 3.9–3.75 (2H, m, $CH_2O$), 3.42–3.26 (2H, m, $CH_2$—$N_3$ and H-4), 3.24 (1H, dd, J=2.7 Hz, J=7.3 Hz, H-6), 3.08–2.8 (2H, m, $SCH_2$), 2.3–1.9 (1H, bs, OH), 1.95–1.54 (4H, m, $CH_2$—$CH_2$) and 1.37 ppm (3H, d, J=6.2 Hz, $CH_3$).

D. Sodium (4R,5S,6S)-4-(3"-azidopropyl)-6-[(1'R)-1'R)-1'-hydroxyethyl]-3-2-hydroxyethyl)thio-7-oxo-1-azabicyclo3.2.0]-hept-2-ene-2-carboxylate

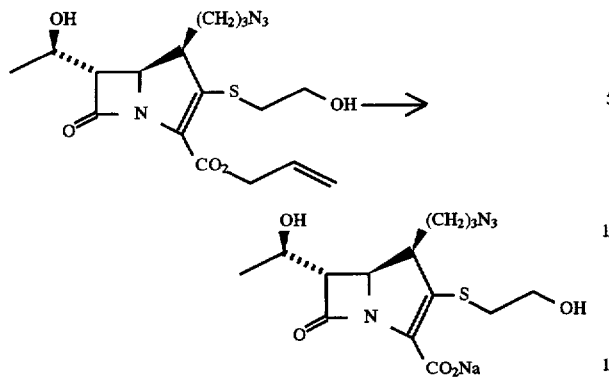

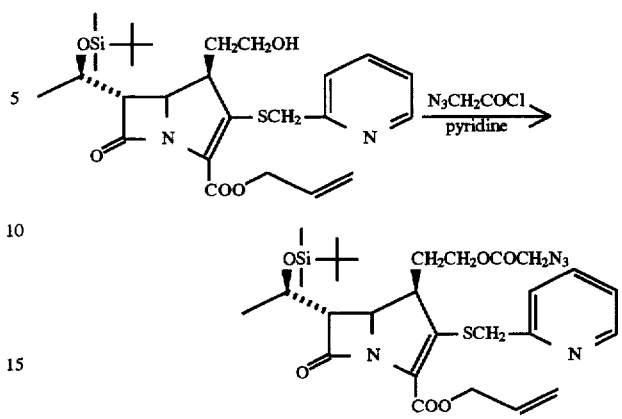

A cold (ice bath) solution of allyl (4R,5S,6S)-4-(3"-azidopropyl)-6-[(1'R)-1'-hydroxyethyl]-3-[(2"-hydroxyethyl)thio]-7-oxo-1-azabicyclo[3.2.0]hept-2-ene-2-carboxylate (63 mg, 0.16 mmol) in $CH_2Cl_2$ (7 mL) was treated with $Pd(PPh_3)_4$ (12 mg, 0.012 mmol) and a 0.5M solution of sodium 2-ethylhexanoate in ethyl acetate (0.32 mL, 0.16 mmol). The mixture was stirred at 5° C. for 40 min, then diluted with diethyl ether (30 mL) and extracted with a cold pH 7.0 buffer solution (3×3.5 mL) and water (1×3 mL). The aqueous extracts were combined, washed with diethyl ether (2×10 mL), passed through a μBondapak $C_{18}$ (15 g) reversed phase column ($H_2O$, 1,2,3,4% $CH_3CN/H_2O$) to give the title compound (30 mg, 50%) after lyophilization.

Purity by HPLC: 98.6% (5% $CH_3CN$/buffer pH 7.40.014M), retention time 8.87 min;

UV ($H_2O$) $\lambda_{max}$: 304 (10.770);

IR (Nujol) $v_{max}$: 3600–3100 (OH), 2100 ($N_3$), 1750 and 1600 cm$^{-1}$ (C=O);

1H NMR ($D_2O$, 200 MHz) δ: 4.35–4.20 (1H, m, H-1'), 4.22 (1H, dd, J=2.4 Hz, J=9.3 Hz, H-5), 3.8–3.7 (2H, m, $CH_2O$), 3.45–3.3 (4H, $CH_2N_3$, H-6 and H-1'), 3.11–2.8 (2H, m, $SCH_2$), 1.95–1.45 (4H, m, $CH_2CH_2$) and 1.33 ppm (3H, d, J=6.4 Hz, $CH_3$).

EXAMPLE 22

Sodium (4R,5S,6S)-6-[(1'R)-1'-hydroxyethyl]-4-(2"-azidoacetoxyethyl)-3-[(pyridin-2-yl)methylthio]-7-oxo-1-azabicyclo[3.2.0]hept-2-ene-2-carboxylate

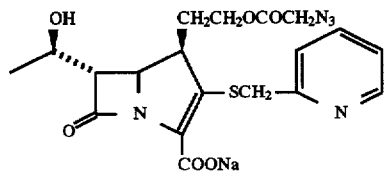

A. Allyl (4R,5S,6S)-6-[(1'R)-1'-(tert-butyldimethylsilyloxyethyl)]-4-(2"-azidoacetoxyethyl)-3-[(pyridin-2-yl)methylthio]-7-oxo-1-azabicyclo[3.2.0]hept-2-ene-2-carboxylate To a solution of allyl (4R,5S,6S)-6-[(1'R)-1'-(tert-butyldimethylsilyloxyethyl)]-4-(2"-hydroxyethyl)-3-[(pyridin-2-yl)methylthio]-7-oxo-1-azabicyclo[3.2.0]hept-2-ene-2-carboxylate (0.5 g, 0.96 mmol) [prepared in Example 6, Step A] in $CH_2Cl_2$ (10 mL) at 0° C., under Argon, was added pyridine (0.1 mL, 1.2 mmol) followed by a solution of azidoacetyl chloride (0.14 g, 1.2 mmol) in $CH_2Cl_2$ (2 mL). The reaction mixture was stirred at 0° C. for 30 min. and then diluted with EtOAc (40 mL) and washed successively with a cold pH 7 phosphate buffer solution and brine. After drying ($MgSO_4$) the solvent was evaporated to a syrup which was chromatographed on silica (2.3×11 cm) packed in $CH_2Cl_2$ and eluted with a mixture of $CH_2Cl_2$ and EtOAc (8:2, gradient elution) to give the title compound as a syrup (0.423 g, 73%).

$^1$H NMR (200 MHz, $CDCl_3$) δ: 0.04 (s, 3H, $SiCH_3$), 0.05 (s, 3H, $SiCH_3$), 0.84 (s, 9H, $SiC(CH_3)_3$), 1.28 (d, $CH_3$, $J_{CH3,1}$=6.12 Hz), 1.70–1.87 (m, 1H, $CH_2$), 2.16–2.33 (m, 1H, $CH_2$), 3.16 (dd, H-6, $J_{5,6}$=2.64 Hz, $J_{6,1}$=7.04 Hz), 3.67 (m, H-4, J=2.1, 8.03, 10.63 Hz), 3.98 (s, $CH_2N_3$) 3.83–4.43 (overlapping, 6H, $CH_2O$, CHOH, H-5, $SCH_2$) 4.57–4.82 (m, $OCH_2$ allyl), 5.18–5.45 (m, =$CH_2$, allyl), 5.82–6.01 (m, CH=, allyl), 7.17 (m, H-5, py, $J_{4,5}$=7.68 Hz, $J_{5,6}$=4.9 Hz), 7.38 (d, H-3, py, $J_{3,4}$=7.83 Hz), 7.66 (dt, H-4, py, $J_{4,6}$=1.8 Hz), 8.45 (m, H-6, py, $J_{3,6}$=0.8 Hz).

B. Allyl (4R,5S,6S)-6-[(1'R)-1'-hydroxyethyl]-4-(2"-azidoacetoxyethyl)-3-[(pyridin-2-yl)methylthio]-7-oxo-1-azabicyclo[3.2.0]-hept-2-ene-2-carboxylate

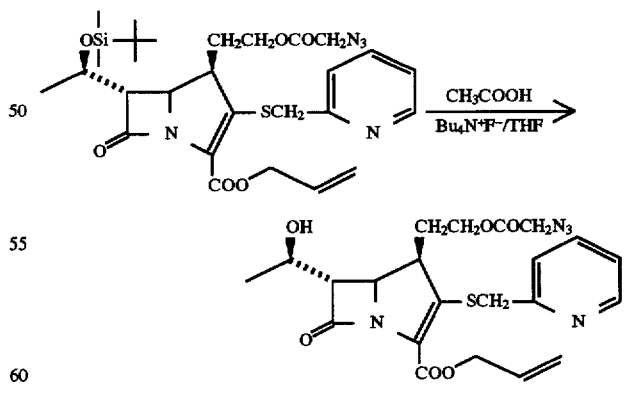

A cold (0° C.) solution of allyl (4R,5S,6S)-6-[(1'R)-1'-(tert-butyldimethylsilyloxyethyl)]-4-(2"-azidoacetoxyethyl)-3-[(pyridin-2-yl)methylthio]-7-oxo-1-azabicyclo[3.2.0]hept-2-ene-2-carboxylate (0.423 g, 0.7 mmol) in dry THF (8 mL) was treated with acetic acid (0.24 mL, 4.22 mmol) followed by a 1M solution of tetrabutylammonium fluoride in THF (2.11 mL, 2.11 mmol). The mixture was stirred between 0° and 5° C. for 120 h at which time ~25% of the starting material remained unreacted. The mixture was neutralized at 0° C. with a 1M NaHCO₃ solution (4.3 mL, 4.22 mmol) and extracted with EtOAc (3×50 mL). The combined organic phase was washed successively with a cold 1M NaHCO₃ solution; water and brine, dried (MgSO₄) and solvent evaporated to give a sticky gum which was chromatographed on silica (2.5×12 cm) packed in CH₂Cl₂ and eluted with a mixture of CH₂Cl₂ and EtOAc (3:7, gradient elution) to give the title compound (0.23 g, 68%).

¹H NMR (200 MHz, CDCl₃ 7.24) δ: 1.38 (d, CH₃, $J_{CH3,1}$=6.24 Hz), 1.71–1.87 (m, 1H, CH₂), 2.26–2.38 (m, 1H, CH₂), 3.24 (dd, H-6, $J_{5,6}$=2.82 Hz, $J_{6,1}$=8.08 Hz), 3.7 (m, H-4, J=2.16, 9.79 Hz), 3.86–4.53 (m, 8H, C$\underline{H}_2$O, C$\underline{H}_2$N₃, C$\underline{H}$OH, H-5, SC$\underline{H}_2$), 4.57–4.85 (m, OC$\underline{H}_2$, allyl), 5.19–5.45 (m, =C$\underline{H}_2$, allyl), 5.83–6.02 (m, CH=, allyl), 7.14–7.21 (m, H-5, py, $J_{3,5}$=1.03 Hz, $J_{4,5}$=7.71 Hz, $J_{5,6}$=4.82 Hz), 7.38 (d, H-3, py, $J_{3,6}$=0.98 Hz, $J_{3,4}$=7.86 Hz), 7.65 (dt, H-4, py, $J_{3,4}$=7.86 Hz, $J_{4,6}$=1.81 Hz), 8.46 (m, H-6, py).

C. Sodium (4R,5S,6S)-6-[(1'R)-1'-hydroxyethyl]-4-(2"-azidoacetoxyethyl)-3-[(pyridin-2-yl)methylthio]-7-oxo-1-azabicyclo[3.2.0]hept-2-ene-2-carboxylate

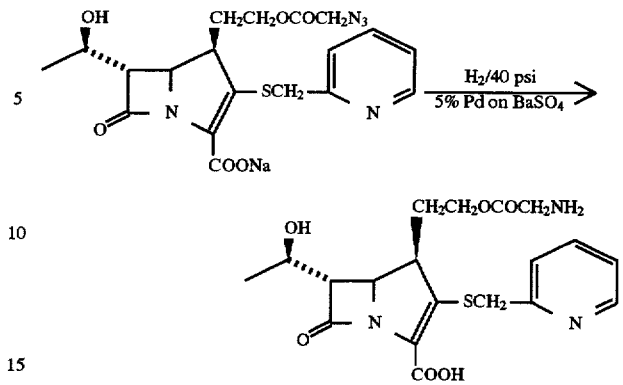

A solution of sodium (4R,5S,6S)-6-[(1'R)-1'-hydroxyethyl]4-(2"-azidoacetoxyethyl)-3-[(pyridin-2-yl)methylthio]-7-oxo-1-azabicyclo[3.2.0]hept-2-ene-2-carboxylate (0.08 g, 0.17 mmol) in a 0.05M solution of pH 7 sodium phosphate buffer (20 mL) was hydrogenated at 0° C. over 5% palladium on BaSO₄ (0.04 g) at 40 psi for 30 min. The catalyst was filtered and washed with water. The

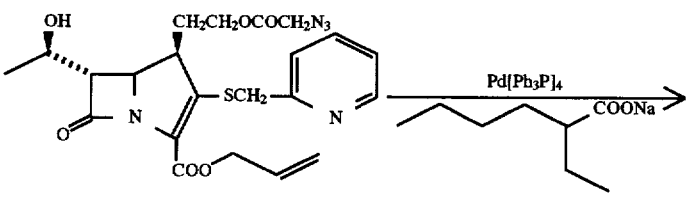 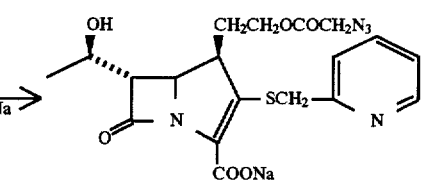

To a cold (0° C.) solution of allyl (4R,5S,6S)-6-[(1'R)-1'-hydroxyethyl]-4-(2"-azidoacetoxyethyl)-3-[(pyridin-2-yl)methylthio]-7-oxo-1-azabicyclo[3.2.0]hept-2-ene-2-carboxylate (0.22 g, 0.46 mmol) in CH₂Cl₂ (10 mL), under Argon, was added Pd[Ph₃P]₄ (0.08 g, 0.07 mmol) followed by a 0.5M solution of sodium 2-ethylhexanoate in EtOAc (1.01 mL, 0.5 mmol). The mixture was stirred at 0° C. for 2 h and then extracted with water (3×15 mL). The combined aqueous phase was passed through a column of μ-Bondapak C-18 reverse phase silica (2.5×10 cm). The title compound was eluted with a mixture of water and CH₃CN (9:1, gradient elution) and was obtained as a white fluffy solid after lyophilization (0.1 g, 48%).

¹H NMR (200 MHz, D₂O) δ: 1.31 (d, CH₃, $J_{CH3,1}$=6.4 Hz), 1.65–1.84 (m, 1H, CH₂), 2.03–2.2 (m, 1H, CH₂), 3.28 (dt, H-4, J=2.72, 11.33 Hz) 3.48 (dd, H-6 $J_{5,6}$=2.64 Hz $J_{6,1}$=6.03 Hz), 4.13 (s, 2H, C$\underline{H}_2$N₃), 4.05–4.35 (m, 6H, C$\underline{H}_2$O, C$\underline{H}$OH, H-5, SC$\underline{H}_2$), 7.39 (m, H-5, py, $J_{4,5}$=7.73 Hz, $J_{5,6}$=4.92 Hz), 7.51 (d, H-3, py, $J_{3,4}$=7.83 Hz), 7.87 (dt, H-4, py, $J_{4,6}$=1.75 Hz), 8.48 (d, H-6, py).

EXAMPLE 23

(4R,5S,6S)-6-[(1'R)-1'-Hydroxyethyl]-4-(2"-aminoacetoxyethyl)-3-[(pyridin-2-yl)methylthio]-7-oxo-1-azabicyclo-[3.2.0]-hept-2-ene-2-carboxylic acid combined aqueous solution was passed through a column of μ-Bondapak C-18 reverse phase silica (2.5×10 cm). The compound was eluted with a mixture of water and CH₃CN (9:1, gradient elution). The first compound obtained was shown to be the sodium (4R,5S,6S)-6-[(1'R)-1'-hydroxyethyl]-4-(2"-hydroxyethyl)-3-[(pyridin-2-yl)methylthio]-7-oxo-1-azabicyclo-[3.2.0]hept-2-ene-2-carboxylate as a result of ester cleavage. The title compound was eluted next and was obtained as a white fluffy solid after lyophilization (0.035 g, 49%).

Purity by HPLC: 93.1% (actually ,98%) U.V. detection at 304 nm, μ-Bondapack C-18 (4 mm×30 cm); 10% CH₃CN in pH 7.4 phosphate buffer; flow rate 1 mL/min; retention time: 5.37 min.

UV (pH 7.4) $\lambda_{max}$: 304 (8260).

IR (Nujol) $v_{max}$: 1750 cm⁻¹ (C=O β-lactam);

¹H NMR (200 MHz, D₂O) δ: 1.29 (d, CH₃, $J_{CH3,1}$=6.4 Hz), 1.69–1.87 (m, 1H, CH₂), 2.06–2.21 (m, 1H, CH₂), 3.27 (dt, H-4, J=2.79, 10.83 Hz), 3.46 (dd, H-6, $J_{5,6}$=2.7 Hz, $J_{6,1}$=6.33 Hz), 3.89 (s, 2H, C$\underline{H}_2$NH₂), 4.04–4.38 (m, 6H, C$\underline{H}_2$O, C$\underline{H}$OH, H-5, SC$\underline{H}_2$), 7.36 (m, H-5, py, $J_{4,5}$=7.73 Hz, $J_{5,6}$=5.08 Hz), 7.5 (d, H-3, py, $J_{3,4}$=7.93 Hz), 7.85 (dt, H-4, py, $J_{4,6}$1.77 Hz, 8.45 (d, H-6 py).

EXAMPLE 24

(4R,5S,6S)-4-(2"-Aminoethyl)-6-[(1'R)-1'-hydroxyethyl]-3-[(pyridin-3-yl)methylthio]-7-oxo-1-azabicyclo[3.2.0]hept-2-ene-2-carboxylic acid A. Allyl (4R,5S,6S)-4-(2"-azidoethyl)-6-[(1'R)-1'-tert-butyldimethylsilyloxyethyl]-3-[(pyridin-3-yl)methylthio]-7-oxo-1-azabicyclo[3.2.0]hept-2-ene-2-carboxylate

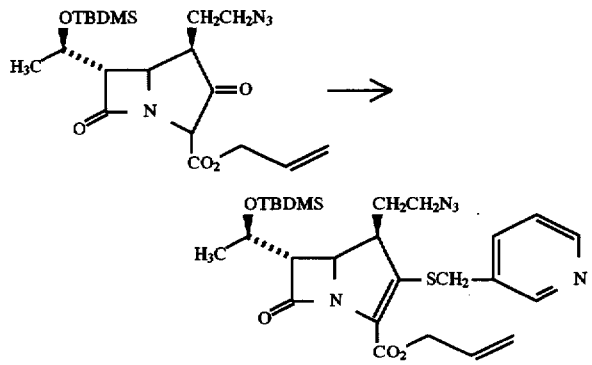

A solution of allyl (4R,5R,6S)-4-(2"-azidoethyl)-6-[(1'R)-1'-tert-butyldimethylsilyloxyethyl]-3,7-dioxo-1-azabicyclo[3.2.0]-heptane-2-carboxylate (6.46 mmol, prepared from 3.0 g, 6.46 mmol of the diazo precursor of Example 2, Step E) in dry $CH_3CN$ (50 mL) was treated at $-15°$ C. with diphenyl chlorophosphate (1.4 mL, 6.75 mmol) and N,N-diisopropylethylamine (1.2 mL, 6.9 mmol) added simultaneously over 5 min. A small crystal of 4-N,N-dimethylaminopyridine was then added and the mixture was slowly warmed up to $0°–5°$ C. over 30 min. Then N,N-diisopropylethylamine (1.4 mL, 8.0 mmol) and 3-mercaptomethylpyridine (1.54 g, 12.3 mmol) in $CH_3CN$ (5 mL) were added dropwise. After 1.5 h at $0°–5°$ C., the reaction mixture was quenched by addition of EtOAc and cold water. The organic phase was washed with 1M $NaHSO_3$, saturated $NaHCO_3$, brine and dried $(MgSO_4)$. Evaporation of the solvent gave an oil which was chromatographed on silica gel (5×11 cm). Elution with a gradient of EtOAc (0–20%) in toluene gave 2.13 g (60%) of the title compound as an oil.

IR (NaCl, film) $v_{max}$: 2100 $(N_3)$, 1775 (C=O of β-lactam) and 1710 $cm^{-1}$ (C=O of ester);

$^1$H NMR (200 MHz, $CDCl_3$) δ: 0.07 and 0.08 (2×s, 2×3H, $SiCH_3$), 0.88 (s, 9H, Sit-Bu), 1.29 (d, J=6.12 Hz, 3H, $CH_3CHO$), 1.6–2.2 (m, 2H, $CH_2$-4), 3.06 (dd, $J_{H6,H5}$=2.70 Hz, $J_{H6,H1}$=7.74 Hz, 1H, H-6), 3.2–3.7 (m, H, $CH_2N_3$ and H-4), 4.05 (dd overlapping with $SCH_2$, $J_{H5,H6}$=2.70 Hz, $J_{H5,H4}$=9.54 Hz, 1H, H-5), 4.07 (ABq, $J_{AB}$15.6 Hz, Δv15.2 Hz, 1H, $SCH_2$), 4.17 (m, 1H, $CH_3CHO$), 4.74 (m, 2H, $CH_2$ of allyl), 5.2–5.5 and 5.8–6.1 (2×m, 2H and 1H, CH of allyl), 7.29 (m, 1H, H-5 of pyridine), 7.79 (m, 1H, H-4 of pyridine), 8.54 (dd, J=15.0 Hz and J=4.8 Hz, 1H, H-6 of pyridine) and 8.62 ppm (d, J=2.0 Hz, 1H, H-2 of pyridine).

B. Allyl (4R,5S,6S)-4-(2"-azidoethyl)-6-[(1'R)-1'-hydroxyethyl]-3-[(pyridin-3-yl)methylthio]-7-oxo-1-azabicyclo-[3.2.0]hept-2-ene-2-carboxylate

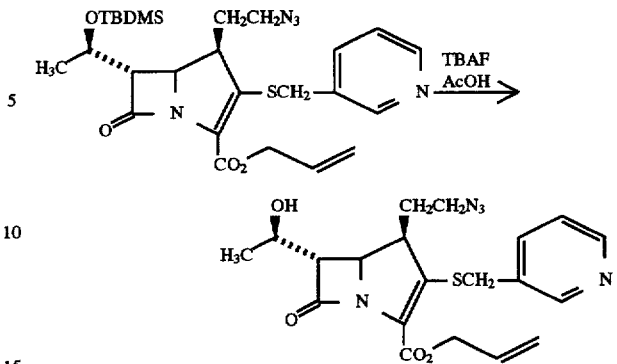

A solution of allyl (4R,5S,6S)-4-(2"-azidoethyl)-6-[(1'R)-1'-tert-butyldimethylsilyloxyethyl]-3-[(pyridin-3-yl)methylthio]-7-oxo-1-azabicyclo[3.2.0]hept-2-ene-2-carboxylate (2.13 g, 3.92 mmol) in dry tetrahydrofuran (60 mL) was treated at $0°–5°$ C. and under nitrogen with acetic acid (1.35 mL, 23.6 mmol) and 12.0 mL (12.0 mmol) of a 1M solution of tetrabutylammonium fluoride in tetrahydrofuran. After five days at $5°$ C., the reaction mixture was diluted with EtOAc, washed with cold saturated $NaHCO_3$, brine and dried $(MgSO_4)$. Evaporation of the solvent gave an oil which was chromatographed on silica gel (4×12 cm) using a gradient of EtOAc (50 to 100%) in toluene as eluent. The first fractions gave 0.33 g (15%) of recovered starting material. The following fractions yielded 0.90 g (54%) of the title compound as a clear oil:

IR (NaCl, film) $v_{max}$: 2100 $(N_3)$, 1775 (C=O of β-lactam) and 1710 $cm^{-1}$ (C=O of ester);

$^1$H NMR (200 MHz, $CDCl_3$) δ: 1.38 (d, J=6.23 Hz, 3H, $CH_3CHO$), 1.6–2.2 (m, 2H,-$CH_2$-4), 3.12 (dd, $J_{H6,H5}$=2.77 Hz, $J_{H6,H1}$=7.89 Hz, 1H, H-6), 3.3–3.7 (m, 3H, $CH_2N_3$ and H-4), 4.05 (ABq, $J_{AB}$=13.4 Hz, Δv23.0 Hz, 2H, $SCH_2$), 4.1–4.3 (m, 2H, H-5 and $CH_3CHO$ overlapping), 4.75 (m, 2H, $CH_2$ of allyl), 5.3–5.5 and 5.9–6.1 (2×m, 2H and 1H, CH of allyl), 7.3 (m, 1H, H-5 of pyridine), 7.72 (m, 1H, H-4 of pyridine), 8.53 (dd, J=1.58 Hz and J=4.8 Hz, 1H, H-6 of pyridine) and 8.6 ppm (d, J=2.0 Hz, 1H, H-2 of pyridine).

C. (4R, 5S,6S)-4-(2"-Aminoethyl)-6-[(1'R)-1'-hydroxyethyl]-3-[(pyridin-3-yl)methylthio]-7-oxo-1-azabicyclo[3.2.0]hept-2-ene-2-carboxylic acid

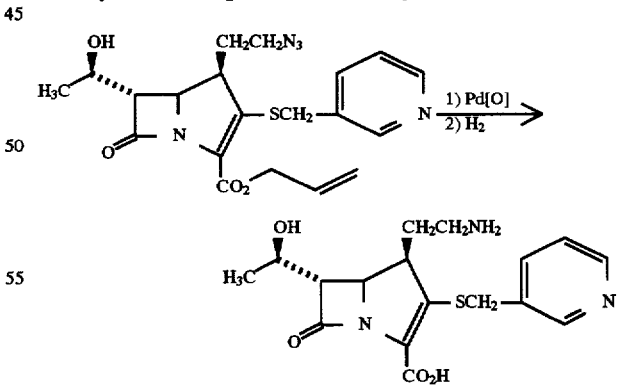

A solution of allyl (4R,5S,6S)-4-(2"-azidoethyl)-6-[(1'R)-1'-hydroxyethyl]-3-[(pyridin-3-yl)methylthio]-7-oxo-1-azabicyclo[3.2.0]hept-2-ene-2-carboxylate (0.90 g, 2.09 mmol) in dry $CH_2Cl_2$ (50 mL) was treated at $0°–5°$ C. and under nitrogen with tetrakis(triphenylphosphine)palladium [0] (0.13 g) and 4.6 mL (2.3 mmol) of a 0.5M solution of potassium 2-ethylhexanoate in EtOAc. After 15 min, the reaction mixture was diluted with diethyl ether (150 mL) and extracted with 0.05M pH 7.0 phosphate buffer (3×75 mL). The combined aqueous phase was adjusted to pH 5.8 with 1M NaH$_2$PO$_4$ and traces of organic solvent were removed in vacuo. The aqueous solution was then hydrogenated over 0.9 g of 30% palladium on Celite at 0°–5° C. and under 45 psi for 1.2 h. The catalyst was then filtered and the filtrate was chromatographed on reversed phase silica gel (μ-Bondapak c-18, 3.5×6.5 cm). Elution with a gradient of CH$_3$CN (0–5%) in water gave the title material as a white amorphous powder after freeze drying. Crystallization in water (30 mL) gave 0.137 g of the title compound as a very fine solid. A second chromatography of the mother liquors gave 0.27 g (total yield 0.397 g, 52%) of the title compound as a white amorphous powder.

Purity by HPLC: 94.5% on μ-Bondapak c-18, 3.9 mm×30 cm, elution 8% CH$_3$CN-HO$_2$O pH 7.4 phosphate buffer, flow rate mL/min, UV detector 300 nm, retention time 5.35 min;

UV (H$_2$O, pH 7.4 phosphate buffer) λ$_{max}$: 268 (6,010) and 302 nm (7,740);

IR (KBr) ν$_{max}$: 1770 (C=O of β-lactam) and 1590 cm$^{-1}$ (C=O of carboxylate);

$^1$H NMR (200 MHz, D$_2$O) δ: 1.30 (d, J=6.29 Hz, 3H, CH$_3$CHO), 1.6–2.2 (m, 2H, CH$_2$-4), 3.04 (broad t, J=8.3 Hz, 2H, CH$_2$NH$_2$), 3.20 (m, 1H, H-4), 3.38 (dd, J$_{H6,H5}$=2.72 Hz, J$_{H6,H1}$=6.45 Hz, 1H, H-6), 4.06 (ABq, J$_{AB}$=13.6 Hz, Δν=24.3, 2H, SCH$_2$), 4.1–4.3 (m, 2H, H-5 and CH$_3$CHO), 7.44 (m, 1H, H-5 of pyridine), 7.85 (d, J=7.8 Hz, 1H, H-4 of pyridine), 8.44 (d, J=4.9 Hz, 1H, H-6 of pyridine) and 8.50 ppm (broad s, 1H, H-2 of pyridine).

EXAMPLE 25

(4R,5S,6S)-4-(2"-N,N-Dimethylaminoethyl)-6-[(1'R)-1'-hydroxyethyl]-3-[(pyridin-3-yl)methylthio]-7-oxo-1-azabicyclo[3.2.0]-hept-2-ene-2-carboxylic acid

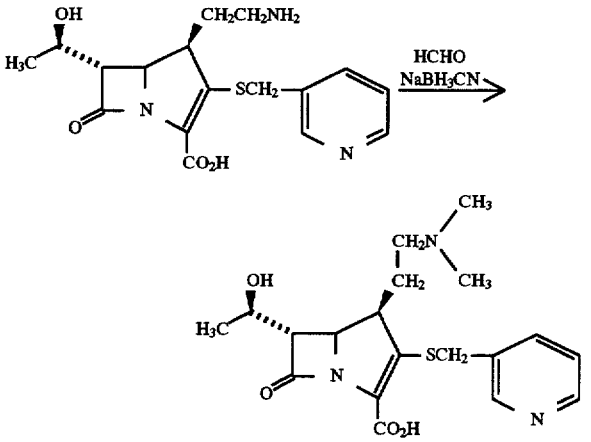

A suspension of (4R,5S,6S)-4-(2"-aminoethyl)-6-[(1'R)-1'-hydroxyethyl]-3-[(pyridin-3-yl)methylthio]-7-oxo-1-azabicyclo[3.2.0]hept-2-ene-2-carboxylic acid from Example 24 (0.150 g, 0.41 mmol) in a mixture of water (3 mL) and acetonitrile (3 mL) was treated at 0°–5° C. with 37% aqueous formaldehyde (0.23 mL, 2.4 mmol), sodium cyanoborohydride (0.048 g, 0.72 mmol) and two drops of acetic acid. After 20 min, the reaction mixture was diluted with 30 mL of 0.2M pH 6.0 phosphate buffer and the traces of organic solvent were removed in vacuo. The aqueous phase was chromatographed twice on reversed phase silica gel (μ-Bondapak c-18, 4×9 cm) using a gradient of acetonitrile (0–5%) in water as eluent. Lyophilization of the UV active fractions gave 0.080 g (~50%) of a white amorphous powder. By HPLC, this product is a mixture of the title dimethylamino compound and N-methyl-N-cyanomethyl compound (Example 26) in a 3:1 ratio. Purification by preparative HPLC (μ-Bondapak c-18, 10 mm×30 cm, elution 5% CH$_3$CN-H$_2$O) gave 0.047 g (29%) of pure dimethylamino title compound.

Purity by HPLC: 97% on μ-Bondapak c-18, 3.9 mm×30 cm, elution 8% CH$_3$CN-H$_2$O pH 7.4 phosphate buffer, flow rate 1 mL/min, retention time 5.42 min.;

UV (H$_2$O, pH 7.4 phosphate buffer) λ$_{max}$: 268 nm (6592) and 302 nm (7,793);

IR (KBr) ν$_{max}$: 1765 (C=O of β-lactam) and 1605 cm$^{-1}$ (C=O of carboxylate);

$^1$H NMR (200 MHz, D$_2$O) δ: 1.30 (d, J=6.37 Hz, 3H, CH$_3$CHO), 1.5–2.2 (m, 2H, CH$_2$-4), 2.87 (s, 6H, N(CH$_3$)$_2$), 3.15 (m, 3H, CH$_2$N and H-4), 3.32 (dd, J$_{H6,H5}$=2.90 Hz, J$_{H6,H1}$=6.80 Hz, 1H, H-6), 4.05 (ABq, J$_{AB}$=14.1 Hz, Δν=29.7 Hz, 2H, SCH$_2$), 4.12 (dd, partially overlapping with SCH$_2$, J$_{H5,H6}$=2.90 Hz, 1H, H-5), 4.22 (m, 1H, CH$_3$CHO), 7.44 (dd, J=5.0 Hz and J=7.9 Hz, 1H, H-5 of pyridine), 7.84 (m, 1H, H-4 of pyridine), 8.44 (dd, J=1.5 Hz, and J=5.0 Hz, 1H, H-6 of pyridine) and 8.50 ppm (d, J=1.8 Hz, 1H, H-2 of pyridine).

EXAMPLE 26

(4R,5S,6S)-4-[2"-(N-Cyanomethyl-N-methylamino)ethyl]-6-[(1'R)-1'-hydroxyethyl]-3-[(pyridin-3-yl)methylthio]-7-oxo-1-azabicyclo[3.2.0]hept-2-ene-2-carboxylic acid

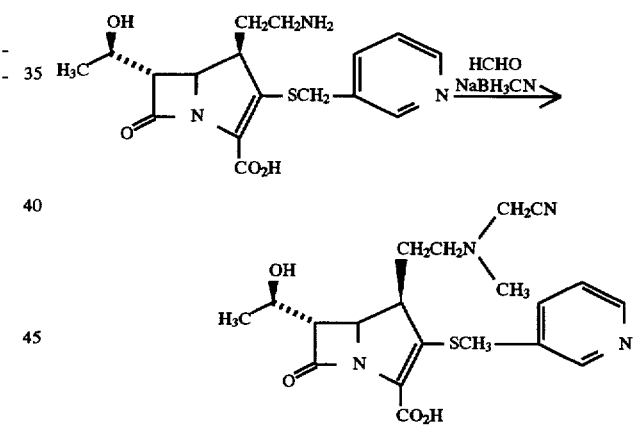

The mixture of products obtained by the reductive alkylation of (4R,5S,6S)-4-(2"-aminoethyl)-6-[(1'R)-1'-hydroxyethyl]-3-[(pyridin-3-yl)methylthio]-7-oxo-1-azabicyclo[3.2.0]hept-2-ene-2-carboxylic acid as described in Example 25 was purified by preparative HPLC (μ-Bondapak c-18). The minor component of the mixture with a longer reaction time gave 0.011 g of the title compound as a white amorphous powder after lyophilization:

Purity by HPLC: 92% on μ-Bondapak c-18, 3.9 mm×30 cm, elution 8% CH$_3$CN-H$_2$O pH 7.4 phosphate buffer, flow rate 1 mL/min, uv detector 302 nm, retention time 23.5 min.;

UV (H$_2$O, pH 7.4 phosphate buffer) λ$_{max}$: 268 and 304 nm;

IR (KBr) ν$_{max}$: 1752 (C=O of β-lactam) and 1605 cm$^{-1}$ (C=O of carboxylate);

$^1$H NMR (200 MHz, D$_2$O) δ: 1.31 (d, J=6.36 Hz, 1H, CH$_3$CHO), 1.4 and 1.9 (2×m, 2×1H, CH$_2$-4), 2.35 (s, 3H, N-CH$_3$), 2.3-2.6 (m, 2H, CH$_2$CH$_2$N), 3.12 (m, 1H, H-4), 3.33 (dd, J$_{H6,H5}$=2.68 Hz, J$_{H6,H1}$=5.95 Hz, 1H, H-6), 3.70 (s, 2H, NCH$_2$CN), 4.09 (ABq, J$_{AB}$=14.14 Hz, Δv29.5 Hz, 2H, SCH$_2$), 4.12 (dd overlapping with SCH$_2$, J$_{H5,H6}$=2.68 Hz, 1H, H-5), 4.24 (m, 1H, CH$_3$CHO), 7.49 (m, 1H, H-5 of pyridine), 7.92 (d, J=8.0 Hz, 1H, H-4 of pyridine), 8.46 (broad d, J=4.3 Hz, 1H, H-6 of pyridine) and 8.54 ppm (broad s, 1H, H-2 of pyridine).

EXAMPLE 27

(4R,5S,6S)-4-(3"-Aminopropyl)-6-[(1'R)-1'-hydroxyethyl]-3-[(2-hydroxyethyl)thio]-7-oxo-1-azabicyclo[3.2.0]hept-2-ene-2-carboxylic acid

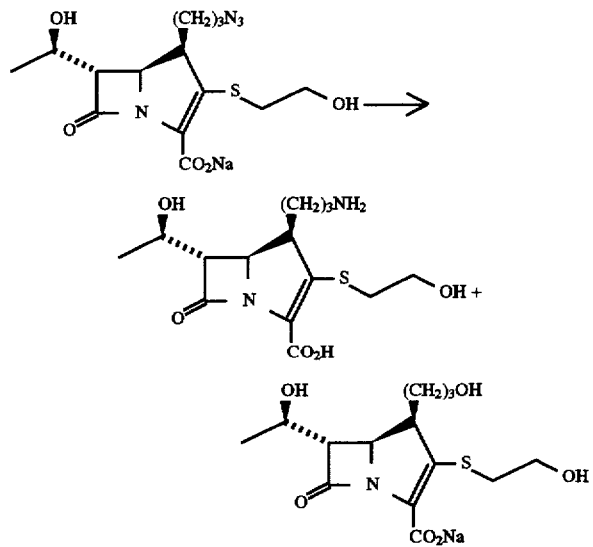

A 0.04M pH 7.0 phosphate buffer solution (50 mL, 2.0 mmol) of sodium (4R,5S,6S)-4-(3"-azidopropyl)-6-[(1' R)-1'-hydroxyethyl]-3-[(2-hydroxyethyl)thio]-7-oxo-1-azabicyclo-[3.2.0]hept-2-en-2-carboxylate obtained from the corresponding allyl ester (404 mg, 1.02 mmol) as described in Example 21 was adjusted at 5° C. to pH 5.8–5.9 with a 1.0M pH 4.2 NaH$_2$PO$_4$ buffer solution. To this mixture was added 30% Pd/Celite (400 mg) and it was shaken on a Parr hydrogenator at 45–50 psi hydrogen for 1.5 h at an initial temperature of 5° C. (ice bath) and final temperature of 15° C. The catalyst was filtered off and the solution was passed through a μBondapak C$_{18}$ reversed phase column (60 g, H$_2$O) to give impure title material contaminated with sodium (4R,5S,6S)-4-(3"-hydroxypropyl)-6-[(1R)-1'-hydroxyethyl]-3-[(2-hydroxyethyl)thio]-7-oxo-1-azabicyclo[3.2.0]hept-2-ene-2-carboxylate (Example 28). This contaminated material dissolved in a 0.01M pH 6.0 phosphate buffer was poured again on a μBondapak C$_{18}$ column (ratio 500/1). The first two volumes of the column were eluted with the pH 6.0 buffer and then elution with water gave 3-aminopropyl pure title compound (95 mg, 28%) and the 3-hydroxypropyl derivative (from 340 mg, 0.85 mmol of allyl ester, 45 mg, 17% as described in Example 28).

Purity of title compound by HPLC: 88% (KH$_2$PO$_4$0.01M, pH 7.4) retention time 5.54 min;

UV (H$_2$O) v$_{max}$: 302 (9000);

IR (Nujol) v$_{max}$: 3600–3100 (OH), 1750 and 1585 cm$^{-1}$ (C=O);

$^1$H NMR (D$_2$O, 200 MHz) δ: 4.33–4.2 (1H, m, H-1'), 4.23 (1H, dd, J=2.5 Hz, J=9.2 Hz, H-5), 3.82–3.67 (2H, m, CH$_2$O), 3.43–3.34 (1H, m H-4), 3.36 (1H, dd, J=2.5 Hz, J=6.6 Hz, H6), 3.09–3.02 (2H, m, CH$_2$N), 3.06–2.79 (2H, 2 sets of m, SCH$_2$), 1.95–1.5 (4H, m, CH$_2$CH$_2$) and 1.33 ppm (3H, d, J=6.4 Hz, CH$_3$).

EXAMPLE 28

Sodium (4R,5S,6S)-4-(3"-hydroxypropyl)-6-[(1'R)-1'-hydroxyethyl]-3-[(2-hydroxyethyl)thio]-7-oxo-1-azabicyclo [3.2.0]-hept-2-ene-2-carboxylate

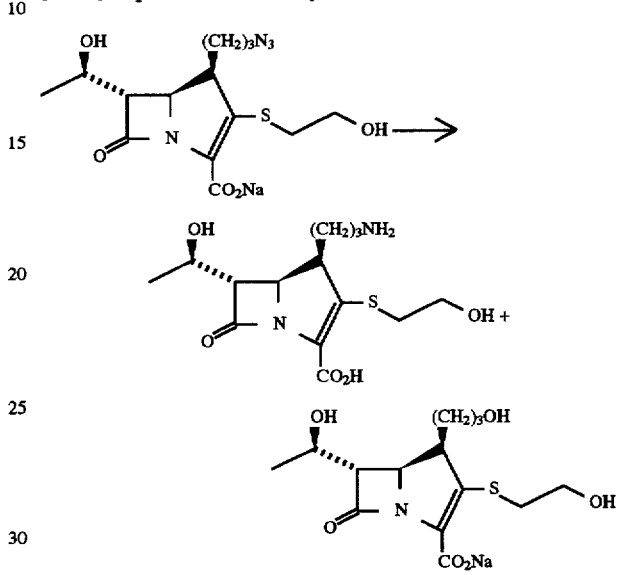

A 0.04M pH 7.0 phosphate buffer solution (50 mL, 2.0 mmol) of sodium (4R,5S,6S)-4-(3"-azidopropyl)-6-[(1' R)-1'-hydroxyethyl]-3-[(2-hydroxyethyl)thio]-7-oxo-1-azabicyclo-[3.2.0]-hept-2-ene-2-carboxylate obtained from the corresponding allyl ester as described in Example 21 (404 mg, 1.02 mmol) was adjusted at 5° C. to pH 5.8–5.9 with a 1.0M pH 4.2 NaH$_2$PO$_4$ buffer solution. To this mixture was added 30% Pd/Celite (400 mg) and it was shaken on a Parr hydrogenator at 45–50 psi hydrogen for 1.5 h at an initial temperature of 5° C. (ice bath) and final temperature of 15° C. The catalyst was filtered off and the solution was passed through a μBondapak C$_{18}$ reversed phase column (60 g, H$_2$O) to give impure title material contaminated with (4R,5S,6S)-4-(3"-aminopropyl)-6-[(1' R)-1'-hydroxyethyl]-3-[(2-hyroxyethyl)thio]-7-oxo-1-azabicyclo[3.2.0]hept-2-ene-2-carboxylate (Example 27). This contaminated material dissolved in a 0.01M pH 6.0 phosphate buffer was poured again on a μBondapak C$_{18}$ column (ratio 500/1). The first two volume of the column were eluted with the pH 6.0 buffer and then elution with water gave 3-aminopropyl compound of Example 27 (95 mg, 28%) and the 3-hydroxypropyl title compound (from 340 mg, 0.85 mmol of allyl ester, 45 mg, 17%).

Purity of title compound by HPLC: 95.2% (KH$_2$PO$_4$, 0.01M pH 7.4), retention time 7.9 min;

UV (H$_2$O) v$_{max}$: 302 (10,300);

IR (Nujol) v$_{max}$: 3600–3100 (OH), 1740 and 1690 cm$^{-1}$ (C=O);

$^1$H NMR (D$_2$O, 200 MHz) δ: 4.35–4.2 (1H, m, H-1'), 4.23 (1H, dd, J=9.2 Hz, J=2.5 Hz, H-5), 3.77 (2H, m, SCH$_2$C H$_2$O), 3.65 (2H, m, CH$_2$O), 3.41 (1H, dd, J=2.5 Hz, J=6.1Hz, H-6), 3.42–3.36 (1H, m, H-4), 3.1–2.8 (2H, 2 sets of m, SCH$_2$), 2.0–1.4 (4H, m, CH$_2$CH$_2$) and 1.33 ppm (3H, d, J=6.4 Hz, CH$_3$).

EXAMPLE 29

Sodium (4R,5S,6S)-4-(3"-azidopropyl)-6-[(1'R)-1'-hydroxyethyl]3-methylthio-7-oxo-1-azabicyclo[3.2.0]hept-2-ene-2-carboxylate

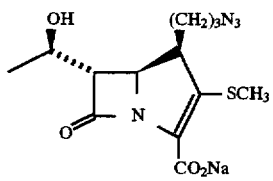

A. Allyl (4R,5S,6S)-4-(3"-azidopropyl)-6-[(1'R)-1'-tert-butyldimethylsilyloxyethyl]-3-methylthio-7-oxo-1-azabicyclo[3.2.0]hept-2-ene-2-carboxylate

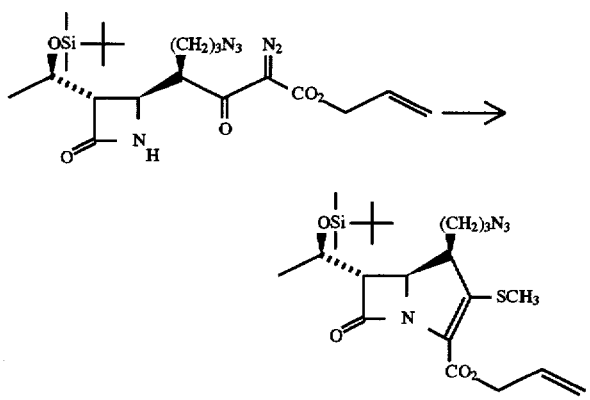

A solution of (3S,4R)-3-[(1'R)-1'-tert-butyldimethylsilyloxyethyl]-4-[(1"R)-1"-(3-azidopropyl)- 3"-diazo-3"-allyl-oxycarbonyl-2"-oxypropyl]azetidin-2-one prepared in Example 7, Step E (2.0 g, 4.2 mmol) and Rh(OAc)$_2$ in benzene (80 mL) was heated under reflux for 20 min. Benzene was removed under vacuum and the resulting bicyclic ketone was diluted with CH$_3$CN (80 mL). It was cooled to −10° C. (ice-MeOH bath) and treated dropwise with diphenyl chlorophosphate (1.0 mL, 4.6 mmol) and N,N-diisopropylethylamine (0.84 mL, 4.6 mmol) and 4-dimethylaminopyridine (2.3 mg). The mixture was stirred for 2 h then N,N-diisopropylethylamine (1.7 mL, 9.2 mmol) was added in, followed by the addition of a stream of CH$_3$SH gas (10 min). The mixture was kept at 5° C. (cold room) for 18 h, then diluted with cold EtOAc (400 mL), washed with cold 1N aqueous HCl (400 mL), ice cold water (200 mL), 1M aqueous NaHCO$_3$ (2×400 mL), ice cold water (3×400 m), brine and dried (MgSO$_4$). The residue obtained (2 g) upon solvent evaporation was passed through a silica gel flash column (100 g, Hexane→20% EtOAc/Hexane) to give the title compound (1.0 g, 50%) as an oil.

IR (CH$_2$Cl$_2$) $v_{max}$: 2100 (N$_3$), 1775 and 1710 cm$^{-1}$ (C=O);

$^1$H NMR (CDCl$_3$, 200 MHz) δ: 5.97–5.89 (1H, m, vinylic H), 5.48–5.21 (2H, m, vinylic H), 4.9–4.6 (2H, m, CH$_2$-vinyl), 4.3–4.15 (1H, m, H-1'), 4.12 (1H, dd, J=2.5 Hz, J=9.4 Hz, H-5), 3.5–3.3 (2H, m, CH$_2$N$_3$), 3.3–3.1 (1H, m, H-4), 3.16 (1H, dd, J=7.4 Hz, J-2.7 Hz, H-6), 2.38 (3H, s, CH$_3$), 1.9–1.5 (4H, m, CH$_2$CH$_2$), 1.31 (3H, d, J=6.1 Hz, CH$_3$), 0.88 (9H, s, tert-butyl), 0.086 and 0.078 ppm (6H, 2s, CH$_3$).

B. Allyl (4R,5S,6S)-4-(3"-azidopropyl)-6-[(1'R)-1'-hydroxyethyl]-3-methylthio-7-oxo-1-azabicyclo[3.2.0]-hept-2-ene-2-carboxylate

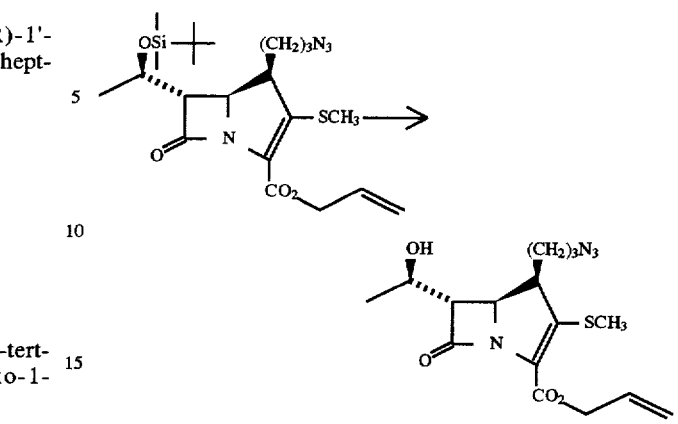

A cold (−20° C.) solution of allyl (4R,5S,6S)-4-(3"-azidopropyl)-6-[(1'R)-1'-tert-butyldimethylsilyloxyethyl]- 3-methylthio-7-oxo-1-azabicyclo[3.2.0]hept-2-ene- 2-carboxylate (1.0 g, 2.1 mmol) in THF (60 mL) was treated with glacial AcOH (1.5 mL, 25.2 mmol) and then with a 1M THF solution of tetrabutylammonium fluoride (12.7 mL, 12.6 mmol). The reaction was kept at 5° C. for 100 h, then neutralized with a 1M aqueous NaHCO$_3$ solution, diluted with EtOAc (200 mL), washed with cold 1M aqueous NaHCO$_3$ solution (1×50 mL), water (2×150 mL), brine (1×150 mL) and dried (MgSO$_4$). The residue (1.2 g) obtained upon solvent evaporation was passed through a silica gel flash column (1/1, Hexane/EtOAc→EtOAc) to give the title compound (0.30 g) and the starting ether (0.42 g) which was retreated again with tetrabutylammonium fluoride under the same conditions to give the title compound (0.13 g); combined yield 0.43 g, 56%.

IR (CH$_2$Cl$_2$) $v_{max}$: 3600 (OH) 2100 (N$_3$) 1775 and 1710 (C=O);

$^1$H NMR (CDCl$_3$, 200 MHz) δ: 6.07–5.87 (1H, m, vinylic H), 5.5–5.21 (2H, m, vinylic-H), 4.87–4.62 (2H, m, CH$_2$-vinylic), 4.3–4.18 (1H, m, H-1'), 4.22 (1H, dd, J=2.6 Hz, J=9.3 Hz, H-5), 3.5–3.3 (2H, m, CH$_2$N$_3$), 3.3–3.2 (1H, m, H-4), 3.23 (1H, dd, J=2.6 Hz, J=7.6 Hz, H-6), 2.37 (3H, s, SCH$_3$), 1.9–1.55 (4H, m, CH$_2$CH$_2$), 1.77 (1H, d, J=4.8 Hz, OH) and 1.39 ppm (3H, d, J=6.3 Hz, CH$_3$).

C. Sodium (4R,5S,6S)-4-(3"-azidopropyl)-6-[(1'R)-1'-hydroxyethyl]-3-methylthio-7-oxo-1-azabicyclo[3.2.0]-hept-2-ene-2-carboxylate

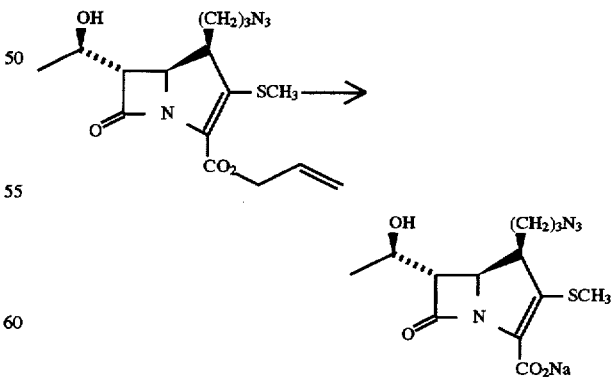

A cold (ice bath) solution of allyl (4R,5S,6S)-4-(3"-azidopropyl)-6-[(1'R)-1'-hydroxyethyl]-3-methylthio- 7-oxo-1-azabicyclo[3.2.0]hept-2-ene-2-carboxylate (50 mg, 0.14 mmol) in CH$_2$Cl$_2$ (2 mL) was treated with Pd(PPh$_3$)$_4$ (5 mg) and a 0.5M solution of sodium 2-ethylhexanoate in EtOAc (0.3 mL, 0.15 mmol). The mixture was diluted with EtOAc (10 mL) and extracted with a 0.05M phosphate buffer solution (1×10 mL, 1×5 mL). The aqueous extracts were combined, washed with diethyl ether and passed through a µBondapak C$_{18}$ reversed phase column (20 g, H$_2$O→2% CH$_3$CN/H$_2$O) to give the title compound (30 mg, 60%).

Purity by HPLC: 97.2% (10% CH$_3$CN/KH$_2$PO$_4$ 0.01M, pH 7.4), retention time 7.56 min;

UV (H$_2$O) $\lambda_{max}$: 304 (8070);

IR (Nujol) $\nu_{max}$: 3600–3100 (OH), 2100 (N$_3$), 1745 and 1595 cm$^{-1}$ (C=O);

$^1$H NMR (D$_2$O, 200 MHz) δ: 4.34–4.2 (1H, m, H-1'), 4.22 (1H, dd, J=2.3 Hz, J=9.0 Hz, H-5), 3.47–3.37 (4H, m, H-6, H-4 and CH$_2$N$_3$), 3.375 (d, J=2.3 Hz, part of dd of H-6), 2.37 (3H, s, CH$_3$), 1.95–1.4 (4H, m, CH$_2$CH$_2$) and 1.35 ppm (3H, d, J=6.4 Hz, CH$_3$).

EXAMPLE 30

(4R,5S,6S)-4-(3"-Aminopropyl)-6-[(1'R)-1'-hydroxyethyl]-3-methylthio-7-oxo-1-azabicyclo[3.2.0]hept-2-ene-2-carboxylic acid

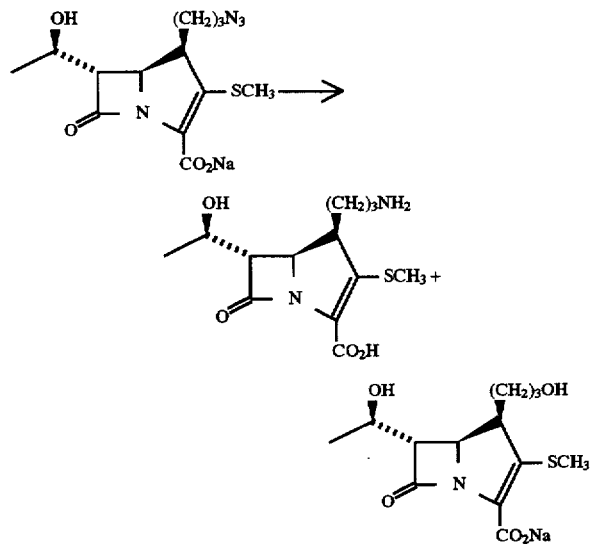

The pH of a cold (ice bath) 0.05M pH 7.0 sodium phosphate buffer (25 mL) of sodium (4R,5S,6S)-4-(3"-azidopropyl)-6-[(1'R)-1'-hydroxyethyl]-3-methylthio-7-oxo-1-azabicyclo[3.2.0]hept-2-ene-2-carboxylate made from the corresponding allyl ester (0.12 g, 0.33 mmol), as described in Example 29, was adjusted to 5.8 with a 1.0M pH 4.2 NaH$_2$PO$_4$ buffer solution. The mixture was then shaken on a Parr hydrogenator at a hydrogen pressure of 45–50 p.s.i. for 90 min at ~10° C. (initial temperature: 5° C.) using 30% Pd/Celite (120 mg) as catalyst. The catalyst was removed by filtration and the solution was passed through a µBondapak C$_{18}$ reversed phase column (50 g, H$_2$O→2% CH$_3$CN/H$_2$O) to give a mixture of two compounds (0.3 g). This lyophilized powder was passed again on the reversed phase column (45 g, 150 mL of 0.05M pH 6.0 phosphate buffer, H$_2$O→2% CH$_3$CN/H$_2$O) to give impure 3-aminopropyl derivative (125 mg) and the 3-hydroxypropyl derivative of Example 31 (20 mg, 20%). The 3-aminopropyl derivative was repurified on the reversed phase column (45 g, H$_2$O→2% CH$_3$CN/H$_2$O) to give the pure title 3-aminopropyl compound (25 mg, 25%).

Purity by HPLC: 96.5% (KH$_2$PO$_4$ buffer 0.01M, pH 7.4), retention time: 7.50 min;

UV (H$_2$O) $\lambda_{max}$: 304 (8580);

IR (Nujol) $\nu_{max}$: 3600–3100 (OH, NH$_2$), 1750 and 1580 (C=O);

$^1$H NMR (D$_2$O, 200 MHz) δ: 4.3–4.2 (1H, m, H-1'), 4.21 (1H, dd, J=2.4 Hz, J=9.1 Hz, H-5), 3.48–3.39 (1H, m, H-4), 3.33 (1H, dd, J=2.4 Hz, J=6.5 Hz, H-6), 3.15–3.0 (2H, m, CH$_2$N), 2.34 (3H, s, SCH$_3$), 1.9–1.5 (4H, m, CH$_2$CH$_2$) and 1.33 ppm (3H, d, J=6.4 Hz, CH$_3$).

EXAMPLE 31

Sodium (4R,5S,6S)-6-[(1'R)-1'-hydroxyethyl]-4-(3"-hydroxypropyl)-3-methylthio-7-oxo-1-azabicyclo[3.2.0]hept-2-ene-2-carboxylate

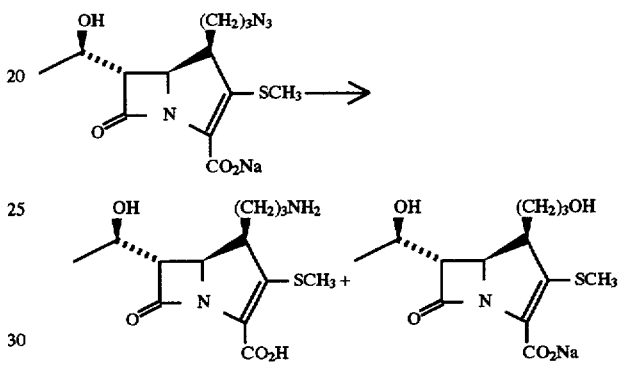

The pH of a cold (ice bath) 0.05M pH 7.0 sodium phosphate buffer (25 mL) of sodium (4R,5S,6S)-4-(3"-azidopropyl)-6-[(1'R)-1'-hydroxyethyl]-3-methylthio-7-oxo-1-azabicyclo[3.2.0]hept-2-ene-2-carboxylate made from the corresponding allyl ester (0.12 g, 0.33 mmol), as described in Example 29, was adjusted to pH 5.8 with a 1.0M pH 4.2 NaH$_2$PO$_4$ buffer solution. The mixture was then shaken on a Parr hydrogenator at a hydrogen pressure of 45–50 p.s.i. for 90 min at ~10° C. (initial temperature: 5° C.) using 30% Pd/Celite (120 mg) as catalyst. The catalyst was removed by filtration and the solution was passed through a µBondapak C$_{18}$ reversed phase column (50 g, H$_2$O→2% CH$_3$CN/H$_2$O) to give the mixture of both title material (0.3 g). This lyophilized powder was passed again on the reversed phase column (45 g, 150 mL of 0.05M pH 6.0 phosphate buffer, H$_2$O→2% CH$_3$CN/H$_2$O) to give the impure 3-aminopropyl compound of Example 30 (125 mg) and the pure 3-hydroxypropyl title compound (20 mg, 20%).

Purity by HPLC: 97.5% (2% CH$_3$CN/pH 7.4 0.01M phosphate buffer), retention time: 7.79 min;

UV (H$_2$O) $\lambda_{max}$: 306 (9700);

IR (Nujol) $\nu_{max}$: 3500–3100 (OH), 1740 and 1590 cm$^{-1}$ (C=O);

$^1$H NMR (D$_2$O, 200 MHz) δ: 4.34–4.18 (1H, m, H-1'), 4.21 (1H, dd, J=2.4 Hz, J=9.3 Hz, H-5), 3.69–3.63 (2H, m, CH$_2$O), 3.46–3.36 (1H, m, H-4), 3.38 (1H, dd, J=2.4 Hz, J=6.3 Hz, H-6), 2.36 (3H, s, SCH$_3$), 1.95–1.4 (4H, m, CH$_2$CH$_2$) and 1.34 ppm (3H, d, J=6.4 Hz, CH$_3$).

EXAMPLE 32

(4R,5S,6S)-4-[3"-(N-Formimidoyl)aminopropyl]-6-[(1'R)-1'-hydroxyethyl]-3-[(2-hydroxyethyl)thio]-7-oxo-1-azabicyclo [3.2.0]hept-2-ene-2-carboxylic acid

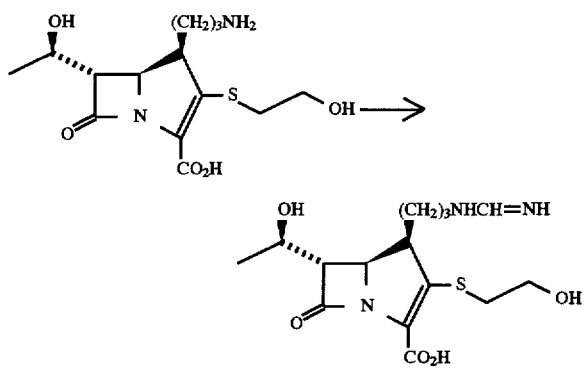

To a cold (ice bath) solution of (4R,5S,6S)-4-(3"-aminopropyl)-6-[(1'R)-1'-hydroxyethyl]-3-[(2-hydroxyethyl)thio]-7-oxo-1-azabicyclo[3.2.0]hept-2-ene-2-carboxylic acid (50 mg, 0.15 mmol) prepared in Example 27 in a 0.04M pH 7.0 phosphate buffer solution (10 mL, 0.4 mmol) was added a 0.1N aqueous NaOH solution in order to bring the pH to 8.2–8.4. To this solution was added portionwise benzylformimidate hydrochloride (257 mg, 1.5 mmol) while maintaining the pH at 8.0–8.5 with the 0.1N aqueous NaOH solution. The mixture was stirred for 10 min and then the pH was adjusted to 7.0 with 0.1N aqueous HCl. The solution was passed through a μ-Bondapak $C_{18}$ column (25 g, $H_2O\rightarrow 2\%$, 4% $CH_3CN/H_2O$) to give the pure title compound (33 mg, 62%) as a lyophilized powder.

Purity by HPLC: 93.8% (2% $CH_3CN/KH_2HPO_4$ 0.01M, pH 7.4), retention time: 5.73 min;

UV ($H_2O$) $\lambda_{max}$: 302 (7651);

IR (Nujol) $\nu_{max}$: 3600–3100 (NH,OH), 1755, 1585 (C=O) and 1710 $cm^{-1}$ (C=NH);

$^1$H NMR ($D_2O$, 200 MHz) δ: 7.83, 7.80 (1H, 2s, NCHN), 4.35–4.2 (1.5H, m, H-1'), 4.21 (0.5H, d, J=2.2 Hz, part of H-5), 3.8–3.7 (2H, m, $CH_2O$), 3.55–3.25 (4H, m, $CH_2N$, H-6, H-4), 3.1–2.8 (2H, 2 sets of m, $SCH_2$), 1.95–1.4 (4H, m, $CH_2CH_2$) and 1.32 ppm (3H, d, J=6.3 Hz, $CH_3$).

EXAMPLE 33

(4R,5S,6S)-4-[3"-(N-Formimidoyl)aminopropyl]-6-[(1'R)-1'-hydroxyethyl]-3-methylthio-7-oxo-1-azabicyclo[3.2.0]hept-2-ene-2-carboxylic acid

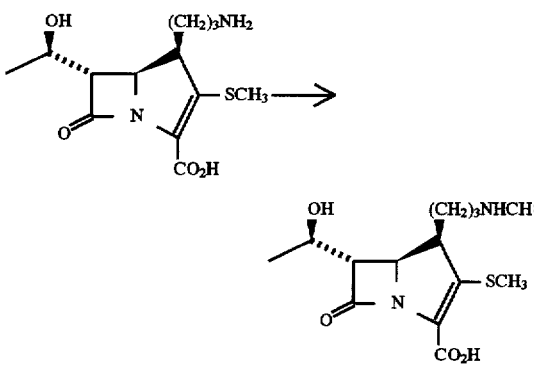

The pH of a cold (ice bath) solution of (4R,5S,6S)-4-(3"-aminopropyl)-6-[(1'R)-1'-hydroxyethyl]-3-methylthio-7-oxo-1-azabicyclo[3.2.0]hept-2-ene-2-carboxylic acid (31 mg, 0.10 mmol) prepared in Example 30 in a 0.05M pH 7.0 phosphate buffer was adjusted to 8.5 with a 0.1N aqueous NaOH solution. To the mixture was added portionwise benzyl formimidate hydrochloride (172 mg, 1 mmol), the pH being kept at 8–8.3 with the 0.1N aqueous NaOH solution, and it was stirred for 15 min. The pH of the mixture was then adjusted to 7.0 and the aqueous solution was passed through μBondapak $C_{18}$ column (15 g, $H_2O$) to give title compound (22 mg, 60%) as a lyophilized powder;

Purity by HPLC: 97.8% (304 nm, 2% $CH_3CN/KH_2P_4$ 0.01M pH 7.4) retention time 8.33 min;

UV ($H_2O$) $\lambda_{max}$: 306 (12,200);

IR (Nujol) $\nu_{max}$: 3600–3100 (OH, $NH_2$), 1750, 1590 (C=O) and 1710 $cm^{-1}$ (C=N);

$^1$H NMR ($D_2O$; 200 MHz) δ: 7.83, 7.80 (1H, 2s, CH), 4.35–4.18 (2H, m, H-1' and H-5), 3.45–3.35 (3H, m, $CH_2N$, H-4), 3.30 (1H, dd, J=2.4 Hz, J=6.2 Hz, H-6), 2.34 (3H, s $SCH_3$), 1.9–1.45 (4H, m, $CH_2CH_2$) and 1.32 ppm (3H, d, J=6.4 Hz, $CH_3$).

EXAMPLE 34

(4R,5S,6S)-4-[3"-(N-Guanidinyl)aminopropyl]-6-[(1'R)-1'-hydroxyethyl]-3-methylthio-7-oxo-1-azabicyclo[3.2.0]hept-2-ene-2-carboxylic acid

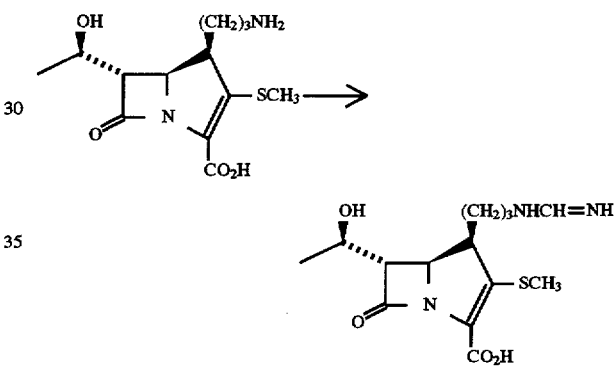

The pH of a cold (ice bath) solution of (4R,5S,6S)-4-(3"-aminopropyl)-6-[(1'R)-1'-hydroxyethyl]-3-methylthio-7-oxo-1-azabicyclo[3.2.0]hept-2-ene-2-carboxylic acid (50 mg, 0.17 mmol) prepared in Example 30 in a 0.05M pH 7.0 phosphate buffer was adjusted to pH 8 with a 0.1N aqueous NaOH solution. To this mixture was added portionwise aminoiminomethanesulfonic acid (211 mg, 1.70 mmol); the pH of the reaction mixture being kept at 7.8–8.0 with the 0.1N aqueous NaOH solution. It was then stirred for 1 h and the pH of the mixture was adjusted to 7.0 with a 0.1N aqueous HCl solution. It was passed through a μBondapak $C_{18}$ reversed phase column (25 g, $H_2O$) to give the title compound (17 mg, 40%) as a lyophilized powder.

Purity by HPLC: 99.4% (304 nm, 2% $CH_3CN/KH_2PO_4$ 0.01M pH 7.4), retention time 9.19 min;

UV ($H_2O$) $\lambda_{max}$: 306 (10,700);

IR (Nujol) $\lambda_{max}$: 3600–3100 ($NH_2$ OH) 1750, 1680 (C=O) and 1660 $cm^{-1}$ (C=N);

$^1$H NMR ($D_2O$, 200 MHz) δ: 4.3–4.17 (1H, m, H-1'), 4.20 (1H, dd, J=2.4 Hz, J=9.1 Hz, H-5), 3.46–3.30 (1H, m, H-4), 3.26 (1H, dd, J=2.5 Hz, J=6.3 Hz, H-6), 3.3–3.2 (2H, m, $CH_2N$), 2.34 (3H, s, $SCH_3$), 1.9–1.4 (4H, m, $CH_2CH_2$) and 1.32 ppm (3H, d, J=6.3 Hz, $CH_3$).

EXAMPLE 35

(4R,5S,6S)-4-[3"-(N-Guanidinyl)aminopropyl]-6-[(1'R)-1'-hydroxyethyl]-3-[(2-hydroxyethyl)thio]-7-oxo-1-azabicyclo-[3.2.0]hept-2-ene-2-carboxylic acid

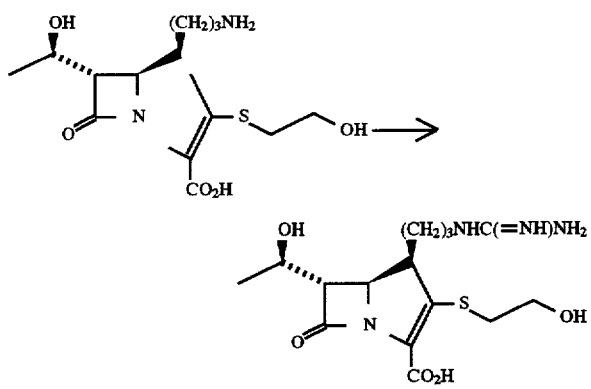

To a cold (ice bath) solution of (4R,5S,6S)-4-(3"-aminopropyl)-6-[(1'R)-1'-hydroxyethyl]-3-[(2-hydroxyethyl)thio]-7-oxo-1-azabicyclo[3.2.0]hept-2-ene-2-carboxylic acid (50 mg, 0.15 mmol) prepared in Example 27 in a 0.04M pH 7.0 aqueous phosphate buffer (10 mL, 0.4 mmol) was added a 0.1N aqueous NaOH solution in order to bring the pH7 to 7.8–8.0. To this solution was added portionwise aminoiminomethanesulfonic acid (186 mg, 1.5 mmol) as described by H. S. Mosher et al. *Tet. Lett.* 29 (26) 3183–86(1988) and the pH was kept between 7.6–7.8. The mixture was stirred for 1 h while maintaining a constant pH (7.6–7.8) with a 0.1N aqueous NaOH solution. The pH of the reaction mixture was adjusted to 7.08 with a 0.1N aqueous HCl solution and then passed through a μ-Bondapak $C_{18}$ reversed phase column (25 g, $H_2O$, 2%, 4% $CH_3CN/H_2O$) to give the title compound (35 mg, 63%) as a lyophilized powder;

Purity by HPLC: 99.1% (2% $CH_3CN$/buffer pH 7.4, 0.01M), retention time 7.5 min;

UV ($H_2O$) $\lambda_{max}$: 304 (7800);

IR (Nujol) $v_{max}$: 3320, 3180 (NH, OH), 1750, 1580 (C=O) and 1665 cm$^{-1}$ (C=N);

$^1$H NMR ($D_2O$, 200 MHz) δ: 4.3–4.2 (2H, m, H-1' and H-5), 3.77 (2H, t, J=6.2 Hz, $CH_2O$), 3.28 (1H, dd, J=2.4 Hz, J=6.2 Hz, H-6), 3.45–3.15 (3H, m, H-4 and $CH_2N$), 3.15–2.8 (2H, 2 sets of m, $SCH_2$), 2.0–1.45 (4H, m, $CH_2CH_2$) and 1.32 (3H, d, J=6.3 Hz, $CH_3$).

EXAMPLE 36

4R,5S,6S)-4-(2"-Aminoethyl)-3-[(2-cyanoethyl)thio]-6-[(1'R)-1'-hydroxyethyl]-7-oxo-1-azabicyclo[3.2.0]hept-2-ene-2-carboxylic acid

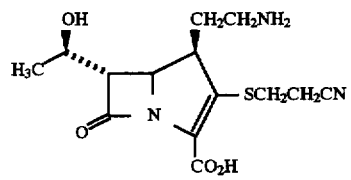

A. Allyl (4R,5R,6S)-4-(2"-azidoethyl)-6-[(1'R)-1'-tert-butyldimethylsilyloxyethyl]-3-[(2-cyanoethyl)thio]-7-oxo-1-azabicyclo[3.2.0]hept-2-ene-2-carboxylate

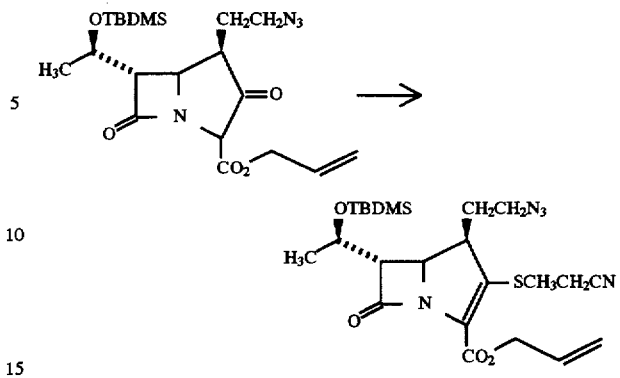

A solution of allyl (4R,5R,6S)-4-(2"-azidoethyl)-6-[(1'R)-1'-tert-butyldimethylsilyloxyethyl]-3,7-dioxo-1-azabicyclo[3.2.0]heptane-2-carboxylate (6.46 mmol, prepared by cyclization of the diazo precursor (3.0 g, 6.46 mmol) prepared in Example 2, Step E) in dry acetonitrile (50 mL) was treated at −15° C. and under nitrogen with diphenyl chlorophosphate (1.4 mL, 6.75 mmol) and N,N-diisopropylethylamine (1.2 mL, 6.9 mmol) added simultaneously over 5 min. A small crystal of 4-N,N-dimethylaminopyridine was then added and the temperature of the mixture was slowly warmed up to 0°–5° C. over 30 min. Then, N,N-diisopropylethylamine (1.2 mL, 6.9 mmol) and β-mercaptopropionitrile (1.13 g, 13.0 mmol) as described by L. Bauer and T. L. Welsh, *J. Org. Chem.*, 26, 1443 (1961) were added and the mixture was stirred at 0°–5° C. for 2 h. The reaction mixture was then diluted with EtOAc (300 mL), washed with water, 1M $NaHSO_3$, saturated $NaHCO_3$, brine and dried ($MgSO_4$). Evaporation of the solvent gave an oil which was chromatographed on silica gel (5×11 cm). Elution with a gradient of EtOAc (0–10%) in toluene gave 3.3 g (~100%) of the title compound as a brown oil contaminated by some polymeric material. This material was used as such for the next step.

IR (NaCl, film) $v_{max}$: 2250 (CN), 2100 ($N_3$), 1775 (C=O of β-lactam) and 1710 cm$^{-1}$ (C=O of ester);

$^1$H NMR (200 MHz, $CDCl_3$) δ: 0.19 (s, 6H, $SiCH_3$), 0.99 (s, 9H, Sit-Bu) 1.41 (d, J=6.11 Hz, 3H, $CH_3CHO$), 1.7–2.2 (m, 2H, $CH_2$-4), 2.7–3.4 (m, 5H, $SCH_2CH_2CN$ and H-6), 3.4–3.8 (m, 3H, $CH_2N_3$ and H-4), 4.3 (m, 2H, H-5 and $CH_3CHO$), 4.85 (m, 2H, $CH_2$ of allyl), 5.3–5.6 and 5.9–6.2 ppm (2×m, 2H and 1H, CH of allyl).

B. Allyl (4R,5S,6S)-4-(2"-azidoethyl)-3-[(2-cyanoethyl)thio]-6-[(1'R)-1'-hydroxyethyl]-7-oxo-1-azabicyclo-[3.2.0]hept-2-ene-2-carboxylate

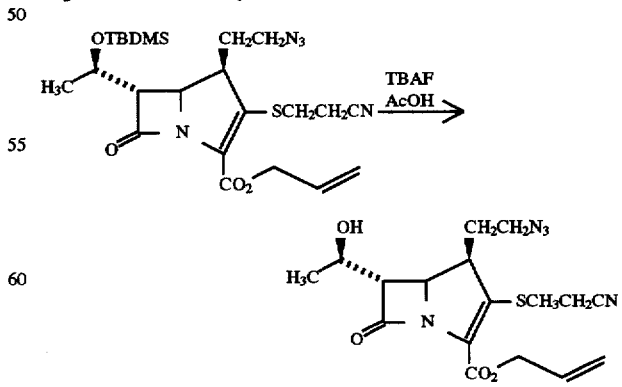

A solution of crude allyl (4R,5S,6S)-4-(2"-azidoethyl)-6-[(1'R)-1'-tert-butyldimethyldimethylsilyloxyethyl]-3-[(2- cyanoethyl)thio]-7-oxo-1-azabicyclo[3.2.0]hept-2-ene-2-carboxylate (3.3 g, 6.4 mmol) from Step A in dry tetrahydrofuran (100 mL) was treated at 0°–5° C. and under nitrogen with acetic acid (2.2 mL, 38.4 mmol) followed by 20 mL (20.0 mmol) of 1M solution of tetrabutylammonium fluoride in tetrahydrofuran. The solution was stored at 5° C. for 8 days. The reaction mixture was then diluted with EtOAc, washed with saturated NaHCO$_3$, brine and dried (MgSO$_4$). Evaporation of the solvent gave an oil which was chromatographed on silica gel (5×11 cm). Elution with a mixture of toluene and EtOAc (1:1) gave 0.92 g (36%, yield from the diazoazetidinone) of the title compound as a clear oil.

IR (NaCl, film) $v_{max}$: 3500 (OH), 2250 (CN), 2105 (N$_3$), 1775 (C=O of β-lactam) and 1710 cm$^{-1}$ (C=O of carboxylate);

$^1$H NMR (200 MHz, CDCl$_3$) δ: 1.40 (d, J=6.23 Hz, 3H, CH$_3$CHO), 1.6–2.1 (m, 2H, CH$_2$-4), 2.7 (m, 2H, CH$_2$CN), 2.9–3.3 (m, 3H, H-6 and SCH$_2$), 3.4–3.7 (m, 3H, H-4 and CH$_2$N$_3$), 4.25 (m overlapping with H-5, 1H, CH$_3$CHO), 4.29 (dd, J$_{H5,H6}$=2.80 Hz, J$_{H5,H4}$=9.69 Hz, 1H, H-5), 4.77 (m, 2H, CH$_2$ of allyl), 5.2–5.5 and 5.9–6.1 ppm (2×m, 2H and 1H, CH of allyl).

C. (4R,5S,6S)-4-(2"-Aminoethyl)-3-[(2-cyanoethyl)thio]-6-[(1'R)-1'-hydroxyethyl]-7-oxo-1-azabicyclo[3.2.0]hept-2-ene-2-carboxylic acid

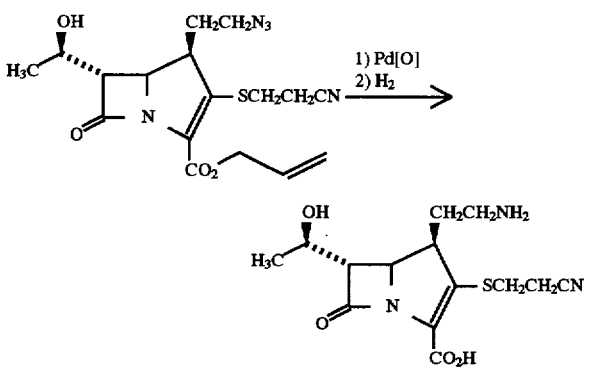

A solution of allyl (4R,5S,6S)-4-(2"-azidoethyl)-3-[(2-cyanoethyl)thio]-6-[(1'R)-1'-hydroxyethyl]-7-oxo-1-azabicyclo[3.2.0]hept-2-ene-2-carboxylate (0.92 g, 2.35 mmol) in dry CH$_2$Cl$_2$ (50 mL) was treated at 0°–5° C. and under nitrogen, with tetrakis (triphenylphosphine)palladium [0] (0.13 g) and 5.2 mL (2.6 mmol) of a 0.5M solution of potassium 2-ethylhexanoate in EtOAc. Then 200 mL of 0.1M pH 6.0 phosphate buffer were added and the organic solvent was evaporated under reduced pressure. The residual aqueous phase was hydrogenated at 0°–5° C. over 2.0 g of 5% palladium on barium sulfate and under 45 psi of hydrogen for 30 min. The catalyst was filtered and the filtrate was concentrated by half under vacuum. After two chromatographies on reversed phase silica gel (μ-Bondapak c-18, 7.5×10.5 cm) using water as eluent, lyophylization of the UV active fractions gave 0.15 g (20%) of the title compound as a white amorphous powder;

Purity by HPLC: 99% on μ-Bondapak c-18, 3.9 mm×30 cm, elution H$_2$O pH 7.4 phosphate buffer, flow rate 1 mL/min, UV detector 304 nm, retention time 4.67 min;

UV (H$_2$O, pH 7.4 phosphate buffer) $λ_{max}$: 298 nm (7,709);

IR (KBr) $v_{max}$: 2250 (CN), 1760 (C=O of β-lactam) and 1590 cm$^{-1}$ (C=O of carboxylate);

$^1$H NMR (200 MHz, D$_2$O) δ: 1.33 (d, J=6.35 Hz, 3H, CH$_3$CHO), 1.8–2.4 (m, 2H, CH$_2$-4), 2.85 (m, 2H, CH$_2$CN), 2.9–3.3 (m, 4H, SCH$_2$ and CH$_2$NH$_2$), 3.45 (m, overlapping with H-6, 1H, H-4), 3.47 (dd, J$_{H6,H5}$=2.90 Hz, J$_{H6,H1}$=6.47 Hz, 1H, H-6), and 4.2–4.4 ppm (m, 2H, H-5 and CH$_3$CHO).

EXAMPLE 37

Sodium (4R,5S,6S)-6-[(1'R)-1'-hydroxyethyl]-4-[2"-(2,5-dioxo-1-pyrrolidinyloxy)ethyl]-3-[(pyridin-2-yl)methylthio]-7-oxo-1-azabicyclo[3.2.0]hept-2-ene-2-carboxylate

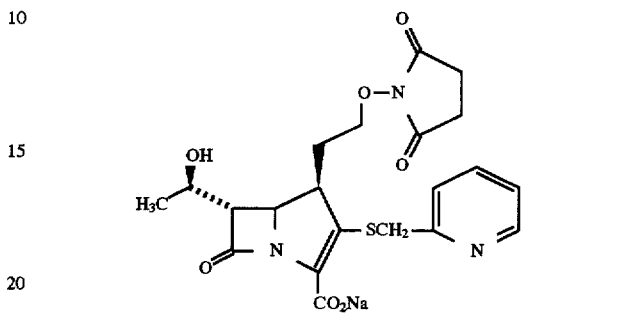

A. Allyl (4R,5S,6S)-6-[(1'R)-1'-(tert-butyldimethylsilyloxyethyl)]-4-[2"-(2,5-dioxo-1-pyrrolidinyloxy)ethyl]-3-[(pyridin-2-yl)methylthio]-7-oxo-1-azabicyclo[3.2.0]hept-2-ene-2-carboxylate

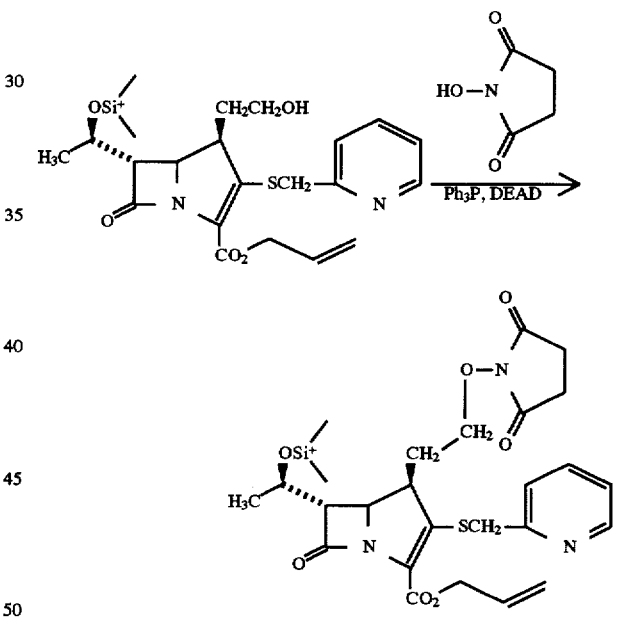

To a mixture of allyl (4R,5S,6S)-6-[(1'R)-1'-(tert-butyldimethylsilyloxyethyl)]-4-(2"-hydroxyethyl)-3-[(pyridin-2-yl)methylthio]-7-oxo-1-azabicyclo[3.2.0]hept-2-ene-2-carboxylate (0.29 g, 0.56 mmol), prepared in Example 6, Step A, N-hydroxysuccinimide (0.07 g, 0.62 mmol) and triphenylphosphine (0.176 g, 0.67 mmol) in dry THF (8 mL) at 0° C., under Argon, was added diethyl azodicarboxylate (0.117 g, 0.67 mmol). The reaction mixture was stirred at 0° C. for 1 hour and at room temperature for an additional hour. The solvent was removed under reduced pressure and the residue was chromatographed on silica (3×9 cm) packed in CH$_2$Cl$_2$ and eluted with a mixture of CH$_2$Cl$_2$ and EtOAc (4:6, gradient elution) to give the title compound mixed with about one equivalent of Ph$_3$P=O (0.465 g).

$^1$H NMR (200 MHz, CDCl$_3$ 7.24) δ: 0.04 (s, 6H, Si(CH$_3$)$_2$), 0.84 (s, 9H, SiC(CH$_3$)$_3$), 1.23 (d, CH$_3$, J$_{CH3,1'}$=

6.07 Hz), 1.73–1.95 (m, 1H, $CH_2$), 2.19–2.33 (m, 1H, $CH_2$), 2.67 (s, 4H, O=C($CH_2$)$_2$C=O), 3.14 (dd, H-6, $J_{5,6}$=2.56 Hz, $J_{6,1}$=6.4 Hz), 3.81 (m, H-4), 3.96–4.33 (overlapping, 6H, $CH_2$O, CHOH, H-5, $SCH_2$), 4.59–4.81 (m, $OCH_2$, allyl), 5.17–5.44 (m, =$CH_2$, allyl), 5.82–5.98 (m, CH=, allyl), 7.16 (m, H-5, py, $J_{4,5}$=7.47 Hz, $J_{5,6}$=4.91 Hz), 8.49 (d, H-6, py).

B. Allyl (4R,5S,6S)-6-[(1'R)-1'-hydroxyethyl]-4-[2"-(2,5-dioxo-1-pyrrolidinyloxy)ethyl]-3-[(pyridin-2-yl)methylthio]-7-oxo-1-azabicyclo[3.2.0]hept-2-ene-2-carboxylate

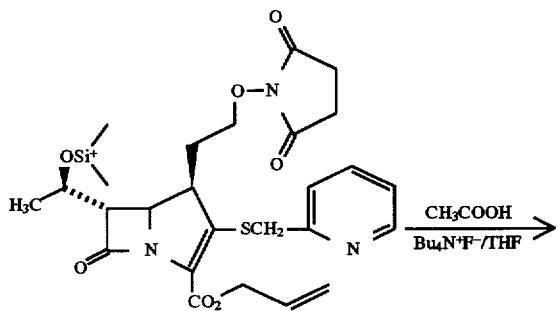

A cold (0° C.) solution of allyl (4R,5S,6S)-6-[(1'R)-1'-(tert-butyldimethylsilyloxyethyl)]-4-[2"-(2,5-dioxo-1-pyrroli-dinyloxy)ethyl]-3-[(pyridin-2-yl)methylthio]-7-oxo-1-azabicyclo[3.2.0]-hept-2-ene-2-carboxylate (0.46 g, 0.75 mmol) from Step A in dry THF (8 mL) was treated, under Argon, with acetic acid (0.26 mL, 4.48 mmol) followed by a 1M solution of tetrabutylammonium fluoride in THF (2.24 mL, 2.24 mmol). The mixture was stirred between 0° and 5° C. for 120 h and then neutralized at 0° C. with a 1M $NaHCO_3$ solution (4.52 mL, 4.48 mmol). The mixture was extracted with EtOAc (3×50 mL) and the combined organic phase was washed successively with a cold 1M $NaHCO_3$ solution, water and brine, dried ($MgSO_4$) and solvent evaporated to give a sticky gum which was chromatographed on silica (3.5×9 cm) packed in $CH_2Cl_2$ and eluted first with a mixture of $CH_2Cl_2$ and EtOAc (50 to 100% EtOAc) and then with a mixture of $CH_3CN$ and EtOAc (1:1 gradient elution) to give the title compound as a foam (0.18 g, 64.3%);

$^1$H NMR (200 MHz, $CDCl_3$ 7.24) δ: 1.37 (d, $CH_3$, $J_{CH3,1}$=6.25 Hz), 1.71–1.9 (m, 1H, $CH_2$), 2.31–2.44 (m, 1H, $CH_2$), 2.7 (s, 4H, O=C($CH_2$)$_2$C=O), 3.25 (dd, H-6, $J_{5,6}$=2.73 Hz, $J_{6,1}$,8.77 Hz), 3.91 (m, H-4), 3.85–4.30 (overlapping, 6H, $CH_2$O, CHOH, H-5, $SCH_2$), 4.58–4.86 (m, $OCH_2$, allyl), 5.19–5.46 (m, $CH_2$, allyl), 5.84–6.03 (m, CH=, allyl), 7.16 (m, H-5, py, $J_{3,5}$=0.93 Hz, $J_{4,5}$=7.67 Hz, $J_{5,6}$=4.04 Hz), 7.34 (m, H-3, py, $J_{3,4}$=7.8 Hz), 7.64 (m, H-4, py, $J_{4,6}$=1.82 Hz), 8.48 (m, H-6, py).

C. Sodium (4R,5S,6S)-6-[(1'R)-1'-hydroxyethyl]-4-[2"-(2,5-dioxo-1-pyrrolidinyloxy)ethyl]-3-[(pyridin-2-yl)methylthio]-7-oxo-1-azabicyclo[3.2.0]hept-2-ene-2-carboxylate

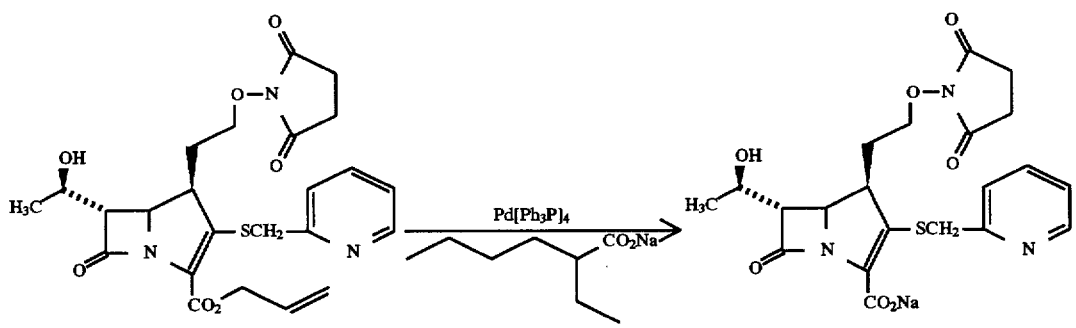

To a cold (0° C.) solution of allyl (4R,5S,6S)-6-[(1'R)-1'-hydroxyethyl]-4-[2"-(2,5-dioxo-1-pyrrolidinyloxy)ethyl]-3-[(pyridin-2-yl)methylthio]-7-oxo-1-azabicyclo[3.2.0]hept-2-ene-2-carboxylate (0.16 g, 0.32 mmol) in $CH_2Cl_2$ (10 mL), under Argon, was added Pd[$Ph_3P$]$_4$ (0.055 g, 0.048 mmol) followed by a 0.5M solution of sodium 2-ethylhexanoate in EtOAc (0.64 mL, 0.32 mmol). The mixture was stirred at 0° C. for 2 h and then extracted with water (3×15 mL). The combined aqueous phase was passed through a column of μ-Bondapak C-18 reverse phase silica (3×11 cm). The title compound was eluted with a mixture of water and $CH_3CN$ (9:1, gradient elution) and was obtained as a white fluffy solid after lyophilization (0.1 g, 64.9%);

Purity by HPLC: 97.6%; UV detection at 304 nm on μ-Bondapak C-18 (4 mm×30 cm), 8% $CH_3CN$ in pH 7.4 phosphate buffer, flow rate 1 mL/min, retention time 9.7 min;

IR (nujol) $v_{max}$: 1750 cm$^{-1}$ (C=O, β-lactam), 1720 cm$^{-1}$ (amide C=O).

UV (pH 7.4) $\lambda_{max}$: 304 (7756).

$^1$H NNR (200 MHz, $D_2O$) δ: 1.25 (d, $CH_3$, $J_{CH3,1}$=6.39 Hz), 1.75–1.91 (m, 1H, $CH_2$), 2.11–2.25 (m, 1H, $CH_2$), 2.82 (s, 4H, O=C($CH_2$)$_2$C=O), 3.41–3.52 (overlapping, 2H, H-4, H-6), 3.98–4.30 (overlapping, 6H, $CH_2$O, CHOH, H-5, $SCH_2$), 7.41 (dd, H-5, py, $J_{3,4}$=7.9 Hz), 7.91 (dt, H-4, py, $J_{4,6}$=1.68 Hz), 8.48 (d, H-6, py).

EXAMPLE 38

(4R,5S,6S)-4-(2"-Aminoethyl)-6-[(1'R)-1'-hydroxyethyl]-3-[(1,2,3-thiadiazol-4-yl)methylthio]-7-oxo-1-azabicyclo-[3.2.0]hept-2-ene-2-carboxylic acid

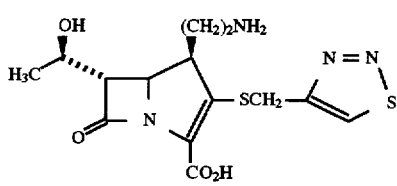

A. Allyl (4R,5S,6S)-4-(2"-azidoethyl)-6-[(1'R)-1'-tert-butyldimethylsilyloxyethyl]-3-[(1,2,3-thiadiazol-4-yl)methylthio]-7-oxo-1-azabicyclo[3.2.0]hept-2-ene-2-carboxylate

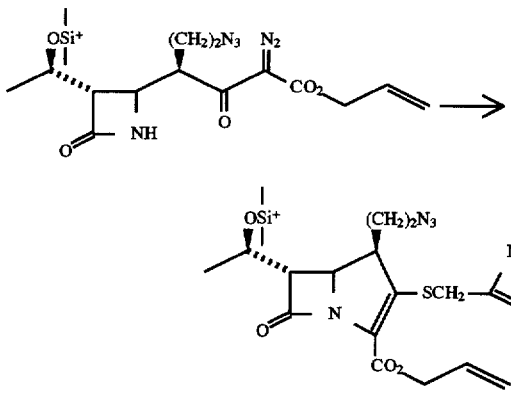

A solution of (3S,4R)-3-[(1'R)-1'-tert-butyldimethylsilyloxyethyl]-4-[(1"R)-1"-(2-azidoethyl)- 3"-diazo-3"-allyloxycarbonyl-2"-oxopropyl]azetidin-2-one (3.7 g, 8.0 mmol prepared as in Example 2, Step E) and Rh(OAc)$_2$ (150 mg) in hot benzene (300 mL) was heated under reflux for 1 h. Filtration and evaporation of benzene gave the crude allyl (4R,5S,6S)-4-(2"-azidoethyl)-6-[(1'R)-1'-tert-butyldimethylsilyloxyethyl]-3,7-dioxo-1-azabicyclo[3.2.0]heptan-2-carboxylate which was dissolved in CH$_3$CN (75 mL), cooled to -15° C. (ice-MeOH bath) and treated dropwise with diphenyl chlorophosphate (1.76 mL, 8.80 mmol) and N,N-diisopropylethylamine (1.54 mL, 8.8 mmol). The mixture was stirred for 1 h and the resulting enol phosphate was treated dropwise with 1,2,3-thiadiazol-4-methyl mercaptan (1.16 g, 8.8 mmol) in CH$_3$CN (1.5 mL) and N,N-diisopropylethylamine (1.54 mL, 8.8 mmol). The reaction mixture was stirred for 1 h and more mercaptan (160 mg, 1.2 mmol) and N,N-diisopropylethylamine (0.20 mL, 1.2 mmol) were added. The mixture was stirred for 1 h, diluted with cold EtOAc (200 mL), washed with cold water (25 mL), 1M aqueous NaHSO$_3$ (3×25 mL), H$_2$O (25 mL), 1N aqueous HCl (25 mL), 1M aqueous NaHCO$_3$ (25 mL), brine (25 mL) and dried (MgSO$_4$). The residue was passed through a silica gel flash pad (125 g, hexane→5%→25% EtOAc/hexane) to give the title compound (2.38 g, 61.5%) and some enol phosphate (640 mg, 0.96 mmol);

IR (CH$_2$Cl$_2$) $v_{max}$: 2100 (N$_3$), 1775 and 1710 cm$^{-1}$ (C=O);

$^1$H NMR (CDCl$_3$, 200 MHz) δ: 8.44 (1H, s, aromatic-H), 6.00–5.83 (1H, m, vinylic-H), 5.46–5.20 (2H, m, vinylic —H), 4.82–4.60 (2H, allylic CH$_2$), 4.774, 4.701, 3.397, 4.324 (2H, ABq, J=14.6 Hz, CH$_2$), 4.25–4.13 (1H, m, H-1'), 4.113 (1H, dd, J=2.7 Hz, J=9.6 Hz, H-5), 3.69–3.55 (2H, m, CH$_2$—N$_3$), 3.46–3.32 (1H, m, H-4), 3.094 (1H, dd, J=2.7 Hz, J=7.4 Hz, H-6), 2.16–1.98, 1.78–1.65 (2H, 2 sets of m, CH$_2$-4), 1.291 (3H, d, J=6.1 Hz, CH$_3$), 0.882 (9H, s, tert-butyl) and 0.080 ppm (6H, s, dimethyl).

B. Allyl (4R,5S,6S)-4-(2"-azidoethyl)-6-[(1'R)-1'-hydroxyethyl]-3-[(1,2,3-thiadiazol-4-yl)methylthio]-7-oxo-1-azabicyclo[3.2.0]hept-2-ene-2-carboxylate

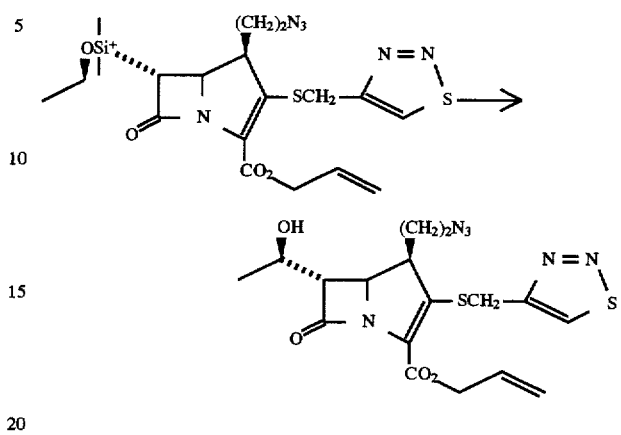

A cold (ice-MeOH bath) solution of allyl (4R,5S,6S)-4-(2"-azidoethyl)-6-[(1'R)-1'-tert-butyldimethylsilyloxyethyl]-3-[(1,2,3-thiadiazol-4-yl)methylthio]-7-oxo-1-azabicyclo[3.2.0]hept-2-ene-2-carboxylate (2.38 g, 4.30 mmol) in anhydrous THF (40 mL) was treated with acetic acid (1.49 mL, 25.8 mmol) and dropwise with a 1M solution of tetrabutylammonium fluoride in THF (12.9 mL, 12.9 mmol). The mixture was then stirred for 48 h at 5° C. It was diluted with EtOAc (150 mL) and washed with water (2×25 mL), 1M aqueous NaHCO$_3$ (2×25 mL), water (1×25 mL), brine (25 mL) and dried (MgSO$_4$). The residue was passed through a silica gel flash column (50 g, CH$_2$Cl$_2$/hexane: 1/1→EtOAc/CH$_2$Cl$_2$: 5→60%) to give the title compound (814 mg, 43%) as an oil;

IR (CH$_2$Cl$_2$) $v_{max}$: 3600 (OH), 2100 (N$_3$), 1780 and 1710 cm$^{-1}$ (C=O);

$^1$H NMR (CDCl$_3$, 200 MHz) δ: 8.46 (1H, s, aromatic —H), 6.04–5.84 (1H, m, vinylic —H), 5.47–5.21 (2H, m, vinylic-H), 4.87–4.59 (2H, m, allylic H), 4.799, 4.725, 4.353, 4.278 (2H, ABq, J=15.0 Hz, CH$_2$-aromatic), 4.216 (1H, dd, J=2.8 Hz, J=6.7 Hz, H-5), 4.72–4.18 (1H, m, H-1'), 3.79–3.67 (1H, m, H-4), 3.66–2.56, 3.52–3.38 (2H, 2 sets of m, CH$_2$—N$_3$), 3.176 (1H, dd, J=2.8 Hz, J=7.9 Hz, H$_6$), 2.20–2.03, 1.88–1.67 (2H, 2 sets of m, CH$_2$-4), 1.874 (1H, d, J=4.3 Hz, OH) and 1.495 ppm (3H, d, J=6.5 Hz, CH$_3$).

C. (4R,5S,6S)-4-(2"-Aminoethyl)-6-[(1'R)-1'-hydroxyethyl]-3-[(1,2,3-thiadiazol-4-yl)methylthio)]-7-oxo-1-azabicyclo[3.2.0]hept-2-ene-2-carboxylic acid

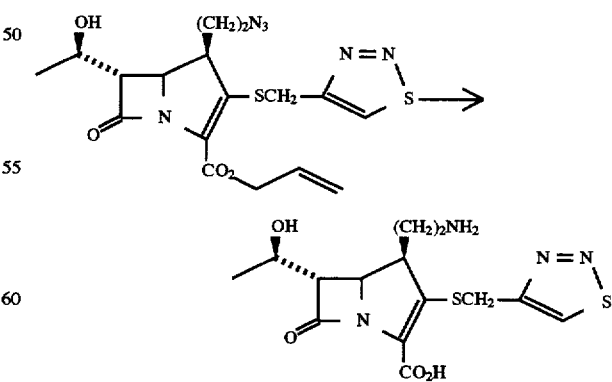

A cold (ice bath) solution of allyl (4R,5S,6S)-4-(2"-azidoethyl)-6-[(1'R)-1'-hydroxyethyl]-3-[(1,2,3-thiadiazol-4-yl)methylthio]-

7-oxo-1-azabicyclo[3.2.0]hept-2-ene-2-carboxylate (465 mg, 1.07 mmol) in CH₂Cl₂ (50 mL) was treated with Pd(PPh₃)₄ (22 mg) and a 0.5M solution of sodium ethyl-2-hexanoate (2.14 mL, 1.07 mmol) in EtOAc. The mixture was stirred for 1 h, diluted with diethyl ether (20 mL) and extracted with a 0.04M aqueous pH 7.0 phosphate buffer (4×5 mL). The aqueous extracts were washed with diethyl ether (2×20 mL) and the pH was adjusted to 5.9. The aqueous solution was then shaken in a Parr hydrogenator at 45–50 psi hydrogen for 1 h at 5°→15° C. (at the end of the reaction) using 30% Pd/Celite (465 mg) as catalyst. The catalyst was removed by filtration and washed with water (2×5 mL). The aqueous layer was passed through a μ-Bondapak C₁₈ reversed phase column (100 g, H₂O→1%→3% CH₃CN/H₂O) to give the title compound (163 mg, 41%) as a lyophilized powder;

Purity: 97.9% by HPLC (300 nm);

UV (H₂O) λ$_{max}$: 300 (ε9240);

IR (Nujol) δ: 1770 and 1580 cm⁻¹ (C=O);

¹H NMR (D₂O, 200 MHz) δ: 8.87 (1H, s, aromatic H), 4.73, 4.67, 4.43, 4.35 (2H, ABq, J=14.0 Hz, CH₂-aromatic), 4.31–4.18 (1H, m, H-1'), 4.157 (1H, dd, J=2.8 Hz, J=9.7 Hz, H-5), 3.417 (1H, dd, J=2.8 Hz, J=6.5 Hz, H-6), 3.38–3.26 (1H, m, H-4), 3.17–3.02 (2H, m, CH₂—N), 2.25–2.07, 1.86–1.65 (2H, 2 sets of m, CH₂-4), and 1.306 ppm (3H, d, J=6.4 Hz, CH₃).

EXAMPLE 39

(4R,5S,6S)-4-(2"-Aminoethyl)-6-[(1'R)-1'-hydroxyethyl]-3-methylthio-7-oxo-1-azabicyclo[3.2.0]hept-2-ene-2-carboxylic acid

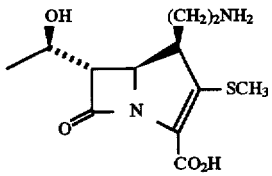

A. Allyl (4R,5S,6S)-4-(2"-azidoethyl)-6-[(1'R)-1'-hydroxyethyl]-3-methylthio-7-oxo-1-azabicyclo[3.2.0]hept-2-ene-2-carboxylate

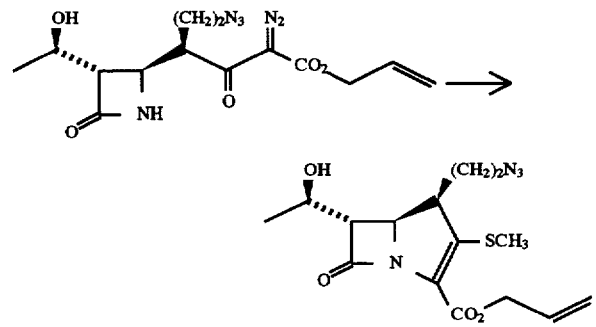

A cold solution (ice-MeOH bath) of allyl (4R,5S,6S)-4-(2"-azidoethyl)-6-[(1'R)-1'-hydroxyethyl]-3,7-dioxo-1-azabicyclo[3.2.0]heptan-2-carboxylate [from (3S,4R)-3-[(1'R)-1'-hydroxyethyl]-4-[(1R)-1"-(2-azidoethyl)-3"-diazo-3"-allyloxy-carbonyl-2"-oxopropyl]azetidin-2-one (2.55 g, 7.00 mmol) as described in Example 38, Step A] in CH₃CN (100 mL) was treated with diphenyl chlorophosphate (1.63 mL, 7.70 mmol), N,N-diisopropylethylamine (1.40 mmL, 7.7 mmol) and 4-dimethylaminopyridine (26 mg). The mixture was stirred for 1 h and the resulting enol phosphate was treated with trimethylsilyl chloride (1.0 mL, 7.7 mmol) and N,N-diisopropylethylamine (1.4 mL, 7.7 mmol). The mixture was stirred (15 min) and N,N-diisopropylethylamine (2.8 mL, 15 mmol) was added followed by the addition of a stream of CH₃SH gas for 10 min. The mixture was allowed to react at 5° C. for 44 h, then diluted with EtOAc (300 mL), washed with an ice cold 1M aqueous NaHCO₃ (3×50 mL) solution, ice cold water (3×50 mL), brine (50 mL) and dried (MgSO₄). The residue (3 g) was diluted with THF (100 mL), treated with 2N aqueous AcOH (17.5 mL, 35 mmol) and stirred for 1 h at 22° C. The mixture was diluted with EtOAc (300 mL), washed with 1M aqueous NaHCO₃ (2×100 mL), H₂O (3×100 mL), brine (100 mL) and dried (MgSO₄). The residue (1.5 g) was passed through a silica gel pad (75 g, hexane/EtOAc: 1/1→EtOAc) to give the title compound (530 mg, 21%) as an oil;

IR (neat) ν$_{max}$: 3600–3200 (OH) 2100 (N₃) 1770 and 1705 cm⁻¹ (C=O);

¹H NMR (CDCl₃, 200 MHz) δ: 6.07–5.87 (1H, m, vinylic H), 5.49–5.22 (2H, m, vinylic —H), 4.88–4.63 (2H, m, allylic CH₂), 4.30–4.19 (1H, m, H-1'), 4.227 (1H, dd, J=2.6 Hz, J=9.4 Hz, H-5), 3.66–3.54 (1H, m, H-4), 3.49–3.34 (2H, m, CH₂N), 3.142 (1H, dd, J=2.6 Hz, J=7.9 Hz, H-6), 2.394 (3H, s, SCH₃), 2.17–1.68 (3H, m, and bs, OH and CH₂-4) and 1.391 ppm (3H, d, J=6.2 Hz, CH₃).

B. Sodium (4R,5S,6S)-4-(2"-azidoethyl)-6-[(1'R)-1'-hydroxyethyl]-3-methylthio-7-oxo-1-azabicyclo[3.2.0]hept-2-ene-2-carboxylate

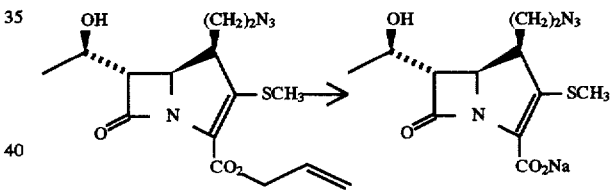

A cold (ice-bath) solution of allyl (4R,5S,6S)-4-(2"-azidoethyl)-6-[(1'R)-1'-hydroxyethyl]-3-methylthio-7-oxo-1-azabicyclo[3.2.0]hept-2-ene-2-carboxylate (0.53 g, 1.5 mmol) in CH₂Cl₂ (5 mL) was treated with Pd(PPh₃)₄ (50 mg) and a 0.5M solution of sodium 2-ethylhexanoate in EtOAc (3.2 mL, 1.6 mmol). The ice bath was removed and the mixture was stirred for 30 min. It was diluted with ethyl acetate (20 mL) and extracted with water (2×10 mL). The aqueous phases were combined, washed with diethyl ether (20 mL) and passed through a reversed phase μ-Bondapak C₁₈ column (50 g, H₂O→5% CH₃CN/H₂O) to give the title compound (0.32 g, 64%) as a lyophilized powder;

¹H NMR (D₂O, 200 MHz) δ: 4.33–4.19 (1H, m, H-1'), 4.221 (1H, dd, J=2.7 Hz, J=9.6 Hz, H-5), 3.63–3.33 (3H, m, H-4, CH₂—N), 3.401 (1H, dd, J=2.7 Hz, J=6.4 Hz, H-6), 2.365 (3H, s, SCH₃), 2.13–1.95, 1.89–1.70 (2H, 2 sets of m, CH₂-4) and 1.334 ppm (3H, d, J=6.4 Hz, CH₃).

C. (4R,5S,6S)-4-(2"-Aminoethyl)-6-[(1'R)-1'-hydroxyethyl]-3-methylthio-7-oxo-1-azabicyclo[3.2.0]hept-2-ene-2-carboxylic acid

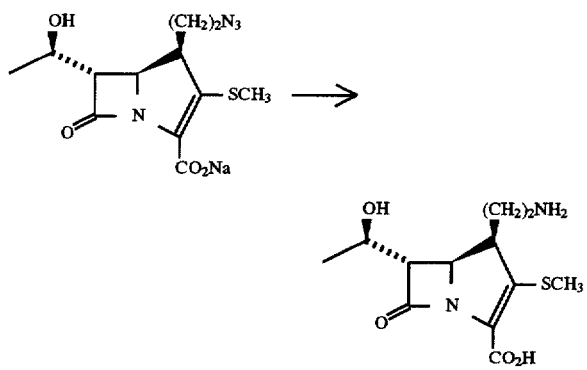

A cold (ice bath) solution of sodium (4R,5S,6S)-4-(2"-azidoethyl)-6-[(1'R)-1'-hydroxyethyl]-3-methylthio-7-oxo-1-azabicyclo[3.2.0]hept-2-ene-2-carboxylate (320 mg, 0.960 mmol) in water (20 mL) was shaken on a Parr hydrogenator at 45–50 psi hydrogen for 90 min using 30% Pd/Celite (320 mg) as catalyst. The catalyst was removed by filtration and the aqueous phase was passed three time on μ-Bondapak $C_{18}$ column (50 g, 800 g and 80 g, $H_2O$) to give the title compound (82 mg, 30 %) as a lyophilized powder;

Purity: 91.8% (HPLC, 304 nm);

UV ($H_2O$) $\lambda_{max}$: 304 (ε8110);

IR (Nujol) δ: 3600–3200 (OH), 1750 and 1600 cm$^{-1}$ (C=O);

$^1$H NMR ($D_2O$, 200 MHz) δ: 4.34–4.21 (1H, m, H-1'), 4.231 (1H, dd, J=2.6 Hz, J=6.6 Hz, H-5), 3.53–3.40 (1H, m, H-4), 3.385 (1H, dd, J=2.6 Hz, J=6.6 Hz, H-6), 3.14–3.05 (2H, m, $CH_2N$), 2.34 (3H, s, $SCH_3$), 2.23–2.80 (2H, 2 sets of m, $CH_2$-4) and 1.335 ppm (3H, d, J=6.3 Hz, $CH_3$).

EXAMPLE 40

(4R,5S,6S)-4-(2"-Guanidinoethyl)-6-[(1'R)-1'-hydroxyethyl]-3-[(1,2,3-thiadiazol-4-yl)methylthio]-7-oxo-1-azabicyclo-[3.2.0]hept-2-ene-2-carboxylic acid

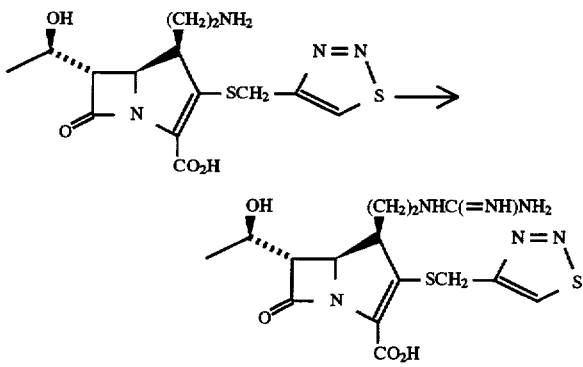

A cold solution (ice bath) of (4R,5S,6S)-4-(2"-aminoethyl)-6-[(1'R)-1'-hydroxyethyl]-3-[(1,2,3-thiadiazol-4-yl) methylthio]-7-oxo-1-azabicyclo[3.2.0]hept-2-ene-2-carboxylic acid (160 mg, 0.432 mmol) from Example 38 in a 0.04M aqueous pH 7.4 phosphate buffer solution (25 mL) was treated with a 0.1N aqueous NaOH solution (to adjust and maintain the pH between 7.6–7.8) and portionwise with aminoiminomethanesulfonic acid (533 mg, 4.30 mmol). The mixture was stirred for 45 min and the pH was adjusted to 6.9 with a 0.1N aqueous HCl solution. The aqueous mixture was passed through a μ-Bondapak $C_{18}$ reversed phase column (50 g, $H_2O \rightarrow 1\%$–5% $CH_3CN/H_2O$) to give the title compound (93 mg, 52%) as a lyophilized powder;

Purity: 99.7% (HPLC, 300 nm);

UV ($H_2O$) $\lambda_{max}$: 302 (ε8300);

IR (Nujol) $v_{max}$: 3400–3100 (OH), 1755 (C=O), 1665 (C=N) and 1585 cm$^{-1}$ (C=O);

$^1$H NMR ($D_2O$, 200 MHz) δ: 8.886 (1H, s, aromatic —H), 4.651, 4.577, 4.421, 4.347 (2H, ABq, J=14.9 Hz, $CH_2$-aromatic), 4.3–4.17 (1H, m, H-1'), 4.143 (1H, dd, J=2.7 Hz, J=9.7 Hz, H-5), 3.405 (1H, dd, J=2.7 Hz, J=6.8 Hz, H-6), 3.38–3.1 (3H, m, H-4 and $CH_2$—N), 2.15–1.95, 1.8–1.55 (2H, 2 set of m, $CH_2$-4) and 1.315 (3H, d, J=6.4 Hz, $CH_3$).

EXAMPLE 41

(4R,5S,6S)-4-(3"-Aminopropyl)-3-[(2-cyanoethyl)thio]-6-[(1'R)-1'-hydroxyethyl]-7-oxo-1-azabicyclo[3.2.0]hept-2-ene-2-carboxylic acid

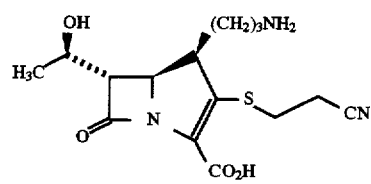

A. Allyl (4R,5S,6S)-4-(3"-azidopropyl)-3-[(2-cyanoethyl)thio]-6-[(1'R)-1'-hydroxyethyl]-7-oxo-1-azabicyclo-[3.2.0]hept-2-ene-2-carboxylate

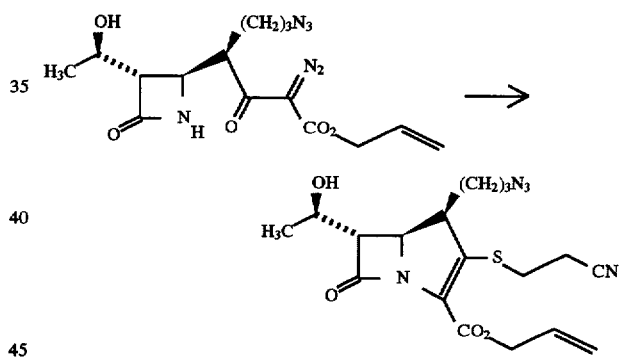

A cold solution (ice-MeOH bath) of allyl (2R,4R,5S,6S)-4-(3"-azidopropyl)-6-[(1'R)-1'-hydroxyethyl]-3,7-dioxo-1-azabicyclo[3.2.0]heptan-2-carboxylate, prepared from (3S,4R)-3-[(1'R)-1'-hydroxyethyl]-4[(1"R)-1"(3"-azidopropyl)-3"-diazo-3"-allyloxycarbonyl-2"-oxopropyl]azetidin-2-one (2.16 g, 5.90 mmol), as prepared in Example 21, Step B in $CH_3CN$ (40 mL) was treated dropwise with diphenyl chlorophosphate (1.3 mL, 6.5 mmol) and N,N-diisopropylethylamine (1.12 mL, 6.5 mmol) and a trace of 4-dimethylaminopyridine. The mixture was stirred for 45 min and the resulting enolphosphate was silylated by the successive addition of trimethylsilyl chloride (0.84 mL, 6.5 mmol) and N,N-diisopropylethylamine (1.12 mL, 6.50 mmol).

The mixture was stirred for 30 min and the resulting enol phosphate silyl ether was treated with cyanoethanethiol (640 mg, 7.37 mmol) and N,N-diisopropylethylamine (1.27 mL, 7.37 mmol). The mixture was stirred for 30 min after which the ice-MeOH bath was replaced by an ice bath and stirring was continued for 30 more minutes. Then cyanoethanethiol (160 mg, 1.84 mmol) and N,N-diisopropylethylamine (0.317 mL, 1.84 mmol) was added in, followed by a stirring period of 1 h. More cyanoethanethiol (160 mg, 1.84 mmol) and N,N-diisopropylethylamine (0.317 mL, 1.84 mmol) was added and after 30 min stirring the mixture was diluted with EtOAc (100 mL), washed with ice cold water (3×40 mL), 1M aqueous NaHSO₃ (3×40 mL), water (40 mL), 1M aqueous NaHCO₃ (40 mL), water (40 mL), brine (40 mL) and dried (MgSO₄). The residue obtained upon solvent evaporation was dissolved in THF (40 mL), cooled to -15° C. (ice-MeOH bath) and treated successively with acetic acid (2 mL, 35.4 mmol) and dropwise with a 1M solution of tetrabutylammonium fluoride in THF (17.7 mL, 17.7 mmol). The mixture was stirred for 40 min, diluted with EtOAc (100 mL), washed with cold 1N aqueous HCl (20 mL), water (2×20 mL), 1M aqueous NaHCO₃ (20 mL), water (2×20 mL), brine and dried (MgSO₄). The residue was passed through a silica gel flash column (50 g, $CH_2Cl_2 \rightarrow 10, 20, 40, 60\%$ EtOAc/$CH_2Cl_2$) to give the title compound as an oil (1.41 g, 59.0%);

IR ($CH_2Cl_2$) $v_{max}$: 3600, 3500 (OH), 2100 ($N_3$), 1780 and 1710 cm⁻¹ (C=O);

¹H NMR (CDCl₃, 200 MHz) δ: 6.07–5.87 (1H, m, vinylic H), 5.50–5.24 (2H, m, vinylic H), 4.89–4.63 (2H, m, allylic-CH₂), 4.279 (1H, dd, J=2.8 Hz, J=9.7 Hz, H-5), 4.3–4.17 (1H, m, H-1'), 3.52–3.36 (2H, m, CH₂N₃), 3.30–3.2 (1H, m, H-4), 3.277 (1H, dd, J=2.8 Hz, J=7.6 Hz, H-6), 3.22–2.93 (2H, m, SCH₂), 2.82–2.56 (2H, m, CH₂CN), 2.0–1.7 (5H, m, OH, CH₂CH₂) and 1.395 ppm (3H, d, J=6.2 Hz, CH₃).

B. (4R,5S,6S)-4-(3"-Aminopropyl)-3-[(2-cyanoethyl)thio]-6-[(1'R)-1'hydroxyethyl]-7-oxo-1-azabicyclo[3.2.0]hept-2-ene-2-carboxylic acid

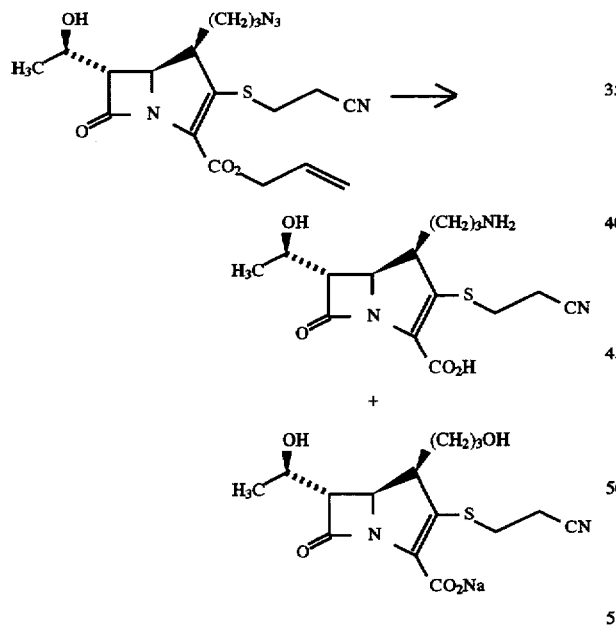

A cold (ice bath) solution of allyl (4R,5S,6S)-4-(3"-azidopropyl)-3-[(2-cyanoethyl)thio]-6-[(1'R)-1'-hydroxyethyl]-7-oxo-1-azabicyclo[3.2.0]hept-2-ene-2-carboxylate (661 mg, 1.63 mmol) in $CH_2Cl_2$ (66 mL) was treated with Pd(PPh₃)₄ (132 mg, 0.110 mmol) and dropwise with a 0.5M solution of sodium ethyl-2-hexanoate (3.3 mL, 1.7 mmol). The mixture was stirred for 50 min, diluted with diethyl ether (250 mL) and extracted with a 0.04M pH 7 phosphate solution (3×10 mL). The aqueous extracts were combined, washed with diethyl ether (2×50 mL) and the pH was lowered to 5.9 with a 1M aqueous NaH₂PO₄ buffer solution. To this mixture (crude sodium salt of (4R,5S,6 S)-4-(3"-azidopropyl)-3-(2-cyanoethylthio)-6-[(1' R)-1'-hydroxyethyl]-7-oxo-1-azabicyclo[3.2.0]hept-2-ene-2-carboxylate) was added Pd/Celite (660 mg) and it was shaken on a Parr hydrogenator at 45–50 psi hydrogen for 1 h at 5° C. (ice bath, initial temperature, 15° C. final temperature). The catalyst was removed by filtration and washed with water (2×10 mL). The aqueous solution was passed through a μ-Bondapak C₁₈ reversed phase column (165 g, $H_2O \rightarrow 1\%$ CH₃CN) to give the 3-aminopropyl title compound and the 3-hydroxypropyl derivative (363 mg) described in Example 42 as 74:26 mixture. The mixture was passed again on the reversed phase column (180 g, pH 6.0, 0.01M phosphate buffer) to give both derivatives with phosphate salts.

The salt of the 3-aminopropyl compound was removed by reversed phase chromatography to give pure title compound (182 mg, 33%);

Purity: 98.3% (HPLC 300 nm);
UV (H₂O) $\lambda_{max}$: 300 (7900);
IR (nujol) $v_{max}$: 1755 and 1585 cm⁻¹ (C=O);

¹H NMR (D₂O, 200 MHz) δ: 4.34–4.21 (1H, m, H-1'), 4.268 (1H, dd, J=2.5 Hz, J=6.8 Hz, H-5), 3.408 (1H, dd, J=2.5 Hz, J=6.5 Hz, H-6), 3.47–3.38 (1H, m, H-4), 3.23–2.91 (4H, m, CH₂NH₂, CH₂S), 2.89–2.80 (2H, m, CH₂CN), 1.92–1.50 (4H, m, CH₂CH₂) and 1.334 ppm (3H, d, J=6.3 Hz, CH₃).

EXAMPLE 42

Sodium (4R,5S,6S)-3-[(2-cyanoethyl)thio]-6-[(1'R)-1'-hydroxyethyl]-4-(3"-hydroxypropyl)-7-oxo-1-azabicyclo-[3.2.0]hept-2-ene-2-carboxylate

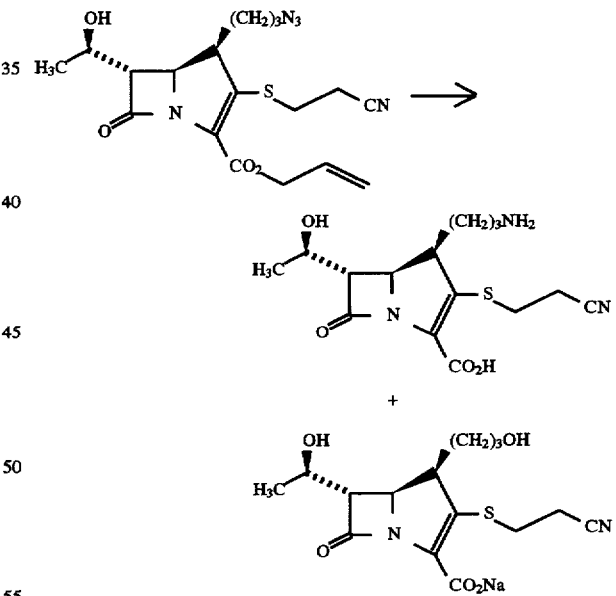

A cold (ice bath) solution of allyl (4R,5S,6 S)-4-(3"-azidopropyl)-3-[(2-cyanoethyl)thio]-6-[(1' R)-1'-hydroxyethyl]-7-oxo-1-azabicyclo[3.2.0]hept-2-ene-2-carboxylate (661 mg, 1.63 mmol) from Example 41, Step A in $CH_2Cl_2$ (66 mL) was treated with Pd(PPh₃)₄ (132 mg, 0.110 mmol) and dropwise with a 0.5M solution of sodium ethyl-2-hexanoate (3.3 mL, 1.7 mmol). The mixture was stirred for 50 min, diluted with diethyl ether (250 mL) and extracted with a 0.04M pH 7 phosphate solution (3×10 mL). The aqueous extracts were combined, washed with diethyl ether (2×50 mL) and the pH was lowered to 5.9 with a 1M aqueous NaH$_2$PO$_4$ buffer solution. To this mixture (crude sodium salt of (4R,5S,6S)-4-(3"- azidopropyl)-3-(2-cyanoethylthio)-6-[(1'R)-1'-hydroxyethyl]-7-oxo-1-azabicyclo[3.2.0]hept-2-ene-2-carboxylate) was added 30% Pd/Celite (660 mg) and it was shaken on a Parr hydrogenator at 45-50 psi hydrogen for 1 h at 5° C. (ice bath, initial temperature, 15° C. final temperature). The catalyst was removed by filtration and washed with water (2×10 mL). The aqueous solution was passed through a μ-Bondapak C$_{18}$ reversed phase column (165 g, H$_2$O→1% CH$_3$CN) to give the 3-aminopropyl compound of Example 41 and the 3-hydroxypropyl title compound (363 mg) as 74:26 mixture. The mixture was passed again on the reversed phase column (180 g, pH 6.0, 0.01M phosphate buffer) to give both derivatives with phosphate salts.

The salt of the 3-hydroxypropyl compound was removed by reversed phase chromatography (H$_2$O) to give the title compound (85 mg, 14%) as a lyophilized powder;

Purity: 92.5% (HPLC 300 nm);

IR (Nujol) ν$_{max}$: 1745 and 1695 cm$^{-1}$ (C=O);

UV (H$_2$O) λ$_{max}$: 302 (9600);

$^1$H NMR (D$_2$O, 200 MHz) δ: 4.34–4.21 (1H, m, H-1'); 4.270 (1H, dd, J=2.4 Hz, J=12.0 Hz, H-5), 3.65, 2H, bt, J=6.0 Hz, CH$_2$O), 3.450 (1H, dd, J=2.5 Az, J=6.0 Hz, H-6); 3.45–3.35 (1H, m, H-4), 3.25–3.06, 3.03–2.9 (2H, 2 sets of m, SCH$_2$), 2.88–2.80 (2H, m, CH$_2$CN), 1.94–1.41 (4H, m, CH$_2$CH$_2$) and 1.331 ppm (3H, d, J=6.4 Hz, CH$_3$).

EXAMPLE 43

(4R,5S,6S)-4-[3"-(N-Formimidoyl)aminopropyl]-3-[(2-cyanoethyl)thio]-6-[(1'R)-1'-hydroxyethyl]-7-oxo-1-azabicyclo-[3.2.0]hept-2-ene-2-carboxylic acid

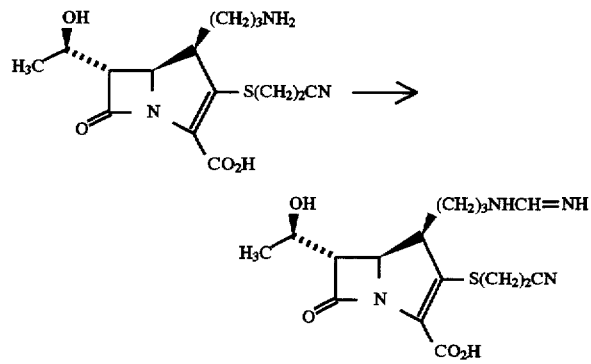

To a cold (ice bath) solution of (4R,5S,6S)-4-(3"-aminopropyl)-3-[(2-cyanoethyl)thio]-6-[(1'R)-1'-hydroxyethyl]-7-oxo-1-azabicyclo[3.2.0]hept-2-ene-2-carbocylic acid (135 mg, 0.400 mmol) from Example 41 in a 0.04M pH 7.0 aqueous phosphate buffer solution (25 mL) was added a 0.1N aqueous NaOH solution to bring the pH to 8.2–8.4 and benzyl formimidate hydrochloride (685 mg, 4.00 mmol) portionwise; the pH of the aqueous mixture being maintained at 8.0–8.4. The mixture was stirred for 10 min and then the pH was lowered to 7.0 with a 0.1N aqueous HCl solution. The solution was passed twice through a μ-Bondapak C$_{18}$ reversed phase column (30 g, H$_2$O→1%, 2% CH$_3$CN/H$_2$O) to give the title compound (99 mg, 69%) as a lyophilized powder;

Purity: 97.8% (HPLC 300 nm);

UV (H$_2$O) λ$_{max}$: 300 (9350);

IR (Nujol) ν$_{max}$: 1760 (C=O), 1710 (C=N) and 1590 cm$^{-1}$ (C=O);

$^1$H NMR (D$_2$O, 200 MHz) δ: 7.83, 7.81 (1H, 2s, CH), 4.725 (1H, dd, J=2.5 Hz, J=6.1 Hz, H-5), 4.31–4.20 (1H, m, H-1'), 3.50–3.35 (4H, m, H-4, H-6 and CH$_2$N), 3.22–3.08 and 3.02–2.91 (2H, 2 sets of m, SCH$_2$), 2.89–2.80 (2H, m, CH$_2$CN), 1.92–1.50 (4H, m, CH$_2$CH$_2$) and 1.323 ppm (3H, d, J=6.4 Hz, CH$_3$).

EXAMPLE 44

(4R,5S,6S)-4-(3"-Aminopropyl)-6-[(1'R)-1'-hydroxyethyl]-3-[(pyridin-4-yl)methylthio]-7-oxo-1-azabicyclo[3.2.0]hept-2-ene-2-carboxylic acid

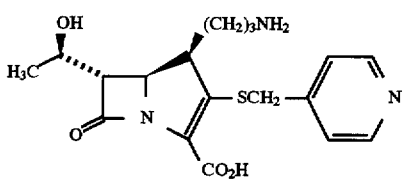

A. Allyl (4R,5S,6S)-4-(3"-azidopropyl)-6-[(1'R)-1'-hydroxyethyl]-3-[(pyridin-4-yl)methylthio]-7-oxo-1-azabicyclo [3.2.0]hept-2-ene-2-carboxylate

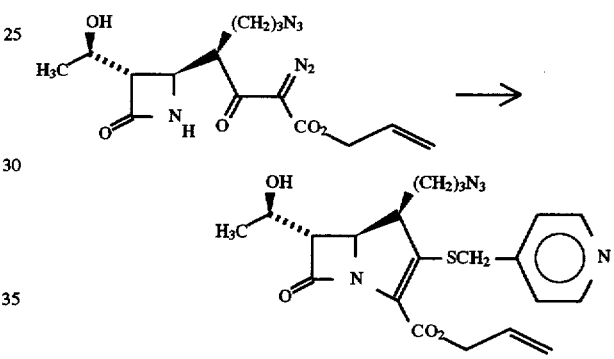

A cold (ice MeOH bath) solution of allyl (4R,5S,6S)-6'-[(1'R)-1'-hydroxyethyl]-4-(3"-azidopropyl)-3,7-dioxo-1-azabicyclo[3.2.0]hept-2-ene-2-carboxylate [from (3 S,4R)-3-[(1'R)-1'-hydroxyethyl]-4-[(1" R)-1"-(3-azidopropyl)-3"-diazo-3"-allyloxycarbonyl-2"-oxopropyl]azetidin-2-one (4.0 g, 11 mmol) as prepared in Example 21, Step B heated under reflux in benzene (300 mL) with Rh(OAc)$_2$ (100 mg) for 45 min] in CH$_3$CN (100 mL) was treated dropwise with diphenyl chlorophosphate (2.6 mL, 12 mmol), N,N-diisopropylethylamine (2.2 mL, 12 mmol) and 4-N,N-dimethylaminopyridine (20 mg). The mixture was stirred for 1 h, then treated with 4-picolyl mercaptan (2.07 g, 16.5 mmol) and N,N-diisopropylethylamine (3.1 mL, 17 mmol) and kept for 18 h at 5° C. The mixture was diluted with ethyl acetate (300 mL), washed with cold 1M aqueous NaHCO$_3$ (1×100 mL), H$_2$O (2×100 mL), 1M aqueous NaHSO$_3$ (1×100 mL), water (2×100 mL), brine (100 mL) and dried (MgSO$_4$). The residue (5 g) was passed through a silica gel flash pad (150 g, hexane/EtOAc→CH$_3$CN) to give the title compound (3.0 g, 62%) as an oil.

IR (CH$_2$Cl$_2$) ν$_{max}$: 3680–3600 (OH), 2100 (N$_3$), 1780 and 1710 cm$^{-1}$ (C=O);

$^1$H NMR (CDCl$_3$, 200 MHz) δ: 8.58–8.55 (2H, m, aromatic —H), 7.29–7.20 (2H, m aromatic H), 6.06–5.86 (1H, m, vinylic —H), 5.49–5.22 (2H, m, vinylic —H), 4.89–4.63 (2H, m, allylic —CH$_2$), 4.27–4.14 (1H, m, H-1'), 4.109 (1H, dd, J=2.7 Hz, J=9.6 Hz, R-5), 4.10, 4.03, 3.98, 3.91 (2H, ABq, J=14.2 Hz, CH$_2$-aromatic), 3.43–3.22 (2H, m, CH$_2$—

N), 3.200 (1H, dd, J=2.7 Hz, J=7.6 Hz, H-6), 3.10–2.98 (1H, m, H-4), 2.19 (1H, bs, OH), 1.91–1.43 (4H, m, CH$_2$CH$_2$-4) and 1.360 (3H, d, J=6.2 Hz, CH$_3$).

B. Sodium (4R,5S,6S)-4-(3"-azidopropyl)-6-[(1'R)-1'-hydroxyethyl]-3-[(pyridin-4-yl)methylthio]-7-oxo-1-azabicyclo[3.2.0]hept-2-ene-2-carboxylate

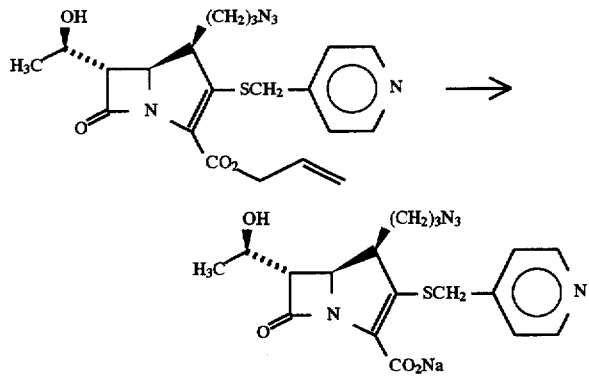

A cold (ice-bath) solution of allyl (4R,5S,6S)-4-(3"-azidopropyl)-6-[(1'R)-1'-hydroxyethyl]-3-[(pyridin-4-yl)methylthio]7-oxo-1-azabicyclo[3.2.0] hept-2-ene -2-carboxylate (3.0 g, 6.8 mmol) in CH$_2$Cl$_2$ (50 mL) was treated with Pd(PPh$_3$)$_4$ (150 mg) and a 0.5M solution of sodium ethyl-2-hexanoate (14 mL, 7 mmol) in ethyl acetate. The mixture was stirred for 60 min, then diluted with hexane/diethyl ether (1/1) and extracted with a 0.05M aqueous phosphate buffer (1×100 mL and 2×25 mL). The aqueous layers were combined, washed with diethyl ether (100 mL) and passed through a μ-Bondapak C$_{18}$ column (300 g, H$_2$O→5% CH$_3$CN/H$_2$O) to give the title compound (0.8 g, 30%);

$^1$H NMR (D$_2$O, 200 MHz) δ: 8.50–8.46 (2H, m aromatic —H), 7.50–7.20 (2H, m, aromatic —H), 4.28–4.15 (1H, m, H-1'), 4.19, 4.11, 4.03, 3.95 (2H, ABq, J=14.6 Hz, CH$_2$-aromatic), 4.073 (1H, dd, J=2.7 Hz, J=9.5 Hz, H-5), 3.37–3.29 (3H, m, H-6 and CH$_2$N), 3.16–3.06 (1H, m, H-4), 1.8–1.38 (4H, 2 sets of m, CH$_2$CH$_2$-4) and 1.288 ppm (3H, d, J=6.4 Hz, CH$_3$).

C. (4R,5S,6S)-4-(3"-Aminopropyl)-6-[(1'R)-1'-hydroxyethyl]-3-[(pyridin-4-yl)methylthio]-7-oxo-1-azabicyclo[3.2.0]-hept-2-ene-2-carboxylic acid

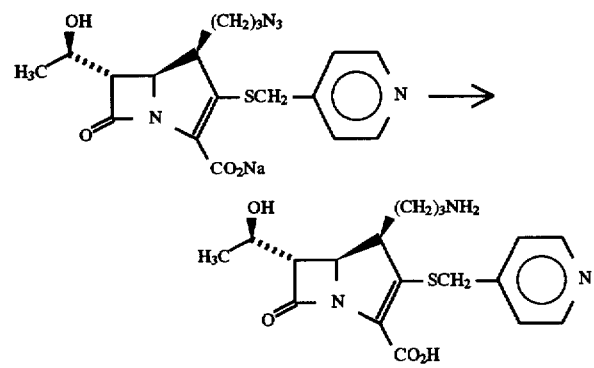

A cold solution of sodium (4R,5S,6S)-4-(3"-azidopropyl)-6-[(1' R)-1'-hydroxyethyl]-3-[(pyridin-4-yl) methylthio]-7-oxo-1-azabicyclo[3.2.0]hept-2-ene-2- carboxylate (270 mg, 0.60 mmol) in water (55 mL) was shaken in a Parr hydrogenator at 5° C. (ice bath) for 2.5 h at 45–50 psi hydrogen using 5% Pd/Alumina (540 mg) as catalyst. The catalyst was removed by filtration and the aqueous solution was passed through a μ-Bondapak C$_{18}$ reversed phase column (50 g, H$_2$O→7% CH$_3$CN/H$_2$O) to give the title compound (127 mg, 53%) as a lyophilized powder;

Purity: 97.2% (HPLC, 300 nm);

UV (H$_2$O) λ$_{max}$: 262 (ε5210), 304 (ε7950);

IR (nujol) ν$_{max}$: 3600–3100 (OH), 1760 and 1600 cm$^{-1}$ (C=O);

$^1$H NMR (D$_2$O, 200 MHz) δ: 8.49–8.46 (2H, m, aromatic —H), 7.52–7.24 (2H, m, aromatic —H), 4.28–4.16 (1H, m H-1'), 4.16, 4.08, 4.02, 3.94 (2H, ABq, J=14.6 Hz, CH$_2$-aromatic), 4.076 (1H, dd, J=2.7 Hz, J=6.5 Hz, H-6), 3.20–3.10 (1H, m, H-4), 3.00–2.93 (2H, m, CH$_2$N), 1.80–1.38 (4H, m, CH$_2$CH$_2$-4) and 1.292 ppm (3H, d, J=6.4 Hz, CH$_3$).

EXAMPLE 45

(4R,5S,6S)-4-(4"-Aminobutyl)-6-[(1'R)-1'-hydroxyethyl]-3-[(pyridin-3-yl)methylthio]-7-oxo-1-azabicyclo[3.2.0]hept-2'-ene-2-carboxylic acid

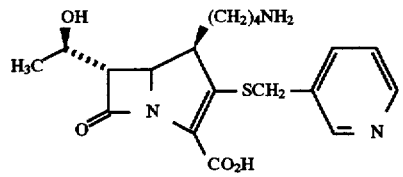

A. 6-Azidohexanoyl chloride

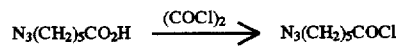

A solution of 6-azidohexanoic acid (151 g, 0.96 mol) [M. Rothe and K. Gehrke, Makromol. Chem. 83, 1 (1965); C.A. 64:4934d.] in dry CH$_2$Cl$_2$ (500 mL) was treated at 22° C. with oxalyl chloride (88.0 mL, 1.0 mmol) added dropwise over 30 min. After 2 h, two drops of N,N-dimethylformamide were added and the solution was stirred at 22° C., under nitrogen, for 18 h. The solvent was then evaporated under vacuum to give the crude acid chloride as a clear oil which was used as such for the next step:

IR (NaCL, film) ν$_{max}$: 2100 (N$_3$) and 1800 cm$^{-1}$ (C=O);

$^1$H NMR (200 MHz, CDCl$_3$) δ: 1.3–1.9 (m, 6H, CH$_2$-3,4 and 5), 2.9 (t, J=7 Hz, 2H, CH$_2$-2) and 3.3 ppm (t, J=6.5 Hz, 2H, CH$_2$-6).

B. 2-Picolyl 6-(azido)thiolhexanoate

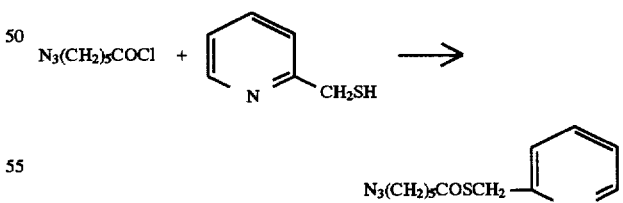

A solution of 2-picolyl mercaptan (130.6 g, 1.04 mol) dry CH$_2$Cl$_2$ (1.3 L) was cooled to 0°–5° C., treated with pyridine (85 mL, 1.05 mol) and a solution of 6-azidohexanoyl chloride (179 g, 1.02 mol) in CH$_2$Cl$_2$ (200 mL) added dropwise over 1 h. After another hour at 0°–5° C., the organic phase was washed with water, saturated NaHCO$_3$, brine and dried (MgSO$_4$). Evaporation of the solvent gave 244 g (90%) of the thioester as a clear oil which was used as such for the next step:

IR (NaCl, film) $v_{max}$: 2100 ($N_3$) and 1680 cm$^{-1}$ (C=O of thioester);

$^1$H NMR (200 MHz, CDCl$_3$) δ: 1.3–1.8 (m, 6H, CH$_2$-3,4, and 5), 2.6 (t, J=7.34 Hz, 2H, CH$_2$-2), 3.25 (t, J=6.7 Hz, 2H, CH$_2$-6), 4.25 (s, 2H, SCH$_2$), 7.16 (m, 1H, H-5 of pyridine), 7.33 (d, J=7.8 Hz, 1H, H-3 of pyridine), 7.62 (m, 1H, H-4 of pyridine) and 8.53 ppm (m, 1H, H-6 of pyridine).

C. O-tert-Butyldimethylsilylether of 2-picolyl 6-(azido) thiolhexanoate

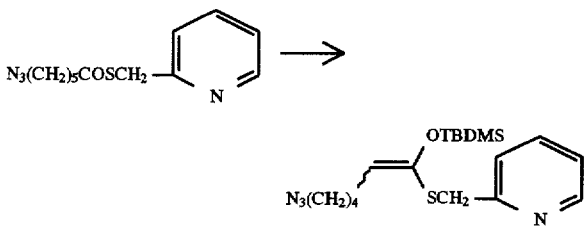

A solution of 2-picolyl 6-(azido)thiolhexanoate (244 g, 0.92 mol) in 1 L of dry CH$_2$Cl$_2$ was cooled to −10° C., treated with triethylamine (260 mL, 1.86 mol) followed by tert-butyldimethylsilyl trifluoromethanesulfonate (318 mL, 1.38 mol) added dropwise over 40 min. The temperature of the mixture was allowed to reach 22° C. and the solution was stirred for 3 h. The reaction mixture was then diluted with hexanes (1.5 L) washed with cold water (2×1 L), saturated NaHCO$_3$, brine and dried (MgSO$_4$). The solution was then treated with activated carbon (neutral), filtered and concentrated under vacuum. The residual black tarry material was extracted with hexanes (1.5 L) and the extract was evaporated to give 315 g (90%) of the crude silyl enolether as a black oil which was used as such for the coupling step. By $^1$H NMR, this product is a 1:1 mixture of E and Z isomer.

IR (NaCl, film) $v_{max}$: 2090 ($N_3$), 1625 and 1590 cm$^{-1}$;

$^1$H NMR (200 MHz, CDCl$_3$) δ: 0.2 and 0.24 (2×s, 6H, SiCH$_3$), 0.97 and 0.98 (2×s, 9H, Si t-Bu), 1.2–1.8 (m, 4H, CH$_2$-4 and 5), 2.0 (m, 2H, CH$_2$—CH=C), 3.17 (m, 2H, C H$_2$N$_3$), 3.95 and 4.03 (2×s, 2H, SCH$_2$), 4.82 and 4.97 (2×t, 1H, J=7.26 Hz, and J=7.58 Hz, 2×1H, CH$_2$—CH=C), 7.14 (m, 1H, H-5 of pyridine), 7.26 (m, 1H, H-3 of pyridine), 7.6 (m, 1H, H-4 of pyridine) and 8.55 ppm (m, 1H, H-6 of pyridine).

D. (3S,4S)-3-[(1'R)-1'-tert-Butyldimethylsilyloxyethyl]-4-[(1"R)-1"-(pyridin-2-yl)methylthiocarbonyl-5"-azidopentyl]-azetidin-2-one

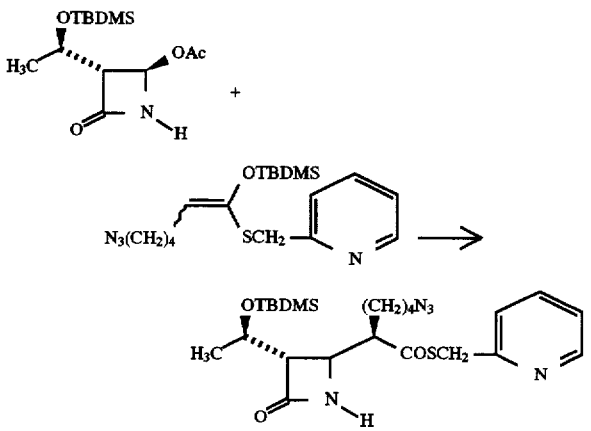

To a cold (0°–5° C.) suspension of freshly fused zinc chloride (151 g, 1.1 mol) in dry dichloromethane (2.6 L) was added 238 g (0.83 mol) of (3S,4R)-4-acetoxy-3-[(1'R)-1'-tert-butyldimethylsilyloxyethyl]-azetidin-2-one followed by a solution of the crude O-tert-butyldimethylsilylether of 2-picolyl 6-(azido)thiolhexanoate (315 g, 0.83 mol) in dry dichloromethane. The temperature of the solution was slowly allowed to reach 22° C. (~3 h) and the resulting homogeneous mixture was stirred for 18 h. The reaction mixture was then washed successively with water, saturated NH$_4$Cl, saturated NaHCO$_3$, water and brine. After drying (MgSO$_4$) evaporation of the solvent gave 494 g of a dark oil which was used as such for the next step. By $^1$H NMR analysis, this crude product was found to be a mixture of 1'R and 1'S pentyl in a 8:2 ratio. Purification of a small aliquot on silica gel (elution toluene-EtOAc, 1:1) gave the pure isomer of the title compound as a white crystalline product: mp 81°–83° C. (hexanes);

UV (EtOH) $\lambda_{max}$: 236 (5576) and 264 nm (4,989);

IR (KBr) $v_{max}$: 2100 ($N_3$), 1758 (C=O of β-lacta), 1718 (C=O of ester) and 1680 cm$^{-1}$ (C=O of thioester);

$^1$H NMR (200 MHz, CDCl$_3$), δ: 0.04 (s, 6H, SiCH$_3$), 0.85 (s, 9H, Sit-Bu), 0.99 (d, J=6.32 Hz, 3H, CH$_3$CHO), 1.2–2.0 (m, 6H, CH$_2$-2,3 and 4 of pentyl) 2.79 (m, 1H, H-1 of pentyl), 3.04 (broad s, 1H, H-3 of azetidinone), 3.23 (t, J=6.56 Hz, 2H, CH$_2$N$_3$), 3.80 (dd, $J_{H3,H4}$=2.08 Hz, $J_{H3,H1}$= 6.97 Hz, 1H, H-3 of azetidinone), 4.14 (m, 1H, CH$_3$C HO) 4.26 (s, 2H, SCH$_2$), 5.85 (broad s, 1H, NH), 7.18 (m, 1H, H-5 of pyridine), 7.32 (d, J=7.8 Hz, 1H, H-3 of pyridine), 7.62 (m, 1H, H-4 of pyridine) and 8.5 ppm (m, 1H, H-6 of pyridine).

Anal. Calcd. for C$_{23}$H$_{37}$N$_5$O$_3$SSi: C, 56.18; H, 7.58; N, 14.24. Found: C, 56.25; H, 7.59; N, 14.10.

E. (3S, 4S)-3-[(1'R)-1'-tert-Butyldimethylsilyloxyethyl]-4-[(1"R)-1"-carboxy-5"-azidopentyl]azetidin-2-one

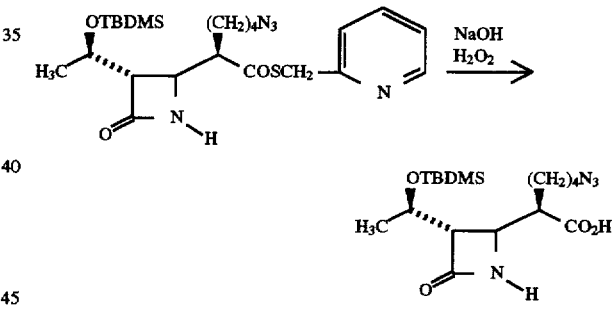

A solution of the crude (3S,4S)-3-[(1'R)-1'-tert-butyldimethylsilyloxyethyl]-4-[(1"R)-1"-(pyridin-2-yl)-methylthiocarbonyl-5"azidopentyl]azetidin-2-one (~400 g, 0.83 mol) in 3 L of tetrahydrofuran was cooled to 0° C. and treated with 30% hydrogen peroxide (1 L, 11.6 mol) added cautiously in portions, followed by 2.8 L of 1M NaOH added dropwise over 2 h. The solution was stirred for two more hours at 0°–5° C. and acidified to pH 2.0 with 3N HCl (~1L). The reaction mixture was then extracted with EtOAc (2 L and 3×1 L) and the combined organic extract was washed with water, 1M NaHSO$_3$, brine and dried (MgSO$_4$). Evaporation of the solvent gave a dark oil which was dissolved in hexanes (2 L) and extracted with saturated NaHCO$_3$ (4×1 L). The combined aqueous phase was cooled to 0°–5° C. and acidified to pH 2 with 3N HCl. The white precipitate formed was collected and washed with water. The moist cake was dissolved in CH$_2$Cl$_2$, dried (MgSO$_4$) and evaporated to give 114 g of the crude product. Crystallization from a mixture of ethyl acetate and hexanes gave 67.4 g (21%) of the pure title acid as white plates; mp=132°–133° C.

IR (KBr) $v_{max}$: 3280 (NH), 2500 (COOH), 2110 ($N_3$), 1760 (sh), 1715 and 1690 cm$^{-1}$ (C=O of acid and β-lactam);

$^1$H NMR (200 MHz, CDCl$_3$) δ: 0.06 and 0.07 (2×s, 2×3H, SiCH$_3$), 0.87 (s, 9H, Si t-Bu), 1.17 (d, J=6.29 Hz, 3H, C H$_3$CHO), 1.4–1.8 (m, 6H, CH$_2$-2, 3 and 4 of pentyl), 2.64 (m, 1H, H-1 of pentyl), 3.14 (m, 1H, H-3), 3.29 (t, J=6.5 Hz, 2H, CH$_2$N$_3$), 3.87 (dd, $J_{H4,H3}$=1.90 Hz, $J_{H4,H1}$=6.22 Hz, 1H, H-4), 4.20 (dq, $J_{H,CH3}$=6.29 Hz, $J_{H,H3}$=4.04 Hz, 1H, CH$_3$ CHO), and 6.46 ppm (s, 1H, NH).

Anal. Calcd. for C$_{17}$H$_{32}$N$_4$O$_4$S: C, 53.10; H, 8.39; N, 14.57. Found: C, 53.08; H, 8.12; N, 14.56.

F. (3S,4R)-4-[(1"R)-1"-(4-Azidobutyl)-3"-allyloxycarbonyl-2"-oxopropyl]-3-[(1'R)-1'-tert-butyldimethylsilyloxyethyl]-azetidin-2-one

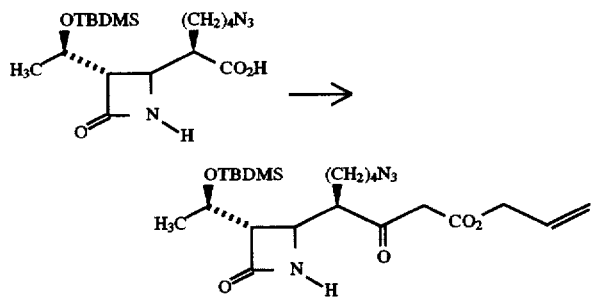

A suspension of (3S,4S)-3-[(1'R)-1'-tert-butyldimethylsilyloxyethyl]-4-[(1"R)-1"-carboxy-5"-azidopentyl]azetidin-2-one (67.0 g, 0.174 mol) in dry CH$_3$CN (1.5 L) was treated at 22° C. and under nitrogen with 1,1-carbonyldiimidazole (31.1 g, 0.192 mol) and the resulting mixture was stirred for 2 h. The solution was then concentrated under vacuum to give the crude imidazolide as an oil: IR (NaCl, film) 2100 (N$_3$), 1755 (C=O of β-lactam) and 1730 cm$^{-1}$ (C=O of imidazolide).

The crude imidazolide in dry CH$_3$CN (200 mL) was then added to a solution of dried magnesium monoallyl malonate (87.0 g, 0.28 mol) in benzene (1.4 L), and the resulting mixture was stirred at 60°–65° C. for 16 h. The cooled reaction mixture was then diluted with ethyl acetate (1L), washed successively with cold water, 0.1N HCl, saturated NaHCO$_3$, water and brine. After drying (MgSO$_4$), evaporation of the solvent gave 80.3 g of the crude keto ester as an oil which was used as such for the next step. Purification of a small aliquot on silica gel gave the pure title compound as a clear oil. By $^1$H NMR this product is a 1:1 mixture of keto and enol form:

IR (NaCl, film) $v_{max}$: 2100 (N$_3$), 1760 (C=O of β-lactam) and 1715 cm$^{-1}$ ;

$^1$H NMR (200 MHz, CDCl$_3$) δ: 0.05 and 0.06 (2×s, 6H, SiCH$_3$), 0.86 (s, 9H, Si t-Bu), 1.10 and 1.17 (2d, J=6.33 Hz, and J=6.28 Hz, 3H, CH$_3$CHO), 1.2–1.8 (m, 6H, CH$_2$-1,2 and 3 of butyl), 2.1–2.3 (m, 1H, H-1 of butyl), 1.2–2.3 (m, 6H, CH$_2$-1,2 and 3 of butyl), 2.9 and 2.97 (2×m, 1H, H-3 of azetidinone), 3.27 (broad t, 2H, CH$_2$N$_3$), 3.54 (s, CH$_2$-3 of oxopropyl, keto form), 3.83 (two overlapping dd, 1H, H-4 of azetidinone), 4.17 (m, 1H, CH$_3$CHO), 4.64 (m, 2H, CH$_2$ of allyl), 5.07 (s, CH-3 of oxopropyl, enol form), 5.2–5.4 and 5.8–6.0 (2×m, 2H and 1H, CH of allyl), and 6.0 ppm (broad s, 1H, NH).

G. (3S,4R)-4-[(1"R)-1"-(4-Azidobutyl)-3"-allyloxycarbonyl-3"-diazo-2"-oxopropyl]-3-[(1'R)-1'-tert-butyldimethyl-silyloxyethyl]azetidin-2-one

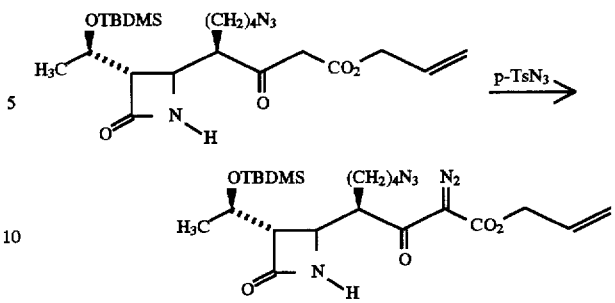

A solution of crude (3S,4R)-4-[(1"R)-1"-(4-azidobutyl)-3"-allyloxycarbonyl-2"-oxopropyl]-3-[(1'R)-1'-tert-butyldimethylsilyloxyethyl]azetidin-2-one (79 g, 0.169 mol) in acetonitrile (400 mL) was cooled to 0°–5° C. and treated with a solution of p-toluenesulfonyl azide (40 g, 0.20 mol) in acetonitrile (500 mL). Then triethylamine (28.3 mL, 0.20 mmol) was added dropwise (5 min) and the resulting mixture was stirred for 2 h. The solvent was then concentrated under vacuum and the residue was triturated with a mixture of diethyl ether and hexanes (1:1). The crystalline p-toluenesulfonamide was collected by filtration and the filtrate was evaporated to give the title diazo compound as an oil (86 g). This material can be used as such for the cleavage of the silyl ether.

Purification of part of the crude (30 g) on silica gel (9×13 cm, elution hexanes-EtOAc, 9:1 to 7:3) gave 17.5 g (correspond to a 59% yield from the acid, two steps) of the title diazo azetidinone as a clear oil:

IR (NaCl, film) $v_{max}$: 2140 (N$_2$), 2100 (N$_3$), 1760 (C=O of β-lactam), 1720 (C=O of ester) and 1650 cm$^{-1}$ ;

$^1$H NMR (200 MHz, CDCl$_3$) δ: 0.05 and 0.06 (2×s, 2×3H, Si CH$_3$), 0.86 (s, 9H, t-Bu), 1.17 (d, J=6.31 Hz, 3H, CH$_3$CHO), 3.04 (m, 1H, H-3 of azetidinone), 3.25 (m, 2H, CH$_2$N$_3$), 3.84 (dd, $J_{H4,H3}$=2.09 Hz, $J_{H4,H1}$=5.33 Hz, 1H, H-4 of azetidinone), 4.07 (m, 1H, H-1 of oxopropyl), 4.17 (dq, $J_{H,CH3}$=6.31 Hz, $J_{H,H3}$=3.94 Hz, 1H, CH$_3$CHO), 4.72 (m, 2H, CH$_2$ of allyl), 5.3–5.4 and 5.9–6.1 (2×m, 2H and 1H, CH of allyl), and 5.84 ppm (s, 1H, NH).

H. (3S,4R)-4-[(1"R)-1"-(4-Azidobutyl)-3"-allyloxycarbonyl-3"-diazo-2"-oxopropyl]-3-[(1'R)-1'-hydroxyethyl]azetidin-2-one

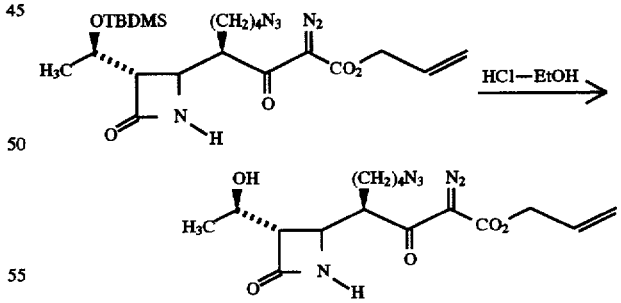

A solution of (3S, 4R)-4-[(1"R)-1"-(4-azidobutyl )-3"-allyloxycarbonyl-3"-diazo-2"-oxopropyl]-3-[(1'R)-1'-tert-butyldimethylsilyloxyethyl]azetidin-2-one (17.5 g, 35.5 mmol) in ethanol (300 mL) was treated at 24° C. with 1N HCl (100 mL) and stirred in the dark for 16 h. The reaction mixture was neutralized with Na$_2$CO$_3$, and concentrated in vacuo. The residual aqueous solution was extracted with ethyl acetate (500 mL and 250 mL) and the combined organic phase was washed with water, brine and dried (MgSO$_4$). Evaporation of the solvent gave a solid which after crystallization from diethyl ether-hexanes and purification of the mother liquors on silica gel (ethyl acetate) gave 11.8 g (88%) of the title compound as white needles: m.p=73°–74° C.;

UV (EtOH) $\lambda_{max}$: 260 nm (8,365);

IR (KBr) vhd max: 3350 (OH) 2160 ($N_2$) 2080 ($N_3$) 1738 (C=O of β-lactam), 1716 (C=O of ester) and 1650 cm$^{-1}$;

$^1$H NMR (200 MHz, CDCl$_3$) δ: 1.30 (d, J=6.33 Hz, 3H, CH$_3$CHO), 1.3–2.0 (m, 6H, CH$_2$-1,2 and 3 of butyl), 2.28 (d, J=3.8 Hz, 1H, OH), 3.0 (dd, J$_{H3,H4}$=2.0 Hz, J$_{H3,H1}$=6.97 Hz, 1H, H-3 of azetidinone), 3.27 (t, J=6.58 Hz, 2H, CH$_2$N$_3$), 3.8 (dd, J$_{H4,H3}$=2.0 Hz, J$_{H4,H1}$=6.55 Hz, 1H, H-4), 3.95 (m, 1H, H-1 of oxopropyl), 4.15 (m, 1H, CH$_3$CHO), 4.73 (m, 2H, CH$_2$ of allyl), 5.3–5.4 and 5.9–6.1 (2×m, 2H and 1H, CH of allyl) and 6.0 ppm (broad s, 1H, NH).

Anal. Calcd. for C$_{16}$H$_{22}$N$_6$O$_5$: C, 50.79; H, 5.86; N, 22.21. Found: C, 50.87; H, 5.87; N, 22.31.

I. Allyl (2R,4R,5R,6S)-4-(4"-azidobutyl)-6-[(1'R)-1'-hydroxyethyl]-3,7-dioxo-1-azabicyclo[3.2.0]heptane-2-carboxylate

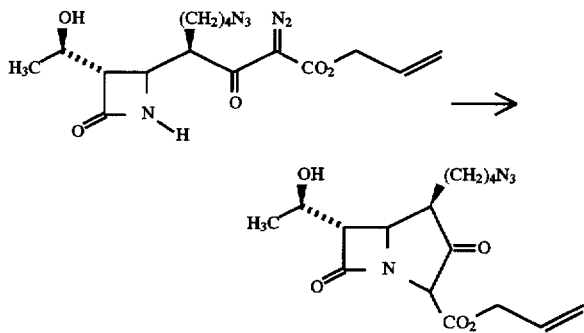

A solution of (3S,4R)-4-[(1"R)-1"-(4-azidobutyl)-3"-allyloxycarbonyl-3"-diazo-2"-oxopropyl]-3-[(1'R)-1'-hydroxyethyl]azetidin-2-one (1.88 g, 4.97 mmol) in dry benzene (60 mL) was treated under nitrogen with rhodium (II) octanoate dimer (0.050 g) and heated under reflux (bath temperature 90° C.) for 20 min. The solvent was then evaporated under vacuum to give the title bicyclic ketone as an oil:

IR (NaCl, film) $v_{max}$: 2100 (N$_3$), 1762 (C=O of β-lactam) and 1745 cm$^{-1}$;

$^1$H NMR (200 MHz, CDCl$_3$) δ: 1.41 (d, J=6.26 Hz, 3H, CH$_3$CHO), 1.4–2.0 (m, 6H, CH$_2$-1,2 and 3 of butyl), 2.7 (m, 1H, H-4), 3.2–3.4 (m, 3H, H-6 and CH$_2$N$_3$ overlapping), 4.28 (dd, J$_{H5,H6}$=2.37 Hz, J$_{H5,H4}$=8.15 Hz, 1H, H-5), 4.3 (m, overlapping with H-5, 1H, CH$_3$CHO), 4.65 (s, 1H, H-2), 4.66 (m, 2H, CH$_2$ of allyl), 5.2–5.4 and 5.8–6.0 ppm (2×m, 2 and 1H, CH of allyl).

J. Allyl (4R,5S,6S)-4-(4"-azidobutyl)-6-[(1'R)-1-hydroxyethyl]-3-[pyridyl-3-yl)methylthio]-7-oxo-1-azabicyclo[3.2.0]hept-2-ene-2-carboxylate

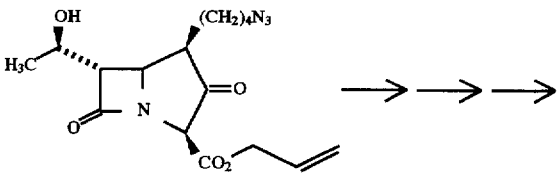

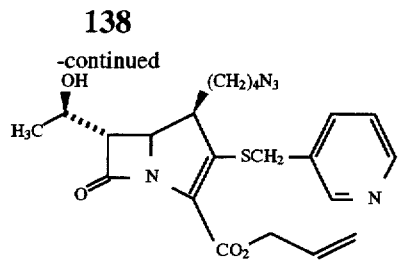

A solution of allyl (2R,4R,5R,6S)-4-(4"-azidobutyl)-6-[(1'R)-1'-hydroxyethyl]-3,7-dioxo-1-azabicyclo[3.2.0]heptane-2-carboxylate (4.97 mmol), in dry CH$_3$CN (30 mL) was cooled to 0°–5° C. and treated with diphenyl chlorophosphate (1.40 g, 5.21 mmol) and N,N-diisopropylethylamine (0.91 mL, 5.21 mmol) added simultaneously over 10 min. A small crystal of 4-N,N-dimethylaminopyridine was then added and the mixture was stirred for 1 h. Then, more N,N-diisopropylethylamine (1.3 mL, 7.4 mmol) was added, followed by 3-picolyl thiol (0.93 g, 7.4 mmol). The reaction mixture was then stirred at 0°–5° C. for 4 h and then quenched by the addition of ethyl acetate (300 mL) and cold water. The organic phase was washed with pH 7.0 phosphate buffer, brine and dried (MgSO$_4$). Evaporation of the solvent gave an oil which was chromatographed on silica gel (3.5×10 cm). Elution with ethyl acetate gave 1.41 g (62%) of the title compound as an oil:

IR (NaCl, film) $v_{max}$: 2100 (N$_3$) 1770 (C=O of β-lactam) and 1705 m$^{-1}$ (C=O of ester);

$^1$H NMR (200 MHz, CDCl$_3$) δ: 1.38 (d, J=6.26 Hz, 3H, CH$_3$CHO), 1.3–2.0 (m, 6H, CH$_2$-1,2 and 3 of butyl), 3.1 (m, 1H, H-4), 3.16 (dd, J$_{H6,H5}$=2.72 Hz, J$_{H6,H1}$=7.33 Hz, 1H, H-6), 3.32 (t, J=6.0 Hz, 2H, CH$_2$N$_3$), 4.02 (ABq, 2H, SCH$_2$), 4.14 (dd, J$_{H5,H6}$=2.72 Hz, J$_{H5,H4}$=9.56 Hz, 1H, H-5), 4.22 (m, 1H, CH$_3$CHO), 4.75 (m, 2H, CH$_2$ of allyl), 5.2–5.5 and 5.9–6.1 (2×m, 2H and 1H, CH of allyl), 7.3 (m, 1H, H-5 of pyridine), 7.7 (m, 1H, H-4 of pyridine) and 8.5 ppm (m, 2H, H-2 and H-6 of pyridine).

K. (4R,5S,6S)-4-(4"-Aminobutyl)-6-[(1'R)-1'-hydroxyethyl]-3-[pyridin-3-yl)methylthio]-7-oxo-1-azabicyclo[3.2.0]hept-2-ene-2-carboxylic acid

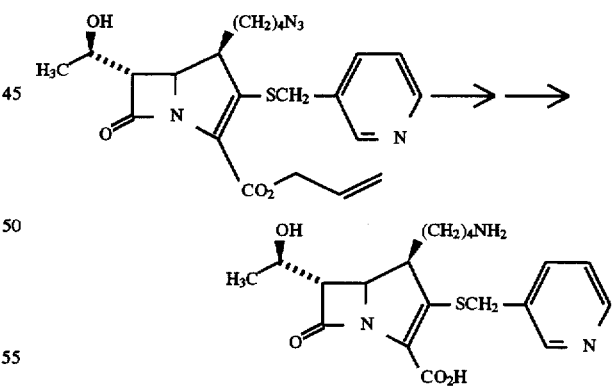

A solution of allyl (4R,5S,6S)-4-(4"-azidobutyl)-6-[(1'R)-1'-hydroxyethyl]-3-[(pyridin-3-yl)methylthio]-7-oxo-1-azabicyclo[3.2.0]hept-2-ene-2-carboxylate (1.12 g, 2.45 mmol) in ethyl acetate (40 mL) was treated at 22° C. and under nitrogen with tetrakis (triphenylphosphine) palladium [0] (0.050 g) and 5.4 mL (2.7 mmol) of a 0.5M solution of potassium 2-ethylhexanoate in ethyl acetate. After 20 min, the reaction mixture was extracted with cold water (3×20 mL) and the combined aqueous phase was maintained under vacuum to remove traces of organic solvent. The aqueous phase was then hydrogenated over 5% palladium on alumina (1.2 g) at 0°–5° C. and under 45 psi of hydrogen for 1.5 h (initial pH 6.8, final pH 9.6). After the addition of 20 mL of 0.2M pH 6.0 phosphate buffer, the catalyst was filtered and the filtrate was chromatographed on reversed phase silica gel (μBondapak $C_{18}$, 3×14 cm). Elution with a gradient of acetonitrile (0–10%) in water gave 0.489 g (51%) of the title compound as a white amorphous powder after freeze drying: $[α]_D^{22}$ –3.5° (c 1.0, $H_2O$);

Purity by HPLC: 98.7% on μBondapak $C_{18}$, 3.9 mm×30 cm, elution 5% $CH_3CN$—$H_2O$, pH 7.4 phosphate buffer, flow rate 1 mL/min, UV detector 300 nm, retention time 9.6 min;

UV ($H_2O$, pH 7.4 phosphate buffer) $ν_{max}$: 268 (5740) and 306 nm (8810);

IR (KBr) $ν_{max}$: 1755 (C=O of β-lactam) and 1585 cm$^{-1}$ (C=O of carboxylate);

$^1$H NMR (200 MHz, $D_2O$) δ: 1.29 (d, J=6.33 Hz, 3H, C$\underline{H}_3$CHO), 1.2–1.8 (m, 6H, $CH_2$-1, 2 and 3 of butyl), 2.96 (t, J=7.6 Hz, 2H, C$\underline{H}_2N_3$), 3.15 (m, 1H, H-4), 3.29 (dd, $J_{H6,H5}$=2.54 Hz, $J_{H6,H1}$=6.36 Hz, 1H, H-6), 4.07 (ABq, $J_{AB}$=14.2 Hz, Δν=24.3 Hz, 2H, $SCH_2$), 4.07 (overlapping with $SCH_2$, 1H, H-5), 4.22 (m, 1H, CH$_3$C$\underline{H}$O), 7.44 (dd, $J_{H5,H6}$=4.95 Hz, $J_{H5,H4}$=7.9 Hz, 1H, H-5 of pyridine), 7.88 (m, 1H, H-4 of pyridine), 8.43 (dd, $J_{H6,H5}$=4.95 Hz, $J_{H6,H4}$=1.52 Hz, 1H, H-6 of pyridine) and 8.52 ppm (d, $J_{H2,H4}$=1.75 ppm, 1H, H-2 of pyridine).

EXAMPLE 46

(4R,5S,6S)-4-(4"-N-Formimidoylaminobutyl)-6-[(1'R)-1'-hydroxy-ethyl]-3-[(pyridin-3-yl)methylthio]-7-oxo-1-azabicyclo[3.2.0]-hept-2-ene-2-carboxylic acid

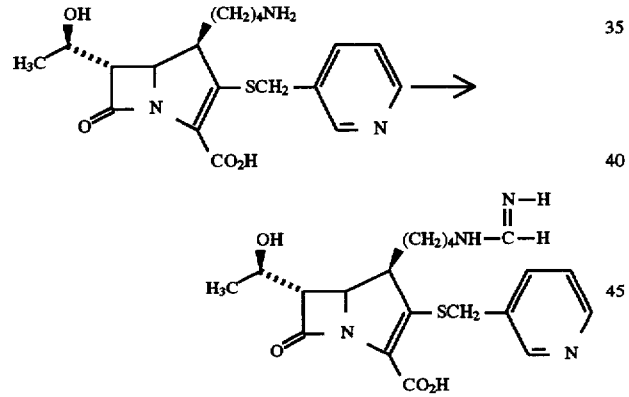

A solution of (4R,5S,6S)-4-(4"-aminobutyl)-6-[(1'R)-1'-hydroxyethyl]-3-[(pyridin-3-yl)methylthio]-7-oxo-1-azabicyclo-[3.2.0]hept-2-ene-2-carboxylic acid from Example 45 (0.175 g, 0.45 mmol) in cold (0°–5° C.) water (15 mL) was adjusted to pH 8.5 with 1M NaOH. Then benzyl formimidate hydrochloride (0.38 g, 2.2 mmol) was added in small portions over 10 min while maintaining the pH to 8–8.5 with 1M NaOH. After another 20 min at 0°–5° C., 20 mL of 0.2M pH 6.0 phosphate buffer was added and the mixture was washed with EtOAc (20 mL). The aqueous phase was then maintained under vacuum to remove traces of organic solvent and chromatographed twice on reversed phase silica gel (μ-Bondapak $C_{18}$, 2×14 cm) using a gradient of acetonitrile (0–5%) in water as eluent. Lyophilization of the UV active fractions gave 0.120 g (64%) of the title compound as a white amorphous solid: $[α]_D^{24}$ –3.2° (c 0.5, $H_2O$);

Purity by HPLC: 99% on μ-Bondapak c18, 3.9 mm×30 cm, elution 10% $CH_3CN$—$H_2O$ pH 7.4 phosphate buffer, flow rate 2 mL/min, UV detector 300 nm, retention time 6.44 min.

UV ($H_2O$, pH 7.4 phosphate buffer) $λ_{max}$: 266 (6,300) and 304 nm (9,600);

IR (KBr) $ν_{max}$: 1755 (C=O of β-lactam) 1715 and 1590 cm$^{-1}$ (C=O of carboxylate);

$^1$H NMR (200 MHz, $D_2O$) δ: 1.28 (d, J=6.34 Hz, 3H, C$\underline{H}_3$CHO), 1.2–1.8 (m, 6H, $CH_2$-1, 2 and 3 of butyl), 3.2 (m, 3H, H-6 and C$\underline{H}_2NH_2$), 4.07 (overlapping with $SCH_2$, 1H, H-5), 4.07 (ABq, $J_{AB}$=14.3 Hz, Δν=23.5 Hz, 2H, $SCH_2$), 4.22 (m, 1H, CH$_3$C$\underline{H}$O), 7.44 (m, 1H, H-5 of pyridine), 7.79 (s, 1H, C$\underline{H}$=NH), 7.89 (m, 1H, H-4 of pyridine), 8.43 (m, 1H, H-6 of pyridine) and 8.52 ppm (m, 1H, H-2 of pyridine).

EXAMPLE 47

(4R,5S,6S)-4-(2"-Aminoethyl)-3-[(3-cyanopropyl)thio]-6-[(1'R)-1'-hydroxyethyl]-7-oxo-1-azabicyclo[3.2.0]hept-2-ene-2-carboxylic acid

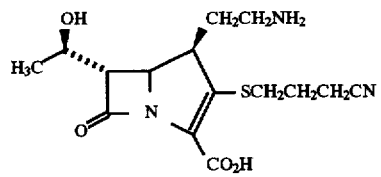

A. Allyl (4R,5S,6S)-4-(2"-azidoethyl)-6-[(1'R)-1'-tert-butyldimethylsilyloxyethyl]-3-(3-cyanopropyl)thio]-7-oxo-1-azabicyclo[3.2.0]hept-2ene-2-carboxylate

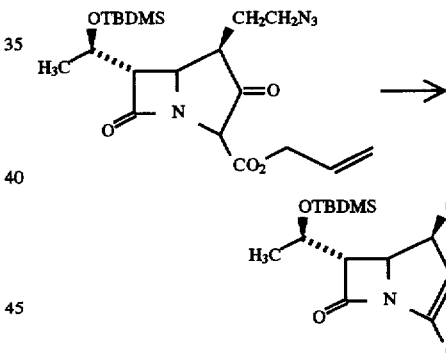

A solution of allyl (4R,5R,6S)-4-(2"-azidoethyl)-6-[(1'R)-1'-tert-butyldimethylsilyloxyethyl]-3,7-dioxo-1-azabicyclo[3.2.0heptane-2-carboxylate (6.46 mmol, prepared by cyclization of 3.0 g, 6.46 mmol of the diazo precursor prepared in Example 2, Step E) in dry acetonitrile (50 mL) was treated at –15° C. and under Argon with diphenyl chlorophosphate (1.4 mL, 6.75 mmol) and N,N-diisopropylethylamine (1.2 mL, 6.9 mmol) added simultaneously over 5 min. A small crystal of 4-N,N-dimethylaminopyridine was then added and the temperature of the mixture was slowly warmed to 0°–5° C. over 30 min. N,N-Diisopropylethylamine (1.2 mL, 6.9 mmol) and 4-mercaptobutyronitrile (1.31 g, 13.0 mmol) [obtained from basic hydrolysis of an aqueous tetrahydrofuran solution of 4-acetylmercaptobutyronitrile (U.S. Pat. No. 3,223,585)] were added and the mixture was stirred at 0°–5° C. for 4 h and overnight at –15° C. The reaction mixture was then diluted with EtOAc (300 mL), washed with water, 1M NaHSO$_3$, saturated NaHCO$_3$, brine and dried (MgSO$_4$).

Evaporation of the solvent gave an oil which was chromatographed on silica gel (5×15 cm). Elution with a mixture of EtOAc and toluene (1:9) gave 2.62 g (78%) of the title compound as a brown oil:

IR (NaCl, film) $v_{max}$: 2250 (CN), 2100 (N$_3$), 1775 (C=O of β-lactam) and 1710 cm$^{-1}$ (C=O of ester).

$^1$H NMR (200 MHz, CDCl$_3$) δ: 0.10 (s, 6H, SiCH$_3$), 0.90 (s, 9H, Si-t-Bu) 1.31 (d, 3H, J=6.11 Hz, CH$_3$CHO), 1.7–2.12 (m, 4H, CH$_2$-4 and CH$_2$CH$_2$—CN), 2.4–3.12 (m, SH, CH$_2$—S, CH$_2$CN and H-6), 3.32–3.7 (m, 3H, CH$_2$N$_3$ and H-4), 4.16 (dd, J$_{4-5}$=9.6 Hz, J$_{5-6}$=2.70 Hz, 1H, H-4), 4.21 (dd, J$_{6-8}$=7.47 Hz, J$_{8-9}$=6.2 Hz, CH$_3$CHO), 4.75 (m, 2H, CH$_2$ of allyl), 5.20–6.50 and 5.96 (2×m, 2H and 1H, CH of allyl).

B. Allyl (4R,5S,6S)-4-(2"-azidoethyl)-3-[(3-cyanopropyl)thio]-6-[(1'R)-1'hydroxyethyl]-7-oxo-1-azabicyclo-[3.2.0]hept-2-ene-2-carboxylate

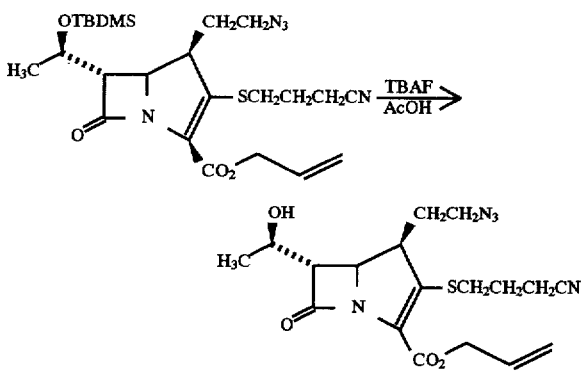

A solution of allyl (4R,5S,6S)-4-(2"-azidoethyl)-6-[(1'R)-1'-tert-butyldimethylsilyloxyethyl]-3-[(3-cyanopropyl)thio]-7-oxo-1-azabicyclo[3.2.0]hept-2-ene-2-carboxylate (2.48 g, 4.77 mmol) in dry tetrahydrofuran (75 mL) was treated at 0°–5° C. and under Argon with acetic acid (1.64 mL, 28.6 mmol) followed by 14.9 mL (14.8 mmol) of 1M solution of tetrabutylammonium fluoride in tetrahydrofuran. The solution was stored at 5° C. for 4½ days. The reaction mixture was then diluted with EtOAc, washed with saturated NaHCO$_3$, brine and dried (MgSO$_4$). Evaporation of the solvent gave an oil which was chromatographed on silica gel (5×15 cm). Elution with a mixture of toluene and EtOAc (9:11) gave 0.91 g (37%, yield from the diazoazetidinone) of the title compound as a yellow oil:

IR (NaCl, film) $v_{max}$: 3500 (OH), 2250 (CN), 2100 (N$_3$), 1775 (C=O of β-lactam) and 1705 cm$^{-1}$ (C=O of carboxylate;

$^1$H NMR (200 MHz, CDCl$_3$) δ: 1.40 (d, 3H, J=6.21 Hz, CH$_3$CHO), 1.6–2.15 (m, 4H, CH$_2$CH$_2$CN and CH$_2$-4), 2.55 (m, 2H, CH$_2$CN), 2.85–3.09 (m, 2H, SCH$_2$), 3.18 (dd, 1H, J$_{6-8}$=7.84 Hz, J$_{5-6}$=2.66 Hz, H-6), 3.37–3.67 (m, 3H, H-4 and CH$_2$N$_3$), 4.26 (m, overlapping with H-5, 1H, CH$_3$C HO), 4.26 (dd, J$_{4,5}$=9.70 Hz, J$_{5-6}$=2.61 Hz, 1H, H-5), 4.78 (m, 2H, CH$_2$ of allyl), 5.24–5.30 and 5.96 (2×m, 2H and 1H, CH of allyl).

C. Sodium (4R,5S,6S)-4-(2"-azidoethyl)-3-[(3-cyanopropyl)thio]-6-[(1'R)-1'-hydroxyethyl]-7-oxo-1-azabicyclo-[3.2.0]-hept-2-ene-2-carboxylate

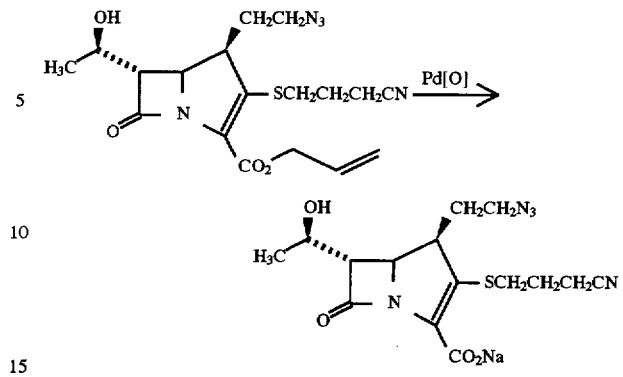

A solution of allyl (4R,5S,6S)-4-(2"-azidoethyl)-3-[(cyanopropyl)thio]-6-[(1'R)-1'-hydroxyethyl]-7-oxo-1-azabicyclo[3.2.0]hept-2-ene-2-carboxylate (900 mg, 2.22 mmol) in dry CH$_2$Cl$_2$ (47 mL) was treated at 0°–5° C. and under Argon, with tetrakis(triphenylphosphine)palladium [0] (123 mg) and 4.9 mL (2.44 mmol) of a 0.5M solution of sodium 2-ethylhexanoate in EtOAc. Then 190 mL of 0.1M phosphate buffer was added and the organic layer was separated. The organic phase was reextracted twice with 50 mL of water and the combined aqueous layers were pumped to remove organic solvent. Chromatography on reversed phase silica gel (Bondapak c-18, 7×10.5 cm) using gradient of acetonitrile in water (0–7%) followed by lyophilization of the UV active fractions gave 580 mg (66%) of the title compound slightly contaminated with sodium 2-ethylhexanoate. This material was used as such for the next step;

IR (NaCl, film) $v_{max}$: 2250 (CN), 2105 (N$_3$), 1750 (C=O of β-lactam) and 1600 (C=O of carboxylate);

$^1$H NMR (200 MHz, D$_2$O) δ: 1.31 (d, J=6.40 Hz, 3H, CH$_3$CHO), 1.71–2.01 (m, 4H, CCH$_2$CH$_2$CN and CH$_2$-4), 2.73 and 2.74 (2t, J=6.94 and J=7.04, 2H, CH$_2$CN), 2.80–3.19 (m, 2H, SCH$_2$), 3.35–3.67 (m, 4H, CCH$_2$N$_3$, H-4 and H-6), 4.29–4.42 (m, 2H, H-5 and CH$_3$CHO).

D. (4R,5S,6S)-4-(2"-Aminoethyl)-3-[(3-cyanopropyl)thio]-6-[(1'R)-1'-hydroxyethyl]-7-oxo-1-azabicyclo[3.2.0]hept-2-ene-2-carboxylic acid

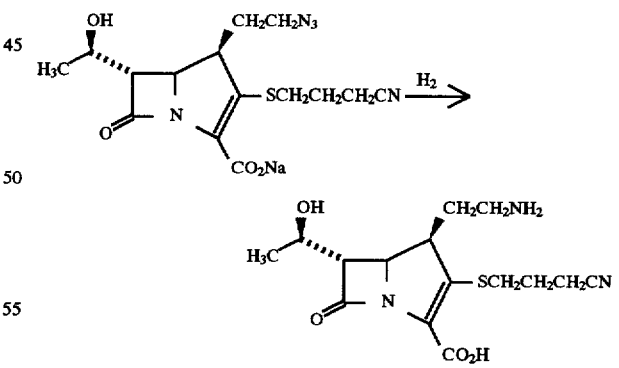

A solution of sodium (4R,5S,6S)-4-(2"-azidoethyl)-3-[(3-cyanopropyl)thio]-6-[(1'R)-1'-hydroxyethyl]-7-oxo-1-azabicyclo[3.2.0]hept-2-ene-2-carboxylate (250 mg, 0.64 mmol) in water was hydrogenated at 0°–5° C. over 250 mg of 5% palladium on alumina and under 45 psi of hydrogen for 1 h. The catalyst was filtered and the filtrate was chromatographed on reversed phase silica gel (Bondapak c-18, 7×10.5 cm) using water as eluent. Lyophilization of the UV active fractions gave 18 mg (8%) of the title compound slightly contaminated with sodium 2-ethylhexanoate as a light yellow amorphous powder and 129 mg (59%) of the pure title compound as an off-white amorphous powder:

Purity by HPLC: 97% μ-Bondapak c-18, 3.9 mm×30 cm, elution 2% CH$_3$CN/H$_2$O pH 7.4 phosphate buffer, flow rate 1 mL/min, uv detector 302 nm, retention time 5.24 min;

UV (H$_2$O, pH7.4 phosphate buffer) λ$_{max}$: 302 nm (5982);

IR (KBr) ν$_{max}$: 2250 (CN), 1760 (C=O of β-lactam) and 1590 cm$^{-1}$ (C=O of carboxylate);

$^1$H NMR (200 MHz, D$_2$O) δ: 1.33 (d, J=6.35 Hz, 3H, CH$_3$CHO), 1.75–2.30 (m, 4H, CH$_2$CH$_2$CN and CH$_2$-4), 2.63 (t, J=7.07 Hz, 2H, CH$_2$CN), 2.69–3.19 (m, 4H, SCH$_2$ and CH$_2$NH$_2$), 3.41 (m, overlapping with H-6, 1H, H-4), 3.44 (dd, J$_{1'-6}$=6.6 Hz, J$_{5-6}$=2.85 Hz, H-6), 4.21–4.33 (m, 2H, H-5 and CH$_3$CHO).

EXAMPLE 48

(4R,5S,6S)-6-[(1'R)-1'-Hydroxyethyl]-4-(2"-aminoethyl)-3-[(pyridin-4-yl)methylthio]-7-oxo-1-azabicyclo[3.2.0]hept-2-ene-2-carboxylic acid

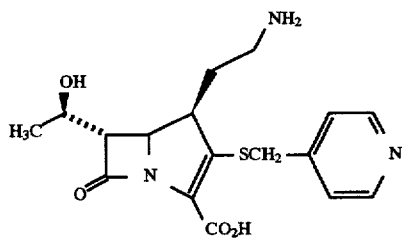

A. Allyl (4R,5S,6S)-6-[(1'R)-1'-tert-butyldimethylsilyloxyethyl]-4-(2"-azidoethyl)-3-[(pyridin-4-yl)methylthio]-7-oxo-1-azabicyclo[3.2.0]hept-2-ene-2-carboxylate

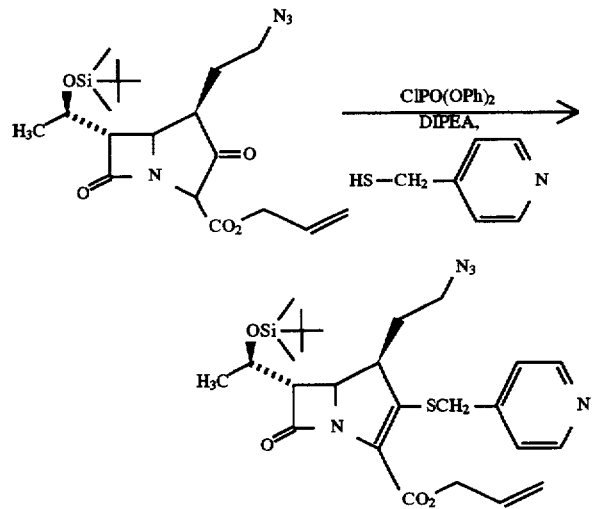

A cold (0° C.) solution of allyl (4R,5R,6S)-6-[(1'R)-1'-(tert-butyldimethylsilyloxyethyl)]-4-(2"-azidoethyl)-3,7-dioxo-1-azabicyclo[3.2.0]heptane-2-carboxylate (4.7 g, 10.76 mmol) prepared as in Example 2 in CH$_3$CN (50 mL) was treated with diphenyl chlorophosphate (2.45 mL, 11.84 mmol) followed by N,N-diisopropylethylamine (2.06 mL, 11.84 mmol) and 4-N,N-dimethylaminopyridine (10 mg). The mixture was stirred at 0° for 2 h, under Argon, after which Argon was bubbled through the solution for 10 min. The enol-phosphate was then treated with 4-picolyl mercaptan (2.02 g, 16.15 mmol) in CH$_3$CN (10 mL) followed by N,N-diisopropylethylamine (2.81 mL, 16.15 mmol) and stirred at 0° C. for 3 hours. The reaction mixture was diluted with EtOAc (350 mL) and washed successively with cold 1M NaHSO$_3$, 1M NaHCO$_3$ and brine. The organic phase was dried (MgSO$_4$) and solvent evaporated to a syrup which was chromatographed on silica (7.5×11 cm) packed in CH$_2$Cl$_2$ and eluted with a mixture of CH$_2$Cl$_2$ and EtOAc (8:2 gradient elution) to give the title compound as a syrup (2.28 g, 39%).

$^1$H NMR (200 MHz, CDCl$_3$ 7.24) δ: 0.04 (s, 3H, SiCH$_3$), 0.06 (s, 3H, SiCH$_3$), 0.86 (s, 9H, SiC(CH$_3$)$_3$), 1.27 (d, CH$_3$, J$_{CH3,1'}$=6.12 Hz), 1.63–1.76 (m, 1H, CH$_2$), 1.93–2.05 (m, 1H, CH$_2$), 3.02 (dd, H-6, J$_{5,6}$=2.68 Hz, J$_{6,1'}$=7.91 Hz), 3.18–3.67 (overlapping, 3H, H-4, CH$_2$N$_3$), 3.9–4.17 (overlapping, 4H, CHOH, H-5, SCH$_2$), 4.6–4.85 (m, OCH$_2$, allyl), 5.2–5.47 (m, =CH$_2$, allyl), 5.84–6.03 (m, CH=, allyl), 7.29 (A of A$_2$B$_2$, H-3,5 py, J$_{2,3}$=5.98 Hz), 8.56 (B of A$_2$B$_2$, H-2,6 py).

B. Allyl (4R,5S,6S)-6-[(1'R)-1'-hydroxyethyl]-4-(2"-azidoethyl)-3-[(pyridin-4-yl)methylthio]-7-oxo-1-azabicyclo[3.2.0]hept-2-ene-2-carboxylate

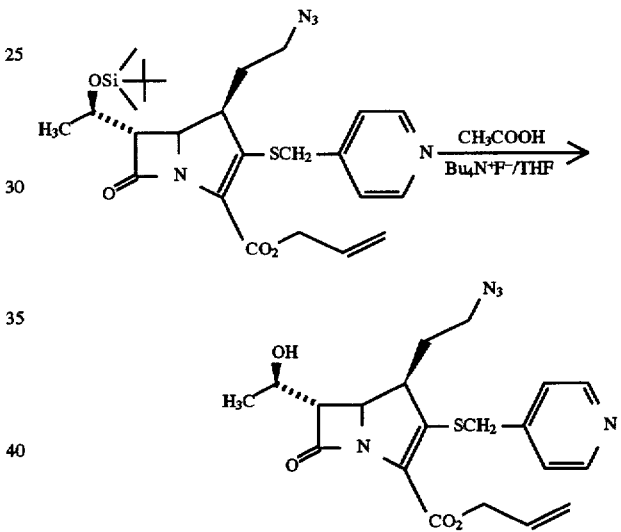

A cold (0° C.) solution of allyl (4R,5S,6S)-6-[(1'R)-1'-tert-butyldimethylsilyloxyethyl]-4-(2"-azidoethyl)-3-[(pyridin-4-yl)methylthio]-7-oxo-1-azabicyclo[3.2.0]hept-2-ene-2-carboxylate (2.26 g, 4.16 mmol) in dry THF (35 mL) was treated, under Argon, with acetic acid (1.43 mL, 24.94 mmol) followed by a 1M solution of tetrabutylammonium floride in THF (12.47 mL, 12.47 mmol). The mixture was stirred between 0° and 5° C. for 120 h and then neutralized at 0° C. with a 1M NaHCO$_3$ solution (25 mL, 25 mmol). The mixture was extracted with EtOAc (3×75 mL) and the combined organic phase was washed successively with a cold 1M NaHCO$_3$ solution, H$_2$O and brine, dried (MgSO$_4$) and solvent evaporated to give a sticky foam which was chromatographed on silica (4.5×11 cm) packed in CH$_2$Cl$_2$ and eluted first with a mixture of CH$_2$Cl$_2$ and EtOAc (50 to 100% EtOAc) and then with a mixture of CH$_3$CN and EtOAc (1:1 gradient elution) to give the title compound as a foam (1.23 g, 69%).

$^1$H NMR (200 MHz, CDCl$_3$ 7.24) δ: 1.36 (d, CH$_3$, J$_{CH3,1'}$=6.23 Hz), 1.64–1.79 (m, 1H, CH$_2$), 1.94–2.09 (m, 1H, CH$_2$), 3.09 (dd, H-6, J$_{5,6}$=2.78 Hz, J$_{6,1'}$=8.08 Hz), 3.19–3.65 (overlapping, 3H, H-4, CH$_2$N$_3$), 3.88–4.23 (overlapping, 4H, CHOH, H-5, SCH$_2$), 4.61–4.88 (m, OCH$_2$, allyl), 5.21–5.47 (m, =CH$_2$, allyl), 5.85–6.04 (m, CHO, allyl), 7.28 (A of A$_2$B$_2$, 2H, H-3,5, py, J$_{2,3}$=6.01 Hz), 8.56 (B of A$_2$B$_2$, 2H, H-2,6; py).

C. Sodium (4R,5S,6S)-6-[(1'R)-1'-hydroxyethyl]-4-(2"-azidoethyl)-3-[(pyridin-4-yl)methylthio]-7-oxo-1-azabicyclo-[3.2.0]hept-2-ene-2-carboxylate

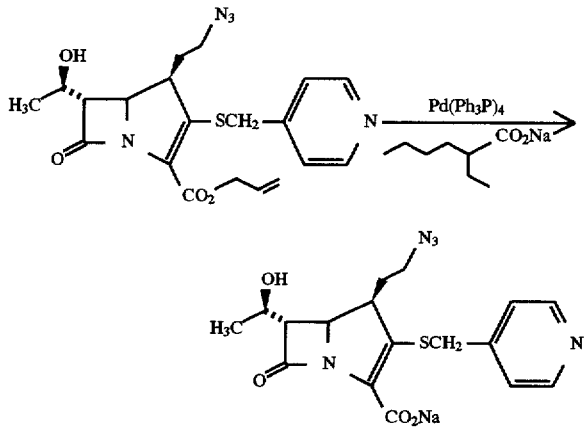

To a cold (0° C.) solution of allyl (4R,5S,6S)-6-[(1'R)-1'-hydroxyethyl]-4-(2"-azidoethyl)-3-[(pyridin-4-yl)methylthio]-7-oxo-1-azabicyclo[3.2.0]hept-2-ene-2-carboxylate (1.23 g, 2.86 mmol) in CH$_2$Cl$_2$ (25 mL), under Argon, was added Pd[Ph$_3$P]$_4$ (0.3 g, 0.26 mmol) followed by a 0.5M solution of sodium 2-ethylhexanoate in EtOAc (5.73 mL, 2.86 mmol). The mixture was stirred at 0° C. for 1 h and then extracted with water (3×25 mL). The combined aqueous phase was passed through a column of µ-Bondapak C-18 reverse phase silica (4.5×11 cm). The title compound was eluted with a mixture of water and CH$_3$CN (9:1, gradient elution) and was obtained as a fluffy solid after lyophilization (0.69 g, 58.5%).

$^1$H NMR (200 MHz, D$_2$O) δ: 1.29 (d, CH$_3$, J$_{CH3,1'}$=6.37 Hz), 1.6–1.78 (m, 1H, CH$_2$), 1.93–2.09 (m, 1H, CH$_2$), 3.14–3.58 (overlapping, 3H, H-4, CH$_2$N$_3$), 3.4 (dd, H-6, J$_{5,6}$=2.64 Hz, J$_{6,1}$=6.22 Hz), 3.96–4.28 (overlapping, 4H, CHOH, H-5, SCH$_2$), 7.5 (A of A$_2$B$_2$, H-3,5, py, J$_{2,3}$=5.35 Hz), 8.49 (br s, B of A$_2$B$_2$, H-2,6, py).

D. (4R,5S,6S)-6-[(1'R)-1'-Hydroxyethyl]-4-(2"-aminoethyl)-3-[(pyridin-4-yl)methylthio]-7-oxo-1-azabicyclo[3.2-0]hept-2-ene-2-carboxylic acid

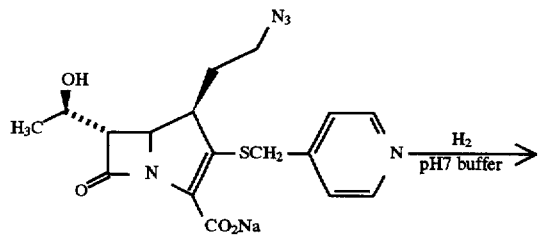

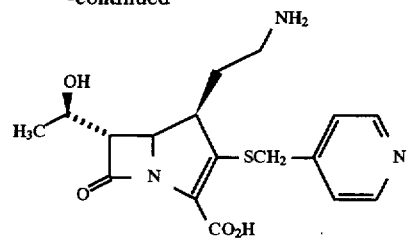

A solution of sodium (4R,5S,6S)-6-[(1'R)-1'-hydroxyethyl]-4-(2"-azidoethyl)-3-[(pyridin-4-yl)methylthio]-7-oxo-1-azabicyclo[3.2.0]hept-2-ene-2-carboxylate (0.16 g, 0.39 mmol) in 40 mL of a 0.05M pH 7 phosphate buffer was hydrogenated at 45 psi over 5% Pd on alumina (0.32 g) at 0° C. for 1 h. After removing the catalyst, the filtrate was passed through a column of µ-Bondapak C-18 reverse phase silica (4.5×11 cm). The title compound was eluted with a mixture of water and CH$_3$CN (95:5, gradient elution) and was obtained as a fluffy solid after lyophilization (0.044 g, 31.4%).

Purity by HPLC: 95.9%; UV detection at 302 nm on µ-Bondapak C-18 (4 mm×30 cm), 10% CH$_3$CN in pH 7.4 phosphate buffer, flow rate 1 mL/min, retention time 7.24 min.

IR (nujol) ν$_{max}$: 1750 cm$^{-1}$ (C=O, β-lactam).

$^1$H NMR (D$_2$O, 200 MHz) δ: 1.31 (d, CH$_3$, J$_{CH3,1'}$=6.35 Hz), 1.65–1.85 (m, 1H, CH$_2$), 2.04–2.22 (m, 1H, CH$_2$), 3.04 (t, 2H, CH$_2$NH$_2$), 3.19 (dt, H-4, J$_{4,5}$=10.05, J=3.44 Hz), 3.4 (dd, H-6, J$_{5,6}$=2.8 Hz, J$_{6,1}$=6.52 Hz), 3.99, 4.13 (AB, SCH$_2$, J$_{gem}$14.39 Hz), 4.11 (dd, H-5), 4.24 (m, H-1'), 7.46 (A of A$_2$B$_2$, H-3,5, py, J$_{2,3}$=6.1 Hz), 8.49 (B of A$_2$B$_2$, H-2-6, py).

EXAMPLE 49

(4R,5S,6S)-3-[(2-Cyanoethyl)thio]-6-[(1'R)-1'-hydroxyethyl]-4-[2"-(N-morpholino)ethyl)-7-oxo-1-azabicyclo[3.2.0]hept-2-ene-2-carboxylic acid

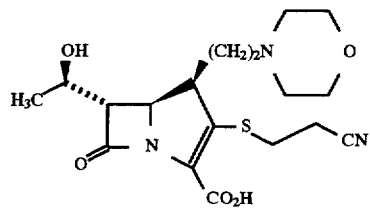

A. Allyl (4R,5S,6S)-4-(2"-tert-butyldimethylsilyloxyethyl)-6-[(1'R)-1'-tert-butyldimethylsilyloxyethyl]-3-[(2-cyanoethyl)-thio]-7-oxo-1-azabicyclo[3.2.0]hept-2-ene-2-carboxylate

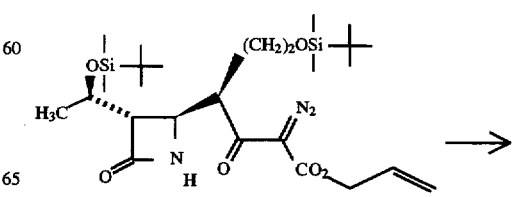

-continued

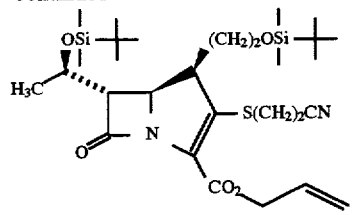

A cold (ice-methanol bath) solution of allyl-(2R,4R,5R,6S)-4-(2"-tert-butyldimethylsilyloxyethyl)-6-[(1'R)-1'-tert-butyldimethylsilyloxyethyl]-3,7-dioxo-1-azabicyclo[3.2.0]heptane-2-carboxylate in CH$_3$CN (160 mL) obtained from the corresponding (3S,4R)-3-[(1'R)-1'-tert-butyldimethylsilyloxyethyl]-4-[(1"R)-1"-(2-tert-butyldimethylsilyloxyethyl)-3"-diazo-3"-allyloxycarbonyl-2"-oxopropyl]azetidin-2-one (15.0 g, 27.0 mmol) was treated successively with diphenyl chlorophosphate (6.2 mL, 30 mmol) and dropwise with N,N-diisopropylethylamine (5.2 mL, 30 mmol) and 4-dimethylaminopyridine (20 mg). The mixture was stirred for 1 h and the resulting enol phosphate was treated with 2-cyanoethanethiol (2.9 g, 33.8 mmol) and N,N-diisopropylethylamine (5.8 mL, 33.8 mmol). The mixture was stirred for 30 min and it was treated twice at 30 min interval with 2-cyanoethane-thiol (600 mg, 6.7 mmol×2) and N,N-diisopropylethylamine (1.16 mL, 6.76 mmol×2). The mixture was diluted with ethyl acetate (400 mL), washed with ice cold water (3×100 mL), ice cold 1M aqueous NaHSO$_3$ (100 mL), ice cold 1N aqueous HCl (100 mL), water (100 mL), cold 1M aqueous NaHCO$_3$ (100 mL), ice cold water (100 mL×2), brine (100 mL) and dried (MgSO$_4$). The mixture was passed through a silica gel flash pad (250 g, Hexane→15% ethyl acetate/Hexane) to give the title compound (11.5 g, 71.6%) as a solid;

IR (neat) $v_{max}$: 2250 (C≡N), 1775 and 1710 cm$^{-1}$ (C=O);

$^1$H NMR (CDCl$_3$, 200 MHz) δ: 6.05–5.85 (1H, m, vinylic H), 5.49–5.21 (2H, m, vinylic H), 4.9–4.55 (2H, m, allylic CH$_2$), 4.27–4.18 (2H, m, H-1' and H-5), 4.195 (part of H-5, d, J=2.6 Hz), 3.89–3.75 (1H, m, HCH—OSi), 3.60–3.45 (2H, m, H-4 and HCH—OSi), 3.35–3.22, 3.12–2.93 (2H, 2 sets of m, SCH$_2$), 3.102 (1H, dd, J=2.5 Hz, J=6.3 Hz, H-6), 2.70–2.60 (2H, m, CH$_2$—CN), 2.04–1.90, 1.80–1.60 (2H, 2 sets of m, CH$_2$-4), 1.267 (3H, d, J=6.1 Hz, CH$_3$), 0.907 and 0.887 (18H, 2s, tert-butyl), 0.084 and 0.074 ppm (12H, 2s, dimethyl).

B. Allyl (4R,5S,6S)-6-[(1'R)-1'-tert-butyldimethylsilyloxyethyl]-3[(2-cyanoethyl)thio]-4-(2"-hydroxyethyl)-7-oxo-1-azabicyclo[3.2.0]hept-2-ene-2-carboxylate

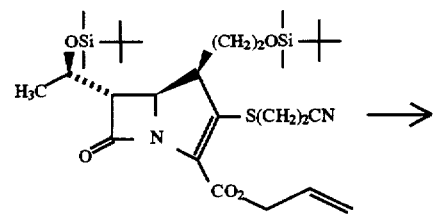

A cold (ice-methanol bath) of allyl (4R,5S,6S)-4-(2"-tert-butyldimethylsilyloxyethyl]-6-[(1'R)-1'-tert-butyldimethylsilyloxyethyl]-3-[(2-cyanoethyl)thio]-7-oxo-1-azabicyclo[3.2.0]hept-2-ene-2-carboxylate (2.0 g, 3.36 mmol) in anhydrous tetrahydrofuran (20 mL) was treated successively with glacial acetic acid (2.2 mL, 40 mmol) and dropwise with a 1M solution of tetrabutylammonium fluoride in tetrahydrofuran (20 mL, 20 mmol). The mixture was stirred for 1 h and then was allowed to react at 5° C. (cold room) for 18 h. The mixture was poured on ice cold saturated NaHCO$_3$ (50 mL) and extracted with ethyl acetate (4×25 mL). The organic layers were combined, washed with ice cold water (25 mL), ice cold 1M aqueous NaHCO$_3$ (2×25 mL), water (2×25 mL), brine (25 mL) and dried (MgSO$_4$). The mixture was passed through a silica gel flash pad (50 g, CH$_2$Cl$_2$→10, 20, 30, 40% EtOAc/CH$_2$Cl$_2$) to give the title compound (1.0 g, 62%) as a semi-solid;

IR (Neat) $v_{max}$: 3600–3200 (OH), 2250 (C≡N), 1770 and 1710 cm$^{-1}$ (C=O);

$^1$H NMR (CDCl$_3$, 200 MHz) δ: 6.03–5.86 (1H, m, vinylic —H), 5.50–5.22 (2H, m, vinylic H), 4.80–4.66 (2H, m, allylic CH$_2$), 4.222 (1H, dd, J=2.7 Hz, J=9.8 Hz, H-5), 4.25–4.19 (1H, m, H-1'), 3.95–3.82, 3.75–3.65 (2H, 2 sets of m, CH$_2$O), 3.59–3.48 (1H, m, H-4), 3.31–3.16, 3.09–2.94 (2H, 2 sets of m, S—CH$_2$), 3.184 (1H, dd, J=2.6 Hz, J=6.9 Hz, H-6), 2.74–2.66 (2H, m, CH$_2$—CN), 2.15–1.95, 1.90–1.70 (2H, 2 sets of m, CH$_2$-4), 1.56 (1H, s, OH), 1.290 (3H, d, J=6.2 Hz, CH$_3$), 0.891 (9H, s, tert-butyl) and 0.090 ppm (6H, s, dimethyl).

C. Allyl (4R,5S,6S)-6-[(1'R)-1'-tert-butyldimethylsilyloxyethyl]-3-[(2-cyanoethyl)thio]-4-[2"-(N-morpholino)ethyl]-7-oxo-1-azabicyclo[3.2.0.]hept-2-ene-2-carboxylate

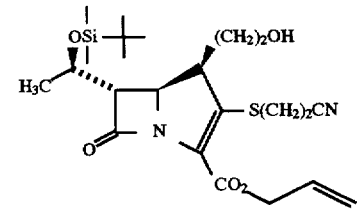

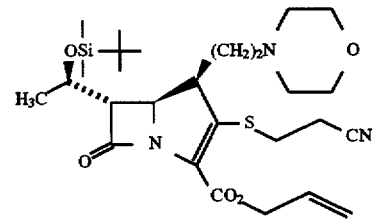

A cold solution (dry ice-acetone) of allyl (4R,5S,6S)-6-[(1'R)-1'-tert-butyldimethylsilyloxyethyl]-3-[(2-cyanoethyl)thio]-4-(2"-hydroxyethyl)-7-oxo-1-azabicyclo[3.2-0]hept-2-ene-2-carboxylate (312 mg, 0.650 mmol) in CH$_2$Cl$_2$ (8 mL) was treated with N,N-diisopropylethylamine (200 µL, 1.72 mmol) and dropwise with trifluoromethanesulfonic anhydride (130 µl, 0.773 mmol). The mixture was stirred for 30 min and then morpholine (350 µl, 4.01 mmol) was added on. The dry-ice bath was removed and was replaced by an ice bath. The mixture was stirred for 3 h after which it was applied directly on a silica gel column (15 g, hexane→hexane/EtOAc→CH₃CN) to give the title compound (420 mg, 100%) as an oil;

IR (neat) $v_{max}$: 1775 and 1710 cm$^{-1}$ (C=O);

$^1$H NMR (CDCl₃, 200 MHz) δ: 6.04–5.84 (1H, m, vinylic-H), 4.85–4.62 (2H, m, allylic-CH₂), 4.192 (1H, dd, J=2.2 Hz, J=11.8 Hz, H-5), 4.29, 4.26, 4.20 (1H, m, part of H-1'), 3.70 (4H, bs, CH₂OCH₂), 3.35–3.16 (3H, m, H-4, H-6, HCHS), 3.03–2.89 (1H, m, HCHS), 2.72–2.55 (2H, m, CH₂CN), 2.52–2.22 (6H, m, (CH₂)₃N), 1.98–1.86 (1H, m, C H-4), 1.69–1.48 (1H, m, CH-4), 1.279 (3H, d, J=6.1 Hz, CH₃), 0.877 (9H, s, tert-butyl) and 0.076 (6H, s, dimethyl).

D. Allyl (4R,5S,6S)-3-[(2-cyanoethyl)thio]-6-[(1'R)-1'-hydroxyethyl]-4-[2"-(N-morpholino)ethyl]-7-oxo-1-azabicyclo[3.2.0]hept-2-ene-2-carboxylate

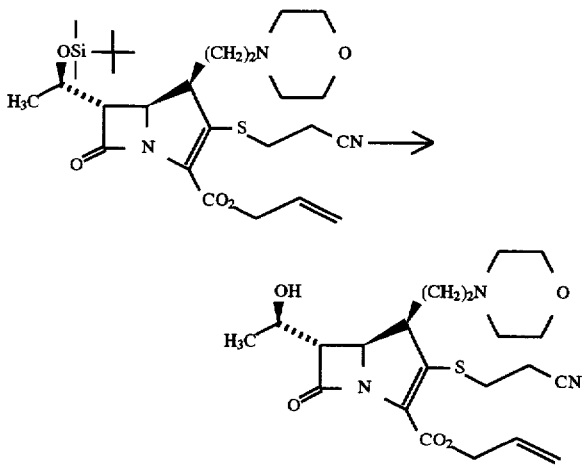

A cold solution (ice-MeOH bath) of allyl (4R,5S,6 S)-6-[(1'R)-1'-tert-butyldimethylsilyloxyethyl]-3-[(2-cyanoethyl)thio]-4-[2"-(N-morpholino)ethyl]-7-oxo-1-azabicyclo-[3.2.0]hept-2-ene-2-carboxylate (420 mg, 764 mmol) in THF (8 mL) was treated first with acetic acid (560 µl, 9.78 mmol) and dropwise with a 1M solution of tetrabutylammonium fluoride in THF (4.55 mL, 4.55 mmol). The mixture was stirred for 30 min and the ice-MeOH bath was replaced by an ice bath. The mixture was then allowed to set in a cold room (5° C.) for 210 h. Then solid NaHCO₃ (600 mg) was added in and the mixture was stirred for 30 min and then applied on 4 preparative TLC plates (2 mm, CH₃CN) to give pure title compound (325 mg, 97%, R$_f$=0.2) but contaminated with some tetrabutylammonium salt;

IR (nujol) $v_{max}$: 3600–3200 (OH), 1770 and 1710 cm$^{-1}$ (C=O);

$^1$H NMR(CDCl₃, 200 MHz) δ: 6.04–5.87 (1H, m, vinylic H), 5.49–5.24 (2H, m, vinylic H), 4.88–4.64 (2H, m, allylic CH₂), 4.276 (1H, dd, J=2.8 Hz, J=9.8 Hz, H-5), 4.3–4.1 (1H, m, H-1'), 3.76–3.7 (4H, bm, CH₂OCH₂), 3.45–3.31 (1H, m, H-4), 3.269 (1H, dd, J=2.9 Hz, J=8.0 Hz, H-6), 3.25–3.16, 3.03–2.90 (2H, 2 sets of m, SCH₂), 2.72–2.35 (8H, CH₂CN, (CH₂)₃N), 2.1–1.9 and 1.8–1.6 (2H, 2 sets of m, CH₂) and 1.388 ppm (3H, d, J=6.2 Hz, CH₃).

E. (4R,5S,6S)-3-[(2-Cyanoethyl)thio]-6-[(1'R)-1'-hydroxyethyl]-4-[2"-(N-morpholino)ethyl]-7-oxo-1-azabicyclo-[3.2.0]-hept-2-ene-2-carboxylic acid

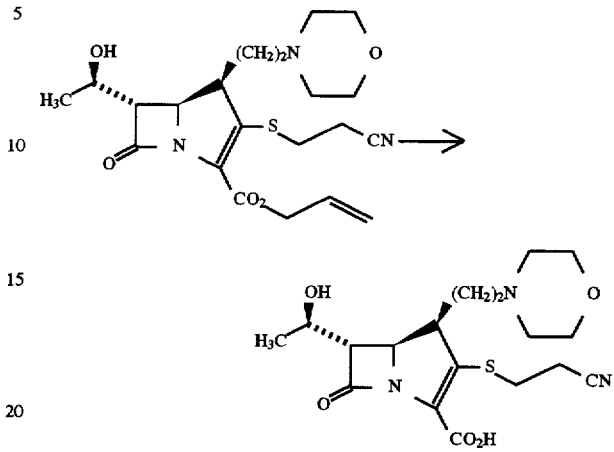

To a cold (ice bath) solution of allyl (4R,5S,6 S)-3-[(2-cyanoethyl)thio]-6-[(1'R)-1'-hydroxyethyl]- 4-[2"-(N-morpholino)ethyl]-7-oxo-1-azabicyclo[3.2.0]hept-2-ene-2-carboxylate (321 mg, 0.737 mmol) in CH₂Cl₂ (6 mL) was added Pd(PPh₃)₄ (14 mg) and a 0.5M solution of potassium ethyl-2-hexanoate (1.5 mL, 0.75 mmol). The ice bath was removed and the mixture was stirred for 1 h. More Pd(PPh₃)₄ was added and stirring was continued for 1 h. It was diluted with diethyl ether and extracted with a 0.05M aqueous pH 7.0 buffer and a pH 7.4 buffer. The aqueous mixture extracted was combined, washed with diethyl ether and passed through a reversed phase µ-Bondapak C₁₈ column (H₂O, 2%→4% CH₃CN/H₂O) to give the title compound (179 mg, 61.4%) as a lyophilized powder;

Purity by HPLC: 99.7% (300 nm);

UV (H₂O) $\lambda_{max}$: 300 (7900);

IR (Nujol) $v_{max}$: 1750 and 1600 cm$^{-1}$ (C=O);

$^1$H NMR (D₂O, 200 MHz) δ: 4271 (1H, dd, J=2.7 Hz, J=6.8 Hz, H-5), 4.4–4.22 (1H, m, H-1'), 3.84–3.80 (4H, m, CH₂OCH₂), 3.424 (1H, dd, J=2.7 Hz, J=6.3 Hz, H-6), 3.43–3.33 (1H, m, H-4), 3.21–3.08, 3.01–2.90 (2H, 2 sets of m, SCH₂), 2.90–2.6 (8H, m, CH₂CN, (CH₂)₃N), 2.2–2.0, 1.90–1.70 (2H, 2 sets of m, CH₂) and 1.336 (3H, d, J=6.3 Hz, CH₃).

EXAMPLE 50

(4R,5S,6S)-4-(3"-Aminopropyl)-3-[(3-cyanopropyl)thio]-6-[(1'R)-1'-hydroxyethyl]-7-oxo-1-azabicyclo[3.2.0]hept-2-ene-2-carboxylic acid

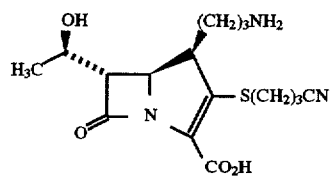

A. Allyl (4R,5S,6S)-4-(3"-azidopropyl)-3-[(3-cyanopropyl)thio]-6-[(1'R)-1'-hydroxyethyl]-7-oxo-1-azabicyclo-[3.2.0] hept-2-ene-2-carboxylate

151

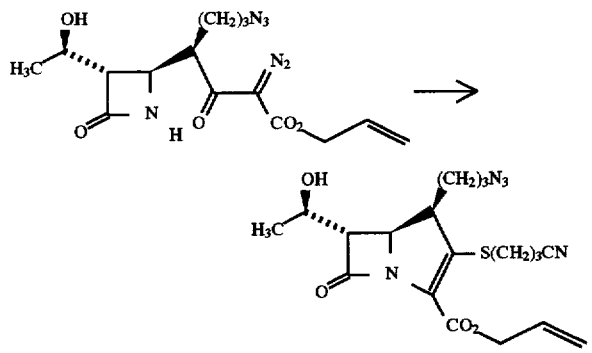

A cold solution (ice-MeOH bath) of allyl (2R,4R,5S,6 S)-4-(3"-azidopropyl)-6-[(1'R )-1'-hydroxyethyl]-3,7-dioxo-1-azabicyclo[3.2.0]heptan-2-carboxylate, prepared from (3 S, 4R)-3-[(1'R)-1'-hydroxyethyl]-4-[(1' R)-1"-(3-azidopropyl)- 3"-diazo-3"-allyloxycarbonyl-2"-oxopropyl]azetidin-2-one (2.00 g, 5.49 mmol), as prepared in Example 21, in $CH_3CN$ (40 mL) was treated dropwise with diphenyl chlorophosphate (1.2 mL, 6.0 mmol) and N,N-diisopropylethylamine (1.03 mL, 6.00 mmol) and a trace of 4-N,N-dimethylaminopyridine. The mixture was stirred for 30 min and the resulting enolphosphate was treated dropwise with cyanopropyl mercaptan (693 mg, 6.86 mmol) and N,N-diisopropylethylamine (1.19 mL, 6.90 mmol). The mixture was stirred for 1 h, then the ice-MeOH bath was replaced by an ice bath and stirring was pursued for 2 more hours. Then more cyanopropyl mercaptan (280 mg, 2.74 mmol) and N,N-diisopropylethylamine (0.480 mL, 2.74 mmol) were added then followed by a stirring period of 18 h at 5° C. (cold room). More thiol (280 mg, 2.74 mmol) and N,N-diisopropylethylamine (0.480 mL, 2.74 mmol) were added and stirring was continued for 3 h after which, the mixture was diluted with ethyl acetate (100 mL), washed with cold 1M aqueous $NaHSO_3$ (2×40 mL), water (40 mL), 1N aqueous HCl (40 mL), water (40 mL), 1M aqueous $NaHCO_3$ (40 mL), water (40 mL), brine (40 mL) and dried ($MgSO_4$). The residue was passed through a silica gel flash column (75 g, EtOAc/Hexane: 1/3→EtOAc) to give the title compound (1.33 g, 59%) as an oil;

IR ($CH_2Cl_2$) $v_{max}$: 3600–3500 (OH), 2250 (CN), 2100 ($N_3$), 1780 and 1710 cm$^{-1}$ (C=O);

$^1$H NMR ($CDCl_3$, 200 MHz) δ: 6.04–5.87 (1H, m, vinylic-H), 5.50–5.23 (2H, m, vinylic-H), 4.89–4.63 (2H, m, allylic $CH_2$), 4.29–4.20 (1H, m, H-1'), 4.248 (1H, dd, J=2.7 Hz, J=9.5 Hz, H-5), 3.50–3.35 (2H, m, $CH_2$__$N_3$), 3.267 (1H, dd, J=2.7 Hz, J=7.6 Hz, H-6), 3.30–3.20 (1H, m, H-4), 3.05–2.85 (2H, m, $SCH_2$), 2.59–2.51 (2H, m, $CH_2CN$), 2.06–1.93 (2H, $CH_2\underline{CH_2}CH_2CN$), 1.93–1.57 (4H, $\underline{CH_2}$—$\underline{CH_2}$—$CH_2N_3$), 1.76 (1H, d, J=3.7 Hz, OH) and 1.393 ppm (3H, d, J=6.3 Hz, $CH_3$).

B. (4R,5S,6S)-4-(3"-Aminopropyl)-3-[(-cyanopropyl)thio]-6-[(1'R)-1'-hydroxyethyl]-7-oxo-1-azabicyclo[3.2.0]hept-2-ene-2-carboxylic acid

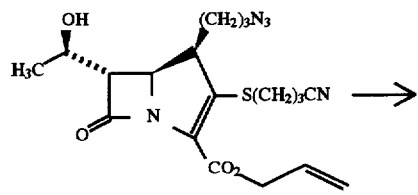

152

-continued

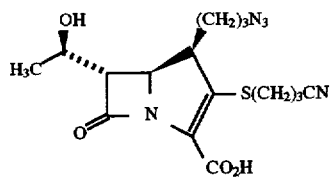

A cold (ice bath) solution of allyl (4R,5S,6 S)-4-(3"-azidopropyl)-3-[(3-cyanopropyl)thio]-6-[(1'R)-1'-hydroxyethyl]-7-oxo-1-azabicyclo[3.2.0]hept-2-ene-2-carboxylate (100 mg, 0.240 mmol) in $CH_2Cl_2$ (10 mL) was treated with Pd(PPh$_3$)$_4$ (220 mg, 0.018 mmol) followed by the dropwise addition of a 0.5M solution of sodium ethyl-2-hexanoate (0.48 mL, 0.24 mmol) in EtOAc. The mixture was stirred for 1.5 h, then diluted with diethyl ether (20 mL) and extracted with water (3×3 mL) and a 0.05M solution of a pH 8.0 phosphate buffer (3×3 mL). The aqueous extracts were combined, washed with diethyl ether (2×5 mL) and then treated at 5° C. (ice bath) at 45–50 psi of hydrogen for 1.25 h using 5% Pd/Alumina (100 mg) as catalyst. The catalyst was removed by filtration, washed with water (2×2 mL) and the aqueous solution was passed through a μ-Bondapak $C_{18}$ column (25 g, $H_2O$→1%, 2% $CH_3CN/H_2O$) to give the title compound (65 mg, 77%) as a white lyophilized powder;

Purity by HPLC: 99.9% (300 nm);

UV ($H_2O$) $\lambda_{max}$: 302 (ε8000);

IR (Nujol) $v_{max}$: 2250 (CN), 1760 and 1595 cm$^{-1}$ (C=O);

$^1$H NMR ($D_2O$, 200 MHz) δ: 4.34–4.32 (2H, m, H-1' and H-5), 4.239, 4.226 (d, J=2.6 Hz, part of H-5), 3.42–3.33 (1H, m, H-4), 3.383 (1H, dd, J=2.7 Hz, J=6.2 Hz, H-6), 3.09–2.94 (3H, m, $CH_2N$ and S-$\underline{H}$CH), 2.85–2.74 (1H, m, S$\underline{H}$C$\underline{H}$), 2.70–2.61 (2H, m, $CH_2CN$), 2.10–1.49 (6H, m, $CH_2\underline{CH_2}CH_2CN$, $CH_2CH_2$) and 1.334 ppm (3H, d, J=6.4 Hz, $CH_3$).

EXAMPLE 51

(4R,5S,6S)-4-[3"-(N-Formimidoyl)aminopropyl]-3-[(3-cyanopropyl)thio]-6-[(1'R)-1'-hydroxyethyl]-7-oxo-1-azabicyclo [3.2.0]hept-2-ene-2-carboxylic acid

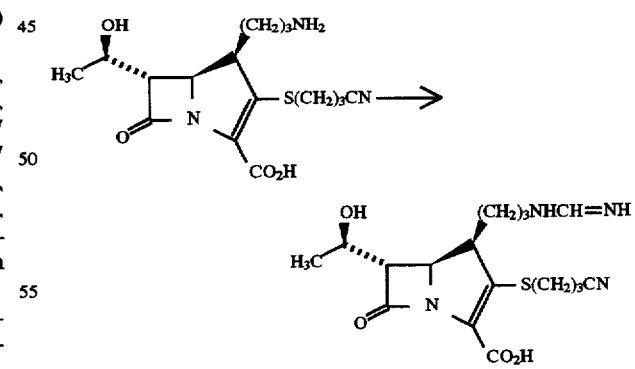

A cold solution (ice bath) of (4R,5S,6 S)-4-(3"-aminopropyl)-3-[(3-cyanopropyl)thio]-6-[(1' R)-1'-hydroxyethyl]-7-oxo- 1-azabicyclo[3.2.0]hept-2-ene-2-carboxylic acid (150 mg, 0.420 mmol) in a 0.04M pH 7.0 phosphate buffer (25 mL) was treated first with a 0.1M aqueous NaOH solution (to raise and maintain the pH to 8–8.4) and portionwise with benzyl formimidate hydrochloride (720 mg, 4.2 mmol). The mixture was stirred for 10 min and the pH of the solution lowered to 7.0 with a 0.1N aqueous HCl solution. The mixture was then passed through a μ-Bondapak C$_{18}$ column (twice, 30 g and 60 g, H$_2$O→1%, 2%, 3%, 4% CH$_3$CN/H$_2$O) to give the title compound (117 mg, 73%) as a lyophilized powder;

Purity by HPLC: 94.4% (300 nm);

UV (H$_2$O) λ$_{max}$: 302 (ε9100);

IR (Nujol) ν$_{max}$: 2250 (CN), 1755 (C=O), 1715 (C=N) and 1590 cm$^{-1}$ (C=O);

$^1$H NMR (D$_2$O, 200 MHz) δ: 7.83, 7.81 (1H, 2s, CH), 4.34–4.22 (2H, m, H-1' and H-4), 4.231 (d, J=2.9 Hz, part of H-4), 3.49–3.32 (4H, m, H-4, H-6 and CH$_2$N), 3.06–2.92, 2.84–2.74 (2H, 2 sets of m, SCH$_2$), 2.70–2.61 (2H, m, CH$_2$CN), 2.10–1.47 (6H, CH$_2$CH$_2$CH$_2$CN, CH$_2$—CH$_2$) and 1.323 ppm (3H, d, J=6.4 Hz, CH$_3$).

EXAMPLE 52

(4R,5S,6S)-4-(4''-Aminobutyl)-3-[(3-cyanopropyl)thio]-6-[(1'R)-1'-hydroxyethyl]-7-oxo-1-azabicyclo[3.2.0]hept-2-ene-2-carboxylic acid

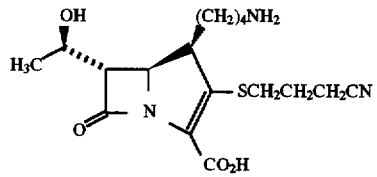

A. Allyl (4R,5S,6S)-4-(4''-azidobutyl)-3-[(3-cyanopropyl)thio]-6-[(1'R)-1'-hydroxyethyl]-7-oxo-1-azabicyclo-[3.2.0]hept-2-ene-2-carboxylate

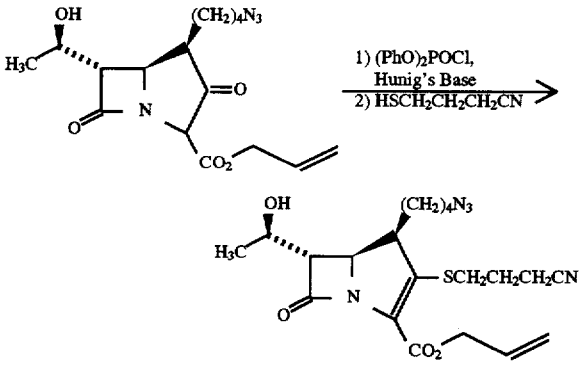

A solution of allyl (4R,5R,6S)-4-(4''-azidobutyl)-6-[(1'R)-1'-hydroxyethyl]-3,7-dioxo-1-azabicyclo[3.2.0]heptane-2-carboxylate (6.71 mmol, prepared by cyclization of 1.54 g, 6.71 mmol of the diazo precursor as described in Example 45) in dry acetonitrile (40 mL) was treated at 0°–5° C. and under nitrogen with diphenyl chlorophosphate (1.53 mL, 7.4 mmol) and N,N-diisopropylethylamine (1.3 mL, 7.5 mmol) added simultaneously over 5 min. A small crystal of 4-N,N-dimethylaminopyridine was then added and the mixture was stirred for 1 h. Then N,N-diisopropylethylamine (1.75 mL, 10.0 mmol) followed by 4-mercaptobutyronitrile (1.01 g, 10.0 mmol) [from basic hydrolysis of 4-acetylmercaptobutyronitrile (U.S. Pat. No. 3,223,585)] were added and the mixture was stirred at 0°–5° C. for 18 h. The reaction mixture was then diluted with EtOAc (300 mL) washed with water, saturated NaHCO$_3$, pH 7.0 phosphate buffer and brine and dried (MgSO$_4$). Evaporation of the solvent gave an oil which was chromatographed on silica gel (4.5×11 cm) using a gradient of EtOAc in toluene (8:2 to 1:1) to give 2.14 g (73%) of the title compound as an oil:

IR (NaCl, film) ν$_{max}$: 2250 (CN), 2100 (N$_3$), 1772 (C=O of β-lactam) and 1710 cm$^{-1}$ (C=O of ester);

$^1$H NMR (200 MHz, CDCl$_3$) δ: 1.39 (d, J=6.25 Hz, 3H, C<u>H</u>$_3$CHO), 1.4–2.1 (m, 8H, CH$_2$-1,2 and 3 of butyl and CH$_2$-2 of cyanopropylthio), 2.55 (m, 2H, C<u>H</u>$_2$CN), 2.8–3.1 (m, 2H, SC<u>H</u>$_2$), 3.2 (dd, J$_{H6,H5}$=2.70 Hz, J$_{H6,H1}$=7.22 Hz, 1H, H-6), 3.2 (m, overlapping with H-6, 1H, H-4), 3.33 (t, J=6.1 Hz, 2H, C<u>H</u>$_2$N$_3$), 4.25 (dd, J$_{H5,H6}$=2.70 Hz, J$_{H5,H4}$=9.49 Hz, 1H, H-5), 4.75 (m, 2H, CH$_2$ of allyl), 5.2–5.5 and 5.9–6.1 ppm (2×m, 2H and 1H, CH of allyl).

B. (4R,5S,6S)-4-(4''-Aminobutyl)-3-[(3-cyanopropyl)thio]-6-[(1'R)-1'-hydroxyethyl]-7-oxo-1-azabicyclo[3.2.0]hept-2-ene-2-carboxylic acid

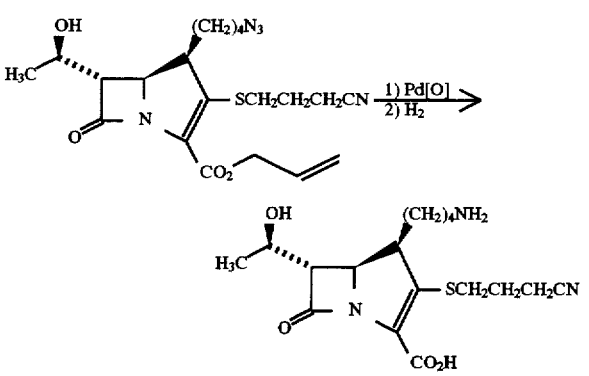

A solution of allyl (4R,5S,6S)-4-(4''-azidobutyl)-3-[(3-cyanopropyl)thio]-6-[(1'R)-1'-hydroxyethyl]-7-oxo-1-azabicyclo[3.2.0]hept-2-ene-2-carboxylate (1.86 g, 4.3 mmol) in dry EtOAc (80 mL) was treated at 24° C. and under nitrogen with tetrakis(triphenylphosphine) palladium [0] (0.10 g) and 9.5 mL (4.75 mmol) of a 0.5M solution of potassium 2-ethylhexanoate in EtOAc. After 30 min, the reaction mixture was extracted with water (2×75 mL) and the combined aqueous phase was hydrogenated over 2.4 g of 5% palladium on alumina at 0°–5° C. under 45 psi of hydrogen for 1 h. Then 40 mL of 0.2M pH 6.0 phosphate buffer were added immediately (initial pH 10.5, final pH 6.9). The catalyst was filtered and the filtrate was chromatographed twice on reverse phase silica gel (μ-Bondapak C-18, 3.5×11 cm) using a mixture of acetonitrile and water (5:95) as eluent. Lyophilisation of the UV active fractions gave 0.839 g (53%) of the title compound as a white amorphous solid;

Purity by HPLC: 99% on μ-Bondapak C-18, 3.9 mm×30 cm, 5% CH$_3$CN—H$_2$O pH 7.4 phosphate buffer, flow rate 1 mL/min, UV detector 300 nm, retention time 7.89 min;

UV (H$_2$O, pH 7.4 phosphate buffer) ν$_{max}$: 302 nm (9,528);

IR (KBr) ν$_{max}$: 2250 (CN), 1755 (C=O of β-lactam) and 1590 cm$^{-1}$ (C=O of carboxylate);

$^1$H NMR (200 MHz, D$_2$O) δ: 1.32 (d, J=6.37 Hz, 3H, C<u>H</u>$_3$CHO), 1.3–2.1 (m, 8H, CH$_2$-1,2 and 3 of butyl and CH$_2$-2 of cyanopropylthio), 2.64 (t, J=7.0, Hz, 2H, C<u>H</u>$_2$CN), 2.6–3.1 (m, 2H, SCH$_2$), 3.0 (t, J-7.6 Hz, 2H, C<u>H</u>$_2$NH$_2$), 3.3 (m, overlapping with H-6, 1H, H-4), 3.35 (dd, J$_{H6,H5}$=2.46 Hz, J$_{H6,H1}$=6.39 Hz, 1H, H-6), 4.22 (dd, J$_{H5,H6}$=2.46 Hz, J$_{H5,H4}$=6.83 Hz, 1H, H-5) and 4.26 ppm (m, 1H, CH$_3$C<u>H</u>O).

EXAMPLE 53

(4R,5S,6S)-4-(4''-Aminobutyl)-6-[(1'R)-1'-hydroxyethyl]-3-[(pyridin-4-yl)methylthio]-7-oxo-1-azabicyclo[3.2.0]hept-2-ene-2-carboxylic acid

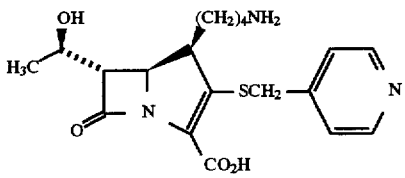

A. Allyl (4R,5S,6S)-4-(4"-azidobutyl)-6-[(1'R)-1'-hydroxyethyl]-3-[(pyridin-4-yl)methylthio]-7-oxo-1-azabicyclo[3.2.0]hept-2-ene-2-carboxylate

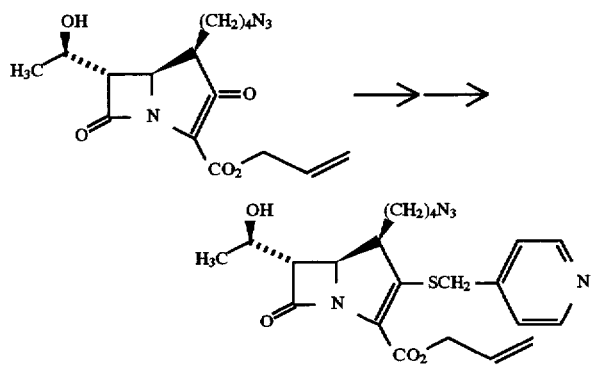

A solution of allyl (4R,5R,6S)-4-(4"-azidobutyl)-6-[(1'R)-1-hydroxyethyl]-3,7-dioxo-1-azabicyclo[3.2.0]heptane-2-carboxylate (5.28 mmol, prepared by cyclization of 2.0 g of the diazo precursor as described in Example 45) in dry acetonitrile (35 mL) was treated at 0°–5° C. and under nitrogen with diphenyl chlorophosphate (1.49 g, 5.5 mmol) and N,N-diisopropylethylamine (0.97 mL, 5.5 mmol) added simultaneously over 5 min. A small crystal of 4-N,N-dimethylaminopyridine was then added and the solution was stirred for 1 h. Then more N,N-diisopropylethylamine (1.4 mL, 7.9 mmol) followed by 4-picolyl mercaptan (1.0 g, 7.9 mmol) were added and the mixture was stirred at 0°–5° C. for 3 h. The reaction mixture was quenched by addition of EtOAc (300 mL) and 0.2M pH 7.0 phosphate buffer. The organic phase was washed with brine, dried (MgSO$_4$) and concentrated. The residue was chromatographed on silica gel (3.5×13 cm) using EtOAc as eluent and gave 1.89 g (78%) of the title compound as a clear oil:

IR (NaCl, film) $v_{max}$: 2100 (N$_3$), 1770 (C=O of β-lactam) and 1710 cm$^{-1}$ (C=O of ester);

$^1$H NMR (200 MHz, CDCl$_3$) δ: 1.37 (d, J=6.27 Hz, 3H, CH$_3$CHO), 1.3–1.9 (m, 6H, CH$_2$-1,2 and 3 of butyl), 3.02 (m, 1H, H-4), 3.14 (dd, J$_{H6,H5}$=2.65 Hz, J$_{H6,H1}$=7.41 Hz, 1H, H-6), 3.31 (t, J=6.1 Hz, CH$_2$N$_3$), 3.98 (ABq, J$_{AB}$=14.22 Hz, Δν15.7 Hz, 2H, SCH$_2$), 4.21(m, 1H, CH$_3$CHO, 4.76 (m, 2H, CH$_2$ of allyl), 5.2–5.5 and 5.9–6.1 (2×m, 2H and 1H, CH of allyl), 7.27 (~d, 2H, H-3 of pyridyl) and 8.57 ppm (~d, 2H, H-2 of pyridyl).

B. (4R,5S,6S)-4-(4"-Aminobutyl)-6-[(1'R)-1'-hydroxyethyl]-3-[(pyridin-4-yl)methylthio]-7-oxo-1-azabicyclo[3.2.0]hept-2-ene-2-carboxylic acid

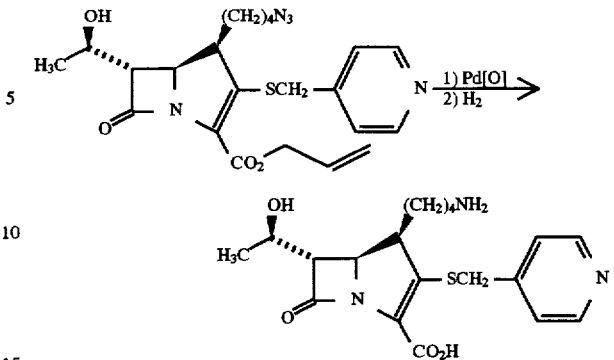

A solution of allyl (4R,5S,6S)-4-(4"-azidobutyl)-6-[(1'R)-1'-hydroxyethyl]-3-[(pyridin-4-yl)methylthio]-7-oxo-1-azabicyclo[3.2.0]hept-2-ene-2-carboxylate (1.80 g, 3.9 mmol) in EtOAc (50 mL) was treated at 22° C. and under nitrogen with tetrakis(triphenylphosphine) palladium [0] (0.1 g) and 8 mL (4.0 mmol) of a 0.5M solution of potassium 2-ethylhexanoate in EtOAc. After 30 min. the reaction mixture was extracted with water (3×50 mL) and the combined aqueous extract was hydrogenated over 2.3 g of 5% palladium on alumina at 0°–5° C. and under 45 psi of hydrogen for 1 h. Then 50 mL of cold 0.2M pH 6.0 phosphate buffer were added (initial pH 10.5, final pH 6.7) and the catalyst was filtered. The filtrate was then chromatographed on reversed phase silica gel (μ-Bondapak c-18, 3×14 cm) using a gradient of acetonitrile (0–5%) in water as eluent.

The first fractions gave, after lyophilisation, 0.050 g (4%) of (4R,5S,6S)-4-(4"-hydroxybutyl)-6-[(1'-hydroxyethyl]-3-[(pyridin-4-yl)methylthio]-7-oxo-1-azabicyclo[3.2.0]hept-2-ene-2-carboxylate (mixture of Na and K salt) as a white solid.

The following fractions gave 0.830 g (54%) of the title compound as a white amorphous solid: [α]$_D^{22}$ –9.5° (c 1.0 H$_2$O);

Purity by HPLC: 97.8% on μ-Bondapak C-18, 3.9 mm×30 cm, 5% CH$_3$CN—H$_2$O pH 7.4 phosphate buffer, flow rate 2 mL/min, UV detector 300 nm, retention time 7.42 min;

UV (H$_2$O, pH 7.4 phosphate buffer) λ$_{max}$: 262 (5,195) and 304 nm (8,370);

IR (KBr) $v_{max}$: 1755 (C=O of β-lactam) and 1600 cm$^{-1}$ (C=O of carboxylate);

$^1$H NMR (200 MHz, D$_2$O) δ: 1.29 (d, J=6.37 Hz, 3H, CH$_3$CHO), 1.2–1.8 (m, 6H, CH$_2$-1,2 and 3 of butyl), 2.94 (t, J=7.5 Hz, CH$_2$NH$_2$), 3.10 (m, 1H, H-4), 3.28 (dd, J$_{H6,5}$=2.53 Hz, J$_{H6,H1}$=6.30 Hz, 1H, H-6), 4.05 (m, 3H, H-5 and SCH$_2$ overlapping), 4.21 (m, 1H, CH$_3$CHO), 7.48 (~d, 2H, H-3 of pyridine), and 8.49 ppm (~d, 2H, H-2 of pyridine).

EXAMPLE 54

(4R,5S,6S)-4-(4"-N-Formimidoylaminobutyl)-6-[(1'R)-1'-hydroxy-ethyl]-3-[(pyridin-4-yl)methylthio]-7-oxo-1-azabicyclo[3.2.0]-hept-2-ene-2-carboxylic acid

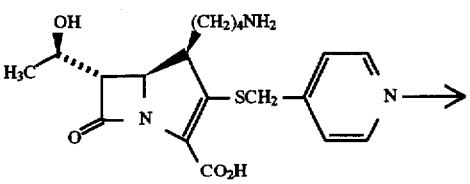

-continued

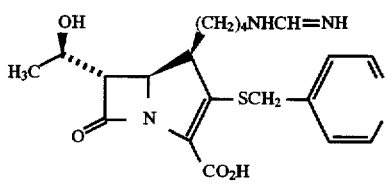

A solution of (4R,5S,6S)-4-(4"-aminobutyl)-6-[(1'R)-1'-hydroxyethyl]-3-[(pyridin-4-yl)methylthio]-7-oxo-1-azabicyclo[3.2.0]hept2-ene-2-carboxylic acid (0.318 g, 0.81 mmol) in cold (0°–5° C.) water (25 mL) was adjusted to pH 8.5 with 1N NaOH. Then benzyl formimidate hydrochloride (0.70 g, 4.06 mmol) was added in small portions over 10 min while maintaining the pH to 8.5 with 1N NaOH. After another 20 min at 0°–5° C., the reaction mixture was quenched by addition of 20 mL of 0.2M pH 6.0 phosphate. The aqueous solution was then washed with EtOAc (20 mL) and then chromatographed on reversed phase silica gel (μ-Bondapak c-18, 3×15 cm) using 0.01M pH 7.0 phosphate buffer and acetonitrile (0–10%) as eluent. The UV active fractions were desalted on the same column using water and acetonitrile (10%) and lyophilized to give 0.153 g (53%) of the title compound as a white amorphous solid: $[\alpha]_D^{24}$ –3.6° (c 0.55, $H_2O$);

Purity by HPLC: 97.5% on μ-Bondapak c-18, 3.9 mm/30 cm, 15% $CH_3CN$—$H_2O$ pH 7.4 phosphate buffer, flow rate 1 mL/min, UV detector 300 nm, retention time 5.8 min;

UV ($H_2O$, pH 7.4 phosphate buffer) $\lambda_{max}$: 262 (5,476) and 304 nm (8,790);

IR (KBr) $\lambda_{max}$: 1750 (C=O of β-lactam), 1715 and 1600 (C=O of carboxylate);

$^1$H NMR (200 MHz, $D_2O$) δ: 1.27 (d, J=6.35 Hz, 3H, C$\underline{H}_3$CHO), 1.1–1.7 (m, 6H, $CH_2$-1,2 and 3 of butyl), 3.11 (m, 1H, H-4), 3.2–3.4 (m, 3H, H-6 and C$\underline{H}_2$NH), 4.08 (m overlapping with $SCH_2$, 1H, H-5), 4.08 (ABq, $J_{AB}$=14.75 Hz, Δν23.2 Hz, $SCH_2$), 4.21 (m, 1H, $CH_3$C$\underline{H}$OH), 7.47 (m, 2H, H-3 of pyridine), 7.78 (s, 1H, C$\underline{H}$=NH) and 8.47 ppm (m, 2H, H-2 of pyridine).

EXAMPLE 55

(4R,5S,6S)-4-[3"-(N-Formimidoyl)aminopropyl]-6-[(1'R)-1'-hydroxyethyl]-3-[(pyridin-4-yl)methylthio]-7-oxo-1-azabicyclo[3.2.0]hept-2-ene-2-carboxylic acid

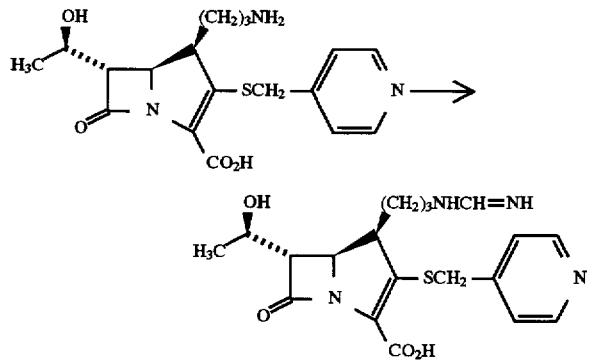

A cold (ice bath) solution of (4R,5S,6S)-4-(3"-aminopropyl)-6-[(1'R)-1'-hydroxyethyl]-3-[(pyridin-4-yl)methylthio]-7-oxo-1-azabicyclo[3.2.0]hept-2-ene-2-carboxylic acid as described in Example 44 (0.16 g, 0.42 mmol) in a 0.05M pH 7.0 aqueous phosphate buffer (30 mL) was treated with a 0.1N aqueous NaOH solution (to raise and maintain the pH around 8.0) and portionwise with benzyl formimidate hydrochloride (720 mg, 4.2 mmole). The mixture was stirred for 30 min, neutralized to pH 7.0 with 1M aqueous $NaH_2PO_4$ and passed twice through a μ-Bondapak $C_{18}$ column ($H_2O$→5% $CH_3CN/H_2O$) to give the title compound (76 mg, 47%) as a lyophilized powder;

Purity: 96.7% (HPLC 304 nm);

UV ($H_2O$) $\lambda_{max}$: 262 (ε7120), 304 (ε10700);

IR (Nujol) $\nu_{max}$: 3600–3100 (OH, $NH_2$), 1755 (C=O), 1710 (C=N) and 1600 cm$^{-1}$ (C=O);

$^1$H NMR ($D_2O$, 200 MHz) δ: 8.48–8.44 (2H, m, aromatic —H), 7.78–7.44 (2H, m, aromatic H), 4.27–4.15 (1H, m, H-1'), 4.14, 4.07, 4.00, 3.93 (2H, ABq, J=Hz, $CH_2$-aromatic), 4.075 (1H, dd, J=2.6 Hz, J=9.3 Hz, H-5), 3.34–3.23 (3H, m, H-5 and $CH_2$—N), 3.303, 3.291 (part of H-6, d, J=2.5 Hz), 3.17–3.07 (1H, m, H-4), 1.70–1.36 (4H, m, $CH_2CH_2$-4), and 1.268 ppm (3H, d, J=6.3 Hz, $CH_3$).

EXAMPLE 56

(4R,5S,6S)-3-[(2-Aminoethyl)thio]-4-(2"-hydroxyethyl)-6-[(1'R)-1'-hydroxyethyl]-7-oxo-1-azabicyclo[3.2.0]hept-2-ene-2-carboxylic acid

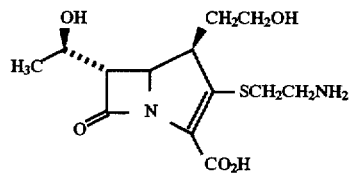

A. Allyl (4R,5S,6S)-4-(2"-tert butyldimethylsilyloxyethyl)-6-[(1'R)-1'-tert butyldimethylsilyloxyethyl]-3-[(2-p-nitrobenzyloxycarbonylaminoethyl)thio]-7-oxo-1-azabicyclo[3.2.0]-hept-2-ene-2-carboxylate

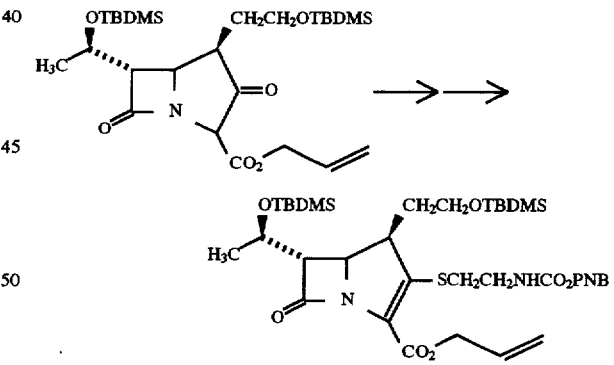

A solution of allyl (4R,5R,6S)-4-(2"-tert-butyldimethylsilyloxyethyl)-6-[(1'R)-1'-tert-butyldimethylsilyloxyethyl]-3,7-dioxo-1-azabicyclo[3.2.0]heptane-2-carboxylate (5.41 mmol, prepared by cyclization of 3.0 g, 5.41 mmol of the diazo precursor as in Example 5) in dry acetonitrile (25 mL) was treated at 0°–5° C. and under nitrogen with diphenyl chlorophosphate (1.18 mL, 5.65 mmol) and N,N-diisopropylethylamine (1.0 mL, 5.65 mmol) added simultaneously over 5 min. Then a small crystal of 4-N,N-dimethylaminopyridine was added and the solution was stirred for 90 min. More N,N-diisopropylethylamine (1.42 mL, 8.1 mmol) followed by p-nitrobenzyl 2-mercaptoethylcarbamate (2.10 g, 8.19 mmol) [I. Shinkai et al., *Synthesis*, 924 (1980)] were added and the mixture was stirred for 16 h. The reaction mixture was then diluted with EtOAc (400 mL) washed with water, brine and dried (MgSO$_4$). After evaporation of the solvent under reduced pressure, the residue was chromatographed on silica gel (3.5×10 cm). Elution with a gradient of ethyl acetate (5–10%) in toluene gave 1.75 g (42%) of the title compound as an oil:

IR (NaCl, film) $v_{max}$: 1772 (C=O of β-lactam) and 1720 cm$^{-1}$ (C=O of carboxylate);

$^1$H NMR (200 MHz, CDCl$_3$) δ: 0.04, 0.05 and 0.08 (3×s, 3H, 3H and 6H, SiCH$_3$), 0.88 (s, 18H, Si t-Bu), 1.27 (d, J=6.14 Hz, 3H, CH$_3$CHO), 1.5–2.1 (m, 2H, CH$_2$CH$_2$OTBDMS), 2.8–3.2 (m, 2H, SCH$_2$), 3.10 (dd, J$_{H6,H5}$=2.49 Hz, J$_{H6,H1}$=6.34 Hz, 1H, H-6), 3.2–3.9 (m, 5H, H-4, CH$_2$OTBDMS and CH$_2$NH), 4.16 (dd, J$_{H5,H6}$=2.49 Hz, J$_{H5,H4}$=9.37 Hz, 1H, H-5), 4.23 (m, 1H, CH$_3$CHO), 4.74 (m, 2H, CH$_2$ of allyl), 5.18 (s, 2H, CH$_2$ of p-nitrobenzyl, 5.2–5.5 and 5.9–6.1 (2×m, 2H and 1H, CH of allyl), 7.5 (d, J=8.7 Hz, 2H, H ortho of p-nitrobenzyl) and 8.22 ppm (d, J=8.7 Hz, 2H, H meta of p-nitrobenzyl).

B. Allyl (4R,5S,6S)-4-(2"-hydroxyethyl)-6-[(1'R)-1'-hydroxy-ethyl]-3-[(2-p-nitrobenzyloxycarbonylaminoethyl)thio]-7-oxo-1-azabicyclo[3.2.0]hept-2-ene-2-carboxylate

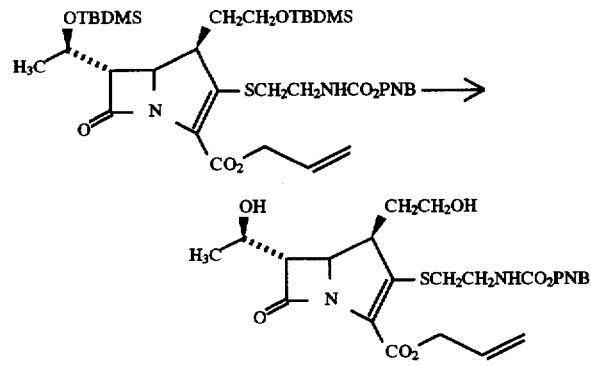

A solution of allyl (4R,5S,6S)-4-(2"-tert-butyldimethylsilyloxyethyl)-6-[(1'R)-1'-tert-butyldimethylsilyloxyethyl]-3-[(2-p-nitrobenzyloxycarbonylaminoethyl)thio]-7-oxo-1-azabicyclo[3.2.0]hept-2-ene-2-carboxylate (1.75 g, 2.29 mmol) in dry tetrahydrofuran (20 mL) was cooled to 0°–5° C. and treated under nitrogen with acetic acid (1.6 mL, 27.5 mmol) followed by 13 mL (13.0 mmol) of a 1.0M solution of tetrabutylammonium fluoride in tetrahydrofuran. After 120 h at 5° C., the reaction mixture was diluted with ethyl acetate (200 mL), washed with water, saturated NaHCO$_3$, 0.2M pH 7.0 phosphate buffer, brine and dried (MgSO$_4$). The residue obtained after evaporation of the solvent was chromatographed on silica gel (3×11 cm) using ethyl acetate and then a mixture of ethyl acetate, acetone and acetonitrile (18:1:1) as eluent.

The first fractions gave 0.78 g (50%) of mono deprotected product, allyl(5S,6S)-6-[(1'R)-1'-tert-butyldimethylsilyloxyethyl]-4-(2"-hydroxyethyl)-3-(2-p-nitrobenzyloxycarbonylaminoethyl)thio]-7-oxo-1-azabicyclo[3.2.0]hept-2-ene-2-carboxylate as an oil.

The following fractions gave 0.23 g (19%) of the title compound as a foam:

IR (NaCl, film) $v_{max}$: 1770 (C=O of β-lactam), 1725 and 1705 cm$^{-1}$ (C=O of ester);

$^1$H NMR (200 MHz, CDCl$_3$) δ: 1.37 (d, J=6.23 Hz, 3H, CH$_3$CHO), 1.7–2.1 (m, 2H, CH$_2$CH$_2$OH), 2.8–3.2 (m, 2H, SCH$_2$), 3.26 (dd, J$_{H6,H5}$=2.55 Hz, J$_{H6,H1}$=7.77 Hz, 1H, H-6), 3.3–3.9 (m, 5H, H-4, CH$_2$OH and CH$_2$NH), 4.1–4.4 (m, 2H, H-5 and CH$_3$CHO overlapping), 4.75 (m, 2H, CH$_2$ of allyl), 5.19 (s, 2H, CH$_2$ of p-nitrobenzyl), 5.2–5.5 and 5.9–6.1 (2×m, 2H and 1H, CH of allyl), 7.5 (d, J=8.7 Hz, 2H, H ortho of p-nitrobenzyl) and 8.22 ppm (d, J=8.7 Hz, H meta of p-nitrobenzyl).

C. (4R,5S,6S)-3-[(2-Aminoethyl)thio]-4-(2"-hydroxyethyl)-6-[(1'R)-1'-hydroxyethyl]-7-oxo-1-azabicyclo[3.2.0]hept-2-ene-2-carboxylic acid

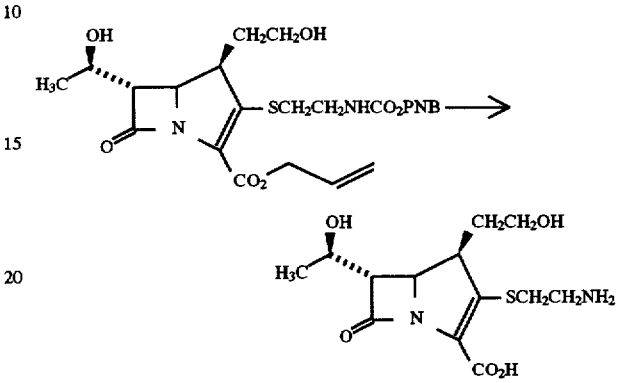

A solution of allyl (4R,5S,6S)-4-(2"-hydroxyethyl)-6-[(1'R)-1'-hydroxyethyl]-3-[(2-p-nitrobenzyloxycarbonylaminoethyl)thio]-7-oxo-1-azabicyclo[3.2.0]hept-2-ene-2-carboxylate (0.99 g, 1.85 mmol) in dry ethyl acetate (40 mL) was treated at 22° C. and under nitrogen with tetrakis(triphenylphosphine)palladium [0] (0.050 g) and 4 mL (2.0 mmol) of a 0.5M solution of potassium 2-ethylhexanoate in ethyl acetate. After 30 min, a precipitate was formed and the reaction mixture was cooled to 0°–5° C. for 2 h. The solid was then filtered and dried under vacuum to give 1.0 g of the intermediate potassium salt as a light brown solid. The solid was then added to a mixture of cold 0.2M pH 7.0 phosphate buffer (40 mL), tetrahydrofuran (20 mL) and diethyl ether (20 mL) and hydrogenated at 0°–5° C. over 1.2 g of 10% palladium on activated carbon and under 45 psi of hydrogen for 1 h. The catalyst was filtered and the filtrate was chromatographed twice on reversed phase silica gel (μBondapak C$_{18}$, 3×14 cm) using a gradient of acetonitrile (0–10%) in water as eluent. Lyophilization of the first fractions gave 0.150 g (26%) of the title compound as a white amorphous solid. The tail fractions also gave 0.450 g of partially reduced material. Crystallization of the first fractions in water (1 mL) gave 0.096 g of the title compound as small cubes:

Purity by HPLC: 99.8% on μBondapak C$_{18}$, 3.9 mm×30 cm, elution 2% CH$_3$CN—H$_2$O pH 7.4 phosphate buffer, flow rate 1 mL/min, uv detector 300 nm, retention time 6.24 min;

UV (water, pH 7.4, phosphate buffer) $\lambda_{max}$: 298 nm (8,510);

IR (KBr) $v_{max}$: 1758 (C=O of β-lactam), 1638, 1618 and 1580 cm$^{-1}$ (C=O of carboxylate);

$^1$H NMR (200 MHz, D$_2$O) δ: 1.32 (d, J=6.42 Hz, 3H, CH$_3$CHO), 1.4–2.2 (m, 2H, CH$_2$-1 of hydroxyethyl), 2.9–3.8 (m, 7H, H-4, SCH$_2$CH$_2$NH$_2$ and CH$_2$OH), 3.49 (dd, J$_{H6,H5}$=2.72 Hz, J$_{H6,H1}$=5.37 Hz, 1H, H-6), and 4.2–4.4 ppm (m, 2H, H-5 and CH$_3$CHO overlapping).

EXAMPLE 57

(4R,5S,6S)-4-[(2"R or S)-Aminopropyl]-6-[(1'R)-1'-hydroxyethyl]-3-[(pyridin-2-yl)methylthio]-7-oxo-1-azabicyclo-[3.2.0]hept-2-ene-2-carboxylic acid; isomer A

161

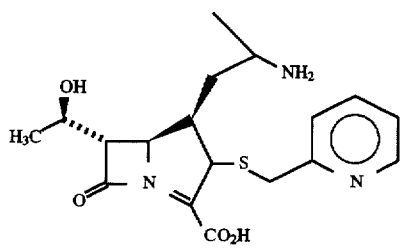

A. 4-Azido-(pyridin-2-yl)methylthiovalerate

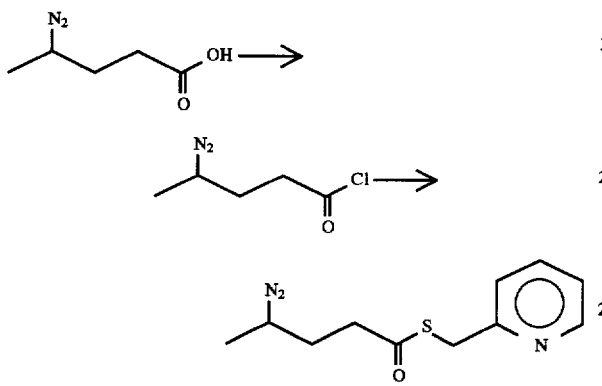

A cold (5° C.) solution of 4-azido valeric acid (59.0 g, 412.2 mmol) and N-methyl imidazole (33.84 g, 412.2 mmol) in CH$_2$Cl$_2$ (1200 mL) was treated dropwise with SOCl$_2$ (15 min). The reaction mixture was stirred at 5° C. for 1 h and 20° C. for 2.5 h. The reaction mixture was again cooled in an ice-bath and treated dropwise this time (15 min) with a solution of 2-mercaptomethyl pyridine (51.6 g, 412.2 mmol) and N-methyl imidazole (37.2 g, 453.4 mmol) in CH$_2$Cl$_2$ (50 mL). After stirring for 15 min at 5° C., the solvent was evaporated and replaced by ethyl acetate (500 mL). The solution was washed with water (250 mL). The organic layers were combined and washed with NaHCO$_3$. Finally after washing with brine, the organic solution was dried (MgSO$_4$) and evaporated to give 97.23 g (94.2%) of the title compound.

IR (CH$_2$Cl$_2$) $v_{max}$: 2110 cm$^{-2}$ (—N$_3$), 1690 cm$^{-1}$ (thioester);

$^1$H NMR (CDCl$_3$) δ: 8.55–8.52 (1H, m, pyridine —H), 7.67–7.58 (1H, m, pyridine-H), 7.35–7.31 (1H, m, pyridine-H), 7.20–7.13 (1H, m, pyridine-H), 4.36 (2H, s, CH$_2$—S), 3.55–3.45 (1H, m, CH—N$_3$), 2.74–2.65 (2H, m, CH$_2$COS), 1.89–1.62 (2H, m, CH$_2$C—N$_3$), 1.28 (3H, d, J: 6.53 Hz, CH$_3$—).

B. Enolsilyl ether of 4-azido-(pyridin-2-yl)methylvalerate

A cold (5° C.) solution of 4-azido-(pyridin-2-yl) methylthiovalerate (97.2 g, 388.4 mmol) and triethylamine (86.5 g, 854.5 mmol) in CH$_2$Cl$_2$ (1000 mL) was treated dropwise (25 min) with tert-butyldimethylsilyl trifluoromethanesulfonate (205.3 g, 776.8 mmol). The ice-bath was allowed to become exhausted and the solution stirred at 20° C. for 15 h. Then the solvent was evaporated and replaced by petroleum ether (1000 mL). The solution was shaken with cold water (500 mL) and the two phases filtered through a pad of Celite. The aqueous layer was discarded and the organic phase washed successively with cold water, aqueous NaHCO$_3$, cold water again and finally brine. The organic solution was dried (MgSO$_4$) and treated with charcoal. After filtration through a pad of Celite, the dark filtrate was given two additional charcoal treatments to finally yield a red solution. After evaporation of the solvent there was obtained 99.4 g (70.2%) of the title compound as a red oil.

IR (CH$_2$Cl$_2$) $v_{max}$: 2110 cm$^{-1}$ (—N$_3$);

$^1$H NMR (CDCl$_3$, 200 MHz) δ: 8.57–8.53 (1H, m, pyridine-H), 7.67–7.58 (1H, m, pyridine-H), 7.30–7.25 (1H, m, pyridine-H), 7.18–7.11 (1H, m, pyridine-H), 5.00 (0.32H, t, J: 7.65 Hz, vinylic H), 4.85 (0.68H, t, J: 7.29 Hz, vinylic-H), 4.05 (0.64H, s, —SCH$_2$), 3.98 (1.36H, s, —SCH$_2$—), 3.34 (0.68H, m, CH—N$_3$), 3.22 (0.32H, m, CH—N$_3$), 2.25–2.15 (2H, m, —CH$_2$—), 1.10 (2.04H, d, J: 6.54 Hz, H$_3$C—), 1.08 (0.96H, d, J: 6.53H, H$_3$C—), 0.99 (9H, 2s, t-butyl), 0.25 and 0.22 ppm (6H, 2s, dimethyl).

C. (3S,4S)-3-[(1'R)-1'-tert-Butyldimethylsilyloxyethyl]-4-[(1"R)-1"-(pyridin-2-yl)methylthiocarbonyl-3"-azidobutyl]-azetidin-2-one

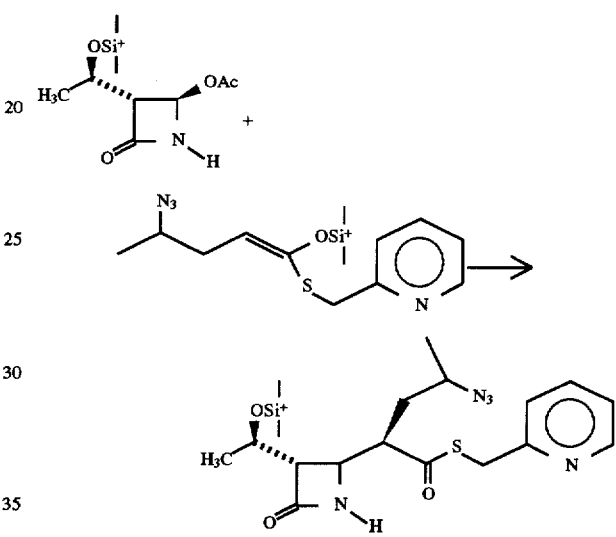

To a cold (5° C.) suspension of fused ZnCl$_2$ (33.4 g, 245 mmol) in CH$_2$Cl$_2$ (500 mL) was added successively (3S, 4R)-4-acetoxy-3-[(1'R)-1'-tert-butyldimethylsilyloxyethyl] azetidin-2-one (70.42 g, 245 mmol) and the tert-butyldimethylsilylenol ether of 4-azido-(pyridin-2-yl) methylthiovalerate from Step B (99.4 g, 272.6 mmol). The ice-bath was allowed to become exhausted while stirring the mixture mechanically overnight (18 h). Then the solvent was evaporated and the viscous residue partitioned between diethyl ether (500 m) and water (100 mL). The aqueous phase was discarded and the organic solution washed successively with water, NaHCO$_3$, water again and finally brine. The organic phase was dried (MgSO$_4$), treated with charcoal, filtered and evaporated. The red viscous oil (142.5 g) thus obtained was purified by chromatography (SiO$_2$, CH$_2$Cl$_2$, 5% CH$_3$CN in CH$_2$Cl$_2$ and ethyl acetate) to give 38.0 g (32.5%) of the title compound as a 1:1 mixture of isomeric compounds at C-3".

IR (CH$_2$Cl$_2$) $v_{max}$: 3405 (NH), 2115 (—N$_3$), 1765 (β-lactam), 1680 cm$^{-1}$ (CO—S);

Less polar isomer A:

$^1$H NMR (CDCl$_3$) δ: 8.56–8.52 (1H, m, pyridine —H), 7.68–7.60 (1H, m, pyridine —H), 7.33–7.26 (1H, m, pyridine), 7.21–7.15 (1H, m, pyridine —H), 5.83 (1H, s, NH), 4.29 (2H, s SCH$_2$—), 4.15 (1H, m, CH'), 3.80 (1H, dd, J: 6.20, 2.14 Hz, H-4), 3.48 (1H, m, CH—N$_3$), 3.16–3.05 (2H, m, H-3, H-1"), 1.96 and 1.44 (2H, 2m, —CH$_2$"), 1.29 (3H, d, J: 6.41, H$_3$C—C—N$_3$), 1.03 (3H, d, J: 6.29, —CH$_3$), 0.854 (9H, s, t-butyl), 0.05 (6H, s, Si(CH$_3$)$_2$).

More polar isomer B:

¹H NMR (CDCl₃) δ: 8.54–8.52 (1H, m, pyridine —H), 7.68–7.59 (1H, m, pyridine —H), 7.36–7.26 (1H, m, pyridine —H), 7.21–7.15 (1H, m, pyridine —H), 5.85 (1H, s, NH), 4.28 (2H, d, J: 5.25 Hz, S—CH₂), 4.17 (1H, m, CH'), 3.89 (1H, dd, J: 2.05, 6.87 Hz, H-4), 3.49 (1H, m, CH—N₃), 3.05 (1H, m, H-3), 2.85 (1H, m, H-1"), 2.05 and 1.57 (2H, 2m, CH₂"), 1.28 (3H, d, J: 6.47, H₃CC—N₃), 1.01 (3H, d, J: 6.32, H₃C), 0.85 (9H, s, t-butyl ), 0.05 (6H, s, Si (CH₃)₂.

D. (3S, 4S )-3-[(1'R)-1'-tert-Butyldimethylsilyloxyethyl]-4-[(1"R)-1"-carboxy-3"-azidobutyl]azetidin-2-one

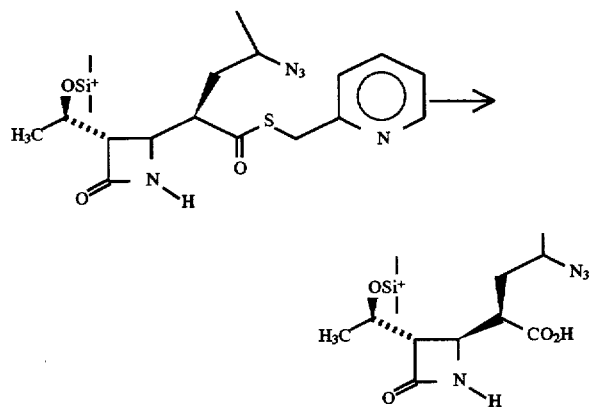

Hydrogen peroxide (30%, 27 mL, 314 mmol) was added to a cold (5° C.) solution of (3S,4S)-3-[(1'R)-1'-tert-butyldimethylsilyloxyethyl]-4-[(1"R)-1"-(pyridin-2-yl)methylthiocarbonyl-3"-azidobutyl]azetidin-2-one (37.5 g, 78.5 mmol) followed by the dropwise addition of 1N NaOH (235.5 mL, 235.5 mmol). The addition was done in 40 min keeping T<10° C. The mixture was stirred for an additional 30 min and then acidified to pH ~1.0 with conc. HCl (30 mL). The solution was extracted with ethyl acetate. The extracts were washed twice with brine, dried (MgSO₄) and evaporated. The solid thus obtained was triturated in petroleum ether and collected by filtration to give 24.0 g (82.6%) of the title compound; mp 123°–125° C. (dec).

IR (CH₂Cl₂) ν$_{max}$: 2110 (—N₃), 1765 (β-lactam), 1740 and 1710 cm⁻¹ (—CO₂H).

Less polar isomer A:

¹H NMR (CDCl₃) δ: 6.35 (1H, s, NH), 4.20 (1H, m, CH'), 3.89 (1H, dd, J: 2.05, 5.50 Hz, H-4), 3.58 (1H, m, CH—N₃), 3.13 (1H, m, H-3), 2.95 (1H, m, H-1"), 1.88 and 1.48 (2H, 2m, —CH₂), 1.34 (3H, d, J: 6.45 Hz, CH₃—C—N₃), 1.19 (3H, d, J: 6.26 —CH₃), 0.87 (9H, s, t-butyl), 0.07 (6H, 2s, Si(CH₃)₂).

More polar isomer B:

¹H NMR (CDCl₃) δ: 6.42 (1H, s, NH), 4.20 (1H, m, CH'), 3.88 (1H, dd, J: 1.94, 6.42 Hz, H-4), 3.55 (1H, m, CH—N₃), 3.15 (1H, m, H-3), 2.74 (1H, m, H-1"), 1.98 and 1.59 (2H, 2m, —CH₂), 1.33 (3H, d, J: 6.50 Hz, H₃CC—N₃), 1.18 (3H, d, J: 6.28, —CH₃), 0.87 (9H, s, t-butyl), 0.068 (6H, 2s, Si(CH₃)₂).

E. (3S,4R)-3-[(1'R)-1'-tert-Butyldimethylsilyloxyethyl]4-[(1"R)-1"-(2-azidopropyl)-3"-allyloxycarbonyl-2"-oxopropyl]azetidin-2-one

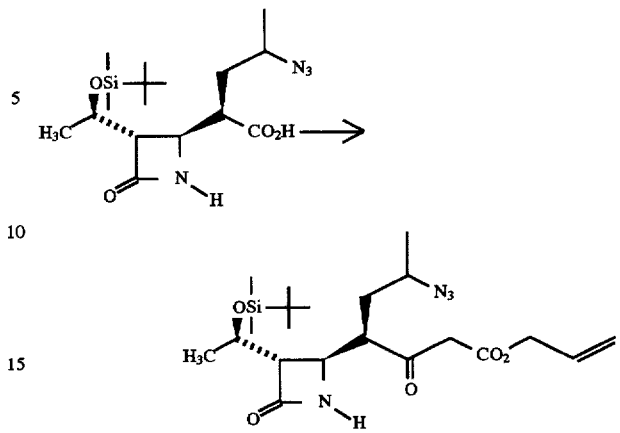

A mixture of (3S,4S)-3-[(1'R)-1'-tert-butyldimethylsilyloxyethyl]-4-[(1"R)-1"-carboxy-3"-azidobutyl]azetidin 2-one (3.48 g, 9.39 mmol) and carbonyldiimidazole (1.70 g, 10.33 mmol) in CH₃CN was stirred at 20° C. for 30 min and then evaporated to dryness to leave a foamy material.

In a separate flask, a suspension of magnesium monoallyl malonate (4.37 g, 14 mmol) in benzene (75 mL) was refluxed collecting the residual water in a Dean Stark trap. After 1.5 h at reflux, this solution was cooled to 20° C. and added to the above imidazolide. This mixture was placed in an oil bath preheated at 70° C. and heated for 18 h. Then the mixture was diluted with an equal volume of ethyl acetate and washed with water, dilute HCl, water again, dilute NaHCO₃ and finally water and brine. The organic phase was dried (MgSO₄) and evaporated. The crude product was purified by chromatography (SiO₂, CH₂Cl₂ then 5–10% CH₃CN in CH₂Cl₂) to give 3.37 g (79.3%) of the title compound as an oil which solidified;

IR (CH₂Cl₂) ν$_{max}$: 2115 (—N₃) 1765 1715 cm⁻¹ (C=O)

Less polar isomer A:

¹H NMR (CDCl₃) δ: 4.6–6.0 (5H, allyl pattern) 4.18 (1H, m, H-1'), 3.80–3.85 (1H, m, H-4), 3.62 (1H, d, —CHC=O), 3.46 (1H, m, CH—N₃), 3.27 (0.6H, m, H-1"), 2.99 and 2.93 (1H, m, H-3), 2.55 (0.4H, m, H-1"), 1.93 and 1.41 (2H, 2m, —CH₂C—N₃) 1.32 and 1.31 (3H, 2d, J: 6.45, 6.40 Hz, CH₃CN₃), 1.19 and 1.12 (3H, 2d, J: 6.27, 6.29 Hz, —CH₃), 0.87 (9H, s, t-butyl), 0.07 and 0.06 (6H, 2s, Si(CH₃)₂).

More polar isomer B:

¹H NMR (CDCl₃) δ: 4.6–6.0 (5H, allyl pattern) 4.17 (1H, m, H-1'), 3.84 (1H, dd, J: 2.1, 5.35 Hz, H-4), 3.63 (1H, d, CH₂CO) 3.48 (1H, m, CHN₃), 3.07 (0.6H, m, H-1"), 2.93 (1H, m, H-3), 2.0 and 1.6 (2H, 2m, CH₂CN₃), 1.27 and 1.32 (3H, 2d, J: 6.5 Hz, CH₃CN₃) 1.09 and 1.18 (3H, 2d, J: 6.25 Hz, CH₃), 0.87 (9H, s, t-butyl), 0.06 (6H, 2s, Si(CH₃)₂).

F. (3S,4R)-3-[(1'R)-1'-tert-Butyldimethylsilyloxyethyl]-4-[(1"R)-1"-(2-azidopropyl)-3"-diazo-3"-allyloxycarbonyl-2"-oxopropyl]azetidin-2-one

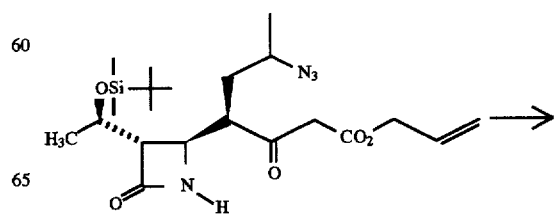

165

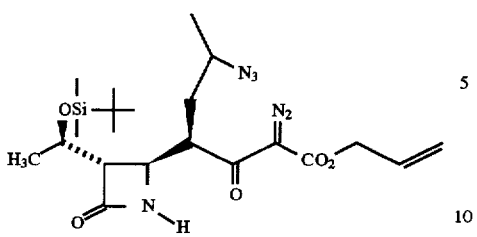

A mixture of p-toluenesulfonyl chloride (442 mg, 2.32 mmol), sodium azide (154 mg, 2.37 mmol) and tetrabutylammonium chloride (12 mg) in CH$_3$CN (15 mL) was stirred at 20° C. for 4 h. Then this mixture was cooled to 5° C. and (3S,4R)-3-[(1'R)-1'-tert-butyldimethylsilyloxyethyl]-4-[(1"R)-1"-(2-azidopropyl)-3"-allyloxycarbonyl-2"-oxopropyl]azetidin-2-one (953 mg, 2.11 mmol) in a minimum amount of CH$_3$CN was added followed, dropwise, by triethylamine (235 mg, 2.32 mmol). The faction mixture was stirred at 5° C. for 1.5 h and then evaporated. The residue was taken up in diethyl ether and washed with water and brine. The organic phase was dried (MgSO$_4$) and evaporated to leave a soft solid. This material was triturated in petroleum ether and the insoluble tosylamide (74.3%) filtered off. The filtrate was evaporated to give a yellow viscous oil which was purified by chromatography (SiO$_2$, CH$_2$Cl$_2$ then 5% CH$_3$CN in CH$_2$Cl$_2$) to give 825 mg (81.7%) of the title compound as a viscous oil;

IR (CH$_2$Cl$_2$) $\lambda_{max}$: 2125 (=N$_2$), 2118 (—N$_3$), 1765 (β-lactam), 1713 cm$^{-1}$ (—CO$_2$—);

Less polar isomer A:

$^1$H NMR (CDCl$_3$) δ: 4.7–6.0 (5H, allyl pattern) 4.31 (1H, m, H-1"), 4.16 (1H, m, H-1'), 3.81 (1H, dd, J: 2.08, 4.90 Hz, H-4), 3.38 (1H, m, CH—N$_3$), 3.05 (1H, m, H-3), 2.69 and 1.39 (2H, 2m, CH$_2$—CN$_3$), 1.28 (3H, d, J: 6.42 Hz, H$_3$CCN$_3$), 1.18 (3H, d, J: 6.29 Hz, —CH$_3$), 0.86 (9H, s, t-butyl), 0.064 and 0.052 (6H, 2s, Si(CH$_3$)$_2$).

More polar isomer B:

$^1$H NMR (CDCl$_3$) δ: 4.7–6.0 (5H, allyl pattern) 4.15 (2H, m, H-1', H-1"), 3.84 (1H, m, H-4), 3.45 (1H, m, CH—N$_3$), 3.05 (1H, m, H-3), 2.10 and 1.5 (2H, 2m, CH$_2$C—N$_3$), 1.27 (3H, d, J: 6.43 Hz, CH$_3$—CN$_3$), 1.17 (3H, d, J: 6.27 Hz, —CH$_3$), 0.87 (9H, s, t-butyl), 0.064 and 0.053 (6H, 2S, Si(CH$_3$)$_2$).

G. (3S,4R)-3-[(1'R)-1'-Hydroxyethyl]-4-[(1"R)-1"-(2-azidopropyl)-3"-diazo-3"-allyloxycarbonyl-2"-oxopropyl]azetidin-2-one

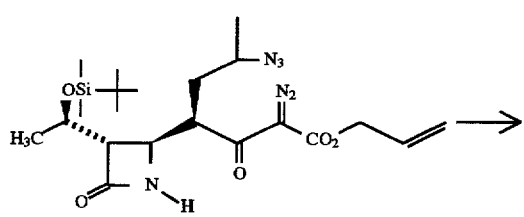 →

166

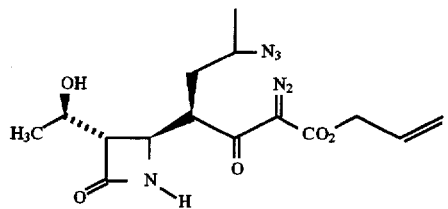

A cold (5° C.) solution of (3S,4R)-3-[(1'R)-1'-tert-butyldimethylsilyloxyethyl]-4-[(1"R)-1"-(2-azidopropyl)-3"-diazo-3"-allyloxycarbonyl-2"-oxopropyl]azetidin-2-one (825 mg, 1.72 mmol) in CH$_3$CN (10 mL) was treated with 4N HCl (0.52 mL, 2.06 mmol). The reaction mixture was stirred at 5° C. for 3.5 h and 20° C. for 1 h. The reaction was then quenched by adding saturated NaHCO$_3$ (3 mL). After being diluted with ethyl acetate, the mixture was washed with water and brine (twice). The organic phase was dried (MgSO$_4$) and evaporated. The crude product was purified by chromatography on silica gel eluting with CH$_2$Cl$_2$ and then ethyl acetate to give 554 mg (88.4%) of the title compound as a yellow oil. The two isomeric compounds were not separated;

IR (CH$_2$Cl$_2$) $\nu_{max}$: 3600 (—OH), 3400 (NH), 2145 (=N$_2$), 2115 (—N$_3$), 1763 (β-lactam), 1713 (C=O).

$^1$H NMR (CDCl$_3$) δ: 4.7–6.0 (5H, allyl pattern), 4.12 (2H, m, H-1' and H-1"), 3.81 (1H, m, H-4), 3.45 (1H, m CH—N$_3$), 3.05 (1H, m, H-3), 2.05 and 1.55 (2H, 2m, CH$_2$CN$_3$), 1.30 (6H, several peaks, 2—CH$_3$).

H. Allyl (4R,5S,6S)-4-(2"-azidopropyl)-6-[(1'R)-1'-hydroxyethyl]-3[(pyridin-2-yl)methylthio]-7-oxo-1-azabicyclo[3.2.0]hept-2-ene-2-carboxylate

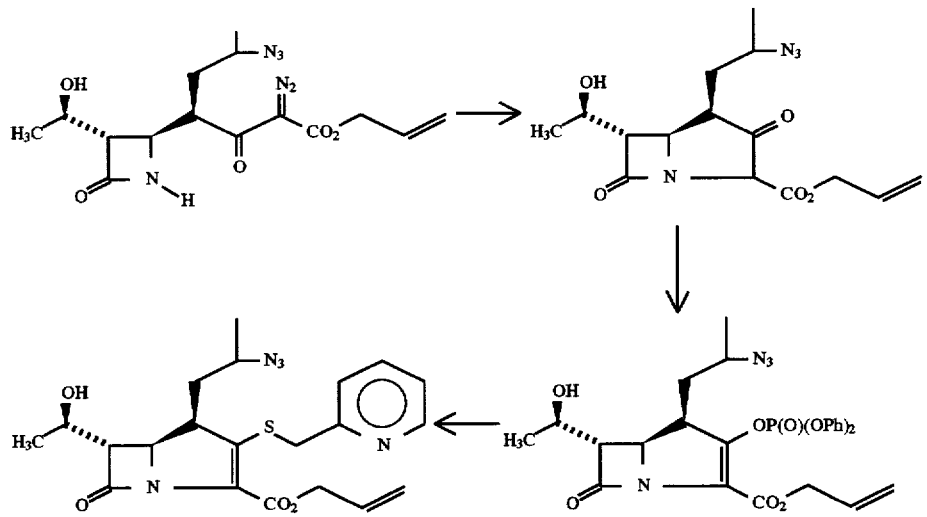

A suspension of rhodium octanoate dimer (55 mg) in C₆H₆ (110 mL) was placed in an oil bath preheated at 130° C. and refluxed for 30 min. Then (3S,4R)-3-[(1'R)-1'-hydroxyethyl]-4-[(1"R)-1"-(2-azidopropyl)-3"-diazo-3"-allyloxycarbonyl-2"-oxopropyl]azetidin-2-one (2.0 g, 5.49 mmol) was added cyclization was completed after 25 min under vigorous reflux. The solvent was evaporated and replaced by CH₃CN (55 mL). This solution was treated with diphenyl chlorophosphate (1.6 g, 6 mmol), N,N-diisopropylethylamine (0.78 g, 6 mmol) and a catalytic amount of 4-N,N-dimethylaminopyridine. After 15 min at 5° C. the reaction was complete. So the reaction mixture was diluted with ethyl acetate and washed with water and brine. After drying (MgSO₄), the organic phase was evaporated and the crude product purified by chromatography (SiO₂/Et₂O) to give 1.63 g (52.0%) of enol phosphate.

The purified enol was dissolved in cold (5° C.) DMF (16 mL) and treated with 2-picolylthiol (465 mg, 3.72 mmol) and N,N-diisopropylethylamine (481 mg, 3.72 mmol). The reaction mixture was stirred at 5° C. for 17 h and 20° C. for 24 h. The solution was then diluted with ethyl acetate (100 mL) and washed with cold brine (3×50 mL), 10% NaHSO₃ (2×25 mL), water and finally brine. The organic phase was dried (MgSO₄) and evaporated to leave a brown viscous oil. Chromatography resulted in the purification and separation of the two isomers of the title compound (SiO₂/cold Et₂O) 470 mg (37%) of the less polar isomer A and 325 mg (25.6%) of the more polar isomer B:

Less polar isomer A

IR (CH₂Cl₂) $v_{max}$: 3600 (—OH), 2115 (—N₃), 1775 (β-lactam), 1710 cm⁻¹ (—CO₂—);

¹H NMR (CDCl₃) δ: 8.55 (1H, m, Ar—H), 7.66 (1H, m, Ar—H), 7.34 (1H, m, Ar—H), 7.19 (1H, m, Ar—H), 4.6–6.0 (5H, allyl pattern), 4.19 (2H, ABq, J: 13.8 Hz, S—CH₂), 4.16–4.24 (2H, m, H-1', H-5), 3.87 (1H, m, CH—N₃), 3.65 (1H, m, H-4), 3.05 (1H, dd, J: 2.70, 7.92 Hz, H-6), 1.6–2.0 (2H, 2m, CH₂CN₃), 1.39 (6H, d, J: 6.15 Hz, 2-CH₃).

More polar isomer B

IR(CH₂Cl₂) $v_{max}$: 3600 (—OH) 2115 (—N₃), 1772 (β-lactam), 1710 cm⁻¹ (—CO₂—);

¹H NMR (CDCl₃) δ: 8.51 (1H, m, Ar—H), 7.64 (1H, m, Ar—H), 7.37 (1H, m, Ar—H), 7.21 (1H, m, Ar—H), 4.6–6.10 (5H, allyl pattern), 4.22 (1H, m, H-1'), 4.14 (1H, dd, J: 2.66, 9.60 Hz, H-5), 4.11 (2H, ABq, J: 14.18 Hz, —SCH₂), 3.75 (1H, m, CH—N₃), 3.62 (1H, m, H-4), 3.32 (1H, dd, J: 2.70, 7.32, H-6), 1.6–2.0 (2H, 2m, —CH₂C—N₃), 1.39 (3H, d, J: 6.42 Hz, —CH₃), 1.38 (3H, d, J: 6.25 Hz, —CH₃).

I. Sodium (4R,5S,6S)-4-[(2"R or S)-azidopropyl]-6-[(1'R)-1'-hydroxy-ethyl]-3[(pyridin-2-yl)methylthio]-7-oxo-1-azabicyclo[3.2.0]hept-2-ene-2-carboxylate; isomer A

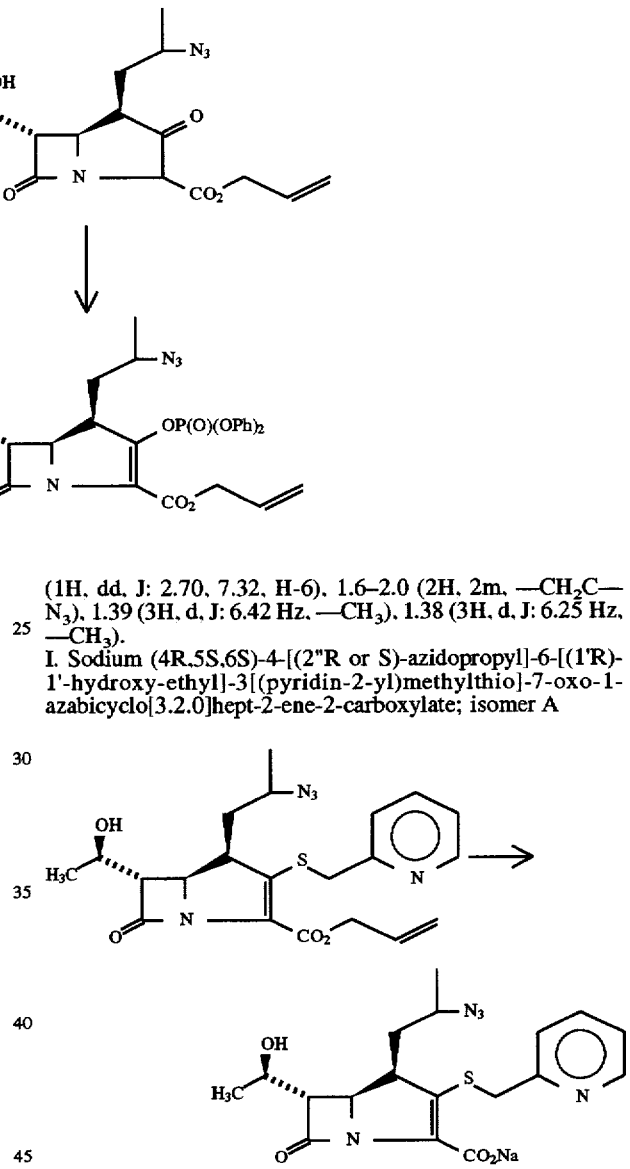

A cold (5° C.) solution of allyl (4R,5S,6S)-4-(2"-azidopropyl)-6-[(1'R)-1'-hydroxyethyl]-3-[(pyridin-2-yl)methylthio]-7-oxo-1-azabicyclo[3.2.0]hept-2-ene-2-carboxylate (500 mg, 1.13 mmol, the less polar isomer A of Step H) in CH₂Cl₂ (50 mL) was treated with 0.5M sodium ethyl hexanoate (2.5 mL, 1.24 mmol) and (PPh₃)₄Pd (131 mg, 0.113 mmol). After stirring for 30 min, the solution was diluted with diethyl ether (100 mL) and extracted with 0.04M buffer (pH 7.0, 3×15 mL). The aqueous extracts were washed with diethyl ether and chromatographed on reversed phase SiO₂ (partisil); elution with water and then 5–15% CH₃CN in water. The pertinent fractions were combined and lyophilized to give 180 mg (38.9%) of the title compound;

¹H NMR (D₂O) δ: 8.50 (1H, m, Ar—H), 7.89 (1H, m, Ar—H), 7.4–7.6 (2H, 2m, 2 Ar—H), 4.26–4.06 (2H, m, H-1', H-5), 4.18 (2H, ABq, J: 14.09, S—CH₂), 3.6 (1H, m, CH—N₃), 3.35 (2H, m, H-6, H-4), 1.8 and 1.56 (2H, 2m, CH₂C—N₃), 1.35 (3H, d, J: 6.71 Hz, —CH₃), 1.32 (3H, d, J: 6.65 Hz, —CH₃).

J. (4R,5S,6S)-4-[(2"R or S)-Aminopropyl]-6-[(1'R)-1'-hydroxyethyl]-3-[(pyridin-2-yl)methylthio]-7-oxo-1-azabicyclo[3.2.0]hept-2-ene-2-carboxylic acid; isomer A

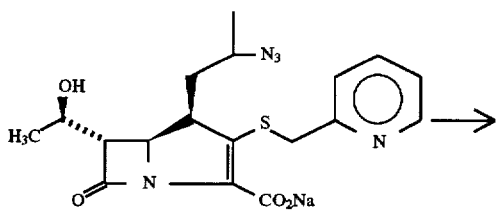

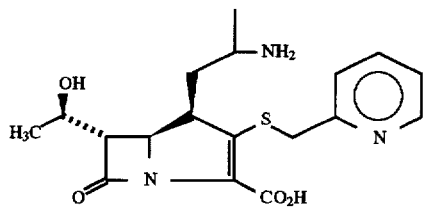

A solution of sodium (4R,5S,6S)-4-(2"-azidopropyl)-6-[(1'R)-1'-hydroxyethyl]-3-[(pyridin-2-yl)methylthio]-7-oxo-1-azabicyclo[3.2.0]hept-2-ene-2-carboxylate (175 mg, 0.425 mmol, the less polar isomer A of Step I) in 0.05M phosphate buffer (pH 6.0, 60 mL) was hydrogenated at 5° C. in the presence of 30% Pd/Celite (350 mg) at a pressure of 45 psi of hydrogen. After 75 min, additional catalyst (100 mg) was added and the reduction continued for 30 more minutes. The catalyst was filtered off and the filtrate chromatographed on reversed phase $SiO_2$ (partisil) eluting with water and then 5% $CH_3CN$ in water. The pertinent fractions were lyophilized to give 50 mg (31.2%) of the title compound; isomer A;

UV ($H_2O$) $\lambda_{max}$: 266 (4093), 300 (3945);

IR (Nujol) $v_{max}$: 1755 (β-lactam), 1595 cm$^{-1}$ (—$CO_2$—);

$^1$H NMR ($D_2O$) δ: 8.46 (1H, m, Ar—H), 7.84 (1H, m, Ar—H), 7.46–7.29 (2H, m, 2 Ar—H), 4.24–4.01 (4H, m, H-1', H-5, —$SCH_2$), 3.17–3.46 (3H, m, H-4, H-6, CH—N—), 1.4–2.0 (2H, 2m, $CH_2C$—N), 1.31 (3H, d, J: 6.53 Hz, —$CH_3$), 1.29 (3H, d, J: 6.31 Hz, —$CH_3$).

EXAMPLE 58

(4R,5S,6S)-4-[(2"S or R)-Aminopropyl]6-[(1'R)-1'-hydroxyethyl]-3-[(pyridin-2-yl)methylthio]-7-oxo-1-azabicyclo-[3.2.0]-hept-2-ene-2-carboxylic acid; isomer B

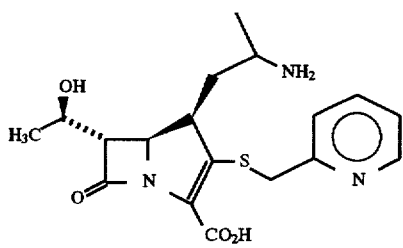

A. Sodium (4R,5S,6S)-4-[(2"S or R)-azidopropyl]-6-[(1'R)-1'-hydroxyethyl]-3-[(pyridin-2-yl)methylthio]-7-oxo-1-azabicyclo-[3.2.0]hept-2-ene-2-carboxylate; isomer B

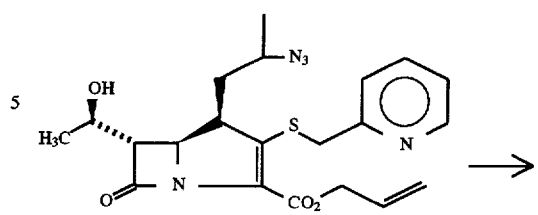

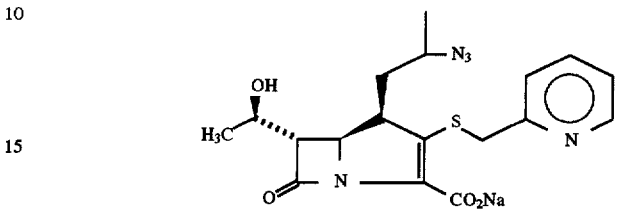

A cold (5° C.) solution of allyl (4R,5S,6S)-4-(2"-azidopropyl)-6-[(1'R)-1'-hydroxyethyl]-3-[(pyridin-2-yl)methylthio]-7-oxo-1-azabicyclo[3.2.0]hept-2-ene-2-carboxylate (340 mg, 0.767 mmol, the more polar isomer B from Example 57, Step H) in $CH_2Cl_2$ (35 mL) was treated with 0.5M sodium ethyl hexanoate (1.7 mL, 0.85 mmol) and $(PPh_3)_4Pd$ (88 mg, 0.08 mmol). After stirring for 30 min, the solution was diluted with diethyl ether (70 mL) and extracted with 0.04M buffer (pH 7.0, 3×10 mL). The aqueous extracts were washed with diethyl ether and chromatographed on reversed phase $SiO_2$ (partisil): elution with water and then 5–15% $CH_3CN$ in water. The pertinent fractions were combined and lyophilized to give 140 mg (44.4%) of the title compound;

$^1$H NMR ($D_2O$) δ: 8.48 (1H, m, Ar—H), 7.88 (1H, m, Ar—H), 7.49 (1H, m, Ar—H), 7.40 (1H, m, Ar—H), 4.02–4.27 (4H, m, H-1', H-5, $SCH_2$), 3.67 (1H, m, CH—$N_3$), 3.43 (1H, dd, J: 2.5, 5.84, H-6), 3.15 (1H, m, H-4), 1.50–1.90 (2H, 2m, $CH_2C$—$N_3$), 1.28 (6H, d, J: 6.35 Hz, 2-$CH_3$).

B. (4R,5S,6S)-4-[(2"S or R)-Aminopropyl]6-[(1'R)-1'-hydroxyethyl]-3-[(pyridin-2-yl)methylthio]-7-oxo-1-azabicyclo[3.2.0]hept-2-ene-2-carboxylic acid; isomer B

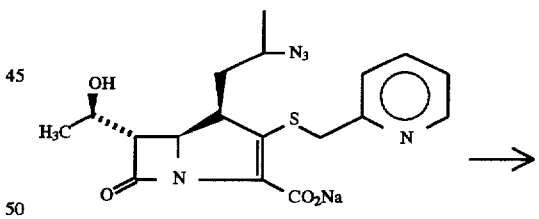

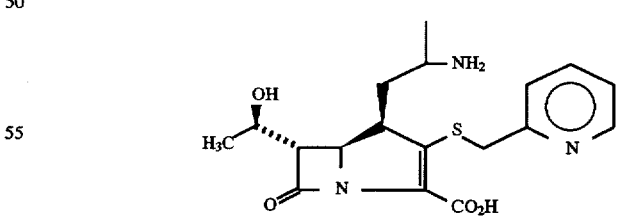

A solution of sodium (4R,5S,6S)-4-(2"-azidopropyl)-6-[(1'R)-1'-hydroxyethyl]-3-[(pyridin-2-yl)methylthio]-7-oxo-1-azabicyclo[3.2.0]hept-2-ene-2-carboxylate (135 mg, 0.328 mmol, the more polar isomer B of Step A) in 0.05M phosphate buffer (pH 6.0, 45 mL) was hydrogenated at 5° C. in the presence of 30% Pd/Celite (270 mg) at a pressure of 40 psi of hydrogen. After 65 min, the catalyst was filtered off and the filtrate chromatographed on reversed phase $SiO_2$ (partisil) eluting with water and then 5% CH₃CN in water. The pertinent fractions were combined and lyophilized to give 60 mg (48.5%) of the title compound;

UV (H₂O) λ$_{max}$: 268 (8362), 302 (9583);

IR (Nujol) ν$_{max}$: 1760 (β-lactam), 1595 cm$^{-1}$ (—CO₂—);

¹H NMR (D₂O) δ: 8.46 (1H, m, Ar—H), 7.83 (1H, m, Ar—H), 7.47 (1H, m, Ar—H), 7.36 (1H, m, Ar—H), 4.01–4.25 (4H, m, H-1', H-5, SCh₂) 3.40 (2H, m, —CH—N dd, J: 2.95, 6.66 H-6), 3.14 (1H, m, H-4), 1.98 and 1.75 (2H, 2m, CH₂—CN), 1.35 (3H, d, J: 6.44 Hz, —CH₃), 1.29 (3H, d, J: 6.37, —CH₃).

EXAMPLE 59

(4R,5S,6S)-3-[(cyanopropyl)thio]-4-(3"-guanidinopropyl)-6-[(1'R)-1'-hydroxyethyl]-7-oxo-1-azabicyclo[3.2.0]hept-2-ene-2-carboxylic acid

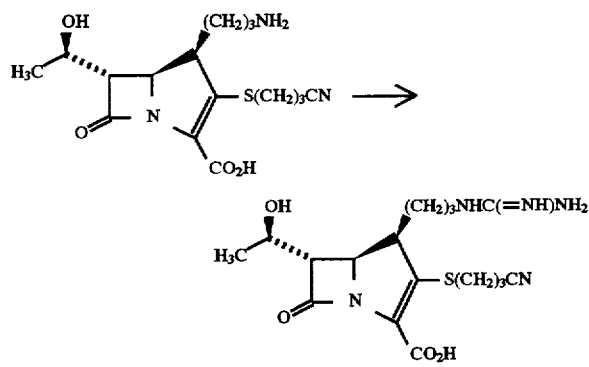

A cold solution (ice bath) of (4R,5S,6S)-4-(3"-aminopropyl)-3-[(3-cyanopropyl)thio]-6-[(1'R)-1'-hydroxyethyl]-7-oxo-1-azabicyclo[3.2.0]hept-2-ene-2-carboxylic acid (150 mg, 0.420 mmol) as described in Example 50 in a 0.04M pH 7.0 aqueous phosphate buffer solution (25 mL) was treated first with a 0.1M aqueous NaOH solution (to raise and maintain the pH between 7.6 and 7.8) and with aminoiminomethanesulfonic acid (520 mg, 4.20 mmol). The mixture was stirred for 2 h and the pH was adjusted to 7.1 with a 0.1N aqueous HCl solution. The mixture was passed through a μ-Bondapak C₁₈ reversed phase column (45 g, H₂O→1%→8% CH₃CN/H₂O) to give the title compound (125 mg, 75%) as a lyophilized powder;

Purity 98.4% (HPLC 300 nm);

UV (H₂O) λ$_{max}$: 302 (ε8230);

IR (Nujol) ν$_{max}$: 2250 (C≡N), 1750 (C=O), 1700 (C=N) and cm$^{-1}$ (C=O);

¹H NMR (D₂O, 200 MHz) δ: 4.33–4.21 (1H, m, H-1'), 4.243 (1H, dd, J=2.5 Hz, J=9.4 Hz, H-4), 3.41–3.23 (3H, m, H-4 and CH₂—N), 3.330 (1H, dd, J=2.5 Hz, J=6.3 Hz, H-6), 3.06–292, 2.85–2.73 (2H, 2 sets of m, SCH₂), 2.71–2.60 (2H, m, CH₂CN), 2.05–1.49 (6H, m, CH₂CH₂CH₂CN and CH₂CH₂) and 1.321 ppm (3H, d, 6.4 Hz, CH₃).

EXAMPLE 60

(4R,5S,6S)-4-(3"-Guanidinopropyl)-6-[(1'R)-1'-hydroxyethyl]-3-[(pyridin-4-yl)methylthio]-7-oxo-1-azabicyclo[3.2.0]hept-2-ene-2-carboxylic acid

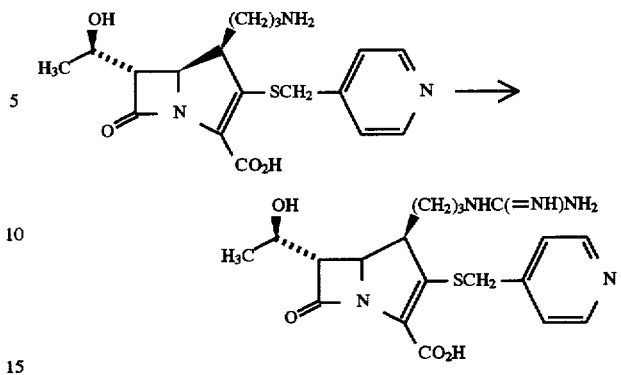

A cold (ice bath) solution of (4R,5S,6S)-4-(3"-aminopropyl)-6-[(1' R)-1'-hydroxyethyl]-3-[(pyridin-4-yl)methylthio]-7-oxo-1-azabicyclo[3.2.0]hept-2-ene-2-carboxylic acid (0.16 g, 0.42 mmol) [Example 44] in a 0.05M pH 7.0 aqueous phosphate buffer (30 mL) was treated with a 0.1N aqueous NaOH solution (to raise and maintain the pH around 7.7–8.1) and aminoiminomethanesulfonic acid (525 mg, 4.2 mmol). The mixture was stirred for 90 min, neutralized to pH 7.0 with a 1.0M aqueous NaH₂PO₄ solution and passed through a μBondapak C₁₈ reversed phase column (30 g, H₂O→8% CH₃CN/H₂O) to give the title compound (85 mg, 57%) as a lyophilized powder;

Purity: 95.2% (HPLC, 304 nm);

UV (H₂O) λ$_{max}$: 304 (ε8,000), 262 (ε5200);

IR (Nujol) ν$_{max}$: 3500–3100 (OH, NH), 1755 (C=O), 1660 (C=N ) and 1600 cm$^{-1}$ (C=O);

¹H NMR (D₂O, 200 MHz) δ: 8.49–8.46 (2H, m, aromatic H), 7.49–7.46 (2H, m, aromatic —H), 4.25–4.16 (1H, m, H-1'), 4.16, 4.09, 4.01, 3.94 (2H, ABq, J=14.4 Hz, CH₂-aromatic), 4.058 (Part of H-5, d, J=2.4 Hz), 3.261 (1H, dd, J=2.5 Hz, J=6.02 Hz, H-6), 3.20–3.07 (3H, m, CH₂N, H-4), 1.8–1.5, 1.5–1.26 (4H, 2 sets of m, CH₂CH₂-4), and 1.280 ppm (3H, d, J=6.4 Hz, CH₃).

EXAMPLE 61

(4R,5S,6S)-3-[(2-Cyanoethyl)thio]-4-(3"-guanidinopropyl)-6-[(1'R)-1'-hydroxyethyl]-7-oxo-1-azabicyclo[3.2.0]hept-2-ene-2-carboxylic acid

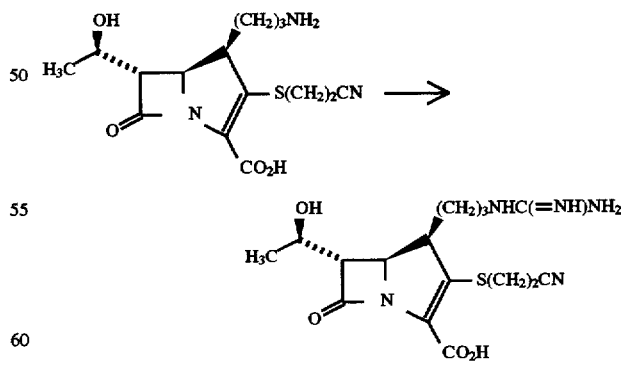

To a cold (ice bath) solution of (4R,5S,6S)-4-(3"-aminopropyl)-3-[(2-cyanoethyl)thio]-6-[(1'R)-1'-hydroxyethyl]-7-oxo-1-azabicyclo[3.2.0]hept-2-ene-2-carboxylic acid (125 mg, 0.37 mmol) [prepared in Example 41] in a 0.04M pH 7.0 aqueous phosphate buffer (25 mL) was added a 0.1N aqueous NaOH and portionwise aminoiminomethanesulfonic acid (458 mg, 3.70 mmol) while maintaining the pH at 7.6–7.8. The mixture was stirred for 2.5 h at 5° C. and the pH was adjusted to 7.05 with a 0.1N aqueous HCl solution. The solution was passed through a μ-Bondapak $C_{18}$ column (38 g, $H_2O$, 1,2,3,4,5% $CH_3CN$/$H_2O$) to give the title compound (98 mg, 70%) as a lyophilized powder;

Purity 98.8% (HPLC, 300 nm);

UV ($H_2O$) $\lambda_{max}$: 300 (ε8990);

IR (Nujol) $v_{max}$: 1755 (C=O), 1665 (C=N) and 1585 $cm^{-1}$ (C=O);

$^1$H NMR ($D_2O$, 200 MHz) δ: 4.34–4.21 (1H, m, H-1'), 4.259 (1H, dd, J=2.6 Hz, J=9.2 Hz, H-5), 3.45–3.33 (1H, m, H-4), 3.351 (1H, dd, J=2.6 Hz, J=6.5 Hz, H-6), 3.29–3.22 (2H, m, $CH_2$—N), 3.18–3.08, 3.02–2.92 (2H, 2 sets of m, $SCH_2$), 2.91–2.80 (2H, m, $CH_2CN$), 1.92–1.44 (4H, m, $CH_2CH_2$) and 1.321 ppm (3H, d, J=6.3 Hz, $CH_3$).

EXAMPLE 62

(4R,5S,6S)-4-(4"-Aminobutyl)-6-[(1'R)-1'-hydroxyethyl]-3-[(1-methyl-1,2,3-triazol-4-yl)methylthio]-7-oxo-1-azabicyclo[3.2.0]-hept-2-ene-2-carboxylic acid

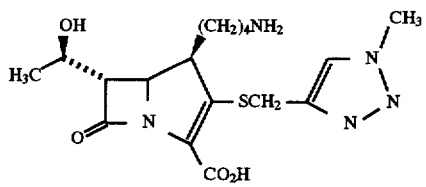

A. Allyl (4R,5S,6S)-4-(4"-azidobutyl)-6-[(1'R)-1'-hydroxyethyl]-3-[(1-methyl-1,2,3-triazol-4-yl)methylthio]-7-oxo-1-azabicyclo[3.2.0]hept-2-ene-2-carboxylate

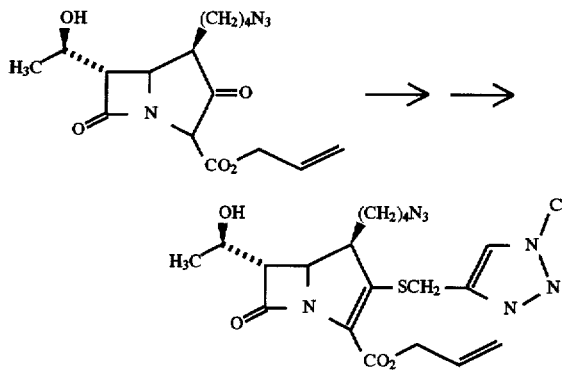

A solution of allyl (4R,5R,6S)-4-(4"-azidobutyl)-6-[(1'R)-1'-hydroxyethyl]-3,7-dioxo-1-azabicyclo[3.2.0]heptane-2-carboxylate (5.28 mmole, prepared by cyclization of 2.0 g, 5.28 mmol of the diazo precursor) in dry acetonitrile (40 mL) was treated at 0°–5° C. and under nitrogen with diphenyl chlorophosphate (1.2 mL, 5.8 mmol) and N,N-diisopropylethylamine (1.0 mL, 5.8 mmol) added simultaneously over 5 min. A small crystal of 4-N,N-dimethylaminopyridine was then added and the clear mixture was stirred at the same temperature for 1 h. Then more N,N-diisopropylethylamine (1.8 mL, 10.6 mmol) followed by 1-methyl-4-mercaptomethyl-1,2,3-triazole (1.36 g, 10.5 mmol) were added and the mixture was stirred for 3 h. The reaction mixture was then quenched by addition of EtOAc (200 mL) and cold water. The organic phase was washed with 1M $NaHSO_3$, saturated $NaHCO_3$, brine and dried ($MgSO_4$). Evaporation of the solvent gave an oil which was chromatographed on silica gel (5×10 cm) using a gradient of EtOAc in toluene (1:1 to EtOAc). Evaporation of the UV active fractions gave 1.51 g (62%) of the title compound as a foam:

IR (NaCl, film) $v_{max}$: 3400 (broad, OH) 2100 ($N_3$), 1770 (C=O of β-lactam) and 1710 $cm^{-1}$ (C=O of ester);

$^1$H NMR (200 MHz, $CDCl_3$) δ: 1.37 (d, J=6.26 Hz, 3H, $CH_3CHO$), 1.3–1.9 (m, 6H, $CH_2$-1,2, and 3 of butyl), 1.92 (d, J=1.9 Hz, 1H, OH), 3.17 (dd, $J_{H6,H5}$=2.66 Hz, $J_{H6,H1}$=7.09 Hz, 1H, H-6), 3.33 (broad t, J=6.2 Hz, 2H, $CH_2N_3$), 3.52 (broad t, J=9.0 Hz, 1H, H-4), 4.07 (ABq, $J_{AB}$=14.75 Hz, Δv=54.4 Hz, 2H, $SCH_2$), 4.08 (s, 3H, $CH_3$-1 of triazole), 4.2 (m, 2H, H-5 and $CH_3CHO$ overlapping), 4.74 (m, 2H, $CH_2$ of allyl), 5.2–5.5 and 5.9–6.1 (2×m, 2H and 1H, CH of allyl) and 7.48 ppm (s, 1H, H-5 of triazole).

B. (4R,5S,6S)-4-(4"-Aminobutyl)-6-[(1'R)-1'-hydroxyethyl]-3-[(1-methyl-1,2,3-triazol-4-yl)methylthio]-7-oxo-1-azabicyclo[3.2.0]hept-2-ene-2,carboxylic acid

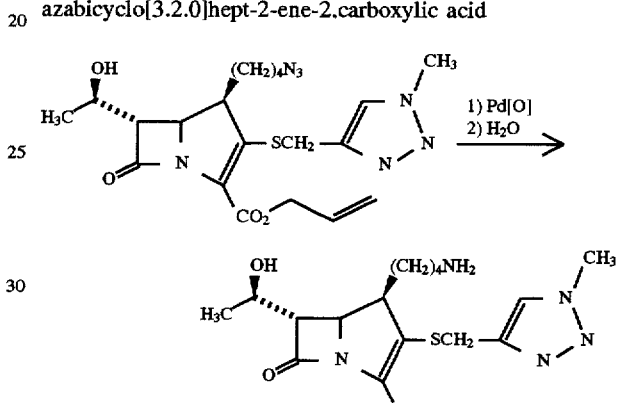

A solution of allyl (4R,5S,6S)-4-(4"-azidobutyl)-6-[(1'R)-1'-hydroxyethyl]-3-[(1-methyl-1,2,3-triazol-4-yl)methylthio]-7-oxo-1-azabicyclo[3.2.0]hept-2-ene-2-carboxylate (1.51 g, 3.27 mmol) in dry EtOAc (75 mL) was treated at 22° C. and under nitrogen with tetrakis (triphenylphosphine)palladium [0] (0.075 g) and 7.2 mL (3.6 mmol) of a 0.5M solution of potassium 2-ethylhexanoate in EtOAc. After 45 min, the reaction mixture was extracted with water (2×75 mL). The combined aqueous phase was maintained under vacuum to remove traces of organic solvent and then hydrogenated at 0°–5° C. over 1.7 g of 5% Pd over alumina at 45 psi of hydrogen for 1 h (final pH 10.5). Then 25 mL of 0.2M pH 6.0 phosphate buffer was added and the catalyst was filtered on a Celite pad. The filtrate was concentrated by half under vacuum and then chromatographed on reversed phase silica gel μ-Bondapak C-18, 3.5×12 cm). Elution with a gradient of acetonitrile (0–5%) in water gave 1.0 g (76%) of the title compound as a white amorphous powder after freeze drying:

Purity by HPLC: 97% on μ-Bondapak C-18, 3.9 mm×30 cm, elution 5% $CH_3CN$—$H_2O1$ pH 7.4 phosphate buffer, flow rate 1 mL/min, UV detector 300 nm, retention time 6.07 min;

UV ($H_2O$, pH 7.4 phosphate buffer) $\lambda_{max}$: 302 nm (9,098);

IR (KBr) $v_{max}$: 1755 (C=O of β-lactam) and 1690 $cm^{-1}$ (C=O of carboxylate);

$^1$H NMR (200 MHz, $D_2O$) δ: 1.30 (d, J=6.35 Hz, 3H, $CH_3CHO$), 1.2–1.9 (m, 6H, $CH_2$-1,2 and 3 of butyl), 3.0 (t, J=7.6 Hz, 2H, $CH_2NH_2$), 3.23 (broad t, 1H, H-4), 3.33 (dd, $J_{H6,H5}$=2.52 Hz, $J_{H6,H1}$=6.33 Hz, 1H, H-6), 4.08 (s, 3H, $CH_3$-1 of triazole), 4.09 (ABq, $J_{AB}$=14.93 Hz, Δv=33.7 Hz, 2H, SCH₂), 4.1 (overlapping with SCH₂, 1H, H-5), 4.24 (m, 1H, CH₃CHO) and 7.87 ppm (s, 1H, H-5 of triazole).

EXAMPLE 63

(4R,5S,6S)-3-[(2-Cyanoethyl)thio]-6-[(1'R)-1'-hydroxyethyl]-4-[2"(1-pyrrolidinyl)ethyl]-7-oxo-1-azabicyclo[3.2.0]hept-2-ene-2-carboxylic acid

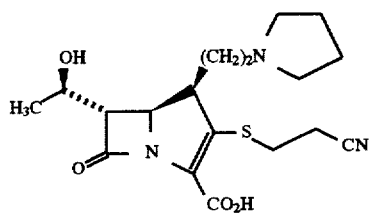

A. Allyl (4R,5S,6S)-6-[(1'R)-1'-tert-butyldimethylsilyloxyethyl]-3-[(2-cyanoethyl)thio]-4-[2"-(1-pyrrolidinyl)ethyl]-7-oxo-1-azabicyclo-[3.2.0]hept-2-ene-2-carboxylate

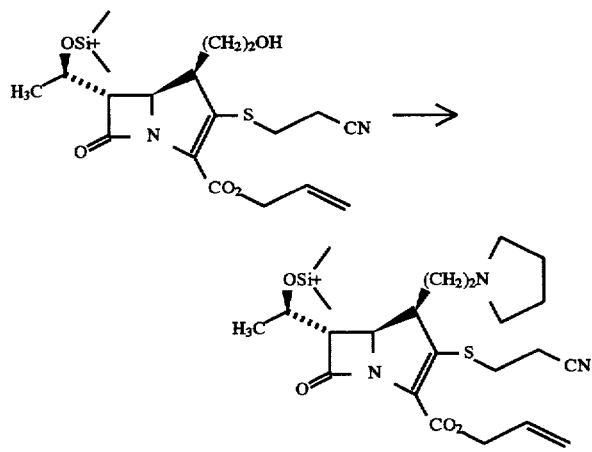

A cold solution (dry ice-acetone bath) of allyl (4R,5S,6 S)-6-[(1'R)-1'-tert-butyldimethylsilyloxyethyl]-3- [(2-cyanoethyl)-thio]-4-(2"-hydroxyethyl)-7-oxo- 1-azabicyclo [3.2.0]hept-2-ene-2-carboxylate (418 mg, 0.870 mmol) in CH₂Cl₂ (10 mL) was treated with N,N-diisopropylethylamine (410 μL, 3.59 mmol) and dropwise with trifluoromethanesulfonic anhydride (209 μL, 1.24 mmol). The mixture was stirred for 30 min and pyrrolidine (530 μL, 6.35 mmol) was added dropwise. The dry ice-acetone bath was replaced by an ice-MeOH bath and the mixture was stirred for 2 h. The reaction mixture was applied on four preparative TLC (2 mm, EtOAc, R=0.2) to give the title compound (355 mg, 75.5%) as an oil;

IR (neat) $v_{max}$: 1780 and 1710 cm⁻¹ (C═O);

¹H NMR (CDCl₃, 200 MHz) δ: 6.05–5.85 (1H, m, vinylic-H), 5.49–5.72 (2H, m, vinylicH), 4.85–4.63 (2H, m, allylic-CH₂), 4.3–4.13 (1H, m, H-1'), 4.193 (1H, dd, J=2.7 Hz, J=9.4 Hz, H-5), 3.224 (1H, dd, J=2.7 Hz, J=9.5 Hz, H-6), 3.37–3.19 (2H, m, H-4 and HCHS), 3.07–2.93 (1H, m, HCHS), 2.72–2.5 (8H, m, CH₂CN and (CH₂)₃N), 2.1–1.8 (6H, m, CH₂-4 and CH₂—CH₂), 1.587 (3H, d, J=6.1 Hz, CH₃), 0.892 (9H, s, tert-butyl) and 0.088 ppm (6H, s, dimethyl).

B. Allyl (4R,5S,6S)-3-[(cyanoethyl)thio]-6-[(1'R)-1'-hydroxyethyl]-4-[2"-(1-pyrrolidinyl)ethyl]-7-oxo-1-azabicyclo[3.2.0]hept-2-ene-2-carboxylate

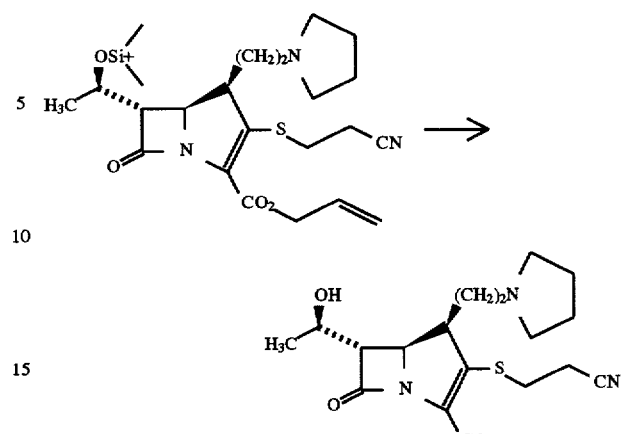

A cold solution (ice-MeOH bath) of allyl (4R,5S,6 S)-6-[(1'R)-1'-tert-butyldimethylsilyloxyethyl]-3-[(2-cyanoethyl)-thio]-4-[2"-(1-pyrrolidinyl)ethyl]-7-oxo-1-azabicyclo[3.2.0]hept-2-ene-2-carboxylate (355 mg, 0.665 mmol) in THF (8 mL) was treated first with acetic acid (500 μL, 8.73 mmol) and dropwise with a 1M solution of tetrabutylammonium fluoride in THF (4.5 mL, 4.5 mmol). The mixture was stirred for 30 min and then was allowed to set in a cold room (5° C.) for 114 h. Then solid NaHCO₃ (1 g) was added and the mixture was stirred for 30 min. It was applied on three preparative TLC plates (2 mm, elution twice with acetone) to give the title compound (220 gm, 78.8%, R_f0.2) contaminated with some tetrabutylammonium salts;

IR (neat) $v_{max}$: 3600–3200 (OH), 1775 and 1710 cm⁻¹ (C═O);

¹H NMR (CDCl₃, 200 MHz) δ: 6.07–5.87 (1H, m, vinylic H), 5.49–5.24 (2H, m, vinylic H), 4.88–4.6 (2H, m, allylic-CH₂), 4.293 (1H, dd, J=3.2 Hz, J=10.4 Hz, H-5), 4.17–4.02 (1H, m, H-1'), 3.366 (1H, dd, J=3.2 Hz, J=9.2 Hz, H-6), 3.2–2.8 (9H, CH₂S, (CH₂)₃N, H-4), 2.7–2.62 (2H, m, CH₂CN), 2.4–2.2 (1H, m, HCH-4), 2.1–1.8 (5H, m, CH₂CH₂, HCH-4) and 1.404 ppm (3H, d, J=6.3 Hz, CH₃).

C. (4R,5S,6S)-3-[(2-Cyanoethyl)thio]-6-[(1'R)-1'-hydroxyethyl]-4-[2"-(1-pyrrolidinyl)ethyl]-7-oxo-1-azabicyclo-[3.2.0]hept-2-ene-2-carboxylic acid

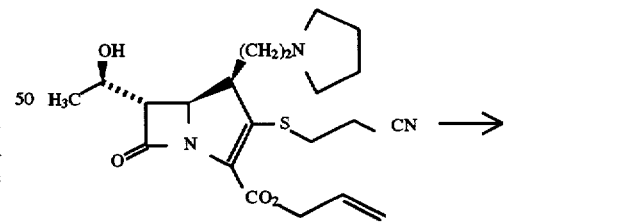

To a cold (ice bath) solution of allyl (4R,5S,6 S)-3-[(2-cyanoethyl)thio]-6-[(1' R)-1'-hydroxyethyl]-4-[2"-(1-pyrrolidinyl)ethyl]-7-oxo-

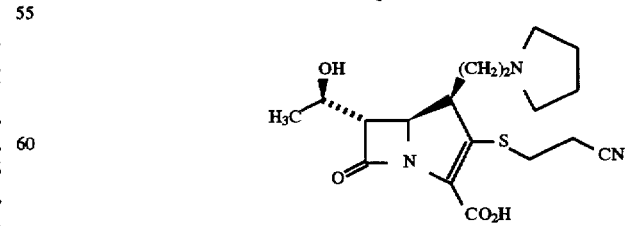

1-azabicyclo[3.2.0]hept-2-ene-2-carboxylate (220 mg, 0.524 mmol) in $CH_2Cl_2$ (8 mL) was added $Pd(PPh_3)_4$ (20 mg) and a 0.5M solution of sodium ethyl-2-hexanoate (1.1 mL, 0.55 mmol) in EtOAc. The mixture was stirred for 30 min after which it was diluted with diethyl ether and a 0.05M aqueous pH 7.0 buffer solution. The organic layer was extracted again with a 0.05M pH 7.4 buffer solution (3×3 mL). The aqueous layers were combined, washed with diethyl ether (25 mL) and passed through a µ-Bondapak $C_{18}$ reversed phase column (25 g, $H_2O$, 2→4% $CH_3CN/H_2O$) to give the title compound (145 mg, 73%) as a lyophilized powder;

Purity by HPLC: 97.2% (300 nm);
UV ($H_2O$) $\lambda_{max}$: 300 ($\epsilon$7500);
IR (Nujol) $\nu_{max}$: 1760 and 1600 cm$^{-1}$ (C=O);
$^1$H NMR ($D_2O$, 200 MHz) δ: 4.33–4.24 (1H, m, H-1'), 4.298 (1H, dd, J=2.9 Hz, J=9.3 Hz, H-5), 3.43 (1H, dd, J=2.9 Hz, J=6.8 Hz, H-6), 3.50–2.4 (7H, m, $(CH_2)_3N$, H-4), 3.21–3.07, 3.01–2.90 (2H, 2 sets of m, $CH_2$—S), 2.88–2.78 (2H, m, $CH_2CN$), 2.24–1.93 (5H, m, $CH_2CH_2$ and $CH_2$-4) and 1.336 ppm (3H, d, J=6.3 Hz, $CH_3$).

EXAMPLE 64

(4R,5S,6S)-4-(4"-Aminobutyl)-3-[(2-carbamoylethyl)thio]-6-[(1'R)-1'-hydroxyethyl]-7-oxo-1-azabicyclo[3.2.0]hept-2-ene-2-carboxylic acid

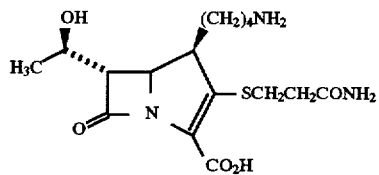

A. Allyl (4R,5S,6S)-4-(4"-azidobutyl)-3-[(2-carbamoylethyl)thio]-6-[(1'R)-1'-hydroxyethyl]-7-oxo-1-azabicyclo[3.2.0]hept-2-ene-2-carboxylate

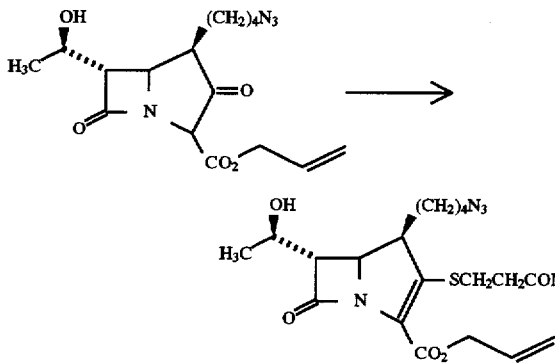

A solution of allyl (4R,5R,6S)-4-(4"-azidobutyl)-6-[(1'R)-1'-hydroxyethyl]-3,7-dioxo-1-azabicyclo[3.2.0]heptane-2-carboxylate (5.28 mmol, prepared by cyclization of 2.0 g, 5.28 mmol of diazo precursor as described in Example 45) in dry acetonitrile (40 mL) was treated at 0°–5° C. and under nitrogen with diphenyl chlorophosphate (1.20 mL, 5.8 mmol) and N,N-diisopropylethylamine (1.0 mL, 5.74 mmol) added simultaneously over 10 min. A small crystal of 4-N,N-dimethylaminopyridine was then added and the mixture was stirred for 1 h. More N,N-diisopropylethylamine (0.92 mL, 5.3 mmol) followed by chlorotrimethysilane (0.67 mL, 5.3 mmol) were added and the mixture was stirred for 10 min. Then N,N-diisopropylethylamine (1.21 mL, 6.9 mmol) followed by 3-mercaptopropionamide (0.73 g, 6.9 mmol)[prepared as described by T. Endo et al., *Chemistry Letters*, 443 (1974) and C. M. Buess, *J. Am. Chem. Soc.*, 77, 6613 (1955)] in N,N-dimethylformamide (2 mL) were added and the solution was then stirred at 0°–5° C. for 18 h. The reaction mixture was quenched by the addition of EtOAc (300 mL) and cold water. The organic phase was washed with saturated $NaHCO_3$, 0.2M pH 7.0 phosphate buffer, brine and dried ($MgSO_4$). Evaporation of the solvent gave an oil which was diluted with tetrahydrofuran (20 mL) and water (5 mL) and treated with acetic acid (2 mL). After 1 h at 22° C. and 18 h at 5° C., the solution was diluted with EtOAc (300 mL) and washed as above. After drying ($MgSO_4$) and evaporation of the solvent, the residue was chromatographed on silica gel (5×10 cm) using a gradient of ethanol (0–10%) in EtOAc as eluent. Evaporation of the UV active fractions gave 1.06 g (46%) of the title ester as an oil:

IR (NaCl, film) $\nu_{max}$: 2100 ($N_3$), 1770 (C=O of β-lactam), 1710 (sh C=O of ester) and 1680 cm$^{-1}$ (C=O of amide);

$^1$H NMR (200 MHz, $CDCl_3$) δ: 1.38 (d, J=6.27 Hz, 3H, $CH_3CHO$), 1.3–1.9 (m, 6H, $CH_2$-1,2,3 of azidobutyl), 2.05 (d, J=2.0 Hz, 1H, OH), 2.53 (~t, J=7 Hz, 2H, S $CH_2CH_2CONH_2$), 3.0–3.3 (m, 4H, $SCH_2$, H-6 and H-4 overlapping), 3.33 (t, J=6.1 Hz, 2H, $CH_2N_3$), 4.26 (dd, $J_{H5,H6}$=2.61 Hz, $J_{H5,H4}$=9.37 Hz, 1H, H-5), 4.26 (overlapping with H-5, 1H, $CH_3CHO$), 4.75 (m, 2H, $CH_2$ of allyl), 5.2–5.5 and 5.9–6.1 (2×m, 2H and 1H, CH of allyl), 5.5 and 5.6 ppm (2 broad s, 2×1H, $CONH_2$).

B. (4R,5S,6S)-4-(4"-Aminobutyl)-3-[(2-carbamoylethyl)thio]-6-[(1'R)-1'-hydroxyethyl]-7-oxo-1-azabicyclo-[3.2.0]hept-2-ene-2-carboxylic acid

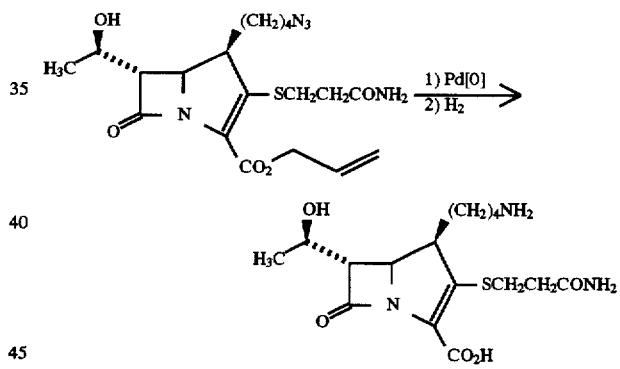

A solution of allyl (4R,5S,6S)-4-(4"-azidobutyl)-3-[(2-carbamoylethyl)thio]-6-[(1'R)-1'-hydroxyethyl]-7-oxo-1-aza-bicyclo[3.2.0]hept-2-ene-2-carboxylate (1.06 g, 2.42 mmol) in EtOAc (50 mL) was treated at 22° C. and under nitrogen with tetrakis(triphenylphosphine)palladium [0] (0.074 g) and 5.3 mL (2.65 mmol) of a 0.5M solution of potassium 2-ethylhexanoate in EtOAc. After 30 min, the reaction mixture was extracted with water (2×50 mL) and the combined aqueous phase was maintained under vacuum to remove traces of organic solvent. The aqueous phase was then hydrogenated over 1.25 g of 5% palladium over alumina at 0°–5° C. and under 45 psi of hydrogen for 1 h. After the addition of 20 mL of 0.2M pH 6.0 phosphate buffer, the catalyst was filtered and the filtrate was chromatographed twice on reversed phase silica gel (µ-Bondapak c-18, 3.5×15 cm). Elution with a gradient of acetonitrile (0–5%) in water gave 0.36 g (40%) of the title compound as a white amorphous powder (93% pure by hplc) after freeze drying. The purity can be increased to 99% by another chromatography on the same column using 0.01M pH 7.0 phosphate buffer instead of water followed by desalting of the product:

Purity by HPLC: 99.5% on µ-Bondapak c-18, 3.9 mm×30 cm, elution 5% $CH_3CN$—$H_2O$, pH 7.4 phosphate buffer, flow rate 0.7 mL/min, UV detector 304 nm, retention time 6.96 min;

UV ($H_2O$, pH 7.4 phosphate buffer) $\lambda_{max}$: 302 nm (8,865);
IR (KBr) $v_{max}$: 1750 (C=O of β-lactam), 1670 (C=O of amide) and 1590 $cm^{-1}$ (C=O of carboxylate);

$^1$H NMR (200 MHz, $D_2O$) δ: 1.33 (d, J=6.37 Hz, 3H, C$\underline{H}_3$CHO), 1.3–2.0 (m, 6H, $CH_2$-1,2 and 3 of butyl), 2.60 (~t, J=6.4 Hz, 2H, C$\underline{H}_2$CONH$_2$), 2.9–3.2 (m, 4H, SC$\underline{H}_2$ and C$\underline{H}_2$NH$_2$ overlapping), 3.4 (m, 2H, H-4 and H-6), 4.23 (dd, $J_{H5,H6}$=2.6 Hz, $J_{H5,H4}$=9.15 Hz, 1H, H-5) and 4.27 ppm (m, 1H, CH$_3$C$\underline{H}$O).

EXAMPLE 65

(4R,5S,6S)-3-[(2"-cyanoethyl)thio]-4-(2-N-formimidoylaminoethyl)-6-[(1'R)-1'-hydroxyethyl]-7-oxo-1-azabicyclo[3.2.0]hept-2-ene-2-carboxylic acid

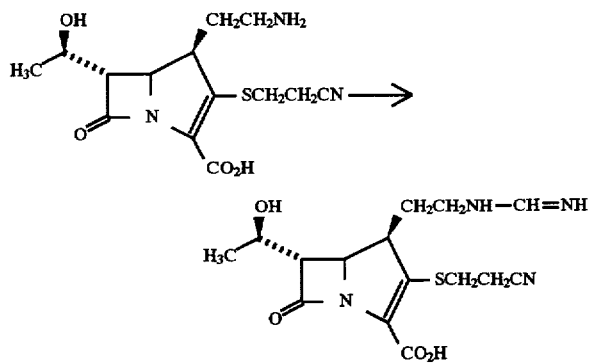

A solution of (4R,5S,6S)-4-(2"-aminoethyl)-3-[(2-cyanoethyl)thio]-6-[(1'R)-1'-hydroxyethyl]-7-oxo-1-azabicyclo[3.2.0]-hept-2-ene-2-carboxylic acid (0.290 g, 0.89 mmol) in 35 mL of cold (0°–5° C.) water was adjusted to pH 8.5 with 1M NaOH and treated with benzyl formimidate hydrochloride (0.76 g, 4.4 mmol) added in small portions over 10 min while maintaining the pH to 8–8.5 (1N NaOH). After 20 min, the reaction mixture was quenched by addition of 25 mL of 0.2M pH 6.0 phosphate buffer and washed with EtOAc. The aqueous phase was maintained under vacuum to remove traces of organic solvent and then chromatographed on reverse phase silica gel (µ-Bondapak c-18, 3.5×12 cm). The column was eluted first with 0.01M pH 7.0 phosphate buffer. The UV active fractions were combined, lyophilized and desalted on the same column using water as eluent. After freeze drying, the title compound was obtained as a white amorphous powder (0.120 g, 38%):

Purity by HPLC: 99% on µ-Bondapak c-18, 3.9 mm×30 cm, elution 1.5% $CH_3CN$—$H_2O$, pH 7.4 phosphate buffer, flow rate 1 mL/min, UV detector 300 nm, retention time 4.91 min;

UV ($H_2O$, pH 7.4 phosphate buffer) $\lambda_{max}$: 300 nm (7,429);
IR (KBr) $v_{max}$: 2250 (weak CN), 1755 (C=O of β-lactam), 1610 (C=N of formimidoyl) and 1580 $cm^{-1}$ (C=O of carboxylate);

$^1$H NMR (200 MHz, $D_2O$) δ: 1.34 (d, J=6.37 Hz, 3H, C$\underline{H}_3$CHO), 1.8–2.3 (m, 2H, CH$_2$-1 of aminoethyl), 2.8–3.2 (m, 4H, SC$\underline{H}_2$C$\underline{H}_2$CN), 3.45 (overlapping with H-6, 1H, H-4), 3.47 (dd, $J_{H6,H5}$=2.92 Hz, $J_{H6,H1}$=6.87 Hz, 1H, H-6), 4.28 (m, 1H, CH$_3$C$\underline{H}$O), 4.32 (dd, $J_{H5,H6}$=2.92 Hz, $J_{H5,H4}$=6.68 Hz, 1H, H-5), and 7.85 ppm (s, 1H, C$\underline{H}$=NH).

EXAMPLE 66

(4R,5S,6S)-4-(3"-Aminopropyl)-3-[(2-carbamoyloxyethyl)thio]-6-[(1'R)-1'-hydroxyethyl]-7-oxo-1-azabicyclo[3.2.0]hept-2-ene-2-carboxylic acid

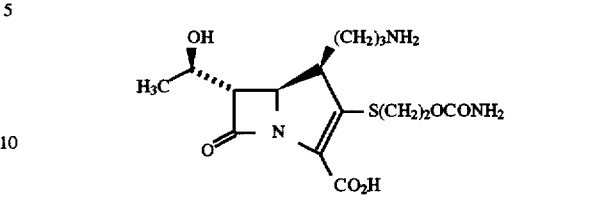

A. Allyl (4R,5S,6S)-4-(3"-azidopropyl)-3-[(2-carbamoyloxyethyl)thio]-6-[(1'R)-1'-hydroxyethyl]-7-oxo-1-azabicyclo-[3.2.0]-hept-2-ene-2-carboxylate

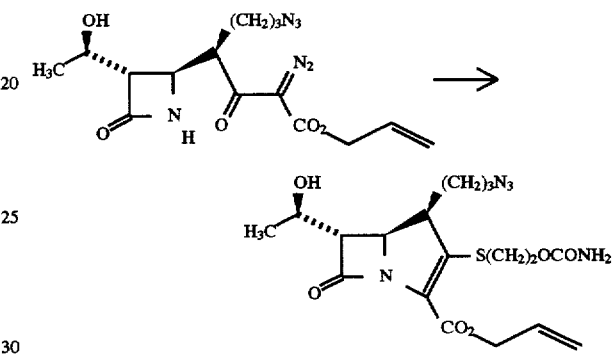

A cold (ice-MeOH bath) solution of allyl (4R,5S,6 S)-4-(3"-azidopropyl)-3-[(2-carbamoyloxyethyl)thio]-6-[(1' R)-1'-hydroxyethyl]-3,7-dioxo-1-azabicyclo[3.2.0]heptan-2-carboxylate, prepared from (3S,4R)-3-[(1' R)-1'-hydroxyethyl]-4-[(1' R)-1"-(3-azidopropyl)-3"-diazo-3"-allyloxycarbonyl-2"-oxopropyl]azetidin-2-one (2.0 g, 5.49 mmol), in $CH_3CN$ (40 mL) was treated with diphenyl chlorophosphate (1.3 mL, 6.0 mmol), N,N-diisopropylethylamine (0.98 mL, 6.0 mmol) and a trace of 4-dimethylaminopyridine. The mixture was stirred for 40 min then the resulting enol phosphate was treated with 2-carbamoyloxyethyl mercaptan (1.33 g, 11.0 mmol) and N,N-diisopropylethylamine (1.7 mL, 11.0 mmol). The mixture was stirred for 24 h at 5° C. then it was treated again with more 2-carbamoyloxyethyl mercaptan (0.65 mL, 5.5 mmol) and N,N-diisopropylethylamine (0.88 mL, 5.5 mmol). After a stirring period of 35 h more, the mixture was diluted with ethyl acetate (200 mL), washed with cold water (2×50 mL), cold 1M aqueous $NaHSO_3$ (2×50 mL), water (50 mL), 1N aqueous HCl (50 mL), water (50 mL), 1M aqueous $NaHCO_3$ (50 mL), water (50 mL), brine (50 mL) and dried ($MgSO_4$). The residue was passed through a silica gel pad (25 g, hexane→ethyl acetate) to give the title compound (1.29 g, 53%) as a yellow semi-crystalline compound;

IR ($CH_2Cl_2$) $v_{max}$: 3680, 3600, 3540, 3420 (OH, $NH_2$), 2100 ($N_3$), 1775, 1740 and 1710 $cm^{-1}$ (C=O);

$^1$H NMR ($CDCl_3$, 200 MHz) δ: 6.04–5.87 (1H, m, vinylic-H), 5.50–5.22 (2H, m, vinylic-H), 4.88–4.63 (4H, m, $NH_2$ and allylic-$CH_2$), 4.37–4.10 (4H, m, H-1', $CH_2O$ and H-4), 4.276 (part of H-4, d, J=2.7 Hz), 3.49–3.35 (3H, m, $CH_2N_3$ and H-4), 3.247 (1H, dd, J=2.7 Hz, J=7.5 Hz, H-6), 3.8–3.09, 2.97–2.63 (2H, 2 sets of m, $SCH_2$), 1.96–1.55 (3H, m, OH and $CH_2CH_2$) and 1.388 ppm (3H, d, J=6.3 Hz, $CH_3$).

B. (4R,5S,6S)-4-(3"-Aminopropyl)-3-[(2-carbamoyloxyethyl)thio]-6-[(1'R)-1'-hydroxyethyl]-7-oxo-1-azabicyclo-[3.2.0]hept-2-ene-2-carboxylic acid

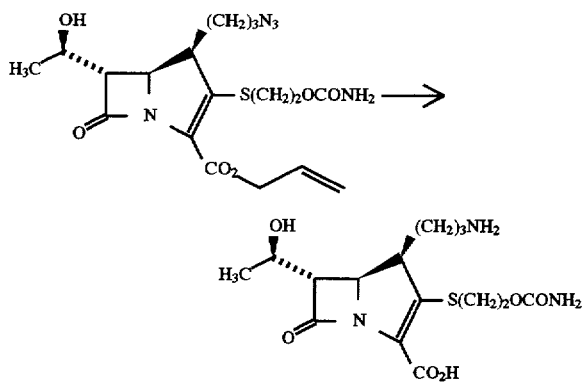

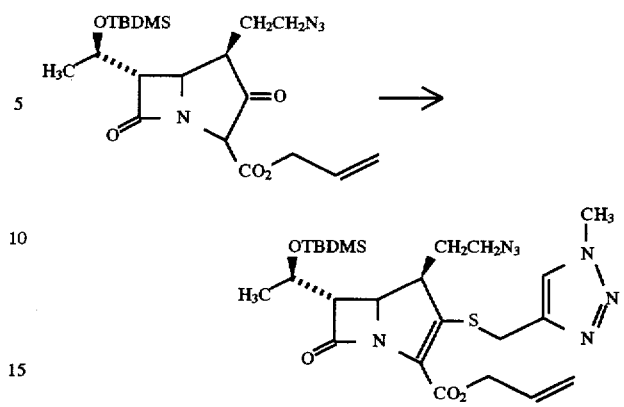

A cold solution (ice bath) of allyl (4R,5S,6S)-4-(3"-azidopropyl)-3-[(2-carbamoxyloxyethyl)thio]-6-[(1'R)-1'-hydroxyethyl]-7-oxo-1-azabicyclo[3.2.0]hept-2-ene-2-carboxylate (520 mg, 1.18 mmol) in $CH_2Cl_2$ (50 mL) was treated with $(PPh_3)_4Pd$ (110 mg, 0.09 mmol) and dropwise with a 0.5M solution of sodium ethyl-2-hexanoate (2.36 mL, 1.18 mmol) in ethyl acetate. The mixture was stirred for 20 min, diluted with diethyl ether (150 mL) and extracted with water (2×20 mL). The aqueous extracts were combined, washed with diethyl ether (2×30 mL) and shaken in a Parr hydrogenator at 45–50 psi hydrogen for 2 h at 0° C. using 5% Pd/Alumina (500 mg) as catalyst. The pH of the solution was adjusted to 6.9 with a 1M aqueous $KH_2PO_4$ solution. The catalyst was removed by filtration and the aqueous solution was passed twice through a µBondapak $C_{18}$ reversed phase column (120 g, $H_2O \rightarrow 1\% \rightarrow 3\%$ $CH_3CN/H_2O$) to give the title compound (155 mg, 35%) lyophilized powder;

Purity: 99.0% (HPLC, 300 nm);

UV ($H_2O$) $\lambda_{max}$: 302 ($\epsilon$10600);

IR (Nujol) $v_{max}$: 1755, 1710 and 1585 $cm^{-1}$ (C=O);

$^1$H NMR ($D_2O$, 200 MHz) $\delta$: 4.34–4.21 (4H, m, H-1', H-5 and $CH_2O$), 3.47–3.35 (1H, m, H-4), 3.356 (1H, dd, J=2.7 Hz, J=6.5 Hz, H-6), 3.21–2.88 (4H, m, $CH_2N$, $SCH_2$), 2.0–1.4 (4H, m, $CH_2CH_2$) and 1.334 ppm (3H, d, J=6.3 Hz, $CH_3$).

EXAMPLE 67

(4R,5S,6S)-4-(2"-Aminoethyl)-3-[(1-methyl-1,2,3-triazol-4-yl)methylthio]-6-[(1'R)-1'-hydroxyethyl]-7-oxo-1-azabicyclo-[3.2.0]hept-2-ene-2-carboxylic acid

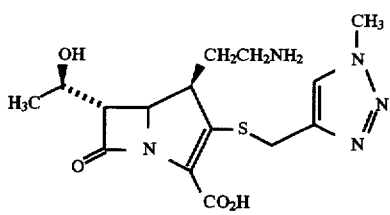

A. Allyl (4R,5S,6S)-(2"-azidoethyl)-6-[(1'R)-1'-tert-butyldimethylsilyloxyethyl]-3-[(1-methyl-1,2,3-triazol-4-yl)-methylthio]-7-oxo-1-azabicyclo[3.2.0]hept-2-ene-2-carboxylate A solution of allyl (4R,5R,6S)-4-(2"-azidoethyl)-6-[(1'R)-1'-tert-butyldimethylsilyloxyethyl]-3,7-dioxo-1-azabicyclo[3.2.0]heptane-2-carboxylate (4.69 mmol, prepared by cyclization of 2.18 g, 4.69 mmol of the diazo precursor as described in Example 2) in dry acetonitrile (36 mL) was treated at −15° C. and under Argon with diphenyl chlorophosphate (1.02 mL, 4.9 mmol) and N,N-diisopropylethylamine (0.87 mL, 5.0 mmol). A small crystal of 4-N,N-dimethylaminopyridine was added and the mixture was stirred at −15° C. for 30 min. N,N-Diisopropylethylamine (0.87 mL, 5.0 mmol) and 1-methyl4-thiomethyl-1,2,3-triazole (1.22 g, 9.4 mmol) were added and the mixture was stirred overnight at −15° C. The reaction mixture was diluted with EtOAc (250 mL) and mixed with a mixture coming from a similar experiment starting from 0.54 mmol of the diazo precursor. The resulting solution was washed with water, 1M $NaHSO_3$ saturated $NaHCO_3$, brine and dried ($MgSO_4$). Evaporation of the solvent gave an oil which was chromatographed on silica gel (5×15 cm). Elution with a mixture of EtOAc and toluene (7:13) gave 1.99 g (69%) of the title compound as a brown oil:

IR (Nujol) $v_{max}$: 2105 ($N_3$), 1775 (C=O of β-lactam) and 1710 (C=O of ester).

$^1$H NMR (200 MHz, $CDCl_3$) $\delta$: 0.09 (s, 6H, $SiCH_3$), 0.89 (s, 9H, Si-t-bu), 1.29 (d, J=6.14 Hz, 3H, $CH_3CHO$), 1.72 and 2.04 (2×m, 2×1H, $CH_2$-4), 3.10 (dd, $J_{1'6}$=7.19 Hz, $J_{5-6}$=2.73 Hz, 1H, H-6), 3.30–3.64 (m, 2H, $CH_2N_3$), 3.65 (ddd, $J_{4-5}$=J=10.06 Hz, J=2.73 Hz, 1H, H-4), 4.01 (d, $J_{gem}$=14.62 Hz, 1H, $CH_2$—S), 4.02–4.35 (m, 2H, H-5 and $CH_3CHO$), 4.08 (s, 3H, $CH_3$—N) 4.26 (d, $J_{gem}$=14.58 Hz, 1H, $CH_2$—S), 4.72 (m, 2H, $CH_2$ of allyl), 5.21–5.47 and 5.95 (2×m, 2H and 1H, CH of allyl), 7.48 (s, 1H, CH of triazole).

B. Allyl (4R,5S,6S)-4-(2"-azidoethyl)-3-[(1-methyl-1,2,3-triazol-4-yl)methylthio]-6-[(1'R)-1'-hydroxyethyl]-7-oxo-1-azabicyclo[3.2.0]hept-2-ene-2-carboxylate

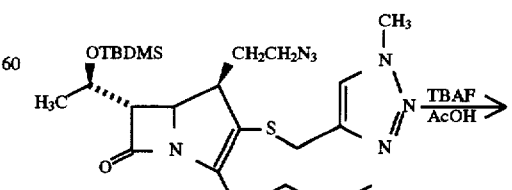

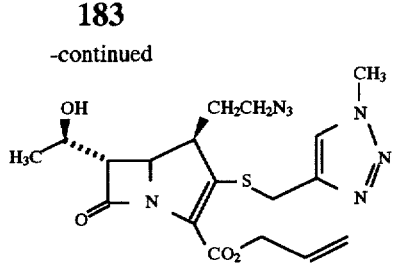

A solution of allyl (4R,5S,6S)-4-(2"-azidoethyl)-6-[(1'R)-1'-tert-butyldimethylsilyloxyethyl]-3-[(1-methyl-1,2,3-triazol-4-yl)methylthio]-7-oxo-1-azabicyclo[3–2.0]hept-2-ene-2-carboxylate (1.99 g, 3.63 mmol) in dry tetrahydrofuran (57 mL) was treated at 0°–5° C. and under Argon with acetic acid (1.25 mL, 21.8 mmol) followed by 11.3 mL (11.3 mmol) of 1M solution of tetrabutylammonium fluoride in tetrahydrofuran. The solution was stored at 5° C. for 10 days. The reaction mixture was then diluted with EtOAc, washed with saturated NaHCO$_3$, brine and dried (MgSO$_4$). Evaporation of the solvent gave an oil which was chromatographed on silica gel (5×15 cm). Elution with a mixture of acetonitrile and EtOAc (3:97) gave 1.09 g (48%, yield from the diazo azetidinone) of the title compound as a foamy light yellow solid:

IR (NaCl, film) $v_{max}$: 3490 (OH), 2105 (N$_3$), 1780 (C=O of β-lactam), and 1710 (C=O of ester).

$^1$H NMR (200 MHz, CDCl$_3$) δ: 1.38 (d, J=6.26 Hz, 3H, CH$_3$CHO), 1.78 and 2.02–2.18 (2×m, 2×1H, CH$_2$–4), 2.07 (d, J=4.42 Hz, 1H, OH), 3.17 (dd, J$_{1'6}$=7.71 Hz, J$_{5-6}$=2.76 Hz, H-6), 3.39–3.65 (m 2H, CH$_2$N$_3$), 3.74 (ddd, J$_{4-5}$:10.40 Hz, J=10.40 Hz, J=2.42 Hz, H-4), 3.95 (d, J$_{gem}$=14.89 Hz, 1H, CH$_2$—S), 4.08 (s, 3H, CH$_3$—N), 4.14–4.27 (m, 1H, CH$_3$CHO), 4.21 (dd, J$_{4-5}$=9.54 Hz, J$_{5-6}$=2.69 Hz, H-5), 4.28 (d, J$_{gem}$=15.05 Hz, 1H, CH$_2$—S), 4.73 (m, 2H, CH$_2$ of allyl), 5.22–5.48 and 5.94 (2×m, 2H and 1H, CH of allyl), 7.48 (s, 1H, CH of triazole).

C. (4R,5S,6S)-4-(2"-Aminoethyl)-3-[(1-methyl-1,2,3-triazol-4-yl)methylthio]-6-[(1'R)-1'-hydroxyethyl]-7-oxo-1-azabicyclo[3.2.0]hept-2-ene-2-carboxylic acid

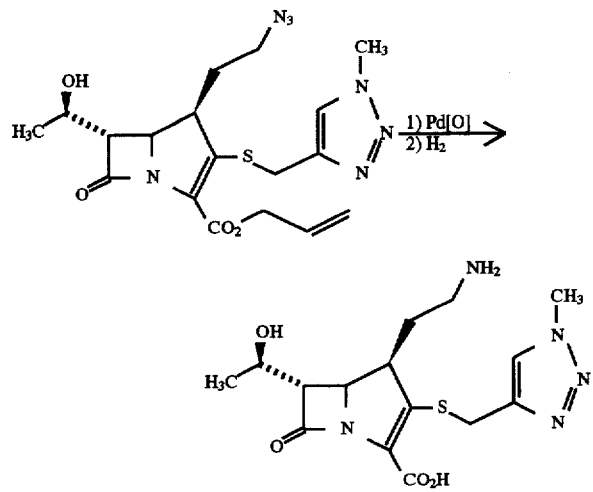

A solution of allyl (4R,5S,6S)-4-(2"-azidoethyl)-3-[(1-methyl-1,2,3-triazol-4-yl)methylthio]-6-[(1'R)-1'-hydroxyethyl]-7-oxo-1-azabicyclo[3.2.0]hept-2-ene-2-carboxylate (495 mg, 1.14 mmol) in dry CH$_2$Cl$_2$ (25 mL) was treated at 0°–5° C. and under Argon, with tetrakis (triphenylphosphine)palladium [0] (83 mg) and 2.5 mL (1.25 mmol) of a 0.5M solution of sodium 2-ethylhexanoate in EtOAc. Then 50 mL of water were added and the organic layer was separated. The organic phase was re-extracted with 3×15 mL of water and the combined aqueous layers were pumped to remove organic solvent. The residual aqueous phase was hydrogenated over 419 mg of 5% palladium on alumina and under 45 psi of hydrogen for 1 hour. The catalyst was filtered and the filtrate was neutralized with a solution of NaH$_2$PO$_4$ 1M (a few drops). The mixture was chromatographed on reversed phase silica gel (ε-bondapak c-18, 7×11 cm) using gradient of acetonitrile in water (0–1%) followed by lyophilization of the UV active fractions gave 290 mg (69%) of the title compound as a light yellow amorphous powder:

Purity by HPLC: 97.3% on μ-bondapak c-18, 3.9 mm×30 cm, elution 1.5% acetonitrile in water pH 7.4 phosphate buffer, flow rate 1 mL/min, UV detector 302 nm, retention time 5.82 min;

UV (H$_2$O, pH 7.4 phosphate buffer) λ$_{max}$: 302 nm (6091);

IR (KBr) $v_{max}$: 1760 (C=O of β-lactam) and 1600 (C=O of carboxylate);

$^1$H NMR (200 Hz, D$_2$O) δ: 1.31 (d, J=6.34 Hz, 3H, CH$_3$CHO), 1.80 and 2.17 (2×m, 2×1H, CH$_2$-4), 3.09 (t, J=8.33 Hz, CH$_2$N$_3$), 3.32 (ddd, J$_{4-5}$=J=10.06 Hz, J=3.06 Hz, 1H, H-4), 3.41 (dd, J$_{7-6}$=6.56 Hz, J$_{5-6}$=2.79 Hz, H-6), 3.95–4.28 (m, 4H, CH$_2$—S, CH$_3$CHO, H-5), 4.08 (s, 3H, CH$_3$—N), 7.85 (s, 1H, CH of triazol).

EXAMPLE 68

(4R,5S,6S)-3-[(3-cyanopropyl)thio]-4-(4"-N-formimidoylaminobutyl)-6-[(1'R)-1'-hydroxyethyl]-7-oxo-1-azabicyclo[3.2.0]hept-2-ene-2-carboxylic acid

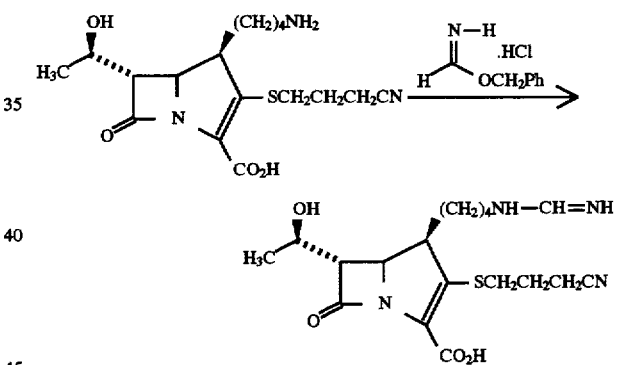

A solution of (4R,5S,6S)-4-(4"-aminobutyl)-3-[(3-cyanopropyl)thio]-6-[(1'R)-1'-hydroxyethyl]-7-oxo-1-azabicyclo-[3.2.0]hept-2-ene-2-carboxylic acid (0.411 g, 1.12 mmol) in water (50 mL) was adjusted to pH 8.5 with 1M NaOH. Then benzylformimidate hydrochloride (0.94 g, 5.4 mmol) was added in small portions over 5 min while maintaining the pH to 8–8.5 with 1M NaOH. After 20 min, 40 mL of 0.2M pH 6.0 phosphate buffer was added and the solution was washed with ethyl acetate and the aqueous phase was maintained under vacuum to remove traces of organic solvent. The aqueous solution was chromatographed at 0°–5° C. on reversed phase silica gel (3.5×15 cm, μ-Bondapak) using a gradient of acetonitrile (0–10%) in 0.01M pH 7.0 phosphate buffer. The UV active fractions were combined, concentrated under vacuum (t<10° C.) and desalted on the same column using water and acetonitrile (0–10%) as eluent. The title compound was obtained as a white amorphous powder (0.224 g, 50%) after freeze drying:

Purity by HPLC: 99% on μBondapak C$_{18}$, 3.9 mm×30 cm, elution 8% CH$_3$CN—H$_2$O, pH 7.4 phosphate buffer, flow rate 1 mL/min, uv detector 304 nm, retention time 6.85 min;

UV (H$_2$O, pH 7.4 phosphate buffer) $\lambda_{max}$: 304 nm (9,324);

IR (KBr) $v_{max}$: 2250 (CN), 1755 (C=O of B-lactam), 1715 (C=N of formimidoyl) and 1590 cm$^{-1}$ (C=O of carboxylate);

$^1$H NMR (200 MHz, D$_2$O) δ: 1.32 (d, J=6.31 Hz, 3H, CH$_3$CHO), 1.3–2.1 (m, 8H, CH$_2$-1,2 and 3 of butyl and CH$_2$-2 of cyanopropyl), 2.64 (t, J=6.9 Hz, 2H, CH$_2$CN), 2.7–3.1 (m, 2H, SCH$_2$), 3.35 (m, 4H, CH$_2$NH, H-4 and H-6 overlapping), 4.2–4.4 (m, 2H, H-5 and CH$_3$CHO overlapping) and 7.79 ppm (s, 1H.

EXAMPLE 69

(4R,5S,6S)-4-(4"-N N-Dimethylaminobutyl)-6-[(1'R)-1'-hydroxyethyl]-3-[(pyridin-3-yl)methylthio]-7-oxo-1-azabicyclo[3.2.0]-hept-2-ene-2-carboxylic acid

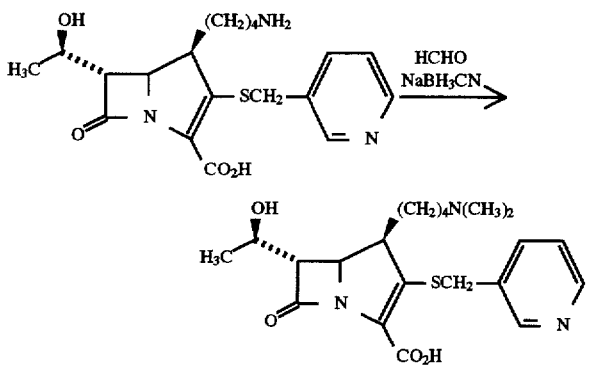

A solution of (4R,5S,6S)-4-(4"-aminobutyl)-6-[(1'R)-1'-hydroxyethyl]-3-[(pyridin-3-yl)methylthio]-7-oxo-1-azabicyclo[3.2.0]hept-2-ene-2-carboxylic acid (0.221 g, 0.56 mmol) in 5 mL of cold water (0°–5° C.) was treated with 37% w/w formaldehyde (0.23 mL, 2.8 mmol) and acetic acid (0.2 mL, 3.5 mmol). The resulting pH was 4.0. Then 0.071 g (1.1 mmol) of sodium borohydride was added all at once followed by another 0.130 g (2.1 mmol) added in small portions over 2 h. The reaction mixture was then quenched by addition of 20 mL of 0.2M pH 7.0 phosphate buffer and then chromatographed on reversed phase silica gel (µBondapak Cl$_{18}$, 2×15 cm). Elution with a gradient of acetonitrile (0–5%) in water gave 0.161 g (68%) of the title compound as a white amorphous solid after freeze drying:

Purity by HPLC: 94% on µBondapak C$_{18}$, 3.9 mm/30 cm, elution 10% CH$_3$CN—H$_2$O pH 7.4 phosphate buffer, flow rate 1.5 mL/min, uv detector 300 nm, retention time 8.19 min;

UV (water, pH 7.4 phosphate buffer) $\lambda_{max}$: 266 (4980) and 304 nm (7,540);

IR (KBr) $v_{max}$: 1758 (C=O of β-lactam) and 1582 cm$^{-1}$ (C=O of carboxylate);

$^1$H NMR (200 MHz, D$_2$O) δ: 1.29 (d, J=6.34 Hz, 3H, CH$_3$CHO), 1.2–1.8 (m, 6H, CH$_2$-1,2 and 3 of butyl), 2.86 (s, 6H, NCH$_3$), 3.1 (m, 3H, CH$_2$N and H-4), 3.29 (dd, J$_{H6,H5}$= 2.54 Hz, J$_{H6,H1}$=6.35 Hz, 1H, H-6), 4.08 (ABq, J$_{AB}$=14.9 Hz, Δv=24.2 Hz, 2H, SCH$_2$), 4.08 (overlapping with SCH$_2$, 1H, H-5), 4.22 (m, 1H, CH$_3$CHO), 7.45 (dd, J=4.9 Hz, and J=7.9 Hz, 1H, H-5 of pyridine), 7.9 (m, 1H, H-4 of pyridine), 8.44 (dd, J=1.5 Hz, and J=4.9 Hz, 1H, H-6 of pyridine) and 8.53 ppm (d, J=1.8 Hz, 1H, H-2 of pyridine).

EXAMPLE 70

(4R,5S,6S)-4-(4"-N-Formimidoylaminobutyl)-6-[(1'R)-1'-hydroxyethyl]-3-[(1-methyl-1,2,3-triazol-4-yl)methylthio]-7-oxo-1-azabicyclo[3.2.0]hept-2-ene-2-carboxylic acid

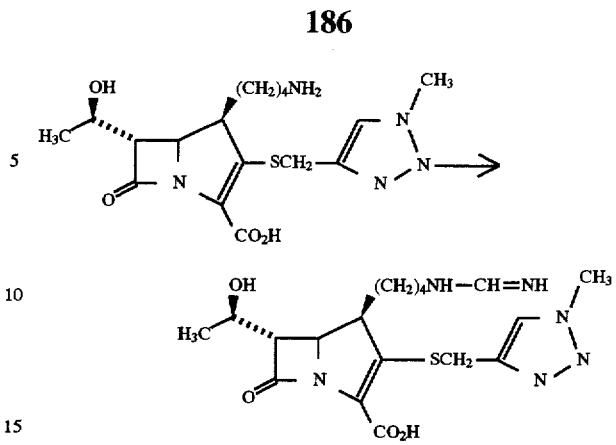

A solution of (4R,5S,6S)-4-(4"-aminobutyl)-6-[(1'R)-1'-hydroxyethyl]-3-[(1-methyl-1,2,3-triazol-4-yl)methylthio]-7-oxo-1-azabicyclo[3.2.0]hept-2-ene-2-carboxylic acid (0.296 g, 0.75 mmol) [prepared in Example 62] in water (30 mL) was treated at 0°–5° C. with benzylformimidate hydrochloride (0.65 g, 3.8 mmol) added in small portions over 10 min while maintaining the pH to 8–8.5 with 1M NaOH. After 30 min, 25 mL of 0.2M pH 6.0 phosphate buffer were added and the resulting mixture was washed with EtOAc (20 mL). The aqueous phase was maintained under vacuum to remove traces of organic solvent and then chromatographed on reversed phase silica gel (µ-Bondapak c-18, 3.5×14 cm). The column was eluted first with a gradient of CH$_3$CN (0–8%) in 0.01M pH 7 phosphate buffer. The UV active fractions were concentrated in vacuo (T<15° C.) and chromatographed again on the same column using water instead of buffer. Lyophilization of the UV active fractions gave 0.21 g (66%) of the title compound as a white amorphous powder:

Purity by HPLC: 98% on µ-Bondapak c-18, 3.9 mm×30 cm, elution 8% CH$_3$CN—H$_2$O, pH 7.4 phosphate buffer, flow rate 1 mL/min, uv detector 304 nm, retention time 6.34 min;

UV (H$_2$O, pH 7.4 phosphate buffer) $\lambda_{max}$: 302 nm (8,586);

IR (KBr) $v_{max}$: 1755 (C=O of β-lactam), 1715 (C=N of formimidoyl) and 1590 cm$^{-1}$ (C=O of carboxylate);

$^1$H NMR (200 MHz, D$_2$O) δ: 1.30 (d, J=6.36 Hz, 3H, CH$_3$CHO), 1.3–1.9 (m, 6H, CH$_2$-1,2 and 3 of butyl), 3.1–3.5 (m, 4H, H-4, H-6 and CH$_2$-4 of butyl overlapping), 4.08 (s, 3H, CH$_3$-1 of triazole), 4.09 (ABq, J$_{AB}$=14.85 Hz, Δv=31.9 Hz, 2H, SCH$_2$), 4.15 (overlapping SCH$_2$ and CH$_3$, 1H, H-5), 4.27 (m, 1H, CH$_3$CHO), 7.8 (broad S, 1H, CH=NH) and 7.87 ppm (s, 1H, H-5 of triazole).

EXAMPLE 71

(4R,5S,6S)-4-(4"-Aminobutyl)-6-[(1'R)-1'-hydroxyethyl]-3-[(2-hydroxyethyl)thio]-7-oxo-1-azabicyclo[3.2.0]hept-2-ene-2-carboxylic acid

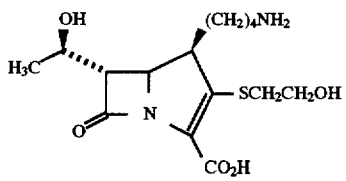

A. Allyl (4R,5S,6S)-4-(4"-azidobutyl)-6-[(1'R)-1'-hydroxyethyl]-3-[(2-hydroxyethyl)thio]-7-oxo-1-azabicyclo[3.2.0]hept-2-ene-2-carboxylate

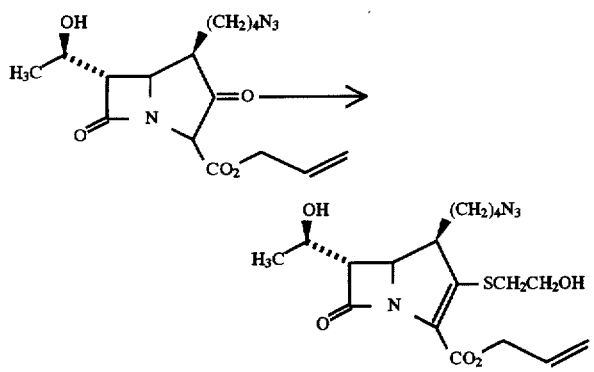

A solution of allyl (4R,5R,6S)-4-(4"-azidobutyl)-6-[(1'R)-1'-hydroxyethyl]-3,7-dioxo-1-azabicyclo[3.2.0]heptane-2-carboxylate (11.8 mmol, prepared by cyclization of 4.47 g, 11.8 mmol of diazo precursor as in Example 45) in dry acetonitrile (50 mL) was cooled to 0°–5° C. and treated with diphenyl chlorophosphate (2.57 mL, 12.4 mmol) and N,N-diisopropylethylamine (2.16 mL, 12.4 mmol) added simultaneously over 5 min. After 1 h, N,N-diisopropylethylamine (2.16 mL, 12.4 mmol) followed by chlorotrimethylsilane (1.57 mL, 12.4 mmol) were added dropwise over 5 min. Then more N,N-diisopropylethylamine (2.16 mL, 12.4 mmol) and 2-mercaptoethanol (1.84 g, 23.5 mmol) were added and the mixture was stirred at 0°–5° C. for 16 h. The reaction mixture was then diluted with ethyl acetate (500 mL), washed with cold water, brine and dried (MgSO$_4$). Evaporation of the solvent gave an oil which was then diluted with tetrahydrofuran (100 mL) and water (20 mL) and treated with acetic acid (2 mL) at 20° C. for 2 h. The solution was diluted again with ethyl acetate, washed with saturated NaHCO$_3$, 0.2M pH 7.0 phosphate buffer and brine. After drying over anhydrous MgSO$_4$, evaporation of the solvent gave an oil which was chromatographed on silica gel (4.5×10 cm). Elution with a mixture of toluene and ethyl acetate (1:1) gave 2.56 g (52%) of the title compound as an oil:

IR (NaCl, film) $v_{max}$: 2100 (N$_3$), 1765 (C=O of β-lactam) and 1705 cm$^{-1}$ (C=O of ester);

$^1$H NMR (200 MHz, CDCl$_3$) δ: 1.38 (d, J=6.29 Hz, 3H, C$\underline{H}_3$CHO), 1.3–2.0 (m, 6H, CH$_2$-1,2 and 3 of butyl), 2.8–3.2 (m, 2H, SC$\underline{H}_2$CH$_2$OH), 3.18 (dd, J$_{H6,H5}$=2.60 Hz, J$_{H6,H1}$=7.18 Hz, 1H, H-6), 3.3 (m, 3H, CH$_2$N$_3$ and H'-4 overlapping), 3.82 (t, J=6.0 Hz, 2H, SCH$_2$C$\underline{H}_2$OH), 4.1–4.3 (m, 2H, H-5 and CH$_3$C$\underline{H}$O overlapping), 4.75 (m, 2H, CH$_2$ of allyl), 5.2–5.5 and 5.9–6.1 ppm (2×m, 2H and 1H, CH of allyl).

B. (4R,5S,6S)-4-(4"-Aminobutyl)-6-[(1'R)-1'-hydroxyethyl]-3-[(2-hydroxyethyl)thio]-7-oxo-1-azabicyclo[3.2.0]hept-2-ene-2-carboxylic acid

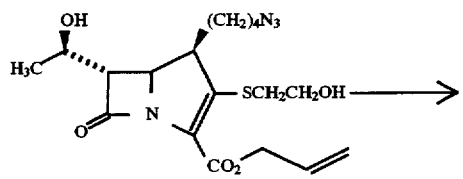

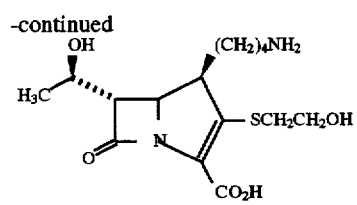

A solution of allyl (4R,5S,6S)-4-(4"-azidobutyl)-6-[(1'R)-1'-hydroxyethyl]-3-[(2-hydroxyethyl)thio]-7-oxo-1-azabicyclo[3.2.0]hept-2-ene-2-carboxylate (2.56 g, 6.2 mmol) in dry ethyl acetate (60 mL) was treated at 22° C. and under nitrogen, with tetrakis(triphenylphosphine)palladium [0] (0.15 g) and 1.25 g (6.9 mmol) of potassium 2-ethylhexanoate. After 2 h, the reaction mixture was extracted with cold water (3×50 mL) and the combined aqueous phase was chromatographed on reversed phase silica gel (μBondapak C$_{18}$, 3×13 cm, elution 5% CH$_3$CN—H$_2$O). The intermediate potassium salt (1.4 g) was then hydrogenated at 0°–5° C. in water (200 mL) over 2.0 g of 5% palladium on alumina under 45 psi of hydrogen for 45 min. After the addition of 60 mL of 0.2M pH 6.0 phosphate buffer, the catalyst was filtered and the filtrate was chromatographed on reversed phase silica gel (μBondapak C$_{18}$, 3×13 cm). Elution with a gradient of acetonitrile (0–5%) in water gave 0.689 g (32%) of the title compound as a white amorphous solid after freeze drying: [α]$_D^{24}$+74.00 (c 1.0, H$_2$O);

Purity by HPLC: 99% on μBondapak C$_{18}$, 3.9 mm×30 cm, elution with pH 7.4 phosphate buffer, flow rate 1 mL/min, retention time (9.68 min);

UV (H$_2$O, pH 7.4 phosphate buffer) $\lambda_{max}$: 304 nm (7.616);

IR (KBr) $v_{max}$: 1750 (C=O of β-lactam) and 1585 cm$^{-1}$ (C=O of carboxylate);

$^1$H NMR (200 MHz, D$_2$O): 1.33 (d, J=6.38 Hz, 3H, C$\underline{H}_3$CHO) 1.3–1.9 (m, 6H, CH$_2$-1,2 and 3 of butyl), 2.8–3.1 (m, 2H, SC$\underline{H}_2$CH$_2$OH), 3.02 (t, J=7.6 Hz, 2H, C$\underline{H}_2$NH$_2$), 3.36 (m, 2H, H-4 and H-6 overlapping), 3.77 (t, J=6.2 Hz, 2H, SCH$_2$C$\underline{H}_2$OH), 4.22 (dd, J$_{H5,H6}$=2.43 Hz, 1H, H-5) and 4.26 ppm (m, overlapping with H-5, 1H, CH$_3$C$\underline{H}$O).

EXAMPLE 72

(4R,5S,6S)-3-[(2-Cyanoethyl)thio]-4-(4"-quanidinobutyl)-6-[(1'R)-1'-hydroxyethyl]-7-oxo-1-azabicyclo[3.2.0]hept-2-ene-2-carboxylic acid

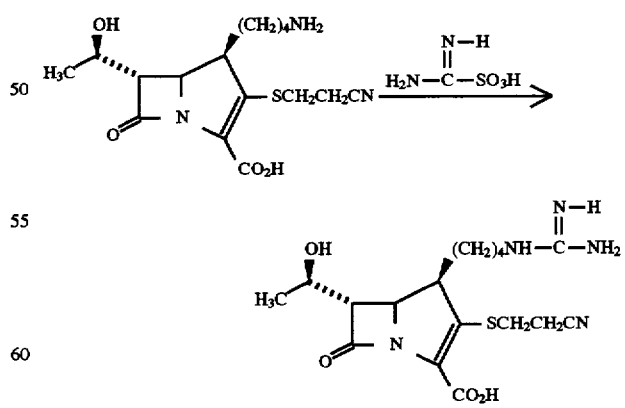

A solution of (4R,5S,6S)-4-(4"-aminobutyl)-3-[(2-cyanoethyl)thio]-6-[(1'R)-1'-hydroxyethyl]-7-oxo-1-azabicyclo [3.2.0]hept-2-ene-2-carboxylic acid (0.300 g, 0.85 mmol) [prepared in Example 17] in cold (0°–5° C.)

water (20 mL) was adjusted to pH 8.0 with 1M NaOH and then treated with aminoiminomethanesulfonic acid (0.35 g, 2.8 mmol) [K. Kim et al., *Tetrahedron Lett.*, 29, 3183 (1988)] added in small portions over 5 min. The pH was maintained at 8–8.5 with 1M NaOH during the addition and for two hours. Then 10 mL of pH 6.0 0.2M phosphate buffer were added and the solution was chromatographed on reversed phase silica gel (μ-Bondapak c-18, 2.5×14 cm). Elution with a gradient of acetonitrile (0–5%) in water gave 0.257 (77%) of the title compound as a white amorphous powder after freeze drying: $[\alpha]_D^{22}$+45.5° (c 1.0, $H_2O$);

Purity by HPLC: 99% on μ-Bondapak c-18, 3.9 mm×30 cm, elution 5% $CH_3CN$—$H_2O$, pH 7.4 phosphate buffer, flow rate 1 mL/min, uv detector 300 nm, retention time 11.1 min;

UV ($H_2O$, pH 7.4 phosphate buffer) $\lambda_{max}$: 302 nm (8,676);

IR (KBr) $v_{max}$: 2250 (weak CN), 1755 (C=O of β-lactam), 1665 (C=N of guanidyl) and 1685 $cm^{-1}$ (C=O of carboxylate);

$^1$H NMR (200 MHz, $D_2O$) δ: 1.32 (d, J=6.39 Hz, 3H, C$\underline{H}_3$CHO), 1.3–1.9 (m, 6H, $CH_2$-1,2 and 3 of butyl), 2.8–3.3 (m, 4H, SC$\underline{H}_2$C$\underline{H}_2$CN), 3.22 (t, J=6.5 Hz, C$\underline{H}_2$NH), 3.36 (dd, $J_{H6,H5}$=2.34 Hz, $J_{H6,H1}$=6.22 Hz, 1H, H-6), 3.4 (overlapping with H-6, 1H, H-4) and 4.2–4.4 ppm (m, 2H, H-5 and CH$_3$C$\underline{H}$O overlapping).

EXAMPLE 73

(4R,5S,6S)-3-[(2-Cyanoethyl)thio]-4-(2"-guanidinoethyl)-6-[(1'R)-1'-hydroxyethyl]-7-oxo-1-azabicyclo[3.2.0]hept-2-ene-2-carboxylic acid

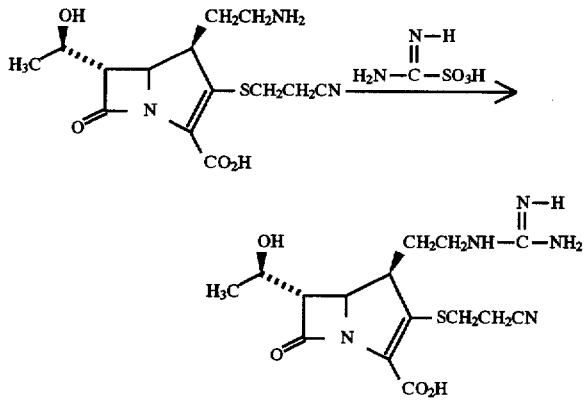

A solution of (4R,5S,6S)-4-(2"-aminoethyl)-3-[(2-cyanoethyl)thio]-6-[(1'R)-1'-hydroxyethyl]-7-oxo-1-azabicyclo[3.2.0]hept-2-ene-2-carboxylic acid (0.185 g, 0.57 mmol) [prepared in Example 36] in cold (0°–5° C.) water (20 mL) was treated with aminoiminomethanesulfonic acid (0.35 g, 2.8 mmol) [K. Kim et al., *Tetrahedron Lett.*, 29, 3183 (1988)] added in small portions over 5 min while maintaining the pH to 8–8.5 with 1M NaOH. The pH was maintained between 8 and 8.5 over 1 h and the reaction mixture was then quenched by addition of 5 mL of 0.2M pH 6.0 phosphate buffer. The solution was chromatographed on reversed phase silica gel (μ-Bondapak c-18, 2.5×14 cm) using a gradient of acetonitrile (0–2%) in water as eluent. Lyophilization of the UV active fractions gave 0.035 g (17%) of the title compound as a white amorphous powder after freeze drying:

Purity by HPLC: 99% on μ-Bondapak c-18, 3.9 mm/30 cm, elution 2% $CH_3CN$—$H_2O$, pH 7.4 phosphate buffer, flow rate 1 mL/min, UV detector 300 nm, retention time 5.98 min;

UV ($H_2O$, pH 7.4 phosphate buffer) $\lambda_{max}$: 300 nm (7,483);

IR (KBr) $v_{max}$: 2255 (weak CN), 1755 (C=O of β-lactam), 1660 (C=N of guanidine) and 1590 $cm^{-1}$ (C=O of carboxylate);

$^1$H NMR (200 MHz, $D_2O$) δ: 1.34 (d, J=6.34 Hz, 3H, C$\underline{H}_3$CHO), 1.7–2.3 (m, 2H, $CH_2$-1 of guanidinoethyl), 2.7–3.4 (m, 7H, SC$\underline{H}_2$C$\underline{H}_2$CN, $CH_2$-2 of guanidinoethyl and H-4), 3.45 (dd, $J_{H6,H5}$=2.69 Hz, $J_{H6,H1}$=6.8 Hz, 1H, H-6) and 4.3 ppm (m, 2H, H-5 and CH$_3$C$\underline{H}$O overlapping).

EXAMPLE 74

(4R,5S,6S)-4-(N-Formimidoyl-4"-aminobutyl)-6-[(1'R)-1'-hydroxyethyl]-3-[(2-hydroxyethyl)thio]-7-oxo-1-azabicyclo[3.2.0]hept-2-ene-2-carboxylic acid

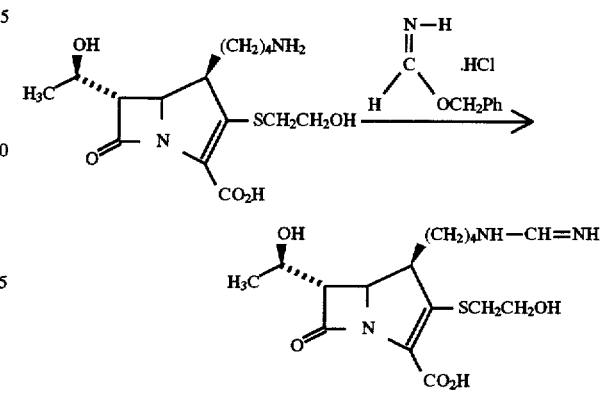

A solution of (4R,5S,6S)-4-(4"-aminobutyl)-6-[(1'R)-1'-hydroxyethyl]-3-[(2-hydroxyethyl)thio]-7-oxo-1-azabicyclo-[3.2.0]hept-2-ene-2-carboxylic acid (0.205 g, 0.59 mmol) in water (20 mL) at 0°–5° C. was adjusted to pH 8.5 with 1M NaOH. Then benzyl formimidate hydrochloride (0.39 g, 2.27 mmol) was added in small portions (10 min) while maintaining the pH to 8–8.5 with 1M NaOH. After 15 min, the reaction mixture was quenched by the addition of 10 mL of 0.2M pH 6.0 phosphate buffer and washed with ethyl acetate (20 mL). The aqueous phase was then chromatographed on reversed phase silica gel (μBondapak $C_{18}$, 2×14 cm) using a gradient of acetonitrile (0–2%) in 0.02M pH 7.0 phosphate buffer as eluent. The UV active fractions were combined, concentrated to 50 mL and desalted on the same column using water instead of buffer. Lyophilization of the UV active fractions gave 0.154 g (69%) of the title compound as a white amorphous solid: $[\alpha]_D^{24}$+67.0° (c 1.0, $H_2O$);

Purity by HPLC: 99% on μBondapak $C_{18}$, 3.9 mm×30 cm, elution 2% $CH_3CN$—$H_2O$, pH 7.4 phosphate buffer, flow rate 1 mL/min, uv detector 300 nm, retention time 10.2 min;

UV ($H_2O$, pH 7.4 phosphate buffer) $\lambda_{max}$: 304 nm (10, 105);

IR (KBr) $v_{max}$: 1750 (C=O of β-lactam), 1715 (C=N of formimidoyl) and 1590 $cm^{-1}$ (C=O of carboxylate);

$^1$H NMR (200 MHz, $D_2O$) δ: 1.32 (d, J=6.37 Hz, 3H, C$\underline{H}_3$CHO), 1.3–1.9 (m, 6H, $CH_2$-1,2 and 3 of butyl), 2.8–3.1 (m, 2H, SC$\underline{H}_2$CH$_2$OH), 3.3–3.5 (m, 4H, H-4, H-6 and C$\underline{H}_2$NH overlapping), 3.77 (t, J=6.21 Hz, 2H, SCH$_2$C$\underline{H}_2$OH), 4.21 (dd, $J_{H5,H6}$=2.25 Hz, 1H, H-5), 4.26 (m overlapping with H-5, 1H, CH$_3$C$\underline{H}$O), and 7.78 ppm (broad s, 1H, C$\underline{H}$=NH).

EXAMPLE 75

(4R,5S,6S)-4-(4"-Aminobutyl)-6-[(1'R)-1'-hydroxyethyl]-3-[(1-N-methylimidazol-5-yl)methylthio]-7-oxo-1-azabicyclo-[3.2.0]hept-2-ene-2-carboxylic acid A. Allyl (4R,5S,6S)-4-(4"-azidobutyl)-6-[(1'R)-1'-hydroxyethyl]-3-[(1-N-methylimidazol-5-yl)methylthio]-7-oxo-1-azabicyclo[3.2.0]hept-2-ene-2-carboxylate

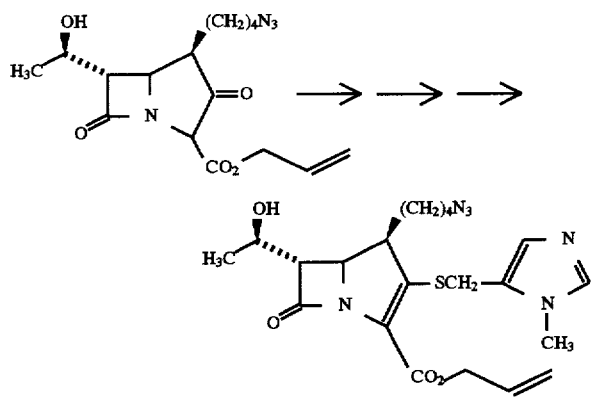

A solution of allyl (4R,5R,6S)-4-(4"-azidobutyl)-6-[(1'R) 1'-hydroxyethyl]-3,7-dioxo-1-azabicyclo[3.2.0]heptane-2-carboxylate (5.28 mmol, prepared by cyclization of 2.0 g, 5.28 mmol of the diazo precursor as in Example 45) in dry $CH_3CN$ (40 mL) was treated at 0°–5° C. and under nitrogen with diphenyl chlorophosphate (1.2 mL, 5.8 mmol) and N,N-diisopropylethylamine (1.0 mL, 5.8 mmol) added simultaneously over 5 min. A small crystal of 4-N,N-dimethylaminopyridine was then added and the mixture was stirred for 40 min. More N,N-diisopropylethylamine (1.84 mL, 10.6 mmol) was added, followed by 5-mercaptomethyl-1-N-methyl imidazole (1.35 g, 10.5 mmol) in dry $CH_3CN$ (3 mL). After 3 h, the reaction mixture was diluted with ethyl acetate, washed with water, saturated $NaHCO_3$, brine and dried ($MgSO_4$). After evaporation of the solvent, the residue was chromatographed on silica gel (4.5×10 cm) using a mixture of ethyl acetate, $CH_3CN$ and acetone (8:1:1 to 4:3:3) as eluent. Evaporation of the UV active fractions gave 1.86 g (76%) of the title compound as an oil:

IR (NaCl, film) $v_{max}$: 2100 ($N_3$), 1770 (C=O of β-lactam) and 1710 cm$^{-1}$ (C=O of ester);

$^1$H NMR (200 MHz, CDCl$_3$) δ: 1.38 (d, J=6.25 Hz, 3H, C$\underline{H_3}$CHO), 1.4–1.9 (m, 6H, CH$_2$-1,2 and 3 of butyl), 3.17 (dd, $J_{H5,H6}$=2.72 Hz, $J_{H3,H4}$=7.36 Hz, 1H, H-6), 3.2 (m, 1H, H-4) 3.32 (t, J=6.0 Hz, 2H, CH$_2$N$_3$), 3.68 (s, 3H, CH$_3$-1 of imidazole), 4.02 (ABq, J$_{AB}$=14.3 Hz, Δv=33.0 Hz, 2H, SCH$_2$), 4.1–4.3 (m, 2H, H-5 and CH$_3$C$\underline{HO}$), 4.74 (m, 2H, CH$_2$ of allyl), 5.2–5.5 and 5.9–6.1 (2×m, 2H and 1H, CH of allyl), 6.93 (s, 1H, H-4 of imidazole), and 7.42 ppm (s, 1H, H-2 of imidazole).

B. (4R,5S,6S)-4-(4"-Aminobutyl)-6-[(1'R)-1'-hydroxyethyl]-3-[(1-N-methylimidazol-5-yl)methylthio]-7-oxo-1-azabicyclo[3.2.0]hept-2-ene-2-carboxylic acid

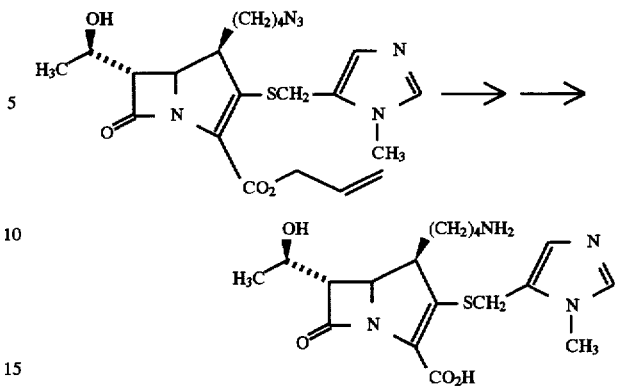

A solution of allyl (4R,5S,6S)-4-(4"-azidobutyl)-6-[(1'R)-1'-hydroxyethyl]-3-[(1-N-methylimidazol-5-yl)methylthio]-7-oxo-1-azabicyclo[3.2.0]hept-2-ene-2-carboxylate (1.86 g, 4.04 mmol) in ethyl acetate (75 mL) was treated at 22° C. and under nitrogen with tetrakis(triphenylphosphine) palladium [0] (0.075 g) and 8.9 mL (4.45 mmol) of a 0.5M solution of potassium 2-ethylhexanoate in ethyl acetate. After 45 min, the reaction mixture was extracted with water (2×75 mL) and the combined aqueous phase was maintained under vacuum to remove traces of organic solvent. The aqueous solution was then hydrogenated at 0°–5° C. over 5% palladium on alumina (2.1 g) under 45 psi of hydrogen for 1 h. Then 30 mL of 0.2M pH 6.0 phosphate buffer were added and the catalyst was filtered. The filtrate was chromatographed twice on reversed phase silica gel (µBondapak $C_{18}$, 3.5×11 cm) using a gradient of acetonitrile (0–8%) in water as eluent. Lyophilization of the UV active fractions gave 0.528 g (33%) of the title compound as a white amorphous powder: $[\alpha]_D^{22}$ –22.4° (c 1.0, H$_2$O);

Purity by HPLC: 97.3% on µBondapak $C_{18}$, 3.9 mm×30 cm, elution 8% $CH_3CN$—$H_2O$ pH 7.4 phosphate buffer, flow rate 1 mL/min, uv detector 302 nm, retention time 5.88 min;

UV (water, pH 7.4 phosphate buffer) $\lambda_{max}$: 302 nm (7,569);

IR (KBr) $v_{max}$: 1755 (C=O of β-lactam) and 1585 cm$^{-1}$ (C=O of carboxylate);

$^1$H NMR (200 MHz, D$_2$O) δ: 1.31 (d, J=6.35 Hz, 3H, C$\underline{H_3}$CHO), 1.3–1.8 (m, 6H, CH$_2$-1,2 and 3 of butyl), 2.99 (t, J=7.6 Hz, 2H, C$\underline{H_2}$NH$_2$), 3.22 (broad t, 1H, H-4), 3.33 (dd, $J_{H6,H5}$=2.56 Hz, $J_{H6,H1}$=6.34 Hz, 1H, H-6), 3.71 (s, 3H, CH$_3$-1 of imidazole), 4.07 (ABq, J$_{AB}$=14.8 Hz, Δv=38.45 Hz, 2H, SCH$_2$), 4.13 (dd overlapping with SCH$_2$, $J_{H5,H6}$=2.56 Hz, 1H, H-5), 4.24 (m, 1H, CH$_3$C$\underline{HO}$), 6.94 (s, 1H, H-4 of imidazole) and 7.66 ppm (s, 1H, H-2 of imidazole).

EXAMPLE 76

(4R,5S,6S)-4-(3"-Aminopropyl)-3-[(2-carbamoylethyl)thio]-6-[(1'R)-1'-hydroxyethyl]-7-oxo-1-azabicyclo[3.2.0]hept-2-ene-2-carboxylic acid

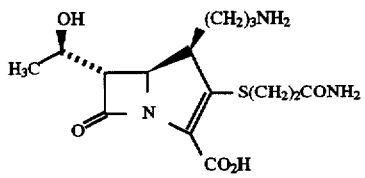

A. Allyl (4R,5S,6S)-4-(3"-azidopropyl)-3-[(2-carbamoylethyl)-thio]-6-[(1'R)-1'-hydroxyethyl]-7-oxo-1-azabicyclo[3.2.0]hept-2-ene-2-carboxylate

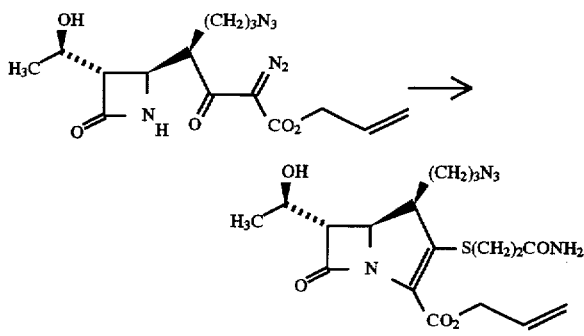

A cold (ice-MeOH bath) of allyl (2R,4R,5R,6 S)-4-(3"-azidopropyl)-6-[(1'R)-1'-hydroxyethyl]-3,7- dioxo-1-azabicyclo[3.2.0]heptane-2-carboxylate, freshly prepared from (3S,4R)-3-[(1'R)-1'-hydroxyethyl]-4-[(1" R)-1"-(3-azidopropyl)- 3"-diazo-3"-allyloxycarbonyl-2"-oxopropyl]azetidin- 2-one (2.00 g, 5.49 mmol) in $CH_3CN$ (50 mL) was treated dropwise with diphenylchlorophosphate (1.3 mL, 6.0 mmol), N,N-diisopropylethylamine (1.1 mL, 6.0 mmol) and a trace of 4-dimethylaminopyridine (10 mg). The mixture was stirred for 1 h and treated with a solution of 2-carbamoylethane thiol (1.16 g, 11.0 mmol) in DMF (5 mL) and N,N-diisopropylethylamine (2.0 mL, 11 mmol). The mixture was stirred for 20 h (cold room). The mixture was treated again with the thiol (580 mg, 5.5 mmol) and N,N-diisopropylethylamine and was stirred for 72 h. It was diluted with ethyl acetate (200 mL), washed with water (2×100 mL), 1M aqueous $NaHCO_3$ (1×100 mL), water (3×100 mL), brine (100 mL) and dried ($MgSO_4$). The residue (2.6 g) was passed through silica gel flash column (75 g, ethyl acetate→acetone) to give the title compound (0.84 g, 36%) as an oil;

IR ($CH_2Cl_2$) $v_{max}$: 3680 3600, 3520, 3410 (OH and $NH_2$) 2100 $N_3$, 1775, 1710, 1690 and 1675 cm$^{-1}$ (C=O);

$^1$H NMR (CDCl$_3$, 200 MHz) δ: 6.03–5.89 (1H, m vinylicH), 5.7, 5.6 (2H, bd, $NH_2$), 5.22 (2H, m, vinylic-H), 4.9–4.6 (2H, m, allylic-$CH_2$), 4.266 (1H, dd, J=2.6 Hz, J=7.5 Hz, H-5), 3.6–3.27 (3H, m, $CH_2N_3$ and H-4), 3.251 (1H, dd, J=2.7 Hz, J=7.2 Hz, H-6), 3.23–2.95 (2H, m, $SCH_2$), 2.6–2.45 (2H, m, $CH_2CON$), 2.25 (1H, bs, OH), 1.95–1.5 (4H, m, $CH_2$—$CH_2$-4) and 1.373 ppm (3H, d, J=6.2 Hz, $CH_3$).

B. (4R,5S,6S)-4-(3"-Aminopropyl)-3-[(2-carbamoylethyl)thio]-6-[(1'R)-1'-hydroxyethyl]-7-oxo-1-azabicyclo-[3.2.0]hept-2-ene-2-carboxylic acid

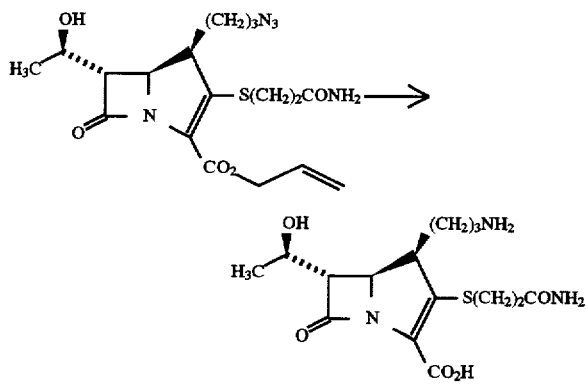

A cold (ice bath) solution of allyl (4R,5S,6 S)-4-(3"-azidopropyl)-3-[(2-carbamoylethyl)thio]-6-[(1' R)-1'-hydroxyethyl]-7-oxo-1-azabicyclo[3.2.0]hept-2-ene-2-carboxylate (0.84 g, 2.0 mmol) in $CH_2Cl_2$ (20 mL) was treated with Pd(PPh$_3$)$_4$ and dropwise with a 0.5M solution of sodium ethyl-2-hexanoate in ethyl acetate (4.2 mL, 2.1 mmol). The mixture was stirred for 45 min, then diluted with ethyl acetate (75 mL) and extracted with ice cold water (1×50 mL and 2×25 mL). The aqueous extracts were combined, washed with diethyl ether and shaken at 5° C. (ice bath) at 45–50 psi hydrogen for 90 min in a Parr hydrogenator using 5% Pd/Alumina (800 g) as catalyst. The pH of the solution was adjusted to 6.9 with a 1M aqueous $KH_2PO_4$ solution. The catalyst was removed by filtration and the aqueous layer was passed through a µBondapak $C_{18}$ reversed phase column (160 g, $H_2O$→4% $CH_3CN/H_2O$) to give the title compound (340 mg, 48%) as a lyophilized powder;

Purity: 94.7% (304 nm, HPLC);

UV ($H_2O$) $\lambda_{max}$: 302 (ε9260);

IR (Nujol) $v_{max}$: 3600–3100 (OH, $NH_2$); 1750–1665 and 1600 cm$^{-1}$ (C=O);

$^1$H NMR ($D_2O$, 200 MHz) δ: 4.35–4.21 (1H, m, H-1'), 4.239 (1H, dd, J=2.6 Hz, J=5.3 Hz, H-5), 3.45–3.36 (1H, m, H-4), 3.385 (1H, dd, J=2.6 Hz, J=6.6 Hz, H-6), 3.2–2.8 (4H, m, $CH_2N$ and $SCH_2$), 2.63–5.55 (2H, m, $CH_2CO$), 2.0–1.45 (4H, m, $(CH_2)_2$-4) and 1.331 ppm (3H, d, J=6.4 Hz, $CH_3$).

EXAMPLE 77

(4R,5S,6S)-4-(4"-N-Formimidoylaminobutyl)-6-[(1'R)-1'-hydroxyethyl]-3-[(1-N-methylimidazol-5-yl)methylthio]-7-oxo-1-azabicyclo[3.2.0]hept-2-ene-2-carboxylic acid

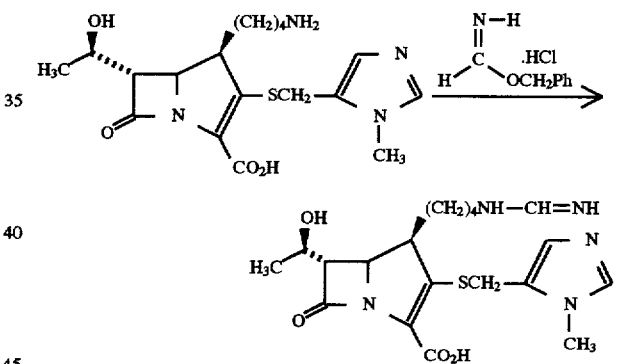

A solution of (4R,5S,6S)-4-(4"-aminobutyl)-6-[(1'R)-1'-hydroxyethyl]-3-[(1-N-methylimidazol-5-yl)methylthio]-7-oxo-1-azabicyclo[3.2.0]hept-2-ene-2-carboxylic acid (0.269 g, 0.68 mmol) in water (30 mL) at 0°–5° C. was adjusted to pH 8.5 with 1M NaOH. Then benzyl formimidate hydrochloride (0.60 g, 3.49 mmol) was added in small portions while maintaining the pH to 8–8.5 with 1M NaOH. After 30 min, the reaction mixture was quenched by addition of 25 mL of 0.2M pH 6.0 phosphate buffer and washed with ethyl acetate. The aqueous phase was then chromatographed on reversed phase silica gel (3.5×12 cm) using a gradient of acetonitrile (0–8%) in 0.01M pH 7.0 phosphate buffer as eluent. The UV active fractions were combined, concentrated and desalted on the same column by eluting with water and acetonitrile. Lyophilization of the UV active fractions gave 0.180 g (63%) of the title compound as a white amorphous powder: $[\alpha]_D^{22}$–23.1° (c 1.0, water);

Purity by HPLC: 97.6% on µBondapak $C_{18}$, 3.9 mm×30 cm, elution 8% $CH_3CN$—$H_2O$ pH 7.4 phosphate buffer, flow rate 1 mL/min, uv detector 302 nm, retention time 9.45 min;

IR (KBr) $v_{max}$: 1750 (C=O of β-lactam), 1715 (C=N of formimidoyl) and 1590 cm$^{-1}$ (C=O of carboxylate);

$^1$H NMR (200 MHz, D$_2$O) δ: 1.30 (d, J=6.34 Hz, 3H, CH$_3$CHO), 1.3–1.8 (m, 6H, CH$_2$-1,2 and 3 of butyl), 3.2–3.5 (m, 4H, H-4, H-6 and CH$_2$N), 3.71 (s, 3H, CH$_3$-1 of imidazole), 4.08 (ABq, J$_{AB}$=14.68 Hz, Δv=37.4 Hz, 2H, SCH$_2$), 4.14 (dd overlapping with SCH$_2$, J$_{5,6}$=2.43 Hz, J$_{H5,H4}$=9.38 Hz, 1H, H-5), 4.24 (m, 1H, CH$_3$CHO), 6.93 (s, 1H, H-4 of imidazole), 7.62 (s, 1H, H-2 of imidazole) and 7.79 ppm (s, 1H, CH=NH).

EXAMPLE 78

(4R,5S,6S)-4-(4"-Guanidinobutyl)-6-[(1'R)-1'-hydroxyethyl]-3-[(pyridin-4-yl)methylthio]-7-oxo-1-azabicyclo[3.2.0]hept-2-ene-2-carboxylic acid

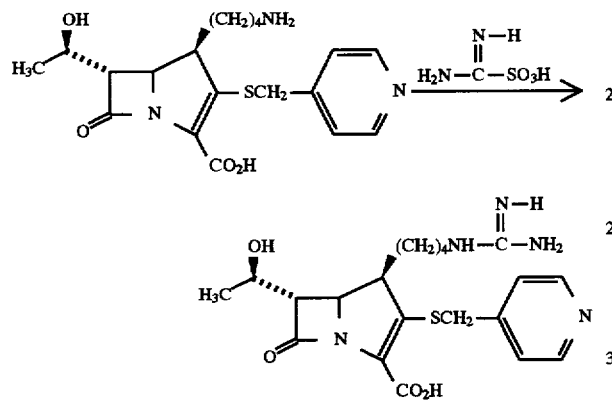

A solution of (4R,5S,6S)-4-(4"-aminobutyl)-6-[(1'R)-1'-hydroxyethyl]-3-[(pyridin-4-yl)methylthio]-7-oxo-1-azabicyclo[3.2.0]hept-2-ene-2-carboxylic acid (0.134 g, 0.34 mmol) in 15 mL of cold water (pH 6.4), was adjusted to pH 8.0 with 1M NaOH. Then 0.170 g (1.36 mmol) of aminoiminomethanesulfonic acid [K. Kim et al., Tet. Lett., 29, 3183 (1988)] was added in small portions over 5 min while maintaining the pH at 8 with 1M NaOH. Three more portions of aminoiminomethanesulfonic acid (3×0.050 g) were added at 30 min intervals and the resulting mixture (some insoluble material) was stirred for a total of 3 h at 0°–5° C. The pH was maintained throughout at 8 with 1M NaOH. Then 15 mL of 0.2M pH 6.0 phosphate buffer was added and the resulting homogeneous solution was chromatographed on reverse phase silica gel (μBondapak C$_{18}$, 2.5×14 cm). Elution with a gradient of acetonitrile (0–10%) in water gave 0.103 g (69%) of the title compound as a white amorphous powder after freeze drying. This lyophilized material is only slightly soluble in water:

Purity by HPLC: 99% on μ-Bondapak c-18, 3.9 mm×30 cm, elution 10% CH$_3$CN—H$_2$O pH 7.4 phosphate buffer, flow rate 1.5 mL/min, UV detector 300 nm, retention time 7.47 min;

UV (H$_2$O, pH 7.4 phosphate buffer) λ$_{max}$: 262 (5,360) and 304 nm (8,765);

IR (KBr) $v_{max}$: 1752 (C=O of β-lactam), 1665 (C=N of guanidine), 1600 cm$^{-1}$ (C=O of carboxylate);

$^1$H NMR (200 MHz, D$_2$O) δ: 1.27 (d, J=6.33 Hz, 3H, CH$_3$CHO), 1.1–1.7 (m, 6H, CH$_2$-1,2,3 of butyl), 3.1 (m, 1H, H-4), 3.15 (t, J=6.4 Hz, 2H, CH$_2$N), 3.26 (dd, J$_{H6,H5}$=2.45 Hz, J$_{H6,H1}$=6.06 Hz, 1H, H-6), 4.05 (ABq, J$_{AB}$=14.76 Hz, Δv=22.9 Hz, 2H, SCH$_2$), 4.05 (overlapping with SCH$_2$, 1H, H-5), 4.21 (m, 1H, CH$_3$CHO), 7.47 (d, J=6.2 Hz, 2H, H-3 of pyridine) and 8.47 ppm (d, J=6.2 Hz, 2H, H-2 of pyridine).

EXAMPLE 79

(4R,5S, 6S )-4-(3"-Aminopropyl)-6-[(1'R)-1'-hydroxyethyl] -3-[(1-N-methylimidazol-5-yl)-methylthio ]-7-oxo-1-azabicyclo-[3.2.0]hept2-ene-2-carboxylic acid

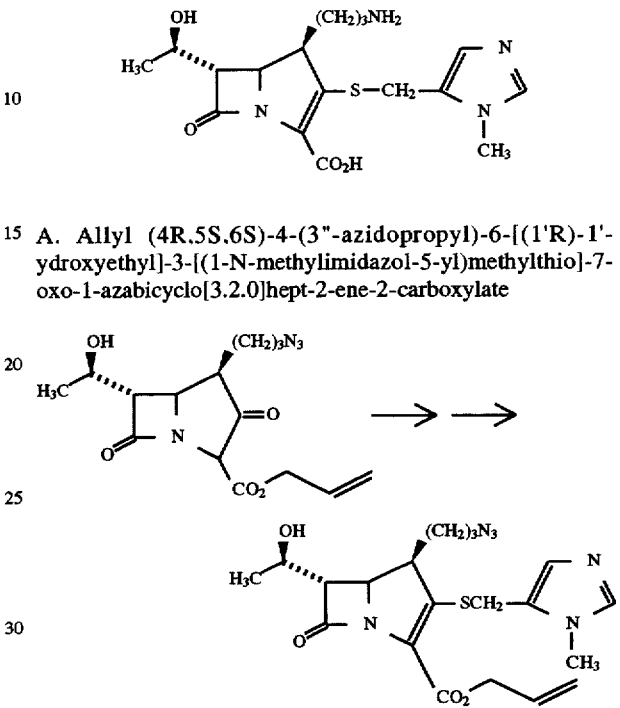

A. Allyl (4R,5S,6S)-4-(3"-azidopropyl)-6-[(1'R)-1'-ydroxyethyl]-3-[(1-N-methylimidazol-5-yl)methylthio]-7-oxo-1-azabicyclo[3.2.0]hept-2-ene-2-carboxylate A solution of allyl (4R,6S)-4-(3"-azidopropyl)-6-[(1'R)-1'-hydroxyethyl]-3,7-dioxo-1-azabicyclo[3.2.0]heptane-2-carboxylate (5 mmol, prepared by cyclization of 1.82 g, 5 mmol of the diazo precursor) in dry CH$_3$CN (75 mL) was treated at 0°–5° C. and under nitrogen with diphenyl chlorophosphate (1.14 mL, 5.5 mmol) and N,N-diisopropylethylamine (0.96 mL, 5.5 mmol). A small crystal of 4-N,N-dimethylaminopyridine was then added and the mixture was stirred for 1 h. A solution of 5-mercaptomethyl-1-N-methyl imidazole (1 g, 7.5 mmol) in dry CH$_3$CN (1 mL) was added followed by N,N-diisopropylethylamine (1.3 mL, 7.5 mmol). After 3 h, the reaction mixture was diluted with EtOAc (150 mL), washed with water, saturated NaHCO$_3$, brine and dried (MgSO$_4$). After evaporation of the solvent, the residue was chromatographed on silica gel (3.5×6.5 cm) using a gradient of CH$_3$CN in EtOAc (25:75→100:0) as eluent then acetone. Fractions which contained the desired compound are combined and concentrated under vacuum to give 1.29 g (58%) of the title compound as an oil:

IR (NaCl, film) $v_{max}$: 2100 (N$_3$) 1775 (C=O of β-lactam) and 1710 cm$^{-1}$ (C=O of ester);

$^1$H NMR (200 MHz, CDCl$_3$) δ: 1.38 (d, J=6.24 Hz, 3H, CH$_3$CHO), 1.4–2.0 (m, 4H, CH$_2$-1 and 2 of propyl), 3.23 (dd, J$_{H5,H6}$=2.69 Hz, J$_{H3,H4}$=7.73 Hz, 1H, H-6), 3.3–3.4 (m, 3H, H-4 and CH$_2$—N$_3$ overlapping), 3.70 (s, 3H, CH$_3$-1 of imidazol), 4.05 (ABq, 2H, SCH$_2$), 4.1–4.3 (m, 2H, H-5 and CH$_3$CHO), 4.75 (m, 2H, CH$_2$ of allyl), 5.2–5.5 and 5.9–6.1 (2×m, 2H and 1H, CH of allyl), 6.94 (s, 1H, H-4 of imidazol), and 7.45 ppm (s, 1H, H-2 of imidazol).

B. (4R,5S,6S)-4-(3"-Aminopropyl)-6-[(1'R)-1'-hydroxyethyl]-3-[(1-N-methylimidazol-5-yl)methylthio]-7-oxo-1-azabicyclo[3.2.0]hept-2-ene-2-carboxylic acid

197

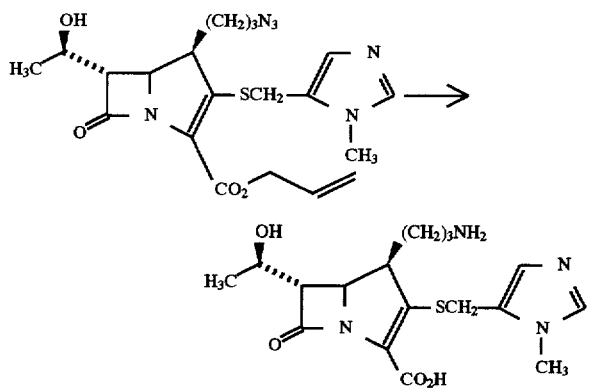

A solution of allyl (4R,5S,6S)-4-(3"-azidopropyl)-6-[(1'R)-1'-hydroxyethyl]-3-[(1-N-methylimidazol-5-yl)methylthio]-7-oxo-1-azabicyclo[3.2.0]hept-2-ene-2-carboxylate (1.25 g, 2.8 mmol) in ethyl acetate (35 mL) was treated at 0°–5° C. and under nitrogen with tetrakis (triphenylphosphine)palladium [0] (0.275 g) and sodium 2-ethylhexanoate (0.450 g). The cold bath was removed and the reaction mixture was stirred at 22° C. for 1 h. Then the reaction mixture was extracted with water (3×60 mL) and the combined aqueous phase was maintained under vacuum to remove traces of organic solvent. The aqueous solution was then hydrogenated at 0°–5° C. over 5% palladium on alumina (1.25 g) under 50 psi of hydrogen for 3 h. The catalyst was filtered, the pH adjusted to 6.2 with 2N HCl. The resulting filtrate was concentrated to about 50 mL and was chromatographed twice on reversed phase silica gel (μBondapak C$_{18}$, 3.5×14 cm) using a gradient of acetonitrile (0–5%) in water eluent. Lyophilization of pure fractions (checked by reversed phase-TLC) gave 0.39 g (38%) of the title compound as an off-white amorphous powder.

Purity by HPLC: 97.8% on μBondapak C$_{18}$, 3.9 mm×30 cm, elution with 8% CH$_3$CN—H$_2$O pH 7.4 phosphate buffer, flow rate 1 mL/min, uv detector 300 nm, retention time 5.00 min;

UV (H$_2$O) λ$_{max}$: 300 nm (7396);

IR (KBr) ν$_{max}$: 1755 (C=O of β-lactam) and 1590 cm$^{-1}$ (C=O of carboxylate);

$^1$H NMR (200 MHz, D$_2$O) δ: 1.31 (d, J=6.36 Hz, 3H, CH$_2$CHO), 1.3–1.9 (m, 3H, CH$_2$-1,2 of propyl), 2.99 (t, J=7.15, 2H, CH$_2$NH$_2$), 3.25 (broad t, 1H, H-4), 3.37 (dd, J$_{H6,H5}$=2.66, J$_{H6,H1}$=6.46 Hz, 1H, H-6), 3.72 (s, 3H, CH$_3$-1 of imidazol), 4.08 (ABq, 2H, SCH$_2$), 4.15–4.3 (m overlapping with SCH$_2$, 2H, H-5 and CH$_2$CHO), 6.96 (s, 1H, H-4 of imidazol and 7.67 ppm (s, 1H, H-2 of imidazol).

EXAMPLE 80

(4R,5S,6S)-4-[3"-(N-Formimidoyl)aminopropyl]-6-[(1'R)-1'-hydroxyethyl]-3-[(1-N-methylimidazol-5-yl)methylthio]-7-oxo-1-azabicyclo[3.2.0]hept-2-ene-2-carboxylic acid

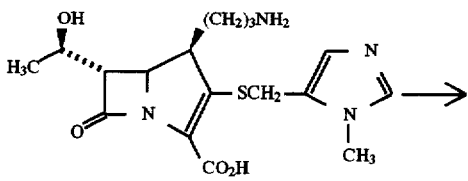

198

—continued

A solution of (4R,5S,6S)-4-[3"-aminopropyl)-6-[(1'R)-1'-hydroxyethyl]-3-[(1-N-methylimidazol-5-yl)methylthio]-7-oxo-1-azabicyclo[3.2.0]hept-2-ene-2-carboxylic acid (300 mg, 0.789 mmol) in water (40 mL) was cooled in an ice bath and the pH of the solution was adjusted to 8 with 1N aqueous NaOH solution. To the mixture was added portionwise benzyl formimidate hydrochloride (5 eq., 3.94 mmol, 0.68 g), the pH being kept at 8–8.5 with 1N aqueous NaOH solution. The reaction mixture was stirred 15 min after the end of addition then the pH was adjusted to 6.5 with 1N aqueous HCl solution and washed with ethyl acetate (2×30 mL). The aqueous phase was concentrated under vacuum without heating and purified on reversed phase silica gel [μBondapak C$_{18}$, 3×5×13 cm, elution with 0.01M pH 6.0 phosphate buffer and gradient of CH$_3$CN (0–3%)]. The pure fractions were lyophilized, repurified on the reversed phase column to remove salts (water→5% CH$_3$CN/H$_2$O) to give 0.115 g (36%) of the title compound as a white amorphous solid after lyophilization.

Purity by HPLC: 99.2% on μBondapak C$_{18}$, 3.9 mm×30 cm, flow rate 1 mL/min, elution 8% CH$_3$CN—KH$_2$PO$_4$ 0.01M pH 7.4, uv detector 300 nm, retention time 6.30 min;

UV (H$_2$O) λ$_{max}$: 300 nm (ε=7853);

IR (KBr) ν$_{max}$: 1755 (C=O of β-lactam), 1715 (C=N and 1590 cm$^{-1}$ (C=O of carboxylate;

$^1$H NMR (200 MHz, D$_2$O) δ: 1.30(d, J=6.37 Hz, CH$_3$), 1.3–1.72 (4H, m, CH$_2$CH$_2$), 3.19–3.40 (3H, m, CH$_2$N and H-6 overlapping), 3.71 (3H, s, N—CH$_3$), 4.08 (ABq, J=14.87 Hz, Δv=45.5 Hz, 2H, SCH$_2$), 4.2 (m, 1H, CH$_3$ CHO), 6.95 (s, 1H, 1H-4 of imidazol), 7.65 (s, 1H, H-2 of imidazol and 7.81 (s, H, CH=NH).

EXAMPLE 81

(4R,5S,6S)-4-(4"-N,N-Dimethylaminobutyl)-6-[(1'R)-1'-hydroxy ethyl]-3-[(pyridin-4-yl)methylthio]-7-oxo-1-azabicyclo-[3.2.0]hept-2-ene-2-carboxylic acid

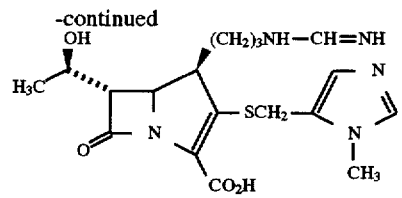

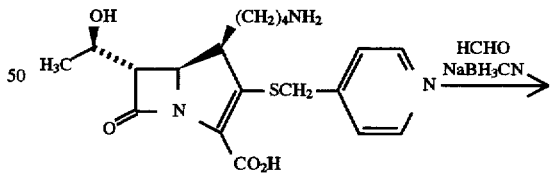

A solution of (4R,5S,6S)-4-(4"-aminobutyl)-6-[(1'R)-1'-hydroxyethyl]-3-[(pyridin-4-yl)methylthio]-7-oxo-1-azabicyclo[3.2.0]hept-2-ene-2-carboxylic acid (0.176 g, 0.45 mmol) in water (8 mL) was treated at 0°–5° C., with 37% formaldehyde (0.2 mL, ~2.5 mmol), acetic acid (0.052 mL, 0.9 mmol) and sodium cyanoborohydride (0.056 g, 0.9 mmol). The final mixture has a pH of 4.2. Completion of the reaction was monitored by HPLC. Over 5 h, sodium cyanoborohydride (6×0.050 g) and formaldehyde (2×0.1 mL) were added while maintaining the pH at 4.5–5 with acetic acid. The reaction mixture was then quenched by addition of 15 mL of 0.2M pH 7.0 phosphate buffer and the pH of the solution was adjusted to 6.5 with 1M NaOH. By HPLC, the product is a 74:20 mixture of dimethyl and N-methyl-N-cyanomethyl derivatives. The solution was chromatographed twice on reversed phase silica gel (μBondapak $C_{18}$, 2.5×18 cm) using a gradient of acetonitrile (0–10%) in water.

Lyophilization of the first fractions gave 0.021 g of the N-methyl-N-cyanomethyl compound.

The following fractions gave 0.104 g (55%) of the title compound as a white amorphous powder: $[\alpha]_D^{22}$+4.0° (c 0.5, water);

Purity by HPLC: 95% on μBondapak $C_{18}$, 3.9 mm×30 cm, elution 10% $CH_3CN$—$H_2O$, pH 7.4 phosphate buffer, flow rate 1 mL/min, retention time 12.0 min;

UV (water, pH 7.4 phosphate buffer) $\lambda_{max}$: 262 (6032) and 304 nm (9.937);

IR (KBr) $\nu_{max}$: 1758 (C=O of β-lactam) and 1600 cm$^{-1}$ (C=O of carboxylate);

$^1$H NMR (200 MHz, $D_2O$) δ: 1.1–1.8 (m, 6H, $CH_2$-1,2 and 3 of butyl), 1.28 (d, J=6.37 Hz, 3H, $CH_3CHO$), 2.85 (s, 6H, $NCH_3$), 2.9–3.2 (m, 3H, H-4 and $CH_2N$), 3.27 (dd, $J_{H6,H5}$=2.54 Hz, $J_{H6,H1}$=6.34 Hz, 1H, H-6), 4.06 (ABq, $J_{AB}$=14.9 Hz, Δν=23.4 Hz, 2H, $SCH_2$), 4.08 (overlapping with $SCH_2$, 1H, H-5), 4.21 (m, 1H, $CH_3CHO$), 7.49 (~d, 2H, H-3 of pyridine) and 8.49 ppm (~d, 2H, H-2 of pyridine).

EXAMPLE 82

(4R,5S,6S)-4-(3"-Aminopropyl)-6-[(1'R)-1'-hydroxyethyl]-3-[(1-methyl-1,2,3-triazol-4-yl)methylthio]-7-oxo-1-azabicyclo[3.2.0]hept-2-ene-2-carboxylic acid

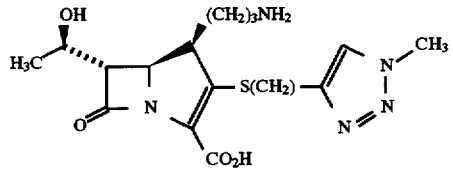

A. Allyl (4R,5S,6S)-4-(3"-azidopropyl)-6-[(1'R)-1'-hydroxyethyl]-3-[(1-methyl-1,2,3-triazol-4-yl)methylthio]-7-oxo-1-azabicyclo[3.2.0]hept-2-ene-2-carboxylate

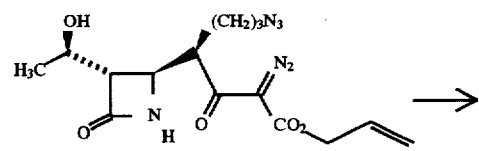

A cold solution (ice-MeOH bath) of allyl (2R,4R, 5R,6 S)-4-(3"-azidopropyl)-6-[(1'R)-1'-hydroxyethyl]-3,7-dioxo-1-azabicyclo[3.2.0]heptan-2-carboxylate, freshly prepared from (3S,4R)-3-[(1'R)-1'-hydroxyethyl]-4-[(1' R)-1"-(3-azidopropyl)-3"-diazo-3"-allyloxycarbonyl-2"-oxopropyl]azetidin-2-one (1.7 g, 4.7 mmol) in $CH_3CN$ (50 mL) was treated with diphenyl chlorophosphate (1.1 mL, 5 mmol), N,N-diisopropylethylamine (0.92 mL, 5.0 mmol) and a trace of 4-dimethylaminopyridine (5 mg). The mixture was stirred for 1 h and the enol phosphate was treated dropwise with 4-mercaptomethyl-1-methyl-1,2,3-triazole (1.21 g, 9.40 mmol) and N,N-diisopropylethylamine (1.84 mL, 10.0 mmol). After a stirring period of 20 h at 5° C. (cold room), the mixture was diluted with ethyl acetate (200 mL), washed with cold 1M aqueous $NaHCO_3$ (2×100 mL), water (2×100 mL), 1M aqueous $NaHSO_3$ (1×100 mL), water (2×100 mL), brine and dried ($MgSO_4$). The residue (3 g) was passed through a silica gel flash pad (150 g, 1/1 hexane/ethyl acetate→ethyl acetate) to give the title compound (1.0 g, 47%) as an oil;

IR ($CH_2Cl_2$) $\nu_{max}$: 3680, 3600, 3400 (OH), 2100 ($N_3$), 775 and 1710 cm$^{-1}$ (C=O);

$^1$H NMR ($CDCl_3$, 200 MHz) δ: 7.489 (1H, s, aromatic-H), 6.02–5.87 (1H, m, vinylic-H), 5.47–5.20 (2H, m, vinylic —H), 4.85–4.59 (2H, m, allylic $CH_2$), 4.274, 4.199, 3.961, 3.886 (2H, ABq, J=15.1 Hz, $CH_2$-aromatic), 4.25–4.12 (1H, m, H-1'), 4.159 (1H, dd, J=2.6 Hz, J=9.6 Hz, H-5), 4.071 (3H, s, N-Me), 3.64–3.53 (1H, m, H-4), 3.49–3.36 (2H, m, $CH_2$—$N_3$), 3.228 (1H, dd, J=2.7 Hz, J=7.3 Hz, H-6), 2.3 (1H, bs, OH), 2.03–1.5 (4H, m, $(CH_2)_2$-4) and 1.357 ppm (3H, d, J=6.3 Hz, $CH_3$).

B. (4R,5S,6S)-4-(3"-Aminopropyl)-6-[(1'R)-1'-hydroxyethyl]-3-[(1-methyl-1,2,3-triazol-4-yl)methylthio]-7-oxo-1-azabicyclo[3.2.0]hept-2-ene-2-carboxylic acid

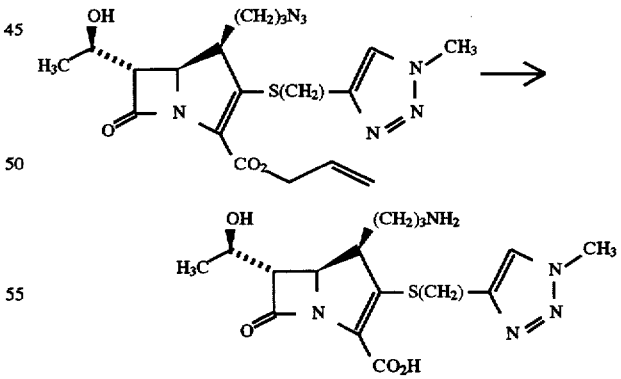

A cold (ice bath) solution of allyl (4R,5S,6 S)-4-(3"-azidopropyl)-6-[(1'R)-1'-hydroxyethyl]-3-[(1-methyl-1,2,3-triazol-4-yl)methylthio]-7-oxo-1-azabicyclo[3.2.0]hept-2-ene-2-carboxylate (1.0 g, 2.2 mmol) in $CH_2Cl_2$ (50 mL) was treated with $Pd(PPh_3)_4$ (100 mg) and dropwise with a 0.5M solution of sodium ethyl-2-hexanoate in ethyl acetate (4.6 mL, 2.3 mmol). The mixture was stirred for 1.5 h, diluted with ethyl acetate (150 mL) and extracted with water (1×75 mL, 2×30 mL). The aqueous extracts were combined, washed with diethyl ether and shaken at 5° C. (ice bath) in a Parr hydrogenator at 45–50 psi of hydrogen for 1 h, using 5% Pd/Alumina as catalyst. More catalyst was then added (1 g) and the mixture was shaken again for 1.5 h more after which the catalyst was removed by filtration. The aqueous portion was passed through a µBondapak C$_{18}$ reversed phase column (200 g, water→5% CH$_3$CN/H$_2$O) to give the title compound (500 mg, 59%) as a lyophilized powder;

Purity: 97.2% (304 nm, HPLC);

UV (H$_2$O) λ$_{max}$: 302 (ε8250);

IR (Nujol) ν$_{max}$: 3600–3100 (OH), 1755 and 1585 cm$^{-1}$ (C=O);

$^1$H nmr (D$_2$O, 200 MHz) δ: 7.866 (1H, s, aromatic H), 4.30–4.18 (1H, m, H-1'), 4.216, 4.143, 4.034, 3.959 (2H, ABq, J=14.7 Hz, CH$_2$-aromatic), 4.085 (3H, s, N—CH$_3$), 4.10–4.08 (1H, m, hidden H-5), 3.356 (1H, dd, J=2.6 Hz, J=6.5 Hz, H-6), 3.33–3.20 (1H, m, H-4), 3.07–3.00 (2H, m, CH$_2$N$_3$), 1.95–1.40 (4H, m, (CH$_2$)$_2$-4) and 1.312 ppm (3H, d J=6.3 Hz, CH$_3$).

EXAMPLE 83

(4R,5S,6S)-3-[(2-Acetamidoethyl)thio]-4-(3"-aminopropyl)-6-[(1'R)-1'-hydroxyethyl]-7-oxo-1-azabicyclo[3.2.0]hept-2-ene-2-carboxylic acid

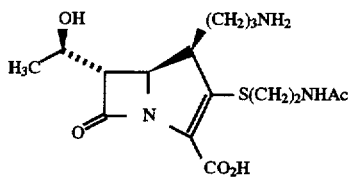

The title compound was obtained from the residual contamination of 2-carbamoylethyl mercaptan with N-acetyl cysteamine in the reaction carried out in Example 76 and was isolated in the usual manner. The title compound was obtained as a lyophilized powder;

Purity: 95% (304 nm, HPLC);

UV (H$_2$O) λ$_{max}$: 302 (ε=7810);

IR (Hnjol) ν$_{max}$: 3600–3100 OH, NH), 1755, 1650 and 1600 cm$^{-1}$ (C=O);

$^1$H nmr (D$_2$O, 200 MHz) δ: 4.30–4.20 (1H, m, H-1'), 4.230 (1H, dd, J=2.6 Hz, J=9.3 Hz, H-5), 3.5–3.3 (4H, m, H-6, H-4 and CH$_2$-NAc), 3.1–2.95 (3H, SHCH and CH$_2$N), 1.9–1.7 (1H, m, SHCH), 1.999 (3H, s, NAc), 1.9–1.5 (4H, m, (CH$_2$)$_2$-4) and 1.332 ppm (3H, d, J=6.4 Hz, CH$_3$).

EXAMPLE 84

(4R,5S,6S)-3-[(2-Carbamoylethyl)thio]-4-[3"-(N-formimidoyl)aminopropyl]-6-[(1'R)-1'-hydroxyethyl]-7-oxo-1-azabicyclo-[3.2.0]hept-2-ene-2-carboxylic acid

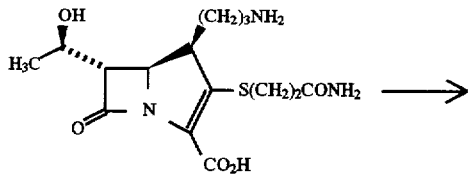

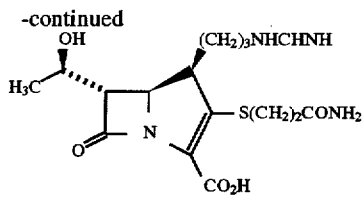

A cold solution (ice bath) of (4R,5S,6S)-4-(3"-aminopropyl)-3-[(2-carbamoylethyl)thio]-6-[(1'R)-1'-hydroxyethyl]-7-oxo-1-azabicyclo[3.2.0]hept-2-ene-2-carboxylic acid (180 mg, 0.500 mmol) in a 0.05M aqueous pH 7.0 aqueous phosphate buffer (50 mL) was treated first with a 0.1N aqueous NaOH solution (to raise and maintain the pH ~8.2) and then portionwise with benzyl formimidate hydrochloride (0.87 g, 5.0 mmol). The mixture was stirred for 20 min and the pH was lowered to 7.0 with a 1M aqueous NaH$_2$PO$_4$ solution. The mixture was passed through a µBondapak C$_{18}$ column (3.6 g, H$_2$O→4% CH$_3$CN/H$_2$O) to give the title compound (110 mg, 57%) as a lyophilized powder;

Purity: 93.1% (HPLC, 302 mm);

UV (H$_2$O) λ$_{max}$: 302 (ε7550);

IR (Nujol) ν$_{max}$: 3600–3100 (NH$_2$, OH), 1750, 1665 and 1590 cm$^{-1}$ (C=O);

$^1$H NMR (D$_2$O, 200 MHz) δ: 4.34–4.22 (2H, m, H-1' and H-5), 4.225 (part of H-5, d, J=2.6 Hz), 3.49–3.34 (4H, m, CH$_2$N$_3$, H-5 and H-4), 3.351 (part of H6, d, J=2.4 Hz), 3.15–2.85 (1H, 2 sets of m, SCH$_2$), 2.71–2.51 (2H, m, CH$_2$CON), 2.0–1.46 (4H, m, (CH$_{22}$-4) and 1.322 ppm (3H, d, J=6.4 Hz, CH$_3$).

EXAMPLE 85

(4R,5S,6S)-4-(4"-Aminobutyl)-6-[(1'R)-1'-hydroxyethyl]-3-[(1,2,3-thiadiazol-4-yl)methylthio]-7-oxo-1-azabicyclo-[3.2.0]hept-2-ene-2-carboxylic acid

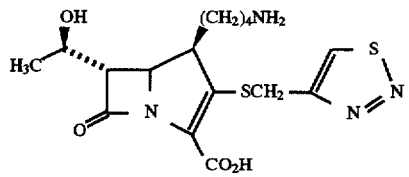

A. Allyl (4R,5S,6S)-4-(4"-azidobutyl)-6-[(1H,)-1'-hydroxyethyl]-3-[(1,2,3-thiadiazol-4-yl)methylthio]-7-oxo-1-azabicyclo[3.2.0]hept-2-ene-2-carboxylate

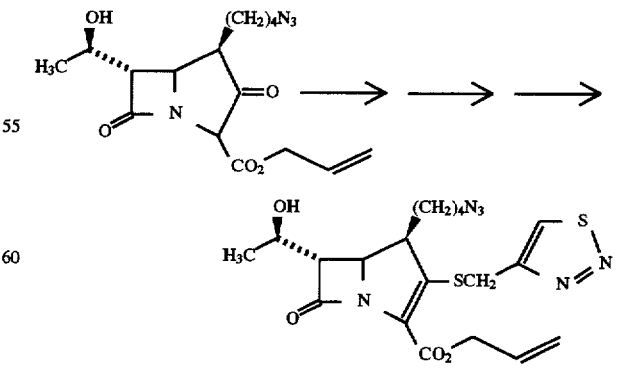

A solution of allyl (4R,5R,6S)-4-(4"azidobutyl)-6-[(1'R)-1'-hydroxyethyl]-3,7-dioxo-1-azabicyclo[3.2.0]heptane-2- carboxylate (5.28 mmol, prepared by cyclization of 2.0 g, 5.28 mmol of diazo precursor), in dry acetonitrile (40 mL) was treated at 0°–5° C. and under nitrogen with diphenyl chlorophosphate (1.2 mL, 5.8 mmol) and N,N-diisopropylethylamine (1.0 mL, 5.7 mmol) added simultaneously over 5 min. A small crystal of 4-N,N-dimethylaminopyridine was then added and the mixture was stirred for 1 h. The solution was then cooled to −20° C. and treated with N,N-diisopropylethylamine (1.84 mL, 10.56 mmol) followed by 4-mercaptomethyl-1,2,3-thiadiazole (1.45 g, 10.96 mmol) in 5 mL of acetonitrile. The temperature was slowly raised to 0° C. over 1 h and the mixture was partitioned between water and ethyl acetate (400 mL). The organic phase was washed with 1M $NaHSO_3$, saturated $NaHCO_3$, brine and dried ($MgSO_4$). Evaporation of the solvent gave an oil which was chromatographed on silica gel (5×11 cm). Elution with a gradient of ethyl acetate in toluene (8:2 to 1:1) gave 1.95 g (79%) of the title compound as an oil:

IR (NaCl, film) $v_{max}$: 2100 ($N_3$), 1770 (C=O of β-lactam) and 1708 $cm^{-1}$ (C=O of ester);

$^1$H NMR (200 MHz, $CDCl_3$) δ: 1.38 (d, J=6.28 Hz, 3H, C$H_3$CHO), 1.3–2.0 (m, 6H, $CH_2$-1,2 and 3 of butyl), 3.18 (dd, $J_{H6,H5}$=2.70 Hz, $J_{H6,H1}$=7.21 Hz, 1H, H-6), 3.34 (t, J=6.1 Hz, 2H, C$H_2$$N_3$), 3.46 (broad t, 1H, H-4), 4.17 (dd, $J_{H5,H6}$=2.70 Hz, $J_{H5,H4}$=9.7 Hz, 1H, H-5), 4.22 (m, 1H, $CH_3$ CHO), 4.50 (ABq, $J_{AB}$=14.95 Hz, Δv=73.5 Hz, 2H, $SCH_2$), 4.74 (m, 2H, $CH_2$ of allyl), 5.2–5.5 and 5.9–6.1 (2×m, 2H and 1H, CH of allyl), and 8.47 ppm (s, 1H, H-5 of thiadiazole).

B. (4R,5S,6S)-4-(4"-Aminobutyl)-6-[(1'R)-1'-hydroxyethyl]-3-[(1,2,3-thiadiazol-4-yl)methylthio]-7-oxo-1-azabicyclo[3.2.0]hept-2-ene-2-carboxylic acid

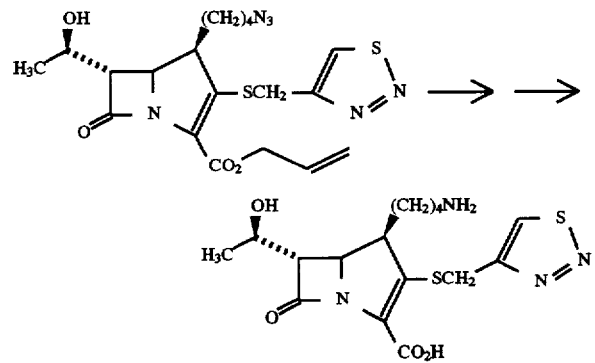

A solution of allyl (4R,5S,6S)-4-(4"-azidobutyl)-6-[(1'R)-1'-hydroxyethyl]-3-[(1,2,3-thiadiazol-4-yl)methylthio]-7-oxo-1-azabicyclo[3.2.0]hept-2-ene-2-carboxylate (1.95 g, 4.2 mmol) in ethyl acetate (75 mL) was treated at 22° C. and under nitrogen with tetrakis(triphenylphosphine)palladium [0] (0.075 g) and 9.2 mL (4.6 mmol) of a 0.5M solution of potassium 2-ethylhexanoate in ethyl acetate. After 45 min, the reaction mixture was extracted with water (2×75 mL) and the combined aqueous extract was maintained under vacuum to remove traces of organic solvent. The aqueous phase was then hydrogenated at 0–5° C. over 2.1 g of 5% palladium on alumina and under 45 psi of hydrogen for 2 h. Then 30 mL of 0.2M pH 6.0 phosphate buffer was added and the catalyst was filtered. The filtrate was chromatographed on reversed phase silica gel (μBondapak $C_{18}$, 3.5×15 cm) using a gradient of acetonitrile (0–8%) in water as eluent.

The first fractions collected gave 0.17 g of (4R,5S,6S)-4-(4"-hydroxybutyl)-6-[(1'R)-1'-hydroxyethyl]-3-(1,2,3-thiadiazol-4-yl)methylthio-7-oxo-1-azabicyclo[3.2.0]hept-2-ene-2-carboxylate (Na, K salt) as a white solid after freeze drying. The following fractions gave 0.576 g (34%) of the title compound as a white amorphous solid:

Purity by HPLC: 97.7% on μBondapak $C_{18}$, 3.9 mm×30 cm, elution 8% $CH_3CN$—$H_2O$, pH 7.4 phosphate buffer, flow rate 0.8 mL/min, retention time 6.75 min;

UV (water, pH 7.4 phosphate buffer) $\lambda_{max}$: 260 (5470) and 302 nm (9,209);

IR (KBr) $v_{max}$: 1755 (C=O of β-lactam) and 1585 $cm^{-1}$ (C=O of carboxylate);

$^1$H NMR (200 MHz, $D_2O$) δ: 1.29 (d, J=6.36 Hz, 3H, C$H_3$CHO), 1.3–1.8 (m, 6H, $CH_2$-1,2 and 3 of butyl), 3.0 (t, J=7.6 Hz, 2H, C$H_2$$NH_2$), 3.21 (broad t, 1H, H-4), 3.32 (dd, $J_{H6,5}$=2.45 Hz, $J_{H6,H1}$=6.25 Hz, 1H, H-6), 4.10 (dd, $J_{H5,H6}$=2.45 Hz, $J_{H5,H4}$=9.42 Hz, 1H, H-5), 4.23 (m, 1H, $CH_3$ CHO), 4.51 (ABq, $J_{AB}$=14.94 Hz, Δv=40.2 Hz, 2H, $SCH_2$), and 8.89 ppm (s, 1H, H-5 of thiadiazole).

EXAMPLE 86

(4R,5S,6S)-4-(4"-N-Formimidoylaminobutyl)-6-[(1'R)-1'-hydroxyethyl]-3-[(1,2,3-thiadiazol-4-yl)methylthio]-7-oxo-1-azabicyclo[3.2.0]hept-2-ene-2-carboxylic acid

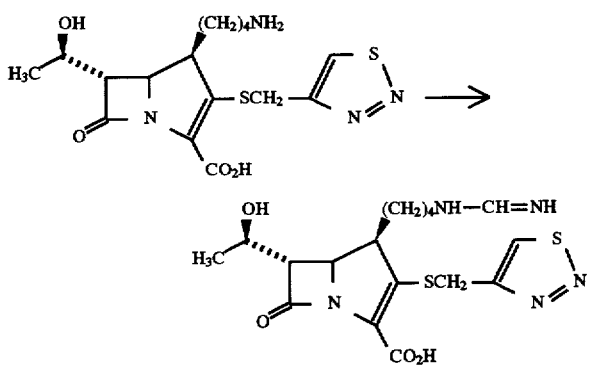

A solution of (4R,5S,6S)-4-(4"-aminobutyl)-6-[(1'R)-1'-hydroxyethyl]-3-[(1,2,3-thiadiazol-4-yl)methylthio]-7-oxo-1-azabicyclo[3.2.0]hept-2-ene-2-carboxylic acid (0.250 g, 0.63 mmol) in water (30 mL) was treated at 0°–5° C. with benzylformimidate hydrochloride (0.60 g, 3.5 mmol) added in small portions over 10 min while maintaining the pH between 8–8.5 with 1M NaOH. After 20 min, 25 mL of 0.2M pH 6 buffer were added and the mixture was washed with ethyl acetate (20 mL). The aqueous phase was maintained under vacuum to remove traces of organic solvent and chromatographed on reversed phase silica gel (μBondapak $C_{18}$, 3.5×15 cm). The column was eluted first with a gradient of acetonitrile (0–8%) in a 0.01M pH 7.0 phosphate buffer. The UV active fractions were combined, lyophilized and chromatographed again on the same column using water instead of buffer. Freeze drying of the UV active fractions gave 0.21 g (78%) of the title compound as a white amorphous solid: $[\alpha]_D^{22}$−28.4° (c 1.0, water);

Purity by HPLC: 98% on μBondapak $C_{18}$, 3.9 mm×30 cm, elution 8% $CH_3CN$—$H_2O$, pH 7.4 phosphate buffer, flow rate 1 mL/min, uv detector 302 nm, retention time 7.8 min;

UV ($H_2O$, pH 7.4 phosphate buffer) $\lambda_{max}$: 258 (5,318) and 302 nm (8,795);

IR (KBr) $v_{max}$: 1755 (C=O of β-lactam), 1710 (C=N of formimidoyl) and 1590 $cm^{-1}$ (C=O of carboxylate);

$^1$H NMR (200 MHz, $D_2O$) δ: 1.29 (d, J=6.39 Hz, 3H, C$H_3$CHO), 1.2–1.8 (m, 6H, $CH_2$-1,2 and 3 of butyl 3.2–3.5 (m, 4H, H-6 and $CH_2$-4 of butyl overlapping), 4.10 (dd, $J_{H5,H6}$=2.47 Hz, $J_{H5,H4}$=9.43 Hz, 1H, H-5), 4.23 (m, 1H, CH$_3$CHO), 4.51 (ABq, $J_{AB}$=15.0 Hz, Δv=39.4 Hz, 2H, SCH$_2$), 7.8 (broad s, 1H, CH=NH), and 8.9 ppm (s, 1H, H-5 of thiadiazole).

EXAMPLE 87

(4R,5S,6S)-4-(4"-Guanidinobutyl)-6-[(1'R)-1'-hydroxyethyl]-3-[(2-hydroxyethyl)thio]-7-oxo-1-azabicyclo[3.2.0]hept-2-ene-2-carboxylic acid

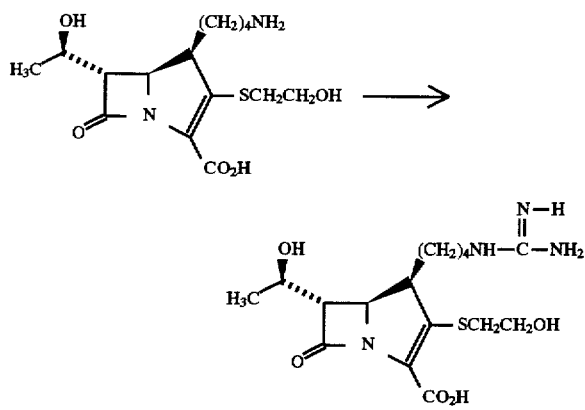

A solution of (4R,5S,6S)-4-(4"-aminobutyl)-6-[(1'R)-1'-hydroxyethyl]-3-[(2-hydroxyethyl)thio]-7-oxo-1-azabicyclo[3.2.0]hept-2-ene-2-carboxylic acid (0.150 g, 0.44 mmol) in cold (0°-5° C.) water (10 mL) was adjusted to pH 8 with 1M NaOH and then treated with aminoiminomethanesulfonic acid (0.216 g, 1.74 mmol) added in small portions over 5 min. The pH was maintained at 8-8.5 throughout the addition and for another three hours with 1M NaOH. The cold reaction mixture was then quenched by the addition of 10 mL of 0.2M pH 6.0 phosphate buffer and then chromatographed on reversed phase silica gel (µBondapak C$_{18}$, 2.5× 16 cm). Elution with a gradient of acetonitrile (0-5%) in water gave 0.115 g (68%) of the title compound after lyophilization of the UV active fractions:

Purity by HPLC: 99% on µBondapak C$_{18}$, 3.9 mm×30 cm, elution 5% CH$_3$CN—H$_2$O, pH 7.4 phosphate buffer, flow rate 1 mn/min, UV detector 300 nm, retention time 7.19 min;

UV (water, pH 7.4 phosphate buffer) $\lambda_{max}$: 304 nm (9,530);

IR (KBr) $v_{max}$: 1750 (C=O of β-lactam), 1665 (C=N of guanidyl) and 1580 cm$^{-1}$ (C=O of carboxylate);

$^1$H NMR (200 MHz, D$_2$O) δ: 1.32 (d, J=6.35 Hz, 3H, CH$_3$CHO), 1.3–1.9 (m, 6H, CH$_2$-1,2 and 3 of butyl), 2.8–3.1 (m, 2H, SCH$_2$), 3.22 (t, J=6.5 Hz, 2H, CH$_2$NH$_2$), 3.32 (dd, $J_{H6,H5}$=2.45 Hz, $J_{H6,H1}$=6.19 Hz, 1H, H-6), 3.35 (overlapping with H-6, 1H, H-4), 3.77 (t, J=6.3 Hz, 2H, CH$_2$OH), 4.21 (dd, $J_{H5,H6}$=2.45 Hz, $J_{H5,H4}$=9.34 Hz, 1H, H-5), and 4.27 ppm (m, 1H, CH$_3$CHO).

EXAMPLE 88

(4R,5S,6S)-S-[(2-Carbamoyloxyethyl)thio]-4-[3"-(N-formimidoyl)aminopropyl]-6-[(1'R)-1'-hydroxyethVl]-7-oxo-1-azabicyclo[3.2.0]hept-2-ene-2-carboxylic acid

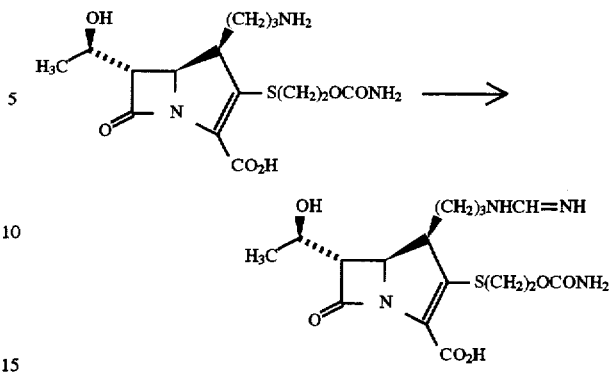

A cold solution (ice bath) of (4R,5S,5S)-4-(3"-aminopropyl)-3-[(2-carbamoyloxyethyl)thio]-6-[(1'R)-1'-hydroxyethyl]-7-oxo-1-azabicyclo[3.2.0]hept-2-ene-2-carboxylic acid (150 mg, 0.40 mmol) in a 0.04M pH 7.0 aqueous phosphate buffer was treated with a 0.1N aqueous NaOH solution (to adjust and maintain the pH at 8.0–8.3) and portionwise with benzyl formimidate hydrochloride (342 mg, 2.0 mmol). The mixture was stirred for 15 min and the pH was adjusted to 7.05 with a 0.1N aqueous HCl solution. The mixture was passed through a µBondapak C$_{18}$ reversed phase column (37.5 g, 0.02M aqueous pH 7.0 phosphate buffer→1%→2%→3%→4% CH$_3$CN/phosphate buffer). The lyophilized powder was passed again through the same reversed phase column (H$_2$O→1%→4% CH$_3$CN/H$_2$O) to give pure title compound (95 mg, 59 %) as a lyophilized powder;

Purity: 98.7% (300 nm, HPLC);

UV (H$_2$O) $\lambda_{max}$: 302 (7520);

IR (Nujol) $v_{max}$: 3600–3100 (OH, NH$_2$), 1750, 1710 and 1585 cm$^{-1}$ (C=O);

$^1$H NMR (D$_2$O, 200 MHz) δ: 7.830, 7.807 (1H, 2s, CH=N), 4.83–4.20 (4H, m, H-1', H$_4$ and CH$_2$O); 3.45–3.33 (4H, m, CH$_2$N, H-6, H-4), 3.19–3.05, 2.98–2.85 (2H, 2 sets of m, S—CH$_2$), 1.95–1.51 (4H, 4-CH$_2$CH$_2$) and 1.320 ppm (3H, d, J=6.4 Hz, CH$_3$).

EXAMPLE 89

(4R,5S,6S)-4-(2"-Aminopropyl)-3-[(2-cyanoethyl)thio]-6-[(1'R)-1'hydroxyethyl]-7-oxo-1-azabicyclo[3.2.0]hept-2-ene-2-carboxylic acid

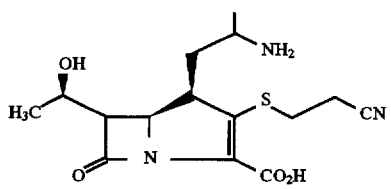

A. Allyl (4R,5S,6S)-4-(2"-azidopropyl)-3-[(2-cyanoethyl)hio]-6-[(1'R)-1'-hydroxyetbyl]-7-oxo-1-azabicyclo[3.2.0]hept-2-ene-2-carboxylate; isomer B

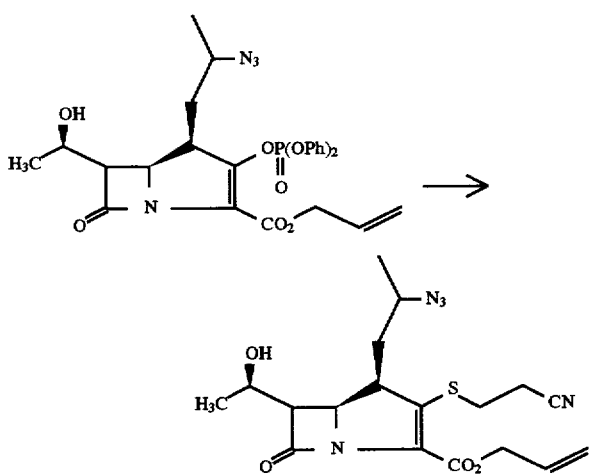

A cold (5° C.) solution of allyl (4R, 5S,6S)-4-(2"-azidopropyl)-3-(diphenylphosphono)-6-[(1'R)-1'-hydroxyethyl]-7-oxo-1-azabicyclo[3.2.0]hept-2-ene-2-carboxylate (1.48 g, 2.6 mmol) [prepared as in Example 57, Step H] in DMF (15 mL) was treated with 3-mercaptopropionitrile (300 mg, 3.44 mmol) and N,N-diisopropylethylamine (445 mg, 3.44 mmol). The ice-bath was allowed to become exhausted and the reaction mixture stirred at 20° C. for a total of 18 h. The solution was diluted with ethyl acetate (100 mL) and washed three times with cold brine. The organic phase was dried (MgSO$_4$) and evaporated to give a mixture which was chromatographed on SiO$_2$ eluting with diethyl ether. Of the two isomeric A and B products produced, the more polar isomer B was purified to give 212 mg (20.1%) of the title compound;

IR (CH$_2$Cl$_2$) $v_{max}$: 3600 (—OH), 2115 (—N$_3$), 1778 (β-lactam), 1710 (—CO$_2$—)

$^1$H NMR (CDCl$_3$) δ: 4.6–6.10 (5H, allyl pattern), 4.21–4.32 (2H, m, H-1', 4.28, dd, J; 2.79, 9.60 Hz, H-5), 3.51–3.69 (2H, m, CH—N$_3$, H-4), 3.23 and 3.0 (2H, 2m, S—CH$_2$), 3.06 (1H, dd, J: 2.72, 8.14 Hz, H-6), 2.72 (2H, m, CH$_2$CN), 1.6–1.9 (2H, m, CH$_2$C—N$_3$), 1.39 (3H, d, J: 6.2 Hz, —CH$_3$), 1.38 (3H, d, J: 6.38 Hz, —CH$_3$).

B. Sodium (4R,5S,6S)-4-(2"-azidopropyl)-3-[(2-cyanoethyl)thio]-6-[(1'R)-1'-hydroxyethyl]-7-oxo-1-azabicyclo[3.2.0]hept-2-ene-2-carboxylate; isomer B

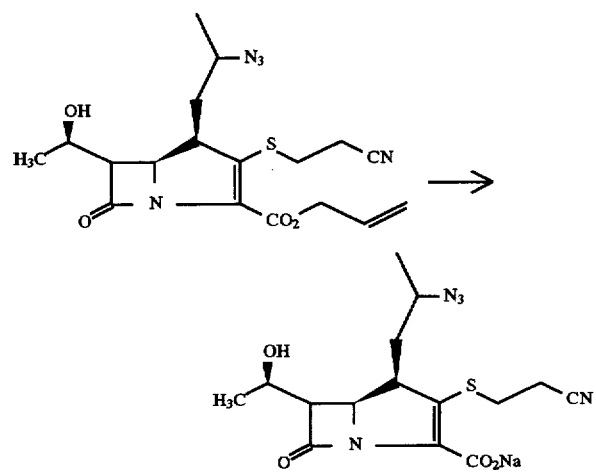

A cold (5° C.) solution of allyl (4R,5S,6S)-4-(2"-azidopropyl)-3-[(2-cyanoethyl)thio]-6-[(1'R)-1'-hydroxyethyl]-7-oxo-1-azabicyclo[3.2.0]hept-2-ene-2-carboxylate (210 mg, 0.52 mmol, the more polar isomer B of Step A) in CH$_2$Cl$_2$ (20 mL) was treated with 0.5M sodium ethyl hexanoate (1.14 mL, 0.57 mmol) and (PPh$_3$)$_4$Pd (60 mg, 0.052 mmol). After stirring for 30 min at 5° C., the solution was diluted with diethyl ether (40 mL) and extracted with 0.04M buffer (pH 7.0, 3×8 mL). The aqueous extracts were combined and chromatographed on reversed phase SiO$_2$ (partisil) eluting with water and then 5% CH$_3$CN in water. The pertinent fractions were combined and lyophilized to give 63 mg (31.3%) of the title compound;

$^1$H NMR (D$_2$O) δ: 4.25–4.35 (2H, m, H-1', H-5), 3.54–3.69 (2H, m, CH—N$_3$, H-4), 3.42 (1H, dd, J: 2.72, 6.38 Hz, H-6), 3.19 and 2.99 (2H, 2m, SCH$_2$), 2.84–2.94 (2H, m, CH$_2$CN), 1.82 (2H, m, CH$_2$—CH$_3$), 1.38 (3H, d, J: 6.52 Hz, —CH$_3$), 1.34 (3H, d, J: 6.47 Hz, —CH$_3$).

C. (4R,5S,6S)-4-(2"-Aminopropyl)-3-[(2-cyanoethyl)thio]-6-[(1'R)-1'-hydroxyethyl]-7-oxo-1-azabicyclo[3.2.0]hept-2-ene-2-carboxylic acid; isomer B

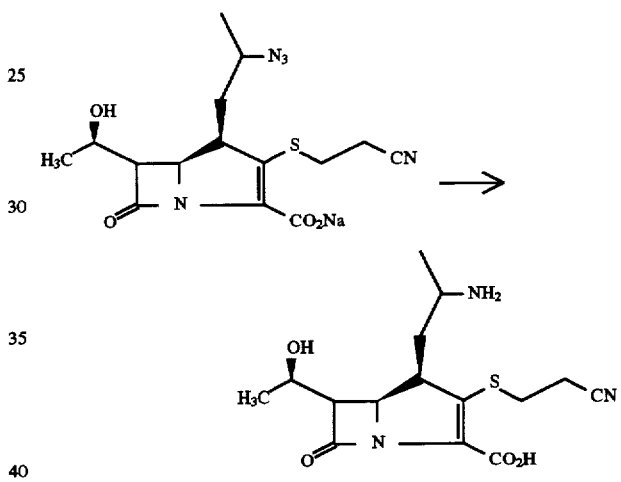

A solution of sodium (4R,5S,6S)-4-(2"-azidopropyl)-3-[(2-cyanoethyl)thio]-6-[(1'R)-1'-hydroxyethyl]-7-oxo-1-azabicyclo[3.2.0]hept-2-ene-2-carboxylate from Step B (63 mg, 0.163 mmol) in 0.05M phosphate buffer (pH 7.0, 20 mL) was hydrogenated at 5° C. in the presence of 30% Pd/Celite (270 mg) at a pressure 45 psi of hydrogen. After 60 min, the catalyst was filtered off and the filtrate chromatographed on reversed phase SiO$_2$ (partisil) eluting with water and then 5% CH$_3$CN in water. The pertinent fractions were combined and lyophilized to give 12 mg (21.7%) of the title compound;

UV (H$_2$O) $\lambda_{max}$: 296 (6200);

IR (Nujol) $v_{max}$: 1755 (β-lactam), 1585 cm$^{-1}$ (—CO$_2$—);

$^1$H NMR (D$_2$O) δ: 4.26–4.40 (2H, m, H-5, H-1'), 3.43–3.69 (3H, m, H-4, CH—N$_3$, H-6), 2.8–3.16 (4H, m, SCH$_2$CH$_2$CN), 1.8–2.2 (2H, m, CH$_2$CH$_3$), 1.43 (3H, d, J: 6.62 Hz, —CH$_3$), 1.35 (3H, d, J: 6.37 Hz, —CH$_3$).

EXAMPLE 90

(4R,5S,6S)-3-[(2-Cyanoethyl)thio]-6-[(1'R)-1'-hydroxyethyl]-4-[2"-(imidazol-1-yl)ethyl]-7-oxo-1-azabicyclo[3.2.0]hept-2-ene-2-carboxylic acid A. Allyl (4R,5S,6S)-6-[(1'R)-1'-tert-butVldimethylsilyloxyethyl]-3-[(2-cyanoethyl)thio]-4-[2"-(imidazol-1-yl)ethyl]-7-oxo-1-azabicyclo[3.2.0]hept-2-ene-2-carboxylate

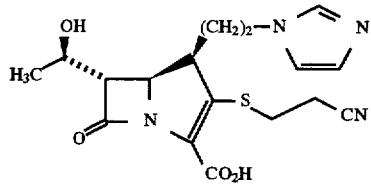

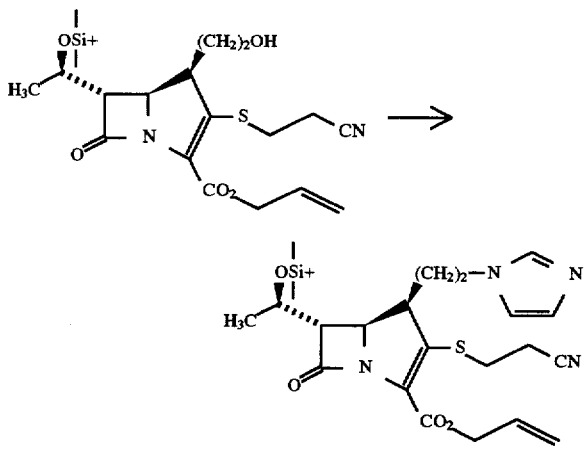

A cold solution (dry ice-acetone bath) of allyl (4R,5R, 6 S)-6-[(1'R)-1'-tert-butyldimethylsilyloxyethyl]-3-[(2-cyanoethyl)thio]-4-(2"-hydroxyethyl)-7-oxo-1-azabicyclo[3.2.0]hept-2-ene-2-carboxylate (370 mg, 0.770 mmol) in CH$_2$Cl$_2$ (10 mL) was treated with N,N-diisopropylethylamine (462 µl, 2.65 mmol) and dropwise with trifluoromethanesulfonic anhydride (231 µl, 1.37 mmol). The mixture was stirred for 30 min and imidazole (200 mg, 2.94 mmol) was added. The dry ice bath was replaced by an ice-MeOH bath end the mixture was stirred for 3.5 h. The mixture was then diluted with cold ethyl acetate, washed with water (3×20 mL), NaHCO$_3$, (20 mL), water (2×20 mL) brine and dried to give the title compound as a solid (350 mg, 85%);

IR (neat) v$_{max}$: 1775 and 1710 cm$^{-1}$ (C=O);

$^1$H NMR (CDCl$_3$, 200 MHz) δ: 7.53 (1H, s, aromatic —H), 7.14 (1H, s, aromatic H), 6.99 (1H, s, aromatic H), 5.97–5.88 (1H, m, vinylic-H), 5.48–5.23 (2H, m vinylic-H), 4.80–4.69 (2H, m, allylic-CH$_2$), 4.255 (1H, dd, J=2.5 Hz, J=9.6 Hz, H-5), 4.35–4.2 (2H, m, H-1'and HC H-imidazole), 4.0–3.9 (1H, m HCH-imidazole), 3.173 (1H, dd, J=2.7 Hz, J=9.0 Hz, H-6), 3.2–3.1 (1H, m, H-4), 3.7–3.5 (4H, SCH$_2$CH$_2$CN), 2.3–2.15, 2.1–1.9 (2H, 2 sets of m, CH$_2$-4), 1.369 (3H, d, J=6.1 Hz, CH$_3$), 0.912 (9H, s, tert-butyl), 0.133 and 0.127 ppm (6H, 2s, CH$_3$).

B. Allyl (4R, 5S,6S)-3-[(2-Cyanoethyl)thio]-6-[(1'R)-1'-hydroxyethyl]-4-[2"-(imidazol-1-yl)ethyl]-7-oxo-1-azabicyclo[3.2.0]hept-2-ene-2-carboxylate

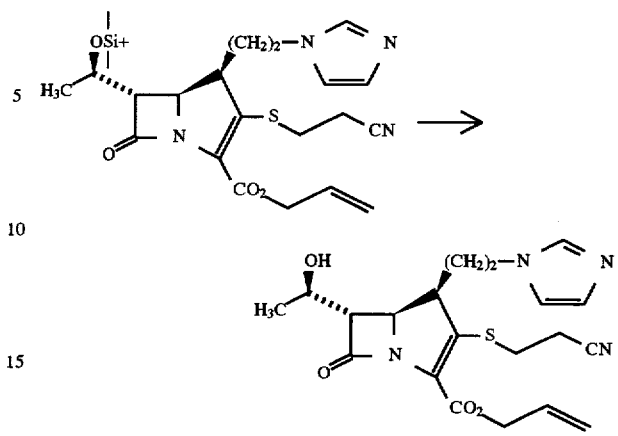

A cold solution (ice-MeOH bath) of allyl (4R,5S,6 S)-6-[(1'R)-1'-tert-butyldimethylsilyloxyethyl]- 3-[(2-cyanoethyl)thio]-4-[2"-(imidazol-1-yl)ethyl]-7-oxo-1-azabicyclo[3.2.0]hept-2-ene-2-carboxylate (425 mg, 0.802 mmol) in tetrahydrofuran (20 mL) was treated first with acetic acid (600 µl, 10.5 mmol) and dropwise with a 1M solution of tetrabutylammonium fluoride in tetrahydrofuran (4.5 mL, 4.5 mmol). The mixture was stirred for 30 min and then was allowed to react at 5° C. (cold room) for 114 h. After that period, solid NaHCO$_3$ (1 g) was added in, and the mixture was stirred for 30 min (ice bath). It was applied on three preparative TLC (2 mm, acetone, Rf=0.2) to give the title compound (120 mg, 36%), contaminated with some tetrabutylammonium fluoride salt;

IR (neat) v$_{max}$: 3600–3100 (OH), 1775 and 1710 cm$^{-1}$ (C=O);

$^1$H NMR (CDCl$_3$, 200 MHz) δ: 7.70 (1H, s, aromatic-H), 7.17 (1H, s, aromatic-H), 7.05 (1H, s, aromatic H ), 6.05–5.99 (1H, m, vinylic H), 5.49–5.24 (2H, m, vinylic-H), 4.9–4.6 (2H, m, allylic-CH$_2$), 4.4–4.2 (4H, m, H-5, H-1' and CH$_2$-imidazole), 3.217 (1H, dd, J=2.9 Hz, J=9.3 Hz, H-6), 3.05–2.90 (1H, m, H-4), 2.75–2.55 (4H, m, SCH$_2$CH$_2$CN), 2.50–2.25, 2.05–1.85 (2H, 2 sets of m, CH$_2$-4), 1.5 (1H, bs, OH) and 1.447 ppm (3H, d, J=5.1 Hz, CH$_3$).

C. (4R,5S,6S)-3-[(2-Cyanoethyl)thio]-6-[(1'R)-1'-hydroxyethyl]-4-[2"-(imidazol-1-yl)ethyl]-7-oxo-1-azabicyclo[3.2.0]hept-2-ene-2-carboxylic acid

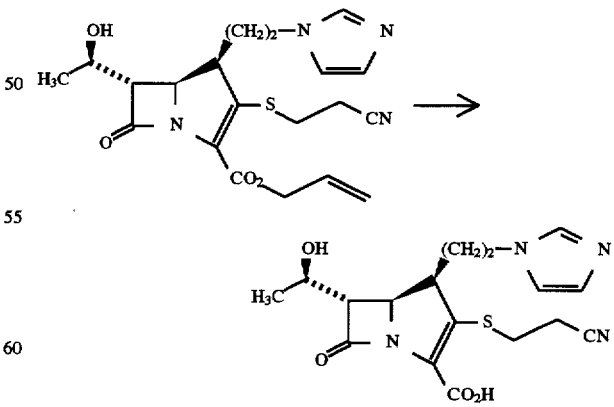

To a cold (ice bath) solution of allyl (4R,5R,6 S)-3-[(2-cyanoethyl)thio]-6-[(1'R)-1'-hydroxyethyl]- 4-[-2"-(imidazol-1-yl)ethyl]-7-oxo-1-azabicyclo[3.2.0]hept-2-ene-2-carboxylate (120 mg, 0.288 mmol) in CH$_2$Cl$_2$ (5 mL) was added Pd(PPh$_3$)$_4$ (20 mg) and a 0.5M solution of sodium ethyl-2-hexanoate (1.0 mL, 0.50 mmol) in ethyl acetate. The mixture was stirred for 30 min and the ice bath was removed. After 30 min the mixture was cooled down again and stirring was continued for 30 more min. The mixture was diluted with diethyl ether (30 mL) and water (5 mL). The phases were separated and the organic layer was extracted again with water (2×5 mL) and 0.05M aqueous pH 7.4 phosphate buffer (3×5 mL). The aqueous extracts were combined, washed with diethyl ether and passed through a reversed phase μBondapak C$_{18}$ column (20 g, H$_2$O→2% CH$_3$CN/H$_2$O) to give a material contaminated with the sodium salt of ethyl-2-hexanoate. The powder was passed through the same column but was eluted with 0.025M pH 6.0 phosphate buffer to give pure title compound and the phosphate salt. The salts were removed through the same reversed phase column (H$_2$O) to give pure title compound (43 mg, 39.6%);

Purity: 99.8% (HPLC 300 nm);

UV (H$_2$O) λ$_{max}$: 300 (7800);

IR ν$_{max}$: 1750 and 1600 cm$^{-1}$ (C=O);

$^1$H NMR (D$_2$O, 200 MHz) δ: 8.00 (1H, s, aromatic H), 7.36 (1H, s, aromatic-H), 7.19 (1H, s, aromatic H), 3.41–3.26 (3H, m, H-5, H-1' and HC$\underline{H}$-imidazole), 4.25–4.05 (1H, m, $\underline{H}$CH-imidazole), 3.528 (1H, dd, J=2.7 Hz, J=6.8 Hz, H6), 3.25–3.10 (1H, m, H-4), 2.74–2.66 (4H, m, SCH$_2$CH$_2$CN), 2.4–2.25, 2.25–2.0 (2H, 2 sets of m, CH$_2$-4), and 1.383 ppm (3H, d, J=6.4 Hz, CH$_3$).

EXAMPLE 91

(4R,5S,6S)-4-(4"-N,N-Dimethylaminobutyl)-6-[(1'R)-1'-hydroxyethyl]-3-[(2-hydroxyethyl)thio]-7-oxo-1-azabicyclo[3.2.0]hept-2-ene-2-carboxylic acid

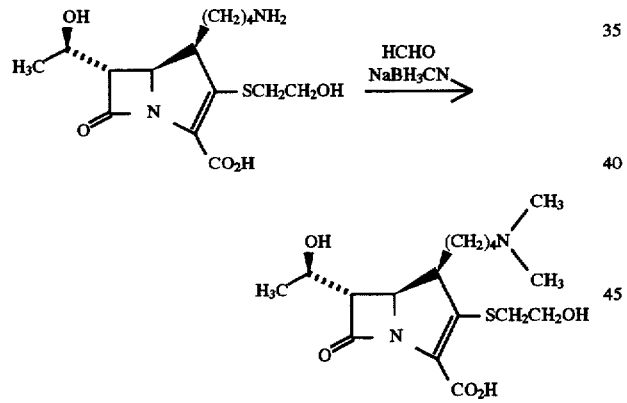

A solution of (4R,5S,6S)-4-(4"-aminobutyl)-6-[(1'R)-1'-hydroxyethyl]-3-[(2-hydroxyethyl)thio]-7-oxo-1-azabicyclo[3.2.0]hept-2-ene-2-carboxylic acid (0.175 g, 0.51 mmol) in cold (0°–5° C.) water (8 mL) was treated with 0.2 mL of 37% aqueous formaldehyde and acetic acid (52 μL, 0.9 mmol). Then sodium cyanoborohydride was added in small portions (5×0.050 g, total 4.0 mmol) over 1 h (pH~5). The reaction mixture was then quenched by the addition of 10 mL of 0.2M pH 7.0 phosphate buffer. HPLC of the crude reaction mixture indicated a mixture of title compound and 4-(4"-N-methyl-N-cyanomethylaminobutyl) compound in a 7:3 ratio. The solution was then chromatographed on reversed phase silica gel (μBondapak C$_{18}$, 2.5×15 cm) using a gradient of acetonitrile (0–5%) in 0.01M pH 7.0 phosphate buffer as eluent. The UV active fractions were combined, concentrated and desalted on the same column using water instead of buffer as eluent. Lyophilization of the pertinent fractions gave 0.077 g (40%) of the title compound as a white amorphous powder: [α]$_D^{24}$+78.5° (c 1.0, H$_2$O);

Purity by HPLC: 98% on μBondapak C$_{18}$, 3.9 mm×30 cm, elution 5% CH$_3$CN—H$_2$O pH 7.4 phosphate buffer, flow rate 1 mL/min, UV detector 300 nm, retention time 6.68 min;

UV (water, pH 7.4 phosphate buffer) λ$_{max}$: 304 nm (8,500);

IR (KBr) ν$_{max}$: 1750 (C=O of β-lactam) and 1590 cm$^{-1}$ (C=O of carboxylate);

$^1$H NMR (200 MHz, D$_2$O) δ: 1.33 (d, J=6.37 Hz, 3H, C$\underline{H}_3$CHO), 1.3–2.0 (m, 6H, CH$_2$-1,2 and 3 of butyl), 2.84 (s, 6H, NCH$_3$), 2.8–3.2 (m 2H, SCH$_2$), 3.11 (t, J=8.0 Hz, 2H, C$\underline{H}_2$N), 3.34 (dd, J$_{H6,H5}$=2.40 Hz, J$_{H6,H1}$=6.41 Hz, 1H, H-6), 3.35 (overlapping with H-6, 1H, H-4), 3.77 (t, J=6.16 Hz, CH$_2$OH), 4.22 (dd, J$_{H5,H6}$=2.40 Hz, J$_{H5,H4}$=10.1 Hz, 1H, H-5) and 4.26 ppm (m, 1H, CH$_3$C$\underline{H}$O).

EXAMPLE 92

(4R,5S,6S)-4-(4"-Aminobutyl)-6-[(1'R)-1'-hydroxyethyl]-3-methylthio-7-oxo-1-azabicyclo[3.2.0]hept-2-ene-2-carboxylic acid

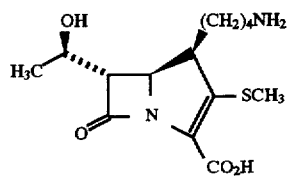

A. Allyl (4R,5S,6S)-4-(4"-azidobutyl)-6-[(1'R)-1'-hydroxyethyl]-3-methylthio-7-oxo-1-azabicyclo[3.2.0]hept-2-ene-2-carboxylate

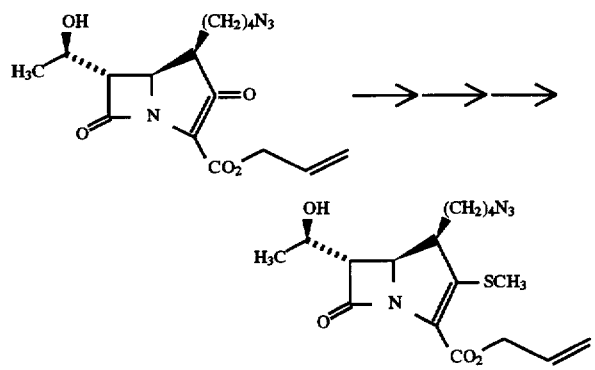

A solution of allyl (4R,5R,6S)-4-(4"-azidobutyl)-6-[(1'R)-1'-hydroxyethyl]-3,7-dioxo-1-azabicyclo[3.2.0]heptane-2-carboxylate (5.28 mmol, prepared from 2.0 g, 5.28 mmol of the diazo precursor) in dry acetonitrile (40 mL) was treated at 0°–5° C. and under nitrogen with diphenyl chlorophosphate (1.2 mL, 5.79 mmol) and N,N-diisopropylethylamine (1.0 mL, 5.74 mmol) added simultaneously over 5 min. A small crystal of 4-N,N-dimethylaminopyridine was added and the mixture was stirred for 40 min. Then N,N-diisopropylethylamine (0.92 mL, 5.28 mmol) followed by chlorotrimethylsilane (0.67 mL, 5.28 mmol) were added and the mixture was stirred for 5 min. The solution was then treated with N,N-diisopropylethylamine (1.84 mL, 10.56 mmol) and excess methanethiol (0.7 g, 15 mmol) was condensed in the solution. The reaction mixture was then stirred at 0°–5° C. for 48 h. After addition of ethyl acetate (400 mL), the organic phase was washed successively with water, 1M NaHSO₃, 1M NaHCO₃, brine and dried (MgSO₄). The solution was then concentrated under reduced pressure, and the residue was diluted with tetrahydrofuran (20 mL) and water (5 mL) and treated at 0°–5° C. with acetic acid (2 mL). The resulting mixture was stored at 0°–5° C. for 16 h. After dilution with ethyl acetate and work-up as above (sat. NaHCO₃, brine, MgSO₄), the product obtained was chromatographed on silica gel (5×10 cm). Elution with a gradient of ethyl acetate in toluene (2:8 to 3:7) gave 1.38 g (69%) of the title compound as a clear oil:

IR (NaCl₃, film) $v_{max}$: 2100 (N₃), 1770 (C=O of β-lactam) and 1705 cm⁻¹ (C=O of ester);

¹H NMR (200 MHz, CDCl₃) δ: 1.39 (d, J=6.26 Hz, 3H, CH₃CHO), 1.4–1.8 (m, 6H, CH₂-1,2 and 3 of butyl), 1.90 (d, J=5.14 Hz, 1H, OH), 2.36 (s, 3H, SCH₃), 3.16 (dd, $J_{H6,H5}$=2.58 Hz, $J_{H6,H1}$=7.38 Hz, 1H, H-6), 3.20 (overlapping with H-6, 1H, H-4), 3.33 (t, J=6.2 Hz, 2H, CH₂N₃), 4.21 (dd, $J_{H5,H6}$=2.58 Hz, $J_{H5,H4}$=9.29 Hz, 1H, H-5), 4.25 (overlapping with H-5, 1H, CH₃CHO), 4.75 (m, 2H, CH₂ of allyl), 5.2–5.5 and 5.9–6.1 ppm (2×m, 2H and 1H, CH of allyl).

B. (4R, 5S, 6S )-4-(4"-Aminobutyl)-6-[(1'R )-1'-hydroxyethyl]-3-methylthio-7-oxo-1-azabicyclo[3.2.0]hept-2-ene-2-carboxylic acid

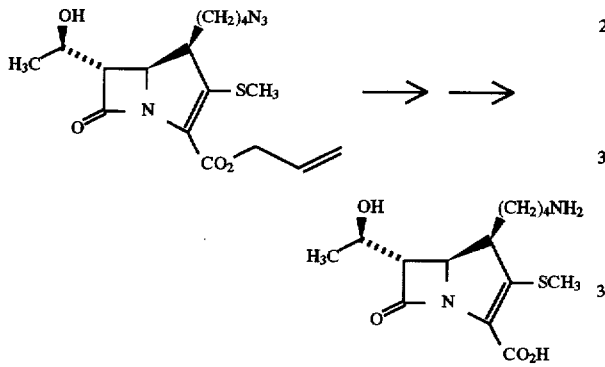

A solution of allyl (4R,5S,6S)-4-(4"-azidobutyl)-6-[(1'R)-1'-hydroxyethyl]-3-methylthio-7-oxo-1-azabicyclo[3.2.0]hept-2-ene-2-carboxylate (1.38 g, 3.63 mmol) in dry ethyl acetate (75 mL) was treated at 22° C. and under nitrogen with tetrakis(triphenylphosphine)palladium [0] (0.12 g) and 8 mL (4.0 mmol) of a 0.5M solution of potassium 2-ethylhexanoate in ethyl acetate. After 1.5 h, the reaction mixture was extracted with cold water (2×75 mL) and the combined aqueous extract was maintained under vacuum to remove traces of organic solvent. The aqueous phase was then hydrogenated at 0°–5° C. over 2 g of 5% palladium on alumina and under 45 psi of hydrogen for 1.2 h. Then 25 mL of 0.2M pH 6.0 phosphate buffer were added and the catalyst was filtered. The filtrate was chromatographed on reversed phase silica gel (µBondapak C₁₈, 3.5×15 cm) using a gradient of acetonitrile (0–4%) in water as eluent. Lyophilization of the uv active fractions gave 0.57 g (50%) of the title compound as a white amorphous powder: $[\alpha]_D^{22}$+97.2° (c 1.0, water);

Purity by HPLC: 98.9% on µBondpak C₁₈, 3.9 mm×30 cm, elution 5% CH₃CN—H₂O, pH 7.4 phosphate buffer, flow rate 0.8 mL/min, UV detector 300 nm, retention time 6.05 min;

UV (water, pH 7.4 phosphate buffer) $\lambda_{max}$: 306 nm (9,475);

IR (KBr) $v_{max}$: 1750 (C=O of β-lactam) and 1580 cm⁻¹ (C=O of carboxylate);

¹H NMR (200 MHz, D₂O) δ: 1.33 (d, J=6.34 Hz, 3H, CH₃CHO), 1.3–1.9 (m, 6H, CH₂-1,2 and 3 of butyl), 2.34 (s, 3H, SCH₃), 3.01 (t, J=7.6 Hz, 2H, CH₂NH₂), 3.31 (dd, $J_{H6,H5}$=2.36 Hz, $J_{H6,H1}$=6.47 Hz, 1H, H-6), 3.39 (broad t, J=9 Hz, 1H, H-4), 4.19 (dd, $J_{H5,H6}$=2.36 Hz, $J_{H5,H4}$=9.06 Hz, 1H, H-5) and 4.26 ppm (m, 1H, CH₃CHO).

EXAMPLE 93

(4R,5S,6S)-4-(3"-Aminopropyl)-6-[(1'R)-1'-hydroxyethyl]-3-[(1,2,3-thiadiazol-4-yl)methlthio]-7-oxo-1-azabicyclo[3.2.0]hept-2-ene-2-carboxylic acid

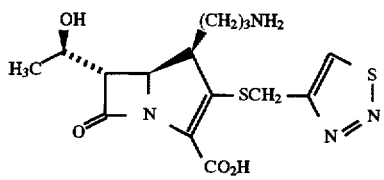

A. Allyl (4R,5S,6S)-4-(3"-azidopropyl)-6-[(1'R)-1'-hydroxyethyl]-3-[(1,2,3-thiadiazol-4-yl)methylthio]-7-oxo-1-azabicyclo[3.2.0]hept-2-ene-2-carboxylate

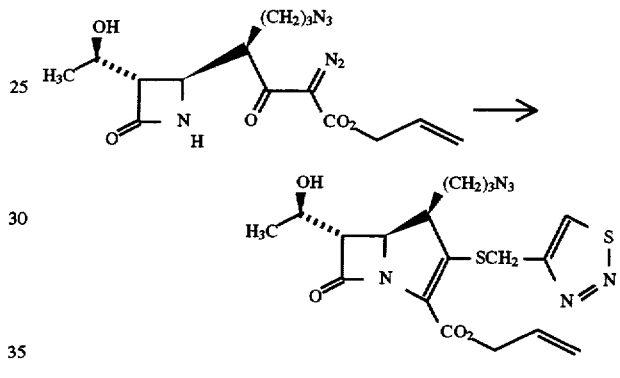

A cold solution (ice-MeOH bath) of allyl (2R,4R,5R, 6S)-4-(3"-azidopropyl)-6-[(1'R)-1'-hydroxyethyl]-3,7-dioxo-1-azabicyclo[3.2.0]heptan-2-carboxylate, freshly prepared from (3S, 4R)-3-[(1'R)-1'-hydroxyethyl]-4-[(1" R)-1"-(3-azidopropyl)- 3"-diazo-3"-allyloxycarbonyl-2"-oxopropyl]azetidin-2-one (1.7 g, 4.7 mmol) in CH₃CN (50 mL) was treated dropwise with diphenyl chlorophosphate (1.1 mL, 5.0 mmol) and N,N-diisopropylethylamine (0.92 mL, 5.0 mmol) and with a trace of 4-N,N-dimethylaminopyridine (5 mg). The mixture was stirred for 1 h and the enol phosphate was treated with 4-mercaptomethyl-1,2,3-thiadiazole (925 mg, 7.0 mmol) and N,N-diisopropylethylamine (1.84 mL, 10.0 mmol). The mixture was stirred for 2 h at 5° C. (ice bath) and more thiol (0.46 g, 3.5 mmol) and N,N-diisopropylethylamine (0.92 mL, 5 mmol) were added. The reaction mixture was left for 18 h at 5° C. (cold room), diluted with ethyl acetate (200 mL), washed with 1M aqueous NaHCO₃, (100 mL) water, (100 mL) 1M aqueous NaHSO₃ (100 mL), water (100 mL), brine (100 mL) and dried (MgSO₄). The residue (4.0 g) was passed through a silica gel flash column (200 g, Hexane/EtOAc 1/1) to give the title compound (0.90 g, 43%) as an oil;

IR (CH₂Cl₂) $v_{max}$: 3680, 3600 (OH), 2100 (N₃), 1775 and 1710 cm⁻¹ (C=O);

¹H NMR (CDCl₃, 200 MHz) δ: 8.477 (1H, s, aromatic-H), 6.02–5.85 (1H, m, vinylic-H), 5.48–5.22 (2H, m, vinylic H), 4.87–4.61 (2H, m, allylic —CH₂), 4.771, 4.696, 4.337, 4.260 (2H, ABq, J=15.2 Hz, CH₂-aromatic), 4.28–4.14 (1H, m, H-1'), 4.162 (1H, dd, J=2.6 Hz, J=9.6 Hz, H-5), 3.60–3.27 (3H, m, CH₂N₃ and H-4), 3.245 (1H, dd, J=2.7 Hz, J=7.5

Hz, H-6), 2.04–1.50 (4H, m, (CH$_2$)$_2$-4), 1.597 (1H, bs, OH) and 1.377 ppm (3H, d, J=6.3 Hz, CH$_3$).

B. (4R,5S,6S)-4-(3"-Aminopropyl)-6-[(1'R)-1'-hydroxyethyl]-3-[(1,2,3-thiadiazol-4-yl)methylthio]-7-oxo-1-azabicyclo[3.2.0]hept-2-ene-2-carboxylic acid

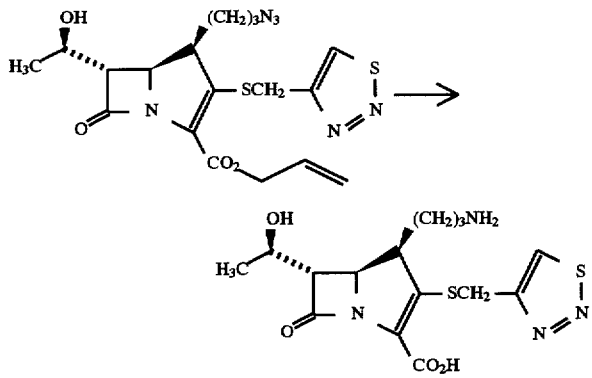

A cold (ice bath) solution of allyl (4R,5S,6S)-4-(3"-azidopropyl)-6-[(1'R)-1'-hydroxyethyl]-3-[(1,2,3-thiadiazol-4-yl)methylthio]-7-oxo-1-azabicyclo[3.2.0]hept-2-ene-2-carboxylate (0.9 g, 2 mmol) in CH$_2$Cl$_2$ (20 mL) was treated with Pd(PPh$_3$)$_4$ (90 mg) followed by the dropwise addition of a 0.5M solution of sodium ethyl-2-hexanoate (4.1 mL, 2.05 mmol) in ethyl acetate. The mixture was stirred for 30 min, then diluted with a 1/1 mixture of ethyl acetate/diethyl ether and was extracted with a 0.05M pH 7.0 aqueous phosphate buffer solution (1×50 mL and 2×25 mL). The aqueous extracts were combined, washed with diethyl ether and passed through a µBondapak C$_{18}$ reversed phase column (180 g, H$_2$O→5% CH$_3$CN/H$_2$O) to give the sodium carboxylate (0.50 g, 61%) as a lyophilized powder;

$^1$H NMR (D$_2$O, 200 MHz) δ: 8.897 (1H, s, aromatic —H), 4.679, 4.605, 4.447, 4.372 (2H, ABq, J=15 Hz, CH$_2$-aromatic), 4.299–4.173 (1H, 5 lines, H-1'), 4.124 (1H, dd, J=2.5 Hz, J=9.5 Hz, H-5), 3.412, 3.401 (part of H-6, d, J=2.5 Hz), 3.41–3.34 (3H, m, H-6 and CH$_2$—N$_3$), 3.31–3.20 (1H m, H-4), 1.9–1.32 (4H, m, (CH$_2$)$_2$-4) and 1.300 ppm (3H, d, J=6.4 Hz, CH$_3$).

The sodium carboxylate (500 mg, 1.22 mmol) in water (75 mL) was shaken at 0° C. (ice bath) in a Parr hydrogenator at 45–50 psi hydrogen for 1 h using 5% Pd/Alumina as catalyst (500 mg). More catalyst (500 mg) was added and the hydrogenation was pursued for one more hour at 0° C. The catalyst was removed by filtration and the pH (10–11) was adjusted to 7.0 with a 1M aqueous NaH$_2$PO$_4$ solution. The mixture was passed through a µBondapak C$_{18}$ reversed phase column (100 g, H$_2$O→5% CH$_3$CN/H$_2$O) to give the final compound (250 mg, 53%) as a lyophilized powder;

Purity: 99.93% (304 nm, HPLC);

UV (H$_2$O) λ$_{max}$: 302 (ε8050);

IR (Nujol) ν$_{max}$: 3600–3100 (OH, NH$_2$), 1755 and 1685 cm$^{-1}$ (C=O);

$^1$H NMR (D$_2$O, 200 MHz) δ: 8.894 (1H, s, aromatic H), 4.660, 4.586, 4.440, 4.365 (2H, ABq, J=14.9 Hz, CH$_2$-aromatic), 4.302–4.174 (1H, 5 lines, H-1'), 4.125 (1H, dd, J=2.6 Hz, J=9.5 Hz, H-5), 3.359 (1H, dd, J=2.7 Hz, J=6.5 Hz, H-6), 3.32–3.22 (1H, m, H-4), 3.06–2.97 (2H, m, CH$_2$—N), 1.83–1.32 (4H, m, (CH$_2$)$_2$-4) and 1.304 ppm (3H, d, J=6.4 Hz, CH$_3$).

EXAMPLE 94

(4R,5S,6S)-4-[3"-(N-Formimidoyl)aminopropyl]-6-[(1'R)-1'-hydroxyethyl]-3-[(1-methyl-1,2,3-triazol-4-yl) methylthio]-7-oxo-1-azabicyclo[3.2.0]hept-2-ene-2-carboxylic acid

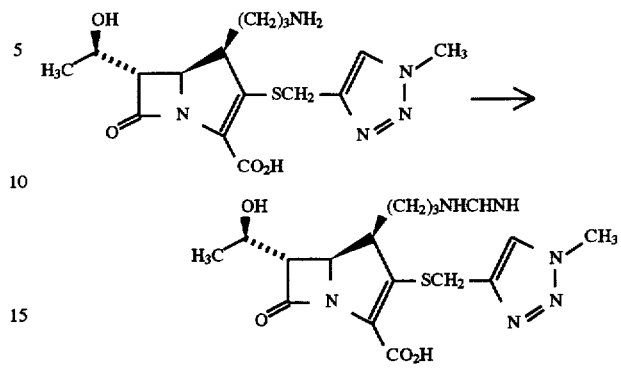

A cold solution (ice bath) of (4R,5S,6S)-4-(3"-aminopropyl)-6-[(1'R)-1'-hydroxyethyl]-3-[(1-methyl-1,2,3-triazol-4-yl)methylthio]-7-oxo-1-azabicyclo[3.2.0]hept-2-ene-2-carboxylic acid (175 mg, 0.460 mmol) in a 0.02M aqueous pH 7.0 phosphate buffer (50 mL) was treated with a 0.10N aqueous NaOH solution (to raise and maintain the pH around 8.0±0.2) and with benzyl formimidate hydrochloride (200 mg, 1.15 mmol). The mixture was stirred for 30 min and then the pH of the solution was lowered to 7.0 with a 1M aqueous NaH$_2$PO$_4$ solution. The mixture was passed through a µBondapak C$_{18}$ reversed phase column (20 g, water→5% CH$_3$CN/H$_2$O) to give the title compound (110 mg, 59%) as a lyophilized powder;

Purity: 97.2% (302 nm, HPLC);

UV (H$_2$O) λ$_{max}$: 302 (ε9260);

IR (Nujol) ν$_{max}$: 3600–3700 (OH), 1750 (C=O), 1710 (C=N) and 1585 cm$^{-1}$ (C=O);

$^1$H NMR (D$_2$O, 200 MHz) δ: 7.867 (1H, s, aromatic —H), 7.834, 7.812 (1H, 2s, CH), 4.30–4.18 (1H, m, H-1'), 4.212, 4.137, 4.031, 3.957 (2H, ABq, J=14.9 Hz, CH$_2$-aromatic), 4.159, 4.112, 4.099 (1H, 1s and 1d, J=2.6 Hz, part of H-5), 4.083 (3H, s, N—CH$_3$), 3.330 (1H, dd, J=2.6 Hz, J=6.1 Hz, H-6), 3.45–3.20 (3H, m, H-4 and CH$_2$N), 1.9–1.32 (4H, m, (CH$_2$)$_2$-4) and 1.300 ppm (3H, d, J=6.4 Hz, CH$_3$).

EXAMPLE 95

(4R,5S,6S)-4-(3"-Guanidinopropyl)-6-[(1'R)-1'-hydroxyethyl]-3-[(1-methyl-1,2,3-triazol-4-yl)methylthio]-7-oxo-1-azabicyclo[3.2.0]hept-2-ene-2-carboxylic acid

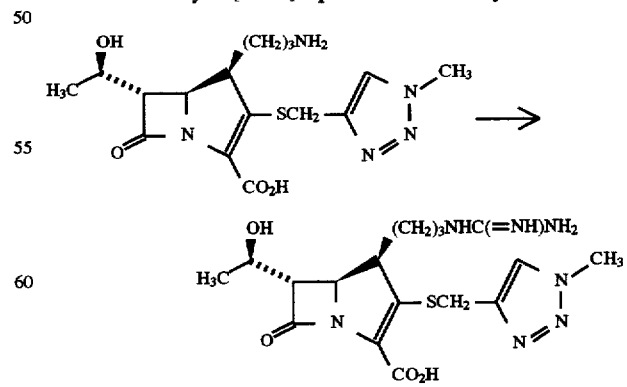

A cold (ice bath) solution of (4R,5S,6S)-4-(3"-aminopropyl)-6-[(1'R)-1'-hydroxyethyl]- 3-[(1- methyl-1,2,3-triazol-4-yl)methylthio]-7-oxo- 1-azabicyclo [3.2.0]hept-2-ene-2-carboxylic acid (170 mg, 0.460 mmol) in a 0.02M pH 7.0 aqueous phosphate buffer (50 mL) was treated first with a 0.1N aqueous NaOH solution (to raise and maintain the pH at 8.0±0.2) and aminoiminomethanesulfonic acid (570 mg, 4.60 mmol). The mixture was stirred for 90 min and then the pH was lowered to 7.0 with a 1M aqueous solution of $NaH_2PO_4$. The mixture was passed through a µBondapak $C_{18}$ reversed phase column (20 g, water→5% $CH_3CN/H_2O$) to give the title compound (130 mg, 74%) as a lyophilized powder;

Purity: 99.85% (302 nm, HPLC);

UV ($H_2O$) $\lambda_{max}$: 302 (ε9150);

IR (Nujol) $v_{max}$: 3600–3100 (NH, OH), 1755 (C=O), 1670–1630 (C=N) and 1590 $cm^{-1}$ (C=O);

$^1H$ NMR ($D_2O$, 200 MHz) δ: 7.871 (1H, s, aromatic H), 4.31–4.16 (1H, 5 lines, H-1'), 4.211, 4.135, 4.037, 3.962 (2H, ABq, J=15 Hz, $CH_2$-aromatic), 4.063 (3H, s, $CH_3$-triazole), 4.155–4.06 (1H, m, hidden H-5), 3.318, 3.306, 3.267 (part of H-6, d+s), 3.32–3.22 (3H, m, $CH_2$—N and H-4), 1.9–1.30 (4H, m, $(CH_2)_2$-4) and 1.29 ppm (3H, d, J=6.4 Hz, $CH_3$).

EXAMPLE 96

(4R,5S,6S)-4-(4"-Aminobutyl)-3-[(2-carbamoyloxy) ethylthio]-6-[(1'R)-1'-hydroxyethyl]-7-oxo-1-azabicyclo [3.2.0]hept-2-ene-2-carboxylic acid

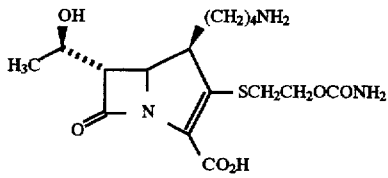

A. Allyl (4R,5S,6S)-4-(4"-azidobutyl)-3-[(2-carbamoyloxy) ethylthio]-6-[(1'R)-1'-hydroxyethyl)]-7-oxo-1-azabicyclo [3.2.0]hept-2-ene-2-carboxylate

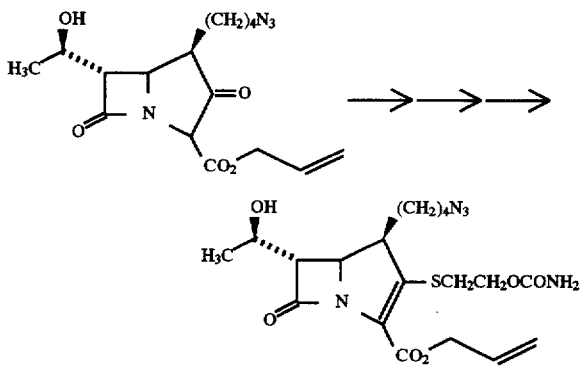

A solution of allyl (4R,5R,6S)-4-(4"-azidobutyl)-6-[(1'R)-1'-hydroxyethyl]-3,7-dioxo-1-azabicyclo[3.2.0]hept-2-ene-2-carboxylate (7.6 mmol, prepared from 2.88 g, 7.6 mmol of the diazo precursor) in dry acetonitrile (35 mL) was treated at 0°–5° C. and under nitrogen with diphenyl chlorophosphate (1.65 mL, 8.0 mmol) and N,N-diisopropylethylamine (1.38 mL, 8.0 mmol) added simultaneously over 5 min. A small crystal of 4-N,N-dimethylaminopyridine was then added and the mixture was stirred for 30 min. Then N,N-diisopropylethylamine (1.38 mL, 8.0 mmol) followed by chlorotrimethylsilane (1.0 mL, 8.0 mmol) were added and the mixture was stirred for 10 min. More N,N-diisopropylethylamine (1.38 mL, 8.0 mmol) followed by 2-carbamoyloxyethanethiol (1.8 g, 15.2 mmol) in acetonitrile were added and the resulting mixture was stirred at 0°–5° C. for 18 h. The reaction mixture was then quenched by addition of cold 0.2M pH 7.0 phosphate buffer (100 mL) and ethyl acetate (500 mL). The organic phase was washed with water, brine and dried ($MgSO_4$). Evaporation of the solvent gave an oil which was dissolved in tetrahydrofuran (50 mL) and water (50 mL) and treated at 0°–5° C. with acetic acid (1.5 mL). The temperature was then slowly allowed to reach 22° C. over 1 h. The reaction mixture was then diluted with ethyl acetate (400 mL) and the work-up was done as above. The residue obtained after evaporation of the solvent was chromatographed twice on silica gel (4×12 cm) using first a mixture of toluene and ethyl acetate (1:1) and then a mixture of dichloromethane and acetonitrile (7:3) as eluent. Evaporation of the UV active fractions gave 1.71 g (49%) of the title compound as an oil:

IR (NaCl, film) $v_{max}$: 2,100 ($N_3$), 1770 (C=O of β-lactam) and 1720 (broad C=O of ester and carbamate);

$^1H$ NMR (200 MHz, $CDCl_3$) δ: 1.39 (d, J=6.25 Hz, 3H, $CH_3CHO$), 1.4–1.8 (m, 6H, $CH_2$-1,2 and 3 of butyl), 2.8–3.2 (m, 5H, $SCH_2$, $CH_2N_3$ and H-4), 3.18 (dd, $J_{H6,H5}$=2.62 Hz, $J_{H6,H1}$=7.17 Hz, 1H, H-6), 4.1–4.4 (m, 4H, H-5, $CH_3CHO$ and $CH_2OCONH_2$ overlapping), 4.6–4.9 (m, 4H, $CH_2$ of allyl and OCO$NH_2$), 5.2–5.5 and 5.9–6.1 ppm (2m, 2H and 1H, CH of allyl).

B. (4R, 5S,6S)-4-(4"-Aminobutyl)-3-[(2-carbamoyloxy) ethylthio]-6-[(1'R)-1'-hydroxyethyl]-7-oxo-1-azabicyclo [3.2.0]hept-2-ene-2-carboxylic acid

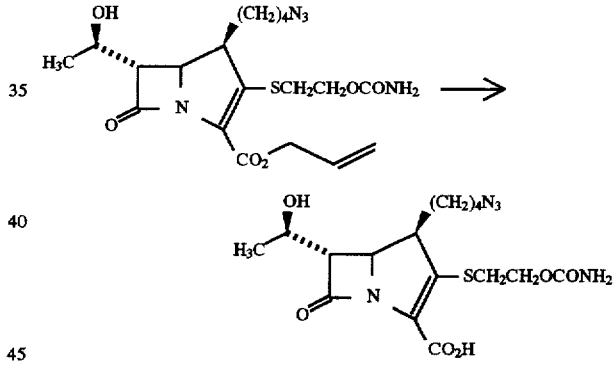

A solution of allyl (4R,5S,6S)-4-(4"-azidobutyl)-3-[(2-carbamoyloxy)ethylthio]-6-[(1'R)-1'-hydroxyethyl]-7-oxo-1-azabicyclo[3.2.0]hept-2-ene-2-carboxylate (1.71 g, 3.77 mmol) in dry ethyl acetate (50 mL) was treated at 22° C. and under nitrogen with tetrakis(triphenylphosphine)palladium [0] (0.100 g) followed by 8 mL (4.0 mmol) of a 0.5M solution of potassium 2-ethylhexanoate in ethyl acetate. The reaction mixture was then extracted with water (3×50 mL) and the combined aqueous extract was chromatographed on reversed phase silica gel (µBondapak $C_{18}$, 3×13 cm). Elution with a gradient of acetonitrile (0–5%) in water gave 1.0 g (59%) of the intermediate potassium salt as a white solid after freeze drying.

The potassium salt was then dissolved in cold water 150 mL and hydrogenated at 0°–5° C. over 1.5 g of 5% palladium over alumina and under 45 psi of hydrogen for 1 h. Then 20 mL of 0.2M pH 6.0 phosphate buffer were added, the catalyst was filtered and the filtrate was chromatographed on reversed phase silica gel (µBondapak $C_{18}$, 3×15 cm). Elution with a gradient of acetonitrile (0–5%) in water gave 0.722 g (83%, 49% combined) of the title compound as a white amorphous powder after lyophilization: $[\alpha]_D^{22}$+ 74.6° (c 1.0 $H_2O$);

Purity by HPLC: 96.4% on µBondapak $C_{18}$, 3.9 mm×30 cm, elution 5% $CH_3CN$—$H_2O$ pH 7.4 phosphate buffer, flow rate 0.8 mL/min, uv detector 300 nm, retention time 5.56 min;

UV (water, pH 7.4 phosphate buffer) $\lambda_{max}$: 302 nm (9,219);

IR (KBr) $v_{max}$: 1750 (C=O of β-lactam), 1720 (C=O of carbamate) and 1585 $cm^{-1}$ (C=O of carboxylate);

$^1$H NMR (200 MHz, $D_2O$) δ: 1.33 (d, J=6.34 Hz, 3H, $CH_3CHO$), 1.3–2.0 (m, 6H, $CH_2$-1,2 and 3 of butyl), 2.9–3.2 (m, 4H, $SCH_2$ and $CH_2NH_2$), 3.36 (dd, $J_{H6,H5}$=2.51 Hz, $J_{H6,H1}$=6.27 Hz, 1H, H-6), 3.4 (m, overlapping with H-6, 1H, H-4) and 4.2–4.4 ppm (m, 4H, H-5, $CH_3\underline{CH}O$ and $\underline{CH_2}OCONH_2$).

EXAMPLE 97

(4R,5S,6S)-4-(3"-Guanidinopropyl)-6-[(1'R)-1'-hydroxyethyl]-3-[(1,2,3-thiadiazol-4-yl)methylthio]-7-oxo-1-azabicyclo[[3.2.0]hept-2-ene-2-carboxylic acid

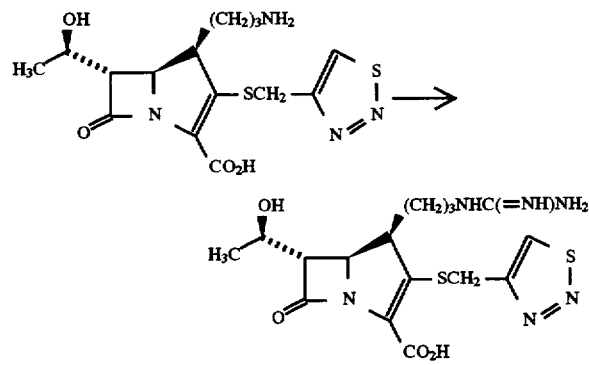

A cold solution (ice bath) of (4R,5R,6S)-4-(3"-aminopropyl)-6-[(1'R)-1'-hydroxyethyl]-3-[(1,2,3-thiadiazol-4-yl)methylthio]-7-oxo-1-azabicyclo[3.2.0]hept-2-ene-2-carboxylic acid (120 mg, 0.31 mmol) in a 0.025M pH 7.0 aqueous phosphate buffer (30 mL) was treated first with a 0.1M aqueous NaOH solution (to raise and maintain the pH to 8.1±0.2) and portionwise with aminoiminomethanesulfonic acid (390 mg, 3.10 mmol). The mixture was stirred for 1.5 h and the pH was lowered to 7.0 with a 1M aqueous $NaH_2PO_4$ solution. The mixture was passed through a µBondapak $C_{18}$ reversed phase column (20 g, water→3% $CH_3CN/H_2O$) to give the title compound (90 mg 68%) as a lyophilized powder;

Purity: 98.5% (302 nm, HPLC);

UV ($H_2O$) $\lambda_{max}$: 302 (ε8400);

IR (Nujol) $v_{max}$: 3600–3100 (OH, $NH_3$), 1750 (C=O), 1770–1730 (C=N) and 1680 $cm^{-1}$ (C=O);

$^1$H NMR ($D_2O$, 200 MHz) δ: 8.896 (1H, s, aromatic H), 4.654, 4.580, 4.446, 4.371 (2H, ABq, J=15 Hz, $CH_2$-aromatic), 4.29–4.17 (1H, 5 lines, H-1'), 4.124 (1H, dd, J=2.5 Hz, J=9.5 Hz, H-5), 3.298 (1H, dd, J=2.5 Hz, J=6.5 Hz, H-6), 3.30–3.10 (3H, m, $CH_2$—N and H-4), 1.90–1.30 (4H, m, $(CH_2)_2$-4) and 1.291 ppm (3H, d, J=6.4 Hz, $CH_3$).

EXAMPLE 98

(4R,5S,6S)-3-[(2-Carbamoyloxyethyl)thio]-4-(4"-N-formimidoylaminobutyl)-6-[(1'R)-1'-hydroxyethyl]-7-oxo-1-azabicyclo[3.2.0]hept-2-ene-2-carboxylic acid

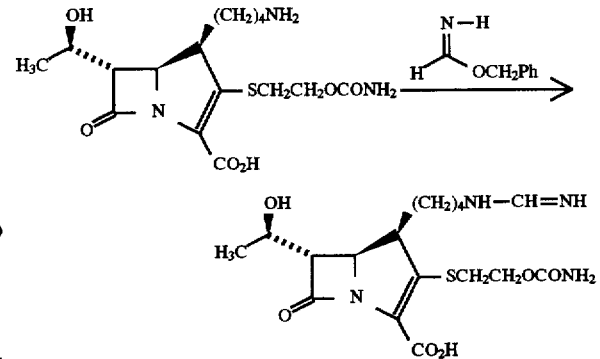

A solution of (4R,5S,6S)-4-(4"-aminobutyl)-3-[(2-carbamoyloxyethyl)thio]-6-[(1'R)-1'-hydroxyethyl]-7-oxo-1-azabicyclo[3.2.0]hept-2-ene-2-carboxylic acid (0.196 g, 0.506 mmol) in cold water (15 mL) was adjusted to pH 8.0 with 1M NaOH and treated at 0°–5° C. with benzylformimidate hydrochloride (0.26 g, 1.5 mmol) added in small portions over 10 min. The pH was maintained at 8–8.5 with 1M NaOH throughout the addition. After 20 min, 10 mL of 0.2M pH 6.0 phosphate buffer were added and the reaction mixture was washed with ethyl acetate. The aqueous phase was then chromatographed first on reversed phase silica gel (µBondapak $C_{18}$, 2.5×15 cm) using a gradient of acetonitrile (0–5%) in 0.02M pH 7.0 phosphate buffer as eluent. The UV active fractions were combined, concentrated (T <5° C.) and desalted on the same column using water instead of buffer as eluent. Lyophilization of the pertinent fractions gave 0.136 g (65%) of the title compound as a white amorphous solid: $[\alpha]_D^{22}$+72.0° (c. 1.0,water);

Purity by HPLC: 98.8% on µBondapak $C_{18}$, 3.9 mm×30 cm, elution 5% $CH_3CN$—$H_2O$, pH 7.4 phosphate buffer, flow rate 1 mL/min, uv detector 300 nm, retention time 6.12 min;

UV (water, pH 7.4 phosphate buffer) $\lambda_{max}$: 302 nm (9,228);

IR (KBr) $v_{max}$: 1750 (C=O of β-lactam), 1715 $cm^{-1}$ (C=O of carbamate and formimidoyl) and 1590 cm (C=O of carboxylate);

$^1$H NMR (200 MHz, $D_2O$) δ: 1.31 (d, J=6.32 Hz, 3H, $\underline{CH_3}CHO$), 1.3–2.0 (m, 6H, $CH_2$-1,2 and 3 of butyl), 2.8–3.2 (m, 2H, $SCH_2$), 3.3–3.5 (m, 4H, H-4, H-6 and $\underline{CH_2}NH$), 4.2–4.4 (m, 3H, $\underline{CH_2}OCONH_2$, H-5 and $CH_3\underline{CH}O$) and 7.79 ppm (broad s, 1H, $\underline{CH}NH$).

EXAMPLE 99

(4R,5S,6S)-4-(2"-Aminoethyl)-3-[(1-methyl-1,3-imidazol-5-yl)methylthio]-6-[(1'R)-1'-hydroxyethyl]-7-oxo-1-azabicyclo[[3.2.0]hept-2-ene-2-carboxylic acid

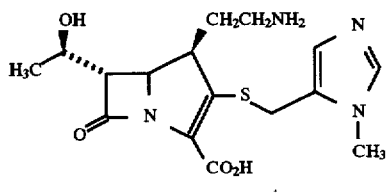

A. Allyl (4R,5S,6S)-4-(2"-azidoethyl)-6-[(1'R)-1'-tert-butyldimethylsilyloxyethyl]-3-[(1-methyl-1,3-imidazol-5-yl)methyl-thio]7-oxo-1-azabicyclo[3.2.0]hept-2-ene-2-carboxylate

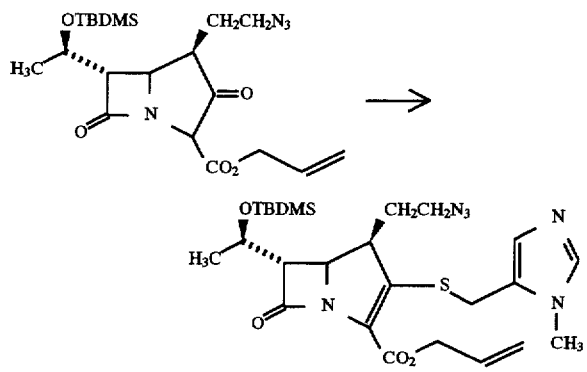

A solution of allyl (4R,5R,6S)-4-(2"-azidoethyl)-6-[(1'R)-1'-tert-butyldimethylsilyloxyethyl]-3,7-dioxo-1-azabicyclo[3.2.0]heptane-2-carboxylate (5.10 mmol, prepared by cyclization of 2.37 g, 5.10 mmol of the diazo precursor) in dry acetonitrile (39 mL) was treated at -15° C. and under Argon with diphenyl chlorophosphate (1.10 mL, 5.3 mmol) and N,N-diisopropylethylamine (0.95 mL, 5.3 mmol). A small crystal of 4-N,N-dimethylaminopyridine was added and the mixture was stirred at -15° C. for 30 min. N,N-Diisopropylethylamine (0.95 mL, 5.4 mmol) and 1-methyl-5-thiomethyl-1,3-imidazole (1.31 g, 10.2 mmol) were added and the mixture was stirred for 3 h at 0° C. The reaction mixture was diluted with EtOAc (272 mL) and washed with water, 1M NaHSO$_3$ saturated NaHCO$_3$, brine and dried (MgSO$_4$). Evaporation of the solvent gave an oil which was chromatographed on silica gel. Elution with a mixture of EtOAc:CH$_3$CN:acetone (12:87:1) gave 1.5 g (54%) of the title compound as a yellow oil:

IR (CH$_2$Cl$_2$) λ$_{max}$: 2100 (N$_3$), 1775 (C=O of β-lactam) and 1710 (C=O of ester).

$^1$H NMR (200 MHz, CDCl$_3$) δ: 0.09 (s, 6H, SiCH$_3$), 0.90 (s, 9H, Si-t-bu), 1.31 (d, J=6.1 Hz, 3H, CH$_3$CHO), 1.7 and 2.0 (2×m, 2×1H, CH$_2$-4), 3.08 (dd, J$_{1',6}$=7.17 Hz, J$_{5,6}$=2.76 Hz, 1H, H-6), 3.3-3.6 (m, 2H, CH$_2$N$_3$), 3.69 (s, 3H, CH$_3$—N), 3.9-4.2 (m, 4H), 4.7 (m, 2H, CH$_2$ of allyl), 5.2-5.5 and 6.0 (2×m, 2H and 1H, CH of allyl), 6.99 and 7.46 (2×s, 2H, imidazoyl).

B. Allyl (4R,5S,6S)-4-(2"-azidoethyl)-3-[(1-methyl-1,3-imidazo-5-yl)methylthio)-6-[(1'R)-1'-hydroxyethyl]-7-oxo-1-azabicyclo[3.2.0]hept-2-ene-2-carboxylate

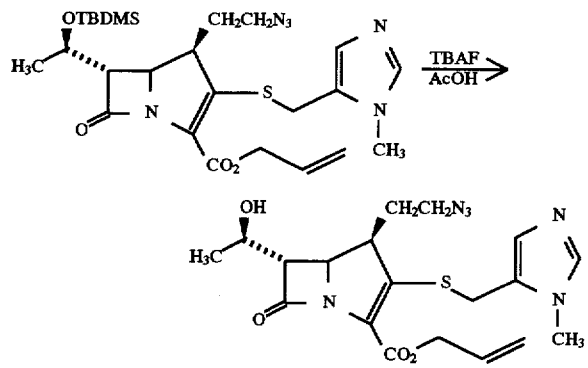

A solution of allyl (4R,5S,6S)-4-(2"-azidoethyl)-6-[(1'R)-1'-tert-butyldimethylsilyloxyethyl]-3-[(1-methyl-1,3-imidazol-5-yl)-methylthio]-7-oxo-1-azabicyclo[3.2.0]hept-2-ene-2-carboxylate (1.50 g, 2.74 mmol) in dry tetrahydrofuran (43 mL) was treated at 0°-5° C. and under Argon with acetic acid (0.94 mL, 16.4 mmol) followed by 8.5 mL (8.5 mmol) of 1M solution of tetrabutylammonium fluoride in tetrahydrofuran. The solution was stored at 5° C. for 8.5 days. The reaction mixture was then diluted with EtOAc, washed with saturated NaHCO$_3$, brine and dried (MgSO$_4$). Evaporation of the solvent gave an oil which was chromatographed on silica gel (4.5×15 cm). Elution with acetone gave 1.87 g (73%) of the title compound as a foamy light yellow solid:

IR (NaCl, film) v$_{max}$: 3200 (broad, OH), 2105 (N$_3$), 1780 (C=O of β-lactam), and 1710 (C=O of ester).

C. (4R,5S,6S)-4-(2"-Aminoethyl)-3-[(1-methyl-1,3-imidazo-5-yl)-methylthio]-6-[(1'R)-1'-hydroxyethyl]-7-oxo-1-azabicyclo[3.2.0]hept-2-ene-2-carboxylate

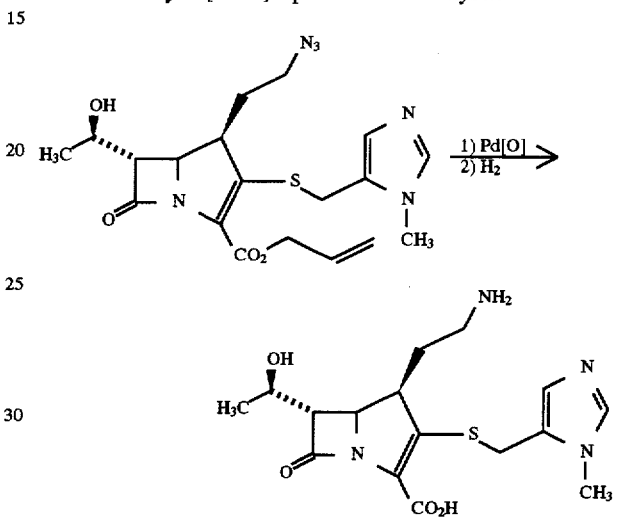

A solution of allyl (4R,5S,6S)-4-(2"-azidoethyl)-3-[(1-methyl-1,3-imidazol-5-yl)-methylthio]-6-[(1'R)-1'-hydroxyethyl]7-oxo-1-azabicyclo[3.2.0]hept-2-ene-2-carboxylate (558 mg, 1.29 mmol) in dry CH$_2$Cl$_2$ (29 mL) was treated at 0°-5° C. and under Argon, with tetrakis(triphenylphosphine)palladium [0] (112 mg) and 2.84 mL (1.42 mmol) of a 0.5M solution of sodium 2-ethylhexanoate in EtOAc. Then 39 mL of water was added and the organic layer was separated. The organic phase was reextracted with 2×22 mL of water and the combined aqueous layers were evaporated to remove organic solvent. The residual aqueous phase was hydrogenated over 396 mg of 5% palladium on alumina and under 45 psi of hydrogen for 1 hour. The catalyst was filtered and the filtrate was neutralized with a solution of NaH$_2$PO$_4$ 1M (a few drops). The mixture was chromatographed on reversed phase silica gel (Bondapak C$_{18}$, 7×11 cm) using a gradient of acetonitrile in water (0-1%) followed by lyophilization of the UV active fractions to give 130 mg of the title compound as a light yellow amorphous powder:

UV (water, pH 7.4 phosphate buffer) λ$_{max}$: 302 nm (6000);

IR (KBr) v$_{max}$: 1765 (C=O of β-lactam) and 1625 (C=O of carboxylate );

1HNMR (200 Hz, D$_2$O) δ: 1.32 (d, J=6.3 Hz, 3H, CH$_3$CHO), 1.7 and 2.1 (2×m, 2×1H, CH$_2$-4), 3.05 (t, J=9.0 Hz, CH$_2$NH$_2$), 3.23 (m, 1H, H-4), 3.41 (dd, J$_{7,6}$=6.5 Hz, J$_{5,6}$=2.7 Hz, H-6), 3.7 (s, 3H, CH$_3$—N), 3.9-4.3 (m, 4H, CH$_2$—S, CH$_3$CHO, H-5), 6.93 and 7.63 (2×s, 2H, imidazoyl).

EXAMPLE 100

(4R,5S,6S)-3-[(2-Carbamoyloxyethyl)thio]-4-(4"-guanidinobutyl)-6-[(1'R)-1'-hydroxyethyl]-7-oxo-1-azabicyclo[3.2.0]hept-2-ene-2-carboxylic acid

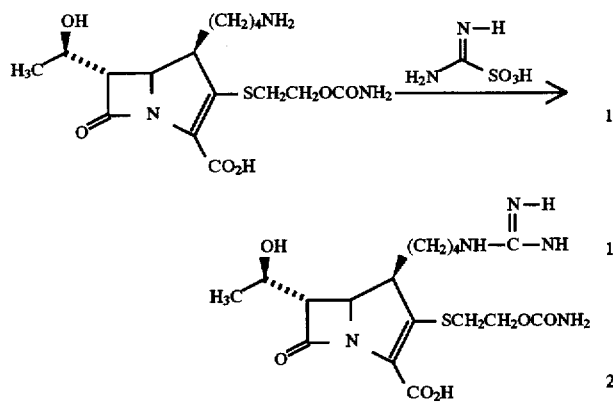

A solution of (4R,5S,6S)-4-(4'-aminobutyl)-3-[(2-carbamoyloxyethyl)thio]-6-[(1'R)-1'-hydroxyethyl]-7-oxo-1-azabicyclo[3.2.0]hept-2-ene-2-carboxylic acid (0.172 g, 0.44 mmol) in cold water (0°–5° C., 13 mL) was adjusted to pH 8.5 with 1M NaOH. Then aminoiminomethanesulfonic acid (0.275 g, 2.21 mmol) was added in small portions over 10 min while maintaining the pH between 8 and 8.5. After 45 min at 0°–5° C., the reaction mixture was quenched by addition of 15 mL of 0.2M pH 6.0 phosphate buffer and chromatographed on reversed phase silica gel (μBondapak C$_{18}$, 2.5×15 cm). Elution with a gradient of acetonitrile (0–5%) in water gave 0.149 g (78%) of the title compound as a white amorphous solid after freeze drying:

Purity by HPLC: 99% on μBondapak C$_{18}$, 3.9 mm×30 cm, elution 10% CH$_3$CN—H$_2$O, pH 7.4 phosphate buffer, flow rate 0.8 mL/min, uv detector 300 nm, retention time 6.0 min;

UV (water, pH 7.4 phosphate buffer) $\lambda_{max}$: 302 nm (9,371);

IR (KBr) $\nu_{max}$: 1750 (sh, C=O of β-lactam), 1730 (broad C=O of carbamate), 1670 (C=O of guanidine) and 1590 cm$^{-1}$ (C=O of carboxylate);

$^1$H NMR (200 MHz, D$_2$O) δ: 1.32 (d, J=6.32 Hz, 3H, CH$_3$CHO), 1.3–1.9 (m, 6H, CH$_2$-1.2 and 3 of butyl), 2.8–3.2 (m, 2H, SCH$_2$), 3.22 (t, J=6.5 Hz, CH$_2$N), 3.34 (dd, J$_{H6,H5}$=2.55 Hz, J$_{H6,H1}$=6.10 Hz, 1H, H-6), 3.36 (m, overlapping with H-6, 1H, H-4) and 4.2–4.4 ppm (m, 4H, CH$_2$O, H-5 and CH$_3$CHO).

EXAMPLE 101

(4R,5S,6S)-3-[(2-Cyanoethyl)thio]-4-(2"-dimethylaminoethyl)-6-[(1'R)-1'-hydroxyethyl]-7-oxo-1-azabicyclo[3.2.0]hept-2-ene-2-carboxylic acid

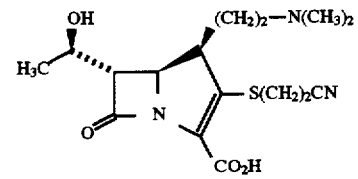

A. Allyl (4R,5S,6S)-6-[(1'R)-1'-tert-butyldimethylsilyloxyethyl]-3[(2-cyanoethyl)thio]-4-(2"-dimethylaminoethyl)-7-oxo-1-azabicyclo[3.2.0]hept-2-ene-2-carboxylate

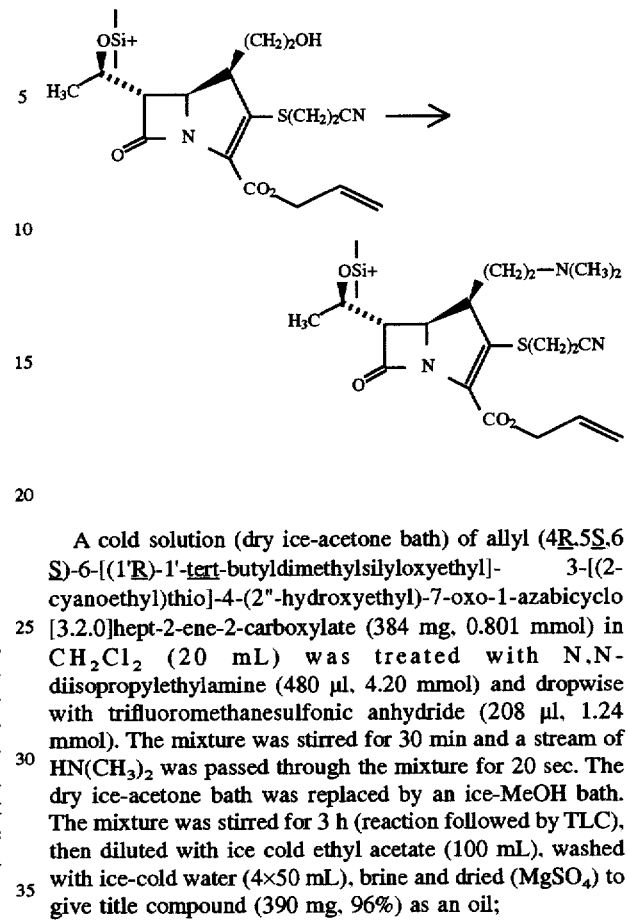

A cold solution (dry ice-acetone bath) of allyl (4R,5S,6S)-6-[(1'R)-1'-tert-butyldimethylsilyloxyethyl]-3-[(2-cyanoethyl)thio]-4-(2"-hydroxyethyl)-7-oxo-1-azabicyclo[3.2.0]hept-2-ene-2-carboxylate (384 mg, 0.801 mmol) in CH$_2$Cl$_2$ (20 mL) was treated with N,N-diisopropylethylamine (480 μl, 4.20 mmol) and dropwise with trifluoromethanesulfonic anhydride (208 μl, 1.24 mmol). The mixture was stirred for 30 min and a stream of HN(CH$_3$)$_2$ was passed through the mixture for 20 sec. The dry ice-acetone bath was replaced by an ice-MeOH bath. The mixture was stirred for 3 h (reaction followed by TLC), then diluted with ice cold ethyl acetate (100 mL), washed with ice-cold water (4×50 mL), brine and dried (MgSO$_4$) to give title compound (390 mg, 96%) as an oil;

IR (neat) $\nu_{max}$: 2250 (C≡N), 1775 and 1710 cm$^{-1}$ (C=O);

$^1$H NMR (CDCl$_3$, 200 MHz) δ: 6.03–4.85 (1H, m, vinylic —H), 5.49–5.22 (2H, m, vinylic H), 4.9–4.6 (2H, m, allylic —CH$_2$), 4.30–4.17 (1H, m, H-1'), 4.205 (1H, dd, J=2.7 Hz, J=9.7 Hz, H-5), 3.40–3.20 (2H, m H-4 and HCH—N), 3.254 (1H, dd, J=2.8 Hz, J=7.0 Hz, H-6), 3.15–2.95 (2H, m, SCH$_2$), 2.72–2.63 (2H, m, CH$_2$CN), 2.5–2.30 (1H, m, HCH—N), 2.254 (6H, s, N(CH$_3$)$_2$), 2.05–1.80 (1H, m, HCH-4), 1.7–1.4 (1H, m, HCH-4), 1.290 (3H, d, J=6.1 Hz, CH$_3$), 0.890 (9H, s, tert-butyl)and 0.086 ppm (6H, s, dimethyl).

B. Allyl (4R,5S,6S)-3-[(2-cyanoethyl)thio]-4-(2"-dimethylaminoethyl)-6-[(1'R)-1'-hydroxyethyl]-7-oxo-1-azabicyclo[3.2.0]hept-2-ene-2-carboxylate

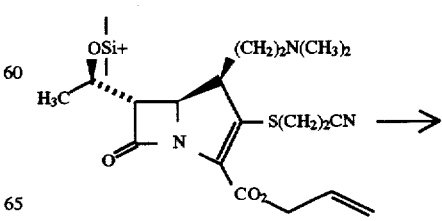

-continued

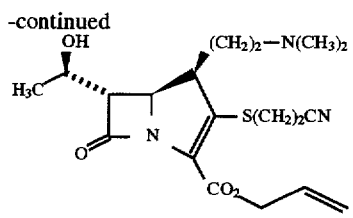

A cold solution (ice-MeOH bath) of allyl (4R,5S,6 S)-6-[(1'R)-1'-tert-butyldimethylsilyloxyethyl]- 3-[(2-cyanoethyl)thio]-4-(2"-dimethylaminoethyl)-7-oxo-1-azabicyclo[3.2.0]hept-2-ene-2-carboxylate (390 mg, 0.768 mmol) in tetrahydrofuran (10 mL) was treated with acetic acid (600 μl, 10.5 mmol) and dropwise with a 1M solution of tetrabutylammonium fluoride in tetrahydrofuran (6.0 mL, 6.0 mmol). The mixture was stirred for 1 h and then was allowed to set in the cold room for 144 h. The mixture was diluted with ethyl acetate (100 mL) and washed with ice cold 1M aqueous $NaHCO_3$ (2×100 mL), cold brine (2×100 mL) and dried ($MgSO_4$) to give the title compound (270 mg, 89%) as a crude oil;

IR (neat) $v_{max}$: 3600–3200 (OH), 1775 and 1710 $cm^{-1}$ (C=O);

$^1$H NMR ($CDCl_3$, 200 MHz) δ: 6.05–1.90 (1H, m, vinylic H), 5.50–5.24 (2H, m, vinylic-H), 4.9–4.6 (2H, m, allylic-H), 4.294, 4.279 (part of H-5, d, J=2.9 Hz), 4.29–4.15 (1H, m, H-1'), 3.45–3.9 (3H, m, H-4 and $SCH_2$), 3.302 (1H, dd, J=2.9 Hz, J=7.9 Hz, H-6), 2.8–2.6 (4H, m, $CH_2$—N and $CH_2CN$), 2.264 (6H, s, $N(CH_3)_2$), 2.0–1.6. (3H, m, $CH_2$-4 and OH) and 1.377 ppm (3H, d, J=6.2 Hz, $CH_3$).

C. (4R,5S,6S)-3-[(2-Cyanoethyl)thio]-4-(2"-dimethylaminoethyl)-6-[(1'R)-1'-hydroxyethyl]-7-oxo-1-azabicyclo[3.2.0]hept-2-ene-2-carboxylic acid

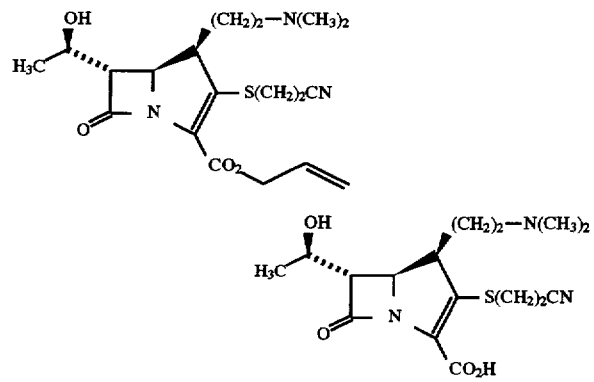

A cold solution (ice bath) of crude allyl (4R,5S,6 S)-3-[(2-cyanoethyl)thio]-4-(2"-dimethylaminoethyl)-6-[(1' R)-1'-hydroxyethyl]-7-oxo-1-azabicyclo[3.2.0]hept-2-ene-2-carboxylate (270 mg, 0.69 mmol) in $CH_2Cl_2$ (5 mL) was treated with $Pd(PPh_3)_4$ (30 mg) and a 0.5M solution of sodium ethyl-2-hexanoate in ethyl acetate (1.44 mL, 0.720 mmol). The mixture was stirred for 45 min, then diluted with a 1/1: ethyl acetate/diethyl ether mixture (20 mL) and extracted with a 0.02M pH 7.0 phosphate buffer (1×20 mL, 2×10 mL). The aqueous extracts were combined, washed with diethyl ether and passed twice through a μBondapak $C_{18}$ reversed phase column (40 g, 0.02M aqueous pH 7.0 phosphate buffer→3% $CH_3$ $CN/H_2O$) to give title compound (70 mg, 30%) as a lyophilized powder;

Purity: 99.5% (298 nm, HPLC);

UV ($H_2O$) $\lambda_{max}$: 298 (ε6960);

IR (Nujol) $v_{max}$: 3600–31200 (OH), 2250 (C≡N), 1750 and 1590 $cm^{-1}$ (C=O);

$^1$H NMR ($D_2O$, 200 MHz) δ: 4.33–4.21 (1H, m, H-1'), 4.289 (1H, dd, J=2.8 Hz, J=9.3 Hz, H-5), 3.429 (1H, dd, J=2.9 Hz, J=6.6 Hz, H-6), 3.48–3.35 (H, m, H-4), 3.21–2.76 (6H, $SCH_2$, $CH_2$—N, $CH_2CN$) 2.758 (6H, s, $N(CH_3)_2$), 2.27–2.14 and 1.98–1.80 (2H, 2 sets of m, $CH_2$-4) and 1.339 ppm (3H, d, J=6.4 Hz, $CH_3$).

EXAMPLE 102

(4R,5S,6S)-4-(4"-Guanidinobutyl)-6-[(1'R)-1'-hydroxyethyl]-3-methylthio-7-oxo-1-azabicyclo[3.2.0]hept-2-ene-2-carboxylic acid

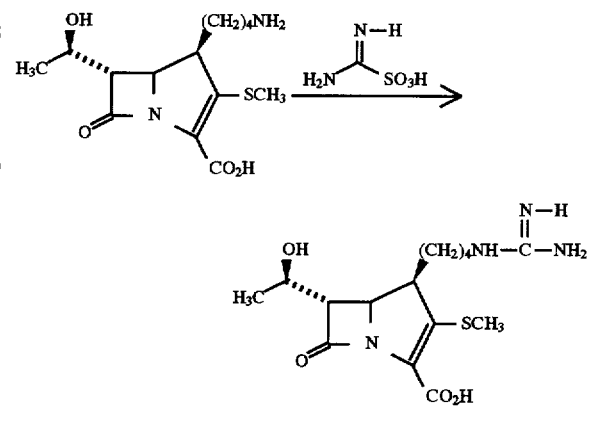

A solution of (4R,5S,6S)-4-(4"-aminobutyl)-6-[(1'R)-1'-hydroxyethyl]-3-methylthio-7-oxo-1-azabicyclo[3.2.0]hept-2-ene- 2-carboxylic acid (0.226 g, 0.72 mmol) in cold water (0°–5° C., 20 mL) was adjusted to pH 8.5 with NaOH 1M and then treated with aminoiminomethanesulfonic acid (0.40 g, 3.22 mmol) added in small portions over 5 min. The pH was maintained at 8–8.5 throughout the addition and for another two hours with 1M NaOH. The reaction mixture was then quenched by the addition of 20 mL of 0.2M pH 6.0 phosphate buffer and chromatographed on reversed phase silica gel (μBondapak $C_{18}$, 3.5×15 cm). Elution with a gradient of acetonitrile (0–5%) in water gave 0.169 g (66%) of the title compound as a white amorphous powder after lyophilization:

Purity by HPLC: 99.8% on μBondapak $C_{18}$, 3.9 mm×30 cm, 5% $CH_3CN$—$H_2O$, pH 7.4 phosphate buffer, flow rate 1.5 mL/min, UV detector 304 nm, retention time 5.77 min;

UV (water, pH 7.4 phosphate buffer) $\lambda_{max}$: 306 nm (9,411);

IR (KBr) $v_{max}$: 1750 (C=O of β-lactam), 1665 (C=N of guanidine) and 1580 $cm^{-1}$ (C=O of carboxylate);

$^1$H NMR (200 MHz, $D_2O$) δ: 1.32 (d, J=6.35 Hz, 3H, $CH_3CHO$), 1.3–1.9 (m, 6H, $CH_2$-1,2 and 3 of butyl), 2.34 (s, 3H, $SCH_3$), 3.22 (t, J=6.5 Hz, 2H, $CH_2N$), 3.28 (dd, $J_{H6,H5}$=2.39 Hz, $J_{H6,H1}$=6.26 Hz, 1H, H-6), 3.38 (broad t, 1H, H-4), 4.19 (dd, $J_{H5,H6}$=2.39 Hz, $J_{H5,H4}$=9.04 Hz, 1H, H5) and 4.27 ppm (m, 1H, $CH_3\underline{C}HO$).

EXAMPLE 103

(4R,5S,5S)-4-(4"-N-Formimidoylaminobutyl)-6-[(1'R)-1'-hydroxyethyl-3-methylthio-7-oxo-1-azabicyclo[3.2.0]hept-2-ene-2-carboxylic acid

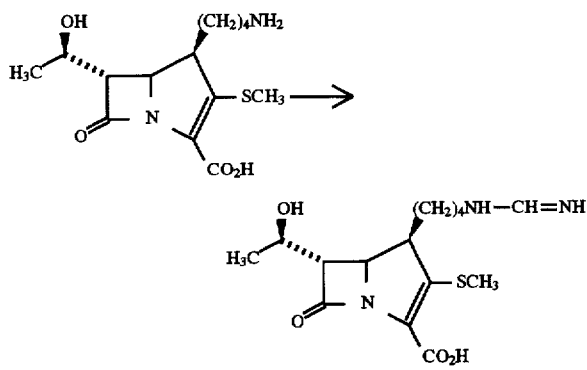

A solution of (4R,5S,6S)-4-(4"-aminobutyl)-6-[(1'R)-1'-hydroxyethyl]-3-methylthio-7-oxo-1-azabicyclo[3.2.0]hept-2-ene-2-carboxylic acid (0.210 g, 0.67 mmol) in water (30 mL) at 0°–5° C. was adjusted to pH 8.5 with 1N NaOH. Then benzyl formimidate hydrochloride (0.60 g, 3.5 mmol) was added in small portions over 10 min while maintaining the pH between 8 and 8.5 with 1N NaOH. After another 20 min at 0°–5° C., the reaction mixture was quenched by addition of 25 mL of 0.2M pH 6.0 phosphate buffer and washed with ethyl acetate (20 mL). The aqueous phase was then maintained under vacuum to remove traces of organic solvent and then chromatographed on reversed phase silica gel (μBondapak $C_{18}$, 3.5×14 cm) using a gradient of acetonitrile (0–5%) in 0.01M pH 7.0 phosphate buffer as eluent. The UV active fractions were combined, concentrated in vacuo (T <5° C.) and chromatographed a second time using water instead of buffer as eluent. Lyophilization of the pertinent fractions gave 0.123 g (54%) of the title compound as a white amorphous powder: $[\alpha]^{22}_D$ +110.3° (c 1.0, water);

Purity by HPLC: 99% on μBondapak $C_{18}$, 3.9 mm×30 cm, elution 3% $CH_3CN$—$H_2O$, pH 7.4 phosphate buffer, flow rate 1.5 mL/min, uv detector 304 nm, retention time 6.48 min;

UV (water, pH 7.4 phosphate buffer) $\lambda_{max}$: 306 nm (10,187);

IR (KBr) $v_{max}$: 1750 (C=O of β-lactam) 1715 (C=N of formimidoyl) and 1580 $cm^{-1}$ (C=O of carboxylate);

$^1$H NMR (200 MHz, $D_2O$) δ: 1.32 (d, J=6.27 Hz, 3H, $CH_3CHO$), 1.3–1.9 (m, 6H, $CH_2$-1,2 and 3 of butyl), 2.34 (s, 3H, $SCH_3$), 3.3–3.5 (m, 4H, H-6, H-4 and $CH_2NH$), 4.18 (dd, $J_{H5,H6}$=1.92 Hz, $J_{H5,H4}$=9.0 Hz, 1H, H-5), 4.26 (m, 1H, $CH_3CHO$) and 7.8 ppm (broad s, 1H, $CH$=NH).

EXAMPLE 104

(4R,5S,6S)-3-[(2-Carbamoyloxyethyl)thio]-4-(4"-N,N-dimethylaminobutyl)-6-[(1'R)-1'-hydroxyethyl]-7-oxo-1-azabicyclo[3.2.0]hept-2-ene-2-carboxylic acid

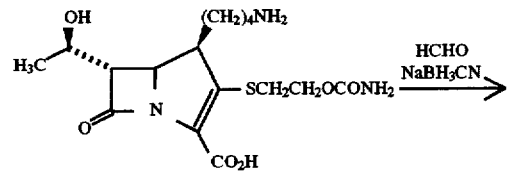

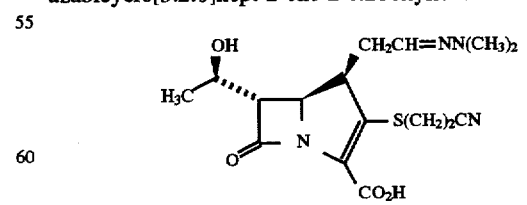

A solution of (4R,5S,6S)-4-(4"-aminobutyl)-3-(2-carbamoyloxyethylthio)-6-[(1'R)-1'-hydroxyethyl]-7-oxo-1-azabicyclo[3.2.0]hept-2-ene-2-carboxylic acid (0.230 g, 0.59 mmol) in water (10 mL) was treated at 0°–5° C. with 0.25 mL (3.0 mmol) of 37% aqueous formaldehyde and 2 mL of 0.2M pH 6.0 phosphate buffer. Then 0.074 g (1.18 mmol) of sodium cyanoborohydride was added all at once and the resulting mixture was stirred at 0°–5° C. for 1 h. By HPLC (μBondapak $C_{18}$) the product was a 51:45 mixture of title dimethyl derivative and of N-methyl-N-cyanomethyl derivative. The crude reaction mixture was chromatographed first on reversed phase silica gel (μBondapak $C_{18}$, 2×15 cm) using a gradient of acetonitrile (0–5%) in 0.02M pH 7.0 phosphate buffer as eluent. The first fractions were combined and desalted on the same column using water instead of buffer as eluent and gave 0.081 g (33%) of the title compound as a white amorphous solid after lyophilization:

Purity by HPLC: 99% on μBondapak $C_{18}$, 3.9 mm×30 cm, elution 5% $CH_3CN$—$H_2O$, pH 7.4 phosphate buffer, flow rate 1 mL/min, uv detector 300 nm, retention time 6.11 min;

UV ($H_2O$, pH 7.4 phosphate buffer) $\lambda_{max}$: 302 (9,036);

IR (KBr) $v_{max}$: 1750 (C=O of β-lactam), 1725 (C=O of carbamate) and 1595 $cm^{-1}$ (C=O of carboxylate);

$^1$H NMR (200 MHz, $D_2O$) δ: 1.32 (d, J=6.34 Hz, 3H, $CH_3CHO$), 1.3–2.0 (m, 6H, $CH_2$-1,2 and 3 of butyl), 2.84 (s, 6H, $NCH_3$), 2.8–3.2 (m, 2H, $SCH_2$), 3.10 (t overlapping with $SCH_2$, J=7.9 Hz, 2H, $CH_2N$), 3.36 (dd, $J_{H6,H5}$=2.30 Hz, 1H, H-6), 3.37 (m, overlapping with H-6, 1H, H-4), and 4.2–4.4 ppm (m, 4H, H-5, $CH_3CHO$ and $CH_2OCONH_2$ overlapping).

EXAMPLE 105

(4R,5S,6S)-4-(2"-Acetaldehydodimethylhydrazone)-3-[(2-cyanoethyl)thio]-6-[(1'R)-1'-hydroxyethyl]-7-oxo-1-azabicyclo[3.2.0]hept-2-ene-2-carboxylic acid A. Allyl (4R,5S,6S)-4-(2"-acetaldehydo)-6-[(1'R)-1'-tert-butyldimethylsilyloxyethyl]-3-[(2-cyanoethyl)thio]-7-oxo-1-azabicycolo[3.2.0]hept-2-ene-2-carboxylate

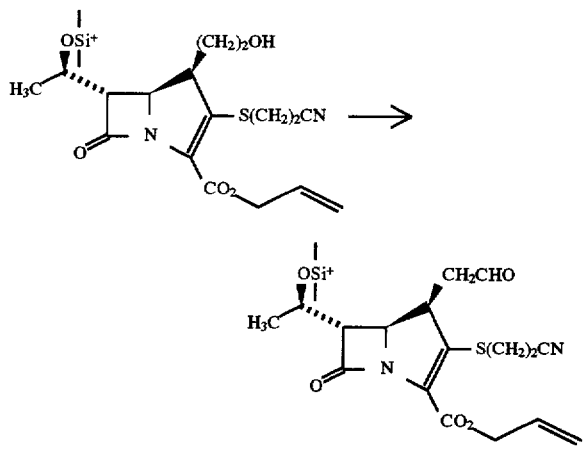

A cold (dry ice-acetone bath) solution of oxalyl chloride (150 μL, 1.65 mmol) in CH$_2$Cl$_2$ (5 mL) was treated dropwise with a solution of DMSO (250 μL, 3.19 mmol) in CH$_2$Cl$_2$ (1 mL). The mixture was stirred for 5 min and then a solution of allyl (4R,5S,6S)-6-[(1'R)-1'-tert-butyldimethylsilyloxyethyl]-3-[(2-cyanoethyl)thio]-4-(2"-hydroxyethyl)-7-oxo-1-azabicyclo[3.2.0]hept-2-ene-2-carboxylate (420 mg, 0.875 mmol) in CH$_2$Cl$_2$ (4 mL) was added dropwise. The mixture was stirred for 15–20 min and triethylamine (1.5 mL, 10.8 mmol) was added. The solution was stirred for 10 more min and then was allowed to warm to room temperature (~10 min). It was diluted with water (25 mL) and CH$_2$Cl$_2$ (40 mL) and the aqueous layer was extracted with CH$_2$Cl$_2$ (4×20 mL). The organic layers were combined, washed with ice cold 5% aqueous HCl (2×20 mL) ice cold water (2×20 mL), ice cold 5% NaHCO$_3$ (2×20 mL), ice cold water (2×20 mL), brine (20 mL) and dried (MgSO$_4$). Evaporation of the solvent gave the title compound (402 mg, 96%) as an oil;

IR (neat) v$_{max}$: 2250 (C≡N), 1775, 1720 and 1710 cm$^{-1}$ (C=O);

$^1$H NMR (CDCl$_3$, 200 MHz) δ: 9.849 (1H, s, CHO), 6.01–5.87 (1H, m, vinylic-H), 5.49–5.22 (2H, m, vinylic —H), 4.80–4.60 (2H, m, allylic —CH$_2$), 4.371 (1H, dd, J=2.7 Hz, J=9.8 Hz, H-5), 4.28–4.18 (1H, 6 lines, H-1'), 3.763 (1H, dt, J=3.5 Hz, J=10.2 Hz, H-4), 3.2–2.77 (5H, m, H-6, SCH$_2$and CH$_2$CHO), 2.70–2.63 (2H, m, CH$_2$CN), 1.161 (3H, d, J=6.2 Hz, CH$_3$), 0.883 (9H, s, tert-butyl) and 0.068 ppm (6H, s, dimethyl).

B. Allyl (4R,5S,6S)-4-(2"-acetaldehydedimethylhydrazone)-6-[(1'R)-1'-tert-butyldimethylsilyloxyethyl]-3-[(2-cyanoethyl)thio]-7-oxo-1-azabicyclo[3.2.0]hept-2-ene-2-carboxylate

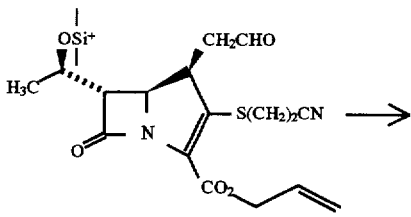

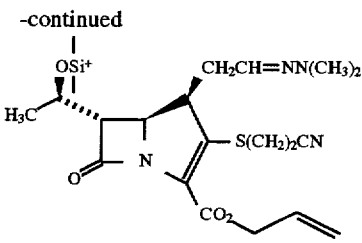

A cold (ice bath) solution of allyl (4R,5S,6S)-4-(2"-acetaldehydo)-6-[(1'R)-1'-tert-butyldimethylsilyloxyethyl]-3-[(2-cyanoethyl)thio]-7-oxo-1-azabicyclo[3.2.0]hept-2-ene-2-carboxylate (402 mg, 0.840 mmol) in anhydrous ethanol (8 mL) was treated with dimethylhydrazine (150 μL, 1.97 mmol). The mixture was allowed to react at 5° C. (cold room) for 24 h after which the solvent was evaporated to leave the title compound (463 mg, 100%) as an oil;

IR (neat) v$_{max}$: 2250 (C≡N), 1775, 1710 (C=O) and 1550 cm$^{-1}$ (C=N);

$^1$H NMR (CDCl$_3$, 200 MHz), δ: 6.474 (1H, bt, J=4.2 Hz, CH=N), 6.04–5.85 (1H, m, vinylic H), 5.48–5.21 (2H, m, vinylic H), 4.85–4.70 (2H, m, allylic —H), 4.298 (1H, dd, J=2.5 Hz, J=9.4 Hz, H-5), 4.28–4.22 (1H, m, H-1'), 3.64–3.55 (1H, m, H-4), 3.319 (1H, dd, J=2.7 Hz, J=3.9 Hz, H-6), 3.25–2.92 (2H, m, SCH$_2$), 2.754 (6H, s, N(CH$_3$)$_2$), 2.73–2.60 (3H, m, CH$_2$CN and HCH-4), 2.55–2.3 (1H, m, HCH-4) 1.148 (3H, d, J=6.2 Hz, CH$_3$), 0.0878 (9H, s, tert-butyl) and 0.066, 0.060 ppm (6H, 2s, dimethyl).

C. Allyl (4R,5S,6S)-4-(2"-acetaldehydedimethylhydrazone)-3-[(2-cyanoethyl)thio]-6-[(1'R)-1'-hydroxyethyl]-7-oxo-1-azabicyclo[3.2.0]hept-2-ene-2-carboxylate

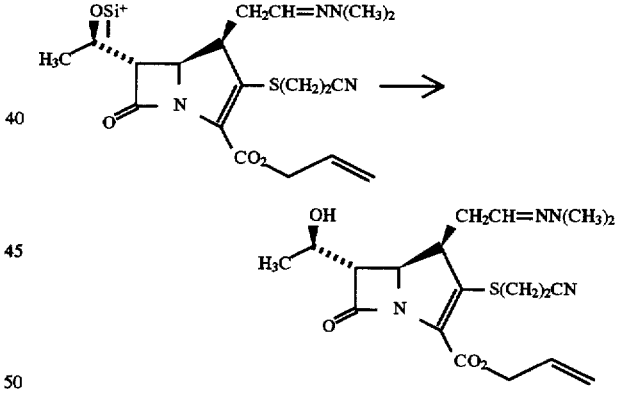

A cold solution (ice-MeOH bath) of allyl (4R,5S,6S)-4-(2"-acetaldehydedimethylhydrazone)-6-[(1'R)-1'-tert-butyldimethylsilyloxyethyl]-3-[(2-cyanoethyl)thio]-7-oxo-1-azabicyclo[3.2.0]hept-2-ene-2-carboxylate (460 mg, 0.883 mmol) in tetrahydrofuran (15 mL) was treated with acetic acid (700 μl, 12.2 mmol) and dropwise with a 1M solution of tetrabutylammonium fluoride in tetrahydrofuran (6.0 mL, 6.0 mmol). The mixture was stirred for 30 min and then was allowed to react at 5° C. (cold room) for 430 h. It was diluted with ice cold ethyl acetate (100 mL) washed with ice cold 5% aqueous NaHCO$_3$ (4×20 mL), water (2×20 mL) brine (20 mL) and dried (MgSO$_4$). Evaporation of the solvent gave the title compound (335 mg, 93%) as a crude oil;

IR (neat) v$_{max}$: 3600–3200 (OH), 2250 (C≡N), 1775, 1710 (C=O) and 1550 cm$^{-1}$ (C=N);

¹H NMR (CDCl₃, 200 MHz) δ: 6.602 (1H, bt, J=4.8 Hz, CH—N), 6.05–5.90 (1H, m, vinylic H), 5.51–5.24 (1H, m, vinylic H), 4.90–4.64 (2H, m, allylic CH₂), 4.311 (1H, dd, J=2.9 Hz, J=9.8 Hz, H-5), 4.20–4.00 (1H, m, H-1'), 3.73–3.60 (1H, m, H-4), 3.307 (1H, dd, J=2.9 Hz, J=8.0 Hz, H-6), 3.18–2.90 (2H, m, SCH₂), 2.773 (6H, s, N(CH₃)₂), 2.87–2.63 (3H, m, CH₂CN and HCH-4), 2.56–2.40 (1H, m, HCH-4), 1.59 (1H, bs, OH) and 1.310 ppm (3H, d, J=6.3 Hz, CH₃).

D. (4R,5S,6S)-4-(2"-Acetaldehydedimethylhydrazone)-3-[(2-cyanoethyl)thio]-6-[(1'R)-1'-hyroxyethyl]-7-oxo-1-azabicyclo[3.2.0]hept-2-ene-2-carboxylic acid

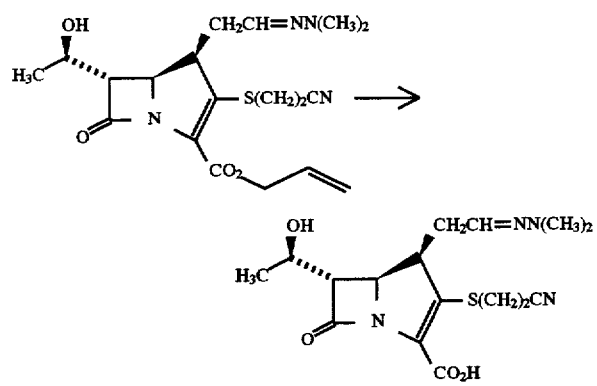

A cold solution ice bath of allyl (4R,5R,6S)-4-(2"-acetaldehydedimethylhydrazone)-3-[(2-cyanoethyl)thio]-6-[(1'R)-1'-hydroxyethyl]-7-oxo-1-azabicyclo[3.2.0]hept-2-ene-2-carboxylate (335 mg, 0.820 mmol) in CH₂Cl₂ (5 mL) was treated with Pd(PPh₃)₄ (35 mg) and dropwise with a 0.5M solution of sodium ethyl-2-hexanoate (1.72 mL, 0.860 mmol) in ethyl acetate. The mixture was stirred for 30 min, then diluted with a 1/1 solution of ethyl acetate/diethyl ether and extracted with a 0.02M pH 7.0 aqueous phosphate buffer (1×30 mL, 2×10 mL). The aqueous extracts were combined, washed with diethyl ether and passed twice on a μBondapak C₁₈ reversed phase column (40 g, 0.02M aqueous phosphate buffer→5% CH₃CN/buffer and 40 g, H₂O→5% CH₃CN/H₂O) to give the title compound (100 mg, 33%) as a lyophilized powder;

Purity: 97.9% (302 nm, HPLC);

UV (H₂O) ν_max: 240 (ε7440) 302 (ε8150);

IR (Nujol) ν_max: 3600–3100 (OH), 2250 (C≡N), 1750 and 1590 (C=O) and 1560 cm⁻¹ (C=N);

¹H NMR (D₂O, 200 MHz) δ: 4.425 (1H, dt, J=5.4 Hz, CH=N), 4.288 (1H, dd, J=2.62 Hz, J=9.5 Hz, H-5), 4.30–4.17 (1H, m, H-1'), 3.79–3.67 (1H, , H-4), 3.518 (1H, dd, J=2.6 Hz, J=5.8 Hz, H-6), 3.30–3.13, 3.05–2.90 (2H, 2 sets of m, SCH₂), 2.90–2.80 (2H, m, CH₂CN), 2.90–2.50 (2H, m, CH₂-4), 2.691 [6H, s, N(CH₃)₂] and 1.274 ppm (3H, d, J=6.4 Hz, CH₃).

EXAMPLE 106

Sodium (4R,5S,6S)-4-(2"-acetaldehydo)-3-[(2-cyanoethyl)thio]-6-[(1'R)-1'-hydroxyethyl]-7-oxo-1-azabicyclo[3.2.0]hept-2-ene-2-carboxylate acid

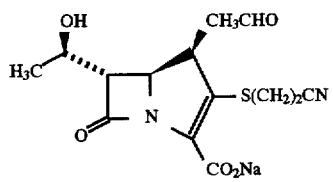

A. Allyl (4R,5S,6S)-4-(2"-acetaldehydo)-3-[(2-cyanoethyl)thio]-6-[(1'R)-1'-hydroxyethyl]--7-oxo-1-azabicyclo[3.2.0]hept-2-ene-2-carboxylate

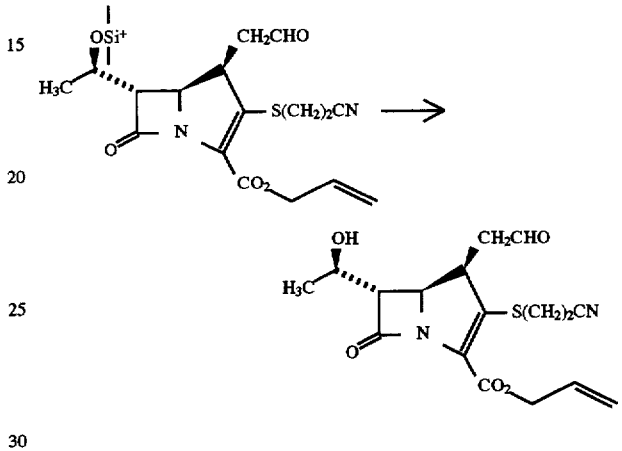

A cold solution of (ice-MeOH bath) of allyl (4R,5S,6S)-4-(2"-acetaldehydo)-6-[(1'R)-1'-tert-butyldimethylsilyloxyethyl]-3-[(2-cyanoethyl)thio]-7-oxo-1-azabicyclo[3.2.0]hept-2-ene-2-carboxylate (200 mg, 0.418 mmol) in tetrahydrofuran (8 mL) was treated with glacial acetic acid (350 mL, 6.1 mmol) and dropwise with a 1M solution of tetrabutylammonium fluoride in tetrahydrofuran (3.0 mL, 3.0 mmol). The mixture was stirred for 30 min and then was allowed to react at (cold room) for 500 hours. It was diluted with ice cold ethyl acetate (50 mL) and with ice cold saturated aqueous NaHCO₃ (4×20 mL), brine (20 mL) and dried (MgSO₄). Evaporation of the solvent left an oil that was applied on a preparative silica gel plate (EtOAc, R_f=0.5) and gave the title compound (40 mg, 26%) as an oil;

IR (neat) ν_max: 3600–330 (OH), 2250 (CN), 1775 and 1720 cm⁻¹ (C=O);

¹H NMR (CDCl₃, 200 MHz) δ: 9.869 (1H, s, CHO), 6.04–5.87 and 5.49–5.25 (3H, m, vinyl H), 4.89–4.65 (2H, m, CH₂-vinyl), 3.416 (1H, dd, J=2.8 Hz, J=9.9 Hz, H-5), 4.24–4.13 (1H, 5 lines, H-1'), 3.84–3.71 (1H, 6 lines, H-4), 3.19–2.81 (3H, m, H-6, CH₂S and CH₂O), 2.75–2.63 (2H, m, CH₂—CN), 1.57 (1H, bs, OH) and 1.298 ppm (3H, d, J=6.3 Hz, CH₃).

B. Sodium (4R,5S,6S)-4-(2"-acetaldehydo)-3-[(2-cyanoethyl)thio]-6-[(1'R)-1'-hydroxyethyl]-7-oxo-1-azabicyclo[3.2.0]hept-2-ene-2-carboxylate acid

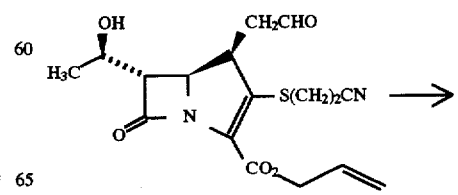

233

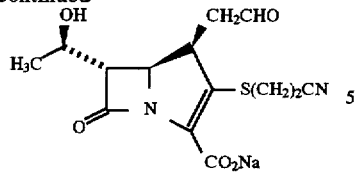

A cold (ice bath) solution of allyl (4R,5S,6 S)-4-(2"-acetaldehydo)-6-[(1'R)-1'-hydroxyethyl]- 3-[(2-cyanoethyl)thio]7-oxo-1-azabicyclo[3.2.0]hept-2-ene-2-carboxylate (40 mg, 0.11 mmol) in dichloromethane (2 mL) was treated with Pd(PPh$_3$)$_4$ (10 mg) and with N-methylaniline (20 μL, excess). The mixture was stirred for 30 min, then diluted with diethyl ether (20 mL) and extracted with a 0.05M pH 7.4 aqueous phosphate buffer (4×5 mL). The aqueous extracts were combined, washed with diethyl ether and passed through a reversed phase μBondpak C$_{18}$ column (9 g, H$_2$O) to give the title compound (10 mg, 26%) as a lyophilized powder;

IR (Nujol) $v_{max}$: 3600–3100 (OH), 2250 (CN), 1755, 1720 and 1600 (C=O);

$^1$H NMR (D$_2$O, 200 MHz) δ: 9.789 (0.5H, s, CHO), 5.244, 5.226, 5.208, 5.189 (0.5H, 4 lines, C$\underline{H}$(OH)$_2$), 4.409 (0.5 H, dd, J=2.7 Hz, J=9.7 Hz, H-5), 4.36–4.20 (1H, m, H-1'), 3.92–3.84 (0.5H, 6 lines, J=3.7 Hz, 10.2 Hz, H-4), 3.556 (0.5 H, dd, J=2.6 Hz, J=5.8 Hz, H-6), 3.56–3.46 (0.5H, m, H-4), 3.27–2.80 (5.5H, m, 0.5 H-6, SCH$_2$, CH$_2$CN and 1H for C$\underline{H}_2$CHO), 2.15–1.90 (1H, m, C$\underline{H}_2$CH(OH)$_2$), 1.336 (1.5H, d, J=6.4 Hz, CH$_3$) and 1.248 ppm (1.5H, d, J=6.5 Hz, CH$_3$).

EXAMPLE 107

Sodium (4R,5S,6S)-3-[(2-cyanoethyl)thio]-6-[(1'R)-1'-hydroxyethyl]-4-(sodium oxycarbonylmethyl)-7-oxo-1-azabicyclo[3.2.0]hept-2-ene-2-carboxylate

234

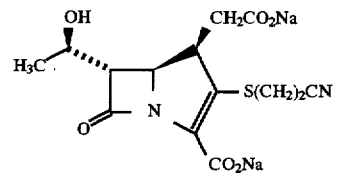

A. Allyl (4R,5S,6S)-4-(allyloxycarbonylmethyl)-3-[(2-cyanoethyl)thio]-6-[(1'R)-1'-tert-butyldimethylsilyloxyethyl]-7-oxo-1-azabicyclo[3.2.0]hept-2-ene-2-carboxylate

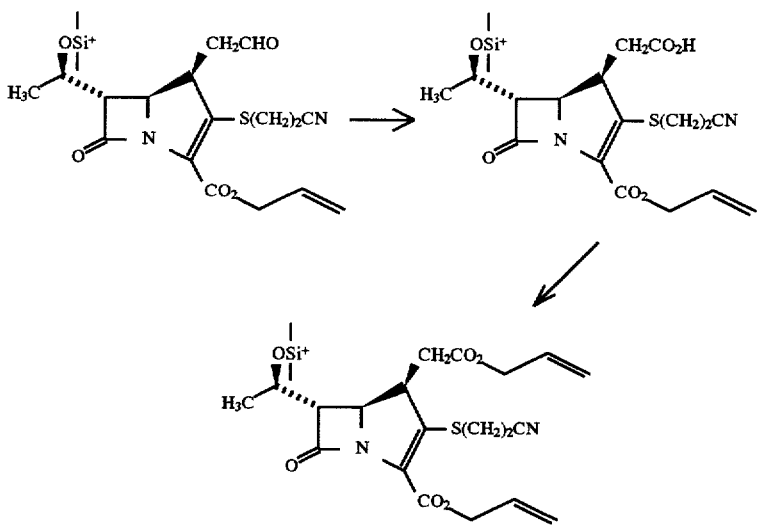

A cold (ice bath) solution of allyl (4R,5S,6 S)-4-(2"-acetaldehydo)-6-[(1'R)-1'-tert-butyldimethylsilyloxyethyl]-3-[(2-cyanoethyl)thio]-7-oxo-1-azabicyclo[3.2.0]hept-2-ene-2-carboxylate (300 mg, 0.627 mmol) in dimethylformamide (10 mL) was treated with pyridinium dichromate (2.0 g, 5.7 mmol) and was stirred for 24 h at 5° C. (cold room). The mixture was diluted with water (100 mL) and the aqueous fraction was extracted with ethyl acetate (5×20 mL). The ethyl acetate extracts were combined, washed with water (2×50 mL), 1% ice cold HCl (50 mL), water (3×50 mL), brine and dried (MgSO$_4$). Evaporation of the solvent left a residue (200 mg) that was dissolved in a 1:1 mixture of dichloromethane and DMF (10 mL). The solution was treated successively with allyl alcohol (1 mL), 1-hydroxybenzotriazole (135 mg, 1.00 mmol) and 1,3-dicyclohexyl carbodiimide (206 mg, 1.00 mmol) and was stirred for 72 h at about 22° C. The ethyl acetate extracts were combined, washed with water (3×20 mL), ice cold 1N aqueous HCl (20 mL), water (2×20 mL), 1M aqueous NaHCO$_3$ (20 mL), water (3×20 mL), brine (20 mL) and dried (MgSO$_4$). The residue upon solvent evaporation was applied on two preparative silica gel plates (2 mm, EtOAc, R$_f$=0.9) to give the title compound (100 mg, 29.8%) as an oil;

IR (neat) $v_{max}$: 2250 (C≡N), 1780, 1735 and 1710 cm$^{-1}$ (C=O);

¹H NMR (CDCl₃, 200 MH) δ: 6.03–5.81, 5.48–5.22 (6H, m, vinylic H), 4.82–4.58 (4H, 2 sets of m, CH₂-vinyl), 3.370 (1H, dd, J=2.7 Hz, J=9.6 Hz, H-5), 4.30–4.19 (1H, 6 lines, H-1'), 3.7 (1H, X part of ABX, J=3.4 Hz, H-4), 3.24–3.11, 3.04–2.90 (2H, 2 sets of m, SCH₂), 3.128 (1H, dd, J=2.7 Hz, J=4.2 Hz, H-6), 2.877, 2.860, 2.792, 2.774 (1H, AB part of ABx, J=3.4 Hz, J=17.1 Hz), 2.601, 2.545, 2.516, 2.460 (1H, AB part of ABX, J=17.1 Hz, J=11.3 Hz, CH₂-4), 2.72–2.63 (2H, m, CH₂CN), 1.147 (3H, d, J=6.3 Hz, CH₃), 0.879 (9H, s, tert-butyl), 0.068 and 0.063 ppm (6H, 2 s, dimethyl).

B. Allyl (4R,5S,6S)-4-(allyloxycarbonylmethyl)-3-[(2-cyanoethyl)thio]-6-[(1'R)-1'-hydroxyethyl]-7-oxo-1-azabicyclo[3.2.0]hept-2-ene-2-carboxylic acid

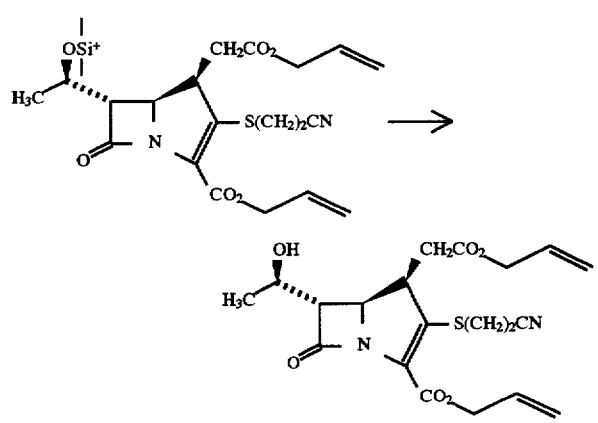

A cold (ice-methanol bath) of allyl (4R,5S,6S)-4-(allyloxycarbonylmethyl)-3-[(2-cyanoethyl)thio]-6-[(1'R)-1'-tert-butyldimethylsilyloxyethyl]-7-oxo-1-azabicyclo[3.2.0]hept-2-ene-2-carboxylate (100 mg, 0.187 mmol) in THF (3 mL) was treated with glacial acetic acid (120 µl, 2.09 mmol) and dropwise with a 1M solution of tetrabutylammonium fluoride in THF (1.3 mL, 1.3 mmol). The mixture was stirred for 30 minutes and then it was allowed to react at 5° C. (cold room) for 430 hours. The mixture was diluted with ice cold ethyl acetate (40 mL), washed with ice cold saturated aqueous NaHCO₃ (4×20 mL), water (2×20 mL), brine (20 mL) and dried (MgSO₄). Evaporation of the solvent left a residue that was applied on a preparative silica gel plate (2 mm, EtOAc, R$_f$=0.75) to give the title compound (23 mg, 29%) as an oil that solidified upon standing;

IR (neat) ν$_{max}$: 3600–3300 (OH), 2250 (C≡N), 1775, 1730 and 1710 cm⁻¹ (C=O);

¹H NMR (CDCl₃, 200 MHz) δ: 6.04–5.83, 5.50–5.24 (6H, 2 sets of m, vinylic-H), 4.89–4.61 (4H, 2 sets of m, CH₂-vinyl), 4.395 (1H, dd, J=3.0 Hz, J=9.8 Hz, H-5), 4.30–4.10 (1H, m, H-1'), 3.803–3.678 (1H, X part of ABX, J=3.4 Hz, H-4), 3.173 (1H, dd, J=3.1 Hz, J=6.9 Hz, H-6), 3.20–3.133, 3.09–2.9 (2.5 H, 2 sets of m, SCH₂ and hidden d of ABq), 2.884, 2.867 (1 part of AB, J=3.4 Hz, CH₂-4), 2.688 (2H, t, J=7.2 Hz, CH₂CN), 2.649, 2.589, 2.562, 2.503 (1H, AB part of ABX, J=11.9 Hz, J=17.5 Hz, CH₂-4), 1.974 (1H, d, J=4.6 Hz, OH) and 1.300 ppm (3H, d, J=6.3 Hz, CH₃).

C. Sodium (4R,5S,6S)-3-[(2-cyanoethyl)thio]-6-[(1'R)-1'-hydroxyethyl]-4-(sodium oxycarbonylmethyl)-7-oxo-1-azabicyclo[3.2.0]hept-2-ene-2-carboxylate

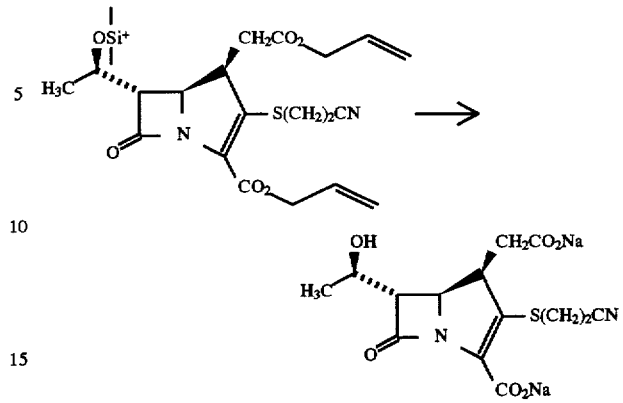

A cold (ice bath) solution of allyl (4R,5S,6S)-4-(allyloxycarbonylmethyl)-3-[(2-cyanoethyl)thio]-6-[(1'R)-1'-hydroxyethyl]-7-oxo-1-azabicyclo[3.2.0]hept-2-ene-2-carboxylate (23 mg, 0.055 mmol) in CH₂Cl₂ (3 mL) was treated successively with Pd(PPh₃)₄, (11 mg) and N-methylaniline (30 µl, 0.22 mmol). The mixture was stirred for 20 min, then was diluted with diethyl ether (10 mL) and extracted with a 0.1M pH 7.0 aqueous phosphate buffer (5×2 mL). The aqueous extracts were combined, washed with diethyl ether and passed through a reversed phase µBondapak C₁₈ column (5 g, H₂O→1% CH₃CN) to give the title compound (10 mg, 50%) as a lyophilized powder;

IR (nujol) ν$_{max}$: 3600–3200 (OH), 2250 (C≡N), 1755 and 1600 cm⁻¹ (C=O);

¹H NMR (D₂O, 200 MHz) δ: 4.328 (1H, dd, J=2.8 Hz, J=9.5 Hz, H-5), 4.297–4.22 (1H, m, H-1'), 3.778–3.653 (1H, x part of ABX, J=3.7 Hz, H-4), 3.419) 1H, dd, J=2.8 Hz, J=4.2 Hz, H-6). 3.30–3.15, 3.01–2.90 (2H, 2 sets of m, SCH₂), 2.90–2.81 (≈2.5H, m, SCH₂CN and 1 d of the B part of ABX), 2.760–2.742 (0.77H, d, J=3.7 Hz, B part of ABX, CH₂CO₂), 2.346, 2.286, 2.262 and 2.203 (1H, A part of ABX, J=11.8 Hz, J=16.7 Hz, CH₂CO₂) and 1.241 ppm (3H, d, J=6.4 Hz, CH₃).

EXAMPLE 108

(4R,5S,6S)-3-{(4S)-4-[(2S)-2-Dimethylaminocarbonyl]pyrrolidinylthio}-6-[(1'R)-1'-hydroxyethyl]-4-(2''-hydroxyethyl)-7-oxo-1-azabicyclo[3.2.0]hept-2-ene-2-carboxylic acid

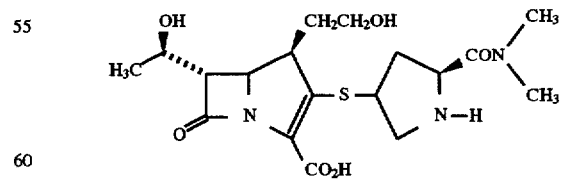

A. Allyl (4R,5R,6S)-3-diphenylphosphoryloxy-6-[(1'R)-1'-tert-butyldimethylsilyloxyethyl]-4-(2''-tert-butyldimethylsilyloxyethyl)-7-oxo-1-azabicyclo[3.2.0]hept-2-ene-2-carboxylate

237

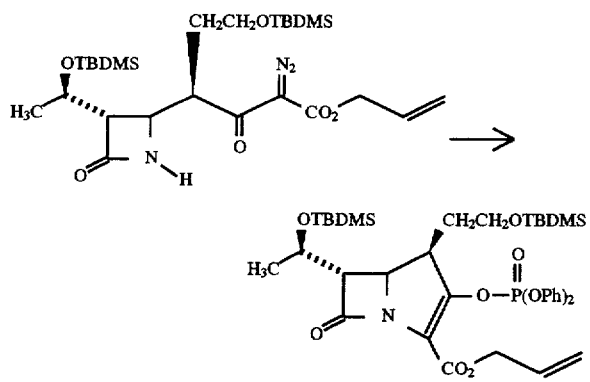

A solution of (3S,4R)-3-[(1'R)-1'-tert-butyldimethylsilyloxyethyl]-4-[(1R)-1-(2-tert-butyldimethylsilyloxyethyl)-3-allyloxycarbonyl-3-diazo-2-oxopropyl]azetidin-2-one (6.93 g, 12.5 mmol) in dry benzene (150 mL) was treated with rhodium (II) octanoate dimer (0.2 g) and heated under reflux (bath temperature 90°–95° C.) for 1 h. The solvent was evaporated under reduced pressure and the residue was dissolved in acetonitrile (80 mL) and cooled to 0°–5° C. Then N,N-diisopropylethylamine (2.40 mL, 13.78 mmol) and diphenyl chlorophosphate (2.85 mL, 13.75 mmol) were added simultaneously over 5 min. A small crystal of 4-N,N-dimethylaminopyridine was then added and the mixture was stirred for 1 h. The reaction mixture was then diluted with ethyl acetate (500 mL) and washed successively with cold water, 0.2M pH 7.0 phosphate buffer, brine and dried (MgSO$_4$). Evaporation of the solvent under vacuum gave an oil which was chromatographed on silica gel (5×12 cm). Elution with a mixture of toluene and ethyl acetate (95:5) gave 5.77 g, (61%) of the title compound as a clear oil:

IR (NaCl, film) $v_{max}$: 1788 (C=O of β-lactam) and 1730 cm$^{-1}$ (C=O of ester);

$^1$H NMR (200 MHz, CDCl$_3$) δ: −0.01, 0.06 and 0.07 (3×s, 6H, 3H and 3H, SiCH$_3$), 0.83 and 0.87 (2×s, 2×9H, Sitert-Bu), 1.27 (d, J=6.14 Hz, 3H, CH$_3$CHO), 1.5–1.8 and 1.9–2.1 (m, 2H, CH$_2$-4), 3.25 (dd, J$_{H6,H5}$=2.77 Hz, J$_{H6,H1}$=6.92 Hz, 1H, H-6), 3.3–3.7 (m, 3H, H-4 and CH$_2$CH$_2$OSi), 4.12 (dd, J$_{H5,H6}$=2.77 Hz, J$_{H5,H4}$=10.35 Hz, 1H, H-5), 4.20 (m, 1H, CH$_3$CHO), 4.64 (broad d, J=5.1 Hz, 2H, CH$_2$ of allyl), 5.1–5.4 and 5.7–6.0 (2×m, 2H and 1H, CH of allyl) and 7.1–7.4 ppm (m, 10H, aromatics).

B. Allyl (4R,5S,6S)-3-((4S)-4-[1-N-allyloxycarbonyl-(2S)-2-dimethylaminocarbonyl]pyrrolidinylthio)-6-[(1'R)-1'-tert-butyldimethylsilyloxyethyl]-4-(2"-tert-butyldimethylsilyloxyethyl)-7-oxo-1-azabicyclo[3.2.0]hept-2-ene-2-carboxylate

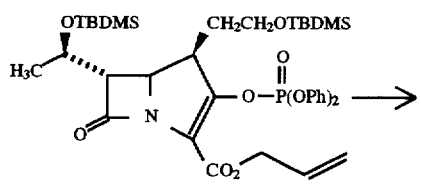

238

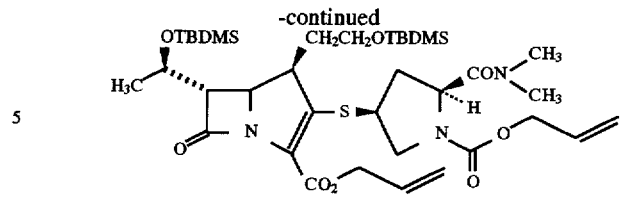

A solution of allyl (4R,5S,6S)-3-diphenylphosphoryloxy-6-[(1'R)-1'-tert-butyldimethylsilyloxyethyl]-4-(2"-tert-butyldimethylsilyloxyethyl)-7-oxo-1-azabicyclo[3.2.0]hept-2-ene-2-carboxylate (1.24 g, 1.63 mmol) in dry acetonitrile (20 mL) was cooled to 0°–5° C. and treated successively with N,N,diisopropylethylamine (0.57 mL, 3.27 mmol) and (2S,4S) 1-N-allyloxycarbonyl-2-dimethylaminocarbonyl-4-mercaptopyrrolidine (0.84 g, 3.27 mmol) [prepared by the general procedures described in European Patent Application EP-126,587] in acetonitrile (3 mL). The reaction mixture was then stirred at 0°–5° C. for 16 h. The solution was then diluted with ethyl acetate (200 mL), washed with water, 0.2M phosphate buffer pH 7.0, brine and dried (MgSO$_4$). Evaporation of the solvent in vacuo gave an oil which was chromatographed on silica gel (2.5×20 cm). Elution with a mixture of toluene and ethyl acetate (1:1) gave 0.80 g (64%) of the title compound as an oil:

IR (NaCl, film) $v_{max}$: 1775 (C=O of β-lactam), 1710 (C=O of ester) and 1660 cm$^{-1}$ (C=O of amide);

$^1$H NMR (200 MHz, CDCl$_3$) δ: 0.03, 0.05 and 0.09 (3×s, 3H, 3H and 6H, SiCH$_3$), 0.87 and 0.89 (2×s, 2×9H, Sit-But), 1.26 (d, J=6.25 Hz, 3H, CH$_3$CHO), 1.6–2.1 (m, 3H, CH$_2$-4 and H-3 of pyrrolidine), 2.6 (m, 1H, H-3 of pyrrolidine), 2.95, 1.97, 3.03 and 3.08 (4 s, total 6H, CON(CH$_3$)$_2$, 3.05 (overlapping with NCH$_3$, 1H, H-6), 3.4–3.6 and 3.7–3.9 (2×m, 3H and 2H, H-4, CH$_2$OSi and H-5 of pyrrolidine), 4.0–4.2 (m, 1H, H-4 of pyrrolidine), 4.2–4.4 (m, 2H, H-5 and CH$_3$CHO), 4.5–4.9 (m, 5H, CH$_2$ of allyl and H-2 of pyrrolidine), 5.1–5.5 and 5.8–6.1 ppm (2×m, 4H and 2H, CH of allyl).

C. Allyl (4R,5S,6S)-3-((4S)-4-[1-N-allyloxycarbonyl-(2S)-2-dimethylaminocarbonyl]pyrrolidinylthio)-6-[(1'R)-1'-hydroxyethyl]-4-(2"-hydroxyethyl)-7-oxo-1-azabicyclo[3.2.0]hept-2-ene-2-carboxylate

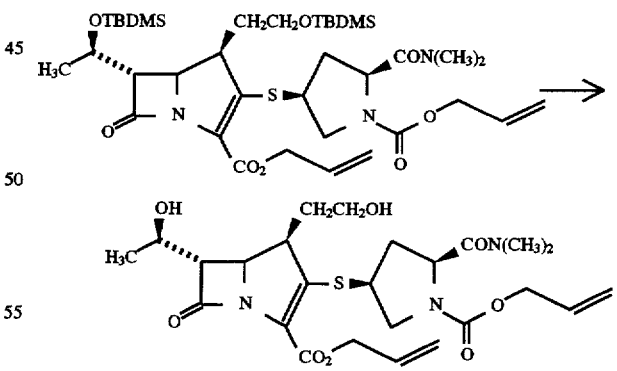

A solution of allyl (4R,5S,6S)-3-((4S)-4-[1-N-allyloxycarbonyl-(2S)-2-dimethylaminocarbonyl]pyrrolidinylthio)-6-[(1'R)-1'-tert-butyldimethylsilyloxyethyl]-4-(2"-tert-butyldimethylsilyloxyethyl)-7-oxo-1-azabicyclo[3.2.0]hept-2-ene-2-carboxylate (0.70 g, 0.91 mmol) in dry tetrahydrofuran (10 mL) was treated dropwise at 0°–5° C. with acetic acid (0.62 mL, 11.0 mmol) followed by 5.5 mL (5.5 mmol) of a 1M solution of tetrabutylammonium fluoride in tetrahydrofuran. The reaction mixture was then stored at 10° C. for 144 h. The solution was then diluted with ethyl acetate (200 mL) washed with cold saturated sodium bicarbonate, brine and dried ($MgSO_4$). Evaporation of the solvent in vacuo gave an oil which was chromatographed on silica gel (2.5×12 cm). Elution with ethyl acetate first gave 0.30 g (50%) of mono deprotected allyl (4R,5S,6S)-3-((4S)-4-[1-N-allyloxycarbonyl-(2S)-2-dimethylaminocarbonyl]pyrrolidinylthio)-6-[(1'R)-1'-tert-butyldimethylsilyloxyethyl]-4-(2"-hydroxyethyl)-7-oxo-1-azabicyclo[3.2.0]hept-2-ene-2-carboxylate [see Example 109, Method B, Step A].

Elution with a mixture of ethyl acetate, acetone and acetonitrile (6:2:2) then gave 0.179 g (36%) of the title carbapenem as an oil contaminated by some tetrabutylammonium salt. This product was used as such for the next step:

IR (NaCl, film) $v_{max}$: 3400 (OH), 1775 (C=O of B-lactam), 1710 (C=O of ester) and 1650 cm$^{-1}$ (C=O of amide);

$^1$H NMR (200 MHz, CDCl$_3$) δ: 1.33 (d, J=6.33, Hz, 3H, CH$_3$CHO), 1.6-2.0 (m, 3H, CH$_2$-4 and H-3 of pyrrolidine), 2.9 (m, 1H, H-3 of pyrrolidine), 2.95, 2.97, 3.03 and 3.09 (4×s, total 6H, NCH$_3$), 3.4-5.0 (broad, 16H), 5.2-5.5 and 6.8-6.1 ppm (4H and 2H, CH of allyl).

D. (4R,5S,6S)-3-((4S)-4-[(2S)-2-Dimethylaminocarbonyl pyrrolidinylthio)-6-[(1'R)-1'-hydroxyethyl]-4-(2"-hydroxyethyl)-7-oxo-1-azabicyclo[3.2.0]hept-2-ene-2-carboxylic acid

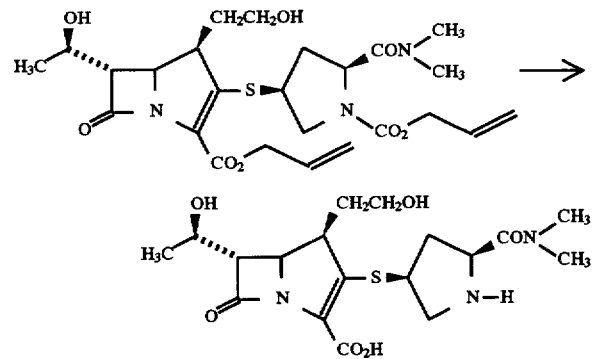

A solution of allyl (4R,5S,6S) 3-((4S)-4-[1-N-allyloxycarbonyl-(2S)-2-dimethylaminocarbonyl]pyrrolidinylthto)-6-[(1'R)-1'-hydroxyethyl]-4-(2"-hydroxyethyl)-7-oxo-1-azablcyclo[3.2.0]hept-2-ene-2-carboxylate (0.33 g, 0.613 mmol) in dichloromethane (10 mL) was treated at 22° C. and under nitrogen with tetrakis (triphenylphosphine)palladium [0] (0.030 g) and N-methylaniline (0.26 mL, 2.45 mmol). After 1 h, the solid formed was collected by filtration and dried under vacuum to give 0.164 g (65%) of the crude title compound as a powder. This solid was chromatographed on reversed phase silica gel (µ-Bondapak c-18, 2.5×14 cm) using a gradient of acetonitrile (0–5%) in water as eluent. Lyophilization of the UV active fractions gave 0.122 g (44%) of the title compound as a white amorphous powder: $[α]_D^{22}$=−58.5° (c 1.0, H$_2$O);

Purity by HPLC: 94.7% on µ-Bondapak c-18, 3.9 mm×30 cm, elution 5% CH$_3$CN—H$_2$O, pH 7.4 phosphate buffer, flow rate 1 mL/min, UV detector 300 nm, retention time 5.9 min;

UV (H$_2$O, pH 7.4 phosphate buffer) $λ_{max}$: 302 nm (8,680);

IR (KBr) $v_{max}$: 1750 (CO of β-lactam), 1650, 1660 (C=O of amide) and 1600 cm$^{-1}$ (C=O of carboxylate);

$^1$H NMR (200 MHz, D$_2$O) δ: 1.32 (d, J=6.37 Hz, 3H, CH$_3$CHO), 1.7–2.2 (m, 3H, CH$_2$-1 of hydroxyethyl and H-3 of pyrrolidine), 3.0 (m overlapping with NCH$_3$, 1H, H-3 of pyrrolidine), 3.0 and 3.07 (2×s, 2×3H, NCH$_3$), 3.3–3.9 (m, 5H, H-4, CH$_2$CH$_2$OH and CH$_2$-5 of pyrrolidine), 3.48 (dd, $J_{H6,H5}$=2.73 Hz, $J_{H6,H1}$=5.91 Hz, 1H, H-6), 3.95 (m, 1H, H-4 of pyrrolidine), 4.2–4.4 (m, 2H, H-5 and CH$_3$CHO overlapping), and 4.83 ppm (t, J=5.8 Hz, 1H, H-2 of pyrrolidine).

EXAMPLE 109

(4R,5S,6S)-4-(2"-Azidoethyl)-3-((4S)-4-[(2S)-2-dimethylaminocarbonyl]pyrrolidinylthio)-6-[(1'R)-1'-hydroxyethyl]-7-oxo-1-azabtcyclo[3.2.0]hept-2-ene-2-carboxylic acid

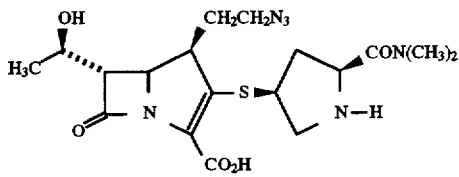

Method A

A. Allyl (4R,5R,6S)-4-(2"-azidoethyl)-3-diphenylphosphoryloxy-6-[(1'R)-1'-tert-butyldimethylsilyloxyethyl]-7-oxo-1-azabicyclo[3.2.0]hept-2-ene-2-carboxylate

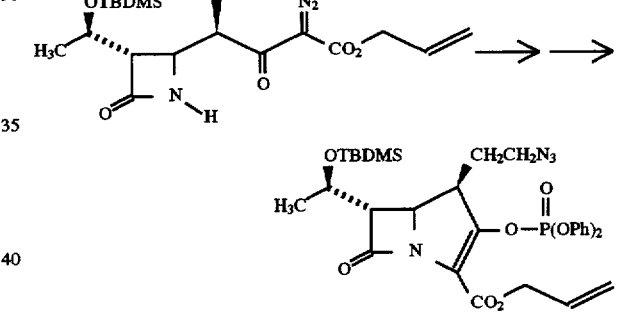

A solution of (3S,4S)-4-[(1R)-1-(2-azidoethyl)-3-allyloxycarbonyl-3-diazo-2-oxopropyl]-3-[(1'R)-1'-tert-butyldimethylsilyloxyethyl]azetidin-2-one (4.0 g, 8.6 mmol) in dry benzene (125 mL) was treated under nitrogen with Rhodium(II)octanoate dimer (0.075 g) and then heated under reflux (bath temperature 90° C.) for 30 min. The solvent was then evaporated under reduced pressure and the intermediate bicyclic ketone was dissolved in dry acetonitrile (60 mL) and cooled to 0°–5° C. The solution was then treated with diphenyl chlorophosphate (2.0 mL, 9.65 mmol) and N,N-diisopropylethylamine (1.68 mL, 9.64 mmol) added simultaneously over 5 min. Then a small crystal of 4-N,N-dimethylaminopyridine was then added and the mixture was stirred at 0°–5° C. for 45 min. The reaction mixture was then diluted with ethyl acetate (500 mL), washed with cold water, 0.2M pH 7.0 phosphate buffer, brine and dried (MgSO$_4$). After evaporation of the solvent under reduced pressure, the residue was chromatographed on silica gel (5×10 cm). Elution with a gradient of ethyl acetate (0–5%) in toluene gave 3.84 g (66%) of the title compound as an oil:

IR (NaCl, film) $v_{max}$: 2100 (N$_3$), 1788 (C=O of β-lactam) and 1730 cm$^{-1}$ (C=O of ester);

$^1$H NMR (200 MHz, CDCl$_3$) δ: 0.07 and 0.08 (2s, 6H, SiCH$_3$), 0.87 (s, 9H, Si-tBu), 1.28 (d, J=6.18 Hz, 3H, $CH_3CHO$), 1.6–2.2 (m, 2H, $CH_2$-4), 3.18 (dd, $J_{H6,H5}$=2.95 Hz, $J_{H6,H1}$=7.38 Hz, 1H, H-6), 3.1–3.5 (m, 3H, $CH_2OH$ and H-4), 4.12 (dd, $J_{H5,H6}$=2.95 Hz, $J_{H5,H4}$=10.54 Hz, 1H, H-5), 4.19 (m, 1H, $CH_3CHO$), 4.65 (m, 2H, $CH_2$ of allyl), 5.1–5.5 and 5.8–6.0 (2m, 2H and 1H, CH of allyl), and 7.2–7.5 (m, 10H, aromatics).

B. Allyl (4R,5S,6S)-3-((4S)-4-[1-N-allyloxycarbonyl-(2S)-2-dimethylaminocarbonyl]pyrrolidinylthio}-4-(2"-azidoethyl)-6-[(1'R)-1'-tert-butyldimethylsilyloxyethyl]-7-oxo-1-azabicyclo[3.2.0]hept-2-ene-2-carboxylate

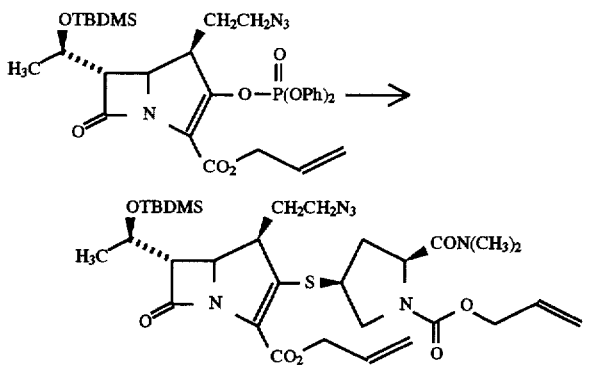

A solution of allyl (4R,5S,6S)-4-(2"-azidoethyl)-3-diphenylphosphoryloxy-6-[(1'R)-1'-tert-butyldimethylsilyloxyethyl]-7-oxo-1-azabicyclo[3.2.0]hept-2-ene-2-carboxylate (3.84 g, 5.74 mmol) in dry acetonitrile (40 mL) was cooled to 0°–5° C. and treated under nitrogen with N,N-diisopropylethylamine (2.0 mL, 11.6 mmol) followed by (2S,4S)-1-N-allyloxycarbonyl-2-dimethylaminocarbonyl-4-mercaptopyrrolidine [prepared according to the general procedures in EP-126,587] (3.0 g, 11.6 mmol) in acetonitrile (7 mL). After 17 h at 0°–5° C., the reaction mixture was diluted with ethyl acetate (500 mL), washed with cold water, saturated sodium bicarbonate, brine and dried ($MgSO_4$). The residue obtained after evaporation of the solvent under reduced pressure was chromatographed on silica gel (5×10 cm) using a mixture of toluene and ethyl acetate (1:1) as eluent and gave 2.47 g (64%) of the title compound as a white foam:

IR (NaCl, film) $v_{max}$: 2100 ($N_3$), 1780 (C=O of β-lactam), 1710 (C=O of ester) and 1660 $cm^{-1}$ (C=O of amide);

$^1H$ NMR (200 MHz, $CDCl_3$) δ: 0.1 (s, 6H, $SiCH_3$), 0.9 (s, 9H, Si-tBu), 1.31 (d, J=6.03 Hz, 3H, $CH_3CHO$), 1.6–2.1 (m, 3H, H-3 of pyrrolidine and $CH_2$-4), 2.6–2.8 (m, 1H, H-3 of pyrrolidine), 2.96, 2.98, 3.05 and 3.11 (4s, total 6H, $NCH_3$), 3.1 (overlapping with $NCH_3$, 1H, H-6), 3.3–3.8 (m, 5H, $CH_2$-5 of pyrrolidine, $CH_2N_3$ and H-4), 4.1 (m, 1H, H-4 of pyrrolidine), 4.1–4.3 (m, 2H, H-5 and $CH_3CHO$), 4.5–4.9 (m, 5H, $CH_2$ of allyl and H-2 of pyrrolidine), 5.1–5.5 and 5.8–6.1 ppm (2×m, 4H and 2H, CH of allyl).

Method B.

A. Allyl (4R,5S,6S)-3-((4S)-4-[1-N-allyloxycarbonyl-(2S)-2-dimethylaminocarbonyl]pyrrolidinylthio)-6-[(1'R)-1'-tert-butyldimethylsilyloxyethyl]-4-(2"-hydroxyethyl)-7-oxo-1-azabicyclo[3.2.0]hept-2-ene-2-carboxylate

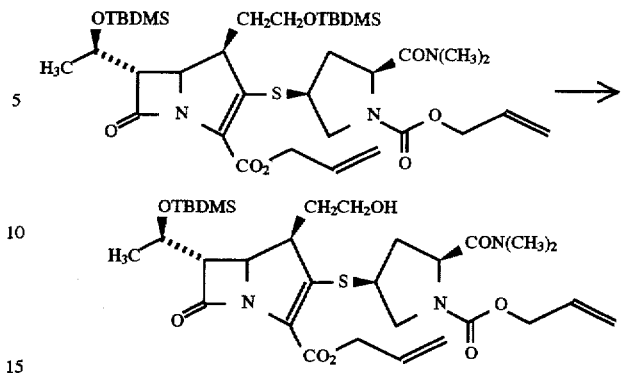

A solution of allyl (4R,5S,6S)-3-((4S)-4-[1-N-allyloxycarbonyl-(2S)-2-dimethylaminocarbonyl]pyrrolidinylthio)-6-[(1'R)-1'-tert-butyldimethylsilyloxyethyl]-4-(2"-tert-butyldimethylsilyloxyethyl)-7-oxo-1-azabicyclo[3.2.0]hept-2-ene-2-carboxylate (2.64 g, 3.44 mmol) [prepared in Example 108, Step B] in dry tetrahydrofuran (50 mL) was treated at 0°–5° C. and under nitrogen with acetic acid (1.2 mL, 21.0 mmol) followed by 10.3 mL (10.3 mmol) of a 1M solution of tetrabutylammonium fluoride in tetrahydrofuran. After 16 h at 10° C., the reaction mixture was diluted with ethyl acetate (400 mL) washed with cold saturated sodium bicarbonate, brine and dried ($MgSO_4$). Evaporation of the solvent under reduced pressure gave an oil which was chromatographed on silica gel (4×8 cm). Elution with ethyl acetate gave 1.82 g (81%) of the title carbapenem as an oil:

IR (NaCl, film) $v_{max}$: 3450 (OH), 1755 (C=O of β-lactam), 1705 (C=O of ester) and 1650 $cm^{-1}$ (C=O of amide);

$^1H$ NMR (200 MHz, $CDCl_3$) δ: 0.09 (s, 6H, $SiCH_3$), 0.89 (s, 9H, Si-tBu), 1.29 (d, J=6.1 Hz, 3H, $CH_3CHO$), 1.6–2.1 (m, 3H, $CH_2CH_2OH$ and H-3 of pyrrolidine), 2.6–2.8 (m, 1H, H-3 of pyrrolidine), 2.96, 2.98, 3.05 and 3.09 (4s, total 6H, $CON(CH_3)_2$), 3.17 (broad dd, $J_{H6,H5}$=2.5 Hz, $J_{H6,H1}$=6.1 Hz, 1H, H-6), 3.46 (~t, 2H, H-5 of pyrrolidine and H-4 overlapping), 3.6–3.9 (m, 3H, $CH_2CH_2OH$ and H-5 of pyrrolidine), 4.1 (m, 1H, H-4 of pyrrolidine), 4.15–4.3 (m, 2H, H-5 and $CH_3CHO$), 4.5–4.9 (m, 5H, $CH_2$ of allyl and H-2 of pyrrolidine), 5.1–5.5 and 5.9–6.1 ppm (2×m, 4H and 2H, CH of allyl).

B. Allyl (4R,5S,6S)-3-((4S)-[1-N-allyloxycarbonyl-(2S)-2-dimethylaminocarbonyl]pyrrolidinylthio)-4-(2"-azidoethyl)-6-[(1'R)-1'-tert-butyldimethylsilyloxyethyl]-7-oxo-1-azabicyclo[3.2.0]hept-2-ene-2-carboxylate

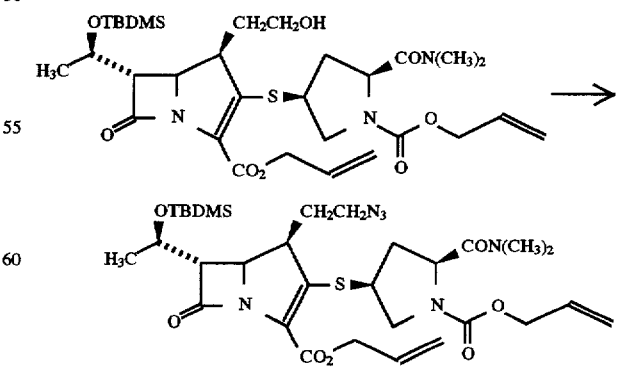

A solution of allyl (4R,5S,6S)-3-((4S)-4-[1-N-allyloxycarbonyl-(2S)-2-dimethylaminocarbonyl]

pyrrolidinylthio)-6-[(1'R)-1'-tert-butyldimethylsilyloxyethyl]-4-(2''-hydroxyethyl)-7-oxo-1-azabicyclo[3.2.0]hept-2-ene-2-carboxylate (1.82 g, 2.79 mmol) in dry tetrahydrofuran (200 mL) at −20° C. and under nitrogen was treated with triphenylphosphine (1.17 g, 4.46 mmol) and 6.5 mL (4.81 mmol) of a 0.74M solution of hydrazoic acid in toluene. Diethyl azodicarboxylate (0.75 mL (4.76 mmol) was then added dropwise and the resulting mixture was stirred for 30 min. The reaction mixture was then diluted with ethyl acetate (500 mL), washed with cold saturated sodium bicarbonate, brine and dried (MgSO$_4$). The solvent was then concentrated in vacuo to give a paste which was triturated at 0°–5° C. with toluene (25 mL) and filtered to remove the crystalline diethyl hydrazinedicarboxylate. The filtrate was concentrated and treated in the same manner with diethyl ether (25 mL) to remove the triphenylphosphine oxide. The filtrate was then chromatographed on silica gel (4×11 cm) using a mixture of toluene and ethyl acetate (1:1) as eluent and gave 2.3 g of the title compound as an oil which was contaminated with triphenylphosphine oxide. The infrared and $^1$H NMR spectra of the product are identical to the spectra of the product obtained in Method A.

C. Allyl (4R,5S,6S)-3-((4S)-4-[1-N-allyloxycarbonyl-(2S)-2-dimethylaminocarbonyl]pyrrolidinylthio)-4-(2''-azidoethyl)-6-[(1'R)-1'-hydroxyethyl]-7-oxo-1-azabicyclo[3.2.0]hept-2-ene-2-carboxylate

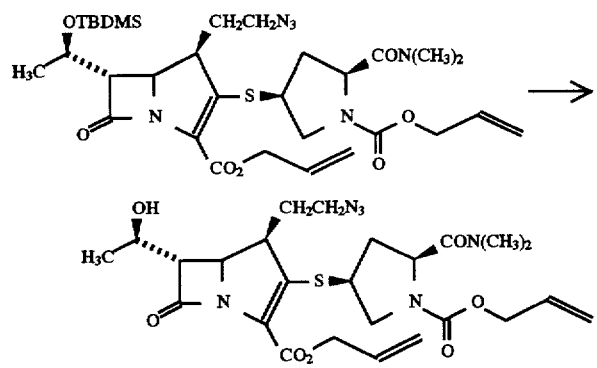

A solution of allyl (4R,5S,6S)-3-((4S)-4-[1-N-allyloxycarbonyl-(2S)-2-dimethylaminocarbonyl]pyrrolidinylthio)-4-(2''-azidoethyl)-6-[(1'R)-1'-tert-butyldimethylsilyloxyethyl]-7-oxo-1-azabicyclo[3.2.0]hept-2-ene-2-carboxylate (2.47 g, 3.65 mmol) in dry tetrahydrofuran (50 mL) was cooled to 0°–5° C. and treated under nitrogen with acetic acid (1.25 mL, 21.8 mmol) followed by 11.0 mL (11.0 mmol) of a 1M solution of tetrabutylammonium fluoride in tetrahydrofuran. The solution was stored at 10° C. for 7 days. The reaction mixture was diluted with ethyl acetate (500 mL), washed with cold saturated sodium bicarbonate, brine and dried (MgSO$_4$). Evaporation of the solvent under reduced pressure gave an oil which was chromatographed on silica gel (4×11 cm). Elution with a gradient of ethyl acetate in toluene (50→100%) gave 1.43 g (70%) of the title compound as a white foam:

IR (NaCl, film) $v_{max}$: 2105 (N$_3$), 1780 (C=O of β-lactam) 1710 (C=O of ester) and 1650 cm$^{-1}$ (C=O of amide);

$^1$H NMR (200 MHz, CDCl$_3$) δ: 1.39 (d, J=6.17 Hz, 3H, CH$_3$CHO), 1.7–2.2 (m, 3H, H-3 of pyrrolidine and CH$_2$-4), 2.6–2.8 (m, 1H, H-3 of pyrrolidine), 2.96, 2.98, 3.06 and 3.10 (4×s, total 6H, NCH$_3$), 3.15 overlapping with NCH$_3$, 1H, H-6), 3.3–3.7 (m, 5H, CH$_2$-5 pyrrolidine, H-4 and CH$_2$N$_3$), 4–4.2 (m, 1H, H-4 of pyrrolidine), 4.2–4.4 (m, 2H, H-5 and CH$_3$CHO), 4.5–4.9 (m, 5H, CH$_2$ of allyl and H-2 of pyrrolidine), 5.1–5.5 and 5.7–6.1 ppm (2×m, 4H, and 2H, CH of allyl).

D. (4R,5S,6S)-4-(2''-Azidoethyl)-3-((4S)-4-[(2S)-2-dimethylaminocarbonyl]pyrrolidinylthio)-6-[(1'R)-1'-hydroxyethyl]-7-oxo-1-azabicyclo[3.2.0]hept-2-ene-2-carboxylic acid

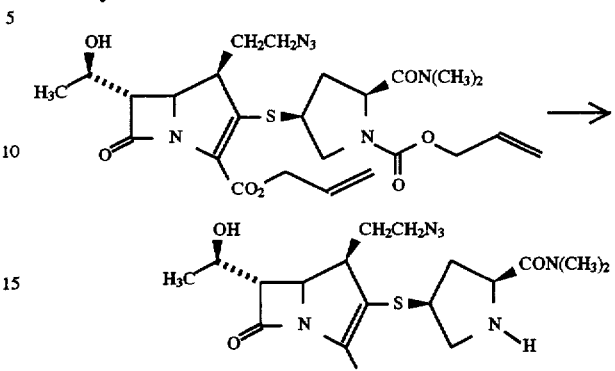

A solution of allyl (4R,5S,6S)-3-((4S)-4-[1-N-allyloxycarbonyl-(2S)-2-dimethylaminocarbonyl]pyrrolidinylthio)-4-(2''-azidoethyl)-6-[(1'R)-1'-hydroxyethyl]-7-oxo-1-azabicyclo[3.2.0]hept-2-ene-2-carboxylate (1.18 g, 2.1 mmol) in dry dichloromethane (40 mL) was treated at 22° C. and under nitrogen with tetrakis(triphenylphosphine)palladium [0] (0.1 g) followed by 0.91 mL (8.4 mmol) of N-methylaniline. After 1 h, the organic phase was extracted with cold water (3×40 mL) and the combined aqueous extract was maintained under vacuum to remove traces of organic solvent. The aqueous phase was then chromatographed on reversed phase silica gel (μ-Bondapak c$_{18}$, 3.5×15 cm) using a gradient of acetonitrile (0–15%) in water as eluent. Lyophilization of the UV active fractions gave 0.50 g (54%) of the title carbapenem as a white amorphous powder: [α]$_D^{22}$–56.2° (c 1.0, H$_2$O);

Purity by HPLC: 96% on μ-Bondapak c-18, 3.9 mm×30 cm, 15% CH$_3$CN—H$_2$O pH 7.4 phosphate buffer, flow rate 1 mL/min, uv detector 302 nm, retention time 7.6 min;

UV (H$_2$O, pH 7.4 phosphate buffer) λ$_{max}$: 302 nm (8,420);

IR (KBr) $v_{max}$: 2100 (N$_3$), 1760 (C=O of β-lactam), 1655 (C=O of amide) and 1600 cm$^{-1}$ (C=O of carboxylate);

$^1$H NMR (200 MHz, D$_2$O) δ: 1.33 (d, J=6.36 Hz, 3H, CH$_3$CHO), 1.7–2.3 (m, 3H, H-3 of pyrrolidine and CH$_2$-4), 3.0 and 3.07 (2×s, 2×3H, NCH$_3$), 3.1 (m, 1H, H-3 of pyrrolidine), 3.3–3.7 (m, 5H, H-5 pyrrolidine, H-4, H-6 and CH$_2$N$_3$), 3.77 (dd, J$_{gem}$=12.15 Hz, J$_{H5,H4}$=6.32 Hz, H-5 of pyrrolidine), 4.0 (m, 1H, H-4 of pyrrolidine), 4.27 (m, 1H, CH$_3$CHO) 4.30 (dd overlapping with CH$_3$CHO, J$_{H5,H6}$=2.7 Hz, H-5) and 4.9 ppm (overlapping with HOD, H-2 of pyrrolidine).

EXAMPLE 110

(4R,5S,6S)-4-(2''-Aminoethyl)-3-{(4S)-4-[(2S)-2-dimethylaminocarbonyl]pyrrolidinylthio}-6-[(1'R)-1'-hydroxyethyl]-7-oxo-1-azabicyclo[3.2.0]hept-2-ene-2-carboxylic acid, acetic acid salt

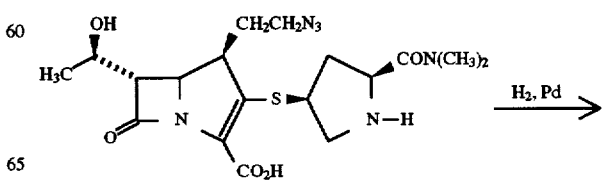

-continued

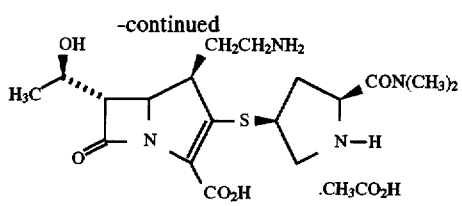

A solution of (4R,5S,6S)-4-(2"-azidoethyl)-3-{(4S)-4-[(2S)-2-dimethylaminocarbonyl]pyrrolidinylthio}-6-[(1'R)-1'-hydroxyethyl]-7-oxo-1-azabicyclo[3.2.0]hept-2-carboxylic acid (0.70 g, 1.60 mmol) in cold water (140 mL) was hydrogenated at 0°–5° C. over 1.9 g of 5% palladium on alumina and under 45 psi of hydrogen for 1 h. Then 0.18 mL (3.2 mmol) of acetic acid was added (pH changed from 8.1 to 4.2) and the catalyst was filtered on a Celite pad. The filtrate was chromatographed on a reversed phase silica gel column (µBondapak $C_{18}$, 2.5×13 cm) using water as eluent. The UV active fractions were combined, lyophilized and chromatographed a second time with the same column. Lyophilization of the pertinent fractions gave 0.35 g (47%) of the title carbapenem as a white amorphous powder: $[\alpha]_D^{22}$ –47.8° (c 1.0, $H_2O$);

Purity by HPLC: 98.8% on µBondapak $C_{18}$, 3.4 mm×30 cm, 5% $CH_3CN$—$H_2O$ pH 7.4 phosphate buffer, flow rate 1 mL/min, uv detector 300 nm, retention time 11.3 min;

UV ($H_2O$, pH 7.4 phosphate buffer) $\lambda_{max}$: 300 nm (8,130);

IR (KBr) $v_{max}$: 1760 (C=O of β-lactam), 1660 (C=O of amide) and 1600 $cm^{-1}$ (broad, C=O of carboxylate).

$^1$H NMR (200 MHz, $D_2O$) δ: 1.35 (d, J=6.35 Hz, 3H, $\underline{CH_3}$CHO), 1.8–2.4 (m, 3H, H-3 of pyrrolidine and $CH_2$-4), 1.94 (s, $\underline{CH_3}CO_2H$), 3.02 and 3.09 (2s, 2×3H, $CON(CH_3)_2$), 2.9–3.2 (m overlapping with $NCH_3$, 3H, H-3 of pyrrolidine and $\underline{CH_2}NH_2$), 3.25–3.5 (m, 2H, H-5 of pyrrolidine and H-4), 3.51 (dd, $J_{H6,H5}$=2.89 Hz, $J_{H6,H1}$=6.44 Hz, 1H, H-6), 3.6–3.75 (m, 1H, H-5 of pyrrolidine), 3.98 (m, 1H, H-4 of pyrrolidine), 4.3 (m, 1H, $CH_3\underline{CHO}$), 4.34 (dd overlapping with $CH_3\underline{CHO}$, $J_{H5,H6}$=2.89 Hz, $J_{H5,H4}$=9.70 Hz, 1H, H-5) and 4.74 ppm (t, J=8.6 Hz, 1H, H-2 of pyrrolidine).

EXAMPLE 111

(4R,5S,6S)-4-(3"-Azidopropyl)-3-{(4S)-4-[(2S)-2-dimethylaminocarbonyl]pyrrolidinylthio}-6-[(1'R)-1'-hydroxyethyl]-7-oxo-1-azabicyclo[3.2.0]hept-2-ene-2-carboxylic acid

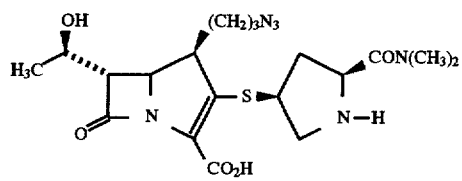

A. Allyl (4R,5S,6S)-3-((4S)-4-[1-N-allyloxycarbonyl)-(2S)-2-dimethylaminocarbonyl]pyrrolidinylthio)-4-(3"-azidopropyl)-6-[(1'R)-1'-hydroxyethyl]-7-oxo-1-azabicyclo[3.2.0]hept-2-ene-2-carboxylate

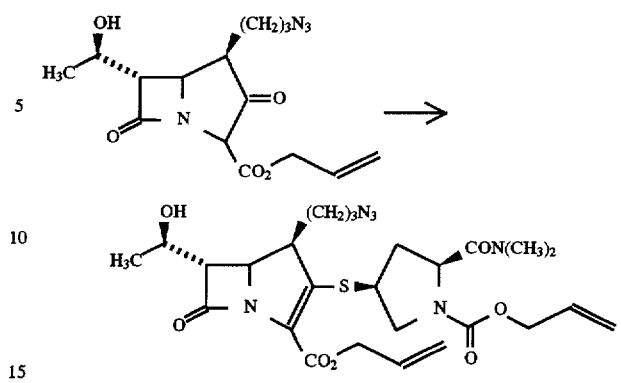

A solution of allyl (2R,4R,5R,6S)-4-(3"-azidopropyl)-6-[(1'R)-1'-hydroxyethyl]-3,7-dioxo-1-azabicyclo[3.2.0]heptane-2-carboxylate (8.23 mmole, prepared by cyclization of 3.0 g, 8.23 mmol of diazo precursor) in dry acetonitrile (60 mL) was treated at 0°–5° C. and under nitrogen with diphenyl chlorophosphate (1.9 mL, 9.18 mmol) and N,N-diisopropylethylamine (1.6 mL, 9.18 mmol) added simultaneously over 5 min. A small crystal of 4-N,N-dimethylaminopyridine was then added and the solution was stirred for 1 h. Then more N,N-diisopropylethylamine (2.0 mL, 11.5 mmol) was added followed by a solution of (2S,4S)-1-N-allyloxycarbonyl-2-dimethylaminocarbonyl-4-mercaptopyrrolidine (3.0 g, 11.65 mmol) in acetonitrile (7 mL) and the resulting mixture was stirred at 0°–5° C. for 18 h. The reaction mixture was quenched by the addition of ethyl acetate (500 mL) and washed with cold water, saturated sodium bicarbonate, brine and dried ($MgSO_4$). Evaporation of the solvent under reduced pressure gave an oil which was chromatographed on silica gel (6.5×12 cm). Elution with a gradient of ethyl acetate in toluene (1:1 to EtOAc) gave 1.59 g (33%) of the title compound as a white foam:

IR (NaCl, film) $v_{max}$: 2100 ($N_3$), 1775 (C=O of β-lactam), 1705 (C=O of ester) and 1650 $cm^{-1}$ (C=O of amide);

$^1$H NMR (200 MHz, $CDCl_3$) δ: 1.37 and 1.39 (2d, J=6.1 Hz, and J=6.18 Hz, 3H, $\underline{CH_3}$CHO), 1.5–2.0 (m, 5H, H-3 of pyrrolidine), $CH_2$-1 and 2 of propyl), 2.6–2.8 (m, 1H, H-3 of pyrrolidine), 2.96, 2.97, 3.05 and 3.1 (4S, total 6H, CON$(CH_3)_2$), 3.1–3.7 (m, 6H, $CH_2$-5 of pyrrolidine, $CH_2N_3$, H-4 and H-6), 4.0 (m, 1H, H-4 of pyrrolidine), 4.1–4.3 (m, 2H, H-5 and $CH_3\underline{CHO}$), 4.5–4.9 (m, 5H, H-2 of pyrrolidine and $CH_2$ of allyl), 5.1–5.5 and 5.8–6.1 ppm (2m, 4H and 2H, CH of allyl).

B. (4R,5S,6S)-4-(3"-Azidopropyl)-3-((4S)-4-[(2S)-2-dimethylaminocarbonyl]pyrrolidinylthio}-6-[(1'R)-1'-hydroxyethyl]-7-oxo-1-azabicyclo[3.2.0]hept-2-ene-2-carboxylic acid

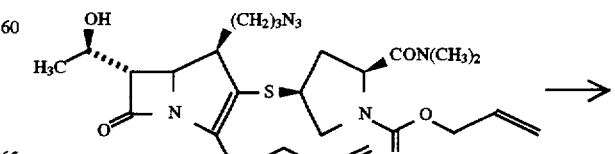

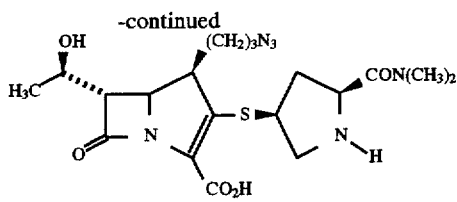

A solution of allyl (4R,5S,6S)-3-((4S)-4-[1-N-allyloxycarbonyl)-(2S)-2-dimethylaminocarbonyl]pyrrolidinylthio)-4-(3"-azidopropyl)-6-[(1'R)-1'-hydroxyethyl]-7-oxo-1-azabicyclo[3.2.0]hept-2-ene-2-carboxylate (1.59 g, 2.76 mmol) in dry dichloromethane (50 mL) was treated at 22° C. and under nitrogen with tetrakis (triphenylphosphine) palladium [0] (0.12 g) followed by 1.2 mL (11.1 mmol) of N-methylaniline. After 3 h the reaction mixture was extracted with water (3×50 mL), and the combined aqueous phase was maintained in vacuo to remove traces of organic solvent. Chromatography of the aqueous phase on reversed phase silica gel (μ-Bondapak $C_{18}$, 3.5×15 cm) using a gradient of acetonitrile (0–15%) in water gave 0.60 g (48%) of the title carbapenem as a white amorphous powder after freeze drying: $[\alpha]_D^{22}$ –47.7° (c 1.0, $H_2O$);

Purity by HPLC: 99% on μ-Bondapak $C_{18}$, 3.9 mm/30 cm, elution 15% $CH_3CN$—$H_2O$, pH 7.4 phosphate buffer, flow rate 1.5 mL/min, UV detector 302 nm, retention time 9.0 min;

UV ($H_2O$, pH 7.4 phosphate buffer) $\lambda_{max}$: 302 nm (9,737);
IR (KBr) $\nu_{max}$: 2100 ($N_3$), 1755 (C=O of β-lactam), 1655 (C=O of amide) and 1600 $cm^{-1}$ (C=O of carboxylate);
$^1H$ NMR (200 MHz, $D_2O$) δ: 1.32 (d, J=6.39 Hz, 3H, $\underline{CH_3}$CHO), 1.4–2.0 (m, 5H, $CH_2$-1 and 2 of propyl and H-3 of pyrrolidine), 2.99 and 3.07 (2s, 2×3H, $CON(CH_3)_2$), 2.9–3.1 (overlapping with $CON(CH_3)_2$, 1H, H-3 of pyrrolidine), 3.2–3.5 (m, 5H, H-5 of pyrrolidine, H-4, H-6 and $CH_2N_3$), 3.63 (dd, $J_{gem}$ 12.25 Hz, $J_{H5,H4}$=6.16 Hz, 1H, H-5 of pyrrolidine), 3.93 (m, 1H, H-4 of pyrrolidine), 4.2–4.4 (m, 2H, H-5 and $\underline{CH_3}$CHO overlapping) and 4.65 ppm (t, J=8.5 Hz, 1H, H-2 of pyrrolidine).

EXAMPLE 112

(4R,5S,6S)-4-(3"-Aminopropyl)-3-((4S)-4-[(2S)-2-dimethylaminocarbonyl]pyrrolidinylthio)-6-[(1'R)-1'-hydroxyethyl]-7-oxo-1-azabicyclo[3.2.0]hept-2-ene-2-carboxylic acid, phosphate salt dibasic

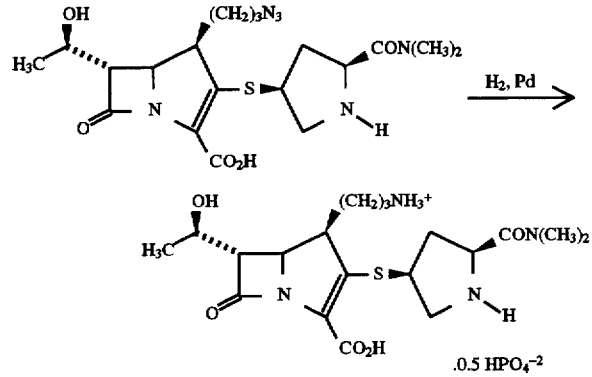

A solution of (4R,5S,6S)-4-(3"-azidopropyl)-3-((4S)-4-[(2S)-2-dimethylaminocarbonyl]pyrrolidinylthio)-6-[(1'R)-1'-hydroxyethyl]- 7-oxo-1-azabicyclo[3.2.0]hept-2-ene-2-carboxylic acid (0.51 g, 1.13 mmol) in cold water (100 mL) was hydrogenated over 0.5 g of 5% palladium on alumina at 45 psi of hydrogen and at 0°–5° C. for 1 h. Then 50 mL of 0.2M pH 6.0 phosphate buffer was added and the catalyst was filtered on a Celite pad. The liltrate was chromatographed on reversed phase silica gel (μ-Bondapak $C_{18}$, 3.5×14 cm) using a gradient of acetonitrile (0–10%) in 0.02M pH 7.0 phosphate buffer as eluent. The UV active fractions were combined and desalted on a similar column (2.5×14 cm) using water instead of buffer as eluent. Lyophilization of the uv active fractions gave 0.25 g (46%) of the title carbapenem as a white amorphous powder: $[\alpha]_D^{22}$ –67.6° (c 1.0, $H_2O$);

Purity by HPLC: 99% on μ-Bondapak $C_{18}$, 3.9 mm×30 cm, elution 8% $CH_3CN$—$H_2O$ pH 7.4 phosphate buffer, flow rate 0.8 mL/min, uv detector 302 nm, retention time 5.68 min;

UV ($H_2O$, pH 7.4 phosphate buffer) $\lambda_{max}$: 302 (10,400);

IR (KBr) $\nu_{max}$: 1760 (C=O of β-lactam), 1645 (C=O of amide) and 1590 $cm^{-1}$ (C=O of carboxylate);

$^1H$ NMR (200 MHz, $D_2O$) δ1.33 (d, J=6.33 Hz, 3H, $\underline{CH_3}$CHO), 1.4–2.0 (m, 5H, H-3 of pyrrolidine and $CH_2$-1 and 2 of propyl), 2.73 (m, 1H, H-3 of pyrrolidine), 2.97 and 3.07 (2s, 2×3H, $CON(CH_3)_2$), 3–3.2 (overlapping with $NCH_3$, 4H, $CH_2$-5 of pyrrolidine and $CH_2NH_2$), 3.34 (broad t, 1H, H-4), 3.38 (dd, $J_{H6,H5}$=2.59 Hz, $J_{H6,H1}$=6.27 Hz, 1H, H-6), 3.73 (m, 1H, H-4 of pyrrolidine), 4.10 (dd collapsed into a t, J=8.0 Hz, 1H, H-2 of pyrrolidine) and 4.2–4.4 ppm (m, 2H, $\underline{CH_3}$CHO and H-5 overlapping).

EXAMPLE 113

(4R,5S,6S)-3-((4S)-4-[(2S)-2-Dimethylaminocarbonyl] pyrrolidinylthio)-4-(3"-guanidinopropyl)-6-[(1'R)-1'-hydroxyethyl]-7-oxo-1-azabicyclo[3.2.0.]hept-2-ene-2-carboxylic acid, phosphate salt dibasic

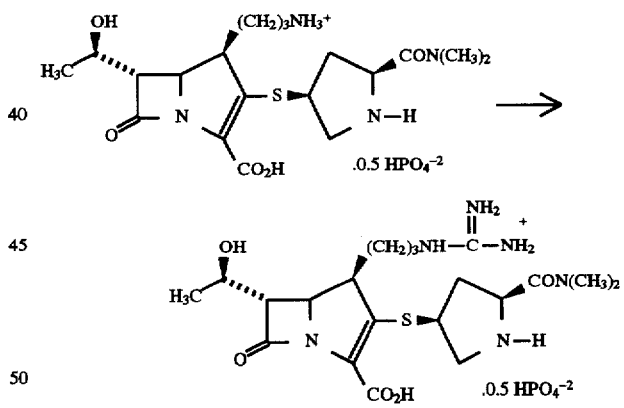

A solution of (4R,5S,6S)-4-(3"-aminopropyl)-3-{(4S)-4-[(2S)-2-dimethylaminocarbonyl]pyrrolidinylthio}-6-[(1'R)-1'-hydroxyethyl]-7-oxo-1-azabicyclo[3.2.0]hept-2-ene-2-carboxylic acid, phosphate salt dibasic (0.14 g, 0.33 mmol) in water (15 mL) at 0°–5° C. was adjusted to pH 8–8.5 with 1N sodium hydroxide and then treated with aminoimino methanesulfonic acid (0.22 g, 1.77 mmol) added in small portions over 5 min. The pH of the reaciton mixture was maintained at 8–8.5 during the addition and for another 2 h. Then 15 mL of 0.2M pH 6.0 phosphate buffer were added and resulting solution was chromatographed on reversed phase silica gel (μBondapak $C_{18}$, 2.5×14 cm). Elution with a gradient of acetonitrile (0–15%) in water gave 0.068 g (45%) of the title compound as a white amorphous powder after freeze drying:

Purity by HPLC: 99% on μBondpak $C_{18}$, 3.9 mm×30 cm, elution 8% $CH_3CN$—$H_2O$, pH 7.4 phosphate buffer, flow rate 1 mL/min, UV detector 302 nm, retention time 7.2 min;

UV ($H_2O$, pH 7.4 phosphate buffer) $\lambda_{max}$: 302 nm (10, 800);

IR (KBr) $v_{max}$: 1755 (C=O of β-lactam), 1640 (C=O of amide) and 1590 $cm^{-1}$ (sh, C=O of carboxylate);

$^1$H NMR (200 MHz, $D_2O$) δ: 1.32 (d, J=6.38 Hz, 3H, C$\underline{H_3}$CHO), 1.4–2.0 (m, 5H, H-3 of pyrrolidine and $CH_2$-1 and 2 of propyl), 2.75 (m, 1H, H-3 of pyrrolidine), 2.97 and 3.08 (2s, 2×3H, $NCH_3$), 3.1–3.4 (m, 5H, $CH_2$-5 of pyrrolidine, $CH_2$N-3 of propyl and H-4), 3.33 (dd, $J_{H6,H5}$=2.55 Hz, $J_{H6,H1}$=6.21 Hz, 1H, H-6), 3.75 (m, 1H, H-4 of pyrrolidine), 4.16 (X part of AMX system, $J_{AX}$=8.8 Hz, $J_{MX}$=7.4 Hz, 1H, H-2 of pyrrolidine), 4.25 (dd overlapping with $CH_3$C$\underline{H}$O, $J_{H5,H6}$=2.55 Hz, 1H, H-5) and 4.27 ppm (m, 1H, $CH_3$C$\underline{H}$O).

EXAMPLE 114

(4R,5S,6S)-4-(2"-Azidoethyl)-3-[(2-aminoethyl)thio]-6-[(1'R)-1'hydroxyethyl]-7-oxo-1-azabicyclo[3.2.0]hept-2-ene-2-carboxylic acid

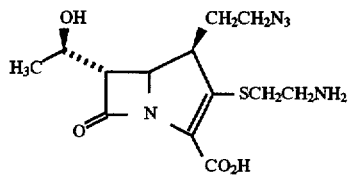

A. Allyl (4R,5S,6S)-3-[(2-allyloxycarbonylaminoethyl)thio]-4-(2"-azidoethyl)-6-[(1'R)-1'-tert-butyldimethylsilyloxyethyl]-7-oxo-1-azabicyclo[3.2.0]hept-2-ene-2-carboxylate

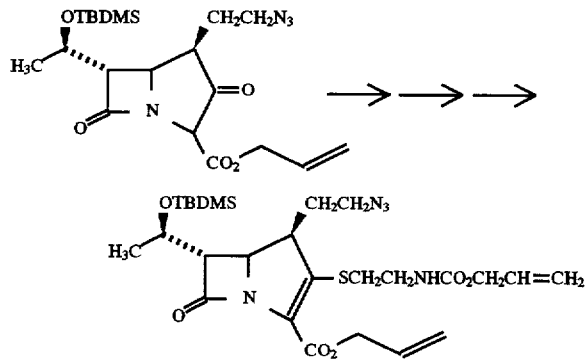

A solution of allyl (2R,4R,5R,6S)-4-(2"-azidoethyl)-6-[(1'R)-1'-tert-butyldimethylsilyloxyethyl]-3,7-dioxo-1-azabicyclo[3.2.0]heptane-2-carboxylate (10.0 mmol, prepared by cyclization of 4.64 g, 10.0 mmol of diazo precursor) in dry acetonitrile (75 mL) was treated at 0°–5° C. and under nitrogen with diphenyl chlorophosphate (2.3 mL, 11.1 mmol) and N,N-diisopropylethylamine (1.9 mL, 10.9 mmol) added simultaneously over 5 min. A small crystal of 4-N,N-dimethylaminopyridine was then added and the resulting mixture was stirred at 0°–5° C. for 30 min. The solution was then treated with more N,N-diisopropylethylamine (6.0 mL, 34.5 mmol) followed by allyl 2-mercaptoethylcarbamate [see Example 116, Step A] (5.1 g, 33.4 mmol) in acetonitrile (5 mL) and the resulting mixture was stirred at 0°–5° C. for 20 h. The solution was then diluted with ethyl acetate (500 mL) washed with water, saturated sodium bicarbonate, brine and dried ($MgSO_4$). The residue obtained after evaporation of the solvent under vacuum was chromatographed on silica gel (5×10 cm) using a gradient of ethyl acetate (0–10%) in toluene as eluent. Evaporation of the pertinent fractions gave 4.37 g (75%) of the title compound as a light yellow oil. By TLC and $^1$H NMR this material was contaminated with some impurities (disulfide) but was used as such in the next step:

IR (NaCl, film) $v_{max}$: 2100 ($N_3$), 1775 (C=O of β-lactam) and 1720 $cm^{-1}$ (broad, C=O of ester);

$^1$H NMR (200 MHz, $CDCl_3$) δ: 0.09 (s, 6H, $SiCH_3$), 0.89 (s, 9H, Si-tBu), 1.30 (d, J=6.05 Hz, 3H, C$\underline{H_3}$CHO), 1.5–2.0 (m, 2H, $CH_2$-4), 2.8–3.6 (m, 8H, SC$\underline{H_2}$C$\underline{H_2}$N, $CH_2N_3$, H-4 and H-6), 4.1–4.3 (m, 2H, H-5 and $CH_3$C$\underline{H}$O), 4.5–4.9 (m, 4H, $CH_2$ of allyl), 5.1–5.5 and 5.8–6.1 ppm (2m, 6H, and 2H, CH of allyl and NH).

B. Allyl (4R,5S,6S)-3-[(2-allyloxycarbonylaminoethyl)thio]-4-(2"-azidoethyl)-6-[(1'R)-1'-hydroxyethyl]-7-oxo-1-azabicyclo[3.2.0]hept-2-ene-2-carboxylate

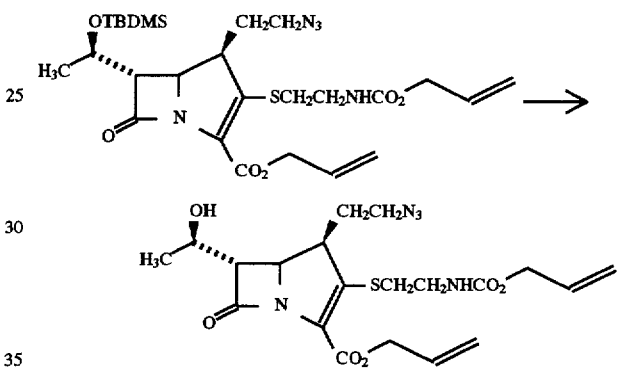

A solution of allyl (4R,5S,6S)-3-[(1-allyloxycarbonylaminoethyl)thio]-4-(2"-azidoethyl)-6-[(1'R)-1'-tert-butyldimethylsilyloxyethyl]-7-oxo-1-azabicyclo[3.2.0]hept-2-ene-2-carboxylate (4.37 g, 7.54 mmol) in dry tetrahydrofuran (120 mL) was treated at 0°–5° C. and under nitrogen with acetic acid (2.7 mL, 47.5 mmol) followed by 24 mL (24.0 mmol) of a 1M solution of tetrabutylammonium fluoride in tetrahydrofuran added dropwise over 5 min. The solution was then stored at 10° C. for 7 days. The reaction mixture was then diluted with ethyl acetate (500 mL), washed with saturated sodium bicarbonate (2×), brine and dried ($MgSO_4$). Evaporation of the solvent under reduced presure gave an oil which was chromatographed on silica gel (6.5×11 cm) using a gradient of ethyl acetate in toluene (7:3 to 1:1) as eluent. Evaporation of the UV active fractions gave 1.17 g (33%) of the title compound as a clear oil:

IR (NaCl) $v_{max}$: 3480 (OH), 2100 ($N_3$), 1770 (C=O of β-lactam) and 1710 $cm^{-1}$ (C=O of ester);

$^1$H NMR (200 MHz, $CDCl_3$) δ: 1.39 (d, J=6.24 Hz, 3H, C$\underline{H_3}$CHO), 1.7–2.1 (m, 2H, $CH_2$-4), 2.7–3.15 (m, 2H, $SCH_2$), 3.18 (dd, $J_{H6,H5}$=2.66 Hz, $J_{H6,H1}$=7.97 Hz, 1H, H-6), 3.2–3.7 (m, 5H, $CH_2NH$, $CH_2N_3$ and H-4), 4.23 (m, overlapping with H-5, 1H, $CH_3$C$\underline{H}$O), 4.25 (dd, $J_{H5,H6}$=2.66 Hz, $J_{H5,H4}$=9.57 Hz, 1H, H-5), 4.57 and 4.75 (2m, 2×2H, $CH_2$ of allyl), 5.1–5.5 and 5.8–6.1 ppm (2m, 6H and 2H, CH of allyl and NH).

C. (4R,5S,6S)-4-(2"-Azidoethyl)-3-[(2-aminoethyl)thio]-6-[(1'R)-1'-hydroxyethyl]-7-oxo-1-azabicyclo[3.2.0]hept-2-ene-2-carboxylic acid

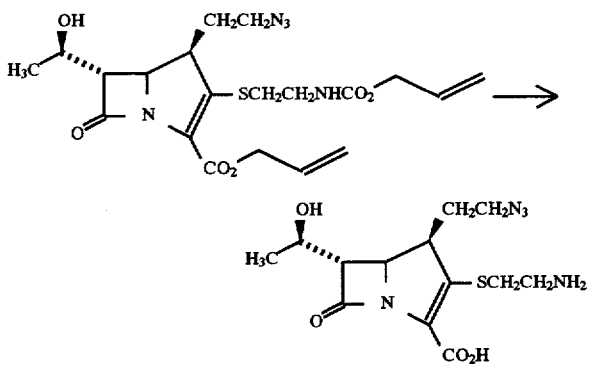

A solution of allyl (4R,5S,6S)-3-[(2-allyloxycarbonylaminoethyl)thio]-4-(2"-azidoethyl)-6-[(1'R)-1'-hydroxyethyl]-7-oxo-1-azabicyclo[3.2.0]hept-2-ene-2-carboxylate (1.17 g, 2.5 mmol) in dry dichloromethane (30 mL) was treated at 22° C. and under nitrogen with tetrakis(triphenylphosphine)palladium [0] (0.072 g) followed by N-methylaniline (1.6 mL, 14.8 mmol). The solution was stirred for 3 h while a precipitated appeared. The reaction mixture was extracted with cold water (3×35 mL) and the combined aqueous phase was maintained under vacuum to remove traces of organic solvent. The solution was then chromatographed on reversed phase silica gel (μBondapak $C_{18}$, 2.5×14 cm) using a gradient of acetonitrile in water as eluent. Lyophilization of the UV active fractions gave 0.37 g (43%) of the title carbapenem as a white amorphous solid: $[\alpha]_D^{?}$ +21.5° (C 1.0, $H_2O$);

Purity by HPLC: 99.2% on μBondapak $C_{18}$ (3.9 mm×30 cm, 10% $CH_3CN$—$H_2O$ pH 7.4 phosphate buffer, flow rate 1 mL/min, uv detector 302 nm, retention time 7.58 min;

UV ($H_2O$, pH 7.4 phosphate buffer) $\lambda_{max}$: 298 nm (7401 nm);

IR (KBr) $v_{max}$: 2100 ($N_3$), 1760 (C=O of β-lactam) and 1590 cm$^{-1}$ (broad, C=O of carboxylate);

$^1H$ NMR (200 MHz, $D_2O$) δ: 1.33 (d, J=6.38 Hz, 3H, $CH_3CHO$), 1.7–2.2 (m, 2H, $CH_2$-4), 2.9–3.7 (broad m, 7H, $SCH_2CH_2NH_2$, $CH_2N_3$ and H-4), 3.50 (dd, $J_{H6,H5}$=2.67 Hz, $J_{H6,H1}$=6.24 Hz, 1H, H-6) and 4.2–4.4 ppm (m, 2H, H-5 and $CH_3CHO$ overlapping).

EXAMPLE 115

(4R,5S,6S)-4-(2"-Aminoethyl)-3-[(2-aminoethyl)thio]-6-[(1'R)-1'-hydroxyethyl]-7-oxo-1-azabicyclo[3.2.0]hept-2-ene-2-carboxylic acid, acetic acid salt

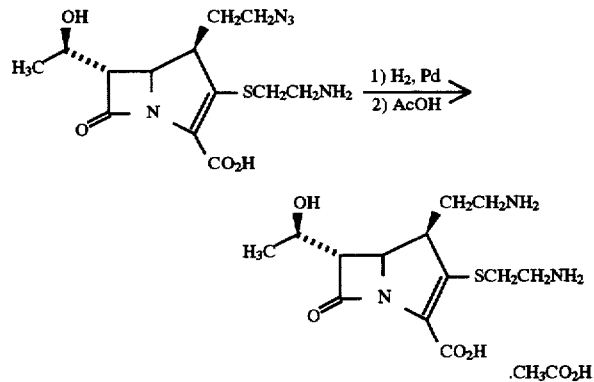

A solution of (4R,5S,6S)-3-[(2-aminoethyl)thio]-4-(2"-azidoethyl)-6-[(1'R)-1'-hydroxyethyl]-7-oxo-1-azabicyclo [3.2.0]hept-2-ene-2-carboxylic acid (0.30 g, 0.88 mmol) in cold water (90 mL) was hydrogenated at 0°–5° C. over 1.2 g of 5% palladium on alumina and under 45 psi of hydrogen for 50 min. Then 0.1 mL (1.6 mmol) of acetic acid was added (pH changed grom 9.3 to 4.3) and the catalyst was filtered on a Celite pad. The filtrate was chromatographed on reversed phase silica gel (2.5×14 cm) using 0.005M aqueous acetic acid as eluent. The product was eluted very fast from the column with the solvent front. The UV active fractions were combined, lyophilized and chromatographed on the same column a second time. Lyophilization gave 0.22 g (66%) of the title carbapenem as a white amorphous powder. By UV and $^1H$ NMR, this product was 60% pure and contained some inorganic salts of acetic acid (based on a UV absorption of 7400 for the azido precursor);

Purity by HPLC: 99% on μBondapak $C_{18}$, 3.9 mm×30 cm, elution 5% $CH_3CN$—$H_2O$ pH 7.4 phosphate buffer, flow rate 0.9 mL/min, uv detector 300 nm, retention time 5.7 min;

UV ($H_2O$, pH 7.4 phosphate buffer) $\lambda_{max}$: 296 nm (4,446);

IR (KBr) $v_{max}$: 1760 (C=O of β-lactam) and 1570 cm$^{-1}$ (broad, C=O of carboxylate);

$^1H$ NMR (200 MHz, $D_2O$) δ: 1.33 (d, J-6.36 Hz, 3H, $CH_3CHO$), 1.9 (s, $CH_3CO_2H$), 1.8–2.4 (m, 2H, $CH_2$-4), 2.8–3.45 (m, 7H, $SCH_2CH_2NH_2$, H-4 and $CH_2NH_2$), 3.49 (dd, $J_{H6,H5}$=2.84 Hz, $J_{H6,H4}$=6.42 Hz, 1H, H-6), 4.2–4.4 ppm (m, 2H, H-5 and $CH_3CHO$).

EXAMPLE 116

(4R,5S,6S)-3-[(2-Aminoethyl)thio]-4-(3"-azidopropyl)-6-[(1'R)-1'-hydroxyethyl]-7-oxo-1-azabicyclo[3.2.0]hept-2-ene-2-carboxylic acid

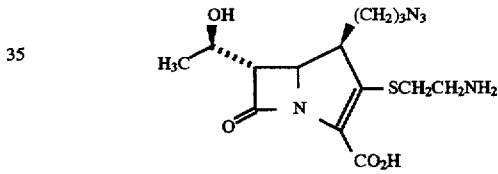

A. Allyl 2-mercaptoethylcarbamate

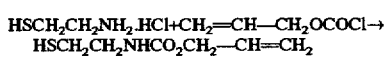

A suspension of 2-aminoethanethiol hydrochloride (4.4 g, 38.7 mmol) in dry acetonitrile (30 mL) was cooled to 0°–5° C. and treated under nitrogen with N,N-diisopropylethylamine (16.0 mL, 91.8 mmol). After 5 min, trimethylsilyl chloride (6.56 mL, 51.7 mmol) was added all at once and the mixture was stirred for 15 min. Then allyl chloroformate (4.24 mL, 40.0 mmol) followed by N,N-diisopropylethylamine (6.9 mL, 29.6 mmol) were added dropwise (10 min) and the resulting mixture was stirred for 30 min at 0°–5° C. and for 2 h at 22° C. Water (100 mL) was then added and the reaction mixture was extracted with dichloromethane (2×100 mL). The combined organic phase was washed with 1N hydrochloric acid (20 mL), 0.2M pH 7.0 phosphate buffer, brine and dried ($Na_2SO_4$). Evaporation of the solvent under reduced pressure gave 6.5 g of the crude thiol as a clear oil which was used immediately for the coupling step. The preparation of the title compound was based on the procedure of I. Shinkai et al, Synthesis, 924, (1980).

$^1H$ NMR (200 MHz, $CDCl_3$) δ: 1.36 (t, J=8.53 Hz, 1H, SH), 2.66 (m, 2H, $SCH_2$), 3.37 (m, 2H, $CH_2N$), 4.57 (m, 2H, $CH_2$ of allyl), 5.2 (broad, 1H, NH), 5.2–5.4 and 5.8–6.1 ppm (2m, 2H and 1H, CH of allyl).

B. Allyl (4R,5S,6S)-3-[(2-allyloxycarbonylaminoethyl)thio]-4-(3"-azidopropyl)-6-[(1'R)-1'-hydroxyethyl]-7-oxo-1-azabicyclo[3.2.0]hept-2-ene-2-carboxylate

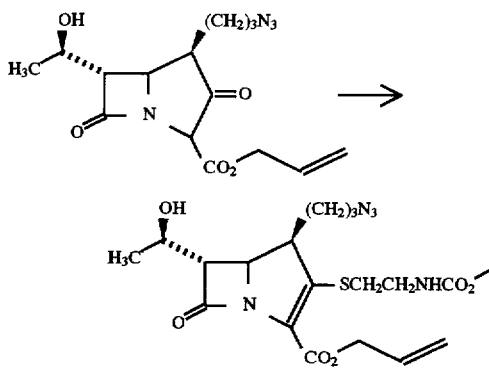

A solution of allyl (4R,5R,6S)-4-(3"-azidopropyl)-6-[(1'R)-1'-hydroxyethyl]-3,7-dioxo-1-azabicyclo[3.2.0]heptane-2-carboxylate (11.0 mmol, prepared by cyclization of 4.0 g, 11.0 mmol of the diazo precursor) in dry acetonitrile (50 mL) was cooled to 0°–5° C. and treated dropwise with diphenyl chlorophosphate (2.3 mL, 11.5 mmol) and N,N-diisopropylethylamine (2.3 mL, 11.5 mmol) added simultaneously over 5 min. A small crystal of 4-N,N-dimethylaminopyridine was then added and the solution was stirred for 1 h. The hydroxyl group was then silylated by the dropwise addition of N,N-diisopropylethylamine (2.3 mL, 11.5 mmol) followed by chlorotrimethylsilane (1.46 mL, 11.5 mmol) and the resulting mixture was stirred for 15 min. Then more N,N-diisopropylethylamine (3.8 mL, 21.9 mmol) and the allyl 2-mercaptoethylcarbamate (3.53 g, 21.9 mmol) were added and the mixture was stirred at 0°–5° C. for 16 h. The reaction mixture was quenched by the addition of ethyl acetate (400 mL) and water. The organic phase was washed with 2% cold aqueous citric acid, 0.2M pH 7.0 phosphate buffer, brine and dried (MgSO$_4$). The solvent was evaporated under reduced pressure and the residue was dissolved in a mixture of tetrahydrofuran (100 mL) and water (50 mL) and treated at 0°–5° C. with acetic acid (5 mL). After 1 h at 0°–5° C. and 2 h at 22° C., the reaction mixture was diluted with ethyl acetate (400 mL), washed successively with cold saturated sodium bicarbonate, 0.2M pH 7.0 phosphate buffer, brine and dried (MgSO$_4$). Evaporation of the solvent under reduced pressure gave an oil which was chromatographed on silica gel (4×12 cm). Elution with a gradient of ethyl acetate in toluene (8:7 to 1:1) gave 3.19 g (61%) of the title compound as an oil:

IR (NaCl, film) $v_{max}$: 3400 (OH), 2100 (N$_3$), 1755 (C=O of β-lactam) and 1705 cm$^{-1}$ (broad, C=O of ester);

$^1$H NMR (200 MHz, CDCl$_3$) δ: 1.39 (d, J=6.25 Hz, 3H, C$\underline{H}_3$CHO), 1.5–2.0 (m, 4H, CH$_2$-1 and 2 of propyl), 2.7–3.2 (m, 2H, SCH$_2$), 3.24 (dd, J$_{H6,H5}$=2.63 Hz, J$_{H6,H1}$=7.46 Hz, 1H, H-6), 3.2–3.6 (m, 5H, CH$_2$N$_3$, CH$_2$N and H-4), 4.24 (dd, J$_{H5,H6}$=2.63 Hz, J$_{H5,H4}$=9.43 Hz, 1H, H-5), 4.24 (overlapping with H-5, 1H, CH$_3$C$\underline{H}$O), 4.56 and 4.75 ppm (2m, 2×2H, CH$_2$ of allyl), 5.1–5.5 (m, 5H, CH of allyl and NH) and 5.8–6.1 ppm (m, 2H, CH of allyl).

C. (4R,5S,6S)-3-[(2-Aminoethyl)thio]-4-(3"-azidopropyl)-6-[(1'R)-1'-hydroxyethyl]-7-oxo-1-azabicyclo[3.2.0]hept-2-ene-2-carboxylic acid

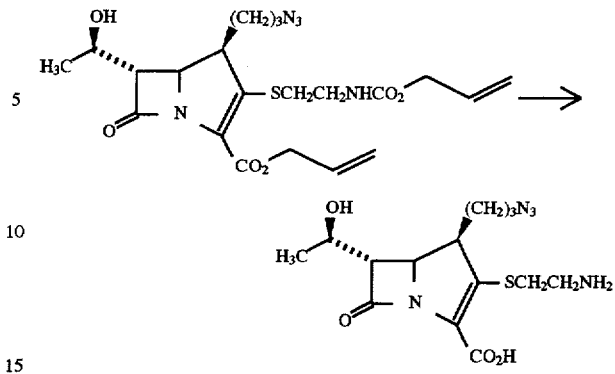

A solution of allyl (4R,5S,6S)-3-[(2-allyloxycarbonylaminoethyl)thio]-4-(3"-azidopropyl)-6-[(1'R)-1'-hydroxyethyl]-7-oxo-1-azabicyclo[3.2.0]hept-2-ene-2-carboxylate (3.19 g, 6.65 mmol) in dry dichloromethane (80 mL) was treated at 22° C. and under nitrogen with tetrakis(triphenylphosphine)palladium [0] (0.19 g) and N-methylaniline (4.3 mL, 40.0 mmol). After 3 h, the reaction mixture which contained a gel-like precipitate was diluted with cold water (200 mL) and adjusted to pH 3.8 with 2N hydrochloric acid to dissolve the amino acid. The cold aqueous phase was collected, washed with dichloromethane, adjusted to pH 6.5 with 1N sodium hydroxide and maintained under vacuum to remove traces of organic solvent. The solution was then chromatographed on reversed phase silica gel (μBondapak C$_{18}$, 3×15 cm) using a gradient of acetonitrile (0–10%) in water as eluent. Lyophilization of the UV active fractions gave 1.28 g (54%) of the title compound as a white amorphous powder: [α]$_D^{22}$+32.6° (c 1.0, H$_2$O);

Purity by HPLC: 99% on μBondapak C$_{18}$, 3.9 mm×30 cm, elution 10% CH$_3$CN—H$_2$O pH 7.4 phosphate buffer, flow rate 1 mL/min, uv detector 300 nm, retention time 13.3 min;

UV (H$_2$O, pH 7.4 phosphate buffer) $\lambda_{max}$: 298 nm (8,425);

IR (KBr) $v_{max}$: 2100 (N$_3$), 1760 (C=O of β-lactam) and 1590 cm$^{-1}$ (C=O of carboxylate);

$^1$H NMR (200 MHz, D$_2$O) δ: 1.33 (d, J=6.37 Hz, 3H, C$\underline{H}_3$CHO), 1.5–2.0 (m, 4H, CH$_2$-1 and 2 of propyl), 2.8–3.5 (m, 5H, SC$\underline{H}_2$C$\underline{H}_2$NH$_2$ and H-4), 3.42 (t, J=6.2 Hz, 3H, CH$_2$N$_3$), 3.47 (dd, J$_{H6,H5}$=2.70 Hz, J$_{H6,H1}$=5.98 Hz, 1H, H-6), 4.26 (dd, J$_{H5,H6}$=2.70 Hz, J$_{H5,H4}$=9.35 Hz, 1H, H-5) and 4.28 ppm (m overlapping with H-5, 1H, CH$_3$C$\underline{H}$O).

EXAMPLE 117

(4R,5S,6S)-4-(3"-Aminopropyl)-3-[(2-aminoethyl)thio]-6-[(1'R)-1'-hydroxyethyl]-7-oxo-1-azabjcyclo[3.2.0]hept-2-ene-2-carboxylic acid, acetic acid salt

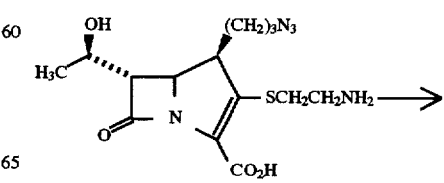

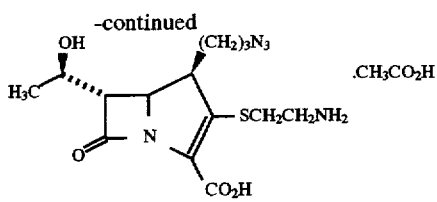

A solution of (4R,5S,6S)-3-[(2-aminoethyl)thio]-4-(3"-azidoethyl)-6-[(1'R)-1'-hydroxyethyl]-7-oxo-1-azabicyclo[3.2.0]hept-2-ene-2-carboxylic acid (0.292 g, 0.82 mmol) in water (90 mL) was hydrogenated at 0°–5° C. over 1.2 g of 5% palladium on alumina and under 45 psi of hydrogen for 1 h. Then 0.1 mL (1.64 mmol) of acetic acid was added and the catalyst was filtered on a Celite pad. The filtrate was then chromatographed on reversed phase silica gel (μBondapak C$_{18}$, 3×12 cm) using 0.005M aqueous acetic acid as eluent. The UV active fractions were combined and lyophilized to give 0.264 g (82%) of the title compound as a white amorphous solid: $[α]_D^{22}$+37.0° (c 1.0, H$_2$O);

Purity by HPLC: 98% on μBondapak C$_{18}$, 3.9 mm×30 cm, elution 5% CH$_3$CN—H$_2$O pH 7.4 phosphate buffer, flow rate 0.8 mL/min, UV detector 300 nm, retention time 4.9 min;

UV (H$_2$O, pH 7.4 phosphate buffer) λ$_{max}$: 298 nm (7,517);

IR (KBr) ν$_{max}$: 1755 (C=O of β-lactam) and 1570 cm$^{-1}$ (broad, C=O of carboxylate);

$^1$H NMR (200 MHz, D$_2$O) δ: 1.33 (d, J=6.34 Hz, 3H, CH$_3$CHO), 1.4–2.0 (m, 4H, CH$_2$-1 and 2 of propyl), 1.92 (s, CH$_3$CO$_2$H), 2.8–3.4 (m, 7H, SCH$_2$CH$_2$NH$_2$, CH$_2$NH$_2$-3 of propyl and H-4), 3.43 (dd, J$_{H6,H5}$=2.73 Hz, J$_{H6,H1}$=6.37 Hz, 1H, H-6), 4.2–4.3 ppm (m, 2H, H-5 and CH$_3$CHO overlapping).

EXAMPLE 118

(4R,5S,6S)-4-(3"-Azidopropyl)-3-[(2-N-formimidoylaminoethyl)thio]6-[(1'R)-1'-hydroxyethyl]-7-oxo-1-azabicyclo[3.2.0]hept-2-ene-2-carboxylic acid

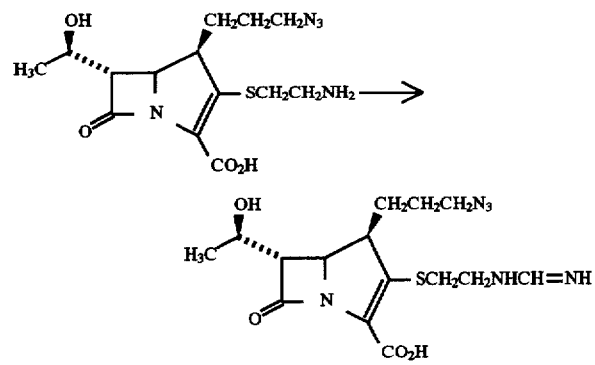

A suspension of (4R,5S,6S)-3-[(2-aminoethyl)thio]-4-(3"azidopropyl)-6-[(1'R)-1'-hydroxyethyl]-7-oxo-1-azabicyclo[3.2.0]hept-2-ene-2-carboxylic acid (0.460 g, 1.29 mmol) in cold water (25 mL) was adjusted to pH 8.5 with 1M sodium hydroxide and treated at 0°–5° C. with benzyl formimidate hydrochloride (0.78 g, 4.52 mmol) added in small portions over 10 min. The pH was maintained at 8–8.5 with 1M sodium hydroxide throughout the addition and for another 25 min. Then 20 mL of 0.2M pH 6 phosphate buffer were added and the reaction mixture was washed with ethyl acetate (20 mL). The aqueous phase was maintained under vacuum to remove traces of organic solvent and then chromatographed on reversed phase silica gel (μBondapak C$_{18}$, 2.5×11 cm). The column was eluted with a gradient of acetonitrile (0–15%) in 0.01M phosphate buffer. The UV active fractions were combined concentrated in vacuo (T <20° C.) and desalted on the same column using water instead of buffer as eluent. Lyophilization of the pertinent fractions gave 0.240 g (48%) of the title compound as a white amorphous powder: $[α]_D^{22}$+16.0 (c 1.0, H$_2$O);

Purity by HPLC: 99.4% on μBondapak C$_{18}$, 3.9 mm×30 cm, elution 20% CH$_3$CN—H$_2$O, pH 7.4 phosphate buffer, flow rate 0.8 mL/min, UV detector 300 nm, retention time 6.06 min;

UV (H$_2$O, pH 7.4 phosphate buffer) λ$_{max}$: 302 nm (9,768);

IR (KBr) ν$_{max}$: 2100 (N$_3$), 1955 (C=O of β-lactam), 1715 (CN of formimidoyl) and 1590 cm$^{-1}$ (C=O of carboxylate);

$^1$H NMR (200 MHz, D$_2$O) δ: 1.33 (d, J=6.35 Hz, 3H, CH$_3$CHO), 1.4–2.0 (m, 4H, CH$_2$-1 and 2 of butyl), 2.8–3.3 (m, 2H, SCH$_2$), 3.3–3.8 (m, 6H, H-6, H-4, CH$_2$N$_3$ and CH$_2$NH), 4.2–4.4 (m, 2H, H-5 and CH$_3$CHO overlapping), 7.76 and 7.83 ppm (2S, 1H, NHCH=NH).

EXAMPLE 119

(4R,5S,6S)-4-(3"-Aminopropyl)-3-[(2-N-formimidoylaminoethyl)thio]-6-[(1'R)-1'-hydroxyethyl]-7-oxo-1-azabicyclo[3.2.0]hept-2-ene-2-carboxylic acid, acetic acid salt

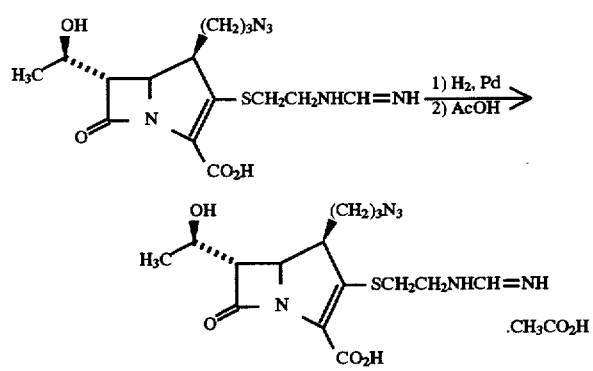

A solution of (4R,5S,6S)-4-(3"-azidopropyl)-3-[(2-N-formimidoylaminoethyl)thio]-6-[(1'R)-1'-hydroxyethyl]-7-oxo-1-azabicyclo[3.2.0]hept-2-ene-2-carboxylic acid (0.180 g, 0.47 mmol) in cold water (70 mL) was hydrogenated at 0°–5° C. over 1.2 g of 5% palladium on alumina and under 45 psi of hydrogen for 1 h. Then acetic acid (0.045 mL, 0.79 mmol) was added and the catalyst was filtered on a Celite pad. The filtrate was then chromatographed on reversed phase silica gel (μBondapak C$_{18}$, 3×10 cm) using 0.005M acetic acid as eluent. Lyophilization of the UV active fractions gave 0.136 g (69%) of the title compound as a white amorphous solid: $[α]_D^{22}$+17.5° (c 1.0 H$_2$O);

Purity by HPLC: 94% on μBondapak C$_{18}$, 3.9 mm×30 cm, elution 5% CH$_3$CN—H$_2$O pH 7.4 phosphate buffer, flow rate 1 mL/min, UV detector 300 nm, retention time 7.57 min;

UV (H$_2$O, pH 7.4 phosphate buffer) λ$_{max}$: 300 nm (6,900);

IR (KBr) 84$_{max}$: 1755 (C=O of β-lactam), 1720 (CN of formimidoyl) and 1570 cm$^{-1}$ (broad, C=O of carboxylate);

$^1$H NMR (200 MHz, D$_2$O) δ: 1.33 (d, J=6.36 Hz, 3H, CH$_3$CHO), 1.5–2.0 (m, 4H, CH$_2$-1 and 2 of propyl), 1.92 (s, 3H, CH$_3$CO$_2$H), 3.04 (t, J=7.0 Hz, 2H, CH$_2$NH$_2$), 3.42 (dd, $J_{H6,H5}$=2.64 Hz, $J_{H6,H1}$=6.31 Hz, 1H, H-6), 2.8–3.7 (m, 5H, SCH$_2$, CH$_2$NHCH=NH and H-4), 4.26 (dd, overlapping with CH$_3$CHO, $J_{H5,H6}$=2.64 Hz, 1H, H-5), 4.28 (m, 1H, CH$_3$CHO), 7.74 and 7.83 ppm (2S, 1H, NHCH=NH).

EXAMPLE 120

(4R,5S,6S)-4-(3"-Aminopropyl)-6-[(1'R)-1'-hydroxyethyl]-3-[2-(1-pyrrolidinyl)ethylthio]-7-oxo-1-azabicyclo[3.2.0]hept-2-ene-2-carboxylic acid, acetic acid salt

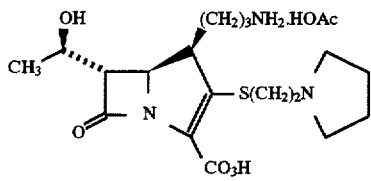

A. Allyl (4R,5S,6S)-4-(3"-azidopropyl)-3-[(2-hydroxyethyl)thio]-6-[(1'R)-1'-triethylsilyloxyethyl]-7-oxo-1-azabicyclo[3.2.0]hept-2-ene-2-carboxylate

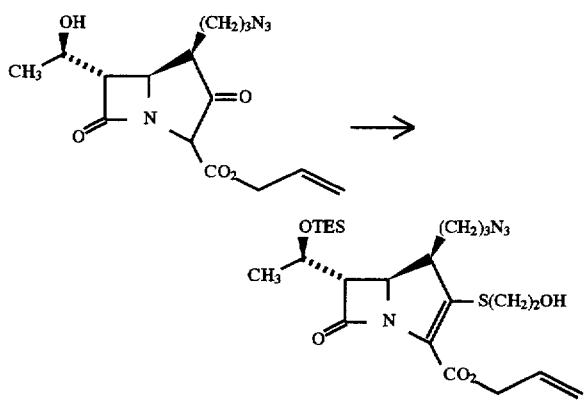

A cold (ice-methanol bath) solution of allyl (2R,4R,5R,6S)-4-(3"-azidopropyl)-6-[(1'R)-1'-hydroxyethyl]-3,7-dioxo-1-azabicyclo[3.2.0]heptan-2-carboxylate [prepared from (3S,4R)-3-[(1'R)-1'-hydroxyethyl]-4-[(1"R)-1"-(3-azidopropyl)-3"-diazo-3"-allyloxycarbonyl-2"-oxopropyl]-azetidin-2-one (1.0 g, 2.75 mmol)] was treated slowly with diphenyl chlorophosphate (0.6 mL, 3.0 mmol) followed by the dropwise addition of diisopropylethylamine (0.52 mL, 3.0 mmol). The mixture was stirred for 1 h, then triethylsilyl chloride (0.5 mL, 3 mmol) and diisopropylethylamine (0.52 mL, 3.0 mmol) were added in. The mixture was stirred for 30 min at −15° C. The resulting silylated enol phosphate was treated with 2-mercaptoethanol (430 mg, 5.5 mmol) in CH$_3$CN (0.5 mL) and diisopropylethylamine (0.95 mL, 5.5 mmol). The mixture was stirred for 19 h at 5°–8° C. (cold room), then diluted with ethyl acetate (50 mL), washed with ice cold water (2×20 mL), 1M aqueous NaHSO$_3$ (3×20 mL), water (20 mL), 1N aqueous HCl (20 mL), water (2×20 mL), 1M aqueous NaHCO$_3$ (20 mL), water (20 mL), brine (20 mL) and dried (MgSO$_4$). The residue was passed through a silica gel flash column (50 g, 0–50% ethyl acetate/hexane) to give the title compound (883 mg, 63%) as an oil.

IR (CH$_2$Cl$_2$) v$_{max}$: 3600 (OH), 2100 (N$_3$), 1775 (C=O β-lactam) and 1710 cm$^{-1}$ (C=O ester);

$^1$H NMR (CDCl$_3$, 200 MHz) δ: 6.05–5.8 (1H, m, vinylic H), 5.49–5.2 (2H, m, vinylic H), 4.9–4.6 (2H, m, allylic CH$_2$), 4.30–4.16 (1H, m, H-1'), 4.145 (1H, dd, J=2.5 Hz, J=9.6 Hz, H-5), 3.803 (2H, t, J=5.9 Hz, CH$_2$O, 3.40–3.28 (2H, m, CH$_2$N$_3$), 3.24–3.28 (1H, m, H-1'), 3.192 (1H, dd, J=2.8 Hz, J=7.5 Hz, H-6), 3.15–2.87 (2H, m, SCH$_2$), 1.89–1.75 (1H, m, part of CH$_2$-4), 1.7–1.45 (3H, m, CH$_2$—CH$_2$ at 4), 1.552 (1H, bs, OH), 1.316 (3H, d, J=6.1 Hz, CH$_3$), 0.998, 0.957 and 0.920 (9H, 3 lines, CH$_3$), 0.662, 0.659, 0.623,0.584, 0.546 and 0.539 ppm (6H, 6 lines, CH$_2$).

B. Allyl (4R,5S,6S)-4-(3"-azidopropyl)-3-[2-(1-pyrrolidinyl)ethylthio]-6-[(1'R)-1'-triethylsilyloxyethyl]-7-oxo-1-azabicyclo[3.2.0]hept-2-ene-2-carboxylate

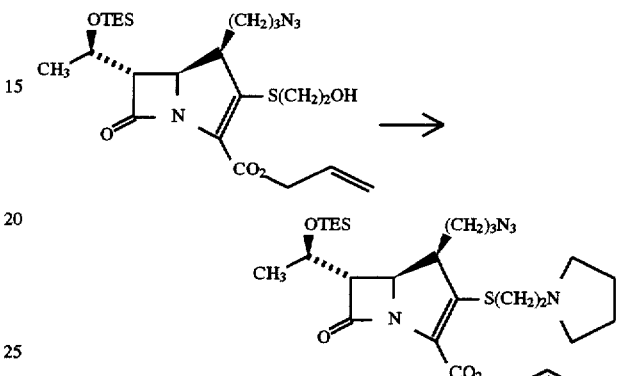

A cold (dry ice-acetone) solution of allyl (4R,5S,6S)-4-(3"-azidopropyl)-3-[(2-hydroxyethyl)thio]-6-[(1'R)-1'-triethylsilyloxyethyl]-7-oxo-1-azabicyclo[3.2.0] hept-2-ene-2-carboxylate (883 mg, 1.73 mmol) in dichloromethane (20 mL) was treated first with diisopropylethylamine (0.80 mL, 4.5 mmol) and dropwise with trifluoromethanesulfonic anhydride (0.35 mL, 2.1 mmol). The mixture was stirred for 20 min and pyrrolidine (0.90 mL, 10.4 mmol) in dichloromethane (1 mL) was added in. Stirring was continued for 30 min at −78° C. (dry ice-acetone) and for 30 min at −15° C. (ice-methanol bath). The reaction mixture was diluted with ethyl acetate (100 mL) and petroleum ether (20 mL), washed with ice cold water (10×25 mL), brine (25 mL), dried (MgSO$_4$) and the residue upon solvent evaporation was passed through a silica gel flash pad (45 g, 33→100% ethyl acetate/hexane, 10%→40% acetone/ethyl acetate) to give title compound (510 mg, 52%) as an oil.

IR (CH$_2$Cl$_2$) v$_{max}$: 2100 (N$_3$), 1775 (C=O β-lactam) and 1710 cm$^{-1}$ (C=O ester);

$^1$H NMR (CDCl$_3$, 200 MHz) δ: 6.03–5.9 (1H, m, vinylic H), 5.49–5.21 (2H, m, vinylic H), 4.9–4.6 (2H, m, allylic CH$_2$), 4.30–4.14 (1H, m, H-1'), 4.121 (1H, dd, J=2.6 Hz, J=9.6 Hz, H-5), 3.4–3.30 (2H, m, CH$_2$N$_3$), 3.23–3.14 (1H, m, H-4), 3.169 (1H, dd, J=2.6 Hz, J=7.6 Hz, H-6), 2.98–2.88, 2.75–2.63 (2H, 2 sets of m, SCH$_2$), 2.63–2.45 (6H, m, CH$_2$N), 1.9–1.5 (8H, m, CH$_2$CH$_2$-4 and CH$_2$CH$_2$ pyrrolidine), 1.317 (3H, d, J=6.1 Hz, CH$_3$), 0.0993, 0.952, 0.916 (9H, 3 lines, CH$_3$), 0.697, 0.658, 0.655, 0.619, 0.579, 0.542 and 0.535 ppm (6H, 7 lines, SiCH$_2$).

C. Allyl (4R,5S,6S)-4-(3"-azidopropyl)-6-[(1'R)-1'-hydroxyethyl]-3-[2-(1-pyrrolidinyl)ethylthio]-7-oxo-1-azabicyclo[3.2.0]hept-2-ene-2-carboxylate

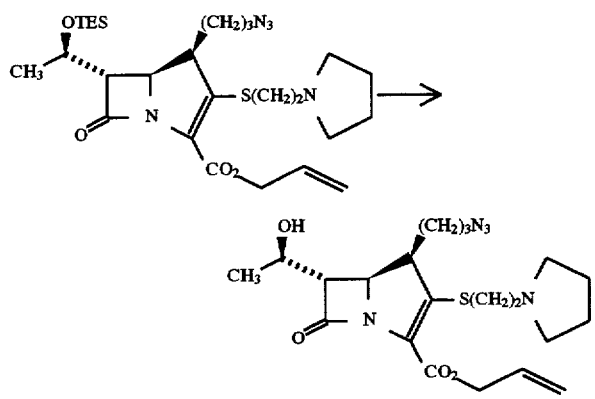

A cold (ice-methanol) solution of allyl (4R,5S,6S)-4-(3"-azidopropyl)-3-[2-(1-pyrrolidinyl)ethylthio]-6-(1'R)-1'-triethylsilylethylsilyloxyethyl]-7-oxo-1-azabicyclo[3.2.0]hept-2-ene-2-carboxylate (500 mg, 0.77 mmol) in anhydrous tetrahydrofuran (5 mL) was treated first with glacial acetic acid (0.290 mL, 5.28 mmol) followed by the dropwise addition of a 1M solution of tetrabutylammonium fluoride in tetrahydrofuran (2.64 mL, 2.64 mmol). The mixture was allowed to stand at -20° C. for 20 h, then diluted with ethyl acetate (25 mL), washed with ice cold 1M aqueous NaHCO₃, (3×10 mL), brine (10 mL) dried (MgSO₄). The residue obtained (370 mg, 94%) upon solvent evaporation was used as such in the next step.

IR (CH₂Cl₂) $v_{max}$: 3600 (OH), 2100 (N₃), 1775 (C=O β-lactam) and 1710 cm⁻¹ (C=O ester);

¹H NMR (CDCl₃, 200 MHz) δ: 6.04–5.90 (1H, m, vinylic H), 5.49–5.22 (2H, m, vinylic H), 4.82–4.62 (2H, m, allylic H), 4.27–4.18 (1H, m, H-1'), 4.217 (1H, dd, J=2.7 Hz, J=9.7 Hz, H-5), 3.45–3.25 (3H, m, CH₂N₃ and H-4), 3.233 (1H, dd, J=2.7 Hz, J=7.6 Hz, H-6), 2.99–2.82, 2.76–2.65 (2H, 2 sets of m, SCH₂), 2.65–2.4 (6H, m, CH₂N), 1.95–1.50 (9H, m, CH₂CH₂-4, OH and CH₂CH₂ pyrrolidine) and 1.388 ppm (3H, d, J=6.2 Hz, CH₃).

D. (4R,5S,6S)-4-(3"-Azidopropyl)-6-[(1'R)-1'-hydroxyethyl]-3-[2-(1-pyrrolidinyl)ethylthio]-7-oxo-1-azabicyclo[3.2.0]hept-2-ene-2-carboxylic acid

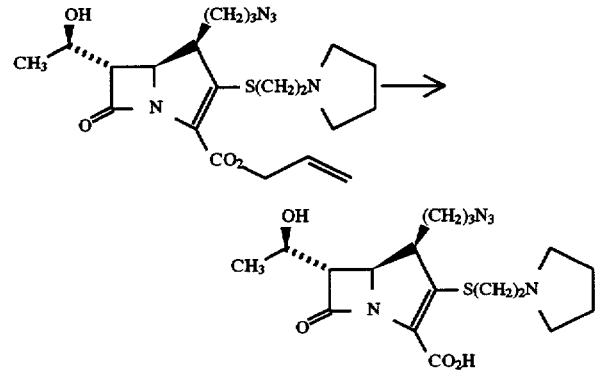

A cold (ice bath) solution of allyl (4R,5S,6S)-4-(3"-azidopropyl)-6-[(1'R)-1'-hydroxyethyl]-3-[2-(1-pyrrolidinyl)ethylthio]-7-oxo-1-azabicyclo[3.2.0]hept-2-ene-2-carboxylate (360 mg, 0.80 mmol) in dichloromethane (20 mL) was treated first with Pd(PPh₃)₄ followed by the dropwise addition of a N-methyl aniline (0.17 mL, 1.6 mmol). The mixture was stirred for 15 min, then a 0.1M pH 7.0 aqueous phosphate buffer (50 mL, 5 mmol) and diethyl ether (50 mL) were added in. The organic phase was extracted again with the 0.1M pH 7.0 buffer (2×15 mL) and water (15 mL). The aqueous extracts were combined, washed with diethyl ether (2×25 mL) and passed through a µBondapak C₁₈ reversed phase column (50 g, 0→30% CH₃CN/H₂O) to give title compound (200 mg, 58%) as a lyophilized powder.

Purity: 99.9% as determined by HPLC (r.t.=7.751, µBondapak C₁₈, 10µ, 15% CH₃CN/KH₂PO₄ 0.01M, pH 7.4);

UV (water) $\lambda_{max}$: 296 (7170);

IR (Nujol) $v_{max}$: 3500–3100 (OH), 2100 (N₃), 1755 (C=O β-lactam) and 1600 cm⁻¹ (C=O carboxylate);

¹H NMR (D₂O, 200 MHz) δ: 4.35–4.20 (1H, m, H-1'), 4.263 (1H, dd, J=2.7 Hz, J=9.4 Hz, H-5), 3.475 (1H, dd, J=2.7 Hz, J=6.1 Hz, H-6), 3.46–3.39 (2H, m, CH₂N), 3.10–2.9 (1H, m, 1H of SCH₂), 2.10–1.85 (5H, m, CH₂CH₂ pyrrolidine and 1H of CH₂-4), 1.80–1.45 (3H, m, CH₂CH₂-4) and 1.331 ppm (3H, d, J=6.4 Hz, CH₃).

E. (4R,5S,6S)-4-(3"-Aminopropyl)-6-[(1'R)-1'-hydroxyethyl]-3-[2-(1-pyrrolidinyl)ethylthio]-7-oxo-1-azabicyclo[3.2.0]hept-2-ene-2-carboxylic acid, acetic acid salt

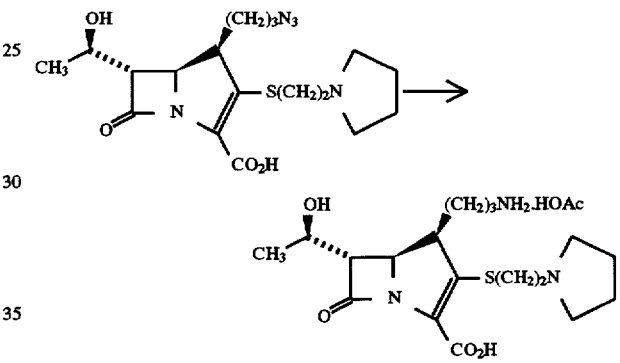

A cold (ice bath) solution of (4R,5S,6S)-4-(3"-azidopropyl)-6-[(1'R)-1'-hydroxyethyl]-3-[2-(1-pyrrolidinyl) ethylthio]-7-oxo-1-azabicyclo[3.2.0]hept-2-ene-2-carboxylic acid (150 mg, 0.34 mmol) in water (30 mL) was shaken in a Parr hydrogenator at 45–50 psi of hydrogen for 1 h using 5% Pd/Alumina (750 mg) as catalyst. The catalyst was removed, washed with water (2×5 mL), and the pH of the solution (9.5) was adjusted to 4.6 with a 1M aqueous acetic acid solution. The aqueous solution was passed twice through a µBondapak C₁₈ reversed phase column (45 g and 35 g, 0.005M aqueous acetic acid, 1%→2% CH₃CN/0.005M aqueous acetic acid) to give the title compound (138 mg, 67%) as a pale yellow lyophilized powder.

Purity: 99.5% as determined by HPLC (r.t.=7.338, µBondapak C₁₈, 10µ, 10% CH₃CN/KH₂PO₄, 0.01M, pH 7.4);

UV (H₂O) $\lambda_{max}$: 296 (8426);

IR (Nujol) $v_{max}$: 3500–3100 (OH, NH₂), 1755 (C=O β-lactam) and 1590 cm⁻¹ (C=O carboxylate);

¹H NMR (D₂O, 200 MHz) δ: 4.33–4.20 (2H, m, H-1'and H-5), 3.412 (1H, dd, J=2.6 Hz, J=6.4 Hz, H-6), 3.5–3.1 (1H, m, CH₂N, H-4, 1H of SCH₂), 3.09, 3.051, 3.016 (2H, 3 lines, CH₂N), 3.10–2.95 (1H, m, 1H of SCH₂), 2.09 (4H, bs, CH₂CH₂ pyrrolidine), 1.92 (2H, s, CH₃CO₂), 2.0–1.45 (4H, m, CH₂CH₂-4) and 1.331 ppm (3H, d, J=6.4 Hz, CH₃).

EXAMPLE 121

(4R,5S,6S)-4-(4"-Aminopentyl)-3-[(2-cyanoethyl)thio]-6-[(1'R)-1'-hydroxyethyl]-7-oxo-1-azabicyclo[3.2.0]hept-2-ene-2-carboxylic acid

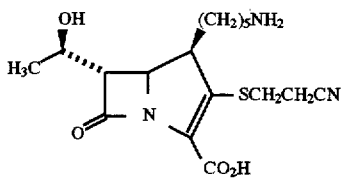

A. 7-Azidoheptanoic acid

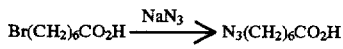

7-Bromoheptanoic acid (50.0 g, 0.24 mol) was added to a solution of sodium hydroxide (9.6 g, 0.24 mol) in 75 ml of water. Then sodium azide (20.9 g, 0.32 mol) was added and the resulting mixture was heated under reflux for 17 h. The solution was then cooled to 0°–5° C., acidified to pH 2.0 with 2N sulfuric acid and extracted with diethyl ether (3×200 mL). The combined organic extract was washed with brine, dried ($MgSO_4$) and evaporated under vacuum to give 40.9 g (100%) of the title acid as an oil. By $^1$H NMR the crude product contained 6% (mole) of the starting bromo acid and was used as such for the acid chloride formation.

IR (NaCl, film) $v_{max}$: 2100 ($N_3$) and 1710 cm$^{-1}$ (C=O of acid);

$^1$H NMR (200 MHz, CDCl$_3$) δ: 1.3–1.8 (m, 8H, CH$_2$-3, 4,5 and 6), 2.36 (t, J=7.35 Hz, 2H, CH$_2$-2) and 3.26 ppm (t, J=6.77 Hz, 2H, CH$_2$-7).

B. 7-Azidoheptanoyl chloride

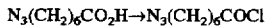

A solution of 7-azidoheptanoic acid from Step A (40.9 g, 0.24 mol) in dry dichloromethane (200 mL) was treated at 22° C. with oxalyl chloride (22.0 mL, 0.25 mol) dropwise over 10 min. After 1 h, two drops of N,N-dimethylformamide were added and the mixture was stirred for another hour. Evaporation of the solvent under reduced pressure gave the crude acid chloride as an oil which was used as such for the next step:

IR (NaCl, film) $v_{max}$: 2100 ($N_3$) and 1800 cm$^{-1}$ (C=O of acid chloride);

$^1$H NMR (200 MHz, CDCl$_3$) δ: 1.3–1.9 (m, 8H, CH$_2$-3, 4,5 and 6), 2.9 (t, J=7.18 Hz, 2H, CH$_2$-2) and 3.27 ppm (t, J=6.7 Hz, 2H, CH$_2$-7).

C. 2-Picolyl 7-azidothiolheptanoate

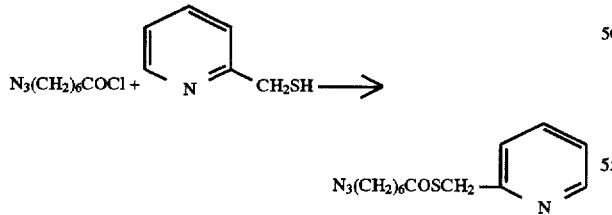

A solution of 2-picolyl mercaptan (30.0 g, 0.24 mol) in dry dichloromethane (400 mL) was treated at 0°–5° C. and under argon with pyridine (21.0 mL, 0.26 mol) followed by a solution of 7-azidheptanoyl chloride (45.5 g, 0.24 mol) in dichloromethane (100 mL) dropwise over 10 min. After 30 min, the reaction mixture was washed with cold saturated sodium bicarbonate, brine and dried (MgSO$_4$). Evaporation of the solvent under reduced pressure gave the crude thioester as a clear oil. Filtration on a silica gel pad (9×11 cm) using a mixture of toluene and ethyl acetate (8:2) as eluent gave 60.3 g (90%) of the title thioester as a clear oil:

IR (NaCl, film) $v_{max}$: 2100 ($N_3$) and 1690 cm$^{-1}$ (C=O of thioester);

$^1$H NMR (200 MHz, CDCl$_3$) δ: 1.2–1.8 (m, 8H, CH$_2$-3, 4,5 and 6), 2.59 (t, J=7.4 Hz, 2H, CH$_2$-2), 3.24 (t, J=6.79 Hz, 2H, CH$_2$-7), 4.25 (s, 2H, SCH$_2$), 7.15 (m, 1H, H-5 of pyridine), 7.33 (d, J=7.8 Hz, 1H, H-3 of pyridine), 7.62 (m, 1H, H-4 of pyridine) and 8.53 ppm (m, 1H, H-6 of pyridine).

D. O-tert-Butyldimethylsilylenol ether of 2-picolyl 7-azidothiolheptanoate

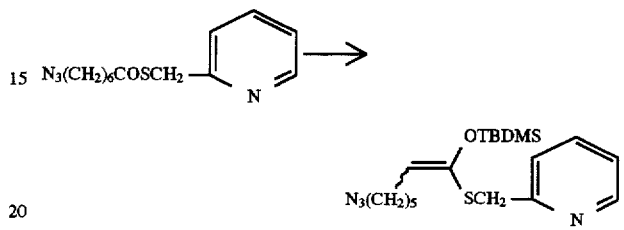

A solution of 2-picolyl 7-azidothiolheptanoate (60.0 g, 0.215 mol) in dry dichloromethane (250 mL) was cooled to −10° C. and treated with triethylamine (60.0 mL, 0.43 mmol). Then 74 mL (0.32 mmol) of tert-butyldimethylsilyl trifluoromethanesulfonate was added dropwise over 40 min. The temperature of the mixture was allowed to reach 20° C. and the solution was stirred for 3 h. The reaction mixture was then diluted with hexanes (600 mL) and washed with cold water (3×), saturated NaHCO$_3$, brine and dried (MgSO$_4$). Evaporation of the solvent gave the crude silyl enol ether as a dark oil which was used as such for the next step. By $^1$H NMR it was a 1:1 mixture of E and Z isomer:

IR (NaCl, film) $v_{max}$: 2100 cm$^{-1}$ ($N_3$);

$^1$H NMR (200 MHz, CDCl$_3$) δ: 0.2 and 0.23 (2×s, 6H, SiCH$_3$), 0.96 and 0.98 (2×s, 9H, Sit-Bu), 1.2–2.1 (m, CH$_2$-4,5 and 6), 3.2 (m, 4H, CH$_2$-3 and 7), 3.95 and 4.03 (2×s, 2H, SCH$_2$), 4.84 and 4.99 (2×t, J=7.22 Hz and J=7.6 Hz, 1H, CH-2), 7.14 (m, 1H, H-5 of pyridine), 7.28 (m, 1H, H-3 of pyridine), 7.61 (m, 1H, H-4 of pyridine) and 8.53 ppm (m, 1H, H-6 of pyridine).

E. (3S,4S)-3-[(1′R)-1′-tert-butyldimethylsilyloxyethyl]-4-[(1″R)-1″-(pyridin-2-yl)methylthiocarbonyl-6″-(pyridin-2-yl)methylthiocarbonyl-6″-azidohexyl]-azetidin-2-one

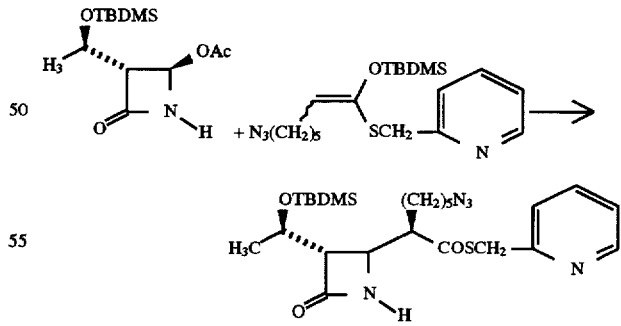

To a cold (0°–5° C.) suspension of freshly fused zinc chloride (38 g, 0.28 mol) in dry dichloromethane (600 mL) was added 60.0 g (0.208 mmol) of (3S,4R)-4-acetoxy-3-[(1′R)-1′-tertbutyldimethylsilyloxyethyl]azetidin-2-one followed by a solution of the crude 0-tert-butyldimethylsilylenol ether of 2-picolyl 7-azidothiolheptanoate (0.215 mol) in dichloromethane (125 mL). The reaction mixture was then stirred at 22° C. for 18 h. The mixture was then washed successively with water, saturated ammonium chloride, saturated sodium bicarbonate, brine and dried (MgSO₄). Evaporation of the solvent under vacuum gave 131 g of the crude thioester as a dark oil which was used as such for the next step. ¹H NMR and HPLC analysis of this mixture indicated a 85:15 mixture of epimers at position 1 of the hexyl (isomer ratio β:α 85:15). Chromatography of an aliquot (4 g) on silica gel (4×20 cm, elution toluene-ethyl acetate, 1:1) gave 1.0 g of the pure title material as an oil followed by mixed fractions (0.25 g) of β and α epimers. Pure β epimer had the following characteristics:

IR (NaCl, film) ν$_{max}$: 2100 (N₃), 1761 (C=O of β-lactam) and 1685 cm⁻¹ (C=O of thioester);

¹H NMR (200 MHz, CDCl₃) δ: 0.04 (s, 6H, SiCH₃), 0.85 (s, 9H, Si t-Bu), 0.99 (d, J=6.32 Hz, 3H, CH₃CHO), 1.2–1.9 (m, 8H, CH₂-2,3,4 and 5 of hexyl), 2.9 (m, 1H, H-1 of hexyl), 3.03 (m, 1H, H-3), 3.22 (t, J=6.73 Hz, 2H, CH₂N₃), 3.79 (dd, J$_{H4,H3}$=2.07 Hz, J$_{H4,H1}$=7.01 Hz, 1H, H-4), 4.14 (qd, J$_{H,CH3}$=6.32 Hz, J$_{H,H3}$=3.60 Hz, 1H, CH₃CHO), 5.86 (broad s, 1H, NH), 7.18 (m, 1H, H-5 of pyridine), 7.32 (d, J=7.8 Hz, 1H, H-3 of pyridine), 7.63 (m, 1H, H-4 of pyridine) and 8.54 ppm (m, 1H, H-6 of pyridine).

F. (3S,4S)-3-[(1'R)-1'-tert-Butyldimethylsilyloxyethyl]-4-[(1"R)-1"-carboxy-6"-azidohexyl]azetidin-2-one

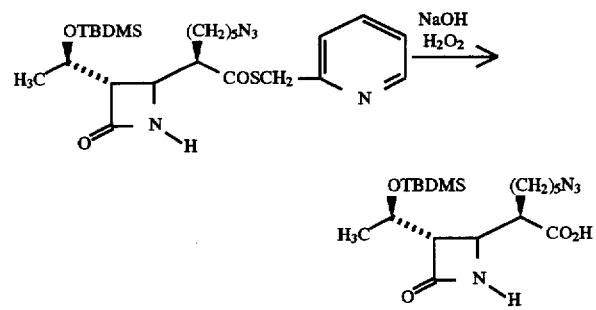

A solution of the crude thioester (~0.2 mmol) from Step E in tetrahydrofuran (700 mL) was cooled to 0°–5° C. and treated dropwise with 150 mL (1.74 mol) of 30% hydrogen peroxide (addition time 15 min). Then 700 mL of 1N sodium hydroxide (2.7 mol) was added dropwise over 1 h. The mixture was allowed to react at 18° C. and the solution was stirred for another hour. The mixture was then diluted with hexanes (700 mL) and the aqueous phase was collected, cooled to 0°–5° C. and acidified to pH 2.0 with concentrated hydrochloric acid. The aqueous solution was then extracted with ethyl acetate (500 mL and 200 mL). The combined organic phase was washed successively with water, 1M sodium bisulfite, brine and dried (MgSO₄). The solvent was then evaporated to a paste which was triturated with hexanes (200 mL). Filtration of the solid gave 16.1 g (19% yield from the acetoxy azetidinone) of the title acid as a white solid. ¹H NMR did not show any α isomer present. Recrystallization from a mixture of ethyl acetate and hexanes gave white plates: mp=145°–147° C. (dec); [α]²⁴$_D$ –7.1° (c 10, CHCl₃).

IR (KBr) ν$_{max}$: 2100 (N₃) and 1715 and 1690 (broad C=O);

¹H NMR (200 MHz, CDCl₃) δ: 0.06 and 0.07 (2×s, 2×3H, SiCH₃), 0.87 (s, 9H, Si t-Bu), 1.17 (d, J=6.31 Hz, 3H, CH₃CHO) 1.2–1.8 (m, 8H, CH₂-2,3,4 and 5 of hexyl), 2.65 (m, 1H, H-1 of hexyl), 3.13 (broad dd, 1H, H-3), 3.26 (t, J=6.7 Hz, 2H, CH₂N₃), 3.86 (dd, J$_{H4,H3}$=1.98 Hz, J$_{H4,H1}$=6.92 Hz, 1H, H-4), 4.20 (dq, J$_{H,CH3}$=6.31 Hz, J$_{H,H3}$=4.0 Hz, 1H, CH₃CHO), and 6.34 ppm (s, 1H, NH).

Anal. Calcd. for C₁₈H₃₄N₄O₄Si: C 54.24, H 8.60, N 14.06; Found: C 54.18, H 8.54, N 13.91.

G. (3S,4R)- 4-[(1"R)-1"-(5-Azidopentyl)-3"-allyloxycarbonyl-2"-oxopropyl]-3-[(1'R)-1'-tert-butyldimethylsilyloxyethyl]azetidin-2-one

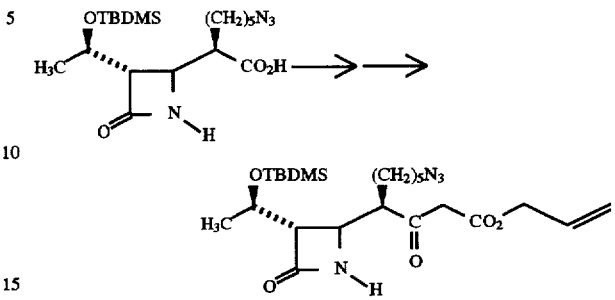

A suspension of (3S,4S)-3-[(1'R)-1'-tert-butyldimethylsilyloxyethyl]-4-[(1"R)-1"-carboxy-6"-azidohexyl]azetidin-2-one (15.0 g, 37.6 mmol) in dry acetonitrile (350 mL) was treated at 22° C. and under nitrogen with 1,1-carbonyldiimidazole (6.7 g, 41.3 mmol). The resulting mixture was stirred for 2 h and the solvent was evaporated under vacuum to give the crude imidazolide as an oil:

IR (NaCl, film) ν$_{max}$: 2100 (N₃), 1760 (C=O of β-lactam) and 1735 cm⁻¹ (C=O of imidazolide).

The crude imidazolide in dry acetonitrile (50 mL) was then added to a solution of magnesium monoallyl malonate (19.0 g, 61.2 mmol) in benzene (300 mL) and the resulting mixture was heated at 65° C. for 28 h. The cooled reaction mixture was diluted with ethyl acetate (500 mL), washed successively with water, cold 1N hydrochloric acid, saturated sodium bicarbonate and brine. After drying (MgSO₄), evaporation of the solvent gave the crude title material as an oil (~20 g) which was used as such for the next step. Chromatography of a small aliquot on silica gel (elution toluene-ethyl acetate 8:2) gave the title material as an oil:

IR (NaCl, film) ν$_{max}$: 2100 (N₃), 1760 (C=O of β-lactam), 1715, 1650 and 1630 cm⁻¹;

¹H NMR (200 MHz, CDCl₃) mixture of keto and enol form in a 1:1 ratio; δ: 0.05 and 0.07 (2s, 6H, SiCH₃), 0.87 (s, 9H, Si t-Bu), 1.1 and 1.17 (2d, J=6.31 Hz, and J=6.33 Hz, 3H, CH₃CHO), 1.2–1.8 (m, 8H, CH₂-1,2,3 and 4 of pentyl), 2.2 (m, H-1 of oxopropyl, enol form), 2.9–3.0 (m, H-3 and H-1 of oxopropyl keto form), 3.26 (t, J=6.7 Hz, CH₂N₃), 3.54 (s, CH₂-3 of oxopropyl, keto form), 3.8 (m, 1H, H-4), 4.2 (m, 1H, CH₃CHO), 4.8 (m, 2H, CH₂ of allyl), 5.07 (s, 1H, H-3 of oxopropyl, enol form), 5.2–5.4 and 5.9–6.1 (2m, 2H and 1H, CH of allyl) and 5.9 ppm (broad s, 1H, NH).

H. (3S,4R)-4-[(1"R)-1"-(5-Azidopentyl)-3"-allyloxycarbonyl-3"-diazo-2"-oxopropyl]-3-[(1'R)-1'-tert-butyldimethylsilyloxyethyl]azetidin-2-one

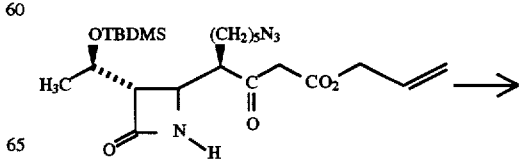

-continued

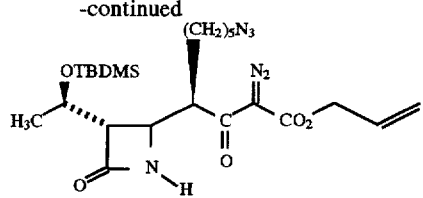

A solution of the crude (3S,4R)-4-[(1"R)-1"-(5-azidopentyl)-3"-allyloxycarbonyl-2"-oxopropyl]-3-[(1'R)-1'-tert-butyldimethylsilyloxyethyl]azetidin-2-one (37.6 mmol) in acetonitrile (100 mL) was treated at 0°–5° C. with a solution of p-toluenesulfonyl azide (9.1 g, 46.1 mmol) in acetonitrile (115 mL) followed by triethylamine (6.5 mL, 46.0 mmol). The reaction mixture was then stirred at 22° C. for 30 min. The solvent was then evaporated under vacuum and the residue was triturated with a mixture of diethyl ether and hexanes (1:1). The crystalline p-toluenesulfonamide was collected by filtration. The filtrate was concentrated under vacuum to give the title compound as an oil. This product was used as such for the next step. Chromatography of an aliquot on silica gel with a mixture of toluene and ethyl acetate (9:1) gave the pure title material as an oil:

IR (NaCl, film) $v_{max}$: 2140 ($N_2$), 2100 ($N_3$), 1760 (C=O of β-lactam), 1720 and 1650 $cm^{-1}$;

$^1$H NMR (200 MHz, CDCl$_3$) δ: 0.05 and 0.06 (2×s, 6H, SiCH$_3$), 0.86 (s, 9H, Si t-Bu), 1.17 (d, J=6.3 Hz, 3H, C$\underline{H}_3$CHO), 1.2–2.0 (m, 8H, CH$_2$-1,2,3 and 4 of pentyl), 3.03 (broad dd, 1H, H-3), 3.24 (t, J=6.7 Hz, 2H, CH$_2$N$_3$), 3.84 (dd, J$_{H4,H3}$=2.07 Hz, J$_{H4,H-1}$=5.37 Hz 1H, H-4) 4.1 (m, 1H, H-1 of oxopropyl), 4.17 (dq, J$_{H,CH3}$=6.3 Hz, J$_{H,H3}$=3.86 Hz, 1H, CH$_3$C$\underline{H}$O), 4.72 (m, 2H, CH$_2$ of allyl), 5.3–5.4 and 5.9–6.1 (2m, 2H and 1H, CH of allyl) and 5.84 ppm (broad s, 1H, NH).

I. (3S,4R)-4-[(1"R)-1"-(5-Azidopentyl)-3"-allyloxycarbonyl-3"-diazo-2"-oxopropyl]-3-[(1'R)-1'-hydroxyethyl]azetidin-2-one

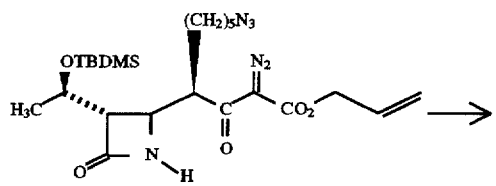

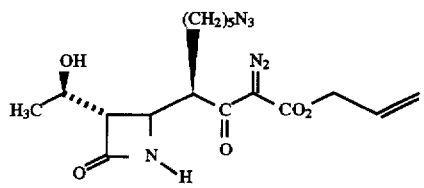

A solution of the crude (3S,4R)-4-[(1"R)-1"-(5-azidopentyl)-3"-allyloxycarbonyl-3"-diazo-2"-oxopropyl]-3-[(1'R)-1'-tert-butyldimethylsilyloxyethyl]azetidin-2-one (37.6 mmol) in ethanol (250 mL) was treated at 5° C. with 100 mL of 1N aqueous hydrochloric acid. After 65 h, the pH of the reaction mixture was adjusted to 6 with sodium bicarbonate and the ethanol was removed under reduced pressure. The residue was diluted with ethyl acetate (500 mL) and the organic phase was washed with water, 0.2M pH 7 phosphate buffer and brine. After drying (MgSO$_4$), the solvent was evaporated under vacuum and the residue was chromatographed on silica gel (9×12 cm, elution with a gradient of ethyl acetate in toluene (1:1) to pure ethyl acetate). Evaporation of the pertinent fractions gave 8.95 (61% for three steps from the carboxylic acid) of the title azetidinone as a solid. Recrystallization from a mixture of diethyl ether and hexanes gave white prisms: mp=65°–66° C.; [α]$^{22}_D$–31.2° (c 1.0, CHCl$_3$).

UV (EtOH) λ$_{max}$: 260 nm (8,440);

IR (KBr) $v_{max}$: 2158 (N$_2$), 2100 (N$_3$), 1730 and 1712 (C=O β-lactam and ester) and 1650 $cm^{-1}$;

$^1$H NMR (200 MHz, CDCl$_3$) δ: 1.29 (d, J=6.3 Hz, 3H, C$\underline{H}_3$CHO), 1.2–1.9 (m, 8H, CH$_2$-1,2,3 and 4 of pentyl), 2.31 (d, J=3.75 Hz, 1H, OH), 2.99 (dd, J$_{H3,H4}$=2.0 Hz, J$_{H3,H1}$=6.93 Hz, 1H, H-3), 3.25 (t, J=6.7 Hz, 2H, CH$_2$N$_3$), 3.82 (dd, J$_{H4,H3}$=2.0 Hz, J$_{H4,H1}$=6.63 Hz, 1H, H-4), 3.95 (m, 1H, H-1 of azidopentyl), 4.11 (m, 1H, CH$_3$C$\underline{H}$O), 4.73 (m, 2H, CH$_2$ of allyl), 5.3–5.4 and 5.9–6.1 (2×m, 2H and 1H, CH of allyl) and 6.0 ppm (broad s, 1H, NH).

Anal. Calcd. for C$_{17}$H$_{24}$H$_6$O$_5$: C 52.09, H 6.16, N 21.42; Found: C 51.85, H 6.04, N 21.33.

J. Allyl (2R,4R,5R,6S)-4-(4"-azidopentyl)-6-[(1'R)-1'-hydroxyethyl]-3,7-dioxo-1-azabicyclo[3.2.0]heptane-2-carboxylate

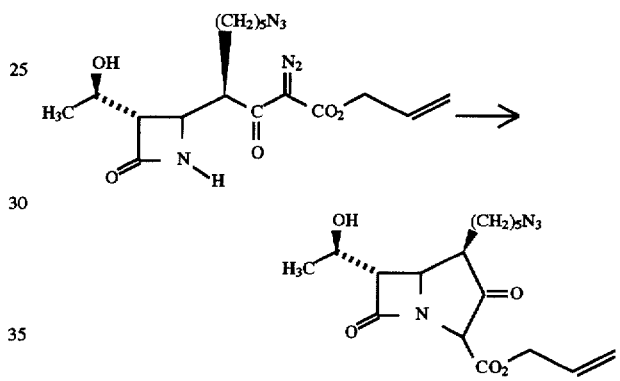

A solution of (3S,4R)-4-[(1"R)-1"-(5-azidopentyl)-3"-allyloxycarbonyl-3"-diazo-2"-oxopropyl]-3-[(1'R)-1'-hydroxyetheyl]azetidin-2-one (2.50 g, 6.37 mmol) in dry benzene (80 mL) was treated under argon with Rhodium (II) octanoate dimer (0.050 g) and heated under reflux (bath temperature 95° C.) for 20 min. The solvent was then evaporated under vacuum to give the crude title bicyclic compound as an oil which was used immediately for the next step:

IR (NaCl, film) $v_{max}$: 2100 (N$_3$), 1760 (C=O of ⊕-lactam) and 1745 $cm^{-1}$ (sh C=O of ketoester);

$^1$H NMR (200 MHz, CDCl$_3$) δ: 1.4 (d, J=6.30 Hz, 3H, C$\underline{H}_3$CHO), 1.4–2.0 (m, 8H, CH$_2$-1, 2, 3 and 4 of pentyl), 2.7 (m, 1H, H-4), 3.2–3.4 (m, 3H, H-6 and CH$_2$N$_3$), 4.26 (dd, J$_{H5,H6}$=2.32 Hz, J$_{H5,H4}$=8.06 Hz, 1H, H-5), 4.28 (m, 1H, CH$_3$C$\underline{H}$O), 4.64 (s, 1H, H-2), 4.66 (m, 2H, CH$_2$ of allyl), 5.2–5.4 and 5.8–6.0 ppm (2×m, 2H and 1H, CH of allyl).

K. Allyl (4R,5S,6S)-4-(4"-azidoethyl)-3-[(2-cyanoethyl)thio]-6-[(1'R)-1'-hydroxyethyl]-7-oxo-1-azabicyclo[3.2.0]hept-2-ene-2-carboxylate

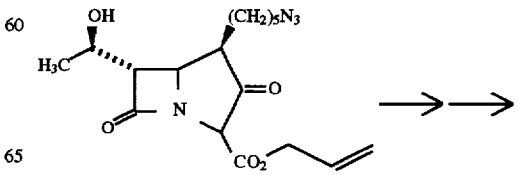

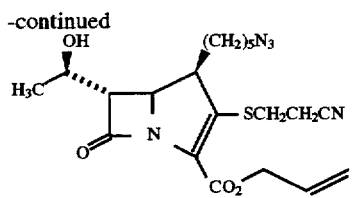

A solution of allyl (2R,4R,5R,6S)-4-(4"-azidopentyl)-6-[(1'R)-1'-hydroxyethyl]-3,7-dioxo-1-azabicyclo[3.2.0]heptane-2-carboxylate (6.37 mmol) in dry acetonitrile (40 mL) was treated at 0°–5° C. and under argon with diphenyl chlorophosphate (1.45 mL, 7.0 mmol) and N,N-diisopropylethylamine (1.22 mL, 7.0 mmol) added simultaneously over 10 min. Then a small crystal of 4-N,N-dimethylaminopyridine was added and the mixture was stirred for 45 min. Then N,N-diisopropylethylamine (2.22 mL, 12.7 mmol) followed by β-mercaptopropionitrile (1.11 g, 12.7 mmol) in acetonitrile (3 mL) were added and the mixture was stirred for 1 h. The reaction mixture was then diluted with ethyl acetate, washed with water, saturated sodium bicarbonate, brine and dried (MgSO$_4$). Evaporation of the solvent gave an oil which was chromatographed on silica gel (5×10 cm). Elution with gradient of ethyl acetate in toluene (8:2 to 7:3) gave 2.52 g (91%) of the title compound as a clear oil.

IR (NaCl, film) $v_{max}$: 2258 (CN), 2100 (N$_3$), 1770 (C=O of β-lactam) and 1710 cm$^{-1}$ (C=O of ester);

$^1$H NMR (200 MHz, CDCl$_3$) δ: 1.38 (d, J=6.28 Hz, 3H, CH$_3$CHO), 1.3–1.9 (m, 8H, CH$_2$-1,2,3 and 4 of pentyl), 1.8 (d, J=4.6 Hz, 1H, OH), 2.7 (~dt, 2H, CH$_2$CN), 2.9–3.2 (m, 2H, SCH$_2$), 3.19 (dd, J$_{H6,H5}$=2.65 Hz, J$_{H6,H1}$=7.34 Hz, 1H, H-6), 3.2 (overlapping with H-6, 1H, H-4), 3.30 (t, J=6.5 Hz, 1H, CH$_2$N$_3$), 4.24 (overlapping with H-5, 1H, CH$_3$CHO), 4.26 (dd, J$_{H5,H6}$=2.65 Hz, J$_{H5,H4}$=9.52 Hz, 1H, H-5), 4.76 (m, 2H, CH$_2$ of allyl), 5.2–5.5 and 5.9–6.1 ppm (2×m, 2H and 1H, CH of allyl).

L. (4R,5S,6S)-4-(5"-Aminopentyl)-3-[(2-cyanoethyl)thio]-6-[(1'R)-1'hydroxyethyl]-7-oxo-1-azabicyclo[3.2.0]hept-2-ene-2-carboxylic acid

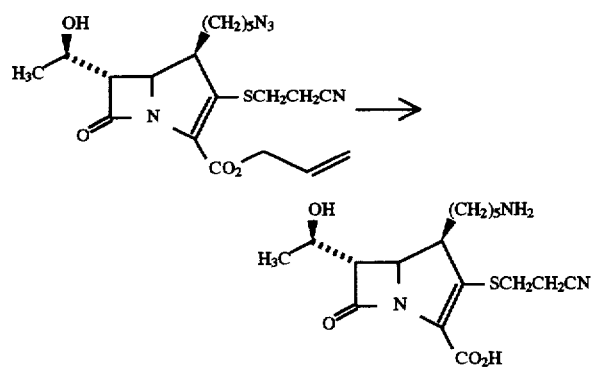

A solution of allyl (4R,5S,6S)-4-(5"-azidopentyl)-3-[(2-cyanoethyl)thio]-6-[(1'R)-1'-hydroxyethyl]-7-oxo-1-azabicyclo[3.2.0]hept-2-ene-2-carboxylate (2.52 g, 5.8 mmol) in dry acetonitrile (125 mL) was treated at 22° C. and under argon with tetrakis(triphenylphosphine)palladium [0] (0.13 g) followed by 12.8 mL (6.4 mmol) of a 0.5M solution of potassium 2-ethylhexanoate in ethyl acetate. After 45 min, the reaction mixture was extracted with water (125 mL) and the aqueous phase was maintained under vacuum to remove traces of organic solvent. The aqueous solution was then hydrogenated at 0°–5° C. over 4.0 g of 5% palladium over alumina under 45 psi of hydrogen for 1 h (initial pH 7, final pH 11). Then 50 mL of 0.2M pH 6.0 phosphate buffer was added and the catalyst was filtered. The filtrate was concentrated by half under vacuum (T <10° C.) and then chromatographed on reversed phase silica gel (μBondapak C$_{18}$, 3.5×14 cm) using a gradient of acetonitrile (0–5%) in water as eluent. Lyophilization of the UV active fractions gave 1.06 g (49%) of the title carbapenem as a white amorphous solid after freeze drying: [α]$^{22}_D$+52.1° (c 1.0, H$_2$O).

Purity by HPLC: 99% on μBondapak C$_{18}$, 3.9mm×30 cm, elution 5% CH$_3$CN—H$_2$O, pH 7.4 phosphate buffer, flow rate 1 mL/min, uv detector 306 nm, retention time.

UV (water, pH 7.4 phosphate buffer) λ$_{max}$: 302 nm (9,055);

IR (KBr) $v_{max}$: 2255 (CN), 1755 (C=O of β-lactam), and 590 cm$^{-1}$ (C=O of carboxylate);

$^1$H NMR (200 MHz, D$_2$O) δ: 1.33 (d, J=6.35 Hz, 3H, CH$_3$CHO), 1.3–1.9 (m, 8H, CH$_2$-1,2,3 and 4 of pentyl), 2.8–3.2 (m, 4H, SCH$_2$CH$_2$CN), 3.0 (t, J=7.4 Hz, 2H, CH$_2$NH$_2$), 3.36 (overlapping with H-6, 1H, H-4), 3.38 (dd, J$_{H6,H5}$=2.53 Hz, J$_{H6,H1}$=6.30 Hz, 1H, H-6), 4.25 (dd overlapping with CH$_3$CHO, J$_{H5,H6}$=2.53 Hz, 1H, H-5) and 4.27 ppm (m, 1H, CH$_3$CHO).

EXAMPLE 122

(4R,5S,6S)-6-[(1'R)-1'-Hydroxyethyl]-3-[(2-hydroxyethyl)thio]-4-(2"-aminoethyl)-7-oxo-1-azabicyclo[3.2.0]hept-2-ene-2-carboxylic acid

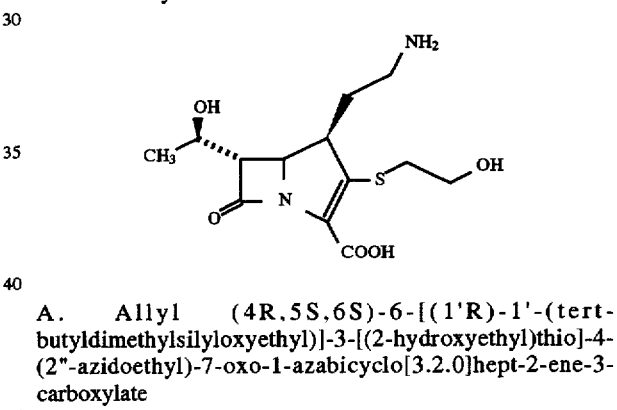

A. Allyl (4R,5S,6S)-6-[(1'R)-1'-(tert-butyldimethylsilyloxyethyl)]-3-[(2-hydroxyethyl)thio]-4-(2"-azidoethyl)-7-oxo-1-azabicyclo[3.2.0]hept-2-ene-3-carboxylate

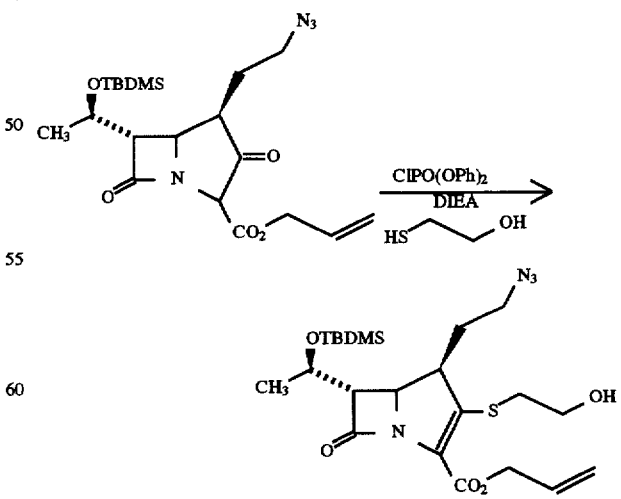

A cold (0° C.) solution of allyl (4R,5S,6S)-6-[(1'R)-1'-(tert-butyldimethylsilyloxyethyl)]-4-(2"-azidoethyl)-3,7- dioxo-1-azabicyclo[3.2.0]heptane-2-carboxylate (0.47 g, 1.08 mmol) in CH₃CN (10 mL) was treated with diphenyl chlorophosphate (0.25 mL, 1.18 mmol) followed by N,N-diisopropylethylamine (0.21 mL, 1.18 mmol) and 4-N,N-dimethylaminopyridine (2 mg). The mixture was stirred at 0° C. for 2 h, under Argon, after which Argon was bubbled through the solution for 15 min. The enol-phosphate was then treated with 2-mercaptoethanol (0.15 mL, 2.15 mmol) in CH₃CN (2 mL) followed by N,N-diisopropylethylamine (0.38 mL, 2.15 mmol) and stirred at 0° C. for 1 h and left in cold (5° C.) for 16 h. The reaction mixture was diluted with EtOAc (50 mL) and washed successively with cold water, 1M NaHSO₃, water, 1N HCl, water, 1M NaHCO₃ and brine. The organic phase was dried (MgSO₄) and solvent evaporated to a syrup which was chromatographed on silica (3.5×11 cm) packed in CH₂Cl₂ and eluted with a mixture of CH₂Cl₂ and EtOAc (8:2, gradient elution) to give the title compound as a syrup (0.35 g, 65.5%).

¹H NMR (200 MHz, CDCl₃ 7.24) δ: 0.06 (s, 6H, Si(CH₃)₂), 0.87 (S, 9H, SiC(CH₃)₃, 1.35 (d, 3H, CH₃, J=6.3 Hz,), 2.85–3.9 (overlap, 8H, CH₂OH, CH₂N₃, H-4, H-6, SCH₂), 4.22 (centre m, 2H, H-5, H-1'), 4.6–4.9 (m, 2H, OCH₂, allyl), 5.2–5.5 (m, 2H, =CH₂, allyl), 5.86–6.05 (m 1H, CH=allyl).

B. Allyl (4R,5S,6S)-6-[(1'R)-1'-hydroxyethyl]-3-[(2-hydroxyethyl)thio]-4-[2"-azidoethyl)-7-oxo-1-azabicyclo[3.2.0]hept-2-ene-2-carboxylate

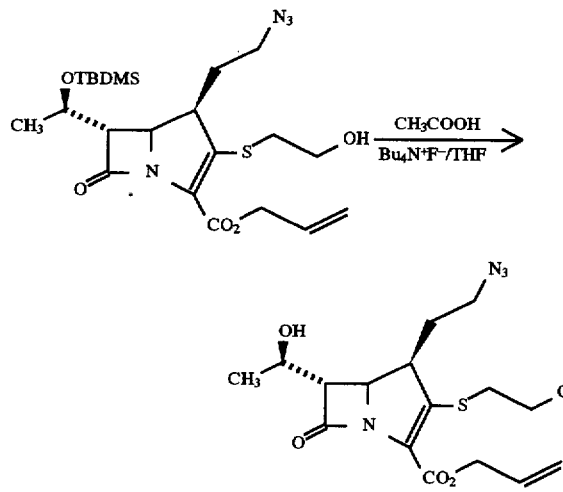

A cold (0° C.) solution of allyl (4R,5S,6S)-6-[(1'R)-1'-(tert-butyldimethylsilyloxyethyl)]-3-[(2-hydroxyethyl)thio]-4-(2"-azidoethyl)-7-oxo-1-azabicyclo[3.2.0]hept-2-ene-2-carboxylate (0.33 g, 0.66 mmol) in dry tetrahydrofuran (5 mL) was treated, under Argon, with acetic acid (0.23 mL, 4 mmol) followed by a 1M solution of tetrabutylammonium fluoride in tetrahydrofuran (1.99 mL, 1.99 mmol). The mixture was stirred between 0° and 5° C. for 168 h and then neutralized at 0° C. with a 1M NaHCO₃ solution (4 mL, 4 mmol). The mixture was extracted with EtOAc (3×50 mL) and the combined organic phase was washed successively with a cold NaHCO₃, water and brine, dried (MgSO₄) and solvent evaporated to give a sticky foam which was chromatographed on silica (3.5×8 cm) packed in CH₂Cl₂ and eluted with a mixture of CH₂Cl₂ and EtOAc (0:100, gradient elution) to give the title compound as a foam (0.09 g, 35.4%).

¹H NMR (200 MHz, CDCl₃) δ: 1.37 (d, 3H, CH₃, J=6.26 Hz), 2.82–3.17 (m, 2H, SCH₂), 3.15 (m, 1H, H-6), 3.34–3.64 (overlap, 3H, CH₂N₃, H-4), 3.82 (t, 2H, CH₂OH, J=5.43 Hz), 4.22 (m, 1H, H-1'), 4.22 (dd, 1H, H-5, J₄,₅=9.64 Hz, J₅,₆=2.78 Hz), 4.62–4.87 (m, 2H, OCH₂, allyl), 5.21–5.49 (m, 2H, =CH₂, allyl), 5.86–6.05 (m, 1H, CH=, allyl).

C. (4R,5S,6S)-6-[(1'R)-1'-Hydroxyethyl]-3-[(2-hydroxyethyl)thio]-4-[2"-aminoethyl)-7-oxo-1-azabicyclo[3.2.0]hept-2-ene-2-carboxylic acid

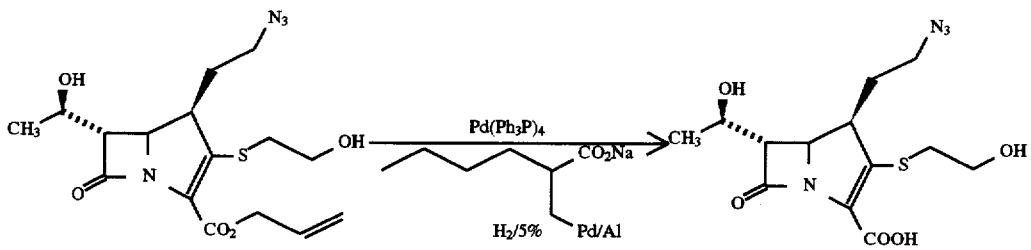

To a cold (0° C.) solution of allyl (4R,5R,6S)-6-[(1'R)-1'-hydroxyethyl]-3-[(2-hydroxyethyl)thio]-4-(2"-azidoethyl)-7-oxo-1-azabicyclo[3.2.0]hept-2-ene-2-carboxylate (0.09 g, 0.24 mmol) in CH₂Cl₂ (10 mL), under Argon, was added Pd[Ph₃P]₄ (0.04 g, 0.035 mmol) followed by a 0.5M solution of 2-ethylhexanoate in EtOAc (0.52 mL, 0.26 mmol). The mixture was stirred at 0° C. for 1 h, diethyl ether (50 mL) was added and extracted with water (3×25 mL). To the combined aqueous extract was added a 0.05M solution of pH 7.0 phosphate buffer (10 mL) and was hydrogenated at 0° C. over 5% palladium on alumina (0.3 g) at 40 psi for 2 h. The catalyst was filtered, washed with water and the combined filtrate was passed through a column of µBondapak C₁₈ reverse phase silica (3.5×9 cm). Appropriate fractions corresponding to the product were lyophilized to a solid which was rechromatographed on µBondapak C₁₈ reverse phase silica (3.5×9 cm). The compound was eluted with water and was obtained as a pale yellow fluffy solid after lyophilization (0.021 g, 28.2%).

Purity by HPLC: 93.9% with UV detection at 302 nm on µBondapak C₁₈ (4 mm×30 cm); pH 6.8 phosphate buffer; flow rate 1 mL/min; retention time: 3.89 min.

UV λ$_{max}$: 302 nm.

IR (Nujol): ν$_{max}$: 1750 cm⁻¹ (C=O, β-lactam);

¹H NMR (200 MHz, D₂O) δ: 1.33 (d, 3H, CH₃, J=6.37 Hz) 1.82–1.98; 2.1–2.27 (m, 2H, CH₂), 2.79–3.23 (overlap, 4H, CH₂NH₂, SCH₂), 3.44 (centre m, 2H, H-4, H-6), 3.76 (m, 2H CH₂OH, J=6.24 Hz) 4.26 (dd, 1H, H-5 J₄,₅=9.14 Hz J₅,₆=2.56 Hz), 4.28 (m, 1H, H-1').

EXAMPLE 123

(4R,5S,6S)-3-[(2-Cyanoethyl)thio]-6-[(1'R)-1'-hydroxyethyl]-4-[2"-(1-N-methylpyrrolidinium)ethyl]-7-oxo-1-azabicyclo[3.2.0]hept-2-ene-2-carboxylate

271

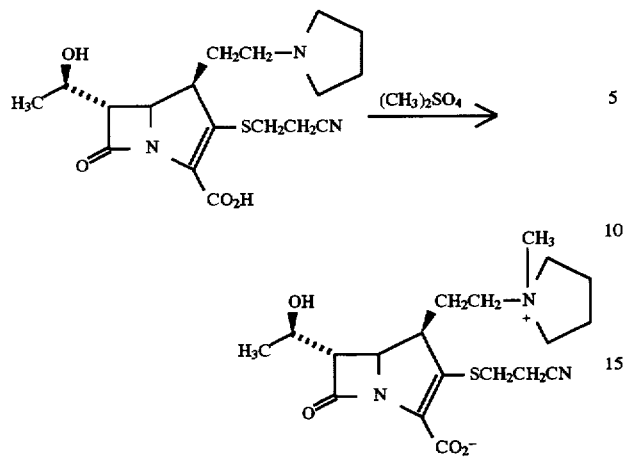

A solution of (4R,5S,6S)-3-[(2-cyanoethyl)thio]-6-[(1'R)-1'-hydroxyethyl]-4-[2"-(1-pyrrolidinyl)-ethyl]-7-oxo-1-azabicyclo[3.2.0]hept-2-ene-2-carboxylic acid (0.150 g, 0.39 mmol) [prepared in Example 63] in a mixture of water (8 mL), acetonitrile (4 mn) and dioxane (5 mL) at 0°–5° C. was adjusted to pH 9.5 with 1M sodium hydroxide. Then dimethyl sulfate (0.22 mL) was added all at once and the pH was maintained at 9–9.5 for 35 min. Then 20 mL of 0.2M pH 6.0 phosphate buffer was added and the solution was maintained under vacuum to remove the organic solvent. The aqueous solution was chromatographed twice on reversed phase silica gel (μBondapak $C_{18}$, 2.5×13 cm) using a gradient of acetonitrile (0–5%) in water as eluent. Lyophilization of the UV active fractions gave 0.056 g (36%) of the pyrrolidinium title compound as a white amorphous solid; $[\alpha]^{22}_D$+57.0° (c 1.0, $H_2O$);

Purity by HPLC: 99% on μBondapak $C_{18}$, 3.9 mm×30 cm, elution 5% $CH_3CN$—$H_2O$, pH 7.4 phosphate buffer, flow rate 1 mL/min, uv detector 300 nm, retention time 6.24 min.

UV (water, pH 7.4 phosphate buffer) $\lambda_{max}$: 298 nm (6.660);

IR (KBr) $v_{max}$: 2250 (CN), 1760 (C=O of β-lactam) and 1600 $cm^{-1}$ (C=O of carboxylate);

$^1$H NMR (200 MHz, $D_2O$) δ: 1.34 (d, J=6.35 Hz, 3H, $CH_3CHO$), 2.0–2.4 (m, 6H, $CH_2$-1 of ethyl and $CH_2$-3,3' of pyrrolidine), 2.8–3.2 (m, 4H, $SCH_2CH_2CN$), 3.11 (s, 3H, $NCH_3$), 3.4–3.7 (m, 8H, H-4, H-6, $CH_2$-2 of ethyl and $CH_2$-2,2' of pyrrolidine), 4.28 (m, 1H, $CH_3CHO$) and 4.31 ppm (dd, $J_{H5,H6}$=3.01 Hz, $J_{H5,H4}$=9.0 Hz, 1H, H-5).

EXAMPLE 124

(4R,5S,6S)-3-[(2-Cyanoethyl)thio]-4-[2"-[N,N-(2-cyanoethyl)methylamino]ethyl]-6-[(1'R)-1'-hydroxyethyl]-7-oxo-1-azabicyclo[3.2.0]hept-2-ene-2-carboxylic acid

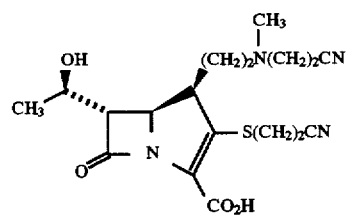

A. Allyl (4R,5S,6S)-6-[(1'R)-1'-tert-butyldimethylsilyloxyethyl]-3-[(2-cyanoethyl)thio]-4-[2"-

272

[N,N-(2-cyanoethyl)methylamino]ethyl]-7-oxo-1-azabicyclo[3.2.0]hept-2-ene-2-carboxylate

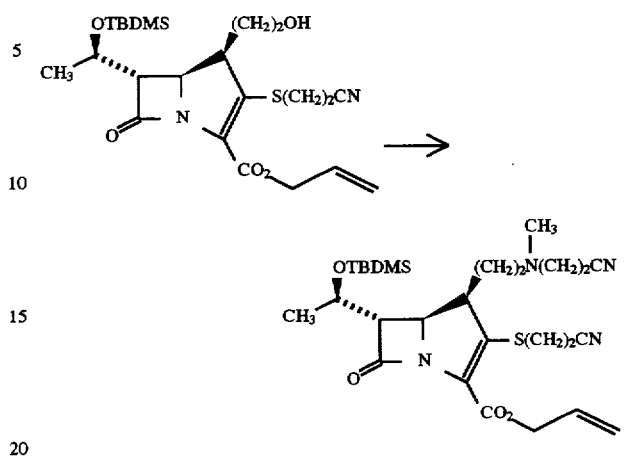

A cold (dry ice-acetone) solution of allyl (4R,5S,6S)-6-[(1'R)-1'-tert-butyldimethylsilyloxyethyl]-3-[(2-cyanoethyl)thio]-4-(2"-hydroxyethyl)-7-oxo-1-azabicyclo[3.2.0]hept-2-ene2-carboxylate (400 mg, 0.830 mmol) in dichloromethane (10 mL) was treated first with diisopropylethylamine (0.380 mL, 2.16 mmol) and then dropwise with trifluoromethanesulfonic anhydride (0.17 mL, 1.0 mmol). The mixture was stirred for 25 min, treated with N-methyl-β-alaninenitrile (0.23 mL, 2.5 mmol) in dichloromethane (0.5 mL) and then stirred for 3 h at −15° C. (dry ice bath replaced by ice-methanol bath). The mixture was allowed to stand in the cold room (5° C.) for 18 h, then diluted with ethyl acetate (20 mL), washed with ice cold 1M aqueous $NaHCO_3$ (5 mL), ice cold water (5 mL), brine (5 mL) and dried ($MgSO_4$). The residue was passed through a silica gel flash pad (15 g, 30→80% ethyl acetate/hexane) to give title compound (315 mg, 69%) as a pale yellow oil.

IR ($CH_2CL_2$) $v_{max}$: 2250 (CN), 1775 (C=O β-lactam) and 1715 $cm^{-1}$ (C=O);

$^1$H NMR ($CDCl_3$, 200 MHz) δ: 6.03–5.86 (1H, m, vinylic H), 5.486–5.224 (2H, m, vinylic H), 4.851–4.666 (2H, m, allylic $CH_2$), 4.29–4.18 (1H, m, H-1'), 4.197, 4.184 (d, J=2.6 Hz, part of H-5), 3.541–3.450 (1H, m, H-4), 3.380–3.242, 3.069–2.929 (2H, 2 sets of m, $SCH_2$), 3.110 (1H, dd, J=2.4 Hz, J=7.0 Hz, H-6), 2.807–2.315 (5H, m, $CH_2N$ and $CH_2CN$), 2.315 (3H, s, $NCH_3$), 2.04–1.87, 1.70–1.55 (2H, 2 sets of m, $CH_2$-4), 1.30 (3H, d, J=6.1 Hz, $CH_3$), 0.895 (9H, s, tert-butyl) and 0.096 ppm (6H, s, dimethyl).

B. Allyl (4R,5R,6S)-3-[(2-cyanoethyl)thio]-4-[2"-[N,N-(2-cyanoethyl)methylamino]ethyl]-6-[(1'R)-1'-hydroxyethyl]-7-oxo-1-azabicyclo[3.2.0]hept-2-ene-2-carboxylate

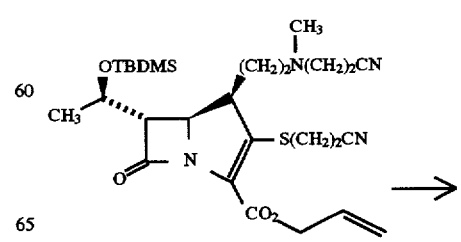

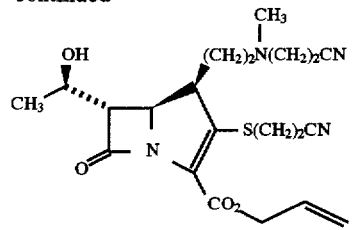

A cold (ice-methanol bath) solution of allyl (4R,5S,6S)-6-[(1'R)-1'-tert-butyldimethylsilyloxyethyl]-3-[(2-cyanoethyl) thio]-4-[2"-[N,N-(2-cyanoethyl)methylamino] ethyl]-7-oxo-1-azabicyclo[3.2.0]hept-2-ene-2-carboxylate (305 mg, 0.560 mmol) in tetrahydrofuran (5 mL) was treated with glacial acetic acid (0.18 mL, 3.4 mmol) and dropwise with a 1M solution of tetrabutylammonium fluoride in tetrahydrofuran (1.68 mL, 1.68 mmol). The mixture was allowed to stand in the cold room for 8 days, then diluted with ethyl acetate (25 mL), washed with ice cold 1M aqueous $NaHCO_3$ (3×5 mL), water (2×5 mL), brine (5 mL) and dried ($MgSO_4$). The residue was passed through a silica gel flash pad (6 g, 40%→100% ethyl acetate/hexane, 1/1 ethyl acetate/acetone) to give title compound (195 mg, 80%) as an oil.

IR ($CH_2Cl_2$) $v_{max}$: 3600, 3500 (OH), 2250 (CN), 1775 (C=Oβ-lactam) and 1710 cm$^{-1}$ (C=O);

$^1$H NMR ($CDCl_3$, 200 MHz) δ: 6.04–5.85 (1H, m, vinylic H), 5.494–5.238 (2H, m, vinylic H), 4.9–4.70 (2H, m, allylic H), 4.282 (1H, dd, J=2.6 Hz, J=9.6 Hz, H-5), 4.29–4.13 (1H, m, H-1'), 3.80–3.70 (1H, m, H-4), 3.35–3.20, 3.05–2.90 (2H, 2 sets of m, $SCH_2$), 3.152 (1H, dd, J=2.6 Hz, J=8.8 Hz, H-6), 2.8–2.6 (4H, m, $CH_2CN$), 2.6–2.45 (2H, m, $CH_2N$), 2.1–1.9, 1.7–1.5 (2H, 2 sets of m, $CH_2$-4), 1.60 (1H, bs, OH) and 1.404 ppm (3H, d, J=6.2 Hz, $CH_3$).

C. (4R,5S,6S)-3-[(2-Cyanoethyl)thio]-4-[2"-[N,N-(2-cyanoethyl)methylamino]ethyl]-6-[(1'R)-1'-hydroxyethyl]-7-oxo-1-azabicyclo[3.2.0]hept-2-ene-2-carboxylic acid

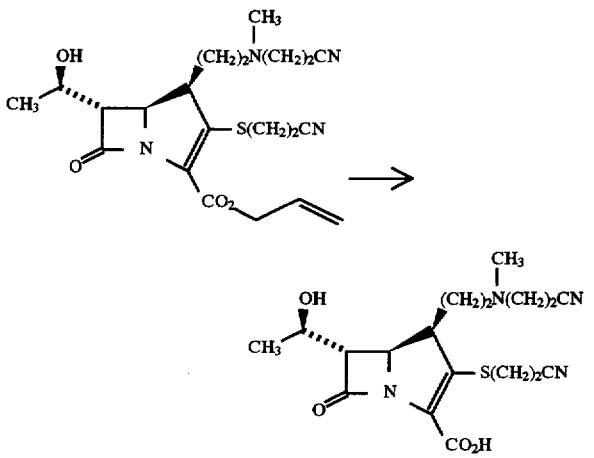

A cold (ice bath) solution of allyl (4R,5S,6S)-3-[(2-cyanoethyl)thio]-4-[2"-[N,N-(2-cyanoethyl) methylamino]ethyl]-6-[(1'R)-1'-hydroxyethyl]-7-oxo-1-azabicyclo[3.2.0]hept-2-ene-2-carboxylate (195 mg, 0.45 mmol) in dichloromethane (12 mL) was treated with $Pd(Ph_3)_4$ (42 mg, 0.034 mmole) and dropwise with a 0.5M solution of potassium 2-ethylhexanoate in ethyl acetate 0.90 mL, 0.45 mmol). The mixture was stirred for 30 min, the diluted with diethyl ether and extracted with a 0.04M aqueous phosphate buffer (3×15 mL) and water (2×15 mL). The aqueous extracts were combined, washed with diethyl ether (2×10 mL) and passed through a μBondapak $C_{18}$ reversed phase column (150 g, 0→3% $CH_3CN/H_2O$) to give title compound (127 mg, 72%) as a lyophilized powder.

Purity: 99.2% as determined by HPLC (r.t.=7.89 min, μBondapak $C_{18}$, 10 μ, 5% $CH_3CN/KH_2PO_4$ 0.01M, pH 7.4);
UV ($H_2O$) $λ_{max}$: 300 (7887);

IR (Nujol) $v_{max}$: 3600–3100 (OH), 2250 (CN), 1745 (C=O β-lactam) and 1595 cm$^{-1}$ (C=O);

$^1$H NMR ($D_2O$, 200 MHz) δ: 4.35–3.25 (2H, m, H-1'and H-5), 3.404 (1H, dd, J=2.6 Hz, J=6.3 Hz, H-6), 3.42–3.30 (1H, m, H-4), 3.25–3.1, 3.03–2.9 (2H, 2 sets of m, $SCH_2$), 2.87–2.81 (4H, m, $CH_2N$), 2.75–2.65, 2.62–2.54 (4H, 2 sets of 3 lines, $CH_2CN$), 2.328 (3H, s, N—$CH_3$), 2.15–1.95, 1.8–1.6 (2H, 2 sets of m, $CH_2$-4) and 1.341 ppm (3H, d, J=6.3 Hz, $CH_3$).

EXAMPLE 125

(4R,5S,6S)-4-[2"-(1-N-Azetidino)ethyl]-3-[(2-cyanoethyl)thio]-6-[(1'R)-1'-hydroxyethyl]-7-oxo-1-azabicyclo[3.2.0]hept-2-ene-2-carboxylic acid

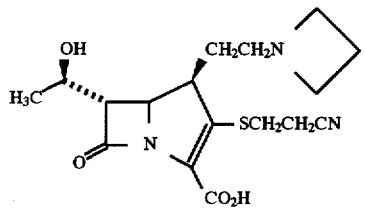

A. Allyl (4R,5S,6S)-6-[(1'R)-1'-tert-butyldimethylsilyloxyethyl]-4-(2"-tert-butyldimethylsilyloxyethyl)-3-[(2-cyanoethyl)thio]-7-oxo-1-azabicyclo[3.2.0]hept-2-ene-2-carboxylate

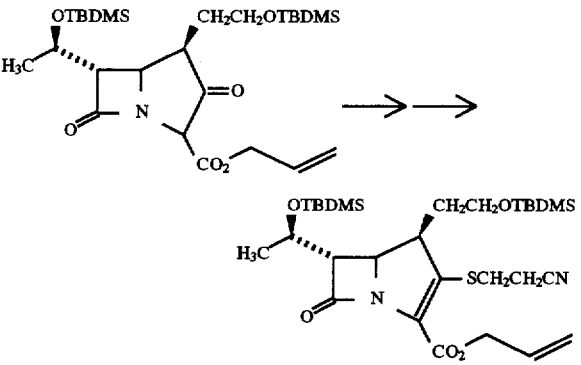

A solution of allyl (2R,4R,5R,6S)-6-[(1'R)-1'-tert-butyldimethylsilyloxyethyl]-4-(2"-tert-butyldimethylsilyloxyethyl)-3,7-dioxo-1-azabicyclo[3.2.0] heptane-2-carboxylate (27.2 mmol, prepared by cyclization of 15.08 g, 27.2 mmol of the diazo precursor) in dry acetonitrile (200 mL) was treated at 0°–5° C. and under nitrogen with diphenyl chlorophosphate (6.3 mL, 30.4 mmol) and N,N-diisopropylethylamine (5.0 mL, 28.7 mmol) added simultaneously over 5 min. A small crystal of 4-N, N-dimethylaminopyridine was then added and the mixture was stirred for 1 h. More N,N-diisopropylethylamine (9.5 mL, 54.5 mmol) followed by β-mercaptopropionitrile (4.6 g, 53.8 mmol) in acetonitrile (10 mL) were added dropwise and the resulting mixture was stirred for 30 min.

The reaction mixture was then diluted with ethyl acetate (1 L), washed with cold water, saturated sodium bicarbonate, 0.2M pH 7.0 phosphate buffer, brine and dried (MgSO$_4$). The solvent was evaporated under reduced pressure and the residue was chromatographed over silica gel (7.5×11 cm) using a gradient of ethyl acetate (0–5%) in toluene as eluent. Evaporation of the UV active fractions gave 11.19 g (69%) of the title material as an oil which solidified upon standing. Recrystallization from hexanes gave the title compound as long needles: mp=95° C.; [α]$^{22}_D$+48.9° (c 1.0, CHCl$_3$).

UV (EtOH) λ$_{max}$: 318 nm (11,930);

IR (KBr) ν$_{max}$: 1770 (C=O of β-lactam) and 1700 cm$^{-1}$ (C=O of ester);

$^1$H NMR (200 MHz, CDCl$_3$) δ: 0.08 and 0.09 (2s, 3H and 9H, SiCH$_3$), 0.89 and 0.91 (2s, 2×9H, Si-tBu), 1.27 (d, J=6.15 Hz, 3H, CH$_3$CHO), 1.6–2.1 (m, 2H, CH$_2$-4), 2.67 (~t, 2H, CH$_2$CN), 2.9–3.1 and 3.2–3.4 (2m, 2H, SCH$_2$), 3.10 (dd, J$_{H6,H5}$=2.52 Hz, J$_{H6,H1}$=6.26 Hz, 1H, H-6), 3.45–3.65 and 3.75–3.9 (2m, 2H and 1H, H-4 and CH$_2$OSi), 4.21 (dd overlapping with CH$_3$CHO, J$_{H5,H6}$=2.52 Hz, 1H, H-5), 4.24 (m, 1H, CH$_3$CHO), 4.74 (m, 2H, CH$_2$ of allyl), 5.2–5.5 and 5.9–6.1 ppm (2m, 2H and 1H, CH of allyl).

Anal. Calcd. for C$_{29}$H$_{50}$N$_2$O$_5$SSi$_2$: C 58.55, H 8.47, N 4.71, S 5.39; Found: C 58.45, H 8.37, N 4.73, S 5.24.

B. Allyl (4R,5R,6S)-6-[(1'R)-1'-tert-butyldimethylsilyloxyethyl]-3-[(2-cyanoethyl)thio]-4-(2"-hydroxyethyl)-7-oxo-1-azabicyclo[3.2.0]hept-2-ene-2-carboxylate

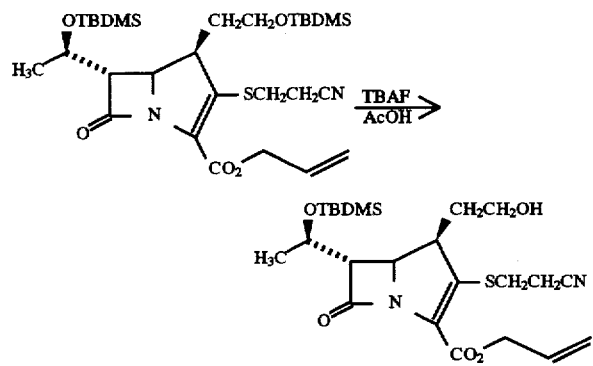

A solution of allyl (4R,5S,6S)-6-[(1'R)-1'-tert-butyldimethylsilyloxyethyl]-4-(2"-tert-butyldimethylsilyloxyethyl)-3-[(2-cyanoethyl)thio]-7-oxo-1-azabicyclo[3.2.0]hept-2-ene-2-carboxylate (11.19 g, 18.8 mmol) in tetrahydrofuran (250 mL) was treated at 0°–5° C. and under nitrogen with acetic acid (6.5 mL, 0.113 mol) followed by 56 mL (56.0 mmol) of a 1.0M solution of tetrabutylammonium fluoride in tetrahydrofuran. The solution was then stored at 10° C. for 18 h. The reaction mixture was then diluted with ethyl acetate (1 L), washed with cold saturated sodium bicarbonate, brine and dried (MgSO$_4$). Evaporation of the solvent under reduced pressure gave an oil which was chromatographed on silica gel (7.5×12 cm). Elution with a gradient of ethyl acetate in toluene (3:7 to 1:1) gave 6.80 g (75%) of the title compound as a thick glass:

IR (NaCl, film) ν$_{max}$: 3500 (OH), 2260 (CN), 1775 (C=O of β-lactam) and 1710 cm$^{-1}$ (C=O of ester);

$^1$H NMR (200 MHz, CDCl$_3$) δ: 0.09 (s, 6H, SiCH$_3$), 0.89 (s, 9H, Si-tBu), 1.29 (d, J=6.13 Hz, 3H, CH$_3$CHO), 1.6–2.1 (m, 2H, CH$_2$-4), 2.70 (~t, 2H, CH$_2$CN), 2.95–3.1 and 3.2–3.4 (2m, 2H, SCH$_2$), 3.18 (dd, J$_{H6,H5}$=2.63 Hz, J$_{H6,H1}$=7.02 Hz, 1H, H-6), 3.54 (broad t, 1H, H-4), 3.6–4.0 (m, 2H, CH$_2$OH), 4.15–4.3 (m, 2H, H-5 and CH$_3$CHO overlapping), 4.75 (m, 2H, CH$_2$ of allyl), 5.2–5.5 and 5.9–6.1 ppm (2m, 2H and 1H, CH of allyl).

C. Allyl (4R,5S,6S)-4-(2"-(1-N-azetidino)ethyl]-6-[(1'R)-1'-tert-butyldimethylsilyloxyethyl]-3-[(2-cyanoethyl)thio]-7-oxo-1-azabicyclo[3.2.0]hept-2-ene-2-carboxylate

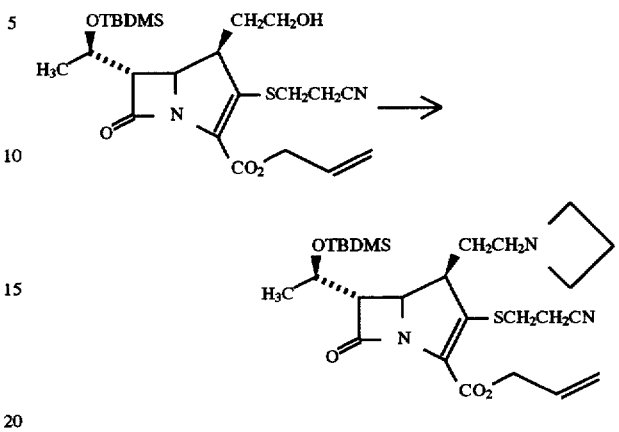

A solution of allyl (4R,5R,6S)-6-[(1'R)-1'-tert-butyldimethylsilyloxyethyl]-3-[(2-cyanoethyl)thio]-4-(2"-hydroxyethyl)-7-oxo-1-azabicyclo[3.2.0]hept-2-ene-2-carboxylate (1.07 g, 2.22 mmol) in dry dichloromethane (18 mL) was cooled to –78° C. and treated under nitrogen with N,N-diisopropylethylamine (0.57 mL, 3.27 mmol) followed by trifluoromethanesulfonic anhydride (0.39 mL, 2.31 mmol) dropwise over 5 min. After 30 min at –78° C., more N,N-diisopropylethylamine (0.57 mL, 3.27 mmol) was added followed by azetidine (0.18 mL, 2.67 mmol) dropwise over 5 min. The reaction mixture was stirred at –78° C. for 30 min, slowly warmed up to –20° C. over 30 min and stirred at this temperature for 1 h. The reaction mixture was then quenched by addition to a cold mixture of ethyl acetate (200 mL) and water (20 mL). The organic phase was washed with brine (2×20 mL), dried (MgSO$_4$) and evaporated under reduced pressure. The residue was chromatographed on silica gel (3.5×12 cm) using acetone as eluent. Evaporation of the UV active fractions gave 0.639 g (55%) of the title compound as an oil. By TLC and $^1$H NMR this material contained 25% of a product resulting from the opening of the β-lactam by the azetidine.

IR (NaCl, film) ν$_{max}$: 2255 (CN), 1775 (C=O of β-lactam), 1712 (C=O of ester), and 1645 (amide of the open product);

$^1$H NMR (200 MHz, CDCl$_3$) δ: 0.08 (s, 6H, SiCH$_3$), 0.88 (s, 9H, Si-tBu), 1.29 (d, J=6.13 Hz, 3H, CH$_3$CHO), 1.4–1.8 (m, 2H, CH$_2$-4), 2.07 (m, 2H, CH$_2$-3 of azetidine), 2.69 (~t, 2H, CH$_2$CN), 2.9–3.5 (broad m, 10H, CH$_2$-2 and 4 of azetidine, CH$_2$-2 of ethyl, H-4 and H-6 and SCH$_2$), 4.15 (dd, J$_{H5,H6}$=2.55 Hz, J$_{H5,H6}$=9.45 Hz 1H, H-5) 4 17 (m, 1H, CH$_3$CHO), 4.73 (m, 2H, CH$_2$ of allyl), 5.2–5.5 and 5.9–6.1 ppm (2m, 2H and 1H, CH of allyl).

D. Allyl (4R,5S,6S)-4-[2"-(1-N-azetidino)ethyl]-3-[(2-cyanoethyl)thio]-6-[(1'R)-1'-hydroxyethyl]-7-oxo-1-azabicyclo[3.2.0]hept-2-ene-2-carboxylate

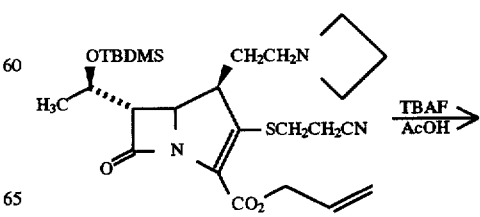

-continued

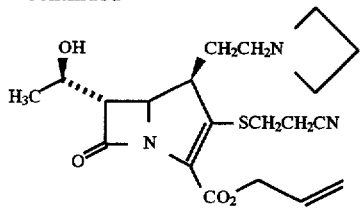

A solution of allyl (4R,5S,6S)-4-[2"-(1-N-azetidino)ethyl]-6-[(1'R)-1'-tert-butyldimethylsilyloxyethyl]-3-[(2-cyanoethyl)thio]-7-oxo-1-azabicyclo[3.2.0]hept-2-ene-2-carboxylate (0.639 g, 1.23 mmol) in dry tetrahydrofuran (8 mL) was cooled to −15° C. and treated under nitrogen with acetic acid (0.42 mL, 3.7 mmol) followed by 3.7 mL (3.7 mmol) of a 1M solution of tetrabutylammonium fluoride in tetrahydrofuran. The solution was then stirred at 0° C. for 140 h. Then 1.2 g of solid powdered sodium bicarbonate was added and the mixture was stirred for 10 min. The organic phase was then chromatographed on silica gel (3.5×3.5 cm) using a mixture of acetone and N,N-dimethylformamide (9:1) as eluent. Evaporation of the pertinent fractions gave 0.39 g (78%) of the title material as an oil. By $^1$H NMR this material was about 50% pure and contained some N,N-dimethylformamide and some tetrabutylammonium salt. This product was used as such for the next step.

IR (NaCl, film) $v_{max}$: 2250 (CN), 1775 (C=O of β-lactam) and 1710 cm$^{-1}$ (C=O of ester);

$^1$H NMR (200 MHz, CDCl$_3$) δ: 1.39 (d, J=6.31 Hz, 3H, CH$_3$CHO), 1.7 (m, 2H, CH$_2$-4), 2.27 (m, 2H, CH$_2$-3 of azetidine), 2.67 (~t, 2H, CH$_2$CN), 2.9–3.2 (m, 2H, SCH$_2$), 3.2–3.4 (m, 4H, H-4, H-6 and CH$_2$-2 of ethyl), 3.58 (t, J=7.6 Hz, CH$_2$-2 and 4 of azetidine), 4.10 (dq, J$_{H5,H6}$=6.31 Hz, J$_{H,H6}$=8.86 Hz, 1H, CH$_3$CHO), 4.28 (dd, J$_{H5,H6}$=3.12 Hz, J$_{H5,H4}$=10.26 Hz, 1H, H-5), 4.75 (m, 2H, CH$_2$ of allyl), 5.2–5.5 and 5.9–6.1 ppm (2m, 2H and 1H, CH of allyl).

E. (4R,5S,6S)-3-[2"-(1-N-Azetidino)ethyl]-3-[(2-cyanoethyl)thio]-6-[(1'R)-1'-hydroxyethyl]-7-oxo-1-azabicyclo[3.2.0]hept-2-ene-2-carboxylic acid

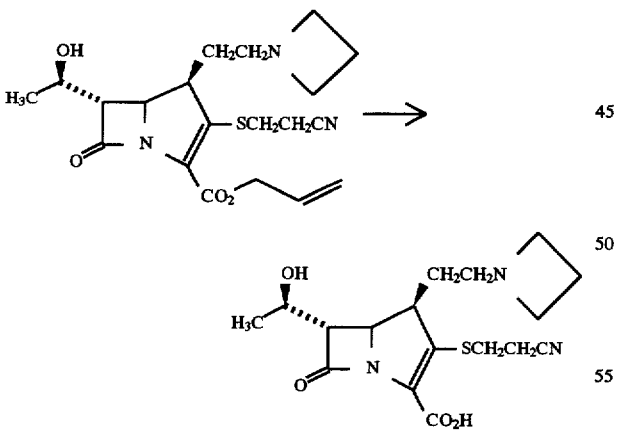

A solution of crude allyl (4R,5S,6S)-4-[2"-(1-N-azetidino)ethyl]-3-[(2-cyanoethyl)thio]-6-[(1'R)-1'-hydroxyethyl]-7-oxo-1-azabicyclo[3.2.0]hept-2-ene-2-carboxylate (0.39 g, 0.96 mmol) in ethyl acetate (15 mL) was treated at 22° C. and under nitrogen with tetrakis(triphenylphosphine)palladium [0] (0.050 g) and 3 mL (1.5 mmol) of a 0.5M solution of potassium 2-ethylhexanoate in ethyl acetate. After 30 min, the reaction mixture was extracted with water (30 mL and 20 mL) and the combined extract was maintained under vacuum to remove traces of organic solvent. Then 8 mL of 0.2M pH6 phosphate buffer were added and the solution was chromatographed on reversed phase silica gel (μBondapak C$_{18}$, 3×13 cm) using a gradient of acetonitrile (0–5%) in water as eluent. The UV active fractions were combined lyophilized and chromatographed a second time on the same column. Final lyophilization gave 0.065 g (19%) of the title carbapenem as a white amorphous powder:

Purity by HPLC: 99.4% on μBondapak C$_{18}$, 3.9 mm×30 cm, elution 5% CH$_3$CN—H$_2$O pH 7.4 phosphate buffer, flow rate 1 mL/min, uv detector 300 nm, retention time 6.41 min.;

UV (H$_2$O, pH 7.4 phosphate buffer) $\lambda_{max}$: 298 nm (8,422);
IR (KBr) $v_{max}$: 2250 (CN), 1760 (C=O of β-lactam) and 1600 cm$^{-1}$ (C=O of carboxylate);

$^1$H NMR (200 MHz, D$_2$O) δ: 1.33 (d, J=6.38 Hz, 3H, CH$_3$CHO), 1.7–2.2 (m, 2H, CH$_2$-4), 2.52 (m, 2H, CH$_2$-3 of azetidine), 2.85 (m, 2H, CH$_2$CN), 2.85–3.2 (m, 2H, SCH$_2$), 3.2–3.5 (m, 3H, CH$_2$-2 of ethyl and H-4), 3.41 (dd overlapping with CH$_2$-2 of ethyl, J$_{H6,H5}$=2.70 Hz, J$_{H6,H1}$=6.86 Hz, 1H, H-6), 4.17 (m, 4H, CH$_2$-2 and 4 of azetidine), and 4.2–4.35 ppm (m, 2H, H-5 and CH$_3$CHO).

EXAMPLE 126

(4R, 5S,6S)-3-[(2-Cyanoethyl)thio]-6-[(1'R)-1'-hydroxyethyl]-4-[2"(4-methylpiperazine-1-yl) ethyl]-7-oxo-1-azabicyclo[3.2.0]hept-2-ene-2-carboxylic acid

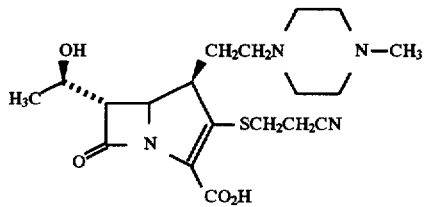

A. Allyl (4R,5S,6S)-6-[(1'R)-1'-tert-butyldimethylsilyloxyethyl]-3-[(2-cyanoethyl)thio]-4-[2"-(4-methylpiperazine-1-yl)ethyl]-7-oxo-1-azabicylo[3.2.0]hept-2-ene-2-carboxylate

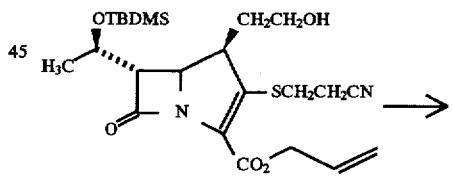

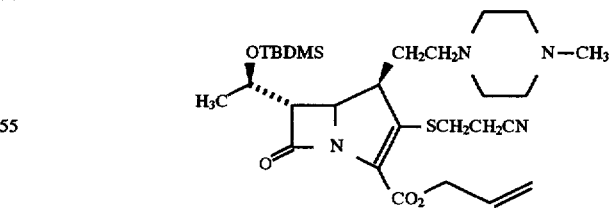

A solution of allyl (4R,5S,6S)-6-[(1'R)-1'-tert-butyldimethylsilyloxyethyl]-3-[(2-cyanoethyl)thio]-4-[2"-(4-methylpiperazine-1-yl)ethyl]-7-oxo-1-azabicyclo[3.2.0.] hept-2-ene-2-carboxylate (1.0 g, 2.08 mmol) in dry dichloromethane (20 mL) was cooled to −78° C. and treated under nitrogen with N,N-diisopropylethylamine (0.54 mL, 3.1 mmol) followed by trifluoromethanesulfonic anhydride (0.40 mL, 2.38 mmol) dropwise over 5 min. After 20 min at −78° C., 1-methylpiperazine (1.0 mL, 9.01 mmol) was added dropwise and the resulting solution was slowly warmed to −20° C. and stirred at that temperature for 1.5 h. The reaction was then quenched by addition of cold ethyl acetate (200 mL) and water. The organic phase was washed with water, brine and dried (MgSO$_4$). Evaporation of the solvent under reduced pressure gave 1.4 g of a clear oil which was used as such for the next step. By $^1$H NMR this product was contaminated by some 1-methylpiperazine.

IR (NaCl, film) $v_{max}$: 2260 (CN), 1775 (C=O of β-lactam) and 1710 cm$^{-1}$ (C=O of ester);

$^1$H NMR (200 MHz, CDCl$_3$) δ: 0.08 (s, 6H, SiCH$_3$), 0.88 (2, 9H, Si-tBut), 1.28 (d, J=6.05 Hz, 3H, CH$_3$CHO), 1.5–2.0 (m, 2H, CH$_2$-4), 2.3 (s, 3H, NCH$_3$), 2.3–2.6 (m, 10H, CH$_2$-2 of ethyl and CH$_2$ of piperazine), 2.6–2.8 (m, 2H, CH$_2$CN), 2.9–3.1 and 3.2–3.4 (m, 2H, SCH$_2$), 3.19 (dd, J$_{H6,H5}$=2.37 Hz, J$_{H6,H1}$=6.6 Hz, 1H, H-6), 3.3 (m, 1H, H-4), 4.19 (dd overlapping with CH$_3$CHO, J$_{H5,H6}$=2.37 Hz, 1H, H-5), 4.22 (m, 1H, CH$_3$CHO), 4.73 (m, 2H, CH$_2$ of allyl), 5.2–5.5 and 5.9–6.1 ppm (2×m, 2H and 1H, CH of allyl).

B. Allyl (4R,5S,6S)-3-[(2-cyanoethyl)thio]-6-[(1'R)-1'-hydroxyethyl]-4-[2"-(4-methylpiperazine-1-yl)ethyl]-7-oxo-1-azabicyclo[3.2.0]hept-2-ene-2-carboxylate

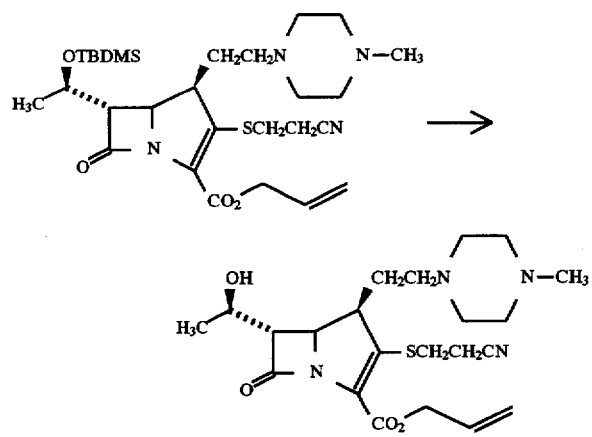

A solution of allyl (4R,5S,6S)-6-[(1'R)-1'-tert-butyldimethylsilyloxyethyl]-3-[(2-cyanoethyl)thio]-4-[2"-(4-methylpiperazine-1-yl)ethyl]-7-oxo-1-azabicyclo[3.2.0]hept-2-ene-2-carboxylate (1.17 g, 2.08 mmol) in dry tetrahydrofuran (50 mL) was cooled to −20° C., and treated dropwise under nitrogen with acetic acid (1.55 mL, 27.1mmol) followed by 14.6 mL (14.6 mmol) of a 1M solution of tetrabutylammonium fluoride in tetrahydrofuran. The solution was then stored at 10° C. for 7 days. The reaction mixture was then diluted with ethyl acetate (300 mL), washed with cold saturated sodium bicarbonate, brine and dried (MgSO$_4$). Evaporation of the solvent under reduced pressure gave 1.45 g of the crude carbapenem. Chromatography on silica gel (3.5×6 cm) using a mixture of acetone and N,N-dimethylformamide (9:1) gave 0.57 g (61%, for two steps) of the title carbapenem as an oil. By $^1$H NMR, this material contained one equivalent of N,N-dimethylformamide.

IR (NaCl, film) $v_{max}$: 2250 (CN), 1770 (C=O of β-lactam) and 1710 cm$^{-1}$ (C=O of ester);

$^1$H NMR (200 MHz, CDCl$_3$) δ: 1.38 (d, J=6.24 Hz, 3H, CH$_3$CHO), 1.6–2.0 (m, 2H, CH$_2$-4), 2.29 (s, 3H, NCH$_3$), 2.3–2.8 (m, 12H, CH$_2$ of piperazine, CH$_2$-2 of ethyl and CH$_2$CN), 2.9–3.1 and 3.2–3.4 (m, 2H, SCH$_2$), 3.24 (dd overlapping with SCH$_2$, J$_{H6,H5}$=2.7 Hz, J$_{H6,H1}$=6.9 Hz, 1H, H-6), 3.42 (m, 1H, H-4), 4.23 (m, 1H, CH$_3$CHO), 4.28 (dd, J$_{H5,H6}$=2.7 Hz, J$_{H5,H4}$=9.5 Hz, 1H, H-5) 4.76 (m 2H CH$_2$ of allyl), 5.2–5.5 and 5.9–6.1 ppm (2×m, 2H and 1H, CH of allyl).

C. (4R,5S,6S)-3-[(2-Cyanoethyl)thio]-6-[(1'R)-1'-hydroxyethyl]-4-[2"-(4-methylpiperazine-1-yl)ethyl]-7-oxo-1-azabicyclo[3.2.0]hept-2-ene-2-carboxylic acid

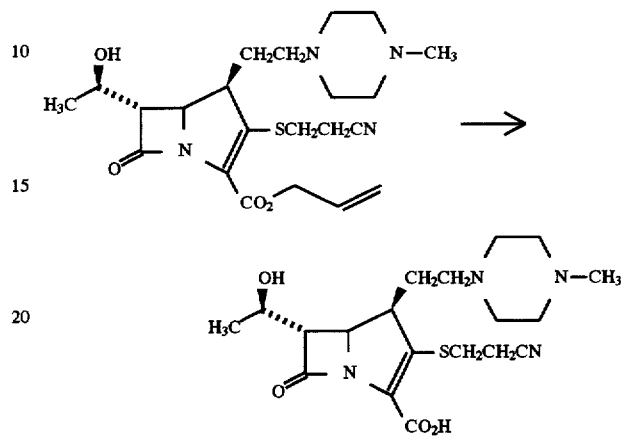

A solution of allyl (4R,5S,6S)-3-[(2-cyanoethyl)thio]-6-[(1'R)-1'-hydroxyethyl]-4-[2"-(4-methylpiperazine-1-yl)ethyl]-7-oxo-1-azabicyclo[3.2.0]hept-2-ene-2-carboxylate (0.57 g, 1.27 mmol) in dry ethyl acetate (25 mL) was treated at 22° C. and under nitrogen with tetrakis (triphenylphosphine) palladium [0] (0.075 g) followed by 2.8 mL (1.4 mmol) of a 0.5M solution of potassium 2-ethylhexanoate in ethyl acetate. After 45 min, the reaction mixture was extracted successively with 50 mL of a 0.1M pH 6.0 phosphate buffer and 25 mL of water. The combined aqueous phase was maintained under vacuum to remove traces of organic solvent and then chromatographed twice on reversed phase silica gel (μ-Bondapak C$_{18}$, 2.5×14 cm). Elution with a gradient of acetonitrile (0–5%) in water gave 0.28 g (54%) of the title carbapenem as a white amorphous powder after freeze drying: [α]$^{22}_D$+35.3° (c 1.0, H$_2$O).

Purity by HPLC: 97% on μ-Bondapak C$_{18}$, 3.9 mm×30 cm, elution 10% CH$_3$CN—H$_2$O Ph 7.4 phosphate buffer flow rate 1 mL/min, uv detector 302 nm, retention time 6.6 min;

UV (H$_2$O, pH 7.4 phosphate buffer) $\lambda_{max}$: 300 nm (8,390);

IR (KBr) $v_{max}$: 2250 (CN), 1755 (C=O of β-lactam) and 1595 cm$^{-1}$ (C=O of carboxylate);

$^1$H NMR (200 MHz, D$_2$O) δ: 1.33 (d, J=6.39 Hz, 3H, CH$_3$CHO), 1.6–2.2 (m, 2H, CH$_2$-4), 2.75 (s, 3H, NCH$_3$), 2.6–3.3 (m, 12H, CH$_2$ of piperazine, SCH$_2$ and CH$_2$-2 of 4-ethyl), 3.3–3.5 (m, 2H, H-4 and H-6 overlapping) and 4.2–4.4 ppm (m, 2H, H-5 and CH$_3$CHO).

EXAMPLE 127

(4R,5S,6S)-4-(3"-Guanidinopropyl)-6-[(1'R)-1'-hydroxyethyl]3-[(2-(1-pyrrolidinyl)ethyl]thio)-7-oxo-1-azabicyclo[3.2.0]hept-2-ene-2-carboxylic acid, acetic acid salt

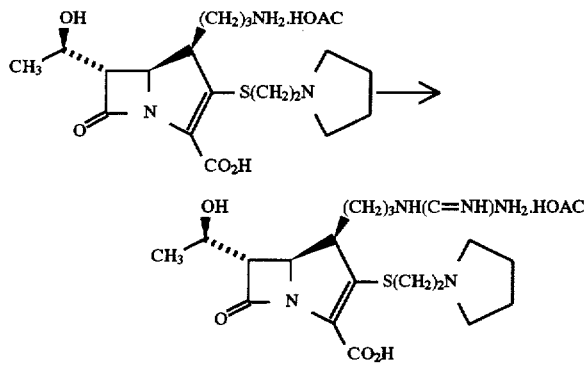

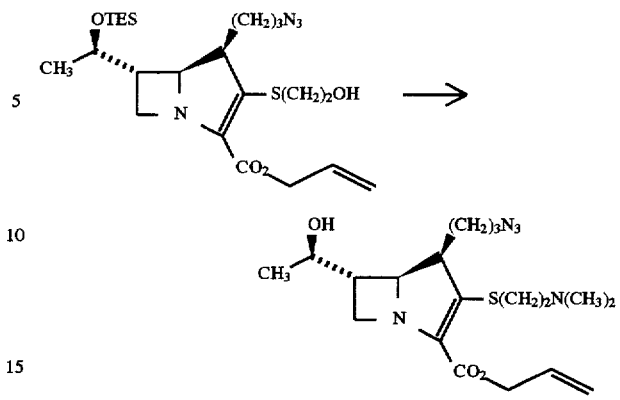

A cold (ice bath) solution of (4R,5S,6S)-4-(3"-aminopropyl)-6-[(1'R)-1'-hydroxyethyl]-3-([2-(1-pyrrolidinyl)ethyl]thio)-7-oxo-1-azabicyclo[3.2.0]hept-2-ene-2-carboxylic acid (from hydrogenolysis of the corresponding azido derivative 115 mg, 0.270 mmol) in a 0.05M aqueous phosphate buffer (15 mL) was treated with 0.1N aqueous NaOH to raise and maintain the pH at 8.0–8.2 during the portionwise addition of aminoiminomethanesulfonic acid (170 mg, 1.30 mmol). The mixture was stirred for 3 h (pH maintained between 8–8.2), then was neutralized with 0.1 Maqueous $NaH_2PO_4$. It was passed through a µBondapak $C_{18}$ reversed phase column (20 g, 0.005M aqueous acetic acid, 1→2% $CH_3CN$/ 0.005M aqueous acetic acid) to give the title compound (75 mg, 57%) as a white lyophilized powder.

Purity: 98.07% as determined by HPLC (r.t.=8.86 min, µBondapak $C_{18}$, 10M, 20% $CH_3CN/KH_2PO_4$ 0.01M, pH 7.4);

UV (water) $\lambda_{max}$: 296 (6723);

IR (Nujol) $v_{max}$: 3400–3100 (OH, $NH_2$), 1760 (C=O of β-lactam), 1670, 1635 (C=N), and 1485 $cm^{-1}$ (C=O of carboxylate);

$^1$H NMR ($D_2O$, 200 MHz), δ: 4.35–4.23 (1H, m, H-1'), 4.264 (1H, dd, J=3.1 Hz, J=9.8 Hz, H-5), 3.399, 3.384 (d, J=3.1 Hz, part of H-6), 3.40–3.138 (11H, m, H-4 (C$\underline{H}_2$—NH, S—C$\underline{H}_2$C$\underline{H}_2$N, C$\underline{H}_2$—N—C$\underline{H}_2$ and part of H-6), 2.12–2.05 (4H, ($CH_2)_2$ pyrrolidine), 1.919 (1.5H, s, $CH_3CO_2$), 1.95–1.4 (2 sets of m, $CH_2CH_2$ at position 4) and 1.320 ppm (3H, d, J=6.4 Hz, $CH_3$).

EXAMPLE 128

(4R,5S,6S)-4-(3"-Aminopropyl)-3-[(2-N,N-dimethylaminoethyl)thio]-6-[(1'R)-1'-hydroxyethyl]-7-oxo-1-azabicyclo[3.2.0]hept-2-ene-2-carboxylic acid, acetic acid salt

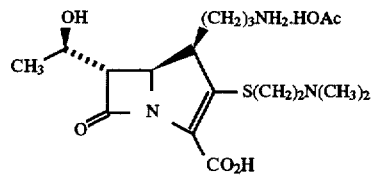

A. Allyl (4R,5S,6S)-4-(3"-azidopropyl)-3-[(2-N,N-dimethyl aminoethyl)thio]-6-[(1'R)-1'-hydroxyethyl]-7-oxo-1-azabicyclo[3.2.0]hept-2-ene-2-carboxylate To a cold (dry ice-acetone bath) solution of allyl (4R,5S,6S)-4-(3"-azidopropyl)-3-[(2-N,N-dimethyl aminoethyl)thio]-6-[(1'R)-1'-triethylsilyloxyethyl]-7-oxo-1-azabicyclo[3.2.0]hept-2-ene-2-carboxylate (3.29 g, 6.45 mmol) in $CH_2Cl_2$ (60 mL) was added N,N-diisopropylethylamine (2.90 mL, 16.8 mmol) followed by the dropwise addition of trifluoromethanesulfonic anhydride (1.29 mL, 7.7 mmol). After a 20 min stirring period, a stream of gaseous dimethyl amine was passed through the reaction mixture for 1.5 min. The mixture was stirred for 15 min at −78° C. and for 30 min at −15° C. (ice-methanol), then diluted with ice cold ethyl acetate (250 mL) and diethyl ether (50 mL), washed with ice cold water (10×50 mL), brine (50 mL) and dried ($MgSO_4$). The residue upon solvent evaporation was dissolved in anhydrous tetrahydrofuran (30 mL), cooled to −15° C. (ice-methanol), then treated with glacial acetic acid (2.1 mL, 38.7 mmol) and a 1M tetrahydrofuran solution of tetrabutylammonium fluoride (19.4 mL, 19.4 mmol) and allowed to stand at −20° C. for 18 h. The mixture was diluted with ice cold ethyl acetate (150 mL), washed with cold 1M aqueous $NaHCO_3$ (3×75 mL), brine (75 mL) and dried ($MgSO_4$). The residue was passed through a silica gel flash column (75 g, 50– 100% ethyl acetate/hexane, 10%→100% acetone/ethyl acetate, 15% methanol/acetone) to give the title compound (605 mg, 22%) as a yellow oil.

IR ($CH_2Cl_2$) $v_{max}$: 3600, 330 (OH), 2100($N_3$), 1775 and 1610 $cm^{-1}$ (C=O);

$^1$H NMR ($CDCl_3$, 200 MHz) δ: 6.1–5.9 (1H, m, vinylic H), 5.5–5.2 (2H, m, vinylic H), 4.88–4.62 (2H, m, allylic $CH_2$), 4.247 (1H, dd, J=2.7 Hz, J=9.5 Hz), 4.3–4.2 (1H, m, H-1'), 3.43–3.2 (3H, m, H-1', $CH_2N_3$), 3.244 (1H, dd, J=2.7 Hz, J=7.4 Hz, H-6), 3.1–2.8 (2H, m, $SCH_3$), 2.65–2.56 (2H, m, $CH_2N$), 2.335 (6H, s, $N(CH_3)_2$), 2.0–1.56 (5H, m, $CH_2$—$CH_2$-4, OH) and 1.391 ppm (3H, d, J=6.3 Hz, $CH_3$).

B. (4R,5S,6S)-4-(3"-Azidopropyl)-3-[(2-N,N-dimethyl aminoethyl)thio]-6-[(1'R)-1'-hydroxyethyl]-7-oxo-1-azabicyclo[3.2.0]hept-2-ene-2-carboxylic acid

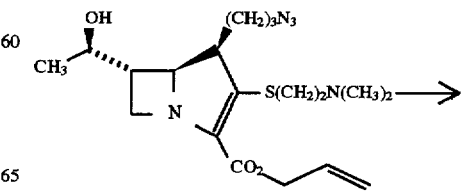

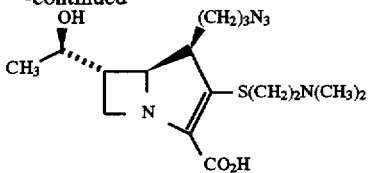

A cold (ice bath) solution of allyl (4R,5S,6S)-4-(3"-azidopropyl)-3-[(2-N,N-dimethylaminoethyl)thio]-6-[(1'R)-1'-hydroxyethyl]-7-oxo-1-azabicyclo[3.2.0]hept-2-ene-2-carboxylate (588 mg, 1.39 mmol) in $CH_2Cl_2$ (35 mL) was treated first with $Pd(PPh_3)_4$ (123 mg, 0.1 mmol) followed by a dropwise addition of N-methyl aniline (0.3 mL, 2.78 mmol). The mixture was stirred for 25 min. Then a 0.1M aqueous pH 7.0 phosphate buffer solution (80 mL) and diethyl ether (150 mL) were added. The phases were separated and the organic phase was extracted with a 0.01M aqueous phosphate pH 7.0 buffer solution (2×30 mL). The aqueous phases were combined, washed with diethyl ether (2×50 mL) and passed through a μBondapak $C_{18}$ reversed phase column (75 g, water, 2%→30% $CH_3CN/H_2O$) to give the title compound (399 mg, 75%) as a pale yellow lyophilized powder.

IR (Nujol) $v_{max}$: 3500–3100 (OH), 2100 ($N_3$), 1750 and 1590 $cm^{-1}$ (C=O);

$^1$H NMR ($D_2O$, 200 MHz) δ: 4.264 (1H, dd, J=2.7 Hz, J=9.3 Hz, H-5), 4.34–4.2 (1H, m, H-1'), 3.475 (1H, dd, J=2.7 Hz, J=6.0 Hz, H-6), 3.5–3.2 (3H, m, $CH_2N_3$ and H-1'), 3.2–2.95 (4H, m, $SCH_2$ and $CH_2N$), 2.0–1.8, 1.8–1.47 (4H, 2 sets of m, H—CH-4 and $HCHCH_2$-4) and 1.33 ppm (3H, d, J=6.3 Hz, $CH_3$).

C. (4R,5S,6S)-4-(3"-Aminopropyl)-3-[(2-N,N-dimethyl aminoethyl)thio]-6-[(1'R)-1'-hydroxyethyl]-7-oxo-1-azabicyclo[3.2.0]hept-2-ene-2-carboxylic acid, acetic acid salt

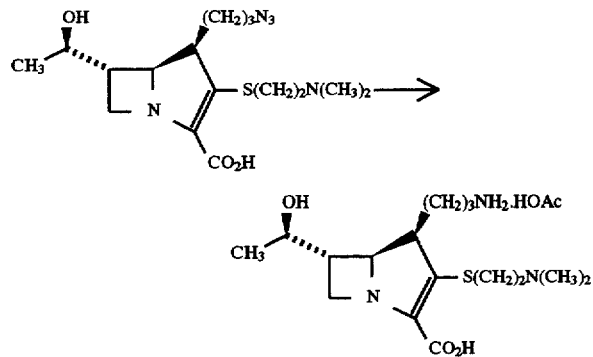

A cold (ice bath) solution of (4R,5S,6S)-4-(2"-azidopropyl)-3-[(2-N,N-dimethyl aminoethyl)thio]-6-[(1'R)-1'-hydroxyethyl]- 7-oxo-1-azabicyclo[3.2.0]hept-2-ene-2-carboxylic acid (250 mg, 0.65 mmol) in water (50 mL) was shaken on a Parr hydrogenator at 45–50 psi of hydrogen, for 1 h using 5% Pd/Alumina as catalyst. More catalyst (600 mg) was then added and the hydrogenation period was pursued for one more hour. The catalyst was removed by filtration and washed with water (3×5 mL). The pH of the aqueous mixture was adjusted to 4.5 with a 1M aqueous acetic acid solution after which it was passed through a μBondapak $C_{18}$ reversed phase column (75 g, 0.005M ice cold aqueous acetic acid, 1% $CH_3CN$/0.005M aqeuous acetic acid) to give the title compound (215 mg, 79%) as a pale yellow lyophilized solid.

Purity: 96.1% as determined by HPLC (r.t.=5.83 min, μBondapak $C_{18}$, 10μ, 10% $CH_3CN/KH_2PO_4$ 0.01M, pH 7.4);

UV (water) $\lambda_{max}$: 296 (8142);

IR (Nujol) $v_{max}$: 3400–3100 (OH, $NH_2$), 1755 and 1600 $cm^{-1}$ (c=O);

$^1$H NMR ($D_2O$, 200 MHz) δ: 4.273 (1H, dd, J=2.7 $H_2$, J=6.9 Hz, H-5), 4.4–4.2 (1H, m, H-1'), 3.458 (1H, dd, J=2.8 Hz, J=6.2 Hz, H-6), 3.4–3.2 (3H, m, $CH_2N$ and H-4), 3.2–3.0 (4H, m, $SCH_2$ and $CH_2N$), 2.91 (6H, s, $(N(CH_3)_2)$, 1.92 (2.5 H, s, $CH_3CO_2H$), 2.0–1.4 (4H, m, $CH_2CH_2$-4) and 1.330 (3H, d, J=6.4 Hz, $CH_3$).

EXAMPLE 129

(4R,5S,6S)-3-{(4S)-4-[(2S)-2-Dimethylaminocarbonyl] pyrrolidinylthio}-4-(2"-quanidinoethyl)-6-[(1'R)-1'-hydroxyethyl]-7-oxo-1-azabicyclo[3.2.0]hept-2-ene-2-carboxylic acid, acetic acid salt

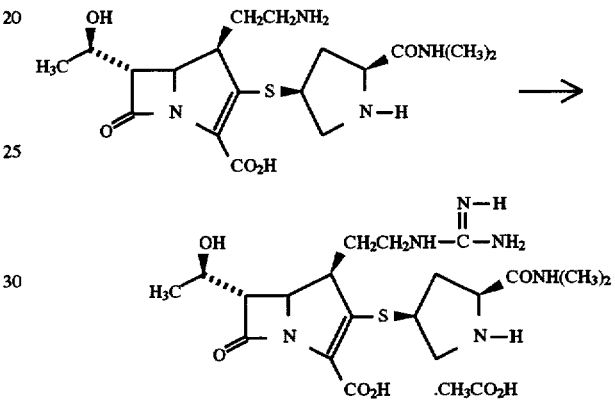

A solution of (4R,5S,6S)-4-(2"-aminoethyl)-3-{(4S)-4-[(2S)-2-dimethylaminocarbonyl]pyrrolidinylthio}-6-[(1'R)-1'-hydroxyethyl]-7-oxo-1-azabicyclo[3.2.0]hept-2-ene-2-carboxylic acid acetic acid salt (0.24 g, 0.51 mmol) in 25 mL of cold (0°–5° C.) water was adjusted to pH 8–8.5 with 1M sodium hydroxide. Then aminoiminomethanesulfonic acid (0.38 g, 3.06 mmol) was added in small portions (5 min) while maintaining the pH at 8–8.5 with 1M sodium hydroxide during the addition and for another 2 h. The pH was then adjusted to 5 with acetic acid and the resulting solution was chromatographed on reversed phase silica gel (μBondapak $C_{18}$, 2.5×15 cm). Elution with a gradient of acetonitrile (0–20%) in 0.005M aqueous acetic acid gave 0.063 g (24%) of the title carbapenem as a white amorphous solid after freeze drying:

Purity by HPLC: 94% on μBondapak $C_{18}$, 3.9 mm×30 cm, elution 5% $CH_3CN$—$H_2O$ Ph 7.4 phosphate buffer, flow rate 1 mL/min, uv detector 302 nm, retention time 15.6 min;

UV ($H_2O$, pH 7.4 phosphate buffer) $\lambda_{max}$: 300 nm (8,011);

IR (KBr) $v_{max}$: 1760 (C=O of β-lactam), 1660 (C=O of amide) and 1600 (C=O of carboxylate);

$^1$H NMR (200 MHz, $D_2O$) δ: 1.33 (d, J=6.32 Hz, 3H, $CH_3CHO$) 1.7–2.2 (m, 3H, H-3 of pyrrolidine and $CH_2$-4), 1.92 (s, $CH_3CO_2H$), 3.0 and 3.07 (2S, 2×3H, $CON(CH_3)_2$), 3–3.1 (m overlapping with $NCH_3$, 1H, H-3 of pyrrolidine), 3.2–3.6 (m, 5H, H-5 of pyrrolidine, H-4, H-6 and $CH_2NH$ of ethyl), 3.65 (dd, $J_{gem}$=12.2 Hz, $J_{H5,H4}$=5.85 Hz, 1H, H-5 of pyrrolidine), 3.9 (m, 1H, H-4 of pyrrolidine), 4.28 (m overlapping with H-5, 1H, $CH_3CHO$), 4.31 (dd, $J_{H5,H6}$=2.75 Hz, $J_{H5,H4}$=9.8 Hz, 1H, H-5) and 4.70 ppm (t, J=8.5 Hz, 1H, H-2 of pyrrolidine).

EXAMPLE 130

(4R,5R,6S)-4-(3"-Aminopropyl)-3-[(N,N-dimethylamidinomethyl)thio]-6-[(1'R)-1'-hydroxyethyl]-7-oxo-1-azabicyclo[3.2.0]hept-2-ene-2-carboxylic acid, acidic acid salt

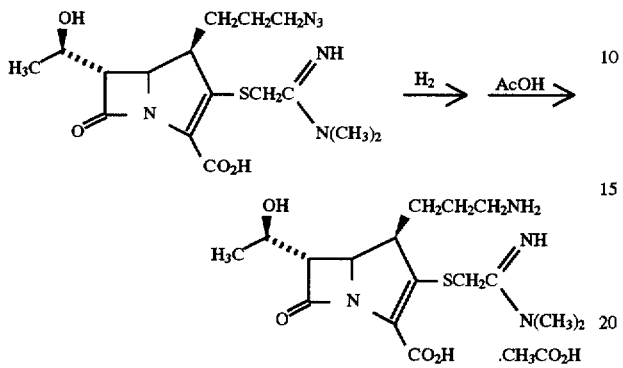

A solution of (4R,5S,6S)-4-(3"-azidopropyl)-3-[(N,N-dimethylaminomethyl)thio]-6-[(1'R)-1'-hydroxyethyl]-7-oxo-1-azabicyclo[3.2.0]hept-2-ene-2-carboxylic acid (0.270 g, 0.68 mmol) in cold water (80 mL) was hydrogenated at 0°–5° C. over 1.2 g of 5% palladium on alumina under 45 psi of hydrogen for 1 h. Then acetic acid (0.08 mn, 1.4 mmol) was added (pH change from 9 to 4) and the catalyst was filtered. The filtrate was chromatographed on reversed phase silica gel (μBondapak $C_{18}$, 3×12 cm) using a gradient of acetonitrile (0–20%) in 0.01M aqueous acetic acid. Lyophilization of the UV active fractions gave 0.200 g of a white amorphous powder which by $^1$H NMR was an equimolar mixture of title material and acetamidine acetate. This mixture was dissolved in ethanol (1 mL) and precipitated with diethyl ether (3 mL). The solid obtained (~0.088 g) was chromatographed on the same column as above to give 0.080 g (27%) of the pure title compound as a white amorphous powder:

Purity by HPLC: 96% on μBondapak $C_{18}$, 3.9 mm×30 cm, elution 3% $CH_3CN$—$H_2O$, pH 7.4 phosphate buffer, flow rate 2 mL/min, uv detector 300 nm, retention time 9.3 min;

UV ($H_2O$, pH 7.4 phosphate buffer) $\lambda_{max}$: 292 nm (5,872);

IR (KBr) $v_{max}$: 1760 (C=O of β-lactam), 1645 (sh) and 1575 cm$^{-1}$ (C=O of carboxylate);

$^1$H NMR (200 MHz, $D_2O$) δ: 1.32 (d, J=6.38 Hz, 3H, C$H_3$CHO), 1.4–2.0 (m, 4H, $CH_2$-1 and 2 of propyl), 1.91 (s, 3H, C$H_3$CO$_2$H), 3–3.4 (m, 3H, H-4 and C$H_2$NH$_2$), 3.12 and 3.29 (2s, 2×3H, N(CH$_3$)$_2$), 3.50 (dd, $J_{H6,H5}$=2.92 Hz, $J_{H6,H1}$=6.32 Hz, 1H, H-6), 3.84 (s, partially exchanged, SCH$_2$), and 4.2–4.4 ppm (m, 2H, H-5 and CH$_3$C$H$O overlapping).

EXAMPLE 131

(4R,5S,6S)-4-[2"-(2-Aminoethylthio)ethyl]-3-[(2-cyanoethylthio]-6-[(1'R)-1'-hydroxyethyl]-7-oxo-1-azabicyclo[3.2.0]hept-2-ene-2-carboxylic acid

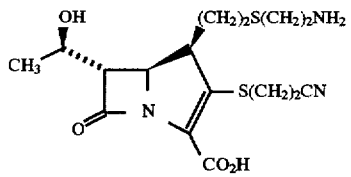

A. Allyl (4R,5S,6S)-4-[2"-(2-allyloxycarbonylaminoethylthio)ethyl]-6-[(1'R)-1'-tert-butyldimethylsilyloxyethyl]-3-[(2-cyanoethyl)thio]-7-oxo-1-azabicyclo-[3.2.0]hept-2-ene-2-carboxylate

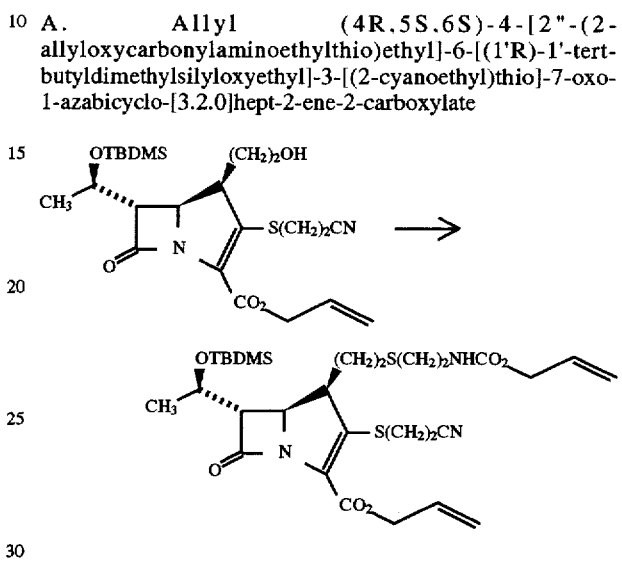

A cold (dry ice-acetone) solution of allyl (4R,5S,6 S)-6-[(1'R)-1'-tert-butyldimethylsilyloxyethyl]-3- [(2-cyanoethyl)thio]-4-(2"-hydroxyethyl)-7-oxo- 1-azabicyclo-[3.2.0]hept-2-ene2-carboxylate (350 mg, 0.73 mmol) in dichloromethane (7 mL) was treated first with diisopropylethylamine (0.34 mL, 1.9 mmol) and then dropwise with trifluoromethanesulfonic anhydride (0.14 mL, 0.88 mmol). The mixture was stirred for 25 min, treated dropwise with N-allyloxycarbonyl cysteamine (354 mg, 2.2 mmol) in dichloromethane (1 mL) and then stirred for 0.5 h at −15° C. (dry ice bath was replaced by an ice-methanol bath). The mixture was treated again with more thiol (177 mg, 1.1 mmol) in dichloromethane (0.5 mL) and diisopropylethylamine (0.13 mL, 0.73 mmol), then stirred for 30 more min. It was diluted with ethyl acetate (30 mL), washed with ice cold 1M aqueous NaHSO$_3$ (2×10 mL) water (10 mL), 1M aqueous NaHCO$_3$ (2×10 mL), water (10 mL), brine (10 mL) and dried (MgSO$_4$). The residue was passed through a silica gel flash column (35 g, 10%→50% ethyl acetate/hexane) to give title compound (321 mg, 70%).

IR (CH$_2$Cl$_2$) $v_{max}$: 3450 (NH), 2250 (CN), 1775 (C=O β-lactam) and 1720 cm$^{-1}$ (C=O ester and carbamoyl);

$^1$H NMR (CDCl$_3$, 200 MHz) δ: 6.03–5.82 (2H, m, vinylic H), 5.48–5.19 (4H, m, vinylic H), 5.1 (1H, bs, NH), 4.9–4.63 (2H, m, allylic CH$_2$), 4.583–4.55 (2H, m, allylic CH$_2$), 4.3–4.13 (1H, m, H-1'), 4.158 (1H, dd, J=2.5 Hz, J=9.5 Hz, H-5), 3.55–3.33 (3H, m, CH$_2$N and H-4), 3.33–3.19, 3.05–2.9 (2H, 2 sets of m, SCH$_2$ at position 3), 3.11 (1H, dd, J=2.7 Hz, J=6.9 Hz, H-6), 2.9–2.63 (6H, 2 sets of m, CH$_2$CN and CH$_2$S), 2.1–1.96, 1.96–1.75 (2H, 2 sets of m, CH$_2$-4), 1.300 (3H, d, J=6.1 Hz, CH$_3$), 0.884 (9H, s, tert-butyl) and 0.090 ppm (6H, s, dimethyl).

B. Allyl (4R,5S,6S)-4-[2"-(2-allyloxycarbonylaminoethylthio)ethyl]-3-[(2-cyanoethyl)thio]-6-[(1'R)-1'-hydroxyethyl]-7-oxo-1-azabicyclo[3.2.0]hept-2-ene-2-carboxylate

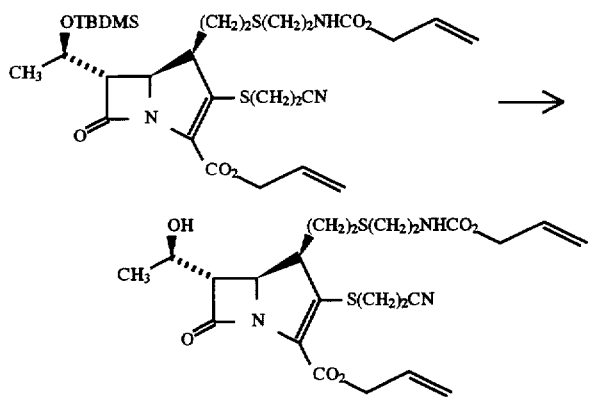

A cold (ice methanol bath) solution of allyl (4R, 5S,6 S)-4-[2"-(2-allyloxycarbonylaminoethylthio)ethyl]-6-[(1' R)-1'-tert-butyldimethylsilyloxyethyl]-3-[(2-cyanoethyl) thio]-7-oxo1-azabicyclo[3.2.0]hept-2-ene-2-carboxylate (310 mg, 0.500 mmol) in tetrahydrofuran (7 mL) was treated with glacial acetic acid (0.16 mL, 3.0 mmol) and dropwise with a 1M solution of tetrabutylammonium fluoride in tetrahydrofuran (1.5 mL, 1.5 mmol). The mixture was allowed to stand in the cold room (5° C.) for 15 days, then diluted with ethyl acetate (30 mL), washed with ice cold 1M aqueous NaHCO₃ (3×15 mL), water (2×15 mL), brine (15 mL) and dried (MgSO₄). The residue was passed through a silica gel flash column (15 g, 40→100% ethyl acetate/ hexane) to give the title compound (155 mg, 60%) as a yellow oil.

IR (CH₂Cl₂) $v_{max}$: 3600 (OH), 3450 (NH), 2250 (CN), 1775 (C=O β-lactam) and 1715 cm⁻¹ (C=O, ester and carbamoyl);

¹H NMR (CDCl₃, 200 MHz) δ: 6.05–5.8 (2H, m, vinylic H), 5.50–5.20 (4H, m, vinylic H), 5.05 (1H, bt, NH), 4.82–4.65 (2H, m, allylic CH₂), 4.586, 4.559 (2H, d, J=5.5 Hz, allylic CH₂), 4.206 (d, J=2.7 Hz, part of H-5), 4.22–4.05 (1H, m, H-1'), 3.7–3.5 (1H, m H-4), 3.5–3.3, 3.3–3.1, 3.1–2.8, 2.8–2.6 (11H, H-6, CH₂N, SCH₂, CH₂CN), 2.1–1.6 (3H, m, CH₂-4 and OH) and 1.427 ppm (3H, d, J=6.1 Hz, CH₃).

C. (4R,5S,6S)-4-[2"-(2-Aminoethylthio)ethyl]-3-[(2-cyanoethyl)thio]-6-[(1'R)-1'-hydroxyethyl]-7-oxo-1-azabicyclo[3.2.0]hept-2-ene-2-carboxylic acid

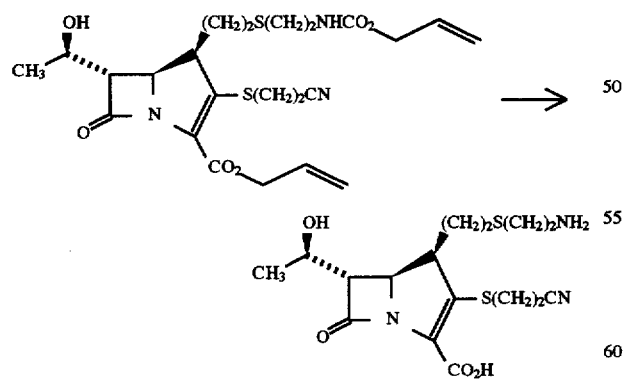

A cold (ice bath) solution of allyl (4R,5S,6 S)-4-[2"-(2-allyloxycarbonylaminoethylthio)ethyl]-3-[(2-cyanoethyl)thio]-6-[(1' R)-1'-hydroxyethyl]-7-oxo-1-azabicyclo [3.2.0]hept-2-ene-2-carboxylate (150 mg, 0.29 mmol) in dichloromethane (8 mL) was treated first with Pd(Pd₃)₄(53 mg, 0.040 mmol) followed by the dropwise addition of N-methyl aniline (0.15 mL, 1.2 mmol). The mixture was stirred for 20 min, then diluted diethyl ether (30 mL) and a 0.1M pH 7.0 aqueous phosphate buffer (15 mL). The organic layer was extracted again with a 0.1M buffer solution (2×7 mL) and water (7 mL).

The aqueous extracts were washed with diethyl ether (2×20 mL) and passed through a μBondapak C₁₈ reversed phase column (45 g, water, 1→6% CH₃CN/water) to give the title compound as a lyophilized powder (31 mg, 28%).

Purity: 98.0% as determined by HPLC (r.t.=6.26 min, μBondapak C₁₈, 10μ, 5% CH₃CN/KH₂PO₄ 0.01M, pH 7.4);

UV (water) $\lambda_{max}$: 300 (10,964);

IR (Nujol) $v_{max}$: 3500–3100 (OH, NH₂), 2250 (CN), 1755 (C=O β-lactam) and 1590 cm⁻¹ (C=O);

¹H NMR (D₂O, 200 MHz) δ: 4.32–4.20 (1H, m, H-1'), 4.244 (d, J=2.7 Hz, part of H-5), 3.608–3.494 (1H, m, H-4), 3.407 (1H, dd, J=2.7 Hz, J=6.6 Hz, H-6), 3.278–3.04 (3H, m, CH₂N and parts of SCH₂ at position 3), 3.03–2.71 (6H, m, SCH₂ at 3, SCH₂ and CH₂CN), 3.70–2.49 (1H, m, part of SCH₂), 2.10–1.95, 1.95–1.75 (2H, 2 sets of m, CH₂-4) and 1.322 ppm (3H, d, J=6.4 Hz, CH₃).

EXAMPLE 132

(4R,5S,6S)-4-(2"-Guanidinoethyl)-6-[(1'R)-1'-hydroxyethyl]-3-[2-(1-pyrrolidinyl)ethylthio]-7-oxo-1-azabicyclo[3.2.0]hept-2-ene-2-carboxylic acid, acetic acid salt

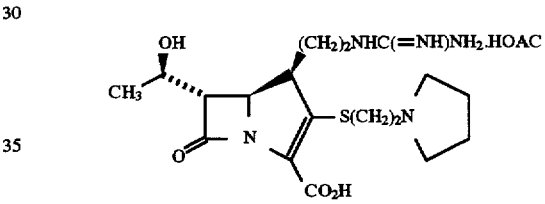

A. Allyl (4R,5S,6S)-4-(2"-azidoethyl)-6-[(1'R)-1'-tert-butyldimethylsiyloxyethyl]-3-[2-[1-pyrrolidinyl)ethylthio]-7-oxo-1-azabicyclo[3.2.0]hept-2-ene-2-carboxylate

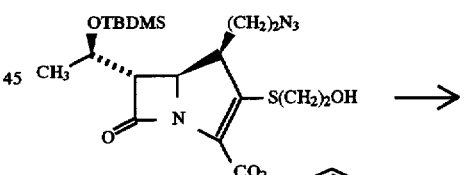

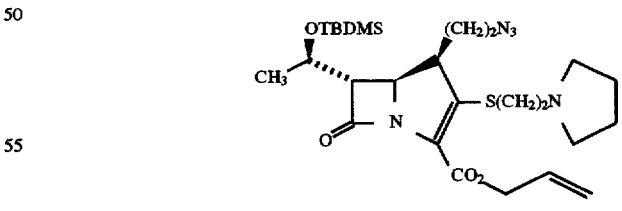

A cold (dry ice-acetone) solution of allyl (4R,5S,6 S)-4(2"-azidoethyl)-6-[(1'B)-1'-tert-butyldimethylsilyloxyethyl]-3-[(2-hydroxyethyl)thio]-7-oxo-1-azabicyclo[3.2.0]hept-2-ene-2-carboxylate (1.0 g, 2.0 mmol) in dry CH₂Cl₂ (20 mL) was treated first with diisopropylethyl amine (0.92 mL, 5.2 mmol) and dropwise with trifluoromethanesulfonic anhydride (0.40 mL, 2.4 mmol). The mixture was stirred for 30 min, pyrrolidine (1.0 mL, 12 mmol) was added in dropwise and it was stirred for 1 h at −15° C. (ice-MeOH). The mixture was diluted with a 1:1 EtOAc/petroleum ether mixture (100 mL) and washed with ice cold water (10×25 mL). The organic fraction was dried (MgSO$_4$) and passed through a silica gel flash pad (60 g, 20%→100% EtOAc/Hexane, 20% acetone/EtOAc) to give the title compound (640 mg, 58%) as an oil.

IR (CH$_2$Cl$_2$) $v_{max}$: 2100 (N$_3$), 1775 and 1720 cm$^{-1}$ (C=O);

$^1$H NMR (CDCl$_3$, 200 MHz) δ: 6.1–5.8 (1H, m, vinylic H), 5.5–5.2 (2H, m, vinylic H), 4.9–4.55 (2H, m, allylic CH$_2$), 4.3–4.1 (1H, m, H-1'), 4.12 (1H, dd, J=2.5 Hz, J=9.5 Hz, H-5), 3.7–3.5 (1H, m, H-4), 3.4–3.2 (2H, m, CH$_2$N$_3$), 3.07 (1H, dd, J=2.5 Hz, J=7.9 Hz, H-6), 3.04–2.76 (2H, 2 sets of m, SCH$_2$), 2.76–2.5 (6H, m, CH$_2$N), 2.15–1.95 (1H, m HC<u>H</u>), 1.9–1.6 (5H, m, (CH$_2$)$_2$ and H—C<u>H</u>), 1.313 (3H, d, J=6.2 Hz, CH$_3$), 0.895 (9H, s, tert-butyl) and 0.094 ppm (6H, s, dimethyl).

B. Allyl (4R,5S,6S)-4-(2"-azidoethyl)-6-[(1'R)-1'-hydroxyethyl]-3-[2-(1-pyrrolidinyl)ethylthio]-7-oxo-1-azabicyclo[3.2.0]hept-2-ene-2-carboxylate

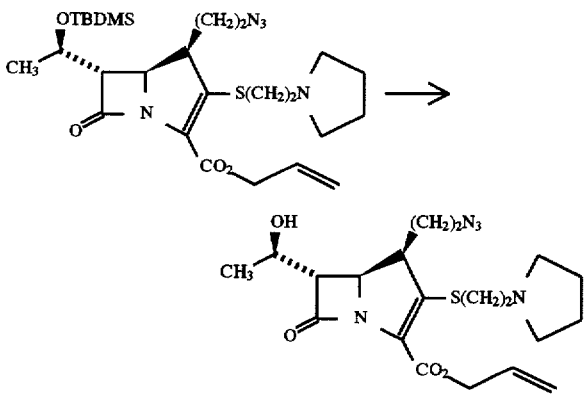

A cold (ice-MeOH bath) solution of allyl (4<u>R</u>,5<u>S</u>,6 <u>S</u>)-4-(2"-azidoethyl)-6-[(1'R)-1'-tert-butyldimethylsilyloxyethyl]- 3-[2-(1-pyrrolidinyl) ethylthio]-7-oxo-1-azabicyclo[3.2.0] hept-2-ene-2-carboxylate (620 mg, 1.1 mmol) in anhydrous tetrahydrofuran (8 mL) was treated first with acetic acid (0.36 mL, 6.6 mmol) followed by the dropwise addition of a 1M tetrahydrofuran solution of tetrabutylammonium fluoride (3.3 mL, 3.3 mmol). The mixture was stirred for 15 min, then at 5° C. (ice bath) for 1 h and it was allowed to stand for twelve days in the cold room (5°–8° C.).

The mixture was diluted with ethyl acetate (30 mL), washed with 1M aqueous NaHCO$_3$ (4×5 mL), brine (5 mL) and dried (MgSO$_4$). The residue was passed through a silica gel flash pad (5 g, ethyl acetate/hexane 50→100%; acetone/ ethyl acetate 20%→100%) to give the title compound (200 mg, 42%) as an oil.

IR (CH$_2$Cl$_2$) $v_{max}$: 3600 (OH), 2100 (N$_3$), 1775 and 1620 cm$^{-1}$ (C=O);

$^1$H NMR (CDCl$_3$, 200 MHz) δ: 6.05–5.95 (1H, m, vinylic H), 5.5–5.2 (2H, m, vinylic H), 4.9–4.6 (2H, m, allylic CH$_2$), 4.3–4.2 (1.5 H, m, H-1' and hidden part of H-5), 4.208 (d, J=2.7 Hz, part of H-5), 3.63–3.53 (1H, m, H-4), 3.49–3.35 (2H, m, CH$_2$N$_3$), 3.155 (1H, dd, J=2.7 Hz, J=7.9 Hz, H-6), 3.09–2.6 (4H, SCH$_2$CH$_2$-pyrrolidine), 2.56 (4H, bs, CH$_2$NCH$_2$), 2.2–1.7 (6H, m, CH$_2$-4 and CH$_2$CH$_2$ for pyrrolidine) and 1.395 ppm (3H, d, J=6.2 Hz, CH$_3$).

C. (4R,5S,6S)-4-(2"-Guanidinoethyl)-6-[(1'R)-1'-hydroxyethyl]-3-[2-(1-pyrrolidinyl)ethylthio]-7-oxo-1-azabicyclo[3.2.0]hept-2-ene-2-carboxylic acid, acetic acid salt

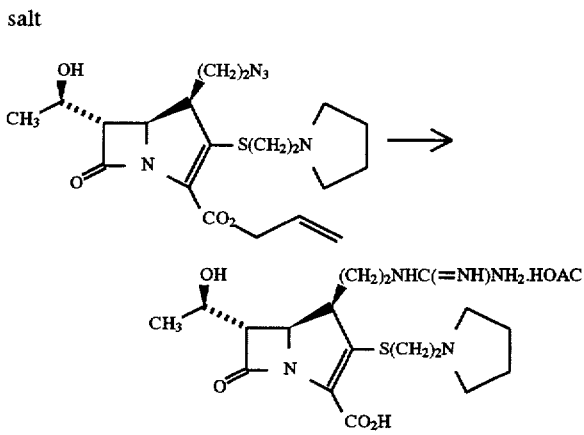

A cold (ice bath) solution of allyl (4<u>R</u>,5<u>S</u>,6 <u>S</u>)-4-(2"-azidoethyl)-6-[(1' <u>R</u>)-1'-hydroxyethyl]-3-[2-(1-pyrrolidinyl) ethylthio]-7-oxo-1-azabicyclo[3.2.0]hept-2-ene-2-carboxylate (160 mg, 0.370 mmol) in CH$_2$Cl$_2$ (12 mL) was treated with Pd[PPh$_3$]$_4$, (30 mg, 0.02 mmol) followed by the dropwise addition of a 0.5M solution of potassium 2-ethylhexanoate in ethyl acetate (0.74 mL, 0.37 mmol). The mixture was stirred for 15 min, then diluted with diethyl ether (70 mL) and extracted with a 0.04M pH 7.0 aqueous phosphate buffer (3×15 mL) and water (1×15 mL). The aqueous extracts were combined, washed with diethyl ether (2×30 mL) and the pH was adjusted (ice bath) to 5.9 with a 1M aqueous NaH$_2$PO$_4$ buffer solution. The aqueous mixture was shaken on a Parr hydrogenator at 45–50 psi of hydrogen at 5° C. (ice bath) for 1 h using 30% Pd/Celite (160 mg) as catalyst. Then more catalyst (100 mg) was added and the hydrogenation was carried out for 30 more minutes. The catalyst was removed by filtration and washed with water (2×5 mL). The pH of the aqueous solution (ice bath) was adjusted to 8.0 with a 0.5M aqueous NaOH solution and aminoiminomethane sulfonic acid (360 mg, 2.96 mmol, 8 eq.) was added in portionwise while maintaining the pH between 7.8–8.0 with the NaOH solution. The reaction mixture was stirred for 3 h (ice bath) after which the pH was adjusted to 7.0 with a 1M aqueous acetic acid solution. The aqueous mixture was passed through a μBondapak C$_{18}$ reversed phase column (60 g) stabilized and eluted with 0.005M aqueous acetic acid solution (1%→2% CH$_3$CN) to give the title compound (45 mg, 26%) as a lyophilized powder.

Purity: 97.5% determined by HPLC (r.t.=7.17 min, μBondapak C$_{18}$, 10μ, 10% CH$_3$CN/KH$_2$PO$_4$ 0.01M, pH 7.4);

UV (water) $\lambda_{max}$: 294 (5427);

IR (Nujol) $v_{max}$: 3400–3100 (NH), 1765, 1000 (C=O) and 1675–1630 cm$^{-1}$ (C=N);

$^1$H NMR (D$_2$O, 200 MHz) δ: 4.35–4.2 (1H, m, H-1'), 4.292 (1H, dd, J=2.9 Hz, J=9.5 Hz, H-5), 3.502 (1H, dd, J=2.9 Hz, J=6.6 Hz, H-6), 3.8–3.0 (9H, m, H-4, SC<u>H</u>$_2$ C<u>H</u>$_2$N, CH$_2$NCH$_2$ of pyrrolidine), 2.2–1.95 (5H, CH$_2$CH$_2$ pyrrolidine, <u>H</u>—CH at position-4), 1.95–1.7 (1H, m, HC— <u>H</u> at position-4), 1.91 (1.5 H, s, CH$_3$CO) and 1.328 ppm (3H, d, J=6.3 Hz, CH$_3$).

EXAMPLE 133

(4R,5S,6S)-4-(3"-Aminopropyl)-3-[(3S)-3-pyrrolidinylthio] -6-[(1'R)-1'-hydroxyethyl]-7-oxo-1-azabicyclo[3.2.0]hept-2-ene-2-carboxylic acid

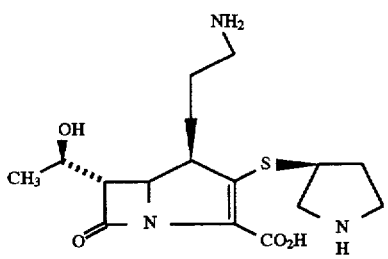

A. (3S)-N-Allyloxycarbonyl-3-mercaptopyrrolidine

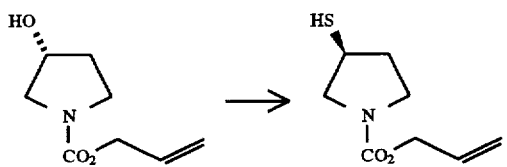

A cold solution (5° C.) of (3R)-N-allyloxycarbonyl-3-hydroxypyrrolidine (1.0 g, 5.84 mmol) in CH$_2$Cl$_2$ was treated with pyridine (0.532 g, 6.72 mmol) followed by trifluoromethanesulfonic anhydride (1.90 g, 6.72 mmol). After stirring for 15 min, the solvent was evaporated, the residue triturated in diethyl ether and filtered. The crude triflate was redissolved in cold (5° C.) CH$_3$CN and while bubbling H$_2$S into the solution, triethylamine (0.71 g, 7 mmol) was added dropwise. Formation of the thiol was completed in 15 min. The solvent was thus evaporated and the crude product purified by chromatography. (SiO$_2$/5% CH$_3$CN in CH$_2$Cl$_2$)to yield 0.787 g (71.9%) of the title compound.

IR (CH$_2$Cl$_2$)$v_{max}$: 1700 (—CO$_2$—), 1650 cm$^{-1}$ (>=<).
$^1$H NMR (CDCl$_3$) δ: 4.50–6.10 (5H, allyl pattern), 3.70–3.90 (1H, m, CH—S—) 3.20–3.70 [4H, m, —(CH$_2$—)$_2$ N], 2.20–2.40 and 1.70–2.00 (2H, 2m, 2 H-4), 1.70 (1H, d, J=6.57, —SH).

B. Allyl (4R,5S,6S)-4-[(3"-azidopropyl)-3-[(3S)-N-(allyloxycarbonyl)-3-pyrrolidinylthio]-6-[(1'R)-1'-hydroxyethyl]-7-oxo-1-azabicyclo[3.2.0]hept-2-ene-2-carboxylate

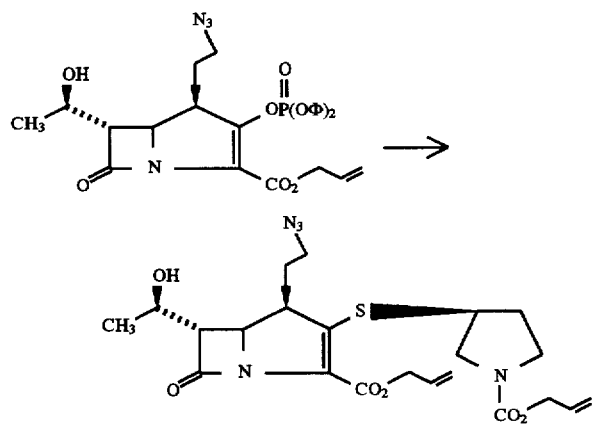

A cold (5° C.) solution of allyl (4R,5S,6S)-4-(3"-azidopropyl)-3-(diphenylphosphono)-6-[(1'R)-1'-hydroxyethyl]-7-oxo-1-azabicyclo[3.2.0]hept-2-ene-2-carboxylate (from 1.09 g, 3 mmol, of diazoketone) in CH$_3$CN was treated with (3S)-N-allyloxycarbonyl-3-mercaptopyrrolidine (0.79 g, 4.2 mmol) followed by diisopropylethylamine (0.54 g, 4.2 mmol). The reaction mixture was stirred at 5° C. for 18 h then diluted with EtOAc and washed successively with brine, dilute hydrochloric acid, dilute bicarbonate and finally brine again. The organic layer was dried (MgSO$_4$) and evaporated. The crude product was purified by chromatography (SiO$_2$/15% CH$_3$CN in CH$_2$Cl$_2$) to yield 441 mg (29.1%) of the title compound.

IR (CH$_2$Cl$_2$) $v_{max}$: 3610 (—OH), 2105 (—H$_3$) 1775 (β-lactam), 1700 (—CO$_2$—), 1650 cm$^{-1}$ (>=<).

$^1$H NMR (CDCl$_3$) δ: 4.50–6.10 (10H, 2 allyl patterns), 4.15–4.25 (2H, m, H-5, H-1'), 3.70–3.90 (2H, m, H-4, —CHS—), 3.0–3.90 (7H, m CH$_2$—N$_3$, H-6, >CH$_2$)$_2$)N—), 1.50–2.40 (6H, m, 2H-1", 2H-2", 2H-4 of pyrrolidine), 1.40 (3H, d, J=6.23, —CH$_2$').

C. (4R,5R,6S)-4-(3"-Azidopropyl)-3-[(3S)-3-pyrrolidinylthio]-6-[(1'R)-1'-hydroxyethyl]-7-oxo-1-azabicyclo[3.2.0]hept-2-ene-2-carboxylic acid

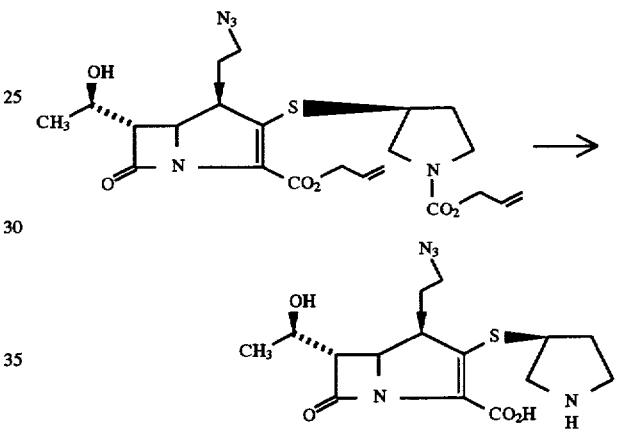

A solution of allyl (4R,5S,6S)-4-(3"-azidopropyl)-3-[(3S)-N-(allyloxycarbonyl)-3-pyrrolidinylthio]-6-[(1'R)-1'-hydroxyethyl]-7-oxo-1-azabicyclo[3.2.0]hept-2-ene-2-carboxylate (0.15 g, 0.3 mmol), triphenylphosphine (0.03 g) and N-methylaniline (0.127 g, 1.19 mmol) in EtOAc (10 mL) was cooled in ice and treated with tetrakis (triphenylphosphine) palladium [0] (0.03 g). The ice bath was removed and the reaction mixture stirred at 20° C. for 30 min. Addition of more tetrakis(triphenylphosphine) palladium [0] (0.025 g) completed the reaction in 45 min. The reaction mixture was then extracted with cold water and the aqueous extracts chromatographed on reversed phase silica gel (Partisil). Elution was done with 0–20% CH$_3$CN in water. The pertinent fractions were lyophilized to give 0.028g (24.5%) of the title compound as a white foam.

IR (Nujol) $v_{max}$: 2100 (—N$_3$), 1765 (β-lactam), 1595 cm$^{-1}$ (—CO$_2$—).

$^1$H NMR (D$_2$O) δ: 4.15–4.35 (2H, m, H-5, H-1'), 3.97 (1H, m, —CH—S—), 3.20–3.70 (8H, m, H-4, H-6, CH$_2$—H$_3$, —CH$_2$)$_2$N), 2.40–2.60 and 1.25–2.20 (6H, m, 2 H-1", 2H-2"2H-4 of pyrrolidine), 1.31 (3H, d, J=6.35, —CH$_3$').

D. (4R,5S,6S)-4-(3"-Aminopropyl)-3-[(3S)-3-pyrrolidinylthio]-6-[(1'R)-1'-hydroxyethyl]-7-oxo-1-azabicyclo-[3.2.0]hept-2-ene-2-carboxylic acid

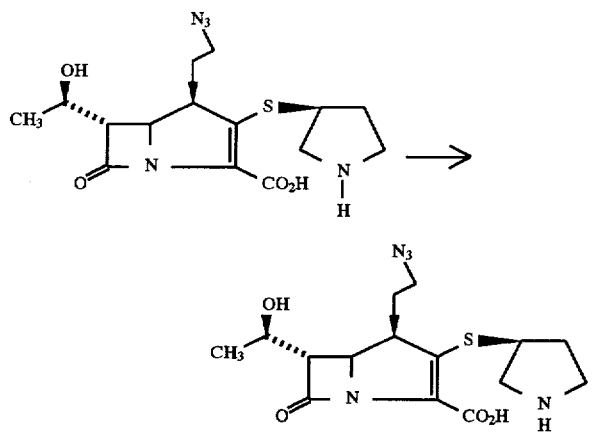

A cold (5° C.) solution of (4R,5R,6S)-4-(3"-azidopropyl)-3-[(3S)-3-pyrrolidinylthio]-6-[(1'R)-1'-hydroxyethyl]-7-oxo-1-azabicyclo[3.2.0]hept-2-ene-2-carboxylic acid (0.042 g, 0.11 mmol) in water (15 mL) was hydrogenated for 1 h at 43 psi, in the presence of 5% Pd/Al$_2$O$_3$ (0.04 g). Then the catalyst was filtered off and the pH of the filtrate lowered to 6.3 by adding 1M NaH$_2$PO$_4$. The aqueous solution was chromatographed on reversed phase silica gel (Partisil) eluting with cold water. Lyophilization of the pertinent fractions gave an impure white solid. A second chromatography, this time eluting with 0.6 ml acetic acid/1L of water gave 0.025 g (54.7%) of the pure title compound as the acetic acid salt.

IR (Nujol) $v_{max}$: 1755 cm$^{-1}$ (β-lactam);

$^1$H NMR (D$_2$O) δ: 4.20–4.40 (2H, m, H-5, H-1'), 3.99 (1H, m, —CH—S), 3.15–3.70 (6H, m, H-6, H-4, —CH$_2$)$_2$ N), 3.05 (2H, m, CH$_2$—N), 2.30–2.60 and 1.50–2.15 (6H, m, 2H-1", 2H-2", 2H-4 of pyrrolidine), 1.33 (3H, d, J: 6.33—CH$_3$'), 1.92 (3H, s, acetic acid).

EXAMPLE 134

(4R,5S,6S)-4-(3"-Aminopropyl)-3-[(2-quanidinoethyl)thio]-6-[(1'R)-1'-hydroxyethyl]-7-oxo-1-azabicyclo[3.2.0]hept-2-ene-2-carboxylic acid, acetic acid salt

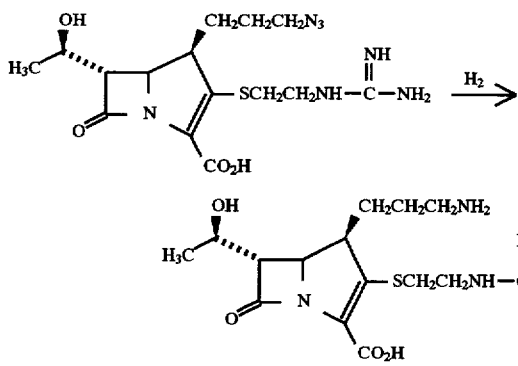

A suspension of (4R,5S,6S)-4-(3"-azidoethyl)-3-[(2-guanidinoethyl)thio]-6-[(1'R)-1'-hydroxyethyl]-7-oxo-1-azabicyclo[3.2.0]hept-2-ene-2-carboxylic acid (0.300 g, 0.76 mmol) in cold water (150 mL) was hydrogenated at 0°–5° C. over 1.0 g of 5% palladium on alumina under 45 psi of hydrogen for 1 h. After the addition of 0.1 mL (1.6 mmol) of acetic acid, the catalyst was filtered and the filtrate was chromatographed twice on reversed phase silica gel (µBondapak C$_{18}$, 2.5×15 cm) using 0.005M acetic acid as eluent. Lyophilization of the UV active fractions gave 0.23 g (70%) of the title carbapenem as a white amorphous solid: [α]$^{22}_D$+32.2° (c 1.0, water).

Purity by HPLC: 99% on µBondapak C$_{18}$, 3.9 mm×30 cm, elution water pH 7.4 phosphate buffer, flow rate 0.8 mL/min, UV detector 302 nm, retention time 8.27 min;

UV (water, pH 7.4 phosphate buffer) λ$_{max}$: 302 nm (6,390);

IR (KBr) $v_{max}$: 1750 (C=O of β-lactam), 1680, 1630 and 1580 cm$^{-1}$ (C=O of carboxylate);

$^1$H NMR (200 MHz, D$_2$O) δ: 1.33 (d, J=6.34 Hz, 3H, CH$_3$CHO), 1.4–2.0 (m, 4H, CH$_2$-1 and 2 of propyl), 1.92 (s, CH$_3$CO$_2$H), 2.8–3.4 (m, 4H, SCH$_2$ and CH$_2$NH$_2$), 3.37 (m, overlapping with H-6, 1H, H-4), 3.40 (dd, J$_{H6,H5}$=2.6 Hz, J$_{H6,H1}$=6.4 Hz, 1H, H-6), 3.48 (t, J=5.8 Hz, 2H, CH$_2$NH—C(NH)NH$_2$), 4.25 (dd, overlapping with CH$_3$ CHO, J$_{H5,H6}$=2.6 Hz, 1H, H-5) and 4.28 ppm (m, 1H, CH$_3$ CHO).

EXAMPLE 135

(4R,5S,6S)-4-(2"-Guanidinoethyl)-3-[(2-quanidinoethyl)thio]-6-[(1'R)-1'-hydroxyethyl]-7-oxo-1-azabicyclo[3.2.0] hept-2-ene-3-carboxylic acid, acetic acid salt

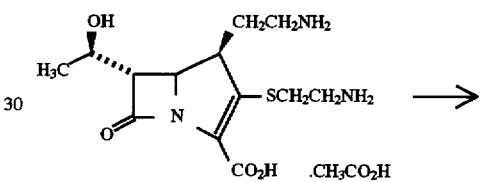

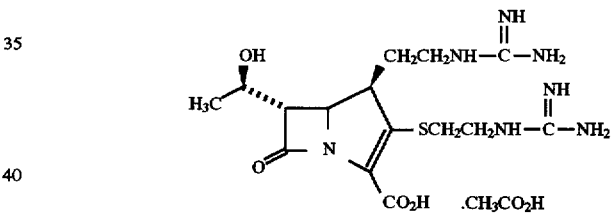

A solution of (4R,5S,6S)-4-(2"-aminoethyl)-3-[(2-aminoethyl)thio]-6-[(1'R)-1'-hydroxyethyl]-7-oxo-1-azabicyclo[3.2.0]hept-2-ene-2-carboxylic acid, acetic acid salt (0.270 g, 0.73 mmol) [prepared in Example 115] in cold water (50 mL) was adjusted to pH 8.5 with 1M aqueous sodium hydroxide and treated at 0°–5° C. with aminoiminomethanesulfonic acid (0.80 g, 6.44 mmol) added in small portions over 5 min while maintaining the pH between 8 and 8.5 with the base. After 2.5 h, the pH was adjusted to 4.5 with acetic acid and the solution was chromatographed twice on reversed phase silica gel (µBondapak C$_{18}$, 2.5×15 cm) using water as eluent. Lyophilization of the UV active fractions gave 0.080 g (23%) of the title carbapenem as a white amorphous solid.

Purity by HPLC: 99% on µBondapak C$_{18}$, 3.9 mm×30 cm, elution 0.01M phosphate buffer, flow rate 2 mL/min, uv detector 300 nm, retention time 6.75 min;

UV (water, pH 7.4 phosphate buffer) λ$_{max}$: 302nm (7,250);

IR (KBr) $v_{max}$: 1755 (C=O of β-lactam), 1670, 1640 and 1570 cm$^{-1}$ (C=O of carboxylate);

$^1$H NMR (200 MHz, D$_2$O) δ: 1.33 (d, J=6.34 Hz, 3H, CH$_3$CHO), 1.7–2.2 (m, 2H, CH$_2$-1 of ethyl), 1.92 (s, CH$_3$CO$_2$H), 2.7–3.2 (m, 2H, SCH$_2$), 3.2–3.7 (m, 6H, H-4, H-6, CH$_2$-2 of ethyl and SCH$_2$CH$_2$N), and 4.2–4.4 ppm (m, 2H, H-5 and CH$_3$CHO).

EXAMPLE 136

(4R,5R,6S)-3-[(2-Cyanoethyl)thio]-6-[(1'R)-1'-hydroxyethyl]-4-[2"-(1-pyridinium)ethyl]7-oxo-1-azabicyclo[3.2.0]hept-2-ene-2-carboxylate

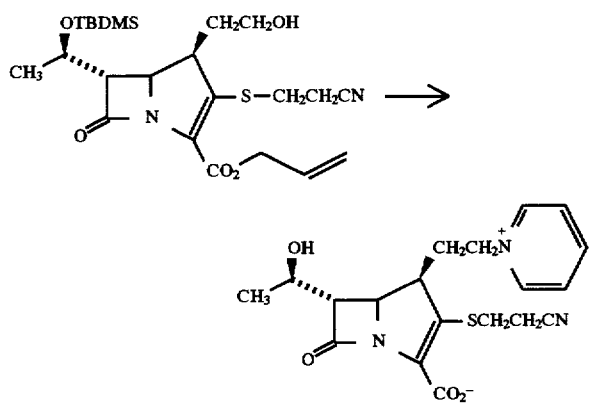

A solution of allyl (4R,5S,6S)-6-[(1'R)-1'-tert-butyldimethylsilyloxyethyl]-3-[(2-cyanoethyl)thio]-4-(2"-hydroxyethyl)-7-oxo-1-azabicyclo[3.2.0]hept-2-ene-2-carboxylate (0.481 g, 1 mmol) [prepared in Example 125] in dry dichloromethane (10 mL) was cooled to −78° C. and treated under Argon with N,N-diisopropylethylamine (0.262 mL, 1.5 mmol) followed by trifluoromethanesulfonic anhydride (0.194 mL, 1.15 mmol) dropwise over 3 min. After 20 min at −78° C., pyridine (0.324 mL, 4 mmol) was added. The reaction mixture was left standing at −20° C. for 18 h, then concentrated under vacuum without heating. The residue was dissolved in dry tetrahydrofuran (20 mL), cooled to −15° C. and treated under Argon with acetic acid (0.76 mL) followed by 6 mL (6 mmol) of a 1M solution of tetrabutylammonium fluoride in tetrahydrofuran. The solution was allowed to stand at 0° C. for 96 h, then tetrakis (triphenylphosphine) palladium [0] (0.090 g) was added followed by N,N-diisopropylethylamine (0.350 mL, 2 mmol). The resulting reaction mixture was stirred under Argon at 0° C. After 3 h the reaction mixture was extracted with cold water (30 mL). The pH of the aqueous phase was adjusted to 6.5 by NaOH 1N then the aqueous extract was washed with diethyl ether and maintained under vacuum to remove traces of organic solvent. The solution was filtered then was chromatographed on reversed phase silica gel (μBondapak C$_{18}$, 3.5×14 cm) using water as eluent. The UV active fractions were combined, lyophilized and chromatographed a second time on the same column using a gradient of acetonitrile (0–1%) in water as eluent. Final lyophilization gave 0.310 g of white amorphous powder which was crystallized in cold methanol (20 mL) to give the pure crystalline title carbapenem (0.262 g, 68%).

Purity by HPLC: 99.96% on μBondapak C$_{18}$, 3.9 mm×30 cm, elution 2% CH$_3$CN-water pH 7.4 phosphate buffer, flow rate 0.8 mL/min, UV detector 300 nm, retention time 9.97 min.;

UV (water, pH 7.4 phosphate buffer) $\lambda_{max}$: 298 nm (8101), 260 nm (7531);

IR (KBr) $\nu_{max}$: 2250 (CN, 1755 (C=O of β-lactam and 1600 cm$^{-1}$ (C=O of carboxylate);

$^1$H NMR (200 MHz, D$_2$O) δ: 1.37 (d, J=6.35, 3H, CH$_3$CHO), 2.2–2.6 (m, 2H, CH$_2$-4), 2.8 (m, 2H, CH$_2$CN), 2.9–3.1 (m, 2H, SCH$_2$), 3.45 (m, 1H, H-4), 3.56 (dd, J$_{H6,H5}$=2.97 Hz, J$_{H6,H1}$=7.04 Hz 1H, H-6) 4.20–4.40 (m, 2H, H-5 and , CH$_3$CHO), 4.81 m, overlapping with HOD signal, 2H, N$^+$—CH $_2$), 8.11 (m, 2H, H-3 and H-5 on pyridinium), 8.59 (m, 1H, H-4 on pyridinium), 8.91 (m, H-2 and H-6 on pyridinium).

EXAMPLE 137

(4R,5S,6S)-6-[(1'R)-1'-Hydroxyethyl]-3-[(2-cyanoethyl)thio]-4-[2"-(β-chloro-L-alanyl-β-chloro-L-alanyl)aminoethyl]-7-oxo-1-azabicyclo[3.2.]-hept-2-ene-2-carboxylic acid

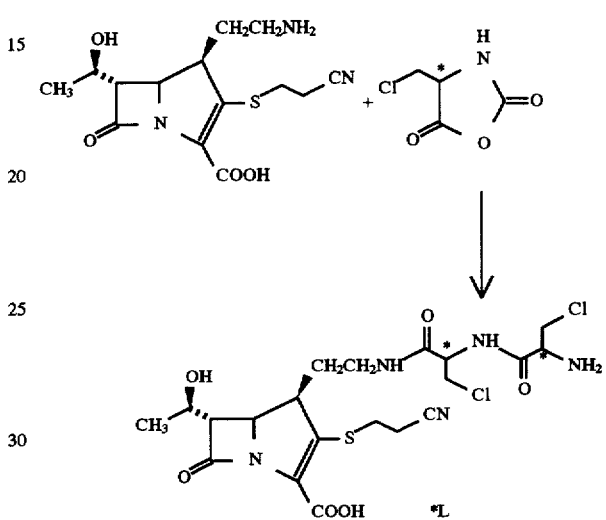

A solution of (4R,5S,6S)-6-[(1'R)-1'-hydroxyethyl]-3-[(2-cyanoethyl)thio]-4-(2"-aminoethyl)-7-oxo-1-azabicyclo [3.2.0]hept-2-ene-2-carboxylic acid (0.475 g, 1.46 mmol) in 0.2M pH 7.0 phosphate buffer (15 mL) was cooled to 0° C. while bubbling Argon through the solution. The pH was adjusted to 10.2 with 1N NaOH and N-carboxyanhydride of β-chloro-L-alanine (0.22 g, 1.46 mmol) in dioxane (1.5 mL) was added in one portion with vigorous stirring. When the pH dropped to 7.2, it was readjusted to 10.2 and left there for 1 h. The reaction was stopped by adjusting the pH to 6.0 with 1N HCl. Argon was bubbled through the solution for 30 min at 0° C. while readjusting the pH to 6.0 whenever it rose above 6.0. The crude reaction mixture was passed through a column of μBondapak C$_{18}$ reverse phase silica (4.5×10.5 cm). Appropriate fractions belonging to the product were combined and lyophilized to a solid which was rechromatographed on μBondapak C$_{18}$ reverse phase silica (4.5×10.5 cm). The slightly less polar title compound, separated very closely from the monopeptide derivative, was eluted with a mixture of water and CH$_3$CN (94:6, gradient elution) and was obtained as a yellowish fluffy solid after lyophilization (0.049 g, 6.8%).

Purity 92.2% by HPLC: UV detection at 300 nm on μBondapak C$_{18}$ (4 mm×30 cm), 10% CH$_3$CN in pH 6.8 phosphate buffer, flow rate 1 mL/min, retention time 8.31 min.

UV $\lambda_{max}$: 300 nm;

IR (Nujol) $\nu_{max}$: 1750 cm$^{-1}$ (C=O, β-lactam).

$^1$H NMR (200 MHz, D$_2$O) δ: 1.37 (d, 3H, CH$_3$, J=6.4 Hz), 1.66–1.77; 2.06–2.16 (m, 2H, CH$_2$), 2.83–2.89 (m, 2H, CH$_2$CN), 2.91–3.04; 3.08–3.21 (m, 2H, SCH$_2$), 3.32–3.41 (m, 3H, CH$_2$NH, H-4), 3.58 (dd, 1H, H-6, J$_{6,1}$=5.88 Hz)

3.78–4.08 (m, 4H, C$_\beta$H$_2$), 4.17 (t, 1H, C$_\alpha$H, J$_{\alpha,\beta}$=4.61 Hz), 4.27 (dd, 1H, H-5, J$_{4,5}$=7.92 Hz, J$_{5,6}$=2.48 Hz), 4.31 (m, 1H, H-1'), 4.76 (t, 1H, C$_\alpha$H, J$_{\alpha,\beta}$=5.37 Hz).

EXAMPLE 138

Sodium (4R,5S,6S)-4-(2"-azidoethyl]-3-[(2-fluoroethyl)thio]-6-[(1'R)-1'-hydroxyethyl]-7-oxo-1-azabicyclo[3.2.0]hept-2-ene-2-carboxylate

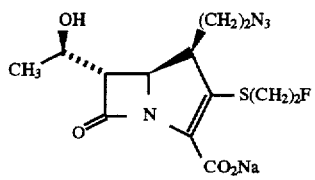

A. Allyl (4R,5R,6S)-4-(2"-azidoethyl)-6-[(1'R)-1'-tert-butyldimethylsilyloxyethyl]-3-[(2-fluoroethyl)thio]-7-oxo-1-azabicyclo[3.2.0]hept-2-ene-2-carboxylate

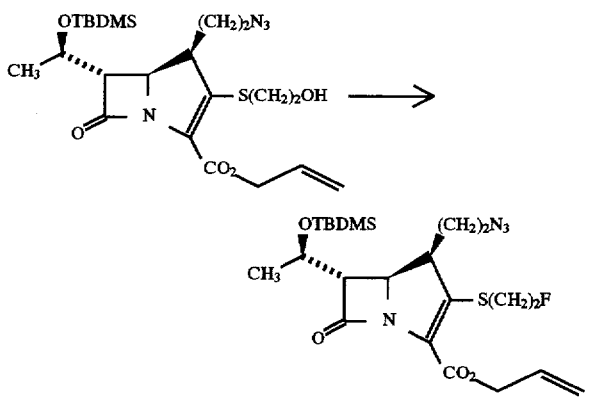

To a cold (ice bath) and well stirred solution of diethylammonium sulfur trifluoride (DAST, 1.05 mL, 8.06 mmol) in CH$_2$Cl$_2$ (20 mL) was added dropwise, over a 10 min period, allyl (4R,5S,6S)-4-(2"-azidoethyl)-6-[(1')-1-tert-butyldimethylsilyloxyethyl]-3-[(2-hydroxyethyl)thio]-7-oxo-1-azabicyclo[3.2.0]hept-2-ene-2-carboxylate in CH$_2$Cl$_2$ (80 mL). The mixture was stirred for 15 min, then quenched with ice cold water (100 mL) and finally diluted with a 1/1 mixture of ethyl acetate/diethyl ether and water (400 mL). The aqueous phase was extracted with ethyl acetate/diethyl ether (1/1, 300 mL) and the organic extracts were combined, washed with ice cold water (2×250 mL), ice cold 1N aqueous HCl, water, 1M aqueous NaHCO$_3$, brine and dried (MgSO$_4$). The residue was passed through a silica gel flash pad (180 g, hexane, 5→25% ethyl acetate/hexane) to give the title compound (1.54 g, 38%) as a yellow oil:

IR (CH$_2$Cl$_2$) v$_{max}$: 2100 (N$_3$), 1775 and 1710 cm$^{-1}$ (C=O);

$^1$H NMR (CDCl$_3$, 200 MHz) δ: 6.05–5.85 (1H, m, vinylic H), 5.49–5.22 (2H, m, vinylic H), 4.9–4.4 (4H, m, allylic CH$_2$ and CH$_2$F), 4.3–4.13 (1H, m, H-1'), 4,145 (1H, dd, J=2.7 Hz, J=9.5 Hz, H-5), 3.7–3.55 (1H, m, H-4), 3.46–3.3 (2H, m, CH$_2$N$_3$), 3.4–3.15, 3.05–2.8 (2H, 2 sets of m, SCH$_2$), 3.088 (1H, dd, J=2.7 Hz, J=7.7 Hz, H-6), 2.13–1.95, 1.85–1.65 (2H, 2 sets of m, CH$_2$-4), 1.309 (3H, d, J=6.1 Hz, CH$_3$), 0.897 (9H, S, tert-butyl) and 0.095 ppm (6H, s, dimethyl).

B. Allyl (4R,5S,6S)-4-[2"-azidoethyl]-3-[(2-fluoroethyl)thio]-6-[(1'R)-1'-hydroxyethyl]-7-oxo-1-azabicyclo[3.2.0]hept-2-ene-2-carboxylate

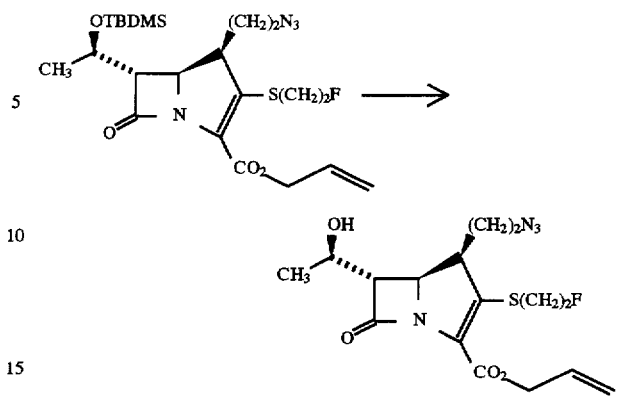

A cold (ice-MeOH) solution of allyl (4R,5S,6S)-4-(2"-azidoethyl)-6-[(1'R)-1'-tert-butyldimethylsilyloxyethyl]-3-[(2-fluoroethyl)thio]-7-oxo-1-azabicyclo[3.2.0]hept-2-ene-2-carboxylate (457 mg, 0.92 mmol) in tetrahydrofuran (8 mL) was treated first with glacial acetic acid (0.3 mL, 5.5 mmol) and then dropwise with a 1M solution of tetrabutylammonium fluoride in tetrahydrofuran (2.75 mL, 2.75 mmol). The mixture was stirred for 10 min and then was allowed to stand in the cold room (5°–8° C.) for nine days. It was then diluted with ethyl acetate (50 mL), washed with ice cold 1M aqueous NaHCO$_3$ (4×25 mL), water (2×25 mL), brine (25 mL) and dried (MgSO$_4$). It was passed through a silica gel flash column (15 g, hexane, ethyl acetate/hexane 10%→50%) to give the title compound (240 mg, 68%) as an oil.

IR (CH$_2$Cl$_2$) v$_{max}$: 3400 (OH), 3100 (N$_3$), 1778 and 1612 cm$^{-1}$ (C=O);

$^1$H NMR (CDCl$_3$, 200 MHz) δ: 6.03–5.9 (1H, m, vinylic H), 5.5–5.2 (2H, m, vinylic H), 4.9–4.35 (4H, m, allylic CH$_2$ and CH$_2$—F), 4.3–4.15 (1H, m, H-1'), 4.248 (1H, dd, J=2.7 Hz, J=9.5 Hz, H-5), 3.7–3.5 (1H, m, H-4), 3.5–3.3 (2H, m, CH$_2$N$_3$), 3.3–2.8 (2H, 2 sets of m, SCH$_2$), 3.160 (1H, dd, J=2.7 Hz, J=8.0 Hz, H-6), 2.15–1.95, 1.84–1.65 (2H, 2 sets of m, CH$_2$-4), 1.834 (1H, d, J=5.1 Hz, OH) and 1.395 ppm (3H, d, J=Hz, CH$_3$).

C. Sodium (4R,5S,6S)-4-(2"-azidoethyl)-3-[(2-fluoroethyl)thio]-6-[(1'R)-1'-hydroxyethyl]-7-oxo-1-azabicyclo[3.2.0]hept-2-ene-2-carboxylate

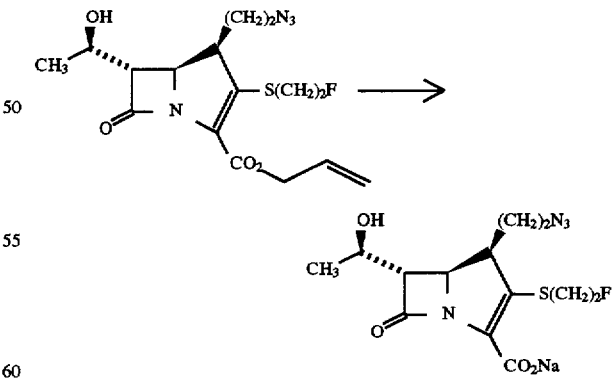

To a cold (ice bath) solution of allyl (4R,5S,6S)-4-(2"-azidoethyl)-3-[(2-fluoroethyl)thio]-6-[(1'R)-1'-hydroxyethyl]-7-oxo-1-azabicyclo[3.2.0]hept-2-ene-2-carboxylate (585 mg, 1.52 mmol) in CH$_2$Cl$_2$ (20 mL) was added Pd(PPh$_3$)$_4$ (142 mg, 0.114 mmol) and dropwise a 0.5M solution of potassium ethyl-2-hexanoate in ethyl acetate (3.0 mL, 1.50 mmol). The mixture was stirred for 20 min, diluted with diethyl ether (80 mL) and extracted with water (4×15 mL). The aqueous extracts were combined, washed with water (2×20 mL) and passed through a µBondapak C$_{18}$ reversed phase column (200 g, 1%→10% CH$_3$CN/water) to give the title compound (40.2 mg, 72%) as an off-white lyophilized solid.

Purity: 97.8% determined by HPLC (r.t.=14.85 min, µBondapak C$_{18}$, 10 µ, 5% CH$_3$CN/KH$_2$PO$_4$ 0.01M, pH 7.4);
UV (H$_2$O) $\lambda_{max}$: 302 (9184);
IR (Nujol) $v_{max}$: 3350 (OH), 2100 (N$_3$), 1750 and 1600 cm$^{-1}$ (C=O);

$^1$H NMR (D$_2$O, 200 MHz) δ: 4.83–4.75, 4.6–4.5 (2H, 2 sets of m, CH$_2$F), 4.35–4.2 (1H, m, H-1'), 4.210 (1H, dd, J=2.8 Hz, J=9.0 Hz, H-5), 3.65–2.9 (6H, m, H-4, SCH$_2$, CH$_2$N$_3$, H-6), 2.17–2.0, 1.9–1.7 (2H, 2 sets of m, CH$_2$-4) and 1.331 ppm (3H, d, J=Hz, CH$_3$).

EXAMPLE 139

(4R,5S,6S)-4-(3"-Aminopropyl)-3-[(4-piperidinyl)thio]-6-[(1'R)-1'-hydroxyethyl]-7-oxo-1-azabicyclo[3.2.0]hept-2-ene-2-carboxylic acid

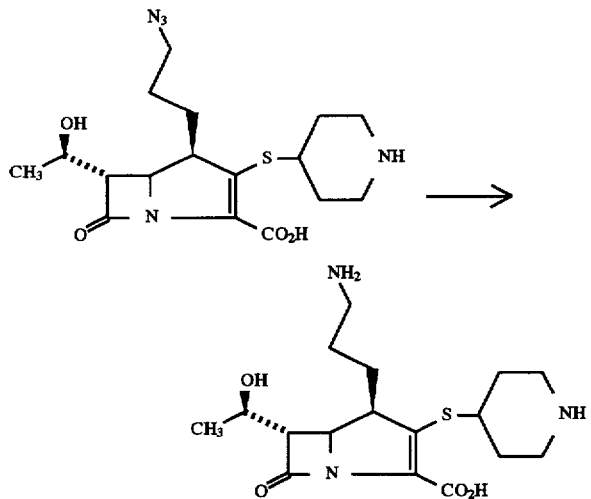

A cold (5° C.) solution of (4R,5S,6S)-4-(3"-azidopropyl)-3-[(4-piperidinyl)thio]-6-[(1'R)-1'-hydroxyethyl]-7-oxo-1-azabicyclo[3.2.0]hept-2-ene-2-carboxylic acid (0.08 g, 0.20 mmol) in water (40 mL) was hydrogenated at 45 psi for 1 h in the presence of 5% Pd/Al$_2$O$_3$ (0.08 g). The catalyst was then filtered off and the pH of the filtrate lowered to 5.0 by adding acetic acid. This acidified aqueous solution was chromatographed on reversed phase silica gel (Partisil) eluting with 15% CH$_3$CN in water. Lyophilization of the pertinent fractions gave 0.066 g (76.8%) of the title compound as the acetic acid salt.

IR (Nujol) $v_{max}$: 1760 (β-lactam), 1580 cm$^{-1}$ (—CO$_2$—).

$^1$H NMR (D$_2$O) δ: 4.20–4.40 (2H, m, H-5, H-1'), 3.25–3.60 [5H, m, H-6, (2 H-2, 2 H-6 of piperidine)], 2.95–3.15 (4H, m, CH$_2$—N, H-4, H-4 of piperidine), 1.50–2.40 [8H, m, 2H-1", 2H-2"(2H-3 2H-5 of piperidine)], 1.93 (3H, s, acetic acid), 1.34 (3H, d, J=6.30, —CH$_3$').

EXAMPLE 140

(4R,5S,6S)-3-[(N,N-Dimethylamidinomethyl)thio]-4-(3"-quanidinopropyl)-6-[(1'R)-1'-hydroxyethyl]-7-oxo-1-azabicyclo[3.2.0]hept-2-ene-2-carboxylic acid, acetic acid salt

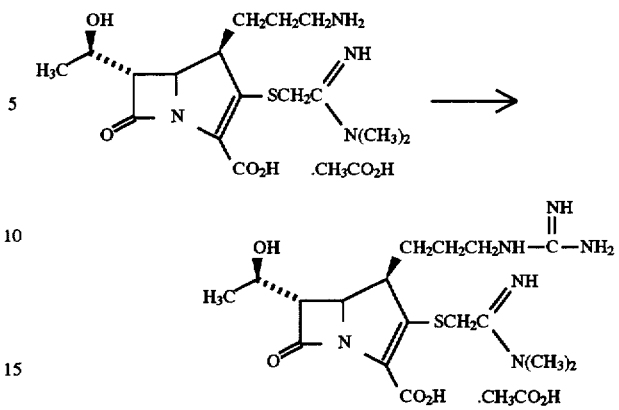

A solution of (4R,5S,6S)-4-(3"-aminopropyl)-3-[(N,N-dimethylamidinomethyl)thio]-6-[(1'R)-1'-hydroxyethyl]-7-oxo-1-azabicyclo[3.2.0]hept-2-ene-2-carboxylic acid (0.203 g, 0.47 mmol) in cold water (0°–5° C., 30 mL) was adjusted to pH 8.5 with 1M aqueous sodium hydroxide and then treated with aminoiminomethanesulfonic acid (0.230 g, 1.85 mmol) added in small portions over 5 min while maintaining the pH at 8–8.5. After 2 h, the pH was adjusted to 4.8 with glacial acetic acid and the solution was chromatographed on reversed phase silica gel (µBondapak C$_{18}$, 2.5×13.5 cm) using 0.01M aqueous acetic acid as eluent. Lyophilization of the UV active fractions gave 0.090 g (40%) of the title carbapenem as a white amorphous solid:

Purity by HPLC: 98% on µBondapak C$_{18}$, 3.9 mm×30 cm, elution 5% CH$_3$CN—H$_2$O, pH 7.4 phosphate buffer, flow rate 1 mL/min, UV detector 292 nm, retention time 7.52 min;

UV (water, pH 7.4 phosphate buffer) $\lambda_{max}$: 292 nm (6,340);

IR (KBr) $v_{max}$: 1760 (C=O of β-lactam), 1680, 1650 and 1580 cm$^{-1}$ (C=O of carboxylate);

$^1$H NMR (200 MHz, D$_2$O) δ: 1.32 (d, J=6.36 Hz, 3H, CH$_3$CHO), 1.4–1.9 (m, 4H, CH$_2$-1 and 2 of propyl), 1.92 (s, CH$_3$CO$_2$H), 3.12 and 3.29 (2s, 2×3H, NCH$_3$), 3.1–3.4 (m, 3H, H-4 and CH$_2$-3 of propyl), 3.44 (dd, J$_{H6,H5}$=2.83 Hz, J$_{H6,H1}$=5.97 Hz, 1H, H-6), 3.86 (s, 2H, SCH$_2$) and 4.2–4.4 ppm (m, 2H, H-5 and CH$_3$CHO overlapping).

EXAMPLE 141

(4R,5S,6S)-3-[(2-N,N-Dimethylaminoethyl)thio]-4-(2"-quanidinoethyl)-6-[(1'R)-1'-hydroxyethyl]-7-oxo-1-azabicyclo[3.2.0]hept-2-ene-2-carboxylic acid, acetic acid salt

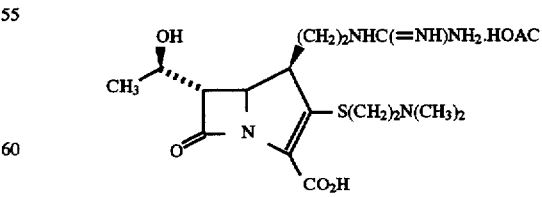

A. Allyl (4R,5S,6S)-4-(2"-azidoethyl)-6-[(1'R)-1'-tert-butyldimethylsilyloxyethyl]-3-[(2-N,N-dimethylaminoethyl)thio]-7-oxo-1-azabicyclo[3.2.0]hept-2-ene-2-carboxylate

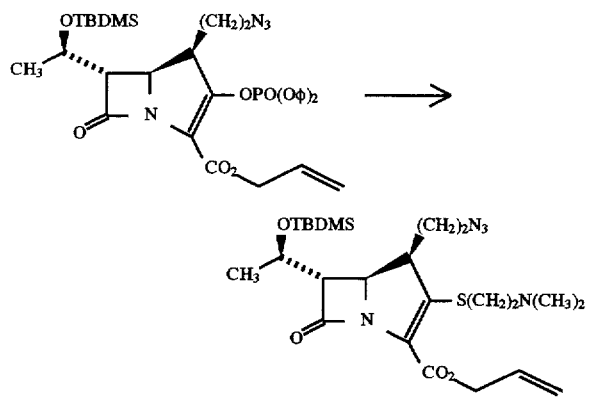

A cold (ice-MeOH bath) solution of enol phosphate prepared from (3S,4R)-3-[(1'R)-1'-tert-butyldimethylsilyloxyethyl]-4-[(1"R)-1"-(2- azidoethyl)-3"-diazo-3"-allyloxycarbonyl-2"-oxopropyl]azetidin-2-one (4.64 g, 10 mmol) in acetonitrile (45 mL) was treated slowly with N,N-dimethylaminoethanethiol (1.05 g, 10.0 mmol) in CH$_3$CN (2 mL) and dropwise with diisopropylethyl amine (1.92 mL, 11.0 mmol). The mixture was stirred for 1.5 h at −10° C.→0° C., then cooled again (ice-methanol) and treated again with the mercaptan (520 mg, 5 mmol) in CH$_3$CN (1 mL) and diisopropylethylamine (0.96 mL, 5.5 mmol). The mixture was stirred for ½ h at −15° and was allowed to set in the refrigerator (−20° C.) for 18 h. It was diluted with a 1:1 mixture of ethyl acetate/diethyl ether (500 mL), washed with ice cold water (5×100 mL), brine (100 mL) and dried (MgSO$_4$). The residue was passed through a silica gel flash column (100 g, 50→100% ethyl acetate/ hexane, 10% acetone/ethyl acetate) to give the title compound (4.0 g, 76%) contaminated with the opened β-lactam side product.

IR (CH$_2$Cl$_2$) v$_{max}$: 2100 N$_3$, 1775 and 1715 cm$^{-1}$ (C=O);

$^1$H NMR (CDCl$_3$, 200 MHz) δ: 6.1–5.8 (1H, m, vinylic H), 5.5–5.1 (2H, m, vinylic 3H), 4.9–4.6 (2H, m, allylic-CH$_2$), 4.3–4.1 (1H, m, H-1'), 4.2–4.15 (1H, dd, H-5), 3.7–3.5 (1H, m, H-4), 3.5–3.3 (2H, m, CH$_2$—N$_3$), 3.071 (1H, dd, J=3.0 Hz, J=7.1 Hz, H-6), 3.1–2.85 (2H, m, SCH$_2$), 2.7–2.4 (2H, m CH$_2$—N), 2.28 (6H, s, N(CH$_3$)$_2$), 2.1–1.6 (2H, m, CH$_2$-4), 1.314 (3H, d, J=6.1 Hz, CH$_3$), 0.897 (9H, s, tert-butyl) and 0.069 ppm (6H, s, dimethyl).

B. Allyl (4R,5S,6S)-4-(2"-azidoethyl)-3-[(2-N,N-dimethylaminoethyl)thio]-6-[(1'R)-6-hydroxyethyl]-7-oxo-1-azabicyclo[3.2.0]hept-2-ene-2-carboxylate

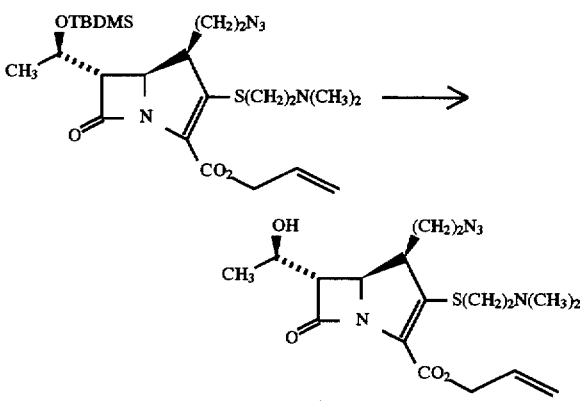

A cold (ice-methanol bath) solution of allyl (4R,5S,6 S)-4-(2"-azidoethyl)-6-[(1'R)-1'- tert-butyldimethylsilyloxyethyl]-3-[(2-N,N-dimethylaminoethyl)thio]-7-oxo-1-azabicyclo[3.2.0] hept-2-ene-2-carboxylate (4.0 g, 7.6 mmol, 37% pure) in tetrahydrofuran was treated first with glacial acetic acid (2.5 mL, 45.6 mmol) and dropwise with a 1M tetrahydrofuran solution of tetrabutylammonium fluoride (22.8 mL, 22.8 mmol). The mixture was allowed to stand at 5° C. for eleven days, then diluted with ethyl acetate (400 mL), washed with ice cold 1M aqueous NaHCO$_3$ (2×25 mL) ice cold water (3×25 mL), brine (25 mL) and dried. The residue was passed through a silica gel flash column (60 g, 10→100% acetone/ ethyl acetate) to give the title compound (473 mg, 41%) as a yellow oil.

IR (CH$_2$Cl$_2$) v$_{max}$: 3610, 3450 (OH), 2110 (N$_3$), 1780 and 1610 cm$^{-1}$ (C=O);

$^1$H NMR (CDCl$_3$, 200 MHz) δ: 6.1–5.9 (1H, m, vinylic H), 5.49–5.22 (2H, m, vinylic H), 4.9–4.6 (2H, m, allylic CH$_2$), 4.235 (1H, dd, J=2.7 Hz, J=9.3 Hz, H-5), 4.33–4.2 (1H, m H-1'), 3.7–3.5 (1H, m, H-4), 3.47–3.3 (2H, m, CH$_2$N$_3$), 3.150 (1H, dd, J=2.7 Hz, J=7.9 Hz, H-6), 3.1–2.9 (2H, m, SCH$_2$), 2.7–2.4 (2H, m, CH$_2$N), 2.284 (6H, s, N(CH$_3$)$_2$), 1.95–1.7 (3H, m, OH, CH$_2$-4) and 1.400 ppm (3H, d, J=6.2 Hz, CH$_3$).

C. (4R,5S,6S)-4-(2"-Azidoethyl)-3-[(2-N,N-dimethylaminoethyl)thio]-6-[(1'R)-1'-hydroxyethyl]-7-oxo-1-azabicyclo[3.2.0]hept-2-ene-2-carboxylic acid

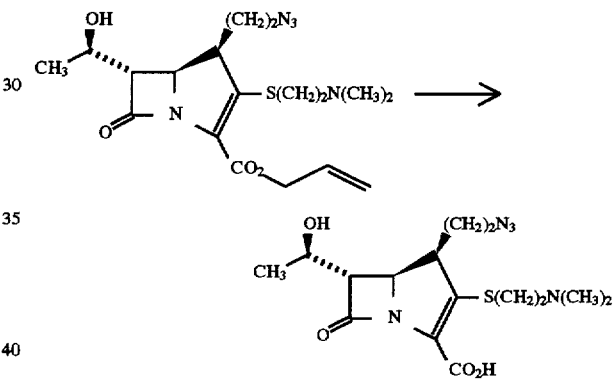

To a cold (ice bath) solution of allyl (4R,5S,6 S)-4-(2"-azidoethyl)-3-[(2-N,N-dimethylamino-ethyl)thio]-6-[(1'R)-1'-hydroxyethyl]-7-oxo-1-azabi-cyclo[3.2.0]hept-2-ene-2-carboxylate (470 mg, 1.14 mmol) in CH$_2$Cl$_2$ (17 mL) was added Pd(PPh$_3$)$_4$ (105 mg, 0.086 mmol) and a 0.5M solution of potassium 2-ethylhexanoate in ethyl acetate (2.28 mL, 1.14 mmol). The mixture was stirred for 15 min, diluted with diethyl ether (100 mL) and extracted with ice cold water (4×20 mL). The organic extracts were combined, washed with diethyl ether (2×40 mL) and passed through a μBondapak C$_{18}$ reversed phase column (67.5 g, water, 1%→10% CH$_3$CN/H$_2$O) to give the title compound (200 mg, 46%) as a yellow lyophilized powder.

IR (Nujol) v$_{max}$: 3400–3100 (OH), 2100 (N$_3$), 1755 and 1600 cm$^{-1}$ (C=O);

$^1$H NMR (D$_2$O, 200 MHz) δ: 4.280 (1H, dd, J=2.4 Hz, J=6.8 Hz, H-5), 4.32–4.2 (1H, m, H-1'), 3.67–3.54 (1H, m, H-4), 3.481 (1H, dd, J=2.7 Hz, J=6.1 Hz, H-6), 3.5–3.34 (2H, m, CH$_2$N$_3$), 3.2–2.92 (4H, m, SCH$_2$ and CH$_2$N), 2.60 (6H, s, N(CH$_3$)$_2$), 2.18–2.02, 1.91–1.75 (2H, 2 sets of m, CH$_2$-4) and 1.329 ppm (3H, d, J=6.1 Hz, CH$_3$).

D. (4R,5S,6S)-3-[(2-N,N-Dimethylaminoethyl)thio]-4-(2"-guanidinoethyl)-6-[(1'R)-1'-hydroxyethyl]-7-oxo-1-azabicyclo[3.2.0]hept-2-ene-2-carboxylic acid, acetic acid salt

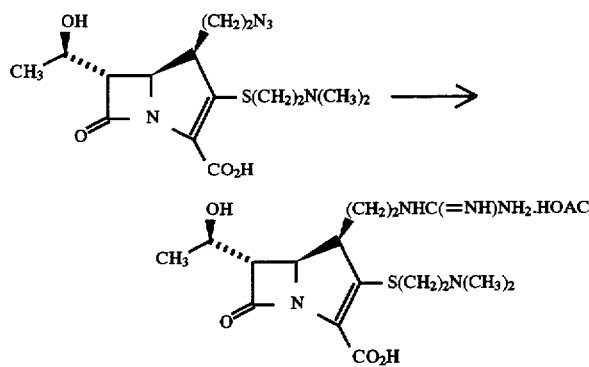

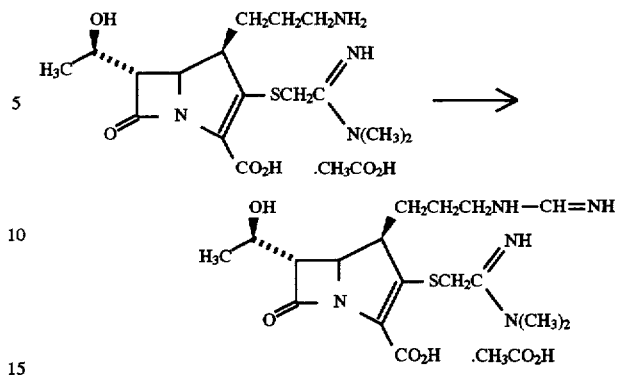

The pH of a cold (ice bath) 0.04M pH 7.0 aqueous phosphate buffer solution (67 mL) of (4R,5S,6 S)-4-(2"-azidoethyl)-3-[(2-N,N-dimethylaminoethyl)thio]-6-[(1'R)-1'-hydroxyethyl]-7-oxo-1- azabicyclo[3.2.0]hept-2-ene- 2-carboxylic acid (190 mg, 0.514 mmol) was adjusted to 5.9 with a 1M aqueous NaH$_2$PO$_4$ solution. The mixture (ice bath) was shaken on a Parr hydrogenator at 45–50 psi of hydrogen for 1 h using 30% Pd/Celite (270 mg) as catalyst. More Pd/Celite was added (270 mg) and the hydrogenation was pursued for one more hour. The catalyst was removed by filtration and washed with water (2×10 mL). The pH of the aqueous solution (ice bath) was adjusted to 7.8–8.0 with a 1N aqueous NaOH solution. Then aminoiminomethanesulfonic acid (354 mg, 2.87 mmol) was added portionwise and the pH was maintained at 7.8–8.0 with the 1N aqueous NaOH solution. The reaction mixture was stirred for a 1.5 h period after which more aminoiminomethanesulfonic acid (124 mg, 1 mmol) was added. The pH was maintained at 7.8–8.0 and the stirring period was pursued for one more hour. At the end of the reaction, the pH was adjusted to 7.0 with a 1.0M aqueous acetic acid solution and the mixture was passed through a µBondapak C$_{18}$ reversed phase column (130 g, ice cold 0.005M aqueous AcOH, 1% CH$_3$CN/0.005M AcOH) to give the title compound (60 mg, 26%) as an off-white lyophilized powder.

Purity: 96.9% as determined by HPLC (r.t.=6.02 min, µBondapak C$_{18}$, 10 µ, 3% CH$_3$CN/KH$_2$PO$_4$ 0.01M, pH 7.4);

UV (H$_2$O) λ$_{max}$: 296 (6089);

IR (Nujol) ν$_{max}$: 3400–3100 (NH, OH), 1760, 1600–1540 (C=O), 1680–1620 cm$^{-1}$ (C=N);

$^1$H NMR (D$_2$O, 200 NH$_2$) δ: 4.33, 4.32 (d, J=2.9 Hz, part of H-5), 4.33–4.2 (m, H-1'and part of H-5), 3.51 (1H, dd, J=2.9 Hz, J=6.6 Hz, H-6), 3.41–3.21 (5H, m, CH$_2$-guanidine, CH$_2$N, H-4), 3.20–2.96 (2H, m, SCH$_2$), 2.91 (6H, s, NCH$_3$), 2.24–2.03, 1.9–1.55 (2H, 2 sets of m, CH$_2$-4), 1.925 (2, 2H, s, CH$_3$CO$_2$) and 1.33 ppm (3H, d, J=6.4 Hz, CH$_3$).

EXAMPLE 142

(4R,5S,6S)-3-[(N,N-Dimethylamidinomethyl)thio]-4-(3"-N-formimidoylaminopropyl)-6-[(1'R)-1'-hydroxyethyl]-7-oxo-1-azabicyclo[3.2.0]hept-2-ene-2-carboxylic acid, acetic acid salt A solution of (4R,5R,6S)-4-(3"-aminopropyl)-3-[(N,N-dimethylamidinomethyl)thio]-6-[(1'R)-1'-hydroxyethyl]-7-oxo-1-azabicyclo[3.2.0]hept-2-ene-2-carboxylic acid, acetic acid salt (0.204 g, 0.474 mmol) in cold water (30 mL, 0°–5° C.) was adjusted to pH 8.5 with 1M aqueous sodium hydroxide and then treated with benzyl formimidate hydrochloride (0.40 g, 2.3 mmol) added in small portions over 5 min while maintaining the pH at 8–8.5 with 1M sodium hydroxide. After 15 min, the pH was adjusted to 5 with concentrated acetic acid and the reaction mixture was washed with ethyl acetate (25 mL). The aqueous phase was maintained under vacuum to remove traces of organic solvent and then chromatographed twice at 4° C. on reversed phase silica gel (µBondapak C$_{18}$, 2.5×14 cm). Elution with 0.01M aqueous acetic acid gave 0.088 g (41%) of the title compound as a white amorphous powder after lyophilization.

Purity by HPLC: 97% on µBondapak C$_{18}$, 3.9 mm/30 cm, elution 3% CH$_3$CN-water, pH 7.4 phosphate buffer, flow rate 0.8 mL/min, UV detector 292 nm, retention time 5.8 min;

UV (water, pH 7.4 phosphate buffer) λ$_{max}$: 292 nm (7.200);

IR (KBr) ν$_{max}$: 1750 (C=O of β-lactam), 1715, 1645 and 1590 cm$^{-1}$ (C=O of carboxylate);

$^1$H NMR (200 MHz, D$_2$O) δ: 1.32 (d, J=6.32 Hz, 3H, CH$_3$CHO), 1.4–1.9 (m, 4H, CH$_2$-1 and 2 of propyl), 1.92 (s, CH$_3$CO$_2$H), 3.12 and 3.28 (2×s, 2×3H, NCH$_3$), 3.0–3.6 (m, 4H, H-4, H-6 and CH$_2$-3 of propyl), 3.84 (s, 2H, SCH$_2$), 4.2–4.4 (m, 2H, H-5 and CH$_3$CHO overlapping) and 7.81 ppm (s, 1H, CH=NH).

EXAMPLE 143

(4R,5R,6S)-4-(3"-N-Formimidoylaminopropyl)- 3-[(2-quanidinoethyl)thio]-6-[(1'R)-1'-hydroxyethyl]-7-oxo-1-azabicyclo[3.2.0]hept-2-ene-2-carboxylic acid, acetic acid salt

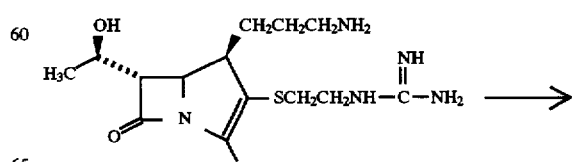

-continued

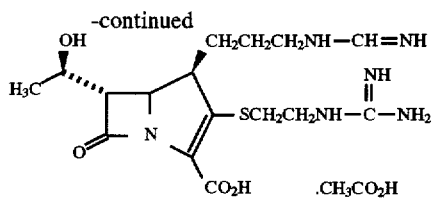

A solution of (4R,5S,6S)-4-(3"-aminopropyl)-3-[(2-guanidinoethyl)thio]-6-[(1'R)-1'-hydroxyethyl]-7-oxo-1-azabicyclo[3.2.0]hept-2-ene-2-carboxylic acid, acetic acid salt (0.300 g, 0.695 mmol) in cold water (30 mL, 0°–5° C.) was adjusted to pH 8.5 with 1M aqueous sodium hydroxide and then treated with benzyl formimidate hydrochloride (0.60 g, 3.5 mmol) added in small portions over 5 min. The pH was maintained at 8–8.5 with 1M sodium hydroxide throughout the addition and for another 15 min. The pH was then adjusted to 5 with concentrated acetic acid and the reaction mixture was washed with ethyl acetate (20 mL). The aqueous phase was then maintained under vacuum to remove traces of organic solvent and then chromatographed at 4° C. on reversed phase silica gel (μBondapak $C_{18}$, 2.5×15 cm). Elution with 0.01M aqueous acetic acid gave 0.190 g (59%) of the title carbapenem as a white amorphous solid after lyophilization: $[\alpha]^{22}_D$+26.6° (c 1.0, water).

Purity by HPLC: 97% on μBondapak $C_{18}$, 3.9 mm×30 cm, elution 2% $CH_3CN$-water, pH 7.4 phosphate buffer, flow rate 1 mL/min, UV detector 300 nm, retention time 6.1 min.;

UV (water, pH 7.4 phosphate buffer) $\lambda_{max}$: 302 nm (8,677);

IR (KBr) $\nu_{max}$: 1755 (C=O of β-lactam), 1710, 1670, 1620 and 1580 cm$^{-1}$ (C=O of carboxylate);

$^1$H NMR (200 MHz, $D_2O$) δ: 1.32 (d, J=6.33 Hz, 3H, $\underline{CH_3}$CHO), 1.4–2.0 (m, 4H, $CH_2$-1 and 2 of propyl), 1.93 (s, $CH_3CO_2H$), 2.8–3.2 (m, 2H, $SCH_2$), 3.3–3.5 (m, 6H, H-4, H-6, $CH_2$-3 of propyl and $SCH_2\underline{CH_2}N$), 4.2–4.4 (m, 2H, H-5 and $CH_3\underline{CHO}$) and 7.8 ppm (s, 1H, $\underline{CH}$=NH).

EXAMPLE 144

(4R,5S,6S)-3-[(2-Guanidinoethyl)thio]-4-(3"-guanidinopropyl)-6-[(1'R)-1'-hydroxyethyl]-7-oxo-1-azabicyclo[3.2.0]hept-2-ene-2-carboxylic acid, acetic acid salt

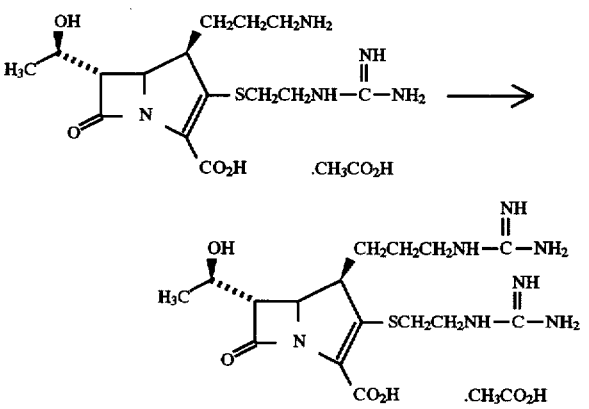

A solution of (4R,5R,6S)-4-(3"-aminopropyl)-3-[(2-guanidinoethyl)thio]-6-[(1'R)-1'-hydroxyethyl]-7-oxo-1-azabicyclo[3.2.0]hept-2-ene-2-carboxylic acid, acetic acid salt (0.300 g, 0.695 mmol) in cold water (30 mL, 0°–5° C.) was adjusted to pH 8.5 with 1N aqueous sodium hydroxide and then treated with aminoiminomethanesulfonic acid (0.43 g, 3.46 mmol) added in small portions over 5 min. The pH was maintained at 8.0–8.5 throughout the addition and for another 2 h with 1M sodium hydroxide. The pH was then adjusted to 5 with glacial acetic acid and the solution was chromatographed on reversed phase silica gel (μBondapak $C_{18}$, 2.5×15 cm). Elution with 0.01M aqueous acetic acid gave 0.213 g (64%) of the title carbapenem as a white amorphous solid after lyophilization: $[\alpha]^{22}_D$+11.3° (c 1.0, water).

Purity by HPLC: 99% on μBondapak $C_{18}$, 3.9 nm×30 cm, elution 2% $CH_3CN$—$H_2O$, pH 7.4 phosphate buffer, flow rate 1 mL/min, UV detector 300 nm, retention time 10.4 min;

UV (water, pH 7.4 phosphate buffer) $\lambda_{max}$: 302 nm (10,260);

IR (KBr) $\nu_{max}$: 1755 (C=O of β-lactam), 1670, 1630 and 1580 cm$^{-1}$ (C=O of carboxylate);

$^1$H NMR (200 MHz, $D_2O$) δ: 1.32 (d, J=6.38 Hz, 3H, $\underline{CH_3CH_3}$CHO), 1.4–2.0 (m, 4H, $CH_2$-1 and 2 of propyl), 1.92 (s, $CH_3CO_2H$), 2.8–3.2 (m, 2H, $SCH_2$), 3.2–3.6 (m, 6H, H-4, H-6, $CH_2$-3 of propyl and $SCH_2\underline{CH_2}N$), 4.23 (dd, $J_{H5,H6}$=2.49 Hz, $J_{H5,H4}$=9.2 Hz, 1H, H-5) and 4.27 ppm (m overlapping with H-5, 1H, $CH_3\underline{CHO}$).

EXAMPLE 145

(4R,5S,6S)-6-[(1'R)-1'-Hydroxyethyl]-3-[(2-cyanoethyl)thio]-4-[2"-(L-alanyl)-aminoethyl]-7-oxo-1-azabicyclo[3.2.0]hept-2-ene-2-carboxylic acid

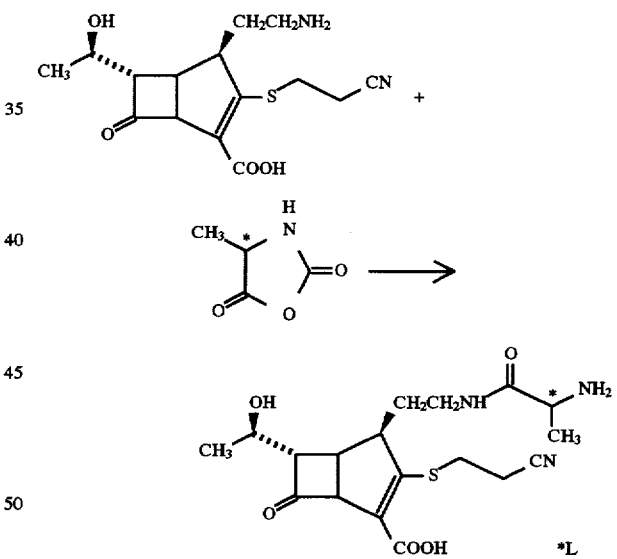

A solution of (4R,5S,6S)-6-[(1'R)-1'-hydroxyethyl]-3-[(2-cyanoethyl)thio]-4-(2"-aminoethyl)-7-oxo-1-azabicyclo[3.2.0]hept-2-ene-2-carboxylic acid (0.512 g, 1.57 mmol) in 0.2M pH 7.0 phosphate buffer (15 mL) was cooled to 0° C. while bubbling Argon through the solution. The pH was adjusted to 10.2 with 1N NaOH and N-carboxyanhydride of L-alanine (0.181 g, 1.57 mmol) in dioxane (1.5 mL) was added in one portion with vigorous stirring. When the pH dropped to 7.2, it was readjusted to 10.2 and left there for 1 h. The reaction was stopped by adjusting the pH to 6.0 with 1N HCl. Argon was bubbled through the solution for 30 min at 0° C. while readjusting the pH to 6.0 whenever it rose above 6.0. The crude reaction mixture was passed through a column of μBondapak $C_{18}$ reverse phase silica (4.5×11.5 cm). Appropriate fractions belonging to the product were combined and lyophilized to a solid which was rechromatographed on μBondapak $C_{18}$ reverse phase silica (4.5×11 cm). The slightly more polar title compound, separated very closely from the dipeptide derivative, was eluted with a mixture of water and $CH_3CN$ (97:3, gradient elution) and was obtained as a yellow fluffy solid after lyophilization (0.099 g, 15.9%).

Purity 96.5% by HPLC: UV detection at 300 nm on μBondapak $C_{18}$ (4 mm×30 cm), 5% $CH_3CN$ in pH 6.8 phosphate buffer, flow rate 0.6 mL/min, retention time 7.25 min.

UV $\lambda_{max}$: 300;

IR (Nujol) $v_{max}$: 1750 $cm^{-1}$ (C=O, β-lactam).

$^1$H NMR (200 MHz, $D_2O$) δ: 1.38 (d, 3H, $CH_3$, J=6.4 Hz,), 1.47 (d, 3H, $CH_3$, J=7.0 Hz), 1.52-1.77; 1.97-2.11 (m, 2H, $CH_2$), 2.82-2.89 (overlap, 2H, $CH_2CN$), 2.91-3.17 (overlap, 2H, $SCH_2$), 3.27-3.43 (overlap, 3H, $CH_2N$, H-4), 3.59 (dd, 1H, H-6, $J_{5,6}$=2.66 Hz, $J_{6,1}$=6.06 Hz), 3.91 (q, 1H, $C_\alpha H$, $J_{\alpha,CH3}$=7.02 Hz), 4.74-4.96 (overlap, 2H, H-5, H-1').

EXAMPLE 146

(4R,5S,6S)-6-[(1'R)-1'-Hydroxyethyl]-3-[(2-cyanoethyl)thio]-4-[2"-(L-alanyl-L-alanyl)-aminoethyl]-7-oxo-1-azabicyclo-[3.2.0]hept-2-ene-2-carboxylic acid

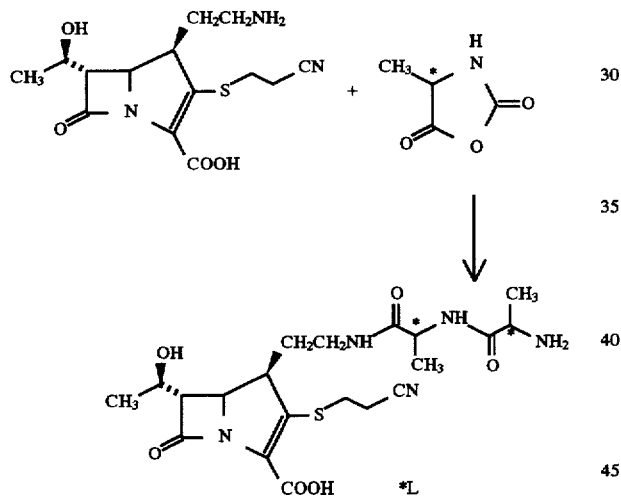

A solution of (4R,5S,6S)-6-[(1'R)-1'-hydroxyethyl]-3-[(2-cyanoethyl)thio]-4-(2"-aminoethyl)-7-oxo-1-azabicyolo-[3.2.0]hept-2-ene-2-carboxylic acid (0.512 g, 1.57 mmol) in 0.2M pH 7.0 phosphate buffer (15 mL) was cooled to 0° C. while bubbling Argon through the solution. The pH was adjusted to 10.2 with 1N NaOH and N-carboxyanhydride of L-alanine (0.181 g, 1.57 mmol) in dioxane (1.5 mL) was added in one portion with vigorous stirring. When the pH dropped to 7.2, it was readjusted to 10.2 and left there for 1 h. The reaction was stopped by adjusting the pH to 6.0 with 1N HCl. Argon was bubbled through the solution for 30 min at 0° while readjusting the pH to 6.0 whenever it rose above 6.0. The crude reaction mixture was passed through a column of μBondapak $C_{18}$ reverse phase silica (4.5×11.5 cm). Appropriate fractions belonging to the product were combined and lyophilized to a solid which was rechromatographed on μBondapak $C_{18}$ reverse phase silica (4.5×11 cm). The slightly less polar title compound, separated very closely from the monopeptide derivative, was eluted with a mixture of water and $CH_3CN$ (96:4, gradient elution) and was obtained as a yellowish fluffy solid after lyophilization (0.069 g, 9.4%).

Purity 96.6% by HPLC: UV detection at 300 nm on μBondapak $C_{18}$ (4 mm×30 cm), 5% $CH_3CN$ in pH 6.8 phosphate buffer, flow rate 0.6 mL/min, retention time 9.1 min.

UV $\lambda_{max}$: 300 nm.

IR (Nujol) $v_{max}$: 1750 $cm^{-1}$ (C=O, β-lactam);

$^1$H NMR (200 MHz, $D_2O$) δ: 1.37 (d, 3H, $CH_3$, J=6.45 Hz), 1.42 (d, 3H, $CH_3$, J=7.39 Hz), 1.46 (d, 3H, $CH_3$, J=8.85 Hz), 1.59-1.75; 1.99-2.14 (m, 2H, $CH_2$), 2.84-2.89 (overlap, 2H, $CH_2CN$), 2.92-3.22 (overlap, 2H, $SCH_2$), 3.3-3.42 (overlap, 3H, $CH_2N$, H-4), 3.59 (dd, 1H, H-6, $J_{5,6}$=2.56 Hz, $J_{6,1}$=5.88 Hz), 3.9 (br, 1H, $C_\alpha H$), 4.25-4.34 (overlap, 3H, H-5, H-1'$C_\alpha H$).

EXAMPLE 147

(4R,5S,6S)-4-(3"-Aminopropyl)-3-[(3-azetidinyl)thio]-6-[(1'R)-1'-hydroxyethyl]-7-oxo-1-azabicyclo[3.2.0]hept-2-ene-2-carboxylic acid

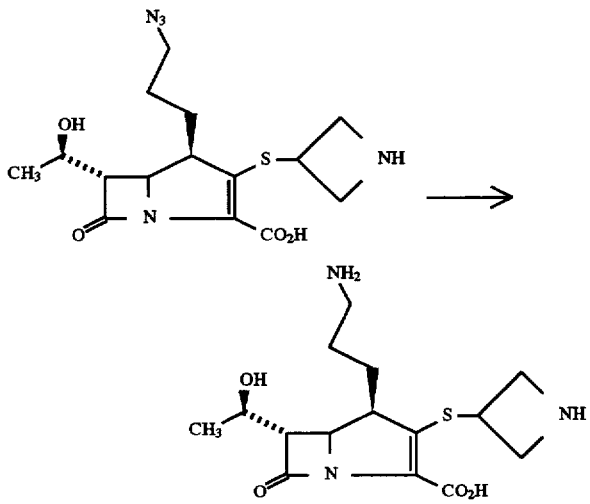

A cold (5° C.) solution of (4R,5S,6S)-4-(3"-azidopropyl)-3-[(3-azetidinyl)thio]-6-[(1'R)-1'-hydroxyethyl]-7-oxo-1-azabicyclo[3.2.0]hept-2-ene-2-carboxylic acid (0.235 g, 0.64 mmol) in water (75 mn) was hydrogenated over 5% Pd/$Al_2O_3$ (0.235 g) under a pressure of 45 psi. After 1 hour, the used catalyst was replaced by some fresh catalyst (0.235 g) and the hydrogenation resumed for one additional hour. At that point, the reaction mixture was filtered, acidified to pH 5.7 with AcOH and finally chromatographed on reversed phase silica gel (Partisil) eluting with water. The material obtained after lyophilization required two additional chromatograph purifications to obtain 0.045 g (17.5%) of the title compound of good purity.

IR (Nujol) $v_{max}$: 1750 $cm^{-1}$ (β-lactam);

$^1$H NMR ($D_2O$) δ: 4.00-4.15 and 4.50-4.70 (4H, 2m, 2H-2, 2H-4 of azetidine), 4.15-4 20 (3H, m, H-5, H-1'CH—S), 3.47 (1H, dd, J=2.72, J=6.33, H-6), 3.00-3.25 (3H, m, $CH_2$—N, H-4), 1.50-1.95 (4H, m, 2H-1", 2H-2"), 1.38 (3H, d, J=6.34, —$CH_3$').

EXAMPLE 148

Potassium (4R,5S,6S)-4-(2"-hydroxyethyl)-6-[(1'R)-1'-hydroxy-ethyl]-3-[(imidazol-4-yl]methylthio]-7-oxo-1-azabicyclo[3.2.0]-hept-2-ene-2-carboxylate

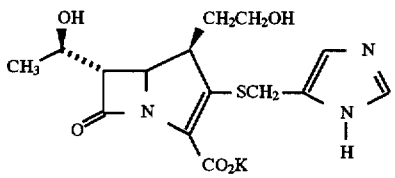

A. Allyl (4R,5S,6S)-6-[(1'R)-1'-tert-butyldimethylsilyloxyethyl]-4-(2"-tert-butyldimethylsilyloxyethyl)-3-[(imidazol-4-yl)methylthio]-7-oxo-1-azabicyclo-[3.2.0]hept-2-ene-2-carboxylate

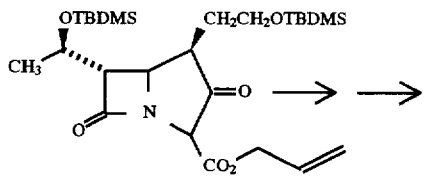

A solution of allyl (4R,5R,6S)-6-[(1'R)-1'-tert-butyldimethylsilyloxyethyl]-4-(2"-tert-butyldimethylsilyloxyethyl)-3,7-dioxo-1-azabicyclo[3.2.0] heptane 2-carboxylate (9.03 mmol, prepared by cyclization of 5.00 g, 9.03 mmol of diazo precursor) in dry acetonitrile (60 mL) was cooled to 0°–5° C. and treated under nitrogen with diphenyl chlorophosphate (2.1 mL, 10.1 mmol) and N,N-diisopropylethylamine (1.7 mL, 9.8 mmol) added simultaneously over 5 min. A small crystal of 4-N,N-dimethylaminopyridine was then added and the mixture was stirred for 1 h. The solution was then cooled to –20° C. and then treated with more N,N-diisopropylethylamine (2.3 mL, 13.2 mmol) followed by 1.22 g (10.7 mmol) of 4(5)-(mercaptomethyl)imidazole in acetonitrile (10 mL). After 3 h at –20° C. and 1 h at 0° C., the reaction mixture was diluted with ethyl acetate (500 mL), washed with saturated sodium bicarbonate, brine, dried (MgSO₄) and evaporated under reduced pressure. The residue was chromatographed on silica gel (5×10 cm). Elution with a mixture of toluene and ethyl acetate (8:2) gave first 5.0 g (73%) of recovered enol phosphate. Then elution with ethyl acetate gave 1.35 g (24%) of the title compound as an oil. By $^1$H NMR this material contained 25% of open product resulting from cleavage of the β-lactam by the thiol.

IR (NaCl, film) ν$_{max}$: 1772 (C=O of β-lactam) and 1708 cm$^{-1}$ (C=O of ester);

$^1$H NMR (200 MHz, CDCl₃) δ: 0.5 (SiCH₃), 0.9 (Si-t-Bu), 1.27 (d, J=6.13H, CH₃CHO), 1.6–2.2 (m, CH₂CH₂OSi), 3.09 (dd, J$_{H8,H6}$=2.45 Hz, J$_{H6,H1}$=6.63 Hz, H-6), 3.5–4.3 (m, H-4, H-5, SCH₂, CH₃CHO, CH₂CH₂OSi), 4.7 (m, CH₂ of allyl), 5.1–5.5 and 5.8–6.1 (2m, CH of allyl), 6.9 (s, H-5 of imidazole) and 7.6 ppm (s, H-2 of imidazole).

B. Allyl (4R,5S,6S)-6-[(1'R)-1'-hydroxyethyl]-4-(2"-hydroxyethyl)-3-[(imidazol-4-yl]methylthio]-7-oxo-1-azabicyclo[3.2.0]hept-2-ene-2-carboxylate

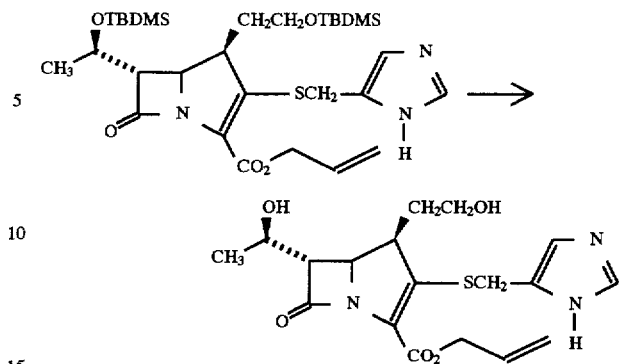

A solution of allyl (4R,5S,6S)-6-[(1'R)-1'-tert-butyldimethylsilyloxyethyl]-4-(2"-tert-butyldimethylsilyloxyethyl)-3-[(imidazol-4-yl)methylthio]-7-oxo-1-azabicyclo[3.2.0]hept-2-ene-2-carboxylate (2.65 g, 4.26 mmol) in tetrahydrofuran (60 mL) was cooled to 0°–5° C. and treated with glacial acetic acid (3.0 mL, 52.4 mmol) followed by 26 mL (26.0 mmol) of a 1.0M solution of tetrabutylammonium fluoride in tetrahydrofuran. The solution was then stored at 5° C. for twelve days. The reaction mixture was then diluted with ethyl acetate (300 mL), washed with saturated sodium bicarbonate, brine and dried. Evaporation of the solvent under reduced pressure gave an oil which was chromatographed on a silica gel pad (5×5 cm) using a gradient of methanol (0–20%) in ethyl acetate as eluent. The product obtained (0.37 g, 20%) contained some tetrabutylammonium salt and was used as such for the deprotection step.

IR (NaCl, film) ν$_{max}$: 1765 (C=O of β-lactam) and 1700 cm$^{-1}$ (C=O of ester).

C. Potassium (4R,5S,6S)-4-(2"hydroxyethyl)-6-[(1'R)-1'-hydroxyethyl]-3-[(imidazol-4-yl)methylthio]-7-oxo-1-azabicyclo[3.2.0]hept-2-ene-2-carboxylate

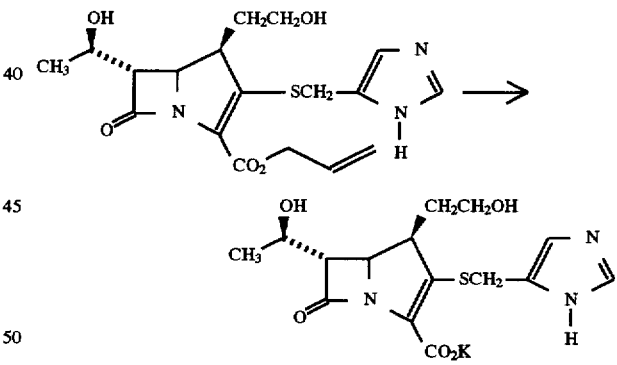

A solution of allyl (4R,5S,6S)-6-[(1'R)-1'-hydroxyethyl]-4-(2"-hydroxyethyl)-3-[(imidazol-4-yl)methylthio]-7-oxo-1-azabicyclo[3.2.0]-hept-2-ene-2-carboxylate (0.37 g, 0.94 mmol) in dry dichloromethane (20 mL) was treated at 22° C. and under nitrogen with tetrakis(triphenylphosphine) palladium[0] and 2.1 mL (1.25 mmol) of a 0.5M solution of potassium 2-ethylhexanoate in ethyl acetate. After 1.2 h, the reaction mixture was extracted with water (2×50 mL) and the combined aqueous extract was chromatographed twice on reversed phase silica gel (μBondapak C₁₈, 3×15 cm) using water as eluent. Lyophilization of the UV active fractions gave 0.081 g (22%) of the title carbapenem as a white amorphous solid:

Purity by HPLC: 100% on μBondapak C₁₈, 3.9 mm×30 cm, elution pH 7.0 phosphate buffer, flow rate 1.5 ml/min, UV detector 300 nm, retention time 9.04 min;

UV (water, pH 7.4 phosphate buffer) $\lambda_{max}$: 304 nm (10,153);

IR (KBr) $v_{max}$: 1750 (C=O of β-lactam) and 1590 cm$^{-1}$ (C=O of carboxylate);

$^1$H NMR (200 MHz, D$_2$O) δ: 1.30 (d, J=6.37 Hz, 3H, C$\underline{H}_3$CHO), 1.5–2.1 (2M, 2H, C$\underline{H}_2$CH$_2$OH) 3.3–3.5 (m, 2H, H-6 and H-4 overlapping), 3.5–3.8 (m, 2H, CH$_2$C$\underline{H}_2$OH), 4.03 (ABq, J$_{AB}$=14.6 Hz, αv=37.0 Hz, 2H, SCH$_2$), 4.13 (dd overlapping with SCH$_2$, J$_{H5,H6}$=2.53 Hz, J$_{H5,H4}$9.60 Hz, 1H, H-5), 4.24 (m, 1H, CH$_3$C$\underline{H}$O), 7.10 (s, 1H, H-5 of imidazole) and 7.79 ppm (s, 1H, H-2 of imidazole).

EXAMPLE 149

(4R,5S,6S)-4-(3"-Azidopropyl)-3-[(3R)-3-pyrrolidinylthio]-6-[(1'R)-1'-hydroxyethyl]-7-oxo-1-azabicyclo[3.2.0]hept-2-ene-2-carboxylic acid

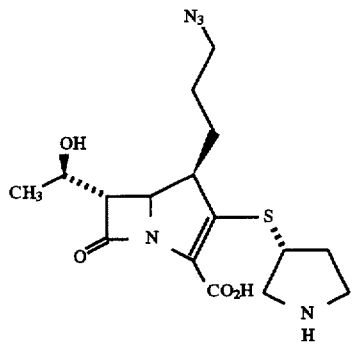

A. (3R)-N-Allyloxycarbonyl-3-hydroxypyrrolidine

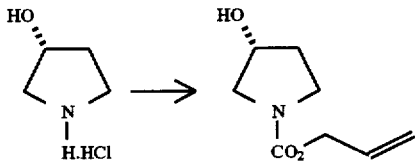

3(R)-Hydroxypyrrolidine .HCl salt (8.0 g, 64.7 mmol) was dissolved in cold (5° C.) 1N NaOH (130 mL, 130 mmol) and treated dropwise with a solution of allyl chloroformate (9.4 g, 77.7 mmol) in acetone (80 mL). The mixture was stirred for 15 min after completion of the addition and then most of the acetone evaporated. The aqueous solution was then extracted with ethyl acetate. The organic extracts were washed with brine, dried (MgSO$_4$) and evaporated. The crude carbamate was purified by chromatography (SiO$_2$/Et$_2$O then EtOAc and CH$_3$CN) to yield 6.28 g (56.7%) of the title compound as a mobile oil.

IR (CH$_2$Cl$_2$) $v_{max}$: 3603, 3440 (—OH), 1697 (—CO$_2$), 1650 (>=<).

$^1$H NMR (CDCl$_3$) δ: 4.8–6.1 (5H, allyl pattern), 4.48 (1H, broad s, H-3), 3.40–3.60 (4H, m, 2H-2, 2H-5), 1.80–2.10 (3H, m, 2H-4, —OH).

B. (3S)-N-Allyloxycarbonyl-3-hydroxypyrrolidine

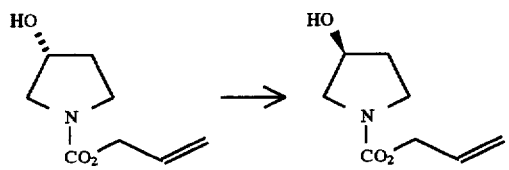

A cold solution (5° C.) of (3R)-N-allyloxycarbonyl-3-hydroxypyrrolidine (2.16 g, 12.62 mmol) in CH$_2$Cl$_2$ was treated with pyridine (1.15 g, 14.5 mmol) and trifluoromethanesulfonic anhydride (4.09 g, 14.5 mmol). After stirring for 15 min, the solvent was evaporated, the residue triturated in diethyl ether and filtered. The filtrate was then evaporated, the crude triflate dissolved in cold (5° C.) CH$_2$Cl$_2$ and treated with a preformed solution of formic acid (0.87 g, 18.93 mmol) and triethylamine (1.9 g, 18.93 mmol) in CH$_2$Cl$_2$. The ice bath was removed and the solution stirred at room temperature for 45 min. Then the reaction mixture was washed with cold water and brine. After drying (MgSO$_4$), the solvent was evaporated and the crude formate purified by chromatography (SiO$_2$; 10% CH$_3$CN in CH$_2$Cl$_2$) to yield 2.13 g (84.7%). This purified material was dissolved in cold (5° C.) tetrahydrofuran and 1N NaOH (11 mL, 11 mmol) was added dropwise. After stirring for 10 min, the reaction mixture was neutralized with HCl, diluted with EtOAc and washed with cold water and brine. After evaporation of the solvent, the product was chromatographed (SiO$_2$/EtOAc) to yield 1.51 g (82.5%) of the title compound.

IR (CH$_2$Cl$_2$) $v_{max}$: 3605, 3440 (—OH), 1695 (—CO$_2$$^-$), 1650 cm$^{-1}$ (>=<).

$^1$H NMR (CDCl$_3$) δ: 4.40–6.10 (5H, allyl pattern), 4.50 (1H, m, H-3), 3.40–3.70 (4H, m, 2H-2, 2H-5), 1.90–2.10 (2H, m, 2H-4). [α]$^{20}$$_D$: +26.9 (130 mg/100 mL, MeOH).

C. (3R) N-Allyloxycarbonyl-3-mercaptopyrrolidine

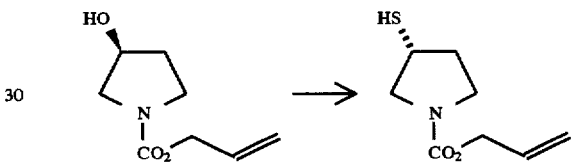

A cold solution (5° C.) of (3S) N-allyloxycarbonyl-3-hydroxypyrrolidine (1.51 g, 8.82 mmol) in CH$_2$Cl$_2$ was treated with pyridine (0.80 g, 10.14 mmol) followed by trifluoromethanesulfonic anhydride (2.86 g, 10.14 mmol). After stirring for 15 min, the solvent was evaporated, the residue triturated in diethyl ether and filtered after evaporating the filtrate, the crude triflate was redissolved in cold (5° C.) CH$_3$CN and while bubbling H$_2$S into the solution, triethylamine (1.07 g, 10.58 mmol) was added dropwise. The starting material disappeared in 30 min. The solvent was then evaporated and the crude thiol purified by chromatography (SiO$_2$/CH$_2$Cl$_2$) to yield 1.25 (75.7%) of the title compound.

1H NMR (CDCl$_3$) δ: 4.60–6.10 (5H, allyl pattern), 3.20–3.90 (5H, m, H-3, 2H-2, 2H-5), 2.20–2.40 (1H, m, H-5), 1.80–2.00 (1H, m, H-5), 1.71 (1H, d, J=6.65, SH).

D. Allyl (4R,5S,6S)-4-(3"-azidopropyl)-3-[(3R)-N-(allyloxycarbonyl)-3-pyrrolidinylthio]-6-[(1'R)-1'-hydroxyethyl]-7-oxo-1-azabicyclo[3.2.0]hept-2-ene-2-carboxylate

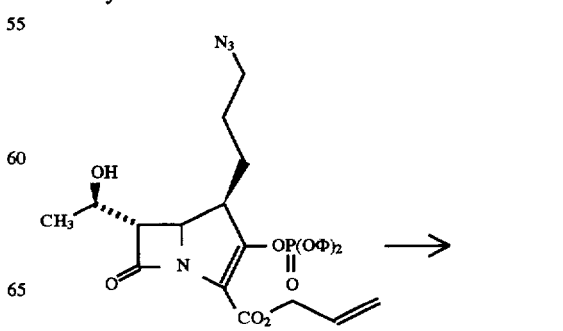

313
-continued

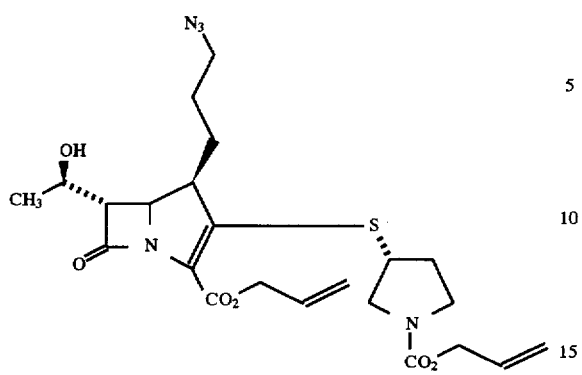

A cold (5° C.) solution of allyl (4R,5S,6S)-4-(3"-azidopropyl)-3-(diphenylphosphono)-6-[(1'R)-1'-hydroxyethyl]-7-oxo-1-azabicyclo[3.2.0]hept-2-ene-2-carboxylate (1.85 g, 3.25 mmol) in DMF (35 mL) was treated with (3R) N-allyloxycarbonyl-3-mercaptopyrrolidine (1.25 g, 6.68 mmol) followed by diisopropylethylamine (0.863 g, 6.68 mmol). The ice bath was removed and after stirring at room temperature for 15 h, the solution was diluted with diethyl ether (90 mL) and washed three times with cold brine. After drying ($MgSO_4$) the organic solution was evaporated and the crude carbapenem purified by chromatography ($SiO_2$, 30% $CH_3CN$ in $CH_2Cl_2$) to yield 1.27 g (77.1%) of the title compound.

IR ($CH_2Cl_2$) $v_{max}$: 3610 (—OH) 2105 (—$N_3$) 1778 (β-lactam), 1700 (—$CO_2^-$), 1650 $cm^{-1}$ (>=<).

$^1$H NMR ($CDCl_3$) δ: 4.5–6.10 (10H, 2 allyl patterns), 4.15–4.30 (2H, m, H-5, H-1), 3.70–3.90 (2H, m, H-4, C—S—), 3.10–3.70 (7H, m, H-6, —$CH_2N_3$, —($CH_2$)$_2$N—), 1.40–2.40 (6H, m, 2H-1", 2H-2", 2H-4 of pyrrolidine), 1.40 (3H, d, J=6.23, —$CH_3$').

E. (4R,5S,6S)-4-(3"-Azidopropyl)-3-[(3R)-3-pyrrolidinylthio]-6-[(1'R)-1'-hydroxyethyl]-7-oxo-1-azabicyclo-[3.2.0]hept-2-ene-2-carboxylic acid

314
-continued

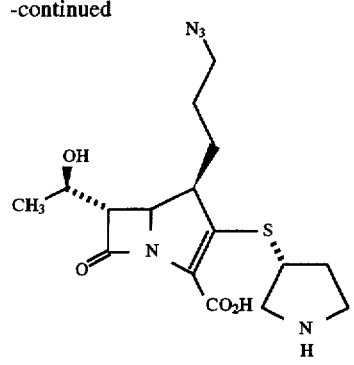

A cold (5° C.) solution of allyl (4R,5S,6S)-4-(3"-azidopropyl)-3-[(3R)-N-(allyloxycarbonyl)-3-pyrrolidinylthio]-6-[(1'R)-1'-hydroxyethyl]-7-oxo-1-azabicyclo[3.2.0]-hept-2-ene-2-carboxylate (0.932 g, 1.84 mmol) in EtOAc (50 mL) was treated with 0.5M sodium ethylhexanoate (11.04 mL, 5.52 mmol) and ($PPh_3$)$_4$Pd (0.90 g). The solution was stirred for 20 h at 5° C. then diluted with EtOAc and extracted with cold water. The aqueous extracts were acidified to pH ~7.0 with AcOH and chromatographed on reversed phase silica gel (partisil). Elution was done with 0–25% $CH_3CN$ in water to yield 15 mg (2.1%) of the title compound. [The major product isolated was the corresponding mono deprotected ester, (31%)].

$^1$H NMR (D2O) δ: 4.20–4.40 (2H, m, H-5, H-1'), 3.95 (1H, m, —CH—S), 2.96–3.42 (1H, m, H-4), 3.1–3.42 (7H, m, H-6, —$CH_2N_3$, —($CH_2$)$_2$N—), 1.50–2.50 (6H, m, 2H-1", 2H-2", 2H-4 of pyrrolidine), 1.33 (3H, d, J-6.37, —$CH_3$').

EXAMPLE 150

(4R,5S,6S)-4-(3"-Aminopropyl)-3-[(3R)-3-pyrrolidinylthio]-6-[(1'R)-1'-hydroxyethyl]-7-oxo-1-azabicyclo[3.3.0]hept-2-ene-2-carboxylic acid

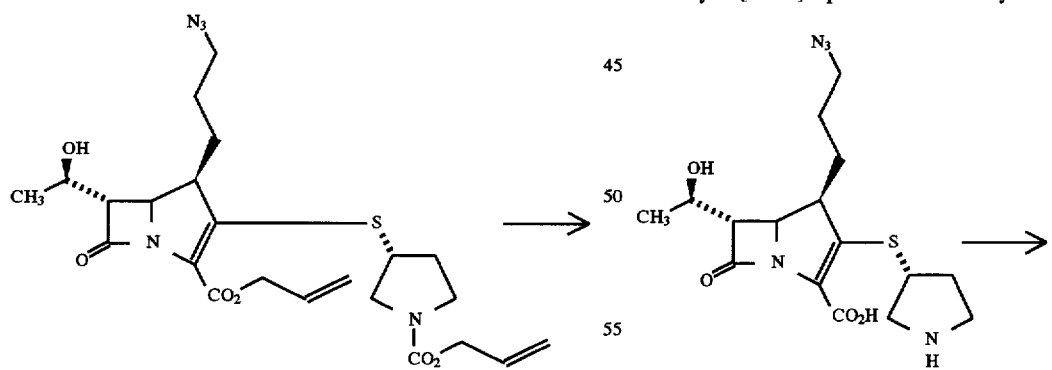

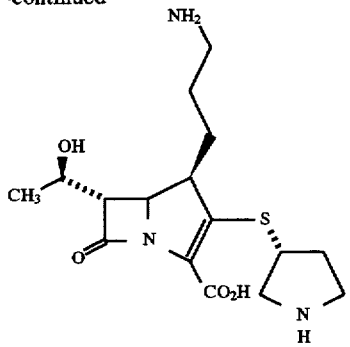

A solution of (4R,5S,6S)-4-(3"-azidopropyl)-3-[(3R)-3-pyrrolidinylthio]-6-[(1'R)-1'-hydroxyethyl]-7-oxo-1-azabicyclo[3.2.0]hept-2-ene-2-carboxylic acid (0.54 g, 0.142 mmol) in cold water (15 mL) was hydrogenated at 5° C. for 1 h at 60 psi of hydrogen in the presence of 5% Pd/Al$_2$O$_3$ (60 mg). Then the catalyst was filtered off and the filtrate acidified to pH=5.5 with acetic acid. Chromatography on reversed phase silica gel (partisil) of this acidified solution gave 30 mg (50.9%) of the title compound as its acetic acid salt.

IR (Nujol) v$_{max}$: 1750 cm$^{-1}$ (β-lactam), 1590 (—CO$_2^{-1}$).

$^1$H NMR (D$_2$O) δ: 4.20–4.40 (2H, m, H-5, H-1'), 3.90–4.10 (1H, m, —CH—S), 3.60–3.70 (1H, m, H-4), 3.20–3.50 (5H, m, H-6, (—CH$_2$)$_2$N—), 3.05 (2H, m, CH$_2$—N—), 1.50–2.60 (6H, m, 2H-1", 2H-2", 2H-4 of pyrrolidine), 1.33 (3H, s, J=6.40, —CH$_3^1$), 1.92 (3H, s, acetic acid).

EXAMPLE 151

Potassium (4R,5S,6S)-4-(2"-azidoethyl)-6-[(1'R)-1'-hydroxyethyl]-3-[(imidazol-4-yl)methylthio]-7-oxo-1-azabicyclo[3.2.0]hept-2-ene-2-carboxylate

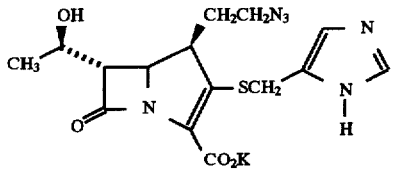

A. Allyl (4R,5S,6S)-4-(2"-azidoethyl)-6-[(1'R)-1'-tert-butyldimethylsilyloxyethy -3-[(imidazol-4-yl)methylthio]-7-oxo-1-azabicyclo[3.2.0]hept-2-ene2-carboxylate

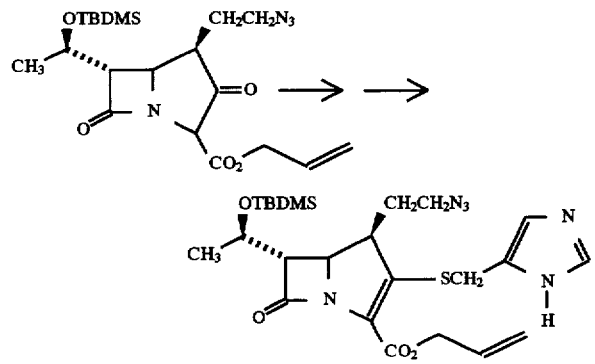

A solution of allyl (4R,5R,6S)-4-(2"-azidoethyl)-6-[(1'R)-1'-tert-butyldimethylsilyloxyethyl]-3,7-dioxo-1-azabicyclo[3.2.0]heptane-2-carboxylate (10.7 mmol, prepared by cyclization of 5.0 g, 10.7 mmol of diazo precursor) in dry acetonitrile (75 mL) was cooled to 0°–5° C. and treated with diphenyl chlorophosphate (2.45 mL, 11.8 mmol) and N,N-diisopropylethylamine (2.06 mL, 11.8 mmol) added simultaneously over 5 min. A small crystal of 4-N,N-dimethylaminopyridine was added and the mixture was stirred for 1 h. The mixture was then cooled to –20° C. and treated with more N,N-diisopropylethylamine (2.06 mL, 11.8 mmol) followed by a solution of 4(5)-(mercaptomethyl) imidazole (1.50 g, 13.1 mmol) in acetonitrile (10 mL). The solution was slowly warmed up to 0°–5° C. and stirred for 3 h. The reaction mixture was then diluted with ethyl acetate (300 mL) washed with saturated sodium bicarbonate, brine and dried (MgSO$_4$). The solvent was evaporated under reduced pressure and the residue was chromatographed on silica gel (5×10 cm). Elution with a mixture of toluene and ethyl acetate (8:2) first gave 3.38 g (47%) of intermediate enol phosphate. Further elution with ethyl acetate gave 1.45 g (25%) of the title compound as an oil.

IR (NaCl, film) vmax: 2100(N$_3$) and 1765 cm$^{-1}$ (C=O of β-lactam).

Allyl (4R,5S,6S)-4-(2"-azidoethyl)-6-[(1'R)-1'-hydroxyethyl]-3-[(imidazol-4-yl)methylthio]-7-oxo-1-azabicyclo[3.2.0]hept-2-ene-2-carboxylate

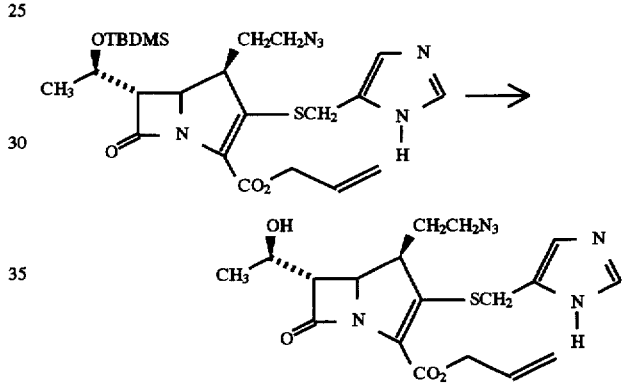

A solution of allyl (4R,5S,6S)-4-(2"-azidoethyl)-6-[(1'R)-1'-tert-butyldimethylsilyloxyethyl)-3-[(imidazol-4-yl) methylthio]-7-oxo-1-azabicyclo[3.2.0]hept-2-ene-2-carboxylate (1.45 g, 2.72 mmol) in tetrahydrofuran (40 mL) was cooled to 0°–5° C. and treated with acetic acid (1.0 mL, 17.5 mmol) followed by 8.2 mL (8.2 mmol) of 1.0M tetrabutylammonium fluoride in tetrahydrofuran. After fourteen days at 0°–5° C., the reaction mixture was diluted with ethyl acetate (400 mL), washed with saturated sodium bicarbonate, brine and dried (MgSO$_4$). The solvent was evaporated under reduced pressure and the residue was chromatographed on silica gel (4×6 cm). Elution with a gradient of methanol (0–20%) in ethyl acetate gave 0.34 g (30%) of the title compound as an oil.

IR (NaCl, film) v$_{max}$: 2100 (N$_3$), 1765 (C=O of β-lactam) and 1700 cm$^{-1}$ (C=O of ester);

$^1$H NMR (200 MHz, CDCl$_3$) δ: 1.38 (d, J=6.25 Hz, 3H, CH$_3$CHO), 1.5–2.1 (m, CH$_2$CH$_2$N$_3$), 3.15 (dd, J$_{H6,H5}$=2.63 Hz, J$_{H6,H1}$=7.72 Hz, 1H, H-6), 3.3–3.7 (m, 3H, H-4 and CH$_2$ CH$_2$N$_3$ overlapping), 4.06 (ABq, J$_{AB}$=14.6 Hz, Δν=45.2 Hz, 2H, SCH$_2$), 4.1–4.4 (m, 2H, H-5 and CH$_3$CHO overlapping), 4.6–4.9 (m, 2H, CH$_2$ of allyl), 5.2–5.5 and 5.9–6.1 (2m, 2H, and 1H, CH of allyl), 6.98 (s, 1H, H-5 of imidazole) and 7.59 ppm (s, 1H, H-2 of imidazole).

C. Potassium (4R,5S,6S)-4-(2"-azidoethyl)-6-[(1'R)-1'-hydroxyethyl)-3-[(imidazol-4-yl]methylthio]-7-oxo-1-azabicyclo[3.2.0]hept-2-ene-2-carboxylate

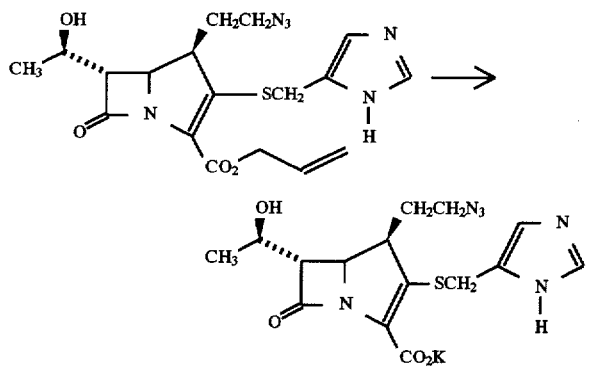

A solution of allyl (4R,5S,6S)-4-(2"-azidoethyl)-6-[(1'R)-1'-hydroxyethyl]-3-[(imidazol-4-yl)methylthio]-7-oxo-1-azabicyclo[3.2.0]hept-2-ene-2-carboxylate (0.304 g, 0.81 mmol) in dichloromethane (20 mL) was treated at 25° C. and under nitrogen with tetrakis(triphenylphosphine)palladium [0](0.040 g) and 1.8 mL (0.9 mmol) of a 0.5M solution of potassium 2-ethylhexanoate in ethyl acetate. After 1.2 h, the reaction mixture was extracted with water (2×50 mL) and the combined extract was chromatographed on reversed phase silica gel (μBondapak $C_{18}$, 2.5×15 cm). The column was eluted with a gradient of acetonitrile (0–5%) in 0.01M pH 7.0 phosphate buffer. The UV active fractions were collected, concentrated and desalted on the same column using water instead of buffer as eluent. Lyophilization of the pertinent fractions gave 0.047 g (14%) of the title carbapenem as a white amorphous solid:

Purity by HPLC: 99% on μBondapak $C_{18}$, 3.9 mm×30 cm, elution 10% $CH_3CN$— water pH 7.4 phosphate buffer, flow rate 1 mL/min, UV detector 302 nm, retention time 6.83 min;

UV (water, pH 7.4 phosphate buffer) $\lambda_{max}$: 304 nm (8,380);

IR (KBr) $v_{max}$: 2100 ($N_3$), 1745 (C=O of β-lactam) and $cm^{-1}$ (C=O of carboxylate);

$^1H$ NMR (200 MHz, $D_2O$) δ: 1.31 (d, J=6.40 Hz, 3H, $CH_3CHO$), 1.6–2.1 (m, 2H, $CH_2CH_2N_3$), 3.2–3.6 (m, 4H, H-6, H-4 and $CH_2CH_2N_3$ overlapping), 4.03 (ABq, $J_{AB}$= 14.52 Hz, Δv=33.6 Hz, 2H, $SCH_2$), 4.14 (dd, $J_{H5,H6}$=2.42 Hz, $J_{H5,H4}$=9.48 Hz, 1H, H-5), 4.24 (m, 1H, $CH_3CHO$), 7.09 (s, 1H, H-5 of imidazole) and 7.72 ppm (s, 1H, H-2 of imidazole).

EXAMPLE 152

(4R,5S,6S)-4-[3"-Amino-(2" R or S)-2"-hydroxypropyl]-3-[(2-cyanoethyl)thio]-6-[(1'R)-1'-hydroxyethyl]-7-oxo-1-azabicyclo[3.2.0]hept-2-ene-2-carboxylic acid

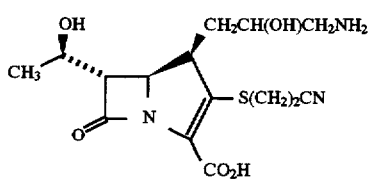

A. (Pyridin-2-yl)methylthio-5-azido-4-(tert-butyldimethylsilyloxy)pentanoate

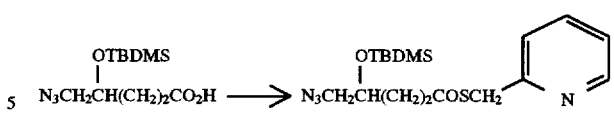

To a cold (ice bath) solution of 5-azido-4-(tert-butyldimethylsilyloxy)pentanoic acid (38 g, 0.14 mmol) from iodolactonization described by P. A. Bartlett et al in *J. Am. Chem. Soc.* 100, 3950 (1978) in dimethyl formamide (250 mL) was added 2-picolyl mercaptan (17.5 g, 0.140 mol), 1,3-dicyclohexylcarbodiimide (30 g, 0.15 mol) and 1-hydroxybenzotriazole (10 g, 0.074 mol). The mixture was stirred for 60 h in the cold room (5°–8° C.), diluted with water (1 L) and extracted with diethyl ether (5×250 mL). The diethyl ether extracts were combined, washed with water (5×250 mL), brine (200 mL), dried and passed through a silica gel flash pad (500 g, Hexane, 5→30% ethyl acetate/hexane) to give the title compound (30 g, %) as an oil.

IR (film) $v_{max}$: 2100 ($N_3$) and 1690 $cm^{-1}$ (C=O).

$^1H$ NMR ($CDCl_3$, 200 MHz) δ: 8.558–8.525 (1H, m, pyridine H-6), 7.672=7.586 (1H, m, pyridine H-4), 7.336 (1H, d, J=7.9 Hz, pyridine H-3), 7,199–7.131 (1H, m, pyridine H-5), 4.257 (2H, s, $CH_2S$, 3.834 (1H, center of 5 lines, J=5.41–2, CHO), 3.197 (2H, center of ABX, J=4.5 Hz, J=5.4 Hz, J=12.5 Hz, $CH_2N_3$), 2.659 (2H, t, J=7.6 Hz, $CH_2CO$), 2.01–1.786 (2H, m, $CH_2$), 0.893 (9H, s, tert-butyl), 0.094 and 0.061 ppm (6H, 2s, dimethyl).

B. (3S,4S)-3-[(1'R)-1'-tert-Butyldimethylsilyloxyethyl]-4-[(1"R)-1"-(pyridin-2-yl)methylthiocarbonyl-4"-azido-(3"R and S)-3"-tert-butyldimethylsilyloxy]butyl]-azetidin-2-one

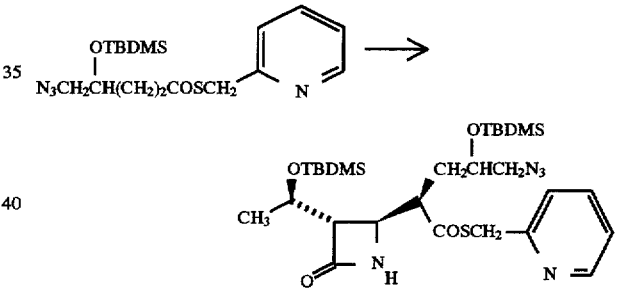

A cold (ice-methanol bath) solution of (pyridin-2-yl)-methylthio-5-azido-4-(tert-butyldimethylsilyloxy) pentanoate (30 g, 78.9 mmol) in dichloromethane (500 mL) was treated with triethylamine (35 mL, 0.25 mol) and dropwise with tert-butyldimethylsilyltrifluoromethanesulfonate (46 mL, 0.20 mmol). At the end of the addition, the mixture was allowed to stand for 18 h at 5°–8° C., then diluted with hexane (1 L), washed with water (5×500 mL), brine (500 mL), dried ($MgSO_4$) and treated with activated charcoal. The residue (20 g, 51%, 0.040 mmol), a red oil, was added to a cold (ice bath) mixture of freshly fused zinc chloride (13 g, 0.096 mol), and (3S,4R)-4-acetoxy-3-[(1'E)-1'-tert-butyl-dimethyl-silyloxyethyl] azetidin-2-one (20 g, 0.069 mol) in dichloromethane (250 mL). It was allowed to stand in a cold room for 18 h, diluted with diethyl ether (11), washed with saturated aqueous $NH_4Cl$ (3×250 mL), water (3×250 mL), ice cold saturated aqueous $NaHCO_3$, water (250 mL), brine (250 mL) and dried ($MgSO_4$). The residue was passed through a silica gel flash column (500 g, Hexane→50% ethyl acetate/hexane) to give the title compounds as separated diastereomers (30 g of each diastereomers, 24% combined yield).

Isomer 1

Rf=0.33 (hexane/ethyl acetate:1/1);

IR (film) $v_{max}$: 3300–3200 (NH), 2700 ($N_3$), 1765 and 1680 cm$^{-1}$ (C=O);

$^1$H NMR (CDCl$_3$, 200 MHz) δ: 8.54–8.51 (1H, m, pyridine-H6), 7.64–7.58 (1H, m, pyridine H-4), 7.314 (1H, d, J=7.8 Hz, pyridine H-3), 7.21–7.14 (1H, m, pyridine H-5), 5.845 (1H, bs, NH), 4.280, 4.269 (2H, 2 lines, part of ABq, CH$_2$S), 4.2–4.05 (1H, m, CHO), 3.832 (1H, dd, J=2.05 Hz, J=6.0 Hz, H-4), 3.83–3.70 (1H, m, CHO), 3.227 (2H, ABX, J=4.6 Hz, J=5.1 Hz, J=12.5 Hz, CH$_2$N$_3$), 3.08–2.95 (2H, m, H-3 and H-1"), 2.15–1.98, 1.67–1.55 (2H, m, CH$_2$-1"), 1.025 (3H, d, J=6.3 Hz, CH$_3$), 0.883, 0.868 (18H, 2s, tert-butyl), 0.070 and 0.047 ppm (3H and 5H, 28, dimethyl.

Isomer 2

Rf=0.42 (hexane/ethyl acetate: 1/1);

IR (film) $v_{max}$: 3250 (NH), 2100 ($N_3$), 1765 and 1685 cm$^{-1}$ (C=O);

$^1$H NMR (CDCl$_3$, 200 MHz) δ: 8.55–8.52 (1H, m, pyridine H-6), 7.67–7.58 (1H, m, pyridine H-4), 7.32 (1H, d, J=7.8 Hz, pyridine H-3), 7.21–7.14 (1H, m, pyridine H-5), 5.90 (1H, bs, NH), 4.336, 4.267, 4.245, 4.174 (2H, ABq, J=14.0 Hz, CH$_2$S), 4.20–4.13 (1H, m, CHO), 3.794 (1H, dd, J=2.1 Hz, J=6.9 Hz, H-4), 3.82–3.75 (1H, m, CHO), 3.207 (2H, ABX, J=3.8 Hz, J=5.2 Hz, J=12.8 Hz, CH$_2$S), 3.048 (1H, bt, J=2.5 Hz, H-3), 2.86–2.75 (1H, m, H-1"), 2.10–1.96, 1.85–1.70 (2H, 2 sets of m, CH$_2$-4), 1.050 (3H, d, J=6.3 Hz, CH$_3$), 0.883, 0.857 (18H, 2s, tert-butyl) and 0.047 ppm (12H, s, dimethyl).

C. (3S,4S)-3-[(1'R)-1'-tert-Butyldimethylsilyloxyethyl]-4-[(1"R)-1"-carboxy-4"-azido-(3" R or S)-3"-tert-butyldimethylsilyloxybutyl]azetidin-2-one

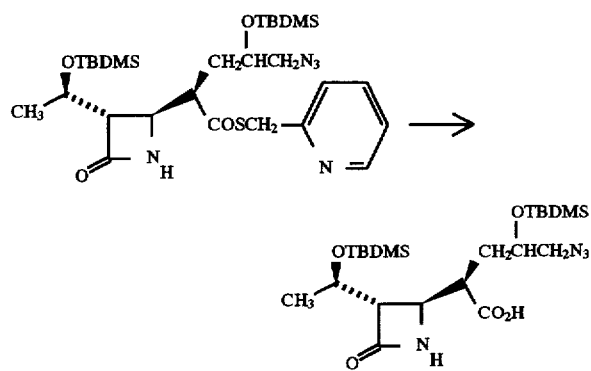

A cold (ice bath) solution of (3S,4S)-3-[(1'R)-1'-tert-butyldimethylsilyloxyethyl]-4-[(1"R)-1"-(pyridin-2-yl)methylthiocarbonyl-4"-azido-(3" R or S)-3"-tert-butyldimethylsilyloxy)butyl]-azetidin-2-one (2.38 g, 3.9 mmol) in tetrahydrofuran (25 mL) was treated with 30% aqueous hydrogen peroxide (1.3 mL, 15.6 mmol), followed by the slow addition of 1M aqueous NaOH (11.7 mL, 11.7 mmol). The mixture was stirred for 30 min, then acidified with 1N aqueous HCl (14 mL) and extracted with ethyl acetate (3×30 mL). The organic extracts were combined, washed with water (2×20 mL), 1M aqueous NaHSO$_3$ (2×20 mL), water (30 mL), brine and dried (MgSO$_4$) to give the title compound (1.8 g, 92%) as an oil.

IR (CH$_2$Cl) $v_{max}$: 3400 (NH), 2100 ($N_3$), 1765, 1740 and 1710 cm$^{-1}$ (C=O); 1H NMR (CDCl$_3$, 200 MHz) δ: 6.329 (1H, bs, NH), 4.23–4.14 (1H, m, CHO), 3.867 (1H, dd, J=2.2 Hz, J=6.4 Hz, H-4), 3.26 (2H, center of ABX, J=4.2 Hz, J=4.7 Hz, J=12.7 Hz, CH$_2$N$_3$), 3.13 (1H, center of m, H-3), 2.70–2.60 (1H, m, H-1"), 2.04–1.7 (2H, m, CH$_2$-1"), 1.171 (3H, d, J=6.3 Hz, CH$_3$), 0.898, 0.869 (18H, 2s, tert-butyl), 0.109, 0.099, 0.070 and 0.062 ppm (12H, 4s, CH$_3$).

D. (3S,4R)-3-[(1'R)-1'-tert-Butyldimethylsilyloxyethyl]-4-[(1"R)-1"-(4-azido-(3 R or S)-3-tert-butyldimethylsilyloxypropyl)-3"-allyloxycarbonyl-2"-oxopropyl]-azetidin-2-one

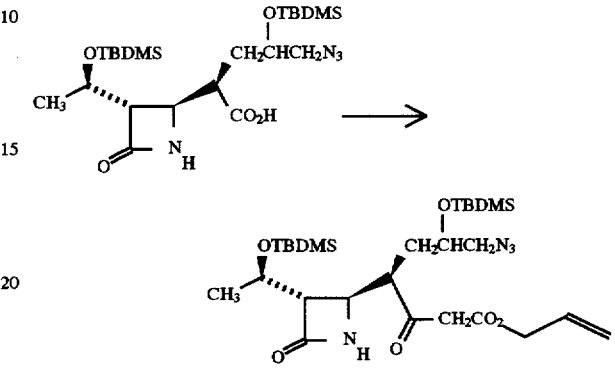

A solution of (3S,4S)-3-[(1'R)-1'-tert-butyldimethylsilyloxyethyl]-4-[(1"R)-1"-carboxy-4"-azido-(3" R or S)-3"-tert-butyldimethylsilyloxybutyl] azetidin-2-one (1.8 g, 3.6 mmol) in toluene (25 mL) was treated with carbonyldiimidazole (642 mg, 3.96 mmol) and then stirred for 1.5 h. The solvent was removed and the residue was dissolved again in toluene. The solvent was removed again and the residue was dried under high vacuum. To this resulting acyl imidazole was added a pre-dried solution (heated for 2.5 h over 3A° and 4A° mole sieves) of magnesium monoallyl malonate (4.5 g, 14.4 mmol) in benzene (40 mL). The mixture was heated for 1.6 h (bath temp. 75° C.), diluted with a 1/1 mixture of diethyl ether and ethyl acetate, washed with ice cold water (2×40 mL) ice cold 1N aqueous HCl (40 mL), water (2×40 mL) brine 40 mL and dried (MgSO$_4$) to give crude title compound (2.29 g,>100%) which was used as such in the next step.

IR (CH$_2$Cl$_2$) $v_{max}$: 3420 (NH), 2120 ($N_3$), 1770 (C=O β-lactam), 1720, 1660 and 1630 cm$^{-1}$ (C=O);

$^1$H NMR (CDCl$_3$, 200 MHz) δ: 12.113 (0.5H, bs, OH enol), 6.03–5.80 (1H, m, vinylic H) 5.927 (1H, bs, NH), 5.387–5.253 (2H, m, vinylic H), 5.058 (2.6H, s, olefinic H of enol), 4.665–4.616 (2H, m, allylic H), 4.24–4.12, 3.883–3.764 (2H, m, H-4 and H-1'), 3.775, 3.764 (d, J=2.1 Hz, part of H-4), 3.680, 3.600, 3.592, 3.513 (2H, ABq, J=15.9 Hz, CH$_2$ of acetoacetate), 3.357–3.269 (1H, m, part of CH$_2$N$_3$), 3.187–3.01 (2H, m, H-1" and part of CH$_2$N$_3$), 2.955 (0.5 H, dd, J=2.1 Hz, J=4.1 Hz, H-3), 2.905 (0.5 H, dt, J=2.6 Hz, part of H-3), 2.256–2.146, 2.065–1.91, 1.836–1.6 (2H, 3 series of m, CH$_2$-4), 1.180 (1.4 H, d, J=6.2 Hz, CH$_3$), 1.086 (1.6 H, d, J=6.3 Hz, CH$_3$)), 0.896 and 0.866 (18H, 2s, tert-butyl), 0.108, 0.091, 0.087, 0.069 and 0.056 ppm (12H, 5s, dimethyl).

E. (3S,4R)-3-[(1'R)-1'-tert-butyldimethylsilyloxyethyl]-4-[(1"R)-1"-(4-azido-(3 R or S)-3-tert-butyldimethylsilyloxypropyl]-3"-diazo-3"-allyloxycarbonyl-2"-oxopropyl]azetidin-2-one

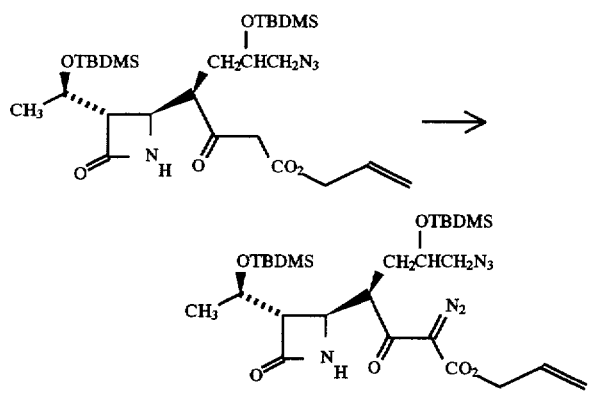

A cold (ice bath) solution of (3S,4R)-3-[(1'R)-1'-tert-butyldimethylsilyloxyethyl]-4-[(1"R)-1"-(4-azido-(3R or S)-3-tert-butyldimethylsilyloxypropyl)-3"-allyloxylcarbonyl-2"-oxopropyl]azetidin-2-one (2.2 g, 3.6 mmol) in CH₃CN (22 mL) was treated first with triethylamine (0.51 mL, 3.6 mmol) and dropwise with tosyl azide (709 mg, 3.6 mL) in CH₃CN (3 mL). The mixture was stirred for 1.5 h and the solvent was removed under vacuum. The residue was triturated with hexane and the solid tosyl amid, was removed by filtration and washed with hexane. The residue upon evaporation of the hexanes fractions was passed through a silica gel flash column (60 g, hexane, 10→40% ether/hexane) to give the title compound (650 mg, 30%) as an oil.

IR (CH₂Cl₂) v$_{max}$: 3410 (NH), 2150 (N₂), 2100 (N₃), 1765 (C=O β-lactam), 1715 and 1650 cm⁻¹ (C=O);

¹H NMR (CDCl₃, 200 MHz) δ: 6.03 –5.832 (1H, m, vinylic H), 5.862 (1H, bs, NH), 5.40–5.29 (2H, m, vinylic H), 4.72–4.689 (2H, m, CH₂ allylic), 4.215– 4.07 (2H, m, CHO and H-1'), 3.805–3.71 (1H, m, H-1"), 3.189 (2H, ABX, J=3.9 Hz, J=5.5 Hz, J=12.7 Hz, CH₂N₃), 3.023 (1H, bt, J=2.5 Hz, H-3), 2.175–2.03, 1.73–1.57 (2H, 2 sets of m, CH₂-1"), 1.162 (3H, d, J=6.4 Hz, CH₃), 0.891, 0.865 (18H, 2s, tert-butyl), 0.094, 0.062 and 0.053 ppm (12H, 3s, dimethyl).

F. Allyl (4R,5R,6S)-4-[3"-azido-(2"R or S)-2"-tert-butyldimethylsilyloxypropyl)-6-[(1'R)-1'-tert-butyldimethylsilyloxyethyl]-3,7-dioxo-1-azabicyclo[3.2.0]-heptan-2-carboxylate

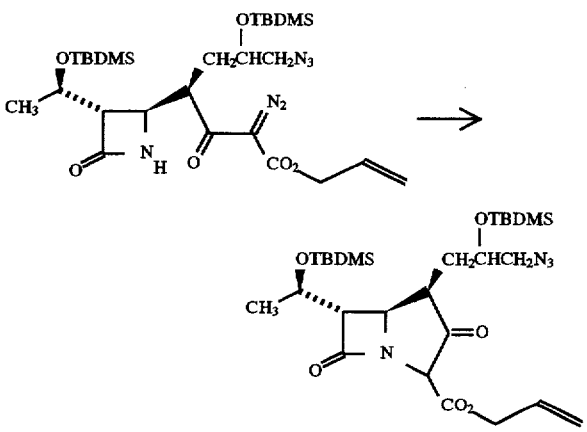

A solution of (3S,4R)-3-[(1'R)-1'-tert-butyldimethylsilyloxyethyl]-4-[(1"R)-1"-[4-azido-(3R or S)-3-tert-butyldimethylsilyloxypropyl]- 3"-diazo-3"-allyloxycarbonyl-2"-oxopropyl]azetidin-2-one (690 mg, 1.1 mmol) in benzene (20 mL) was heated under reflux in the presence of Rh(OAc)₂ (17 mg) for 45 min. More catalyst (17 mg) was added and the heating period was continued for 30 more min. The catalyst was removed by filtration and benzene was removed under vacuum to give the title compound (700 mg, 100%) as an oil.

IR (CH₂Cl₂) v$_{max}$: 2110 (N₃), 1770 and 1745 cm⁻¹ (C=O);

¹H NMR (CDCl₃, 200 MHz) δ: 6.0–5.79 (1H, m, vinylic H), 5.38–5.24 (2H, m, vinylic H), 4.72 –4.88 (2H, m, allylic CH₂), 4.633 (1H, s, CH-2), 4.58–4.28 (1H, m, H-1'), 4.325 (1H, dd, J=2.5 Hz, J=8.4 Hz, H-5), 3.91–3.82 (1H, m, CHO) 3.40–3.2 (2H, m, CH₂N₃), 3.246 (1H, dd, J=2.5 Hz, J=4.3 Hz, H-6), 2.839 (1H, bq, J=7.9 Hz, H-4), 1.84–1.72 (2H, m, CH₂-4), 1.270 (3H, d, J=6.2 Hz, CH₃), 0.897 (18H, s, tert-butyl), 0.112, 0.099, 0.092 and 0.083 ppm (12H, 4s, dimethyl).

G. Allyl (4R,5S,6S)-4-[3"-azido-("2R or S)-2"-tert-butyldimethylsilyloxypropyl]-6-[(1'R)-1'-tert-butyldimethylsilyloxyethyl]-3-[(2-cyanoethyl)thio]-7-oxo-1-azabicyclo[3.2.0]hept-2-ene-2-carboxylate

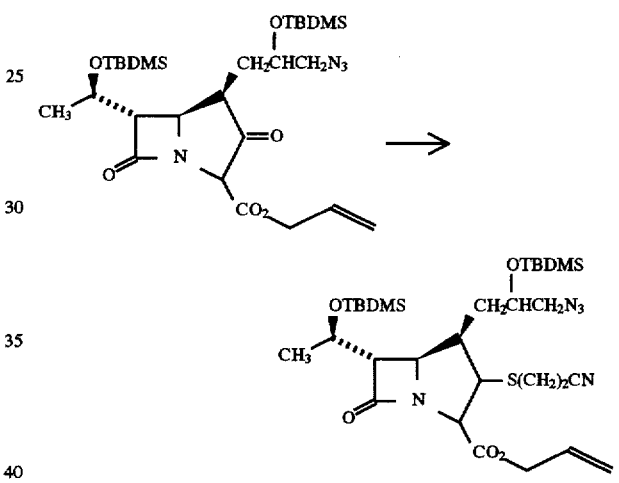

A cold (ice-methanol bath) solution of allyl (4R,5S,6S)-4-[3"-azido-(2" R or S)-2-tert-butyldimethylsilyloxypropyl]- 6-[(1R)-1'-tert-butyldimethylsilyloxyethyl]-3,7-dioxo-1-azabicyclo [3.2.0]hept-2-ene-2-carboxylate (from 690 mg, 1.1 mol of diazo) in CH₃CN (8 mL) was treated dropwise with diphenyl chlorophosphate (0.26 mL, 1.32 mmol) and diisopropylethyl amine (0.23 mL, 1.32 mmol) and a trace amount of 4-N,N-dimethylaminopyridine (20 mg). The mixture was stirred for 1 h and then two portions of cyanoethyl mercaptan (130 mg, 1.5 mmol and 52 mg, 0.60 mmol) and diisopropylethyl amine (0.26 mL, 1.50 mmol and 0.10 mL, 0.60 mmol) were successively added within 1 h period. The mixture was stirred for 1.5 h, diluted with ethyl acetate (25 mL), washed with ice cold water (3×10 mL), 1M aqueous NaHSO₃ (3×10 mL), water (2×10 mL), 1N aqueous HCl (10 mL), water (2×10 mL), 1M aqueous NaHCO₃ (10 mL), water (10 mL), brine (10 mL) and dried (MgSO₄). The residue was passed through a silica gel flash column (25 g, petroleum ether, 10→40% diethyl ether/petroleum ether) to give the title compound (442 mg, 62%) as an oil.

IR (CH₂Cl₂) v$_{max}$: 2250 (CN), 2110 (N₃), 1775 (C=O β-lactam), 1710 cm (C=O);

¹H NMR (CDCl₃, 200 MHz) δ: 6.03–5.84 (1H, m, vinylic H), 5.48–5.20 (2H, m vinylic H), 4.85–4.6 (2H, m, allylic CH₂), 4.38–4.3 (1H, m H-1), 4.284 (1H, dd, J=2.5 Hz, J=9.5

Hz, H-5), 3.65–3.50 (1H, m, CHO), 3.47–2.93 (5H, m, H-4, CH₂N₃, SCH₂), 3.205 (1H, dd, J=2.5 Hz, J=6.4 Hz, H-6), 2.699, 2.664, 2.632 (2H, m, CH₂CN), 1.90–1.75 (2H, m, CH₂-4), 1.245 (3H, d, J=6.2 Hz, CH₃), 0.935 and 0.898 (18H, 2s, tert-butyl), 0.143 and 0.091 (12H, 2s, dimethyl).

H. Allyl (4R,5S,6S)-4-[3"-azido-(2"R or S)-2"-hydroxypropyl]-6-[(1'R)-1'-hydroxyethyl]-3-[(2-cyanoethyl)thio]-7-oxo-1-azabicyclo[3.2.0]hept-2-ene-2-carboxylate

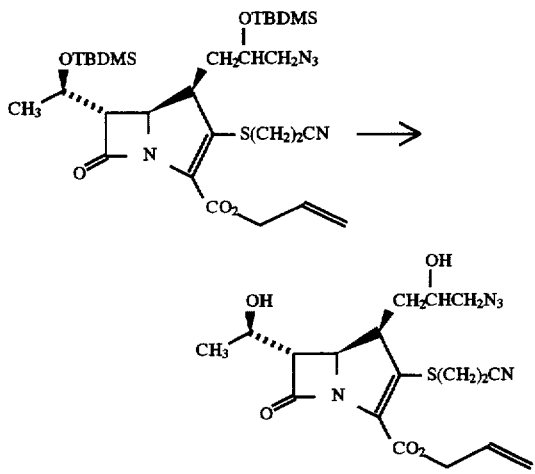

A cold (ice-methanol bath) solution of allyl (4R,5S,6S)-4-[3"-azido-(2" R or S)-2"-tert-butyldimethylsilyloxy-propyl]-6-[(1'R)-1'-tert-butyldimethylsilyloxyethyl]-3-[(2-cyanoethyl)thio]-7-oxo-1-azabicyclo[3.2.0]-hept-2-ene-2-carboxylate (440 mg, 0.68 mmol) in tetrahydrofuran (6 mL) was treated with glacial acetic acid (0.94 mL, 17 mmol) and dropwise with a 1M tetrabutylammonium fluoride solution in tetrahydrofuran (6.8 mL, 6.8 mmol). The mixture was stirred for 15 days at 8° C., then diluted with ethyl acetate (40 mL), washed with ice cold water (4×10 mL), 1M aqueous NaHCO₃ (2×10 mL), water (10 mL), brine and dried (MgSO₄). The residue was applied on preparative silica gel plate (ethyl acetate/hexane: 4/1) to give the title compound (185 mg, 65%) as an oil.

IR (CH₂Cl₂) $v_{max}$: 3600, 3450 (OH), 2250 (CN), 2110 (N₃), 1775 (C=O β-lactam) and 1710 cm⁻¹ (C=O);

¹H NMR (CDCl₃, 200 MHz) δ:6.04–5.87 (1H, m, vinylic H), 5.493–4.24 (2H, m, vinylic H), 4.88–4.64 (2H, m, allylic H), 4.294 (1H, dd, J=2.6 Hz, J=9.7 Hz, H-5), 4.3–4.17 (1H, m, H-1'), 3.9–3.67 (2H, m, CHO and H-4), 3.382, 3.353 (2H, 2 lines, CH₂N₃), 3.35–3.23 (1H, m, 1 proton of SCH₂), 3.159 (1H, dd, J=2.6 Hz, J=8.0 Hz, H-6), 3.05–2.91 (1H, m, 1 proton of SCH₂), 3.91 (1H, bs, OH), 2.81–2.63 (2H, m, CH₂CN), 2.377 (1H, bs, OH), 1.94–1.64 (2H, m, CH₂-4) and 1.388 ppm (3H, d, J=6.2 Hz, CH₃).

I. Sodium (4R,5S,6S)-4-[3"-azido-(2"R or S)-2"-hydroxypropyl]-6-[(1'R)-1'-hydroxyethyl]-3-[(2-cyanoethyl)thio]-7-oxo-1-azabicyclo[3.2.0]hept-2-ene-2-carboxylate

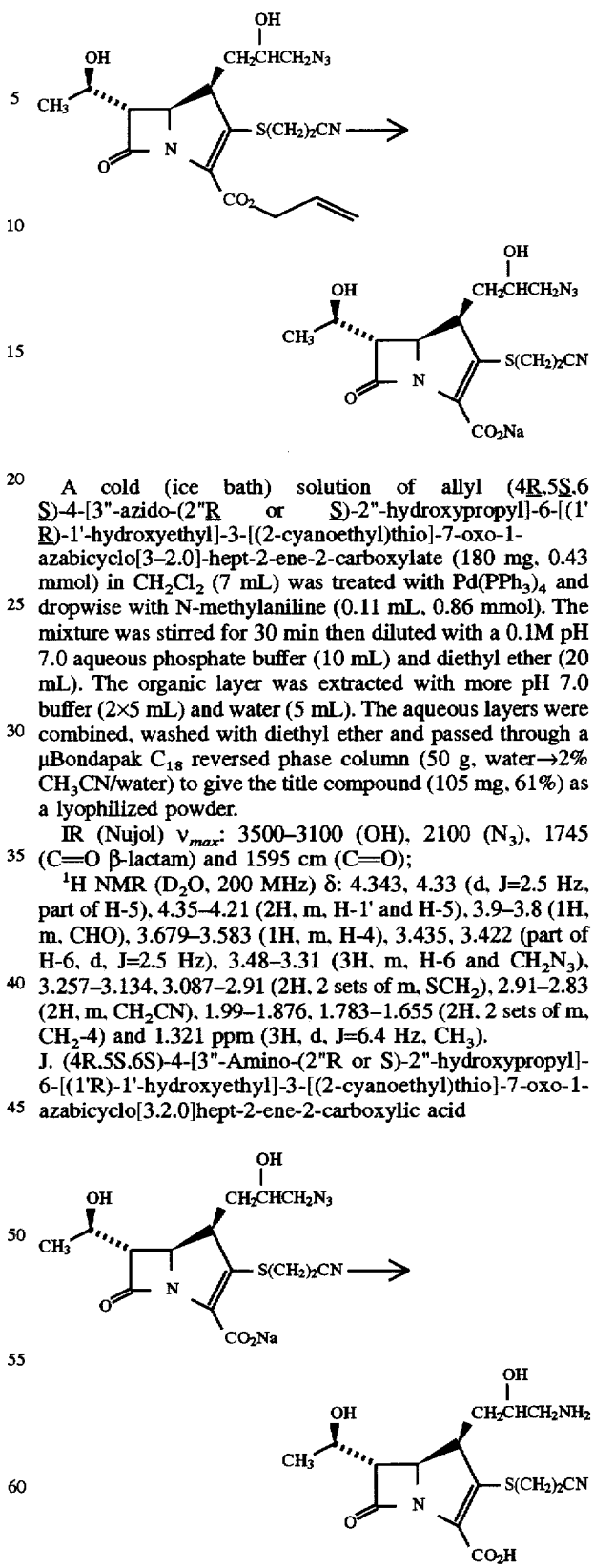

A cold (ice bath) solution of allyl (4R,5S,6 S)-4-[3"-azido-(2"R or S)-2"-hydroxypropyl]-6-[(1' R)-1'-hydroxyethyl]-3-[(2-cyanoethyl)thio]-7-oxo-1-azabicyclo[3–2.0]-hept-2-ene-2-carboxylate (180 mg, 0.43 mmol) in CH₂Cl₂ (7 mL) was treated with Pd(PPh₃)₄ and dropwise with N-methylaniline (0.11 mL, 0.86 mmol). The mixture was stirred for 30 min then diluted with a 0.1M pH 7.0 aqueous phosphate buffer (10 mL) and diethyl ether (20 mL). The organic layer was extracted with more pH 7.0 buffer (2×5 mL) and water (5 mL). The aqueous layers were combined, washed with diethyl ether and passed through a μBondapak C₁₈ reversed phase column (50 g, water→2% CH₃CN/water) to give the title compound (105 mg, 61%) as a lyophilized powder.

IR (Nujol) $v_{max}$: 3500–3100 (OH), 2100 (N₃), 1745 (C=O β-lactam) and 1595 cm (C=O);

¹H NMR (D₂O, 200 MHz) δ: 4.343, 4.33 (d, J=2.5 Hz, part of H-5), 4.35–4.21 (2H, m, H-1' and H-5), 3.9–3.8 (1H, m, CHO), 3.679–3.583 (1H, m, H-4), 3.435, 3.422 (part of H-6, d, J=2.5 Hz), 3.48–3.31 (3H, m, H-6 and CH₂N₃), 3.257–3.134, 3.087–2.91 (2H, 2 sets of m, SCH₂), 2.91–2.83 (2H, m, CH₂CN), 1.99–1.876, 1.783–1.655 (2H, 2 sets of m, CH₂-4) and 1.321 ppm (3H, d, J=6.4 Hz, CH₃).

J. (4R,5S,6S)-4-[3"-Amino-(2"R or S)-2"-hydroxypropyl]-6-[(1'R)-1'-hydroxyethyl]-3-[(2-cyanoethyl)thio]-7-oxo-1-azabicyclo[3.2.0]hept-2-ene-2-carboxylic acid

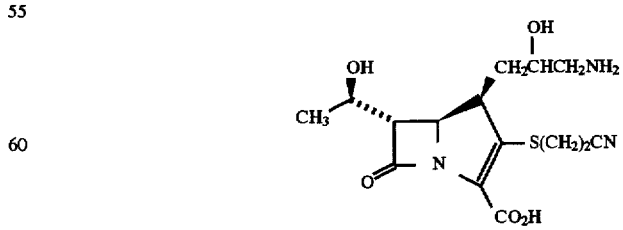

A cold (ice bath) solution of sodium (4R,5S,6 S)-4-[3"-azido-(2"R or S)-2"-hydroxypropyl]-6-[(1' R)-1'-hydroxyethyl]-3-[(2-cyanoethyl)thio]-7-oxo-1- azabicyclo[3.2.0]-hept-2-ene-2-carboxylate (105 mg, 0.26 mmol) in water (20 mL) was shaken on a Parr hydrogenator for 1 h at 45–50 psi of hydrogen, using 5% Pd/Alumina as catalyst. The catalyst was removed by filtration and washed with water (2×2 mL). The pH of the aqueous reaction mixture was adjusted to 7.05 with a 0.1M aqueous $NaH_2PO_4$ solution. The neutralized solution was passed through a μBondapak $C_{18}$ reversed phase column (50 g, water) to give the title compound (65 mg, 43%) as a white lyophilized powder.

Purity: 98.2% as determined by HPLC (r.t.=5.92 min, μBondapak $C_{18}$, 10μ, $KH_2PO_4$ 0.01M, pH 7.4);

UV (water) $\lambda_{max}$: 300 (8008);

IR (Nujol) $\nu_{max}$: 3600–3100 (OH, $NH_2$), 2250 (CN), 1750 (C=O β-lactam) and 1590 $cm^{-1}$ (C=O);

$^1H$ NMR ($D_2O$, 200 MHz) δ: 4.312 (1H, dd, J=2.8 Hz, J=9.7 Hz, H-5), 4.32–4.207 (1H, m, H-1'), 3.948–3.849 (1H, m CHO), 3.68–3.575 (1H, m, H-4), 3.380 (1H, dd, J=2.8 Hz, J=6.6 Hz, H-6), 3.235, 3.219, 3.169, 3.154 (1H, part of ABX, J=3.1 Hz, J=13.2 Hz, $CH_2N_3$), 3.23–3.11 (1H, m, 1 proton of $SCH_2$), 3.008–2.95 (2H, m, part of $CH_2CN$ and part of $SCH_2$), 2.88–2.82 (2H, m, $CH_2CN$), 2.002–1.699 (2H, m, $CH_2$-4) and 1.328 ppm (3H, d, J=6.4 Hz, $CH_3$).

EXAMPLE 153

(4R,5S,6S)-6-[R]-1'-Hydroxyethyl]-3-benzylthio-4-[2"-(N-benzyl-N-methyl)aminoethyl]-7-oxo-1-azabicyclo[3.2.0]-hept-2-ene-2-carboxylic acid

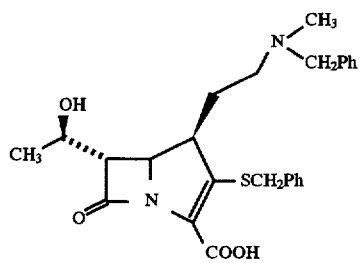

A. Allyl (4R,5S,6S)-6-[(1'R)-1'-(tert-butyldimethylsilyloxyethyl)]-3-benzylthio-4-[2"-tert-butyldimethylsilyloxyethyl)]-7-oxo-1-azabicyclo[3.2.0]hept-2-ene-2-carboxylate

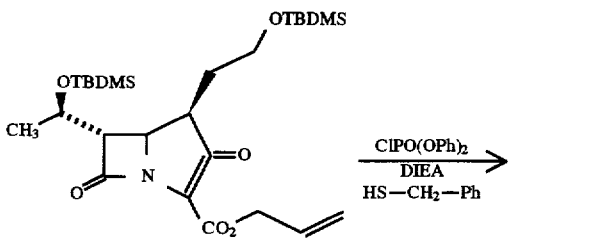

A cold (0° C.) solution of allyl (4R,5S,6S)-6-[(1'R)-1'-(tert-butyldimethylsilyloxyethyl)]-4-[2"-tert-butyldimethylsilyloxyethyl]-3,7-dioxo-1-azabicyclo[3-2.0] heptane-2-carboxylate (4.75 g, 9.03 mmol) in $CH_3CN$ (50 mL) was treated with $ClPO(OPh)_2$ (2.06 mL, 9.93 mmol) followed by N,N-diisopropylethylamine (1.73 mL, 9.93 mmol) and 4-N,N-dimethylaminopyridine (10 mg). The mixture was stirred at 0° C. for 2.5 h, under Argon, after which Argon was bubbled through the solution for 10 min. The enol-phosphate was then treated with benzylmercaptan (2.54 mL, 21.58 mmol) followed by N,N-diisopropylethylamine (3.8 mL, 21.68 mmol) and stirred at 0° C. for 20 h. The reaction mixture was diluted with EtOAc (300 mL) and washed successively with cold 1M $NaHSO_3$, water and brine, dried ($MgSO_4$) and solvent evaporated to a syrup which was chromatographed on silica (9×10 cm) packed in hexane and eluted with a mixture of hexane and EtOAc (85:15, gradient elution) to give the title compound as a foam (4.35 g, 76.2%).

$^1H$ NMR (200 MHz, $CDCl_3$, 7.24) δ: 0.05 (s, 12H, $Si(CH_3)_2$), 0.857, 0.86 (2s, 18H, $SiC(CH_3)_2$), 1.26 (d, 3H, $CH_3$), 1.62–1.78; 1.98.2.12 (m, 2H, $CH_2$), 3.05 (dd, 1H, H-6, $J_{6,1}$=6.93 Hz), 3.45–3.6 (m, 1H, H-4), 3.53–3.8 (centers m, 2H, $CH_2O$), 4.03 (dd, 1H, H-5, $J_{5,6}$=2.38 Hz, $J_{4,5}$=9.21 Hz), 4.1 (tight AB, 2H, $SCH_2$), 4.18 (m, 1H, H-1'), 4.59–4.82 (m, 2H, $OCH_2$, allyl), 5.17–5.46 (m, 2H, =$CH_2$, allyl), 5.83–6.02 (m, 1H, CH=, allyl), 7.16–7.34 (m, 5H, phenyl).

B. Allyl (4R,5S,6S)-6-[(1'R)-1'-(tert-butyldimethylsilyloxyethyl)]-3-benzylthio-4-(2"-hydroxyethyl]-7-oxo-1-azabicyclo[3.2.0]hept-2-ene-2-carboxylate

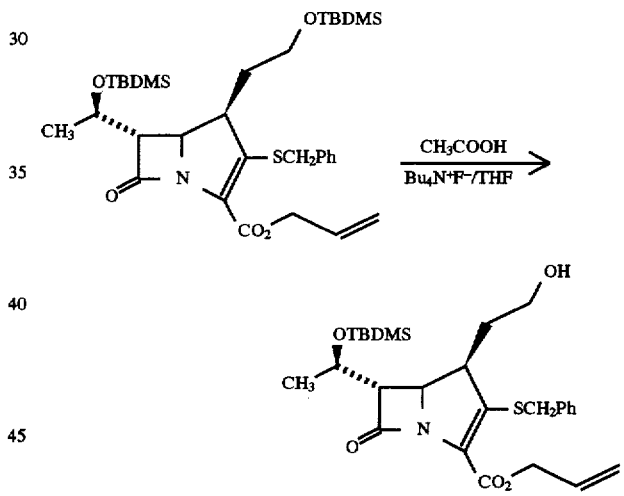

A cold (0° C.) solution of allyl (4R,5S,6S)-6-[(1'R)-1'-(tert-butyldimethylsilyloxyethyl)]-3-benzylthio-4-[2"-tert-butyldimethylsilyloxyethyl]-7-oxo-1-azabicyclo-[3.2.0] hept-2-ene-2-carboxylate (4.35 g, 6.88 mmol) in drytetrahydrofuran (65 mL) was treated, under Argon, with acetic acid (2.36 mL, 41.26 mmol) followed by a 1M solution of tetrabutylammonium fluoride in tetrahydrofuran (20.63 mL, 20.63 mmol). The mixture was stirred at 0° C. for 5 h and left at −20° C. for 18 h after which it was neutralized at 0° C. with a 1M $NaHCO_3$ solution (42 mL, 42 mmol). The mixture was extracted with EtOAc (3×75 mL) and the combined organic phase was washed successively with cold 1M $NaHCO_3$, water and brine, dried ($MgSO_4$) and solvent evaporated to give a foam which was chromatographed on silica (7.5×8 cm) packed in $CH_2Cl_2$ and eluted with a mixture of $CH_2Cl_2$ and $CH_3CN$ (8:2, gradient elution) to give the title compound as a foam (2.49 g, 69.9%).

$^1H$ NMR (200 MHz, $CDCl_3$, 7.24) δ: 0.04, 0.05 (2 s, 6H, $Si(CH_3)_2$), 0.86 (s, 9H, $SiC(CH_3)_2$), 1.26 (d, 3H, $CH_3$), 1.63–1.8; 1.98–2.14 (m, 2H, CH₂), 3.12 (dd, 1H, H-6, J₆,₁=7.46 Hz), 3.45 (m, 1H, H-4, J=2.19, 9.45, 11.5 Hz), 3.63, 3.82 (centers of m, 2H, CH₂O), 4.01 (dd, 1H, H-5, J₅,₆=2.59 Hz, J₄,₅=9.45 Hz), 4.03–4.13 (AB, 2H, SCH₂, J=13.26 Hz), 4.155 (m, 1H, H-1'), 4.59–4.84 (m, 2H, OCH₂, allyl), 5.18–5.46 (m, 2H, =CH₂, allyl), 5.83–6.03 (m, 1H, CH=, allyl), 7.19–7.38 (m, 5H, phenyl).

C. Allyl (4R,5S,6S)-6-[(1'R)-1'-(tert-butyldimethylsilyloxyethyl)]-3-benzylthio-4-[2"-(N-benzyl-N-methyl)aminoethyl]-7-oxo-1-azabicyclo[3.2.0]hept-2-ene-2-carboxylate

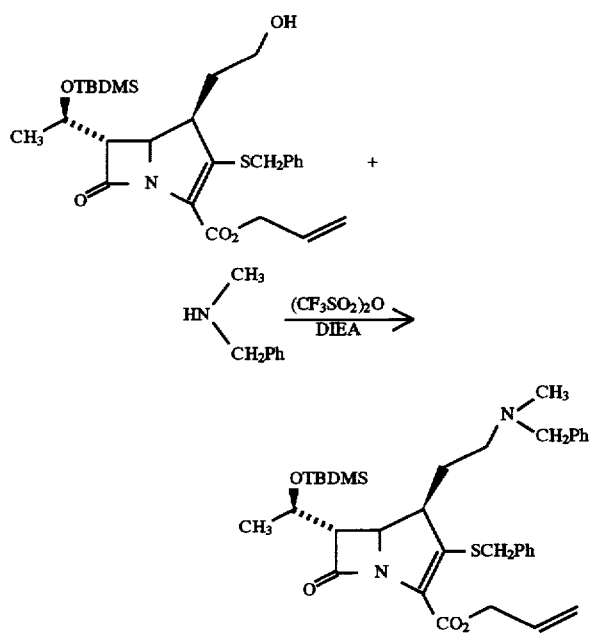

A solution of allyl (4R,5S,6S)-6-[(1'R)-1'-(tert-butyldimethylsilyloxyethyl)]-3-benzylthio-4-[2"-hydroxyethyl]-7-oxo-1-azabicyclo[3.2.0]hept-2-ene-2-carboxylate (0.5 g, 0.97 mmol) in dry CH₂Cl₂ (15 mL) was cooled to −78° C. under Argon and treated with diisopropylethylamine (0.185 mL, 1.06 mmol) followed by (CF₃SO₂)₂O (0.18 mL, 1.06 mmol). After 1 h at −78° C., N-benzyl-N-methylamine (0.75 mL, 5.8 mmol) was added and the mixture was stirred at −78° C. for 1 h and at 0° C. for 5 h and left at 5° C. for 16 h. The reaction mixture was diluted with EtOAc (200 mL) and washed with cold water and brine, dried (MgSO₄) and solvent evaporated to a syrup which was chromatographed on silica (4.5×13 cm) packed in CH₂Cl₂. The title compound was eluted with a mixture of CH₂Cl₂ and EtOAc (7:3, gradient elution) to give a syrup (0.4 g, 66.7%).

¹H NMR (200 MHz, CDCl₃ 7.24) δ: 0.036, 0.045 (2 s, 6H, Si(CH₃)₂), 0.86 (s, 9H, SiC(CH₃)₃), 1.07 (d, 3H, CH₃, J=6.16 Hz), 2.26 (S, 3H, NCH₃), 3.18 (m, 1H, H-4, J=1.94, 9.27, 11.37 Hz), 3.44–3.56 (AB, 2H, NCH₂, J_AB=13.15 Hz), 3.94 (dd, 1H, H-5, J₅,₆=2.47 Hz J₄,₅=9.32 Hz), 4.0–4.1 (AB, 2H, SCH₂, J_AB=13.21 Hz), 4.14 (m, 1H, H-1'), 4.7–4.8 (m, 2H, OCH₂, allyl), 5.19–5.48 (m 2H, =CH₂, allyl), 5.85–6.04 (m, 1H, CH=, allyl), 7.19–7.78 (m, 10H, phenyl).

D. Allyl (4R,5S,6S)-6-[(1'R)-1'-hydroxyethyl]-3-benzylthio-4-[2"-(N-benzyl-N-methyl)aminoethyl]-7-oxo-1-azabicyclo[3.2.0]hept-2-ene-2-carboxylate

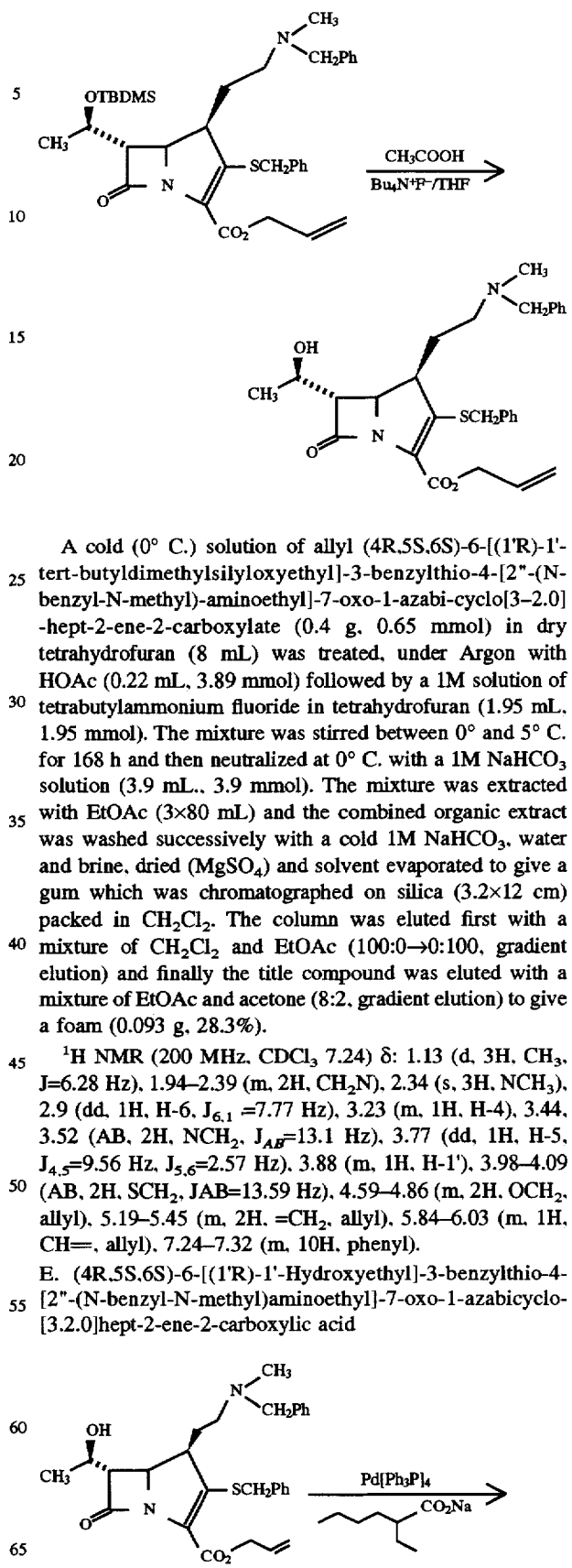

A cold (0° C.) solution of allyl (4R,5S,6S)-6-[(1'R)-1'-tert-butyldimethylsilyloxyethyl]-3-benzylthio-4-[2"-(N-benzyl-N-methyl)-aminoethyl]-7-oxo-1-azabi-cyclo[3–2.0]-hept-2-ene-2-carboxylate (0.4 g, 0.65 mmol) in dry tetrahydrofuran (8 mL) was treated, under Argon with HOAc (0.22 mL, 3.89 mmol) followed by a 1M solution of tetrabutylammonium fluoride in tetrahydrofuran (1.95 mL, 1.95 mmol). The mixture was stirred between 0° and 5° C. for 168 h and then neutralized at 0° C. with a 1M NaHCO₃ solution (3.9 mL, 3.9 mmol). The mixture was extracted with EtOAc (3×80 mL) and the combined organic extract was washed successively with a cold 1M NaHCO₃, water and brine, dried (MgSO₄) and solvent evaporated to give a gum which was chromatographed on silica (3.2×12 cm) packed in CH₂Cl₂. The column was eluted first with a mixture of CH₂Cl₂ and EtOAc (100:0→0:100, gradient elution) and finally the title compound was eluted with a mixture of EtOAc and acetone (8:2, gradient elution) to give a foam (0.093 g, 28.3%).

¹H NMR (200 MHz, CDCl₃ 7.24) δ: 1.13 (d, 3H, CH₃, J=6.28 Hz), 1.94–2.39 (m, 2H, CH₂N), 2.34 (s, 3H, NCH₃), 2.9 (dd, 1H, H-6, J₆,₁ =7.77 Hz), 3.23 (m, 1H, H-4), 3.44, 3.52 (AB, 2H, NCH₂, J_AB=13.1 Hz), 3.77 (dd, 1H, H-5, J₄,₅=9.56 Hz, J₅,₆=2.57 Hz), 3.88 (m, 1H, H-1'), 3.98–4.09 (AB, 2H, SCH₂, JAB=13.59 Hz), 4.59–4.86 (m, 2H, OCH₂, allyl), 5.19–5.45 (m, 2H, =CH₂, allyl), 5.84–6.03 (m, 1H, CH=, allyl), 7.24–7.32 (m, 10H, phenyl).

E. (4R,5S,6S)-6-[(1'R)-1'-Hydroxyethyl]-3-benzylthio-4-[2"-(N-benzyl-N-methyl)aminoethyl]-7-oxo-1-azabicyclo-[3.2.0]hept-2-ene-2-carboxylic acid -continued

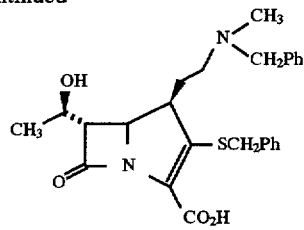

To a cold (0° C.) solution of allyl (4R,5S,6S)-6-[(1'R)-1'-hydroxyethyl]-3-benzylthio-4-[2"-(N-benzyl-N-methyl)-aminoethyl]-7-oxo-1-azabicyclo[3.2.0]hept-2-ene-2-carboxylate (0.093 g, 0.18 mmol) in $CH_2Cl_2$ (5 mL), under Argon, was added $Pd[Ph_3P]_4$ (0.026 g, 0.023 mmol) followed by a 0.5M solution of 2-ethyl hexanoate in EtOAc (0.37 mL, 0.18 mmol). The mixture was stirred at 0° C. for 50 min, diluted with diethyl ether (50 mL) and extracted with 0.1M pH 7.0 phosphate buffer (3×10 mL). The combined aqueous extract was passed through a column of µBondapak $C_{18}$ reverse phase silica (3.2×7 cm). The title compound was eluted with a mixture of water and $CH_3CN$ (7:3, gradient elution) and was obtained as a fluffy solid (0.067 g, 78.2%).

Purity: 99.9% by HPLC, UV detection at $\lambda_{max}$: 304 nm, on µBondapak $C_{18}$ (4 mm×30 cm), pH 6.8 phosphate buffer, flow rate 1 mL/min, retention time: 7.22 min.

UV $\lambda_{max}$: 304 nm.

IR (Nujol) $v_{max}$: 1750 cm$^{-1}$ (C=O, β-lactam).

$^1$H NMR (200 MHz, $D_2O$) δ: 1.12 (d, 3H, $CH_3$, J=6.35 Hz), 1.38, 1.94 (centres m, 2H, $CH_2$), 2.38 (s, 3H, $NCH_3$), 2.47 (centre m, 2H, $CH_2CN$), 3.04 (m, overlap, 1H, H-6), 3.05 (m, overlap, 1H, H-4), 3.72 (tight AB, 2H, $NCH_2$), 4.05 (dd, 1H, H-5), 3.96, 4.09 (AB, 2H, $SCH_2$, $J_{AB}$=13.8 Hz), 4.11 (m, 1H, H-1'), 7.35–7.54 (m, 10H, phenyl).

EXAMPLE 154

(4R,5S,6S)-3-[(2—Cyanoethyl)thio]-6-[(1'R)-1'-hydroxyethyl]-4-(3-N-methylaminopropyl)-7-oxo-1-azabicyclo-[3.2.0]hept-2-ene-2-carboxylic acid

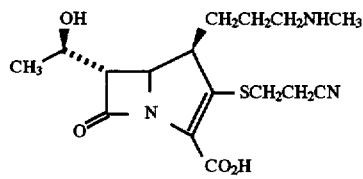

A. 5-N-Allyloxycarbonyl-N-methylaminovaleric acid

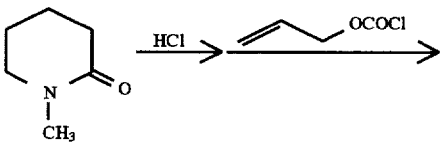

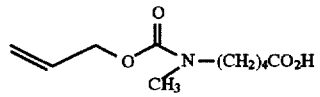

A mixture of 1-methyl-2-piperidone (13.0 g, 0.115 mmol) and 100 mL of 6N hydrochloric acid was heated under reflux for 8 h. The solvent was evaporated to dryness and the residual amino acid as described by M. Maeda, et. al., *Chem. Pharm. Bull.* 32, 4157 (1984) was diluted with cold water (0°–5° C., 100 mL). The pH was adjusted to 8.5 with solid sodium carbonate and allyl chloroformate (12.2 mL, 0.115 mmol) was added dropwise while maintaining the pH to 8–8.5. After 30 min at 0° C. and another 30 min at 22° C., the reaction mixture was washed with diethyl ether and the aqueous phase was adjusted to pH 3 with concentrated hydrochloric acid. The aqueous solution was extracted with diethyl ether (3×200 mL) and the combined organic extract was washed with brine and dried ($MgSO_4$). Evaporation of the solvent gave 22.9 g (93%) of the title acid as an oil.

IR (NaCl, film) $v_{max}$: 1740, 1710 and 1680 cm$^{-1}$ (sh);

$^1$H NMR (200 MHz, $CDCl_3$) δ: 1.5–1.7 (m, 4H, $CH_2$-3 and (4), 2.35–2.45 (m, 2H, $CH_2$-2), 2.90 (s, 3H, $NCH_3$), 3.25–3.35 (m, 2H, $CH_2N$), 4.55–4.6 (m, 2H, $CH_2$ of allyl), 5.15–5.35 and 5.85–6.05 ppm (2m, 2H and 1H, CH of allyl).

B. 5-N-Allyloxycarbonyl-N-methylaminovaleryl chloride

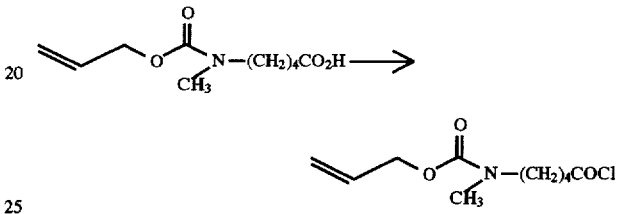

A solution of 5-N-allyloxycarbonyl-N-methylaminovaleric acid (35.26 g, 0.164 mol) in dry dichloromethane (175 mL) was treated dropwise at 22° C. with oxalyl chloride (15.7 mL, 0.180 mol). After 10 min, 4 drops of N,N-dimethylformamide were added and the reaction mixture was stirred for 2.0 h, while the evacuation of gas slowly ceased. The solvent and excess reagent were evaporated under reduced pressure and the residual acid chloride was used as such for the next step:

IR (NaCl, film) $v_{max}$: 1800 (C=O of acid chloride), 1740 (sh), 1705 and 1670 cm$^{-1}$ (sh);

$^1$H NMR (200 MHz, $CDCl_3$) δ: 1.5–1.8 (m, 4H, $CH_2$-3 and 4), 2.90 (s, 3H, $NCH_3$), 2.9–3.0 (m, 2H, $CH_2$-2), 3.29 (t, 2H, $CH_2N$), 4.55–4.6 (m, 2H, $CH_2$ of allyl), 5.15–5.35 and 5.8–6.0 ppm (2m, 2H and 1H, CH of allyl).

C. 2-Picolyl-5-(N-allyloxycarbonyl-N-methylamino]thiolvalerate

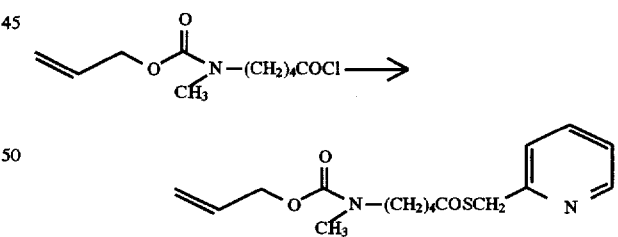

A solution of 2-picolyl mercaptan (20.5 g, 0.164 mol) in dry dichloromethane (350 mL) was treated at 0° C. and under nitrogen with pyridine (16.0 mL, 0.197 mol) followed by a solution of 5-N-allyloxycarbonyl-N-methylaminovaleryl chloride (46.0 g, 0.164 mol) in dichloromethane (75 mL) added dropwise over 10 min. After 1.5 h at 0°–5° C., the reaction mixture was washed with saturated sodium bicarbonate, brine and dried ($MgSO_4$). Evaporation of the solvent under reduced pressure gave an oil which was filtered through a silica gel pad (7.5×12 cm) using a mixture of toluene and ethyl acetate (1:1) as eluent. Evaporation of the UV active fractions gave 48.4 g (92%) of the title material as a clear oil:

IR (NaCl, film) $v_{max}$: 1700 and 1690 (sh) cm$^{-1}$;

$^1$H NMR (200 MHz, D$_2$O) δ: 1.5–1.7 (m, 4H, CH$_2$-3 and 4), 2.61 (t, J=7.0 Hz, 2H, CH$_2$-2), 2.87 (s, 3H, NCH$_3$), 3.26 (t, J=6.6 Hz, 2H, CH$_2$-5), 4.24 (s, 2H, CH$_2$Pyr), 4.55–4.6 (m, 2H, CH$_2$ of allyl), 5.15–5.3 and 5.9–6.05 (2 m, 2H and 1H, H of allyl), 7.1–7.2 (m, 1H, H-5 of pyridine), 7.33 (d, J=7.8 Hz, 1H, H-3 of pyridine), 7.62 (m, 1H, H-4 of pyridine) and 8.5–8.55 ppm (m, 1H, H-6 of pyridine).

D. tert-Butyldimethylsilylenol ether of 2-picolyl-5-(N-allyloxycarbonyl-N-methylamino)thiolvalerate

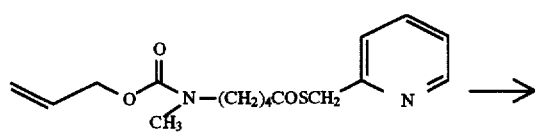

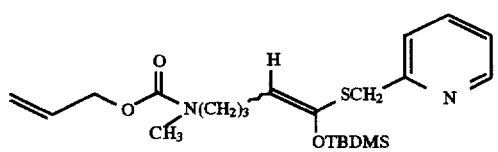

A solution of 2-picolyl 5-(N-allyloxycarbonyl-N-methylamino)thiolvalerate (51.3 g, 0.159 mol) in dry dichloromethane (225 mL) was cooled to −10° C. and treated with triethylamine (44 mL, 0.315 mol) followed by tertbutyldimethylsilyl trifluoromethanesulfonate (56 mL, 0.243 mol) dropwise over 40 min. After warming to 22° C., the solution was stirred for 3 h. The reaction mixture was then diluted with hexane (1 L) and washed with cold water (3×300 mL). The combined aqueous washings were extracted with hexanes (300 mL) and the combined organic extracts were washed with brine and dried (MgSO$_4$). After treating with activated carbon, the solvent was evaporated under vacuum to give the crude silyl enol ether as a dark oil which was used as such for the next step. By $^1$H NMR, the product was a 1:1 mixture of E and Z isomers.

IR (NaCl film) $v_{max}$: 1705 cm$^{-1}$ (C=O of carbamate);

$^1$H NMR (200 MHz, CDCl$_3$) δ: 2.83 and 2.85 (2s, NCH$_3$), 3.96 and 4.03 (2s, CH$_2$Pyr), 4.85 (t, J=5 Hz, CH=CSO) and 5.0 ppm (broad t, CH=CSO).

E. (3S,4S)-3-[(1'R)-1'-tert-Butyldimethylsilyloxyethyl]-4-[(1R)-1-(2-pyridyl)methylthiocarbonyl-4-(N-allyloxycarbonyl-N-methylamino)butyl]azetidin-2-one

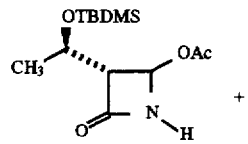

+

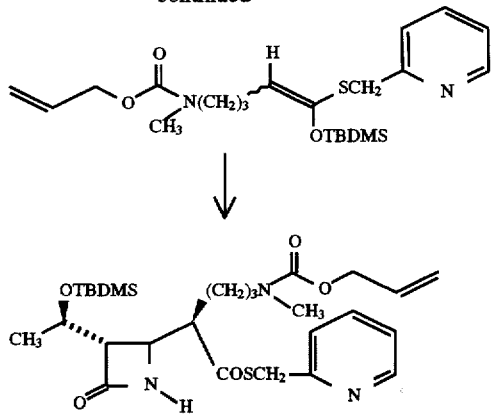

To a suspension of freshly fused zinc chloride (35.0 g, 0.256 mol) in dry dichloromethane (400 mL) was added at 22° C. solid 4R-acetoxy-3S-[(1'R)-1'-tert-butyldimethylsilyl-oxyethyl]azetidin-2-one (36.5 g, 0.127 mol) followed by a solution of the crude silyl enol ether (0.159 mol) in dry dichloromethane (50 mL). The reaction mixture was then stirred at 22° C. for 18 h. The mixture was then washed with water, saturated ammonium chloride, saturated sodium bicarbonate, brine and dried (MgSO$_4$). Evaporation of the solvent under reduced pressure gave an oil which was chromatographed on silica gel (15×12 cm). Elution with a gradient of ethyl acetate (50–100%) in toluene gave 34.16 g (49%) of the title material as an oil. By $^1$H NMR this product was a 84:16 mixture of β and α isomers.

IR (NaCl, film) $v_{max}$: 1765 (C=O of β-lactam), 1705 (sh) and 1685 cm$^{-1}$ (C=O of carbamate and thioester);

$^1$H NMR (200 MHz, CDCl$_3$, major isomer, β) δ: 0.04 (s, 6H, SiCH$_3$), 0.85 (s, 9H, Si-t-Bu), 0.97 (d, J=6.33 Hz, 3H, CH$_3$CHO), 1.3–1.8 (m, 4H, CH$_2$-2 and 3 of butyl), 2.83 (s, 3H, NCH$_3$), 2.83 (m overlapping with NCH$_3$, 1H, H-1 of butyl), 3.03 (broad t, 1H, H-3), 3.1–3.4 (m, 2H, CH$_2$N), 3.79 (dd, J$_{H4,H3}$=1.96 Hz, J$_{H4,H1}$=7.16 Hz, 1H, H-4), 4.1–4.25 (m, 1H, CH$_3$CHO), 4.26 (s, 2H, CH$_2$Pyr), 4.55–4.6 (m, 2H, CH$_2$ of allyl), 5.15–5.35 (m, 2H, CH of allyl), 5.85–6.1 (m, 2H, NH and CH of allyl), 7.15–7.20 (m, 1H, H-5 of pyridine), 7.32 (d, J=7.78 Hz, 1H, H-3 of pyridine), 7.55–7.65 (m, 1H, H-4 of pyridine) and 8.5–8.55 ppm (m, 1H, H-6 of pyridine).

F. Imidazolide of (3S,4S)-3-[(1'R)-1'-tert-butyldimethylsilyloxyethyl]-4-[(1R)-1-carboxy-4-(N-allyloxycarbonyl-N-methylamino)butyl]azetidin-2-one

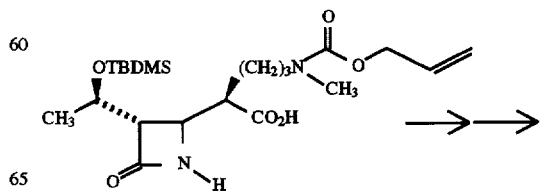

333

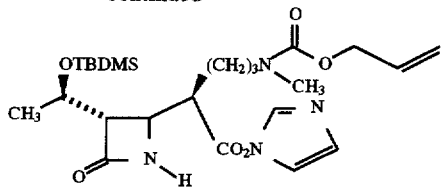

A solution of (3S,4S)-3-[(1'R)-1'-tert-butyldimethylsilyloxyethyl]-4-[(1R)-1-carboxy-4-(N-allyloxycarbonyl-N-methylamino)butyl]azetidin-2-one (13.56 g, 31.6 mmol) in dry acetonitrile (300 mL) was treated at 22° C. and under nitrogen with 1,1-carbonyldiimidazole (5.64 g, 34.8 mmol). After 3 h, the solvent was evaporated under reduced pressure and the crude imidazolide was used as such for the next step.

IR (NaCl, film) $v_{max}$: 1760, 1740 and 1700 cm$^1$.

G. (3S,4S)-3-[(1'R)-1'-tert-Butyldimethylsilyloxyethyl]-4-[(1R)-1-carboxy-4-(N-allyloxycarbonyl-N-methyl-amino)butyl]azetidin-2-one

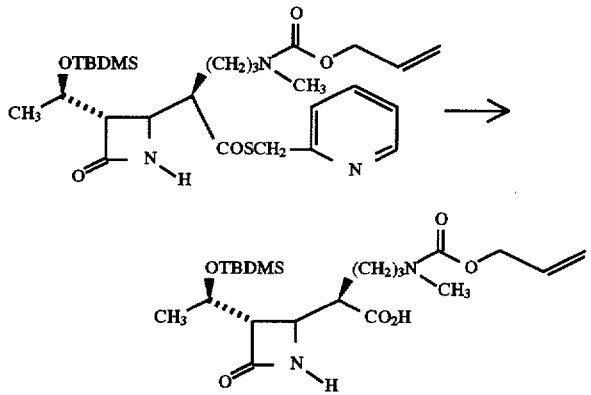

A solution of (3S,4S)-3-[(1'R)-1'-tert-butyldimethylsilyloxyethyl]-4-[(1R)-1-(2-pyridyl)methylthiocarbonyl-4-(N-allyloxycarbonyl-N-methylamino)butyl]azetidin-2-one (32.16 g, 58.5 mmol) in dry tetrahydrofuran (250 mL) was treated dropwise at 0°–5° C. with 30% hydrogen peroxide (20 mL, 0.23 mol) (addition time 5 min) followed by 64 mL (64.0 mmol) of 1N aqueous sodium hydroxide (addition time 20 min). The reaction mixture is then stirred at 22° C. for 1 h. Then hexane (500 mL) was added and the mixture was stirred for another 10 min. The aqueous phase formed was collected and the organic phase was extracted with 100 mL of 0.1N sodium hydroxide. The combined aqueous extracts were cooled to 0°–5° C., acidified to pH 2 with concentrated hydrochloric acid and extracted with ethyl acetate (2×350 mL). The combined organic extracts were washed with 1M sodium bisulfite, brine and dried (MgSO$_4$). Evaporation of the solvent under reduced pressure gave 13.56 g (52%) of the crude title acid as a foam. $^1$H NMR indicated a δ: 2 mixture of β and α isomers.

IR (NaCl, film) $v_{max}$: 1740 (C=O of β-lactam) and 1700 (broad, C=O of carbamate and acid);

$^1$H NMR (200 MHz, CDCl$_3$) δ: 0.05 and 0.06 (2s, 6H, SiCH$_3$), 0.86 (s, 9H, Si-t-Bu), 1.15 (d, J=6.30 Hz, 3H, CH$_3$CHO), 1.4–1.8 (m, 4H, CH$_2$-2 and 3 of propyl), 2.6–2.7 (m, 1H, H-1 of butyl), 2.89 (s, 3H, NCH$_3$), 3.12 (broad t, 1H, H-3), 3.2–3.5 (m, 2H, CH$_2$N), 3.86 (dd, J$_{H4,H3}$=1.84 Hz, J$_{H4,H1}$=6.38 Hz, 1H, H-4), 4.19 (dq, J$_{H,CH_3}$=6.30, J$_{H,H3}$=3.8 Hz, 1H, CH$_3$CHO), 4.55–4.6 (m, 2H, CH$_2$ of allyl),

334

5.15–5.35 and 5.8–6.05 (2m, 2H and 1H, CH of allyl) and 6.53 ppm (broad s, 1H, NH).

H. (3S,4R)-3-[(1'R)-1'-tert-Butyldimethylsilyloxyethyl]-4-{(1R)-[(3-N-allyloxycarbonyl-N-methylamino)propyl]-3-allyloxycarbonyl-2-oxopropyl}azetidin-2-one

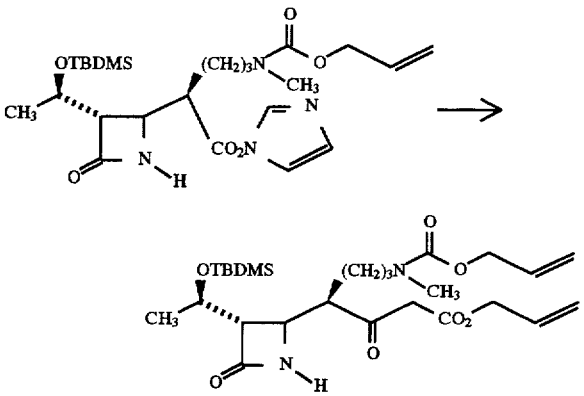

A solution of the crude imidazole (31.6 mmol) in dry acetonitrile (50 mL) was added to a mixture of magnesium monoallyl malonate (16.0 g, 51.5 mmol) in dry benzene (300 mL) and the resulting mixture was maintained at 65° C. for 16 h. The cooled reaction mixture was then diluted with ethyl acetate (500 mL) washed with cold 1N aqueous hydrochloric acid, saturated sodium bicarbonate and brine. After drying (MgSO$_4$), the organic phase was evaporated under reduced pressure and the residual oil was used as such for the next step. Chromatography of a small aliquot on silica gel (elution toluene-ethyl acetate 9:1 to 1:1) gave the title compound as an oil. $^1$H NMR indicated a 1:1 mixture of keto and enol form.

IR (NaCl, film) $v_{max}$: 1760 (C=O of β-lactam) and 1705 cm$^{-1}$;

$^1$H NMR (200 MHz, CDCl$_3$) δ: 0.05 and 0.06 (2s, SiCH$_3$), 0.86 (s, Si-t-Bu), 1.09 and 1.16 (2d, J=6.31 Hz, J=6.29 Hz, CH$_3$CHO), 1.3–1.8 (m, CH$_2$-1 and 2 of butyl), 2.1 (m, H-1 of oxopropyl, keto form), 2.88 (s, NCH$_3$), 2.8–3.1 (m, H-3), 3.2–3.3 (m, CH$_2$N), 3.55 (s, CH$_2$-3 of oxopropyl keto form), 3.82 (2 dd overlapping, H-4), 4.1 (m, 1H, CH$_3$CHO), 4.57 and 4.63 (2m, CH$_2$ of allyl), 5.08 (s, CH-3 of oxopropyl, enol form), 5.15–5.4 (m, CH of allyl) and 5.8–6.1 ppm (m, CH of allyl and NH).

I. (3S,4R)-3-[(1'R)-1'-tert-Butyldimethylsilyloxyethyl]-4-{(1R]-1-[{3-N-allyloxycarbonyl-N-methylamino)propyl]-3-allyloxycarbonyl-3-diazo-2-oxopropyl}-azetidin-2-one

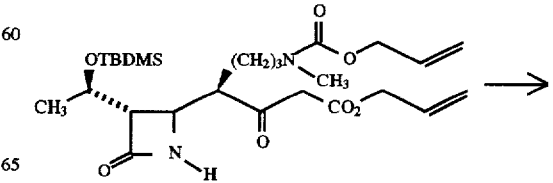

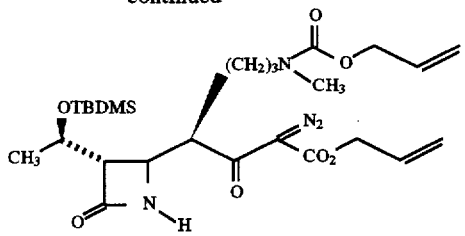

A solution of (3S,4R)-3-[(1'R)-1'-tert-butyldimethylsilyloxyethyl]-4-{(1R)-1-[(3-N-allyloxycarbonyl-N-methylamino)propyl]-3-allyloxycarbonyl-2-oxopropyl}-azetidin-2-one (crude from the previous step, 31.6 mmol) in acetonitrile (100 mL) was cooled to 0°–5° C. and treated with a solution of p-toluenesulfonyl azide (6.45 g, 32.7 mmol) in acetonitrile (35 mL). Then N,N-diisopropylethylamine (4.6 mL, 33.0 mmol) was added dropwise over 5 min and the resulting mixture was stirred for 45 min at 22° C. The solvent was then evaporated under reduced pressure and the residue was triturated with a mixture of diethyl ether and hexanes (1:1, 100 mL). The crystalline p-toluenesulfonamide was collected by filtration and washed with a mixture of diethyl ether and hexanes (1:1). The filtrate and the washing were evaporated under reduced pressure to give the crude diazooazetidinone which was used as such for the next step. Purification of a small aliquot on silica gel (elution toluene ethyl acetate 1:1) gave the title compound as an oil.

IR (NaCl, film) $v_{max}$: 2140 (N$_2$), 1760 (C=O of β-lactam), 1710 and 1650 cm ;

$^1$H NMR (200 MHz, CDCl$_3$) δ: 0.05 and 0.06 (2s, 6H, SiCH$_3$), 0.86 (s, 9H, Si-t-Bu), 1.15 (d, J=6.35 Hz, 3H, CH$_3$CHO), 1.3–1.9 (m, 4H, CH$_2$-1 and 2 of propyl), 2.87 (s, 3H, NCH$_3$), 3.03 (m, 1H, H-3), 3.23 (broad t, J=6.7 Hz, CH$_2$N), 3.84 (dd, J$_{H4,H3}$=2.09 Hz, J$_{H4,H1}$=5.51 Hz, 1H, H-4), 4.0–4.15 (m, 1H, H-1 of oxopropyl), 4.15–4.25 (m, 1H, CH$_3$CHO), 4.5–4.6 and 4.7–4.8 (2m, 2×2H, CH$_2$ of allyl), 5.1–5.3 (m, 4H, CH of allyl) and 5.8–6.1 ppm (m, 3H, CH of allyl and NH).

J. (3S,4R)-4-{(1R)-1-[(3-N-Allyloxycarbonyl-N-methylamino)propyl]-3-allyloxycarbonyl-3-diazo-2-oxopropyl}-3-[(1'R)-1'-hydroxyethyl]azetidin-2-one

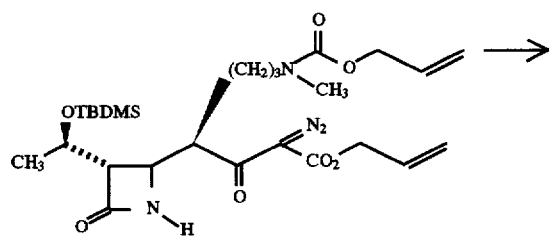

A solution of (3S,4R)-3-[(1'R)-1'-tert-butyldimethylsilyloxyethyl]-4-{(1R)-1-[(3-N-allyloxycarbonyl-N-methylamino)propyl]-3-allyloxycarbonyl-3-diazo-2-oxopropyl}-azetidin-2-one (31.6 mmol, crude from the previous step) in ethanol (175 mL) was cooled to 0°–5° C. and treated with 1N aqueous hydrochloric acid (100 mL). After 18 h at 5° C., the pH was adjusted to 6 with solid sodium bicarbonate and the ethanol was evaporated under reduced pressure. The residue was diluted with ethyl acetate (300 mL) and the organic phase was washed with 0.2M pH 7.0 phosphate buffer and brand brine. After drying (MgSO$_4$), the solvent was evaporated under reduced pressure and the residue was chromatographed on silica gel (9×11 cm). Elution with a mixture of toluene and ethyl acetate (1:1) gave 5.92 g (43%, yield for 5 steps from the acid) of the title compound as an oil.

IR (NaCl, film) $v_{max}$: 3450 and 3280 (broad OH and NH), 2140 (N$_2$), 1755 (C=O of β-lactam), 1700 (broad) and 1645 cm$^{-1}$;

$^1$H NMR (200 MHz, CDCl$_3$) δ: 1.29 (d, J=6.33 Hz, 1H, CH$_3$HO), 1.4–1.8 (m, 4H, CH$_2$-1 and 2 of propyl), 2.88 (s, 3H, NCH$_3$), 2.9 (broad, 1H, H-3), 3.1–3.4 (m, 2H, CH$_2$N), 3.80 (dd, J$_{H4,H3}$=1.98 Hz, J$_{H4,H1}$=6.95 Hz, 1H, H-4), 3.9–4.0 (m, 1H, H-1 of oxopropyl), 4.1 (m, 1H, CH$_3$CHO), 4.55–4.6 and 4.7–4.75 (2m, 2×2H, CH$_2$ of allyl), 5.2–5.45 and 5.9–6.1 (2m, 4H and 2H, CH of allyl) and 6.6 ppm (broad s, NH).

K. Allyl (2R,4R,5R,6S)-4-[(3"-N-allyloxycarbonyl-N-methylamino]propyl]-6-[(1'R)-1'-hydroxyethyl]-3,7-dioxo-1-azabicyclo[3.2.0]heptane-2-carboxylate

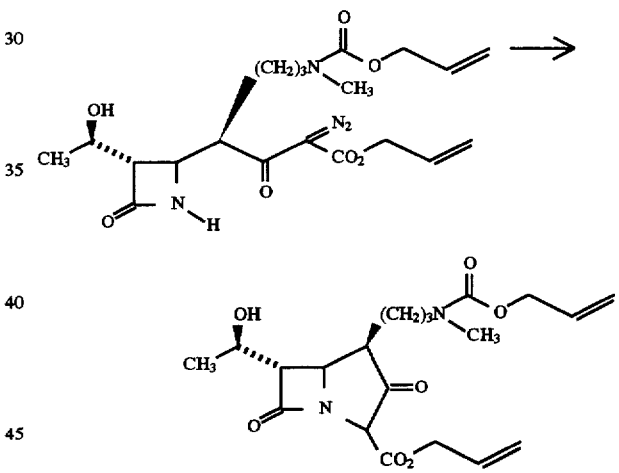

A solution of (3S,4R)-4-{(1R)-1-[(3-N-allyloxycarbonyl-N-methylamino)propyl]-3-allyloxycarbonyl-3-diazo-2-oxopropyl}-3-[(1'R)-1'-hydroxyethyl]azetidin-2-one(2.00 g, 4.58 mmol) in dry benzene (80 mL) was heated under reflux in presence of rhodium octanoate dimer (0.050 g) for 30 min. The solvent was evaporated under reduced pressure and the title bicyclic product was used as such for the next step.

IR (NaCl, film) $v_{max}$: 3450 (OH), 1762 (C=O of β-lactam), 1645 (sh) and 1690 cm$^{-1}$;

$^1$H NMR (200 MHz, CDCl$_3$) δ: 1.43 (broad d, J=6.1 Hz, 3H, CH$_3$CHO), 1.5–2.0 (m, 4H, CH$_2$-1 and 2 of propyl), 2.9 (m, 1H, H-4 of propyl), 2.92 (s, 3H, NCH$_3$), 3.1–3.4 (m, 3H, H-6 and CH$_2$N), 4.1–4.3 (m, 1H, CH$_3$CHO), 4.3 broad dd, 1H, H-5), 4.56 and 4.66 (2m, 2×2H, CH$_2$ of allyl), 5.15–5.4 and 5.8–6.15 ppm (2m, 4H and 2H, CH of allyl).

L. Allyl (4R,5S,6S)-4-[(3"-N-allyloxycarbonyl-N-methylamino)propyl]-3-[(2-cyanoethyl)thio]-6-[(1'R)-1'-hydroxyethyl]-7-oxo-1-azabicyclo[3.2.0]hept-2-ene-2-carboxylate

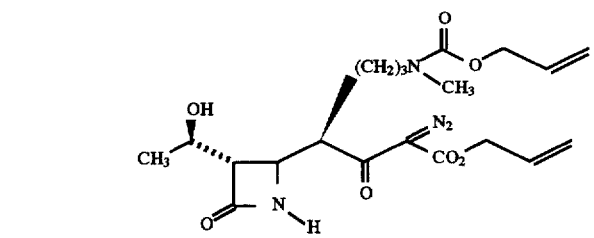

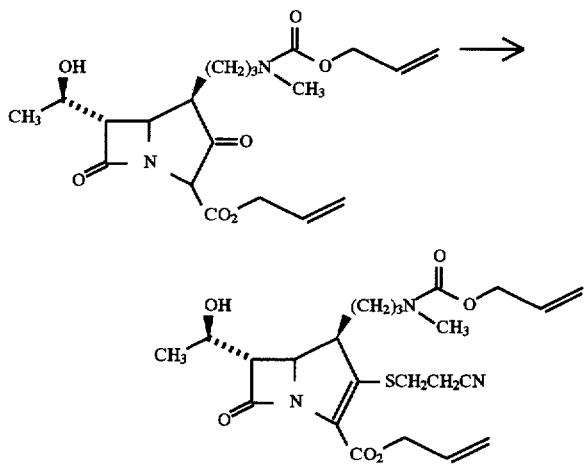

A solution of the crude bicyclic ketone prepared in Step K (4.58 mmol) in dry acetonitrile (40 mL) was treated at 0°–5° C. and under nitrogen with diphenyl chlorophosphate (1.04 mL, 5.02 mmol) and N,N-diisopropylethylamine (0.88 mL, 5.06 mmol) added simultaneously over 2 min. A small crystal of 4-N,N-dimethylaminopyridine was added and the mixture was stirred for 45 min. Then more N,N-diisopropylethylamine (0.80 mL, 4.60 mmol) followed by a solution of β-mercaptopropionitrile (0.40 g, 4.60 mmol) in acetonitrile (2 mL) were added and the resulting mixture was stirred for 1 h. The reaction mixture was then diluted with ethyl acetate (300 mL) washed with cold water, saturated sodium bicarbonate, brine and dried ($MgSO_4$). Evaporation of the solvent under reduced pressure gave an oil which was chromatographed on silica gel (5×10 cm). Elution with a gradient of ethyl acetate in toluene (1:1 to EtOAc) gave 1.45 g (67%) of the title compound as an oil.

IR (NaCl, film) $v_{max}$: 3450 (OH), 2250 (CN), 1775 (C=O of β-lactam) and 1700 $cm^{-1}$ (C=O of ester and carbamate);

$^1$H NMR (200 MHz, $CDCl_3$) δ: 1.44 (broad d, J=6.0 Hz, 3H, $CH_3$CHO), 1.5–2.0 (m, 4H, $CH_2$-1 and 2 of propyl), 2.67 (broad t, 2H, $SCH_2CH_2CN$), 2.94 (s, 3H, $NCH_3$), 2.9–3.5 (m, 4H, H-6, H-4 and $CH_2N$), 4.06 (m, 1H, $CH_3$CHO), 4.28 (dd, $J_{H5,H6}$=2.78 Hz, $J_{H5,H4}$=9.79 Hz, 1H, H-5), 4.57 and 4.76 (2m, 2×2H, $CH_2$ of allyl), 5.2–5.5 and 5.8–6.1 ppm (2m, 4H and 2H, CH of allyl).

M. (4R,5S,6S)-3-[(2-Cyanoethyl)thio]-6-[(1'R)-1'-hydroxyethyl]-4-(3"-N-methylaminopropyl)-7-oxo-1-azabicyclo[3.2.0]hept-2-ene-2-carboxylic acid

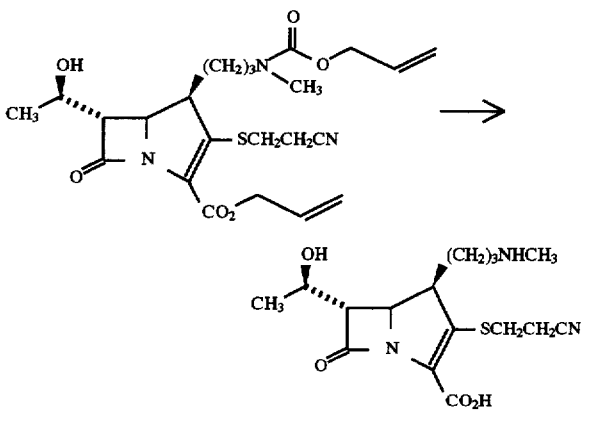

A solution of allyl (4R,5S,6S)-4-[(3"-N-allyloxycarbonyl-N-methylamino)propyl]-3-[(2-cyanoethyl)thio]-6-[(1'R)-1'-hydroxyethyl]-7-oxo-1-azabicyclo[3.2.0]hept-2-ene-2-carboxylate (0.760 g, 1.59 mmol) in dry dichloromethane (25 mL) was treated at 22° C. and under nitrogen with N-methylaniline (1.0 mL, 9.23 mmol) followed by tetrakis (triphenylphosphine)palladium[O] (0.060 g). After 3 h, the reaction mixture was extracted with water (2×25 mL) and 0.05M pH 6.0 phosphate buffer (35 mL). The combined aqueous extract was chromatographed on reversed phase silica gel (3×13 cm) using a gradient of acetonitrile (0–10%) in water as eluent. Lyophilization of the first fractions gave 0.156 g (27%) of the title compound as a white amorphous solid: $[α]^{22}_D$+57.9° (c 1.0, water).

Purity by HPLC: 99.7% on μBondapak $C_{18}$, 3.9 mm×30 cm, elution 5% $CH_3CN$—$H_2O$ pH 7.4 phosphate buffer, flow rate 0.7 mL/min, UV detector 302 nm, retention time 6.37 min;

UV (water pH 7.4 phosphate buffer) $λ_{max}$: 300 nm (9,050);

IR (KBr) $v_{max}$: 2250 (CN), 1755 (C=O of β-lactam) and 1590 $cm^{-1}$ (C=O of carboxylate);

$^1$H NMR (200 MHz, $D_2O$) δ: 1.33 (d, J=6.35 Hz, 3H, $CH_3$CHO), 1.5–2.0 (m, 4H, $CH_2$-1 and 2 of propyl), 2.72 (s, 3H, $CH_3$N), 2.75–2.9 (m, 2H, $SCH_2CH_2CN$), 2.9–3.25 (m, 2H, $CH_2$N), 3.40 (dd, $J_{H6,H5}$=2.61 Hz, $J_{H6,H1}$=6.53 Hz, 1H, H-6), 3.42 (m overlapping with H-6, 1H, H-4) and 4.2–4.35 ppm (m, 2H, H-5 and $CH_3$CHO overlapping).

EXAMPLE 155

When the general procedures of the foregoing text and examples are repeated with the appropriate intermediate and mercaptan compound, there is thereby produced a compound or salt thereof having the formula

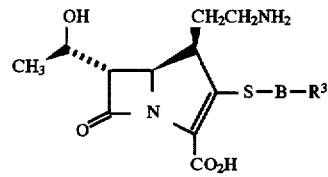

wherein B—$R^3$ is

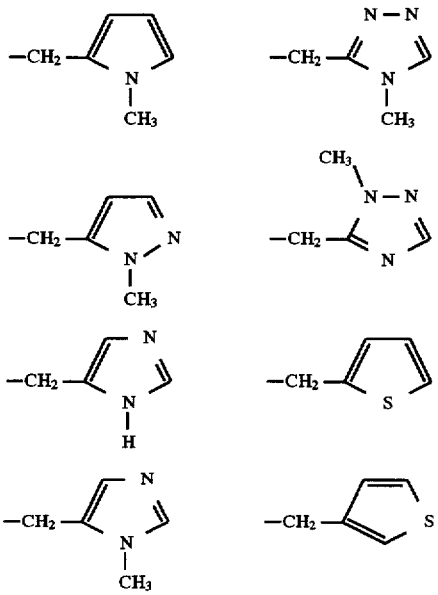

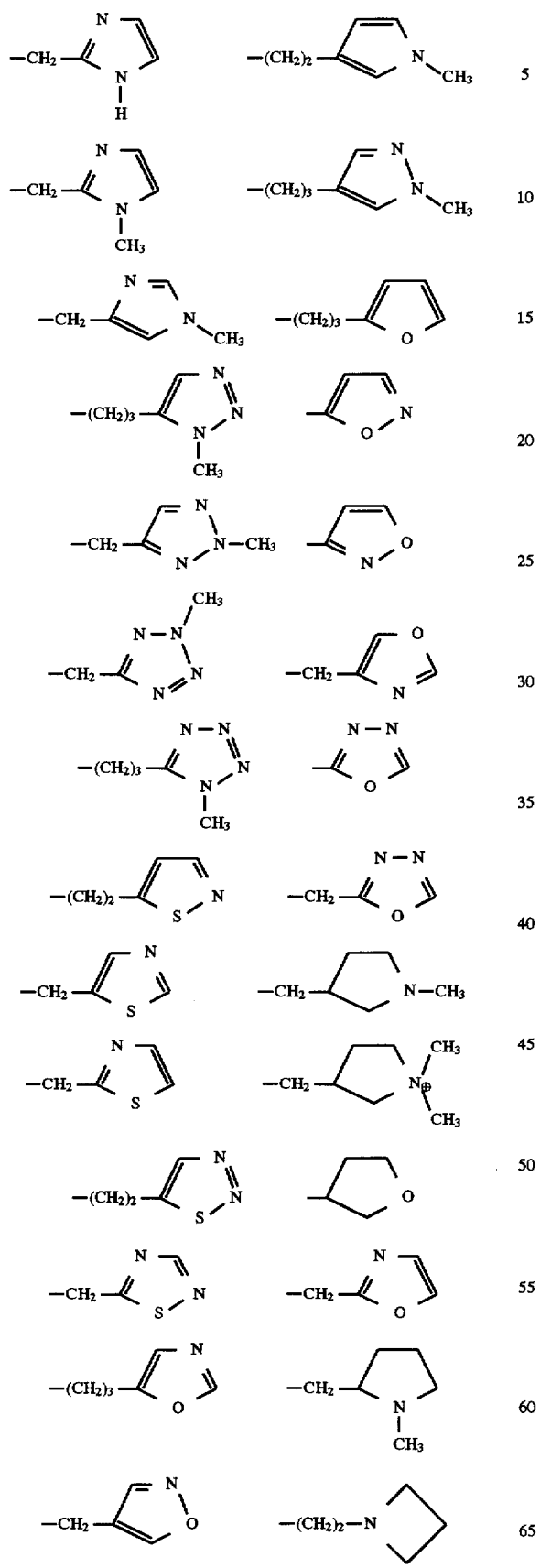
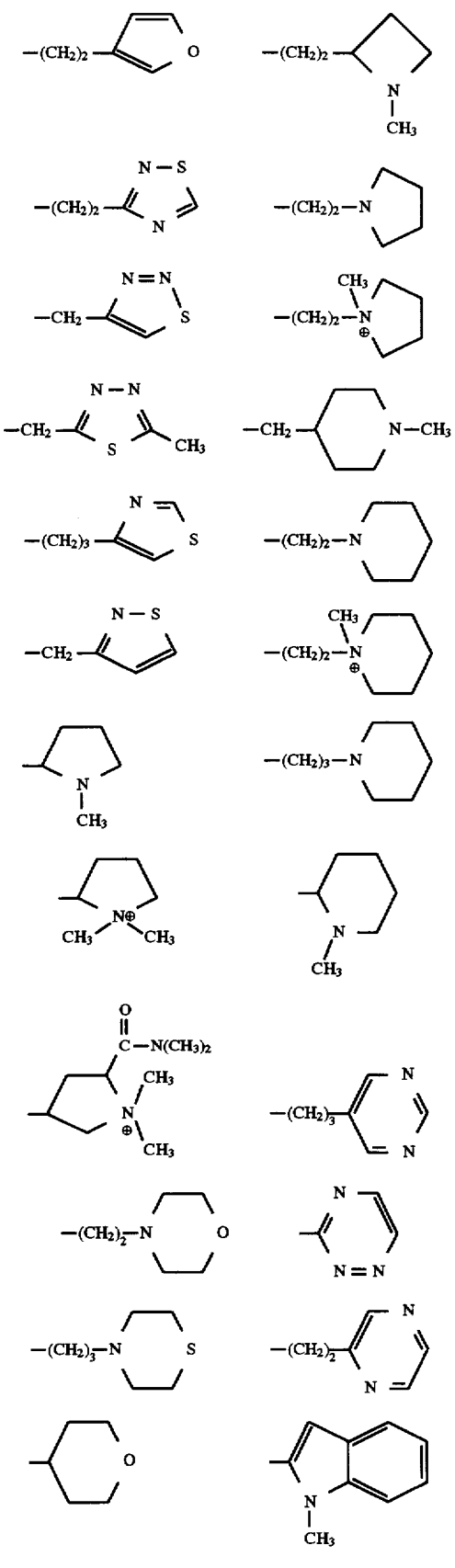

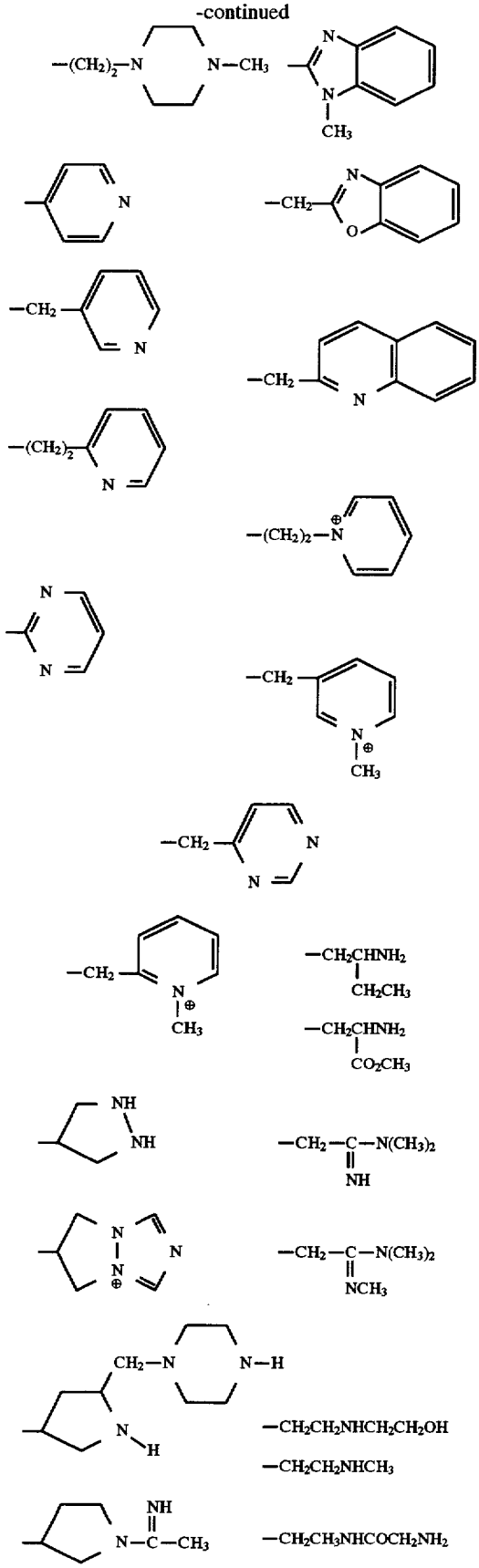
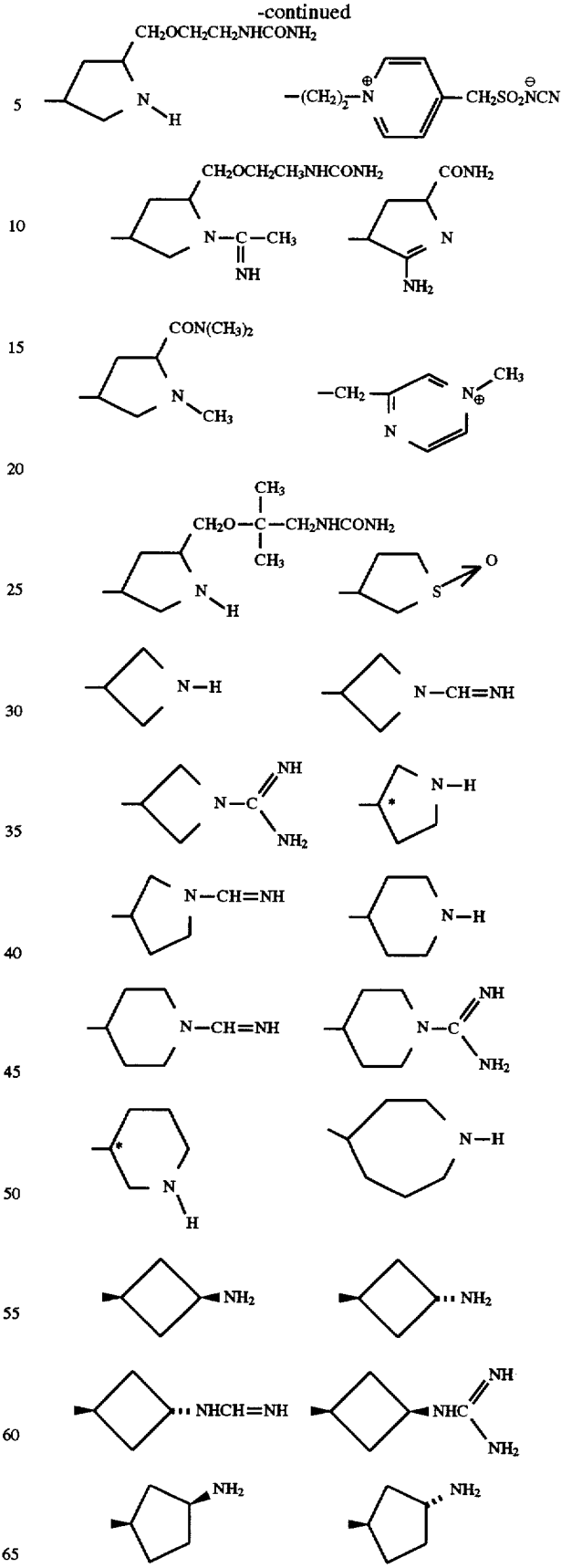

EXAMPLE 156

When the general procedures of the foregoing text and examples are repeated with the appropriate intermediate and mercaptan compound, there is thereby produced a compound or salt thereof having the formula wherein B—$R^3$ is 345
-continued
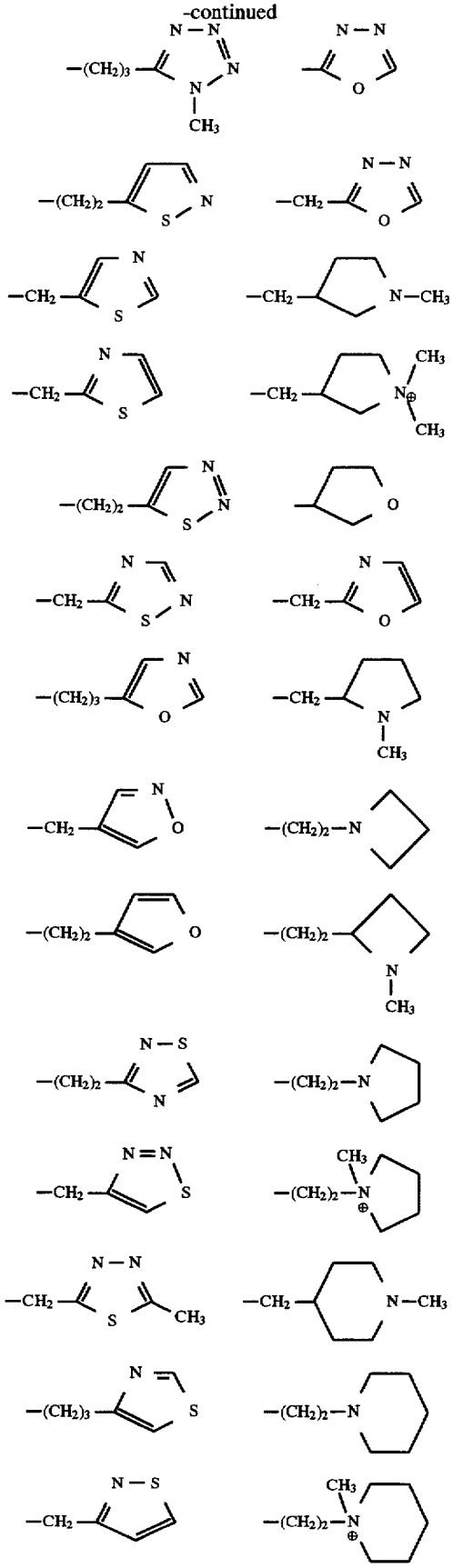
346
-continued
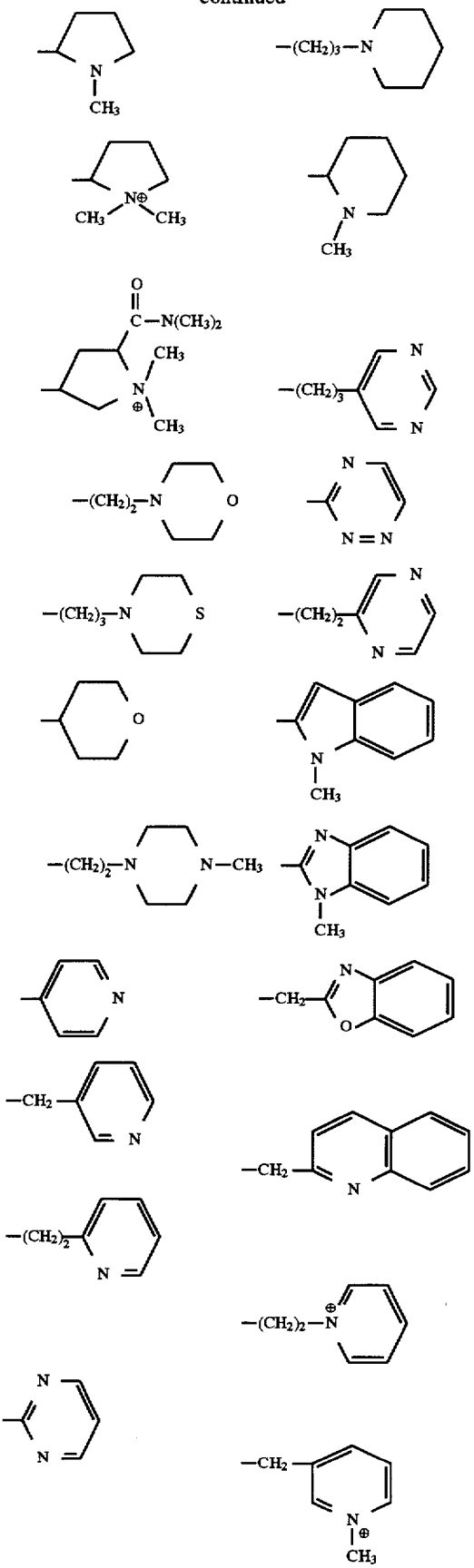

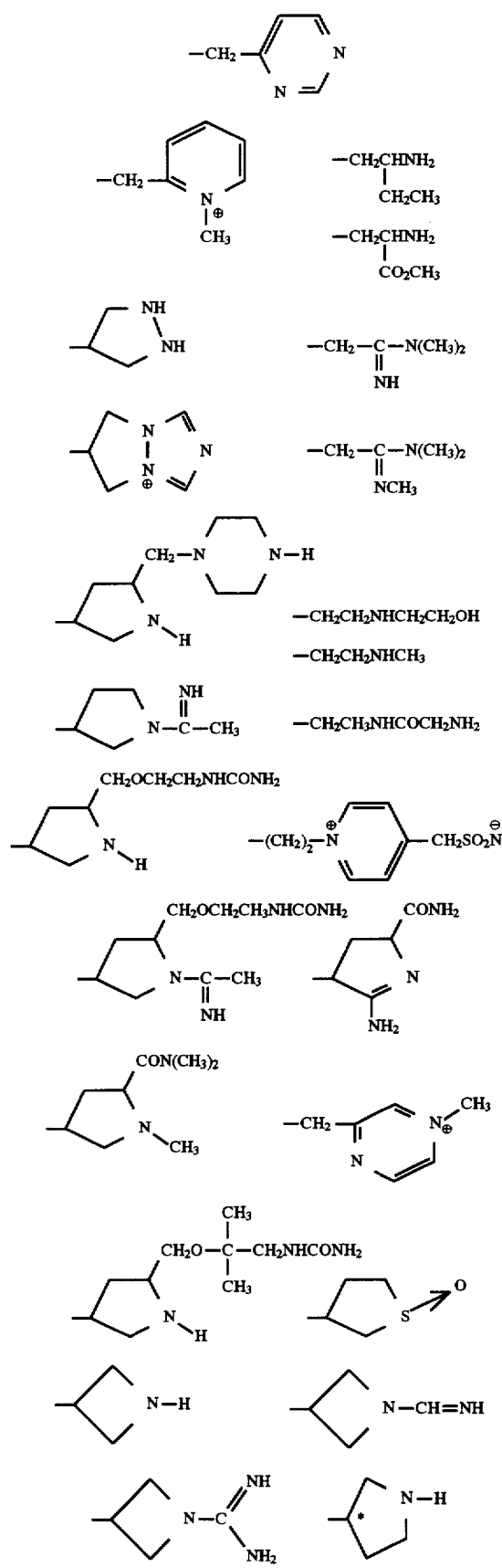
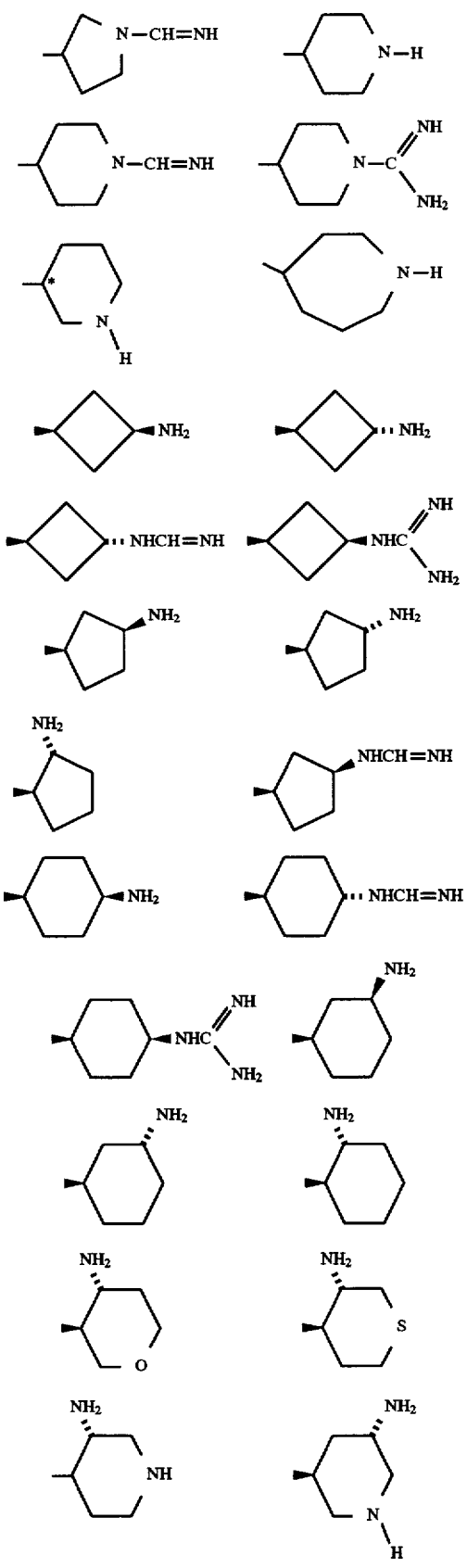

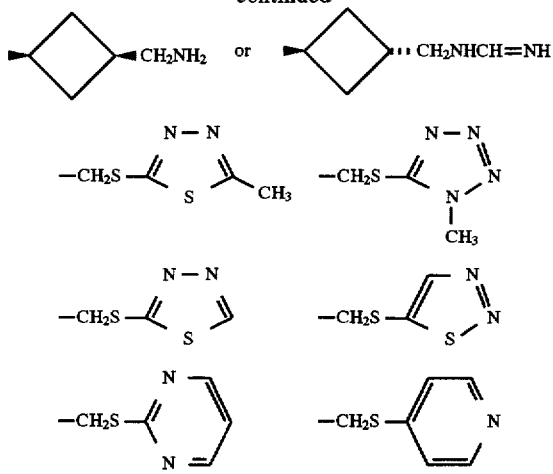

EXAMPLE 157

(4R,5S,6S)-3-[(2-Aminoethyl)thio]-6-[(1'R)-1'-hydroxyethyl]-4-[(2"S)-(2"-pyrrolidinyl)methyl]-7-oxo-1-azabicyclo[2.0]-hept-2-ene-2-carboxylic acid acetic acid salt

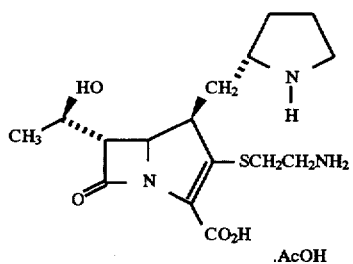

A. (S)-1-Allyloxycarbonyl-2-(hydroxymethyl)pyrrolidine

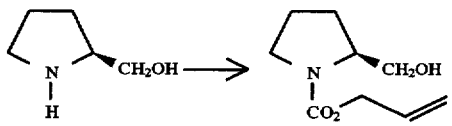

A solution of (S)-2-(hydroxymethyl)pyrrolidine (5.05 g, 0.05 mol) in cold 1.0N sodium hydroxide solution (1 eq, 50 mL) was treated dropwise over 45 min at 0°–5° C. with a solution of allyl chloroformate (1.2 eq, 0.06 mol, 6.6 mL) in acetone (60 mL). After 15 min, the acetone was evaporated and the residue was extracted with ethyl acetate (2×75 mL). The combined organic phases were washed with water, saturated sodium bicarbonate, brine and dried ($MgSO_4$). Evaporation of the solvent under reduced pressure and distillation with a Kugelrohr apparatus (0.1 mm Hg, 80°–100° C.) gave 8.5 g (92%) of the title carbamate as a pinkish oil:

IR (NaCl) $v_{max}$: 3425 (OH), 1690 $cm^{-1}$ (C=O of carbamate);

$^1H$ NMR (200 MHz, $CDCl_3$) δ:1.5–2.1 (m, 4H, $CH_2$-3 and $CH_2$-4), 3.3–3.6 (2×m, 2H, $CH_2$—OH), 3.6–3.7 (m, 2H, N—$CH_2$), 3.9–4.1 (m, 1H, CH-2), 4.5–4.6 (m, 2H, $CH_2$ of allyl), 5.15–5.35 and 5.8–6.0 ppm (2m, 2H and 1H, CH of allyl).

B. (S)-1-Allyloxycarbonyl-2-formyl-pyrrolidine

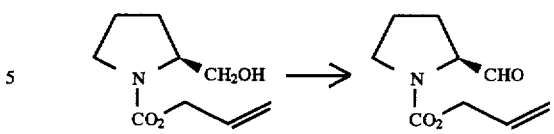

A solution of oxalyl chloride (4 mL, 44 mmol) in dry dichloromethane (96 mL) was cooled to –60° C. under argon and treated dropwise (ca 5 min) with a dry solution of dimethylsulfoxide (6.8 mL, 88 mmol) in dichloromethane (16 mL). The reaction mixture was stirred for 2 min and a solution of (S)-1-allyloxocarbonyl-2-(hydroxymethyl) pyrrolidine (7.4 g, 40 mmol) in dry dichloromethane (40 mL) was added dropwise within 6 min, then stirring was continued for an additional 15 min. Triethylamine (28 mL, 200 mmol) was added and the reaction mixture was stirred for 5 min and then allowed to warm to room temperature (ca 60 min). Cold water (200 mL) was added and the reaction mixture was extracted with diethyl ether (2×200 mL). The organic layers were combined, washed with dilute 1N HCl (200 mL), water, saturated sodium bicarbonate, brine and dried ($MgSO_4$). Evaporation of the solvent under reduced pressure gave 6.2 g (85%) of the title aldehyde as an oil:

IR (NaCl, film) vmax: 1735 (C=O of formyl) and 1700 $cm^{-1}$ (C=O of carbamate);

$^1H$ NMR (200 MHz, $CDCl_3$) δ: 1.8–2.3 (m, 4H, $CH_2$-3 and $CH_2$-4), 3.4–3.7 (m, 2H, $CH_2$—N), 4.1–4.4 (m, 1H, H-2), 4.5–4.7 (m, 2H, $CH_2$ of allyl), 5.1–5.4 and 5.8–6.1 (2m, 2H and 1H, CH of allyl), 9.51 and 9.57 ppm (2d, 1H, CHO, J=2.4 Hz and J=1.65 Hz).

C. Ethyl 3-[(2'S)-2'-(1'-allyloxycarbonylpyrrolidinyl)] acrylate

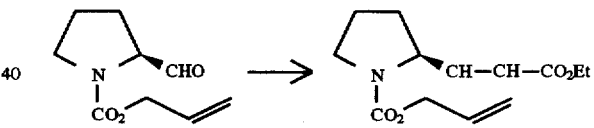

A solution of (S)-1-allyloxycarbonyl-2-formylpyrrolidine (6.2 g, 33.84 mmol) in dry methanol (30 mL) was cooled to 0°–5° C. under argon then treated portionwise with (carbethoxymethylene) triphenylphosphorane (1.2 eq, 14.2 g, 40.6 mmol). The reaction mixture was stirred for 2 h at 0° C. and 2 h at 25° C., then the methanol was evaporated. The residue was diluted with dry diethyl ether (100 mL), the solid was filtered, washed with diethyl ether and the filtrate was concentrated to dryness. Purification of the residue by flash chromatography (silica gel 230–400 mesh, 6.5×11 cm) using gradients of toluene -AcOEt (100:0→80:20) as eluent gave 7.83 g (91.4%) of the title acrylate as an oil:

$[α]_D^{24}$=38.6° (C 1.1, $CHCl_3$);

IR (NaCl, film) vmax: 1700–1720 (broad, CO of carbamate and ester);

$^1H$ NMR (200 MHz, $CDCl_3$) δ: 1.27 (t, J=7.17 Hz, 3H, $CH_3$ of ester), 1.6–2.4 (m, 4H, $CH_2$-3 and $CH_2$-4), 3.4–3.7 (m, 2H, $CH_2$N), 4.17 (q, J=7.06 Hz, 2H, $CH_2$ of ester), 4.5–4.6 (m, 3H, $CH_2$ of allyl and CH-2), 5.1–7.2 ppm (set of m, 5H, CH of allyl and CH of acrylate).

D. Methyl 3-[(2'S)-2'-(1'-allyloxycarbonylpyrrolidinyl)] propanoate

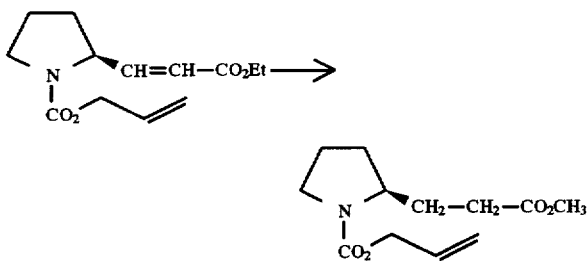

A mixture of ethyl 3-[(2'S)-2'-(1'-allyloxycarbonyl pyrrolidinyl)]acrylate (7.7 g, 30.4 mmol) and magnesium turnings (7.4 g, 304 mmol) in dry methanol (250 mL) was stirred under argon for 4 h. An exothermic reaction took place and the internal temperature increased until methanol was refluxed. The reaction mixture was cooled to room temperature and 1N HCl was added carefully until the solids were completely dissolved and the residue was extracted with diethyl ether, then washed with water, brine and dried (MgSO$_4$). Evaporation of the solvent under reduced pressure gave 6.8 g (92.7%) of the title ester as a clear oil with suitable purity to be used in the next step. An aliquot was distilled with a Kugelrohr apparatus (50 μm, 100° C.):

[α]$_D^{24}$=−47.1° (C=0.94, CHCl$_3$);

IR (NaCl, film) v$_{max}$: 1735 (C=O of ester) and 1700 cm$^{-1}$ (C=O of carbamate);

$^1$H NMR (200 MHz, CDCl$_3$) δ: 1.5–2.4 (m, 8H, CH$_2$-3' and CH$_2$-4' of pyrrolidine and —C$\underline{H}_2$C$\underline{H}_2$CO$_2$CH$_3$), 3.3–3.6 (m, 2H, C$\underline{H}_2$—N), 3.66 (s, 3H, CH$_3$ of ester), 3.9–4.0 (m, 1H, CH-2 of pyrrolidine), 4.5–4.6 (m, 2H, CH$_2$ of allyl), 5.15–5.35 and 5.8–6.0 ppm (2m, 2H and 1H, CH of allyl).

E. 3-[(2'S)-2'-(1'-Allyloxycarbonylpyrrolidinyl)]propanoic acid

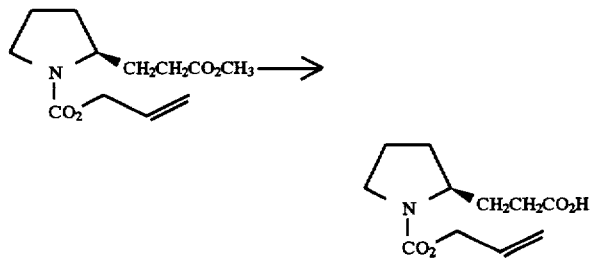

A solution of methyl 3-[(2'S)-2'-(1'-allyloxycarbonylpyrrolidinyl)]propanoate (6.5 g, 26.9 mmol) in methanol (27 mL) was treated dropwise with 3N sodium hydroxide solution (1.3 eq, 11.7 mL) at room temperature. After 45 min, most of the methanol was evaporated under vacuum and the residue was washed with diethyl ether (25 mL). The aqueous phase was acidified to pH 1.8 by 1N HCl solution then extracted with diethyl ether (2×25 mL). The combined organic phases were washed with brine and dried (MgSO$_4$). Evaporation of the solvent under reduced pressure gave 5.55 g (90.8%) of the title acid as a clear oil:

[α]$_D^{24}$=−36.5° (Cl, CHCl$_3$);

IR (NaCl, film) v$_{max}$: 1650–1740 cm$^{-1}$ (broad, C=O of acid and carbamate);

$^1$H NMR (200 MHz, CDCl$_3$) δ: 1.6–2.1 and 2.35–2.45 (2m, 8H, CH$_2$-3' and CH$_2$-4' of pyrrolidine and —C$\underline{H}_2$—CH$_2$CO$_2$H), 3.35–3.5 (m, 2H, C$\underline{H}_2$—N), 3.9–4.0 (m, 1H, CH-2' of pyrrolidine), 4.55–4.6 (m, 2H, CH$_2$ of allyl), 5.17–5.35 and 5.84–6.04 (2m, 2H and 1H, CH of allyl).

F. 3-[(2'S)-2'-(1'-Allyloxycarbonylpyrrolidinyl)]propanoyl chloride

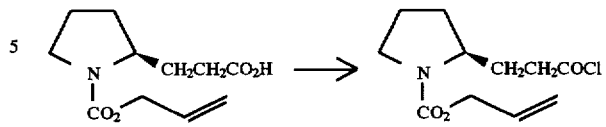

A solution of 3-[(2'S)-2'-(1'-allyloxycarbonylpyrrolidinyl)]propanoic acid (5.5 g, 24.42 mmol) in dry dichloromethane (13 mL) was treated dropwise with oxalyl chloride (2.4 mL, 2.7 mmol). A drop of N,N-dimethylformamide was added and the resulting mixture was stirred at 22° C. for 18 h. Evaporation of the solvent under reduced pressure gave the crude acid chloride as an orange oil which was used as such in the next step:

IR (NaCl film) v$_{max}$: 1800 (C=O of acid chloride) and 1695 cm$^{-1}$ (C=O of carbamate).

G. 2'-Picolyl 3-[(2"S)-2"-(1"-allyloxycarbonylpyrrolidinyl)] thiolpropanoate

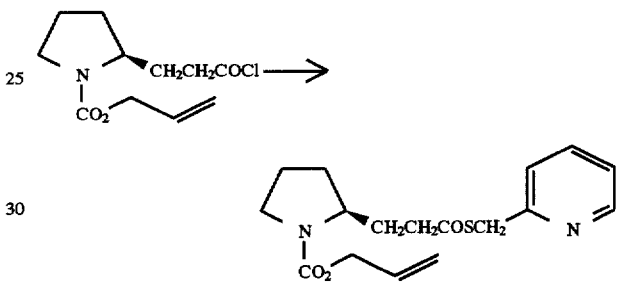

A solution of 2-picolyl mercaptan (2.9 g, 23.2 mmol) in dry dichloromethane (25 mL) was cooled to 0°–5° C. and treated under argon with pyridine (2.4 mL, 29.3 mmol) followed by a solution of crude 3-[(2"S)-2'-(1'-allyloxycarbonylpyrrolidinyl)]propanoyl chloride (max. 24.42 mmol) in dry dichloromethane (5 mL) added dropwise. After 2 h, the reaction mixture was diluted with diethyl ether (100 mL) and washed with cold water (2×50 mL), saturated sodium bicarbonate (50 mL), brine and dried (MgSO$_4$). Evaporation of the solvent under reduced pressure gave an oil which was chromatographed on silica gel (230–400 mesh, 4×11 cm). Elution with a gradient of toluene in ethyl acetate (100:0→70:30) gave 7.36 g (94%) of the title thioester as a yellow oil:

IR (NaCl, film) v$_{max}$: 1695 cm$^{-1}$ (broad, C=O);

$^1$H NMR (200 MHz, CDCl$_3$) δ: 1.6–2.1 (m, 6H, CH$_2$-3" and CH$_2$-4" of pyrrolidine and CH$_2$-3), 2.5–2.7 (m, 2H, CH$_2$-2), 3.3–3.5 (m, 2H, C$\underline{H}_2$—N), 3.8–4.0 (m, 1H, CH-2" of pyrrolidine), 4.24 (s, 2H, S-C$\underline{H}_2$), 4.5–4.6 (m, 2H, CH$_2$ of allyl), 5.15–5.35 and 5.8–6.1 (2m, 2H and 1H, CH of allyl), 7.12–7.19 (m, 1H, H-5 of pyridine), 7.33 (d, J=7.81 Hz, 1H, H-3 of pyridine), 7.6–7.7 (m, 1H, H-4 of pyridine) and 8.52 ppm (broad d, J=4.4 Hz, H-6 of pyridine).

H. t-Butyldimethylsilylenol ether of 2'-picolyl 3-[(2"S)-2"-(1"-alloxycarbonylpyrrolidinyl)]thiolpropanoate

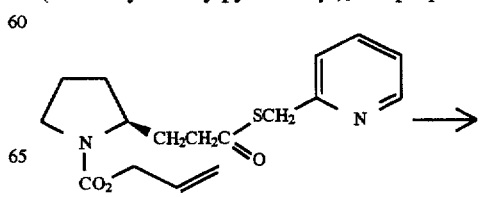

-continued

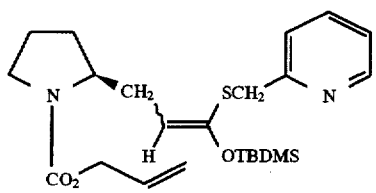

A solution of 2'-picolyl 3-[(2"S)-2"-(1"-allyloxycarbonylpyrrolidinyl)]thiolpropanoate (5.06 g, 22.27 mmol) in dry dichloromethane (30 mL) was cooled to −10° C. and treated under argon with triethylamine (7.8 mL, 55.7 mmol) followed by tert-butyldimethylsilyl trifluromethanesulfonate (10.2 mL, 44.54 mmol) added dropwise over 30 min. The dark solution was then stirred at 22° C. for 3 h. The reaction mixture was then diluted with hexane (100 mL) and washed with cold water (3×100 mL), brine and dried (MgSO$_4$). Evaporation of the solvent under reduced pressure gave the crude title material as a dark oil which was used immediately in the next step:

IR (NaCl film) vmax: 1680–1700 (broad, C=O of carbamate);

$^1$H NMR (200 MHz, CDCl$_3$) δ: 3.95 (broad s, SCH$_2$) and 4.8 and 4.95 ppm (2m, C$\underline{H}$=CSO).

I. (3S,4S)-3-[(1'R)-1'-tert-Butyldimethylsilyloxyethyl]-4-[(1R)-1-(2-pyridyl)methylthiocarbonyl-2-(N-allyloxycarbonyl-(2"S)-2"-pyrrolidinyl)ethyl]azetidin-2-one.

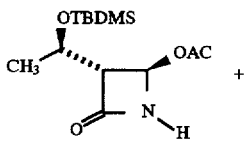

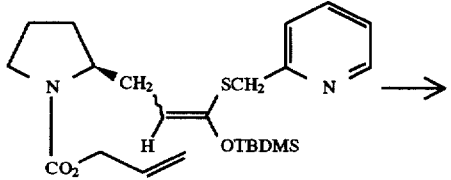

To a suspension of freshly fused zinc chloride (2.44 g, 17.9 mmol) in dry dichloromethane (45 mL) was added at 5° C. and under argon solid 4R-acetoxy-3S-[(1'R)-1'-tert-butyldimethylsilyloxyethyl]azetidin-2-one (14.9 mmol, 4.3 g) followed by a solution of crude silylenol ether prepared in Step H (22 mmol) in dry dichloromethane (10 mL). The resulting mixture was slowly warm up to 22° C. and stirred 18 h. The reaction mixture was then washed with cold saturated ammonium chloride, cold water, saturated sodium bicarbonate and brine. After drying (MgSO$_4$) and evaporation of the solvent under reduced pressure, a red oil residue was obtained which was chromatographed on silica gel (5.2×11 cm) using a gradient of ethyl acetate in toluene (0:100 to 100:0). The title compound was obtained as a clear red oil (2 g, 24%). By $^1$H NMR this product was pure β-isomer:

IR (NaCl, film) 1765 (C=O of lactam) and 1680–1700 cm$^{-1}$ (broad, C=O of carbamate and C=O of thioester);

$^1$H NMR (200 MHz, CDCl$_3$) δ: 0.04 (s, 6H, SiCH$_3$), 0.85 (s, 9H, si-t-Bu), 0.94 (d, J=5.8 Hz, C$\underline{H}_3$CHO), 1.6–2.2 and 2.6–2.8 (broad m, 6H, B—CH$_2$ and CH$_2$-3' and CH$_2$-4' of pyrrolidyl), 2.95 (m, 1H, H-3), 3.2–3.5 (m, 2H, N—CH$_2$—5' of pyrrolydyl), 3.8 (m, 2H, H-4 and CH—2" of pyrrolidine), 4–4.2 (m, 1H, CH$_3$C$\underline{H}$O), 4.6 (m, 2H, 5-CH$_2$), 5.1–5.4 (m,2H, CH$_2$ of allyl), 5.8–6.0 (m, 1H, CH of allyl), 7.1–7.4 (m, 3H, H-3 and H-5 of pyridine and CH of allyl), 7.6 (m, 1H, H-4 of pyridine) and 8.54 (m, 1H, H-6 of pyridine).

J. (3S,4S)-3-[(1'R)-1'-tert-Butyldimethylsilyloxyethyl]-4-[(1R)-1-carboxy-2-(N-allyloxycarbonyl-(2"S)-2"-pyrrolidinyl)ethyl]azetidin-2-one.

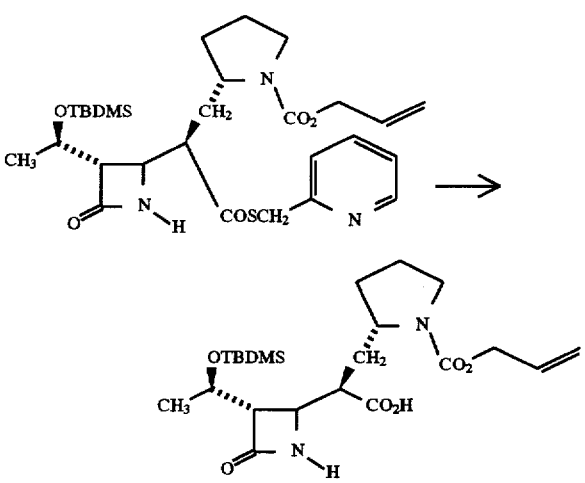

A solution of (3S,4R)-3-[(1'R)-1-tert-butyldimethyl silyloxyethyl]-4-[(1R)-1-(2-pyridyl)methylthiocarbonyl-2-(N-allyloxycarbonyl-(2"S)-2"-pyrrolidinyl)ethyl]azetidin-2-one (2 g, 3.56 mmol) in tetratrydrofuran (12 mL) was cooled to 5° C. and treated slowly with 30% hydrogen peroxide (1.2 mL). Then 1.0M aqueous sodium hydroxide were added dropwise then the stirring was continued for another 30 min. The reaction mixture was diluted with hexanes and the aqueous phase was collected. The organic phase was extracted a second time with cold water, the combined aqueous extracts were washed with hexanes, cooled to 0°–5° C. and acidified to pH 2 with 1.0N hydrochloric acid. The solution was extracted with ethyl acetate (2×) and the combined organic extract was washed with 1M aqueous sodium bisulfite and brine. After drying (MgSO$_4$), evaporation of the solvent under vacuum gave 1.388 g of the crude acid as a semi-solid residue. Crystallization from a mixture of ethyl acetate and hexanes gave 1.24 g (79%) of the title acid as white solid: m.p.=153°–154° C.;

$[\alpha]_D^{24}$=−2° (C=0.2, CHCl$_3$);

IR (KBr) v$_{max}$: 1740 (C=O of β-lactam), 1705 (C=O of carbamate) and 1665 cm$^{-1}$ C=O of carboxylic acid);

$^1$H NMR (200 MHz, CDCl$_3$) δ: 0.05 and 0.06 (2s, 3H, SiCH$_3$), 0.86 (s, 9H, Si-t-Bu), 1.23 (d, J=6.26 Hz, 3H, CH$_3$CHO) 1.6–2.2 (m, 5H, CH$_2$-3' and CH$_2$-4' of pyrrolidyl and one H of β-CH$_2$), 2.65 (m, 1H, one H of β-CH$_2$), 2.80 (m, 1H, H-3), 3.5 (m, 2H, N—CH$_2$ of pyrrolidyl), 3.9 (m, 1H, H-4), 4.15 (m, 2H, CH of pyrrolidyl and CH$_3$C$\underline{H}$O), 4.6 (m, 2H, CH$_2$ of allyl), 5.3 (m, 2H, CH of allyl), 5.9–6.0 (m, 1H, CH of allyl), 6.1 (broad s, 1H, NH), Anal. Calcd. for C$_{22}$H$_{38}$N$_2$O$_6$Si: C 58.12; H 8.42; N 6.16 Found: C 57.52; H 8.33; N 6.04.

355

K. (3S,4R)-3-[(1'R)-1'-tert-Butyldimethylsilyloxyethyl]-4-{(1R)-1-[(N-allyloxycarbonyl-(2"S)-2"-pyrrolidinyl)methyl]-3-allyloxycarbonyl-2-oxopropyl}azetidin-2-one

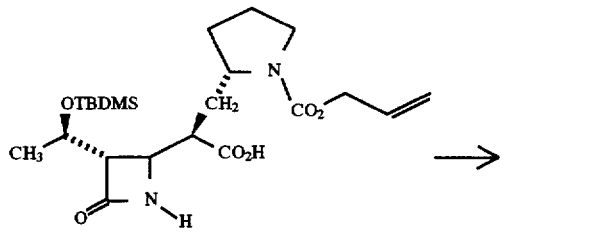

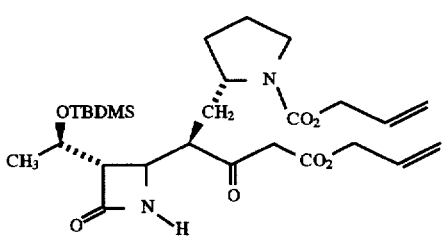

A solution of (3S,4S)-3-[(1'R)-1'-tert-butyldimethylsilyloxyethyl]-4-[(1R)-1-carboxy-2-(N-allyloxycarbonyl)-(2"S)-2"-pyrrolidinyl)ethyl]azetidine-2-one (1.1 g, 2.42 mmol) in dry acetonitrile (21 mL) was treated at 22° C. and under argon with 1,1-carbonyldiimidazole (0.450 g, 2.75 mmol) and the resulting mixture was stirred for 2 h. Evaporation of the solvent under reduced pressure gave the crude imidazolide which was then dissolved in dry acetonitrile (3 mL) and added to a mixture of magnesium monoallyl malonate (1.3 g, 4 mmol) in dry benzene (20 mL) and the resulting mixture was heated at 65° C. for 18 h. The mixture was then diluted with ethyl acetate washed with 0.1N hydrochloric acid, cold water, saturated sodium bicarbonate, brine and dried (MgSO₄). Evaporation of the solvent gave the crude title material as an oil which solidified on standing and was used as such in the next step. By ¹H NMR this product is a 1:1 mixture of keto and enol form:

IR (NaCl film) $v_{max}$: 1760 (C=O of β-lactam) and 1700 cm⁻¹ (broad, allyl carbamate and allyl ester)

¹H NMR (200 MHz, CDCl₃) δ: 1.09 and 1.17 ppm, 2d, J=6.22 Hz and 6.30 Hz, CH₃CHO).

L. (3S,4R)-3-[(1'R)-1'-tert-Butyldimethylsilyloxyethyl]-4-{(1'R)-1-[(N-allyloxycarbonyl-(2"S)-2"-pyrrolidinyl)methyl]-3-allyloxycarbonyl-3-diazo-2-oxopropyl}-azetidin-2-one

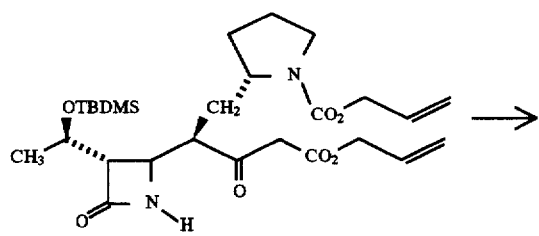

356
-continued

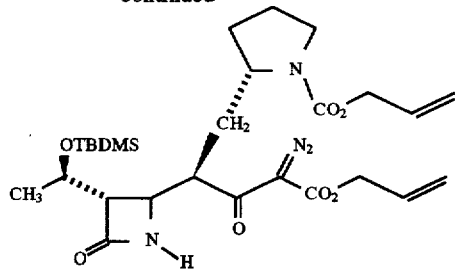

A solution of crude (3S,4R)-3-[(1'R)-1'-tert-butyldimethylsilyloxyethyl]-4-{(1R)-1-[(N-alloxycarbonyl-(2"S)-2"-pyrrolidinyl)methyl]-3-allyloxycarbonyl-2-oxopropyl}azetidin-2-one (2.3 mmol) in dry acetonitrile (5 mL) was treated at 0°–5° C. with a solution of p-toluenesulfonyl azide (0.54 g, 2.76 mmol) in acetonitrile (7 mL). Triethylamine (0.38 mL, 2.76 mmol) was then added and the solution was stirred at 22° C. for 2 h. The solvent was then evaporated under reduced pressure and the residue was triturated with a 1:1 cold (5° C.) mixture of diethyl ether and hexanes (30 mL). The crystalline p-toluene sulfonamide was collected and washed with a mixture of diethyl ether and hexanes. The filtrate and washings were combined and evaporated under reduced pressure to give 1.57 g of the crude title material as an oil which was used as such in the next step. TLC (toluene:ethylacetate, 1:1) (silica gel) RF=0.49.

M. (3S,4R)-4-{(1R)-1-[(N-Allyloxycarbonyl-(2"S)-2"-pyrrolidinyl)methyl]-3-allyloxcarbonyl-3-diazo-2-oxopropyl}-3-[(1'R)-1'-hydroxyethyl]azetidin-2-one

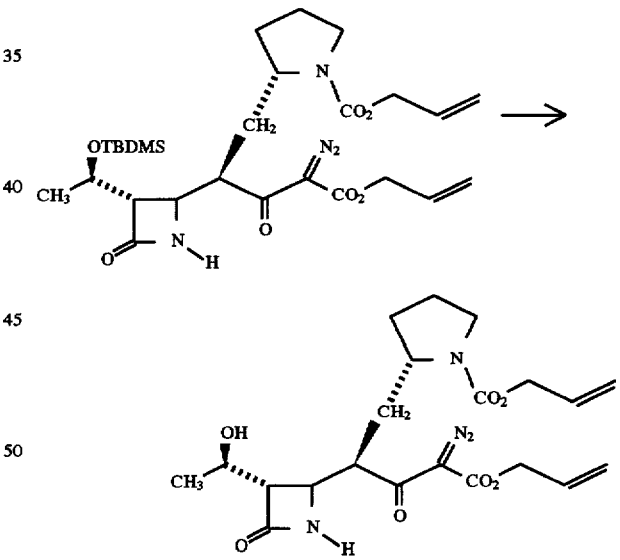

A solution of crude (3S,4R)-3-[(1'R)-1'-tert-butyldimethylsilyloxyethyl]-4-{(1R)-1-[(N-allyloxycarbonyl-(2"S)-2"-pyrrolidinyl)methyl]-3-allyloxycarbonyl-3-diazo-2-oxopropyl}azetidin-2-one (max 2.3 mmol) in ethanol (22 mL) was cooled to 0°–5° C. and treated with 1N aqueous hydrochloric acid (12 mL). After 18H at 5° C., the pH was adjusted to 8 with solid sodium bicarbonate and the residue was diluted with ethyl acetate and washed with saturated aqueous sodium bicarbonate, brine and dried (MgSO₄). Evaporation of the solvent and chromatography of the residue on silica gel (2.2×11 cm, elution with a gradient of ethyl acetate in toluene (10:90) to ethyl acetate followed by CH₃CN gave 0.75 g (74%, for 3 steps from the acid) of the title material as a beige foam:

IR (NaCl, film) $v_{max}$: 2140 (=N₂), 1755 (C=O of β-lactam), 1710 and 1690 cm⁻¹ (co of allyl);

¹H NMR (400 MHz, CDCl₃) δ: 1.32 (d, J=6.27 Hz, 3H, C$\underline{H}$₃CHO), 1.6–2.1 (m, 6H, C$\underline{H}$₂C$\underline{H}$₂CH₂N of pyrrolidinyl and C$\underline{H}$₂-pyrrolidinyl), 2.77 (broad s, 1H, OH), 3.01 (d, 1H, J=7.44 Hz, H-3), 3.3–3.4 (m, 2H, CH₂—N of pyrrolidinyl), 3.8–4.2 (m, 4H, N—CH of pyrrolidinyl, CH₃C$\underline{H}$O, H-4, H-1 of oxopropyl), 4.4–4.8 (2 m, 4H, CH₂ of allyl), 5.2–5.5 and 5.8–6.0 (2 m, 4H and 2H, CH of allyl) and 6.5 ppm (m, 1H, NH).

N. Allyl (2R,4R,5R,6S)-4-[(N-allyloxycarbonyl-(2"S)-2"-pyrrolidinyl)methyl]-6-[(1'R)-1'-hydroxyethyl]-3,7-dioxo-1-azabicyclo[3.2.0]heptane-2-carboxylate

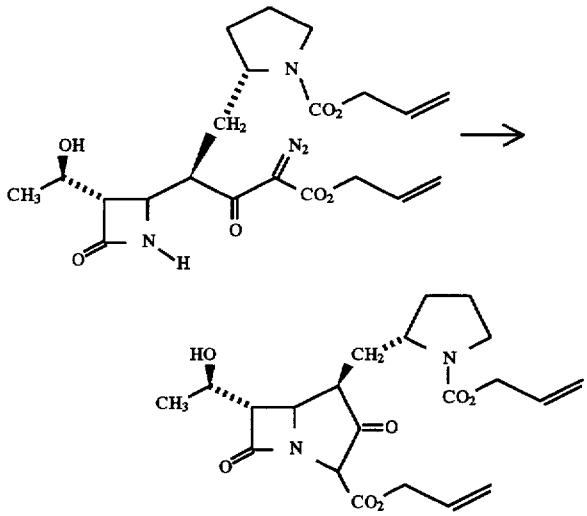

A solution of (3S,4R)-4-{(1R)-1-{(N-allyloxycarbonyl-(2"S)-2"-pyrrolidinyl)methyl]-3-allyloxocarbonyl-3-diazo-2-oxopropyl}-3-[(1'R)-1'-hydroxyethyl]azetidin-2-one (0.421 g, 1.0 mmol) in dry benzene (18 mL) was treated under argon with rhodium octanoate dimer (15 mg) and heated under reflux for 20 min. Evaporation of the solvent under reduced pressure gave the bicyclic ketone as an oil which was used as such in the next step:

IR (NaCl, film) $v_{max}$: 1765 (C=O of β-lactam), 1740 (Sh) and 1670 cm⁻¹;

¹H NMR (200 MHz, CDCl₃) δ: 1.47 (d, 3H, J=6.05 Hz, C$\underline{H}$₃CHO), 1.5–2.1 (m, 6H, C$\underline{H}$₂C$\underline{H}$₂CH₂N of pyrrolidinyl and C$\underline{H}$₂-pyrrolidinyl), 2.5–2.7 (m, 1H, H4), 3.2–3.7 (m, CH₂—N of pyrrolidinyl and H-6), 3.9–4.3 (m, 2H, N—CH of pyrrolidinyl, CH₃C$\underline{H}$O), 4.41 (dd, J$_{H5,H6}$=2.84, J$_{H5,H4}$= 9.0 Hz, 1H, H-5), 4.5–4.7 (m, 4H, CH₂ of allyl), 5.2–5.4 and 5.9–6.0 (2 m, 4H and 2H, CH of allyl).

O. Allyl (4R,5S,6S)-4-[(N-allyloxycarbonyl-(2"S)-2"-pyrrolidinyl)methyl]-3-[N-allyloxycarbonyl-(2-aminoethyl)thio]-6-[(1'R)-1'-hydroxyethyl]-7-oxo-1-azabicylo[3.2.0]hept-2-ene-2-carboxylate

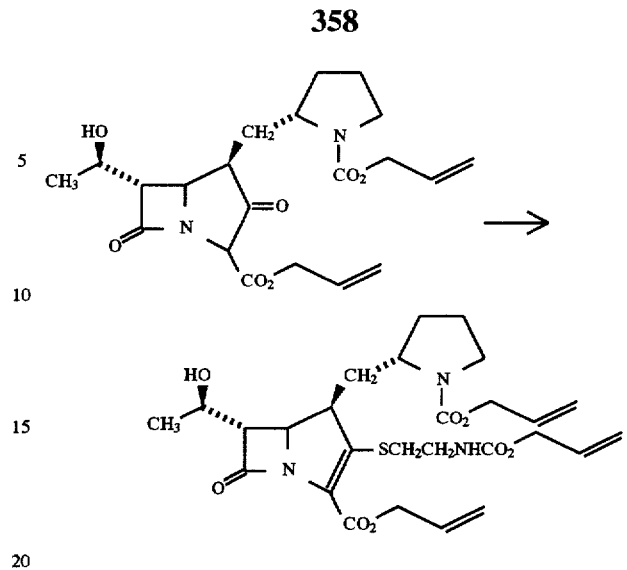

A solution of allyl (2R,4R,5R,6S)-4-[(N-allyloxycarbonyl-(2"S)-2"-pyrrolidinyl)methyl]-6-[(1'R)-1'-hydroxyethyl]-3,7-dioxo-1-azabicyclo[3.2.0]heptane-2-carboxylate (0.785 mmol, prepared by cyclization of 0.330 g, 0.785 mmol of the diazo precursor) in dry acetonitrile (10 mL) was treated at 0°–5° C. and under argon with diphenyl chlorophosphate (0.18 mL, 0.863 mmol) and N,N-diisopropylethylamine (0.15 mL, 0.863 mmol) added simultaneously over 1 min. A small crystal of 4-N,N-dimethylaminopyridine was then added and the mixture was stirred for 1.5 h. Trimethylsilylchloride (0.110 mL, 0.863 mmol) was then added followed by N,N-diisopropylethylamine (0.150 mL, 0.863 mmol) and the reaction mixture was stirred 2 h at 5° C. More N,N-diisopropylethylamine (0.275 mL, 1.57 mmol) was added followed by a solution of allyl 2-mercaptoethyl carbamate (0.25 g, 1.5 mmol) in acetonitrile (1 mL) and the resulting mixture was stirred at 0°–5° C. for 24 h. The reaction mixture was then diluted with ethyl acetate (50 mL), washed with cold 0.01N aqueous hydrochloric acid (50 mL), diluted sodium bisulfite, water, saturated sodium bicarbonate, brine and dried (MgSO₄). Evaporation of the solvent under reduced pressure gave an oil which was chromatographed on silica gel (2.5×10 cm). Elution with a gradient of ethyl acetate in toluene (0:100 to ethyl acetate) gave 0.10 g (22%) of the title carbapenem as an oil:

IR (NaCl, film) $v_{max}$: 1775 (C=O of β-lactam) and 1700 cm⁻¹ (broad, C=O of allyl);

¹H NMR (200 MHz, CDCl₃) δ: 1.44 (d, 3H, CH₃CHO), 1.5–2.1 (m, 6H, CH₂CH₂CH₂N of pyrrolidinyl and 4-C$\underline{H}$₂ pyrrolidinyl), 2.7–3.0 (2m, 2H, S—CH₂), 3.1–3.6 (m, 5H, CH₂NH₂, CH₂N (pyrrolidinyl) and H-4), 3.9–4.3 (2m, 2H, CH₃C$\underline{H}$O and C$\underline{H}$N of pyrrolydinyl), 4.35 (dd, J$_{H5,H6}$=3.10 Hz, J$_{H5,H6}$=10.37 Hz, 1H, H-5), 4.5–4.9 (2m, 6H, CH₂ of allyl), 5–5.5 and 5.8–6.1 ppm (2m, 9H, CH of allyl).

P. (4R,5S,6S)-3-[(2-Aminoethyl)thiol]-6-[(1'R)-1'-hydroxyethyl]-4-[(2"S)-(2"-pyrrolidinyl)methyl]-7-oxo-1-azabicyclo[3.2.0]hept-2-ene-2-carboxylic acid acetic acid salt

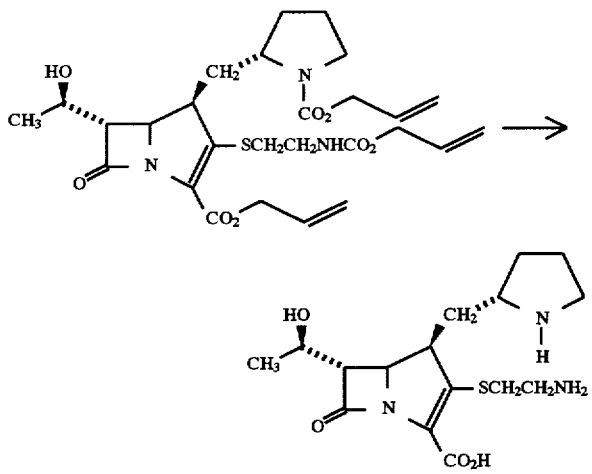

A solution of allyl (4R,5S,6S)-4-[(N-allyloxocarbonyl-(2"S)-2"-pyrrolidinyl)methyl]-3-[N-allyloxycarbonyl-(2-aminoethyl)thio]-6-[(1'R)-1'-hydroxyethyl]-7-oxo-1-azabicyclo[3.2.0]hept-2-ene-2-carboxylate (0.1 g, 0.177 mmol) in dry dichloromethane (10 mL) was treated at 22° C. and under argon with a solution of tri-n-butyltinhydride (0.206 g, 0.708 mmol) in dichloromethane (1 mL), acetic acid (0.40 mL, 0.708 mmol) and tetrakis (triphenylphosphine)palladium[[O] (20 mg). After 20 min, the reaction mixture was extracted with water (2×10 mL) and the combined aqueous extract was washed with dichloromethane (20 mL). After concentration under reduced pressure the aqueous extract was chromatographed on reversed phase silica gel (μ-Bondapak C-18, 2×10 cm) using 0.01N acetic acid as eluent. Pure fractions were freeze-dried and gave 55 mg (79%) of the title compound as an off-white amorphous solid:

Purity by HPLC: 95.0% on μ-Bondapak C-18, 3.9 mm×30 mm, solution 5% $CH_3CN-H_2O$, pH 7.4 phosphate buffer, flow rate 1 mL/min, UV detector 300 mn, retention time 8.48 min;

UV ($H_2O$, pH 7.4 phosphate buffer) $\lambda_{max}$: 294 nm (6953);

IR (KBr) $v_{max}$: 1760 (C=O of β-lactam) and 1600 cm$^{-1}$ (C=O of carboxylate);

$^1$H NMR (400 MHz, $D_2O$) δ: 1.33 (d, J=6.35 Hz, 3H, C$\underline{H}_3$CHO), 1.73–1.82 and 2.36–2.43 (2×m, 2H, β-$CH_2$), 2.00–2.20 (m, 4H, $CH_2$-3' and $CH_2$-4' of pyrrolidyl), 2.90–2.97 and 3.08–3.15 (2m, 3H, S—$CH_2$ and H-6), 3.26–3.39 (m, 4H, C$\underline{H}_2$—$NH_2$ and $CH_2$—N of pyrrolidyl), 3.50–3.53 (m, 1H, H-5), 3.58–3.65 (m, 1H, N—CH of pyrrolidyl) and 4.24–4.32 ppm (m, 2H, $CH_3$C$\underline{H}$O and H-5).

EXAMPLES 158–318

Following the general procedures of the foregoing text and examples with the appropriately selected starting materials and reagents as exemplified by the present invention, the following 4-substituted alkyl carbapenem compounds having the formula and $^1$H NMR data as indicated in the Tables were produced.

| EX. NO. | STRUCTURES | NMR DATA |
|---|---|---|
| 158 | 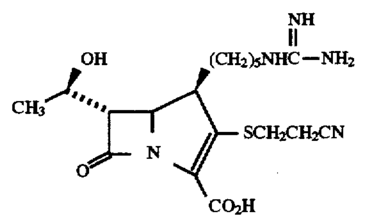 | $^1$H NMR(200 MHz, $D_2O$)δ: 1.32(d, J=6.38Hz, 3H, $CH_3$CHO), 1.3–1.9 (m, 8H, $CH_2$-1,2,3 and 4 of pentyl), 2.8–3.3(m, 4H, S$CH_2CH_2$CN), 3.18(t, J=6.7Hz, 2H, $CH_2NH_2$), 3.35(overlapping with H-6, 1H, H-4), 3.38(dd, J$_{H6,H5}$=2.44Hz, J$_{H6,H1}$=6.15Hz, 1H, H-6), 4.24(dd overlapping with $CH_3$CHO, J$_{H5,H6}$=2.44Hz, 1H, H-5) and 4.27 ppm(m, 1H, $CH_3$C$\underline{H}$O). |
| 159 | 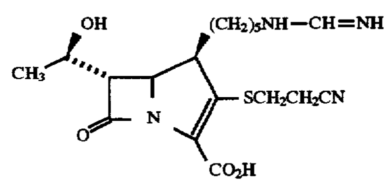 | $^1$H NMR(200 MHz, $D_2O$)δ: 1.32(d, J=6.38Hz, 3H, $CH_3$CHO), 1.3–1.9 (m, 8H, $CH_2$-1,2,3 and 4 of pentyl), 2.8–2.9(m, 2H, $CH_2$CN), 2.9–3.2(m, 2H, S$CH_2$), 3.31(t, J=6.8Hz, 2H, $CH_2$N), 3.38(dd, J$_{H6,H5}$=2.24Hz, J$_{H6,H1}$=6.24Hz, 1H, H-6), 3.38(overlapping with H6, 1H, H-4), 4.24(dd, overlapping with $CH_3$C$\underline{H}$O, J$_{H5,H6}$= 2.24Hz, 1H, H-5), 4.27(m, 1H, $CH_3$C$\underline{H}$O), and 7.8 ppm(s, 1$\overline{H, C\underline{H}}$=NH). |
| 160 | 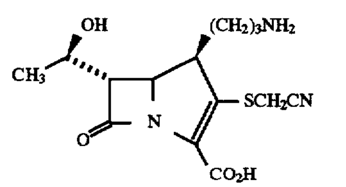 | $^1$H NMR ($D_2O$, 200 MHz)δ: 4.337(1H, dd, J=2.8Hz, J=9.3Hz, H-5), 4.35–4.25(1H, m, H-1'), 3.902, 3.814, 3.785, 3.696(2H, ABq, J=17.6Hz, S$CH_2$CN), 3.507–3.409(1H, m, H-4), 3.448(1H, dd, J=2.8 Hz, J=6.3Hz, H-6), 3.093, 3.057, 3.021(2H, 3 lines, J=7.3Hz, $CH_2$N), 2.1–1.40(4H, m, $CH_2CH_2$-4) and 1.340 ppm(3H, d, J=6.4Hz, $CH_3$). |
| 161 | 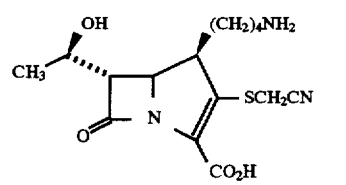 | $^1$H NMR(200 MHz, $D_2O$)δ: 1.33(d, J=6.38Hz, 3H, $CH_3$CHO), 1.3–2.0(m, 6H, $CH_2$-1,2 and 3 of butyl), 3.02(t, J=7.5Hz, 2H, C$\underline{H_2}^{NH}{}_2$), 3.4 (m, overlapping with H-6, 1H, H-4), 3.43(dd, J$_{H6,H5}$=2.63Hz, J$_{H6,H1}$= 6.25Hz, 1H, H-6), 3.79(ABq, J$_{AB}$=17.6Hz, Δv=14.7Hz, 2H, S$CH_2$), 4.29(m, 1H, $CH_3$C$\underline{H}$O) and 4.32 ppm(dd, J$_{H5,H6}$=2.63Hz, J$_{H5,H4}$=9.32 Hz, 1H, H-5). |

| EX. NO. | STRUCTURES | NMR DATA |
|---|---|---|
| 162 | 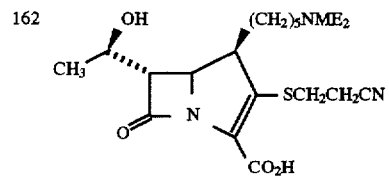 | $^1$H NMR(200 MHz, $D_2O$)δ: 1.33(d, J=6.35Hz, 3H, C$\underline{H}_3$CHO), 1.3–1.9(m, 8H, CH$_2$-1,2,3 and 4 of pentyl), 2.85(s, 6H, NCH$_3$), 2.8–3.2(m, 6H, SCH$_2$CH$_2$CN and CH$_2$-5 of pentyl), 3.36(overlapping with H-6, 1H, H-4), 3.38(dd, J$_{H6,H5}$=2.50Hz, J$_{H6,H1}$=6.20Hz, 1H, H-6), 4.24(dd, overlapping CH$_3$CHO, J$_{H5,H6}$=2.50Hz, 1H, H-5) and 4.27 ppm(m, 1H, CH$_3$C$\underline{H}$O). |
| 163 | 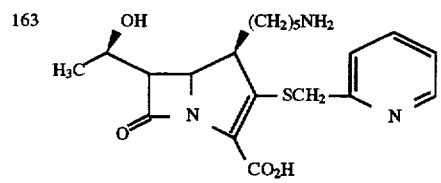 | $^1$H NMR(200 MHz, $D_2O$)δ: 1.29(d, J=6.36Hz, 3H, C$\underline{H}_3$CHO), 1.2–1.8(m, 8H, CH$_2$-1,2,3 and 4 of pentyl), 2.97(t, J=7.6Hz, 2H, CH$_2$N$_3$), 3.14 (broad t, J=8.5Hz, 1H, H-4), 3.29(dd, J$_{H6,H5}$=2.47Hz, J$_{H6,H1}$=6.24 Hz, 1H, H-6), 4.05(dd overlapping with SCH$_2$, J$_{H5,H6}$=2.47Hz, J$_{H5,H4}$= 9.34Hz, 1H, H-5), 4.14(ABq, J$_{AB}$=14.26Hz, Δν=21.7Hz, 2H, SCH$_2$), 4.21(m, 1H, CH$_3$C$\underline{H}$O), 7.37(m, 1H, H-5 of pyridine), 7.52(d, J=7.9 Hz, 1H, H-3 of pyridine), 7.86(m, 1H, H-4 of pyridine), and 8.46 ppm(m, 1H, H-6 of pyridine). |
| 164 | 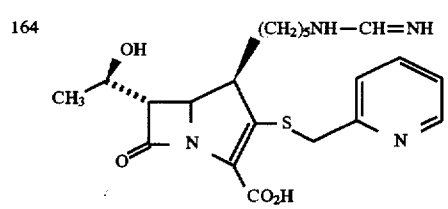 | $^1$H NMR(200 MHz, $D_2O$)δ: 1.28(d, J=6.34Hz, 3H, C$\underline{H}_3$CHO), 1.2–1.7 (m, 8H, CH$_2$-1,2,3 and 4 of pentyl), 3.15(broad t, 1H, H-4), 3.2– 3.4(m, 3H, H-6 and C$\underline{H}_2$NH$_2$ overlapping)4.7(overlapping with SCH$_2$, 1H, H-6), 4.13(ABq, J$_{AB}$=14.32, Δν=22.6Hz, 2H, SCH$_2$), 4.21(m, 1H, CH$_3$C$\underline{H}$O), 7.36(m, 1H, H-5 of pyridine)7.52(d, J=7.82Hz, 1H, H-3 of pyridine), 7.77(s, 1H, C$\underline{H}$=NH), 7.85(m, 1H, H-4 of pyridine) and 8.46 ppm(d, J=8.5Hz, 1H, H-6 of pyridine). |
| 165 | 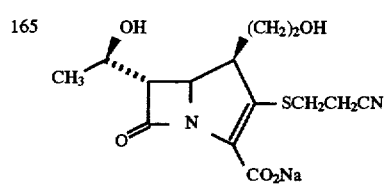 | $^1$H NMR($D_2O$, 200 MHz)δ: 4.35–4.20(2H, m, H-1' and H-5), 3.80–3.55 (2H, m, CH$_2$O), 3.531–3.41(1H, m, H-4), 3.465(1H, dd, J=2.7Hz, J=6.0Hz, H-6), 3.25–3.12, 3.03–2.89(2H, 2 sets of m, SCH$_2$), 2.89– 2.81(2H, m, CH$_2$CN), 2.15–1.95, 1.82–1.70(2H, 2 sets of m, CH$_2$-4) and 1.322 ppm(3H, d, J=6.4Hz, CH$_3$). |
| 166 | 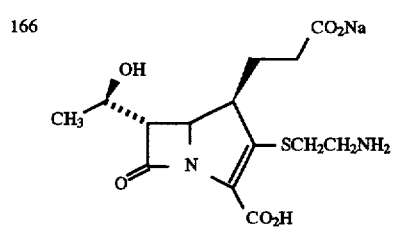 | $^1$H NMR($D_2O$)δ 1.37(d, 3H, 6.4Hz), 1.66–1.74(m, 1H), 2.14–2.48 (m, 3H), 2.91–3.42(m, 5H), 3.51(dd, 1H, J=2.7, 6.0Hz), 4.28(dd, 1H, J=2.7, 8.3Hz), 4.31(dq, 1H, J=6.0, 6.4Hz)HPLC purity 95%; half life(phosphate buffer, pH 7.4, 0.07M, 37° C.)86 h. |
| 167 | 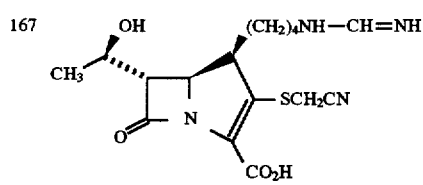 | $^1$H NMR(200 MHz, $D_2O$)δ: 1.32(d, J=6.37Hz, 3H, C$\underline{H}_3$CHO), 1.3–2.0(m, 6H, CH$_2$-1,2 and 3 of butyl),3.3–3.5(m, 4H, H-4, H-6 and C$\underline{H}_2$NH$_2$ overlapping), 3.8(ABq partially exchanged, SCH$_2$CN), 4.2–4.4(m, 2H, H-5 and CH$_3$C$\underline{H}$O), and 7.8 ppm(s, 1H, C$\underline{H}$=NH). |
| 168 | 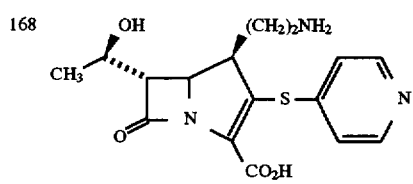 | $^1$H NMR(200 MHz, CDCl$_3$ 7.24 δ): −0.12, −0.14(2s, 6H, Si(CH$_3$)$_2$), 0.06 (s, 6H, Si(CH$_3$)$_2$), 0.72, 0.87(2m, 2×9H, Sic(CH$_3$)$_2$), 1.22(d, 3H, CH$_3$, J=6.56Hz), 1.5–1.6; 1.79–1.96(m, 2H, CH$_2$), 3.2–3.58(overlap, 4H, CH$_2$O, H-4, H-6), 4.23(dd, 1H, H-5, J$_{5,6}$=2.72Hz, J$_{4,5}$=9.7Hz), 4.25(m, 1H, H-1'), 4.63–4.85(m, 2H, OCH$_2$, allyl), 5.2–5.47(m, 2H, =CH$_2$, allyl), 5.84–6.03(m, 1H, CH=, allyl), 7.26(B of A$_2$B$_2$, 2H, H-3,5, py), 8.5(A of A$_2$B$_2$, 2H, H-2,6 py). |
| 169 | 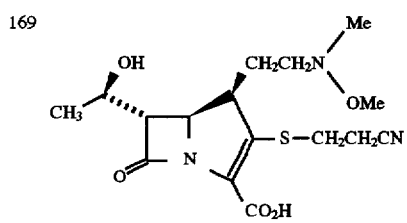 | $^1$H NMR($D_2O$ 200 MHz)δ: 4.34–4.216(2H, m, H-1' and H-5), 4.301, 4.286(d, J=2.9Hz, part of H-5), 3.579(3H, s, OCH$_3$), 3.486, 3.473 (d, J=2.7Hz, part of H-6), 3.49–3.34(2H, m, H-6 and H-4), 3.235– 3.104, 3.04–2.90(2H, 2 sets of m, SCH$_2$), 2.90–2.764(4H, m, CH$_2$N and CH$_2$CN), 2.640(3H, s, NCH$_3$), 2.20–2.03, 1.86–1.65(2H, 2 sets of m, CH$_2$-4) and 1.331 ppm(3H, d, J=6.4Hz, CH$_3$). |

5,672,701

-continued

| EX. NO. | STRUCTURES | NMR DATA |
|---|---|---|
| 170 | (structure: carbapenem with OH, CH₃, (CH₂)₃NH₂, S-pyridine, CO₂H) | $^1$H NMR(D$_2$O, 200 MHz)δ: 8.459–8.427(2H, m, pyridine H), 7.505–7.470(2H, m, pyridine H), 4.371(1H, dd, J=2.9Hz, J=9.9Hz H-5), 4.389–4.23(1H, m, H-1'), 3.434(1H, dd, J=2.9Hz, J=6.2Hz, H6), 3.304–3.20(1H, m, H-4), 2.839, 2.805, 2.774(2H, 3 lines, CH$_2$N), 1.8–1.4(4H, m, CH$_2$CH$_2$-4) and 1.316 ppm(3H, d, J=6.4Hz, CH$_3$). |
| 171 | (structure: carbapenem with OH, CH₃, CH₂CH₂-N-pyrroline, SCH₂CH₂CN, COOH) | $^1$H NMR(200 MHz, CDCl$_3$ 7.24 δ): 0.06(s, 6H, 6H(CH$_3$)$_2$), 0.87(s, 9H, SiC(CH$_3$)$_3$), 1.27(d, 3H, CH$_3$, J=6.14Hz), 1.52–1.99(m, 2H, CH$_2$), 2.53–3.42(overlap, 8H, CH$_2$N—, SCH$_2$, CH$_2$CN, H-4, H-6), 3.47(s, 4H, N—(CH$_2$)$_2$, pyrroline), 4.18(m, 1H, H-5), 4.21(m, 1H, H-1'), 4.61–4.84(m, 2H, OCH$_2$, allyl), 5.2–5.48(m, 2H, =CH$_2$, allyl), 5.77(s, 2H, HC=CH, pyrroline), 5.84–6.03(m, 1H, CH=, allyl). |
| 172 | (structure: carbapenem with OH, CH₃, CH₂CH₂N(CH₃)CH₂CO₂H, SCH₂CH₂CN, CO₂Na) | $^1$H NMR(D$_2$O, 200 MHz)δ: 4.311–4.20(2H, m, H-5 and H-1'), 3.773 (2H, s, NCH$_2$CO$_2$), 3.432, 3.329(2 lines, J=2.5Hz, part of H-6), 3.50–3.20(5H, H-4, H-6, 1H of SCH$_2$, CH$_2$N), 3.21–3.08(1H, m, 1H of SCH$_2$), 2.959(3H, s, NCH$_3$), 2.893–2.796(2H, m, CH$_2$CN), 2.40–2.20, 2.10–1.90(2H, 2 sets of m, CH$_2$-4) and 1.330 ppm(3H, d, J=6.3Hz, CH$_3$). |
| 173 | (structure: carbapenem with OH, CH₃, (CH₂)₄NH-C(O)-CH₂NH₂, SCH₂CH₂CN, CO₂H · CH₃CO₂H) | $^1$H NMR(200 MHz, D$_2$O)δ: 1.33(d, J=6.37Hz, 3H, CH$_3$CHO), 1.3–1.9 (m, 6H, CH$_2$-1,2 and 3 of butyl), 2.75–2.9(m, 2H, CH$_2$CN), 2.9–3.3 (m, 2H, SCH$_2$), 6.5(t, J=3.27Hz, CH$_2$-4 of butyl), 3.3–3.5(m, 2H, H-6 and H-4 overlapping), 3.74(s, 2H, CH$_2$NH$_2$) and 4.2–4.4 ppm(m, 2H, H-5 and CH$_3$CHO). |
| 174 | (structure: carbapenem with OH, CH₃, CH₂CH₂NH₂, S-pyrimidine, CO₂H) | $^1$H NMR(CDCl$_3$, 200 MHz)δ: 8.54(2H, d, J: 4.83, aromatic-H), 7.07 (1H, t, J: 4.88, aromatic —H), 6.02–4.60(5H, allylic pattern), 4.24 (1H, m, H-4), 4.11(1H, m, H-1'), 3.95(1H, dd, J: 2.71, 8.48, H-5), (1H, m, H-4), 4.11(1H, m, H-1'), 3.95(1H, dd, J: 2.71, 8.48, H-5), 3.42(2H, m, =CH$_2$=N$_3$), 3.36(1H, dd, J: 8.16, 2.68, H-6), 2.15–1.50 (3H, 2m, =CH$_2$=, 1.96: =OH), 1.41(3H, d, J: 6.25, 1'-CH$_3$). |
| 175 | (structure: carbapenem with OH, CH₃, CH₂CH₂N(CH₃)CH₂CH₂OH, SCH₂CH₂CN, CO₂H) | $^1$H NMR(D$_2$O, 200 MHz)δ: 4.3–4.22(1H, m, H-1' and part of H-5), 4.259(d, J=2.9Hz, part of H-5), 3.896, 3.869, 3.842(2H, 3 lines, CH$_2$O), 3.443(1H, dd, J=2.5Hz, J=6.6Hz, H-6), 3.46–3.36(1H, m, H-4), 3.21–3.05(5H, m, CH$_2$=N and 1H of SCH$_2$), 3.05–2.88(1H, m, 1H of SCH$_2$), 2.88–2.80(2H, m, CH$_2$CN), 2.75(3H, s, NCH$_3$), 2.3–2.15, 2.0–1.8(2H, 2 sets of m, CH$_2$-4) and 1.338 ppm(3H, d, J=6.4Hz, CH$_3$). |
| 176 | (structure: carbapenem with OH, CH₃, CH₂CH₂NHCCH₂NH₂ (with C=O), SCH₂CH₂CN, COOH) | $^1$H NMR(200 MHz, D$_2$O)δ: 1.36(d, 3H, CH$_3$; J=6.37Hz), 1.63–1.82; 1.99–2.13(m, 2H CH$_2$), 2.81–2.89(m, 2H, CH$_2$CN), 2.91–2.99; 3.02–3.17(m, 2H, SCH$_2$), 3.35(m centre, 3H, CH$_2$NH, H-4), 3.59(dd, 7H, H-6, J$_{5,6}$=2.67Hz, J$_{6,1}$=5.94Hz), 4.06(s, 2H, CH$_2$N$_3$), 4.29(dd, 1H, H-5, J$_{4,5}$=10.04Hz), 4.31(m, 1H, H-1'). |

| EX. NO. | STRUCTURES | NMR DATA |
|---|---|---|
| 177 | (structure: carbapenem with OH, CH₃ hydroxyethyl; CH₂CH₂N⁺(CH₃)₃ side chain; SCH₂CH₂CN; CO₂⁻) | ¹H NMR(200 MHz, D₂O)δ: 1.34(d, J=6.35Hz, 3H, $\underline{CH_3}$CHO), 2.0–2.4(m, 2H, CH₂-4), 2.7–3.2(m, 4H, S$\underline{CH_2CH_2}$CN), 3.19(s, 9H, N(CH₃)₃), 3.3–3.7(m, 4H, H-6, H-4 and $\underline{CH_2}$N(CH₃)₃), 4.28(m, 1H, CH₃$\underline{CHO}$) and 4.31 ppm(dd, $J_{H5,H6}$=3.05Hz, $J_{H5,H4}$=9.90Hz, 1H, H-5). |
| 178 | (structure: carbapenem with OH, CH₃; CH₂CH₂CH₂NHC(=NH)H amidine; SCH₂CH₂N(CH₃)CH₃; CO₂H · CH₃CO₂H) | ¹H NMR(D₂O, 200 MHz)δ: 4.4–4.2(2H, m, H-1' and H-5), 3.43(1H, dd, J=2.7Hz, J=6.0Hz, H-6), 3.46–3.2(5H, CH₂N, CH₂N and H-4), 3.2–2.93(2H, m, SCH₂), 2.90(6H, s, N(CH₃)₂), 1.92(2.3H, s, CH₃CO₂), 2.0–1.35(4H, m, CH₂CH₂-4) and 1.319 ppm(3H, d, J=6.4Hz, CH₃). |
| 179 | (structure: carbapenem with OH, CH₃; CH₂CH₂N(CH₃)CH₂CH₂N₃; SCH₂CH₂CN; CO₂H) | ¹HMR (D₂O, 200 MHz)δ: 4.286(1H, dd, J=2.8Hz, J=9.7Hz, H-5), 4.35–4.27(1H, m, H-1'), 3.673(2H, t, J=5.7Hz, CH₂N₃), 3.426(1H, dd, J=2.8Hz, J=6.6Hz, H-6), 3.44–3.35(1H, m, H-1'), 3.2–2.75 (8H, SCH₂, CH₂N and CH₂CN), 2.58(3H, s, NCH₃), 2.25–2.0, 1.9–1.7 (2H, 2 sets of m, CH₂-4) and 1.342 ppm(3H, d, J=6.4Hz, CH₃). |
| 180 | (structure: carbapenem with OH, CH₃; CH₂CH₂NHC(=O)CH₂CH₂NH₂; SCH₂CH₂CN; COONa) | ¹H NMR(200 MHz, D₂O)δ: 1.37(d, 3H, CH₃, J=6.4 Hz), 1.63–1.85; 1.99–2.14(m, 2H, CH₂), 2.57(t, 2H, C(=O)CH₂, J=6.19Hz), 2.82–2.89 (m 2H, CH₂CN), 2.93–3.0; 3.03–3.23(m, 2H, SCH₂), 3.31–3.42(m, 3H, CH₂NH, H-4), 3.61(dd, 1H, H-6, $J_{5,6}$=2.72Hz, $J_{6,1}$=6.96Hz), 3.64 (t, 2H, CH₂N₃), 4.3(dd, 1H, H-5, $J_{4,5}$=10.01Hz), 4.32(m, 1H, H-1'). |
| 181 | (structure: carbapenem with OH, CH₃; (CH₂)₃N₃; SCH₂C(=N-H)N(CH₃)CH₃; CO₂H) | ¹H NMR(200 MHz, D₂O)δ: 1.32(d, J=6.36Hz, 3H, ($\underline{CH_3}$CHO), 1.4–2.0 (m, 4H, CH₂-1 and 2 of propyl), 3.13 and 3.30 (2×s, 2×3H, N(CH₃)₂), 3.1–3.3(m, 1H, H-4), 3.42(t, J=6.2Hz, 2H, CH₂N₃), 3.53(dd, $J_{H6,H5}$=2.91Hz, $J_{H6,H1}$=5.93Hz, 1H, H-6), 3.88(ABq², $J_{AB}$=15.2 Hz, Δv=11.8Hz, 2H, SCH₂), and 4.2–4.4 ppm(m, 2H, H-5 and CH₃$\underline{CHO}$). |
| 182 | (structure: carbapenem with OH, CH₃; (CH₂)₃N₃; S-CH₂CH₂-N(CH₃)CH₂CO₂H; CO₂Na) | ¹H NMR(D₂O, 200 MHz)δ: 4.35–4.25(1H, m, H-1'), 4.272(1H, dd, J=2.7Hz, J=9.5Hz, H-5), 3.665(2H, s, CH₂CO₂), 3.452(1H, dd, J=2.7Hz, J=6.2Hz, H-6), 3.5–3.2(5H, m, CH₂N, CH₂N₃, H-4), 3.2–3.0 (2H, m, SCH₂), 2.858(3H, s, CH₃N), 2.0–1.5(4H, m, CH₂CH₂-4) and 1.335 ppm(3H, d, J=6.4Hz, CH₃). |
| 183 | (structure: carbapenem with OH, CH₃; CH₂CH₂N(CH₃)CH₂CH₂NHC(=NH)NH₂ guanidine; SCH₂CH₂CN; CO₂H · CH₃CO₂H) | ¹H NMR(D₂O, 200 MHz)δ: 4.313–4.21(2H, m, H-1' and H-5), 3.7–3.58 (2H, m, CH₂-guanidine), 3.424(1H, dd, J=2.6Hz, J=6.8Hz, H-6), 3.5–3.05(7H, m, H-1', CH₂N, SCH₂), 3.05–2.86(2H, m, CH₂CN), 2.84 (3H, s, NCH₃), 2.3–2.1, 2.1–2.9(2H, 2 sets of m, CH₂-4), 1.92(3H, s, CH₃CHO₂) and 1.334 ppm(3H, d, J=6.3Hz, CH₃). |

| EX. NO. | STRUCTURES | NMR DATA |
|---|---|---|
| 184 | (structure) | ¹H NMR(D₂O, 200 MHz)δ: 4.312, 4.299(d, J=2.6Hz part of H-5), 4.34–4.21(m, part of H-5 and H-1'), 3.410(1H, dd, J=2.6Hz, J=6.6 Hz, H-6), 3.5–2.8(11H, H-4, CH₂N, SC₂, CH₂CN), 2.86–2.62. (3H, 2s, NCH₃), 1.933(3H, s, CH₃CO₂), 2.3–2.1, 2.0–1.8(2H, 2m, CH₂-4) and 1.337 ppm(3H, d, J=6.3Hz, CH₃). |
| 185 | (structure) | ¹NMR(200 MHz, D₂O)δ: 1.39(d, 3H, CH₃, J=6.28Hz), 1.74–1.79; 2.05–2.11(m, 2H, CH₂), 2.53(t, 2H, C(=O)CH₂), 2.84–3.21(overlap, 4H, SCH₂, CH₂CN), 3.34–3.44(overlap, 3H, CH₂NH, H-4), 3.61(m, 1H, H-6), 3.88(t, 2H, CH₂OH, J=6.0Hz), 4.32(m, 1H, H-5), 4.33(m, 1H, H-1'). |
| 186 | (structure) | ¹H NMR δ 1.34(d, 3H, J=6.4Hz), 1.62–1.81(m, 1H), 2.18(d quintets, 1H, J=2.8, 7.9Hz), 2.42–2.54(m, 2H), 2.85–3.41(m, 5H), 2.94(s, 3H), 3.07(s, 3H), 3.48(dd, 1H, J=2.4, 5.6Hz); half-life phosphate buffer, pH 7.4, 0.07M, 37° C.)50 h; HPLC purity 94%. |
| 187 | (structure) | ¹H NMR(200 MHz, D₂O)δ: 1.37(d, 3H, CH₃, J=6.34Hz), 1.73–1.91; 2.09–2.16(m, 2H, CH₂), 2.78–3.5(overlap, 7H, CH₂NH, H-4), 3.47 (dd, 1H, H-6, J₆,₁=6.84Hz), 4.31(m, 1H, H-1'), 4.32(m, 1H, H-5, J₅,₆=2.74Hz, J₄,₅=9.08Hz). |
| 188 | (structure) | ¹H NMR(D₂O, 200 MHz)δ: 4.30–4.20(2H, m, H-1' and H-5), 3.420 (1H, dd, J=2.5Hz, J=6.1Hz, H-6), 3.50–3.30(3H, m, H-4 and CH₂N₃), 3.20–2.90, 2.90–2.75(2 sets of m, 4H, SCH₂), 2.171(3H, s, SCH₃), 1.95–1.50(4H, m, CH₂CH₂-4) and 1.331 ppm(3H, d, J=6.4Hz, CH₃). |
| 189 | (structure) | ¹H NMR(200 MHz, D₂O)δ: 1.35(d, J=6.37Hz, 3H, CH₃CHO), 1.5–2.0 (m, 4H, CH₂-1 and 2 of propyl), 2.8–3.3(m, 4H, SCH₂CH₂CN), 3.14(s, 9H, NCH₃), 3.3–3.6(m, 4H, H-4, H-6 and CH₂-3 of propyl) and 4.2–4.4 ppm(m, 2H, H-5 and CH₃CHO overlapping). |
| 190 | (structure) | ¹H NMR(D₂O, 200 MHz)δ: 4.35–4.20(1H, m, H-1'), 4.251(1H, dd, J=2.6Hz, J=9.5Hz, H-5), 3.375(1H, dd, J=2.6Hz, J=6.4Hz, H-6), 3.40–3.32(1H, m, H-4), 3.16–2.85(4H, m, SCH₂ and CH₂N), 2.84–2.74 (2H, m, SCH₂), 2.166(3H, s, SCH₃)1.94–1.54(4H, m, CH₂CH₂-4) and 1.333 ppm(3H, d, J=6.4Hz, CH₃). |
| 191 | (structure) | ¹H NMR(CDCl₃, 200 MHz)δ: 8.53–8.50(1H, m, H-6), 7.70–7.62(1H, m, H-4), 7.371, 7.33(1H, d, J=7.8Hz, pyridine H-3), 7.226–7.164(1H, m, pyridine H-5), 6.06–5.85(2H, m, vinylic H), 5.470–5.221(4H, m, vinylic H), 4.867–4.592(4H, 2 sets of m, allylic H), 4.290(1H, dd, J=2.8Hz, J=9.6Hz, H-5), 4.269, 4.198, 4.068, 3.999(2H, ABq, J=13.7 Hz, CH₂-pyridine), 4.27–4.10(1H, m, H-1'), 4.068–3.953(1H, m, H-4), 3.092(1H, dd, J=2.8Hz, J=7.1Hz, H-6), 2.971, 2.957, 2.883, 2.869, 2.531, 2.470, 2.443, 2.382(2H, ABX, J=2.9Hz, J=12.2Hz, J=17.6Hz, CH₂CO₂), 2.045(1H, bs, OH) and 1.291 ppm(3H, d, J=6.3Hz, CH₃). |

| EX. NO. | STRUCTURES | NMR DATA |
|---|---|---|
| 192 | 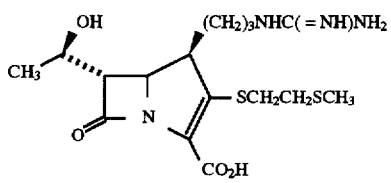 | $^1$H NMR($D_2O$, 200 MHz)δ: 4.40–4.20(1H, m, H-1'), 4.239(1H, dd, J=2.7 Hz, J=9.5Hz, H-5), 3.324(1H, dd, J=2.7, J=6.4Hz, H-6), 3.40–3.20 (3H, m, H-4 and $CH_2CN$), 3.2–2.87(2H, m, $SCH_2$), 2.85–2.74(2H, m, $SCH_2$), 2.164(3H, s, $SCH_3$), 1.90–1.45(4H, m, $CH_2CH_2$-4) and 1.322 ppm (3H, d, J=6.4Hz, $CH_3$). |
| 193 | 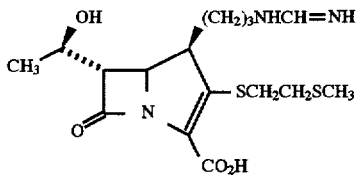 | $^1$H NMR($D_2O$, 200 MHz)δ: 7.836, 7.815(1H, 2s, NCH=N), 4.334–4.22(1H, m, H-1'), 4.224(d, J=-2.5Hz, part of H-5), 3.383 or 3.334(d, J=2.8 Hz, part of H-6), 3.45–3.30(4H, H-4, H-6 and $CH_2N$), 3.15–2.86, 2.86–2.71(4H, 2 sets of m, $SCH_2$), 2.162(3H, s, $SCH_3$), 1.90–1.47(4H, m, $CH_2CH_2$-4) and 1.322 ppm(3H, d, J=6.3Hz, $CH_3$). |
| 194 | 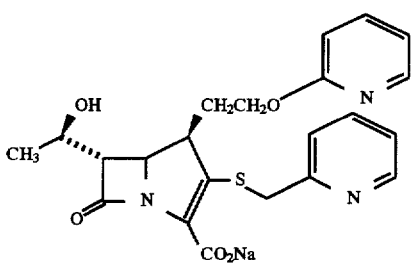 | $^1$H NMR(200 MHz, $CDCl_3$ 7.24 δ): 1.29(d, 3H, $CH_3$, J=6.11Hz), 1.85–2.02(m, 1H, $CH_2$), 2.24–2.38(m, 1H, $CH_2$), 3.46(dd, 1H, H-6, $J_{5,6}$=2.54Hz, $J_{6,1'}$=6.91Hz), 3.72(m, 1H, H-4, J=1.96, 11.42Hz), 4.03–4.36(overlap, 1H, $CH_2O$), 4.08(dd overlap, 1H, H-5), 4.32 (AB, 2H, $SCH_2$, $J_{AB}$=13.8Hz), 4.48–4.82(m, 3H, $OCH_2$ allyl, $CH_2O$), 5.17–5.46(m, 2H, =$CH_2$, allyl), 5.82–6.01(m, 1H, CH=, allyl), 6.72 (d, 1H, H-3', $J_{3',4}$=8.36Hz py), 6.83(m, 1H, H-5' py), 7.16(m, 1H, H-5, py), 7.35(d, 1H, H-3, $J_{3,4}$=7.81Hz py), 7.52(m, 1H, H-4' py), 7.64(m, 1H, H-4, $J_{3,4}$=$J_{4,5}$=7.69Hz, $J_{4,6}$=1.78Hz py), 8.08 (m, 1H, H-6' py), 8.49(m, 1H, H-6, $J_{5,6}$=5.57Hz, $J_{4,6}$=$J_{3,6}$=0.92Hz py). |
| 195 | 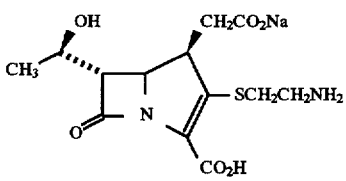 | $^1$H NMR($D_2O$, 200 MHz)δ: 4.334(1H, dd, J=2.6Hz, J=9.4Hz, H-5), 3.50–4.20(1H, m, H-1'), 3.72–3.59(1H, m, H-4), 3.465, 3.449, 3.430(1H, 3 lines, H-6), 3.36–3.09(3H, m, $CH_2N$ and 1H of $SCH_2$), 3.02–2.897(1H, m, 1H of $SCH_2$), 2.842, 2.822, 2.759, 2.739, 2.369, 2.312, 2.287, 2.229(2H, ABX, J=3.9Hz, J=11.6Hz, J=16.7Hz, $CH_2CO$), and 1.242 ppm(3H, d, J=6.4Hz, $CH_3$). |
| 196 | 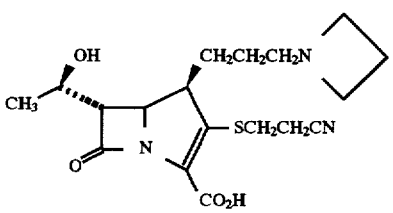 | $^1$H NMR(200 MHz, $D_2O$)δ: 1.32(d, J=6.34Hz, 3H, $\underline{CH_3}CHO$), 1.4–2.0 (m, 4H, $CH_2$-1 and 2 of propyl), 2.3–2.7(m, 2H, $CH_2$-3 of azetidine), 2.8–3.2(m, 4H, $SCH_2CH_2CN$), 3.25(broad t, J=7Hz, 2H, $CH_2$-3 of propyl), 3.37(dd, $J_{H6,H5}$=2.78Hz, $J_{H6,H1}$=6.38Hz, 1H, H-6), 3.4 (m overlapping with H-6, 1H, H-4) and 4.0–4.4 ppm(m, 6H, H-5, $CH_3CHO$ and $CH_2$2-2 and 4 of azetidine overlapping). |
| 197 | 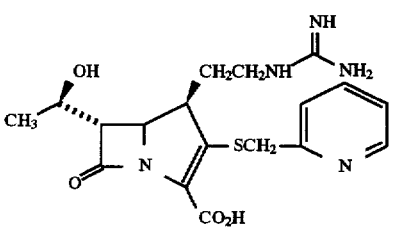 | $^1$H NMR($D_2O$, 200 MHz)δ: 8.47–8.44(1H, m, aromatic H), 7.88–7.79 (1H, m, aromatic H), 7.490, 7.450(1H, d, J=7.9Hz, aromatic H), 7.39–7.3(1H, m, aromatic H), 4.25–4.14(1H, m, H-1'), 4.21, 4.14, 4.07, 4.00(2H, ABq, J=14.1Hz, $CH_2$-pyridine), 4.119, 4.106(d, J=2.6Hz, part of H-5), 3.331(1H, dd, J=6.8Hz, J=2.6Hz, H-6), 3.31–2.95(3H, m, H-4 and $CH_2$), 2.0–1.8, 1.6–1.4(2H, 2m, $CH_2$=N) and 1.285(3H, d, J=6.4Hz, $CH_3$). |
| 198 | 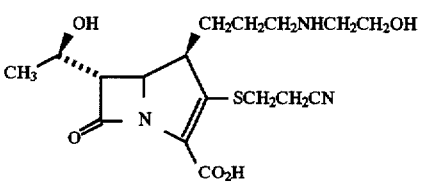 | $^1$H NMR(200 MHz, $D_2O$)δ:1.33(d, J=6.35Hz, 3H, $\underline{CH_3}CHO$), 1.4–2.0(m, 4H, $CH_2$-1 and 2 of propyl), 2.8–3.5(m, 8H, $SCH_2\overline{CH_2}CN$, $NCH_2CH_2OH$ and $CH_2$-3 of propyl), 3.41(dd, $J_{H6,H1}$=2.53Hz, $J_{H6,H1}$=6.67Hz, 1H, $\overline{H}$-6), 3.42(m, overlapping with H-6, 1H, H-4), 3.84(t, J=5.2Hz, 2H, $CH_2OH$) and 4.21–4.4 ppm(m, 2H, H-5 and $CH_3\underline{CHO}$). |

| EX. NO. | STRUCTURES | NMR DATA |
|---|---|---|
| 199 | (structure: carbapenem with OH, CH₃, (CH₂)₃N(CH₂CH₂OH)₂, SCH₂CH₂CN, CO₂H) | ¹H NMR(200 MHz, D₂O)δ: 1.33(d, J=6.28Hz, 3H, C$\underline{H}_3$CHO), 1.4–2.0 (m, 4H, CH₂-1 and 2 of propyl), 2.8–3.6(m, 11H, H-4, NC$\underline{H}_2$CH₂OH, SC$\underline{H}_2$CH₂CN, CH₂-3 of propyl), 3, 42(dd overlapping with the previous m, $J_{H6,H5}$=1.9Hz, $J_{H6,H1}$=7.1Hz, 1H, H-6), 3.90(t, J=5.2Hz, 4H, C$\underline{H}_2$OH), and 4.2–4.4 ppm(m, 2H, H-5 and CH₃C$\underline{H}$O overlapping). |
| 200 | (structure: carbapenem with OH, CH₃, (CH₂)₄NHCCHNH₂ with CH₂Cl, SCH₂CH₂CN, COOH, *L-) | ¹H NMR(200 MHz, D₂O)δ: 1.35(d, 3H, CH₃, J=6.39Hz), 1.45–1.9 (overlap, 6H, (CH₂)₃), 2.83–3.37(overlap, 7H, H-4, CH₂CN, SCH₂, CH₂NH), 3.425(dd, 1H, H-6, $J_{5,6}$=2.49Hz, $J_{6,1}$=5.93Hz), 3.85(centre of m, 3H, CH, C$_\beta$H₂), 4.25(dd, overlap 1H, H-5), 4.29(m, 1H, H-1'). |
| 201 | (structure: carbapenem with OH, CH₃, CH₂CH₂NHC(=NH)NH₂, SCH₂CH₂OH, CO₂H) | ¹H NMR(D₂O, 200 MHz)δ: 4.33–4.19(1H, m, H-1'), 4.248(1H, dd, J=2.5 Hz, J=8.8Hz, H-5), 3.787, 3.755, 3.726(2H, 3 lines, CH₂O), 3.400 (1H, dd, J=2.5Hz, J=6.9Hz, H-6), 3.5–3.15(3H, m, H-4 and CH₂N), 3.04–2.76(2H, m, SCH₂), 2.2–2.04, 1.87–1.68(2H, 2 sets of m, CH₂ at 4) and 1.33 ppm(3H, d, J=6.3Hz, CH₃). |
| 202 | (structure: carbapenem with OH, CH₃, CH₂CH₂-N⁺ pyrrolidinium with allyl, SCH₂CH₂CN, CO₂⁻) | ¹H NMR(200 MHz, D₂O)δ: 1.33(d, J=6.32Hz, 3H, C$\underline{H}_3$CHO), 2.0–2.4(m, 8H, CH₂-1 of ethyl and CH₂-3 and 3' of pyrrolidinium), 2.8–3.2(m, 4H, SC$\underline{H}_2$CH₂CN), 3.2–3.8(m, 8H, H-4, H-6, CH₂-2 of ethyl, CH₂-2 and 2' of pyrrolidinium), 3.9–4.1(m, CH₂ of allyl), 4.2–4.4(m, 2H, H-5 and CH₃C$\underline{H}$O overlapping), 5.7–5.9 and 6.0–6.2 ppm(2m, 2H and 1H, CH of allyl). |
| 203 | (structure: carbapenem with OH, CH₃, (CH₂)₃NHC(=NH)NH₂, S-(CH₂)₃-CN, CO₂H) | ¹H NMR(200 MHz, D₂O)δ: 1.34(d, J=6.33Hz, 3H, C$\underline{H}_3$CHO), 1.7–2.3(m, 4H, C$\underline{H}_2$CH₂N and SCH₂C$\underline{H}_2$CN), 2.60–3.02(m, 4H, SC$\underline{H}_2$CH₂CH₂CN), 3.20–3.46(m, 4H, CH₂N, H-6 and H-4) and 4.2–4.4 ppm(m, H-5, CH₃C$\underline{H}$O). |
| 204 | (structure: carbapenem with OH, CH₃, CH₂CH₂CH₂N₃, CH₂CH₂NH-C(=NH)-NH₂, CO₂H) | ¹H NMR(200 MHz, D₂O)δ: 1.33(d, J=6.33Hz, 3H, C$\underline{H}_3$CHO), 1.4–2.0(m, 4H, CH₂-1 and 2 of propyl), 2.8–3.2(m, 2H, SCH₂), 3.2–3.6(m, 6H, H-4, H-6, C$\underline{H}_2$N₃ and C$\underline{H}_2$N) and 4.2–4.4 ppm(m, 2H, H-5 and CH₃C$\underline{H}$O overlapping). |
| 205 | (structure: carbapenem with OH, CH₃, CH₂CH₂NH-C(=NH)-NH₂, SCH₂-pyridyl, CO₂H) | ¹H NMR(200 MHz, D₂O)δ: 1.30(d, J=6.33Hz, 3H, C$\underline{H}_3$CHO), 1.4–2.1(m, 2H, CH₂-1 of aminoethyl), 3.0–3.4(m, 3H, CH₂-2 of aminoethyl and H-4), 3.35(dd, $J_{H6,H5}$=2.63Hz, $J_{H6,H1}$=6.77Hz, 1H, H-6), 4.03(ABq, $J_{AB}$=14.1Hz, Δv=24.4Hz, 2H, SCH₂), 4.1(m overlapping with SCH₂, 1H, H-5), 4.22(m, 1H, CH₃C$\underline{H}$O), 7.43(m, 1H, H-5 of pyridine), 7.86(m, 1H, H-4 of pyridine), 8.43(m, 1H, H-6 of pyridine) and 8.47 ppm(d, J=1.9Hz, 1H, H-2 of pyridine). |

| EX. NO. | STRUCTURES | NMR DATA |
|---|---|---|
| 206 | (structure: carbapenem with OH, CH₃; side chain CH₂CH₂NHCCHNH₂ with O*, CH₂Cl, CH₂CN; SCH₂CH₂CN; COOH) *L− | $^1$H NMR(200 MHz, D$_2$O)δ: 1.37(d, 3H, CH$_3$, J=6.36Hz), 1.65–1.82; 2.16–2.02(m, 2H, CH$_2$), 2.81–2.92(m, 2H, CH$_2$CN), 2.94–3.02; 3.03–3.21(m, 2H, SCH$_2$), 3.26–3.51(overlap, 3H, CH$_2$NH, H-4), 3.59(dd, 1H, H-6, J$_{5,6}$=2.68Hz, J$_{6,1'}$=6.02Hz), 3.87–4.04(m, 2H, C$_β$H$_2$), 4.11 (t, 1H, C$_α$H, J$_{α,β}$=4.57Hz), 4.27–4.38(overlap, 2H, H-5, H-1') |
| 207 | (structure: carbapenem with OH, CH₃; CH₂CH₂CH₂NH-C(=NH)-NH₂; SCH₂CH₂N(CH₃)₂; CO₂H · CH₃CO₂H) | $^1$H NMR(D$_2$O, 200 MHz)δ: 4.275(1H, dd, J=2.7Hz, J=12.4Hz, H-5), 4.35–4.2(1H, m, H-1'), 3.395(1H, dd, J=2.7Hz, J=6.2Hz, H-6), 3.45–2.95(7H, CH$_2$-guanidine, CH$_2$N, SCH$_2$ and H-4), 2.90(6H, s, N(CH$_3$)$_2$), 1.92(1.8H, s, CH$_3$CO$_2$), 1.9–1.4(4H, m, CH$_2$CH$_2$-4) and 1.32 ppm(3H, d, J=6.4Hz, CH$_3$). |
| 208 | (structure: carbapenem with OH, CH₃; CH₂CH₂OH; SCH₂CH₂NH-C(=NH)-NH₂; CO₂H) | $^1$H NMR(200 MHz, D$_2$O)δ: 1.32(d, J=6.41Hz, 3H, C$\underline{H_3}$CHO), 1.6–2.2(m, 2H, C$\underline{H_2}$CH$_2$OH), 2.8–3.2(m, 2H, SC$\underline{H_2}$CH$_2$), 3.3–3.8(m, 6H, H-6, H-4, SC$\underline{H_2}$CH$_2$N and CH$_2$CH$_2$OH) and 4.2–4.4 ppm(m, 2H, H-5 and CH$_3$C$\underline{H}$O overlapping). |
| 209 | (structure: carbapenem with OH, CH₃; CH₂CH₂NH-C(=NH)-NH₂; SCH₂-pyridine(4); COOH) | $^1$H NMR(200 MHz, D$_2$O)δ: 1.3(d, 3H, CH$_3$, J=6.33Hz), 1.54–1.69; 1.93–2.04(m, 2H, CH$_2$), 2.98–3.29(overlap, 3H, CH$_2$NH, H-4), 3.36 (dd, 1H, H-6, J$_{6,1'}$=6.78Hz)4.08(1H, H-5, J$_{5,6}$=2.66Hz), 2.97, 4.1(AB, 2H, SCH$_2$, J$_{gem}$=14.72Hz), 4.22(m, 1H, H-1'), 7.45(B of 4.1(AB, 2H, SCH$_2$, J$_{gem}$=14.72Hz), 4.22(m, 1H, H-1'), 7.45(B of A$_2$B$_2$, 2H, H-3,5 py), 8.48(A of A$_2$B$_2$, 2H, H-2, 6 py, J=6.01Hz). |
| 210 | (structure: carbapenem with OH, CH₃; CH₂CH₂OH; SCH₂CH₂NHCH=NH; CO₂H) | $^1$H NMR(200 MHz, D$_2$O)δ: 1.32(d, J=6.41Hz, 3H, C$\underline{H_3}$CHO), 1.6–2.2(m, 2H, C$\underline{H_2}$CH$_2$OH, 2.8–3.3(m, 2H, SCH$_2$), 3.47(dd, J$_{H6,H5}$=2.71Hz, J$_{H6,H1}$=6.0Hz, 1H, CH$_3$C$\underline{H}$O), 3.4–3.8(m, 5H, H-4, CH$_2$N and CH$_2$O), 4.2–4.4(m, 2H, H-5 and CH$_3$C$\underline{H}$O overlapping), 7.76 and 7.84 ppm(2s, 1H, C$\underline{H}$=NH). |
| 211 | (structure: carbapenem with OH, CH₃; CH₂OH; S-CH₂-pyridine(2); CO₂Na) | $^1$H NMR(400 MHz, D$_2$O)δ 1.28(d, 3H, J=6.3Hz), 3.35(m, 1H, J=5.7, 2.1, 9.3Hz), 3.55(dd, 1H, J=6.1, 2.6Hz), 3.77(dq, 2H, J$_A$=3.78, J$_B$=3.76, J$_{AB}$=12.0Hz, J$_{AX}$=5.7, J$_{BX}$=2.1Hz), 4.07(dd, 1H, J=2.6, 9.3Hz), 4.11(d, 1H, J=14.3Hz), 4.21(d, 1H, J=14.3Hz), 4.23 (dq, 1H, J=6.3, 6.1Hz), 7.35–8.47(m, 4H, arom.); HPLC purity 99%. |
| 212 | (structure: carbapenem with OH, CH₃; (CH₂)₃N₃; SCH₂-imidazole; CO₂K) | $^1$H NMR(200 MHz, D$_2$O)δ: 1.31(d, J=6.36Hz, 3H, C$\underline{H_3}$CHO), 1.3–1.9 (m, 4H, CH$_2$-1 and 2 of propyl), 3.2–3.5(m, 4H, H-4, H-6 and CH$_2$-3 of propyl), 4.03(ABq, J$_{AB}$=14.7Hz, Δν=27.8Hz, 2H, SCH$_2$), 4.13 (dd, J$_{H5,H6}$=2.50Hz, J$_{H5,H4}$=9.30Hz, 1H, H-5), 4.24(m, 1H, CH$_3$C$\underline{H}$O), 7.09(s, 1H, H-5 of imidazole) and 7.75 ppm(d, J=1.0Hz, 1H, H-2 of imidazole). |
| 213 | (structure: carbapenem with OH, CH₃; CH₂CH₂N₃; SCH₂CH₂CN; CO₂K) | $^1$H NMR(200 MHz, D$_2$O)δ: 1.33(d, J=6.4Hz, 3H, C$\underline{H_3}$CHO), 1.7–2.2(2m, 2H, CH$_2$-4), 2.8–3.7(m, 8H, —SC$\underline{H_2}$C$\underline{H_2}$CN, C$\underline{H_2}$N$_3$, H-4, H-6), 4.2–4.4(m, 2H, H-5 and CH3C$\underline{H}$O overlapping). |

| EX. NO. | STRUCTURES | NMR DATA |
|---|---|---|
| 214 | (structure) | J=46.7Hz, CH$_2$F), 4.34–4.21(1H, m, H-1'), 4.268(1H, dd, J=2.7Hz, J=9.4Hz, H-5), 3.51–3.39(1H, m, H-4), 3.435(1H, dd, J=2.7Hz, J=6.5Hz, H-6), 3.32–2.91(4H, m, CH$_2$N and SCH$_2$), 2.23–2.1, 1.97–1.81(2H, 2 sets of m, CH$_2$-4) and 1.331 ppm(3H, d, J=6.4Hz, CH$_3$). |
| 215 | (structure) | $^1$H NMR(D$_2$O, 200 MHz)δ: 4.57–4.47(1H, 1 set of m, 1H of CH$_2$F), 4.34–4.13(1H, m, H-1'), 4.271(1H, dd, J=2.8Hz, J=8.9Hz, H-5), 3.426(1H, dd, J=2.8Hz, J=6.8Hz, H-6), 3.50–2.88(5H, SCH$_2$, CH$_2$N, H-4), 2.21–2.05, 1.88–1.69(2H, 2 sets of m, CH$_2$-4) and 1.343 ppm (3H, d, J=6.3Hz, CH$_3$). |
| 216 | (structure) | $^1$H NMR(D$_2$O)δ: 4.15–4.30(2H, m, H-5, H-1'), 3.00–3.60[9H, m, —CH$_2$N$_3$, H-4, H-6, (H-4, 2H-2, 2H-6 of piperidine)], 1.40–2.30 [8H, m, 2H-1'',(2H-2'', (2H-3, 2H-5 of piperidine)], 1.31(3H, d, J: 6.35, —CH$_3^1$. |
| 217 | (structure) | $^1$H NMR(200 MHz, D$_2$O)δ: 1.31(d, J=6.44Hz, 3H, CH$_3$CHO), 1.3–1.9(m, 4H, CH$_2$-1 and 2 of propyl), 3.0(broad t, 2H, CH$_2$NH$_2$), 3.3(m, 1H, H-4), 3.33(dd overlapping with H-4, J$_{H6,H5}$=2.42Hz, J$_{H6,H1}$=6.34Hz, 1H, H-6), 4.0(ABq, J$_{AB}$=14.65Hz, Δv=24.6Hz, 2H, SCH$_2$), 4.13(dd overlapping with SCH$_2$, J$_{H5,H6}$=2.42Hz, 1H, H-5), 4.25(m, 1H, CH$_3$CHO), 7.09(s, 1H, H-5 of imidazole) and 7.73 ppm(m, 1H, H-2 of imidazole). |
| 218 | (structure) | $^1$H NMR(200 MHz, D$_2$O)δ: 1.30(d, J=6.32Hz, 3H, CH$_3$CHO), 1.3–1.8 (m, 4H, CH$_2$-1 and 2 of propyl), 3.1–3.4(m, 4H, H-4, H-6 and CH$_2$-3 of propyl), 4.0(ABq, J$_{AB}$=14.52Hz, Δv=23.0Hz, 2H, SCH$_2$), 4.13(dd overlapping with SCH$_2$, J$_{H5,H6}$=2.26Hz, 1H, H-5), 4.24(m, 1H, CH$_3$CHO), 7.08(s, 1H, H-5 of imidazole) and 7.7 ppm(s, 1H, H-2 of imidazole) |
| 219 | (structure) | $^1$H NMR(200 MHz, D$_2$O)δ: 1.32(d, J=6.38Hz, 3H, CH$_3$CHO), 1.8–2.3(2m, 2H, CH$_2$-4), 2.5–3.3(m, 6H, S—CH$_2$CH$_2$CN, CH$_2$—CN), 2.4–3.6(m, 2H, H-4 and H-6), 4.2–4.4 m, 2H, H-5 and CH$_3$CHO overlapping). |
| 220 | (structure) | $^1$H NMR(200 MHz, D$_2$O)δ: 1.32(d, J=6.37Hz, 3H, CH$_3$CHO), 1.7–1.9 and 2.1–2.3(2×m, 2H, CH$_2$CH$_2$N), 2.85(m, 2H, CH$_2$CN), 3.04(s, 6H, N(CH$_3$)$_2$, overlapping)2.9–3.6(m, 6H, SCH$_2$, CH$_2$N, H-6, H-4) and 4.2–4.4 ppm(m, 2H, H-5 and CH$_3$CHO). |
| 221 | (structure) | $^1$H NMR(200 MHz, D$_2$O)δ: 1.32(d, J=6.32Hz, 3H, CH$_3$CHO), 1.4–1.9(m, 4H, CH$_2$-1 and 2 of propyl), 1.93(s, CH$_3$CO$_2$H), 2.8–3.2(m, 2H, SCH$_2$), 3.2–3.7(m, 6H, H-4, H-6, CH$_2$-3 of propyl and CH$_2$-2 of ethylthio), 4.2–4.4(m, 2H, H-5 and CH$_3$CHO overlapping), 7.75, 7.80 and 7.84 ppm (3s, total 2H, CH=NH). |

| EX. NO. | STRUCTURES | NMR DATA |
|---|---|---|
| 222 | (structure: carbapenem with OH, CH₃, (CH₂)₃NH-C(=NH)NH₂ group, SCH₂CH₂NHCH=NH, CO₂H) | ¹H NMR(200 MHz, D₂O)δ: 1.31(d, J=6.33Hz, 3H, C$\underline{H_3}$CHO), 1.4–1.9 (m, 4H, CH₂-1 and 2 of propyl), 1.94(s, C$\underline{H_3}$CO₂H), 2.8–3.2(m, 2H, SCH₂), 3.2–3.7(m, 6H, H-4, H-6, CH₂-3 of propyl and CH₂-2 of ethylthio), 4.2–4.4(m, 2H, H-5 and CH₃C$\underline{H}$O overlapping), 7.5 and 7.8 ppm(2s, total 1H, C$\underline{H}$=NH). |
| 223 | (structure: carbapenem with OH, CH₃, CH₂CH₂N₃, SCH₂CH₂NHCNH₂ (NH), CO₂H) | ¹HMR(200 MHz, D₂O)δ: 1.33(d, J=6.33Hz, 3H, C$\underline{H_3}$CHO), 1.7–2.2(m, 2H, C$\underline{H_2}$CH₂N₃), 2.8–3.2(m, 2H, SCH₂), 3.3–3.7(m, 6H, H-6, H-4, C$\underline{H_2}$NH and CH₂N₃), and 4.2–4.35 ppm(m, 2H, H-5 and CH₃C$\underline{H}$O). |
| 224 | (structure: carbapenem with OH, CH₃, CH₂CH₂N₃, SCH₂CH₂NH-CH=NH, CO₂H) | ¹H NMR(200 MHz, D₂O)δ: 1.33(d, J=6.29Hz, 3H, C$\underline{H_3}$CHO), 1.7–2.2(m, 2H), C$\underline{H_2}$CH₂N₃), 2.8–3.3(m, 2H, SC$\underline{H_2}$), 3.3–3.8(m, 6H, H-4, H-6, C$\underline{H_2}$NH and C$\underline{H_2}$N₃), 4.2–4.4(m, 2H, H-5 and CH₃C$\underline{H}$O overlapping), 7.76 and 7.84 ppm(2s, 1H, C$\underline{H}$=NH). |
| 225 | (structure: carbapenem with OH, CH₃, (CH₂)₃N₃, S-azetidinyl(N-H), CO₂H) | (D₂O)δ: 4.55–4.65 and 3.95–4.10(4H, 2m, 2H-2, 2H-4 of azetidine), 4.20–4.40(3H, m, H-1', H-5, CH—S), 3.35–3.50(3H, m, —CH₂N₃, H-6), 3.15(1H, m, H-4), 1.50–1.95(4H, m, 2H-1" , 2H-2"), 1.34(3H, d, J: 6.38, —CH₃¹). |
| 226 | (structure: carbapenem with OH, CH₃, CH₂CH₂CN, SCH₂CH₂NH₂, CO₂H) | ¹H NMR(200 MHz, D₂O), δ: 1.32(d, J=6.38Hz, 3H, C$\underline{H_3}$CHO), 1.8–2.3 (2m, 2H, CH₂-4), 2.4–3.4(broad m, 7H, SCH₂CH₂NH₂, CH₂CN and H-4), 3.46(dd, J$_{H6,H5}$=2.92Hz, J$_{H6,1}$=6.41Hz, 1H, H-6) and 4.2 to 4.35 ppm (m, 2H, H-5 and CH₃C$\underline{H}$O overlapping). |
| 227 | (structure: carbapenem with OH, CH₃, CH₂CH₂CN, SCH₂CH₂NHC(=NH)NH₂, CO₂H) | ¹H NMR(200 MHz, D₂O)δ: 1.33(d, J=6.26 3H, C$\underline{H_3}$CHO), 1.8–2.4(2m, 2H, CH₂-4), 2.4–3.6(broad m, 8H, S—C$\underline{H_2}$C$\underline{H_2}$N, CH₂CN, H-4 and H-6), 4.2–4.4(m, 2H, H-5 and CH₃C$\underline{H}$O). |
| 228 | (structure: carbapenem with OH, CH₃, CH₂CH=O, SCH₂CH₂N₃, CO₂Na) | ¹H NMR(D₂O, 200 MHz)δ: 9.706(0.5H, s, CHO); 5.16, 5.14, 5.12, 5.10(0.5H, 4 lines, J=3.9Hz, CH(OD)₂), 4.324(0.5H, dd, J=2.8Hz, J=9.8Hz, H-5), 4.250(0.5H, dd, J=2.8Hz, J=9.8Hz), 4.30–4.13(1H, m, H-1'), 3.90–3.70(0.5H, m, H-4 of CH₂CHO), 3.55–3.40(2.5H, CH₂N₃, H-4 of CH₂CH(OD)₂), 3.21–2.74(4H, m, H-6, SCH₂ and C$\underline{H_2}$CHO), 2.10–1.75(1H, m, C$\underline{H_2}$CH(OD)₂), 1.263(1.5H, d, J=6.4Hz, CH₃) and 1.171 ppm(1.5H, d, J=6.4Hz, CH₃). |
| 229 | (structure: carbapenem with OH, CH₃, (CH₂)₃NH₂, SCH₂-triazolyl, CO₂Na) | ¹H NMR(200 MHz, CDCl₃)δ: 1.20–1.8(m, 4H, CH₂CH₂-4), 1.30(d, 3H, J=6.37Hz, C$\underline{H_3}$CHO), 2.98(m, 2H, CH₂NH₂), 3.21–3.35(m, 2H, H-4 and H-6), 4.02–4.27(m, 4H, CH₂—S, H-5 and CH₃C$\underline{H}$O), 7.70(s, 1H, CH of triazol). By UV at 37° C. in a pH 7.4 phosphate buffer, the half-life was measured to be 85 h. |

-continued

| EX. NO. | STRUCTURES | NMR DATA |
|---|---|---|
| 230 | (structure) | $^1$NMR(200 MHz, CDCl$_3$)δ: 1.24–1.80(m, 4H, CH$_2$CH$_2$-4), 1.26(d, 3H, J=6.29Hz, CH$_3$CHO), 3.21(m, 1H, H-4), 3.35(dd, 1H, J=6.03Hz, J$_{5,6}$=2.40Hz, H-6), 3.55(m, 2H, CH$_2$OH), 4.02–4.23(m, 4H, CH$_2$—S, H-5 and CH$_3$CHO), 7.80(9, 1H, CH of triazol). By UV at 37° C. in a pH 7.4 phosphate buffer, the half-life was measured to be 170 h. |
| 231 | (structure) | $^1$H NMR(200 MHz, D$_2$O)δ: 1.38(d, 3H, CH$_3$, J=6.54Hz), 1.42(d, 3H, CH$_3$, J=7.32Hz), 1.48(3H, CH$_3$), 1.59–1.75; 1.99–2.14(m, 2H, CH$_2$), 2.84–2.89(overlap, 2H, CH$_2$CN), 2.92–3.22(overlap, 2H, SCH$_2$), 3.3–3.42(overlap, 3H, CH$_2$N, H-4), 3.59(dd, 1H, H-6, J$_{5,6}$=2.56Hz, J$_{6,1}$=5.88Hz), 3.9(br, 1H, C$_\alpha$H), 4.25–4.34(overlap, 3H, H-5, H-1', C$_\alpha$H). |
| 232 | (structure) | $^1$H NMR(200 MHz, CDCl$_3$ 7.24 δ): 0.04(s, 6H, Si(CH$_3$)$_2$), 0.85(s, 9H, SiC(CH$_3$)3), 1.05(d, 3H, CH$_3$, J=6.18Hz), 1.51–1.66; 1.85–2.0(m, 2H, CH$_2$), 2.24(s, 3H, NCH$_3$), 2.29–2.5(m, 2H, CH$_2$N), 2.61(centre m, 2H, CH$_2$CN), 2.9, 3.19(centre m, 2H, SCH$_2$), 3.07(dd, 1H, H-6, J$_{6,1}$=5.66 Hz), 3.3(m, 1H, H-4, J=2.12, 11.29Hz), 3.42, 3.58(AB, 2H, NCH$_2$Ph, J=13.23Hz), 4.08(dd, 1H, H-5, J$_{5,6}$=2.61, J$_{4,5}$=9.52Hz), 4.11(m, 1H, H-1'), 4.61–4.81(m, 2H, OCH$_2$, allyl), 5.19–5.47(m, 2H, =CH$_2$, allyl), 5.83–6.02(m, 1H, CH=, allyl), 7.2–7.36(m, 5H, phenyl). |
| 233 | (structure) | $^1$H NMR(200 MHz, D$_2$O)δ: 1.34(d, J=6.40Hz, 3H, CH$_3$CHO), 1.8–2.2 (m,2H, CH$_2$CH$_2$N$_3$), 3.3–3.7(m, 4H, H-6, H4 and CH$_2$CH$_2$N$_3$), 3.81(ABq, J$_{AB}$=17.6Hz, Δv=28.6Hz, 2H, SCH$_2$), 4.28(m, 1H, CH$_3$CHO) and 4.35 ppm(dd, J$_{H5,H6}$=2.77Hz, J$_{H5,H4}$=9.58Hz, 1H, H-5). |
| 234 | (structure) | $^1$H NMR(200 MHz, D$_2$O)δ: 1.34(d, J=6.39Hz, 3H, CH$_3$CHO), 1.7–2.3(m, 2H, CH$_2$CH$_2$N) 3.2–3.6(m, 3H, H-4 and CH2CH2N), 3.5(dd, J$_{H6,H5}$=2.80Hz, J$_{H6,H1}$=6.80Hz, 1H, H-6), 3.78(ABq, J$_{AB}$=17.6Hz, Δv=14.1Hz, 2H, SCH$_2$), 4.29(m, 1H, CH$_3$CHO) and 4.35 ppm(dd, J$_{H5,H6}$=2.80Hz, J$_{H5,H4}$=9.64Hz, 1H, H-5). |
| 235 | (structure) | $^1$H NMR(200 MHz, D$_2$O)δ: 1.33(d, J=6.38Hz, 3H, CH$_3$CHO), 1.7–2.2(m, 2H, CH$_2$CH$_2$N$_3$), 3.14 and 3.30(2d, 2×3H, NCH$_3$), 3.3–3.7(m, 4H, H-4, H-6 and CH$_2$N$_3$), 3.88(ABq, 2H, SCH$_2$), and 4.2–4.35 ppm(m, 2H, H-5 and CH$_3$CHO). |
| 236 | (structure) | $^1$H NNR(200 MHz, D$_2$O)δ: 1.32(d, J=6.38Hz, 3H, CH$_3$CHO), 1.4–2.9(m, 4H, CH$_2$-1 and 2 of propyl), 2.8–3.2(m, 4H, SCH$_2$CH$_2$CN), 3.07(s, 3H, NCH$_3$), 3.2–3.6(m, 4H, H-4, H-6 and CH$_2$N overlapping), 4.2–4.4(m, 2H, H-5 and CH$_3$CHO), 7.78 and 7.89 ppm(2s, 1H, CH=NH). |

| EX. NO. | STRUCTURES | NMR DATA |
|---|---|---|
| 237 | 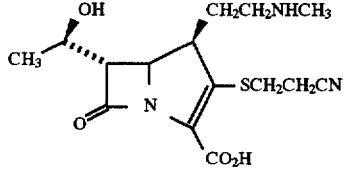 | $^1$H NMR(200 MHz, D$_2$O)δ: 1.31(d, J=6.38Hz, 3H, C$\underline{H}_3$CHO), 1.8–2.3(m, 2H, C$\underline{H}_2$CH$_2$N), 2.71(m, 3H, NCH$_3$), 2.8–3.2(m, 6H, SC$\underline{H}_2$CH$_2$CN and CH$_2$C$\underline{H}_2$N), 3.35–3.5(m, 2H, H-6 and H-4), and 4.2–4.4 ppm(m, H-5 and CH$_3$C$\underline{H}$O). |
| 238 | 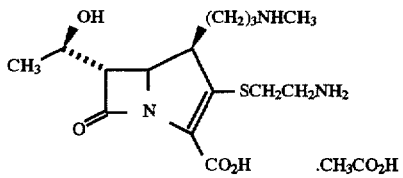 | $^1$H NMR(200 MHz, D$_2$O)δ: 1.33(d, J=6.35Hz, 3H, C$\underline{H}_3$CHO), 1.5–2.0(m, 4H, CH$_2$-1 and 2 of propyl), 1.92(s. CH$_3$CO$_2$H), 2.72(s, 3H, NCH$_3$), 2.8–3.4(m, 8H, H-4, H6, CH$_2$-3 of propyl and SC$\underline{H}_2$CH$_2$NH$_2$), 3.42(dd, J$_{H6,H5}$=2.72Hz, J$_{H6,H1}$=6.36Hz, 1H, H-6), and 4.2–4.4 ppm(m, 2H, H-5 and CH$_3$C$\underline{H}$O). |
| 239 | 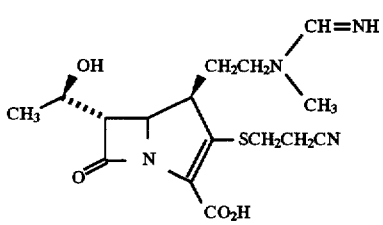 | $^1$H NMR(200 MHz, D$_2$O)δ: 1.33(d, J=6.34Hz, 3H, C$\underline{H}_3$CHO), 1.8–2.3(m, 2H, C$\underline{H}_2$CH$_2$N$_3$), 2.75–2.9(m, 2H, C$\underline{H}_2$CN), 2.9–3.2(m, 2H, SCH$_2$), 3.11(s, 3H, NCH$_3$), 3.25–3.5(m, 1H, H-4), 3.44(dd, J$_{H6,H5}$=2.78Hz, J$_{H6,H1}$=6.97 Hz, 1H, H-6), 3.65(broad t, 2H, CH$_2$N), 4.2–4.4(m, 2H, H-5 and CH$_3$C$\underline{H}$O and 7.9 ppm(s, 1H, C$\underline{H}$=N). |
| 240 | 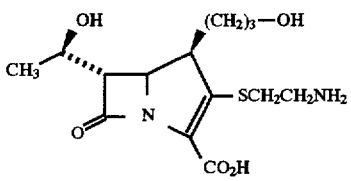 | $^1$H NMR(D$_2$O, 400 MHz)δ: 4.29(1H, quint J=6.6Hz, H-1'); 4.27(1H, dd, J=6.9Hz, J=2.4Hz, H-5); 3.66(2H, t, J=6.2Hz, CH$_2$O); 3.48(1H, dd, J=6.0Hz, J=2.7Hz, H-6); 3.36–3.26 and 3.24–3.10.(4H, 2 sets of m, H-4, CH$_2$N, part of SCH$_2$); 2.98–2.91(1H, m, part of SCH$_2$); 1.91–1.89 and 1.71–1.49(4H, 2 sets of m, CH$_2$CH$_2$-4) and 1.34 ppm(3H, d, J=6.4Hz, CH$_3$). |
| 241 | 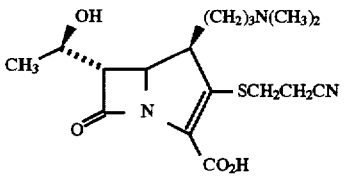 | $^1$H NMR(200 MHz, D$_2$O)δ: 1.32(d, J=6.34Hz, 3H, C$\underline{H}_3$CHO), 1.4–2.0(m, 4H, CH$_2$-1 and 2 of propyl), 2.85(s, 6H, NCH$_3$), 2.8–3.3(m, 6H, SCH$_2$CH$_2$CN and CH$_2$-3 of propyl), 3.40(dd, J$_{H6,H5}$=2.7Hz, J$_{H6,H1}$=6.5Hz, 1H, H-6), 3.4–3.5(m overlapping with H-6, 1H, H-4), and 4.2–4.35 ppm (m, 2H, H-5 and CH$_3$C$\underline{H}$O). |
| 242 | 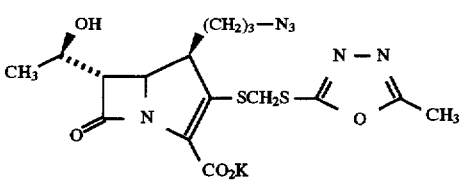 | $^1$H NMR(200 MHz, D$_2$O)δ: 1.34(d, J=6.33Hz, 3H, C$\underline{H}_3$CHO), 1.5–2.0(m, 4H, CH$_2$-1 and 2 of propyl), 2.56(s, 3H, CH$_3$ of oxadiazole), 3.3–3.5(m, 4H, H-4, H-6 and CH$_2$-3 of propyl), 4.2–4.4(m, 2H, H-5 and CH$_3$C$\underline{H}$O), and 4.56 ppm(ABq, J$_{AB}$=13.91Hz, Δv=24.5Hz, 2H, SCH$_2$). |
| 243 | 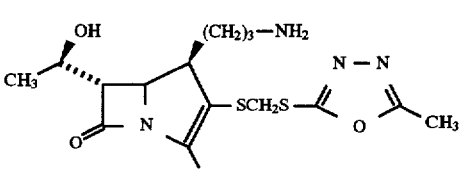 | $^1$H NMR(200 MHz, D$_2$O)δ: 1.33(d, J=6.36Hz, 3H, C$\underline{H}_3$CHO), 1.5–2.0(m, 4H, CH$_2$-1 and 2 of propyl), 2.56(s, 3H, CH$_3$ of oxadiazole), 3.04(t, J=7.1Hz, 2H, CH$_2$-3 of propyl), 3.3–3.5(m, 2H, H-4 and H-6), 4.2–4.35 (m, 2H, H-5 and CH$_3$C$\underline{H}$O), and 4.54 ppm(ABq, J$_{AB}$=13.96Hz, Δv=24.56 Hz, 2H, SCH$_2$). |
| 244 | 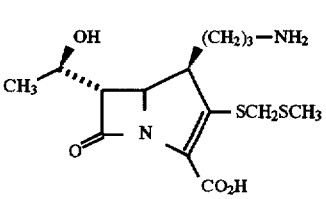 | $^1$H NMR(200 MHz, D$_2$O)δ: 1.31(d, J=6.33Hz, 3H, C$\underline{H}_3$CHO), 1.40–2.0(m, 4H, CH$_2$-1 and 2 of propyl), 2.19(s, 3H, SCH$_3$), 3.03(t, J=7.0Hz, 2H, C$\underline{H}_2$NH$_2$), 3.3–3.5(m, 2H, H-4 and H-6), 3.90(ABq, J$_{AB}$=13.7Hz, Δv=31.1Hz, SCH$_2$) and 4.2–4.4 ppm(m, 2H, H-5 and CH$_3$C$\underline{H}$O overlapping). |

| EX. NO. | STRUCTURES | NMR DATA |
|---|---|---|
| 245 | (structure: carbapenem with OH, CH₃, CH₂CH₂NH₂, SCH₂C(=NH)N(CH₃)₂, CO₂H ·AcOH) | ¹H NMR(200 MHz, D₂O)δ: 1.31(d, J=6.35Hz, 3H, C$\underline{H_3}$CHO), 1.8–2.3(m, 2H, C$\underline{H_2}$CH₂NH₂), 1.90(s, CH₃CO₂H), 3.09 and 3.26(2m, 2×3H, NCH₃), 3.0–3.4(m, 3H, H-4 and CH₂C$\underline{H_2}$NH₂), 3.54(dd, J$_{H6,H5}$=3.1Hz, J$_{H6,H1}$=6.42Hz, 1H, H-6), 3.81(s, 2H, SCH₂), and 4.2–4.4 ppm(m, 2H, H-5 and CH₃C$\underline{H}$O). |
| 246 | (structure: carbapenem with OH, CH₃, CH₂CH₂CH₂NH—CH=NH, SCH₂SCH₃, CO₂H) | ¹H NMR(200 MHz, D₂O)δ: 1.29(d, J=6.35Hz, 3H, CH₃CHO), 1.3–2.0(m, 4H, CH₂-1 and 2 of propyl), 2.18(s, 3H, SCH₃), 3.3–3.5(m, 4H, H-4, H-6 and CH₂-3 of propyl), 3.89(ABq, J$_{AB}$=13.69Hz, Δv=29.0Hz, 2H, SCH₂), 4.15–4.3(m, 2H, H-5 and CH₃C$\underline{H}$O), 7.78 and 7.8 ppm(2s, 1H, C$\underline{H}$=N). |
| 247 | (structure: carbapenem with OH, CH₃, CH₂CH₂CHO, SCH₂CH₂NH₂, CO₂H) | ¹H NMR(D₂O, 200 MHz)δ: 9.72(0.2H, s, CHO); 5.10(0.5H, t, J=5.2 Hz, CH(OH)₂, hydrated form); 4.31–4.24(2H, m, H-1' and one part of H-5), 4.267(dd, J=2.6Hz, J=9.2Hz, part of H-5); 3.50(1H, dd, J=5.8Hz, J=2.7Hz, H-6); 3.45–3.07(4H, m, H-4, CH₂N, part of SCH₂); 3.01–2.84(1H, m, part of SCH₂); 2.77–2.67(0.7H, m, CH₂CO aldehydic form); 2.31–2.20 and 1.99–1.46(4H, 2 sets of m, CH₂CH₂-4) and 1.33 ppm(3H, d, J=6.4Hz, CH₃). |
| 248 | (structure: carbapenem with OH, CH₃, CH₂CH₂NH—C(=NH)—NH₂, SCH₂C(=NH)N(CH₃)₂, CO₂H) | ¹H NMR(400 MHz, D₂O)δ: 1.33(d, J=6.37Hz, 3H, C$\underline{H_3}$CHO), 1.7–1.85 and 2.05–2.15(2m, 2H, CH₂-1 of ethyl), 1.92(s, CH₃CO₂H), 3.12 and 3.28(2s, 2×3H, NCH₃), 3.2–3.4(m, 3H, H-4 and CH₂-2 of ethyl), 3.55(dd, J$_{H6,H5}$=3.09Hz, J$_{H6,H1}$=6.66Hz, 1H, H-6), 1.45(m, 1H, CH₃C$\underline{H}$O), and 4.31 ppm(dd, J$_{H5,H6}$=3.09Hz, J$_{H5,H4}$=10.0Hz, 1H, H-5). |
| 249 | (structure: carbapenem with OH, CH₃, (CH₂)₃NH—C(=NH)—NH₂, SCH₂SCH₃, CO₂H) | ¹H NMR(200 MHz, D₂O)δ: 1.31(d, J=6.34Hz, 3H, C$\underline{H_3}$CHO), 1.4–2.0 (m, 4H, CH₂1 and 2 of propyl)2.21(s, 3H, SCH₃), 3.2–3.5(m, 4H, H-4, H-6 and CH₂-3 of propyl), 3.91(ABq, J$_{AB}$=13.65Hz, Δv=27.8Hz, 2H, SCH₂) and 4.2–4.4 ppm(m, 2H, H-5 and CH₃C$\underline{H}$O). |
| 250 | (structure: carbapenem with OH, CH₃, CH₂CH₂CH₂N-pyrrolidine, SCH₂CH₂CN, CO₂H) | ¹H NMR(400 MHz, D₂O)δ: 1.33(d, J=6.38Hz, 3H, C$\underline{H_3}$CHO), 1.5–1.9(m, 4H, CH₂-1 and 2 of propyl), 1.9–2.2(m, 4H, CH₂-3 and 4 of pyrrolidine), 2.8–2.9(m, 2H, SC$\underline{H_2}$CH₂CN), 2.9–3.0 and 3.1–3.2(m, 2H, SC$\underline{H_2}$CH₂CN), 3.0–3.1, 3.2–3.3 and 3.6–3.7(3m, 3×2H, CH₂-3 of propyl and CH₂-2 and 5 of pyrrolidine), 3.39(dd, J$_{H6,H5}$=2.66Hz, J$_{H6,H1}$=6.49Hz, 1H, H-6), 3.43(broad t, 1H, H-4), and 4.25–4.35 ppm (m, 2H, H-5 and CH₃C$\underline{H}$O overlapping). |
| 251 | (structure: carbapenem with OH, CH₃, (CH₂)₃NH—CH=NH, SCH₂S-oxadiazole-CH₃, CO₂H) | ¹H NMR(200 MHz, D₂O)δ: 1.30(d, J=6.33Hz, 3H, C$\underline{H_3}$CHO), 1.4–2.0(m, 4H, CH₂-1 and 2 of propyl), 2.54(s, 3H, CH₃-2 of oxadiazole), 3.3–3.5(m, 4H, H-6, H-4 and CH₂-3 of propyl), 4.2–4.3(m, 2H, H-5 and CH₃C$\underline{H}$O), 4.53(ABq, J$_{AB}$=13.95Hz, Δv=20.0Hz, 2H, SCH₂) and 7.8 ppm(s, 1H, C$\underline{H}$=NH). |
| 252 | (structure: carbapenem with OH, CH₃, (CH₂)₃OH, SCH₂CH₂—N-pyrrolidine, CO₂H) | ¹H NMR(D₂O, 200 MHz)δ: 4.22(d, J=2.6Hz, part of H-5), 4.35–4.21 (1H, m, H-1'), 3.629(t, J=5.5Hz, C$\underline{H_2}$OH), 3.468(1H, dd, J=2.6Hz, J=6.0Hz, H-6), 3.41–310(8H, m, H-4, CH₂—N, CH₂-pyrrolidine and part of SCH₂), 3.07–2.90(1H, m, part of SCH₂), 2.05(4H, m, CH₂-pyrrolidine), 2.0–1.8, 1.8–1.4(4H, 2 sets of m, C$\underline{H_2}$—CH₂OH, CH₂-4) and 1.307 ppm(3H, d, J=6.35Hz, CH₃). |

| EX. NO. | STRUCTURES | NMR DATA |
|---|---|---|
| 253 | (structure) | ¹H NMR(200 MHz, D₂O)δ: 1.30(d, J=6.25Hz, 3H, C$\underline{H_3}$CHO), 1.4–1.9(m, 4H, CH₂-1 and 2 of propyl), 2.54(s, 3H, CH₃-2 of oxadiazole), 3.1–3.5 (m, 4H, H-4, H-6 and CH₂-3 of propyl), 4.1–4.3(m, 2H, H-5 and CH₃C$\underline{H}$O), and 4.52 ppm(ABq, J$_{AB}$=14.3Hz, Δν=23.7Hz, 2H, SCH₂). |
| 254 | (structure) | ¹H NMR(D₂O, 200 MHz)δ: 4.317(d, J=2.1Hz, part of H-5), 4.38–4.24 (1H, m, H-1'), 3.441(1H, dd, J=2.7Hz, J=6.25 H&, H-6), 3.16–2.92 (1H, m, part of S—CH₂), 3.72–3.21(14H, m, H-4, NCH₂-pyrrolidine, CH₂N and part of SCH₂), 2.07–2.05(8H, m, CH₂-pyrroline), 1.92(2H, s, CH₃CO₂), 2.40–2.21, 1.87–1.65, 1.65–1.49(4H, 3 sets of m, CH₂-4, CH₂—CH₂N) and 1.335 ppm(3H, d, J=6.3Hz, CH₃). |
| 255 | (structure) | ¹H NMR(D₂O, 200 MHz)δ: 6.08–5.91(1H, m, H-vinylic), 5.74–5.64(2H, m, CH₂-vinylic), 4.29(1H, d, J=3.0Hz, part of H-5), 4.30–4.24(1H, m, H-1'), 3.90(2H, d, J=7.0Hz, CH₂), 3.40(1H, dd, J=2.8Hz, J=6.6 Hz, H-6), 3.71–3.08(13H, m, H-4, CH₂N, CH₂-pyrrolidine and part of SCH₂), 3.05–2.90(1H, m, part of SCH₂), 2.185(4H, m, CH₂-pyrrolidine quat), 2.03(4H, m, CH₂-pyrrolidine), 1.912(2H, s, CH₃CHO₂), 2.3–1.7 (3H, m, C$\underline{H_2}$—CH₂N, part of CH₂-4), 1.65–1.54(1H, m, part of CH₂-4) and 1.328 ppm(3H, d, J=6.3Hz, CH₃). |
| 256 | (structure) | ¹H NMR(D₂O, 400 MHz)δ: 8.479(1H, d, J=5.1Hz, pyridine-H), 7.89–7.84(1H, m, pyridine-H), 7.527(1H, d, J=7.8Hz, pyridine-H), 7.396–7.364(1H, m, pyridine H), 4.270, 4.235, 4.149, 4.114(2H, ABq, J=13.9 Hz, CH₂-pyridine), 4.27–4.20(1H, m, H-1'), 4.115–4.09(1H, partly hidden H-5), 3.488(1H, dd, J=3.5Hz, J=9.0Hz, H-6), 3.53–3.38(2H, m, CH₂-4), 3.118(1H, dd, J=7.9Hz, J=13.94Hz, H-4), 1.439(9H, s, tert-butyl) and 1.270 ppm(3H, d, J=6.4Hz, CH₃). |
| 257 | (structure) | ¹H NMR(D₂O)δ: 1.26(d, 3H, J=6.2Hz), 1.5–1.7(m, 1H), 1.8–2.0(m, 1H), 2.38(t, 2H, J=7.5Hz), 2.7–3.4(m, 4H), 3.32(s, 3H), 3.71(t, 2H, J=6.0Hz), 4.16(dd, 1H, J=2.4, 9.4Hz), 4.23(m, 1H), 4.83–5.06 (m, 2H), 7.49(s, 5H); HPLC purity 99%. |
| 258 | (structure) | ¹H NMR(200 MHz, D₂O)δ: 1.31(d, J=6.36Hz, 3H, CH₃CHO), 1.3–2.0(m, 4H, CH₂-1 and 2 of propyl), 3.15–3.3(m, 1H, H-4), 3.4(t, J=6.1Hz, C$\underline{H_2}$H₃), 3.49(dd, J$_{H6,H5}$=2.8Hz, J$_{H6,H1}$=5.55Hz, 1H, H-6), 3.8(ABq, partially exchanged D₂O, J$_{AB}$=6.9Hz, Δν=11.4Hz, SCH₂), and 4.2–4.4 ppm(m, 2H, H-5 and CH₃C $\underline{H}$O). |
| 259 | (structure) | ¹H NMR(200 MHz, D₂O)δ: 1.31(d, J=6.32Hz, 3H, C$\underline{H_3}$CHO), 1.8–2.3(m, 2H, C$\underline{H_2}$CH₂N), 2.72(s, 3H, NCH₃), 2.7–3.05(m, 2H, SCH₂), 3.05–3.2(m, 2H, C$\underline{H_2}$CH₂N), 3.3–3.5(m, 2H, H-6 and H-4), 3.73(t, J=6.0Hz, 2H, CH₂C$\underline{H_2}$OH) and 4.2–4.3 ppm(m, 2H, H-5 and CH₃C$\underline{H}$O). |

-continued

| EX. NO. | STRUCTURES | NMR DATA |
|---|---|---|
| 260 | (structure: carbapenem with OH, CH₃ stereochem, CH₂CH₂CH₂N₃ side chain, SCH₂C(=NH)NHCH₃, CO₂H) | ¹H NMR(200 MHz, D₂O)δ: 1.31(d, J=6.35Hz, 3H, C$\underline{H_3}$CHO), 1.4–2.0(m, 4H, CH₂-1 and 2 of propyl), 2.95(s, 3H, NCH₃), 3.2(m, 1H, H-4), 3.41 (t, J=6.05Hz, 2H, CH₂N₃), 3.49(dd, $J_{H6,H5}$=2.81Hz, $J_{H6,H1}$=6.0Hz, 1H H-6), 3.8(s, partially exchanged, SCH₂) and 4.2–4.4 ppm(m, 2H, H-5 and CH₃C$\underline{H}$O). |
| 261 | (structure: carbapenem with OH, CH₃, CH₂CH₂N(CH₃)CH=NH side chain, SCH₂CH₂OH, CO₂H) | ¹H NMR(200 MHz, D₂O)δ: 1.34(d, J=6.28Hz, 3H, C$\underline{H_3}$CHO), 1.9–2.4(m, 2H, CH₂CH₂N), 2.8–3.1(m, 2H, SCH₂), 3.12 and 3.30(2s, 3H, NCH₃), 3.3–3.5(m overlapping with H-6, 1H, H-4), 3.41(dd, $J_{H6,H5}$=2.43Hz, $J_{H6,H1}$=6.93Hz, 1H, H-6), 3.66(broad t, J=7.7Hz, 2H, CH₂N), 3.75(t, J=6.1 Hz, 2H, CH₂OH), and 4.2–4.4 ppm(m, 2H, H-5 and CH₃CHO). |
| 262 | (structure: carbapenem with OH, CH₃, CH₂CH₂CH₂NH₂, SCH₂C(=NH)NHCH₃, CO₂H·AcOH) | ¹H NMR(200 MHz, D₂O)δ: (d, J=6.34Hz, 3H, C$\underline{H_3}$CHO), 1.4–2.0(m, 2H, CH₂-1 and 2 of propyl), 1.92(s, C$\underline{H_3}$CO₂H), 2.95(s, 3H, NCH₃), 3.05(t, J=7.0Hz, 2H, C$\underline{H_2}$NH₂), 3.24(m, 1H, H-4), 3.47(dd, $J_{H6,H5}$=2.89Hz, $J_{H6,H1}$=6.35Hz, 1H, H-6), 3.78(s, 2H, SCH₂) and 4.2–4.4 ppm (m, 2H, H-5 and CH₃C$\underline{H}$O). |
| 263 | (structure: carbapenem with OH, CH₃, CH₂CH₂NHCH₃, SCH₂CH₂OCONH₂, CO₂H) | ¹H NMR(200 MHz, D₂O)δ: 1.33(d, J=6.37Hz, 3H, C$\underline{H_3}$CHO), 1.8–2.3(m, 2H, C$\underline{H_2}$CH₂N), 2.75(s, 3H, NCH₃), 2.8–3.25(m, 4H, SC$\underline{H_2}$CH₂O and CH₂C$\underline{H_2}$N), 3.42(dd, $J_{H6,H5}$=2.64Hz, $J_{H6,H1}$=6.72Hz, 1H, H-6), 3.45(m overlapping with H-6, 1H, H-4), and 4.2–4.4 ppm(m, 2H, H-5 and CH₃C$\underline{H}$O). |
| 264 | (structure: carbapenem with OH, CH₃, CH₂CH₂NHCH₃, S-(R)-pyrrolidinyl, CO₂H) | ¹H NMR(200 MHz, D₂O)δ: 1.33(d, J=6.34Hz, 3H, C$\underline{H_3}$CHO), 1.9–2.55 (m, 4H, β-CH₂ and CH₂-4 of pyrrolidyl), 2.75(s, 3H, N$\underline{H}$CH₃), 3.1–3.7 (m, 8H, 2×CH₂N of pyrrolidyl, C$\underline{H_2}$NHCH₃, H-4 and H-6), 4.0(m, 1H, S—CH) and 4.2–4.4 ppm(m, 2$\underline{H}$, CH₃C$\underline{H}$O and H-5). |
| 265 | (structure: carbapenem with OH, CH₃, CH₂CH₂CH₂NH₂, SCH₂C(=NH)NH₂, CO₂H·AcOH) | ¹H NMR(200 MHz, D₂O)δ: 1.33(d, J=6.35Hz, 3H, C$\underline{H_3}$CHO), 1.5–2.0(m, 4H, CH₂-1 and 2 of propyl), 1.92(s, CH₃CO₂H), 3.05(broad t, J=7.0 Hz, 2H, C$\underline{H_2}$NH₂), 3.3(m, 1H, H-4), 3.46(dd, $J_{H6,H5}$=2.83Hz, $J_{H6,H1}$=6.33Hz, 1H, H-6), 3.79(ABq, $J_{AB}$=15.8Hz, Δν=6.4Hz, 2H, SCH₂), and 4.2–4.4 ppm(m, 2H, H-5 and CH₃C$\underline{H}$O). |
| 266 | (structure: carbapenem with OH, CH₃, CH₂CH₂N(CH₃)CH=NH, SCH₂CH₂OCONH₂, CO₂H) | ¹H NMR(200 MHz, D₂O)δ: 1.35(d, J=6.34Hz, 3H, C$\underline{H_3}$CHO), 1.8–2.3(m, 2H, CH₂CH₂N), 2.9–3.2(m, 2H, SCH₂), 3.11 and 3.30(2s, 3H, NCH₃), 3.3–3.5(m overlapping with H-6, 1H, H-4), 3.42(dd, $J_{H6,H5}$=2.67Hz, $J_{H6,H1}$=7.0Hz, 1H, H-6), 3.66(broad t, J=7.5Hz, 2H, CH₂N), and 4.15–4.4 ppm(m, 4H, H-5, CH₃C$\underline{H}$O and C$\underline{H_2}$O). |
| 267 | (structure: carbapenem with OH, CH₃, CH₂CH₂CO₂Na, SCH₂CH₂OH, CO₂Na) | ¹H NMR(D₂O)δ 1.34(d, 3H, J=6.3Hz), 1.56–1.76(m, 1H), 2.07–2.44(m, 3H), 2.73–3.20(m, 3H), 3.44(dd, 1H, J=2.5, 6.1 Hz), 3.66–3.86(m, 2H), 4.23(dd, 1H, J=2.5, 9.2Hz), 4.23(quin., 1H, J=6.2Hz); HPLC purity 90%. |

| EX. NO. | STRUCTURES | NMR DATA |
|---|---|---|
| 268 | [structure with OH, CH₃, CH₂CH₂NHCH₃, SCH₂-pyridine, CO₂H] | ¹H NMR(200 MHz, D₂O)δ: 1.28(d, J=6.37Hz, 3H, CH₃CHO), 1.5–1.85 and 1.95–2.2(2m, 2H, CH₂-1 of ethyl), 2.70(s, 3H, NCH₃), 3.0(t, J=8.5Hz, 2H, CH₂N), 3.1–3.25(m, 1H, H-4), 3.33(dd, J<sub>H6,H5</sub>=2.82Hz, J<sub>H6,H1</sub>=6.66Hz, 1H, H-6), 4.05(m overlapping with SCH₂, 1H, H-5), 4.09(ABq, J<sub>AB</sub>=13.8Hz, Δν=22.1Hz, 2H, SCH₂), 4.2(m, 1H, CH₃CHO), 7.35(m, 1H, H-5 of pyridine), 7.45(d, J=7.9Hz, 1H, H-3 of pyridine), 7.83(m, 1H, H-4 of pyridine) and 8.44 ppm(m, 1H, H-6 of pyridine). |
| 269 | [structure with OH, CH₃, CH₂CH₂N(CH₃)—CH=NH, S-CH₂-pyridine, CO₂H] | ¹H NMR(400 MHz, D₂O)indicated a 75:25 mixture of Z and E formamidinium isomers: Major isomer δ: 1.24(d, J=6.4Hz, 3H, CH₃CHO), 1.5–2.0 (m, 2H, CH₂CH₂N), 2.95(m, overlapping with NCH₃, 1H, H-4), 2.98(s, 3H, NCH₃), 3.26(dd, J<sub>H6,H5</sub>=2.89Hz, J<sub>H6,H1</sub>=6.95Hz, 1H, H-6), 3.3–3.6(m, 2H, CH₂CH₂N), 4.02(dd, J<sub>H5,H6</sub>=2.89Hz, J<sub>H5,H4</sub>=9.72Hz, 1H, H-5), 4.04(ABq, J<sub>AB</sub>=13.96Hz, Δν=53.5Hz, 2H, SCH₂), 4.15(m, 1H, CH₃CHO), 7.29–7.33(m, 1H, H-5 of pyridine), 7.37–7.42(m, 1H, H-3 of pyridine), 7.76(s, 1H, CH=NH), 7.75–7.82(m, 1H, H-4 of pyridine) and 8.39–8.42 ppm(m, 1H, H-6 of pyridine). |
| 270 | [structure with OH, CH₃, (CH₂)₃N₃, SCH₂CH₂-N-piperazine-N—CH₃, CO₂H] | ¹H NMR(D₂O, 400 MHz)δ: 4.242(1H, dd, J=2.6Hz, J=9.3Hz, H-5), 4.30, 4.288, 4.273, 4.257, 4.241(1H, 5 lines, J=6.3Hz, J=6.2Hz, H-1'), 3.455(1H, dd, J=2.7Hz, J=6.0Hz, H-6), 3.424(2H, t, J=6.0 Hz, CH₂N₃), 3.346–3.289(1H, m, H-4), 3.081–2.972, 2.929–2.801(2H, 2 sets of m, CH₂—S), 2.770, 2.753, 2.734(2H, 3 lines, CH₂N), 3.20–2.60 (8H, m, CH₂-piperazine), 2.644(3H, bs, N—CH₃), 1.918–1.874, 1.750–1.537(4H, 2 sets of m, CH₂CH₂-4) and 1.330 ppm(3H, d, J=6.4Hz, CH₃). |
| 271 | [structure with OH, CH₃, CH₂CH₂N(CH₃)—CH=NH, S-(R)-pyrrolidine-CH=NH, CO₂H] | ¹H NMR(200 MHz, D₂O)δ: 1.33(d, J=6.32Hz, 3H, CH₃CHO), 1.8–2.6(m, 4H, β-CH₂ and CH₂-4 of pyrrolidyl), 3.1 and 3.3(2s, 3H, NHCH₃), 3.2–4.1(m, 9H, 2×N—CH₂of pyrrolidyl, CH₂NHCH₃, H-4, H-6 and S—CH), 4.2–4.4(m, 2H, CH₃#CHO and H-5) and 7.81, 7.90, 8.00 ppm(3m, 2H, CH=NH). |
| 272 | [structure with OH, CH₃, CH₂CH₂CH₂NH—C(=NH)—NH₂, SCH₂C(=NH)NH₂, CO₂H] | ¹H NMR(200 MHz, D₂O)δ: 1.31(d, J=6.35Hz, 3H, CH₃CHO), 1.4–2.0(m, 4H, CH₂-1 and 2 of propyl), 1.93(s, CH₃CO₂H), 3.1–3.35(m, 3H, H-4 and CH₂NH), 3.39(dd, J<sub>H6,H5</sub>=2.81Hz, J<sub>H6,H1</sub>=6.0Hz, 1H, H-6), 3.79 (AB system partially exchanged with D₂O, SCH₂), and 4.2–4.4 ppm(m, 2H, H-5 and CH₃CHO). |
| 273 | [structure with OH, CH₃, (CH₂)₃OH, SCH₂CH₂-N-piperazine-N—CH₃, CO₂H] | ¹H NMR(D₂O, 400 MHz)δ: 4.092(1H, 5 lines, J=6.3Hz, H-1'), 4.068 (1H, dd, J=2.6Hz, J=9.4Hz, H-5), 3.478(2H, t, J=6.2Hz, CH₂O), 3.260(1H, dd, J=2.6Hz, J=6.1Hz, H-6), 3.165–3.109(1H, m, H-4), 3.1–2.4(8H, bm, piparazine-H), 2.877–2.876, 2.759–2.687(2H, 2 sets of m, SCH₂), 2.614–2.580(2H, m, CH₂N), 2.530(3H, bs, NCH₃), 1.75–1.66, 1.58–1.47, (2H, 2 sets of m, CH₂-4), 1.46–1.27(2H, 2 sets of m, CH₂) and 1.159 ppm(3H, d, J=6.3Hz, CH₃). |
| 274 | [structure with OH, CH₃, CH₂CH₂NHCH₃, SCH₂CH₂N-pyrrolidine, CO₂H] | ¹H NMR(200 MHz, D₂O)δ: 1.32(d, J=6.36Hz, 3H, CH₃CHO), 1.91(s, 3H, OCH₃), 1.9–2.4(m, 6H, CH₂-1 of ethyl and CH₂-3,4 of pyrrolidine), 2.73(s, 3H, NCH₃), 2.9–3.5(m, 11H, H-4, CH₂-2 of ethyl, CH₂-2 and 5 of pyrrolidine and SCH₂CH₂N), 3.49(dd, J<sub>H6,H5</sub>=2.97 Hz, J<sub>H6,H1</sub>=6.46Hz, 1H, H-6), and 4.2–4.4 ppm(m, 2H, H-5 and CH₃CHO). |

| EX. NO. | STRUCTURES | NMR DATA |
|---|---|---|
| 275 | (structure) | $^1$H NMR(400 MHz, D$_2$O)δ: 1.32(d, J=6.43Hz, 3H, C$\underline{H_3}$CHO), 1.7–1.85 and 2.0–2.1(2m, 2H, C$\underline{H_2}$CH$_2$N$_3$), 2.96(s, 3H, NCH$\overline{_3}$), 3.3(m, 1H, H-4), 3.38–3.45 and 3.55–3.62(2m, 2H, CH$_2$CH$_2$N$_3$), 3.53(dd, J$_{H6,H5}$=2.95Hz, J$_{H6,H1}$=6.18Hz, 1H, H-6), 3.82(A part of a partly exchanged AB system, SC$\underline{H_2}$), 4.27(m, 1H, CH$_3$C$\underline{H}$O), and 4.28 ppm(dd, J$_{H5,H6}$=2.95 Hz, J$_{H5,H4}$=9.65Hz, 1H, H-5). |
| 276 | (structure) | $^1$H NMR(400 MHz, D$_2$O)δ: 4.107(1H, center of 5 lines, J=6.4Hz, J=6.7Hz, H-1'), 4.081(1H, dd, J=2.6Hz, J=9.5Hz, H-5), 3.225(1H, dd, J=2.7Hz, J=6.4Hz, H-6), 3.191, 3.185, 3.167, 3.161, 3.143, 3.136(1H, 6 lines, H-4), 2.907–2.863(2H, m, CH$_2$N), 2.846–2.790, 2.749–2.678(2H, 2 sets of m, CH$_2$—S), 2.636(3H, s, NCH$_3$), 3.3–2.56 (10H, m, NCH$_2$), 1.903 and 1.749(0.83 and 2.18H, CH$_3$), 1.75–1.515 1.448–1.353(4H, 2 sets of m, CH$_2$CH$_2$-4) and 1.162 ppm(3H, d, J=6.4 Hz, CH$_3$). |
| 277 | (structure) | $^1$H NMR(D$_2$O, 400 MHz)δ: 4.273(1H, 5 lines, J=6.4Hz, H-1'), 4.38 (1H, dd, J=2.6Hz, J=9.4Hz, H-5), 3.334(1H, dd, J=2.6Hz, J=6.2Hz, H-6), 3.32–3.18(3H, m, CH$_2$-guanidine and H-4), 3.5–2.7(10H, series of m, CH$_2$N), 3.03–2.70, 2.93–2.859(2H, 2 sets of m, CH$_2$S), 2.859(3H, s, NCH$_3$), 1.923(1.6H, s, CH$_3$CO$_2$), 1.883–1.802, 1.763–1.592, 1.569–1.473(4H, m, CH$_2$CH$_2$-4), and 1.319 ppm(3H, d, J=6.3Hz, CH$_3$). |
| 278 | (structure) | $^1$H NMR(400 MHz, D$_2$O)δ: 1.32(d, J=6.36Hz, 3H, C$\underline{H_3}$CHO), 1.7–1.85 and 2.05–2.15(2m, 2H, CH$_2$-1 of ethyl), 1.92(s, C$\underline{H_3}$CO$_2$H), 2.94(m, 3H, NHC$\underline{H_3}$), 3.2–3.4(m, 3H, H-4 and CH$_2$-2 of ethyl), 3.51(dd, J$_{H6,H5}$=3.04 Hz, J$_{H6,H1}$=6.70Hz, 1H, H-6), 3.76 ABq, J$_{AB}$=15.6Hz, Δν=17.5Hz, 2H, SCH$_2$), 4.27(m, 1H, CH$_3$C$\underline{H}$O), and 4.29 ppm(dd, J$_{H5,H6}$=3.04Hz, J$_{H5,H4}$=9.91Hz, 1H, H-5). |
| 279 | (structure) | $^1$H NMR(400 MHz, D$_2$O)δ: 1.32(d, J=6.35Hz, 3H, C$\underline{H_3}$CHO), 1.8–1.92 and 2.12–2.2(2m, 2H, CH$_2$-1 of ethyl), 1.92(s, CH$_3$CO$_2$$\overline{H}$), 2.94 s, 3H, NCH$_3$), 3.05–3.2(m, 2H, CH$_2$-2 of ethyl), 3.29(m, 1H, H-4), 3.53(dd, J$_{H6,H5}$=3.06Hz, J$_{H6,H1}$=6.45Hz, 1H, H-6), 3.76(ABq, J$_{AB}$=15.6Hz, Δν= 11.9Hz, 1H, SCH$_2$), 4.28(m, 1H, CH$_3$C$\underline{H}$O) and 4.30 ppm(dd, J$_{H5,H6}$=3.06 Hz, J$_{H5,H4}$=9.90Hz, 1H, H-5). |
| 280 | (structure) | $^1$H NMR(400 MHz, D$_2$O)δ: 1.34(d, J=6.41Hz, 3H, CH$_3$CHO), 1.85–1.95 and 2.25–2.35(2m, 2H, C$\underline{H_2}$CH$_2$N), 2.75(s, 3H, NCH$_3$), 3.16(m, 2H, CH$_2$C$\underline{H_2}$N), 3.48(m, 1H, H-4), 3.49(dd, J$_{H6,H5}$=2.93Hz, J$_{H6,H1}$=6.62Hz, 1H, H-6), 3.80(ABq, J$_{AB}$=17.6Hz, Δν=42.1Hz, 2H, SCH$_2$), 4.29(m, 1H, CH$_3$C$\underline{H}$O) and 4.35 ppm(dd, J$_{H5,H6}$=2.93Hz, J$_{H5,H4}$=9.69Hz, 1H, H-5). |
| 281 | (structure) | $^1$H NMR(D$_2$O, 400 MHz)δ: 4.267(1H, dd, J=2.6Hz, J=12.1Hz, H-5); 4.301–4.238(1H, m, H-1'), 3.63–3.573(1H, m, part of CH$_2$—N$_3$), 3.448 (1H, dd, J=2.7Hz, J=6.2Hz, H-6), 3.50–3.378(2H, m, part of CH$_2$N$_3$ and H-4), 3.055–2.985, 2.915–2.840(2H, 2 sets of m, SCH$_2$), 2.95–2.65 (10H, m, CH$_2$N), 2.481(3H, s, NCH$_3$), 2.123–2.038, 1.863–1.772(2H, 2 sets of m, CH$_2$-4) and 1.335 ppm(3H, d, J=6.4Hz, CH$_3$). |
| 282 | (structure) | $^1$H NMR(400 MHz, D$_2$O)δ: 1.32(d, J=6.38Hz, 3H, CH$_3$CHO), 1.45–1.95(m, 4H, CH$_2$-1 and 2 of propyl), 2.12(s, 3H, CH$_3$CO$_2$), 2.78–2.92(m, 2H, CH$_2$CN), 2.92–3.01 and 3.12–3.2(2m, 2H, SCH$_2$), 3.39(m, 1H, H-4), 3.44 (dd, J$_{H6,H5}$=2.65Hz, J$_{H6,H1}$=6.05Hz, 1H, H-6), 4.12–4.2(m, 2H, CH$_2$OAc), 4.27(dd, J$_{H5,H6}$=2.65Hz, J$_{H5,H4}$=9.25Hz, 1H, H-5) and 4.28 ppm(m, 1H, CH$_3$C$\underline{H}$O). |

| EX. NO. | STRUCTURES | NMR DATA |
|---|---|---|
| 283 | 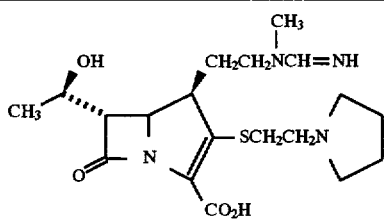 | $^1$H NMR(200 MHz, D$_2$O)δ: 1.33(d, J: 6.30Hz, 3H, C$\underline{H}_3$CHO), 1.91(s, C$\underline{H}_3$CO$_2$H), 1.8–2.3(m, 6H, CH$_2$-1 of ethyl and CH$_2$-3 and 4 of pyrrolidine), 3.09(s, 3H, NCH$_3$)3.0–3.8(m, 12H), 4.2–4.4(m, 2H, H-5 and CH$_3$C$\underline{H}$O), 7.80 and 7.88 ppm(2s, 1H, C$\underline{H}$=NH). |
| 284 | 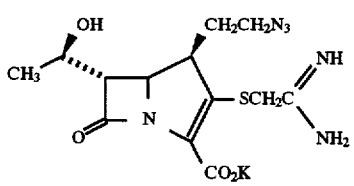 | $^1$H NMR(400 MHz, D$_2$O)δ: 1.32(d, J=6.34Hz, 3H, C$\underline{H}_3$CHO), 2.75–1.85 and 2.0–2.15(2m, 2H, CH$_2$-1 of ethyl), 3.3–3.38(m, 1H, H-4), 3.38–3.45 and 3.55–3.62(2m, 2H, CH$_2$-2 of ethyl), 3.53(dd, J$_{H6,H5}$=2.91Hz, J$_{H6,H1}$=6.17Hz, 1H, H-6), 3.8(AB system partially exchanged), 4.27 (m, 1H, CH$_3$C$\underline{H}$O) and 4.29 ppm(dd, J$_{H5,H6}$=2.91Hz, J$_{H5,H4}$=9.69Hz, 1H, H-5). |
| 285 | 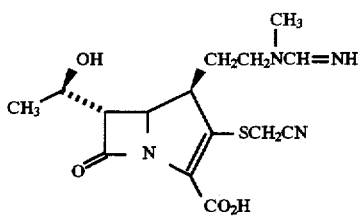 | $^1$H NMR(400 MHz, D$_2$O)this product is a 8:2 mixture of Z and E formamidinium isomers; major isomer δ: 1.35(d, J=6.39H, 3H, CH$_3$CHO), 1.9–2.0 and 2.25–2.35(2m, 2H, CH$_2$-1 of ethyl), 3.11(s, 3H, N—CH$_3$), 3.39–3.48(m, 1H, H-4), 3.48(dd, J$_{H5,H6}$=2.97Hz, J$_{H6,H1}$=6.85 Hz, 1H, H-6), 3.6–3.7(m, 2H, CH$_2$-2 of ethyl), 3.79 ABq, J$_{AB}$=17.55 Hz, Δν=33.6Hz, 2H, SCH$_2$), 4.29(m, 1H, CH$_3$C$\underline{H}$O), 4.35(dd, J$_{H5,H6}$=2.97 Hz, J$_{H5,H4}$=9.70Hz, 1H, H-5), and 7.89 ppm(s, 1H, C$\underline{H}$=NH); minor isomer δ: 1.36(d, J=6.31Hz, C$\underline{H}_3$CHO), 3.30(s, NC$\underline{H}_3$), 3.53(dd, J$_{H6,H5}$=3.14Hz, J$_{H6,H1}$=7.51Hz, H-6), 3.79(ABq, J$_{AB}$=17.55Hz, Δν=48.6 Hz, SCH$_2$), 4.38(dd, J$_{H5,H6}$=3.14Hz, J$_{H5,H4}$=9.93Hz, H-5) and 7.80 ppm (s, C$\underline{H}$=NH). |
| 286 | 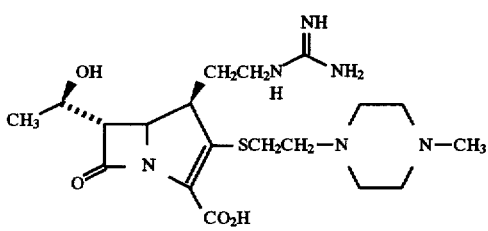 | $^1$H NMR(D$_2$O, 400 MHz)δ: 4.284(d, J=2.5Hz, part of H-5), 4.30–4.24 (1H, m, H-1'), 3.435(1H, dd, J=2.5Hz, J=6.6Hz, H-6), 3.42–3.31, 3.30–3.22(5H, 2 sets of m, CH$_2$-guanidine, H-4 and CH$_2$N), 2.97–2.923, 2.901–2.829(2H, 2 sets of m, CH$_2$S), 3.4–2.74(8H, m, CH$_2$-piperazine), 1.918(3H, s, NCH$_3$), 2.17–2.08, 1.37–1.25(2H, 2 sets of m, CH$_2$-4), 1.918(2H, s, CH$_3$CO$_2$) and 1.335 ppm(3H, d, J=6.3Hz, CH$_3$). |
| 287 | 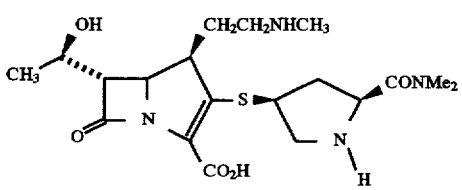 | $^1$H NMR(400 MHz, D$_2$O)δ: 1.33(d, J=6.35Hz, 3H, C$\underline{H}_3$CHO), 1.8–2.0 and 2.15–2.3(2m, 2H and 1H, CH$_2$-1 of ethyl and H-3 of pyrrolidine), 1.92 (s, CH$_3$CO$_2$H), 2.75, 3.00 and 3.07(3s, 3×3H, NCH$_3$ and CON(CH$_3$)$_2$), 2.9–3.1(m, 1H, H-3 of pyrrolidine), 3.05–3.25(m, 2H, CH$_2$-2 of ethyl), 3.34(m, 1H, H-4), 3.35(dd, J$_{gem}$=12.32Hz, J$_{H5,H4}$=4.43Hz, 1H, H-5 of pyrrolidine), 3.47(dd, J$_{H6,H5}$=2.96Hz, J$_{H6,H1}$=6.60Hz, 1H, H-6), 3.56(dd, J$_{gem}$=12.32Hz, J$_{H5,H4}$=6.05Hz, 1H, H-5 of pyrrolidine), 3.87–3.95(m, 1H, H-4 of pyrrolidine), 4.28(m, 1H, CH$_3$C$\underline{H}$O), 4.30(dd, J$_{H5,H6}$=2.96Hz, J$_{H5,H4}$=9.74Hz, 1H, H-5), and 4.62 ppm(broad t, J=8.5Hz, 1H, H-2 of pyrrolidine). |
| 288 | 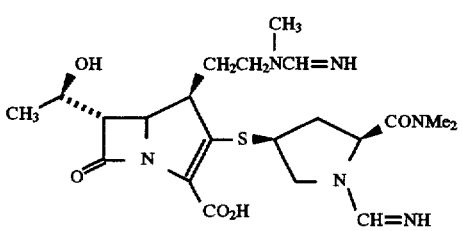 | $^1$H NMR(200 MHz, D$_2$O). This product is a mixture of Z and E (formimidinium isomers: δ: 1.33(d, J=6.32Hz, 3H, C$\underline{H}_2$CHO), 1.8–2.3(m, 3H, CH$_2$-1 of ethyl and H-3 of pyrrolidine), 2.98, 2.99, 3.09 and 3.28(4s, total 9H, NCH$_3$), 3.0–4.2(m, 8H, H-4, H-6, CH$_2$-2 of ethyl, H-3 of pyrrolidine, H-4 of pyrrolidine and CH$_2$-5 of pyrrolidine), 4.2–4.4(m, pyrrolidine, H-4 of pyrrolidine and CH$_2$-5 of pyrrolidine), 4.2–4.4(m, 2H, H-5 and CH$_3$C$\underline{H}$O), 5.06 and 7.8Hz(2t, J 7.7Hz and J=7.8Hz, 1H, H-2 of pyrrolidine), 7.8, 7.83, 7.89 and 8.09 ppm(4S, total 2N, C$\underline{H}$=NH). |
| 289 | 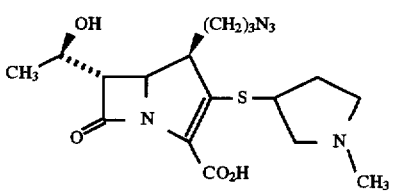 | $^1$H NMR(D$_2$O)δ: 4.29(1H, dd, J: 2.82, J: 6.40, H-6). 4.28(1H, m, H-1'), 4.02(1H, unresolved s, —S—CH—), 3.5–4.0(4H, broad unresolved m, —CH$_2$)$_2$N-pyrrolidine), 3.48(1H, dd, J: 2.76, J: 5.96, H-5), 3.42(2H, t, J: 6.41 —CH$_2$N=), 3.27(1H, m, H-4), 2.99, 2.98(3H, 2s, 2 N—CH$_3$), 2.6 and 2.1(2H, 2 unresolved m, 2 CH-4 of pyrrolidine), 1.50–1.95(4H, m, 2 CH-1', 2-CH-2"), 1.33(3H, d, J: 6.44, 3-CH'). |

| EX. NO. | STRUCTURES | NMR DATA |
|---|---|---|
| 290 | 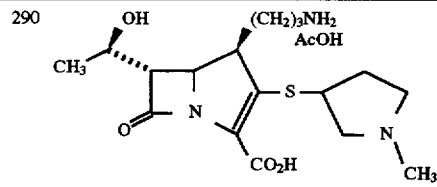 | $^1$H NMR(D$_2$O)δ: 4.30(1H, dd, J: 2.82, J: 6.91, H-6), 4.28(1H, m, H-1') 4.0(1H, m, CH—S), 3.35–3.78 [5H, broad unresolved m, —CH$_2$)$_2$N— of pyrrolidine; 3.43(1H, dd, J: 2.47, Jt 6.45, H-5)], 3.30(1H, m, H-4), 3.05(2H, m, 2 CH-3"), 2.96 and 2.95(3H, 2S, 2-N—CH$_3$), 2.00–2.20 and 2.45–2.70(2H, 2 m, 2 CH-4 of pyrrolidine), 1.92(s, CH$_3$CO$_2$—), 1.50–1.95(4H, m, 2 CH-1" , 2 CH-2"), 1.33(3H, d, J: 6.36, 3 CH-1'). |
| 291 | 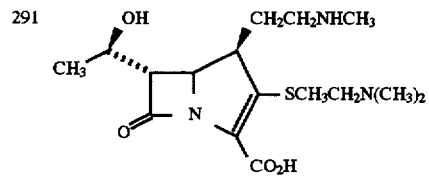 | $^1$H NMR(400 MHz, D$_2$O)δ: 1.33(d, J=6.35Hz 3H, CH$_3$CHO), 1.8–1.95 and 2.15–2.25(2m, 2H, CH$_2$-1 of ethyl), 1.92(s, CH$_3$CO$_2$H), 2.74(broad s, 9H, NCH$_3$), 2.9–3.2(m, 6H, SCH$_2$CH$_2$N and CH$_2$-2 of ethyl), 3.34(m, 1H, H-4), 3.48(dd, J$_{H6,H5}$=3.0Hz, J$_{H6,H1}$=6.50Hz, 1H, H-6), 4.28(m, 1H, CH$_3$CHO) and 4.30 ppm(dd, J$_{H5,H6}$=3.0Hz, J$_{H5,H4}$=9.87Hz, 1H, H-5). |
| 292 | 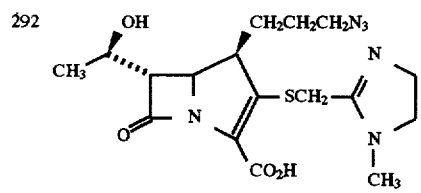 | $^1$H NMR(400 MHz)δ: 1.33(d, J=6.44Hz, 3H, CH$_3$CHO), 1.4–2.0(m, 4H, CH$_2$-1 and 2 of propyl), 3.13(s, 3H, NCH$_3$), 3.15–3.25(m, 1H, H-4), 3.43(t, J=6.55Hz, 2H, CH$_2$N$_3$), 3.53(dd, J$_{H6,H5}$=3.0Hz, J$_{H6,H1}$=6.0Hz, 1H, H-6), 3.8–4.0(m, 4H, CH$_2$-4 and 5 of imidazoline), 4.28(m, overlapping with H-5, 1H, CH$_3$CHO), and 4.28 ppm(dd, J$_{H5,H6}$=3.0Hz, J$_{H5,H4}$=9.9Hz, 1H, H-5). |
| 293 | 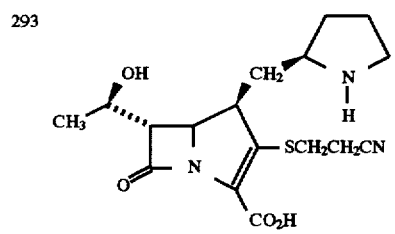 | $^1$H NMR(400 MHz, D$_2$O)δ: 1.33(d, J=6.36Hz, 3H, CH$_3$CHO), 1.73–1.83 and 2.38–2.46(2×m, 2H, β-CH$_2$), 2.00–2.20(m, 4H, CH$_2$-3' and CH2-4' of pyrrolidyl), 2.75–2.90(m, 2H, CH2CN), 2.92–3.11(2m, 2H, SCH2), 3.30–3.45(m, 3H, H-6 and CH2—N of pyrrolidyl), 3.5(m, 1H, H04), 3.65(m, 1H, N—CH-2' of pyrrolidyl) and 4.24–4.33e ppm(m, 2H, CH3CHO and H-5). |
| 294 | 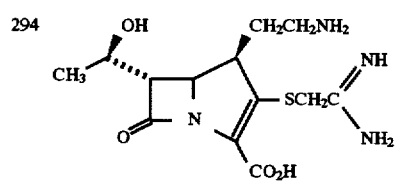 | $^1$H NMR(200 MHz, D$_2$O)δ: 1.32(d, J=6.38Hz, 3H, CH$_3$CHO), 1.92(s, CH$_3$CO$_2$H), 1.8–2.0 and 2.05–2.15(2m, 2H, CH$_2$-1 of ethyl)), 3.0–3.2(m, 2H, CH$_2$-2 of ethyl), 3.2–3.4(m, 1H, H-4)3.52(dd, J$_{H6,H5}$=3.04Hz, J$_{H6,H1}$=6.45Hz, 1H, H-6), 3.76(ABq, J$_{AB}$=15.71Hz, Δv=6.5Hz, 2H, SCH$_2$), and 4.2–4.4 ppm(m, 2H, H-5 and CH$_3$CHO overlapping). |
| 295 | 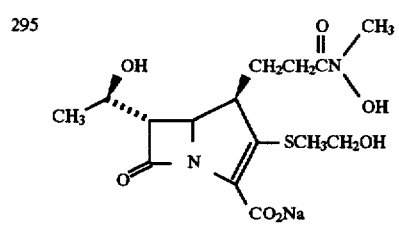 | $^1$H NMR(D$_2$O)δ 1.32(d, 3H, J=6.3Hz), 1.6–1.9(m, 1H), 2.1–2.3(m, 1H), 2.59(t, 2H, J=7.3Hz), 2.8–3.1(m, 2H), 3.25(s, 3H), 3.3–3.4 (m, 1H), 3.46(dd, 1H, J=2.3, 5.7Hz), 3.75(t, 2H, J=6.0Hz), 4.23 (dd, 1H, J=2.3, 8.9 Hm), 4.27(quin, 1H, J=6.3Hz); HPLC purity 99%. |
| 296 | 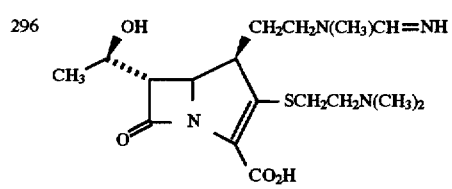 | $^1$HMR(200 MHz, D$_2$O)mixture of E and Z isomers of formamidinium δ: 1.34(d, J=6.35Hz, 3H, CH$_3$CHO), 1.92(s, CH$_3$CO$_2$H), 1.8–2.0 and 2.1–2.25(2m, 2H, CH$_2$-1 of ethyl), 2.90(s, 6H, N(CH$_3$)$_2$), 3.11 and 3.29 (2s, 3H, NCH$_3$), 2.9–3.4(m, 5H, H-4, SCH$_2$CH$_2$N), 3.51(dd, J$_{H6,H5}$=2.95Hz, J$_{H6,H1}$=6.75Hz, 1H, H-6), 3.6–3.8(m,2H,CH$_2$-2 of ethyl), 4.2–4.4(m, 2H, H-5 and CH$_3$CHO), 7.81 and 7.89 ppm(2s, 1H, CH=NH). By UV at 37° C. in a pH 7.4 phosphate buffer the half-life was measured to be 10.3 h. |
| 297 | 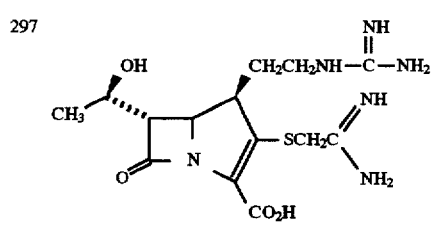 | $^1$H NMR(400 MH&, D$_2$O)δ: 1.32(d, J=6.39Hz, 3H, CH$_3$CHO), 1.73–1.85 and 2.15–2.3(2m, 2H, CH$_2$-1 of ethyl), 1.94(s, 3H, CH$_3$CO$_2$H), 3.22–3.39(m, 3H, H-4 and CH$_2$-2 of ethyl) , 3.51(dd, J$_{H6,H5}$=3.01Hz, J$_{H6,H1}$=6.66Hz, 1H, H-6), 3.77(ABq, J$_{AB}$=15.69Hz, Δv=16.24Hz, 2H, SCH$_2$), 4.27(m, 1H, CH$_3$CHO), and 4.30 ppm(dd, J$_{H5,H6}$=3.01Hz, J$_{H5,H4}$=9.89Hz, 1H, H-5). By UV at 37° C. in pH 7.4 phosphate buffer the half-life was measured to be 13 h. |

| EX. NO. | STRUCTURES | NMR DATA |
|---|---|---|
| 298 | 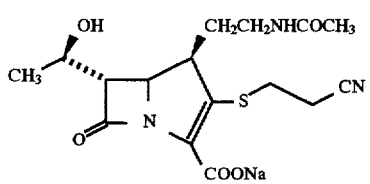 | ¹H NMR(400 MHz, D₂O)δ: 1.35(d, 3H, CH₃, J=7.05Hz), 1.64–1.73; 1.98–2.07(m, 2H, CH₂), 2.02(s, 3H, COCH₃), 2.82–2.86(m, 2H, CH₂CN), 2.91–3.12(m, 2H, SCH₂), 3.2–3.37(overlap, 3H, H-4, CH₂NH), 3.56(dd, 1H, H-6, J₅,₆=2.755Hz, J₆,₁=6.01Hz), 4.27(dd, 1H, H-5, J₄,₅=9.38Hz), 4.29 (q, 1H, H-1'). |
| 299 | 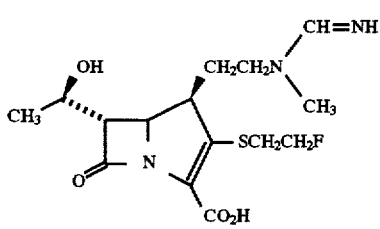 | ¹H NMR(400 MHz, D₂O): (8:2 mixture of Z and E formamidinium isomers) major isomer δ: 1.34(d, J=6.39Hz, 3H, CH₃CHO), 1.8–2.3(2m, 2H, CH₂CH₂N), 2.9–3.2(m, 2H, SCH₂), 3.12(s, 3H, NCH₃), 3.38(m, 1H, H-4), 3.41(dd, J_{H6,H5}=2.8Hz, J_{H6,H1}=6.95Hz, 1H, H6), 3.65(m, 2H, CH₂N), 4.2–4.35(m, 2H, H-5 and CH₃CHO), 4.5–4.75(m, J_{H,F}=46.7Hz, 2H, CH₂F) and 7.9 ppm(s, 1H, CH=NH); minor isomer δ: 1.35(d, J=6.32H, CH₃CHO), 3.30(s, NCH₃), 3.46(dd, J_{H6,H5}=2.97Hz, J_{H6,H1}=7.53Hz, H-6) and 7.83 ppm(s, CH=NH). |
| 300 | 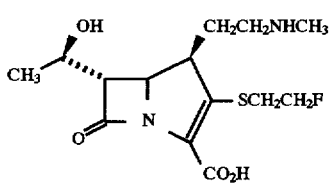 | ¹H NMR(400 MHz, D₂O)δ: 1.35(d, J=6.43Hz, 3H, CH₃CHO), 1.85–1.95 and 2.15–2.25(2m, 2H, CH₂CH₂N), 2.75(s, 3H, NCH₃), 2.9–3.3(m, 4H, SCH₂ and CH₂N), 3.42(dd, J_{H6,H5}=2.87Hz, J_{H6,H1}=6.65Hz 1H, H-6), 3.43(m, 1H, H-4), 4.26(dd, J_{H5,H6}=2.87Hz, J_{H5,H4}=9.45Hz, 1H, H-5), 4.27(m, 1H, CH₃CHO) and 4.55–4.75 ppm(2m, J_{HF}=46.8Hz, 2H, CH₂F). |
| 301 | 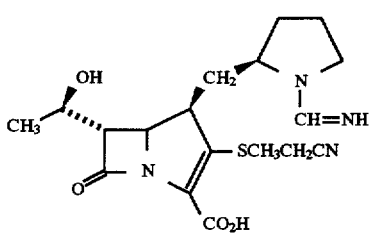 | ¹H NMR(400 MHz, D₂O)d: 1.33(d, J=6.40Hz, 3H, CH₃CHO), 1.86–1.94 and 2.25–2.34(2m, 2H, β-CH₂), 2.0–2.5(m, 4H, CH₂-3' and CH₂-4' of pyrrolidyl), 2.75–2.90(m, 2H, CH₂CN), 2.90–3.1(2m, 2H, S—CH₂), 3.4(m, 1H, H-6), 3.5–3.6(m, 3H, N—CH₂ of pyrrolidyl and H-4), 4.05(m, 1H, NCH-2' of pyrrolidyl), 4.25–4.35(m, 2H, CH₃CHO and H-5) and 8.00 ppm(s, 1H, CH=NH). |
| 302 | 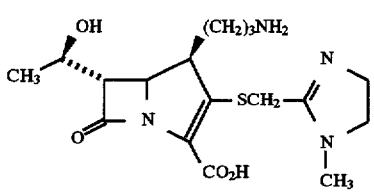 | ¹H NMR(400 MHz D₂O)δ: 1.33(d, J=6.42Hz, 3H, CH₃CHO), 1.5–2.0(m, 4H, CH₂-1 and 2 of propyl), 1.92(s, CH₃CO₂H), 3.06(m, 4H, CH₂NH₂), 3.12(s, 3H, NCH₃), 3.25(m, 1H, H-4), 3.50(dd, J_{H6,H5}=3.00Hz, J_{H6,H1}=6.29Hz, 1H, H-6), 3.75–4.0(m, 6H, SCH₂ and CH₂-4 and 5 of imidazoline), 4.28(m, 1H, CH₃CHO) and 4.30 ppm(dd, J_{H5,H6}=3.00Hz, J_{H5,H4}=9.95Hz, 1H, H-5). |
| 303 | 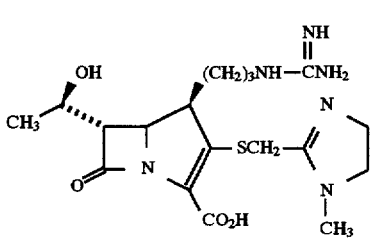 | ¹H NMR(200 MHz, D₂O)δ: 1.29(d, J=6.35Hz, 3H, CH₂CHO), 1.3–1.9(m, 4H, CH₂-1 and 2 of ethyl), 1.9(s, CH₃CO₂H), 3.09(s, 3H, NCH₃), 3.42 (dd, J_{H6,H5}=2.83Hz, J_{H6,H1}=6.00Hz, 1H, H-6), 3.0–3.4 and 3.6–4.0(m, 9H, H-4, CH₂-3 of propyl, SCH₂ and CH₂-4 and 5 of imidazoline), and 4.2–4.4 ppm(m, 2H, H-5 and CH₃CHO). |
| 304 | 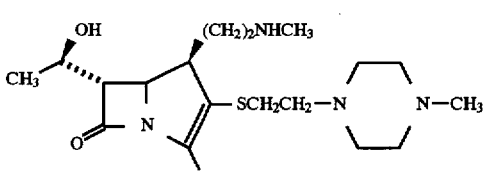 | ¹H NMR(400 MHz, D₂O)δ: 1.33(d, J=6.40Hz, 3H, CH₃CHO), 1.85–1.95 and 2.15–2.25(2m, 2H, CH₂-1 of ethyl), 1.93(5, CH₃CO₂H), 2.75 and 2.86 (2s, 2×3H, NCH₃), 2.7–3.3(series of m, 14H, CH₂-2 of ethyl, SCH₂CH₂N and CH₂ of piperazine), 3.36(m, 1H, H-4), 3.44(dd, J_{H6,H5}=2.89Hz, J_{H6,H1}=6.60Hz, 1H, H-6) 4.27(m, 1H, CH₃CHO) and 4.28 ppm(dd, J_{H5,H6}=2.89Hz, J_{H5,H4}=9.71Hz, 1H, H-5). |

| EX. NO. | STRUCTURES | NMR DATA |
|---|---|---|
| 305 | (structure: carbapenem with OH, CH₃, side chain CH=NH, (CH₂)₂N—CH₃, SCH₂CH₂—N-piperazine-N—CH₃, CO₂H) | ¹H NMR(200 MHz, D₂O)δ: 1.34(d, J=6.34Hz, 3H, C$\underline{H_3}$CHO), 1.8–2.3(2m, 2H, CH₂-1 of ethyl), 1.94(s, CH₃CO₂H), 2.87, 3.11 and 3.3(3s, total 6H, NCH₃), 2.7–3.4(broad series of m, 13H, H-4, SC$\underline{H_2}$CH₂N and CH₂ of piperazine), 3.45(dd, J$_{H6,H5}$=2.68 Hz, J$_{H6,H1}$=6.79Hz, 1H, H-6), 3.66(m, 2H, CH₂-2 of ethyl), 4.2–4.4(m, 2H, H-5 and CH₂C$\underline{H}$O), 7.81 and 7.90 ppm(2s, 1H, C$\underline{H}$=NH). |
| 306 | (structure: carbapenem with OH, CH₃, CH₃CH₂NHCH₃ side, SCH₂CH₂N₃, CO₂H) | ¹H NMR(200 MHz, CDCl₃)δ: 1.41(d, J=6.17Hz, 3H, C$\underline{H_3}$CHO), 1.4–1.7 and 2.1–2.3(2m, 2H, C$\underline{H_2}$CH₂N), 2.97(s, 3H, NCH₃), 2.8–3.6(series of m, 8H, H-4, H-6, SC$\underline{H_2}$CH₂N₃ and CH₂C$\underline{H_2}$N), 4.1–4.3(m, 1H, CH₃C$\underline{H}$O), 4.26(dd, J$_{H5,H6}$=2.96Hz, J$_{H5,H4}$=10.12Hz, 1H, H-5), 4.5–4.9(m, 4$\underline{H}$, CH₂ of allyl), 5.2–5.5 and 5.8–6.1 ppm(2m, 4H and 2H, CH of allyl). |
| 307 | (structure: carbapenem with OH, CH₃, CH₂CH₂N(CH₃)CH=NH side, SCH₂CH₂N₃, CO₂H) | ¹H NMR(400 MHz, D₂O): the product in a 8:2 mixture of Z and E formamidinium isomers; major isomer δ: 1.34(d, J=6.36Hz, 3H, C$\underline{H_3}$CHO)1.85–2.0 and 2.15–2.25(m, 2H, C$\underline{H_2}$CH₂N), 2.85–3.1(m, 2H, SC$\underline{H_2}$), 3.12(s, 3H, NCH₃) 3.39(m, 1H, H-$\overline{4}$), 3.42(dd, J$_{H6,H5}$=2.83Hz, J$_{H6,H1}$=6.91Hz, 1H, H-6), 3.55(m, 2H, CH₂N₃), 3.66(m, 2H, CH₂N), 4.25–4.35(m, 2H, H-5 and CH₃C$\underline{H}$O) and 7.91 ppm(s, 1H, C$\underline{H}$=NH): minor isomers: 1.35(d, J=6.34Hz, C$\underline{H_3}$CHO), 3.30(s, NCH₃), 3.47(dd, J$_{H6,H1}$=2.94Hz, J$_{H6,H4}$=7.54Hz, H-6), and 7.83 ppm(s, C$\underline{H}$=NH). |
| 308 | (structure: carbapenem with OH, CH₃, CH₂CH₂NH₂ side, SCH₂-phenyl, COOH) | ¹H NMR(400 MHz, D₂O)δ: 1.29(d, 3H, CH₃, J=6.17 Hz), 1.65–1.75; 2.0–2.1(m, 2H, CH₂), 2.9–3.05(m, 2H, CH₂N), 3.2(dt, 1H, H-4, J$_{4,5}$=9.94 Hz), 3.34(dd, 1H, H-6, J$_{5,6}$=2.83Hz, J6, 6.48Hz, 4.0, 4.11(AB, 2H, SCH₂, J=13.69Hz), 4.11(dd, 1H, H-5), 4.22(q, 1H, H-1'), 7.41–7.43 (m, 5H, phenyl). |
| 309 | (structure: carbapenem with OH, CH₃, CH₂CH₂N₃ side, S-pyrrolidine N—H, CO₂H) | ¹H NMR(D₂O)δ: 4.30(1H, dd, J=2.87, 9.68, H-5), 4.26(1H, m, H-1'), 4.08(1H, m, SCH—), 4.0–3.8(1H, unresolved m, N—CH pyrrolidine), 3.70–3.55(2H, 2 m, CH—N₃, N—CH pyrrolidine), 3.5(1H, dd, J=2.80, 6.14, H-6), 3.45–3.30(3H, m, H-4, CH—N₃, N—CH pyrrolidine), 3.30–3.10 (1H, unresolved m, N—CH pyrrolidine), 3.00 and 2.96(3H, 2S, 2 N—CH₃), 2.8–2.4(1H, unresolved m, CH-4 pyrrolidine), 2.25–1.97(2H, unresolved m, CH-4 pyrrolidins, C-H-1"), 1.87–1.75(1H, unresolved m, CH-1"), 1.31(3H, d, J=6.36, CH₃'). |
| 310 | (structure: carbapenem with OH, CH₃, CH₂CH₂NH₂ side, S-pyrrolidine N—CH₃, CO₂H) | ¹H NMR(D₂O)δ: 4.35–4.25(2H, 2m, H-1', H-6), 4.0(1H, m, —SCH), 3.8–3.6(2H, unresolved m, 2N—CH pyrrolidine), 3.50(1H, 2dd, J': 2.94, 6.44, J²: 2.74, 6.30, H-5), 3.45–3.37(2H, unresolved m, 2 N—CH pyrrolidine), 3.33(1H, dt, J: 3.4, 10.2, H-4), 3.14(2H, m, —CH₂N), 2.98 and 2.97(3H, 2S, N—CH₃), 2.7–2.5(1H, m, CH-4 pyrrolidine), 2.25–2.00(2H, m, CH-4 pyrrolidine, CH-1"), 1.92(3H, s, acetate), 1.95–1.70(1H, m, CH-1"), 1.33(3H, d, J: 6.38, —CH₃'). |
| 311 | (structure: carbapenem with OH, CH₃, CH₂CH₂NCH=NH with CH₃, SCH₂CH₂NH₂, CO₂H) | ¹H NMR(200 MHz, water)δ: 1.34(d, J=5.88Hz, 3H, CH₃CHO), 1.8–2.3 (2m, 2H, C$\underline{H_2}$CH₂NCH₃), 1.93(s, CH₃CO₂H), 2.8–3.8(m, 7H, H-4, SCH₂C$\underline{H_2}$N, CH₂C$\underline{H_2}$NCH₃), 3.10(s, 3H, NCH₃), 3.48(dd, J$_{H6,H5}$=2.69Hz, J$_{H6,H1}$=6.79Hz, 1H, H-6), 4.2–4.4(m, 2H, H-5 and CH₃C$\underline{H}$O), 7.81 and 7.90 ppm(2s, 1H, C$\underline{H}$=NH). |
| 312 | (structure: carbapenem with OH, CH₃, CH₂CH₂OH side, SCH₂CH₂-piperazine-N—CH₃, CO₂H) | ¹NMR(D₂O, 400 MHz)δ: 4.254(1H, dd, J=2.7Hz, J=9.4Hz, H-5), 4.301–4.239(1H, dq, J=6.2Hz, J=6.3Hz, H-1'), 3.789–3.733, 3.645–3.581 (2H, 2 sets of m, CH₂—O), 3.436(1H, dd, J=2.6Hz, J=6.0Hz, H-6), 3.432, 3.376(1H, m, H-4); 3.055–3.008, 2.920–2.822(2H, 2 sets of m, CH₂—S), 3.0–2.64(10H, m, CH₂N), 2.544(3H, s, N—CH₃), 2.095–2.012, 1.802–1.725(2H, 2 sets of m, CH₂-4) and 1.321 ppm(3H, d, J=6.4Hz, CH₃). |

| EX. NO. | STRUCTURES | NMR DATA |
|---|---|---|
| 313 | (structure: carbapenem with OH, CH₃, CH₂CH₂N₃, SCH₂-imidazoline-NCH₃, CO₂H) | $^1$H NMR(400 MHz, D₂O)δ: 1.32(d, J=6.38Hz, 3H, CH₃CHO), 1.75–1.85 and 2.02–2.11(2m, 2H, CH₂-1 of ethyl), 3.13(s, 3H, NCH₃), 3.32(m, 1H, H-4), 3.39–4.8 and 3.55–3.64(2m, 2H, CH₂N₃), 3.56(dd, $J_{H6,H5}$=3.0Hz, $J_{H6,H1}$=6.13Hz, 1H, H-6), 3.8–4.0(m, 4H, CH₂-4 and 5 of imidazoline), 4.27(m, 1H, CH₃CHO) and 4.31 ppm(dd, $J_{H5,H6}$=3.0Hz, $J_{H5,H4}$=10.03Hz, 1H, H-5). |
| 314 | (structure: carbapenem with OH, CH₃, CH₂CH₂N₃, SCH₂CH₂-piperazine-NH, CO₂H) | $^1$H NMR(D₂O, 400 MHz)δ: 4.263(2H, dd, J=2.8Hz, J=9.6Hz, H-5), 4.299–4.235(1H, dq, J=6.2Hz, J=6.4Hz, H-1'), 3.634–3.573, 3.466–3.372 (2H, 2 sets of m, CH₂N₃), 3.454(1H, dd, J=2.8Hz, J=6.2Hz, H-6), 3.444–3.372(1H, m, H-4), 3.303, 2.91, 3.277(4H, 3 lines, CH₂N-piparazine), 3.066–2.998, 2.934–2.878(2H, 2 sets of m, SCH₂), 2.896–2.857(4H, m CH₂N piperazine), 2.786, 2.769, 2.751(2H, m, CH₂N), 2.122–2.037, 1.863–1.772(2H, 2 sets of m, CH₂-4) and 1.331 ppm(3H, dq J=6.3Hz, CH₃. |
| 315 | (structure: carbapenem with OH, CH₃, CH₂CN, SCH₂CH₂CN, CO₂Na) | $^1$H NMR(D₂O, 400 MHz)δ: 4.38(1H, dd, J=2.9Hz, J=9.6Hz, H-5); 4.31 (1H, quint, J=6.2Hz, H-1'); 3.86–3.80(1H, m, H-4); 3,62(1H, dd, J=2.9Hz, J=5.5Hz, H-6); 3.23–3.16(1H, m, part of SCH₂); 3.02–2.89 (3H, m, part of SCH₂, CH₂CN-3); 2.86–2.83(2H, m, CH₂CN-4) and 1.33 ppm (3H, d, J=6.4Hz, CH₃). |
| 316 | (structure: carbapenem with OH, CH₃, (CH₂)₂NHC(=NH)NH₂, S-CH₂CH₂-piperazine-NH, CO₂H) | $^1$H NMR(D₂O, 400 MHz)δ: 4.286(1H, dd, J=2.55Hz, J=6.93Hz, H-5), 4.32–4.24(1H, m, H-1'), 3.435(1H, dd, J=2.6Hz, J=6.75Hz, H-6) 3.42–3.33, 3.32–3.22(3H, 2 sets of m, CH₂—NH, H-4), 3.284(4H, t, J=5.2Hz, CH₂-guanidine), 3.0–2.8(2H, m, S—CH₂), 2.88–2.82(4H, m, CH₂-guanidine), 2.741(2H, t, J=7.25Hz, CH₂—N), 2.18–2.05, 1.85–1.72 (1H, 2 sets of m, CH₂-4), 1.918(2H, S, CH₃CO₂) and 1.337 ppm(3H, d, J=6.34Hz, CH₃). |
| 317 | (structure: carbapenem with (CH₂)₃N₃, S—CH₂-pyridine, CO₂K) | $^1$H NMR(400 MHz, D₂O)δ: 8.475(1H, d, J=4.5Hz, pyridine-H), 7.88–7.83 1H, m, pyridine-H 7.524(1H, d, J=7.9Hz, pyridine-H), 7.413–7.362 (1H, m, pyridine-H), 4.235, 4.199, 4.098, 4.063(2H, ABq, J=14.3Hz, CH₂-pyridine), 4.191–4.147(1H, 7 lines, J=2.8H, J=5.5H, H-5), 3.370, 3.357, 3.327, 3.314(1H, part of ABX, J=5.5Hz, J=17.1Hz, H-6-β), 3.35–3.25(2H, m, CH₂N₃), 3.17–3.10(1H, m, H-5), 3.060, 3.053, 3.017, 3.010(1H, part of ABX, J=2.8Hz, J=17.1Hz, H-16-α), 1.70–1.54, 1.52–1.40 and 1.37–1.27 ppm(4H, 3 sets of m, CH₂CH₂-4). |
| 318 | (structure: carbapenem with (CH₂)₃NH₂, S—CH₂-pyridine, CO₂K) | $^1$H NMR(200 MHz, D₂O)δ: 8.46(1H, d, J=4.2Hz, pyridine-H), 7.90–7.81 (1H, m, pyridine-H), 7.52(1H, d, J=7.9Hz, pyridine-H), 7.40–7.20 (1H, m, pyridine-H), 4.228–4.158, 4.109, 4.038(2H, ABq, J=14.1Hz, CH₂), 4.22–4.11(1H, m, H-5), 3.415, 3.388, 3.329, 3.302(1H, part of ABX, J=5.4Hz, J=17.2Hz, H-6β), 3.231–3.134(1H, m, H-4), 3.060, 3.046(2 lines of ABX, J=2.8Hz, part of H-6α), 3.001–2.93, 2.3H, m, CH₂N and part of H-6α) and 1.729–1.55, 1.487–1.313 ppm(4H, 2 sets of m, CH₂CH₂-4). |

EXAMPLE 319

When the general procedures of the foregoing text and examples are repeated with the appropriate intermediate and mercaptan compound, there is thereby produced a compound or salt thereof having the formula

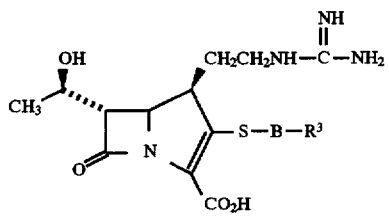

wherein B—R³ is
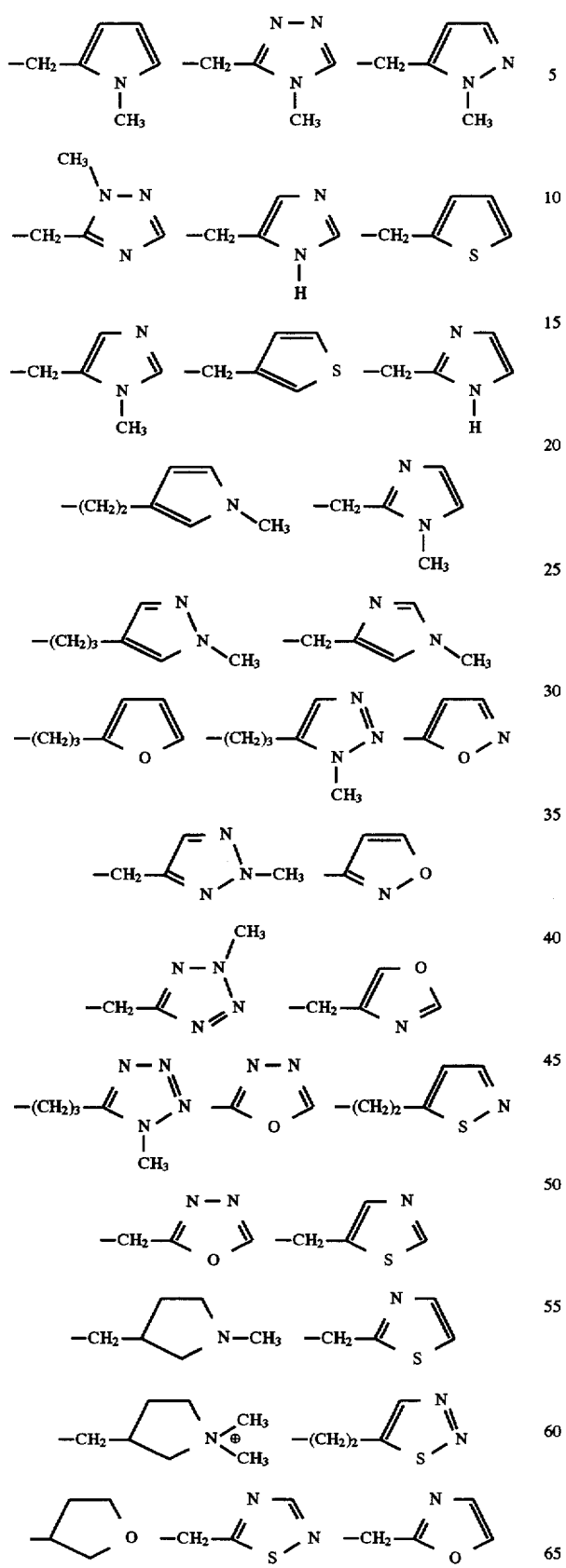
-continued
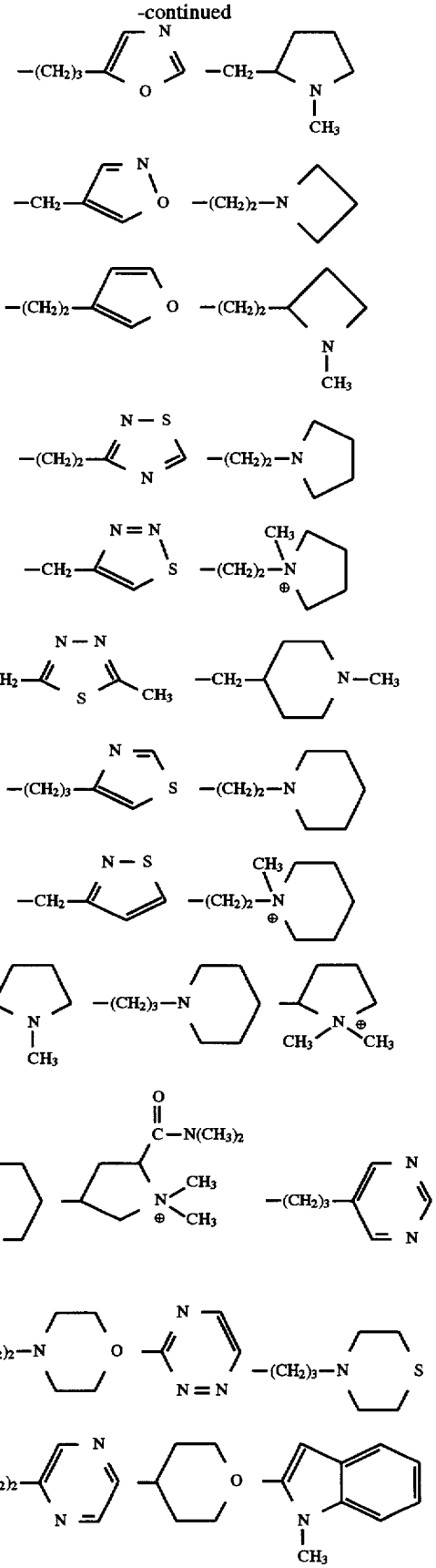

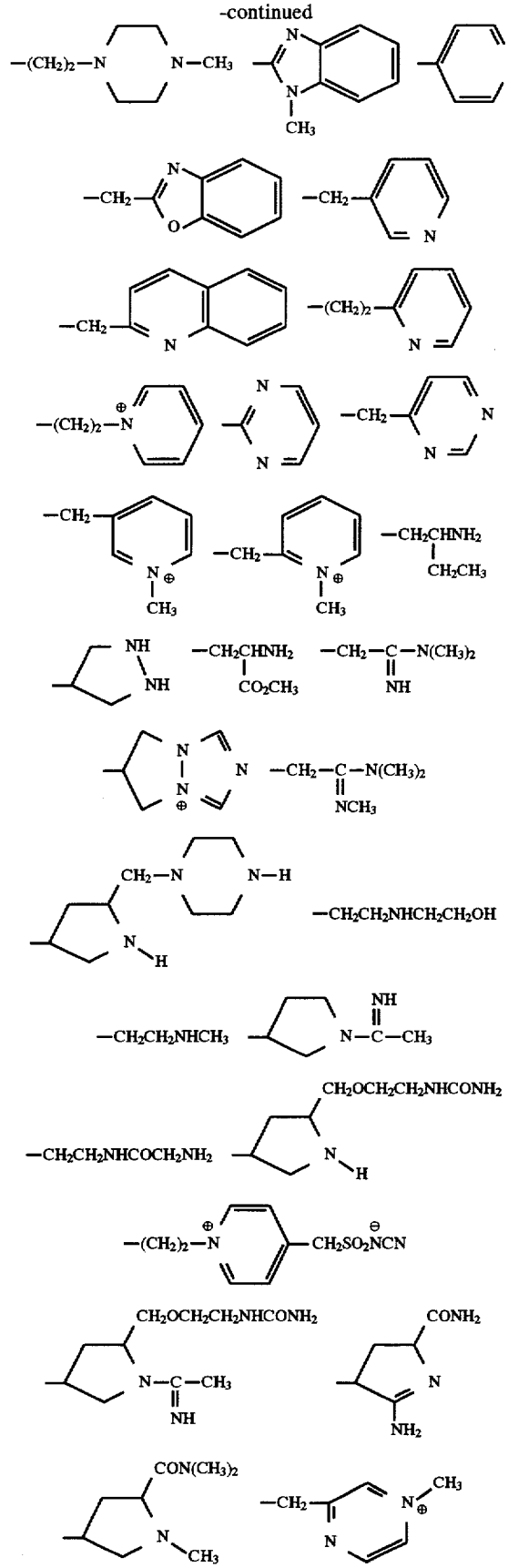
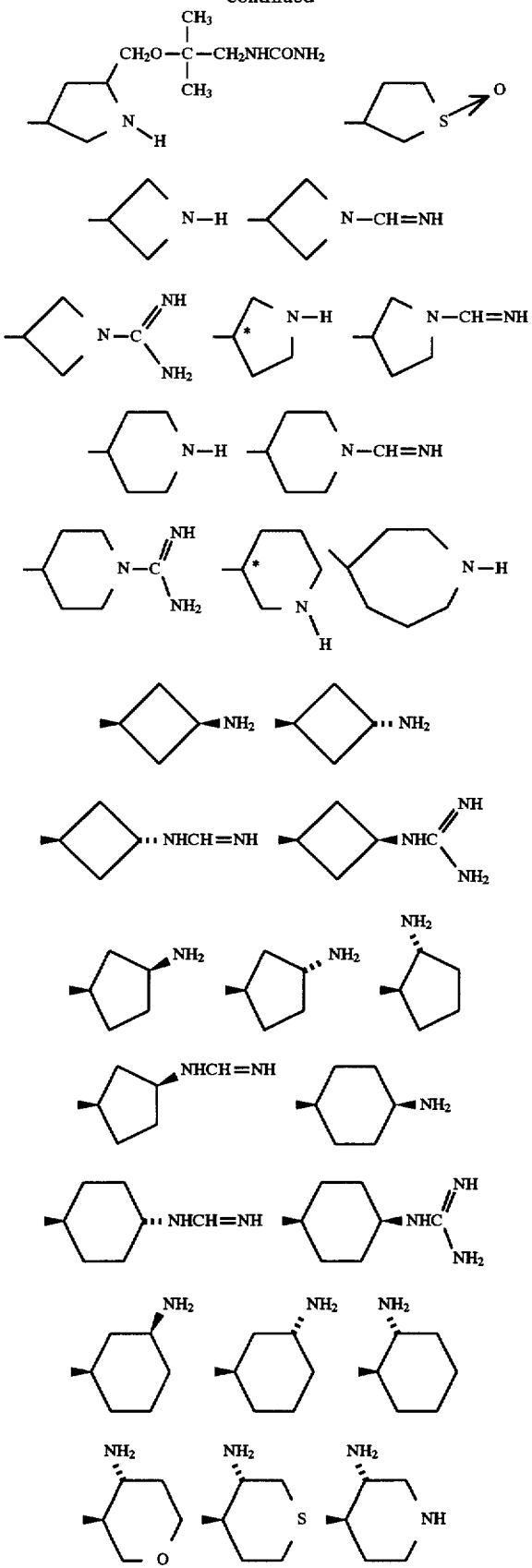

-continued
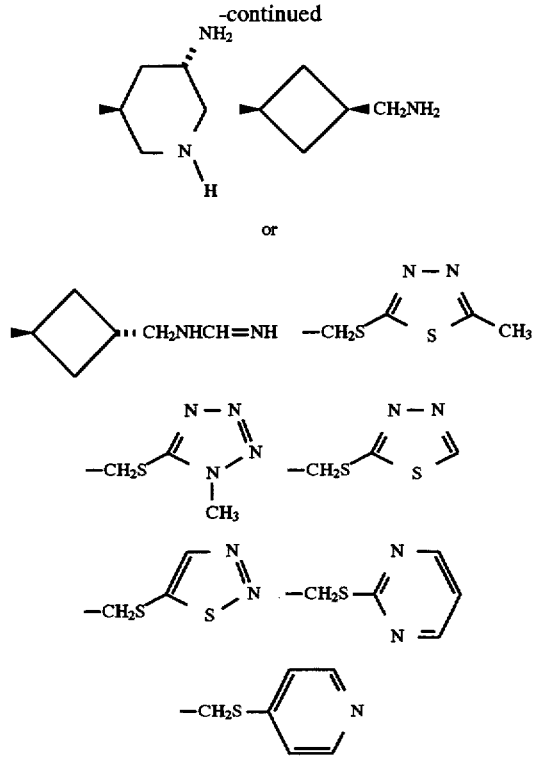
EXAMPLE 320
When the general procedures of the foregoing text and examples are repeated with the appropriate intermediate and mercaptan compound, there is thereby produced a compound or salt thereof having the formula
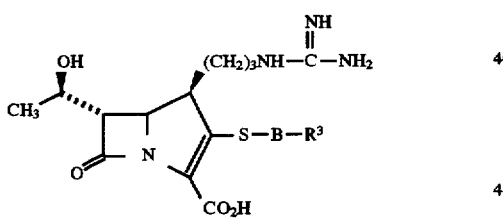
wherein B—R³ is
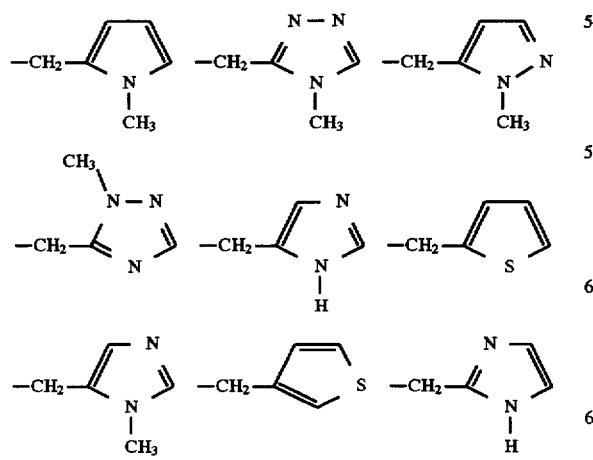
-continued
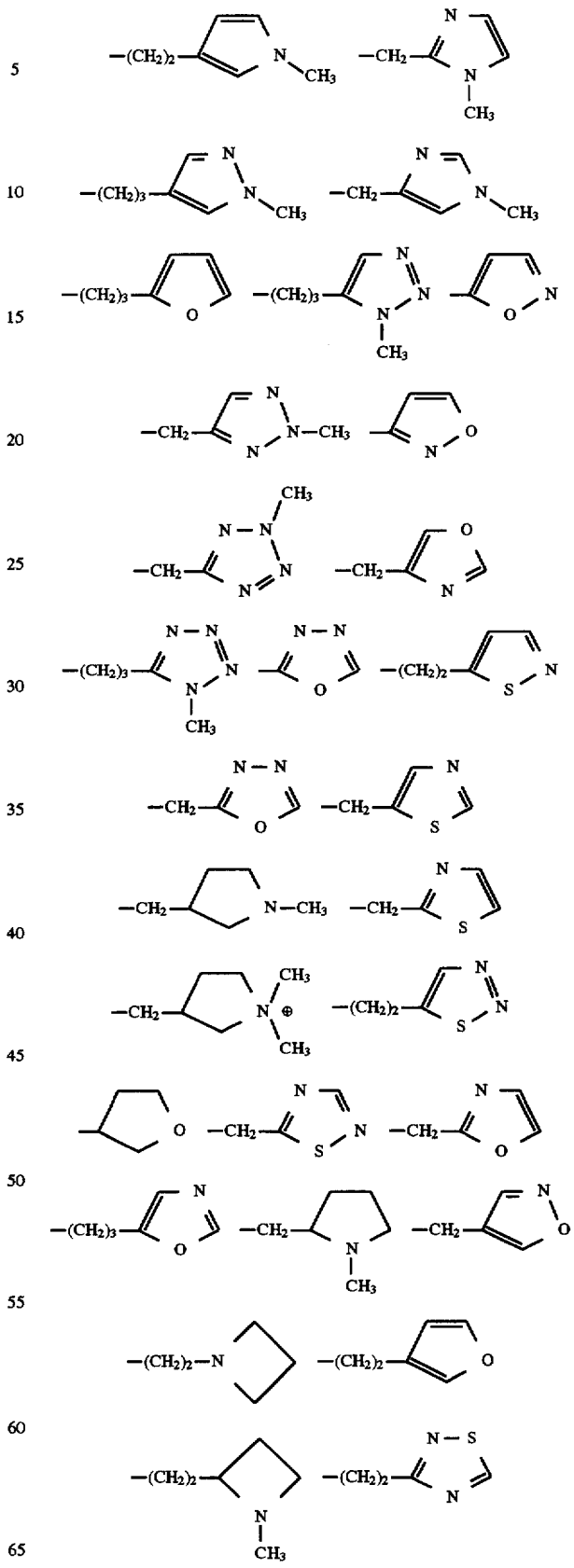

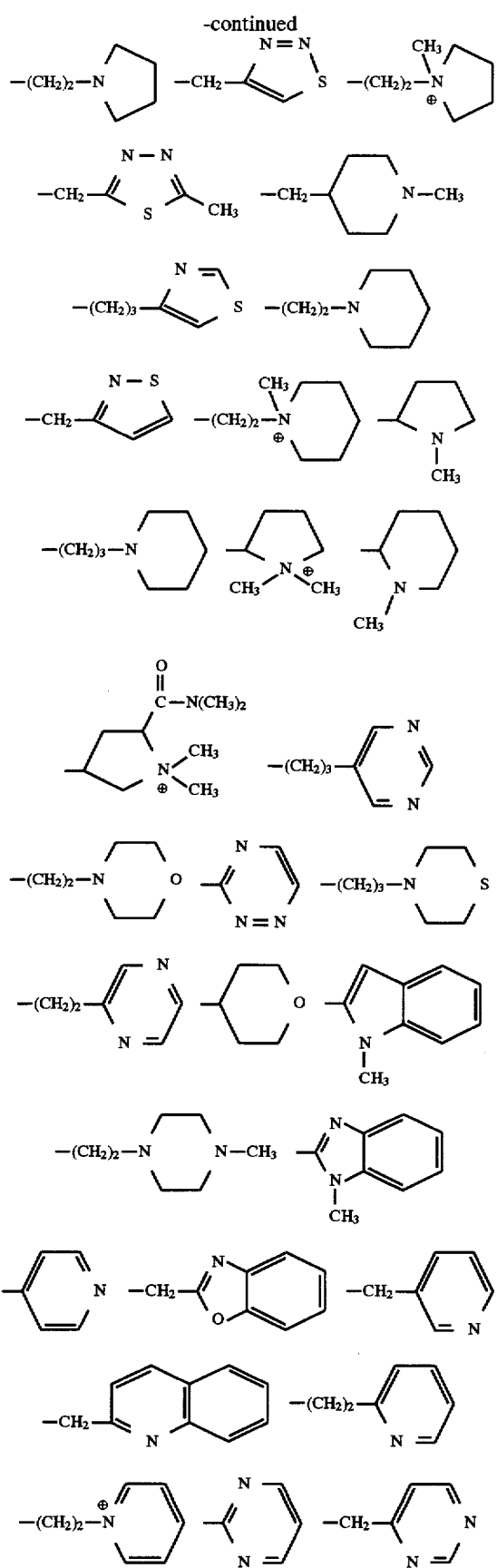
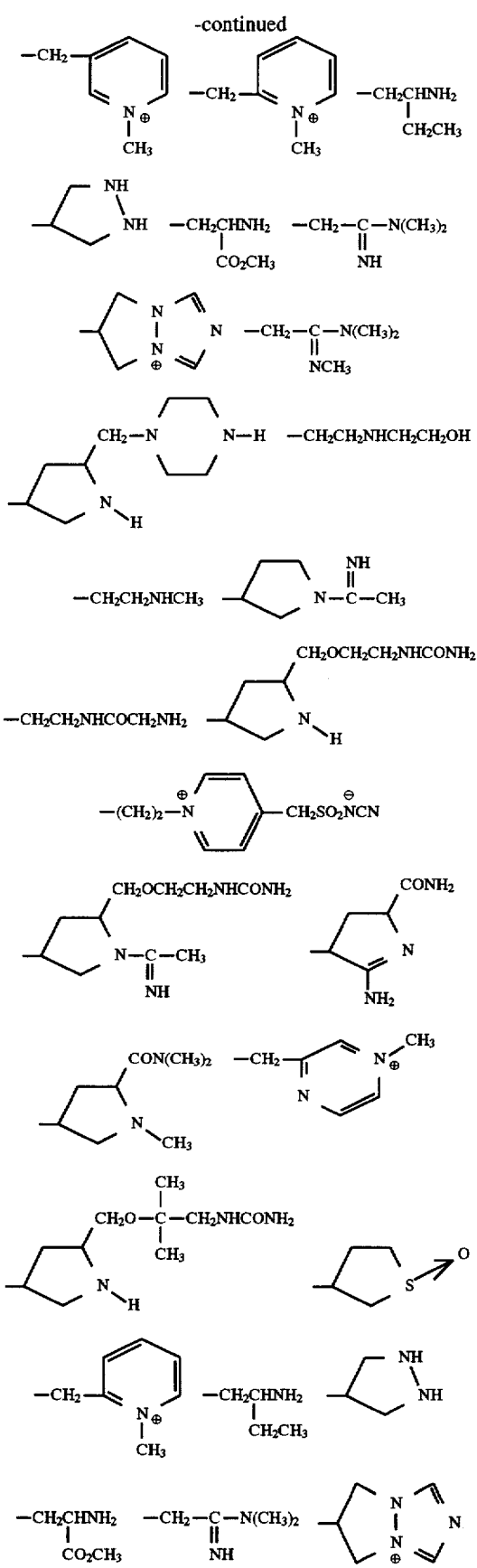

411
-continued

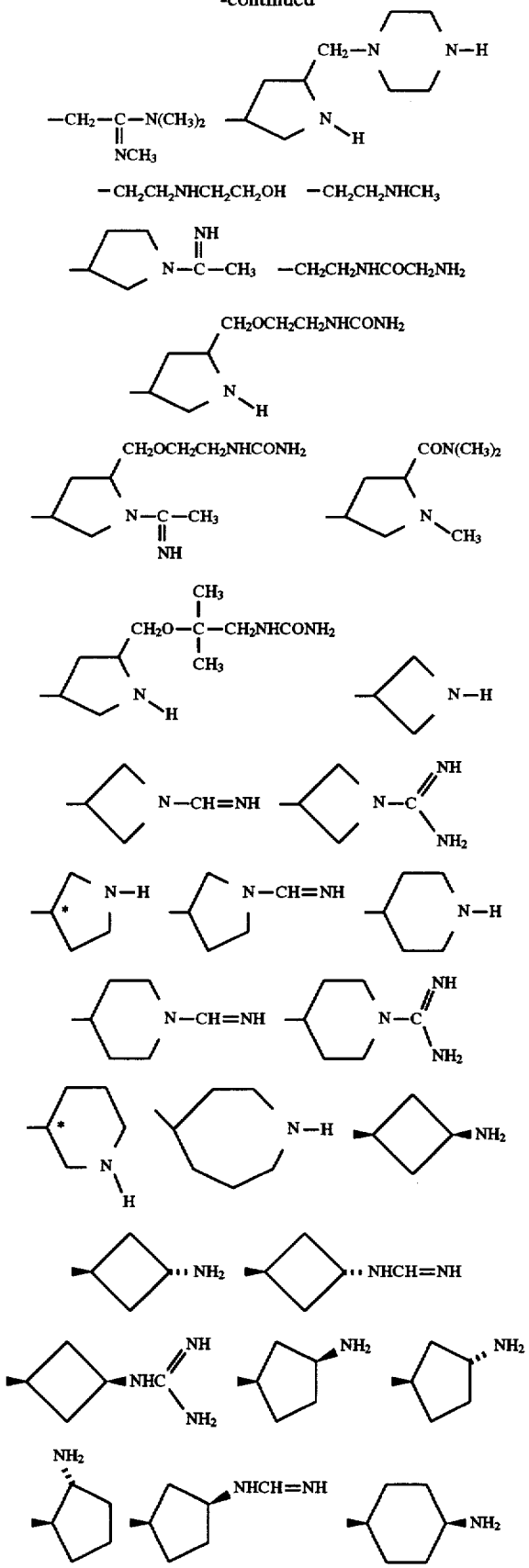

412
-continued

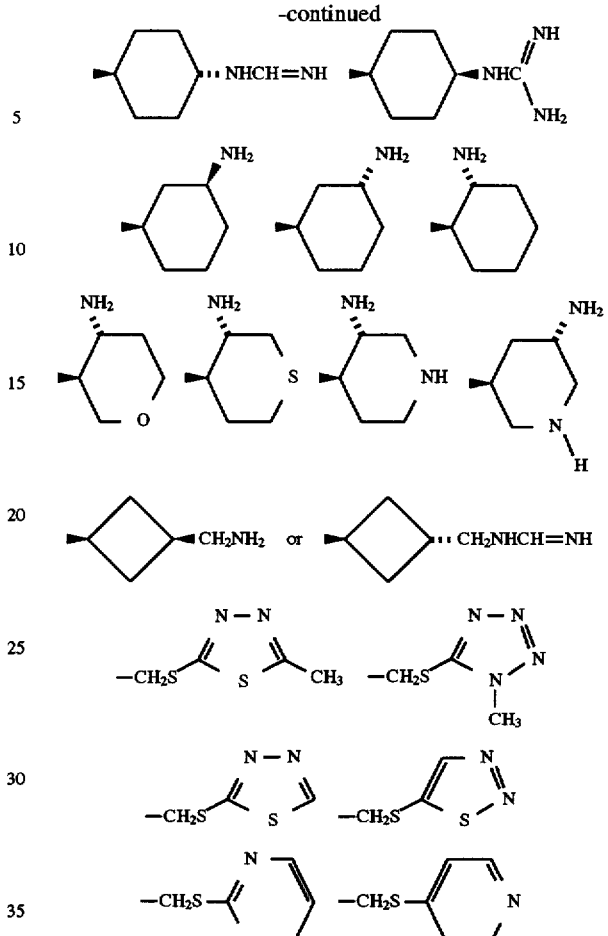

What is claimed is:
1. A compound of the formula

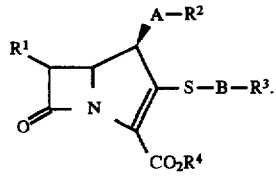

wherein
R$^1$ is hydrogen, C$_{1-2}$ alkyl, —CH$_2$OH, —CH$_2$NH$_2$,

A is an unsubstituted or hydroxy-substituted straight or branched C$_{1-10}$ alkylene group or a straight or branched C$_{1-10}$ alkylene group having an intervening heteroatom selected from oxygen, sulfur and nitrogen;

R$^2$ is hydroxy, halogen, C$_{1-4}$ alkoxy, nitrile, azido, a quaternary ammonio group, —NR$^5$R$^6$,

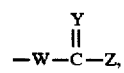

azetidinyl, or a 5- or 6-membered heterocyclic group selected from heteroaromatic and heteroalicyclic joined through a carbon atom thereof;

B is a straight or branched $C_{1-6}$ alkylene group or a direct bond when $R^3$ is joined to the sulfur atom through a carbon atom thereof;

$R^3$ is a residue of an organic group;

$R^4$ is hydrogen, a removable carboxy-protecting group or a physiologically hydrolyzable ester group;

$R^5$ and $R^6$ each are independently hydrogen, $C_{1-6}$ alkyl, $C_{1-4}$ alkoxy, hydroxyethyl, azidoethyl, aminoethyl, and when $R^5$ is hydrogen or $C_{1-4}$ alkyl, $R^6$ is hydroxy, $C_{1-4}$ alkoxy, amino, $C_{1-4}$ alkylamino, di($C_{1-4}$)-alkylamino, substituted $C_{1-4}$ alkyl wherein said alkyl substituent is selected from hydroxy, azido, amino, guanidino, nitrile, carboxy, formimidoyl and phenyl, or an acyl residue of an amino acid or peptide; or $R^5$ and $R^6$, taken together with the nitrogen atom to which they are attached, is an unsubstituted or substituted heterocyclic group having 1 to 2 ring members and having up to four heteroatoms in each ring independently selected from oxygen, nitrogen and sulfur, wherein said substituent is selected from the group consisting of $C_{1-4}$ alkyl, $C_{1-4}$ alkoxy, trifluoromethyl, hydroxy, halogen, amino, nitrile, carboxy, formimidoyl, carbamido, carbamoyl, $C_{1-4}$ alkylamino and amino($C_{1-4}$)alkyl;

W is a direct bond, oxygen, sulfur or $NR^{10}$;

Y is oxygen or $NR^{10}$;

Z is hydrogen, hydroxy, $C_{1-4}$ alkyl, $C_{1-4}$ alkoxy, $-NR^7R^8$, amino($C_{1-4}$)alkyl, azido($C_{1-4}$)alkyl or hydroxy($C_{1-4}$)alkyl;

$R^7$ and $R^8$ each are independently hydrogen, $C_{1-4}$ alkyl, hydroxy, benzyloxy or alkanoyl; and $R^{10}$ is hydrogen, $C_{1-4}$ alkyl, $C_{1-4}$ alkylamino or di($C_{1-4}$) alkylamino;

or a non-toxic pharmaceutically acceptable salt thereof.

2. A compound of claim 1 having the formula

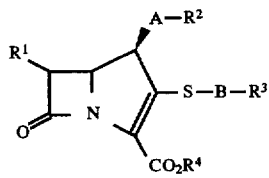

wherein $R^1$ is hydrogen, $C_{1-2}$ alkyl, $-CH_2OH$, $-CH_2NH_2$,

A is an unsubstituted or hydroxy-substituted straight or branched $C_{1-10}$ alkylene group or a straight or branched $C_{1-10}$ alkylene group having an intervening heteroatom selected from oxygen, sulfur and nitrogen;

$R^2$ is hydroxy, halogen, $C_{1-4}$ alkoxy, nitrile, azido, a quaternary ammonio group, $-NR^5R^6$,

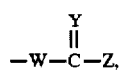

azetidinyl, or a 5- or 6-membered heterocyclic group selected from heteroaromatic and heteroalicyclic joined through a carbon atom thereof;

B is a straight or branched $C_{1-6}$ alkylene group or a direct bond when $R^3$ is joined to the sulfur atom through a carbon atom thereof;

$R^3$ is hydrogen, $C_{3-6}$ cycloalkyl or substituted $C_{3-6}$ cycloalkyl, $C_{5-6}$ cycloalkenyl or substituted $C_{5-6}$ cycloalkenyl, phenyl or substituted phenyl, hydroxy, $C_{1-4}$ alkoxy, $C_{1-4}$ alkylthio, phenylthio or substituted phenylthio, halogen, nitrile, nitro, $-NR^7R^8$, $-\oplus R^9R^9R^9$,

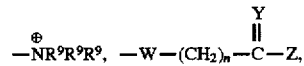

or an unsubstituted or substituted heterocyclic group selected from heteroaromatic, heteroalicyclic,

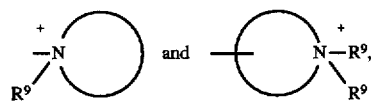

having from one to two rings with 4 to 7 ring members in each ring and having up to four heteroatoms in each ring independently selected from oxygen, nitrogen and sulfur, in which said heterocyclic group may be joined through a sulfur atom attached to a carbon atom of said heterocyclic group, wherein said $C_{3-6}$ cycloalkyl, $C_{5-6}$ cycloalkenyl, phenyl and heterocyclic substituent is selected from the group consisting of one or two $C_{1-4}$ alkyl, $C_{1-4}$ alkoxy, trifluoromethyl, hydroxy, halogen, amino, $C_{1-4}$ alkylamino, di($C_{1-4}$)alkylamino, nitrile, carboxy, formimidoyl, carbamido, carbamoyl, amino ($C_{1-4}$)alkyl, $C_{1-4}$ alkylamino($C_{1-4}$)alkyl, di($C_{1-4}$) alkylamino($C_{1-4}$)alkyl, $C_{1-4}$ alkoxycarbonyl, $C_{1-4}$ alkoxycarbonyl($C_{1-4}$)alkyl, amino($C_{1-4}$)alkylamino ($C_{1-4}$) alkyl and $C_{1-4}$ alkylcarbonyloxy, and said heterocyclic group may also be substituted with

$R^4$ is hydrogen, a removable carboxy-protecting group or a physiologically hydrolyzable ester group;

$R^5$ and $R^6$ each are independently hydrogen, $C_{1-6}$ alkyl, $C_{1-4}$ alkoxy, hydroxyethyl, azidoethyl, aminoethyl, and when $R^5$ is hydrogen or $C_{1-4}$ alkyl, $R^6$ is hydroxy, $C_{1-4}$ alkoxy, amino, $C_{1-4}$ alkylamino, di($C_{1-4}$)alkylamino, substituted ($C_{1-4}$)alkyl wherein said alkyl substituent is selected from hydroxy, azido, amino, guanidino, nitrile, carboxy, formimidoyl and phenyl, or an acyl residue of an amino acid or peptide; or $R^5$ and $R^6$, taken together with the nitrogen atom to which they are attached, is an unsubstituted or substituted azetidino, or an unsubstituted or substituted 5- or 6-membered heterocyclic group having up to four heteroatoms in each ring independently selected from oxygen, nitrogen and sulfur, wherein said substituent is selected from the group consisting of $C_{1-4}$ alkyl, $C_{1-4}$ alkoxy, trifluoromethyl, hydroxy, halogen, amino, nitrile, carboxy, formimidoyl, carbamido, carbamoyl, $C_{1-4}$ alkylamino and amino($C_{1-4}$)alkyl;

n is an integer of from 0 to 2; inclusive;

W is a direct bond, oxygen, sulfur or $NR^{10}$;

Y is oxygen or $NR^{10}$;

Z is hydrogen, hydroxy, $C_{1-4}$ alkyl, $C_{1-4}$ alkoxy, $-NR^7R^8$, amino($C_{1-4}$)alkyl, azido($C_{1-4}$)alkyl or hydroxy($C_{1-4}$)alkyl;

$R^7$ and $R^8$ each are independently hydrogen, $C_{1-4}$ alkyl, hydroxy, benzyloxy, or alkanoyl;

$R^9$ is a $C_{1-4}$ alkyl or $C_{2-4}$ alkenyl; and $R^{10}$ is hydrogen, $C_{1-4}$ alkyl, $C_{1-4}$ alkylamino or di($C_{1-4}$) alkylamino;

or a non-toxic pharmaceutically acceptable salt thereof.

3. A compound of claim 1 having the formula

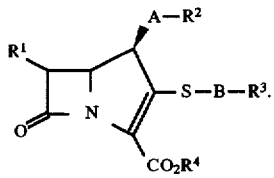

wherein
$R^1$ is

A is an unsubstituted or hydroxy-substituted straight or branched $C_{1-10}$ alkylene group or a straight or branched $C_{1-10}$ alkylene group having an intervening heteroatom selected from oxygen, sulfur and nitrogen;

$R^2$ is hydroxy, fluoro, $C_{1-4}$ alkoxy, nitrile, azido, a quaternary ammonio group, $-NR^5R^6$,

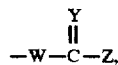

azetidinyl, or a 5- or 6-membered heterocyclic group selected from heteroaromatic and heteroalicyclic joined through a carbon atom thereof;

B is a straight or branched $C_{1-6}$ alkylene group or a direct bond when $R^3$ is joined to the sulfur atom through a carbon atom thereof;

$R^3$ is hydrogen, $C_{3-6}$ cycloalkyl or substituted $C_{3-6}$ cycloalkyl, $C_{5-6}$ cycloalkenyl or substituted $C_{5-6}$ cycloalkenyl, phenyl or substituted phenyl, hydroxy, $C_{1-4}$ alkoxy, $C_{1-4}$ alkylthio, phenylthio or substituted phenylthio, halogen, nitrile, $-NR^7R^8$,

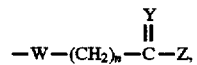

or an unsubstituted or substituted heterocyclic group selected from heteroaromatic, heteroalicyclic,

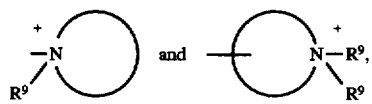

having from one to two rings with 5 to 6 ring members in each ring and having up to four heteroatoms in each ring independently selected from oxygen, nitrogen and sulfur, in which said heterocyclic group may be joined through a sulfur atom attached to a carbon atom of said heterocyclic group, wherein said $C_{3-6}$ cycloalkyl, $C_{5-6}$ cycloalkenyl, phenyl and heterocyclic substituent is selected from the group consisting of one or two $C_{1-4}$ alkyl, $C_{1-4}$ alkoxy, trifluoromethyl, hydroxy, halogen, amino, $C_{1-4}$ alkylamino, di($C_{1-4}$)alkylamino, nitrile, carboxy, formimidoyl, carbamido, carbamoyl, amino ($C_{1-4}$)alkyl, $C_{1-4}$ alkylamino($C_{1-4}$)alkyl, di($C_{1-4}$) alkylamino($C_{1-4}$)alkyl, $C_{1-4}$ alkoxycarbonyl, $C_{1-4}$ alkoxycarbonyl($C_{1-4}$)alkyl, amino($C_{1-4}$)alkylamino ($C_4$)alkyl and $C_{1-4}$ alkylcarbonyloxy, and said heterocyclic group may also be substituted with

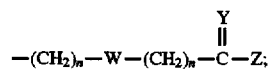

$R^4$ is hydrogen, a removable carboxy-protecting group or a physiologically hydrolyzable ester group;

$R^5$ and $R^6$ each are independently hydrogen and $C_{1-6}$ alkyl, and when $R^5$ is hydrogen or $C_{1-4}$ alkyl, $R^6$ is hydroxy, $C_{1-4}$ alkoxy, amino, $C_{1-4}$ alkylamino, di($C_{1-4}$)alkylamino, substituted ($C_{1-4}$)alkyl wherein said alkyl substituent is selected from hydroxy, azido, amino, guanidino, nitrile, carboxy, formimidoyl and phenyl, or an acyl residue of an amino acid or peptide; or $R^5$ and $R^6$, taken together with the nitrogen atom to which they are attached, is an unsubstituted or substituted azetidino, or an unsubstituted or substituted 5- or 6-membered heterocyclic group having up to two heteroatoms in each ring independently selected from oxygen, nitrogen and sulfur, wherein said substituent is selected from the group consisting of $C_{1-4}$ alkyl, hydroxy, amino, nitrile, formimidoyl, $C_{1-4}$ alkylamino and amino($C_{1-4}$)alkyl;

n is an integer of from 0 to 2; inclusive;

W is a direct bond, oxygen, sulfur or $NR^{10}$;

Y is oxygen or $NR^{10}$;

Z is hydrogen, hydroxy, $C_{1-4}$ alkyl, $C_{1-4}$ alkoxy, $NR^7R^8$, amino($C_{1-4}$)alkyl, azido($C^{1-4}$)alkyl or hydroxy($C_{1-4}$) alkyl;

$R^7$ and $R^8$ each are independently hydrogen, $C_{1-4}$ alkyl, hydroxy, benzyloxy or alkanoyl;

$R^9$ is a $C_{1-4}$ alkyl or $C_{2-4}$ alkenyl; and $R^{10}$ is hydrogen, $C_{1-4}$ alkyl, $C_{1-4}$ alkylamino or di($C_{1-4}$) alkylamino;

or a non-toxic pharmaceutically acceptable salt thereof.

4. A compound of claim 1 having the formula

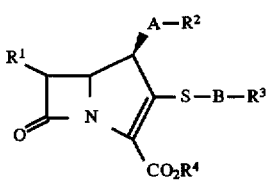

wherein
$R^1$ is

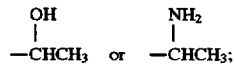

A is a straight or branched $C_{1-10}$ alkylene group;

417

$R^2$ is hydroxy, nitrile, azido, —$NR^5R^6$ or

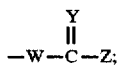

B is a straight or branched $C_{1-6}$ alkylene group or a direct bond when $R^3$ is joined to the sulfur atom through a carbon atom thereof;

$R^3$ is hydrogen, $C_{3-6}$ cycloalkyl or substituted $C_{3-6}$ cycloalkyl, phenyl or substituted phenyl, hydroxy, $C_{1-4}$ alkoxy, $C_{1-4}$ alkylthio, phenylthio or substituted phenylthio, halogen, nitrile, —$NR^7R^8$,

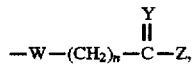

or an unsubstituted or substituted heterocyclic group selected from heteroaromatic and heteroalicyclic, having from one to two rings with 5 to 6 ring members in each ring and having up to four heteroatoms in each ring independently selected from oxygen, nitrogen and sulfur, in which said heterocyclic group may be joined through a sulfur atom attached to a carbon atom of said heterocyclic group, wherein said $C_{3-6}$ cycloalkyl, phenyl and heterocyclic substituent is selected from the group consisting of one or two $C_{1-4}$ alkyl, $C_{1-4}$ alkoxy, trifluoromethyl, hydroxy, halogen, amino, $C_{1-4}$ alkylamino, di($C_{1-4}$)alkylamino, nitrile, carboxy, formimidoyl, carbamido, carbamoyl, amino($C_{1-4}$) alkyl, $C_{1-4}$ alkylamino($C_{1-4}$)alkyl, di($C_{1-4}$)alkylamino ($C_{1-4}$)alkyl, $C_{1-4}$ alkoxycarbonyl, $C_{1-4}$ alkoxycarbonyl ($C_{1-4}$)alkyl, amino($C_{1-4}$)alkylamino($C_4$)alkyl and $C_{1-4}$ alkylcarbonyloxy, and said heterocyclic group may also be substituted with

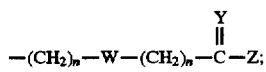

$R^4$ is hydrogen, a removable carboxy-protecting group or a physiologically hydrolyzable ester group;

$R^5$ and $R^6$ each are independently hydrogen and $C_{1-6}$ alkyl, and when $R^5$ is hydrogen or $C_{1-4}$ alkyl $R^6$ is substituted ($C_{1-4}$)alkyl wherein said alkyl substituent is selected from hydroxy, azido, amino, guanidino, nitrile, carboxy, formimidoyl and phenyl, or an acyl residue of an amino acid or peptide; or $R^5$ and $R^6$, taken together with the nitrogen atom to which they are attached, is an unsubstituted or substituted azetidino, or an unsubstituted or substituted 5- or 6-membered heterocyclic group having up to four heteroatoms in each ring independently selected from oxygen, nitrogen and sulfur, in which said heterocyclic group may be joined through a sulfur atom attached to a carbon atom of said heterocyclic group, wherein said substituent is selected from the group consisting of $C_{1-4}$ alkyl, amino, formimidoyl, $C_{1-4}$ alkylamino and amino($C_{1-4}$)alkyl;

n is an integer of from 0 to 2; inclusive;

W is a direct bond, oxygen, sulphur or $NR^{10}$;

Y is oxygen or $NR^{10}$;

Z is hydrogen, hydroxy, $C_{1-4}$ alkyl, $C_{1-4}$ alkoxy, $NR^7R^8$, amino($C_{1-4}$)alkyl, azido($C_{1-4}$)alkyl or hydroxy($C_{1-4}$) alkyl;

$R^7$ and $R^8$ each are independently hydrogen, $C_{1-4}$ alkyl, hydroxy, benzyloxy or alkanoyl;

418

$R^9$ is a $C_{1-4}$ alkyl or $C_{2-4}$ alkenyl; and $R^{10}$ is hydrogen, $C_{1-4}$ alkyl, $C_{1-4}$ alkylamino or di($C_{1-4}$) alkylamino;

or a non-toxic pharmaceutically acceptable salt thereof.

5. A compound of claim 1 having the formula

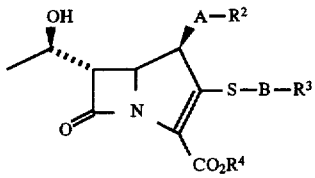

wherein

A is a straight or branched $C_{1-10}$ alkylene group;

$R^2$ is hydroxy, nitrile, azido, —$NR^5R^6$ or

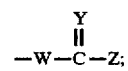

B is a straight or branched $C_{1-6}$ alkylene group or a direct bond when $R^3$ is joined to the sulfur atom through a carbon atom thereof;

$R^3$ is hydrogen, substituted $C_{3-6}$ cycloalkyl, substituted phenyl, hydroxy, $C_{1-4}$ alkoxy, $C_{1-4}$ alkylthio, substituted phenylthio, halogen, nitrile, —$NR^7R^8$,

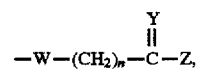

or an unsubstituted or substituted heterocyclic group selected from heteroaromatic and heteroalicyclic, having a 5- or 6-membered ring and having up to four heteroatoms in each ring independently selected from oxygen, nitrogen and sulfur, in which said heterocyclic group may be joined through a sulfur atom attached to a carbon atom of said heterocyclic group, wherein said $C_{3-6}$ cycloalkyl, phenyl and heterocyclic substituent is selected from the group consisting of one or two $C_{1-4}$ alkyl, $C_{1-4}$ alkoxy, trifluoromethyl, hydroxy, halogen, amino, $C_{1-4}$ alkylamino, di($C_{1-4}$)alkyl-amino, nitrile, carboxy, formimidoyl, $C_{1-4}$ alkoxycarbonyl, $C_{1-4}$ alkoxycarbonyl($C_{1-4}$)alkyl, amino($C_{1-4}$)alkylamino ($C_{1-4}$)alkyl and $C_{1-4}$ alkylcarbonyloxy, and said heterocyclic group may also be substituted with

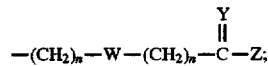

$R^4$ is hydrogen, a removable carboxy-protecting group or a physiologically hydrolyzable ester group;

$R^5$ and $R^6$ each are independently hydrogen and $C_{1-6}$ alkyl, and when $R^5$ is hydrogen or $C_{1-4}$ alkyl, $R^6$ is substituted ($C_{1-4}$)alkyl wherein said alkyl substituent is selected from hydroxy, azido, amino, guanidino, nitrile, carboxy, formimidoyl and phenyl, or an acyl residue of an amino acid or peptide; or $R^5$ and $R^6$, taken together with the nitrogen atom to which they are attached, is azetidino, pyrrolidino, pyrrolinio, piperidino, morpholino, thiomorpholino, piperazino, N-methylpiperazino, imidazoyl;

n is an integer of from 0 to 2; inclusive;

W is a direct bond, oxygen, sulphur or $NR^{10}$;

Y is oxygen or NR$^{10}$;

Z is hydrogen, hydroxy, C$_{1-4}$ alkyl, C$_{1-4}$ alkoxy, NR$^7$R$^8$, amino(C$_{1-4}$)alkyl, azido(C$_{1-4}$)alkyl or hydroxy(C$_{1-4}$) alkyl;

R$^7$ and R$^8$ each are independently hydrogen, C$_{1-4}$ alkyl, hydroxy, benzyloxy or alkanoyl;

R$^9$ is a C$_{1-4}$ alkyl or C$_{2-4}$ alkenyl; and

R$^{10}$ is hydrogen, C$_{1-4}$ alkyl, C$_4$ alkylamino or di(C$_{1-4}$) alkylamino;

or a non-toxic pharmaceutically acceptable salt thereof.

6. A compound of claim 1 having the formula

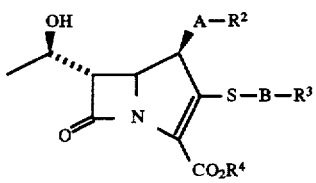

wherein

A is a straight or branched C$_{1-8}$ alkylene group;

R$^2$ is —NR$^5$R$^6$ or

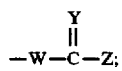

B is a straight or branched C$_{1-4}$ alkylene group or a direct bond when R$^3$ is joined to the sulfur atom through a carbon atom thereof;

R$^3$ is hydrogen, substituted C$_{3-6}$ cycloalkyl, substituted phenyl, hydroxy, C$_{1-4}$ alkoxy, C$_{1-4}$ alkylthio, substituted phenylthio, fluoro, nitrile, —NR$^7$R$^8$,

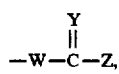

or an unsubstituted or substituted heterocyclic group selected from heteroaromatic and heteroalicyclic, having a 5- or 6-membered ring and having up to four heteroatoms in each ring independently selected from oxygen, nitrogen and sulfur, wherein said C$_{3-6}$ cycloalkyl, phenyl and heterocyclic substituent is selected from the group consisting of methyl, methoxy, trifluoromethyl, hydroxy, halogen, amino, C$_{1-4}$ alkylamino, di(C$_{1-4}$)alkylamino, nitrile, carboxy, C$_{1-4}$ alkoxycarbonyl, C$_{1-4}$ alkoxycarbonyl(C$_{1-4}$) alkyl, amino(C$_{1-4}$)alkylamino(C$_{1-4}$)alkyl and C$_{1-4}$ alkylcarbonyloxy, and said heterocyclic group may also be substituted with

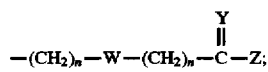

R$^4$ is hydrogen, a removable carboxy-protecting group or a physiologically hydrolyzable ester group;

R$^5$ and R$^6$ each are independently hydrogen and C$_{1-6}$ alkyl, and when R$^5$ is hydrogen or C$_{1-4}$ alkyl, R$^6$ is substituted (C$_{1-4}$)alkyl wherein said alkyl substituent is selected from hydroxy, azido, amino, guanidino, nitrile, carboxy, formimidoyl and phenyl, or an acyl residue of an amino acid or peptide; or R$^5$ and R$^6$, taken together with the nitrogen atom to which they are attached, is azetidino, pyrrolidino, pyrrolinio, piperidino, morpholino, thiomorpholino, piperazino, N-methylpiperazino, imidazoyl;

n is an integer of from 0 to 2; inclusive;

W is a direct bond, oxygen, sulphur or NR$^{10}$;

Y is oxygen or NR$^{10}$;

Z is hydrogen, hydroxy, C$_{1-4}$ alkyl, C$_{1-4}$ alkoxy, NR$^7$R$^8$, amino(C$_{1-4}$)alkyl, azido(C$_{1-4}$)alkyl or hydroxy(C$_{1-4}$) alkyl;

R$^7$ and R$^8$ each are independently hydrogen, C$_{1-4}$ alkyl, hydroxy, benzyloxy or alkanoyl;

R$^9$ is a C$_{1-4}$ alkyl or C$_{2-4}$ alkenyl; and

R$^{10}$ is hydrogen, C$_{1-4}$ alkyl, C$_{1-4}$ alkylamino or di(C$_{1-4}$) alkylamino;

or a non-toxic pharmaceutically acceptable salt thereof.

7. A compound of claim 1 wherein R$^2$ is amino.

8. A compound of claim 1 wherein R$^2$ is dimethylamino.

9. A compound of claim 1 wherein R$^2$ is N-formimidoylamino.

10. A compound of claim 1 wherein R$^2$ is guanidino.

11. A compound of claim 1 wherein R$^2$ is pyrrolidino.

12. A compound of claim 1 wherein R$^2$ is methylamino.

13. The compound of claim 1 which is (4R,5S,6S)-4-(2"-aminoethyl)-6-[(1'R)-1'-hydroxyethyl]-3-[(pyridin-2-yl) methylthio]-7-oxo-1-azabicyclo[3.2.0]hept-2-ene-2-carboxylic acid or a non-toxic pharmaceutically acceptable salt thereof.

14. The compound of claim 1 which is (4R,5S,6S)-4-(3"-aminopropyl)-6-[(1'R)-1'-hydroxyethyl]-3-[(pyridin-2-yl) methylthio]-7-oxo-1-azabicyclo[3.2.0]hept-2-ene-2-carboxylic acid or a non-toxic pharmaceutically acceptable salt thereof.

15. The compound of claim 1 which is (4R,5S,6S)-4-(2"-aminoethyl)-6-[(1'R)-1'-hydroxyethyl]-3-[(1-methylpyridinium-2-yl)methylthio]-7-oxo-1-azabicyclo[3.2.0]hept-2-ene-2-carboxylic acid or a non-toxic pharmaceutically acceptable salt thereof.

16. The compound of claim 1 which is (4R,5S,6S)-4-(4"-aminobutyl)-3-[(2-cyanoethyl)thio]-6-[(1'R)-1'-hydroxyethyl]-7-oxo-1-azabicyclo[3.2.0]hept-2-ene-2-carboxylic acid or a non-toxic pharmaceutically acceptable salt thereof.

17. The compound of claim 1 which is (4R,5S,6S)-3-[(2-cyanoethyl)thio]-4-[4"-(N-formimidoyl)aminobutyl]-6-[(1'R)-1'-hydroxyethyl]-7-oxo-1-azabicyclo[3.2.0]hept-2-ene-2-carboxylic acid or a non-toxic pharmaceutically acceptable salt thereof.

18. The compound of claim 1 which is (4R,5S,6S)-3-[(2-cyanoethyl)thio]-4-(4"-N,N-dimethylaminobutyl)-6-[(1'R)-1'-hydroxyethyl]-7-oxo-1-azabicyclo[3.2.0]hept-2-ene-2-carboxylic acid or a non-toxic pharmaceutically acceptable salt thereof.

19. The compound of claim 1 which is (4R,5S,6S)-4-(2"-aminoethyl)-6-[(1'R)-1'-hydroxyethyl]-3-[(pyridin-3-yl) methylthio]-7-oxo-1-azabicyclo[3.2.0]hept-2-ene-2-carboxylic acid or a non-toxic pharmaceutically acceptable salt thereof.

20. The compound of claim 1 which is (4R,5S,6S)-4-(2"-N,N-dimethylaminoethyl)-6-[(1'R)-1'-hydroxyethyl]-3-[(pyridin-3-yl)methylthio]-7-oxo-1-azabicyclo[3.2.0]-hept-2-ene-2-carboxylic acid or a non-toxic pharmaceutically acceptable salt thereof.

21. The compound of claim 1 which is (4R,5S,6S)-4-[2"-(N-cyanomethyl-N-methylamino)ethyl]-6-[(1'R)-1'-hydroxyethyl]-3-[(pyridin-3-yl)methylthio]-7-oxo-1-azabicyclo-[3.2.0]hept-2-ene-2-carboxylic acid or a non-toxic pharmaceutically acceptable salt thereof.

22. The compound of claim 1 which is (4R,5S,6S)-4-(3"-aminopropyl)-6-[(1'R)-1'-hydroxyethyl]-3-[(2-hydroxyethyl)thio]-7-oxo-1-azabicyclo[3.2.0]hept-2-ene-2-carboxylic acid or a non-toxic pharmaceutically acceptable salt thereof.

23. The compound of claim 1 which is (4R,5S,6S)-4-[3"-(N-formimidoyl)aminopropyl]-6-[(1'R)-1'-hydroxyethyl]-3-[(2-hydroxyethyl)thio]-7-oxo-1-azabicyclo[3.2.0]hept2-ene-2-carboxylic acid or a non-toxic pharmaceutically acceptable salt thereof.

24. The compound of claim 1 which is (4R,5S,6S)-4-[3"-(N-formimidoyl)aminopropyl]-6-[(1'R)-1'-hydroxyethyl]-3-methylthio-7-oxo-1-azabicyclo[3.2.0]hept-2-ene-2-carboxylic acid or a non-toxic pharmaceutically acceptable salt thereof.

25. The compound of claim 1 which is (4R,5S,6S)-4-[3"-(N-guanidinyl)aminopropyl]-6-[(1'R)-1'-hydroxyethyl]-3-methylthio-7-oxo-1-azabicyclo[3.2.0]hept-2-ene-2-carboxylic acid or a non-toxic pharmaceutically acceptable salt thereof.

26. The compound of claim 1 which is (4R,5S,6S)-4-[3"-(N-guanidinyl)aminopropyl]-6-[(1'R)-1'-hydroxyethyl]-3-[(2-hydroxyethyl)thio]-7-oxo-1-azabicyclo[3.2.0]hept-2-ene-2-carboxylic acid or a non-toxic pharmaceutically acceptable salt thereof.

27. The compound of claim 1 which is (4R,5S,6S)-4-(2"-aminoethyl)-3-[(2-cyanoethyl)thio]-6-[(1'R)-1'-hydroxyethyl]-7-oxo-1-azabicyclo[3.2.0]hept-2-ene-2-carboxylic acid or a non-toxic pharmaceutically acceptable salt thereof.

28. The compound of claim 1 which is (4R,5S,6S)-4-(2"-aminoethyl)-6-[(1'R)-1'-hydroxyethyl]-3-[(1,2,3-thiadiazol-4-yl)methylthio]-7-oxo-1-azabicyclo[3.2.0]hept-2-ene-2-carboxylic acid or a non-toxic pharmaceutically acceptable salt thereof.

29. The compound of claim 1 which is (4R,5S,6S)-4-(2"-guanidinoethyl)-6-[(1'R)-1'-hydroxyethyl]-3-[(1,2,3-thiadiazol-4-yl)methylthio]-7-oxo-1-azabicyclo[3.2.0]hept-2-ene-2-carboxylic acid or a non-toxic pharmaceutically acceptable salt thereof.

30. The compound of claim 1 which is (4R,5S,6S)-4-(3"-aminopropyl)-3-[(2-cyanoethyl)thio]-6-[(1'R)-1'hydroxyethyl]-7-oxo-1-azabicyclo[3.2.0]hept-2-ene-2-carboxylic acid or a non-toxic pharmaceutically acceptable salt thereof.

31. The compound of claim 1 which is (4R,5S,6S)-3-[(2-cyanoethyl)thio]-6-[(1'R)-1'-hydroxyethyl]-4-(3"-hydroxypropyl)-7-oxo-1-azabicyclo[3.2.0]hept-2-ene-2-carboxylic acid or a non-toxic pharmaceutically acceptable salt thereof.

32. The compound of claim 1 which is (4R,5S,6S)-4-[3"-(N-formimidoyl)aminopropyl]-3-[(2-cyanoethyl)thio]-6-[(1'R)-1'-hydroxyethyl]-7-oxo-1-azabicyclo[3.2.0]hept-2-ene-2-carboxylic acid or a non-toxic pharmaceutically acceptable salt thereof.

33. The compound of claim 1 which is (4R,5S,6S)-4-(2"-aminoethyl)-3-[(3-cyanopropyl)thio]-6-[(1'R)-1'-hydroxyethyl]-7-oxo-1-azabicyclo[3.2.0]hept-2-ene-2-carboxylic acid or a non-toxic pharmaceutically acceptable salt thereof.

34. The compound of claim 1 which is (4R,5S,6S)-6-[(1'R)-1'-hydroxyethyl]-4-(2"-aminoethyl)-3[(pyridin-4-yl)methyl- thio]-7-oxo-1-azabicyclo[3.2.0]hept-2-ene-2-carboxylic acid or a non-toxic pharmaceutically acceptable salt thereof.

35. The compound of claim 1 which is (4R,5S,6S)-3-[(2-cyanoethyl)thio]-4-(3"-guanidinopropyl)-6-[(1'R)-1'-hydroxyethyl]-7-oxo-1-azabicyclo[3.2.0]hept-2-ene-2-carboxylic acid or a non-toxic pharmaceutically acceptable salt thereof.

36. The compound of claim 1 which is (4R,5S,6S)-3-[(2-cyanoethyl)thio]-6-[(1'R)-1'-hydroxyethyl]-4-[2"(1-pyrrolidinyl)ethyl]-7-oxo-1-azabicyclo[3.2.0]hept-2-ene-2-carboxylic acid or a non-toxic pharmaceutically acceptable salt thereof.

37. The compound of claim 1 which is (4R,5S,6S)-4-(2"-aminoethyl)-3-[(1-methyl-1,2,3-triazol-4-yl)methylthio]-6-[(1'R)-1'-hydroxyethyl]-7-oxo-1-azabicyclo[3.2.0]hept-2-ene-2-carboxylic acid or a non-toxic pharmaceutically acceptable salt thereof.

38. The compound of claim 1 which is (4R,5S,6S)-4-(4"-aminobutyl)-6-[(1'R)-1'-hydroxyethyl]-3-[(2-hydroxyethyl)thio]-7-oxo-1-azabicyclo[3.2.0]hept-2-ene-2-carboxylic acid or a non-toxic pharmaceutically acceptable salt thereof.

39. The compound of claim 1 which is (4R,5S,6S)-3-[(2-cyanoethyl)thio]-4-(4"-guanidinobutyl)-6-[(1'R)-1'-hydroxyethyl]-7-oxo-1-azabicyclo[3.2.0]hept-2-ene-2-carboxylic acid or a non-toxic pharmaceutically acceptable salt thereof.

40. The compound of claim 1 which is (4R,5S,6S)-3-[(2-cyanoethyl)thio]-4-(2"-guanidinoethyl)-6-[(1'R)-1'-hydroxyethyl]-7-oxo-1-azabicyclo[3.2.0]hept-2-ene-2-carboxylic acid or a non-toxic pharmaceutically acceptable salt thereof.

41. The compound of claim 1 which is (4R,5S,6S)-4-(3"-aminopropyl)-6-[(1'R)-1'-hydroxyethyl]-3-[(1-methyl-1,2,3-triazol-4-yl)methylthio]-7-oxo-1-azabicyclo[3.2.0]hept-2-ene-2-carboxylic acid or a non-toxic pharmaceutically acceptable salt thereof.

42. The compound of claim 1 which is (4R,5S,6S)-3-[(2-carbamoyloxyethyl)thio]-4-[3"-(N-formimidoyl)aminopropyl]-6-[(1'R)-1'-hydroxyethyl]-7-oxo-1-azabicyclo[3.2.0]hept-2-ene-2-carboxylic acid or a non-toxic pharmaceutically acceptable salt thereof.

43. The compound of claim 1 which is (4R,5S,6S)-4-(4"-aminobutyl)-3-[(2-carbamoyloxy)ethylthio]-6-[(1'R)-1'-hydroxyethyl]-7-oxo-1-azabicyclo[3.2.0]hept-2-ene-2-carboxylic acid or a non-toxic pharmaceutically acceptable salt thereof.

44. The compound of claim 1 which is (4R,5S,6S)-4-(3"-guanidinopropyl)-6-[(1'R)-1'-hydroxyethyl]-3-[(1,2,3-thiadiazol-4-yl)methylthio]-7-oxo-1-azabicyclo[3.2.0]hept-2-ene-2-carboxylic acid or a non-toxic pharmaceutically acceptable salt thereof.

45. The compound of claim 1 which is (4R,5S,6S)-3-[(2-carbamoyloxyethyl)thio]-4-(4"-N,N-dimethylaminobutyl)-6-[(1'R)-1'-hydroxyethyl]-7-oxo-1-azabicyclo[3.2.0]hept-2-ene-2-carboxylic acid or a non-toxic pharmaceutically acceptable salt thereof.

46. The compound of claim 1 which is (4R,5S,6S)-4-(2"-acetaldehydo)-3-[(2-cyanoethyl)thio]-6-[(1'R)-1'-hydroxyethyl]-7-oxo-1-azabicyclo[3.2.0]hept-2-ene-2-carboxylic acid or a non-toxic pharmaceutically acceptable salt thereof.

47. The compound of claim 1 which is (4R,5S,6S)-3-[(2-cyanoethyl)thio]-6-[(1'R)-1'-hydroxyethyl]-4-(hydroxycarbonylmethyl)-7-oxo-1-azabicyclo[3.2.0]hept-2-ene-2-carboxylate or a non-toxic pharmaceutically acceptable salt thereof.

48. The compound of claim 1 which is (4R,5S,6S)-3-{(4S)-4-[(2S)-2-dimethylaminocarbonyl]pyrrolidinylthio}-6-[(1'R)-1'-hydroxyethyl]-4-(2"-hydroxyethyl)-7-oxo-1-azabicyclo-[3.2.0]hept-2-ene-2-carboxylic acid or a non-toxic pharmaceutically acceptable salt thereof.

49. The compound of claim 1 which is (4R,5S,6S)-4-(2"-aminoethyl)-3-{(4S)-4-[(2S)-2-dimethylaminocarbonyl]-pyrrolidinylthio}-6-[(1'R)-1'-hydroxyethyl]-7-oxo-1- azabicyclo[3.2.0]hept-2-ene-2-carboxylic acid or a non-toxic pharmaceutically acceptable salt thereof.

50. The compound of claim 1 which is (4R,5S,6S)-4-(3"-aminopropyl)-3-{(4S)-4-[(2S)-2-dimethylaminocarbonyl]-pyrrolidinylthio}-6-[(1'R)-1'-hydroxyethyl]-7-oxo-1-azabicyclo[3.2.0]hept-2-ene-2-carboxylic acid or a non-toxic pharmaceutically acceptable salt thereof.

51. The compound of claim 1 which is (4R,5S,6S)-3-((4S)-4-[(2S)-2-dimethylaminocarbonyl]pyrrolidinylthio)-4-(3"-guanidinopropyl)-6-[(1'R)-1'-hydroxyethyl]-7-oxo-1-azabicyclo[3.2.0]hept-2-ene-2-carboxylic acid or a non-toxic pharmaceutically acceptable salt thereof.

52. The compound of claim 1 which is (4R,5S,6S)-4-(2"-aminoethyl)-3-[(2-aminoethyl)thio]-6-[(1'R)-1'-hydroxyethyl]-7-oxo-1-azabicyclo[3.2.0]hept-2-ene-2-carboxylic acid or a non-toxic pharmaceutically acceptable salt thereof.

53. The compound of claim 1 which is (4R,5S,6S)-4-(3"-aminopropyl)-3-[(2-aminoethyl)thio]-6-[(1'R)-1'-hydroxyethyl]-7-oxo-1-azabicyclo[3.2.0]hept-2-ene-2-carboxylic acid or a non-toxic pharmaceutically acceptable salt thereof.

54. The compound of claim 1 which is (4R,5S,6S)-4-(3"-aminopropyl)-3-[(2-N-formimidoylaminoethyl)thio]-6-[(1'R)-1'-hydroxyethyl]-7-oxo-1-azabicyclo[3.2.0]hept-2-ene-2-carboxylic acid or a non-toxic pharmaceutically acceptable salt thereof.

55. The compound of claim 1 which is (4R,5S,6S)-6-[(1'R)-1'-hydroxyethyl]-3-[(2-hydroxyethyl)thio]-4-(2"-aminoethyl)-7-oxo-1-azabicyclo-[3.2.0]hept-2-ene-2- carboxylic acid or a non-toxic pharmaceutically acceptable salt thereof.

56. The compound of claim 1 which is (4R,5S,6S)-3-[(2-cyanoethyl)thio]-6-[(1'R)-1'-hydroxyethyl]-4-[2"-(1-N-methylpyrrolidinium)ethyl]-7-oxo-1-azabicyclo[3.2.0]hept-2-ene-2-carboxylate or a non-toxic pharmaceutically acceptable salt thereof.

57. The compound of claim 1 which is (4R,5S,6S)-3-[(2-cyanoethyl)thio]-6-[(1'R)-1'-hydroxyethyl]-4-[2"-(4-methyl- piperazine-1-yl)ethyl]-7-oxo-1-azabicyclo[3.2.0] hept-2-ene-2-carboxylic acid or a non-toxic pharmaceutically acceptable salt thereof.

58. The compound of claim 1 which is (4R,5S,6S)-4-(3"-guanidinopropyl)-6-[(1'R)-1'-hydroxyethyl]3-([2-(1-pyrrolidinyl)ethyl]thio)-7-oxo-1-azabicyclo[3.2.0]-hept-2-ene-2-carboxylic acid or a non-toxic pharmaceutically acceptable salt thereof.

59. The compound of claim 1 which is (4R,5S,6S)-4-(3"-aminopropyl)-3-[(2-N,N-dimethyl aminoethyl)thio]-6-[(1'R)-1'-hydroxyethyl]-7-oxo-1-azabicyclo[3.2.0]hept-2-ene-2-carboxylic acid or a non-toxic pharmaceutically acceptable salt thereof.

60. The compound of claim 1 which is (4R,5S,6S)-3-{(4S)-4-[(2S)-2-dimethylaminocarbonyl]pyrrolidinylthio}-4-(2"-guanidinoethyl)-6-[(1'R)-1'-hydroxyethyl]-7-oxo-1-azabicyclo[3.2.0]hept-2-ene-2-carboxylic acid salt or a non-toxic pharmaceutically acceptable salt thereof.

61. The compound of claim 1 which is (4R,5S,6S)-4-(3"-aminopropyl)-3-[(N,N-dimethylamidinomethyl)thio]-6-[(1'R)-1'-hydroxyethyl]-7-oxo-1-azabicyclo[3.2.0]hept-2-ene-2-carboxylic acid or a non-toxic pharmaceutically acceptable salt thereof.

62. The compound of claim 1 which is (4R,5S,6S)-4-(2"-guanidinoethyl)-6-[(1'R)-1'-hydroxyethyl]-3-[2-(1-pyrrolidinyl)ethylthio]-7-oxo-1-azabicyclo[3.2.0]-hept-2-ene-2-carboxylic acid or a non-toxic pharmaceutically acceptable salt thereof.

63. The compound of claim 1 which is (4R,5S,6S)-4-(3"-aminopropyl)-3-[(3S)-3-pyrrolidinylthio]-6-[(1'R)-1'-hydroxyethyl]-7-oxo-1-azabicyclo[3.2.0]hept-2-ene-2-carboxylic acid or a non-toxic pharmaceutically acceptable salt thereof.

64. The compound of claim 1 which is (4R,5S,6S)-4-(3"-aminopropyl)-3-[(2-guanidinoethyl)thio]-6-[(1'R)-1'-hydroxyethyl]-7-oxo-1-azabicyclo[3.2.0]hept-2-ene-2-carboxylic acid or a non-toxic pharmaceutically acceptable salt thereof.

65. The compound of claim 1 which is (4R,5S,6S)-4-(2"-guanidinoethyl)-3-[(2-guanidinoethyl)thio]-6-[(1,R)-1'-hydroxyethyl]-7-oxo-1-azabicyclo[3.2.0]hept-2-ene-2-carboxylic acid salt or a non-toxic pharmaceutically acceptable salt thereof.

66. The compound of claim 1 which is (4R,5S,6S)-6-[(1'R)-1'-hydroxyethyl]-3-[(2-cyanoethyl)thio]-4-[2"-(β-chloro-L-alanyl-β-chloro-L-alanyl) aminoethyl]-7-oxo-1-azabicyclo[3.2.]-hept-2-ene-2-carboxylic acid or a non-toxic pharmaceutically acceptable salt thereof.

67. The compound of claim 1 which is (4R,5S,6S)-4-(2"-azidoethyl)-3-[(2-fluoroethyl)thio]-6-[(1'R)-1'-hydroxyethyl]-7-oxo-1-azabicyclo[3.2.0]hept-2-ene-2-carboxylate or a non-toxic pharmaceutically acceptable salt thereof.

68. The compound of claim 1 which is (4R,5S,6S)-4-(3"-aminopropyl)-3-[(4-piperidinyl)thio]-6-[(1'R)-1'-hydroxyethyl]-7-oxo-1-azabicyclo[3.2.0]hept-2-ene-2-carboxylic acid or a non-toxic pharmaceutically acceptable salt thereof.

69. The compound of claim 1 which is (4R,5S,6S)-4-(2"-aminoethyl)-3-[(N,N-dimethylamidinomethyl)thio]-6-[(1'R)-1'-hydroxyethyl]-7-oxo-1-azabicyclo[3.2.0]hept-2-ene-2-carboxylic acid or a non-toxic pharmaceutically acceptable salt thereof.

70. The compound of claim 1 which is (4R,5S,6S)-3-[(N,N-dimethylamidinomethyl)thio]-4-(2"-guanidinoethyl)-6-[(1'R)-1'-hydroxyethyl]-7-oxo-1-azabicyclo[3.2.0]hept-2-ene-2-carboxylic acid or a non-toxic pharmaceutically acceptable salt thereof.

71. The compound of claim 1 which is (4R,5S,6S)-3-[(3R)-(pyrrolidin-3-yl)thio]-4-[2"-N-methylaminoethyl]-6-[(1'R)-1'-hydroxyethyl]-7-oxo-1-azabicyclo[3.2.0]hept-2-ene-2-carboxylic acid or a non-toxic pharmaceutically acceptable salt thereof.

72. The compound of claim 1 which is (4R,5S,6S)-4-(2"-N-formimidoyl-N-methylaminoethyl)-3-{[(3R)-(N-formimidoyl-pyrrolidin-3-yl)]thio}-6-[(1'R)-1'-hydroxyethyl]-7-oxo-1-azabicyclo[3.2.0]hept-2-ene-2-carboxylic acid or a non-toxic pharmaceutically acceptable salt thereof.

73. The compound of claim 1 which is (4R,5S,6S)-4-(3"-aminopropyl)-6-[(1'R)-1'-hydroxyethyl]-3-{[2-(4-methylpiperazin-1-yl)ethyl]thio}-7-oxo-1-azabicyclo-[3.2.0]hept-2-ene-2-carboxylic acid or a non-toxic pharmaceutically acceptable salt thereof.

74. The compound of claim 1 which is (4R,5S,6S) 3-{(4S)-4-[(2S)-2-dimethylaminocarbonylpyrrolidinyl]thio}-6-[(1'R)-1'-hydroxyethyl]-4-(2"-N-methylaminoethyl)-7-oxo-1-azabicyclo-[3.2.0]hept-2-ene-2-carboxylic acid or a non-toxic pharmaceutically acceptable salt thereof.

75. The compound of claim 1 which is (4R,5S,6S)-3-[(2-fluoroethyl)thio]-6-[(1'R)-1'-hydroxyethyl]-4-(2"-N-methylaminoethyl)-7-oxo-1-azabicyclo[3.2.0]hept-2-ene-2-carboxylic acid or a non-toxic pharmaceutically acceptable salt thereof.

76. The compound of claim 1 which is (4R,5S,6S)-3-[(2-aminoethyl)thio]-6-[(1'R)-1'-hydroxyethyl]-4-[(2"S)-(2"- pyrrolidinyl)methyl]-7-oxo-1-azabicyclo[3.2.0]hept-2-ene-2-carboxylic acid or a non-toxic pharmaceutically acceptable salt thereof.

77. The compound of claim 1 which is (4R,5S,6S)-4-[3"-amino-(2" R or S)-2"-hydroxypropyl]-3-[(2-cyanoethyl) thio]-6-[(1'R)-1'-hydroxyethyl]-7-oxo-1-azabicyclo[3.2.0]hept-2-ene-2-carboxylic acid or a non-toxic pharmaceutically acceptable salt thereof.

* * * * *